US011254985B2

(12) United States Patent
Molloy et al.

(10) Patent No.: US 11,254,985 B2
(45) **Date of Patent: *Feb. 22, 2022**

(54) DIAGNOSTIC GENE MARKER PANEL FOR COLORECTAL CANCER

(71) Applicants: CLINICAL GENOMICS PTY. LTD., North Ryde (AU); COMMONWEALTH SCIENTIFIC AND INDUSTRIAL RESEARCH ORGANISATION, Australian Capital Territory (AU)

(72) Inventors: Peter Molloy, Chatswood (AU); Lawrence Lapointe, West Pennant Hills (AU); Susanne Pedersen, Windsor Downs (AU)

(73) Assignees: CLINICAL GENOMICS PTY. LTD., New South Wales (AU); COMMONWEALTH SCIENTIFIC AND INDUSTRIAL RESEARCH ORGANIZATION, Australian Capital Territory (AU)

( * ) Notice: Subject to any disclaimer, the term of this patent is extended or adjusted under 35 U.S.C. 154(b) by 204 days.

This patent is subject to a terminal disclaimer.

(21) Appl. No.: 14/400,313

(22) PCT Filed: May 10, 2013

(86) PCT No.: PCT/AU2013/000481

§ 371 (c)(1),
(2) Date: Nov. 10, 2014

(87) PCT Pub. No.: WO2013/166558

PCT Pub. Date: Nov. 14, 2013

(65) Prior Publication Data

US 2015/0141275 A1 May 21, 2015

Related U.S. Application Data

(60) Provisional application No. 61/646,174, filed on May 11, 2012.

(51) Int. Cl.

| | |
|---|---|
| ***C12Q 1/68*** | (2018.01) |
| ***C12P 19/34*** | (2006.01) |
| ***C12Q 1/6886*** | (2018.01) |

(52) U.S. Cl.

CPC ...... *C12Q 1/6886* (2013.01); *C12Q 2600/112* (2013.01); *C12Q 2600/118* (2013.01); *C12Q 2600/154* (2013.01)

(58) Field of Classification Search

CPC ............ C12Q 1/6886; C12Q 2600/112; C12Q 2600/154; C12Q 2600/118; G01N 2800/06

See application file for complete search history.

(56) References Cited

U.S. PATENT DOCUMENTS

| | | | | |
|---|---|---|---|---|
| 4,883,750 | A | 11/1989 | Whiteley et al. | 435/6.16 |
| 5,143,854 | A | 9/1992 | Pirrung et al. | 436/518 |
| 5,786,146 | A | 7/1998 | Herman et al. | 435/6.12 |
| 5,837,832 | A | 11/1998 | Chee et al. | 506/16 |
| 5,972,602 | A | 10/1999 | Hyland et al. | 435/6.11 |
| 6,033,854 | A | 3/2000 | Kurnit et al. | 435/6.12 |
| 6,174,670 | B1 | 1/2001 | Wittwer et al. | 435/6.12 |
| 6,180,349 | B1 | 1/2001 | Ginzinger et al. | 435/6.11 |
| 7,186,512 | B2 | 3/2007 | Martienssen et al. | 435/6.16 |
| 7,459,274 | B2 | 12/2008 | Lakey et al. | 435/6.12 |
| 7,901,880 | B2 | 3/2011 | Jeddeloh et al. | 435/6.12 |
| 7,910,296 | B2 | 3/2011 | Jeddeloh et al. | 435/6.12 |
| 8,501,403 | B2 | 8/2013 | Molloy et al. | 435/6.1 |
| 8,669,050 | B2 | 3/2014 | James et al. | 435/6.1 |
| 9,765,397 | B2 * | 9/2017 | McEvoy | C12Q 1/6876 |
| 2005/0053967 | A1 | 3/2005 | James et al. | 435/6.11 |
| 2005/0069879 | A1 | 3/2005 | Berlin | 435/6.11 |
| 2005/0153316 | A1 | 7/2005 | Jeddeloh et al. | 435/6.12 |
| 2005/0158739 | A1 | 7/2005 | Jeddeloh et al. | 435/6.12 |
| 2005/0272065 | A1 | 12/2005 | Lakey et al. | 435/6.12 |
| 2009/0325810 | A1 | 12/2009 | Lapointe et al. | 506/7 |
| 2010/0233683 | A1 | 9/2010 | Molloy et al. | 435/6.1 |
| 2010/0292094 | A1 | 11/2010 | Lapointe et al. | 506/9 |
| 2011/0098189 | A1 | 4/2011 | Lapointe et al. | 506/9 |

(Continued)

FOREIGN PATENT DOCUMENTS

| | | |
|---|---|---|
| EP | 0 320 308 | 11/1993 |
| JP | 6742726 A | 8/2020 |

(Continued)

OTHER PUBLICATIONS

Kim, M.S. et al. Cancer Metastasis Rev (2010) 29:181-206.*

(Continued)

*Primary Examiner* — Stephen T Kapushoc

(74) *Attorney, Agent, or Firm* — Knobbe, Martens, Olson & Bear LLP

(57) ABSTRACT

The present invention relates generally to a method of screening for the onset, predisposition to the onset and/or progression of a neoplasm. More particularly, the present invention relates to a method of screening for the onset, predisposition to the onset and/or progression of a neoplasm by screening for changes to the methylation levels of a panel of gene markers including BCAT1, IKZF1, IRF4, GRASP and/or CAHM. The method of the present invention is useful in a range of applications including, but not limited to, those relating to the diagnosis and/or monitoring of colorectal neoplasms, such as colorectal adenocarcinosis.

14 Claims, 226 Drawing Sheets

Specification includes a Sequence Listing.

(56) References Cited

U.S. PATENT DOCUMENTS

| | | | | |
|---|---|---|---|---|
| 2011/0160072 | A1 | 6/2011 | Lapointe et al. | 506/9 |
| 2013/0059734 | A1 | 7/2013 | Molloy et al. | 506/23 |
| 2013/0338020 | A1* | 12/2013 | Ross | C12Q 1/6886 506/9 |
| 2014/0155280 | A1 | 6/2014 | Lapointe et al. | 506/7 |
| 2015/0010951 | A1 | 1/2015 | Lapointe et al. | 435/91.21 |
| 2015/0152505 | A1* | 6/2015 | Lapointe | C12Q 1/6886 435/6.11 |
| 2017/0191135 | A1* | 7/2017 | Pedersen | C12Q 1/6886 |

FOREIGN PATENT DOCUMENTS

| | | | |
|---|---|---|---|
| WO | WO 96/17958 | 6/1996 | |
| WO | WO 98/49557 | 11/1998 | |
| WO | WO 2000/070090 | 11/2000 | |
| WO | WO 2007/109850 | 10/2007 | |
| WO | WO 2009/043112 | 4/2009 | |
| WO | WO 2009/052571 | 4/2009 | |
| WO | WO 2010/135786 | 12/2010 | |
| WO | WO 2011/144718 | 11/2011 | |
| WO | WO 2012/034170 | 3/2012 | |
| WO | WO-2012034170 A1 * | 3/2012 | C12Q 1/6886 |
| WO | WO 2013/026104 | 2/2013 | |
| WO | WO 2013/170314 | 11/2013 | |

OTHER PUBLICATIONS

Weisenberger, D.J. et al. "Comprehensive DNA Methylation Analysis on the Illumina Infinium Assay Platform" Illumina Applicantion Note (2010), form www.illumina.com.*
Costello, J.F. et al. The Jopurnal of Biological Chemistry, vol. 269, No. 25, Isaue of Jun. 24, pp. 1722g-17237, 1994.*
Juppner, H. Bone vol. 17, No. 2, Supplement, Aug. 1995:39S-42S.*
HumanMethylation27 Product Support Files content list (.xlsx) for the HumanMethylation27 BeadChip,four pages printed on Dec. 8, 2017 from https://support.illumina.com/downloads.html (Year: 2017).*
Irizarry R.A. et al, Nature Genetics, Feb. 2009, vol. 41, No. 2, p. 178-186, also data from Supplementary Data Tables 2 and 1. (Year: 2009).*
Li, X. et al. Molecular and Clinical Oncology 1: 153-160, 2013 (Year: 2013).*
Brenner H. et al. Statistics in Medicine, vol. 16, 981-991 (1997) (Year: 1997).*
DNA-based Molecular Diagnostic Techniques: Research Needs for Standardization and Validation of the Detection of Aquatic Animal Pathogens and Diseases, editd by Peter Walker and Rohana Subasinghe. FAO Fisheries Technical Paper. No.395. Rome, FAO. (Year: 2000).*
Grothey, A. et al. J Clin Oncol 26:5326-5334. (Year: 2008).*
Letter/Written Disclosure of the Information Disclosure Statement for the above-referenced application, dated Apr. 16, 2015, 2 pages.
Narang et al., "Improved phosphotriester method for the synthesis of gene fragments," Methods Enzymol 68:90-98 (1979).
Nevrivy et al.,"Interaction of GRASP, a protein encoded by a novel retinoic acid-induced gene, with members of the cytohesin family of guanine nucleotide exchange factors," J Biol. Chem. 275(22):16827-16836 (2000).
Nielsen et al., "Synthesis of 2'-O.3'-C-linked bicyclic nucleosides and bicyclic oligonucleotides," J. Chem. Soc. Perkin Trans., 1:3423-3433 (1997).
Olek, A. and J. Walter, "The pre-implantation ontogeny of the H19 methylation imprint," Nat. Genet. 17(3): 275-276 (1997).
Orum et al., "Detection of the factor V Leiden mutation by direct allele-specific hybridization of PCR amplicons to photoimmobilized locked nucleic acids." Clin. Chem. 45:1898-1905 (1999).
Orum et al., "Single base pair mutation analysis by PNA directed PCR clamping." Nucl. Acids Res., 21:5332-5336 (1993).
Oster et al., "Identification and validation of highly frequent CpG island hypermethylation in colorectal adenomas and carcinomas," Int. J. Cancer 129:2855-2566 (2011).
Pathak et al.,"IRF4 is a suppressor of c-Myc induced B cell leukemia," PLoS One 6:e22628, 9 pages (2011).
Pedersen et al., "CAHM, a long non-coding RNA gene hypermethylated in colorectal neoplasia," Epigenetics 9(8):1071-1082 (2014).
Rand et al, "Bisulphite differential denaturation PCR for analysis of DNA methylation." Epigenetics 1:94-100 (2006).
Rand et al.,"Headloop suppression PCR and its application to selective amplification of methylated DNA sequences." Nucl. Acids Res. 33;e127, 11 pages (2005).
Rein et al.,"Identifying 5-methylcytosine and related modifications in DNA genomes." Nucl. Acids Res. 26(10): 2255-2264 (1998).
Ross et al., "Identification of differentially methylated regions using streptavidin bisulfite ligand methylation enrichment (SuBLiME), a new method to enrich for methylated DNA prior to deep bisulfite genomic sequencing," Epigenetics 8(1):113-127 (2013).
Sadri, R. and P.J. Hornsby, "Rapid analysis of DNA methylation using new restriction enzyme sites created by bisulfite modification." Nucl. Acids Res. 24:5058-5059 (1996).
SantaLucia, J., "A unified view of polymer, dumbbell, and oligonucleotide DNA nearest-neighbor thermodynamics." Proc. Natl. Acad. Sci. USA, 95:1460-1465 (1998).
Shames et al., "Methods for detecting DNA methylation in tumors: from bench to bedside," Cancer Lett. 251:187-198 (2007).
Simeonov, A. and T. Nikiforov, "Single nucleotide polymorphism genotyping using short, fluorescently labeled locked nucleic acid (LNA) probes and fluorescence polarization detection" Nucl. Acids Res., 30(17):e91, 5 pages (2002).
Singer-Sam et al., "A quantitative HpaII-PCR assay to measure methylation of DNA from a small number of cells." Nucl. Acids Res. 18:687 (1990).
Singer-Sam et al., "A sensitive, quantitative assay for measurement of allele-specific transcripts differing by a single nucleotide." PCR Methods Appl. 1:160-163 (1992).
Singh, S.K. and J. Wengel, "Universality of LNA-mediated high-affinity nucleic acid recognition," Chem. Commun. 1247-1248 (1998).
Slattery et al., "Interferon-signaling pathway: associations with colon and rectal cancer risk and subsequent survival," Carcinogenesis 32(11):1660-1667 (2011).
Southern et al., "Analyzing and comparing nucleic acid sequences by hybridization to arrays of oligonucleotides: evaluation using experimental models." Genomics, 13:1008-1017 (1992).
Szabo, P.E. and J.R. Mann, "Allele-specific expression and total expression levels of imprinted genes during early mouse development: implications for imprinting mechanisms." Genes Dev. 9: 3097-3108 (1995).
Toyota et al., "Identification of differentially methylated sequences in colorectal cancer by methylated CpG island amplification." Cancer Res. 59:2307-2312 (1999).
Uhlmann et al., "Evaluation of a potential epigenetic biomarker by quantitative methyl-single nucleotide polymorphism analysis," Electrophoresis, 23:4072-4079 (2002).
Wedemeyer et al., "Flow cytometric quantification of competitive reverse transcription-PCR products." Clin. Chem. 48(9):1398-1405 (2002).
Weissleder et al., "In vivo magnetic resonance imaging of transgene expression." Nature Medicine 6:351-354 (2000).
Weitzel, J., "Genetic cancer risk assessment. Putting it all together," Cancer 86 (11 Suppl): 2483-2492 (1999).
Worm et al., "In-tube DNA methylation profiling by fluorescence melting curve analysis." Clin. Chem. 47(7):1183-1189 (2001).
Xiong, Z. and P.W. Laird, "COBRA: a sensitive and quantitative DNA methylation assay." Nucl. Acids Res. 25:2532-2534 (1997).
Yamashita et al., "DNA methylation of interferon regulatory factors in gastric cancer and noncancerous gastric mucosae," Cancer Sci. 101:1708-1716 (2010).
Written Opinion, dated Jul. 1, 2013, in connection with International Patent Application No. PCT/AU2013/000481, 4 pages.
International Search Report, dated Jul. 1, 2013, in connection with International Patent Application No. PCT/AU2013/000481, 6 pages.
International Preliminary Report on Patentability, dated Nov. 11, 2014, in connection with International Patent Application No. PCT/AU2013/000481, 5 pages.

(56) References Cited

OTHER PUBLICATIONS

Letter/Written Disclosure of the Information Disclosure application, dated Apr. 15, 2015, 2 pages.
Abrams, E. and V. Stanton, "Use of denaturing gradient gel electrophoresis to study conformational transitions in nucleic acids." Methods Enzymol., 212:71-104 (1992).
Adorjan et al., "Tumour class prediction and discovery by microarray-based DNA methylation analysis," Nucl. Acids Res., 30:e21, 9 pages (2002).
Alon et al., "Broad patterns of gene expression revealed by clustering analysis of tumor and normal colon tissues probed by oligonucleotide arrays." Proc. Natl. Acad. Sci. USA: 96:6745-6750 (1999).
Ammerpohl et al., "Hunting for the 5th base: Techniques for analyzing DNA methylation." Biochim Biophys Acta. 1790:847-862 (2009).
Beaucage, S. and M. Caruthers, "Deoxynucleoside phosphoramidites—A new class of key intermediates for deoxypolynucleotide synthesis," Tetrahedron Letters 22:1859-1862 (1981).
Bianco et al., "Methylation-sensitive, single-strand conformation analysis (MS-SSCA): A rapid method to screen for and analyze methylation." Hum. Mutat., 14:289-293 (1999).
Bonner, W. and R. Laskey, "A film detection method for tritium-labelled proteins and nucleic acids in polyacrylamide gels," Eur. J. Biochem. 46:83-88 (1974).
Breslauer et al., "Predicting DNA duplex stability from the base sequence," Proc. Natl. Acad. Sci. USA, 83: 3746-3750 (1986).
Caruthers et al., "Chemical synthesis of deoxyoligonucleotides by the phosphoramidite method," Methods Enzymol. 154:287-313 (1988).
Chen, X. and P. Kwok, "Template-directed dye-terminal incorporation (TDI) assay: a homogeneous DNA diagnostic method based on fluorescence resonance energy transfer," Acids Res. 25:347-353 (1997).
Clark et al., "DNA methylation: bisulphite modification and analysis," Nat Protoc. 1:2353-2364 (2006).
Clark et al., "High sensitivity mapping of methylated cytosines." Nucl. Acids Res. 22:2990-2997 (1994).
Cottrell et al., "A real-time PCR assay for DNA-methylation using methylation-specific blockers," Nucl. Acids Res. 32:e10, 8 pages (2003).
DeGraves et al., "High-sensitivity quantitative PCR platform," Biotechniques 34(1):106-110, 112-115 (2003).
Deiman et al., "Characteristics and applications of nucleic acid sequence-based amplification (NASBA)," Mol. Biotechnol. 20(2):163-179 (2002).
Deng et al., "Detection of CpG methylation in human mismatch repair gene hMLH1 promoter by denaturing high-performance liquid chromatography (DHPLC)." Chin. J. Cancer Res., 12:171, 191 (2000).
Eads et al., "MethyLight: a high-throughput assay to measure DNA methylation," Nucl. Acids Res. 28:e32, 8 pages (2000).
Eads et al.,"CpG island hypermethylation in human colorectal tumors is not associated with DNA methyltransferase overexpression," Cancer Res. 59:2302-2306 (1999).
Egholm et al., "Peptide nucleic acids (PNA). Oligonucleotide analogs with an achiral peptide backbone," J. Am. Chem. Soc., 114:1895-1897 (1992).
Egholm et al., "PNA hybridizes to complementary oligonucleotides obeying the Watson-Crick hydrogen-bonding rules," Nature, 365:566-568 (1993).
Fodor et al., "Light-directed, spatially addressable parallel chemical synthesis," Science 767-773 (1991).
Frommer et al., "A genomic sequencing protocol that yields a positive display of 5-methylcytosine residues in individual DNA strands," Proc. Natl. Acad. Sci. USA 89:1827-1831 (1992).
Gibson et al., "A novel method for real time quantitative RT-PCR," Genome Research 6:995-1001 (1996).
Golub et al., "Molecular classification of cancer: class discovery and class prediction by gene expression monitoring," Science, 286:531-537 (1999).
Gonzalgo et al., "Identification and characterization of differentially methylated regions of genomic DNA by methylation-sensitive arbitrarily primed PCR," Cancer Res. 57:594-599 (1997).
Gonzalgo, M. and P. Jones, "Rapid quantitation of methylation differences at specific sites using methylation-sensitive single nucleotide primer extension (Ms-SNuPE)." Nucleic Acids Res. 25:2529-2531 (1997).
Gregory, R. and R. Feil, "Analysis of chromatin in limited numbers of cells: a PCR-SSCP based assay of allele-specific nuclease sensitivity," Nucleic Acids Res., 27:e32, 4 pages (1999).
Havelange et al., "IRF4 mutations in chronic lymphocytic leukemia," Blood 118:2827-2829 (2011).
Herman et al., "Methylation-specific PCR: a novel PCR assay for methylation status of CpG islands," Proc. Natl. Acad. Sci. USA 93:9821-9826 (1996).
Holland et al., "Detection of specific polymerase chain reaction product by utilizing the 5'->3' exonuclease activity of Thermus aquaticus DNA polymerase." Proc. Natl. Acad. Sci. USA, 88:7276-7280 (1991).
Javierre et al., "Long-range epigenetic silencing associates with deregulation of Ikaros targets in colorectal cancer cells," Mol. Cancer Res. 9(8):1139-1151 (2011).
Kawai et al., "Comparison of DNA methylation patterns among mouse cell lines by restriction landmark genomic scanning," Mol. Cell. Biol. 14:7421-7427 (1994).
Kibriya et al., "A genome-wide DNA methylation study in colorectal carcinoma." BMC Med Genomics, 4:50, 16 pages (2011).
Kristensen, L.S. and L.L. Hansen, "PCR-based methods for detecting single-locus DNA methylation biomarkers in cancer diagnostics, prognostics, and response to treatment," Clin Chem. 55:1471-1483 (2009).
Kuppuswamy et al., "Single nucleotide primer extension to detect genetic diseases: experimental application to hemophilia B (factor IX) and cystic fibrosis genes," Proc. Natl. Acad. Sci. USA 88:1143-1147 (1991).
Landegren et al., "Reading bits of genetic information: methods for single-nucleotide polymorphism analysis," Genome Res., 8(8):769-776 (1998).
LaPointe et al., "Discovery and validation of molecular biomarkers for colorectal adenomas and cancer with application to blood testing," Plos One 7(1):e29059, 10 pages (2012).
Lee et al., "Allelic discrimination by nick-translation PCR with fluorogenic probes," Nucleic Acid Res. 21:3761-3766 (1993).
Markowitz, S. and M. Bertagnolli, "Molecular origins of cancer: Molecular basis of colorectal cancer," N. Engl. J. Med. 361(25):2449-2460 (2009).
Martinez et al., "Primary bone marrow lymphoma: an uncommon extranodal presentation of aggressive non-hodgkin lymphomas," Am. J. Surg Pathol. 36:296-304 (2012).
Messing, J., "New M13 vectors for cloning," Methods Enzymol, 101:20-78 (1983).
Mhlanga, M. and L. Malmberg, "Using molecular beacons to detect single-nucleotide polymorphisms with real-time PCR." Methods 25:463-471 (2001).
Mitchell et al., "A panel of genes methylated with high frequency in colorectal cancer," BMC Cancer 14:54, 15 pages (2014).
Moore et al., "Measuring transferrin receptor gene expression by NMR imaging," Biochim Biophys Acta., 1402:239-249 (1988).
Letter/Written Disclosure of the Supplemental Information Disclosure Statement for the above-referenced application, filed herewith on Jan. 3, 2017, 2 pages.
Pedersen et al., "135: Discovery and Validation of a Novel DNA Methylation Biomarker for Colorectal Cancer with Application to Blood Testing," Gastroenterology 142(5):Suppl 1 pp. S-33, Abstract 135 (2012).
Communication Pursuant to Rule 164(1) EPC (Partial Supplementary European Search Report), dated Jan. 5, 2016, in connection with corresponding European Patent Application No. 13788103.3, 8 pages.

(56) References Cited

OTHER PUBLICATIONS

Extended European Search Report, dated Apr. 21, 2016, in connection with corresponding European Patent Application No. 13788103.3, 11 pages.
Office Action issued in JP application No. 2018-136763, dated Dec. 22, 2020.
Zhang, W. et al. "Predicting genome-wide DNA methylation using methylation marks, genomic position, and DNA regulatory elements" Zhang et al. Genome Biology (2015) 16: 14 (Year: 2015).

* cited by examiner

FIG. 1

>hg19_refGene_NM_181711 range=chr12:52398748-52409671 5'pad=0 3'pad=0 strand=+ repeatMasking=none

Genomic Sequence of GRASP (SEQ ID NO: 89)

```
   1  CCCACCCCCCACAGATGCTGTCTGTCAGGAGCAGGCAACAGACGGTCCTGGGGTCCATCT
   1  GGGTGGGGGGTGTCTACGACAGACAGTCCTCGTCCGTTGTCTGCCAGGACCCCAGGTAGA

  61  GTGCTAATGCTTCACAATAGAGTCCCATGTTTCCCCACTGACACCCCCTCGGCCCCTCAG
  61  CACGATTACGAAGTGTTATCTCAGGGTACAAAGGGGTGACTGTGGGGGAGCCGGGGAGTC

 121  CTGATGGCCACTTGGTGGTGCCAAGGCGGGAGGTGGGAGGAGGGAGAAGAAGGCACTAAG
 121  GACTACCGGTGAACCACCACGGTTCCGCCCTCCACCCTCCTCCCTCTTCTTCCGTGATTC

 181  AGAGCTACCTCTTAGCTCCTGGCAGTCCTCAATCCACCCCGGCCCCCCACCCAACAAGCA
 181  TCTCGATGGAGAATCGAGGACCGTCAGGAGTTAGGTGGGGCCGGGGGGTGGGTTGTTCGT

 241  TCCTGCCATCTGGACTTGTGCAATCACTGAGGGGCGGAAAAGCACCCTCTTCCACCCACA
 241  AGGACGGTAGACCTGAACACGTTAGTGACTCCCCGCCTTTTCGTGGGAGAAGGTGGGTGT

 301  CCTCTTGTAGGGGATGGGGGCCTAGAGGACTGGGGGTGGGGAGGAGAACACAGAGTCAAG
 301  GGAGAACATCCCCTACCCCCGGATCTCCTGACCCCCACCCCTCCTCTTGTGTCTCAGTTC

 361  GAGACTAGAGAAGAAGACTGAGCCAGGCGCAAGAACTGAGACAGGCAGGAGGCAGAAAGT
 361  CTCTGATCTCTTCTTCTGACTCGGTCCGCGTTCTTGACTCTGTCCGTCCTCCGTCTTTCA

 421  CTTTCCTGGCCTCGCAGGTGGACGTGGCCATTGCCCCTCTGTGCTCCTTATGCCACGTGT
 421  GAAAGGACCGGAGCGTCCACCTGCACCGGTAACGGGGAGACACGAGGAATACGGTGCACA

 481  CTAACACAGCACATGTGCAAGGTACCACTCCCTACCAGGCCAAGAGCCTCTGTAACCCCA
 481  GATTGTGTCGTGTACACGTTCCATGGTGAGGGATGGTCCGGTTCTCGGAGACATTGGGGT

 541  GTGCCCAGCCAGTACCTGGCACACAGCAGGGCTTAAATGTTGGACAACATCACAGAGTGG
 541  CACGGGTCGGTCATGGACCGTGTGTCGTCCCGAATTTACAACCTGTTGTAGTGTCTCACC

 601  TTAGATTGCAGGCTCTGGAACCAGGCTGCCTGGCTTTGAATCTCAGCTCTGCCGCTGAGT
 601  AATCTAACGTCCGAGACCTTGGTCCGACGGACCGAAACTTAGAGTCGAGACGGCGACTCA

 661  GACTTAGGGCAAATTACTTATCTTCTCTGGGCCTCAGTTTCCTCATCTGTAAGGGAGGAT
 661  CTGAATCCCGTTTAATGAATAGAAGAGACCCGGAGTCAAAGGAGTAGACATTCCCTCCTA

 721  AATGGTGCTTATTTCGTAGGGTTGTTATGAAGACCAAGTGAGTTAATGCATGTATGTAAA
 721  TTACCACGAATAAAGCATCCCAACAATACTTCTGGTTCACTCAATTACGTACATACATTT

 781  AGGACACACAGAACAAACAGTGTGCATAGCACATGCTAAGTGCTCAATAAATGTTAACTG
 781  TCCTGTGTGTCTTGTTTGTCACACGTATCGTGTACGATTCACGAGTTATTTACAATTGAC

 841  TGAAGGCATAACAGATTTGGGAAGACTGGGGGAGGAGGGAGGGGACAGACAAGGGCACCG
 841  ACTTCCGTATTGTCTAAACCCTTCTGACCCCCTCCTCCCTCCCCTGTCTGTTCCCGTGGC

 901  CATTGCCGCCTCTGCTTCTTGGCCGATGGGTGTTGGGACATGGAGTCCCCAGCCTGTGCT
 901  GTAACGGCGGAGACGAAGAACCGGCTACCCACAACCCTGTACCTCAGGGGTCGGACACGA

 961  GCTGACGCCCTGTGGTGGCTAGCCGCTCTTTAGACACCAGACGCTGCCTTCCACTTCCTC
 961  CGACTGCGGGACACCACCGATCGGCGAGAAATCTGTGGTCTGCGACGGAAGGTGAAGGAG

1021  CTCTCACTTCTTATTCGGGCACCACTGACGACAGAGACTTCGGCTGGGCCATTCCCGCCT
1021  GAGAGTGAAGAATAAGCCCGTGGTGACTGCTGTCTCTGAAGCCGACCCGGTAAGGGCGGA

1081  CTCCTACCGCCTGGCAGCCATGGTAACAGCCTGGGGGATGGTCCCTAAGATGGGGTCAGA
1081  GAGGATGGCGGACCGTCGGTACCATTGTCGGACCCCCTACCAGGGATTCTACCCCAGTCT

1141  GAACGGCTGAGCATGGCCATCCCCCCAGCCCTGAACTCCCACTCAGCCTGGGCTCATCCC
1141  CTTGCCGACTCGTACCGGTAGGGGGGTCGGGACTTGAGGGTGAGTCGGACCCGAGTAGGG

1201  AACCTCCTGAGTCAAGTCCACAGTAAGCGTCTGTCTCCTGGGAAGGGGGATCTGACCCCG
1201  TTGGAGGACTCAGTTCAGGTGTCATTCGCAGACAGAGGACCCTTCCCCCTAGACTGGGGC
```

FIG. 1 (cont'd)

1261 GCATCAGGAGCTGAGGAAAGGTGTTGCCAGCAGGGATCACTCAAGCCCCTTGGAGGGGAC
1261 CGTAGTCCTCGACTCCTTTCCACAACGGTCGTCCCTAGTGAGTTCGGGGAACCTCCCCTG

1321 AGGCCAGAACTAAGCCTACTGCTTTCAGGGTTTCCACCTCTTCCCTTCTTCCTAGACGTG
1321 TCCGGTCTTGATTCGGATGACGAAAGTCCCAAAGGTGGAGAAGGGAAGAAGGATCTGCAC

1381 CGAACAGGGGGCAGCCTCTTTCAGCTCTTCTGGGGCAGCTGCGTCAAGGGAAAATCCTGG
1381 GCTTGTCCCCCGTCGGAGAAAGTCGAGAAGACCCCGTCGACGCAGTTCCCTTTTAGGACC

1441 GCCCTCTCCCTCCCTGGGGGCTTCTGCGCAGTGAGTTCAGGGAGTCTCCTCCCTCCTCCA
1441 CGGGAGAGGGAGGGACCCCCGAAGACGCGTCACTCAAGTCCCTCAGAGGAGGGAGGAGGT

1501 TCGGGCCTCCACCCCTACTCCTGCGCAGCCCCGCTGCCGCTCTCCCTGCCCTGGAGTCTC
1501 AGCCCGGAGGTGGGGATGAGGACGCGTCGGGGCGACGGCGAGAGGGACGGGACCTCAGAG

1561 CTGCAGCCCCTTGGATCTCCGTGACTCTCCCTACCTCCCCGACTCCCCAGGCTTCTTACA
1561 GACGTCGGGGAACCTAGAGGCACTGAGAGGGATGGAGGGGCTGAGGGGTCCGAAGAATGT

1621 GTGACCTCTTACCGTGCCCCACTCCATGAATCGCCAGAGCTATTCGTCCCTAAATTTCAA
1621 CACTGGAGAATGGCACGGGGTGAGGTACTTAGCGGTCTCGATAAGCAGGGATTTAAAGTT

1681 ACCTTGCGCAATGTCCCTTCACAGACCCCTCCAGGTATCACGCAGCCCCGAGCCCCGAGC
1681 TGGAACGCGTTACAGGGAAGTGTCTGGGGAGGTCCATAGTGCGTCGGGGCTCGGGGCTCG

1741 CCCGCCCCGGGGGCCTCATCCCGCCCCTTCGCGTCCGCGGCTCGTTTTCCCCCACTGAGC
1741 GGGCGGGGCCCCCGGAGTAGGGCGGGGAAGCGCAGGCGCCGAGCAAAAGGGGGTGACTCG

1801 GCCCAGCTCCCGCAGTTTCCCCGGCCGTCGAGCGCCGTGGGCGGGGCTCCAGGGCGGCGG
1801 CGGGTCGAGGGCGTCAAAGGGGCCGGCAGCTCGCGGCACCCGCCCCGAGGTCCCGCCGCC

1861 CGCCTCGCGGGGAGGGTCCTCCGTGCTGGGGGCGAGGCCACCCGAGGCAGCTCCCCGCCC
1861 GCGGAGCGCCCCTCCCAGGAGGCACGACCCCCGCTCCGGTGGGCTCCGTCGAGGGGCGGG

1921 GCCCCCAACCCCGCCCCGCTCTCGGAGCCTATAAAGGGAGGCGACCCGCGGCCCGCCCGG
1921 CGGGGGTTGGGGCGGGGCGAGAGCCTCGGATATTTCCCTCCGCTGGGCGCCGGGCGGGCC

1981 CTGGCATCCCCCAGCCGCCGCCAGCCCCGCCGAGGGGAGCCAGCGCCGTCTCTGAGGGGC
1981 GACCGTAGGGGGTCGGCGGCGGTCGGGGCGGCTCCCCTCGGTCGCGGCAGAGACTCCCCG

2041 GTCCGGCGCCGGAGCCATGACCCTCCGCCGACT*CAGGAAGCTGCAGCAGAAGGAGGAGGC*
2041 CAGGCCGCGGCCTCGGTACTGGGAGGCGGCTGA*GTCCTTCGACGTCGTCTTCCTCCTCCG*

2101 *GGCGGCCACCCCGGACCCCGCCGCCCGGACTCCCGACTCGGAAGTCGCGCCCGCCGCTCC*
2101 *CCGCCGGTGGGGCCTGGGGCGGCGGGCCTGAGGGCTGAGCCTTCAGCGCGGGCGGCGAGG*

2161 *GGTCCCGACCCCGGGACCCCCTGCCGCAGCCGCCACCCCTGGGCCCCCAGCGGACGAGCT*
2161 *CCAGGGCTGGGGCCCTGGGGGACGGCGTCGGCGGTGGGGACCCGGGGGTCGCCTGCTCGA*

2221 *GTACGCGGCGCTGGAGGACTATCACCCTGCCGAGCTGTACCGCGCGCTCGCCGTGTCCGG*
2221 *CATGCGCCGCGACCTCCTGATAGTGGGACGGCTCGACATGGCGCGCGAGCGGCACAGGCC*

2281 *GGGCACCCTGCCCCGCCGAAAGGTGCGTCCCCCGCCCGCCTTCAGGATCTGCTCAGCCCC*
2281 *CCCGTGGGACGGGGCGGCTTTCCACGCAGGGGGCGGGCGGAAGTCCTAGACGAGTCGGGG*

2341 *TCTCCGACTCCCTACAGGGCCTGCTGACTCCG*CAGTGCCCTCTCCTCGGCGTCCGCGGAG
2341 *AGAGGCTGAGGGATGTCCCGGACGACTGAGGC*GTCACGGGAGAGGAGCCGCAGGCGCCTC

2401 TCCCCCACCTTCTTCCCCGGCCCGCTGGGTGCCTCGACTCCCCGCGTTCCCCGCTGCTGC
2401 AGGGGGTGGAAGAAGGGGCCGGGCGACCCACGGAGCTGAGGGGCGCAAGGGGCGACGACG

2461 GAAGGCCGTGGCCCTCGCCTGCACACCGCGCCCAGGCTCGGTGGCTCTTAACTCCGCGCC
2461 CTTCCGGCACCGGGAGCGGACGTGTGGCGCGGGTCCGAGCCACCGAGAATTGAGGCGCGG

2521 CCATGCACGCCCCCTCTCTCCCTCCTTGACTCCTCCCAGCACCCCCCTTCTCCTACCCGC
2521 GGTACGTGCGGGGGAGAGAGGGAGGAACTGAGGAGGGTCGTGGGGGGAAGAGGATGGGCG

2581 TCCATCTGGCTTTCTGCCCCCCATGCCCCGCCTCCCCGTGGCCAGGTGTCCTGGGTCCCC
2581 AGGTAGACCGAAAGACGGGGGGTACGGGGCGGAGGGGCACCGGTCCACAGGACCCAGGGG

FIG. 1 (cont'd)

2641 AGGAGCCCCTCGCCCGAGGGACAGAGACAGCCCCAGGCAAGTTGAAGGTCCGAGAGCCCC
2641 TCCTCGGGGAGCGGGCTCC*CTGTCTCTGTCGGGGTCCGTTCAACTTCCAGGCTCTCGGGG*

2701 CGGTGGGAGAAGCGGGCCGGTGGCTGCGCCGCGTGCGTTCTCACTCTGAGGAAGTGCGTG
2701 *GCCACCCTCTTCGCCCGGCCACCGACGCGGCGCACGCAAGAGTGAGACTCCTTCACGCAC*

2761 GGGAGCCGCTGACTCCGGATAGCACACCCTTCCGAGGGGACTCCCCGATTCCTGGGCTGG
2761 *CCCTCGGCGACTGAGGCCTATCGTGTGGGAAGGCTCCCCTGAGGGGCTAAGGACCCGACC*

2821 GGGCCTGCCGCCTGGCCCCACGTCTGACGTACGGGGCGCGAGGGCCACTGCTCCCTGGAC
2821 *CCCGGACGGCGGACCGGGGTGCAGACTGCATGCCCCGCGCTCCCGGTGACGAGGGACCTG*

2881 TTCTGTCGGAACCGGACGCAGTGGGAGGGGTCGCAGGGCGCCCGCGGGGCAGGAAGGATG
2881 *AAGACAGCCTTGGCCTGCGTCACCCTCCCCAGCGTCC*CGCGGGCGCCCCGTCCTTCCTAC

2941 CGGGCCGCGCCCACCTCTGAGTCCCCTCTGCCAGCCTCTTCCTCTGGCCCCAGGAGACCT
2941 GCCCGGCGCGGGTGGAGACTCAGGGGAGACGGTCGGAGAAGGAGACCGGGGTCCTCTGGA

3001 GAGGCTCAGAACCTACACAACACCAGGTTAAGAAGAGGGGCCTGGTGGCCTTTCCTCACC
3001 CTCCGAGTCTTGGATGTGTTGTGGTCCAATTCTTCTCCCCGGACCACCGGAAAGGAGTGG

3061 CAGCCGCCCTCCTTCGCCCCGGCCCCCAGCTAGCCCCCACACAATGAACAGCTTGTTGAG
3061 GTCGGCGGGAGGAAGCGGGGCCGGGGGTCGATCGGGGGTGTGTTACTTGTCGAACAACTC

3121 AATTTGCATTTTATGAAAATCATGTTGAAAGACAAAGGGGTCTCTCTGTGCTGCCCAGTC
3121 TTAAACGTAAAATACTTTTAGTACAACTTTCTGTTTCCCCAGAGAGACACGACGGGTCAG

3181 CTTCCTCCCTGGCCGTTTGGGAACTGTCCCCACCCCTGAGGCCAATCTGGTTCTGAACCT
3181 GAAGGAGGGACCGGCAAACCCTTGACAGGGGTGGGGACTCCGGTTAGACCAAGACTTGGA

3241 TCTCTTCCTTGCCTTGGGCAGCTTTGGGGGAGGGTTAGCAAAGGCACAGAACAGAAAGGC
3241 AGAGAAGGAACGGAACCCGTCGAAACCCCCTCCCAATCGTTTCCGTGTCTTGTCTTTCCG

3301 CCTGGGCTGTGCAGGCTCCAAAGAAAAGGGCTGCTCTGGGACTGGACCTCCTCCCAGGAC
3301 GGACCCGACACGTCCGAGGTTTCTTTTCCCGACGAGACCCTGACCTGGAGGAGGGTCCTG

3361 CAAAAAGTTAGGGAGGGTGAGAGACTACTTTAGTTTATCAAGGACCCTGAAGAGACAGGA
3361 GTTTTTCAATCCCTCCCACTCTCTGATGAAATCAAATAGTTCCTGGGACTTCTCTGTCCT

3421 ACCTTCATCTCTCATCCTTCCTCCACACCCCCCACCACCACCCCTAAAGAACTCCCAGTC
3421 TGGAAGTAGAGAGTAGGAAGGAGGTGTGGGGGGTGGTGGTGGGGATTTCTTGAGGGTCAG

3481 TCGGTCCTTTAGTGAGACTTGCTGACAAGTTTGACATCTAAGATGTTTTGTCCCAGAAAG
3481 AGCCAGGAAATCACTCTGAACGACTGTTCAAACTGTAGATTCTACAAAACAGGGTCTTTC

3541 CACAAAATATATGGCAATGGAGAGAGAGACCCAGGTATAGCTGGGCACAGCTGGTCACCT
3541 GTGTTTTATATACCGTTACCTCTCTCTCTGGGTCCATATCGACCCGTGTCGACCAGTGGA

3601 GCAGCTGGGATCCACAACTGGTCCTTGAAACGGCCTGTACCTTAGGAGACCTGGCACCTC
3601 CGTCGACCCTAGGTGTTGACCAGGAACTTTGCCGGACATGGAATCCTCTGGACCGTGGAG

3661 TGACCCCACATTCTGGCTGGGATTGCCAGCCCTTCGGGACAGGGTCCCTGACCCCAGCCC
3661 ACTGGGGTGTAAGACCGACCCTAACGGTCGGGAAGCCCTGTCCCAGGGACTGGGGTCGGG

3721 TCCCAAGCCACTGTCTGTAGCTGAGAAATTAGATGGAGAGACCCAACTGGCAGAAGGTCC
3721 AGGGTTCGGTGACAGACATCGACTCTTTAATCTACCTCTCTGGGTTGACCGTCTTCCAGG

3781 TCGGAGCACCTTGATAGGTGAGCCCAGGGGACACCTATCCTCTGAATCCCACTGGGGAAG
3781 AGCCTCGTGGAACTATCCACTCGGGTCCCCTGTGGATAGGAGACTTAGGGTGACCCCTTC

3841 AGCCCCTGCCTCAGCTTTGGGAGTCTGGATGGCCTGAGCCTCTACAGACATGGGCCCTAG
3841 TCGGGGACGGAGTCGAAACCCTCAGACCTACCGGACTCGGAGATGTCTGTACCCGGGATC

3901 GGGTGGAGACCATTTTAGAATAATGATCTCCCCACCTGCTGCCAGTGTGGAAACCAGCAA
3901 CCCACCTCTGGTAAAATCTTATTACTAGAGGGGTGGACGACGGTCACACCTTTGGTCGTT

3961 GGGCTTAGAGGTTCATGGATCTGGAACCCAGGAGGATGGTTGTGTCCCTGCAGTCCCAGG
3961 CCCGAATCTCCAAGTACCTAGACCTTGGGTCCTCCTACCAACACAGGGACGTCAGGGTCC

FIG. 1 (cont'd)

4021 TATGAAGGTAAGGCCTGTAGAGAAAGTTGAGGAGTGGTGCCAGTAGTGGCACTTGGCAAA
4021 ATACTTCCATTCCGGACATCTCTTTCAACTCCTCACCACGGTCATCACCGTGAACCGTTT

4081 TAGTTCCACCAGCACCAAAACAGGTGTGGATGTGGAGCTGGGAAGGGGCAGACAGGAAGT
4081 ATCAAGGTGGTCGTGGTTTTGTCCACACCTACACCTCGACCCTTCCCCGTCTGTCCTTCA

4141 GGGTCGCTGTGTCCAGGGTAACCTCTCAGTGTCTGCTCAAGGACAGTCCCGCCTTACCTG
4141 CCCAGCGACACAGGTCCCATTGGAGAGTCACAGACGAGTTCCTGTCAGGGCGGAATGGAC

4201 CTCCTTCTGACCATCTTACTGCCCAGGGCTCAGGATTCCGCTGGAAGAATCTCAGCCAGA
4201 GAGGAAGACTGGTAGAATGACGGGTCCCGAGTCCTAAGGCGACCTTCTTAGAGTCGGTCT

4261 GTCCTGAACAGCAGCGGTGAGTCACCAACACCCAGCCCCTGCCATGGTCCAAAGGGGTGA
4261 CAGGACTTGTCGTCGCCACTCAGTGGTTGTGGGTCGGGGACGGTACCAGGTTTCCCCACT

4321 GGTGCTGGGTTGGGGGGTGCCAGGACAGCATCTCAGCCTAGCGAGGGTAGTCATTCTCCT
4321 CCACGACCCAACCCCCCACGGTCCTGTCGTAGAGTCGGATCGCTCCCATCAGTAAGAGGA

4381 AGCCTTTAAACATGGCTCCCCCGCTGGGAGTGAGGGCAGGTGGGGGTGAGGGCTGTGTGA
4381 TCGGAAATTTGTACCGAGGGGGCGACCCTCACTCCCGTCCACCCCCACTCCCGACACACT

4441 AGGGGGTGGCAGAGAAAGGAGGTAGGGACTTTTGAGTCATTAGGTGCTCTTCAACACACC
4441 TCCCCCACCGTCTCTTTCCTCCATCCCTGAAAACTCAGTAATCCACGAGAAGTTGTGTGG

4501 CCCAGTCCCTGCCAGTTACCCCTCCCTGGGGAGATCTGGATGAACGGATGTGGGAGTTGG
4501 GGGTCAGGGACGGTCAATGGGGAGGGACCCCTCTAGACCTACTTGCCTACACCCTCAACC

4561 GAGGGGGTGTAGGCAAAGTCTATGGGGAACGTCCTAACCCAGGCCTCCTGGGCTCCCCTG
4561 CTCCCCCACATCCGTTTCAGATACCCCTTGCAGGATTGGGTCCGGAGGACCCGAGGGGAC

4621 AGCCCTCCTAGCCTTGGCAAACCCCACGGGCCCAGACCTTAGCCAGGCTGTGTCCAGCTG
4621 TCGGGAGGATCGGAACCGTTTGGGGTGCCCGGGTCTGGAATCGGTCCGACACAGGTCGAC

4681 CTTGGGGCTGGCTGCCCCTGCCTCCAGAATGTCAGTCCTCTTCTGGTCCCAGCCTGTGGC
4681 GAACCCCGACCGACGGGGACGGAGGTCTTACAGTCAGGAGAAGACCAGGGTCGGACACCG

4741 AGCCCTCTTAGGAGGGATCTGAGCGTGGGCAGAAGTAGGTGCTGACTCCAGGCCCTGGGA
4741 TCGGGAGAATCCTCCCTAGACTCGCACCCGTCTTCATCCACGACTGAGGTCCGGGACCCT

4801 CCCCACAGTTTCCCTTCTCTACTCATGTCCCATCCCTGATTTGGGCTTGACTTTCTCTAA
4801 GGGGTGTCAAAGGGAAGAGATGAGTACAGGGTAGGGACTAAACCCGAACTGAAAGAGATT

4861 AATGGATCAGCAAACTGACCTGCTAGCCAGATTGGCCTGTTTGGCCCTTGAGCTAATAAT
4861 TTACCTAGTCGTTTGACTGGACGATCGGTCTAACCGGACAAACCGGGAACTCGATTATTA

4921 TTTTAAAGAGTTGTAAAAATAAAAACAAATAACAATATATGACAGAGATCATAAGGGGCC
4921 AAAATTTCTCAACATTTTTATTTTTGTTTATTGTTATATACTGTCTCTAGTATTCCCCGG

4981 TGCAAAGAAAGCCTAAAGTATTTACCATTTGGCCCTTTGCAGAAAAAGTTTGCTGACCCT
4981 ACGTTTCTTTCGGATTTCATAAATGGTAAACCGGGAAACGTCTTTTTCAAACGACTGGGA

5041 TCCAAAAAACCCTAGAACATTGGGGTAGACGCGGAACTCCCAGCCACCCTGCTCCCTGCC
5041 AGGTTTTTTGGGATCTTGTAACCCCATCTGCGCCTTGAGGGTCGGTGGGACGAGGGACGG

5101 CCAATAGTACAGAGAGGGGAAAGGCCTGCTGTTCAGAGTGAGAGGGGCTCGAGCTGGAGT
5101 GGTTATCATGTCTCTCCCCTTTCCGGACGACAAGTCTCACTCTCCCCGAGCTCGACCTCA

5161 GGGGAGGTGCTGCTCAGCATTTGGGGGAATCTCTGGGTCAGGCTGGAAGCGGAGAAGCCT
5161 CCCCTCCACGACGAGTCGTAAACCCCCTTAGAGACCCAGTCCGACCTTCGCCTCTTCGGA

5221 GGTCTCCAGGGCCTTTCCGAGGCTGAGCTACTTGAAGGGGCCTTTGGAGGCTGCTTTAAC
5221 CCAGAGGTCCCGGAAAGGCTCCGACTCGATGAACTTCCCCGGAAACCTCCGACGAAATTG

5281 TGTGCCTCTGGCTGGGCGGGAAGGAAGGGGGTGGGAGTGGGCAGAGGAAACTCTGGGCTC
5281 ACACGGAGACCGACCCGCCCTTCCTTCCCCCACCCTCACCCGTCTCCTTTGAGACCCGAG

5341 CCCCAGCAGGCGAGGATCTGGAGCAGCTCCAGACCATTGTGTCCAGCGGGCAGGCCTTCA
5341 GGGGTCGTCCGCTCCTAGACCTCGTCGAGGTCTGGTAACACAGGTCGCCCGTCCGGAAGT

FIG. 1 (cont'd)

```
5401 GTGCGGGAAGGGGCGGCCTCGAGGCTCCCCTCCCCCAGCCCCCACATCTGGTGGGCTGGC
5401 CACGCCCTTCCCCGCCGGAGCTCCGAGGGGAGGGGGTCGGGGGTGTAGACCACCCGACCG

5461 CCCAGCATAGCTGGGAGGAGCAGCTGTGGTCTTGCTGAGCCTCGTGACTGGCCTCTGGGG
5461 GGGTCGTATCGACCCTCCTCGTCGACACCAGAACGACTCGGAGCACTGACCGGAGACCCC

5521 GTGGGGCCAGTCCTCTCTCCAAAGCTGTGGAACAGAGGAGGCTCCAGGCTGTGGCTGAAT
5521 CACCCCGGTCAGGAGAGAGGTTTCGACACCTTGTCTCCTCCGAGGTCCGACACCGACTTA

5581 TTCGGGCCTTAGCTAGTCAGTAAGTGGTACTGTAGGGCTCACTGGAAAGCTGGGATGGGG
5581 AAGCCCGGAATCGATCAGTCATTCACCATGACATCCCGAGTGACCTTTCGACCCTACCCC

5641 CTAAAAAACTCAGCCGGCTCATCCTTCAGGGGACCGGCCCTTCTCTGTGCTTCCCTCCCA
5641 GATTTTTTGAGTCGGCCGAGTAGGAAGTCCCCTGGCCGGGAAGAGACACGAAGGGAGGGT

5701 CCACTAGAGGCTGGATTGGTTCTCTGTGGCTCCATGAGGCTGATTTCAATTGGGTATGGG
5701 GGTGATCTCCGACCTAACCAAGAGACACCGAGGTACTCCGACTAAAGTTAACCCATACCC

5761 AAAGACATTCCAATAATCTGTGATGAGACTGAGCTGTCACTGGAGACAGAGTCCTGCTGG
5761 TTTCTGTAAGGTTATTAGACACTACTCTGACTCGACAGTGACCTCTGTCTCAGGACGACC

5821 AATGTTCTAGACCAGTTGCCAATATCCAGGGAGGCCCAAGCTATGGGACTTCTACACCTT
5821 TTACAAGATCTGGTCAACGGTTATAGGTCCCTCCGGGTTCGATACCCTGAAGATGTGGAA

5881 TTAATCCTAATTGTCTTGACCCCTGTGTCTCTTGCAGGAAAGTGCTGACGTTGGAGAAGG
5881 AATTAGGATTAACAGAACTGGGGACACAGAGAACGTCCTTTCACGACTGCAACCTCTTCC

5941 AGGATAACCAGACCTTCGGCTTTGAGATCCAGGTGGGAGAAGCTGCACACAGGGGTCAGG
5941 TCCTATTGGTCTGGAAGCCGAAACTCTAGGTCCACCCTCTTCGACGTGTGTCCCCAGTCC

6001 GGGGTTGGATGACCAGCCTGAGGGATGAACGGACTTGTCCCAACCCTGGGCTGAGGGTCC
6001 CCCCAACCTACTGGTCGGACTCCCTACTTGCCTGAACAGGGTTGGGACCCGACTCCCAGG

6061 CCTTGTCCATTACAGACTTATGGCCTTCACCACCGGGAGGAGCAGCGTGTGGAAATGGTG
6061 GGAACAGGTAATGTCTGAATACCGGAAGTGGTGGCCCTCCTCGTCGCACACCTTTACCAC

6121 ACCTTTGTCTGCCGAGTTCATGAGTCTAGCCCTGCCCAGCTGGCTGGGCTCACACCAGGT
6121 TGGAAACAGACGGCTCAAGTACTCAGATCGGGACGGGTCGACCGACCCGAGTGTGGTCCA

6181 GGGGCCTGAGCCCAGGACACCCAGGTCTGGGAAGGGGATATGACCTTACTCCCAAGCAAA
6181 CCCCGGACTCGGGTCCTGTGGGTCCAGACCCTTCCCCTATACTGGAATGAGGGTTCGTTT

6241 GGGGGTGAGCAATCTCTCCTGAAATCAATTCCTCTTCCTTTTCCTTCTTTGAGAAGGCCA
6241 CCCCCACTCGTTAGAGAGGACTTTAGTTAAGGAGAAGGAAAAGGAAGAAACTCTTCCGGT

6301 GAAAGAAGAATGGATAGAATCTGGGCTTTGGATCTAGGCAAATTTGCCATGTACTGTGTG
6301 CTTTCTTCTTACCTATCTTAGACCCGAAACCTAGATCCGTTTAAACGGTACATGACACAC

6361 ATCTTGCACAGCCCCATCTACAAAATGAGGGTAATAATGCATCCAAACATCACAGTGCGG
6361 TAGAACGTGTCGGGGTAGATGTTTTACTCCCATTATTACGTAGGTTTGTAGTGTCACGCC

6421 CAAGGGGATTCCCTGGGCACACTGCCAGGGCCTAATTAATGGTGGATGATGCTGCTGCTG
6421 GTTCCCCTAAGGGACCCGTGTGACGGTCCCGGATTAATTACCACCTACTACGACGACGAC

6481 CTCTGATTCCTCCCAGCAACCCTGGCAGTCAGCATGGGCAGGAGCCAGGGAAGAAGCAAC
6481 GAGACTAAGGAGGGTCGTTGGGACCGTCAGTCGTACCCGTCCTCGGTCCCTTCTTCGTTG

6541 ATTCCATTAAGTCTGTTTGATATTGGGGATCAGGCCAATCCTGCCCCAAAATGGGCCCAG
6541 TAAGGTAATTCAGACAAACTATAACCCCTAGTCCGGTTAGGACGGGGTTTTACCCGGGTC

6601 TGCTGAGGAACCGATGTTACTCCCTTTTAAAAAATTAGAAACTTTTTTTTTTTTTAAGAG
6601 ACGACTCCTTGGCTACAATGAGGGAAAATTTTTTAATCTTTGAAAAAAAAAAAAATTCTC

6661 ACAGGGCCTCAGTCTGTCACCCAGGCTAGAGTGCAGTGGCGTAATCATAACTCACTATAA
6661 TGTCCCGGAGTCAGACAGTGGGTCCGATCTCACGTCACCGCATTAGTATTGAGTGATATT

6721 CCTTGAACTCCTGGGCTCAAGCGATCCTCCTCTTGCCTCTGCCTCCCAAAGCAATATGTT
6721 GGAACTTGAGGACCCGAGTTCGCTAGGAGGAGAACGGAGACGGAGGGTTTCGTTATACAA
```

FIG. 1 (cont'd)

6781 ACTTCCTCTAACAAGGAAATTATGCTTCAGCAGGAGATCCCTGGATTGAGCAGATCTAGA
6781 TGAAGGAGATTGTTCCTTTAATACGAAGTCGTCCTCTAGGGACCTAACTCGTCTAGATCT

6841 GTCCCCAGGTTCCAGGAAGGGCAGCCTGAAACTGTATGAATCAATCCCCCCTCCACCATC
6841 CAGGGGTCCAAGGTCCTTCCCGTCGGACTTTGACATACTTAGTTAGGGGGGAGGTGGTAG

6901 TTTGCCCCTAAGCCCCTACCTCCTTCCCACTTACCAGCAGCCCGTGCTAGCTATCTTAGT
6901 AAACGGGGATTCGGGGATGGAGGAAGGGTGAATGGTCGTCGGGCACGATCGATAGAATCA

6961 CCATTTTCTGTTACCATAACAGAATACCTGATACTGGGTAATTATAAAGAAAAGAGGTTT
6961 GGTAAAAGACAATGGTATTGTCTTATGGACTATGACCCATTAATATTTCTTTTCTCCAAA

7021 ATTTAGCTCATGGTTCTGGAGGCTGGGAAGTTCAAGACTGGGTGGCCGCATCAGGTGAGG
7021 TAAATCGAGTACCAAGACCTCCGACCCTTCAAGTTCTGACCCACCGGCGTAGTCCACTCC

7081 GCCTCATGCTGCGTTCTGACATGATGGATGGCATCTCATGGCAGGAACGCCTGCAAGAGT
7081 CGGAGTACGACGCAAGACTGTACTACCTACCGTAGAGTACCGTCCTTGCGGACGTTCTCA

7141 GGTGAGTAGGCACACGCAAAAGAGACAAAACATGGGTGATCTTGCTTTATAGCAACCCAC
7141 CCACTCATCCGTGTGCGTTTTCTCTGTTTTGTACCCACTAGAACGAAATATCGTTGGGTG

7201 TCGCCAGGTAACTAAACCAGTCCTACCAGAGCAAGAACTCACTCCCCAAAAACAGCATGG
7201 AGCGGTCCATTGATTTGGTCAGGATGGTCTCGTTCTTGAGTGAGGGGTTTTTGTCGTACC

7261 ATCCCTTCACTGGGCAGATCCTTCATGGCCCAAATGCCACTTTTTTTGAGATGGAGTTTC
7261 TAGGGAAGTGACCCGTCTAGGAAGTACCGGGTTTACGGTGAAAAAAACTCTACCTCAAAG

7321 GCTCTTGTTGCCCAGGCTGGAGTGCAATGGCATGATCTCAGCTCACTGCAGCCTCTGCCT
7321 CGAGAACAACGGGTCCGACCTCACGTTACCGTACTAGAGTCGAGTGACGTCGGAGACGGA

7381 CCCAGATTCAAGCAATTCTCCTGCCTCAGCCTCCCGAGTAGCTGGGATTACAGGCACTGG
7381 GGGTCTAAGTTCGTTAAGAGGACGGAGTCGGAGGGCTCATCGACCCTAATGTCCGTGACC

7441 CCACCAAGCCCAGCTCATTTTTGTATTTTTAGTAGAGATGGGGTTTTGCCTTGTTGGCCA
7441 GGTGGTTCGGGTCGAGTAAAAACATAAAAATCATCTCTACCCCAAAACGGAACAACCGGT

7501 GGCTGGTCTCGAACTCCTGACCTCAGGTGATCCACCCGCCTCGGCCTCCCAAAGTGCTGG
7501 CCGACCAGAGCTTGAGGACTGGAGTCCACTAGGTGGGCGGAGCCGGAGGGTTTCACGACC

7561 GATTACAGGTGTGAGCCACGGCGCTCGGCCCCAAATGCCTCTTAAAGGTCCTACCATCTC
7561 CTAATGTCCACACTCGGTGCCGCGAGCCGGGGTTTACGGAGAATTTCCAGGATGGTAGAG

7621 TCAGCACTGTTACGTTGGGGATGAAGCCTCAACATGAGTTTTGGGGACAAACAATATTTA
7621 AGTCGTGACAATGCAACCCCTACTTCGGAGTTGTACTCAAAACCCCTGTTTGTTATAAAT

7681 AATGGTAGCAGTAGCCAAGTGGTATACTACAACTTCTCAAAGTAGTTTCAAATCCACTCT
7681 TTACCATCGTCATCGGTTCACCATATGATGTTGAAGAGTTTCATCAAAGTTTAGGTGAGA

7741 CCCTCCCCATCATCCCTGAAGCATCCACAGCAGGGATCCATACCCCTTTTTACAGATAGG
7741 GGGAGGGGTAGTAGGGACTTCGTAGGTGTCGTCCCTAGGTATGGGGAAAAATGTCTATCC

7801 AATGGGGCCCTGACATGGGGCACACTGTGCTTGAGGTCAGGAAGCTCTCCAGTGGTGCAG
7801 TTACCCCGGGACTGTACCCCGTGTGACACGAACTCCAGTCCTTCGAGAGGTCACCACGTC

7861 GGTAGCAGAACTATCCCTCTGGGGGCCAGTCATTCCCTGTGCTTCTCTCCCACCACCAGA
7861 CCATCGTCTTGATAGGGAGACCCCCGGTCAGTAAGGGACACGAAGAGAGGGTGGTGGTCT

7921 GGCTGGACTGATTATCTGTGGATCCATGAGGCCATGCCATGCCTGGGGCCAGGGTCGGTT
7921 CCGACCTGACTAATAGACACCTAGGTACTCCGGTACGGTACGGACCCCGGTCCCAGCCAA

7981 CCCAGCTGGGTGCTGCTCACCTGCTCTTCCCTGAATTGACTGGGTCTTATGGCCAGCGTG
7981 GGGTCGACCCACGACGAGTGGACGAGAAGGGACTTAACTGACCCAGAATACCGGTCGCAC

8041 GACTGGACAGAAATAACCAAATCTGAGGGTAGCCCAGGGTCCTGGGTGGGCTTAGCTTTG
8041 CTGACCTGTCTTTATTGGTTTAGACTCCCATCGGGTCCCAGGACCCACCCGAATCGAAAC

8101 GGACAGAACTTCTTTTTTTTTTTTTTTTTTTTGAGACGGAGTCTCGCTCTGTCGCCCAGG
8101 CCTGTCTTGAAGAAAAAAAAAAAAAAAAAAAACTCTGCCTCAGAGCGAGACAGCGGGTCC

FIG. 1 (cont'd)

```
8161  CTGGAGTGCAGTGGCGCGATCTCGGCTCACTGCAAGCTCCGCCTCCCGGGTTCACGCCAT
8161  GACCTCACGTCACCGCGCTAGAGCCGAGTGACGTTCGAGGCGGAGGGCCCAAGTGCGGTA

8221  TCTCCTGCCTCAGCCTCCCGAGTAGCTGGGACTACAGGCGCCTGCTACCACGCCCGGCTA
8221  AGAGGACGGAGTCGGAGGGCTCATCGACCCTGATGTCCGCGGACGATGGTGCGGGCCGAT

8281  ATTTTTTGTATTTTTAGTAGAGACGGGGTTTCACCGTGTTAGCCAGGATGGTCTCGATCT
8281  TAAAAAACATAAAAATCATCTCTGCCCCAAAGTGGCACAATCGGTCCTACCAGAGCTAGA

8341  CCTGACCTCGTGATCCGCCCGCCTCGGCCTCCCAAAGTGCTGGGATTACAGGCGTGAGCC
8341  GGACTGGAGCACTAGGCGGGCGGAGCCGGAGGGTTTCACGACCCTAATGTCCGCACTCGG

8401  ACCGCGCCCGGCCGGACAGAACTTCTTGAGGGCAGAGTGAGGGTGTTGGGTGTGTGAGGT
8401  TGGCGCGGGCCGGCCTGTCTTGAAGAACTCCCGTCTCACTCCCACAACCCACACACTCCA

8461  CCCCACCCTTTGGCTGGGGTGCTGGGCGTGGACAACCTGGTAGTCACTACAGGCCCACAA
8461  GGGGTGGGAAACCGACCCCACGACCCGCACCTGTTGGACCATCAGTGATGTCCGGGTGTT

8521  GAATGGCTGTGGTTCTGTGTGTTTGGATCGAGTATGAGAGATGTCAGAGGAGATCTACAG
8521  CTTACCGACACCAAGACACACAAACCTAGCTCATACTCTCTACAGTCTCCTCTAGATGTC

8581  AGAACCATGAGGAGTTGGAGGAGGGAGTTCAGGAGTATTCCCTGGAGTTACTACCCACCC
8581  TCTTGGTACTCCTCAACCTCCTCCCTCAAGTCCTCATAAGGGACCTCAATGATGGGTGGG

8641  TTCTCCCCTTTCTGGCTAAGGTAGGAGGCTGGTATTCTAGCATGCCCCATGGAGCAAATC
8641  AAGAGGGGAAAGACCGATTCCATCCTCCGACCATAAGATCGTACGGGGTACCTCGTTTAG

8701  TAACCCCCTTGTCTGCCTGGCAGGGGACACCATCGCCAGCGTCAATGGCCTGAATGTGGA
8701  ATTGGGGGAACAGACGGACCGTCCCCTGTGGTAGCGGTCGCAGTTACCGGACTTACACCT

8761  AGGCATCCGGCATCGAGAGATTGTGGACATCATTAAGGCGTCAGGCAATGTTCTCAGGTA
8761  TCCGTAGGCCGTAGCTCTCTAACACCTGTAGTAATTCCGCAGTCCGTTACAAGAGTCCAT

8821  TGTCTGGGAGCCGAGGTGCCTGAATTCCTGAGCTCAGCCTCTTGGTATTTCCTCAGCCTG
8821  ACAGACCCTCGGCTCCACGGACTTAAGGACTCGAGTCGGAGAACCATAAAGGAGTCGGAC

8881  TGGCTCACTCAGGCTTTGATTCTCCAACCTCAGACTGGAAACTCTATATGGGACATCAAT
8881  ACCGAGTGAGTCCGAAACTAAGAGGTTGGAGTCTGACCTTTGAGATATACCCTGTAGTTA

8941  TCGGAAGGCAGAACTGGAGGCTCGTCTGCAGTACCTGAAGGTAGGGGAACCTAGATAACG
8941  AGCCTTCCGTCTTGACCTCCGAGCAGACGTCATGGACTTCCATCCCCTTGGATCTATTGC

9001  TCCAGCCTCCACCCTCCTCTTCCCAAGCCTCTGCCCTGTGGGGGGTCACTTACAGCTGAA
9001  AGGTCGGAGGTGGGAGGAGAAGGGTTCGGAGACGGGACACCCCCCAGTGAATGTCGACTT

9061  TCTCCTGTAACTGAAGATTTCTTTTGTCTACTCCCTGATCCCTCGTCTGTACCCACGTCC
9061  AGAGGACATTGACTTCTAAAGAAAACAGATGAGGGACTAGGGAGCAGACATGGGTGCAGG

9121  TGCTAGTTTCCTGCTAGCTTGTGACAGTGGGGTGGGGACTGTCTCTTGCAGCAAACCCTG
9121  ACGATCAAAGGACGATCGAACACTGTCACCCCACCCCTGACAGAGAACGTCGTTTGGGAC

9181  TATGAGAAGTGGGGAGAGTACAGGTCCCTAATGGTGCAGGAGCAGCGGCTGGTGCATGGT
9181  ATACTCTTCACCCCTCTCATGTCCAGGGATTACCACGTCCTCGTCGCCGACCACGTACCA

9241  GAGTAGATCCCGGGGTGTGAGGGGCCACTTGTTCTGCTACAGACACCCCATCTGCGCTTC
9241  CTCATCTAGGGCCCCACACTCCCCGGTGAACAAGACGATGTCTGTGGGGTAGACGCGAAG

9301  CCCCTCAGAACTGGCGGGTTCTAGTAAAGAACGGTTTACTAGTAAACCTCCACAGTAAAG
9301  GGGGAGTCTTGACCGCCCAAGATCATTTCTTGCCAAATGATCATTTGGAGGTGTCATTTC

9361  CAAGGTTTGTTGAGCTACTACTACTTTGGGTACTGCCGCAGCCACATTTCTGGTTATTCT
9361  GTTCCAAACAACTCGATGATGATGAAACCCATGACGGCGTCGGTGTAAAGACCAATAAGA

9421  CACACTAGCCCTCTGCAGGTAAGTAACAGATAGTGTCATCTTCACTTTACAGAGGGGAAC
9421  GTGTGATCGGGAGACGTCCATTCATTGTCTATCACAGTAGAAGTGAAATGTCTCCCCTTG

9481  ACCAGGGCTCAAAGAGTTTGTGTCAATTATTTCCGAGGCCCGTTTGTGCTAAGCGGCCCC
9481  TGGTCCCGAGTTTCTCAAACACAGTTAATAAAGGCTCCGGGCAAACACGATTCGCCGGGG
```

FIG. 1 (cont'd)

```
9541   CATAAGGATCTGAGTGATAATTCCTGATTTGCGGGTGAGGGAAGTAGGGTCTCAGGTTTG
9541   GTATTCCTAGACTCACTATTAAGGACTAAACGCCCACTCCCTTCATCCCAGAGTCCAAAC

9601   TGCCTGGCCAGGGCCACAGAGATGGTCAGCAGGACGGAGCGGGGACGCCCCGCCCATGCC
9601   ACGGACCGGTCCCGGTGTCTCTACCAGTCGTCCTGCCTCGCCCCTGCGGGGCGGGTACGG

9661   CTCCGACCCTTTGCAGAGGCCACCACGGTCCAGGCCTGACCCGCCCCCTACCTCTCCCGT
9661   GAGGCTGGGAAACGTCTCCGGTGGTGCCAGGTCCGGACTGGGCGGGGGATGGAGAGGGCA

9721   CTCTGCGCAGGCCTGGTGGTGAAGGACCCCAGCATCTACGACACGCTGGAGTCGGTGCGC
9721   GAGACGCGTCCGGACCACCACTTCCTGGGGTCGTAGATGCTGTGCGACCTCAGCCACGCG

9781   TCCTGCCTCTACGGCGCGGGCCTGCTCCCGGGCTCGCTGCCCTTCGGGCCTCTGCTCGCC
9781   AGGACGGAGATGCCGCGCCCGGACGAGGGCCCGAGCGACGGGAAGCCCGGAGACGAGCGG

9841   GTGCCCGGGCGTCCCCGCGGAGGCGCCCGACGGGCCAGGGGCGACGCCGACGACGCCGTC
9841   CACGGGCCCGCAGGGGCGCCTCCGCGGGCTGCCCGGTCCCCGCTGCGGCTGCTGCGGCAG

9901   TACCACACGTGCTTCTTCGGGGACTCCGAGCCGCCGGCGCTGCCGCCCCCGCCGCCCCCG
9901   ATGGTGTGCACGAAGAAGCCCCTGAGGCTCGGCGGCCGCGACGGCGGGGGCGGCGGGGGC

9961   GCCCGCGCCTTCGGCCCGGGCCCCGCCGAGACCCCTGCCGTGGGGCCGGGCCCTGGGCCG
9961   CGGGCGCGGAAGCCGGGCCCGGGGCGGCTCTGGGGACGGCACCCCGGCCCGGGACCCGGC

10021  CGGGCCGCGCTGAGCCGCAGCGCCAGTGTGCGGTGCGCGGGCCCTGGCGGGGGCGGAGGC
10021  GCCCGGCGCGACTCGGCGTCGCGGTCACACGCCACGCGCCCGGGACCGCCCCCGCCTCCG

10081  GGGGGCGCGCCGGGCGCGCTCTGGACTGAGGCTCGCGAGCAGGCCCTATGCGGCCCCGGC
10081  CCCCCGCGCGGCCCGCGCGAGACCTGACTCCGAGCGCTCGTCCGGGATACGCCGGGGCCG

10141  CTGCGCAAAACCAAGTACCGCAGCTTCCGCCGGCGGCTGCTCAAGTTCATCCCCGGACTC
10141  GACGCGTTTTGGTTCATGGCGTCGAAGGCGGCCGCCGACGAGTTCAAGTAGGGGCCTGAG

10201  AACCGCTCCCTGGAGGAGGAGGAGAGCCAGCTGTAGGGGCGGGGGCGGGCAGGGAGGTAT
10201  TTGGCGAGGGACCTCCTCCTCCTCTCGGTCGACATCCCCGCCCCCGCCCGTCCCTCCATA

10261  TTATTTATTTATTCGCAACAGCCAGCGCTAAAAGAGGGGGAGGCCGAGCCAAGAGGACCC
10261  AATAAATAAATAAGCGTTGTCGGTCGCGATTTTCTCCCCCTCCGGCTCGGTTCTCCTGGG

10321  CAGGAGCCCAGAGCAGCGGGAGAGGGTCCTTCCTAGCCTCGGCCCGCCGGGTCGGTTCCT
10321  GTCCTCGGGTCTCGTCGCCCTCTCCCAGGAAGGATCGGAGCCGGGCGGCCCAGCCAAGGA

10381  GGCTGGTGTCTGCTGAGGGAGTGGGGGGCCCAGCCCCTTCTCTTCTCCCCCGCCAAACCA
10381  CCGACCACAGACGACTCCCTCACCCCCCGGGTCGGGGAAGAGAAGAGGGGGCGGTTTGGT

10441  CAGTGGGAGCTGGGGCAGGGGGAGAGCCAGGCAATCGGGGGCCAAAGATGGGGGTGCTCG
10441  GTCACCCTCGACCCCGTCCCCCTCTCGGTCCGTTAGCCCCCGGTTTCTACCCCCACGAGC

10501  CCTACAGTCTGCATCTGTAGTGCCTTGTGGGGTATCCAGGAACACCCTCCCAGCAGGGGA
10501  GGATGTCAGACGTAGACATCACGGAACACCCCATAGGTCCTTGTGGGAGGGTCGTCCCCT

10561  TGGGAACCCTGTCCCATGAAGCCCTCTCCTCAGCTTTACTTGCTCCCCCGCCCTTAGCCT
10561  ACCCTTGGGACAGGGTACTTCGGGAGAGGAGTCGAAATGAACGAGGGGGCGGGAATCGGA

10621  TGGGGAGAAATGGCCCGTGGTGGGCTGACCCCCCACCCTCCACACACACAGTTCCATGAC
10621  ACCCCTCTTTACCGGGCACCACCCGACTGGGGGGTGGGAGGTGTGTGTGTCAAGGTACTG

10681  CCAGCGGGCCCCCAGGGGCATCAGGTGCTGGTCCTCCTCCCTCCTGGCCTCGACCCCTAA
10681  GGTCGCCCGGGGGTCCCCGTAGTCCACGACCAGGAGGAGGGAGGACCGGAGCTGGGGATT

10741  GGGCTTCGCCCCTCCCAGGGGCCTGTAACTAAGTCGGGTCCTGCCAGGCAGGGGGCCTGT
10741  CCCGAAGCGGGGAGGGTCCCCGGACATTGATTCAGCCCAGGACGGTCCGTCCCCCGGACA

10801  GTTCTGTGCCCCTTGGGAGACAGGAACTGGCGAGTTCAGGTGGGGTGGGGACAGCACAGA
10801  CAAGACACGGGGAACCCTCTGTCCTTGACCGCTCAAGTCCACCCCACCCCTGTCGTGTCT

10861  CTGTTCCACCGTTGTGCATATTGTTGCTTCTGAACCACAAACTGTATAAATGGATGGTTT
10861  GACAAGGTGGCAACACGTATAACAACGAAGACTTGGTGTTTGACATATTTACCTACCAAA

10921  TTTG
10921  AAAC
```

FIG. 2

>hg19_refGene_NR_037593 range=chr6:163834097-163836982 5'pad=0 3'pad=0 strand=- repeatMasking=none

Genomic Sequence of CAHM (SEQ ID NO: 90)

```
   1 AGCATAATTTCGGTCTCCTACGGAATTTCTTTAAACTAACGAGCCCCACACTGACTTCCA
   1 TCGTATTAAAGCCAGAGGATGCCTTAAAGAAATTTGATTGCTCGGGGTGTGACTGAAGGT

  61 CTTAGTATTGAACAGCTGCACCAACTCCCCAACCACGAAACCCCGCTTTAGTCCTCACGG
  61 GAATCATAACTTGTCGACGTGGTTGAGGGGTTGGTGCTTTGGGGCGAAATCAGGAGTGCC

 121 GAGGGGAGAGCTCCCGAACGCGGGGCGGTGGGGGTCCGCGCAGAGCAGGCTCGGGAGGCC
 121 CTCCCCTCTCGAGGGCTTGCGCCCCGCCACCCCCAGGCGCGTCTCGTCCGAGCCCTCCGG

 181 GAGCGGAGGAGCGGGGCCCGCGCCGGGCACACGCGTCCTCCAGGCCGGCGGCGCGGCGTG
 181 CTCGCCTCCTCGCCCCGGGCGCGGCCCGTGTGCGCAGGAGGTCCGGCCGCCGCGCCGCAC

 241 GGCCTGCTCTCGGGAGGGCTCGGCGAGGACCACCGAGTCCGCGCAGCCCCCGCCGACCTC
 241 CCGGACGAGAGCCCTCCCGAGCCGCTCCTGGTGGCTCAGGCGCGTCGGGGGCGGCTGGAG

 301 TCGGAAATGTGACCGCCGAAGCTAGAGGGGCCGCAGGGCTCACCCCGCAGCCCTCCGCAA
 301 AGCCTTTACACTGGCGGCTTCGATCTCCCCGGCGTCCCGAGTGGGGCGTCGGGAGGCGTT

 361 CGCGCCAACTTGGACGCCAGCGGCGCGGGGTCCCGGCCGGGCAGGGGGCGTCCGGCACCG
 361 GCGCGGTTGAACCTGCGGTCGCCGCGCCCCAGGGCCGGCCCGTCCCCCGCAGGCCGTGGC

 421 GCGGGTCCACCCCGGCCCGCCCGCCCGCCGCAAGCCCGGCCCGGCACCTCCTTTGTGCGC
 421 CGCCCAGGTGGGGCCGGGCGGGCGGGCGGCGTTCGGGCCGGGCCGTGGAGGAAACACGCG

 481 CCTCCTGGCCTCCCAGTCCCCCCGGCGCTCGGTCCCGCCCGGCCGTGACCTTCCCGCCCT
 481 GGAGGACCGGAGGGTCAGGGGGGCCGCGAGCCAGGGCGGGCCGGCACTGGAAGGGCGGGA

 541 CCCCACCATCCCAAGCGGGGAAAGGGGCCGCCCCGGCGGGGGTCGGGCCGGGGCCGGGGC
 541 GGGGTGGTAGGGTTCGCCCCTTTCCCCGGCGGGGCCGCCCCCAGCCCGGCCCCGGCCCCG

 601 CCTGGAGACGCTCACCTTCGTCCAGCAGCCGCTCGAGGTGGTTGAAGATCCCGCAGAAGT
 601 GGACCTCTGCGAGTGGAAGCAGGTCGTCGGCGAGCTCCACCAACTTCTAGGGCGTCTTCA

 661 TGGGCAGGCTGCTCATGAGCTTCTTGTCGTTCATCAGCTGCATCAGGTAATCTGGGGTGG
 661 ACCCGTCCGACGAGTACTCGAAGAACAGCAAGTAGTCGACGTAGTCCATTAGACCCCACC

 721 GCTTCGGCTTCTCCTTCGTTTCCATTTCCCCGACCATATTCCAGGCTCCGCAGCTCACTC
 721 CGAAGCCGAAGAGGAAGCAAAGGTAAAGGGGCTGGTATAAGGTCCGAGGCGTCGAGTGAG

 781 CGCCCGCCGCCGCCGCCGCCGCCGCCGGAGAGGAGGGAGGGGCGGGGGCGAGCCCCGGCC
 781 GCGGGCGGCGGCGGCGGCGGCGGCGGCCTCTCCTCCCTCCCCGCCCCCGCTCGGGGCCGG

 841 GCGGGCCGCTCGGGACCCGGCGTCCCGCTCCGCGCCGGCTCCCGCTCTGGCTCCCGCGCC
 841 CGCCCGGCGAGCCCTGGGCCGCAGGGCGAGGCGCGGCCGAGGGCGAGACCGAGGGCGCGG

 901 GAGCCCCGGGGCGGCCGGCACCGCGCGCTCGCCCGCCCCCCGCAGGCACTTTCCGCCCGG
 901 CTCGGGGCCCCGCCGGCCGTGGCGCGCGAGCGGGCGGGGGGCGTCCGTGAAAGGCGGGCC

 961 GCCCGACGCGCTCCCAGCCGCCGCCGCTCTCGGCCGCCCGGCTCGGCGCGTCCCTCACGA
 961 CGGGCTGCGCGAGGGTCGGCGGCGGCGAGAGCCGGCGGGCCGAGCCGCGCAGGGAGTGCT

1021 GGCCGGCGGGCGGGCGGGAGGCGGGTCTCGGCTGGCCGAGTGCGGGCGCGGGGCGCGGGC
1021 CCGGCCGCCCGCCCGCCCTCCGCCCAGAGCCGACCGGCTCACGCCCGCGCCCCGCGCCCG

1081 TGCTGGCGCCGGACGAGGAGGAGCCGGGGCCGCCGCTCGCTCGGCTGGTCGAGCCCGCTC
1081 ACGACCGCGGCCTGCTCCTCCTCGGCCCCGGCGGCGAGCGAGCCGACCAGCTCGGGCGAG

1141 AGCGCCGCCGCCGCCTGTGCCGCGGGCTCGGGGGGTCTCTCTGGGCTGGTCCCCGCCGCG
1141 TCGCGGCGGCGGCGGACACGGCGCCCGAGCCCCCCAGAGAGACCCGACCAGGGGCGGCGC

1201 GCGCCTCTGCCGCTGCCGCCGCGCTCCGACTGCGCTCCTCCTCTTCCTCCTCCTCCTTCT
1201 CGCGGAGACGGCGACGGCGGCGCGAGGCTGACGCGAGGAGGAGAAGGAGGAGGAGGAAGA
```

FIG. 2 (cont'd)

1261 CCTCCTCCTCCTCCTCACTCACTTGGCGGCGGAGTTCGCCTCAGTTCAGGCGGCGCTGCC
1261 GGAGGAGGAGGAGGAGTGAGTGAACCGCCGCCTCAAGCGGAGTCAAGTCCGCCGCGACGG

1321 AGCGGCGGCGGCAGCAGCGGCGGCGGCGGGGGAGGGGCAGCGGCGCGGGGAGGGCCGGG
1321 TCGCCGCCGCCGTCGTCGCCGCCGCCGCCCCCCTCCCCGTCGCCGCGCCCCTCCCGGCCC

1381 GGCGGGCGGCGGGCGGGGCCGCGCAGGGCGGCCGTTAGCGGGTCCCGGCCGGCGCGCTCC
1381 CCGCCCGCCGCCCGCCCCGGCGCGTCCCGCCGGCAATCGCCCAGGGCCGGCCGCGCGAGG

1441 CGCTGCCTGCTGCCCGCCGCCCCGCGACCGGGGCAGCCGCCGGCGCCGCGCCCCCTCCTC
1441 GCGACGGACGACGGGCGGCGGGGCGCTGGCCCCGTCGGCGGCCGCGGCGCGGGGGAGGAG

1501 CCTGCCTCCCCGGCGGGGCGGGCGACGGGGGCAACGGGAGTGTGACGGACTGCGGCGCTC
1501 GGACGGAGGGGCCGCCCCGCCCGCTGCCCCCGTTGCCCTCACACTGCCTGACGCCGCGAG

1561 GGCGGGCCTGGGCGCAAGGACTGGGTCGCCGCCGTGCGGGGCGCCCGGGGCGGGTGGGTG
1561 CCGCCCGGACCCGCGTTCCTGACCCAGCGGCGGCACGCCCCGCGGGCCCCGCCCACCCAC

1621 TGGGCTGCGGGGCCGACGGCCGCGGGGGGGCGCGGGGCTTTCCACGGCACGGGGCGGGT
1621 ACCCGACGCCCCGGCTGCCGGCGCCCCCCCGCGCCCCGAAAGGTGCCGTGCCCCGCCCA

1681 GGGGCTGCGGGCGCGGTCGGGGCTGGCGCGGCAGGCGAGAGGAATTCCAGCGGGACGCGC
1681 CCCCGACGCCCGCGCCAGCCCCGACCGCGCCGTCCGCTCTCCTTAAGGTCGCCCTGCGCG

1741 CAGCGCTGCCTCCGCCTCGCCTCCCGTTACTATAGTTTTTTCAGAACCTCTTATCCACCC
1741 GTCGCGACGGAGGCGGAGCGGAGGGCAATGATATCAAAAAAGTCTTGGAGAATAGGTGGG

1801 CGCAGAAGAGAAATTTTTTTTTAACGTCCTGTTGCTTCACGGGGGACTTTCGGGGTGGGC
1801 GCGTCTTCTCTTTAAAAAAAAATTGCAGGACAACGAAGTGCCCCCTGAAAGCCCCACCCG

1861 ATCACGTGGCCCGACACGTAGCCGTGGGGCTCCAGAGCGCGTGCGCGCGTCGAGCCCGGT
1861 TAGTGCACCGGGCTGTGCATCGGCACCCCGAGGTCTCGCGCACGCGCGCAGCTCGGGCCA

1921 CGCCACGCCCCTTCCGAGGGTCGCTCCGCCCCCGTCGGGCCCCGCGAGCGCGCGGTGGGG
1921 GCGGTGCGGGGAAGGCTCCCAGCGAGGCGGGGGCAGCCCGGGGCGCTCGCGCGCCACCCC

1981 GAGGGGAGGGCCCCGGAGCGCGCCTGCGTGGGGCGGGGGCGGCAGCCGACTAGGGGCTGG
1981 CTCCCCTCCCGGGGCCTCGCGCGGACGCACCCCGCCCCCGCCGTCGGCTGATCCCCGACC

2041 GTCTGGCCGTTTAGGGCCGGGTCTTGGCCCGTCGCC*CACGGTGCGGAGGGCTGGTGGGCT*
2041 CAGACCGGCAAATCCCGGCCCAGAACCGGGCAGCGGGTGCCACGCCTCCCGACCACCCGA

2101 *TTCCTTGGCCGTCGGGCCCGCCACGGCGCGGGTCTTGGCTGCGGGGCGGAGGTGGGGCGG*
2101 AAGGAACCGGCAGCCCGGGCGGTGCCGCGCCCAGAACCGACGCCCCGCCTCCACCCCGCC

2161 *GAGAGCCGAGGATAAGAGTTTGAGGCTTTTCGAGGCGCGTGCCGCGGCGTCCGCCTCTGC*
2161 CTCTCGGCTCCTATTCTCAAACTCCGAAAAGCTCCGCGCACGGCGCCGCAGGCGGAGACG

2221 *GGGACTCTGCGCCGGGCGCCCTCGGCCGGCGCGCCCGGCTCCCGCTTTGTCGCCGAGGGA*
2221 CCCTGAGACGCGGCCCGCGGGAGCCGGCCGCGCGGGCCGAGGGCGAAACAGCGGCTCCCT

2281 *AGCACGCGCGACGCCCCTCCCGTCGCCGCCGTGGCTTCTTTCGGTGTTCGTGATTTGCTG*
2281 TCGTGCGCGCTGCGGGGAGGGCAGCGGCGGCACCGAAGAAAGCCACAAGCACTAAACGAC

2341 *AGAGGCTGGAAAGCAGCACGGC*GGAGAGGAGCCTTGCACTCGCCAGGCGGGAAGCCTGCG
2341 TCTCCGACCTTTCGTCGTGCCGCCTCTCCTCGGAACGTGAGCGGTCCGCCCTTCGGACGC

2401 CGGACACGCGTGCGCACCCACGGGGCGGCGGGCGGGCGTGGGGGGTCCGGGCCACGCGGG
2401 GCCTGTGCGCACGCGTGGGTGCCCCGCCGCCCGCCCGCACCCCCCAGGCCCGGTGCGCCC

2461 CGACGCGCCTCTAGGGAAGCGA*TCTTGTTGCACCTTCCCGTTATTCTGAAAGCAAATCGT*
2461 GCTGCGCGGAGATCCCTTCGCT*AGAACAACGTGGAAGGGCAATAAGACTTTCGTTTAGCA*

2521 *AGCCAGACCCGAGCGCAGCGGCTTAGCAAATAATAAGGGGAGCGTCAGTCGTGCTCGAAA*
2521 *TCGGTCTGGGCTCGCGTCGCCGAATCGTTTATTATTCCCCTCGCAGTCAGCACGAGCTTT*

2581 *TGCTTCCTTCGCGATGGCGTCAGTGTTCCGTGAGGGAATGAAGCCGCAGTAGGAAATAAA*
2581 *ACGAAGGAAGCGCTACCGCAGTCACAAGGCACTCCCTTACTTCGGCGTCATCCTTTATTT*

FIG. 2 (cont'd)

```
2641  GAGGCTGTGCGCGTAGTCTGAAAAGCAGAAGTCAACATTTTTACAGATGAAGAAAGAATA
2641  CTCCGACACGCGCATCAGACTTTTCGTCTTCAGTTGTAAAAATGTCTACTTCTTTCTTAT

2701  CGGAGGCAAGAGGTCTTTCTCTGCAGTTTGGTGGATTTCCAACATTTAGACTTGTTTGGA
2701  GCCTCCGTTCTCCAGAAAGAGACGTCAAACCACCTAAAGGTTGTAAATCTGAACAAACCT

2761  AGAATTTCCTCAGCTGCACCAATGAAGTCCTTGATCTATAGAAGTCGGCAGTCCCTAAAT
2761  TCTTAAAGGAGTCGACGTGGTTACTTCAGGAACTAGATATCTTCAGCCGTCAGGGATTTA

2821  CTACGTCTGCATTTTGTTGCAAATCCTTTATAACATTCCATTAAAATAATGCAGAGTTAT
2821  GATGCAGACGTAAAACAACGTTTAGGAAATATTGTAAGGTAATTTTATTACGTCTCAATA

2881  TTAATA
2881  AATTAT
```

FIG. 3

>hg19_refGene_NM_001195286 range=chr6:389739-411443 5'pad=0 3'pad=0 strand=+ repeatMasking=none

Genomic Sequence of IRF4 (SEQ ID NO: 91)

```
   1  AGATTAGCAATTACATTTAAAAACAAGGTAGTGGTGTGAAGGCTCAGAGTTTCACACAAC
   1  TCTAATCGTTAATGTAAATTTTTGTTCCATCACCACACTTCCGAGTCTCAAAGTGTGTTG

  61  GACTGTTGTTCTGAACTAAAAGCAGAGGATGTGGATGAGTGAGGGGAGGGTATGTTGAAA
  61  CTGACAACAAGACTTGATTTTCGTCTCCTACACCTACTCACTCCCCTCCCATACAACTTT

 121  ATGACTAAACCCGGTGCAGAGGACACGTATACGAAAGTGCAAAAAGCTCTCATTTGCCAT
 121  TACTGATTTGGGCCACGTCTCCTGTGCATATGCTTTCACGTTTTTCGAGAGTAAACGGTA

 181  TTTTTGTCCTCAGCAAACTCCTCTCTGGTATGTTTGTGAACGTTTGAGGGAAAGGTAACA
 181  AAAAACAGGAGTCGTTTGAGGAGAGACCATACAAACACTTGCAAACTCCCTTTCCATTGT

 241  CTGATTAAAATATAATGCAACAAGAAGGCAACGATCTTTGCTTTGTTCACTGATGTGTTC
 241  GACTAATTTTATATTACGTTGTTCTTCCGTTGCTAGAAACGAAACAAGTGACTACACAAG

 301  CAAGTGCCTAGGACGGTTCCTGACAAGTAGCAGGTGCTCAAAATACATTTGTCAAGTGAA
 301  GTTCACGGATCCTGCCAAGGACTGTTCATCGTCCACGAGTTTTATGTAAACAGTTCACTT

 361  TAAATCTGTGAAAGGAAAGGAAGAAAAACAGGTTGTGACCAGAACTTTTTGTGAACAAAA
 361  ATTTAGACACTTTCCTTTCCTTCTTTTTGTCCAACACTGGTCTTGAAAAACACTTGTTTT

 421  CCCTGTTGTTTATTACATAGACTTTGGTAATGGAAAACTTACTTGGGTGAAATAAAAAAT
 421  GGGACAACAAATAATGTATCTGAAACCATTACCTTTTGAATGAACCCACTTTATTTTTTA

 481  GGCATCCTGTTAATTTCTGAGAACGTCTGTTGGTTTTAGGAAAAGCATACCTATCCATAC
 481  CCGTAGGACAATTAAAGACTCTTGCAGACAACCAAAATCCTTTTCGTATGGATAGGTATG

 541  CTCACTACCTGTTTTGCTCTAGCCTAAACATAGATTCTTCTTTGGTTAGGAGACATTGAC
 541  GAGTGATGGACAAAACGAGATCGGATTTGTATCTAAGAAGAAACCAATCCTCTGTAACTG

 601  CCAATATATAAGATTAAAACAAAAACTGAGAAATAAGTGAAATCAAAAGCTTTTCAAAAG
 601  GGTTATATATTCTAATTTTGTTTTTGACTCTTTATTCACTTTAGTTTTCGAAAAGTTTTC

 661  TTGCAGGTTGACCTACGGTGGTGGTGGTCTAAAATCATATAGAAACCAGAGATCTGATGG
 661  AACGTCCAACTGGATGCCACCACCACCAGATTTTAGTATATCTTTGGTCTCTAGACTACC

 721  TTTACCTGAAAATGCGAAGTAAATGCACATACTCAGCATCTCAGACGATCGAAAGCTCAA
 721  AAATGGACTTTTACGCTTCATTTACGTGTATGAGTCGTAGAGTCTGCTAGCTTTCGAGTT

 781  CGGGTGAAAGCTCAGGGGGTTAATTTTGCGATTAAGGACATCTTGGAAAAGTATGTAAAA
 781  GCCCACTTTCGAGTCCCCCAATTAAAACGCTAATTCCTGTAGAACCTTTTCATACATTTT

 841  TCCCTGGTCCACTTAAGTATTATTCCTATTTTGGGCTTTTATTTATTTATTTTGAGATGG
 841  AGGGACCAGGTGAATTCATAATAAGGATAAAACCCGAAAATAAATAAATAAAACTCTACC

 901  AGTCTTGCTCTGTCGCCCACCTCGGCTCACTGCAACTTCAGCCTCCCGGGTTCAAGCGAT
 901  TCAGAACGAGACAGCGGGTGGAGCCGAGTGACGTTGAAGTCGGAGGGCCCAAGTTCGCTA

 961  TCTCGTGGCTCGTCCTCTCAAGTAGCTGGGGCCACGCCCGGCTAATTTTTGTATTTTTAG
 961  AGAGCACCGAGCAGGAGAGTTCATCGACCCCGGTGCGGGCCGATTAAAAACATAAAAATC

1021  TAGAGATGGGGTTTCACCGTGTTGGCCAGGCTGGTCTCGAACTCCTGACCTCAGGCGATC
1021  ATCTCTACCCCAAAGTGGCACAACCGGTCCGACCAGAGCTTGAGGACTGGAGTCCGCTAG

1081  CACCGCCTCGGCCTCCCAAAGTGCTGGGATTACAGGCTTGAGCCACAGCGCCTGGCCTAT
1081  GTGGCGGAGCCGGAGGGTTTCACGACCCTAATGTCCGAACTCGGTGTCGCGGACCGGATA

1141  TTTGGGCTTTTATACCCCACTGGTAAACTGCTTTCCTCCAGGTTGAGGTTAAAACGACAT
1141  AAACCCGAAAATATGGGGTGACCATTTGACGAAAGGAGGTCCAACTCCAATTTTGCTGTA

1201  CATTTTAAGGTGAACTGAAGTCTGGAAGTGATTAAGCACTTGGATCCTTAGGGAGCCTCT
1201  GTAAAATTCCACTTGACTTCAGACCTTCACTAATTCGTGAACCTAGGAATCCCTCGGAGA
```

FIG. 3 (cont'd)

1261 CCCCGCCCCCATCTCTTTCATGCTAAGATAATTAAAACTTCGGGGCCGGGGCATTGTCTG
1261 GGGGCGGGGGTAGAGAAAGTACGATTCTATTAATTTTGAAGCCCCGGCCCCGTAACAGAC

1321 AGTCACTTCAATTCACCAGCCTAATAGATGCAAAAGGATGTAAGCATGTCAGACACGCAG
1321 TCAGTGAAGTTAAGTGGTCGGATTATCTACGTTTTCCTACATTCGTACAGTCTGTGCGTC

1381 AGACAGTATTTGAATCAAGCTTAATAGCTCAAGGGAGCTGGGCCATTTCCTATTTTCTTT
1381 TCTGTCATAAACTTAGTTCGAATTATCGAGTTCCCTCGACCCGGTAAAGGATAAAAGAAA

1441 TTAGTGAGTGCGATGTTCTCTAAACACCGCGGAGAGGCAGGGTTCCCGGTGATGGCCTTG
1441 AATCACTCACGCTACAAGAGATTTGTGGCGCCTCTCCGTCCCAAGGGCCACTACCGGAAC

1501 CCGAGGGTGCTCCCGCAACCTCCACCTCCAGTTCTCTTTGGACCATTCCTCCGTCTTCCG
1501 GGCTCCCACGAGGGCGTTGGAGGTGGAGGTCAAGAGAAACCTGGTAAGGAGGCAGAAGGC

1561 TTACACGCTCTGCAAAGCGAAGTCCCCTTCGCACCAGATTCCCGCTACTACACGCCCCCC
1561 AATGTGCGAGACGTTTCGCTTCAGGGGAAGCGTGGTCTAAGGGCGATGATGTGCGGGGGG

1621 ATTTCCCGCCCTGGCCACATCGCTGCAGTTTAGTGATTGACTGGCCTCCTGAGGTCCTGG
1621 TAAAGGGCGGGACCGGTGTAGCGACGTCAAATCACTAACTGACCGGAGGACTCCAGGACC

1681 CGCAAAGGCGAGATTCGCATTTCGCACCTCGCCCTTCGCGGGAAACGGCCCCAGTGACAG
1681 GCGTTTCCGCTCTAAGCGTAAAGCGTGGAGCGGGAAGCGCCCTTTGCCGGGGTCACTGTC

1741 TCCCCGAAGCGGCGCGCGCCCGGCTGGAGGTGCGCTCTCCGGGCGCGGCGCGCGGAGGGT
1741 AGGGGCTTCGCCGCGCGCGGGCCGACCTCCACGCGAGAGGCCCGCGCCGCGCGCCTCCCA

1801 CGCCAAGGGCGCGGGAACCCCACCCCGGCCGCGGCAGCCCCCAGCCTTCACGCCGGCCCT
1801 GCGGTTCCCGCGCCCTTGGGGTGGGGCCGGCGCCGTCGGGGGTCGGAAGTGCGGCCGGGA

1861 GAGGCTCGCCCGCCCGGCCGGCCCCGGCTCTCGGCTTGCAAAGTCCCTCTCCCCAGTCCA
1861 CTCCGAGCGGGCGGGCCGGCCGGGGCCGAGAGCCGAACGTTTCAGGGAGAGGGGTCAGGT

1921 ACCCCCGGCCCCCACAGGCCTCGGCGCCCCGCCCCGCCCCAGGCCCCGCCCCAGAGAGTT
1921 TGGGGGCCGGGGGTGTCCGGAGCCGCGGGGCGGGGCGGGGTCCGGGGCGGGGTCTCTCAA

1981 CTATAAAGTTCCTCTTTCCCACCTCGCACTCTCAGTTTCACCGCTCGATCTTGGGACCCA
1981 GATATTTCAAGGAGAAAGGGTGGAGCGTGAGAGTCAAAGTGGCGAGCTAGAACCCTGGGT

2041 CCGCTGCCCTCAGCTCCGAGTCCAGGGCGAGGTAAGGGCTGGAGTCGGGCAGGAGGAGGG
2041 GGCGACGGGAGTCGAGGCTCAGGTCCCGCTCCATTCCCGACCTCAGCCCGTCCTCCTCCC

2101 GTGTGAGGCTGATACCAGAGAGGACCCGGAGCGCGAACCAGAGGTTCGACCTCCAGGGCA
2101 CACACTCCGACTATGGTCTCTCCTGGGCCTCGCGCTTGGTCTCCAAGCTGGAGGTCCCGT

2161 GCGCAGGGTACCCCGGCTTCGGAGCGGGAAGGGAGCGCGCCCCGTCCTGGAGCTCCGACT
2161 CGCGTCCCATGGGGCCGAAGCCTCGCCCTTCCCTCGCGCGGGGCAGGACCTCGAGGCTGA

2221 CCCACCCCATCTGCGCTGAGCCGGAGGCGCTGGTTTGGGCTCCAAGGCCCGCCTCCTTGG
2221 GGGTGGGGTAGACGCGACTCGGCCTCCGCGACCAAACCCGAGGTTCCGGGCGGAGGAACC

2281 CTCTGCCCGAGCCTCCC*CGCCTGCCCTCCGCGCTCCTGCGACGGGGTCGCCACAAGCTGG*
2281 GAGACGGGCTCGGAGGGGCGGACGGGAGGCGCGAGGACGCTGCCCCAGCGGTGTTCGACC

2341 *ACGGGATGAGCTAACCGGACTGTCGGGGCCCCAGGAGTGGCTGAGGCGGGGCCGTCCAAG*
2341 TGCCCTACTCGATTGGCCTGACAGCCCCGGGGTCCTCACCGACTCCGCCCCGGCAGGTTC

2401 *GCACCCA*CACAAGACGGCACAACTGCCTGCGAGAAACAGGCCCGGCCCTGTGGACCCCAA
2401 CGTGGGTGTGTTCTGCCGTGTTGACGGACGCTCTTTGTCCGGGCCGGGACACCTGGGGTT

2461 TCCGAGGCTCCTTCCCCTGCTCTTCGTTCCTAAGGGGCCCAAGCTCACGGCGGCCTCCGG
2461 AGGCTCCGAGGAAGGGGACGAGAAGCAAGGATTCCCCGGGTTCGAGTGCCGCCGGAGGCC

2521 CGCGGTGCTCACCCGCTGGCGCAGGAGGAGGAGGAGCTCCACATTTGGGTCGCTCCGAGC
2521 GCGCCACGAGTGGGCGACCGCGTCCTCCTCCTCCTCGAGGTGTAAACCCAGCGAGGCTCG

2581 CTTGCGTGCGGTGGCCTAGCCGGCCTGGCGCGGTCCCTGCCTCCCAGGCTCCGCAGCTGT
2581 GAACGCACGCCACCGGATCGGCCGGACCGCGCCAGGGACGGAGGGTCCGAGGCGTCGACA

FIG. 3 (cont'd)

```
2641  CGTCGCCCTCTCCCGCGCCCTCCCCGCCTCCGCTCTCCCGGGCCTGCTCCGGGGTCCGGC
2641  GCAGCGGGAGAGGGCGCGGGAGGGGCGGAGGCGAGAGGGCCCGGACGAGGCCCCAGGCCG

2701  GGACGCTCTGCGCGCGGAATCCCCCGTACTGGGGCTGCAGCCCCCGCGTCTGCGCCACTT
2701  CCTGCGAGACGCGCGCCTTAGGGGGCATGACCCCGACGTCGGGGGCGCAGACGCGGTGAA

2761  GTCGTTTGCAGAGCCCACTTAGTGCGCGCTAGCTGGGCAGGGATAGGGGTCCTATTCGGG
2761  CAGCAAACGTCTCGGGTGAATCACGCGCGATCGACCCGTCCCTATCCCCAGGATAAGCCC

2821  GCGAAGGGTCTGGATGCGAGCAGAGAAAGCGGAGGGTGGAGGAACCCGGGGCTGCGCCCC
2821  CGCTTCCCAGACCTACGCTCGTCTCTTTCGCCTCCCACCTCCTTGGGCCCCGACGCGGGG

2881  TGGAACGCCCGGCCGCAGGCGAGGTCCTCCGCGCGTGGAGGCCGCCAGGGGAGTGGAAAC
2881  ACCTTGCGGGCCGGCGTCCGCTCCAGGAGGCGCGCACCTCCGGCGGTCCCCTCACCTTTG

2941  TGACAGAGTCGCGGGGAAGGGGCGAGAAGCGGGTTGGGAGTGAGCGAAGGCAAGCGAGAG
2941  ACTGTCTCAGCGCCCCTTCCCCGCTCTTCGCCCAACCCTCACTCGCTTCCGTTCGCTCTC

3001  CTGCGAGTGAGTGCGGAAGGAGGGCCAGGAGGGGTGGCGGCTGGGTGGGGAGAGAGGGTG
3001  GACGCTCACTCACGCCTTCCTCCCGGTCCTCCCCACCGCCGACCCACCCCTCTCTCCCAC

3061  CAAGACGAGCGGCGCGTGTCGGGAGCCTTTGGGCTGCGGGTGCGTTACAGGAGAGCAGGC
3061  GTTCTGCTCGCCGCGCACAGCCCTCGGAAACCCGACGCCCACGCAATGTCCTCTCGTCCG

3121  GGGTAGGAGCCTTCGCGGGGGCCGAGCTCGGAAGGCGGACGGCTGTGCCCGCCCAGGGGA
3121  CCCATCCTCGGAAGCGCCCCCGGCTCGAGCCTTCCGCCTGCCGACACGGGCGGGTCCCCT

3181  TGCGCCCGGGCCGGCCGCGAAGGTGCCTTCTTCCGGGGGCCCGGACGACCCTGACACGGC
3181  ACGCGGGCCCGGCCGGCGCTTCCACGGAAGAAGGCCCCCGGGCCTGCTGGGACTGTGCCG

3241  ACGCGCGCGCTTCGCAGCCTCAAAGACTCCGGGGCCTCGTGGTCACTGGCGCAGGGGATC
3241  TGCGCGCGCGAAGCGTCGGAGTTTCTGAGGCCCCGGAGCACCAGTGACCGCGTCCCCTAG

3301  GGGGCGGGGTGCCCGGAGTGCGGTGCCTCGTGGCTGAAGGGCAGCTCTTCTCCCCGCAGT
3301  CCCCGCCCCACGGGCCTCACGCCACGGAGCACCGACTTCCCGTCGAGAAGAGGGGCGTCA

3361  GCAGAGCAGAGCGGGCGGAGGACCCCGGGCGCGGGCGCGGACGGCACGCGGGGCATGAAC
3361  CGTCTCGTCTCGCCCGCCTCCTGGGGCCCGCGCCCGCGCCTGCCGTGCGCCCCGTACTTG

3421  CTGGAGGGCGGCGGCCGAGGCGGAGAGTTCGGCATGAGCGCGGTGAGCTGCGGCAACGGG
3421  GACCTCCCGCCGCCGGCTCCGCCTCTCAAGCCGTACTCGCGCCACTCGACGCCGTTGCCC

3481  AAGCTCCGCCAGTGGCTGATCGACCAGATCGACAGCGGCAAGTACCCCGGGCTGGTGTGG
3481  TTCGAGGCGGTCACCGACTAGCTGGTCTAGCTGTCGCCGTTCATGGGGCCCGACCACACC

3541  GAGAACGAGGAGAAGAGCATCTTCCGCATCCCCTGGAAGCACGCGGGCAAGCAGGACTAC
3541  CTCTTGCTCCTCTTCTCGTAGAAGGCGTAGGGGACCTTCGTGCGCCCGTTCGTCCTGATG

3601  AACCGCGAGGAGGACGCCGCGCTCTTCAAGGTCTCCGGCCTCGGGAGCCGGCGGGGGCGC
3601  TTGGCGCTCCTCCTGCGGCGCGAGAAGTTCCAGAGGCCGGAGCCCTCGGCCGCCCCCGCG

3661  GCCGGGGAGGGCCCAGAGACAGAGCCCGGGGTCCCCGGCGCCGCCTCCGAGGCGAGCCCA
3661  CGGCCCCTCCCGGGTCTCTGTCTCGGGCCCCAGGGGCCGCGGCGGAGGCTCCGCTCGGGT

3721  GGGGACCGCGCGGGGCGGACGGGCGGGCGGCGGAGGCATCAGGTGGCGTCGCCGGAGCCG
3721  CCCCTGGCGCGCCCCGCCTGCCCGCCCGCCGCCTCCGTAGTCCACCGCAGCGGCCTCGGC

3781  CAGGAGGAGGAAAGGAGGCCTCGGCTCTCAGCGGGACCGCGGGGGCCGGGAGCCGGGTCC
3781  GTCCTCCTCCTTTCCTCCGGAGCCGAGAGTCGCCCTGGCGCCCCCGGCCCTCGGCCCAGG

3841  TGGGCGCGTGGAGGCTGCAGGGAAACCGCTGAAGGCCCGGCCGGGCCCGGGGAAGGGCGG
3841  ACCCGCGCACCTCCGACGTCCCTTTGGCGACTTCCGGGCCGGCCCGGGCCCCTTCCCGCC

3901  CCAAAGGCTTGAGGGGTTTTGCGCGTTCGTCCGTGCGTTCTCGTTTCCACGCAAGCCTCC
3901  GGTTTCCGAACTCCCCAAAACGCGCAAGCAGGCACGCAAGAGCAAAGGTGCGTTCGGAGG

3961  CGCCCTTCCTCCGGGCTCCCGTCTGCCGCCTCCGTCCGTGGGTCCCCCTCGCCCTCTCCG
3961  GCGGGAAGGAGGCCCGAGGGCAGACGGCGGAGGCAGGCACCCAGGGGGAGCGGGAGAGGC
```

FIG. 3 (cont'd)

```
4021  TGCGTCCGCGCCTGTGCCGGCGGCTGTTTTCGTCTCTCACCGCGTCTCTGTTTCTCTTTT
4021  ACGCAGGCGCGGACACGGCCGCCGACAAAAGCAGAGAGTGGCGCAGAGACAAAGAGAAAA

4081  CGCTGCTTTTCTCTCTGAGTCTCTCTCTCTCCATGTTTTTCCTGAGGTCAGCCTCTCTTC
4081  GCGACGAAAAGAGAGACTCAGAGAGAGAGAGGTACAAAAAGGACTCCAGTCGGAGAGAAG

4141  TCGCTCCTGCTAGCTCTCTGCGGGTACTCCCACCTCTGTCTTTCTCTTTGTGTGTCTCTG
4141  AGCGAGGACGATCGAGAGACGCCCATGAGGGTGGAGACAGAAAGAGAAACACACAGAGAC

4201  TCTCTCTCTTTCCCCCATCGCAGTGGAACTCAGGGCCTCTGTCTAGAGCTGTCTCCCTTG
4201  AGAGAGAGAAAGGGGGTAGCGTCACCTTGAGTCCCGGAGACAGATCTCGACAGAGGGAAC

4261  CCCTTTGCGCGAGTGCACACACGTGTGTCGTTGTTACGATTGTTCTCCCCTAAGGCAGTT
4261  GGGAAACGCGCTCACGTGTGTGCACACAGCAACAATGCTAACAAGAGGGGATTCCGTCAA

4321  TACCCAGAGAACTACGTGTCTGGGCCCAGCCCCCACCTGTGGGCAGAGCAGGGGAAGGGG
4321  ATGGGTCTCTTGATGCACAGACCCGGGTCGGGGGTGGACACCCGTCTCGTCCCCTTCCCC

4381  ACTTCCTCCGGGAATTTGGTCTCAATTTGCTCTCAGAGTGCCTCAGCTGTGCTGCCATCC
4381  TGAAGGAGGCCCTTAAACCAGAGTTAAACGAGAGTCTCACGGAGTCGACACGACGGTAGG

4441  AGATGTCTCCTGTGGGTGACAGCTCACACCACAGCTGTCCTTAGTCCTAGGCAAGCTCAC
4441  TCTACAGAGGACACCCACTGTCGAGTGTGGTGTCGACAGGAATCAGGATCCGTTCGAGTG

4501  TCAGACACTGGGTGGGTAGAGCCCCCTCAAGGAACCTCCGCATCTCACTCTACCGGTTAT
4501  AGTCTGTGACCCACCCATCTCGGGGGAGTTCCTTGGAGGCGTAGAGTGAGATGGCCAATA

4561  AAATACCCAGAAAATGTGTCTTCAACTTGGCAGTGATAGGGTCCAAGATGGAAAATCATT
4561  TTTATGGGTCTTTTACACAGAAGTTGAACCGTCACTATCCCAGGTTCTACCTTTTAGTAA

4621  TTCCTAGAGCATAGCTGGGGTCTTTCAGTTTACGTTCTGAGCAACGGTGTAAATCTGAAG
4621  AAGGATCTCGTATCGACCCCAGAAAGTCAAATGCAAGACTCGTTGCCACATTTAGACTTC

4681  GACCTATGCGCCATTCTTTCTTTTAGAAATACAATTTCAAGATTCCTTATAAAATATCTG
4681  CTGGATACGCGGTAAGAAAGAAAATCTTTATGTTAAAGTTCTAAGGAATATTTTATAGAC

4741  TATTTTGGGTTTAGCATGGTGGCTCACACCTGTAATCCCAGCACTTTGGGAAGATGAGGT
4741  ATAAAACCCAAATCGTACCACCGAGTGTGGACATTAGGGTCGTGAAACCCTTCTACTCCA

4801  GGAAGGATGCCTATGCAACATAGTGAGACCCTGCCTCTGCAAAAAATAATAATTAAAAAA
4801  CCTTCCTACGGATACGTTGTATCACTCTGGGACGGAGACGTTTTTTATTATTAATTTTTT

4861  ATTAGCCAGGCATGGTGGTGAACACCTGTAGGCCGAGGGCCCAGCTACTCTAGAGGCTGA
4861  TAATCGGTCCGTACCACCACTTGTGGACATCCGGCTCCCGGGTCGATGAGATCTCCGACT

4921  GATAGGAGGACCCTAGAACTCAGGAGTTCGATGCTGCGGTGAGCTATCATCGTGCCACTG
4921  CTATCCTCCTGGGATCTTGAGTCCTCAAGCTACGACGCCACTCGATAGTAGCACGGTGAC

4981  TACTCTAGCCTGGGCAGCAGAGCAGGACTCTGATTCCAAAAAGAAAGCTAATAAACCAGA
4981  ATGAGATCGGACCCGTCGTCTCGTCCTGAGACTAAGGTTTTTCTTTCGATTATTTGGTCT

5041  CATGTATTTTGACTTTTCGTTCTCTTCATTCTTTCCCACCAGGCTTGGGCACTGTTTAAA
5041  GTACATAAAACTGAAAAGCAAGAGAAGTAAGAAAGGGTGGTCCGAACCCGTGACAAATTT

5101  GGAAAGTTCCGAGAAGGCATCGACAAGCCGGACCCTCCCACCTGGAAGACGCGCCTGCGG
5101  CCTTTCAAGGCTCTTCCGTAGCTGTTCGGCCTGGGAGGGTGGACCTTCTGCGCGGACGCC

5161  TGCGCTTTGAACAAGAGCAATGACTTTGAGGAACTGGTTGAGCGGAGCCAGCTGGACATC
5161  ACGCGAAACTTGTTCTCGTTACTGAAACTCCTTGACCAACTCGCCTCGGTCGACCTGTAG

5221  TCAGACCCGTACAAAGTGTACAGGATTGTTCCTGAGGGAGCCAAAAAAGGTAGGGGCTCT
5221  AGTCTGGGCATGTTTCACATGTCCTAACAAGGACTCCCTCGGTTTTTTCCATCCCCGAGA

5281  CCTGAATTTGGGTCACCTAACAGAGGCAGCCAGATCCTTGAGGCACCTTAACTTCATTCT
5281  GGACTTAAACCCAGTGGATTGTCTCCGTCGGTCTAGGAACTCCGTGGAATTGAAGTAAGA

5341  GAGCATCACTTTCTAGCTTTCCTTTTGTATTGCCTGCCTGCCTGCCTTCTGCCTCACAGT
5341  CTCGTAGTGAAAGATCGAAAGGAAAACATAACGGACGGACGGACGGAAGACGGAGTGTCA
```

FIG. 3 (cont'd)

```
5401  GAAGCCCAGCCTCCTTGCCTGAGTTATGTGGGTCACAAGTTGAAATTCCTGTGGGGTTCA
5401  CTTCGGGTCGGAGGAACGGACTCAATACACCCAGTGTTCAACTTTAAGGACACCCCAAGT

5461  GCATAGGAGAATTAATCACACTGTATGCCTCAATGTATATGGGGGGGGGTGCATTGAATA
5461  CGTATCCTCTTAATTAGTGTGACATACGGAGTTACATATACCCCCCCCCACGTAACTTAT

5521  TGTGTTTTCCAGTTAGTCTTTCAAAAAAAAAAAGAAAAAAGAAAACTGGATAACTTGTTA
5521  ACACAAAAGGTCAATCAGAAAGTTTTTTTTTTTCTTTTTTCTTTTGACCTATTGAACAAT

5581  AAATTTACTTATCTAATAGTCTTTAGTGAGTGACTATTTTGCAGAAAAGGAGTAATGAGA
5581  TTTAAATGAATAGATTATCAGAAATCACTCACTGATAAAACGTCTTTTCCTCATTACTCT

5641  GGAATATCTCATCACTATGCATGGTAATAAAACTGTCAACTTTTAAAGTGTAACATGGTC
5641  CCTTATAGAGTAGTGATACGTACCATTATTTTGACAGTTGAAAATTTCACATTGTACCAG

5701  AGCTGAGGTGTTTATTAAAAGTCAGATTCCTGGACCCCTCTTTTCAAGATTCTGACCAGT
5701  TCGACTCCACAAATAATTTTCAGTCTAAGGACCTGGGGAGAAAAGTTCTAAGACTGGTCA

5761  GTGTCTGGAAGAGAGCTCAGGAATCTGCATCTGGAACAAATCCTTCAGGTGACCTCACTT
5761  CACAGACCTTCTCTCGAGTCCTTAGACGTAGACCTTGTTTAGGAAGTCCACTGGAGTGAA

5821  GGGAAACATCTGGCTGGCGGGGTCCTTTATGTCACAAGGCACATTCGCATGCCATCTGTC
5821  CCCTTTGTAGACCGACCGCCCCAGGAAATACAGTGTTCCGTGTAAGCGTACGGTAGACAG

5881  ATGTATTTCTTTACCTGTCCTGTACAACTCAGACCTTGTAGAAAAAAATCAGTTTAATAG
5881  TACATAAAGAAATGGACAGGACATGTTGAGTCTGGAACATCTTTTTTTAGTCAAATTATC

5941  CATGAAAAAATAACTTCCCAAGGGAGTTGCTGAAAAATACCTTATTTGTCAACACCGTGT
5941  GTACTTTTTTATTGAAGGGTTCCCTCAACGACTTTTTATGGAATAAACAGTTGTGGCACA

6001  TATGCATTCTAAGAATTAAATGCTCAGGTATTTTTACAAGATTTGACATTTAGTTAGGTC
6001  ATACGTAAGATTCTTAATTTACGAGTCCATAAAAATGTTCTAAACTGTAAATCAATCCAG

6061  AGTTCCTGTTTTTACGTTGTGCCATTTCCCTTTTCCCCAAACATGTAGGAGCCAAGCAGC
6061  TCAAGGACAAAAATGCAACACGGTAAAGGGAAAAGGGGTTTGTACATCCTCGGTTCGTCG

6121  TCACCCTGGAGGACCCGCAGATGTCCATGAGCCACCCCTACACCATGACAACGCCTTACC
6121  AGTGGGACCTCCTGGGCGTCTACAGGTACTCGGTGGGGATGTGGTACTGTTGCGGAATGG

6181  CTTCGCTCCCAGCCCAGGTATGGTGGAGGGCACTGGGCTCCCTGAGGGCGAGGCTGTGTG
6181  GAAGCGAGGGTCGGGTCCATACCACCTCCCGTGACCCGAGGGACTCCCGCTCCGACACAC

6241  GGCCAGCTGCCCACATGGCCAGAGAACCACAGCAGCCCAGACAGCAGAACTTGCCATTTG
6241  CCGGTCGACGGGTGTACCGGTCTCTTGGTGTCGTCGGGTCTGTCGTCTTGAACGGTAAAC

6301  CTATGGCTGCTCCAACAGCCCAGAAAAACCCCAGGTCACTGAACGAATGTCTCACTTTCC
6301  GATACCGACGAGGTTGTCGGGTCTTTTTGGGGTCCAGTGACTTGCTTACAGAGTGAAAGG

6361  ACACGGTGCTGCCATTGGTGTGGATTTTAAGTTGGGGAGGGTCGGGCGTGTCCGCCTGTT
6361  TGTGCCACGACGGTAACCACACCTAAAATTCAACCCCTCCCAGCCCGCACAGGCGGACAA

6421  GGAATATGCTTCTCAGGTCTTCTGGGAAACAGATGTTTTGTGGAAGTGGAAGATTTTGGA
6421  CCTTATACGAAGAGTCCAGAAGACCCTTTGTCTACAAAACACCTTCACCTTCTAAAACCT

6481  AGTAGTGCCTTATCATGTGAAACCACAGGGCAGCTGATCTCTTCAGGCTTTCTTGATGTG
6481  TCATCACGGAATAGTACACTTTGGTGTCCCGTCGACTAGAGAAGTCCGAAAGAACTACAC

6541  AATGACAGCTTTGTTTCATCCACTTTGGTGGGTAAAAGAAGGCAAATTCCCCTGTGGTAC
6541  TTACTGTCGAAACAAAGTAGGTGAAACCACCCATTTTCTTCCGTTTAAGGGGACACCATG

6601  TTTTGGTGCCAGGTTTAGCCATATGACGAAGCTTTACATAAAACAGTACAAGTATCTCCA
6601  AAAACCACGGTCCAAATCGGTATACTGCTTCGAAATGTATTTTGTCATGTTCATAGAGGT

6661  TTGTCCTTTATGATCCTCCATGAGTGTTTTCACTTAGTCTGATGAAGGGTTCACTCCAGT
6661  AACAGGAAATACTAGGAGGTACTCACAAAAGTGAATCAGACTACTTCCCAAGTGAGGTCA

6721  CTTTTCGGATGATAAAATGCTTCGGCTGTCAGTCTAATAAGGGATTCCCTGAGGAGTTTG
6721  GAAAAGCCTACTATTTTACGAAGCCGACAGTCAGATTATTCCCTAAGGGACTCCTCAAAC
```

FIG. 3 (cont'd)

```
6781  GAGGCTGTAAGAGCACCCCCCGTCTCAATGCCAGTGCTTCTTATCTCAGCCTCTCCTGCA
6781  CTCCGACATTCTCGTGGGGGGCAGAGTTACGGTCACGAAGAATAGAGTCGGAGAGGACGT

6841  CTCCTTTACCCCCGTCTCGATGCCAGTGCTTCCTATCTCAGCCTCTCCTGCACTCCTTTA
6841  GAGGAAATGGGGGCAGAGCTACGGTCACGAAGGATAGAGTCGGAGAGGACGTGAGGAAAT

6901  CCCCCGTCTCGATGCCAGTGCTTCCTATCTCAGCCTCTCCTGCACTCCTTTACCCCCGTC
6901  GGGGGCAGAGCTACGGTCACGAAGGATAGAGTCGGAGAGGACGTGAGGAAATGGGGGCAG

6961  TCGATGCCAGTGCTTCTTATCTCAGCCTCTCCTGCACTCCTTTACCCCCGTCTCAATGCC
6961  AGCTACGGTCACGAAGAATAGAGTCGGAGAGGACGTGAGGAAATGGGGGCAGAGTTACGG

7021  AGTGCTTCCTATCTCAGCCTCTCCTGCACTCCTTTAACCCCGTCTCGATGCCAGTGCTTC
7021  TCACGAAGGATAGAGTCGGAGAGGACGTGAGGAAATTGGGGCAGAGCTACGGTCACGAAG

7081  TTATCTCAGCCTCTCCTGCACTCCTTTACCCCCGTCTCAATGCCAGTGCTTCCTATCTCA
7081  AATAGAGTCGGAGAGGACGTGAGGAAATGGGGGCAGAGTTACGGTCACGAAGGATAGAGT

7141  GCCTCTCCTGCACTCCTTTACCCCCGTCTCAATGCCAGTGCTTCCTATCTCAGCCTCTCC
7141  CGGAGAGGACGTGAGGAAATGGGGGCAGAGTTACGGTCACGAAGGATAGAGTCGGAGAGG

7201  TGCACTCCTTTACCCCCGTCTCGATGCCAGTGCTTCTTATCTCAGCCTCTCCTGCACTCC
7201  ACGTGAGGAAATGGGGGCAGAGCTACGGTCACGAAGAATAGAGTCGGAGAGGACGTGAGG

7261  TTTACCCCCGTCTCGATGCCAGTGCTTCCTATCTCAGCCTCTCCTGCACTCCTTTACCCC
7261  AAATGGGGGCAGAGCTACGGTCACGAAGGATAGAGTCGGAGAGGACGTGAGGAAATGGGG

7321  CGTCTCAATGCCAGTGCTTCTTATCTCAGCCTCTCCTGCACTCCTTTAGCAGGTTCACAA
7321  GCAGAGTTACGGTCACGAAGAATAGAGTCGGAGAGGACGTGAGGAAATCGTCCAAGTGTT

7381  CTACATGATGCCACCCCTCGACCGAAGCTGGAGGGACTACGTCCCGGATCAGCCACACCC
7381  GATGTACTACGGTGGGGAGCTGGCTTCGACCTCCCTGATGCAGGGCCTAGTCGGTGTGGG

7441  GGAAATCCCGTACCAATGTCCCATGACGTTTGGACCCCGCGGCCACCACTGGCAAGGCCC
7441  CCTTTAGGGCATGGTTACAGGGTACTGCAAACCTGGGGCGCCGGTGGTGACCGTTCCGGG

7501  AGCTTGTGAAAATGGTAAGGAGGATACCAGTGCAGGAAATAGAAGAGCTAATTGCTAATG
7501  TCGAACACTTTTACCATTCCTCCTATGGTCACGTCCTTTATCTTCTCGATTAACGATTAC

7561  TGGCCATGGGCCATGGCGAATCCTGGTCTGTCCTGGGCAGCACCAAAGCTCTTTCCCCTT
7561  ACCGGTACCCGGTACCGCTTAGGACCAGACAGGACCCGTCGTGGTTTCGAGAAAGGGGAA

7621  CTTAGAGGCTGCGTGTGCAGCTCGGGGAGAGGGGGGTTTCTCACTCCTGTGGGATGGTG
7621  GAATCTCCGACGCACACGTCGAGCCCCTCTCCCCCCAAAAGAGTGAGGACACCCTACCAC

7681  GCATCCCACAGCCAAGTTTACTCTCAGGATCCATGCTAGGCACTGCCCTTCGTGGGATCT
7681  CGTAGGGTGTCGGTTCAAATGAGAGTCCTAGGTACGATCCGTGACGGGAAGCACCCTAGA

7741  TATTTAAACACCACAGAGATCACTCCAGGCAGTGGAAAACAGCCCCCCACTTTTTATATA
7741  ATAAATTTGTGGTGTCTCTAGTGAGGTCCGTCACCTTTTGTCGGGGGGTGAAAAATATAT

7801  GAGAGGAGATTGTGGAAGCTCATAAATAATAAGTAGGGATGCTGGGAGATTATTGAGCTG
7801  CTCTCCTCTAACACCTTCGAGTATTTATTATTCATCCCTACGACCCTCTAATAACTCGAC

7861  GTATATTTCTCTCGAATAGTGGTGTGTTCATTGTTGCTATTGTTGGAATTAGAGGTGATA
7861  CATATAAAGAGAGCTTATCACCACACAAGTAACAACGATAACAACCTTAATCTCCACTAT

7921  CTAAAAAAGGAACGGAAAAATACCATGGCAAACACATAAAACGTCTCTACAGGTGCCTAC
7921  GATTTTTTCCTTGCCTTTTTATGGTACCGTTTGTGTATTTTGCAGAGATGTCCACGGATG

7981  CTACCACTGGGTCCCAGAAAGACTTGCTGATTGTGGATTAGATGTGGTCCCCTGCCCTCG
7981  GATGGTGACCCAGGGTCTTTCTGAACGACTAACACCTAATCTACACCAGGGGACGGGAGC

8041  GGAGTTCCCCAGACATCAAAATGAGCTCCCTCAGCAGAAGCTCTCATTAGCTGGGTGCAG
8041  CCTCAAGGGGTCTGTAGTTTTACTCGAGGGAGTCGTCTTCGAGAGTAATCGACCCACGTC

8101  GGAGAATCTAGCAATGCGGTAACTCAGGCCTTCAGGACTTTTGAGTTAGTTACTTAAATG
8101  CCTCTTAGATCGTTACGCCATTGAGTCCGGAAGTCCTGAAAACTCAATCAATGAATTTAC
```

FIG. 3 (cont'd)

```
8161  GAAGTCCTGAGACAGGTCAACACACTGAACCCTTTGGATGTTTTAGGAATATTTGTTCCT
8161  CTTCAGGACTCTGTCCAGTTGTGTGACTTGGGAAACCTACAAAATCCTTATAAACAAGGA

8221  TTGCAATTTGGCCTTTTTTTCCCCAGTCATGTTCAGGTTATCCTTGGCTGCAGGTAGTGA
8221  AACGTTAAACCGGAAAAAAAGGGGTCAGTACAAGTCCAATAGGAACCGACGTCCATCACT

8281  AGAGGTGTACCACTCTTTAATGTTTGTACTGAGTGGCATGTTCACAAAAAAGCTCAGAAT
8281  TCTCCACATGGTGAGAAATTACAAACATGACTCACCGTACAAGTGTTTTTTCGAGTCTTA

8341  TCAGTTGCATTGGCTTTTCAAGAGGGATTTGCAGCAAGGGCTGGTTTCCAATATGGTAGT
8341  AGTCAACGTAACCGAAAAGTTCTCCCTAAACGTCGTTCCCGACCAAAGGTTATACCATCA

8401  GGAGGAATTGGCTAACATAAAACTAGCTCCTGAAATTCAGACTTGCGTTTACTGCTCTGG
8401  CCTCCTTAACCGATTGTATTTTGATCGAGGACTTTAAGTCTGAACGCAAATGACGAGACC

8461  CTCTATGGAATTAGTAACCATGGGAAAGAGGCAATGCTTAGAACTGTGTAAAGTGATGGA
8461  GAGATACCTTAATCATTGGTACCCTTTCTCCGTTACGAATCTTGACACATTTCACTACCT

8521  GTAGGTAGAGACCTGTCTTGAAGCATCGGTAACAGTAAATGAAGCAGCAGCAAGATCAGG
8521  CATCCATCTCTGGACAGAACTTCGTAGCCATTGTCATTTACTTCGTCGTCGTTCTAGTCC

8581  TGTTCTGTGCCACATTCTTTTTCCATTCATGTTTCATACAACATTGTCTTCAGGAACATG
8581  ACAAGACACGGTGTAAGAAAAAGGTAAGTACAAAGTATGTTGTAACAGAAGTCCTTGTAC

8641  GTTCAGTGTTCTCCCAACCCACAAGAGACAAGCAAAATAAAAATGGACTAAATAATTTGC
8641  CAAGTCACAAGAGGGTTGGGTGTTCTCTGTTCGTTTTATTTTTACCTGATTTATTAAACG

8701  TAGTTTTTAATTGGGCTCTTTGGCACAGACTCAAGTAGACCTGAACTCTCAGCTCTGTTG
8701  ATCAAAAATTAACCCGAGAAACCGTGTCTGAGTTCATCTGGACTTGAGAGTCGAGACAAC

8761  TGAACCCGCTTTGTGAACAAGGACAAAGCATGTCATCTGTCTCTGAGCCTCAGTCTCCCT
8761  ACTTGGGCGAAACACTTGTTCCTGTTTCGTACAGTAGACAGAGACTCGGAGTCAGAGGGA

8821  GTTAGTCAGTTACAGAGAGAGCGCTCCAAGTTTCCTTCCAAAGCTGTGCACTGGCTCGTT
8821  CAATCAGTCAATGTCTCTCTCGCGAGGTTCAAAGGAAGGTTTCGACACGTGACCGAGCAA

8881  TCTCCATCAGCTTTGGTTTTCCAGTTGGTCTCCAGCTCATCTTTGCCTCACAAGAGCGTG
8881  AGAGGTAGTCGAAACCAAAAGGTCAACCAGAGGTCGAGTAGAAACGGAGTGTTCTCGCAC

8941  CCCTGCTAGTTGCTGGTGCTGGGAGTGGGTGGGAAGGTGATTGGGCGCCAGCCCCTTCCT
8941  GGGACGATCAACGACCACGACCCTCACCCACCCTTCCACTAACCCGCGGTCGGGGAAGGA

9001  TCCCAGGCTTCACACACACACCCCAGGAAGCCCCGCGGTGCGTCGGACTCTCTGTCTAGA
9001  AGGGTCCGAAGTGTGTGTGTGGGGTCCTTCGGGGCGCCACGCAGCCTGAGAGACAGATCT

9061  CATCATCTGATTTTTATTTGCAAATGCAGGTTGCCAGGTGACAGGAACCTTTTATGCTTG
9061  GTAGTAGACTAAAAATAAACGTTTACGTCCAACGGTCCACTGTCCTTGGAAAATACGAAC

9121  TGCCCCACCTGAGTCCCAGGCTCCCGGAGTCCCCACAGAGCCAAGCATAAGGTCTGCCGA
9121  ACGGGGTGGACTCAGGGTCCGAGGGCCTCAGGGGTGTCTCGGTTCGTATTCCAGACGGCT

9181  AGCCTTGGCGTTCTCAGGTGAGTGCAGGGTTTGCTCCTGGAGGCACCGCAGGAGGCCAGC
9181  TCGGAACCGCAAGAGTCCACTCACGTCCCAAACGAGGACCTCCGTGGCGTCCTCCGGTCG

9241  CTCTGCTGCCAGCTCTGTCATCTTTGGGCAGATTCGATGGGACTTTAGACACTTGCTTTG
9241  GAGACGACGGTCGAGACAGTAGAAACCCGTCTAAGCTACCCTGAAATCTGTGAACGAAAC

9301  CTCCCTCTGGGGTCTGGAGTAGATGTAGACACATCCTGTGTGTGAGGTGACCAGGGTGAT
9301  GAGGGAGACCCCAGACCTCATCTACATCTGTGTAGGACACACACTCCACTGGTCCCACTA

9361  TTAGGAGCACCATTAGAAAACCTGACATCACTGCTTGTGGTTCTGCTGACCGTTTCAGCC
9361  AATCCTCGTGGTAATCTTTTGGACTGTAGTGACGAACACCAAGACGACTGGCAAAGTCGG

9421  ACTGGCTTGAATGGAGTCATTTTGGCTTCTTCACTGGCACCTCTCTGAATTTCTAGGAAT
9421  TGACCGAACTTACCTCAGTAAAACCGAAGAAGTGACCGTGGAGAGACTTAAAGATCCTTA

9481  GTGCCTTTACCTTTACCGAGGGCCCCTCTTCAGCCAACATTCTCACGATGTGGAATAATT
9481  CACGGAAATGGAAATGGCTCCCGGGGAGAAGTCGGTTGTAAGAGTGCTACACCTTATTAA
```

FIG. 3 (cont'd)

```
 9541  GCTTGGAAGTGTAGAAGGGCTTCTCATTTTGAGAAGCTGATCATCCTTCCAGGTTGAGCC
 9541  CGAACCTTCACATCTTCCCGAAGAGTAAAACTCTTCGACTAGTAGGAAGGTCCAACTCGG

 9601  ACAAATAAGTCCTCCTCCTCTACTCCCTGGGGACATTAGTTCTGGTCCCTCATCTCTAAA
 9601  TGTTTATTCAGGAGGAGGAGATGAGGGACCCCTGTAATCAAGACCAGGGAGTAGAGATTT

 9661  ACATTGATGTGCCTAAGAGTAATACACATTTTGGTCTTCCTCTGAACTTTAATATAGCTT
 9661  TGTAACTACACGGATTCTCATTATGTGTAAAACCAGAAGGAGACTTGAAATTATATCGAA

 9721  GCAAACAAATATGGATTCAATCTGATTTTTAAAGTTTTATTTCTAAAAAAAAAAAAAAAA
 9721  CGTTTGTTTATACCTAAGTTAGACTAAAAATTTCAAAATAAAGATTTTTTTTTTTTTTTT

 9781  TCCCTGCACCATGGAGATCTTACCTACTATAAAGAAGGCACCTCTAGGCTTGGCAAGCAC
 9781  AGGGACGTGGTACCTCTAGAATGGATGATATTTCTTCCGTGGAGATCCGAACCGTTCGTG

 9841  ACGTGCTATATGTATATTTATTTTTCAGATAATATTTTGGATTGTTTTTAAATGGGATTT
 9841  TGCACGATATACATATAAATAAAAAGTCTATTATAAAACCTAACAAAAATTTACCCTAAA

 9901  GTTTTTATATTAAAACCAAATAGCTTAAGGTTTGGAATTCTCATCTTGCCCTCTGGCATC
 9901  CAAAAATATAATTTTGGTTTATCGAATTCCAAACCTTAAGAGTAGAACGGGAGACCGTAG

 9961  TTTAAAAATCAGTGATGAAAAATACTAACTAAATTCTGAAGGTTTCAGGGAGGCGAGAGT
 9961  AAATTTTTAGTCACTACTTTTTATGATTGATTTAAGACTTCCAAAGTCCCTCCGCTCTCA

10021  TGTGGCACTTTTGCTGCTCAGAGGGGAGCTGGAGTTTGACCTACCAGCTCTTTCTAGTTG
10021  ACACCGTGAAAACGACGAGTCTCCCCTCGACCTCAAACTGGATGGTCGAGAAAGATCAAC

10081  TGAATGAGGCTTGCACCTTTTTTTCTGAGGTGCTCGTGAGTAACTGAGGATGCCCTTTGG
10081  ACTTACTCCGAACGTGGAAAAAAAGACTCCACGAGCACTCATTGACTCCTACGGGAAACC

10141  GAGGAGGTGCTTCTGAGCAGGAAGGCTTGTGTTTGTTTTTAGAAACTTTCAAACCCTTGT
10141  CTCCTCCACGAAGACTCGTCCTTCCGAACACAAACAAAAATCTTTGAAAGTTTGGGAACA

10201  CTTGAACACCTAAGACTTGTGTGGGTGCCTGAAGAGTAGGAAATAAACAGCTATTTATAT
10201  GAACTTGTGGATTCTGAACACACCCACGGACTTCTCATCCTTTATTTGTCGATAAATATA

10261  CTCGGCAACCTCGTGATTTCTGATGACATTAAATGAAATGAAACCTGCCCCGAGAATCAC
10261  GAGCCGTTGGAGCACTAAAGACTACTGTAATTTACTTTACTTTGGACGGGGCTCTTAGTG

10321  CTCGAATGGCCAACACCCACTCTCTTTGGGGCGCACTGTCTGACTCGCTTTCAGACAGTG
10321  GAGCTTACCGGTTGTGGGTGAGAGAAACCCCGCGTGACAGACTGAGCGAAAGTCTGTCAC

10381  TGTTGAAGCAGAGAATTGAGACAGTGATGTGGGTTAAGTCTCAAAACCTGCTGTTGAGGA
10381  ACAACTTCGTCTCTTAACTCTGTCACTACACCCAATTCAGAGTTTTGGACGACAACTCCT

10441  ATAAGATAGTTTTGTGGGTTTCTTTTTTTGGTATGCATGATACAGATTAATTATCAGCCA
10441  TATTCTATCAAAACACCCAAAGAAAAAAACCATACGTACTATGTCTAATTAATAGTCGGT

10501  TGAGCACATTTATTAGATAACTGTGATTCCCATTGATTTTGGGGTTCCATACAGTTACCA
10501  ACTCGTGTAAATAATCTATTGACACTAAGGGTAACTAAAACCCCAAGGTATGTCAATGGT

10561  GTGGCAGCTGCCTCCTGTCTGTGCCACTCCCCTGCGGTCTGGCTGAGGAGCTTGTGCAAA
10561  CACCGTCGACGGAGGACAGACACGGTGAGGGGACGCCAGACCGACTCCTCGAACACGTTT

10621  CCCAGCTTGGTTCTTTCAACTCATGGGCGATATTTTAAAGAGGCTTCTGAAATCAGCAAA
10621  GGGTCGAACCAAGAAAGTTGAGTACCCGCTATAAAATTTCTCCGAAGACTTTAGTCGTTT

10681  ACGTTTGTAAATGGATTCATCTTGTTTAAAGTTTCAGAGAGCGCAGTTTTAGAGTTCTTT
10681  TGCAAACATTTACCTAAGTAGAACAAATTTCAAAGTCTCTCGCGTCAAAATCTCAAGAAA

10741  TCAAACTTAAACACAAAGCCCAGTGGGAATTTCAGCAGACTTTACATGAACTTTTAGAGT
10741  AGTTTGAATTTGTGTTTCGGGTCACCCTTAAAGTCGTCTGAAATGTACTTGAAAATCTCA

10801  ATTTTTCTCATTAATTTCTTTCTTTTCACAAGAATTAATTTTGTGATAAAAACACCACAT
10801  TAAAAAGAGTAATTAAAGAAAGAAAAGTGTTCTTAATTAAAACACTATTTTTGTGGTGTA

10861  ATCCAGTGTGGAAAACTAATTTAAAAATCAGAAAAACAAAAATGGAAAATAAAAATATCA
10861  TAGGTCACACCTTTTGATTAAATTTTTAGTCTTTTTGTTTTTACCTTTTATTTTTATAGT
```

FIG. 3 (cont'd)

```
10921  CATTCTACCACCCAGAAATCACCATTAAGGCCTCAGTGCTTACCCTTTAATGTGTGTATG
10921  GTAAGATGGTGGGTCTTTAGTGGTAATTCCGGAGTCACGAATGGGAAATTACACACATAC

10981  TGAGTGTGTTTATATATAAATTATATAGACATAAATAATTAAGCACCTAATTCTATATAT
10981  ACTCACACAAATATATATTTAATATATCTGTATTTATTAATTCGTGGATTAAGATATATA

11041  AATTTATATATGTACACACACACACACACACACACACATTTGCTTTTTACCTAAATGATG
11041  TTAAATATATACATGTGTGTGTGTGTGTGTGTGTGTGTAAACGAAAAATGGATTTACTAC

11101  TCATGTTATTATTTTGGGGACGTTTCAGGTATGTGGACCGACTTGCTTCTTTCTGAAACA
11101  AGTACAATAATAAAACCCCTGCAAAGTCCATACACCTGGCTGAACGAAGAAAGACTTTGT

11161  CCGTTATATTTTTTGCTAGTATAAATTAAACTTAGGGTTCATTTCCTCCAAAGTAAAAAT
11161  GGCAATATAAAAAACGATCATATTTAATTTGAATCCCAAGTAAAGGAGGTTTCATTTTTA

11221  TGATTTGCTTAAAGATGAATTTTCATTCAGTGACACATGACTTAAATGACATCACCACTA
11221  ACTAAACGAATTTCTACTTAAAAGTAAGTCACTGTGTACTGAATTTACTGTAGTGGTGAT

11281  TCATCATCATAATTCACAAATAAGACTTAGCAAGTTCTTAATAGTGATGCTCTATAATAG
11281  AGTAGTAGTATTAAGTGTTTATTCTGAATCGTTCAAGAATTATCACTACGAGATATTATC

11341  GAATTCAACTTACATTTCCAGAAAATTAATGAAAGATACACTTGTTCCTTAAAAAAAGAG
11341  CTTAAGTTGAATGTAAAGGTCTTTTAATTACTTTCTATGTGAACAAGGAATTTTTTTCTC

11401  TCGGTGGCCACATACGTTTGTAATATGCTGGTTTAGACAGATTAAATGGGTTTCTTTCCA
11401  AGCCACCGGTGTATGCAAACATTATACGACCAAATCTGTCTAATTTACCCAAAGAAAGGT

11461  CGGGACTTCTCCAAGTGTTGACCGAGCTCATGCTGTCTGTGGATCTCTGGGGGAGACAAG
11461  GCCCTGAAGAGGTTCACAACTGGCTCGAGTACGACAGACACCTAGAGACCCCCTCTGTTC

11521  GGCACGCTGTGTTTCCCAGGCCTCCTTGACGCGGGAACCTTTTGTTCCCCCACGGGACAT
11521  CCGTGCGACACAAAGGGTCCGGAGGAACTGCGCCCTTGGAAAACAAGGGGGTGCCCTGTA

11581  GTGGGACACTAGAGTTCCACCACAGGTGCTTGGCTCTGTGGAGTCGTTGGCCTCGAGGTG
11581  CACCCTGTGATCTCAAGGTGGTGTCCACGAACCGAGACACCTCAGCAACCGGAGCTCCAC

11641  GTGTCCTTGGCCCCCAGCACTGACTCCGGAGCTCTGTGTTTGCAGACTGCCGGCTGCACA
11641  CACAGGAACCGGGGGTCGTGACTGAGGCCTCGAGACACAAACGTCTGACGGCCGACGTGT

11701  TCTGCCTGTACTACCGGGAAATCCTCGTGAAGGAGCTGACCACGTCCAGCCCCGAGGGCT
11701  AGACGGACATGATGGCCCTTTAGGAGCACTTCCTCGACTGGTGCAGGTCGGGGCTCCCGA

11761  GCCGGATCTCCCATGGACATACGTATGACGCCAGCAACCTGGACCAGGTCCTGTTCCCCT
11761  CGGCCTAGAGGGTACCTGTATGCATACTGCGGTCGTTGGACCTGGTCCAGGACAAGGGGA

11821  ACCCAGAGGACAATGGCCAGAGGAAAAACATTGAGAAGCTGCTGAGCCACCTGGAGAGGG
11821  TGGGTCTCCTGTTACCGGTCTCCTTTTTGTAACTCTTCGACGACTCGGTGGACCTCTCCC

11881  GCGTGGTCCTCTGGATGGCCCCCGACGGGCTCTATGCGAAAAGACTGTGCCAGAGCAGGA
11881  CGCACCAGGAGACCTACCGGGGGCTGCCCGAGATACGCTTTTCTGACACGGTCTCGTCCT

11941  TCTACTGGGACGGGCCCCTGGCGCTGTGCAACGACCGGCCCAACAAACTGGAGAGAGACC
11941  AGATGACCCTGCCCGGGGACCGCGACACGTTGCTGGCCGGGTTGTTTGACCTCTCTCTGG

12001  AGACCTGCAAGCTCTTTGACACACAGCAGTTCTTGTCAGGTAAGGCACCTCGTTATCTGT
12001  TCTGGACGTTCGAGAAACTGTGTGTCGTCAAGAACAGTCCATTCCGTGGAGCAATAGACA

12061  TAGAATGGAGGTGGTGATGGCCTGCCTGCCACAGGGGTCAGAAACCACAGGGTCCCTCCC
12061  ATCTTACCTCCACCACTACCGGACGGACGGTGTCCCCAGTCTTTGGTGTCCCAGGGAGGG

12121  ACCCCAGGCTGAGGTCTTCCTCCTGTTGACTTCGGCGCCCACTGGGCTTGGGGCTTGACT
12121  TGGGGTCCGACTCCAGAAGGAGGACAACTGAAGCCGCGGGTGACCCGAACCCCGAACTGA

12181  CCAGTAGAGATCTTCTGTCTGGCTCTGTTGTGGGCAGAGAGTCCGGATCAGATGGTCCAG
12181  GGTCATCTCTAGAAGACAGACCGAGACAACACCCGTCTCTCAGGCCTAGTCTACCAGGTC

12241  GTGGACCATGGCTCAGGCTGTTCTCTTGCAATTCTGGTTTTCAGCAGTCGCCTCTTAAAA
12241  CACCTGGTACCGAGTCCGACAAGAGAACGTTAAGACCAAAAGTCGTCAGCGGAGAATTTT
```

FIG. 3 (cont'd)

```
12301  CAGTTCCATTTCATTGCACTATGATCTCGACAAATACGTCTGCTGATGTGGCGGCTCTTT
12301  GTCAAGGTAAAGTAACGTGATACTAGAGCTGTTTATGCAGACGACTACACCGCCGAGAAA

12361  TCAGGTTCCCAGAAAAATCATAAAGGTTGGAAGCATATTGTTAACATTCTTGGTTGTCAG
12361  AGTCCAAGGGTCTTTTTAGTATTTCCAACCTTCGTATAACAATTGTAAGAACCAACAGTC

12421  GTGTGTCACCCTCATGCAGATGCTGGCCCACGAGTGAGACGGAGGGTGGAGTGGACTGTA
12421  CACACAGTGGGAGTACGTCTACGACCGGGTGCTCACTCTGCCTCCCACCTCACCTGACAT

12481  CTGGTTTTGCACAGGAGAAGTTATAGGAGAGTGCTATAAGTTGGCTCTGTGATATGAACA
12481  GACCAAAACGTGTCCTCTTCAATATCCTCTCACGATATTCAACCGAGACACTATACTTGT

12541  TTTCTAAGCATATTTTTCAGAACCAGTGAGTTTTGTTTTTCTACCTTGGATTTCATGACA
12541  AAAGATTCGTATAAAAAGTCTTGGTCACTCAAAACAAAAAGATGGAACCTAAAGTACTGT

12601  ATTCAGCGAACCTCTGGCTGGCTTCTGTGAAGCCCCTCGCCCTGTCATGCTGGGCTTCCT
12601  TAAGTCGCTTGGAGACCGACCGAAGACACTTCGGGGAGCGGGACAGTACGACCCGAAGGA

12661  CACTGGCTTTGTGGGGCTGTCCAGGTGGAGGGAGCCTCCCGCGTGGGAGGGAGCTGCTCT
12661  GTGACCGAAACACCCCGACAGGTCCACCTCCCTCGGAGGGCGCACCCTCCCTCGACGAGA

12721  ACCCGCCACTCGCCACCCCACCGCCAACTCTTCCTCTGCCTTTTCCCAGTCCTGTCCCTT
12721  TGGGCGGTGAGCGGTGGGGTGGCGGTTGAGAAGGAGACGGAAAAGGGTCAGGACAGGGAA

12781  CCTGAGCCCCTTCAGAAACTCCTGTGTCTTTGATTTCTCATGTGCCTCCCCTTTTCTTGA
12781  GGACTCGGGGAAGTCTTTGAGGACACAGAAACTAAAGAGTACACGGAGGGGAAAAGAACT

12841  ATGTGCTTCTTCATTCAACTTATTTAAAATAAAAATATGACACGTCTGTGTGCTCTGGCA
12841  TACACGAAGAAGTAAGTTGAATAAATTTTATTTTTATACTGTGCAGACACACGAGACCGT

12901  CTGTTGACATGTGCTCGTACTTCTGGGTGTAAGTGACCCAAGTTTTTGTAAGCTCATCCA
12901  GACAACTGTACACGAGCATGAAGACCCACATTCACTGGGTTCAAAAACATTCGAGTAGGT

12961  GATTTTCTTTTGGTGCCCAAAGCAAATATGTCCCCAGATAACTAAGCTTCAGGCCAGGTG
12961  CTAAAAGAAAACCACGGGTTTCGTTTATACAGGGGTCTATTGATTCGAAGTCCGGTCCAC

13021  TGGTGGCCCATGCCTGTAATCCCAGCACTTTAGGAGGCTGAGGTGGGCAGATCACTTGAG
13021  ACCACCGGGTACGGACATTAGGGTCGTGAAATCCTCCGACTCCACCCGTCTAGTGAACTC

13081  GCCAGGAGTTCAAGACCAGCCTGGCCAACATGGCAAAACCCCGTCTCTACTAAAGATACA
13081  CGGTCCTCAAGTTCTGGTCGGACCGGTTGTACCGTTTTGGGGCAGAGATGATTTCTATGT

13141  AAAATTAGCTGGGCGTGATGGTGGGCGCCTGTAATCCCAGCTACTCAGGAGGATGAGGCA
13141  TTTTAATCGACCCGCACTACCACCCGCGGACATTAGGGTCGATGAGTCCTCCTACTCCGT

13201  CAAGAATCGCTTGAACCTGTGGGAGGCGGAGGTTGCAGTGAGCTGAGATCGCACCACGGT
13201  GTTCTTAGCGAACTTGGACACCCTCCGCCTCCAACGTCACTCGACTCTAGCGTGGTGCCA

13261  GCTGCAGTTTGCAGGACAGAGCGAGACTCCATTGCCCCCCGCACCACAAAAAAATAACTA
13261  CGACGTCAAACGTCCTGTCTCGCTCTGAGGTAACGGGGGGCGTGGTGTTTTTTTATTGAT

13321  AGCTCACACAGAGGCTGACCATAGGAAGAGGGAGAACTGTGCTGGTTCCCCGAGGCGGCG
13321  TCGAGTGTGTCTCCGACTGGTATCCTTCTCCCTCTTGACACGACCAAGGGGCTCCGCCGC

13381  GCAAGTGAGGAAGTCACCTGGGGCTGGACACCTCTCATTCTAAGGGCAGAACCATCCCCA
13381  CGTTCACTCCTTCAGTGGACCCCGACCTGTGGAGAGTAAGATTCCCGTCTTGGTAGGGGT

13441  AGCCCTGGCCAGGGCGGTCCCATCCTTCTTGGGGTTGGGCATGGTGTTCATGGGGGACCA
13441  TCGGGACCGGTCCCGCCAGGGTAGGAAGAACCCCAACCCGTACCACAAGTACCCCCTGGT

13501  AGGAAATTGAAGGGCAACTGGGGGGACCCCCCCTCCCCTGTCAGCATCTCCTGTGTCTGC
13501  TCCTTTAACTTCCCGTTGACCCCCCTGGGGGGGAGGGGACAGTCGTAGAGGACACAGACG

13561  CTTGGGATCTGGAAGAGCTCACATGGGCCAGGAAGGCTAAGGCCCACTGGGCCTGGATTT
13561  GAACCCTAGACCTTCTCGAGTGTACCCGGTCCTTCCGATTCCGGGTGACCCGGACCTAAA

13621  CTGAAGACTCTGGACCTTGGTGCCAGTGGATTCAGAAGATACCACAAGGTGAGGGCTTTC
13621  GACTTCTGAGACCTGGAACCACGGTCACCTAAGTCTTCTATGGTGTTCCACTCCCGAAAG
```

FIG. 3 (cont'd)

```
13681  TAATGAAAGTGTCACAAGGAACTGGCACTGGCTTTTCTGAGTGCCTCTTGCTGGGCGTTT
13681  ATTACTTTCACAGTGTTCCTTGACCGTGACCGAAAAGACTCACGGAGAACGACCCGCAAA

13741  TTAGGGAGGTAGAGCCCCCGTGGTGACTAAGCTGGAAGGTGCACATTGAGTCACAGGTGC
13741  AATCCCTCCATCTCGGGGGCACCACTGATTCGACCTTCCACGTGTAACTCAGTGTCCACG

13801  ACTGCGTGAGAGACAGCACAGGCAGGGGGTGGACGCCTGTGAGTGTCCTGGGGCTGTAGA
13801  TGACGCACTCTCTGTCGTGTCCGTCCCCCACCTGCGGACACTCACAGGACCCCGACATCT

13861  CTTGCGCGACTAGAACTTACTATTAATCTGTGAGCAAGAGCTGGTCTTGGCTTTCATTCC
13861  GAACGCGCTGATCTTGAATGATAATTAGACACTCGTTCTCGACCAGAACCGAAAGTAAGG

13921  TTCCTCTGTAACCAAGGGCTGTGCTCTTTGCCCACTGCAGCCTCTCACCTCAAAGTGTTC
13921  AAGGAGACATTGGTTCCCGACACGAGAAACGGGTGACGTCGGAGAGTGGAGTTTCACAAG

13981  ACTGAGGTTCAAGGAGGATGCTGTGAACGTAAAAACTGCAGCTGTGCCAACCAGCTTCTG
13981  TGACTCCAAGTTCCTCCTACGACACTTGCATTTTTGACGTCGACACGGTTGGTCGAAGAC

14041  CATAATTAAGGATTCCCACCAAACACTCTCATGTTATCTAGGGTTGGAGCCATGCTTTCT
14041  GTATTAATTCCTAAGGGTGGTTTGTGAGAGTACAATAGATCCCAACCTCGGTACGAAAGA

14101  CAGAGAATTGTGCCAACTCGCCATTCTGATTAGCCTGTGTAGGTGTAGTCTCAGATCACG
14101  GTCTCTTAACACGGTTGAGCGGTAAGACTAATCGGACACATCCACATCAGAGTCTAGTGC

14161  GCAGTGTGAATGTATTTTACAGATTCTGACTAAGTCATTTGGGTTTGATTTGAATTCTGG
14161  CGTCACACTTACATAAAATGTCTAAGACTGATTCAGTAAACCCAAACTAAACTTAAGACC

14221  AAAAAAAAAAAAGCAGGAAGTCAAATAGTCCTGTAAGTTAGCTAGAAACTTCTGTTCAGT
14221  TTTTTTTTTTTTCGTCCTTCAGTTTATCAGGACATTCAATCGATCTTTGAAGACAAGTCA

14281  TGAAGAGAACAGTGGAGATCTTTGATATCTTCCTATTCAGGTCTGCACAGCACTAGGGAC
14281  ACTTCTCTTGTCACCTCTAGAAACTATAGAAGGATAAGTCCAGACGTGTCGTGATCCCTG

14341  AGCCCCCAGGGCCCGGCCCGAGGGTGTGTATCTGATAAGGACGCGTCTGTTCTGCAGAAG
14341  TCGGGGGTCCCGGGCCGGGCTCCCACACATAGACTATTCCTGCGCAGACAAGACGTCTTC

14401  CTGTAGCGGCTCCTGTGTCAACTCGTTTCTTTTGCGGGCGTGACATTTTATTGTAGCTAC
14401  GACATCGCCGAGGACACAGTTGAGCAAAGAAAACGCCCGCACTGTAAAATAACATCGATG

14461  AGGCAGAAGATTTGTCTTGTGTACAGGGGAGGGAGCATGGGCTAAAGTCAGGGGATGGGC
14461  TCCGTCTTCTAAACAGAACACATGTCCCCTCCCTCGTACCCGATTTCAGTCCCCTACCCG

14521  ACTTGTCTTTCCAACAATGTTCCAGTCCGTTTTGTATCTTTTGGGTAGGTGTGGTGGCTT
14521  TGAACAGAAAGGTTGTTACAAGGTCAGGCAAAACATAGAAAACCCATCCACACCACCGAA

14581  CAGGATGTACATGTGTATATCCACAAGCGGGAGGCCAGGGGGGCTGCCCCACTCCTGTTC
14581  GTCCTACATGTACACATATAGGTGTTCGCCCTCCGGTCCCCCCGACGGGGTGAGGACAAG

14641  TCAAGTCAAGTTACTGTTCCATCCCTGGAGACAGGCAAGAAGTCTACTCAGAGTTACACA
14641  AGTTCAGTTCAATGACAAGGTAGGGACCTCTGTCCGTTCTTCAGATGAGTCTCAATGTGT

14701  GTTCAGGCATAGTGACAGTGGGACTCAGCTGCCGATGGCTGGTGCTCAGTCACCACGTTG
14701  CAAGTCCGTATCACTGTCACCCTGAGTCGACGGCTACCGACCACGAGTCAGTGGTGCAAC

14761  ACGTTACATATTTTCTGTGGTGCCTGAGTTACGTGGATGTCCGCAGTAGCACAGATACTG
14761  TGCAATGTATAAAAGACACCACGGACTCAATGCACCTACAGGCGTCATCGTGTCTATGAC

14821  GATTATGTGGGCTCTGTAGTGAGGGGATGAGGTTTTAAAATGATCCTGGGATGTCGAAAC
14821  CTAATACACCCGAGACATCACTCCCCTACTCCAAAATTTTACTAGGACCCTACAGCTTTG

14881  ATTCTGATTTTTTAAATGAAAACTTGTCCATGGCATAAATTGGTCTTTTGCCATTGCGTG
14881  TAAGACTAAAAAATTTACTTTTGAACAGGTACCGTATTTAACCAGAAAACGGTAACGCAC

14941  ACTACGTTTCTTGTTCTTTATCTCCCGACTTCACTGTGGTCTACTACCTTTTGAATCTTC
14941  TGATGCAAAGAACAAGAAATAGAGGGCTGAAGTGACACCAGATGATGGAAAACTTAGAAG

15001  GTGGGTCCAATGCTGCAAAGCAGTGTTCTTTAGCTGTCGACTAGTTCCTCTTGAAGAATC
15001  CACCCAGGTTACGACGTTTCGTCACAAGAAATCGACAGCTGATCAAGGAGAACTTCTTAG
```

FIG. 3 (cont'd)

15061 GAGGGAGACCGAGGGCCCTGGGGGGAAAGCACCCAAAGGAATGCATACATGCTATTTTGT
15061 CTCCCTCTGGCTCCCGGGACCCCCCTTTCGTGGGTTTCCTTACGTATGTACGATAAAACA

15121 ATCTGAGATGTTCACATCAAGAGCCCCACTCAGCGGAGTAAGAGTGCTCATTCCTCTTGC
15121 TAGACTCTACAAGTGTAGTTCTCGGGGTGAGTCGCCTCATTCTCACGAGTAAGGAGAACG

15181 AGTGTTCAGAATCACAGTAAGCTCTTGCTTCCTGTTTAACCTGGTGTGTTCGGTGATGAG
15181 TCACAAGTCTTAGTGTCATTCGAGAACGAAGGACAAATTGGACCACACAAGCCACTACTC

15241 GGTTTCTGAACATGGTCTCTTTCTTGTGGGCTTCTACAGAGCTGCAAGCGTTTGCTCACC
15241 CCAAAGACTTGTACCAGAGAAAGAACACCCGAAGATGTCTCGACGTTCGCAAACGAGTGG

15301 ACGGCCGCTCCCTGCCAAGATTCCAGGTGACTCTATGCTTTGGAGAGGAGTTTCCAGACC
15301 TGCCGGCGAGGGACGGTTCTAAGGTCCACTGAGATACGAAACCTCTCCTCAAAGGTCTGG

15361 CTCAGAGGCAAAGAAAGCTCATCACAGCTCACGTGAGTCCTCAGTTACACTCCTACCATA
15361 GAGTCTCCGTTTCTTTCGAGTAGTGTCGAGTGCACTCAGGAGTCAATGTGAGGATGGTAT

15421 GTGGCTTCCTGTTCTTTGTAAAGGCCAGAGTTTCATTTAGAAAAGTCCCAAATGAAAAGT
15421 CACCGAAGGACAAGAAACATTTCCGGTCTCAAAGTAAATCTTTTCAGGGTTTACTTTTCA

15481 AAATGTCAAATGACCTGGAAAAATAAGCGTAACCCTTAAACTAGTGAGGGAGGAAGCATG
15481 TTTACAGTTTACTGGACCTTTTTATTCGCATTGGGAATTTGATCACTCCCTCCTTCGTAC

15541 GTCCAACGAGCAGCACAGTCTGAGGACTCACGTGCTCCTCCCAGACTTGAGATCTGCTCA
15541 CAGGTTGCTCGTCGTGTCAGACTCCTGAGTGCACGAGGAGGGTCTGAACTCTAGACGAGT

15601 TCAAAGAACCAGGGAGGACAGCCTCAAAGGAGGGTGCCTCTTTCCCCATCTTTTTTATTT
15601 AGTTTCTTGGTCCCTCCTGTCGGAGTTTCCTCCCACGGAGAAAGGGGTAGAAAAAATAAA

15661 TTCAGGAAAGTTGTCGTATTTCCATTTTATAGGGATTGAAAAAGATTGATGGTTAAAGTT
15661 AAGTCCTTTCAACAGCATAAAGGTAAAATATCCCTAACTTTTTCTAACTACCAATTTCAA

15721 GCCCTTTAAAATTCTCCAGGTTAAGATTGCTGTAAGAATGCTATCTAGCTAGTGGATCTT
15721 CGGGAAATTTTAAGAGGTCCAATTCTAACGACATTCTTACGATAGATCGATCACCTAGAA

15781 CATTCAATGGAAAAGCTTTTCCCAAATGAGAAACTATCCATTCCCTGGAGGCATTTTGTA
15781 GTAAGTTACCTTTTCGAAAAGGGTTTACTCTTTGATAGGTAAGGGACCTCCGTAAAACAT

15841 GGTCTCTGCAGCTGTGTCCTAGCACCTCTTTTATTTCTGGAATTTTAGAAATTATTTAAT
15841 CCAGAGACGTCGACACAGGATCGTGGAGAAAATAAAGACCTTAAAATCTTTAATAAATTA

15901 TATTGGGCATATGATATTTGAAAGAGGCTGAATCTTTCAAGGAATTCAAGCAAATCAGAC
15901 ATAACCCGTATACTATAAACTTTCTCCGACTTAGAAAGTTCCTTAAGTTCGTTTAGTCTG

15961 CCTCTCGTAATGTTCTCTAGCATAGCTCAAGATGGGTTCAACTGTGGCAAGTAACACTAA
15961 GGAGAGCATTACAAGAGATCGTATCGAGTTCTACCCAAGTTGACACCGTTCATTGTGATT

16021 AAGGGTAGGGTTAGGATTAGGGTTAGAGTTTTCTTTTTTATGAGAAAAGGTTTCCATAGA
16021 TTCCCATCCCAATCCTAATCCCAATCTCAAAAGAAAAAATACTCTTTTCCAAAGGTATCT

16081 TAACATGAAGCATTAATTTGCCATGGGAAACAGAATCTTGAACCCTTAAGACTTTTGAAT
16081 ATTGTACTTCGTAATTAAACGGTACCCTTTGTCTTAGAACTTGGGAATTCTGAAAACTTA

16141 TTGAAAACTTCACATTGCTACATACTTGCAAGCATTATTAACGGGCTTGCATGCTGAGCA
16141 AACTTTTGAAGTGTAACGATGTATGAACGTTCGTAATAATTGCCCGAACGTACGACTCGT

16201 ATACCAGGTAAAAGTTACACCCCCTAACATCAAAGTTCTCATCATGTTCTAGCTCTGATG
16201 TATGGTCCATTTTCAATGTGGGGGATTGTAGTTTCAAGAGTAGTACAAGATCGAGACTAC

16261 CTATTTCTCATTGAGAACTGAAATGAAACATGGTTTAATCTTGAACATACAACCCCCCTT
16261 GATAAAGAGTAACTCTTGACTTTACTTTGTACCAAATTAGAACTTGTATGTTGGGGGGAA

16321 CTTGATTTTAAAAACAAAGACCAGCCAACCAACCAGTATATAATCCCATAGACTCAGGAG
16321 GAACTAAAATTTTTGTTTCTGGTCGGTTGGTTGGTCATATATTAGGGTATCTGAGTCCTC

16381 TTTTCTCATGAGTTCTCTCCAGTGATTGACTTAATAATTGATATGATTGTTGAAATAATA
16381 AAAAGAGTACTCAAGAGAGGTCACTAACTGAATTATTAACTATACTAACAACTTTATTAT

FIG. 3 (cont'd)

```
16441  ACTGATACATTGTTAACAACAGGAATTGCTAAATGACTAAATAAACTTGGCATTGATAAG
16441  TGACTATGTAACAATTGTTGTCCTTAACGATTTACTGATTTATTTGAACCGTAACTATTC

16501  CAGCATTTAAGAAGTTGATGATCGGCCGGGCACAGTGGCTCACGCCTGTAATCCCGGCAC
16501  GTCGTAAATTCTTCAACTACTAGCCGGCCCGTGTCACCGAGTGCGGACATTAGGGCCGTG

16561  TTTGGGAGGCTGAGGCGGGCAGATCATGTGGTCAGGAGTTCGAGACCAGCCTGACCAACA
16561  AAACCCTCCGACTCCGCCCGTCTAGTACACCAGTCCTCAAGCTCTGGTCGGACTGGTTGT

16621  TGGTGAAACCCCCTCTCTACTAAAAATACAAAAATTAGCCGGGCGTGGTGGTGCGCACCT
16621  ACCACTTTGGGGGAGAGATGATTTTTATGTTTTTAATCGGCCCGCACCACCACGCGTGGA

16681  GTAATCCCAGCTACTCGGGAGGCTGAAGCAAGGGAGTCACTTGAACCCAGGAGTCAGAGC
16681  CATTAGGGTCGATGAGCCCTCCGACTTCGTTCCCTCAGTGAACTTGGGTCCTCAGTCTCG

16741  TTGCAGTGAGCCGAGATTGCACCACTGCACTCCAGCCTGGGTGACAGAGTGAGACTCTGT
16741  AACGTCACTCGGCTCTAACGTGGTGACGTGAGGTCGGACCCACTGTCTCACTCTGAGACA

16801  CTCAAAAAAAAAACAAAAAAAGAAGTTGATGATCAGCTCAGCTATCACATCAATCCAGTT
16801  GAGTTTTTTTTTTGTTTTTTTCTTCAACTACTAGTCGAGTCGATAGTGTAGTTAGGTCAA

16861  TTAAAGTTGACATGGATGCAAGTCACTGTCCTCTAAGTCAGGGAAAGATGGATCCCCAGA
16861  AATTTCAACTGTACCTACGTTCAGTGACAGGAGATTCAGTCCCTTTCTACCTAGGGGTCT

16921  TGACCCCCTCATGCTGAAGACGAGGCTGCGTGGTCCATAAAATGAATAAACACACGTGTA
16921  ACTGGGGGAGTACGACTTCTGCTCCGACGCACCAGGTATTTTACTTATTTGTGTGCACAT

16981  CACCTATGAGTTCCACTTTTAAAAATTATTAATTTAATTCATTTCAGGTACTTAGGAGTT
16981  GTGGATACTCAAGGTGAAAATTTTTAATAATTAAATTAAGTAAAGTCCATGAATCCTCAA

17041  TAGCTTAAGTCGTCATATATAAAATACAGTCTCTAATATCATGATTGATGGAGAGCATTC
17041  ATCGAATTCAGCAGTATATATTTTATGTCAGAGATTATAGTACTAACTACCTCTCGTAAG

17101  AGCTTGCCTTAGATGCTGTAAATTCAGGAAAAGCTGAACATTAAGGCGTTTTTGTTTTTT
17101  TCGAACGGAATCTACGACATTTAAGTCCTTTTCGACTTGTAATTCCGCAAAAACAAAAAA

17161  GGTGAGTGTGATCCACGCTAATAACCAGACAGTATAAATTTGAGGCCAGTTAGCTTCTCT
17161  CCACTCACACTAGGTGCGATTATTGGTCTGTCATATTTAAACTCCGGTCAATCGAAGAGA

17221  TTTTCCACAATAGTAGTTTTGTTGTTGTTTAACTTTACTTTTTATTTCTTTTACCTCTGG
17221  AAAAGGTGTTATCATCAAAACAACAACAAATTGAAATGAAAAATAAAGAAAATGGAGACC

17281  TTGAGAACTATACAGATTACCTAGAAATCAAATCATTCAGGATGAGCTCCTTGTTTCTTT
17281  AACTCTTGATATGTCTAATGGATCTTTAGTTTAGTAAGTCCTACTCGAGGAACAAAGAAA

17341  CAAACTGCAGTTGTGGAAAAACAAAATCATTGGCCTAAATTACCCTGCAGATTCCCTCAG
17341  GTTTGACGTCAACACCTTTTTGTTTTAGTAACCGGATTTAATGGGACGTCTAAGGGAGTC

17401  ACTTCCTTTTAATTTGATCACTTTACTTGATTTGATGCAGTTTTAGTTAAATGTACATTT
17401  TGAAGGAAAATTAAACTAGTGAAATGAACTAAACTACGTCAAAATCAATTTACATGTAAA

17461  TAAGTGGCAGTCGATTTGAAAGTAACATCTTTAACCCAGAATTAAGTCACTTTGGCTGTT
17461  ATTCACCGTCAGCTAAACTTTCATTGTAGAAATTGGGTCTTAATTCAGTGAAACCGACAA

17521  TTTTTACATGTTGATCTATGGAAGGACTAACCAAAAAATTGCTTCTTTAGATGGCTCCAA
17521  AAAAATGTACAACTAGATACCTTCCTGATTGGTTTTTTAACGAAGAAATCTACCGAGGTT

17581  ATATGAAATGTTTTGATGTGTTCTAGGATGTAACTTTGGGCTTTACGTTACTGTCTCCTT
17581  TATACTTTACAAAACTACACAAGATCCTACATTGAAACCCGAAATGCAATGACAGAGGAA

17641  AGAATCTGAGTGCTGTTTAATAGTGAGCCAGTTGCAGGATATCTCAGTAATGTCTTTTTA
17641  TCTTAGACTCACGACAAATTATCACTCGGTCAACGTCCTATAGAGTCATTACAGAAAAAT

17701  AAATCTCTTATTAAAGGTAGAACCTCTGCTAGCCAGACAACTATATTATTTTGCTCAACA
17701  TTTAGAGAATAATTTCCATCTTGGAGACGATCGGTCTGTTGATATAATAAAACGAGTTGT

17761  AAACAGTGGACATTTCCTGAGGGGCTACGATTTACCAGAACACATCAGCAATCCAGAAGA
17761  TTTGTCACCTGTAAAGGACTCCCCGATGCTAAATGGTCTTGTGTAGTCGTTAGGTCTTCT
```

FIG. 3 (cont'd)

```
17821  TTACCACAGATCTATCCGCCATTCCTCTATTCAAGAATGAAAAATGTCAAGATGAGTGGT
17821  AATGGTGTCTAGATAGGCGGTAAGGAGATAAGTTCTTACTTTTTACAGTTCTACTCACCA

17881  TTTCTTTTTCCTTTTTTTTTTTTTTTTTTTGATACGGGGATACGGGGTCTTGCTCTGTCT
17881  AAAGAAAAAGGAAAAAAAAAAAAAAAAAAACTATGCCCCTATGCCCCAGAACGAGACAGA

17941  CCCAGGCTGGAGTGCAGTGACACAATCTCAGCTCACTGTGACCTCCGCCTCCTGGGTTCA
17941  GGGTCCGACCTCACGTCACTGTGTTAGAGTCGAGTGACACTGGAGGCGGAGGACCCAAGT

18001  AGAGACTCTCCTGCCTCAGCCTCCCTGGTAGCTGGGATTACAGGTGTGAGCCACTGCACC
18001  TCTCTGAGAGGACGGAGTCGGAGGGACCATCGACCCTAATGTCCACACTCGGTGACGTGG

18061  CACCCAAGACAAGTGATTTTCATTGTAAATATTTGACTTTAGTGAAAGCGTCCAATTGAC
18061  GTGGGTTCTGTTCACTAAAAGTAACATTTATAAACTGAAATCACTTTCGCAGGTTAACTG

18121  TGCCCTCTTACTGTTTTGAGGAATTCAGAAGTGGAGATTTCAGTTCAGCGGTTGAGGAGA
18121  ACGGGAGAATGACAAAACTCCTTAAGTCTTCACCTCTAAAGTCAAGTCGCCAACTCCTCT

18181  ATTGCGGCGAGACAAGCATGGAAAATCAGTGACATCTGATTGGCAGATGAGCTTATTTCA
18181  TAACGCCGCTCTGTTCGTACCTTTTAGTCACTGTAGACTAACCGTCTACTCGAATAAAGT

18241  AAAGGAAGGGTGGCTTTGCATTTCTTGTGTTCTGTAGACTGCCATCATTGATGATCACTG
18241  TTTCCTTCCCACCGAAACGTAAAGAACACAAGACATCTGACGGTAGTAACTACTAGTGAC

18301  TGAAAATTGACCAAGTGATGTGTTTACATTTACTGAAATGCGCTCTTTAATTTGTTGTAG
18301  ACTTTTAACTGGTTCACTACACAAATGTAAATGACTTTACGCGAGAAATTAAACAACATC

18361  ATTAGGTCTTGCTGGAAGACAGAGAAAACTTGCCTTTCAGTATTGACACTGACTAGAGTG
18361  TAATCCAGAACGACCTTCTGTCTCTTTTGAACGGAAAGTCATAACTGTGACTGATCTCAC

18421  ATGACTGCTTGTAGGTATGTCTGTGCCATTTCTCAGGGAAGTAAGATGTAAATTGAAGAA
18421  TACTGACGAACATCCATACAGACACGGTAAAGAGTCCCTTCATTCTACATTTAACTTCTT

18481  GCCTCACACGTAAAAGAAATGTATTAATGTATGTAGGAGCTGCAGTTCTTGTGGAAGACA
18481  CGGAGTGTGCATTTTCTTTACATAATTACATACATCCTCGACGTCAAGAACACCTTCTGT

18541  CTTGCTGAGTGAAGGAAATGAATCTTTGACTGAAGCCGTGCCTGTAGCCTTGGGGAGGCC
18541  GAACGACTCACTTCCTTTACTTAGAAACTGACTTCGGCACGGACATCGGAACCCCTCCGG

18601  CATCCCCCACCTGCCAGCGGTTTCCTGGTGTGGGTCCCTCTGCCCCGCCCTCCTTCCCAT
18601  GTAGGGGGTGGACGGTCGCCAAAGGACCACACCCAGGGAGACGGGGCGGGAGGAAGGGTA

18661  TGGCTTTCTCTCCTTGGCCTTTCCTGGAAGCCAGTTAGTAAACTTCCTATTTTCTTGAGT
18661  ACCGAAAGAGAGGAACCGGAAAGGACCTTCGGTCAATCATTTGAAGGATAAAAGAACTCA

18721  CAAAAAACATGAGCGCTACTCTTGGATGGGACATTTTTGTCTGTCCTACAATCTAGTAAT
18721  GTTTTTTGTACTCGCGATGAGAACCTACCCTGTAAAAACAGACAGGATGTTAGATCATTA

18781  GTCTAAGTAATGGTTAAGTTTTCTTGTTTCTGCATCTTTTTGACCCTCATTCTTTAGAGA
18781  CAGATTCATTACCAATTCAAAAGAACAAAGACGTAGAAAAACTGGGAGTAAGAAATCTCT

18841  TGCTAAAATTCTTCGCATAAAGAAGAAGAAATTAAGGAACATAAATCTTAATACTTGAAC
18841  ACGATTTTAAGAAGCGTATTTCTTCTTCTTTAATTCCTTGTATTTAGAATTATGAACTTG

18901  TGTTGCCCTTCTGTCCAAGTACTTAACTATCTGTTCCCTTCCTCTGTGCCACGCTCCTCT
18901  ACAACGGGAAGACAGGTTCATGAATTGATAGACAAGGGAAGGAGACACGGTGCGAGGAGA

18961  GTTTGTTTGGCTGTCCAGCGATCAGCCATGGCGACACTAAAGGAGGAGGAGCCGGGGACT
18961  CAAACAAACCGACAGGTCGCTAGTCGGTACCGCTGTGATTTCCTCCTCCTCGGCCCCTGA

19021  CCCAGGCTGGAGAGCACTGCCAGGACCCACCACTGGAAGCAGGATGGAGCTGACTACGGA
19021  GGGTCCGACCTCTCGTGACGGTCCTGGGTGGTGACCTTCGTCCTACCTCGACTGATGCCT

19081  ACTGCACACTCAGTGGGCTGTTTCTGCTTATTTCATCTGTTCTATGCTTCCTCGTGCCAA
19081  TGACGTGTGAGTCACCCGACAAAGACGAATAAAGTAGACAAGATACGAAGGAGCACGGTT

19141  TTATAGTTTGACAGGGCCTTAAAATTACTTGGCTTTTTCCAAATGCTTCTATTTATAGAA
19141  AATATCAAACTGTCCCGGAATTTTAATGAACCGAAAAAGGTTTACGAAGATAAATATCTT
```

FIG. 3 (cont'd)

```
19201  TCCCAAAGACCTCCACTTGCTTAAGTATACCTATCACTTACATTTTTGTGGTTTTGAGAA
19201  AGGGTTTCTGGAGGTGAACGAATTCATATGGATAGTGAATGTAAAAACACCAAAACTCTT

19261  AGTACAGCAGTAGACTGGGGCGTCACCTCCAGGCCGTTTCTCATACTACAGGATATTTAC
19261  TCATGTCGTCATCTGACCCCGCAGTGGAGGTCCGGCAAAGAGTATGATGTCCTATAAATG

19321  TATTACTCCCAGGATCAGCAGAAGATTGCGTAGCTCTCAAATGTGTGTTCCTGCTTTTCT
19321  ATAATGAGGGTCCTAGTCGTCTTCTAACGCATCGAGAGTTTACACACAAGGACGAAAAGA

19381  AATGGATATTTTAAATTCATTCAACAAGCACCTAGTAAGTGCCTGCTGTATCCCTACATT
19381  TTACCTATAAAATTTAAGTAAGTTGTTCGTGGATCATTCACGGACGACATAGGGATGTAA

19441  ACACAGTTCAGCCTTTATCAAGCTTAGTGAGCAGTGAGCACTGAAACATTATTTTTTAAT
19441  TGTGTCAAGTCGGAAATAGTTCGAATCACTCGTCACTCGTGACTTTGTAATAAAAAATTA

19501  GTTTAAAAAGTTTCTAATATTAAAGTCAGAATATTAATACAATTAATATTAATATTAACT
19501  CAAATTTTTCAAAGATTATAATTTCAGTCTTATAATTATGTTAATTATAATTATAATTGA

19561  ACAGAAAAGACAAACAGTAGAGAACAGCAAAAAAATAAAAAGGATCTCCTTTTTTCCCAG
19561  TGTCTTTTCTGTTTGTCATCTCTTGTCGTTTTTTTATTTTTCCTAGAGGAAAAAAGGGTC

19621  CCCAAATTCTCCTCTCTAAAAGTGTCCACAAGAAGGGGTGTTTATTCTTCCAACACATTT
19621  GGGTTTAAGAGGAGAGATTTTCACAGGTGTTCTTCCCCACAAATAAGAAGGTTGTGTAAA

19681  CACTTTTCTGTAAATATACATAAACTTAAAAAGAAAACCTCATGGAGTCATCTTGCACAC
19681  GTGAAAAGACATTTATATGTATTTGAATTTTTCTTTTGGAGTACCTCAGTAGAACGTGTG

19741  ACTTTCATGCAGTGCTCTTTGTAGCTAACAGTGAAGATTTACCTCGTTCTGCTCAGAGGC
19741  TGAAAGTACGTCACGAGAAACATCGATTGTCACTTCTAAATGGAGCAAGACGAGTCTCCG

19801  CTTGCTGTGGAGCTCCACTGCCATGTACCCAGTAGGGTTTGACATTTCATTAGCCATGCA
19801  GAACGACACCTCGAGGTGACGGTACATGGGTCATCCCAAACTGTAAAGTAATCGGTACGT

19861  ACATGGATATGTATTGGGCAGCAGACTGTGTTTCGTGAACTGCAGTGATGTATACATCTT
19861  TGTACCTATACATAACCCGTCGTCTGACACAAAGCACTTGACGTCACTACATATGTAGAA

19921  ATAGATGCAAAGTATTTTGGGGTATATTATCCTAAGGGAAGATAAAGATGATATTAAGAA
19921  TATCTACGTTTCATAAAACCCCATATAATAGGATTCCCTTCTATTTCTACTATAATTCTT

19981  CTGCTGTTTCACGGGGCCCTTACCTGTGACCCTCTTTGCTGAAGAATATTTAACCCCACA
19981  GACGACAAAGTGCCCCGGGAATGGACACTGGGAGAAACGACTTCTTATAAATTGGGGTGT

20041  CAGCACTTCAAAGAAGCTGTCTTGGAAGTCTGTCTCAGGAGCACCCTGTCTTCTTAATTC
20041  GTCGTGAAGTTTCTTCGACAGAACCTTCAGACAGAGTCCTCGTGGGACAGAAGAATTAAG

20101  TCCAAGCGGATGCTCCATTTCAATTGCTTTGTGACTTCTTCTTCTTTGTTTTTTTAAATA
20101  AGGTTCGCCTACGAGGTAAAGTTAACGAAACACTGAAGAAGAAGAAACAAAAAAATTTAT

20161  TTATGCTGCTTTAACAGTGGAGCTGAATTTTCTGGAAAATGCTTCTTGGCTGGGGCCACT
20161  AATACGACGAAATTGTCACCTCGACTTAAAAGACCTTTTACGAAGAACCGACCCCGGTGA

20221  ACCTCCTTTCCTATCTTTACATCTATGTGTATGTTGACTTTTTAAAATTCTGAGTGATCC
20221  TGGAGGAAAGGATAGAAATGTAGATACACATACAACTGAAAAATTTTAAGACTCACTAGG

20281  AGGGTATGACCTAGGGAATGAACTAGCTATGAAATACTCAGGGTTAGGAATCCTAGCACT
20281  TCCCATACTGGATCCCTTACTTGATCGATACTTTATGAGTCCCAATCCTTAGGATCGTGA

20341  TGTCTCAGGACTCTGAAAAGGAACGGCTTCCTCATTCCTTGTCTTGATAAAGTGGAATTG
20341  ACAGAGTCCTGAGACTTTTCCTTGCCGAAGGAGTAAGGAACAGAACTATTTCACCTTAAC

20401  GCAAACTAGAATTTAGTTTGTACTCAGTGGACAGTGCTGTTGAAGATTTGAGGACTTGTT
20401  CGTTTGATCTTAAATCAAACATGAGTCACCTGTCACGACAACTTCTAAACTCCTGAACAA

20461  AAAGAGCACTGGGTCATATGGAAAAAATGTATGTGTCTCCCAGGTGCATTTCTTGGTTTA
20461  TTTCTCGTGACCCAGTATACCTTTTTTACATACACAGAGGGTCCACGTAAAGAACCAAAT

20521  TGTCTTGTTCTTGAGATTTTGTATATTTAGGAAAACCTCAAGCAGTAATTAATATCTCCT
20521  ACAGAACAAGAACTCTAAAACATATAAATCCTTTTGGAGTTCGTCATTAATTATAGAGGA
```

FIG. 3 (cont'd)

```
20581  GGAACACTATAGAGAACCAAGTGACCGACTCATTTACAACTGAAACCTAGGAAGCCCCTG
20581  CCTTGTGATATCTCTTGGTTCACTGGCTGAGTAAATGTTGACTTTGGATCCTTCGGGGAC

20641  AGTCCTGAGCGAAAACAGGAGAGTTAGTCGCCCTACAGAAAACCCAGCTAGACTATTGGG
20641  TCAGGACTCGCTTTTGTCCTCTCAATCAGCGGGATGTCTTTTGGGTCGATCTGATAACCC

20701  TATGAACTAAAAAGAGACTGTGCCATGGTGAGAAAAATGTAAAATCCTACAGTGAAATGA
20701  ATACTTGATTTTTCTCTGACACGGTACCACTCTTTTTACATTTTAGGATGTCACTTTACT

20761  GCAGCCCTTACAGTATTGTTACCACCAAGGGCAGGTAGGTATTAGTGTTTGAAAAAGCTG
20761  CGTCGGGAATGTCATAACAATGGTGGTTCCCGTCCATCCATAATCACAAACTTTTTCGAC

20821  GTCTTTGAGCGAGGGCATAAATACAGCTAGCCCCAGGGGTGGAACAACTCTGGGAGTCTT
20821  CAGAAACTCGCTCCCGTATTTATGTCGATCGGGGTCCCCACCTTGTTGAGACCCTCAGAA

20881  GGGTACTCGCACCTCTTGGCTTTGTTGATGCTCCGCCAGGAAGGCCACTTGTGTGTGCGT
20881  CCCATGAGCGTGGAGAACCGAAACAACTACGAGGCGGTCCTTCCGGTGAACACACACGCA

20941  GTCAGTTACTTTTTTAGTAACAATTCAGATCCAGTGTAAACTTCCGTTCATTGCTCTCCA
20941  CAGTCAATGAAAAAATCATTGTTAAGTCTAGGTCACATTTGAAGGCAAGTAACGAGAGGT

21001  GTCACATGCCCCCACTTCCCCACAGGTGAAAGTTTTTCTGAAAGTGTTGGGATTGGTTAA
21001  CAGTGTACGGGGGTGAAGGGGTGTCCACTTTCAAAAAGACTTTCACAACCCTAACCAATT

21061  GGTCTTTATTTGTATTACGTATCTCCCGAAGTCCTCTGTGGCCAGCTGCATCTGTCTGAA
21061  CCAGAAATAAACATAATGCATAGAGGGCTTCAGGAGACACCGGTCGACGTAGACAGACTT

21121  TGGTGCGTGAAGGCTCTCAGACCTTACACACCATTTTGTAAGTTATGTTTTACATGCCCC
21121  ACCACGCACTTCCGAGAGTCTGGAATGTGTGGTAAAACATTCAATACAAAATGTACGGGG

21181  GTTTTTGAGACTGATCTCGATGCAGGTGGATCTCCTTGAGATCCTGATAGCCTGTTACAG
21181  CAAAAACTCTGACTAGAGCTACGTCCACCTAGAGGAACTCTAGGACTATCGGACAATGTC

21241  GAATGAAGTAAAGGTCAGTTTTTTTTTGTATTGATTTTCACAGCTTTGAGGAACATGCAT
21241  CTTACTTCATTTCCAGTCAAAAAAAAACATAACTAAAAGTGTCGAAACTCCTTGTACGTA

21301  AAGAAATGTAGCTGAAGTAGAGGGGACGTGAGAGAAGGGCCAGGCCGGCAGGCCAACCCT
21301  TTCTTTACATCGACTTCATCTCCCCTGCACTCTCTTCCCGGTCCGGCCGTCCGGTTGGGA

21361  CCTCCAATGGAAATTCCCGTGTTGCTTCAAACTGAGACAGATGGGACTTAACAGGCAATG
21361  GGAGGTTACCTTTAAGGGCACAACGAAGTTTGACTCTGTCTACCCTGAATTGTCCGTTAC

21421  GGGTCCACTTCCCCCTCTTCAGCATCCCCCGTACCCCACTTTCTGCTGAAAGAACTGCCA
21421  CCCAGGTGAAGGGGGAGAAGTCGTAGGGGGCATGGGGTGAAAGACGACTTTCTTGACGGT

21481  GCAGGTAGGACCCCAGAGGCCCCCAAATGAAAGCTTGAATTTCCCCTACTGGCTCTGCGT
21481  CGTCCATCCTGGGGTCTCCGGGGGTTTACTTTCGAACTTAAAGGGGATGACCGAGACGCA

21541  TTTGCTGAGATCTGTAGGAAAGGATGCTTCACAAACTGAGGTAGATAATGCTATGCTGTC
21541  AAACGACTCTAGACATCCTTTCCTACGAAGTGTTTGACTCCATCTATTACGATACGACAG

21601  GTTGGTATACATCATGAATTTTTATGTAAATTGCTCTGCAAAGCAAATTGATATGTTTGA
21601  CAACCATATGTAGTACTTAAAAATACATTTAACGAGACGTTTCGTTTAACTATACAAACT

21661  TAAATTTATGTTTTTAGGTAAATAAAAACTTTTAAAAATTTGTTA
21661  ATTTAAATACAAAAATCCATTTATTTTTGAAAATTTTTAAACAAT
```

FIG. 4

>hg19_refGene_NM_001178092 range=chr12:24962958-25102393

Genomic Sequence of BCAT1 (SEQ ID NO: 92)

```
   1  AGTAGGGAGGTGGGCAGGAGCCAGTGATGACGGAATGGCAATCACATTTGACCTCTGATC
   1  TCATCCCTCCACCCGTCCTCGGTCACTACTGCCTTACCGTTAGTGTAAACTGGAGACTAG

  61  TGTTTATTTCCTCCTCCTTGACGTCTCCATATAAATGTTACACGGGCATCCCCACACTCG
  61  ACAAATAAAGGAGGAGGAACTGCAGAGGTATATTTACAATGTGCCCGTAGGGGTGTGAGC

 121  GATACGCACCCACAGTGGCTGATTCGGGGGTAACCGTGTCATTTGCTTGCAACACTGGCA
 121  CTATGCGTGGGTGTCACCGACTAAGCCCCCATTGGCACAGTAAACGAACGTTGTGACCGT

 181  CCTCTGCCCTGCACCCCGGGAGTGAGCAGTGAGTGAGGCTCGGGTCTGGGCGCTGGCTCC
 181  GGAGACGGGACGTGGGGCCCTCACTCGTCACTCACTCCGAGCCCAGACCCGCGACCGAGG

 241  GAATCTTCGGGCTGGGAGAGACTCCACCATCTGGGGGCGGCCTGGGGGAGCAGCCTTAGT
 241  CTTAGAAGCCCGACCCTCTCTGAGGTGGTAGACCCCCGCCGGACCCCCTCGTCGGAATCA

 301  GTCTTCCTGCTGATGCAATCCGCTAGGTCGCGAGTCTCCGCCGCGAGAGGGCCGGTCTGC
 301  CAGAAGGACGACTACGTTAGGCGATCCAGCGCTCAGAGGCGGCGCTCTCCCGGCCAGACG

 361  AATCCAGCCCGCCACGTGTACTCGCCGCCGCCTCGGGCACTGCCCCAGGTCTTGCTGCAG
 361  TTAGGTCGGGCGGTGCACATGAGCGGCGGCGGAGCCCGTGACGGGGTCCAGAACGACGTC

 421  CCGGGACCGCGCTCTGCAGCCGCAGACCCGGTCCACACGGCCAGGGGCTACGACCCTTGG
 421  GGCCCTGGCGCGAGACGTCGGCGTCTGGGCCAGGTGTGCCGGTCCCCGATGCTGGGAACC

 481  GATCTGCCCTCCGCTCAGCTCGAGCTTCCCTCGTGGCCGACGGAACAATGAAGGTAACTA
 481  CTAGACGGGAGGCGAGTCGAGCTCGAAGGGAGCACCGGCTGCCTTGTTACTTCCATTGAT

 541  CTTATGGTTTTGTCCGTGTTTTACAAAAATGTGTGCGTGAATCGAACCGGCGATTTCTCC
 541  GAATACCAAAACAGGCACAAAATGTTTTTACACACGCACTTAGCTTGGCCGCTAAAGAGG

 601  AAGAAACATAGTTGGCAGGGAGGGGAGGAAGGCGAGACAACCATGGCTTATATCCCCCGC
 601  TTCTTTGTATCAACCGTCCCTCCCCTCCTTCCGCTCTGTTGGTACCGAATATAGGGGGCG

 661  AAACGTCTCAGTATCTTCTTTATCAATCGTAGTTTGCGGGGACCGTGCATTCTGTTCAGA
 661  TTTGCAGAGTCATAGAAGAAATAGTTAGCATCAAACGCCCCTGGCACGTAAGACAAGTCT

 721  TTTCGGTTTAACCTCCACTCGCAGGACGTGCCTTCTCGGACTTTTTCACATTCGCTTTTG
 721  AAAGCCAAATTGGAGGTGAGCGTCCTGCACGGAAGAGCCTGAAAAAGTGTAAGCGAAAAC

 781  GGAACGGAGGTGAAAGTCTGCTACAGCTCCCTCCCCTGCTTGTGAAGTTTGGAAAGGAAG
 781  CCTTGCCTCCACTTTCAGACGATGTCGAGGGAGGGGACGAACACTTCAAACCTTTCCTTC

 841  TGAGGGCTTCTCTCAGTTTCTCCTATGCACAGGAGGTGGGGAATTTTGGAGAGGAGGTCT
 841  ACTCCCGAAGAGAGTCAAAGAGGATACGTGTCCTCCACCCCTTAAAACCTCTCCTCCAGA

 901  GGGGATGTCCCGGGCTGTAAATGCGCTTTCCTGCAGCGTGTGTTCGTGATGCAGGAGGGA
 901  CCCCTACAGGGCCCGACATTTACGCGAAAGGACGTCGCACACAAGCACTACGTCCTCCCT

 961  GCGGCTGGAAGAGTTGACCCGGGTGGAGAGGGGAGGGAGAACGATCTTTTCACTGTTAAA
 961  CGCCGACCTTCTCAACTGGGCCCACCTCTCCCCTCCCTCTTGCTAGAAAAGTGACAATTT

1021  AGCAGAAGGCCCCTCTTATTTTGTTTCTTGTGGAAATTAAAGCTTCTAGGAGTTACAAAT
1021  TCGTCTTCCGGGGAGAATAAAACAAAGAACACCTTTAATTTCGAAGATCCTCAATGTTTA

1081  GATAGACGCCTAAGGGCATTCATTTGTTAAACCAGTGAGCACCCTAATGGCTCTGATCTT
1081  CTATCTGCGGATTCCCGTAAGTAAACAATTTGGTCACTCGTGGGATTACCGAGACTAGAA

1141  GCTAATCAAGGATAATTAGCCTAGCTGCCTATTATTTCTGACTATTTAGGTGTAGGGATG
1141  CGATTAGTTCCTATTAATCGGATCGACGGATAATAAAGACTGATAAATCCACATCCCTAC

1201  TACACCGTTGAGTGTTTTGTTTTCCTAGTTTCACACACTGGAAAACTGCAATCGCATATA
1201  ATGTGGCAACTCACAAAACAAAAGGATCAAAGTGTGTGACCTTTTGACGTTAGCGTATAT

1261  AAACCCGAAGAGCAACTTTTTCCAAGGAAAGTGAAGGATGGGCAGATATTCTTGCCATCT
1261  TTTGGGCTTCTCGTTGAAAAAGGTTCCTTTCACTTCCTACCCGTCTATAAGAACGGTAGA
```

FIG. 4 (cont'd)

```
1321  AACATTTTGGAATTGAGATGACCATAATGCAATCTGAACTTCTGGTAGGAATAAAGCCTC
1321  TTGTAAAACCTTAACTCTACTGGTATTACGTTAGACTTGAAGACCATCCTTATTTCGGAG

1381  GTTTCAGAGTTTCTAAGGAGGGAGATGAAGCGTGGTTCTCAACTGCTCTTATCTACAACC
1381  CAAAGTCTCAAAGATTCCTCCCTCTACTTCGCACCAAGAGTTGACGAGAATAGATGTTGG

1441  CATCCCAGACCATAGTTTCACTTAGAAGAAATAATATGTAAATAGCGCCTTTGTTGCCAA
1441  GTAGGGTCTGGTATCAAAGTGAATCTTCTTTATTATACATTTATCGCGGAAACAACGGTT

1501  ACAAAAACTTTCACTACAATTAAACAGTAACCGAGTGGAAACTATGCGTTTTTGTATTCA
1501  TGTTTTTGAAAGTGATGTTAATTTGTCATTGGCTCACCTTTGATACGCAAAAACATAAGT

1561  ACAGAGATCACACAACTTTTCTTCTATAGTTAGAGGTTCTATTTCTGGCTTCCTCATGCT
1561  TGTCTCTAGTGTGTTGAAAAGAAGATATCAATCTCCAAGATAAAGACCGAAGGAGTACGA

1621  TGTTTCATTTCAGATGAAAAACACACTTTAGTTGATTATAGCTTTAGTAAGTAAAAGGAG
1621  ACAAAGTAAAGTCTACTTTTTGTGTGAAATCAACTAATATCGAAATCATTCATTTTCCTC

1681  AAAACTAAGAATGAACAGTCTTGCTTTTCCAGCTTTTTCCTGTCCATGTGCAGTTGTGGT
1681  TTTTGATTCTTACTTGTCAGAACGAAAAGGTCGAAAAAGGACAGGTACACGTCAACACCA

1741  TAATTACGCGTTTTTGTAGGTCCAAAAACCCCTGTCCCTTCCACAAGATACTTTTATAAC
1741  ATTAATGCGCAAAAACATCCAGGTTTTTGGGGACAGGGAAGGTGTTCTATGAAAATATTG

1801  ATGGGGAACTAGGTAAGATATCTACAAGTAGTCTCTTTTCTGTTTCCTGATATTTCCTAA
1801  TACCCCTTGATCCATTCTATAGATGTTCATCAGAGAAAAGACAAAGGACTATAAAGGATT

1861  GATTAAGAAAGAAATGATTGTATTCTAGGTATGATCGAAGAAGTATGGAAGGTTCCATTA
1861  CTAATTCTTTCTTTACTAACATAAGATCCATACTAGCTTCTTCATACCTTCCAAGGTAAT

1921  AGTTAGTTTTATCACAATATTTCAAACATCTTTCCACTTATCTCTTAAATATGTATTGCT
1921  TCAATCAAAATAGTGTTATAAAGTTTGTAGAAAGGTGAATAGAGAATTTATACATAACGA

1981  ATCACAAGCTTGATTTTTTAAAAAAATGTTATTTGCACATGGCATCTTGATTGCCTTTGT
1981  TAGTGTTCGAACTAAAAAATTTTTTTACAATAAACGTGTACCGTAGAACTAACGGAAACA

2041  CCTCAGCAAATTCTCCGGGCTTAAGTCATGCATGAGCTTGTATTTTAAGACAGACACATG
2041  GGAGTCGTTTAAGAGGCCCGAATTCAGTACGTACTCGAACATAAAATTCTGTCTGTGTAC

2101  CAGAATGGGCAACTTGGATAAGAAACATAGGATATACACTGAGTAGCATGTGTACAAAAA
2101  GTCTTACCCGTTGAACCTATTCTTTGTATCCTATATGTGACTCATCGTACACATGTTTTT

2161  TGGTAAGTGAGTATTATGACTTAATAAATTTAGATGGGGATTTAAAAATGATACACATGT
2161  ACCATTCACTCATAATACTGAATTATTTAAATCTACCCCTAAATTTTTACTATGTGTACA

2221  AAATGGGATTGGAGGCAAGGGAAGTCCGTGTGTGTGTGTGTGTGTGTGTGTGTGTGTGTG
2221  TTTACCCTAACCTCCGTTCCCTTCAGGCACACACACACACACACACACACACACACACAC

2281  TGTGTGTGTGTGGAGGGAAGACGGGAGGCCTAGTGGGGAGAGAGGTTTTACATTCCAGAC
2281  ACACACACACACCTCCCTTCTGCCCTCCGGATCACCCCTCTCTCCAAAATGTAAGGTCTG

2341  ACAGGATGTGGCCCCTCAGGCTAGGCTCAGAGATGTAAAGCTAGTTAAGCTGGCCTAACA
2341  TGTCCTACACCGGGGAGTCCGATCCGAGTCTCTACATTTCGATCAATTCGACCGGATTGT

2401  AAAGGGTGGTGGTTAGAAAAAGGAAAAAAAGAGGTGGGGGTTGGGGAGGAAAAGAATTTA
2401  TTTCCCACCACCAATCTTTTTCCTTTTTTTCTCCACCCCCAACCCCTCCTTTTCTTAAAT

2461  ATGCTGGCCAATATTTTCATCTGATAAGTTTCAGTAATGAGTAATTTCACTGGATTTCAG
2461  TACGACCGGTTATAAAAGTAGACTATTCAAAGTCATTACTCATTAAAGTGACCTAAAGTC

2521  AACTACAGAGAGAAAAGGGGAAAAATATTTTTCCTTTTTTACGCAAGAATTTCTCTTGCT
2521  TTGATGTCTCTCTTTTCCCCTTTTTATAAAAAGGAAAAAATGCGTTCTTAAAGAGAACGA

2581  TTTCAGCTCATTAGAACCAGATCTAATTATTTGAAATGAGTTTAAAACCTTATTATGAAA
2581  AAAGTCGAGTAATCTTGGTCTAGATTAATAAACTTTACTCAAATTTTGGAATAATACTTT

2641  GGAAGTTGAAAACATTCGATCACAATTGAGTTTTGTACTATGGACTAAAACCAAGATGTG
2641  CCTTCAACTTTTGTAAGCTAGTGTTAACTCAAAACATGATACCTGATTTTGGTTCTACAC
```

FIG. 4 (cont'd)

```
2701  CTTTCTGTCAGTAGCTGTGCAACTCCCTGAAAAAAGAAAAATAGCGCAGAGCGATCTGAG
2701  GAAAGACAGTCATCGACACGTTGAGGGACTTTTTTCTTTTTATCGCGTCTCGCTAGACTC

2761  CTTTGTGAAGGCTACACAATTTATCAGGCCCAGAGAGATAGGAGTGTGAGACTTCAGTCA
2761  GAAACACTTCCGATGTGTTAAATAGTCCGGGTCTCTCTATCCTCACACTCTGAAGTCAGT

2821  CGTCCCCCCGTACGCATGCGCAGGAGTAATTATTTAAAGACATTTTGTTCCTGACTAACT
2821  GCAGGGGGGCATGCGTACGCGTCCTCATTAATAAATTTCTGTAAAACAAGGACTGATTGA

2881  GCCTCACTCATTATGTTCCTGGAATTTGTGATACAAAAAAACAATGTTTAGCCTATCAAT
2881  CGGAGTGAGTAATACAAGGACCTTAAACACTATGTTTTTTTGTTACAAATCGGATAGTTA

2941  AGTTTATATAGTTTATGTTATTTTAATATAAATTCTTCTCAACTTAGAAACTGCCTCTTT
2941  TCAAATATATCAAATACAATAAAATTATATTTAAGAAGAGTTGAATCTTTGACGGAGAAA

3001  TTTCTTTTAAAAACCCACTTGTAACTGCTGTATATATTCAGGGCAACTTGATTTGGTGTT
3001  AAAGAAAATTTTTGGGTGAACATTGACGACATATATAAGTCCCGTTGAACTAAACCACAA

3061  TCGTTGGTTGCAGTCCTCAAATTTGACCTCAATATACTCTCTACTTATATAAATTTTGTC
3061  AGCAACCAACGTCAGGAGTTTAAACTGGAGTTATATGAGAGATGAATATATTTAAAACAG

3121  TCAGTTTTGTCCGTAGGCTGACATTCCAATTGTTTTCCTAATTATATATTTTGTTCCTTA
3121  AGTCAAAACAGGCATCCGACTGTAAGGTTAACAAAAGGATTAATATATAAAACAAGGAAT

3181  TTTCTCATGTCTAGAAATAAAGCTAGGGAAGTAAACAGCTGGAAAACTGATAGTGGTGTT
3181  AAAGAGTACAGATCTTTATTTCGATCCCTTCATTTGTCGACCTTTTGACTATCACCACAA

3241  ATTAACCTAACTGAGAGGGCTGGGCTTATGAGTAAATTATTCCTGTGCATAAATGAAAGA
3241  TAATTGGATTGACTCTCCCGACCCGAATACTCATTTAATAAGGACACGTATTTACTTTCT

3301  TTGTTTCTAAATGGCAGCTATGTTGAGCCTTTGTATTAGTTACATCTTTTGGGGTTTCAG
3301  AACAAAGATTTACCGTCGATACAACTCGGAAACATAATCAATGTAGAAAACCCCAAAGTC

3361  GTTGCCAGCTTCTTTAAATGGCCTCTTCTCAACTGGTATAGGAAGTTGGAAAATAAAGAA
3361  CAACGGTCGAAGAAATTTACCGGAGAAGAGTTGACCATATCCTTCAACCTTTTATTTCTT

3421  CTTTCTTTATTTCCCTTTAGTGTTGGTAACCACAGTTTCTTTAAATAACAGATGCCCACC
3421  GAAAGAAATAAAGGGAAATCACAACCATTGGTGTCAAAGAAATTTATTGTCTACGGGTGG

3481  CCAGGGAAACCCAGTGGCATGATCAGCCTTATGCTCAGGAAGGTTTGGTTGCTATACTGG
3481  GGTCCCTTTGGGTCACCGTACTAGTCGGAATACGAGTCCTTCCAAACCAACGATATGACC

3541  AGAGTGAGAATCTGGGACCTTCCATGATAGACATAATTGTGCCAGCTATCCTCTACTTTC
3541  TCTCACTCTTAGACCCTGGAAGGTACTATCTGTATTAACACGGTCGATAGGAGATGAAAG

3601  TATATGATGCTATCATTCTTTTTTCTTTTCTTTTTTTTGACAGAATCTCACTGTGTTGTT
3601  ATATACTACGATAGTAAGAAAAAAGAAAAGAAAAAAAACTGTCTTAGAGTGACACAACAA

3661  CAGGCTGGAGTGCCGCAGAGTGATCTCTACTCACTGCAACCTCTGCCTCCTAGGTTCAAG
3661  GTCCGACCTCACGGCGTCTCACTAGAGATGAGTGACGTTGGAGACGGAGGATCCAAGTTC

3721  CAATTCTTGTGCCTCAGCCTCCTGAGAAGCTGGGATTACCACCATGCCCAGCTAATTTTC
3721  GTTAAGAACACGGAGTCGGAGGACTCTTCGACCCTAATGGTGGTACGGGTCGATTAAAAG

3781  GTATTTTTTTGTAAAGACGGAGTTTTGCCATGTTGGCCAGGCTGGTCTGGAACTCCTGGC
3781  CATAAAAAAACATTTCTGCCTCAAAACGGTACAACCGGTCCGACCAGACCTTGAGGACCG

3841  CTCAAGCGATCTGCCCATCTCGGCCTCCCAAAGTGCTGGGATTACAGGCATGTGCTATCA
3841  GAGTTCGCTAGACGGGTAGAGCCGGAGGGTTTCACGACCCTAATGTCCGTACACGATAGT

3901  TTCTTTTTGAGCACAGGAGGAAACTATGGCTGATCTGCTCATTTTACTGTCAAAAATATA
3901  AAGAAAAACTCGTGTCCTCCTTTGATACCGACTAGACGAGTAAAATGACAGTTTTTATAT

3961  GGCAGCTTTTGTATTGTAACATTATCCCCTTAACAGCTGTCCAACTGGTCTATACATTTC
3961  CCGTCGAAAACATAACATTGTAATAGGGGAATTGTCGACAGGTTGACCAGATATGTAAAG

4021  ACCTAACATATGGTAAATGTTCCTACTGTTGGCCTTTCCTGAGCCTCTGTCCATTCAACT
4021  TGGATTGTATACCATTTACAAGGATGACAACCGGAAAGGACTCGGAGACAGGTAAGTTGA
```

FIG. 4 (cont'd)

```
4081  AAGGCCACTGCAATGGGATTGTATGCAGTTCAGCCAAGAAATAAATGTGAGGTGCAACTC
4081  TTCCGGTGACGTTACCCTAACATACGTCAAGTCGGTTCTTTATTTACACTCCACGTTGAG

4141  ACATTTTTTAAATGTTTCAAAATTAAGCATTTAGGTGCTTTTATTCATAAACATGACTTT
4141  TGTAAAAAATTTACAAAGTTTTAATTCGTAAATCCACGAAAATAAGTATTTGTACTGAAA

4201  GCAAATATTGGTAAACAGTTTCATCATAAGACCTTGTCAGTGACTCACAATGTCAATGGT
4201  CGTTTATAACCATTTGTCAAAGTAGTATTCTGGAACAGTCACTGAGTGTTACAGTTACCA

4261  GAACGCAAAGGAGAATCTGTCTTTTCTGGAACACCAGGTTCAGGTATCAGTTTCAACTAT
4261  CTTGCGTTTCCTCTTAGACAGAAAAGACCTTGTGGTCCAAGTCCATAGTCAAAGTTGATA

4321  GCTTATAATTTGTGCTCTAAAGTCCACAAAGCTAAATTATCTTTCCCCTAAAAATTGAGT
4321  CGAATATTAAACACGAGATTTCAGGTGTTTCGATTTAATAGAAAGGGGATTTTTAACTCA

4381  ACTCATATCCTTAAAATAGCTTGGAAATTAGATTACCTTATGAATACAGCATAGCATGTC
4381  TGAGTATAGGAATTTTATCGAACCTTTAATCTAATGGAATACTTATGTCGTATCGTACAG

4441  ACATAAACGTTTTTCTACTGTTATACCTTTTTGGTGGGAAAGACTATTTTGCAAAACATT
4441  TGTATTTGCAAAAAGATGACAATATGGAAAAACCACCCTTTCTGATAAAACGTTTTGTAA

4501  TTTCTTGTGTTCAGTAATTAATGGGAAAAACAAACTCTAAAAGAAAGAGACAGTTATGTC
4501  AAAGAACACAAGTCATTAATTACCCTTTTTGTTTGAGATTTTCTTTCTCTGTCAATACAG

4561  CCAAAAATACAGGAAAATGGAAGAATGGAAACAGGGAAGACCAATAAAGAAAAAAATAGA
4561  GGTTTTTATGTCCTTTTACCTTCTTACCTTTGTCCCTTCTGGTTATTTCTTTTTTTATCT

4621  GGAAATTACAAGTAATAAACTGAAGTCATACTGAAAAACATATGGCTCTTTCTTATTGAA
4621  CCTTTAATGTTCATTATTTGACTTCAGTATGACTTTTTGTATACCGAGAAAGAATAACTT

4681  AGTTGTGAAATACTTGCAAAACTCAGCTAGTTCCATTAAGAATAGTCTTTAATCTAAAAA
4681  TCAACACTTTATGAACGTTTTGAGTCGATCAAGGTAATTCTTATCAGAAATTAGATTTTT

4741  GAACAAATTCATTTGTCAGTTCTTTATTTCGGTGTGTAGATTTGAATGTTTCATCAATTG
4741  CTTGTTTAAGTAAACAGTCAAGAAATAAAGCCACACATCTAAACTTACAAAGTAGTTAAC

4801  CATTTACGGTTTATCCCTCAGTGTGAGAACTGTTTTTGCTGTTTTGACTATAAATGGATA
4801  GTAAATGCCAAATAGGGAGTCACACTCTTGACAAAAACGACAAAACTGATATTTACCTAT

4861  TCTGCTTTAGGAAGACTTAGGAAGCCTGGGACATAGGATTACAGATCAAATTCTATTTGA
4861  AGACGAAATCCTTCTGAATCCTTCGGACCCTGTATCCTAATGTCTAGTTTAAGATAAACT

4921  CTCCATAGAAGTTGAGACGGAAGGAGCACCTGTTGGGATATTCTAGACCAAACATTCCAC
4921  GAGGTATCTTCAACTCTGCCTTCCTCGTGGACAACCCTATAAGATCTGGTTTGTAAGGTG

4981  AGCTGTCTCTTAACGTGACTGACAAAGAGACACAGTTGAGACGAAGTTTGGGTATATCCT
4981  TCGACAGAGAATTGCACTGACTGTTTCTCTGTGTCAACTCTGCTTCAAACCCATATAGGA

5041  GGGATGAGGCCAAGGGTGGATTTGCACAGGATGGTCACAGGGCAGTTGTTAGCATTCCAC
5041  CCCTACTCCGGTTCCCACCTAAACGTGTCCTACCAGTGTCCCGTCAACAATCGTAAGGTG

5101  CACTACATAAAAGGGTGATTTTGCCAAGTGCATTTCATTTCATTTCAGTTGATTTAGATA
5101  GTGATGTATTTTCCCACTAAAACGGTTCACGTAAAGTAAAGTAAAGTCAACTAAATCTAT

5161  CCAAGTTATATTGTTTTGACTTTAGGACTAGATGTGAGTTCAGGAATTTGAAATCATAAT
5161  GGTTCAATATAACAAAACTGAAATCCTGATCTACACTCAAGTCCTTAAACTTTAGTATTA

5221  AAATGTTTCCTTGAACTTTGAAGATAAAAGGTAGAGTTAAAAGACAGCTGCGAAGTCTAC
5221  TTTACAAAGGAACTTGAAACTTCTATTTTCCATCTCAATTTTCTGTCGACGCTTCAGATG

5281  ATGGGGAAGCATAATACATGACTCAGGGTTCCATGGTTTTCAGTGTCGGTGAGTGCTCTG
5281  TACCCCTTCGTATTATGTACTGAGTCCCAAGGTACCAAAAGTCACAGCCACTCACGAGAC

5341  TACACTTATAAGAATAGTGCTGGTGTTTATAGAAGAAACACATGCAGGTTTGAGGCAAGA
5341  ATGTGAATATTCTTATCACGACCACAAATATCTTCTTTGTGTACGTCCAAACTCCGTTCT

5401  CTTCCTTGCTTAATTGGTGCTTTTGCTTTCCATTTTCTAAATGCCATGCAAACTACTTTT
5401  GAAGGAACGAATTAACCACGAAAACGAAAGGTAAAAGATTTACGGTACGTTTGATGAAAA
```

FIG. 4 (cont'd)

```
5461  TTTTTTTTCTTTTGTTGAGACGGAGTCTTGCTCTGTCACCCAGGCTGGAGTACAGTGGTG
5461  AAAAAAAAGAAAACAACTCTGCCTCAGAACGAGACAGTGGGTCCGACCTCATGTCACCAC

5521  CGATCTCGGCTCACTGCAAGCTCCGCCTCCTGGGTTCACGCCATTCTCCTGCCTCAGCTT
5521  GCTAGAGCCGAGTGACGTTCGAGGCGGAGGACCCAAGTGCGGTAAGAGGACGGAGTCGAA

5581  CCTGAGTAGCTGGGACTACAGGCGCCCGCCACCACGCCCGGCTAATTTTTTGTATTTTTT
5581  GGACTCATCGACCCTGATGTCCGCGGGCGGTGGTGCGGGCCGATTAAAAAACATAAAAAA

5641  GTAGAGACGGGGTTTCACCATGTTAGCCAGGAAGGTCTTGATCTCCTGACCTCGTGATCT
5641  CATCTCTGCCCCAAAGTGGTACAATCGGTCCTTCCAGAACTAGAGGACTGGAGCACTAGA

5701  GCCCGCCTCGGCCACCCAAGGTGCTGGGATTACAGGCGTGAGCCACCGCTCCCGGCCTCA
5701  CGGGCGGAGCCGGTGGGTTCCACGACCCTAATGTCCGCACTCGGTGGCGAGGGCCGGAGT

5761  AACTACTTTAACTGAAAACATTCTTCTAAGGAAAGCATCAGAAAACTTACTAGAATTGCT
5761  TTGATGAAATTGACTTTTGTAAGAAGATTCCTTTCGTAGTCTTTTGAATGATCTTAACGA

5821  TAAGAATAAATAAATAATACAAATAAAAGAGCAAAATGAGAAAGTAGACAGACTCCTAGT
5821  ATTCTTATTTATTTATTATGTTTATTTTCTCGTTTTACTCTTTCATCTGTCTGAGGATCA

5881  CTATTGTGCTATTGATCTCTCCAGGTTCTAGGCTTTCTTGGGTCTGACACCACTTTGTAA
5881  GATAACACGATAACTAGAGAGGTCCAAGATCCGAAAGAACCCAGACTGTGGTGAAACATT

5941  ATTTTTTTTTTTTTTTTTTTTTTTTTCCAGATAGGGTCTCATTCTGTCACCTAGGCTGGA
5941  TAAAAAAAAAAAAAAAAAAAAAAAAAGGTCTATCCCAGAGTAAGACAGTGGATCCGACCT

6001  GTGCAGTGGTACAATCATGGCTCACTTCAGCTTCAACCTCCTGGGCTCAAGTGATCTTCC
6001  CACGTCACCATGTTAGTACCGAGTGAAGTCGAAGTTGGAGGACCCGAGTTCACTAGAAGG

6061  TGCCTCAGCTCCCTGAGTAGCTGGGACCACAGGCATGTGCCACCACGCCCGGTGAATTTT
6061  ACGGAGTCGAGGGACTCATCGACCCTGGTGTCCGTACACGGTGGTGCGGGCCACTTAAAA

6121  TGTATTTTTTGTAGAGATGGGGTTTCTCCATGTTGCACTGGCTGGTCTTGAACTCCTGGG
6121  ACATAAAAAACATCTCTACCCCAAAGAGGTACAACGTGACCGACCAGAACTTGAGGACCC

6181  CTCCAGTGATCCACCCACCTTGGCCTCCAAAGTGCTGGGATTACAGGCATCCGTCACTGC
6181  GAGGTCACTAGGTGGGTGGAACCGGAGGTTTCACGACCCTAATGTCCGTAGGCAGTGACG

6241  ACTGGGCCAGTTTGTAAATCTTATGAAAAGTATGGCCAATCTTTTGCAAAATGTGCAAAC
6241  TGACCCGGTCAAACATTTAGAATACTTTTCATACCGGTTAGAAAACGTTTTACACGTTTG

6301  ACATATAGACACAAAGTTTTATATCTAAATTATTGGTTATTAAAGCCAGGACAATAGAGT
6301  TGTATATCTGTGTTTCAAAATATAGATTTAATAACCAATAATTTCGGTCCTGTTATCTCA

6361  GCATATAGCATGGAAGACAGGTAGAAAAGACTGAAATGGTTTAGTTATTCAGAGCAGTGG
6361  CGTATATCGTACCTTCTGTCCATCTTTTCTGACTTTACCAAATCAATAAGTCTCGTCACC

6421  AGGGCTATTGGCTCTTGCCTTTGCAGTCAGCTGAGATATGAAACTATATAAGCAGAAGCT
6421  TCCCGATAACCGAGAACGGAAACGTCAGTCGACTCTATACTTTGATATATTCGTCTTCGA

6481  TCACGCTGCCATTTGAATATTGAAAATCTCCACTTTTAGTTCAAGAGATAAACAACCAAT
6481  AGTGCGACGGTAAACTTATAACTTTTAGAGGTGAAAATCAAGTTCTCTATTTGTTGGTTA

6541  GGTTTGTTTGTTCACAGCACATAAGTTATCACTTTCTTCTCTGTTTCATCCCATCAAGAT
6541  CCAAACAAACAAGTGTCGTGTATTCAATAGTGAAAGAAGAGACAAAGTAGGGTAGTTCTA

6601  CTAAGGTGTATAGTTACAGAATAGAACTCGGTTCATACCATATGCACCCTAATTTCTTCG
6601  GATTCCACATATCAATGTCTTATCTTGAGCCAAGTATGGTATACGTGGGATTAAAGAAGC

6661  ATCTTCAACTAGTTTGGAAGTGTGTGTGGGTGTTTTCTTAGCCAAGGTTAATATGCAATT
6661  TAGAAGTTGATCAAACCTTCACACACACCCACAAAAGAATCGGTTCCAATTATACGTTAA

6721  TCTTAGTGGAGTGTAGGAGTTTGGGGTGCCTAGCCTTCCTACTTCCCACTTAGATAACTT
6721  AGAATCACCTCACATCCTCAAACCCCACGGATCGGAAGGATGAAGGGTGAATCTATTGAA

6781  CCCCTACCTGTTGTACCTGTCAAAGGAGAAGGCCAGTATGGCCATGTTCTTTGCAGGTGA
6781  GGGGATGGACAACATGGACAGTTTCCTCTTCCGGTCATACCGGTACAAGAAACGTCCACT
```

FIG. 4 (cont'd)

```
6841  CTCCACCTTAGCCACAGCTGATTGTAACAAGGGTGTATATTTGGCCCAAGTCCAGCCATC
6841  GAGGTGGAATCGGTGTCGACTAACATTGTTCCCACATATAAACCGGGTTCAGGTCGGTAG

6901  TTTTTTTTTTTTTTTTGAGGCGGAGTCTTGTTCTGTCACCCACGCTGGAGTGCAGTGGTG
6901  AAAAAAAAAAAAAAAACTCCGCCTCAGAACAAGACAGTGGGTGCGACCTCACGTCACCAC

6961  TGATTTTGGCTCACTGCAACCTCTGCCTCCCGGGTTCAAGCAATTCTCCTGCCTCAGCCT
6961  ACTAAAACCGAGTGACGTTGGAGACGGAGGGCCCAAGTTCGTTAAGAGGACGGAGTCGGA

7021  CCTGAGTAGCTGGGATTACAGACACCCACGACCACGCTTGGCTTTGTATTTTTGTATTTT
7021  GGACTCATCGACCCTAATGTCTGTGGGTGCTGGTGCGAACCGAAACATAAAAACATAAAA

7081  TAGTAGAGACGGGGTTTCTCCATGTTGGCCAGGCTGGTCTAGAACTCTTGACCTCAAGTG
7081  ATCATCTCTGCCCCAAAGAGGTACAACCGGTCCGACCAGATCTTGAGAACTGGAGTTCAC

7141  ATCCGCCCGCCTTGGCCTCCCAAACTACTGGGATTACATGCCCAGCCAGCCATCTTTTAC
7141  TAGGCGGGCGGAACCGGAGGGTTTGATGACCCTAATGTACGGGTCGGTCGGTAGAAAATG

7201  TTCTTTCTTATTCTCTTATTCCACATATTCAAGCAGGTACCACGTCCTGTGGACTCTGTC
7201  AAGAAAGAATAAGAGAATAAGGTGTATAAGTTCGTCCATGGTGCAGGACACCTGAGACAG

7261  TTCTCTGAATCTATAGGTTCTCTCTTTCCCATTGCCCTGCATACTGGTTTATGCTCTCAT
7261  AAGAGACTTAGATATCCAAGAGAGAAAGGGTAACGGGACGTATGACCAAATACGAGAGTA

7321  TACTTCTCGCTTGAATTATTCCAAAAGTCTCCCAACTGGTCTGAAGCTTAATTTTCATTA
7321  ATGAAGAGCGAACTTAATAAGGTTTTCAGAGGGTTGACCAGACTTCGAATTAAAAGTAAT

7381  TGTGCTGTTCGATGTCATTCCACCACGCAAAATCTATGGCTTCTCCATTGTCTCCTGAGT
7381  ACACGACAAGCTACAGTAAGGTGGTGCGTTTTAGATACCGAAGAGGTAACAGAGGACTCA

7441  TTAGTTTAGTGCATGAGACCGTTTAAAATCTACCTACACCTCTTCTATGTGCATGCATTT
7441  AATCAAATCACGTACTCTGGCAAATTTTAGATGGATGTGGAGAAGATACACGTACGTAAA

7501  CTCTAGTCATAAGAGAGGATTTGATCTATCTCAAAATGTGTTCTTATATTTGCATTTACT
7501  GAGATCAGTATTCTCTCCTAAACTAGATAGAGTTTTACACAAGAATATAAACGTAAATGA

7561  GGTTTTTAACTCCCTCCATCCTATCTATAATTTGCACCATGTTGCTCACCATGCAGCCCA
7561  CCAAAAATTGAGGGAGGTAGGATAGATATTAAACGTGGTACAACGAGTGGTACGTCGGGT

7621  CTCCCCAGACACCTTGTGAGAACAGTGATCATGTTTTTGCAGTGGAATGAACATGGGCGA
7621  GAGGGGTCTGTGGAACACTCTTGTCACTAGTACAAAAACGTCACCTTACTTGTACCCGCT

7681  AAGGTGGGAAGGTATGCATAGATTTACATTTTGAAGTCAGGAAATAAGATACTGATCAAT
7681  TTCCACCCTTCCATACGTATCTAAATGTAAAACTTCAGTCCTTTATTCTATGACTAGTTA

7741  GCTTTAATTCGACTGTGCTTTTTACCTTTTCCTCTGTTGTAGCATGAACCTTGCCCCAAA
7741  CGAAATTAAGCTGACACGAAAAATGGAAAAGGAGACAACATCGTACTTGGAACGGGGTTT

7801  AAGATATTGATCATATGCTGCAACTCCTCTGCACTTACCTTTTCTTCTACCATGGCAGGA
7801  TTCTATAACTAGTATACGACGTTGAGGAGACGTGAATGGAAAAGAAGATGGTACCGTCCT

7861  ACCTTGCACCATTGTTGGTGCTTTACAGATATTGGTTGAGTTAAATCGAGAGCCTATTTC
7861  TGGAACGTGGTAACAACCACGAAATGTCTATAACCAACTCAATTTAGCTCTCGGATAAAG

7921  TGGACTTTCAAGATTCAGATTAATTGATTCTGTTTTATACTTCTCTGTTTTTGAATGGCA
7921  ACCTGAAAGTTCTAAGTCTAATTAACTAAGACAAAATATGAAGAGACAAAAACTTACCGT

7981  CATACATCTTTCCACACTTGGATTTCTTTGAAGTTAAAGCTTTAATTGACTTCCAAAAGA
7981  GTATGTAGAAAGGTGTGAACCTAAAGAAACTTCAATTTCGAAATTAACTGAAGGTTTTCT

8041  CAGAGGATTATAAAAACACAGAGAACAGTAAAGTATTTACACGGTCTTAATGCCTATTGC
8041  GTCTCCTAATATTTTTGTGTCTCTTGTCATTTCATAAATGTGCCAGAATTACGGATAACG

8101  CAAACACATATAGCTGCTATTAATGCCTATTGCCAGACTCATATAGCTGCAAACTCATGT
8101  GTTTGTGTATATCGACGATAATTACGGATAACGGTCTGAGTATATCGACGTTTGAGTACA

8161  AGCTTAATGCCCATTGCCAAACTCATATAGCTGCTATATATGTCTACTGGAAAACTCACA
8161  TCGAATTACGGGTAACGGTTTGAGTATATCGACGATATATACAGATGACCTTTTGAGTGT
```

FIG. 4 (cont'd)

```
8221  TAGCTGGTTGATTTTAAATTGATTGTAGGAAAATTCATACAAAAAGATGCTACATAGGAA
8221  ATCGACCAACTAAAATTTAACTAACATCCTTTTAAGTATGTTTTTCTACGATGTATCCTT

8281  TATAAACTGAACACCACAAAAATCGTAATGAACAAACTCAGTAATGCCAGCCTGTTCAAT
8281  ATATTTGACTTGTGGTGTTTTTAGCATTACTTGTTTGAGTCATTACGGTCGGACAAGTTA

8341  CACTAGTTTTCAGATTAAGGCAGTATGCAAAGGGAAACATCCTTGGAATGGTCTTAGAAT
8341  GTGATCAAAAGTCTAATTCCGTCATACGTTTCCCTTTGTAGGAACCTTACCAGAATCTTA

8401  ATAGAACAAAGTCATGTGTTTGGGAATCTTAACCAATTCCAATACTGTTCAACATGTTTT
8401  TATCTTGTTTCAGTACACAAACCCTTAGAATTGGTTAAGGTTATGACAAGTTGTACAAAA

8461  TCTTTGTTGCAAACAATGCAGTTTTTAAGCAAACTAATGAATGCATACCCTGACAAACAA
8461  AGAAACAACGTTTGTTACGTCAAAAATTCGTTTGATTACTTACGTATGGGACTGTTTGTT

8521  ATCCAACAAAAGAGGTACTTAGAGCAGTGTTCATTGAATCCTAGAATTTTGAAAGAAAAA
8521  TAGGTTGTTTTCTCCATGAATCTCGTCACAAGTAACTTAGGATCTTAAAACTTTCTTTTT

8581  ATCTATTAGGTCATTTTGGGCTTTTACTTCTGCTGAAGAAGGATTGTTCTTTTGAGTTTA
8581  TAGATAATCCAGTAAAACCCGAAAATGAAGACGACTTCTTCCTAACAAGAAAACTCAAAT

8641  TTTTTCTAGCTTTCAGTTCTATTCCATTTAAATGCCTCGAGAAATAGGACTTCTCAAATT
8641  AAAAAGATCGAAAGTCAAGATAAGGTAAATTTACGGAGCTCTTTATCCTGAAGAGTTTAA

8701  CCCTGTGGAGAGTTCTGGCACCTACTATATTCACTTTTGAAAGTCTCCTGATAACTGATT
8701  GGGACACCTCTCAAGACCGTGGATGATATAAGTGAAAACTTTCAGAGGACTATTGACTAA

8761  TCCTTTTTCTTTTGGTTATACACATCAACTATTCATGGTTGGCTCTGCTGATAGTTTTCC
8761  AGGAAAAAGAAAACCAATATGTGTAGTTGATAAGTACCAACCGAGACGACTATCAAAAGG

8821  ATGATTCTTTATGCTTATTTAAAAGAAATCATATAACATTAATCATATAACATATAACCA
8821  TACTAAGAAATACGAATAAATTTTCTTTAGTATATTGTAATTAGTATATTGTATATTGGT

8881  TTACTTGGTTATAAAGCATGATATTAACTAAACTGGCTTTTAAAAATTCAATAACATTAG
8881  AATGAACCAATATTTCGTACTATAATTGATTTGACCGAAAATTTTTAAGTTATTGTAATC

8941  AGCAAATATTTTATTAATATTGTCAGTAGTTCCATGAATATATAGATGTAGGATGTCAAT
8941  TCGTTTATAAAATAATTATAACAGTCATCAAGGTACTTATATATCTACATCCTACAGTTA

9001  AAAGTTTATGCCCCTTAATAACTGAGTGTGTTAATGTTGTATTTGCTGGTTAACTGGCAC
9001  TTTCAAATACGGGGAATTATTGACTCACACAATTACAACATAAACGACCAATTGACCGTG

9061  CTTCCCTCCTTTTGATCAATGTTCTTAGAACAGTATGTACAGGAGTACTTTAGTCTACCA
9061  GAAGGGAGGAAAACTAGTTACAAGAATCTTGTCATACATGTCCTCATGAAATCAGATGGT

9121  CTTGATATTCAAGGACAACACTTCGAAGCTTGAAATGAGGGATTGTTTTAACCATATTAA
9121  GAACTATAAGTTCCTGTTGTGAAGCTTCGAACTTTACTCCCTAACAAAATTGGTATAATT

9181  CGTAACTGCATAGTTTGCAATAGATTTAATGATTCAACATCATTGTTAATATTTAGTTTA
9181  GCATTGACGTATCAAACGTTATCTAAATTACTAAGTTGTAGTAACAATTATAAATCAAAT

9241  ATTAAAAGTGCCTTATATTAACTTGTACACATGTGAAATGACTTATCAACAAGATTATTT
9241  TAATTTTCACGGAATATAATTGAACATGTGTACACTTTACTGAATAGTTGTTCTAATAAA

9301  ATTGCAGCATTGTTTGTGATTACAAAGAGTGGAAGTCATTTGCATAGTCATTAGGCGTAA
9301  TAACGTCGTAACAAACACTAATGTTTCTCACCTTCAGTAAACGTATCAGTAATCCGCATT

9361  AAAATAATGACATTAAAAGAAAACAATTGAGGAAAGAACCAGTAAGCTCTCAGGTAGAGA
9361  TTTTATTACTGTAATTTTCTTTTGTTAACTCCTTTCTTGGTCATTCGAGAGTCCATCTCT

9421  TAAAAAGAAAGTTACCGTGAGCCTTTTCACTGTATATATTTATATATTTGATTTTTGACA
9421  ATTTTTCTTTCAATGGCACTCGGAAAAGTGACATATATAAATATATAAACTAAAAACTGT

9481  CGTGAGTTTATTATAATCAAGATTGAATGAAAAAAATTGAAGCCTTTTAATGAAATTAGC
9481  GCACTCAAATAATATTAGTTCTAACTTACTTTTTTTAACTTCGGAAAATTACTTTAATCG

9541  TTGACACCAGAGTCATTATCAAGAAAATCTGAAATACTGGTACCTATGCACATTTGATTT
9541  AACTGTGGTCTCAGTAATAGTTCTTTTAGACTTTATGACCATGGATACGTGTAAACTAAA
```

FIG. 4 (cont'd)

```
 9601   TATTATTTTTAGTTTTATTATTTTTTGAGACAGAGTCTTGCTCTGTCGCCCAGACTGGAG
 9601   ATAATAAAAATCAAAATAATAAAAAACTCTGTCTCAGAACGAGACAGCGGGTCTGACCTC

 9661   TGAAGTGGTGTGATCTCAGCTCACTGCAATCTCCAGCCTCCCAGGTTCAAGCGATTCTCC
 9661   ACTTCACCACACTAGAGTCGAGTGACGTTAGAGGTCGGAGGGTCCAAGTTCGCTAAGAGG

 9721   TCAGCCTCCCGAGTAGCTGGGATTACAGATGCCTGCCACCATGCTTGGCTAGTTTTTGTA
 9721   AGTCGGAGGGCTCATCGACCCTAATGTCTACGGACGGTGGTACGAACCGATCAAAAACAT

 9781   TTTTTAGTAGTGACGGAGTTTTGCCATGCTGGCCAGGCTGATCTCAAACTCCTGACCTCA
 9781   AAAAATCATCACTGCCTCAAAACGGTACGACCGGTCCGACTAGAGTTTGAGGACTGGAGT

 9841   GGTGGTCCACCTGCCTCAGCCTCCCAAAGTGTTGGGATTACAGGCGTGAGCCACTGCACC
 9841   CCACCAGGTGGACGGAGTCGGAGGGTTTCACAACCCTAATGTCCGCACTCGGTGACGTGG

 9901   CGGCCATTTAAGCAAATTTTAGTTAAGACCAGTAACATATTTTTGACAGTATTTCCGAAG
 9901   GCCGGTAAATTCGTTTAAAATCAATTCTGGTCATTGTATAAAAACTGTCATAAAGGCTTC

 9961   TGTTGTATTTAATTTAACTAATTGAAAATTATCTATTAAGAAAGCAAGTTAAATGTAATG
 9961   ACAACATAAATTAAATTGATTAACTTTTAATAGATAATTCTTTCGTTCAATTTACATTAC

10021   TGTATACTTCATAGTATACACATTATAATGATTCATAGTAACCATTATATGAAGAGTGTC
10021   ACATATGAAGTATCATATGTGTAATATTACTAAGTATCATTGGTAATATACTTCTCACAG

10081   TAAACTTTTCTTCAAATCTACCATTTATATAGTACAATAATGACCAGCAAACAATGGCTA
10081   ATTTGAAAAGAAGTTTAGATGGTAAATATATCATGTTATTACTGGTCGTTTGTTACCGAT

10141   AGTTTTACTTAATTAGACATTTGTGTAGCTCCTACCAAGGCTACCAGACTTTGTACCCAG
10141   TCAAAATGAATTAATCTGTAAACACATCGAGGATGGTTCCGATGGTCTGAAACATGGGTC

10201   TAACAGGAAAACAGAAATAATTCAAGCATTATTCTCACTCTTGAGAAACAATTCTATTTA
10201   ATTGTCCTTTTGTCTTTATTAAGTTCGTAATAAGAGTGAGAACTCTTTGTTAAGATAAAT

10261   GGGAGATATACATAAAAAGCAAAGGTGGCTGGGTGCAGTGGCTCATGCCTGTAATCCCAG
10261   CCCTCTATATGTATTTTTCGTTTCCACCGACCCACGTCACCGAGTACGGACATTAGGGTC

10321   CACTTTGGGAGGCCAAGGCAGGCAGATCACTTGAGGCCAGGAGTTCGAGACTAGCCTGAC
10321   GTGAAACCCTCCGGTTCCGTCCGTCTAGTGAACTCCGGTCCTCAAGCTCTGATCGGACTG

10381   CAACATGGTGAAACCCTGTTTCTACTAAACATACAAAAATTAGCTGGGTGTGGTGGCATG
10381   GTTGTACCACTTTGGGACAAAGATGATTTGTATGTTTTTAATCGACCCACACCACCGTAC

10441   CACCTGCAATCCCAGCTACTGGGCAGGCTGAGGCAGATAATTGCTTGAACCTGGGAGGTG
10441   GTGGACGTTAGGGTCGATGACCCGTCCGACTCCGTCTATTAACGAACTTGGACCCTCCAC

10501   GAGGCTACAGTGAGCTGAGATTGCACCACTGTACTCCAGCCTGGGTGACAGAGCGAGACT
10501   CTCCGATGTCACTCGACTCTAACGTGGTGACATGAGGTCGGACCCACTGTCTCGCTCTGA

10561   CCATCTCAATGAATAAATAAATAAATAAATAAATAGCAAAGGCAATAATGTGCATATAGT
10561   GGTAGAGTTACTTATTTATTTATTTATTTATTTATCGTTTCCGTTATTACACGTATATCA

10621   AGGTGCTACAGTAGAAGTCTGCACAAGGTTCTGTGTATGTGGAAAAGACAAGTCAGAAAA
10621   TCCACGATGTCATCTTCAGACGTGTTCCAAGACACATACACCTTTTCTGTTCAGTCTTTT

10681   ATTAGGAAAGGCTTTATTGGGAGGTGACATTTAAGCAGAATCACGAAAGAAGACCTGATG
10681   TAATCCTTTCCGAAATAACCCTCCACTGTAAATTCGTCTTAGTGCTTTCTTCTGGACTAC

10741   AACATGGGGGTAAGAGCACTTGTACACAACCCCATACTCCTGGGCTCAGACTCACTTGCT
10741   TTGTACCCCCATTCTCGTGAACATGTGTTGGGGTATGAGGACCCGAGTCTGAGTGAACGA

10801   CATTCCCTAATCATAGAAGACCTTGAGGAAAAGCATGCTGGGGTTCCCTTCCAGCCCACT
10801   GTAAGGGATTAGTATCTTCTGGAACTCCTTTTCGTACGACCCCAAGGGAAGGTCGGGTGA

10861   GGTAAATACAGAGAGGCCTAAGCACCCAACATCCCCCAGGGAATACACCACTGGGACTTA
10861   CCATTTATGTCTCTCCGGATTCGTGGGTTGTAGGGGGTCCCTTATGTGGTGACCCTGAAT

10921   AAGCATTGGCAACCCAGCACCCAGTTAAATTCCCCTTGTCACTGTTTCCACATTGTCCCC
10921   TTCGTAACCGTTGGGTCGTGGGTCAATTTAAGGGGAACAGTGACAAAGGTGTAACAGGGG
```

FIG. 4 (cont'd)

```
10981  ATCACCTTCACTCTCTTGATGCTCTGCATTTTCTCTCTTAACTCGACCCACAGTAGACCC
10981  TAGTGGAAGTGAGAGAACTACGAGACGTAAAAGAGAGAATTGAGCTGGGTGTCATCTGGG

11041  TCCCACTCAAATCTGCCCCCAATAACCTTTGCAACCAATATTACCGCACTACACTTTATC
11041  AGGGTGAGTTTAGACGGGGGTTATTGGAAACGTTGGTTATAATGGCGTGATGTGAAATAG

11101  TTCCCTAAGGGTTTCCTGCTCCTCCTGGTCTTAGGTGAGGTCATTTCTCTGCCAGCCTTT
11101  AAGGGATTCCCAAAGGACGAGGAGGACCAGAATCCACTCCAGTAAAGAGACGGTCGGAAA

11161  AAAGTGGAAGCTGCTCATTTTCTCTGTCCCTCATCCAGGGCTGGAGTGGGACTGATGCCC
11161  TTTCACCTTCGACGAGTAAAAGAGACAGGGAGTAGGTCCCGACCTCACCCTGACTACGGG

11221  TTCACCCTGCCCAGTACTGTTTCCACATGAGACTCCTTGCATAGCATCTGCTCTCTGCTA
11221  AAGTGGGACGGGTCATGACAAAGGTGTACTCTGAGGAACGTATCGTAGACGAGAGACGAT

11281  CTCAGACCAGGAGTCTGTGCTCTCTCTTCCTCTAACCATCATTGGAAGACACCCCAGTCC
11281  GAGTCTGGTCCTCAGACACGAGAGAGAAGGAGATTGGTAGTAACCTTCTGTGGGGTCAGG

11341  CTCTGGCCCCATTATCCACTGTAGATTTTAGCACTTACCTCCTCTCTTCCCTCCCATGTG
11341  GAGACCGGGGTAATAGGTGACATCTAAAATCGTGAATGGAGGAGAGAAGGGAGGGTACAC

11401  CTGTTTTCCCATTTATTTTAAGGTGCATGTGGATGGCCCATTCCCCTTCCTGGCATCTTA
11401  GACAAAAGGGTAAATAAAATTCCACGTACACCTACCGGGTAAGGGGAAGGACCGTAGAAT

11461  ATCCCTTTAATTTCTCATTTCCATTAATTTGCTACATTCCTCATATGCCAGCTACCCCTA
11461  TAGGGAAATTAAAGAGTAAAGGTAATTAAACGATGTAAGGAGTATACGGTCGATGGGGAT

11521  TGGCCATATCCCAGACCTTTGAATCACACACCAAATTCCATCAAGTCCTATGAGTCATTT
11521  ACCGGTATAGGGTCTGGAAACTTAGTGTGTGGTTTAAGGTAGTTCAGGATACTCAGTAAA

11581  TTGGTCCAAGACCTATCTTACATCTATGCAGTGCTATCTATTTTAACAACCATGTGCCCA
11581  AACCAGGTTCTGGATAGAATGTAGATACGTCACGATAGATAAAATTGTTGGTACACGGGT

11641  GTTTAGGCCACTGTCTTCTCTTCACTGAATATATGTGTTCCTGTTTTTTCTCATCCCCAT
11641  CAAATCCGGTGACAGAAGAGAAGTGACTTATATACACAAGGACAAAAAAGAGTAGGGGTA

11701  TTGTTTCCCAGACACAATTTGTTCTCCAGAGCAGAGTGATCACATCAGTCACCTGCTATA
11701  AACAAAGGGTCTGTGTTAAACAAGAGGTCTCGTCTCACTAGTGTAGTCAGTGGACGATAT

11761  AAAACTCCTCAACCCGGTGGGGCATGGTGACTCACAGCCCCAGCACTGTAATCCCAGCAC
11761  TTTTGAGGAGTTGGGCCACCCCGTACCACTGAGTGTCGGGGTCGTGACATTAGGGTCGTG

11821  TTTGGGAGGCTGAGGTGGGAGGATCACTTGAGCACAGGAGGAGCTGAAGTGATCTGTGAT
11821  AAACCCTCCGACTCCACCCTCCTAGTGAACTCGTGTCCTCCTCGACTTCACTAGACACTA

11881  CACGTCACTGCACTCCAGCCTGGGCTACAGAGTGACACCCTATCTCAAAAACAAGCAAAC
11881  GTGCAGTGACGTGAGGTCGGACCCGATGTCTCACTGTGGGATAGAGTTTTTGTTCGTTTG

11941  AAACAAACAAACAAAAACCAACAAAAAATTTTTATTAAGCAAAAAACCTCTTCAACCTC
11941  TTTGTTTGTTTGTTTTTGGTTGTTTTTTAAAAATAATTCGTTTTTTGGAGAAGTTGGAG

12001  TTCCTGTTATGTTTTGAATAAAAGCTAAAGTCCCCACCATGCTCCAGAAGTTCCCAAGGG
12001  AAGGACAATACAAAACTTATTTTCGATTTCAGGGGTGGTACGAGGTCTTCAAGGGTTCCC

12061  ATCTGGTCCTTCTCATCTTTACAGCCTCATCTTGTTTTGCCGTTTCCACCTCCCTCATCC
12061  TAGACCAGGAAGAGTAGAAATGTCGGAGTAGAACAAAACGGCAAAGGTGGAGGGAGTAGG

12121  CCCAAACTCTTTTTCTTCAGGGCCTTTGCACTTGCTGATGCCTCTGCCTGGAAGGTCTTC
12121  GGGTTTGAGAAAAAGAAGTCCCGGAAACGTGAACGACTACGGAGACGGACCTTCCAGAAG

12181  TTCTGATTCCCCATCCAGGGGTGCCTTATCACCCTGCCCTGCCAACCTCAGATTGGATGC
12181  AAGACTAAGGGGTAGGTCCCCACGGAATAGTGGGACGGGACGGTTGGAGTCTAACCTACG

12241  TACTTCCTCAAAGAGACCCTTGGGACTCCCATGTTTCCCAGGCTTTCAGTGCCCTCATCT
12241  ATGAAGGAGTTTCTCTGGGAACCCTGAGGGTACAAAGGGTCCGAAAGTCACGGGAGTAGA

12301  CAACTTGTAATGATTGTATTGGGGTGATTATTTGTATGACTTTGGGATTGATATCTGACT
12301  GTTGAACATTACTAACATAACCCCACTAATAAACATACTGAAACCCTAACTATAGACTGA
```

FIG. 4 (cont'd)

```
12361  CTTCCACTAGACCATACATTTCTTGAGAGCAGAGAGCATATCCAGTTTTTTTACCACTGT
12361  GAAGGTGATCTGGTATGTAAAGAACTCTCGTCTCTCGTATAGGTCAAAAAAATGGTGACA

12421  GCAACCATATGTCGTCCAATGCTTGGCCCATAATAGGGGGTTGGTGAATGTGGTAGGCTG
12421  CGTTGGTATACAGCAGGTTACGAACCGGGTATTATCCCCCAACCACTTACACCATCCGAC

12481  AGTCATAGCCCCCAAGGATGCCCATAGCCTCATCCCCAGAAGCTTTCATGGTAAAAGGGA
12481  TCAGTATCGGGGGTTCCTACGGGTATCGGAGTAGGGGTCTTCGAAAGTACCATTTTCCCT

12541  TTTTGCAGATTGTGATTAAGTTATGGATCTTGAGATGGAGAGATTATCCTTGATTATCTA
12541  AAAACGTCTAACACTAATTCAATACCTAGAACTCTACCTCTCTAATAGGAACTAATAGAT

12601  AATAGGTCCAATATAATCAGTAGCGTCTTTATAAGAGAGAGGCAGAGGGTCAAAAGCAGA
12601  TTATCCAGGTTATATTAGTCATCGCAGAAATATTCTCTCTCCGTCTCCCAGTTTTCGTCT

12661  ATCAGAGAAGGAGATGCCACAGTGGAAGCAAAGGGGTGTGTGTGTATGTGTGTGTGTATG
12661  TAGTCTCTTCCTCTACGGTGTCACCTTCGTTTCCCCACACACACATACACACACACATAC

12721  TGTGTGTGTGTGTGTGAGAGAGAGAGATTGAGATTTAAAGAGCTCCATTACTTGATCTGA
12721  ACACACACACACACACTCTCTCTCTCTAACTCTAAATTTCTCGAGGTAATGAACTAGACT

12781  GGATAAGGATGAGCCAAAGAATGCAGGTGGCTTGTAGAAGCTGGAGAAGCCAAGAAAACA
12781  CCTATTCCTACTCGGTTTCTTACGTCCACCGAACATCTTCGACCTCTTCGGTTCTTTTGT

12841  TTCTCACTCTAGAGCCTCCAGAAGGAATGCAGCTCTGCTGACACCTTGATTTGGAACTTC
12841  AAGAGTGAGATCTCGGAGGTCTTCCTTACGTCGAGACGACTGTGGAACTAAACCTTGAAG

12901  CAGAACCATAAGATAATAATTTTGTGTAGTTTTGAGGCTGGGCTCATGCCTGTAATTCCA
12901  GTCTTGGTATTCTATTATTAAAACACATCAAAACTCCGACCCGAGTACGGACATTAAGGT

12961  GCACTTTGGGAGGCCAAGGTGGGTGGATCACTTGAGGTCAGGAGTTTGAGACTAGCCTGG
12961  CGTGAAACCCTCCGGTTCCACCCACCTAGTGAACTCCAGTCCTCAAACTCTGATCGGACC

13021  CCAACATGGTGAAACCCTGTATGTACTAAATATACAAAAATTAGCCAGGTGTGGTGGTGC
13021  GGTTGTACCACTTTGGGACATACATGATTTATATGTTTTTAATCGGTCCACACCACCACG

13081  ACGCCTATAGACCCAACTACTTGGGAAGCTGGGGCAGGAGAATCACTTGAACCCGGGAGG
13081  TGCGGATATCTGGGTTGATGAACCCTTCGACCCCGTCCTCTTAGTGAACTTGGGCCCTCC

13141  TAGAGATTGCAGTAAGCTAAGATTGTGCCACTGCACTCCAGCCTGGGCTACAGCGTGAGA
13141  ATCTCTAACGTCATTCGATTCTAACACGGTGACGTGAGGTCGGACCCGATGTCGCACTCT

13201  CTTCGTCAGAAAAAAAGAATAATTTTGTATAATTTCAGGCCACAAAGTCTGCAGTCATCT
13201  GAAGCAGTCTTTTTTTCTTATTAAAACATATTAAAGTCCGGTGTTTCAGACGTCAGTAGA

13261  GTTACAACAGCAGTAGTACACGAATACAGATTTTGGTACCTGGAAATGGTGTGCTACTGT
13261  CAATGTTGTCGTCATCATGTGCTTATGTCTAAAACCATGGACCTTTACCACACGATGACA

13321  AACAGATACCTAAACAATGTGGAAGTGGCTTTTGAATTGGGTGTTGGGCAGCATGTGGAA
13321  TTGTCTATGGATTTGTTACACCTTCACCGAAAACTTAACCCACAACCCGTCGTACACCTT

13381  GAATTTTGAGAAGCATGATAGGAAAAGCCTAGCTTGCCTTAGAAAGACTGTTAGTAGAAG
13381  CTTAAAACTCTTCGTACTATCCTTTTCGGATCGAACGGAATCTTTCTGACAATCATCTTC

13441  TAGGGATGTTAAAGGCGCTGCTGGTGAGGACTTGGAAGTGAAGAGCATGGTAAAGAAAAT
13441  ATCCCTACAATTTCCGCGACGACCACTCCTGAACCTTCACTTCTCGTACCATTTCTTTTA

13501  GTGTTTCATTTTAGAGAATATCAAAGTCATTGTAGAAGGTTGGCAGAAGTGTAGGTTTTC
13501  CACAAAGTAAAATCTCTTATAGTTTCAGTAACATCTTCCAACCGTCTTCACATCCAAAAG

13561  ATAATGTGTTGTTGGTGAGGGCTGAGAAAGAAATGAGGACCATGTTTAGGGAAACTGGAG
13561  TATTACACAACAACCACTCCCGACTCTTTCTTTACTCCTGGTACAAATCCCTTTGACCTC

13621  GAAAAAGATCCTTGTCATACAGTGGAATGAAACTGTGGAATTGTGTCTTACAGTTATATG
13621  CTTTTTCTAGGAACAGTATGTCACCTTACTTTGACACCTTAACACAGAATGTCAATATAC

13681  GGAAGCAGAATTTGTTTGAACTTGGATATTTGGCTTAGCTTTCCAAGTAAAGTATTGAAG
13681  CCTTCGTCTTAAACAAACTTGAACCTATAAACCGAATCGAAAGGTTCATTTCATAACTTC
```

FIG. 4 (cont'd)

```
13741  GTGTAGCCTGGTTTTCTCTTGCTGTTTTATAGTAAAATGCCCGAGAAAAAGGGATAAATT
13741  CACATCGGACCAAAAGAGAACGACAAAATATCATTTTACGGGCTCTTTTTCCCTATTTAA

13801  GAGGTAGGAACTGTTAAGAAAAAGGAACAAAGACATGATGACTTGGGAAATTCTCAGGAT
13801  CTCCATCCTTGACAATTCTTTTTCCTTGTTTCTGTACTACTGAACCCTTTAAGAGTCCTA

13861  ACCTGGTTTGTAAAAGATGCTAGAATTAGAAGATTCATTGTCAGGAAAGTGTGCTCTGGA
13861  TGGACCAAACATTTTCTACGATCTTAATCTTCTAAGTAACAGTCCTTTCACACGAGACCT

13921  GAGGAAGCCAAGGGTGAGTTCCTTGTGGCGTAGGTTAGGGGCTGTGGCAGGGATGCAGGG
13921  CTCCTTCGGTTCCCACTCAAGGAACACCGCATCCAATCCCCGACACCGTCCCTACGTCCC

13981  AAGAGATGATGGTGACTTGGACTAGGGGTCTGACGGGGTATGGGAAAATAGAGAGGAATG
13981  TTCTCTACTACCACTGAACCTGATCCCCAGACTGCCCCATACCCTTTTATCTCTCCTTAC

14041  AGTTGATTCTGTTGGGACTTTGTATTGAGTTCCTTGATTCCATAAGTGGAAACACATGTA
14041  TCAACTAAGACAACCCTGAAACATAACTCAAGGAACTAAGGTATTCACCTTTGTGTACAT

14101  GAGCTCTCTTTCCTGGCCACCTAAGCTCTCTGACCATATCCCTGACTCTCTCCAGAATGC
14101  CTCGAGAGAAAGGACCGGTGGATTCGAGAGACTGGTATAGGGACTGAGAGAGGTCTTACG

14161  CTTGGCTTCATGTCCACGTGAGGACAAATCATATTTTTCTGCATTTTGCGTGCTGGATTC
14161  GAACCGAAGTACAGGTGCACTCCTGTTTAGTATAAAAAGACGTAAAACGCACGACCTAAG

14221  CTCTCTGGACTAAAGATCCAATGAGAGGTGGTTTCTAGCTTTCTGCTCTTTCCCACAACA
14221  GAGAGACCTGATTTCTAGGTTACTCTCCACCAAAGATCGAAAGACGAGAAAGGGTGTTGT

14281  CTCCGTCAGTGAGTCTTCTGGATGTCCTATAGGCAACTCACTGGATCCACTTGGTCTGTG
14281  GAGGCAGTCACTCAGAAGACCTACAGGATATCCGTTGAGTGACCTAGGTGAACCAGACAC

14341  GAAGAATCACTACCACATCCATTTCACCTTGGGCACAGACTAGAAGGTGAGGCAGTCATG
14341  CTTCTTAGTGATGGTGTAGGTAAAGTGGAACCCGTGTCTGATCTTCCACTCCGTCAGTAC

14401  TCCTGCAGTCACTGGGTAGCTTACAAGTGCTAATACAGCAATAGCTTAATTAGAGAGAGA
14401  AGGACGTCAGTGACCCATCGAATGTTCACGATTATGTCGTTATCGAATTAATCTCTCTCT

14461  GAGAAGAAGAAGAATGTTATGGAGCCTGTTTCTAGAGAGGAAACCACAATATCTTGATCA
14461  CTCTTCTTCTTCTTACAATACCTCGGACAAAGATCTCTCCTTTGGTGTTATAGAACTAGT

14521  AGAGACCCTAAAACTGGAAGAACCAGAGCAGCTGGTATCAAAATGTGGAAAAAACTGAGA
14521  TCTCTGGGATTTTGACCTTCTTGGTCTCGTCGACCATAGTTTTACACCTTTTTTGACTCT

14581  TGTGGCAAGTGGTACAACTGATAGCCAAGGAGGAAAAATTTGTATCCCCCTGTAATCCCA
14581  ACACCGTTCACCATGTTGACTATCGGTTCCTCCTTTTTAAACATAGGGGGACATTAGGGT

14641  GCACTTTGGGAGGCTGAAACAGGTGGATCACCTGAGGTCAGGAGTTCGAGACCAGCCTGG
14641  CGTGAAACCCTCCGACTTTGTCCACCTAGTGGACTCCAGTCCTCAAGCTCTGGTCGGACC

14701  CCAATATGGTGAAACCCTGTCTCTACTAAAAATACAAAAATTAGCTGGGCGTGGTGGTGT
14701  GGTTATACCACTTTGGGACAGAGATGATTTTTATGTTTTTAATCGACCCGCACCACCACA

14761  GCACCTATAGTCCCAGCTACTTGGGAGGCTGAGGCAGGAAAATTGCTTGAACCTGGGAGC
14761  CGTGGATATCAGGGTCGATGAACCCTCCGACTCCGTCCTTTTAACGAACTTGGACCCTCG

14821  AGAGGTTGCAGTGAGCCAAGATCGCACCACTGCACTCCAGCCTGGGTGACAAGAGTTAAA
14821  TCTCCAACGTCACTCGGTTCTAGCGTGGTGACGTGAGGTCGGACCCACTGTTCTCAATTT

14881  CTCTGTCTCAAAAAAATAAAAAGAAAAGTTTGTACCCTCTTCTTTTCTCTTGCCTCAGGA
14881  GAGACAGAGTTTTTTTATTTTTCTTTTCAAACATGGGAGAAGAAAAGAGAACGGAGTCCT

14941  TAACTGAGATTCTTATAATGCATTTATTGAACAAATATTTGAGGAGTACTCATTATGTAA
14941  ATTGACTCTAAGAATATTACGTAAATAACTTGTTTATAAACTCCTCATGAGTAATACATT

15001  GCATCAGACACTGCTCAAGGTCTTGAGGCTGTGAGGGTGTATTAGTCCGTTTTCACACTG
15001  CGTAGTCTGTGACGAGTTCCAGAACTCCGACACTCCCACATAATCAGGCAAAAGTGTGAC

15061  CTATAAAGAACTACCTGAGACTGGGTGATTTATAAAGAAAAGAGGTTTAACTGAATTACA
15061  GATATTTCTTGATGGACTCTGACCCACTAAATATTTCTTTTCTCCAAATTGACTTAATGT
```

FIG. 4 (cont'd)

```
15121   GTTCATCATGGCCAGAAAGGCCTCAGGAAACTTACAATCATGGCAGAAGGTGAAGAGGAA
15121   CAAGTAGTACCGGTCTTTCCGGAGTCCTTTGAATGTTAGTACCGTCTTCCACTTCTCCTT

15181   GCAAGGCACATCTTACATGGTGGCAGGAGACACAGTGAGAAGGGAGAAGTGCCACACTTT
15181   CGTTCCGTGTAGAATGTACCACCGTCCTCTGTGTCACTCTTCCCTCTTCACGGTGTGAAA

15241   TAAACCATCAGATCTTATGATGATATAGGAGTTAAGAAGAAATCACTTAGGTAGATAGTG
15241   ATTTGGTAGTCTAGAATACTACTATATCCTCAATTCTTCTTTAGTGAATCCATCTATCAC

15301   AGGGTACGGGAGTCCTTGGTAAGGCTTTTCTTTTAAATGAAAAGCAGCCCCACACATAGA
15301   TCCCATGCCCTCAGGAACCATTCCGAAAAGAAAATTTACTTTTCGTCGGGGTGTGTATCT

15361   CAAGCAAGCTGGGAGCTTGCACGGGTGAATGCCGGCAGAAACTAGGAACCAGACACGTTA
15361   GTTCGTTCGACCCTCGAACGTGCCCACTTACGGCCGTCTTTGATCCTTGGTCTGTGCAAT

15421   AGATGGCGGCTCCATTTTCCCTTCTCTGCCAGCCAAGTGTACAGTAAGGAGCAGACAAGC
15421   TCTACCGCCGAGGTAAAAGGGAAGAGACGGTCGGTTCACATGTCATTCCTCGTCTGTTCG

15481   TGGTGCCGGCCAAGAGGAGAATTCATGTGCATAATAAGATTAGGGTGGGGTGACCAGCCT
15481   ACCACGGCCGGTTCTCCTCTTAAGTACACGTATTATTCTAATCCCACCCCACTGGTCGGA

15541   TCCCAGTGCGCTATGTGAACATCATACCTGATTGAACCAATCTGTGAGCCCTATGTAAAT
15541   AGGGTCACGCGATACACTTGTAGTATGGACTAACTTGGTTAGACACTCGGGATACATTTA

15601   CAGACACCACCTCCTCAAGCCTGACTATAAAATCTGGTGCATTCGCCACCCGCCGGTGTT
15601   GTCTGTGGTGGAGGAGTTCGGACTGATATTTTAGACCACGTAAGCGGTGGGCGGCCACAA

15661   TCCTCTCAGAAGTCCCCTCTCTCTCATTAGAGAGAGGGCTGTTTTCCTTTCTCCTTCTTC
15661   AGGAGAGTCTTCAGGGGAGAGAGAGTAATCTCTCTCCCGACAAAAGGAAAGAGGAAGAAG

15721   TGCCTATTAACCTGTGCTCCTAAACTCCCTGTGTGTGTCTGTTCTGAATTTTCCCGGCAT
15721   ACGGATAATTGGACACGAGGATTTGAGGGACACACACAGACAAGACTTAAAAGGGCCGTA

15781   GAGAGGATGAACCTGGGGTATATACCCCAGAAAACATAGCCACTTAAGTGAGAACTCACT
15781   CTCTCCTACTTGGACCCCATATATGGGGTCTTTTGTATCGGTGAATTCACTCTTGAGTGA

15841   CACTATTCACCCCCAAGATCCAATCACCTTCGACCAGGTTCCTCCCCTGGCGTGAGGGGA
15841   GTGATAAGTGGGGGTTCTAGGTTAGTGGAAGCTGGTCCAAGGAGGGGACCGCACTCCCCT

15901   TTAAAATTCCACATGAGGTTTGAGTAGGGACACAGAGCCAAACCAAACCATATCAGAGGG
15901   AATTTTAAGGTGTACTCCAAACTCATCCCTGTGTCTCGGTTTGGTTTGGTATAGTCTCCC

15961   TGAAGAGCAGGTAAAGTTGCAGCTCTCCTGCAACTTGCAGGGAAAGGCCATATAACACAT
15961   ACTTCTCGTCCATTTCAACGTCGAGAGGACGTTGAACGTCCCTTTCCGGTATATTGTGTA

16021   GGTTATGAGCACAAACTGGGACTGGACTGCAGGTGTGTGAGCCCCAGCTTTGCTATTGAG
16021   CCAATACTCGTGTTTGACCCTGACCTGACGTCCACACACTCGGGGTCGAAACGATAACTC

16081   TGACCACCAGCAAGTTATTAAACTGTGCCTCAGTTTTTTGTTTATGAAATGGTGGTATT
16081   ACTGGTGGTCGTTCAATAATTTGACACGGAGTCAAAAAAACAAATACTTTACCACCATAA

16141   AGTACAACCCACCTCTCATGGATGATGTGAGGATTAAATAAAATAACATGTTGCCAGGCA
16141   TCATGTTGGGTGGAGAGTACCTACTACACTCCTAATTTATTTTATTGTACAACGGTCCGT

16201   CAGTGGTGCACACCTGTAATCTCGGCACATTGGGAGGCTGAGGCCCGAGGGTTACTTGAG
16201   GTCACCACGTGTGGACATTAGAGCCGTGTAACCCTCCGACTCCGGGCTCCCAATGAACTC

16261   GTTAGAAGCCTGAGACCTGCCTGGCCAACATAGCGAAACCTCATCTCTGCTTAAAATACA
16261   CAATCTTCGGACTCTGGACGGACCGGTTGTATCGCTTTGGAGTAGAGACGAATTTTATGT

16321   AAAAAAAAAAAAAAAAAAAAAAAAAAAAAAGGCCAGGCGTGGTGGCTCATGCTTGTAATC
16321   TTTTTTTTTTTTTTTTTTTTTTTTTTTTTTCCGGTCCGCACCACCGAGTACGAACATTAG

16381   CCAGCACTTTGGGAGGCCGAGGCGGGTGGATCACAAGGTCAGGAGTTTGAGACCAGCCTG
16381   GGTCGTGAAACCCTCCGGCTCCGCCCACCTAGTGTTCCAGTCCTCAAACTCTGGTCGGAC

16441   GCCAATATGGTGAATCCCCGTCTCTACTAAAAATACAAAAATTAGCCAAGTGTGGTGGTG
16441   CGGTTATACCACTTAGGGGCAGAGATGATTTTTATGTTTTTAATCGGTTCACACCACCAC
```

FIG. 4 (cont'd)

```
16501  GGCACCTGTAGTCCCAGCTACTCGGGAGGCTGAGGCAGGAGAATCACTTGAACCTGGGAG
16501  CCGTGGACATCAGGGTCGATGAGCCCTCCGACTCCGTCCTCTTAGTGAACTTGGACCCTC

16561  GCAGAAGTTGCAGTGAGCCGAGGTTGCGCCACTGCACTCCAGCCTGGGCGACGGAGCGAG
16561  CGTCTTCAACGTCACTCGGCTCCAACGCGGTGACGTGAGGTCGGACCCGCTGCCTCGCTC

16621  ACTCCATCTCAAAACAAAACAAAAAAACCAAAAAAATTAACCAGGCATGGTGGCACACAC
16621  TGAGGTAGAGTTTTGTTTTGTTTTTTTGGTTTTTTTAATTGGTCCGTACCACCGTGTGTG

16681  CTGTAATCCCAGCTACTCAGGAGGCTGAGGCAGGAGAATCACTTGAACCCAGGAGGTGGA
16681  GACATTAGGGTCGATGAGTCCTCCGACTCCGTCCTCTTAGTGAACTTGGGTCCTCCACCT

16741  GGTTGCAGTGAGTTAAGATTGTGCCACTGCACTCCAGCCTGTGCGATAGAAGGAGACAGT
16741  CCAACGTCACTCAATTCTAACACGGTGACGTGAGGTCGGACACGCTATCTTCCTCTGTCA

16801  CTGCAACAAAGATCCAAAAACAAATATAAAGCACTTATAACAGGGTCTGGTCTGAAATAA
16801  GACGTTGTTTCTAGGTTTTTGTTTATATTTCGTGAATATTGTCCCAGACCAGACTTTATT

16861  GTACTATGTAAGTACTGTAAGTATTAACTAATATTATTACAATTTATCCTCATATAGTAA
16861  CATGATACATTCATGACATTCATAATTGATTATAATAATGTTAAATAGGAGTATATCATT

16921  CATATCAAATATTTTCAGTCAGTGATGCAATATGAATAAAATGAAATGATGCAGTAGTGA
16921  GTATAGTTTATAAAAGTCAGTCACTACGTTATACTTATTTTACTTTACTACGTCATCACT

16981  CAGAACTGAGAGAAAGCTGGTACAAATTTATACTGACTGGTCAGGGAAAGCTTCACAGAA
16981  GTCTTGACTCTCTTTCGACCATGTTTAAATATGACTGACCAGTCCCTTTCGAAGTGTCTT

17041  AAGGTGAACTTTCAGCTGACACCTGAGTACCATGGTCTGGAGGTAAGAGTGTCCCATGCA
17041  TTCCACTTGAAAGTCGACTGTGGACTCATGGTACCAGACCTCCATTCTCACAGGGTACGT

17101  TATGGAACAGCAAATGAAACTTCCCAGAGCATAATCTGAGAGGGGAGATTTCAGGAGTGG
17101  ATACCTTGTCGTTTACTTTGAAGGGTCTCGTATTAGACTCTCCCCTCTAAAGTCCTCACC

17161  AGCCACATCATTGAAGTTCCTTAGTCCTGGTAAGTGTGGATTTTATTCTAAGTGTGGTGA
17161  TCGGTGTAGTAACTTCAAGGAATCAGGACCATTCACACCTAAAATAAGATTCACACCACT

17221  AATGCCCCTGAGAGGTTTTGAGTAGTAGATGGAATTCCATTTTTAAAAGTCACTGGTGAG
17221  TTACGGGGACTCTCCAAAACTCATCATCTACCTTAAGGTAAAAATTTTCAGTGACCACTC

17281  TCAAGTAGTGTACTATGGTTACATTTTTTTCCCCTTATACCTCATTTTGTTTTTCCTGCA
17281  AGTTCATCACATGATACCAATGTAAAAAAAGGGGAATATGGAGTAAAACAAAAAGGACGT

17341  GTTAATTCTTGCATTATTTCCTTTTATTTACTTACCTTACTATATATTTATTATGAATTC
17341  CAATTAAGAACGTAATAAAGGAAAATAAATGAATGGAATGATATATAAATAATACTTAAG

17401  TTTCCAATTCCCAACTTCCTGACAGCCTCTCAATGTAATTTTACTTAGGTTAAATGTATC
17401  AAAGGTTAAGGGTTGAAGGACTGTCGGAGAGTTACATTAAAATGAATCCAATTTACATAG

17461  TGACAGTTCATTTTCTTTTTTGTCTCTGTACTCTTTCTGCTACCATTCTCATTCTTGCAC
17461  ACTGTCAAGTAAAAGAAAAAACAGAGACATGAGAAAGACGATGGTAAGAGTAAGAACGTG

17521  TAATTTGTGCTGGTTTCTCTCTGAGCCAGCTGCACAGCTGCCTGCCTAAGACTTCCTCTT
17521  ATTAAACACGACCAAAGAGAGACTCGGTCGACGTGTCGACGGACGGATTCTGAAGGAGAA

17581  GGCATCTTTTACCCTCTCTCTGTGTTACATCCCCGGTTTTCTGAATCGTGTGGCGTTCTC
17581  CCGTAGAAAATGGGAGAGAGACACAATGTAGGGGCCAAAAGACTTAGCACACCGCAAGAG

17641  CTTTTTACTTTACTTCCTCATTTGTGTTGCACGTATGCTCTAGTTGTTTTTAGATAAAGA
17641  GAAAAATGAAATGAAGGAGTAAACACAACGTGCATACGAGATCAACAAAAATCTATTTCT

17701  GTGCATCAGAGGTAGATGTTTTGATTCCTTACATGCCTGACTTTTTGTTCTACTTTTGCT
17701  CACGTAGTCTCCATCTACAAAACTAAGGAATGTACGGACTGAAAAACAAGATGAAAACGA

17761  CTAGGTTAATACTTGATTTTGAATAATATCCTAGGTTAGAAATGATTTTTCGTCAGAATT
17761  GATCCAATTATGAACTAAAACTTATTATAGGATCCAATCTTTACTAAAAAGCAGTCTTAA

17821  TTAAGGGAATTGCTTTTCTGTTGTCTAGTTTCCTGTGTTACTGATAGGAAGTCCAAAGGG
17821  AATTCCCTTAACGAAAAGACAACAGATCAAAGGACACAATGACTATCCTTCAGGTTTCCC
```

FIG. 4 (cont'd)

```
17881  GCTCGTATTTCAGGTCCTTTTTATGTGTAACCTGTTTTTTGTTCCTTGAGGTATTCAGGG
17881  CGAGCATAAAGTCCAGGAAAAATACACATTGGACAAAAAACAAGGAACTCCATAAGTCCC

17941  TCTCTTTTTATTGCTAATTTGGGGAGCTTTATCATAACATGGGTCCTTAGTCATTCATCC
17941  AGAGAAAAATAACGATTAAACCCCTCGAAATAGTATTGTACCCAGGAATCAGTAAGTAGG

18001  TAGAAAATTTTCCTTTCCTATATCTTTGATGATTTCGTCTCCTCTGCTTTCCCTCTTTTC
18001  ATCTTTTAAAAGGAAAGGATATAGAAACTACTAAAGCAGAGGAGACGAAAGGGAGAAAAG

18061  TCATTCTTAAACTTCTATTTGTTTGACATTAGACCTCCTTGTTTGATCTTCTAATTTAAT
18061  AGTAAGAATTTGAAGATAAACAAACTGTAATCTGGAGGAACAAACTAGAAGATTAAATTA

18121  TTTTCTCTCCTAGTGTCCAATTTTTGAGGTGGGAGAAAGATCTCATCAATGTTATCTTTC
18121  AAAAGAGAGGATCACAGGTTAAAAACTCCACCCTCTTTCTAGAGTAGTTACAATAGAAAG

18181  AGCCTTTCCCCTGAATTTTAAAATTTTACTCTTCATATTTCTTCTGATTAATCCTTTAAA
18181  TCGGAAAGGGGACTTAAAATTTTAAAATGAGAAGTATAAAGAAGACTAATTAGGAAATTT

18241  AAAATAGCATCCTGGGCCAGGTGCAGTGGCTCACACCTGTAATCCCAGCACTTTGGAAGG
18241  TTTTATCGTAGGACCCGGTCCACGTCACCGAGTGTGGACATTAGGGTCGTGAAACCTTCC

18301  CTGAGCGGGGAGTGGATCACCTGAGGTCAGGAGCTCAAGACCAGTCTGGCCAACATGATG
18301  GACTCGCCCCTCACCTAGTGGACTCCAGTCCTCGAGTTCTGGTCAGACCGGTTGTACTAC

18361  AAACCCTGTCTCTACTAAAAATACAAAAACTTAGCCAGGCGTGGTGGTGGGCTCCTGTAG
18361  TTTGGGACAGAGATGATTTTTATGTTTTTGAATCGGTCCGCACCACCACCCGAGGACATC

18421  TCCCAGCTACTTGGGAGGCTGAGACAGGAGAATCACCAGAACCTGGGAGGTGGAGGTTGT
18421  AGGGTCGATGAACCCTCCGACTCTGTCCTCTTAGTGGTCTTGGACCCTCCACCTCCAACA

18481  AGTGAGCTGAGATTGTGTGCCATTGTACTCCAACCTGGGTGACAGAGCAAGACTCTATCT
18481  TCACTCGACTCTAACACACGGTAACATGAGGTTGGACCCACTGTCTCGTTCTGAGATAGA

18541  CAAAAAAAAAAAAAAAAAAAAAAGGGCCCTGTTCCACTGAGGCTTCAGTGCGGAGCATGG
18541  GTTTTTTTTTTTTTTTTTTTTTTCCCGGGACAAGGTGACTCCGAAGTCACGCCTCGTACC

18601  AGGGATACTACCTCCAAATTCCAAACACGTTTGACACATCTAAAGAACCTTCTAAAGGAT
18601  TCCCTATGATGGAGGTTTAAGGTTTGTGCAAACTGTGTAGATTTCTTGGAAGATTTCCTA

18661  GACTAAACTAATTCTGCAAGCTTTAGCCTCTAACTTATCTCCAATTTATATTTAATAGAA
18661  CTGATTTGATTAAGACGTTCGAAATCGGAGATTGAATAGAGGTTAAATATAAATTATCTT

18721  GGCTGGAAATTGAACAGAAAGGAAATAAGATTATTTGGAAATAAAAAATTGTCAGCCAAG
18721  CCGACCTTTAACTTGTCTTTCCTTTATTCTAATAAACCTTTATTTTTTAACAGTCGGTTC

18781  CAAGGAGAGCTTGGCATTTCTGGAAACTTCTTTACCCTGGAAGAGGTAAAAAAGTGATTC
18781  GTTCCTCTCGAACCGTAAAGACCTTTGAAGAAATGGGACCTTCTCCATTTTTTCACTAAG

18841  TCCCATTCCCCCAACAGGGCATTCACTAAAAATTAAGTGAGAAATGCTTTGCCTAGAGGA
18841  AGGGTAAGGGGGTTGTCCCGTAAGTGATTTTTAATTCACTCTTTACGAAACGGATCTCCT

18901  TCTGTAGCTTGCGAACACTTGACTTGTGCCACTGGTGTACGGAACATAGCAGTGTCAGCT
18901  AGACATCGAACGCTTGTGAACTGAACACGGTGACCACATGCCTTGTATCGTCACAGTCGA

18961  CTGCCCTGGGACAGTCAAGGCTGGCTGGTGCTGCCTGTGGTTAGAGTCAAGAGAGGGGTC
18961  GACGGGACCCTGTCAGTTCCGACCGACCACGACGGACACCAATCTCAGTTCTCTCCCCAG

19021  TTCAGTGGGTGCAGTTTGCAGTTCCAGAGTTTAGTAGAGCAAAGACGTCATGAACTATGT
19021  AAGTCACCCACGTCAAACGTCAAGGTCTCAAATCATCTCGTTTCTGCAGTACTTGATACA

19081  GAACTCTGAGGAAAGGTGTCATAGAAACACCTCAAAAGGACACTGTCTAAGAAGGCTACT
19081  CTTGAGACTCCTTTCCACAGTATCTTTGTGGAGTTTTCCTGTGACAGATTCTTCCGATGA

19141  TGCTGGGGCAAGGAGACCCCAGGGGTCAGAGGCTGTGTAGGGAATAATGCCAGAGCTGGG
19141  ACGACCCCGTTCCTCTGGGGTCCCCAGTCTCCGACACATCCCTTATTACGGTCTCGACCC

19201  GTTGAAGGAGAATCCTTAGAGGTGAGACAGAATGTGCATCATTGCAGTGGGGCTGTGCAA
19201  CAACTTCCTCTTAGGAATCTCCACTCTGTCTTACACGTAGTAACGTCACCCCGACACGTT
```

FIG. 4 (cont'd)

```
19261  GGCAGTGGTCTCCACAGGAGGTGAGGACAAGGGGGAGGGGAGGTTGTGAAGAATCCGTAA
19261  CCGTCACCAGAGGTGTCCTCCACTCCTGTTCCCCCTCCCCTCCAACACTTCTTAGGCATT

19321  GTGACCATGATGCAATAGAAAGCCAGAATTTGGGCATTTGCCATAGGAGAGGGCCCCCAG
19321  CACTGGTACTACGTTATCTTTCGGTCTTAAACCCGTAAACGGTATCCTCTCCCGGGGGTC

19381  TGCCAGATTATAATGGTCACAGACAAATGAGATTTTTAACCATTTCCTCTAATTCATGGT
19381  ACGGTCTAATATTACCAGTGTCTGTTTACTCTAAAAATTGGTAAAGGAGATTAAGTACCA

19441  CCACACTTAACCCCGTGGGTCCTGGAAACAGCAGCTGGAGAATGGAGAGGAAAGTGATGT
19441  GGTGTGAATTGGGGCACCCAGGACCTTTGTCGTCGACCTCTTACCTCTCCTTTCACTACA

19501  GGGAGAGAGAAAACTTTCTTTACCCTTTTCATAACTGAGTTTATGAAGTAAACTGACAGT
19501  CCCTCTCTCTTTTGAAAGAAATGGGAAAAGTATTGACTCAAATACTTCATTTGACTGTCA

19561  AGAAAGATAAATAGGAGAAAAGACATAAATTTATTTTGTGCGTACACATGGGAGTCCCAT
19561  TCTTTCTATTTATCCTCTTTTCTGTATTTAAATAAAACACGCATGTGTACCCTCAGGGTA

19621  AAAATATGAGACTCAAAGAAAGGCCAGATGATTGAAGTTTATATAGTATTCCTGAGCTAC
19621  TTTTATACTCTGAGTTTCTTTCCGGTCTACTAACTTCAAATATATCATAAGGACTCGATG

19681  AGAAAAGGAATCAGGGCTTGGGGCTTATTGAGGGGAGGTGGTGACAGGTTATAAGAGGGT
19681  TCTTTTCCTTAGTCCCGAACCCCGAATAACTCCCCTCCACCACTGTCCAATATTCTCCCA

19741  GAGGAGAGGAAGTGTATAGCAAGCATAGGTTGTCTTGTTATGCAGATAAAAAGTCTCTCA
19741  CTCCTCTCCTTCACATATCGTTCGTATCCAACAGAACAATACGTCTATTTTTCAGAGAGT

19801  GGTGATAAAAGTTGTCTCAGAGTCCCCCATCAGAAGAATAGGTAATAGCCTGTGACAAGG
19801  CCACTATTTTCAACAGAGTCTCAGGGGGTAGTCTTCTTATCCATTATCGGACACTGTTCC

19861  TCTACCTGTCCAATCTTCTCCCTGGTGATAAAATCTTCCCTGGTTGATGAGATTCTTATC
19861  AGATGGACAGGTTAGAAGAGGGACCACTATTTTAGAAGGGACCAACTACTCTAAGAATAG

19921  AAAGTTTTTTTCTTTATAGATATAAATTTTGTTTACAAAAAGACAGTTTTTCAGAGCTAC
19921  TTTCAAAAAAAGAAATATCTATATTTAAAACAAATGTTTTTCTGTCAAAAAGTCTCGATG

19981  TCCTGTGTCTACAGTGTCTCAGAATAACTAACTGGAAATACATCAAATAAGCATATCCTG
19981  AGGACACAGATGTCACAGAGTCTTATTGATTGACCTTTATGTAGTTTATTCGTATAGGAC

20041  ATGTGGCATATTCTGGTCATATTTTGGGATGGTGCGTCCTGAGCTCCAATGCTGAAAAAA
20041  TACACCGTATAAGACCAGTATAAAACCCTACCACGCAGGACTCGAGGTTACGACTTTTTT

20101  CAGGAACCCCATTTCTGTTGGATGTGCCAACCTAAAATAATCAAAAGGGTCAGAATCTAG
20101  GTCCTTGGGGTAAAGACAACCTACACGGTTGGATTTTATTAGTTTTCCCAGTCTTAGATC

20161  TTTAAAGATACTTTATTCAAGTGCAAAGTTTAAGGACAGTGCTAGGGAAACACGGATCCC
20161  AAATTTCTATGAAATAAGTTCACGTTTCAAATTCCTGTCACGATCCCTTTGTGCCTAGGG

20221  AAAGAATGGAAGTCAGCGTTCTGAACTTTAGAAGTTTGGGATTGTTTATAGAGAGAGAGT
20221  TTTCTTACCTTCAGTCGCAAGACTTGAAATCTTCAAACCCTAACAAATATCTCTCTCTCA

20281  TTAGGGAAGCTTAACAGAATTTCAACATCTTTCTGTGTAAGGCTTAATGCCTAGTTACAA
20281  AATCCCTTCGAATTGTCTTAAAGTTGTAGAAAGACACATTCCGAATTACGGATCAATGTT

20341  TGATCTGATTAGTCAAGGTGGTCACTTTCATTTGAGAAAGGCATATTTAACATTTCACGG
20341  ACTAGACTAATCAGTTCCACCAGTGAAAGTAAACTCTTTCCGTATAAATTGTAAAGTGCC

20401  GCTGGGAGCGGTGGTTCATGCCTGTAATCTCAGCACTTTGGGAGGCCGAGGCGGGCAGAT
20401  CGACCCTCGCCACCAAGTACGGACATTAGAGTCGTGAAACCCTCCGGCTCCGCCCGTCTA

20461  CATCTGAGGTCAGGAGTTCGAGGCCAGCCTGGCCAATATGGGGAAACCCCTTCTCTACTA
20461  GTAGACTCCAGTCCTCAAGCTCCGGTCGGACCGGTTATACCCCTTTGGGGAAGAGATGAT

20521  AAAATACAATACAATAAAATAAAATAAAATAAAAAAAATTAGCCGGGCATGGTGCACGTG
20521  TTTTATGTTATGTTATTTTATTTTATTTTATTTTTTTTAATCGGCCCGTACCACGTGCAC

20581  CCTGTAATCCCAGCTACTTGGGAAGCTGAGGCAGGAGAATTGCTTGAACCTGGGAGGCAG
20581  GGACATTAGGGTCGATGAACCCTTCGACTCCGTCCTCTTAACGAACTTGGACCCTCCGTC
```

FIG. 4 (cont'd)

```
20641  AGGTTGTGGTGAGCTGAGATTGCACCATTGCACTCCAGCCTGGGCAACAAGAATGAAACT
20641  TCCAACACCACTCGACTCTAACGTGGTAACGTGAGGTCGGACCCGTTGTTCTTACTTTGA

20701  CCATCTCAAACAACAACAACAACAACAACAACAACAACAACAACAACAACAACAAACATT
20701  GGTAGAGTTTGTTGTTGTTGTTGTTGTTGTTGTTGTTGTTGTTGTTGTTGTTGTTTGTAA

20761  TCACACTGAAGGTGTAACAGTCATGGGTTTGTATTTTCGTTTTTCTTGGTTTTTTTTTTT
20761  AGTGTGACTTCCACATTGTCAGTACCCAAACATAAAAGCAAAAAGAACCAAAAAAAAAAA

20821  TTTTTTTGAGACTGTCTCGCTCTGTATTGCAGGCTGGCATGGCACAATCACAGCTCGCTG
20821  AAAAAAACTCTGACAGAGCGAGACATAACGTCCGACCGTACCGTGTTAGTGTCGAGCGAC

20881  CAGCTTCGATTTTGTGGGCTCAAGTGATCCTACCACCTCAGTCTCCCGACTAGCTGGGAC
20881  GTCGAAGCTAAAACACCCGAGTTCACTAGGATGGTGGAGTCAGAGGGCTGATCGACCCTG

20941  CACAGTCATGTGCCACCACACCCGGCTAATTTATTTTTTATTTCTTATAGAGACCAGATC
20941  GTGTCAGTACACGGTGGTGTGGGCCGATTAAATAAAAAATAAAGAATATCTCTGGTCTAG

21001  CCCCTTTTGCCCAGGCTGGTCTCAAACTCCTGGACTCAAACAATTCTCCTGCCTCAGCCT
21001  GGGGAAAACGGGTCCGACCAGAGTTTGAGGACCTGAGTTTGTTAAGAGGACGGAGTCGGA

21061  CCCAAAGTGCCTGGATTACAGGCATGGGCTACTGTGCTCATCCCATGGGGTCTTTTGTGC
21061  GGGTTTCACGGACCTAATGTCCGTACCCGATGACACGAGTAGGGTACCCCAGAAAACACG

21121  CAACTGGTGTGAGTTAGGTACAGGACAATAAAGGAGGCAGTTAATCCATTAATCCATAAC
21121  GTTGACCACACTCAATCCATGTCCTGTTATTTCCTCCGTCAATTAGGTAATTAGGTATTG

21181  AAAGATCAGTGAAGGGGGAAGGTCTGGTCTCTGGTCTCTCCTAGTCATTTACAGAACTAG
21181  TTTCTAGTCACTTCCCCCTTCCAGACCAGAGACCAGAGAGGATCAGTAAATGTCTTGATC

21241  AACGATGAGAAGAGAGTGAATCTATAACCTAAGAAGCAGAATTGCAAACATGCTATGTGA
21241  TTGCTACTCTTCTCTCACTTAGATATTGGATTCTTCGTCTTAACGTTTGTACGATACACT

21301  CTCAGTTTCCAGTACTTAACTTCTCCCTTGGCATAATAAATAATTTTAGAGAGTTTTAAG
21301  GAGTCAAAGGTCATGAATTGAAGAGGGAACCGTATTATTTATTAAAATCTCTCAAAATTC

21361  AATTTTGTTTTCTTTTACAGATGTTAACAACCTCAGCTTGCTGGGGGCTGGTGGTGGTGG
21361  TTAAAACAAAAGAAAATGTCTACAATTGTTGGAGTCGAACGACCCCCGACCACCACCACC

21421  CTGCTCAGACAGTAAAGCATTGAATGCAATGTGAGGTCAAAGTTTTATTACAGATCATAC
21421  GACGAGTCTGTCATTTCGTAACTTACGTTACACTCCAGTTTCAAAATAATGTCTAGTATG

21481  CGGTCTTTTAAGTACTTGCAGCAAGATTTTCCTAATACTTAAAAGTGACTGGAAACTCAA
21481  GCCAGAAAATTCATGAACGTCGTTCTAAAAGGATTATGAATTTTCACTGACCTTTGAGTT

21541  TAGGATCAGTGTGATCTTCTCCAGATAGGGATGGTAGATTTTTGAAAGTGGGTGTGAAGG
21541  ATCCTAGTCACACTAGAAGAGGTCTATCCCTACCATCTAAAAACTTTCACCCACACTTCC

21601  GCAGTAATGAGAGAAAAATAAAACTATTTCTGGTTGTACTCTCCCAAGTCAAGGTCATTC
21601  CGTCATTACTCTCTTTTTATTTTGATAAAGACCAACATGAGAGGGTTCAGTTCCAGTAAG

21661  AATGAATGGTTATATAGATTTGCATCAAAAGTCCCTGTTTTCAGCCTCACCTTTGGAAAC
21661  TTACTTACCAATATATCTAAACGTAGTTTTCAGGGACAAAAGTCGGAGTGGAAACCTTTG

21721  ACCTGGATTCTCTATTCTGAGACTTTCTGAGATGAGGGAAAGGTGGCTTCTCATCAGTAT
21721  TGGACCTAAGAGATAAGACTCTGAAAGACTCTACTCCCTTTCCACCGAAGAGTAGTCATA

21781  CTCCTTCTTTGTGCAATACAGTTTCAGTTCTTTCTAATCTACAGAGTTAGTTCCTTCTCT
21781  GAGGAAGAAACACGTTATGTCAAAGTCAAGAAAGATTAGATGTCTCAATCAAGGAAGAGA

21841  ACTGTCAGCTTTCTACCTTCCAAAATGTGTTAATGTCACTCATTATCATGTTTCCCATTC
21841  TGACAGTCGAAAGATGGAAGGTTTTACACAATTACAGTGAGTAATAGTACAAAGGGTAAG

21901  TCTTTCCCTTATGGTTTAAACTTTAAAAGACAATGGTATTTGTTTAAGTGAATATCTAAA
21901  AGAAAGGGAATACCAAATTTGAAATTTTCTGTTACCATAAACAAATTCACTTATAGATTT

21961  AAGATGTGGAGAAAGATTCATGTGTTCAGTCTACCATGTTTAATTGGAGTCACTGGTAGA
21961  TTCTACACCTCTTTCTAAGTACACAAGTCAGATGGTACAAATTAACCTCAGTGACCATCT
```

FIG. 4 (cont'd)

```
22021  TTTTTAAGGAAAAATAACATTCTAGGTTTTTCCAGTATTGCTATGTAGCTTGTCTATGTA
22021  AAAAATTCCTTTTTATTGTAAGATCCAAAAAGGTCATAACGATACATCGAACAGATACAT

22081  GATCACCTTGCATTCTTCTGTTTCTCTCTTATAACTTGATTTTTTTCTTTTCTTTTCTTT
22081  CTAGTGGAACGTAAGAAGACAAAGAGAGAATATTGAACTAAAAAAAGAAAAGAAAAGAAA

22141  TCTTTTTTTTTCGAGACAGAGTCTCACTTTGTCACCCAGGCTGGAGTACAGTGGCACAAT
22141  AGAAAAAAAAAGCTCTGTCTCAGAGTGAAACAGTGGGTCCGACCTCATGTCACCGTGTTA

22201  CTCGTCTCATTGCTGCCTCCATCTCCTGGGTTCAAGTGATTCTCCCACCTCACCTTCCCA
22201  GAGCAGAGTAACGACGGAGGTAGAGGACCCAAGTTCACTAAGAGGGTGGAGTGGAAGGGT

22261  AATAGCCGGGATTACAGACATCTTATAACTTGATTTTTACTCATTTCATTATCATCCAAG
22261  TTATCGGCCCTAATGTCTGTAGAATATTGAACTAAAAATGAGTAAAGTAATAGTAGGTTC

22321  AGATGAAATTTAACTCAAAGCAAATGACTATTGTTTCAAATACAAATCTTAATCAGGGAG
22321  TCTACTTTAAATTGAGTTTCGTTTACTGATAACAAAGTTTATGTTTAGAATTAGTCCCTC

22381  AAAAGATTATAACTTATAGTTGAACTGGGGTTTGGAGATTATATGTGTTTTTTAAAATTA
22381  TTTTCTAATATTGAATATCAACTTGACCCCAAACCTCTAATATACACAAAAAATTTTAAT

22441  TTCTGTCCCACATGTAACATACAAGTGAGGATTTTAAAAATTTGTCTGCAGTTTTTTTTT
22441  AAGACAGGGTGTACATTGTATGTTCACTCCTAAAATTTTTAAACAGACGTCAAAAAAAAA

22501  TTTTAATTGATCATTCTTGGGTGTTTCTCGCAGAGGGGGATTTGGCAGGGTCATAGGACA
22501  AAAATTAACTAGTAAGAACCCACAAAGAGCGTCTCCCCCTAAACCGTCCCAGTATCCTGT

22561  ATAGTGGAGGGAAGGTCAGCAGATAAACGAGTGAACAAAGGTCTCTGGTTTTCCTAGGCA
22561  TATCACCTCCCTTCCAGTCGTCTATTTGCTCACTTGTTTCCAGAGACCAAAAGGATCCGT

22621  GAGGACCCTGCGGCCTTCCGCAGTGTTTGTGTCCCTGGGTACTTGAGATTAGGGAGTGGT
22621  CTCCTGGGACGCCGGAAGGCGTCACAAACACAGGGACCCATGAACTCTAATCCCTCACCA

22681  GATGACTCTTAAAGAGCATGCTGCCTTCAAGCATCTGTTTAACAAAGCACATCTTGCACC
22681  CTACTGAGAATTTCTCGTACGACGGAAGTTCGTAGACAAATTGTTTCGTGTAGAACGTGG

22741  GCCCTTAATCCATTTAACCCTGAGTGGACACAGCACATGTTTCAGAGAGCACCGGGTTGG
22741  CGGGAATTAGGTAAATTGGGACTCACCTGTGTCGTGTACAAAGTCTCTCGTGGCCCAACC

22801  GGGTAAGGTCATAGATCAACAGCATCCCAAGGCAGAAGAATTTTTCTTAGTACAGAACAA
22801  CCCATTCCAGTATCTAGTTGTCGTAGGGTTCCGTCTTCTTAAAAAGAATCATGTCTTGTT

22861  AATGGAGTCTCCTATGTCTACTTCTTTCTACACAGACACAGCAACAATCTGATTTCTCTA
22861  TTACCTCAGAGGATACAGATGAAGAAAGATGTGTCTGTGTCGTTGTTAGACTAAAGAGAT

22921  TCTTTTCCCCACATTTCCCCCTTTTCTATTCCACAAAACCGCCATTGTCATCATGGCCCG
22921  AGAAAAGGGGTGTAAAGGGGGAAAAGATAAGGTGTTTTGGCGGTAACAGTAGTACCGGGC

22981  TTCTCAATGAGCTGTTGGGTACACCTCCCAGACGGGGTGGCGGCCGGGCAGAGGGGCTCC
22981  AAGAGTTACTCGACAACCCATGTGGAGGGTCTGCCCCACCGCCGGCCCGTCTCCCCGAGG

23041  TCACTTCCCAGAAGGGGTGGCCTGGCAGAGGCACCCCCAACCTCCCTCCCGGACGGGGCG
23041  AGTGAAGGGTCTTCCCCACCGGACCGTCTCCGTGGGGGTTGGAGGGAGGGCCTGCCCCGC

23101  GCTGGCCAGGCGGGGGCTGCCCCCAACTTCCCAGACGGGGTGGCTGCTGGGCGGAGGGGC
23101  CGACCGGTCCGCCCCCGACGGGGGTTGAAGGGTCTGCCCCACCGACGACCCGCCTCCCCG

23161  TCTTTACTTCTCAGATGGGGCGGCTGCCGGGTGGAGGGGCTCCTCACTTCTCAGACGGGG
23161  AGAAATGAAGAGTCTACCCCGCCGACGGCCCACCTCCCCGAGGAGTGAAGAGTCTGCCCC

23221  CGGCCGGGCAGAGGCGCTCCTCACCTCCCAGACGGGGCAGCAGGGCAGAGGCGCTCCCCA
23221  GCCGGCCCGTCTCCGCGAGGAGTGGAGGGTCTGCCCCGTCGTCCCGTCTCCGCGAGGGGT

23281  CATCTCAGACGATGGGCGGCCGGGCAGAGACGCTCCTCACTTCCTAGACGGGATGGCAGC
23281  GTAGAGTCTGCTACCCGCCGGCCCGTCTCTGCGAGGAGTGAAGGATCTGCCCTACCGTCG

23341  CGGGAAGAGGCGCTCCTCACTTCCCAGACTGGGCAGCCAGGCAGAGGGGCTCCTCACATC
23341  GCCCTTCTCCGCGAGGAGTGAAGGGTCTGACCCGTCGGTCCGTCTCCCCGAGGAGTGTAG
```

FIG. 4 (cont'd)

23401 CCAGACGATGGGCAGCCAGGCAGAGAAGCTCCTCACTTCCCAGATGGGGTGGCGGCCGGG
23401 GGTCTGCTACCCGTCGGTCCGTCTCTTCGAGGAGTGAAGGGTCTACCCCACCGCCGGCCC

23461 CAGAGGCTGCAATCTCGGCACTTTGGGAGGCCAAGGCAGGCGGCTGGGAGGTGGAGGTTG
23461 GTCTCCGACGTTAGAGCCGTGAAACCCTCCGGTTCCGTCCGCCGACCCTCCACCTCCAAC

23521 TAGCGAGCCGAGATCACGCCACTACACTCCAGCTTGGGCAACATTGAGCACTGAGTGAAC
23521 ATCGCTCGGCTCTAGTGCGGTGATGTGAGGTCGAACCCGTTGTAACTCGTGACTCACTTG

23581 GAGACTCCGTCTGCAATCCCGGCACCTCGGGAGGCCGAGGCTGGCAGATCACTCCCGGTT
23581 CTCTGAGGCAGACGTTAGGGCCGTGGAGCCCTCCGGCTCCGACCGTCTAGTGAGGGCCAA

23641 AGGAGCTGGAGACCAGCCCGGCCAACACAGCGAAACCCCGTCTCCACCAAAAAAATACGA
23641 TCCTCGACCTCTGGTCGGGCCGGTTGTGTCGCTTTGGGGCAGAGGTGGTTTTTTTATGCT

23701 AAACCAGTCAGGCATGGTGGCGCGCGCCTGCAATCACAGGCACTCGGCAGGCTGAGGCAG
23701 TTTGGTCAGTCCGTACCACCGCGCGCGGACGTTAGTGTCCGTGAGCCGTCCGACTCCGTC

23761 GACAATCAGGCAGGGAGGTTGCAGTGAGCAGAGATGGCAGCAGTACAGTCCAGCTTCGGC
23761 CTGTTAGTCCGTCCCTCCAACGTCACTCGTCTCTACCGTCGTCATGTCAGGTCGAAGCCG

23821 TTGGCATCAGAGGGAGACCGTGGAAAGAGAGGGAGAGGGAGACCGTGGGGAGAGGGAGAG
23821 AACCGTAGTCTCCCTCTGGCACCTTTCTCTCCCTCTCCCTCTGGCACCCCTCTCCCTCTC

23881 GGGGAGGGGGAGCTGCAATTTTTTATTTAGCAATTTCCAAACCTATTGTGTTAGGCAGGG
23881 CCCCTCCCCCTCGACGTTAAAAAATAAATCGTTAAAGGTTTGGATAACACAATCCGTCCC

23941 TTCTCCAGGGAAACAGAACCAATAGGGCATATCTATATCTATATTTATATCTTTATCTAT
23941 AAGAGGTCCCTTTGTCTTGGTTATCCCGTATAGATATAGATATAAATATAGAAATAGATA

24001 ATCTATATCTATAATCTTTCTATCTATCTATCAAGAGATCGAGAGAGAGAGATTTATTTT
24001 TAGATATAGATATTAGAAAGATAGATAGATAGTTCTCTAGCTCTCTCTCTCTAAATAAAA

24061 AAGGAATTGGTTCATGTGATTGTGGGAGCTGGCAAGTCTGAAATCCATAGGGCAAGTTGG
24061 TTCCTTAACCAAGTACACTAACACCCTCGACCGTTCAGACTTTAGGTATCCCGTTCAACC

24121 TCAGCTGGAAATTCTGGTAAGAGTTGATGTTGCAGTCGTGAGTCTGAAATTTGCAGGGCA
24121 AGTCGACCTTTAAGACCATTCTCAACTACAACGTCAGCACTCAGACTTTAAACGTCCCGT

24181 GGTCAGGTACAGTATCTATTGCAATTGCAGTCCTGAGGCCAAATTCCTTCTTCAGGAAAC
24181 CCAGTCCATGTCATAGATAACGTTAACGTCAGGACTCCGGTTTAAGGAAGAAGTCCTTTG

24241 CTCCGTCTTTTTTGCTGTTAAGGCCTTCAACTAATTGGATGAAGCCCTCCCACATTGAGG
24241 GAGGCAGAAAAAACGACAATTCCGGAAGTTGATTAACCTACTTCGGGAGGGTGTAACTCC

24301 GCAATCTGCTTTACTCAAAGTCTGCTGATTTAAATGGTAATCACATCTAAAAAATACTTT
24301 CGTTAGACGAAATGAGTTTCAGACGACTAAATTTACCATTAGTGTAGATTTTTTATGAAA

24361 CACAGCAACATTTGAACTTGTGTTGTCTAAGCAATTGGGCACTATAGCTTAGCCAAGCAG
24361 GTGTCGTTGTAAACTTGAACACAACAGATTCGTTAACCCGTGATATCGAATCGGTTCGTC

24421 ACACATGAAATTAACCATCACTCTGTAGAGATGAAAGAACTACTGTTTCAAAAAACAACT
24421 TGTGTACTTTAATTGGTAGTGAGACATCTCTACTTTCTTGATGACAAAGTTTTTTGTTGA

24481 GTTTTTGAATCCGTCATTTATCAACGGATTCACCCAATGGTTAACCTTTCTATATGCTTT
24481 CAAAAACTTAGGCAGTAAATAGTTGCCTAAGTGGGTTACCAATTGGAAAGATATACGAAA

24541 CTCTTTCTCCCAAGTACTGAATCATATGAAAATAAATTATGGTTGTGATATTTCCTATCT
24541 GAGAAAGAGGGTTCATGACTTAGTATACTTTTATTTAATACCAACACTATAAAGGATAGA

24601 AAATACTTCATATGGGACATTCTCCTACATAGCACACCTAAGAAGATTAGTATTAATTCA
24601 TTTATGAAGTATACCCTGTAAGAGGATGTATCGTGTGGATTCTTCTAATCATAATTAAGT

24661 GAGAGATCATGTCATATCTGGTTCATATATAATTTTCCCTAGCTGACCTCAAAATGTGTT
24661 CTCTCTAGTACAGTATAGACCAAGTATATATTAAAAGGGATCGACTGGAGTTTTACACAA

24721 TGTTTTGTTTACATATTACTCTTTATAGTTATGTTTCTTTTAATACGGATCAATATTTGT
24721 ACAAAACAAATGTATAATGAGAAATATCAATACAAAGAAAATTATGCCTAGTTATAAACA

FIG. 4 (cont'd)

```
24781  GTGTTTTTGCTGCTATTTTTTTTAATGACATTGTTTTGAATAATTCAGGCTCATTGGCTA
24781  CACAAAAACGACGATAAAAAAAATTACTGTAACAAAACTTATTAAGTCCGAGTAACCGAT

24841  TTTCACATCCTGAATTTCTCTAATTTTATCTTTATGATTAGAGCCAGGCTCTAATTCTTG
24841  AAAGTGTAGGACTTAAAGAGATTAAAATAGAAATACTAATCTCGGTCCGAGATTAAGAAC

24901  GCAAGAATAACACTGAAGTGAGGTTGTGTACTCCTAATTGCCCTGCATCAAAGACACATG
24901  CGTTCTTATTGTGACTTCACTCCAACACATGAGGATTAACGGGACGTAGTTTCTGTGTAC

24961  ATATGCATTGGTTCCTGCATTAGTCATGTTAAGTTTGATTAGCTGGTGAAGGTGGTCGCC
24961  TATACGTAACCAAGGACGTAATCAGTACAATTCAAACTAATCGACCACTTCCACCAGCGG

25021  ACCATTTCTCACTCTTGTAAAGGGACATTTTCTCCTTTTAAATTAATATGTAATTTGTGG
25021  TGGTAAAGAGTGAGAACATTTCCCTGTAAAAGAGGAAAATTTAATTATACATTAAACACC

25081  CACAAGACTTTGAGACTGTGTAAATATCCCATTCTCTGACAACCTTTCTTCTGATGACTT
25081  GTGTTCTGAAACTCTGACACATTTATAGGGTAAGAGACTGTTGGAAAGAAGACTACTGAA

25141  TAGCATTAACTGATCTAATTATATCATTCTTGGCATTGAGTAGCATTCTTGTGTAAAGAA
25141  ATCGTAATTGACTAGATTAATATAGTAAGAACCGTAACTCATCGTAAGAACACATTTCTT

25201  GGGGTTCTCTTTCTCTCCCTCCTCTCATTATAATTTGTTACTGTTATTTTCTTACAAGTT
25201  CCCCAAGAGAAAGAGAGGGAGGAGAGTAATATTAAACAATGACAATAAAAGAATGTTCAA

25261  ACTAAGAATTACTCAAAGGCAGTATTTTTCAATAAATCATTGGTAATTTATGGTCTTCTC
25261  TGATTCTTAATGAGTTTCCGTCATAAAAAGTTATTTAGTAACCATTAAATACCAGAAGAG

25321  ACTCTAGAAAAGGGAGGATGGGTCAGAAAGCTGAGGGGAAAAAAAGGGAGGAAACGAGAA
25321  TGAGATCTTTTCCCTCCTACCCAGTCTTTCGACTCCCCTTTTTTTCCCTCCTTTGCTCTT

25381  TGTATATTATCGACATAATCGGTTGAAAATGTCTAGTGCTGTAATTATGCCATCATGCAG
25381  ACATATAATAGCTGTATTAGCCAACTTTTACAGATCACGACATTAATACGGTAGTACGTC

25441  ATTAAAAAGCCACCTGTGAAAAATCAACTTGTATTGTTTTGTTTTGTTTGATTTTTAATA
25441  TAATTTTTCGGTGGACACTTTTTAGTTGAACATAACAAAACAAAACAAACTAAAAATTAT

25501  AATCCTTATAGTGTATGAATAAAAATTAAATTAATTGATCAGTATCTTCACTAATGGCAG
25501  TTAGGAATATCACATACTTATTTTTAATTTAATTAACTAGTCATAGAAGTGATTACCGTC

25561  AGAAGGGGATGGACTGAGCAGATTCTGCTTTTCACTCTGATATTTGTTAATTGCCCTGTG
25561  TCTTCCCCTACCTGACTCGTCTAAGACGAAAAGTGAGACTATAAACAATTAACGGGACAC

25621  TGGTCTGAAGACCTGGGTTCTAGTACCAGCTCTCCCTCTGCAGACAGGTGTGTTACTTTG
25621  ACCAGACTTCTGGACCCAAGATCATGGTCGAGAGGGAGACGTCTGTCCACACAATGAAAC

25681  GTCAAGGCAATCAATCTTCTTGATACTCAGTTTGGTTCTCTCTGATTTGAGCATAAGAAA
25681  CAGTTCCGTTAGTTAGAAGAACTATGAGTCAAACCAAGAGAGACTAAACTCGTATTCTTT

25741  TATACTTGAAGGCCGGGCATGGTGGCTTATGCCTGTAATTCCAGCACTATGGGAAGCCGA
25741  ATATGAACTTCCGGCCCGTACCACCGAATACGGACATTAAGGTCGTGATACCCTTCGGCT

25801  GGTGGGAGGATCGCTTGGGCTCAGGAGTTTGAGACCAGGCTGGGCAACATGGCAAAACCT
25801  CCACCCTCCTAGCGAACCCGAGTCCTCAAACTCTGGTCCGACCCGTTGTACCGTTTTGGA

25861  CAACTCTACAAAAAACAAACAAAAAATTAGCCAGGCATGGTGGTGCACGCCTGTAGTCCC
25861  GTTGAGATGTTTTTTGTTTGTTTTTTAATCGGTCCGTACCACCACGTGCGGACATCAGGG

25921  AGCTACTCAGGAGGTTGAGGCAGGAGAATCCTGGGAGGCAGAGGTTGCAGTGATCTGAGA
25921  TCGATGAGTCCTCCAACTCCGTCCTCTTAGGACCCTCCGTCTCCAACGTCACTAGACTCT

25981  TTGTGCCACTGCACTCCAGCCTGGGAGCCTGGGTGACAGAGAGAGACCCTGTCTAAAATA
25981  AACACGGTGACGTGAGGTCGGACCCTCGGACCCACTGTCTCTCTCTGGGACAGATTTTAT

26041  TATATATACACACACTTGAATGCTTCATGTCCCTTGCTCAGTGACAGCCCCGTCCTCTGC
26041  ATATATATGTGTGTGAACTTACGAAGTACAGGGAACGAGTCACTGTCGGGGCAGGAGACG

26101  TTCTGCACAGTTGACCAAGGCTTCTCAGTCTACTCCTGTGTAGAAAAGAATTAAAGCAGG
26101  AAGACGTGTCAACTGGTTCCGAAGAGTCAGATGAGGACACATCTTTTCTTAATTTCGTCC
```

FIG. 4 (cont'd)

```
26161  CCTGAGGCTGCTAGTCTTAGAAAGGCTTGCAAAGTTGGCCCTTGTCTGGTGTCTGGGAAC
26161  GGACTCCGACGATCAGAATCTTTCCGAACGTTTCAACCGGGAACAGACCACAGACCCTTG

26221  TTGAATTTCTGGAGGGTTCTCACCATTCCCTGAAAAGAATGGCTCACGATGCCTAAAATA
26221  AACTTAAAGACCTCCCAAGAGTGGTAAGGGACTTTTCTTACCGAGTGCTACGGATTTTAT

26281  TTTGTACAAACAATGAAGTTTCTGCTGAACATCTGCTTCCTTCTGGGAGTCTGGAATTTT
26281  AAACATGTTTGTTACTTCAAAGACGACTTGTAGACGAAGGAAGACCCTCAGACCTTAAAA

26341  AGGATGTGCTAGGTAGGGGTGTTTACATGACAGCCCCACATAAAAACCTTGGGCACTGAG
26341  TCCTACACGATCCATCCCCACAAATGTACTGTCGGGGTGTATTTTTGGAACCCGTGACTC

26401  TGTCTAATGAGATTCCCTAGTAAGTAATATTTTACACATATTATCACAACTCATTGCTGG
26401  ACAGATTACTCTAAGGGATCATTCATTATAAAATGTGTATAATAGTGTTGAGTAACGACC

26461  AGGAGTTAAGTGCATCCTGTGTGACTCCACTGGGAGAGGACTCTGGGAAGCACATGTCTG
26461  TCCTCAATTCACGTAGGACACACTGAGGTGACCCTCTCCTGAGACCCTTCGTGTACAGAC

26521  ATTTCCTTTGTCCCATGTGCCTTTTCCTTTTGCTGATTTTTGCCTTGTAAATTTTTTTTT
26521  TAAAGGAAACAGGGTACACGGAAAAGGAAAACGACTAAAAACGGAACATTTAAAAAAAAA

26581  TTTTTTTTGAGAGACAGAGTCTTACTCTGTTGCCCAGACTGGAGTTCAGTGGCCCCATGT
26581  AAAAAAAACTCTCTGTCTCAGAATGAGACAACGGGTCTGACCTCAAGTCACCGGGGTACA

26641  CGGCTCACTGCAGCCTCTGCCTCCTGGATTCAAGCAATTCTCCTGCCTCAGCCTCCCGAG
26641  GCCGAGTGACGTCGGAGACGGAGGACCTAAGTTCGTTAAGAGGACGGAGTCGGAGGGCTC

26701  TAGCTGGGACTACAGGCGCGCGCTGCCACACCGGCTAATTTTTGTATTTTTAGTAGAGAC
26701  ATCGACCCTGATGTCCGCGCGCGACGGTGTGGCCGATTAAAAACATAAAAATCATCTCTG

26761  GGGGTTTCACCATGTTGGCCAGGATGGTCTTGATCTCCTGACCTCGTGATCCGCCTGCCT
26761  CCCCAAAGTGGTACAACCGGTCCTACCAGAACTAGAGGACTGGAGCACTAGGCGGACGGA

26821  CGGCCTCCCAAAGTGCTGGAATTATAGGCCTGGGCCACTGTGCCTGGCCATAATTTTTAT
26821  GCCGGAGGGTTTCACGACCTTAATATCCGGACCCGGTGACACGGACCGGTATTAAAAATA

26881  CCTGTAATAAATTATAGTCGAAAGTATTGAGTCCTGTGAATCAACTTAGAGAATCACCAA
26881  GGACATTATTTAATATCAGCTTTCATAACTCAGGACACTTAGTTGAATCTCTTAGTGGTT

26941  ACTGCTTCCAATTTTCTCATATGTAAAATGGGTTGCTATAATAATGATGATATCTACCTT
26941  TGACGAAGGTTAAAAGAGTATACATTTTACCCAACGATATTATTACTACTATAGATGGAA

27001  ATAGGGTTGTTTTAAGTATGAAAAATATGGTGAAATATGTGTGAAACTAGGGGCCGGATG
27001  TATCCCAACAAAATTCATACTTTTTATACCACTTTATACACACTTTGATCCCCGGCCTAC

27061  TAGGATGAGTCATACAGTGGGTGGTTATTATTACGGATCATATTAACTCTTCAGGTAAAA
27061  ATCCTACTCAGTATGTCACCCACCAATAATAATGCCTAGTATAATTGAGAAGTCCATTTT

27121  ACCATCTTGTAGCTGGGCAAGGTGGCACATGCCTGTAGTCCCAGCTACTTGGGGGACTGA
27121  TGGTAGAACATCGACCCGTTCCACCGTGTACGGACATCAGGGTCGATGAACCCCCTGACT

27181  GGCAGGTGGATCGCTTGAGCCTAGGAGTTCAAGGCTGTAGTACGCTATGATCACGTCTAT
27181  CCGTCCACCTAGCGAACTCGGATCCTCAAGTTCCGACATCATGCGATACTAGTGCAGATA

27241  CAATAGCCACTGGACTCCAGCCTGGACAATGTAATGAGAGTCTGTCTCAAAAAAAAGGAA
27241  GTTATCGGTGACCTGAGGTCGGACCTGTTACATTACTCTCAGACAGAGTTTTTTTTCCTT

27301  CAATCTTGTGTTTGCGTGTGTGCTCATGTCTTTGTTGGAATAATACTGACACAGTCACTC
27301  GTTAGAACACAAACGCACACACGAGTACAGAAACAACCTTATTATGACTGTGTCAGTGAG

27361  AAATTAACTCTCAAATCTTTGATTATTCATTTGATGGGAACAACAGGTTTATGTGCCAGC
27361  TTTAATTGAGAGTTTAGAAACTAATAAGTAAACTACCCTTGTTGTCCAAATACACGGTCG

27421  TTATCAGGACCCCTAGTTCTTTCATTAAAGTGTGTATGTGTGTGTGTATGTGTGTATGTG
27421  AATAGTCCTGGGGATCAAGAAAGTAATTTCACACATACACACACACATACACACATACAC

27481  TGCACATGTGTGCTAGTTTTCTTATCTAACGACGAAGTCCTTTGGGAGGTTTACTTTTTC
27481  ACGTGTACACACGATCAAAAGAATAGATTGCTGCTTCAGGAAACCCTCCAAATGAAAAAG
```

FIG. 4 (cont'd)

27541 ATTACTATTTTTTTCATGCTTTCCTTTGATGTGCACCTGGCAATTTATAGAGCCAATGTG
27541 TAATGATAAAAAAAGTACGAAAGGAAACTACACGTGGACCGTTAAATATCTCGGTTACAC

27601 TACTACATATTCTGCTGCAGAAAATGACAGAGGTGAGGAAGGAGCAGGAAGCAGATTTAG
27601 ATGATGTATAAGACGACGTCTTTTACTGTCTCCACTCCTTCCTCGTCCTTCGTCTAAATC

27661 AAAGGAATGTTACAGTTTATCAAGTTGTGACTAATGGAAGCTATTAAAACAAAAGGTACC
27661 TTTCCTTACAATGTCAAATAGTTCAACACTGATTACCTTCGATAATTTTGTTTTCCATGG

27721 AACCCATCTTAAATATTCACTGCCTCTACAACTATTTTTCTATAACTGTTGTTCCTTGTC
27721 TTGGGTAGAATTTATAAGTGACGGAGATGTTGATAAAAAGATATTGACAACAAGGAACAG

27781 AGCTCTGGGGTGGAGGGAATATTCCTGAATGTTTTATTAAGTAATTCAAAGATCTTCCTA
27781 TCGAGACCCCACCTCCCTTATAAGGACTTACAAAATAATTCATTAAGTTTCTAGAAGGAT

27841 GGTATGTGTATCAAAGATCCTATGATGTATCTGTCTTGTAAATTGAGACTGGCATATATT
27841 CCATACACATAGTTTCTAGGATACTACATAGACAGAACATTTAACTCTGACCGTATATAA

27901 GGGCTTACATTACTGGGAAAAATGTATGTCATCATCATTGGTGAAAAAGAGTTTCCATAG
27901 CCCGAATGTAATGACCCTTTTTACATACAGTAGTAGTAACCACTTTTTCTCAAAGGTATC

27961 CAGTTTTTTCTAAGTAGAGAGATAAATGAATCAGACTTTTGGAGGAGGTATGTTTTAACT
27961 GTCAAAAAAGATTCATCTCTCTATTTACTTAGTCTGAAAACCTCCTCCATACAAAATTGA

28021 CACTGGAGGATCACACCAAGTCTGAACATCTAAGGAACCCTAGTGGAAAACTGGTTTTCC
28021 GTGACCTCCTAGTGTGGTTCAGACTTGTAGATTCCTTGGGATCACCTTTTGACCAAAAGG

28081 TGTATGCTGCTCTAGCGATCTGAGGAAAGGCCTAAAAAAAGCCAGTGTCCCTGTGATATT
28081 ACATACGACGAGATCGCTAGACTCCTTTCCGGATTTTTTTCGGTCACAGGGACACTATAA

28141 GTGAAATACATATATGTGGTCTTTGTTCCTGTTTCCTGGCATACAAGTACTAAAAATCCT
28141 CACTTTATGTATATACACCAGAAACAAGGACAAAGGACCGTATGTTCATGATTTTTAGGA

28201 TGGAATCTCCAAAGTGCTGTCTTTTTGTATATTAGTGTTGACTGATAGCTTCAGAGTGGG
28201 ACCTTAGAGGTTTCACGACAGAAAAACATATAATCACAACTGACTATCGAAGTCTCACCC

28261 GCTGGTCAAGTTGATCACCAATGGCCAGTGGTTTAATCAGTCATGCCTATGTAATGAAGC
28261 CGACCAGTTCAACTAGTGGTTACCGGTCACCAAATTAGTCAGTACGGATACATTACTTCG

28321 CTCCATGAAAATCCAAAGGGAATGGACTGGGGAGCTTCTAAGAAGTGTTTTTTACCTTCC
28321 GAGGTACTTTTAGGTTTCCCTTACCTGACCCCTCGAAGATTCTTCACAAAAAATGGAAGG

28381 CGTGAGCCTCCTGTGCTGAACACGTGGAGGGTCACGGGAAGGTAAGCAAAAATTCATTCA
28381 GCACTCGGAGGACACGACTTGTGCACCTCCCAGTGCCCTTCCATTCGTTTTTAAGTAAGT

28441 CATGCTGGGAGGGTGGCACATCCCAACTCCACGAGGACAAAAGCTCCTGTGCTCAGAACC
28441 GTACGACCCTCCCACCGTGTAGGGTTGAGGTGCTCCTGTTTTCGAGGACACGAGTCTTGG

28501 CTTCCAGACTTGGACCTTGTATCTCTTCATTGGCTTTTATTTGTATTTTAAAAAATATCC
28501 GAAGGTCTGAACCTGGAACATAGAGAAGTAACCGAAAATAAACATAAAATTTTTTATAGG

28561 TGAGTGATAAACTGGTAGATGTAAGTGTCTTCCTCAGTTCTGTGAACCACGCTAGCAAAT
28561 ACTCACTATTTGACCATCTACATTCACAGAAGGAGTCAAGACACTTGGTGCGATCGTTTA

28621 TAATCAAACCGGAAGAGGGGGTCATGGCAACCCCAACTTGAAACCTGTTGGTCAGCAGTT
28621 ATTAGTTTGGCCTTCTCCCCCAGTACCGTTGGGGTTGAACTTTGGACAACCAGTCGTCAA

28681 CCAGAGACCTGAACTTATGACTGGTTGGAAGGACGGGGTGCTCTTGTGGGACTGAGCCCT
28681 GGTCTCTGGACTTGAATACTGACCAACCTTCCTGCCCCACGAGAACACCCTGACTCGGGA

28741 CAACTTGTGGATCTGATGCTATCTCTGGGTAGACAGTGTTGGAGCTGAATTGGAGGACAC
28741 GTTGAACACCTAGACTACGATAGAGACCCATCTGTCACAACCTCGACTTAACCTCCTGTG

28801 CTAGCTTGTGTCCACTGCAGAACTGATTGCTTGCTTCCTGCTGGGGAGAAATCCCTATAT
28801 GATCGAACACAGGTGACGTCTTGACTAACGAACGAAGGACGACCCCTCTTTAGGGATATA

FIG. 4 (cont'd)

```
28861  ATTTTGGGGTCCAGAAGTCTTCCGTGTTGATTGTTTTTGTGTGAGAGCAGAGGAAAAATG
28861  TAAAACCCCAGGTCTTCAGAAGGCACAACTAACAAAAACACACTCTCGTCTCCTTTTTAC

28921  GTTTGAGAGTTTTTCGGGAAACAGCCCCTCTTAGTATAGTGGTAGAAACACTCCAAAAAT
28921  CAAACTCTCAAAAAGCCCTTTGTCGGGGAGAATCATATCACCATCTTTGTGAGGTTTTTA

28981  AAAATATGCTACCCCAAAAATAAAAAATGAAAATAAAAATAAAAATCTGGAGTGGTCAGT
28981  TTTTATACGATGGGGTTTTTATTTTTTACTTTTATTTTTATTTTTAGACCTCACCAGTCA

29041  TTGCCAAGAGGATTTATGGAGCATCTAAGGTCAAGCATTACTTCTCAGCCCTGCAGCAGG
29041  AACGGTTCTCCTAAATACCTCGTAGATTCCAGTTCGTAATGAAGAGTCGGGACGTCGTCC

29101  CCTCTAATTAAGCCATGCCACAGAGTGCGGTTTGCAGAGAGGTGGAGTTCCTGTGGATTC
29101  GGAGATTAATTCGGTACGGTGTCTCACGCCAAACGTCTCTCCACCTCAAGGACACCTAAG

29161  ATTCTTCTCTCTAAAATTATAAATAACGCAGCTTCCAAACATGCCATATTACCTCACAAG
29161  TAAGAAGAGAGATTTTAATATTTATTGCGTCGAAGGTTTGTACGGTATAATGGAGTGTTC

29221  GTCTAAAGACTCAATATGAATCTTCAACTTAACAATTATAACTGACACAGATTGAGATCT
29221  CAGATTTCTGAGTTATACTTAGAAGTTGAATTGTTAATATTGACTGTGTCTAACTCTAGA

29281  TCCTGGATGCTGAAATAGGCTTTACATGATTTATCTCATTTAGTTCTCATAAAACTCTAT
29281  AGGACCTACGACTTTATCCGAAATGTACTAAATAGAGTAAATCAAGAGTATTTTGAGATA

29341  TATTAATATTATTTTACAGATAGAGAAATGGAAGCACAGAGAGGGTAAGTGTATTAGTCC
29341  ATAATTATAATAAAATGTCTATCTCTTTACCTTCGTGTCTCTCCCATTCACATAATCAGG

29401  ATTTTTATGCTGCTAATAAAGACATACCCAAGACAGGGTAATTTATACAGAAAAAGAGGT
29401  TAAAAATACGACGATTATTTCTGTATGGGTTCTGTCCCATTAAATATGTCTTTTTCTCCA

29461  TTAATGGACTCACATTTCCACATGGCTGGGAGGCCTCACAATCATGGCAGAAGGCAAAAG
29461  AATTACCTGAGTGTAAAGGTGTACCGACCCTCCGGAGTGTTAGTACCGTCTTCCGTTTTC

29521  GCACTTCTTACCTGGTGGTGGCAAGACAGAAAATGAGAACCAAGCGAAAGGGGTTTCCCC
29521  CGTGAAGAATGGACCACCACCGTTCTGTCTTTTACTCTTGGTTCGCTTTCCCCAAAGGGG

29581  TTATAAAACCATCAGGTAACATGAGACAATTATTCACTACCACAGAAACTATATGGGGGA
29581  AATATTTTGGTAGTCCATTGTACTCTGTTAATAAGTGATGGTGTCTTTGATATACCCCCT

29641  AACCGCCCCCATGATTCAGTTATCTTCCATTGGGTCCCTCCCACAACACGTGGAGCTACA
29641  TTGGCGGGGGTACTAAGTCAATAGAAGGTAACCCAGGGAGGGTGTTGTGCACCTCGATGT

29701  ATTCAAGATGAGATTTGTGTGGAGACATAGCTAACCCATATCAGTAAGTAATTAGACAAA
29701  TAAGTTCTACTCTAAACACACCTCTGTATCGATTGGGTATAGTCATTCATTAATCTGTTT

29761  CCTTGCAAAGCTAGTAAGTGGTATTGCTGGAATTAAATCTGCCAATGTCACTCCAGAGTC
29761  GGAACGTTTCGATCATTCACCATAACGACCTTAATTTAGACGGTTACAGTGAGGTCTCAG

29821  TATGTGATTTACTGGTATATTATAGGGTCTACCTATAAGCTTGATAACCTTATGTTAGAA
29821  ATACACTAAATGACCATATAATATCCCAGATGGATATTCGAACTATTGGAATACAATCTT

29881  CAAATAACCATGACATATTCTGTTCAGTAGTTTGCATTTCCTTTTGACTCCTACAGGGGA
29881  GTTTATTGGTACTGTATAAGACAAGTCATCAAACGTAAAGGAAAACTGAGGATGTCCCCT

29941  GGAGGCCGAGGTTCAGGGACATTAAAGTGGGGTTTAGAGACATTAGGTGGTTTACCCAAG
29941  CCTCCGGCTCCAAGTCCCTGTAATTTCACCCCAAATCTCTGTAATCCACCAAATGGGTTC

30001  CTTTATCTACTAGATACTAGATAATTGTCTATCTGACAATAAAGCTAGAACTTACACCCA
30001  GAAATAGATGATCTATGATCTATTAACAGATAGACTGTTATTTCGATCTTGAATGTGGGT

30061  GCTGGACAATGGAGCTACAGCTTAAAACAAAATCTTCTAATGAGCTCAGAACTCATGGCT
30061  CGACCTGTTACCTCGATGTCGAATTTTGTTTTAGAAGATTACTCGAGTCTTGAGTACCGA

30121  TAATAAGATTTGGGAAAAGTCCTGCGGACATTTCACTGTCTATCCAGAAATGCGAGGAAG
30121  ATTATTCTAAACCCTTTTCAGGACGCCTGTAAAGTGACAGATAGGTCTTTACGCTCCTTC
```

FIG. 4 (cont'd)

```
30181  TTAGGAGAAAAGGCAAAGTATCTCATAGACAGATAAAGGCAGTTCAGTAAGTAGCCTGAA
30181  AATCCTCTTTTCCGTTTCATAGAGTATCTGTCTATTTCCGTCAAGTCATTCATCGGACTT

30241  TAAATAGCCATATTTAAAATCTAATTTGGTTCTTTTGTGCCTAACACAATTGACTTTATG
30241  ATTTATCGGTATAAATTTTAGATTAAACCAAGAAAACACGGATTGTGTTAACTGAAATAC

30301  CTGGTATCTATTTTCTGCTCTGTCTCTCTTTCTGTCTCTACTTATGTGTGTATGCATGTG
30301  GACCATAGATAAAAGACGAGACAGAGAGAAAGACAGAGATGAATACACACATACGTACAC

30361  TTATAAAATATATCAGCCCATTGATCAATTTTTAATTTAAGCAAAAACATGGTAGATTAA
30361  AATATTTTATATAGTCGGGTAACTAGTTAAAAATTAAATTCGTTTTTGTACCATCTAATT

30421  TATATTCAATCAATTTATTGAGTAGATATTTATCGAGGCTCACACATTTATCTGACTGTG
30421  ATATAAGTTAGTTAAATAACTCATCTATAAATAGCTCCGAGTGTGTAAATAGACTGACAC

30481  TACTAAGCACTGGAAACCCAAAGAGAATGAAGTCACTGCCTAGACAGTTGGAGGCTGACA
30481  ATGATTCGTGACCTTTGGGTTTCTCTTACTTCAGTGACGGATCTGTCAACCTCCGACTGT

30541  CATAAACAAGCAGGGTAATAATCAAGTGTCATAACTAGTCTATTACATGCAATGTTAAAC
30541  GTATTTGTTCGTCCCATTATTAGTTCACAGTATTGATCAGATAATGTACGTTACAATTTG

30601  TAGCATCTCTACCATGCAAAACTTGTGCTCTTGGGGATACAGGAAGACTTTCCAGAGAAG
30601  ATCGTAGAGATGGTACGTTTTGAACACGAGAACCCCTATGTCCTTCTGAAAGGTCTCTTC

30661  TACACAGGACAGGAATGTGTTAGGAAACCAGTCAGTTCCCAGGTCCTCGATCAGGTCACA
30661  ATGTGTCCTGTCCTTACACAATCCTTTGGTCAGTCAAGGGTCCAGGAGCTAGTCCAGTGT

30721  GTGACTTGCGATTCTATTTTGAACATAGGTCTTAAATCTTTATTTTGATAGCAAGGGTTT
30721  CACTGAACGCTAAGATAAAACTTGTATCCAGAATTTAGAAATAAAACTATCGTTCCCAAA

30781  TAAACTTTTGATATATGATATACTTCTGAAAATCAAATTTCATATTCTAAAATTAAGTAT
30781  ATTTGAAAACTATATACTATATGAAGACTTTTAGTTTAAAGTATAAGATTTTAATTCATA

30841  TTTTGCCCTTAACTAACTTGAACATAATACTATAATACATTAACATATATTATTAATAAT
30841  AAAACGGGAATTGATTGAACTTGTATTATGATATTATGTAATTGTATATAATAATTATTA

30901  AAATAGGACCCCTGGAAGTCCAAGAGAGACATGAGGCTTATTTGGTATGTTAAAATCATA
30901  TTTATCCTGGGGACCTTCAGGTTCTCTCTGTACTCCGAATAAACCATACAATTTTAGTAT

30961  CAGGAAGTGTTGTTAAATAAGAAATGGTGTTACACTTTCTTTGAGTTATATTTATATGGA
30961  GTCCTTCACAACAATTTATTCTTTACCACAATGTGAAAGAAACTCAATATAAATATACCT

31021  TATGTTGTTAATATGTGTTCCAACATTGTATGAGATTCCTAAAAATCTGATATGGACATC
31021  ATACAACAATTATACACAAGGTTGTAACATACTCTAAGGATTTTTAGACTATACCTGTAG

31081  CAGTGTGGTTGTTGGGTCCTCTATGAGCCTAGGGAGCACTGGCCGGTTACCTTGCATCCA
31081  GTCACACCAACAACCCAGGAGATACTCGGATCCCTCGTGACCGGCCAATGGAACGTAGGT

31141  TTCATGTCAGCGTTGGTAGTGTCAGGCACCCGATGGTTCTTAGAAGAGTACTTAGCTCTA
31141  AAGTACAGTCGCAACCATCACAGTCCGTGGGCTACCAAGAATCTTCTCATGAATCGAGAT

31201  CTCTGCAGTGTCTGAAGTTGCTGGATATATACCTGCTGTATAAACTGCTGACTAGGGCGC
31201  GAGACGTCACAGACTTCAACGACCTATATATGGACGACATATTTGACGACTGATCCCGCG

31261  TGCAGTTTACTTACTGTCTTCTCATGGGGACCTTCCCCTTCAACTCTTTCCTCTTGGGTT
31261  ACGTCAAATGAATGACAGAAGAGTACCCCTGGAAGGGGAAGTTGAGAAAGGAGAACCCAA

31321  TCACATCTTGGGTGGGGAGTTTCATCCTAGTAGTTTGCCTGAGAATACAGGTGAACCCAC
31321  AGTGTAGAACCCACCCCTCAAAGTAGGATCATCAAACGGACTCTTATGTCCACTTGGGTG

31381  AGAACAAAGTGGACTTCGAAAGCATCTCCTTGGAGTGAGACTTTGCTTCTTTCTCTTTGC
31381  TCTTGTTTCACCTGAAGCTTTCGTAGAGGAACCTCACTCTGAAACGAAGAAAGAGAAACG

31441  TAGCACCATCTTGTACCTTATCGTCATGAACTTTGTTGGCTGAATCATTCCCATTTACTT
31441  ATCGTGGTAGAACATGGAATAGCAGTACTTGAAACAACCGACTTAGTAAGGGTAAATGAA

31501  AATTGAAGAGTAAGAGACTGGAACAATGCTCACTTTGATTTTCCTGGATAAGAGTTAAGA
31501  TTAACTTCTCATTCTCTGACCTTGTTACGAGTGAAACTAAAAGGACCTATTCTCAATTCT
```

FIG. 4 (cont'd)

31561 GTTCTTGAGATGGCAGCTTGTTTGACACATGAATTTTCTTCAAATTTGTGCTTACTACCA
31561 CAAGAACTCTACCGTCGAACAAACTGTGTACTTAAAAGAAGTTTAAACACGAATGATGGT

31621 ACTGATTTGGTGTGGAGGAGAGCCCAGAGAAGTTCCCTCTCTCTGTCAGAACAACTTTGT
31621 TGACTAAACCACACCTCCTCTCGGGTCTCTTCAAGGGAGAGAGACAGTCTTGTTGAAACA

31681 AACATTTATTAACCTGACTTCTGCCTTCAATTAACTGTAACCTTTTGCCTTCCAAATTAA
31681 TTGTAAATAATTGGACTGAAGACGGAAGTTAATTGACATTGGAAAACGGAAGGTTTAATT

31741 AAAGTTCCACATTACTCCAAAAATAAAAAGTGAAAATAAAAATAAAAGGCTGATATGTCA
31741 TTTCAAGGTGTAATGAGGTTTTTATTTTTCACTTTTATTTTTATTTTCCGACTATACAGT

31801 TGGTATATGCAGTAAATTGCTTTATTCTGATTTTTTTTTCTAAAAGCCTTTTGCAAATCC
31801 ACCATATACGTCATTTAACGAAATAAGACTAAAAAAAAAGATTTTCGGAAAACGTTTAGG

31861 TGAAGTGCTGTGTATTCAAGGAAATTCATGAAAGGGACCTTGACAAGTAGTCTTAAATAC
31861 ACTTCACGACACATAAGTTCCTTTAAGTACTTTCCCTGGAACTGTTCATCAGAATTTATG

31921 AGGTTTCTGATAACTTTGGAGATCACACCTTTGGACTAGGTAAAAACATCCAAAACTCGT
31921 TCCAAAGACTATTGAAACCTCTAGTGTGGAAACCTGATCCATTTTTGTAGGTTTTGAGCA

31981 CTGGGCGCAGTGGCTCACGCCTGTAATCCCAGCACTTTGGGAGGCCAAGGCAGGCGGATC
31981 GACCCGCGTCACCGAGTGCGGACATTAGGGTCGTGAAACCCTCCGGTTCCGTCCGCCTAG

32041 ACGAGGTCAGGAGATCGAGACCATCCTGGCTAACACGGTGAAACCCCATCTCTACTAAAA
32041 TGCTCCAGTCCTCTAGCTCTGGTAGGACCGATTGTGCCACTTTGGGGTAGAGATGATTTT

32101 ACACAAAAACAAAATTAGCCGGGCGTGGTGGCGGGCGCCTGTAGTTCCAGCTACCCGGCA
32101 TGTGTTTTTGTTTTAATCGGCCCGCACCACCGCCCGCGGACATCAAGGTCGATGGGCCGT

32161 GGCTGAGGCGGAAGAATGGCGCGAAGCGGCAAGACGGAGCTTGCAGTGAGCCGAGATCGC
32161 CCGACTCCGCCTTCTTACCGCGCTTCGCCGTTCTGCCTCGAACGTCACTCGGCTCTAGCG

32221 GCCACTGCACTCCAGCCTCAAAAAAAAAAAAAAAAAAAAAAAAAAAGTCCAAAGCTCTAATG
32221 CGGTGACGTGAGGTCGGAGTTTTTTTTTTTTTTTTTTTTTTTTTTTCAGGTTTCGAGATTAC

32281 AAAAACTGATGCATTCATGCAGATTGCTAACCCAACATCAAGGAGAACGAGAATTACATG
32281 TTTTTGACTACGTAAGTACGTCTAACGATTGGGTTGTAGTTCCTCTTGCTCTTAATGTAC

32341 GGACTGAGTGAATGAAGGATTGAAATTACTATTTTAAAGGGTTTTTGTTTGAAACATTAC
32341 CCTGACTCACTTACTTCCTAACTTTAATGATAAAATTTCCCAAAAACAAACTTTGTAATG

32401 TGATTTTTTTTATGTTTTGTTTTCCAGACTCAAGAAAATATTTTTTTTCTTTTGAGCTAT
32401 ACTAAAAAAAATACAAAACAAAAGGTCTGAGTTCTTTTATAAAAAAAAGAAAACTCGATA

32461 TTATAGCTTACAGCATTGGGGTAAAGTATACTTCTGTGAGCAAAATGGAAACATTTACCT
32461 AATATCGAATGTCGTAACCCCATTTCATATGAAGACACTCGTTTTACCTTTGTAAATGGA

32521 TTCTTTCTACCTGAATTCTTCAGAATTTGGAAACTATTCATTAGTGTTCTTATTTTCTGG
32521 AAGAAAGATGGACTTAAGAAGTCTTAAACCTTTGATAAGTAATCACAAGAATAAAAGACC

32581 CAATATAGTTATTTGCATAAGTTCAATAAGAACCTATTTTCGGCTGTGCATGGTGGCTCA
32581 GTTATATCAATAAACGTATTCAAGTTATTCTTGGATAAAAGCCGACACGTACCACCGAGT

32641 TGCCTGTAATCCCAGCACCTTGGGAGGGCGAGGCCGGTGGATCACAAGGTCAGGAGTTTG
32641 ACGGACATTAGGGTCGTGGAACCCTCCCGCTCCGGCCACCTAGTGTTCCAGTCCTCAAAC

32701 AGAACAGCCTGGCCAAGATGGTGAAACCCCGTCTCTACTAAAACTACAAAGATTAACCAG
32701 TCTTGTCGGACCGGTTCTACCACTTTGGGGCAGAGATGATTTTGATGTTTCTAATTGGTC

32761 GCGCGGTGGCAGGCGCCTGTAATCCCAGCTACTCGGGAGGCTGAGGCAGGAGAATAGCTT
32761 CGCGCCACCGTCCGCGGACATTAGGGTCGATGAGCCCTCCGACTCCGTCCTCTTATCGAA

32821 GAACCTTGGGTGGCAGAGGTTGCAGTGAGCCGAGATCGCACCACTGCGCTCCAGCCTAGG
32821 CTTGGAACCCACCGTCTCCAACGTCACTCGGCTCTAGCGTGGTGACGCGAGGTCGGATCC

FIG. 4 (cont'd)

```
32881  GGACAAGAGCGAGACTCTATCTCAAAACAAACAAACAAAAAAACAAAAAGCAAACAAACA
32881  CCTGTTCTCGCTCTGAGATAGAGTTTTGTTTGTTTGTTTTTTTGTTTTTCGTTTGTTTGT

32941  AAAAAAGAGCTTATTTTCTTTTGTAACTGGACACATGGAAACAGTGGTTATTTTACCAAG
32941  TTTTTTCTCGAATAAAAGAAAACATTGACCTGTGTACCTTTGTCACCAATAAAATGGTTC

33001  GCTTTGACTGGAATGTCTTTTTTTTGAGTGCAACCGGACTGCTTCGAGGGATTGAGGTTG
33001  CGAAACTGACCTTACAGAAAAAAAACTCACGTTGGCCTGACGAAGCTCCCTAACTCCAAC

33061  ACTTTATACAGCCAGTAGACTTGGAAAAAGACACACCTGGTACCTTGCCCACACAATTCC
33061  TGAAATATGTCGGTCATCTGAACCTTTTTCTGTGTGGACCATGGAACGGGTGTGTTAAGG

33121  TTTATAGCGTTTCTAACTTTGCAATAAGTAAAGAATGTCACTTTCTGACAGGCCCAGGGA
33121  AAATATCGCAAAGATTGAAACGTTATTCATTTCTTACAGTGAAAGACTGTCCGGGTCCCT

33181  CCTCAAGATATTTTGGAGACGTTGAAAAGAGAGCAATTCACCCAATTCATACAGGTTTTA
33181  GGAGTTCTATAAAACCTCTGCAACTTTTCTCTCGTTAAGTGGGTTAAGTATGTCCAAAAT

33241  CAGGCACAGTCTGATGGCGAATCTTTGGCTTGGCTTCATTGCTTCAAGAGTTTGTTTTTT
33241  GTCCGTGTCAGACTACCGCTTAGAAACCGAACCGAAGTAACGAAGTTCTCAAACAAAAAA

33301  TGACACGGAATCTCACTCTGTCACCCATTCTGGAGTGCAGTGGTGAGATCTTGGCTCACT
33301  ACTGTGCCTTAGAGTGAGACAGTGGGTAAGACCTCACGTCACCACTCTAGAACCGAGTGA

33361  GAAACCTCTGCTTCCTGGATTCAAGTGATTCTCCTGCTTCAGCCTCCCGAGTAGCTGGGA
33361  CTTTGGAGACGAAGGACCTAAGTTCACTAAGAGGACGAAGTCGGAGGGCTCATCGACCCT

33421  TTACAGGCATGTGTTGCTACTCCCAGCTAATTTTTTGTATTTTTGGTAGAGATGAGGTTT
33421  AATGTCCGTACACAACGATGAGGGTCGATTAAAAAACATAAAAACCATCTCTACTCCAAA

33481  CACCATGTTGCCCAGGGTGGTCTTGAACTCCTGACCTCAGGTGATCCACCCACCTCAGCC
33481  GTGGTACAACGGGTCCCACCAGAACTTGAGGACTGGAGTCCACTAGGTGGGTGGAGTCGG

33541  TCCCAAAGTGCTGGGATTACAGGCGTGAGCCACTGTGCCCAGCCCTTGAGAGGTTTCAAA
33541  AGGGTTTCACGACCCTAATGTCCGCACTCGGTGACACGGGTCGGGAACTCTCCAAAGTTT

33601  AGTCTTAATCTGAGATTCCTTATGAAAAAATTCCAACAAAGCCAACTTAAGAGCCATCCC
33601  TCAGAATTAGACTCTAAGGAATACTTTTTTAAGGTTGTTTCGGTTGAATTCTCGGTAGGG

33661  TGTAGAAAATATATCTATTTAAATATCGTCTGTTTTATGCCACAATGTTTGTTTTGCGTT
33661  ACATCTTTTATATAGATAAATTTATAGCAGACAAAATACGGTGTTACAAACAAAACGCAA

33721  GCAAGCCGTTATCTCCTAGGCATGGGTAATCCACTTTGAGAGGAAAATCCAGACATCATT
33721  CGTTCGGCAATAGAGGATCCGTACCCATTAGGTGAAACTCTCCTTTTAGGTCTGTAGTAA

33781  GTGCCTAATTTGCTGCCACCTGTGTCTGTGCTGGATCTTACCAGGGTTAGCTTTATTTTC
33781  CACGGATTAAACGACGGTGGACACAGACACGACCTAGAATGGTCCCAATCGAAATAAAAG

33841  TTTCAACTGGCAAAATTCTGATAAAGCATGTAGCTTCACGGTAGAGCAAAAAGTGTAACT
33841  AAAGTTGACCGTTTTAAGACTATTTCGTACATCGAAGTGCCATCTCGTTTTTCACATTGA

33901  TAATTGAAAGTCATGACTTTCAGGAGTCTAATGATGCTAATATATTTTCTTCTAGAGAGG
33901  ATTAACTTTCAGTACTGAAAGTCCTCAGATTACTACGATTATATAAAAGAAGATCTCTCC

33961  TGTCTTTATTGTATGTAATTCCCTGAAGAAATGTAAAGATTTATCTAATTCCTATTGCTC
33961  ACAGAAATAACATACATTAAGGGACTTCTTTACATTTCTAAATAGATTAAGGATAACGAG

34021  TGACAGGCGTGCTCAATAGAAGCATTGAAGTAAAATAAAAATAACCTTTTTAATCTGTGT
34021  ACTGTCCGCACGAGTTATCTTCGTAACTTCATTTTATTTTTATTGGAAAAATTAGACACA

34081  ATTTCTCTTGCCCACCAAGATATTTAATTTTTTTCTTGATCTTTGCTTTTGTTTATGTGA
34081  TAAAGAGAACGGGTGGTTCTATAAATTAAAAAAAGAACTAGAAACGAAAACAAATACACT

34141  AGATATTTATGTCTATATCATTTCTGTATATATCACAGAAAAGTTTTCACTTGCTTGACA
34141  TCTATAAATACAGATATAGTAAAGACATATATAGTGTCTTTTCAAAAGTGAACGAACTGT

34201  TTTTATTCTACAATGATTTTTAGTTTAAGTTTAAAGAATGGCTACATTCAGATTTATTTT
34201  AAAATAAGATGTTACTAAAAATCAAATTCAAATTTCTTACCGATGTAAGTCTAAATAAAA
```

FIG. 4 (cont'd)

```
34261  CACAACTATAGTCCTGCTAAACTGCCTTTGTTGAAAACTCAGTTTTTATAATAAATAAAA
34261  GTGTTGATATCAGGACGATTTGACGGAAACAACTTTTGAGTCAAAAATATTATTTATTTT

34321  AATATCAAAGCAAAAAAAAAAGAGCCTTCATGATAAATCACCATTCTTACTGCACTTTAA
34321  TTATAGTTTCGTTTTTTTTTTCTCGGAAGTACTATTTAGTGGTAAGAATGACGTGAAATT

34381  GCAGATAATCATGCCAGAGACTAAACTGACTTTGCAAATAAATTAGTTTTATTATTATTA
34381  CGTCTATTAGTACGGTCTCTGATTTGACTGAAACGTTTATTTAATCAAAATAATAATAAT

34441  TCTTTGTGGGTAAAAGTTGGGATGACTGTAGAAGAGAAAATTATATTTCAGAAGAAAATT
34441  AGAAACACCCATTTTCAACCCTACTGACATCTTCTCTTTTAATATAAAGTCTTCTTTTAA

34501  ATACCATACTTGTTATTAGATTCTAGTCTTGATAATTGTTTTTTTGAGTTTTTGTTATTT
34501  TATGGTATGAACAATAATCTAAGATCAGAACTATTAACAAAAAAACTCAAAAACAATAAA

34561  GCCTACAATTTGGGCTGAATCCTGAATTCCTTCCTGGGTACAAGTCTCCAAACTAATGTT
34561  CGGATGTTAAACCCGACTTAGGACTTAAGGAAGGACCCATGTTCAGAGGTTTGATTACAA

34621  TCCTAATTTTTCTACCATTTTTCTGTCTTGGAATCACCAAGCCCTGCAGGCTTTAGCTAG
34621  AGGATTAAAAAGATGGTAAAAAGACAGAACCTTAGTGGTTCGGGACGTCCGAAATCGATC

34681  ACAACTTGATATAAACTTTGGAAGAAATAATGACAGCAACTTAATATATGAGCAGTGTTC
34681  TGTTGAACTATATTTGAAACCTTCTTTATTACTGTCGTTGAATTATATACTCGTCACAAG

34741  ATGTCAGCTGATGTATGGATTACTCAGAAGGTTTACTTGAACACCTGATTCAAACTATAA
34741  TACAGTCGACTACATACCTAATGAGTCTTCCAAATGAACTTGTGGACTAAGTTTGATATT

34801  TCCAGAAATATCTGTAAGATTGCCACTGCAATCTGAAGCTACTTCAGAGACTCTAGGAAA
34801  AGGTCTTTATAGACATTCTAACGGTGACGTTAGACTTCGATGAAGTCTCTGAGATCCTTT

34861  ATTAGTTTATAGACAACTCCAGATGTTAATCTTTGTTTTTCTTTTGTTTTCATGGAAATG
34861  TAATCAAATATCTGTTGAGGTCTACAATTAGAAACAAAAAGAAAACAAAAGTACCTTTAC

34921  CCTTTTATTAAACATCTGATTGCTTGATTCATAGAGGCCTGACTTTGGTGGAAGCAACAC
34921  GGAAAATAATTTGTAGACTAACGAACTAAGTATCTCCGGACTGAAACCACCTTCGTTGTG

34981  CACTGCCTGAAATGAGATATAACTGTTAACCGTTTAATTGGAGCGGCCTGTTCTCACGAC
34981  GTGACGGACTTTACTCTATATTGACAATTGGCAAATTAACCTCGCCGGACAAGAGTGCTG

35041  TGCAAGACTAGTTCAATGGCTTATAAAATAATCCACCCGCTGGGCACAGTAGTTCACACC
35041  ACGTTCTGATCAAGTTACCGAATATTTTATTAGGTGGGCGACCCGTGTCATCAAGTGTGG

35101  TGTAATCTCAGCACTTTGGGAGGCTGAGGTGGGCAAATTGCTTGAGCTCAGGAGTTCGAG
35101  ACATTAGAGTCGTGAAACCCTCCGACTCCACCCGTTTAACGAACTCGAGTCCTCAAGCTC

35161  ACCAGCCAGAGCAACATGGTGAAACCCTGTCTCTACCAAAAATATAAAAAATTAGCCGGG
35161  TGGTCGGTCTCGTTGTACCACTTTGGGACAGAGATGGTTTTTATATTTTTTAATCGGCCC

35221  CATAGTAGCATGTGCCTGTGGTCCCAGCTCCTCGGGAGGTGGATGTGGGAGGATTGCCTG
35221  GTATCATCGTACACGGACACCAGGGTCGAGGAGCCCTCCACCTACACCCTCCTAACGGAC

35281  AGCCTGGGAGGCAGAGCTTGCAGTGAGCTGAGATTATGACACTGCACTCTAGCCTGGGCA
35281  TCGGACCCTCCGTCTCGAACGTCACTCGACTCTAATACTGTGACGTGAGATCGGACCCGT

35341  ATACAGTGAGACCCCATCTCAAAAAAAAAAAAAAAAAGATAATCTACCAACCCAATTTCTC
35341  TATGTCACTCTGGGGTAGAGTTTTTTTTTTTTTTTTTCTATTAGATGGTTGGGTTAAAGAG

35401  AACTGGGGAATGTTGGGCTCCTGCTCTCCTGTCTCTGACCTTTCATTCTCCCTTGAGGCT
35401  TTGACCCCTTACAACCCGAGGACGAGAGGACAGAGACTGGAAAGTAAGAGGGAACTCCGA

35461  AGCCATCAAGACTACAACCCCTCTTCCCCAAAGTGGGCCATAGAAACAAAACCCCTTTTC
35461  TCGGTAGTTCTGATGTTGGGGAGAAGGGGTTTCACCCGGTATCTTTGTTTTGGGGAAAAG

35521  CCCAAAGCCAACCATAAAACCTAAAAATAGTACTCTAACTTCCACCACCCCCAGCCTGTC
35521  GGGTTTCGGTTGGTATTTTGGATTTTTATCATGAGATTGAAGGTGGTGGGGGTCGGACAG
```

FIG. 4 (cont'd)

```
35581  TGTGTAAGGCCATAAAGAAATTATCTGACTCACTTTGTTTGACTGAAGGTTATAAGACCC
35581  ACACATTCCGGTATTTCTTTAATAGACTGAGTGAAACAAACTGACTTCCAATATTCTGGG

35641  CCATTCCAGAGAGGGTCCAGCACCACACCCAGAAGGAAGAAATGCATGCTCAGAGAGGCA
35641  GGTAAGGTCTCTCCCAGGTCGTGGTGTGGGTCTTCCTTCTTTACGTACGAGTCTCTCCGT

35701  AGAAGGGTCCAGACAGACAGGCTGTGCTGGATTTCCCTGCTCAGTCTATTAGCATTAGAC
35701  TCTTCCCAGGTCTGTCTGTCCGACACGACCTAAAGGGACGAGTCAGATAATCGTAATCTG

35761  CATACCTTTTTTGTCCAATCATATTTCTACGTGGCTCTCCATACTTTGTTTAACCTAACC
35761  GTATGGAAAAAACAGGTTAGTATAAAGATGCACCGAGAGGTATGAAACAAATTGGATTGG

35821  TAAGGGGGCTCAGGGTTTTGGCCTGGGCATTGTCTGTTGGGGAATAGAGTGAGTCATCCC
35821  ATTCCCCCGAGTCCCAAAACCGGACCCGTAACAGACAACCCCTTATCTCACTCAGTAGGG

35881  CAGCTCATGGGTTTGCATCCAGTTCTTGTTGTAAAAGGCCCAAAGCCTGTTGGATGGCAA
35881  GTCGAGTACCCAAACGTAGGTCAAGAACAACATTTTCCGGGTTTCGGACAACCTACCGTT

35941  CCCTGAGCCATCGTGGAAGGGGGGTTCCAGTTTCACAAATAGATACTCAGACAGCCAAAC
35941  GGGACTCGGTAGCACCTTCCCCCCAAGGTCAAAGTGTTTATCTATGAGTCTGTCGGTTTG

36001  TACCATCTACTTGGTGCCAACGTTTGCACTGTGGTCAAAGACTTACCTAGCACAGACTGA
36001  ATGGTAGATGAACCACGGTTGCAAACGTGACACCAGTTTCTGAATGGATCGTGTCTGACT

36061  ACAAATCTTCCCATCTGTCACATAAATGTCCCCAAGCAATGTTGAAGCACATGCCAGGAT
36061  TGTTTAGAAGGGTAGACAGTGTATTTACAGGGGTTCGTTACAACTTCGTGTACGGTCCTA

36121  CGGCCTTGCTAGGTCCTGCTTGGTAGATAAGCAAATGGCTTCCTTGTGGTGTTTTTATTC
36121  GCCGGAACGATCCAGGACGAACCATCTATTCGTTTACCGAAGGAACACCACAAAAATAAG

36181  TATTTTGTCTCATTAACACTACAACTTTGTGTTATCTACTTGATAATCTGTAATTGTAAA
36181  ATAAAACAGAGTAATTGTGATGTTGAAACACAATAGATGAACTATTAGACATTAACATTT

36241  TACATACAGGATTATGTAATTTGTGTAAATACATAATGACAGACTTCTGAAAACTGGTAT
36241  ATGTATGTCCTAATACATTAAACACATTTATGTATTACTGTCTGAAGACTTTTGACCATA

36301  TTTTTACTTGGTGTCCATTTGAAGCTGTTTTAGGTTCTGTGGCACATGAACCAATGGCAT
36301  AAAAATGAACCACAGGTAAACTTCGACAAAATCCAAGACACCGTGTACTTGGTTACCGTA

36361  TTAAAAAGCATACTCTCCTTGCTCTTAAAAAAACAAACAAAACAAAACAAAAACTGTCCA
36361  AATTTTTCGTATGAGAGGAACGAGAATTTTTTTGTTTGTTTTGTTTTGTTTTTGACAGGT

36421  TTAAAATTTTTGTATTTTTGTAAAGACAGGGTTTCACCATAAAAATGGACAGTTTCCCTT
36421  AATTTTAAAAACATAAAAACATTTCTGTCCCAAAGTGGTATTTTTACCTGTCAAAGGGAA

36481  ATATCTTTGGGTCTTCGTTCTGTAGGCTCTCGTGTCACATAAAATTATGATCAAATAAAT
36481  TATAGAAACCCAGAAGCAAGACATCCGAGAGCACAGTGTATTTTAATACTAGTTTATTTA

36541  TTGTATGACTTTTCTCCTATTAATCTGCCCCTTGTCAATGATTTTGAGCAACCTTCTGAA
36541  AACATACTGAAAAGAGGATAATTAGACGGGGAACAGTTACTAAAACTCGTTGGAAGACTT

36601  GAAAGTGATGGGGAAGTATTCCCTTTGCTGCCACAAGGTATATATCAGATAAGTCAGTCT
36601  CTTTCACTACCCCTTCATAAGGGAAACGACGGTGTTCCATATATAGTCTATTCAGTCAGA

36661  ATTTTCTTGAACATATATCACATTCATAGGAAAAACACTTTTTCCAAAAGATTACTGTCT
36661  TAAAAGAACTTGTATATAGTGTAAGTATCCTTTTTGTGAAAAAGGTTTTCTAATGACAGA

36721  TCCCAAATACCCACGTTCTCCATTTTTTTTTTTTTTTTTTTAGAGATGGGGTCTCACTGTG
36721  AGGGTTTATGGGTGCAAGAGGTAAAAAAAAAAAAAAAAAAATCTCTACCCCAGAGTGACAC

36781  TTGTCCAGGCTAGTCTCAAGCTTCTGGACTCAAGCAATCCTCTCACCTCAGCTTCCCAAA
36781  AACAGGTCCGATCAGAGTTCGAAGACCTGAGTTCGTTAGGAGAGTGGAGTCGAAGGGTTT

36841  GTGCTGTGATTACAGACATAAGCCATCACGCCCGGCCCCATTTTCTCCTTTGGGTGTATG
36841  CACGACACTAATGTCTGTATTCGGTAGTGCGGGCCGGGGTAAAAGAGGAAACCCACATAC

36901  TATATTGCTCATTGTCAGGCATCAACCATTTCTCTTCTCTGAGATGGAGTCTCACTCTGT
36901  ATATAACGAGTAACAGTCCGTAGTTGGTAAAGAGAAGAGACTCTACCTCAGAGTGAGACA
```

FIG. 4 (cont'd)

36961 CACCCAGGCTGGAGTGCAGTGGCGCAATCTTGGCTCACTGCAAGCTCTGCCTCCCTGGTT
36961 GTGGGTCCGACCTCACGTCACCGCGTTAGAACCGAGTGACGTTCGAGACGGAGGGACCAA

37021 CACGCCATTCTCCTGCCTCAGCCTCCCGAGTAGCTGGGACTACAGGTGCCCACCACTACG
37021 GTGCGGTAAGAGGACGGAGTCGGAGGGCTCATCGACCCTGATGTCCACGGGTGGTGATGC

37081 CCCGGCTAATTTTTTTGTATTTCTTTTTTGGTAGAGACGGGGTTTCACCGTGTTAGACAG
37081 GGGCCGATTAAAAAAACATAAAGAAAAAACCATCTCTGCCCCAAAGTGGCACAATCTGTC

37141 GATGGTCTCAATCTCCTGACCTCGTGATCCGCCCGCCTCGGCCTCCCAAAGTGCTGGGAT
37141 CTACCAGAGTTAGAGGACTGGAGCACTAGGCGGGCGGAGCCGGAGGGTTTCACGACCCTA

37201 TACAGGTGTGAGCCACTGCGCCCAGCCCTCTTCTAATTTTTTATATTTATCATGTATTTA
37201 ATGTCCACACTCGGTGACGCGGGTCGGGAGAAGATTAAAAAATATAAATAGTACATAAAT

37261 CTAGAACTGGTTTATTTTCGTGAGCATATGTTGTGGATTCTACTATAAATAATGCACTTA
37261 GATCTTGACCAAATAAAAGCACTCGTATACAACACCTAAGATGATATTTATTACGTGAAT

37321 ATAATCATTAATAAAACTTAAATCCTTTCCGTCTTGATTGTGGCCTTTTCTTTTTGCTAT
37321 TATTAGTAATTATTTTGAATTTAGGAAAGGCAGAACTAACACCGGAAAAGAAAAACGATA

37381 TAATTTCCTCAGCATAGGTTAACCTGAACTCTTAAAAGCTATTTAGGTACTGGTATAAAA
37381 ATTAAAGGAGTCGTATCCAATTGGACTTGAGAATTTTCGATAAATCCATGACCATATTTT

37441 CAAAATTTTCTCCAAAGCAATCCAGTATATAATATCTGGATTTTAAAAAAGCAGCCTCAT
37441 GTTTTAAAAGAGGTTTCGTTAGGTCATATATTATAGACCTAAAATTTTTTCGTCGGAGTA

37501 TTAATTAGGATTAATTTCTCCTTTCAGAAGTTAAGTGATTCTGTTTCTGTAAAACGCAAA
37501 AATTAATCCTAATTAAAGAGGAAAGTCTTCAATTCACTAAGACAAAGACATTTTGCGTTT

37561 ATTATAAGCTTAATTGTTTTCCACACAGGAAATGAAATTCCTAATCTTTTTATCCAGAAT
37561 TAATATTCGAATTAACAAAAGGTGTGTCCTTTACTTTAAGGATTAGAAAAATAGGTCTTA

37621 CTTCATGTGTTTGTCTCTCTGTCCATCTGTCACTCCTTTTTAAGGTACCTGGAGATGACC
37621 GAAGTACACAAACAGAGAGACAGGTAGACAGTGAGGAAAAATTCCATGGACCTCTACTGG

37681 TAGAGGCTTGCCACGCTTAGGGTTTCCTCCCTGTGCAGAAGAAGATGGGAAGTGCAAATG
37681 ATCTCCGAACGGTGCGAATCCCAAAGGAGGGACACGTCTTCTTCTACCCTTCACGTTTAC

37741 AGGACGAGGGGTGGGGAGGGAAGAGGGAGTCAGGTGATTCAGCAAGTGCAGGAGCCCACA
37741 TCCTGCTCCCCACCCCTCCCTTCTCCCTCAGTCCACTAAGTCGTTCACGTCCTCGGGTGT

37801 GACTAAGCTCAGGAATTTGCACTTTGTCTGCTCGCAGAGTGAGTTTCATCGTGGTGTGTA
37801 CTGATTCGAGTCCTTAAACGTGAAACAGACGAGCGTCTCACTCAAAGTAGCACCACACAT

37861 TATATTGAGATATGCAACAGACTCCACTGGAATGTCAGAAGAACTTATGTTTATTTTTCC
37861 ATATAACTCTATACGTTGTCTGAGGTGACCTTACAGTCTTCTTGAATACAAATAAAAAGG

37921 TCTAACATGTGGGAAAGATTAAACTGTATTTGTATTTAACTCACATAGATTGGCACGTGC
37921 AGATTGTACACCCTTTCTAATTTGACATAAACATAAATTGAGTGTATCTAACCGTGCACG

37981 TCATTCTGTGTGTCACCCTGCCACGCTGTCACAAACTTCGAGCAGGGTCCTGAGGGGAGA
37981 AGTAAGACACACAGTGGGACGGTGCGACAGTGTTTGAAGCTCGTCCCAGGACTCCCCTCT

38041 GGAGGGCATAGCTCCTGCTCCCAGGGGGTTGCCTGTGTAGCCCTGCGCATTCATTCTCTT
38041 CCTCCCGTATCGAGGACGAGGGTCCCCCAACGGACACATCGGGACGCGTAAGTAAGAGAA

38101 CCAGAGGGTTGTGATTTGTGGCGGTCTGTGTGAGCCTGGTTAAGGAGAGTTACAGATTAT
38101 GGTCTCCCAACACTAAACACCGCCAGACACACTCGGACCAATTCCTCTCAATGTCTAATA

38161 GTCATCTGGTGTTAACTGATAATCTTTGCAAAAGGGACATTGGCTTTAAGAGATGTCTGC
38161 CAGTAGACCACAATTGACTATTAGAAACGTTTTCCCTGTAACCGAAATTCTCTACAGACG

38221 AAAAAAAACTCTAAACAAACATAAATAAAAATTTAAAAGGATAAAGCCAGAATAATAATG
38221 TTTTTTTTGAGATTTGTTTGTATTTATTTTTAAATTTTCCTATTTCGGTCTTATTATTAC

FIG. 4 (cont'd)

```
38281  AAAATATTAGTAATGTAAAACAAGGAAATGTGTCATGTTTTTCATGATAACTAATATTTT
38281  TTTTATAATCATTACATTTTGTTCCTTTACACAGTACAAAAAGTACTATTGATTATAAAA

38341  TTCAATTTTTTTTTTTTTTTAAGACAGTCTCACTCTGTCACCAGGCTGGAGTCAGTAGTG
38341  AAGTTAAAAAAAAAAAAAAAATTCTGTCAGAGTGAGACAGTGGTCCGACCTCAGTCATCAC

38401  CGATCTTGGCTCACTGCAACCTCCACCTCCCAGGTTCACACAATTCTCATGTCTCAGCCT
38401  GCTAGAACCGAGTGACGTTGGAGGTGGAGGGTCCAAGTGTGTTAAGAGTACAGAGTCGGA

38461  CCTGAGTAGCTGGGTTTACAGGCACTCGCCACCATGCCCAGCTAATTTTTGTATTTTTAG
38461  GGACTCATCGACCCAAATGTCCGTGAGCGGTGGTACGGGTCGATTAAAAACATAAAAATC

38521  TAAAGACAGGGTTTTACCATGTTGGCCAGGCTGGTCTCAAACTCCTGACCTCAGGTGATC
38521  ATTTCTGTCCCAAAATGGTACAACCGGTCCGACCAGAGTTTGAGGACTGGAGTCCACTAG

38581  GGCCGCCTTGGCCTCCCAAAGTGCTGGGATTACAGGCGTGTGCCACTGTGCCTGGCCCCA
38581  CCGGCGGAACCGGAGGGTTTCACGACCCTAATGTCCGCACACGGTGACACGGACCGGGGT

38641  GTTCTTATTATAAGTTCTCCATTAACCATATCATGAGATTAAAAAAACAACAATGATTTC
38641  CAAGAATAATATTCAAGAGGTAATTGGTATAGTACTCTAATTTTTTTGTTGTTACTAAAG

38701  ATCGGAACTGACAAATAGTGGGTGACACAATTTTGATCATCAAGAAGACTTTAAAAGAAG
38701  TAGCCTTGACTGTTTATCACCCACTGTGTTAAAACTAGTAGTTCTTCTGAAATTTTCTTC

38761  GATTTGTATCACTGTCATTACTGATTACTTGGCCCTTGTGTATACTGGGCCTTTAGCTAG
38761  CTAAACATAGTGACAGTAATGACTAATGAACCGGGAACACATATGACCCGGAAATCGATC

38821  GGCTGGTACAATAAAATAACCATAGTTAGAAAGATATTTTAAAGGATTACTTATTTCATG
38821  CCGACCATGTTATTTTATTGGTATCAATCTTTCTATAAAATTTCCTAATGAATAAAGTAC

38881  TTTATCTCACCCTTTTATCCCTATTTTTGGGCATGATTTATTATTATTAGGTTTTTAAAT
38881  AAATAGAGTGGGAAAATAGGGATAAAAACCCGTACTAAATAATAATAATCCAAAAATTTA

38941  AAATAATGAAATAAGCATGTTAGGTTTGCATGCTGCTTTGGTTAACATTGCTATATAACC
38941  TTTATTACTTTATTCGTACAATCCAAACGTACGACGAAACCAATTGTAACGATATATTGG

39001  AACCACCCCAAACTTTGTGGCCTTAAAACAATAATTTATTTATTTATTTATTTATTTATT
39001  TTGGTGGGGTTTGAAACACCGGAATTTTGTTATTAAATAAATAAATAAATAAATAAATAA

39061  TATTTATTTATTTATTTATTTTTGAGACAGAGTCTCGCTATGTCACCCAGGCTGGAGTGC
39061  ATAAATAAATAAATAAATAAAAACTCTGTCTCAGAGCGATACAGTGGGTCCGACCTCACG

39121  AGCGGCATGATCTCGGCTCACTGCAACCTCCACCTCCTGGGTTCAAGTGATCCTCCTGCC
39121  TCGCCGTACTAGAGCCGAGTGACGTTGGAGGTGGAGGACCCAAGTTCACTAGGAGGACGG

39181  TCAGCCTCCCGTAGAGCTGGGATTACAGGCACCCGCCATCAAGCCCAGCTAATTTTTCCT
39181  AGTCGGAGGGCATCTCGACCCTAATGTCCGTGGGCGGTAGTTCGGGTCGATTAAAAAGGA

39241  TTATTTTTAGTAGAGACGGGGTTTCACCATGTTGGCCAGGTTGGTCTCGAACTCCTGATC
39241  AATAAAAATCATCTCTGCCCCAAAGTGGTACAACCGGTCCAACCAGAGCTTGAGGACTAG

39301  TCAGGTGATATGCCTGCTTTGGCCTCCCAAAGTGCTGGGATTACAGGTGTGAGCCACTGT
39301  AGTCCACTATACGGACGAAACCGGAGGGTTTCACGACCCTAATGTCCACACTCGGTGACA

39361  GCATGGCCAACAATAATTTATTTTTATCTCTCATGGTCTCTAGATTGCCTGGGCCCGGCT
39361  CGTACCGGTTGTTATTAAATAAAAATAGAGAGTACCAGAGATCTAACGGACCCGGGCCGA

39421  GAGCAGTCTGAGTCAGCCTTATGGTCTCTCATGTGTTTTTAATCAGTCATGAGGGGCCGG
39421  CTCGTCAGACTCAGTCGGAATACCAGAGAGTACACAAAAATTAGTCAGTACTCCCCGGCC

39481  CATCATCTGAAGGCTTGACTGGGCTGGATGTTTAAGACAGCCACTCACAGGGCTGACAGT
39481  GTAGTAGACTTCCGAACTGACCCGACCTACAAATTCTGTCGGTGAGTGTCCCGACTGTCA

39541  GATGCTGGATGTTGCACTGTTGACTAATGAGCCTGCACGTGGCTCCTCCATGTGATTTGG
39541  CTACGACCTACAACGTGACAACTGATTACTCGGACGTGCACCGAGGAGGTACACTAAACC
```

FIG. 4 (cont'd)

```
39601  GCTATTTATAGCTGGGGTGACTGGGTTCTAGGTGGGGTAGTTCCAAGATCCTTCCAAGAG
39601  CGATAAATATCGACCCCACTGACCCAAGATCCACCCCATCAAGGTTCTAGGAAGGTTCTC

39661  GAAGAAAGCAGAAACTGCCTGGCCAGTTAGTGTATATGCTTAGTCTTAGAACAGTGTCAC
39661  CTTCTTTCGTCTTTGACGGACCGGTCAATCACATATACGAATCAGAATCTTGTCACAGTG

39721  TTCCATATTTCTCCATAGTCCATTAATCAAAGCAGTTACAGGAAGCAGACAGACAGGAAG
39721  AAGGTATAAAGAGGTATCAGGTAATTAGTTTCGTCAATGTCCTTCGTCTGTCTGTCCTTC

39781  GGAAAACACAATGCAACAGAAGGAGAGATTGAAGTGTTGGCAGCTGCAAGCCAAGAAACA
39781  CCTTTTGTGTTACGTTGTCTTCCTCTCTAACTTCACAACCGTCGACGTTCGGTTCTTTGT

39841  CCTGGGTTACCAGAAGCTAGAAGAAGAAAGGTAGGATTCTCCCCTACAGGTTCCAAAGGA
39841  GGACCCAATGGTCTTCGATCTTCTTCTTTCCATCCTAAGAGGGGATGTCCAAGGTTTCCT

39901  AGCTGGGCCTGTCCACACCTCACCTCTGGAACTATGAGACAATCACTTTCTGTGGGTTTA
39901  TCGACCCGGACAGGTGTGGAGTGGAGACCTTGATACTCTGTTAGTGAAAGACACCCAAAT

39961  AGCTACCCAGTTTGTGGCACTTTGTTACTACCGTCCTAGGCAAATGATACAGTAACTACA
39961  TCGATGGGTCAAACACCGTGAAACAATGATGGCAGGATCCGTTTACTATGTCATTGATGT

40021  TACACAGTACATAGAATTGCTCATTTTACTTCGTTGAATGGGACTTGGCATTGAATAAGC
40021  ATGTGTCATGTATCTTAACGAGTAAAATGAAGCAACTTACCCTGAACCGTAACTTATTCG

40081  CCAAATGAGAATTCTTTTGTCAAGATTTTTTTATGGCTCACTTTTCCAGAGACGTGACAT
40081  GGTTTACTCTTAAGAAAACAGTTCTAAAAAAATACCGAGTGAAAAGGTCTCTGCACTGTA

40141  GGCAGGAGTAAGGGGAGGGTTTGGCAGGTAGGAATTATACTCATCTGTCATTGTCTTCCC
40141  CCGTCCTCATTCCCCTCCCAAACCGTCCATCCTTAATATGAGTAGACAGTAACAGAAGGG

40201  AATACCAACCAGGAAGCATGTAAATAATAGCTGTGCAGTTTGTTTTCTGAACCAAACTGG
40201  TTATGGTTGGTCCTTCGTACATTTATTATCGACACGTCAAACAAAAGACTTGGTTTGACC

40261  GCCTTATTTTTTTTAAAGAAACTTTATTAAACAAACAAAAACCTAGAAACACTAGATGTA
40261  CGGAATAAAAAAAATTTCTTTGAAATAATTTGTTTGTTTTTGGATCTTTGTGATCTACAT

40321  TATTTTTAAGGTTTCTCTCACATAATATCCTAATCATCAGTATACCGTAATCCAAGGGCT
40321  ATAAAAATTCCAAAGAGAGTGTATTATAGGATTAGTAGTCATATGGCATTAGGTTCCCGA

40381  ACATATAACTGAAAAATAAATGGGTCTTAAAAAAATTAAAACATGGTATATAACACTAGC
40381  TGTATATTGACTTTTTATTTACCCAGAATTTTTTTAATTTTGTACCATATATTGTGATCG

40441  TAACATGTACTGAGCAGTTACTAAGTGCTAAGTACTGCTAAGTCCTTTATAGATATCTTC
40441  ATTGTACATGACTCGTCAATGATTCACGATTCATGACGATTCAGGAAATATCTATAGAAG

40501  ATGTTGAGTGTCGTCACTGCCCATTACTTACTCTGAGTTTAAATATGAGACTCAAAAGAG
40501  TACAACTCACAGCAGTGACGGGTAATGAATGAGACTCAAATTTATACTCTGAGTTTTCTC

40561  GTTAGTAATTTGCCAAAAGTCATAGGGCTTATAAGTGATAGAACCAGGATAACGAATCTC
40561  CAATCATTAAACGGTTTTCAGTATCCCGAATATTCACTATCTTGGTCCTATTGCTTAGAG

40621  AACCAAGGGACTTCAATGCCCAAACCGGTGCTCAGACTGTAGCCCCATGTAGTTAGCTAT
40621  TTGGTTCCCTGAAGTTACGGGTTTGGCCACGAGTCTGACATCGGGGTACATCAATCGATA

40681  TTACATTTGAAAAAATTTTTAATGTTTATTATTTTTTTTAAGACAGGGTCTTGCTCTGTC
40681  AATGTAAACTTTTTTAAAAATTACAAATAATAAAAAAAATTCTGTCCCAGAACGAGACAG

40741  ACCTAGGCTGGAGTGGAGTGGTGTGATCTTGGCTCACTGCAACCTCCACCTCCTGGGCTC
40741  TGGATCCGACCTCACCTCACCACACTAGAACCGAGTGACGTTGGAGGTGGAGGACCCGAG

40801  AAGTGATCCTCTCATCTCAGCCTCCCAAGTAGCTGGGACCACAGGTGTATGGCACCACGC
40801  TTCACTAGGAGAGTAGAGTCGGAGGGTTCATCGACCCTGGTGTCCACATACCGTGGTGCG

40861  CCAACTAATTTGTTGTGTTCTTGGTAGAGGTGAGTTTCACCATGTTGCCCAGGCTGGTCT
40861  GGTTGATTAAACAACACAAGAACCATCTCCACTCAAAGTGGTACAACGGGTCCGACCAGA
```

FIG. 4 (cont'd)

```
40921  TGAACTCCTGAGCTCAAGTGACCTGCCCACTTGCCTCACCCTCCTAAAGTGGGGGGATTA
40921  ACTTGAGGACTCGAGTTCACTGGACGGGTGAACGGAGTGGGAGGATTTCACCCCCCTAAT

40981  CAGGTGTGAGCCACCATGCCCGGCCCAGCTATTTACATTTAAATATAAATTAAAATGAAA
40981  GTCCACACTCGGTGGTACGGGCCGGGTCGATAAATGTAAATTTATATTTAATTTTACTTT

41041  CAAGATTAAAAATTCGGTTTCTCAATCACACTAACCACACTTGAAGTGCTCAGTAGCTAC
41041  GTTCTAATTTTTAAGCCAAAGAGTTAGTGTGATTGGTGTGAACTTCACGAGTCATCGATG

41101  ATGTGGCTTAGTGGCTACCTGGCAGATATAGAACGTTTCCATCAGCACAGAAAGTTCTAC
41101  TACACCGAATCACCGATGGACCGTCTATATCTTGCAAAGGTAGTCGTGTCTTTCAAGATG

41161  TGGAAAGCATTGATCCAATCTCTTTGAACAGTCACAATGCATATAAAGTCCTTATTATGA
41161  ACCTTTCGTAACTAGGTTAGAGAAACTTGTCAGTGTTACGTATATTTCAGGAATAATACT

41221  CTGTACAAGGGAAGACAACGAGTAGAGGAAGGCAGAAAATAGGAAAAAAGGAAGAAGAAA
41221  GACATGTTCCCTTCTGTTGCTCATCTCCTTCCGTCTTTTATCCTTTTTTCCTTCTTCTTT

41281  GATTTAGGGTGAGGGAGAGCAGTTCTATGAAGAAAAGAAGCTCATATCTAGGAGTGGAGT
41281  CTAAATCCCACTCCCTCTCGTCAAGATACTTCTTTTCTTCGAGTATAGATCCTCACCTCA

41341  GGACCCTGAGAACATGTTAGTCTATTATATTCTAAACTTTGGCAGTTAAAATTCCAAAGT
41341  CCTGGGACTCTTGTACAATCAGATAATATAAGATTTGAAACCGTCAATTTTAAGGTTTCA

41401  ATATTAAGTACATGCTTTCTAAAATATTAGAGAGCTGCAGTTCAACAGATTTTTAACTCT
41401  TATAATTCATGTACGAAAGATTTTATAATCTCTCGACGTCAAGTTGTCTAAAAATTGAGA

41461  CCACAGCATGTCCGGCACTGGGTGAGGTGGGATGGCTAGGTGAATAATATAGGCATTGTC
41461  GGTGTCGTACAGGCCGTGACCCACTCCACCCTACCGATCCACTTATTATATCCGTAACAG

41521  ATGTGTGTTCGTGTGAAGAGACCACCAAACAGGCTTTGTGTGAGCAATAAAGCTTTTTAA
41521  TACACACAAGCACACTTCTCTGGTGGTTTGTCCGAAACACACTCGTTATTTCGAAAAATT

41581  TCACCTGGGTACAGGCGGGCCGAGTCTGAAAAGAGAGTCAGCAAAGGGTGGTGGGATTAT
41581  AGTGGACCCATGTCCGCCCGGCTCAGACTTTTCTCTCAGTCGTTTCCCACCACCCTAATA

41641  AATTAGTTCTTAGAGGTTTGGGATAGGCGGTGGAGTAGGAACAATTTTTTGTGGGCAGGG
41641  TTAATCAAGAATCTCCAAACCCTATCCGCCACCTCATCCTTGTTAAAAAACACCCGTCCC

41701  GATGGATCTTACAAAGTACATTCTCAAGGGCGAGGAGAATATTACAAAGTACCTTAAGGG
41701  CTACCTAGAATGTTTCATGTAAGAGTTCCCGCTCCTCTTATAATGTTTCATGGAATTCCC

41761  CAGGGAAGGATATTACAAAGTACCTTCTCAAGGGTGGGGAGGGTGTATCATACAAAGTGC
41761  GTCCCTTCCTATAATGTTTCATGGAAGAGTTCCCACCCCTCCCACATAGTATGTTTCACG

41821  ATTCACAAGGGTGGGGAAATATCACAAAGTACATTATCGCAAGGGCAGGGAGGGTGTATT
41821  TAAGTGTTCCCACCCCTTTATAGTGTTTCATGTAATAGCGTTCCCGTCCCTCCCACATAA

41881  GTCACAAAGTCAATTGATCGGTTAGGGTGGGGCAGGAACAAATCACAACAGTGGAATGTC
41881  CAGTGTTTCAGTTAACTAGCCAATCCCACCCCGTCCTTGTTTAGTGTTGTCACCTTACAG

41941  ATCAGTTAAGGCAGGAACCTGCTATTTTCACTTTTGTTGATCTTCAGTTGCTTCAGGCCA
41941  TAGTCAATTCCGTCCTTGGACGATAAAAGTGAAAACAACTAGAAGTCAACGAAGTCCGGT

42001  TCTGGATGTATACGTGCAGGTCACAGGGGATATGATGGATTAGCTTGGGCTCAGAGGCCT
42001  AGACCTACATATGCACGTCCAGTGTCCCCTATACTACCTAATCGAACCCGAGTCTCCGGA

42061  GACAGACATGAACTTCCCATCATAAAATTAGAAGAGCATTAATCAAATGATTAGAATAAA
42061  CTGTCTGTACTTGAAGGGTAGTATTTTAATCTTCTCGTAATTAGTTTACTAATCTTATTT

42121  ATATTACCATTATTTTGAAATGGCAAGCATTGTATGTAAATAAACAGCAGAGGAACCCAC
42121  TATAATGGTAATAAAACTTTACCGTTCGTAACATACATTTATTTGTCGTCTCCTTGGGTG

42181  TGTAGCCTAGACAGGGTTCAGAGACGTTCCTGCCAAGGACATGGCACAGGGACTGAACAA
42181  ACATCGGATCTGTCCCAAGTCTCTGCAAGGACGGTTCCTGTACCGTGTCCCTGACTTGTT

42241  GGAAGGATGACAGTGCCTGGCAAAGGCAGGGAATGTTACAGGTATTTGGGCACCTGTGAG
42241  CCTTCCTACTGTCACGGACCGTTTCCGTCCCTTACAATGTCCATAAACCCGTGGACACTC
```

FIG. 4 (cont'd)

```
42301  AAGGCCTGATGTCCGAAAGGACTGAAATAAATTAAATGTGTGGGGGGAGAGAGAAAGAAA
42301  TTCCGGACTACAGGCTTTCCTGACTTTATTTAATTTACACACCCCCCTCTCTCTTTCTTT

42361  GAGCCTAGCAAAAGGTGAGCTGGAGAGTCAGAGGCAGAAGGCAGAATCTGGGATGGGCTG
42361  CTCGGATCGTTTTCCACTCGACCTCTCAGTCTCCGTCTTCCGTCTTAGACCCTACCCGAC

42421  GGAGCTTGCCAATCATTTTGTCAAATGGGTGATGTGAAGCCTTGAAGGTTTTTTGACCAA
42421  CCTCGAACGGTTAGTAAAACAGTTTACCCACTACACTTCGGAACTTCCAAAAAACTGGTT

42481  GAGGAGATGTCTTCAGATTTGCGTTTGAGACATTTTCACTGGTTGTCATGCTAAGAATGG
42481  CTCCTCTACAGAAGTCTAAACGCAAACTCTGTAAAAGTGACCAACAGTACGATTCTTACC

42541  CTTAAAGAGAAGCAAGGCTGGGGTCAGAGGAGCTGCTTGGAAGCTGTTTGGTACTAGGAT
42541  GAATTTCTCTTCGTTCCGACCCCAGTCTCCTCGACGAACCTTCGACAAACCATGATCCTA

42601  GCGGATAACATGGTTGGAGAAATGGCAACTGTCAGGGTATTTGGAGCAAGAATGGATAGA
42601  CGCCTATTGTACCAACCTCTTTACCGTTGACAGTCCCATAAACCTCGTTCTTACCTATCT

42661  CATTGGTGATCATCACTTGGATGCATTTGAGGGACAACTGCTATGTTTCTACTAGAGCAA
42661  GTAACCACTAGTAGTGAACCTACGTAAACTCCCTGTTGACGATACAAAGATGATCTCGTT

42721  CTACATAGAGCAGGAGTAAGCAACTTACAGTCCACAGACCACATTTGCTCTGTCCCGTTT
42721  GATGTATCTCGTCCTCATTCGTTGAATGTCAGGTGTCTGGTGTAAACGAGACAGGGCAAA

42781  TTCAAATACAGTTTAATGGAAACAGAGCCATGCCCGTTCTTTCACCTATTCTGCATGGCT
42781  AAGTTTATGTCAAATTACCTTTGTCTCGGTACGGGCAAGAAAGTGGATAAGACGTACCGA

42841  GACATCAGGCATGGTTCTAAGTAATATACATAAGTTTCATATATTAATGCTCATCTATCC
42841  CTGTAGTCCGTACCAAGATTCATTATATGTATTCAAAGTATATAATTACGAGTAGATAGG

42901  CAGTTGACAAACATGAAGTGTTGCTATTGTCTCATTTTACAGCGGAGAAAACTGACATAG
42901  GTCAACTGTTTGTACTTCACAACGATAACAGAGTAAAATGTCGCCTCTTTTGACTGTATC

42961  AGATTCTCTTTCGCACCCATAGCTTCAGTTACCACCTCTATGCCAATGATTCAATAATAC
42961  TCTAAGAGAAAGCGTGGGTATCGAAGTCAATGGTGGAGATACGGTTACTAAGTTATTATG

43021  CTCTAATCCAGACCTCTTCTCTGAGCTTCAGACAGGCAGATCTCTCACAGCCAGTCTTGG
43021  GAGATTAGGTCTGGAGAAGAGACTCGAAGTCTGTCCGTCTAGAGAGTGTCGGTCAGAACC

43081  AGACACTTCAGAAATCATAGGTCCCAAACCAGACTCCTCCTCATCCCCTCAAACACATTC
43081  TCTGTGAAGTCTTTAGTATCCAGGGTTTGGTCTGAGGAGGAGTAGGGGAGTTTGTGTAAG

43141  TTTTTCAACATTCCTTTTTTCTTAGTGAACATCACCAAATAGATAAGCAAGTCAGATCCA
43141  AAAAAGTTGTAAGGAAAAAAGAATCACTTGTAGTGGTTTATCTATTCGTTCAGTCTAGGT

43201  AGGAGGCCTCCTTGGCACTTCTCTCATCCTTGTCCCACCTTATATCATCTATTTTTCTTT
43201  TCCTCCGGAGGAACCGTGAAGAGAGTAGGAACAGGGTGGAATATAGTAGATAAAAAGAAA

43261  TTCTTTTTTTTTGAGATGGTGTCTCACTGTGTCACCCAGGCAAGTGCAGTGGTGTGATCC
43261  AAGAAAAAAAAACTCTACCACAGAGTGACACAGTGGGTCCGTTCACGTCACCACACTAGG

43321  TGGCCCACTGCAGCCTCAACCTCACCAAGTTCAGGTAATCCTCTCACCTTAATCCCGTGA
43321  ACCGGGTGACGTCGGAGTTGGAGTGGTTCAAGTCCATTAGGAGAGTGGAATTAGGGCACT

43381  GTAGCTGGGACTACAGGCACATGCCACCGAGCCCGGCTAATTTTTGTATTTTTACCAGAG
43381  CATCGACCCTGATGTCCGTGTACGGTGGCTCGGGCCGATTAAAAACATAAAAATGGTCTC

43441  ACAGGGTTTTGCCATGTTGCCCAGGCTGCCACCTTATCTCCATTCTTGCTGAAATCTGGC
43441  TGTCCCAAAACGGTACAACGGGTCCGACGGTGGAATAGAGGTAAGAACGACTTTAGACCG

43501  TGTTTCTCTCCACTTCTATTACCAACCACCAGCCAAATCTGACTTATTAAAAGGATCATC
43501  ACAAAGAGAGGTGAAGATAATGGTTGGTGGTCGGTTTAGACTGAATAATTTTCCTAGTAG

43561  TCGTATGTGGGTTCTGTAATAGCTTCTTCAAAATCCATTCCTCTCCACCCAGACCCTCTT
43561  AGCATACACCCAAGACATTATCGAAGAAGTTTTAGGTAAGGAGAGGTGGGTCTGGGAGAA
```

FIG. 4 (cont'd)

```
43621  CCAATCTCCAAACTGCAGCCAATACCTTCAATTCTGTCACCGCTCCTGCATACTCCACCT
43621  GGTTAGAGGTTTGACGTCGGTTATGGAAGTTAAGACAGTGGCGAGGACGTATGAGGTGGA

43681  AATCCTTAACCTTTCAATGGTTTCTCTTGCCCCTAGGTTAAGCTAAATTGAAAACTGCTA
43681  TTAGGAATTGGAAAGTTACCAAAGAGAACGGGGATCCAATTCGATTTAACTTTTGACGAT

43741  AAGCTACAGCTTCTTAGTGTAACTAGTAAGTACAGTGACTACTATGTCTGGTTTACTTCA
43741  TTCGATGTCGAAGAATCACATTGATCATTCATGTCACTGATGATACAGACCAAATGAAGT

43801  GCTGTTGCTGACTAATAGCACTTCTTGAATGAAGAAATTATATTACCGTACTGTAGGGAA
43801  CGACAACGACTGATTATCGTGAAGAACTTACTTCTTTAATATAATGGCATGACATCCCTT

43861  AAATTTGTACTTCAATGGAAAACTGAATTATTTAGAGCAAACCTTTAAGGTTATCTGATT
43861  TTTAAACATGAAGTTACCTTTTGACTTAATAAATCTCGTTTGGAAATTCCAATAGACTAA

43921  CTGATTCCATGGGCCCTTTCATTGGGTCTTACATTGTTTCATTGTTTTTGAGTTATTTTA
43921  GACTAAGGTACCCGGGAAAGTAACCCAGAATGTAACAAAGTAACAAAAACTCAATAAAAT

43981  CAGATGACTGATAGAAATGCAAAATAATTATTGCATGCAGTCATGCAAGTAAAATCTGAA
43981  GTCTACTGACTATCTTTACGTTTTATTAATAACGTACGTCAGTACGTTCATTTTAGACTT

44041  GGTCAGGGTTCAATTAACTTCTCTCCCCTACTGTGGAAGAAGCCAATTTCATTTGCATAT
44041  CCAGTCCCAAGTTAATTGAAGAGAGGGGATGACACCTTCTTCGGTTAAAGTAAACGTATA

44101  TCATTTCAATATTTCTGACCTATAAACATGCCTGTTCTTTGAACCAGTTTTTATATCTGC
44101  AGTAAAGTTATAAAGACTGGATATTTGTACGGACAAGAAACTTGGTCAAAAATATAGACG

44161  CTGGTAACTTCATTAAATGATTTAAATAAACTCTATAATTTAGTTTATTTTATACCTGTA
44161  GACCATTGAAGTAATTTACTAAATTTATTTGAGATATTAAATCAAATAAAATATGGACAT

44221  TGACAGTCAGGCTTTTACCTTATTTTTGCTTTTTAAAATTATTCTTTAGCTCTCCCTAAG
44221  ACTGTCAGTCCGAAAATGGAATAAAAACGAAAAATTTTAATAAGAAATCGAGAGGGATTC

44281  GCACTACTTGGCTGGCCCTTTGGCTACTCACTAGCCCAAGCTCCATCCTCTTCTGTCTAC
44281  CGTGATGAACCGACCGGGAAACCGATGAGTGATCGGGTTCGAGGTAGGAGAAGACAGATG

44341  CGCAGCCCCAGGCTCTCTTTTGGCCCTTTGTTCCAGCCCTCCTCAGAGAAGTTCTTTTGT
44341  GCGTCGGGGTCCGAGAGAAAACCGGGAAACAAGGTCGGGAGGAGTCTCTTCAAGAAAACA

44401  CCTGGAACTCACTTTCATACCAGGTGCTCTTCATCCCTTCTTCCTTTAGTAAATTTCTTT
44401  GGACCTTGAGTGAAAGTATGGTCCACGAGAAGTAGGGAAGAAGGAAATCATTTAAAGAAA

44461  AATCTTTCAGATTTCTGCTCAAGGATCACTTGCTGAAAGCCTTTCCAGGCCTTTCTGAGT
44461  TTAGAAAGTCTAAAGACGAGTTCCTAGTGAACGACTTTCGGAAAGGTCCGGAAAGACTCA

44521  CAATACAATCCATTATTAGAGGCTCTTAGAGCACAGGCAGCACTTGTTATAATTTTACAT
44521  GTTATGTTAGGTAATAATCTCCGAGAATCTCGTGTCCGTCGTGAACAATATTAAAATGTA

44581  CTGTCTGTGGGATTCCTTAACACTTTCTAACACAATTAACACTTTTCTCTCTGGCTGGGG
44581  GACAGACACCCTAAGGAATTGTGAAAGATTGTGTTAATTGTGAAAAGAGAGACCGACCCC

44641  GCAATGCATGATAACAGGATGATGGTATGCTCTCAACCCTCCCCCAGCAACTAGCCCAGT
44641  CGTTACGTACTATTGTCCTACTACCATACGAGAGTTGGGAGGGGGTCGTTGATCGGGTCA

44701  GCTTCGAACATGGTGGATAGATACACCGTTTTTATTTTAGACAGATTTTTGAGTAGCAAG
44701  CGAAGCTTGTACCACCTATCTATGTGGCAAAAATAAAATCTGTCTAAAAACTCATCGTTC

44761  TACCTACTGCTCAGGAGACAGATGGACTGAAAAAATATATTTGGGAGTCATCAGCACATA
44761  ATGGATGACGAGTCCTCTGTCTACCTGACTTTTTTATATAAACCCTCAGTAGTCGTGTAT

44821  GGTGCAGCCATGAAAATGCACGAGAAGCAAAACCATTGGCAGGAACAAAATGAAGGCTAT
44821  CCACGTCGGTACTTTTACGTGCTCTTCGTTTTGGTAACCGTCCTTGTTTTACTTCCGATA

44881  TAGAGACCTTATTTAGGTGGAATAATTGGACAGAAGCCCTTAATGGGGAGGAAATAGAAG
44881  ATCTCTGGAATAAATCCACCTTATTAACCTGTCTTCGGGAATTACCCCTCCTTTATCTTC

44941  CAGTTAATACAGATGGAGGCCGGGCGCCGTGGCTCACGCCTGTAATCCTAGCACTTTGGG
44941  GTCAATTATGTCTACCTCCGGCCCGCGGCACCGAGTGCGGACATTAGGATCGTGAAACCC
```

FIG. 4 (cont'd)

```
45001  AGGCTGAGATAGGTGGGTGGCTTGAGTCCAGGAGTTTGAGAGCAGCCTGGGCAACATAGC
45001  TCCGACTCTATCCACCCACCGAACTCAGGTCCTCAAACTCTCGTCGGACCCGTTGTATCG

45061  AAAACCCGGTCTCTACAAAAAATACAAAAATTAGCCCGGCGTGGTGGCGCAGGCCTGTAG
45061  TTTTGGGCCAGAGATGTTTTTTATGTTTTTAATCGGGCCGCACCACCGCGTCCGGACATC

45121  TCCCGGCTACTGGGGAGGCTGAGATGGGAGAATTGCTTGAACCGGGGAGGCGGATGTTGC
45121  AGGGCCGATGACCCCTCCGACTCTACCCTCTTAACGAACTTGGCCCCTCCGCCTACAACG

45181  AATTAGACGAGATCGCGCCACTGCACTCCAGCCTGGGCGACAGAGCGAGACTCCGTCTCA
45181  TTAATCTGCTCTAGCGCGGTGACGTGAGGTCGGACCCGCTGTCTCGCTCTGAGGCAGAGT

45241  AAACAACAAGGACAAAACTTATCTTATAAGCGACCCTGGACTTCCAGGGACACTCGCCGC
45241  TTTGTTGTTCCTGTTTTGAATAGAATATTCGCTGGGACCTGAAGGTCCCTGTGAGCGGCG

45301  TCTATGGTGGTACGTGACCTGCCTGGACTCTGTGGTCTTTGGAGCTTGGGACCCCACCCC
45301  AGATACCACCATGCACTGGACGGACCTGAGACACCAGAAACCTCGAACCCTGGGGTGGGG

45361  AGCGTAAGAGGCCTTTCTGTGCCTTGTATAAAGGAGAGGAAAAGTGTAGGTTTTCTGAGT
45361  TCGCATTCTCCGGAAAGACACGGAACATATTTCCTCTCCTTTTCACATCCAAAAGACTCA

45421  TGATAAGATTAGAGCTACAGTATATTATCAGTAGCGTTGTATGAAACCATTTAAAAAACC
45421  ACTATTCTAATCTCGATGTCATATAATAGTCATCGCAACATACTTTGGTAAATTTTTTGG

45481  AAACCGGATTTAACCGCTTTCACCCAGAATAAACTGCCCTCCCCCTCTTTCCAAGATCAA
45481  TTTGGCCTAAATTGGCGAAAGTGGGTCTTATTTGACGGGAGGGGGAGAAAGGTTCTAGTT

45541  GTCAGCCCCAGTTACCACTTCCTATTAATTTAAAAACCAGGAAGGCTCATAATTTAGGCT
45541  CAGTCGGGGTCAATGGTGAAGGATAATTAAATTTTTGGTCCTTCCGAGTATTAAATCCGA

45601  GACGTTGCCCCAGGCGAACACTGCATATAAGACAATAGCTATTCCAATCCTCCTTTCCCT
45601  CTGCAACGGGGTCCGCTTGTGACGTATATTCTGTTATCGATAAGGTTAGGAGGAAAGGGA

45661  TTCTAAACCGAATAGTACTTCTAACATCACTTTTCCAGTCCTCTTTCTAAATATTGCGAT
45661  AAGATTTGGCTTATCATGAAGATTGTAGTGAAAAGGTCAGGAGAAAGATTTATAACGCTA

45721  CACGAGCCTACATCGGAAAACTATGAAAACAGTATGATTGGAGCTCTTGATGGTCTGCTT
45721  GTGCTCGGATGTAGCCTTTTGATACTTTTGTCATACTAACCTCGAGAACTACCAGACGAA

45781  TGCCTGAAAACGATGAAAGGCATTGAGATCTTTGGGCAGAAATGGCCCTTAGGGAATGCG
45781  ACGGACTTTTGCTACTTTCCGTAACTCTAGAAACCCGTCTTTACCGGGAATCCCTTACGC

45841  AGCCTGGTAGCCCCATAACACCCCGAGTTACAAATTCGGTTTGGGTAGGTGGCGCAGGGA
45841  TCGGACCATCGGGGTATTGTGGGGCTCAATGTTTAAGCCAAACCCATCCACCGCGTCCCT

45901  AATCTAAAAGCTGGATTCACGTTCTCCCCCTTCAGTTTGCACATAGCGGTCAGTGGCAGA
45901  TTAGATTTTCGACCTAAGTGCAAGAGGGGGAAGTCAAACGTGTATCGCCAGTCACCGTCT

45961  CAAGAGCAGACGCACAAATGTCAATCCCCGCCCGCAAACTCTCGAGGGCAGAAACTGCTT
45961  GTTCTCGTCTGCGTGTTTACAGTTAGGGGCGGGCGTTTGAGAGCTCCCGTCTTTGACGAA

46021  TTTGTCAGTTGGATTTGGAGTCGGTGGAAAAGCTGCCCTAATGTAGTTTCTCCGAGGTTT
46021  AAACAGTCAACCTAAACCTCAGCCACCTTTTCGACGGGATTACATCAAAGAGGCTCCAAA

46081  CCTTAGCCTTGACCGAGGGGCGCTTCCCGGCCATTCACCTAGAGGTTGTTTAATAAACAA
46081  GGAATCGGAACTGGCTCCCCGCGAAGGGCCGGTAAGTGGATCTCCAACAAATTATTTGTT

46141  GGATGCTCGCGAAATATCTGCGCTTGGAAAGGCGCTCGTTCGTGGCGCGCATTCTCGGGC
46141  CCTACGAGCGCTTTATAGACGCGAACCTTTCCGCGAGCAAGCACCGCGCGTAAGAGCCCG

46201  CTCCGCAAGCGACCCCGGTGACAGGGACAACCGCTTCGGTTTTAGCGACTGCAGACAGAC
46201  GAGGCGTTCGCTGGGGCCACTGTCCCTGTTGGCGAAGCCAAAATCGCTGACGTCTGTCTG

46261  TGGGACGAGACGGTTGGAGGCTCCTCCCCAAGGGATGCTGGAGGGGTTGCGTCGTACCCT
46261  ACCCTGCTCTGCCAACCTCCGAGGAGGGGTTCCCTACGACCTCCCCAACGCAGCATGGGA
```

FIG. 4 (cont'd)

```
46321  GCGCCTGGCCCTGGCGCGCGGCCCCAGGTCGTGGTACCCAGCGCCCTATGGGCCGTGCGC
46321  CGCGGACCGGGACCGCGCGCCGGGGTCCAGCACCATGGGTCGCGGGATACCCGGCACGCG

46381  CGGGGCTTGGCCACACCGCCTGCTTTCGCTTCCAGCCGCGCGCTCCGTGCCACTGCCGCT
46381  GCCCCGAACCGGTGTGGCGGACGAAAGCGAAGGTCGGCGCGCGAGGCACGGTGACGGCGA

46441  CTCTGCAGCCCCGCGTCCCCGCAGCCTCCCCATGGCCAGCCCGCTTCGCTCCGCTGCGGC
46441  GAGACGTCGGGGCGCAGGGGCGTCGGAGGGGTACCGGTCGGGCGAAGCGAGGCGACGCCG

46501  CCTTGCCCGCCAGGTACCTCGAACCCGGGCGTTTGCGGAAGGGGGGAGGATTGGAACCCG
46501  GGAACGGGCGGTCCATGGAGCTTGGGCCCGCAAACGCCTTCCCCCCTCCTAACCTTGGGC

46561  GGTCTCGGTAGCTCGCGGGCCTGGCCGGGCGCCTTGTCGCCGTTTCCTGCACCATCCTCC
46561  CCAGAGCCATCGAGCGCCCGGACCGGCCCGCGGAACAGCGGCAAAGGACGTGGTAGGAGG

46621  TTCGCCTTGCCCTCCATTCCGCCTCCAGCGAGGCGTCTTCCCTTCCCCGCATCCCTGCCC
46621  AAGCGGAACGGGAGGTAAGGCGGAGGTCGCTCCGCAGAAGGGAAGGGGCGTAGGGACGGG

46681  GAAATCTGGAGTCCCAGCCTGCAATCTCCACCTCTTCGAGGTTCCCGCTGCCCAGGTCTA
46681  CTTTAGACCTCAGGGTCGGACGTTAGAGGTGGAGAAGCTCCAAGGGCGACGGGTCCAGAT

46741  GCACCCTCATGGGTAACCCGCTCCGGAGCGTGGCGAGGACCGCCACGGGGGACGTGAGGG
46741  CGTGGGAGTACCCATTGGGCGAGGCCTCGCACCGCTCCTGGCGGTGCCCCCTGCACTCCC

46801  TAGCTATGGACTCGCTCTGAGGGAGGAGGCGGGAGCTGAATCTCTGGGCTGCCAGAACCC
46801  ATCGATACCTGAGCGAGACTCCCTCCTCCGCCCTCGACTTAGAGACCCGACGGTCTTGGG

46861  ACAGCCACATCCTACGTGACTCTGCCACCCCAAAATATTTTGACCGCAGCCTTCTGCCTC
46861  TGTCGGTGTAGGATGCACTGAGACGGTGGGGTTTTATAAAACTGGCGTCGGAAGACGGAG

46921  CTTGGATCTCTTCCTTCCCCACCCCCACCCCCGTAGTTATTTAGCAGATTACGCATTAAA
46921  GAACCTAGAGAAGGAAGGGGTGGGGGTGGGGGCATCAATAAATCGTCTAATGCGTAATTT

46981  ACAAATGTCTGCAGGTTTTCCCAATTAGTCCCGCTTCCCTGTGTCTTTATCTTTTAAATT
46981  TGTTTACAGACGTCCAAAAGGGTTAATCAGGGCGAAGGGACACAGAAATAGAAAATTTAA

47041  GCCCACTAATACCATGAGGTTTAAGGTGTGGGGTGGATGCTGCGGCATCGGAGGACCCTG
47041  CGGGTGATTATGGTACTCCAAATTCCACACCCCACCTACGACGCCGTAGCCTCCTGGGAC

47101  CTGGTGGAGGAAATGGTTCACGCCCGTCCCCGTTCCCTTTGCAGGCTTGCTATTGTGCGT
47101  GACCACCTCCTTTACCAAGTGCGGGCAGGGGCAAGGGAAACGTCCGAACGATAACACGCA

47161  CTGTGATTGACAAGACCACGAGGCTGAGCGCGCCCTGGAGATTTTTCTATAAATGGCTTA
47161  GACACTAACTGTTCTGGTGCTCCGACTCGCGCGGGACCTCTAAAAAGATATTTACCGAAT

47221  ACACCCCAGTCTAGACTATTTGCTCGGATATAAGGGAGACAATTGTTTTTTTGTTCTTTG
47221  TGTGGGGTCAGATCTGATAAACGAGCCTATATTCCCTCTGTTAACAAAAAAACAAGAAAC

47281  CCGGCGAACCCTGGCTCTGTAGGGCTGACCTGGAATTTAACCAGTCTTCCCTGAGCCGGC
47281  GGCCGCTTGGGACCGAGACATCCCGACTGGACCTTAAATTGGTCAGAAGGGACTCGGCCG

47341  GGAGGAGGACAAAAACCGCCGCGACCCCGGCAGGGTGGGAAGTGCAGGGCAGCGCTCCCA
47341  CCTCCTCCTGTTTTTGGCGGCGCTGGGGCCGTCCCACCCTTCACGTCCCGTCGCGAGGGT

47401  AGACACGCTTGTTGGAGGTTCGGGCCTGGGTGCTTGGTTGTCTGAGCCTCCTTTTTTGTG
47401  TCTGTGCGAACAACCTCCAAGCCCGGACCCACGAACCAACAGACTCGGAGGAAAAAACAC

47461  TTTGCCTGGGTCCTGGAGAGGAGCGCACGGTATCATGGTGAGCGTCACGTAGGTTACCCC
47461  AAACGGACCCAGGACCTCTCCTCGCGTGCCATAGTACCACTCGCAGTGCATCCAATGGGG

47521  GGGTCCCGCTTACCCACCTGCATTTACTTAATGGTGGTTTAATTCTTCTTTAAGGATTGC
47521  CCCAGGGCGAATGGGTGGACGTAAATGAATTACCACCAAATTAAGAAGAAATTCCTAACG

47581  AGTAACGGATGCTCCGCAGAGTGTACCGGAGAAGGAGGATCAAAAGAGGTGGTGGGGACT
47581  TCATTGCCTACGAGGCGTCTCACATGGCCTCTTCCTCCTAGTTTTCTCCACCACCCCTGA

47641  TTTAAGGTAAGTTGCTTGCCAGAGGCTTAGTGTCTAAAGCAACGTTCAACTGAATAAATC
47641  AAATTCCATTCAACGAACGGTCTCCGAATCACAGATTTCGTTGCAAGTTGACTTATTTAG
```

FIG. 4 (cont'd)

47701 CATTTCTTGTTGAGATTCGGGGAAATTTTCACTGTGTGGGTTACCCAGTTCCTAGGTTGT
47701 GTAAAGAACAACTCTAAGCCCCTTTAAAAGTGACACACCCAATGGGTCAAGGATCCAACA

47761 GTTGCCAGACTTTTAAAATTCCACTCTTAGAGGAAAAAAAGCCATTTAGAGAGTGACAGT
47761 CAACGGTCTGAAAATTTTAAGGTGAGAATCTCCTTTTTTTCGGTAAATCTCTCACTGTCA

47821 ACATTCATCACAACAAAAATTATCTAGCAGCTAATTGCTGATTTTATTTTGAGTCATATA
47821 TGTAAGTAGTGTTGTTTTTAATAGATCGTCGATTAACGACTAAAATAAAACTCAGTATAT

47881 TTTTTCTTGAAAAATAGTCAATGCGTAAATATTAAACTAGTTGTTTATCAGATTCCATAA
47881 AAAAAGAACTTTTTATCAGTTACGCATTTATAATTTGATCAACAAATAGTCTAAGGTATT

47941 TACGTACAAACCTTCAGTCTACTTGTAGAAAAAGTTAAACTGTGATTTTTCTCTTTCAGT
47941 ATGCATGTTTGGAAGTCAGATGAACATCTTTTTCAATTTGACACTAAAAAGAGAAAGTCA

48001 AGCACATAACACTCTACAGTGAAAGTGTTGCATTTTCTTCTTTTCTATCTGAATTGCGGG
48001 TCGTGTATTGTGAGATGTCACTTTCACAACGTAAAAGAAGAAAAGATAGACTTAACGCCC

48061 GTTTATATAGTAAATAGCTCATACTTCAAACAGTGAGAAACAAAGCACGTTGAAAACTGT
48061 CAAATATATCATTTATCGAGTATGAAGTTTGTCACTCTTTGTTTCGTGCAACTTTTGACA

48121 ACAAATACAAATGTAAGATGTAATATTATTTTTTCTATAAGTCTATCTCCTACCCTCCCT
48121 TGTTTATGTTTACATTCTACATTATAATAAAAAAGATATTCAGATAGAGGATGGGAGGGA

48181 CCTCGTGGAGGTTTTAGCTTCTTCTTTTTATGCCTAGTGCTGCTCTTCTGCCTGTTTGAG
48181 GGAGCACCTCCAAAATCGAAGAAGAAAAATACGGATCACGACGAGAAGACGGACAAACTC

48241 TCACTGTCAATTGTCATCAGACAATTGACACAGAGTGTCCTAATGATCTCACATCCTGGC
48241 AGTGACAGTTAACAGTAGTCTGTTAACTGTGTCTCACAGGATTACTAGAGTGTAGGACCG

48301 GGTTCAGAGAGGGAAGGAAACTTGACTCATCAGTTTCTCACACATTGAGCTCTCTCACAG
48301 CCAAGTCTCTCCCTTCCTTTGAACTGAGTAGTCAAAGAGTGTGTAACTCGAGAGAGTGTC

48361 TGTGCTGGAGACTGTGCCATGCATTGGACATCCAAAGGTGAATTCAAGATTAGGTCTCTA
48361 ACACGACCTCTGACACGGTACGTAACCTGTAGGTTTCCACTTAAGTTCTAATCCAGAGAT

48421 CTTGCAAGGAATTTTTATTTTATTTTTCTTTTTCCTTCTCTTGCTGTCATCTTAGCAAGG
48421 GAACGTTCCTTAAAAATAAAATAAAAAGAAAAAGGAAGAGAACGACAGTAGAATCGTTCC

48481 ATTTTTTAAAAAGCAAAATTAGAATATTGCAATTTCTTTTCTGTTTTTTGAGACAGGGTC
48481 TAAAAAATTTTTCGTTTTAATCTTATAACGTTAAAGAAAAGACAAAAAACTCTGTCCCAG

48541 TCGCTCTGTCACCCAGGCTGGAGTGCAGTGGCACGATCTCAGCTCACTGCAATCTCTGCC
48541 AGCGAGACAGTGGGTCCGACCTCACGTCACCGTGCTAGAGTCGAGTGACGTTAGAGACGG

48601 TCCCAGGTTCAAGTGATTCTCCTGCCTCAGCCTCCTGAGTAGCTGAGATTACAGGCATGT
48601 AGGGTCCAAGTTCACTAAGAGGACGGAGTCGGAGGACTCATCGACTCTAATGTCCGTACA

48661 GCCATCACGCCCAGCTAATTTTGTATTTTTAGTAGAGATGGGGTTATCACCATGTTAGCC
48661 CGGTAGTGCGGGTCGATTAAAACATAAAAATCATCTCTACCCCAATAGTGGTACAATCGG

48721 AGGCTGGTCTCGAACTCCTGGCCTCATGCAATCCACCTCCCAAAGTGCTGGGATTGCAGG
48721 TCCGACCAGAGCTTGAGGACCGGAGTACGTTAGGTGGAGGGTTTCACGACCCTAACGTCC

48781 CGTGAGCCACCAAGCCTAGCCTGAAGAATTCTTTGCAAAGAAAAATATCAACTCAAATTT
48781 GCACTCGGTGGTTCGGATCGGACTTCTTAAGAAACGTTTCTTTTTATAGTTGAGTTTAAA

48841 AAATAATCTTTTCCTTTCTTTTTCTTTTTTTTGAGACAGAGTCTTGTTCTGTTGCCCAGA
48841 TTTATTAGAAAAGGAAAGAAAAAGAAAAAAAACTCTGTCTCAGAACAAGACAACGGGTCT

48901 CTGAAGTGCAGTGGCACCATCAATTAGGTATCACTTTCAGCCTTGATCTCTCAGACTCAA
48901 GACTTCACGTCACCGTGGTAGTTAATCCATAGTGAAAGTCGGAACTAGAGAGTCTGAGTT

48961 GTGATCCTCTTAGCCTCTCAAGTACCTGAGACTATCGGCTTGCATGCCATCAGGCCCAAC
48961 CACTAGGAGAATCGGAGAGTTCATGGACTCTGATAGCCGAACGTACGGTAGTCCGGGTTG

FIG. 4 (cont'd)

```
49021  TAATTTCGTCATTTTTTGTAGAGATGGGATCTCCCTGTGTTGCCCAGACTGATCTCCAAC
49021  ATTAAAGCAGTAAAAAACATCTCTACCCTAGAGGGACACAACGGGTCTGACTAGAGGTTG

49081  TCCTGGGCTTGTGCAACCCTCCCACCTCGGCCTCCCAAAATGCTGGGTCACAGGCATAAG
49081  AGGACCCGAACACGTTGGGAGGGTGGAGCCGGAGGGTTTTACGACCCAGTGTCCGTATTC

49141  CCACAATGCCTGGCCATAAATAATCTTTTTTATTTGTTAATTTAGATTTCTGTATATTAG
49141  GGTGTTACGGACCGGTATTTATTAGAAAAAATAAACAATTAAATCTAAAGACATATAATC

49201  GTTTTATTTAGGGGAATTGCCTGTTTACACTCATGTATTTACACATCAAAACATGAGTTA
49201  CAAAATAAATCCCCTTAACGGACAAATGTGAGTACATAAATGTGTAGTTTTGTACTCAAT

49261  TGGTGGATGTATTCACAGCACATATGTAATAAGGCATGTGTAAAAATGATATTGATAATT
49261  ACCACCTACATAAGTGTCGTGTATACATTATTCCGTACACATTTTTACTATAACTATTAA

49321  TAGGGAATAAAAATGGTAGATTTTATAGACCATCTTTGTTTTTGATATACTTTTCTCTGT
49321  ATCCCTTATTTTTACCATCTAAAATATCTGGTAGAAACAAAAACTATATGAAAAGAGACA

49381  CTCAAAAAACAAAAACAAAAACAAACAAACAAACAAAATATATATATATAGCCTACATTG
49381  GAGTTTTTTGTTTTTGTTTTTGTTTGTTTGTTTGTTTTATATATATATATCGGATGTAAC

49441  TTGTTAACTATAATCACCCTACTCTGCTATGAACAGTAGACTTTATCGCTTCTATCTAAC
49441  AACAATTGATATTAGTGGGATGAGACGATACTTGTCATCTGAAATAGCGAAGATAGATTG

49501  TGTATGTTTGTACTCATTAACCAACCTCTCTTCCTCCACCTACACCCTTCCCACCCCCTG
49501  ACATACAAACATGAGTAATTGGTTGGAGAGAAGGAGGTGGATGTGGGAAGGGTGGGGGAC

49561  CCATCTTCTGATATCTATCATTCTATGAGTACTCTCTTCCTCCATGAGATCAACTTTTTT
49561  GGTAGAAGACTATAGATAGTAAGATACTCATGAGAGAAGGAGGTACTCTAGTTGAAAAAA

49621  TTTTAGCTCTCACGTATGAGTGAGAACATGCAATATTTGTTTTTCTGGGTTTTTTTTTTT
49621  AAAATCGAGAGTGCATACTCACTCTTGTACGTTATAAACAAAAAGACCCAAAAAAAAAAA

49681  TTCTGTGTTTGGCTTATTTCGCTTACCATAATGACTTCCAGTTCCATCCATGTTGCTACA
49681  AAGACACAAACCGAATAAAGCGAATGGTATTACTGAAGGTCAAGGTAGGTACAACGATGT

49741  AATGACACGATTTTACTCTTTTTTAATGGCTGAGTAGTATTCCATTGTGTATATGCACCA
49741  TTACTGTGCTAAAATGAGAAAAAATTACCGACTCATCATAAGGTAACACATATACGTGGT

49801  CATTTTATTTGTTCATTGATGGACACTTAGGTGATTCCATGTCTTGACTATTGTGAATAG
49801  GTAAAATAAACAAGTAACTACCTGTGAATCCACTAAGGTACAGAACTGATAACACTTATC

49861  TGCTGTAATAAACATGGGACTGCAGATATCCCTTTGATATACTGATTTCCTTTCCTTTGG
49861  ACGACATTATTTGTACCCTGACGTCTATAGGGAAACTATATGACTAAAGGAAAGGAAACC

49921  AAAATACCCAGTAGTAGGATTGTTGGTTTATATGGTCATTCTACTTTTAGTTTTTTTTTT
49921  TTTTATGGGTCATCATCCTAACAACCAAATATACCAGTAAGATGAAAATCAAAAAAAAAA

49981  GGAAAGCTTCATACCATTTTCCACAGTAGATAAACTAATTTACATTCTTACCAACAGTGT
49981  CCTTTCGAAGTATGGTAAAAGGTGTCATCTATTTGATTAAATGTAAGAATGGTTGTCACA

50041  ATAAGCGTTCTCTTTTCTCTGTATCCTCATCAGCATCTGTTATTTTTTGTCTTTCTAATA
50041  TATTCGCAAGAGAAAAGAGACATAGGAGTAGTCGTAGACAATAAAAAACAGAAAGATTAT

50101  ATAACCATTCTAACTGTGGTTGCTTTTGACATATTTCTCTACCTTTTTGTTAATCTACAT
50101  TATTGGTAAGATTGACACCAACGAAAACTGTATAAAGAGATGGAAAAACAATTAGATGTA

50161  CATTTATAACATTTCATATGGCCTTTTGGGTCTCTCTTGGGTAGTTTTCGTATTTCTTCT
50161  GTAAATATTGTAAAGTATACCGGAAAACCCAGAGAGAACCCATCAAAAGCATAAAGAAGA

50221  CCCCTCCCCATTTATGATGCAGTCATATTACATGAGGATGCAGTTTTGCAGCAGGGCCTA
50221  GGGGAGGGGTAAATACTACGTCAGTATAATGTACTCCTACGTCAAAACGTCGTCCCGGAT

50281  GCAATGAGATACGTTGTTACACATCCTGGCGAATCTTTCTGTGGACTCTAGGATCCTCTT
50281  CGTTACTCTATGCAACAATGTGTAGGACCGCTTAGAAAGACACCTGAGATCCTAGGAGAA

50341  CATTTGCAAGAGGTCAGCCATCTATTTCTTCCAATTCCTCCAGCTTCACATATCTCCACA
50341  GTAAACGTTCTCCAGTCGGTAGATAAAGAAGGTTAAGGAGGTCGAAGTGTATAGAGGTGT
```

FIG. 4 (cont'd)

```
50401  GAATGCAACACTGCAAATCTGCAGTTCTCTTCATGATCCTCTTTATTAGATTTTAAAAGA
50401  CTTACGTTGTGACGTTTAGACGTCAAGAGAAGTACTAGGAGAAATAATCTAAAATTTTCT

50461  GTATCTCCAAAAGATGAACATAGTGCCTAAGGCTTTCCAAATGGAGTAAGAATAATGCAC
50461  CATAGAGGTTTTCTACTTGTATCACGGATTCCGAAAGGTTTACCTCATTCTTATTACGTG

50521  AAGAACCTAGAATAAAGTTATTAAATGTCTGATACAGTTGTAATACAGACTTGATTTTTG
50521  TTCTTGGATCTTATTTCAATAATTTACAGACTATGTCAACATTATGTCTGAACTAAAAAC

50581  AAAAATGTGGCCAATGAAGAGAAGAGCAAATGTGCTATACGATGGTGAGCAAAAGGTGTT
50581  TTTTTACACCGGTTACTTCTCTTCTCGTTTACACGATATGCTACCACTCGTTTTCCACAA

50641  GACAGGCCTGGCATGGTGACTCACCCCTGTAATCCCAGCACTTTGGGAGGCTGAGGTGGG
50641  CTGTCCGGACCGTACCACTGAGTGGGGACATTAGGGTCGTGAAACCCTCCGACTCCACCC

50701  TGGATCATTTGAGGTCAGGAGTTTGAGACTAGCCTGGCCAACATGGTGAAACCCTGTTTG
50701  ACCTAGTAAACTCCAGTCCTCAAACTCTGATCGGACCGGTTGTACCACTTTGGGACAAAC

50761  TATTAAAAATACAAAAATTAGCCAGGTGCGATGACACATGCCTGTAATCCCAGCTACCTG
50761  ATAATTTTTATGTTTTTAATCGGTCCACGCTACTGTGTACGGACATTAGGGTCGATGGAC

50821  GGAGGCTGAGGCTTGAGACTTGCTTGAACCGGGGAGGCGGAGGTTGCAGCGAGCCGAGAT
50821  CCTCCGACTCCGAACTCTGAACGAACTTGGCCCCTCCGCCTCCAACGTCGCTCGGCTCTA

50881  TGTGCCACTGCACTCCAGCCTGGGCAACAGAGCAAAAAAAAAAAAAAAAAAAAAAAAAAG
50881  ACACGGTGACGTGAGGTCGGACCCGTTGTCTCGTTTTTTTTTTTTTTTTTTTTTTTTTTC

50941  TGTTGACTGAACCCTGGCTGAAACAGTTTTCAGGTGCTTTCAACAAATTTACACTTCCCT
50941  ACAACTGACTTGGGACCGACTTTGTCAAAAGTCCACGAAAGTTGTTTAAATGTGAAGGGA

51001  GCCCTGAGCCTCCCTATTTCAGAACAAATGATTACCCAACTGCAAACTTTGAATTAGGAA
51001  CGGGACTCGGAGGGATAAAGTCTTGTTTACTAATGGGTTGACGTTTGAAACTTAATCCTT

51061  GTTGTTTTTAATATGCCCTGTTTTTCTCAATATTTCTTGCCATTTCACAATCAGTTATTG
51061  CAACAAAAATTATACGGGACAAAAAGAGTTATAAAGAACGGTAAAGTGTTAGTCAATAAC

51121  TGGCATTCCAATTCTTCCACAAACATATGATGTGAAACATCCTGACTTCGATGTCATCAG
51121  ACCGTAAGGTTAAGAAGGTGTTTGTATACTACACTTTGTAGGACTGAAGCTACAGTAGTC

51181  GGAATGTGGAGCATTGGAAAGAGACAGATTAATTATGCAGAAGAAAGTATCATTTGACAA
51181  CCTTACACCTCGTAACCTTTCTCTGTCTAATTAATACGTCTTCTTTCATAGTAAACTGTT

51241  AATATTATTTTTATTTATCTTTGGAAAGGAAATCTAGAAAAAGAAAATACTTTTTAAAGA
51241  TTATAATAAAAATAAATAGAAACCTTTCCTTTAGATCTTTTTCTTTTATGAAAAATTTCT

51301  ACACTGATAAAAATTGTTTATAAAATTTGTTTCCTTTAGGAAACAAATCGTTCCCTTAAA
51301  TGTGACTATTTTTAACAAATATTTTAAACAAAGGAAATCCTTTGTTTAGCAAGGGAATTT

51361  ACTACATTTCATATCTGCCCCAAACGAGTCACATGTCTTCAGCTAATATTGCTTGTTTAC
51361  TGATGTAAAGTATAGACGGGGTTTGCTCAGTGTACAGAAGTCGATTATAACGAACAAATG

51421  GTTTGAACTTTATTCAATTCTATCACCTAGTAATTTAGTATTCTTAGGTAATTTCTCTTT
51421  CAAACTTGAAATAAGTTAAGATAGTGGATCATTAAATCATAAGAATCCATTAAAGAGAAA

51481  GAGCTCAGGTTAAAAGTTGTTATTTTTAGTTTTCAGAGTTGCAGAATTTTTTTTTCAAGT
51481  CTCGAGTCCAATTTTCAACAATAAAAATCAAAAGTCTCAACGTCTTAAAAAAAAAGTTCA

51541  AGAGAAAAGTTCATGATGAGATTCTGAAGCCACCTAATCGTATATTACTTTGAAAAACTG
51541  TCTCTTTTCAAGTACTACTCTAAGACTTCGGTGGATTAGCATATAATGAAACTTTTTGAC

51601  GATATATGCCGGGCGCGGTAGCTCACACCTGTAATCCCAGCACTTTCAGAGGCCGAGGTG
51601  CTATATACGGCCCGCGCCATCGAGTGTGGACATTAGGGTCGTGAAAGTCTCCGGCTCCAC

51661  GGTGGGTCACCTGAGGTCAGGAGTTCGAGACCAGCCTGGTCAACATGGTGAAACCCCATC
51661  CCACCCAGTGGACTCCAGTCCTCAAGCTCTGGTCGGACCAGTTGTACCACTTTGGGGTAG
```

FIG. 4 (cont'd)

51721 TCTACCAAAAATACAAAACTTAGCCGGGTGTTGTGGCACATGCCTGTAGTCCCAGCTACT
51721 AGATGGTTTTTATGTTTTGAATCGGCCCACAACACCGTGTACGGACATCAGGGTCGATGA

51781 CAGGAGGCTGAAGCAGGAGAATCACTTGAACCTGGGAGGCGGAGGTTGCAGTGAGCCCAG
51781 GTCCTCCGACTTCGTCCTCTTAGTGAACTTGGACCCTCCGCCTCCAACGTCACTCGGGTC

51841 ATCACATCACTGCTCTTCCGCCTGGGTGACAGAGTGAGACTCCATCTAAAAGAAAAAGCA
51841 TAGTGTAGTGACGAGAAGGCGGACCCACTGTCTCACTCTGAGGTAGATTTTCTTTTTCGT

51901 AAACAAAACAAAACTGGATACAGGGCAGTGCTTAGGTACAAATCAGAAAGTTAGAGGTTG
51901 TTTGTTTTGTTTTGACCTATGTCCCGTCACGAATCCATGTTTAGTCTTTCAATCTCCAAC

51961 CTATTCATATCATTAAGAAATAATGTGTCTTACGAAAGAATGTAGCAGTTTACTGAAATA
51961 GATAAGTATAGTAATTCTTTATTACACAGAATGCTTTCTTACATCGTCAAATGACTTTAT

52021 GAAGTCATACCTAGAAATGTAATAATTTATCTTTAATTGTCAGAAATTTAACTGATATTA
52021 CTTCAGTATGGATCTTTACATTATTAAATAGAAATTAACAGTCTTTAAATTGACTATAAT

52081 TGAAGTTCTAATTATAAGAACACTTATTTGAGGTTAAAAATTACCTTATTCTATCCCTGC
52081 ACTTCAAGATTAATATTCTTGTGAATAAACTCCAATTTTTAATGGAATAAGATAGGGACG

52141 TTTGCCGCTAATTTGATCTCTCTGGATTAGTGGGTTATTGTGGGTCCTATGGGTATTTTA
52141 AAACGGCGATTAAACTAGAGAGACCTAATCACCCAATAACACCCAGGATACCCATAAAAT

52201 AGGAGAGGTCTCAGAAAACTAAAAATTATATATACTGGATCATAATCATTCTTGTCACCC
52201 TCCTCTCCAGAGTCTTTTGATTTTTAATATATATGACCTAGTATTAGTAAGAACAGTGGG

52261 ACTCTCATCTTTCTGTTTTTGTTTTGTGTTTTACTACCCTTCCCCTTTTACTAAGTAGTC
52261 TGAGAGTAGAAAGACAAAAACAAAACACAAAATGATGGGAAGGGGAAAATGATTCATCAG

52321 TTAGTAGAAGAAAATTTGCATTAAGTTTGTCGTACTGTATTGATATGGCTCCAAATGTTT
52321 AATCATCTTCTTTTAAACGTAATTCAAACAGCATGACATAACTATACCGAGGTTTACAAA

52381 CTTAGCCCAGGGTCCTCCCCATTCACTGATAAAAGCTAACTAAGGTAAATCACAGGTGTT
52381 GAATCGGGTCCCAGGAGGGGTAAGTGACTATTTTCGATTGATTCCATTTAGTGTCCACAA

52441 TATTGTGCAAGAATACTGTGAAACTATTCATGTAATAAAAAGTTTGTGTTAGAATTTCAC
52441 ATAACACGTTCTTATGACACTTTGATAAGTACATTATTTTTCAAACACAATCTTAAAGTG

52501 TCTCTTTAAATCCTGGACATCTTCTGTGAGTGTATCTGAAAGCAGCCAGACATCTTCAGT
52501 AGAGAAATTTAGGACCTGTAGAAGACACTCACATAGACTTTCGTCGGTCTGTAGAAGTCA

52561 ATTTAAGAAACCCTTTACTATTCTGTGTGCTAGGCACTGTGTTAGCTTTGGAATTCAACT
52561 TAAATTCTTTGGGAAATGATAAGACACACGATCCGTGACACAATCGAAACCTTAAGTTGA

52621 GTGAATACTCTAGCCAGACTTCTTGTCTAAATAGTCCAGAATAGGGGTTGCTAAACTTTC
52621 CACTTATGAGATCGGTCTGAAGAACAGATTTATCAGGTCTTATCCCCAACGATTTGAAAG

52681 TTTCTTTTTTTTTGAGATGGAGTTCCACTCTTATTGCCCAGGCTGGAGTGCACTGGTGTG
52681 AAAGAAAAAAAAACTCTACCTCAAGGTGAGAATAACGGGTCCGACCTCACGTGACCACAC

52741 TCTCTGCTGACTGCAACCTCTGCCTCCCAGGTTCAAGCAGTTCTCCTGCCTCAGCCTCCC
52741 AGAGACGACTGACGTTGGAGACGGAGGGTCCAAGTTCGTCAAGAGGACGGAGTCGGAGGG

52801 AAGTAGCTGGGATTACAGGCGCCCACCACTACACTCAGTTAATTTTTGTATTTTTAGTAG
52801 TTCATCGACCCTAATGTCCGCGGGTGGTGATGTGAGTCAATTAAAAACATAAAAATCATC

52861 AGACAGGGTTGTGCTGTTTGCCAGGTTGATCTCAAACTCCTGACCTTTGGTGATCCACCC
52861 TCTGTCCCAACACGACAAACGGTCCAACTAGAGTTTGAGGACTGGAAACCACTAGGTGGG

52921 GCCTCGGCCTCCCAAAGTGTTGGGATTCAGGGTGTGCCACTGTGCCCGGCCTGCTAAACT
52921 CGGAGCCGGAGGGTTTCACAACCCTAAGTCCCACACGGTGACACGGGCCGGACGATTTGA

52981 TTCTTAAATGGCTAGATGATAAATATTTTAGGCTTGAGGGCCATCAGGTTTCTGTTACAA
52981 AAGAATTTACCGATCTACTATTTATAAAATCCGAACTCCCGGTAGTCCAAAGACAATGTT

53041 CTAGTTGGCTGTGCTGCCACTGAAGATACAAGAATGGCGTGACTATGTTCCAATAACATT
53041 GATCAACCGACACGACGGTGACTTCTATGTTCTTACCGCACTGATACAAGGTTATTGTAA

FIG. 4 (cont'd)

```
53101  TTAATTTCAAAACAGGCCAGCTGGCTGCATTTGGTCTGCAAGTAAAGTCTGCCTGACCCC
53101  AATTAAAGTTTTGTCCGGTCGACCGACGTAAACCAGACGTTCATTTCAGACGGACTGGGG

53161  CTACCTAGTCCAGAGGACAACGGGAGAGAAAAGGGATTCAAAGATAAAAATAATTTAGCT
53161  GATGGATCAGGTCTCCTGTTGCCCTCTCTTTTCCCTAAGTTTCTATTTTTATTAAATCGA

53221  GGAATATATTTCTTTAAATAAACTTATTATACTTAGTAAAAAGTCTTAAATTAACGTTTT
53221  CCTTATATAAAGAAATTTATTTGAATAATATGAATCATTTTTCAGAATTTAATTGCAAAA

53281  TACTTGAATTAAATAGTGGTAAAACAGGCTGGGCACAGTGGCTCATGCCTGTAATCTTAG
53281  ATGAACTTAATTTATCACCATTTTGTCCGACCCGTGTCACCGAGTACGGACATTAGAATC

53341  AACTTTGGGAGGTCGAGGCAGGCAGATTGCTTAAGCCCAGGAGTTCGAGACCAGCCTGGG
53341  TTGAAACCCTCCAGCTCCGTCCGTCTAACGAATTCGGGTCCTCAAGCTCTGGTCGGACCC

53401  CAACATAGTGAGTCCCTATCTCTAAAAAAAATACAAAATAATAATAATAATGGTAGAACA
53401  GTTGTATCACTCAGGGATAGAGATTTTTTTTATGTTTTATTATTATTATTACCATCTTGT

53461  AAGTCAATTTTTTATTGAAACTTGGCATTTTATTGGCATATTACAAAGTAGCATTACTAG
53461  TTCAGTTAAAAAATAACTTTGAACCGTAAAATAACCGTATAATGTTTCATCGTAATGATC

53521  ACTAGCCTGAACATTACAGTAATATTCTGTCCTTAATGCCTTTTGTGTCACTGTAATATG
53521  TGATCGGACTTGTAATGTCATTATAAGACAGGAATTACGGAAAACACAGTGACATTATAC

53581  AGCTTTCTGTTTGTTTTGGAATATGTTTTCAGCCTGAATATTATTCTAAAAATACAATTT
53581  TCGAAAGACAAACAAAACCTTATACAAAAGTCGGACTTATAATAAGATTTTTATGTTAAA

53641  ACTATCATTCATAATATATCAAATGACTCACGTAGCTGCAAGGCAGTGAATTAAACAGAA
53641  TGATAGTAAGTATTATATAGTTTACTGAGTGCATCGACGTTCCGTCACTTAATTTGTCTT

53701  TTAGATCATTTTAAAAATAATGATAAGAGCTGATGATGTAAAGTGAAGGTCTGTATTTAA
53701  AATCTAGTAAAATTTTTATTACTATTCTCGACTACTACATTTCACTTCCAGACATAAATT

53761  TTTGGGAGGGAAAAGACTTTTTTTGTATATTCAAAGAGATGGAGTTTGACATCCCTTCAC
53761  AAACCCTCCCTTTTCTGAAAAAAACATATAAGTTTCTCTACCTCAAACTGTAGGGAAGTG

53821  AACCTGTTACAGGTTGAACTTGCCCCTGTTTTTTTAACTGATCAAAAAGTTCCTTCTCTT
53821  TTGGACAATGTCCAACTTGAACGGGGACAAAAAAATTGACTAGTTTTTCAAGGAAGAGAA

53881  GTGTTTCTTTTTTTCTTCTCTTTTCTCTTCTTTTCTTTTCTTTTTTTTTTTTCTGAGACA
53881  CACAAAGAAAAAAAGAAGAGAAAAGAGAAGAAAAGAAAAGAAAAAAAAAAAAGACTCTGT

53941  GAGTCTTGCTCTGTCTCCCAGGCTGGAGTGCAGTGGTGCGATCTTGACTCTCTGCAACCT
53941  CTCAGAACGAGACAGAGGGTCCGACCTCACGTCACCACGCTAGAACTGAGAGACGTTGGA

54001  CCGCCTCCCGGGTTCAAGTGATTTTCCTGCCTCAGCCTCCTGAGTAGCTGCGACTACAGG
54001  GGCGGAGGGCCCAAGTTCACTAAAAGGACGGAGTCGGAGGACTCATCGACGCTGATGTCC

54061  TGCATGCCACCACGCCTGGCTAATTTTTAGTATTTTTAGTAGAGACGGGGTTTCACCATG
54061  ACGTACGGTGGTGCGGACCGATTAAAAATCATAAAAATCATCTCTGCCCCAAAGTGGTAC

54121  TTAGCTAGGATGGTCTCAATCTCCAAACCTTGTGATCTGCATGCCTCGGCTTCCCAAAGT
54121  AATCGATCCTACCAGAGTTAGAGGTTTGGAACACTAGACGTACGGAGCCGAAGGGTTTCA

54181  GCTGGTCTCCTGTGTTTTTGTCAGCATTCCACAGATGCTATAAAGTTAGTGGTGGTATCG
54181  CGACCAGAGGACACAAAAACAGTCGTAAGGTGTCTACGATATTTCAATCACCACCATAGC

54241  CATGCAATTTGTACGCTTAATGTTTGGCCATTTGCAGTGGGCAAACTGGCTATGTCGGGA
54241  GTACGTTAAACATGCGAATTACAAACCGGTAAACGTCACCCGTTTGACCGATACAGCCCT

54301  GCTGGTGAGATGCTGCTTGTGGGGAGTTGTTTCCTATTACTCTGATTTATCTTTGTTTAA
54301  CGACCACTCTACGACGAACACCCCTCAACAAAGGATAATGAGACTAAATAGAAACAAATT

54361  ATAAGAGTTCCTTTGTTCACTGTTTCCTCCACACAGAACAGAGGATTTATATCTTAGTGT
54361  TATTCTCAAGGAAACAAGTGACAAAGGAGGTGTGTCTTGTCTCCTAAATATAGAATCACA
```

FIG. 4 (cont'd)

```
54421  TCATTCTCAACTTTCCTGTTTTCAAAGAGGAAAACATTTGCTTCACTTTGCTCATTTCTT
54421  AGTAAGAGTTGAAAGGACAAAAGTTTCTCCTTTTGTAAACGAAGTGAAACGAGTAAAGAA

54481  CTCCAGTGCACCCAGAGGATTTTGAAGGCTTATGCCAACAATTCTTTGGGGCAGTTGGAG
54481  GAGGTCACGTGGGTCTCCTAAAACTTCCGAATACGGTTGTTAAGAAACCCCGTCAACCTC

54541  TGTAACCATTGCTAAATAGCAGTTCAGTACTTAATGACATTCATTTTAGTTTAACAAATC
54541  ACATTGGTAACGATTTATCGTCAAGTCATGAATTACTGTAAGTAAAATCAAATTGTTTAG

54601  ATTGTGAGTGTTGCCATTTTTTATTAGGGAAAACATCTCTTTCATCTTTCCCAAATACTC
54601  TAACACTCACAACGGTAAAAAATAATCCCTTTTGTAGAGAAAGTAGAAAGGGTTTATGAG

54661  AACATGAGTCCTATGGTGAGAGTGAAAAAGGGTTGTATTCTTTTTTTGCATCATCTTACC
54661  TTGTACTCAGGATACCACTCTCACTTTTTCCCAACATAAGAAAAAAACGTAGTAGAATGG

54721  CCATCTGCTATTTTGTCCCTCTTCTATATATCACTGAAATTTGGTTCTGATATTCTATTA
54721  GGTAGACGATAAAACAGGGAGAAGATATATAGTGACTTTAAACCAAGACTATAAGATAAT

54781  GGCAGTGTACATTGCAGAGATTATGAATAACTGGCCGAATTCTGAATGCAGGCATGATTT
54781  CCGTCACATGTAACGTCTCTAATACTTATTGACCGGCTTAAGACTTACGTCCGTACTAAA

54841  GTTCAGCTCAGAGTGTTAAATTTCTGTGTTAGCTGCTAACCTTTAAAAGTCAATTGATTT
54841  CAAGTCGAGTCTCACAATTTAAAGACACAATCGACGATTGGAAATTTTCAGTTAACTAAA

54901  CCTTTTTTTTTTCCCCTCTGTATAATCTAGCCAGCGAATGCTCAGTAGCTTTTCTGTAA
54901  GGAAAAAAAAAAGGGGAGACATATTAGATCGGTCGCTTACGAGTCATCGAAAAGACATT

54961  ATAGTGATGATTTTTCTTCCCCAGGCTAAAGACCTAATAGTCACACCAGCTACCATTTTA
54961  TATCACTACTAAAAAGAAGGGGTCCGATTTCTGGATTATCAGTGTGGTCGATGGTAAAAT

55021  AAGGAAAAACCAGACCCCAATAATCTGGTTTTTGGAACTGTGTTCACGGATCATATGCTG
55021  TTCCTTTTTGGTCTGGGGTTATTAGACCAAAAACCTTGACACAAGTGCCTAGTATACGAC

55081  ACGGTGGAGTGGTCCTCAGAGTTTGGATGGGAGAAACCTCATATCAAGCCTCTTCAGAAC
55081  TGCCACCTCACCAGGAGTCTCAAACCTACCCTCTTTGGAGTATAGTTCGGAGAAGTCTTG

55141  CTGTCATTGCACCCTGGCTCATCAGCTTTGCACTATGCAGTGGAAGTAAGTACATGGGAA
55141  GACAGTAACGTGGGACCGAGTAGTCGAAACGTGATACGTCACCTTCATTCATGTACCCTT

55201  TTAAAGAGAGTGACATGCTTGCACTTCACTGTGGGTACTAAGTAGCTTCTCCTGCTAAAA
55201  AATTTCTCTCACTGTACGAACGTGAAGTGACACCCATGATTCATCGAAGAGGACGATTTT

55261  TAGCTCTTGGGCAGTATGGGCTTTATCATATTTACCAGAGGAAGCCGAAAATGTCTTTAA
55261  ATCGAGAACCCGTCATACCCGAAATAGTATAAATGGTCTCCTTCGGCTTTTACAGAAATT

55321  AAGTTTTCCTATAGACAGTTGGATTGAAGATAAATCTTAGCAGCTAATTTTTCAGATAAT
55321  TTCAAAAGGATATCTGTCAACCTAACTTCTATTTAGAATCGTCGATTAAAAAGTCTATTA

55381  CTTGCATTTTCTGTGACGTCAATAAAAAAATTATTTAAAGCAAATAGAAAGGACAGCTGG
55381  GAACGTAAAAGACACTGCAGTTATTTTTTTAATAAATTTCGTTTATCTTTCCTGTCGACC

55441  TGGGAAAATTGGCAATTAAAAAGCCAGCACTGTTGATAATTTAATAAGTCACCTTTCTTC
55441  ACCCTTTTAACCGTTAATTTTTCGGTCGTGACAACTATTAAATTATTCAGTGGAAAGAAG

55501  TTAGATCTTCTAATAATTGAGAAAGGGTCATTGAGAACAATATTATGATTTGATTTTAAT
55501  AATCTAGAAGATTATTAACTCTTTCCCAGTAACTCTTGTTATAATACTAAACTAAAATTA

55561  GCTAACTCCACATTTTTATGACCAGTAATAATGTCTAGTTATGCATGTTAAGGGACATGT
55561  CGATTGAGGTGTAAAAATACTGGTCATTATTACAGATCAATACGTACAATTCCCTGTACA

55621  AATTAAATGTCCTCCTTCAGCCATGAGTTGAAATAATTTTAAGCATAAAATGTTTAAAGA
55621  TTAATTTACAGGAGGAAGTCGGTACTCAACTTTATTAAAATTCGTATTTTACAAATTTCT

55681  ATTCTTTCTCTGGTCCTTTTCAGGGTGCACAATTAACCAGATGCACAGTATACTTCCCAT
55681  TAAGAAAGAGACCAGGAAAAGTCCCACGTGTTAATTGGTCTACGTGTCATATGAAGGGTA

55741  TGTCTTGATTCTCATTGTATTTTACTTTTGAATGATTTGGACATCTTTCCCAGAATAATA
55741  ACAGAACTAAGAGTAACATAAAATGAAAACTTACTAAACCTGTAGAAAGGGTCTTATTAT
```

FIG. 4 (cont'd)

```
55801  GGGGTGCTGGAAATAATAATAGTCTTCCTATTAAGTGCTAAAATATGGTAATAGTAAAAT
55801  CCCCACGACCTTTATTATTATCAGAAGGATAATTCACGATTTTATACCATTATCATTTTA

55861  ATTAATAGATTAATGATAAAATAACAACTTTTGTTTACTGAATTCCTGCAATACGTTCTG
55861  TAATTATCTAATTACTATTTTATTGTTGAAAACAAATGACTTAAGGACGTTATGCAAGAC

55921  TATTATGTTCCATATATGAATCATCTCATTTAATTACCTTAAGTGAGAAGGCATGTGATT
55921  ATAATACAAGGTATATACTTAGTAGAGTAAATTAATGGAATTCACTCTTCCGTACACTAA

55981  AAGCATTCAGGCTTTGAAGTCAGACATCCTGGGCTCAAATTCGGTCTCATTTGCTCCATA
55981  TTCGTAAGTCCGAAACTTCAGTCTGTAGGACCCGAGTTTAAGCCAGAGTAAACGAGGTAT

56041  GGAACCTTTATGACTTGAGGAATTTAATCATTTGTGCTTTAATTTCTTTATCTATAAAAT
56041  CCTTGGAAATACTGAACTCCTTAAATTAGTAAACACGAAATTAAAGAAATAGATATTTTA

56101  TGGGGTAGTTATAATATCTATCTTACAGTGATCTCATAAGTATAAAATAAAGTAATTTAT
56101  ACCCCATCAATATTATAGATAGAATGTCACTAGAGTATTCATATTTTATTTCATTAAATA

56161  CTAAGCATATAGAGTCATATCTGGTGCATAGCGAGAGCCCAGTTGTTAGCAATAATAATT
56161  GATTCGTATATCTCAGTATAGACCACGTATCGCTCTCGGGTCAACAATCGTTATTATTAA

56221  AACTCTTGAAGCAGTGGTCTCATCCATTATAAAAGGAGGCTCAGAAGAGTTGTTTCTTGA
56221  TTGAGAACTTCGTCACCAGAGTAGGTAATATTTTCCTCCGAGTCTTCTCAACAAAGAACT

56281  CTAATATTACACAGCAGTAAGGGTGGAGCTAAGGTTCCAATGAGAAGCTTCTTTCTGTTA
56281  GATTATAATGTGTCGTCATTCCCACCTCGATTCCAAGGTTACTCTTCGAAGAAAGACAAT

56341  TATAGCCCCTACATGTATACACCAAAATTACTAGGATGCTTTTGCAATTAACTCCTTCAA
56341  ATATCGGGGATGTACATATGTGGTTTTAATGATCCTACGAAAACGTTAATTGAGGAAGTT

56401  AATTATAAATTCATATAATTTTGGAAAGATATTCACTGTCCATATGTATCCACAAAATGT
56401  TTAATATTTAAGTATATTAAAACCTTTCTATAAGTGACAGGTATACATAGGTGTTTTACA

56461  TGAATTTAGGAATCTAAGTTTCTGTTCCCAGCTCTTCCTGTTATGTCAATTTGAATGAGT
56461  ACTTAAATCCTTAGATTCAAAGACAAGGGTCGAGAAGGACAATACAGTTAAACTTACTCA

56521  TCTTTCATTATTTGCCACAAGCCCTCACCATGTCATAAGGTATAATAAAGAACAGGTGAA
56521  AGAAAGTAATAAACGGTGTTCGGGAGTGGTACAGTATTCCATATTATTTCTTGTCCACTT

56581  ATGAAGTGCTTTTATTTATTTATTTTTCAGACAGATTCTTGCTCTGTCACCCAGGCTGGA
56581  TACTTCACGAAAATAAATAAATAAAAAGTCTGTCTAAGAACGAGACAGTGGGTCCGACCT

56641  GTGCAGTGGCACGATCGTGGCTCACTGCAGCCTCAAACTCCTGGGCTCAAGCAAACCTCG
56641  CACGTCACCGTGCTAGCACCGAGTGACGTCGGAGTTTGAGGACCCGAGTTCGTTTGGAGC

56701  TACCTCAGCCTCCTGAGTAGCTGGGACCACAGACACATGTCACCATGTCTGGCTAATTTT
56701  ATGGAGTCGGAGGACTCATCGACCCTGGTGTCTGTGTACAGTGGTACAGACCGATTAAAA

56761  TACATATTTTGTTGAGACTGGGTTTTGCCATGTTGCCCAGGCTGGTCTCAAACTCCTGGG
56761  ATGTATAAAACAACTCTGACCCAAAACGGTACAACGGGTCCGACCAGAGTTTGAGGACCC

56821  CTCAAGCAATCCTCTTGCCTTGGCTTCTTCAAGTGCTGGGATGACAGCCATGAGCCACTG
56821  GAGTTCGTTAGGAGAACGGAACCGAAGAAGTTCACGACCCTACTGTCGGTACTCGGTGAC

56881  CTCCTGGCTATGTGCTTTTAAATTTGAAAGGAATAATATGCCCAAGCCCAGGTCACTGGT
56881  GAGGACCGATACACGAAAATTTAAACTTTCCTTATTATACGGGTTCGGGTCCAGTGACCA

56941  TCTCAAACTTAATGTGCATCAGAATCAGCTGGCTACATCTCCAGAGTTTCTCATTTCTAA
56941  AGAGTTTGAATTACACGTAGTCTTAGTCGACCGATGTAGAGGTCTCAAAGAGTAAAGATT

57001  CAAGTGTCCAGATCATGTTAATTTTGTCGCTCCAGGGACCACATTTTGGGAATTGCTGGC
57001  GTTCACAGGTCTAGTACAATTAAAACAGCGAGGTCCCTGGTGTAAAACCCTTAACGACCG

57061  CTATGGGAAGTAAATGAGAAATGATTTAATGTCATTTTTGGAAGTTAAAAAAGATTTTGG
57061  GATACCCTTCATTTACTCTTTACTAAATTACAGTAAAAACCTTCAATTTTTTCTAAAACC
```

FIG. 4 (cont'd)

```
57121  TGGTCACTGGTTTTTGAAAACTCTTTGAAGGCTGGGTGGGGTGGTTCACATCTGTAATTT
57121  ACCAGTGACCAAAAACTTTTGAGAAACTTCCGACCCACCCCACCAAGTGTAGACATTAAA

57181  CAGCAGTTTCGGGGAGATGGGGTTCTTGGGAAATGAGCCCTCCACCCATGGGATCTGATG
57181  GTCGTCAAAGCCCCTCTACCCCAAGAACCCTTTACTCGGGAGGTGGGTACCCTAGACTAC

57241  CTATTTCCACGTAGATAATGTCAGAGTCGTTCAAACCAGAGTGACTCCATCCTGAATAGG
57241  GATAAAGGTGCATCTATTACAGTCTCAGCAAGTTTGGTCTCACTGAGGTAGGACTTATCC

57301  GGCTGGGTAAAATAAGGCTGAGACCTACTGGGCTGCAACATGATGAGACCCTGACTCTAT
57301  CCGACCCATTTTATTCCGACTCTGGATGACCCGACGTTGTACTACTCTGGGACTGAGATA

57361  TGAAACAAAACAAAACAAAACAAAACAAAACAAAACAAAAAACGGCCAGGCGAGGTGGCT
57361  ACTTTGTTTTGTTTTGTTTTGTTTTGTTTTGTTTTGTTTTTTGCCGGTCCGCTCCACCGA

57421  CACGCCTGTAATACCAGCACTTTGGGAGGCCAAGGCGGGCGGATCACGAGGTCAGGAGAT
57421  GTGCGGACATTATGGTCGTGAAACCCTCCGGTTCCGCCCGCCTAGTGCTCCAGTCCTCTA

57481  CGAGACCATCCTGGCTAACATGGTGAAACCCCATCTCTACTAAAAATAGAAAAAAAAAAA
57481  GCTCTGGTAGGACCGATTGTACCACTTTGGGGTAGAGATGATTTTTATCTTTTTTTTTTT

57541  AAAATTAGCCGGGCGTGGTGGCAGGCGCCTGTAGTCCAAGCTACTTAGGAGGCTGAGGCA
57541  TTTTAATCGGCCCGCACCACCGTCCGCGGACATCAGGTTCGATGAATCCTCCGACTCCGT

57601  GGAAAATGACGTGAACCCAGGAGGCGGAGTTTGCAGTGAGCCGAGATCACGCCGCTGCAC
57601  CCTTTTACTGCACTTGGGTCCTCCGCCTCAAACGTCACTCGGCTCTAGTGCGGCGACGTG

57661  TCCACACTGGGTGACAGAGCAAGACTCCATCTCAAAAAAAAAAAACAAAAACCTCTTTGG
57661  AGGTGTGACCCACTGTCTCGTTCTGAGGTAGAGTTTTTTTTTTTTGTTTTTGGAGAAACC

57721  CCATCTATTTAGATGAGTTGGAATGCTACTTTGATTGGTTTTGCCAATTTAGATTTTTGT
57721  GGTAGATAAATCTACTCAACCTTACGATGAAACTAACCAAAACGGTTAAATCTAAAAACA

57781  AATTAGGGTAGTTTAAAAAAACTCTCAAATTACTGTTATCCTTTGTTAAAAACCAAAATC
57781  TTAATCCCATCAAATTTTTTTGAGAGTTTAATGACAATAGGAAACAATTTTTGGTTTTAG

57841  TTTTATTATTAGTCTTCTGCTTACAATATAAGTAAAATAAATGTTTTGTATTAATAACTG
57841  AAAATAATAATCAGAAGACGAATGTTATATTCATTTTATTTACAAAACATAATTATTGAC

57901  GATTGTATATTGCATGGTTACCACTATGTAACAAAATTAATAGCTTAAAATTACAAGCGT
57901  CTAACATATAACGTACCAATGGTGATACATTGTTTTAATTATCGAATTTTAATGTTCGCA

57961  CATTTTAAAATTATTTTTCATGTTTCTGGGGTTGACTAGGATGGCTAAGTGGTTTTTGCT
57961  GTAAAATTTTAATAAAAAGTACAAAGACCCCAACTGATCCTACCGATTCACCAAAAACGA

58021  TGGGGTCCGTCACACGGTTGCTGTCAGTGGCTGGGGTTAGAGTCAGCTCACAGGCTTCCT
58021  ACCCCAGGCAGTGTGCCAACGACAGTCACCGACCCCAATCTCAGTCGAGTGTCCGAAGGA

58081  AACTCATATGGTGCTGGAGGGAGTGTCTCTTAGCATGCTAATGCTTCATAATTTGTGTAT
58081  TTGAGTATACCACGACCTCCCTCACAGAGAATCGTACGATTACGAAGTATTAAACACATA

58141  AATGAACAGTGAGGATGACCAGAGGTCACTTTCATTGCCATCTGGGCTGCAAAACTCAAG
58141  TTACTTGTCACTCCTACTGGTCTCCAGTGAAAGTAACGGTAGACCCGACGTTTTGAGTTC

58201  GAGTTGAAGGCTCTTCCGGCATTACTTGTTCTCCATGTGGTCTCCTCAGGATGGCAGTCA
58201  CTCAACTTCCGAGAAGGCCGTAATGAACAAGAGGTACACCAGAGGAGTCCTACCGTCAGT

58261  CAGAGTAGGCAGCCTTCTTATGTGCTGACCTAGGGCCCAAAATCTGTATGTGTCAGTTGA
58261  GTCTCATCCGTCGGAAGAATACACGACTGGATCCCGGGTTTTAGACATACACAGTCAACT

58321  CTGAGCCCAGATGGAAGCTCTATTGCTGTTTACGCCCTAGCCTCAAAACTACTCTTTCAA
58321  GACTCGGGTCTACCTTCGAGATAACGACAAATGCGGGATCGGAGTTTTGATGAGAAAGTT

58381  GAAAAATTCTCCAACCGAGTTTTTCCTCTACTCTCACACCACCACAACAATAGTCAACAT
58381  CTTTTTAAGAGGTTGGCTCAAAAAGGAGATGAGAGTGTGGTGGTGTTGTTATCAGTTGTA

58441  AGGAGACTTCTATGATCAAAGGTGTAGGGATTTCTCCCCACCACCAAGCAGTGAACCCCA
58441  TCCTCTGAAGATACTAGTTTCCACATCCCTAAAGAGGGGTGGTGGTTCGTCACTTGGGGT
```

FIG. 4 (cont'd)

```
58501  GCTGGGTGTCCTCCAATTCAATTCTCACACTGTTATTACGGGAAAGGTGTCCCAATCCAG
58501  CGACCCACAGGAGGTTAAGTTAAGAGTGTGACAATAATGCCCTTTCCACAGGGTTAGGTC

58561  TCCCCAAGAGGTTCTTGGATGTTGCACAAGAAAGAATTTGGGGAGAGTCCACAAAGTAAA
58561  AGGGGTTCTCCAAGAACCTACAACGTGTTCTTTCTTAAACCCCTCTCAGGTGTTTCATTT

58621  ATAAAATTTATTAAGAAAGTAAAGGAAAAAAAGAATGGCTACTCCGTAGACAGAGGAGCT
58621  TATTTTAAATAATTCTTTCATTTCCTTTTTTTCTTACCGATGAGGCATCTGTCTCCTCGA

58681  CCGAGGGCTGCTGGTTGGCTATTTTAATGGTTATTTCTTGATCATTTGCTAAAGAAGGGG
58681  GGCTCCCGACGACCAACCGATAAAATTACCAATAAAGAACTAGTAAACGATTTCTTCCCC

58741  TAGATTATTCATAAATTTTCCAGAAAAGGGATGGGCAATTCCTGGAACTGAGGGTTCCTC
58741  ATCTAATAAGTATTTAAAAGGTCTTTTCCCTACCCGTTAAGGACCTTGACTCCCAAGGAG

58801  CCCTTTTTAGACCTTGTAGGTTAACTTCCCACCATTGCCATGGCCTCTGTAAATTGTCGT
58801  GGGAAAAATCTGGAACATCCAATTGAAGGGTGGTAACGGTACCGGAGACATTTAACAGCA

58861  GACACTGGTAGGAGTGTCTGTTAGCATGCTAATGCATTATAATTAGCTTATAATGAGCAG
58861  CTGTGACCATCCTCACAGACAATCGTACGATTACGTAATATTAATCGAATATTACTCGTC

58921  CGAGGACGGCCAGACATCCCTTTCATTGCCATATGGGATTTGGCAGGTTTTGGCTGGCTT
58921  GCTCCTGCCGGTCTGTAGGGAAAGTAACGGTATACCCTAAACCGTCCAAAACCGACCGAA

58981  CTTTACCACATCTTGTTTTATCAGTGGGGTCTTTGTAACCTGTATGTTGTGCCGACCTCC
58981  GAAATGGTGTAGAACAAAATAGTCACCCCAGAAACATTGGACATACAACACGGCTGGAGG

59041  TATCTCATCCTGTGACCTAGAATACTAACCTCCTGAGAATGCAGCCCAGTAGGTTTCAGC
59041  ATAGAGTAGGACACTGGATCTTATGATTGGAGGACTCTTACGTCGGGTCATCCAAAGTCG

59101  CTTATTTTACCCAGCCCCTAATCAGGATGGAGTCGCTCTGGTCCAAACACCTCTGACATT
59101  GAATAAAATGGGTCGGGGATTAGTCCTACCTCAGCGAGACCAGGTTTGTGGAGACTGTAA

59161  ATCCACCTGGAAATAGTGTCAGATCCCATGGGTTAAGGGCTCATTCCCCAAGACCCTAAC
59161  TAGGTGGACCTTTATCACAGTCTAGGGTACCCAATTCCCGAGTAAGGGGTTCTGGGATTG

59221  CACCCTCACCTGGCCCAGACACAAGTCACAAGTCCTGTCCTCTGGAATGTCTGACTGAGA
59221  GTGGGAGTGGACCGGGTCTGTGTTCAGTGTTCAGGACAGGAGACCTTACAGACTGACTCT

59281  GGCATCAAGTTGGAGTTCCCATGACCCCCTCTTCTGGTTTGATTAATTTACTGGAGCAGC
59281  CCGTAGTTCAACCTCAAGGGTACTGGGGGAGAAGACCAAACTAATTAAATGACCTCGTCG

59341  TCACAAAACTCAGGGAAACACTTAGGTTTAGTGGTTTATTATAAAGGATACTGCAAAGTG
59341  AGTGTTTTGAGTCCCTTTGTGAATCCAAATCACCAAATAATATTTCCTATGACGTTTCAC

59401  TATAGATGAAGCGATGTGTAGGGTGAGGTATCGGGGGATAGAGTGCAGGGCTTCCATGCC
59401  ATATCTACTTCGCTACACATCCCACTCCATAGCCCCCTATCTCACGTCCCGAAGGTACGG

59461  CTCCCGGGGTGTGCCACCCTTTAGGAACCTTCATGTGTTCTGCTATCCGGAAGCTCACTG
59461  GAGGGCCCCACACGGTGGGAAATCCTTGGAAGTACACAAGACGATAGGCCTTCGAGTGAC

59521  AACTCATTCTTTTGGGTTTTTATGGAAGCTTCACGTCAATATTCCTTCCCCTGGGGTATG
59521  TTGAGTAAGAAAACCCAAAAATACCTTCGAAGTGCAGTTATAAGGAAGGGGACCCCATAC

59581  AGGCAGGACCTTCACCGGAGAGGGTCTTTTATTTTATTTCATTATTTTTAAAATATAAGA
59581  TCCGTCCTGGAAGTGGCCTCTCCCAGAAAATAAAATAAAGTAATAAAAATTTTATATTCT

59641  TGGGGTCTTGCTATGTAGCCTAGGGTGGTATTGAATTCCTGGGCCCAAGTAAGCCTCCCG
59641  ACCCCAGAACGATACATCGGATCCCACCATAACTTAAGGACCCGGGTTCATTCGGAGGGC

59701  CCTCTGCCTCCGAAAGTGCTGGGACTACAGGCATGAGCCACCCAGCCCCTTTGGAGAGGA
59701  GGAGACGGAGGCTTTCACGACCCTGATGTCCGTACTCGGTGGGTCGGGGAAACCTCTCCT

59761  TCTTAAGACTCACAGTTAGAAAGGAGGGCAGGAGAAGGTCAGAGAGATTCTGCTTCCTGC
59761  AGAATTCTGAGTGTCAATCTTTCCTCCCGTCCTCTTCCAGTCTCTCTAAGACGAAGGACG
```

FIG. 4 (cont'd)

```
59821  CCCTGAGGCCTAACACACCCAGCATTATAACAAAAGACTGTAACAAGGGCTATGGGAGTT
59821  GGGACTCCGGATTGTGTGGGTCGTAATATTGTTTTCTGACATTGTTCCCGATACCCTCAA

59881  ACCAGCCAGGAACTGTAAATCACACAGTATTATTTCTGCCTTACTCTTATCAGTCATGAT
59881  TGGTCGGTCCTTGACATTTAGTGTGTCATAATAAAGACGGAATGAGAATAGTCAGTACTA

59941  GGTTACAAAGGCCTGTCCAAGTTCAAAAGGAGGAAAAAAGCACTCCACTTCTTGATGAGG
59941  CCAATGTTTCCGGACAGGTTCAAGTTTTCCTCCTTTTTTCGTGAGGTGAAGAACTACTCC

60001  AAGGTCAGGGTTCTGGAAGAGCATGGGGGACTGGAAATATTGTTCGGCCATTTCATGGAA
60001  TTCCAGTCCCAAGACCTTCTCGTACCCCCTGACCTTTATAACAAGCCGGTAAAGTACCTT

60061  AATACAGTCTGTAATAGACATCAGTGATAAATGGGGAGATATGGTGGATGTATTGTTTTC
60061  TTATGTCAGACATTATCTGTAGTCACTATTTACCCCTCTATACCACCTACATAACAAAAG

60121  CTCTGAGTGCCAAATTGGGTTCTAAGATTTCACAGGCCAGATATTATTGAAGTGGCTACG
60121  GAGACTCACGGTTTAACCCAAGATTCTAAAGTGTCCGGTCTATAATAACTTCACCGATGC

60181  TTGTCTGGGGTATATACCTTGGGGTTCGTCATTTTGTGCCAGGAAAATTTAGGACAAGGA
60181  AACAGACCCCATATATGGAACCCCAAGCAGTAAAACACGGTCCTTTTAAATCCTGTTCCT

60241  CTCACACGAGGAGTTTAGGAGTGGAGGTTTAATAGGCAGAAGAGAAACAGAAACAGTTCT
60241  GAGTGTGCTCCTCAAATCCTCACCTCCAAATTATCCGTCTTCTCTTTGTCTTTGTCAAGA

60301  TTCTGTAGGGAGAGAGGGATCTTCGAGGGAAAAGACCATCCAGCAGCAGATGAGCTGGAT
60301  AAGACATCCCTCTCTCCCTAGAAGCTCCCTTTTCTGGTAGGTCGTCGTCTACTCGACCTA

60361  TTTATAGTCAGGTTTGAGGAGGAAGTGTCTGATTTACTTAGGGCTAACAGGTTGGTTTGA
60361  AAATATCAGTCCAAACTCCTCCTTCACAGACTAAATGAATCCCGATTGTCCAACCAAACT

60421  TCAGGTATGACGTTTACATAGCACACCGGGAAGTCTGGTTGCCCCACCCTAATCCTTTTA
60421  AGTCCATACTGCAAATGTATCGTGTGGCCCTTCAGACCAACGGGGTGGGATTAGGAAAAT

60481  TGCAAATGGACTTTCCTAGTTGATTGGAGCTATCTTGTCTGCTCCTTACTGTACAGGTGG
60481  ACGTTTACCTGAAAGGATCAACTAACCTCGATAGAACAGACGAGGAATGACATGTCCACC

60541  CTGACAAAGAGAAGGGAAGATGGAGCCGCCATCTTGAACATGATTGACGCAGCTGTGGAT
60541  GACTGTTTCTCTTCCCTTCTACCTCGGCGGTAGAACTTGTACTAACTGCGTCGACACCTA

60601  ATCTATGTCTGCAGCTTGATTTTACAGGCTGCTCTTCTTTAGAAAGGGGCTGCTTTTCAT
60601  TAGATACAGACGTCGAACTAAAATGTCCGACGAGAAGAAATCTTTCCCCGACGAAAAGTA

60661  TAAAACAAAAACCTTACTGAGGACTCTTGTACCCTCACTATCTGCAGGTGATTTCTTAAC
60661  ATTTTGTTTTTGGAATGACTCCTGAGAACATGGGAGTGATAGACGTCCACTAAAGAATTG

60721  TCCTGTATCATTATTATAGTGTCATAGGAATCTAGGAAGTGTGATTGCCTTCTGGAGAGA
60721  AGGACATAGTAATAATATCACAGTATCCTTAGATCCTTCACACTAACGGAAGACCTCTCT

60781  ACTTCAGGGTCCCTGGATTTTCTCACTAATCATATTCATTTCATTCCCTGTTTACCTGTT
60781  TGAAGTCCCAGGGACCTAAAAGAGTGATTAGTATAAGTAAAGTAAGGGACAAATGGACAA

60841  TAATAAATGTTGAGTGGCTACTATGTGCCCAGGGCTGTGCAAGGTGCCTGGAATAGGATG
60841  ATTATTTACAACTCACCGATGATACACGGGTCCCGACACGTTCCACGGACCTTATCCTAC

60901  GCAAGCAAACCAACCATGACCTTGCTCTCAAAGAATTGTTTTCTTTCTTTCTTTTTTTTC
60901  CGTTCGTTTGGTTGGTACTGGAACGAGAGTTTCTTAACAAAAGAAAGAAAGAAAAAAAAG

60961  TGAGACAAGGTCTTGCTCTGTCGCCCAGGCTGGAGTGCAGTGGCCTGATCTCAGCTCACT
60961  ACTCTGTTCCAGAACGAGACAGCGGGTCCGACCTCACGTCACCGGACTAGAGTCGAGTGA

61021  GCAACTTCCACCTCCTGGCTTCAACAGATTCTCCTCCCTCAGCCTCCCAGGTAGCTGGGA
61021  CGTTGAAGGTGGAGGACCGAAGTTGTCTAAGAGGAGGGAGTCGGAGGGTCCATCGACCCT

61081  TTATAGGTGCCCACCACCATGCCCGGCTAATTTTTGTATTTTTAGTAGAGACAGGGTTTC
61081  AATATCCACGGGTGGTGGTACGGGCCGATTAAAAACATAAAAATCATCTCTGTCCCAAAG

61141  ATCATGTTGGCCAGGCTAGTCTCAAACTCCTGACCTCAAGTGATCCGCCTGCCTCAGTGC
61141  TAGTACAACCGGTCCGATCAGAGTTTGAGGACTGGAGTTCACTAGGCGGACGGAGTCACG
```

FIG. 4 (cont'd)

```
61201  CGAGATTACAGGCATGAGCCACTGCACCTGGCCTGTTTTCTGTCTTTTTTTTTTAACCCC
61201  GCTCTAATGTCCGTACTCGGTGACGTGGACCGGACAAAAGACAGAAAAAAAAAATTGGGG

61261  CACATGGAAAGTTAGGCAGGGATTTAATTTCAAAGAGTTTCTTCCCAAATATTGTGGTGA
61261  GTGTACCTTTCAATCCGTCCCTAAATTAAAGTTTCTCAAAGAAGGGTTTATAACACCACT

61321  AACATCTAGTCCATTTATGTTTCAGGCTTTTTCATAGATATTACTGTTTCTCTTAGACTG
61321  TTGTAGATCAGGTAAATACAAAGTCCGAAAAAGTATCTATAATGACAAAGAGAATCTGAC

61381  ACAGACTTAGGACATCACATGATTGAATGTCAACCTGACTTTTAAGTTCAATAATAGTTT
61381  TGTCTGAATCCTGTAGTGTACTAACTTACAGTTGGACTGAAAATTCAAGTTATTATCAAA

61441  CATTTTTTAAATGCAAAATTAAATAGGAGTAATATCCTTGAACATGTTTCTCCTTCACTC
61441  GTAAAAAATTTACGTTTTAATTTATCCTCATTATAGGAACTTGTACAAAGAGGAAGTGAG

61501  ATCGGACCTATTGAGTCTAGAATCCATTTTATTTTGAGAGCTCCAACTACATGTGGTTTC
61501  TAGCCTGGATAACTCAGATCTTAGGTAAAATAAAACTCTCGAGGTTGATGTACACCAAAG

61561  TGTTAATATCTGAAAGTAATTTTTAATATCTGAAAGTTTCAAATAGTGATAATATTTGAA
61561  ACAATTATAGACTTTCATTAAAAATTATAGACTTTCAAAGTTTATCACTATTATAAACTT

61621  GGTTTCAAATAGTGGAGGAGAGACGCAAACTGCGAGTAGGGAACGCGGATTGAAGGAAAT
61621  CCAAAGTTTATCACCTCCTCTCTGCGTTTGACGCTCATCCCTTGCGCCTAACTTCCTTTA

61681  GAAAAGTTGATAATAGGCACTTCATTTTCAGATTATAACAAATATTTAGTGAAATAAAGC
61681  CTTTTCAACTATTATCCGTGAAGTAAAAGTCTAATATTGTTTATAAATCACTTTATTTCG

61741  ATAATTTTAAAAAATGGATAAGACATGTATGTACTATTTAATGTGTACTAATAAATGAAT
61741  TATTAAAATTTTTTACCTATTCTGTACATACATGATAAATTACACATGATTATTTACTTA

61801  GCTCATATTTGCCATCCAGATAAAGAAATAGAACAGTTGAACATCACAGAAGCCCTCGCG
61801  CGAGTATAAACGGTAGGTCTATTTCTTTATCTTGTCAACTTGTAGTGTCTTCGGGAGCGC

61861  TGTCCCATTCAGATCACAAACTCTATCTTTCTACTGGTAACCATTATTCTTACTTTTGTG
61861  ACAGGGTAAGTCTAGTGTTTGAGATAGAAAGATGACCATTGGTAATAAGAATGAAAACAC

61921  ATAACCTTTCTTTGCTTTCCTTTATGGAGTGTGTAGATTCTTAACACTATAGTTTTGCCT
61921  TATTGGAAAGAAACGAAAGGAAATACCTCACACATCTAAGAATTGTGATATCAAAACGGA

61981  CTTTTTGAACTTCATGTAAATGAAAAAATGTATATATTTTGTGTTTGTGTGCATGTGTGT
61981  GAAAAACTTGAAGTACATTTACTTTTTTACATATATAAAACACAAACACACGTACACACA

62041  GTGTGTGCTTGCACACGTGTGAATACCCCTTATTGTTTGAGCTTAGTATTATGTAAGATC
62041  CACACACGAACGTGTGCACACTTATGGGGAATAACAAACTCGAATCATAATACATTCTAG

62101  TAACCAGGAAGGACCAACCTAACATTTGTGGGGCCTGGGACCTAAGTATAGACAGAGATG
62101  ATTGGTCCTTCCTGGTTGGATTGTAAACACCCCGGACCCTGGATTCATATCTGTCTCTAC

62161  ACATGGTCCACTCCATATCTGTTCCCATCCCAGTTCTGCCCTGTGCTACAAGGGGTCTTC
62161  TGTACCAGGTGAGGTATAGACAAGGGTAGGGTCAAGACGGGACACGATGTTCCCCAGAAG

62221  CAGACACTGCATAGGTACCCATACCACCTGCAGGCAGATGACCTTTGCCTGTCCTTTGGA
62221  GTCTGTGACGTATCCATGGGTATGGTGGACGTCCGTCTACTGGAAACGGACAGGAAACCT

62281  GTTAGGCCTGGGTACCCTACTAGTGGTGTCTGCTCTTGGGATGATAAACCCGAGGGGCTT
62281  CAATCCGGACCCATGGGATGATCACCACAGACGAGAACCCTACTATTTGGGCTCCCCGAA

62341  ATCAGCTTTATATATATATATATATATATATATATATATTTTTTTTTTTTTTTTTTTTAG
62341  TAGTCGAAATATATATATATATATATATATATATATATAAAAAAAAAAAAAAAAAAAATC

62401  CTAGCATCTCTCTCGTTCTTCCAGGCTGGAGAGCAGTGGTGTGATCTTGGCTCACTGTAA
62401  GATCGTAGAGAGAGCAAGAAGGTCCGACCTCTCGTCACCACACTAGAACCGAGTGACATT

62461  TCTCCACCTCCTGGGTTCAAGCGATTCTCCTGCCTCAGCCTCCCAAGTAGCTGAGATTAC
62461  AGAGGTGGAGGACCCAAGTTCGCTAAGAGGACGGAGTCGGAGGGTTCATCGACTCTAATG
```

FIG. 4 (cont'd)

```
62521  AGGCACGTGCCACTATGCCTGGCTAATTTTTGTATTTTTAGTAGAGACTGGGTTTCACCA
62521  TCCGTGCACGGTGATACGGACCGATTAAAAACATAAAAATCATCTCTGACCCAAAGTGGT

62581  TGTTGGCATGTGAGCCACTATGCCCGGCCTCTTTTTTTTTTTTTTTTAAGAGACAGGGTC
62581  ACAACCGTACACTCGGTGATACGGGCCGGAGAAAAAAAAAAAAAAAATTCTCTGTCCCAG

62641  TTACTATGTTGCCCAGGCTGGTGTTGAACTCCTGGCCTCAATAGATCCTCTGTCCTTGGT
62641  AATGATACAACGGGTCCGACCACAACTTGAGGACCGGAGTTATCTAGGAGACAGGAACCA

62701  CTCCCAAAGTGCTGGCTCAGTCATTATGTTCTTTACTGCCATCCATTGCAGTATAAAAAG
62701  GAGGGTTTCACGACCGAGTCAGTAATACAAGAAATGACGGTAGGTAACGTCATATTTTTC

62761  AATAACAGTTTTCCCTCAGAATATTCTTGGTGAAACAGTAACAATTATTAATTTTATTAA
62761  TTATTGTCAAAAGGGAGTCTTATAAGAACCACTTTGTCATTGTTAATAATTAAAATAATT

62821  ATCTTGGCTCTTGAGCAAATGTCATTTTAATATTCTGTGTGATAAAATAGCAATGTCACA
62821  TAGAACCGAGAACTCGTTTACAGTAAAATTATAAGACACACTATTTTATCGTTACAGTGT

62881  TAAAGTGCTTTTACATACTTAAGTACTATGGTTGTCTGAAGAAAAAGGAGTTGTGTGATT
62881  ATTTCACGAAAATGTATGAATTCATGATACCAACAGACTTCTTTTTCCTCAACACACTAA

62941  GTCTTGAGTTTGTAAGTGGAACTACTTTTTTCATCGAGCACCGTTTTTACTTGAAATAAC
62941  CAGAACTCAAACATTCACCTTGATGAAAAAAGTAGCTCGTGGCAAAAATGAACTTTATTG

63001  AAAGTATGAATATGAATGCAGATTTGGCCATTTGGCAGATTTTTATTTATTTATTTGAGA
63001  TTTCATACTTATACTTACGTCTAAACCGGTAAACCGTCTAAAAATAAATAAATAAACTCT

63061  CAAGGTCTTGCTGTGTCACCCAGACTGGGGTGCAGCTCACTGCAGCCTTTACCTCCTGGG
63061  GTTCCAGAACGACACAGTGGGTCTGACCCCACGTCGAGTGACGTCGGAAATGGAGGACCC

63121  CTCAAGTGATCCTCCTGCCTCAGCCTCCTTAGTTGCTGGGACCACAGGTGTGCAGCACCA
63121  GAGTTCACTAGGAGGACGGAGTCGGAGGAATCAACGACCCTGGTGTCCACACGTCGTGGT

63181  TGCTCAGCTAATTTTTAAATTTTTTGTGGAGACAAGGTCTGACCATGTTGCCCAGGCTGG
63181  ACGAGTCGATTAAAAATTTAAAAAACACCTCTGTTCCAGACTGGTACAACGGGTCCGACC

63241  TCTCGAACTCCTGGGCTCCAGCAATCCTCTCGCTTCAGCTTCTCAAAGTGCTGGAATTAC
63241  AGAGCTTGAGGACCCGAGGTCGTTAGGAGAGCGAAGTCGAAGAGTTTCACGACCTTAATG

63301  AGGCGTGAGCCACGGTTCCCAGCTCGCCTTTTCATATGTTTATTGGGTTGCTAAATATGT
63301  TCCGCACTCGGTGCCAAGGGTCGAGCGGAAAAGTATACAAATAACCCAACGATTTATACA

63361  TCTTATTTGAAGTGCCCACTTGTTCAAGTTTTTTGTTCACTTTTTTATTGCTGTCTTTAT
63361  AGAATAAACTTCACGGGTGAACAAGTTCAAAAAACAAGTGAAAAAATAACGACAGAAATA

63421  AATTTTTTGATGACAAGAAATATGTTTAAATTAAAGGCAGTTTTGTCAATCTGCCTTATG
63421  TTAAAAAACTACTGTTCTTTATACAAATTTAATTTCCGTCAAAACAGTTAGACGGAATAC

63481  TTTGGAATTTGTTGTGTCTTTAAAGACTCTTTTCCTGCCCTTATATTATAAAGATATCTT
63481  AAACCTTAAACAACACAGAAATTTCTGAGAAAAGGACGGGAATATAATATTTCTATAGAA

63541  ATAGTATTGATATTGTCATTCACAGTTAGGTCTTTAATCCTAGAAGTTGATTTTTGTATG
63541  TATCATAACTATAACAGTAAGTGTCAATCCAGAAATTAGGATCTTCAACTAAAAACATAC

63601  AAGTAAGGGCCCAATTTATTTTTTTCCACCTATGTATACCCAGTTTTCCCAGCACCATTT
63601  TTCATTCCCGGGTTAAATAAAAAAAGGTGGATACATATGGGTCAAAAGGGTCGTGGTAAA

63661  AAACGGGCGGTACTTTCCCCTCTGATATGTCATGATGACACCTTTGTCATGTACACATGA
63661  TTTGCCCGCCATGAAAGGGGAGACTATACAGTACTACTGTGGAAACAGTACATGTGTACT

63721  GTTTGCTTCTGGATCTCTATTTGTGTTCAGTTGTTTTACTTGTCTGCATAAATGCCACAG
63721  CAAACGAAGACCTAGAGATAAACACAAGTCAACAAAATGAACAGACGTATTTACGGTGTC

63781  TCTTGGTTTCTCAGTCATTATAATGAGCCTTGCCTGCTAGGAAGGGTCCTTCTACTTTGT
63781  AGAACCAAAGAGTCAGTAATATTACTCGGAACGGACGATCCTTCCCAGGAAGATGAAACA
```

FIG. 4 (cont'd)

```
63841  TCTCCAAGAGTGCCTTGGATATTCTTGGTCATTTTCTTTCCATATAATTTTTAGATTTGG
63841  AGAGGTTCTCACGGAACCTATAAGAACCAGTAAAAGAAAGGTATATTAAAAATCTAAACC

63901  TTTATCAAGTCGATAAACTTTTGTCATGCAGTTTTTTAAAAGAAAATAAAGTGCCCTAAT
63901  AAATAGTTCAGCTATTTGAAAACAGTACGTCAAAAAATTTTCTTTTATTTCACGGGATTA

63961  GTGATTTTTTTTAATTTGGATTACATTGAATACATAAATCAGTTTGGGGAAAATCAACAT
63961  CACTAAAAAAAATTAAACCTAATGTAACTTATGTATTTAGTCAAACCCCTTTTAGTTGTA

64021  CTTTATAATATTGAGGCTTTTTATCCATGAGCATGAAATTGCTTTCTACATTAATAACTT
64021  GAAATATTATAACTCCGAAAAATAGGTACTCGTACTTTAACGAAAGATGTAATTATTGAA

64081  GGTAAAGTTTTATATTTTCCTTATGGATCTTTCACTTCTTTTGTTAGATTTTTCTCCACC
64081  CCATTTCAAAATATAAAAGGAATACCTAGAAAGTGAAGAAAACAATCTAAAAAGAGGTGG

64141  TAAGTACTGTATCTTTTAATTCTACTGTAAATAGTGTTTTTATTTTTTAACTGCTGCTAT
64141  ATTCATGACATAGAAAATTAAGATGACATTTATCACAAAAATAAAAAATTGACGACGATA

64201  TACATAGGAATATAATTTTGCATCTGGCCAGCTTGCCTAAACAGATGATTTCAAAATATT
64201  ATGTATCCTTATATTAAAACGTAGACCGGTCGAACGGATTTGTCTACTAAAGTTTTATAA

64261  ATCTGTCAGATTTTCTGTGTTCTCTATCTCTGTAATCATATCATCTATGTTTTATGATCT
64261  TAGACAGTCTAAAAGACACAAGAGATAGAGACATTAGTATAGTAGATACAAAATACTAGA

64321  ATGACAGTTATATTTTTTCATCTCCAAGCTGATATTTTAAATTTCATTATTCTTGCTTTA
64321  TACTGTCAATATAAAAAAGTAGAGGTTCGACTATAAAATTTAAAGTAATAAGAACGAAAT

64381  TACTGGTTGTACATATTCAGTTAGAGTGATTGCAGTAGGCAATTTGCGATGTTCCCAATT
64381  ATGACCAACATGTATAAGTCAATCTCACTAACGTCATCCGTTAAACGCTACAAGGGTTAA

64441  TGATAAGGAAAGCTTTTACATTTTACCATTAAGTATAACGTTTGCGAGCTTATTATAGCT
64441  ACTATTCCTTTCGAAAATGTAAAATGGTAATTCATATTGCAAACGCTCGAATAATATCGA

64501  ATCCTTTGTCACTTAGGGAAGTTATCTTTGTTTTTTAGTTATCTAGGAAACTAAAAAATC
64501  TAGGAAACAGTGAATCCCTTCAATAGAAACAAAAAATCAATAGATCCTTTGATTTTTTAG

64561  AGAAAAGTTAGTTTGATTTTATCAGATACATCTGCTACATCTAATGAGATGATCATATAG
64561  TCTTTTCAATCAAACTAAAATAGTCTATGTAGACGATGTAGATTACTCTACTAGTATATC

64621  TTTTTTTCCTCCCATAAACTGTGAATATAATGAATCACATTAATTGATTTTTTTAAATGT
64621  AAAAAAAGGAGGGTATTTGACACTTATATTACTTAGTGTAATTAACTAAAAAAATTTACA

64681  TAAACCAATCTCCATTTCTGGGATAAATTCAACTTAGTCATGTTGTATTAGCCTTTTGTA
64681  ATTTGGTTAGAGGTAAAGACCCTATTTAAGTTGAATCAGTACAACATAATCGGAAAACAT

64741  TATCTTATATCTATAATACTGAATGAGATTATCATACTCTTTACATGTATTTGAAGCCAT
64741  ATAGAATATAGATATTATGACTTACTCTAATAGTATGAGAAATGTACATAAACTTCGGTA

64801  GTCATTAAGTGCATACAATTTTTATTAAATTTTTAATTGACAAATAATTGTATTTATTTA
64801  CAGTAATTCACGTATGTTAAAAATAATTTAAAAATTAACTGTTTATTAACATAAATAAAT

64861  TGGGGTACGATGTAGTGTTTTGATATATGTTTACATTGTAGAGTGACTAAATCAAGCTAA
64861  ACCCCATGCTACATCACAAAACTATATACAAATGTAACATCTCACTGATTTAGTTCGATT

64921  TTAGCATACTCATCACTGAACATATTTATCATTTCTTGTGGTGAGAACATTTGAAATTTA
64921  AATCGTATGAGTAGTGACTTGTATAAATAGTAAAGAACACCACTCTTGTAAACTTTAAAT

64981  ATCTCTTAGCAATTTTGAAATATATGATACATTATTATTAACTACAGTCACCATGCTGTG
64981  TAGAGAATCGTTAAAACTTTATATACTATGTAATAATAATTGATGTCAGTGGTACGACAC

65041  CGATAGGTCTCAAAAACTTATTCCTCCTAATTGAAATTTTGTTCCCTTTGACCAACATCT
65041  GCTATCCAGAGTTTTTGAATAAGGAGGATTAACTTTAAAACAAGGGAAACTGGTTGTAGA

65101  TCCAATTCCCCAACCCCTAGCCTCCTCTGGTAACCACCATTCTACTCTCTACTTCCATTA
65101  AGGTTAAGGGGTTGGGGATCGGAGGAGACCATTGGTGGTAAGATGAGAGATGAAGGTAAT
```

FIG. 4 (cont'd)

```
65161  GTTTGACTTTTTCAGTCCACATATGAGTGAAATCGTGCAGTATTTGTCTTTCTGTACTTG
65161  CAAACTGAAAAAGTCAGGTGTATACTCACTTTAGCACGTCATAAACAGAAAGACATGAAC

65221  TCTTGTTTCACTTAGCATAATGTCCAACGGGTTCCCCATGTCATTGTAAATGATGGAATT
65221  AGAACAAAGTGAATCGTATTACAGGTTGCCCAAGGGGTACAGTAACATTTACTACCTTAA

65281  TTCTTTTTTATAGCTAAATAACATTCCATCATGTATACATACCACATTTTCTTTATCGAT
65281  AAGAAAAAATATCGATTTATTGTAAGGTAGTACATATGTATGGTGTAAAAGAAATAGCTA

65341  TCATCTGTTGATGGACAGTTAGGTTGCTTCTGTATCCTGGCTATTGTGAATAATGCTACA
65341  AGTAGACAACTACCTGTCAATCCAACGAAGACATAGGACCGATAACACTTATTACGATGT

65401  ATAAACATGAGAGCACAGATACCTCATGCTGATTTCAATTCCTTTGGATAAGGGTCCCCA
65401  TATTTGTACTCTCGTGTCTATGGAGTACGACTAAAGTTAAGGAAACCTATTCCCAGGGGT

65461  AACCCCAGGCTATGGAACAGCAGTGGTATGTGTGGCCTGTTAGGTACTGGATCGCACTGT
65461  TTGGGGTCCGATACCTTGTCGTCACCATACACACCGGACAATCCATGACCTAGCGTGACA

65521  AGGAGGTGAGCAGCTGCGAGTGAGCATTACCACCTGAGCTCCATCTCATCTCAGATCAGT
65521  TCCTCCACTCGTCGACGCTCACTCGTAATGGTGGACTCGAGGTAGAGTAGAGTCTAGTCA

65581  GGCAGCATTAGGTTCTCATAGGAGTGTGAACCCTATTGTGAACTGTGCATTGCAGGAATC
65581  CCGTCGTAATCCAAGAGTATCCTCACACTTGGGATAACACTTGACACGTAACGTCCTTAG

65641  TAGGTGGTGCACTTTTTATGAGAATCTAATGCTTGATGATCTGAGGTAGAATGATTGCAC
65641  ATCCACCACGTGAAAAATACTCTTAGATTACGAACTACTAGACTCCATCTTACTAACGTG

65701  TCTGCAAGACTCCCCACGCTCATCCCTGTGGAAAAATTATCTTCCACAAAACTGGTCCCT
65701  AGACGTTCTGAGGGGTGCGAGTAGGGACACCTTTTTAATAGAAGGTGTTTTGACCAGGGA

65761  GGTGCCAAAAAGGTTGGGGACTGCTGCTTTTGGATATATACCCAGAAGTGGGATTGCTGA
65761  CCACGGTTTTTCCAACCCCTGACGACGAAAACCTATATATGGGTCTTCACCCTAACGACT

65821  AGCATATGGTAGTTTAATTTTAATTTTAATTTAATTTAGTTTAATTAATTTATTTTTAGC
65821  TCGTATACCATCAAATTAAAATTAAAATTAAATTAAATCAAATTAATTAAATAAAAATCG

65881  ACCTAGGCTGGAATGCAGCAGTGCAATCATAGCTCACTGCAGCTTCCAATTCCTGACCTC
65881  TGGATCCGACCTTACGTCGTCACGTTAGTATCGAGTGACGTCGAAGGTTAAGGACTGGAG

65941  AAGCCATCCTCCCAACTCAGCCTCCCAAATTTCTGGAACTACAGGAATGAGCCATCTCAC
65941  TTCGGTAGGAGGGTTGAGTCGGAGGGTTTAAAGACCTTGATGTCCTTACTCGGTAGAGTG

66001  TCAGCCCTATTTTTAGTGTTGGGAAGAATCTCAAAAAGTAATGACTGTACTAATTTACAC
66001  AGTCGGGATAAAAATCACAACCCTTCTTAGAGTTTTTCATTACTGACATGATTAAATGTG

66061  CGCTACCCTCAGTATACAAGGGTTCCATATCCTCACTAATACTTATCTTTTATCTTTTTG
66061  GCGATGGGAGTCATATGTTCCCAAGGTATAGGAGTGATTATGAATAGAAAATAGAAAAAC

66121  ATAGTAGCCATTCTAAGTATGTATAGTTTTAAAATTATGAAGTTTAAATTGAACCTTAGG
66121  TATCATCGGTAAGATTCATACATATCAAAATTTTAATACTTCAAATTTAACTTGGAATCC

66181  AAGTTGCTACTCTGTCACCAGGCTGGAGTGCAGCAGCGTGATCTTGGTTCACCACAATCT
66181  TTCAACGATGAGACAGTGGTCCGACCTCACGTCGTCGCACTAGAACCAAGTGGTGTTAGA

66241  CCGCCTCCTGGGTTTAAGCAATTCTCCTGGCTCAGCCTCCCAAGTAGCTGGGACTACAGG
66241  GGCGGAGGACCCAAATTCGTTAAGAGGACCGAGTCGGAGGGTTCATCGACCCTGATGTCC

66301  CACATGCTACCATGCCTGGCTCATTTTTATATTTTTGGTAGAGATGGGTTTCACCATGTT
66301  GTGTACGATGGTACGGACCGAGTAAAAATATAAAAACCATCTCTACCCAAAGTGGTACAA

66361  GTCCAGGCTGGTCTCGAACTCCTGACCTCAAGTGATCCAACAGCCTTGGCCTCCCAACGT
66361  CAGGTCCGACCAGAGCTTGAGGACTGGAGTTCACTAGGTTGTCGGAACCGGAGGGTTGCA

66421  GTTGGGATTACAGACGTGAGCCATCACACCCAGCCTTGAAGTTGCCTTTTTTATCTTCAG
66421  CAACCCTAATGTCTGCACTCGGTAGTGTGGGTCGGAACTTCAACGGAAAAAATAGAAGTC

66481  TAGTGCTTCTTGGCTTAAATTCTTTTGTTTTATAAATAGTAATGGAAGCTTGCCAGTTTT
66481  ATCACGAAGAACCGAATTTAAGAAAACAAAATATTTATCATTACCTTCGAACGGTCAAAA
```

FIG. 4 (cont'd)

```
66541  ATTTTAGAAAGTATTTGCAGGCCAGGTGCAGTGGCTCATGCCTGTAATCCCAGCACTTTG
66541  TAAAATCTTTCATAAACGTCCGGTCCACGTCACCGAGTACGGACATTAGGGTCGTGAAAC

66601  GGAGGCCGAGGCAGGCACATCACTTGAGCCCAGGAGTTCGAGACCAGCCTAGGCAACATG
66601  CCTCCGGCTCCGTCCGTGTAGTGAACTCGGGTCCTCAAGCTCTGGTCGGATCCGTTGTAC

66661  GCAAAACCTCGTCTCTACAAAAAATACAAAAAATTAACTTGGGCGTGGTGGTGCGCGCCT
66661  CGTTTTGGAGCAGAGATGTTTTTTATGTTTTTTAATTGAACCCGCACCACCACGCGCGGA

66721  GTAGTCCCAGCTACTCTGGAGGCTGAGGTGGGAGGATTGCTTGAACCCAGGGGGTAGAGG
66721  CATCAGGGTCGATGAGACCTCCGACTCCACCCTCCTAACGAACTTGGGTCCCCCATCTCC

66781  TTGCAGTGAGCCAAGATCTTGCCACTGAACTTCATTCAGCCTGGGTGACAGAGAAAAACA
66781  AACGTCACTCGGTTCTAGAACGGTGACTTGAAGTAAGTCGGACCCACTGTCTCTTTTTGT

66841  ACTCTGTCTCAAAAAAAAAAAATAAATAATAAAAAATAAAGTATTTGCATGATATATCTT
66841  TGAGACAGAGTTTTTTTTTTTTATTTATTATTTTTTATTTCATAAACGTACTATATAGAA

66901  TTTCTGTCTTTTTGATTCAGATATTGTCAGCTGAGTCCAATCTAACAAACTTATATTTTA
66901  AAAGACAGAAAAACTAAGTCTATAACAGTCGACTCAGGTTAGATTGTTTGAATATAAAAT

66961  ACCGAAGCTTTAGTACTGTTATATTTAATAAACTAATAATATATTTGCACTTAAATACAA
66961  TGGCTTCGAAATCATGACAATATAAATTATTTGATTATTATATAAACGTGAATTTATGTT

67021  CATCTAATTTTATGCTTTTTAATTATACATGATTTGTATTTCTTTTTTTCCCATGTAAGT
67021  GTAGATTAAAATACGAAAAATTAATATGTACTAAACATAAAGAAAAAAAGGGTACATTCA

67081  TTTTAGGGTATACATCTTTAAAGGCCTTACTTTTCATTATCGTTCAGTTTAACTTATTTT
67081  AAAATCCCATATGTAGAAATTTCCGGAATGAAAAGTAATAGCAAGTCAAATTGAATAAAA

67141  CTAATTTCCATTTTTCTTCTGTGACCTATGGTTTAGTTAGTGGTGGATTTATTTTCCAAA
67141  GATTAAAGGTAAAAAGAAGACACTGGATACCAAATCAATCACCACCTAAATAAAAGGTTT

67201  ATATGGATGGTGTCCAGTCAAACTTTTGGTATTGATTTCTGGCTTATCTTGTGTTTGGAA
67201  TATACCTACCACAGGTCAGTTTGAAAACCATAACTAAAGACCGAATAGAACACAAACCTT

67261  AATATGTGAATTCTACAGCTGGTCTGTGTAAGAGTTCTCTGTATCAGTTAGGGAAGTTTG
67261  TTATACACTTAAGATGTCGACCAGACACATTCTCAAGAGACATAGTCAATCCCTTCAAAC

67321  TTCTTCCTGTTGTTCATATCTTGCATATCTTTACTAAGGTTTAGCCTGTTTGTTCTATAA
67321  AAGAAGGACAACAAGTATAGAACGTATAGAAATGATTCCAAATCGGACAAACAAGATATT

67381  ATTACTTAGAGAAGCTGTGTTAAATTTTCCCACTAAAATTATTGATTTTTGTCTTTCTCT
67381  TAATGAATCTCTTCGACACAATTTAAAAGGGTGATTTTAATAACTAAAAACAGAAAGAGA

67441  GTATTTATCAGTATGTATCTACTGAAGTCTTTTCAAATCCCTGATCAGTGGTTTGTTCAG
67441  CATAAATAGTCATACATAGATGACTTCAGAAAAGTTTAGGGACTAGTCACCAAACAAGTC

67501  GACAGCACTTTGATTGAGGGAGGTGACGTGGCTTAACATAGTATGGTCTTGAGCTGCCTG
67501  CTGTCGTGAAACTAACTCCCTCCACTGCACCGAATTGTATCATACCAGAACTCGACGGAC

67561  GTTTCTGTGATTTAGGGACTGAACCAGCTCTGGTCACATCTGGATTATCTACTATCCAGC
67561  CAAAGACACTAAATCCCTGACTTGGTCGAGACCAGTGTAGACCTAATAGATGATAGGTCG

67621  ATTCAAATGAACCAGATTACATGAAAGGATATGGGGGTACTCTTTGGGGGCCACGGTGCC
67621  TAAGTTTACTTGGTCTAATGTACTTTCCTATACCCCCATGAGAAACCCCCGGTGCCACGG

67681  ACAAGGCCTTTGGTTTCGATCTCCATTGCCTAGGGAATTAACCTGTGCTGTGTGATTCTA
67681  TGTTCCGGAAACCAAAGCTAGAGGTAACGGATCCCTTAATTGGACACGACACACTAAGAT

67741  GATGTTTTCTTCCTGCTCCCTTAAATAACACCTAAATGTGTTATTCAGCAGTGTGGCTCC
67741  CTACAAAAGAAGGACGAGGGAATTTATTGTGGATTTACACAATAAGTCGTCACACCGAGG

67801  TGCTAAGCAGAGGAGAACTCGGAATTCCTACCAAATTCTGATAATAAAATAACTTTCCTC
67801  ACGATTCGTCTCCTCTTGAGCCTTAAGGATGGTTTAAGACTATTATTTTATTGAAAGGAG
```

FIG. 4 (cont'd)

67861 CACCTCAACCATTGTTTTTACCAGTCCTGTCAACTGTTAGCTTTCCTGGATTTAATGATC
67861 GTGGAGTTGGTAACAAAAATGGTCAGGACAGTTGACAATCGAAAGGACCTAAATTACTAG

67921 TCAAGTTGAGGTCAATGTCAACAGCTTTATGGGATGAATAAGATGAACGCCCATAGGAAA
67921 AGTTCAACTCCAGTTACAGTTGTCGAAATACCCTACTTATTCTACTTGCGGGTATCCTTT

67981 GTCAGTCTCTTGAACACGGGTTGTTTTCTTTTGGTTACCCTCTAAGATTTTTTCTCTTTG
67981 CAGTCAGAGAACTTGTGCCCAACAAAAGAAAACCAATGGGAGATTCTAAAAAAGAGAAAC

68041 ATCTCCAGTTATTTGAAGGATTGAAGGCATTTCGAGGAGTAGATAATAAAATTCGACTGT
68041 TAGAGGTCAATAAACTTCCTAACTTCCGTAAAGCTCCTCATCTATTATTTTAAGCTGACA

68101 TTCAGCCAAACCTCAACATGGATAGAATGTATCGCTCTGCTGTGAGGGCAACTCTGCCGG
68101 AAGTCGGTTTGGAGTTGTACCTATCTTACATAGCGAGACGACACTCCCGTTGAGACGGCC

68161 TATGTAAGTGTAGGAGTTTCTTTTGTGTTTCTTTTAATGTAACGGGTCACGGTGTTGACC
68161 ATACATTCACATCCTCAAAGAAAACACAAAGAAAATTACATTGCCCAGTGCCACAACTGG

68221 ACCAAATAAATAATTTCTGAATAGTTAGATAAATATTCAGTACAAACCATATGAACATTA
68221 TGGTTTATTTATTAAAGACTTATCAATCTATTTATAAGTCATGTTTGGTATACTTGTAAT

68281 ACATTATTTCTGATCTACTTTAGTTAGGTAAAAATACAAGAAAATGGCCGGGCACGGTGG
68281 TGTAATAAAGACTAGATGAAATCAATCCATTTTTATGTTCTTTTACCGGCCCGTGCCACC

68341 TTCACTCCTATAATCCCAGCACTCTGGGAGACTGAGGTGGGTGGATCACTTGAAACCAGG
68341 AAGTGAGGATATTAGGGTCGTGAGACCCTCTGACTCCACCCACCTAGTGAACTTTGGTCC

68401 AATTGGAGACAAGCCTGGCCAACATGGTGAAACACCATCTCTGCAAAAAATACAAAAATT
68401 TTAACCTCTGTTCGGACCGGTTGTACCACTTTGTGGTAGAGACGTTTTTTATGTTTTTAA

68461 AGCCGGGTTTGGTGGCACATGCCTGTGGTCCCATCGGTGTGGCTGAGGCATGAGAATTGC
68461 TCGGCCCAAACCACCGTGTACGGACACCAGGGTAGCCACACCGACTCCGTACTCTTAACG

68521 TTGAACCTGGCAGGTGGAGGCTGCAGTGAGCCAAGATAATCACATCACTGCCCTCCAGCC
68521 AACTTGGACCGTCCACCTCCGACGTCACTCGGTTCTATTAGTGTAGTGACGGGAGGTCGG

68581 TAAGCCGCAAAGTGAGACTCTGTAAAAAAAAAAAACAAAAAACAAAAAACCCAAGAAAAT
68581 ATTCGGCGTTTCACTCTGAGACATTTTTTTTTTTTGTTTTTTGTTTTTTGGGTTCTTTTA

68641 AATATCATTTGGCAATTCCACAATTTTTTAAAATCAGTGTCTGTGGGGGATTCATATGCA
68641 TTATAGTAAACCGTTAAGGTGTTAAAAAATTTTAGTCACAGACACCCCCTAAGTATACGT

68701 AGTGAGAGATGAAAGAGTAAGGAAGAAAAATGTATCTCAACCTAAAATAATATTTGAAGA
68701 TCACTCTCTACTTTCTCATTCCTTCTTTTTACATAGAGTTGGATTTTATTATAAACTTCT

68761 CCACATGAAATTAATATTGAAAATGGAAAATATGGTGTGCAGCACAGGTATTTTGCGGAT
68761 GGTGTACTTTAATTATAACTTTTACCTTTTATACCACACGTCGTGTCCATAAAACGCCTA

68821 ATTTTGCCTAATTGCTTTAGATGCTAGCAAGATATAGTAACTTAATTATTTTGATATTTT
68821 TAAAACGGATTAACGAAATCTACGATCGTTCTATATCATTGAATTAATAAAACTATAAAA

68881 ATCTTAAGTAATGTTTTGAGATAAAAAGATATCAAAATGGTTTCTCATGGCCATTGAATC
68881 TAGAATTCATTACAAAACTCTATTTTTCTATAGTTTTACCAAAGAGTACCGGTAACTTAG

68941 GTGGCTGTCACAATGTTTCTTATGGAGCAGAAATCATTGTAAGATGGGTTAGATTTTTTT
68941 CACCGACAGTGTTACAAAGAATACCTCGTCTTTAGTAACATTCTACCCAATCTAAAAAAA

69001 TTTGAGAGAGAGTCTCACTCTGTCACCCAAGCTATAGTGCAGTGGCACAATCTTGGCTCA
69001 AAACTCTCTCTCAGAGTGAGACAGTGGGTTCGATATCACGTCACCGTGTTAGAACCGAGT

69061 CTACAACCTCCACCTCCGGGGTTCAAGTGATTCTTGTGCCTCAGCCTCCTTAGTATCTGG
69061 GATGTTGGAGGTGGAGGCCCCAAGTTCACTAAGAACACGGAGTCGGAGGAATCATAGACC

69121 GATTACAAGTGCACGCAGCCATGCCCAGCTTAATTTTTTTAAAAATTATTTTTAGTGGAG
69121 CTAATGTTCACGTGCGTCGGTACGGGTCGAATTAAAAAAATTTTTAATAAAAATCACCTC

FIG. 4 (cont'd)

69181 ACATGATTTCACCATGTTAGCCAGGCTGGACTTGAACTTCTGGCCTCAAGTGATCTGCCT
69181 TGTACTAAAGTGGTACAATCGGTCCGACCTGAACTTGAAGACCGGAGTTCACTAGACGGA

69241 GCCTCAGCCTCCCAAAGTTCTGGGATTACAGGCATGAGCCACCGTGCCCAGCTTCAGGGA
69241 CGGAGTCGGAGGGTTTCAAGACCCTAATGTCCGTACTCGGTGGCACGGGTCGAAGTCCCT

69301 TTTAGCCCAACCTATGCATTCAGGAAGCCTGAGGACGGCTAAATCCAAGTGTTCTTCATT
69301 AAATCGGGTTGGATACGTAAGTCCTTCGGACTCCTGCCGATTTAGGTTCACAAGAAGTAA

69361 CCTCTGCCTATTTTTGTAACCCGCATTTCACCCATCTCCTTTGGAGGCCATAATATAGTA
69361 GGAGACGGATAAAAACATTGGGCGTAAAGTGGGTAGAGGAAACCTCCGGTATTATATCAT

69421 GCAGAGGGGAAATTAAGGTAAATTCTTTGGACTAGGGCATAGTTTCGCTCTTCTTCTCAT
69421 CGTCTCCCCTTTAATTCCATTTAAGAAACCTGATCCCGTATCAAAGCGAGAAGAAGAGTA

69481 TACAGCTAGATCACTGGGGAAAAGTCTTTAAAATGGGGCTGGAAGGAAAGGGAAGTAATA
69481 ATGTCGATCTAGTGACCCCTTTTCAGAAATTTTACCCCGACCTTCCTTTCCCTTCATTAT

69541 TTTGTTAGACATCAATTTTGCTACCAAACTGTGTTATGTAGTTTCACATTCCTTATCTGT
69541 AAACAATCTGTAGTTAAAACGATGGTTTGACACAATACATCAAAGTGTAAGGAATAGACA

69601 GTAATCACAGCAGTAAGGCGTTGCTAAGAAGATTATTTGTTGTACAGTTTATTAGTGCCT
69601 CATTAGTGTCGTCATTCCGCAACGATTCTTCTAATAAACAACATGTCAAATAATCACGGA

69661 TTGTACAGAGAAGAAAACTTGAGTCCAGAGAGATTAAATGACTTGTCTGAAGTCACAAAG
69661 AACATGTCTCTTCTTTTGAACTCAGGTCTCTCTAATTTACTGAACAGACTTCAGTGTTTC

69721 AGCAAAAGGACAGGGCAAGAAATTAGATCCAGGTGTTTTTATTCCTGGTCAAGTTCTCTT
69721 TCGTTTTCCTGTCCCGTTCTTTAATCTAGGTCCACAAAAATAAGGACCAGTTCAAGAGAA

69781 CTCACTGAATTCTGTCTCTAGACAGCAATACCAGGGGCTGAGGCAGGTGCTACAGGGTTC
69781 GAGTGACTTAAGACAGAGATCTGTCGTTATGGTCCCCGACTCCGTCCACGATGTCCCAAG

69841 ACCTATATGATTGGCAGTCCCAATTTCTATAACATTACTACATTATTATTGCTGTTACAG
69841 TGGATATACTAACCGTCAGGGTTAAAGATATTGTAATGATGTAATAATAACGACAATGTC

69901 GTCAATATTTAAATAGACAAATTCTGACTTCATGAGCTTTACTCAGATGCTTATGACTGA
69901 CAGTTATAAATTTATCTGTTTAAGACTGAAGTACTCGAAATGAGTCTACGAATACTGACT

69961 CTCATTTCTACCTTAGGTGACCCATCACATCTCTGAAAGTATGTTTCTCTACTTTGCAAG
69961 GAGTAAAGATGGAATCCACTGGGTAGTGTAGAGACTTTCATACAAAGAGATGAAACGTTC

70021 TGAGCAGAGACTAAATTATTTTATGAAGTATCACCCATCTAGTAGATGTAATTTTTTTTT
70021 ACTCGTCTCTGATTTAATAAAATACTTCATAGTGGGTAGATCATCTACATTAAAAAAAAA

70081 CTTTAGAAATAAAGTGCTCTTTGCTTTTGCCCATTTTCCTATTGGGTTATCTATCTCTTC
70081 GAAATCTTTATTTCACGAGAAACGAAAACGGGTAAAAGGATAACCCAATAGATAGAGAAG

70141 ATTGACTTTGGGGATATCCAAATATATATACCAGTTAAAATTCTTTGTTGATCATGCTAC
70141 TAACTGAAACCCCTATAGGTTTATATATATGGTCAATTTTAAGAAACAACTAGTACGATG

70201 CAATAACTTCACCCAGTTTGTTGCTTTACATCTTTTGAAGAACGGAAGTCTTTAAGTTTC
70201 GTTATTGAAGTGGGTCAAACAACGAAATGTAGAAAACTTCTTGCCTTCAGAAATTCAAAG

70261 AAATAGTCACATTTTATCCATTTTTTTCCTTCATGATTTGTGTTTTACATCTCCTACTTA
70261 TTTATCAGTGTAAAATAGGTAAAAAAAGGAAGTACTAAACACAAAATGTAGAGGATGAAT

70321 AGAATCCTTTCCTACCTTAAGGTCACAGAGATATTTTGTACTTTTTAAATAAAGTCTTAG
70321 TCTTAGGAAAGGATGGAATTCCAGTGTCTCTATAAAACATGAAAAATTTATTTCAGAATC

70381 TATTTTGTCACATTTAAGTATATCATCTAATTAGAATTGATTGGGGGGTATGGTAAGATG
70381 ATAAAACAGTGTAAATTCATATAGTAGATTAATCTTAACTAACCCCCCATACCATTCTAC

70441 TAGGGATCTAATCTTATCTTTCACATGTGGATAGCTCGTCATCCCATCACAATTTTTGGG
70441 ATCCCTAGATTAGAATAGAAAGTGTACACCTATCGAGCAGTAGGGTAGTGTTAAAAACCC

FIG. 4 (cont'd)

```
70501  GGGAAAATCAGAAAAAAATTGTTTGGTTTTATTATTACTTTAAAATTTTTTTTATTGGTAC
70501  CCCTTTTAGTCTTTTTTAACAAACCAAAATAATAATGAAATTTTAAAAAAAATAACCATG

70561  CATAAATTATACATATTTATGAGGTACACTGATGTTTTCATGCATGCATATAATGTGTAA
70561  GTATTTAATATGTATAAATACTCCATGTGACTACAAAAGTACGTACGTATATTACACATT

70621  TGATTAGGACAAATAAGAAAGAAATAAATAAAAATTAGGATAATTAGGATATCCATCACC
70621  ACTAATCCTGTTTATTCTTTCTTTATTTATTTTTAATCCTATTAATCCTATAGGTAGTGG

70681  TCAAACATTTCTTATTTTTTTGTGTTGGGATTATTAATTTTTTAACAGTTTAAATGCTTC
70681  AGTTTGTAAAGAATAAAAAAACACAACCCTAATAATTAAAAAATTGTCAAATTTACGAAG

70741  AGTGAGGATCATTTATTATTGCCACATTGTGAGAAAATTCTGTCATTTATTATGTTTTTC
70741  TCACTCCTAGTAAATAATAACGGTGTAACACTCTTTTAAGACAGTAAATAATACAAAAAG

70801  ATTCTTTCAGGTATTTGACAAAGAAGAGCTCTTAGAGTGTATTCAACAGCTTGTGAAATT
70801  TAAGAAAGTCCATAAACTGTTTCTTCTCGAGAATCTCACATAAGTTGTCGAACACTTTAA

70861  GGATCAAGAATGGGTCCCATATTCAACATCTGCTAGTCTGTATATTCGTCCTACATTCAT
70861  CCTAGTTCTTACCCAGGGTATAAGTTGTAGACGATCAGACATATAAGCAGGATGTAAGTA

70921  TGGAACTGAGGTGCAAACTGACTCTTTATTTTGGGGTACTTTGCTGGGCAAGTTATTATT
70921  ACCTTGACTCCACGTTTGACTGAGAAATAAAACCCCATGAAACGACCCGTTCAATAATAA

70981  GTTTATTGTTGTTTGAAACTTCTAGCATATAGTTTGCAGTAGCCCCCCAGTAGCATCATT
70981  CAAATAACAACAAACTTTGAAGATCGTATATCAAACGTCATCGGGGGGTCATCGTAGTAA

71041  AATGACTTCTTCCTTCTGATTGTCAAGATTAGAGGTAGCAAACATTTTCTGTGAAGCGCC
71041  TTACTGAAGAAGGAAGACTAACAGTTCTAATCTCCATCGTTTGTAAAAGACACTTCGCGG

71101  AATCAGTAAATATTTTTTGGCTTTGTGGCCATATAGTTTCTAATAAGAAATTAGATCCCT
71101  TTAGTCATTTATAAAAAACCGAAACACCGGTATATCAAAGATTATTCTTTAATCTAGGGA

71161  ACCTCTTACCATACCCCAAAATCAATTATAATTCGATTATATACTTAAATGTGACAAAAT
71161  TGGAGAATGGTATGGGGTTTTAGTTAATATTAAGCTAATATATGAATTTACACTGTTTTA

71221  ACTAAGACGTTTATTAAGAAATACAAAATATCTCTGTGACCTTAGGTAGGAAATGATTTT
71221  TGATTCTGCAAATAATTCTTTATGTTTTATAGAGACACTGGAATCCATCCTTTACTAAAA

71281  TTTTTTTTGAGGTCTCTCTCTGGTTTTTTTTTTTTTGCCCACGTTGTCGCTTAGGCTGGGG
71281  AAAAAAAACTCCAGAGAGAGACCAAAAAAAAAAAAACGGGTGCAACAGCGAATCCGACCCC

71341  TGCAGTGATGCAATCACGGCTGACTGCAGCTTTGACCTCCTGGGCTCAAGTGATCCTCCT
71341  ACGTCACTACGTTAGTGCCGACTGACGTCGAAACTGGAGGACCCGAGTTCACTAGGAGGA

71401  GCCTCAGCTTCCCAAGTAGCTAGTACTACAGGCATGTGCTACCATGCCTAGCTAATTTTT
71401  CGGAGTCGAAGGGTTCATCGATCATGATGTCCGTACACGATGGTACGGATCGATTAAAAA

71461  AAATTTTTTGTAGAGATGATGTCTCACTCTGTTGTCCTGGCTGGTCTCAAACTCCTGGCC
71461  TTTAAAAAACATCTCTACTACAGAGTGAGACAACAGGACCGACCAGAGTTTGAGGACCGG

71521  TCTAGCAATCCTCCCACCTTGGCCTCCCAAAGTCCTGGGATTACAGGCATGAGCCACTTC
71521  AGATCGTTAGGAGGGTGGAACCGGAGGGTTTCAGGACCCTAATGTCCGTACTCGGTGAAG

71581  ACCTGACCGGAGAGGATTCTTAAACTCTGCCATTTTAGTACTAAAGCAGCCATAGACAGC
71581  TGGACTGGCCTCTCCTAAGAATTTGAGACGGTAAAATCATGATTTCGTCGGTATCTGTCG

71641  ACATAAATGAGTAAATGCAGTGCTGTTTGCCTTGCCCAATTAAGACTAGTCATTATTTTC
71641  TGTATTTACTCATTTACGTCACGACAAACGGAACGGGTTAATTCTGATCAGTAATAAAAG

71701  TAAGTTTACAAGTGCAGTGCCTCCCATTGTGGCAGTACTTCTCTGAGGTAGAAATGGTTT
71701  ATTCAAATGTTCACGTCACGGAGGGTAACACCGTCATGAAGAGACTCCATCTTTACCAAA

71761  TAAAATTTAGGGGAGGGAGAGCTGCTAATTTTCATTTTCATGAGGTCTTGGGATTACTTG
71761  ATTTTAAATCCCCTCCCTCTCGACGATTAAAAGTAAAAGTACTCCAGAACCCTAATGAAC

71821  GCATGGAGTGAGAATGGAGGTTCCCCTTCCCACATAGAAAAATGGTGAAAATAAAGTTCA
71821  CGTACCTCACTCTTACCTCCAAGGGGAAGGGTGTATCTTTTTACCACTTTTATTTCAAGT
```

FIG. 4 (cont'd)

```
71881  CAGTGGGAGTTAAGGAAGGAAATTGAAGAGCTGGGATGGTAGGTTTAAATAACATGACCT
71881  GTCACCCTCAATTCCTTCCTTTAACTTCTCGACCCTACCATCCAAATTTATTGTACTGGA

71941  TATGATTTCCTGGTGGGTCACAGTCTCTTGGTTGGGTGCCCTTGTGAATAAAGGCATGGA
71941  ATACTAAAGGACCACCCAGTGTCAGAGAACCAACCCACGGGAACACTTATTTCCGTACCT

72001  TTGGGCATGCCTGGAGGGGCCAAGGCCTTTTGAGCGGACGAGTATGTTTATATGAAGACC
72001  AACCCGTACGGACCTCCCCGGTTCCGGAAAACTCGCCTGCTCATACAAATATACTTCTGG

72061  CTGTCACCTGTCTCTGGTATCTGCTAGGCAGCTGTGGCTTGAGAGTGTGATATTGAGGGA
72061  GACAGTGGACAGAGACCATAGACGATCCGTCGACACCGAACTCTCACACTATAACTCCCT

72121  TAATTGATGGAAGGAGATTGAATGTGGCTGGCAGGTAAAGAGATAGGGAACATATGGAGA
72121  ATTAACTACCTTCCTCTAACTTACACCGACCGTCCATTTCTCTATCCCTTGTATACCTCT

72181  TATTTAGAATAAGAGAGTGTGAGATAGAGCGCTTTTGCTATAGCCTAGCCATTCTGTTCT
72181  ATAAATCTTATTCTCTCACACTCTATCTCGCGAAAACGATATCGGATCGGTAAGACAAGA

72241  CTACTAAGTGTTGCGGGGTTACCAGGTTTTCTACTAGGCTGTATGAATGCAAAAGGTAGA
72241  GATGATTCACAACGCCCCAATGGTCCAAAAGATGATCCGACATACTTACGTTTTCCATCT

72301  GAGATATATAGGGCCATGGAATAAATACCGAAGTGTTTTCTTTGGTATCCTTGATACCTT
72301  CTCTATATATCCCGGTACCTTATTTATGGCTTCACAAAAGAAACCATAGGAACTATGGAA

72361  TCGAAAGCCGTGTAAGGATCTAGATAATGAATTTCGTGAATTGCAGTCTCTCTGACAAGT
72361  AGCTTTCGGCACATTCCTAGATCTATTACTTAAAGCACTTAACGTCAGAGAGACTGTTCA

72421  TTTAAAGAATAGGAACAATTTTAAAAAGTCATCTACTTCCATAAGTTTTTTGACATTTTA
72421  AAATTTCTTATCCTTGTTAAAATTTTTCAGTAGATGAAGGTATTCAAAAAACTGTAAAAT

72481  AGATAATTGAATTTTTTTTTTTCAGCTTTTAAGTTCCAGGGTACATGTGCAGGTAGGTGT
72481  TCTATTAACTTAAAAAAAAAAAGTCGAAAATTCAAGGTCCCATGTACACGTCCATCCACA

72541  GTTATATAGGTAAATGTAAGCCATGGTGGTTTGCTGTACAAATCAACCCATCACCTAGGT
72541  CAATATATCCATTTACATTCGGTACCACCAAACGACATGTTTAGTTGGGTAGTGGATCCA

72601  ATTAAGCCCAGCATCCATTAGCTATTCTTCCTGATGCTCTTCCTCCTCCCGCCCCTTCCG
72601  TAATTCGGGTCGTAGGTAATCGATAAGAAGGACTACGAGAAGGAGGAGGGCGGGGAAGGC

72661  ACAGACCCTAGTATGTGCTGCTCCCTGCATGTGCCCATGTGTTCTCATTGTTCAGCTCCC
72661  TGTCTGGGATCATACACGACGAGGGACGTACACGGGTACACAAGAGTAACAAGTCGAGGG

72721  ACTTATAAGAGAACATGCAGTGTTTGGTTTTCTTTTAATATTATTTTTAACTTTATGATA
72721  TGAATATTCTCTTGTACGTCACAAACCAAAAGAAAATTATAATAAAAATTGAAATACTAT

72781  GGAAGGAGTACTTTTTAAAGTTGGTTGAAACATTGTTACTGATCTCAAAGCACTACCTTC
72781  CCTTCCTCATGAAAAATTTCAACCAACTTTGTAACAATGACTAGAGTTTCGTGATGGAAG

72841  CAGTTATTCTGAGATACTTTTTCAGTCTAAGATCTGATACTCCTATTCCTGGTTTGTTGA
72841  GTCAATAAGACTCTATGAAAAAGTCAGATTCTAGACTATGAGGATAAGGACCAAACAACT

72901  GAGTTTTTGTCATGAATGGATGTTGGATTTTGTCAATTGCTTTTTTTGAATCTCTTGACA
72901  CTCAAAAACAGTACTTACCTACAACCTAAAACAGTTAACGAAAAAAACTTAGAGAACTGT

72961  TGATTATGTGGTTTTGTACTTTATTACATTATTAATGAATGAATTATATCAATTTATTTT
72961  ACTAATACACCAAAACATGAAATAATGTAATAATTACTTACTTAATATAGTTAAATAAAA

73021  TGGATGTTAAATCAACCTTATTTTCCTAAGCTAAATCCTACTTGGTCATTGTGAATAATC
73021  ACCTACAATTTAGTTGGAATAAAAGGATTCGATTTAGGATGAACCAGTAACACTTATTAG

73081  CATTTTTTTATCTTGCTATATTCAGTTTGCTAATATTTTAAGAATTTTTGTTTCACTGTT
73081  GTAAAAAAATAGAACGATATAAGTCAAACGATTATAAAATTCTTAAAAACAAAGTGACAA

73141  CATGAAATATATTGATCTAGTTTTCATTTTTCTTTTCTTTCTTTTTTTTTTTTTTTTTTA
73141  GTACTTTATATAACTAGATCAAAAGTAAAAAGAAAAGAAAGAAAAAAAAAAAAAAAAAAT
```

FIG. 4 (cont'd)

```
73201  CATCTCCCTCCTCTTCCTCTTGATCTAGTTTTCTAATACAGCTGCACTCCAACTTACGAT
73201  GTAGAGGGAGGAGAAGGAGAACTAGATCAAAAGATTATGTCGACGTGAGGTTGAATGCTA

73261  GGTCCTACTTAGGAGTTTTTGACTGTATGATGTTTGAAAACAATATGAGTTTAGTAGAAA
73261  CCAGGATGAATCCTCAAAAACTGACATACTACAAACTTTTGTTATACTCAAATCATCTTT

73321  CTTACTTTGAGTACACATACCATTCTGTTTTTTTGCTTTTAGTACAGTATTCAATAAATT
73321  GAATGAAACTCATGTGTATGGTAAGACAAAAAAACGAAAATCATGTCATAAGTTATTTAA

73381  ATGTGAGATAACCAATACTTTATTATAAAATAATACACTTTTAGATGATTCTGCCCTACC
73381  TACACTCTATTGGTTATGAAATAATATTTTATTATGTGAAAATCTACTAAGACGGGATGG

73441  ATAGGCTAATGTAATTGTTCTGAGCACATTTAAGATAGGATAAGCTAAGATACGATGGAT
73441  TATCCGATTACATTAACAAGACTCGTGTAAATTCTATCCTATTCGATTCTATGCTACCTA

73501  GTTTGGTAGGTTAGGTATATTAAATGCATTTTCACCTTAAGGATATTTTCAACTTAGGAT
73501  CAAACCATCCAATCCATATAATTTACGTAAAAGTGGAATTCCTATAAAAGTTGAATCCTA

73561  GAGTTTATTGAGTTGTAACCCCATCACAAGTTGAGGAACATCTATGTATCTAATTCCATG
73561  CTCAAATAACTCAACATTGGGGTAGTGTTCAACTCCTTGTAGATACATAGATTAAGGTAC

73621  ATTCAGTAAATTCTTTAGACTGCCAAAATCCTGTAATCTAGAGTTAGACAAGATCTTAAA
73621  TAAGTCATTTAAGAAATCTGACGGTTTTAGGACATTAGATCTCAATCTGTTCTAGAATTT

73681  TCAGGTTTTGTGGTCCATCTTGTAGTCATGATCATTCTCACTATTAGGGAATTCTTAACT
73681  AGTCCAAAACACCAGGTAGAACATCAGTACTAGTAAGAGTGATAATCCCTTAAGAATTGA

73741  TTTTGCATTTGAATCACCGAGGTGTTATTTAAAATACACATATGGAATCCAAGCTCCAGA
73741  AAAACGTAAACTTAGTGGCTCCACAATAAATTTTATGTGTATACCTTAGGTTCGAGGTCT

73801  GACTCTGAGTAGATCTGGTGAGTGATTGTGATGCCTGCCCACATTCAAGAACCTTAGTAC
73801  CTGAGACTCATCTAGACCACTCACTAACACTACGGACGGGTGTAAGTTCTTGGAATCATG

73861  AAAAGCCCTGCTGAATGGTTCTCTTTCACTATACACTCTATCAACTTATGTACTTGATCA
73861  TTTTCGGGACGACTTACCAAGAGAAAGTGATATGTGAGATAGTTGAATACATGAACTAGT

73921  CACTTTGGACCTCAAAATCAATAATTTTTAAAAATCTACTTCCTAAGTTGTGAGGTACGA
73921  GTGAAACCTGGAGTTTTAGTTATTAAAAATTTTTAGATGAAGGATTCAACACTCCATGCT

73981  ATTGAAGGAAATAATGAATACTATTTGGGGAGTCAACATTATTTATTAACGAATACCATT
73981  TAACTTCCTTTATTACTTATGATAAACCCCTCAGTTGTAATAAATAATTGCTTATGGTAA

74041  TGGGGAGCCGACATTATTTATATTTGGTTGGTATATTTGTATCAACTATCATTTTCTAAT
74041  ACCCCTCGGCTGTAATAAATATAAACCAACCATATAAACATAGTTGATAGTAAAAGATTA

74101  TAATGGTATAGGCAGAATAAACCATCACTTGTGATTCAGAAAGGAACATGATACAAATAA
74101  ATTACCATATCCGTCTTATTTGGTAGTGAACACTAAGTCTTTCCTTGTACTATGTTTATT

74161  CATCCAATAATGTATATGGATTTAAATAGATCTGCCCCCTACAGATGTTACGCAATTCAT
74161  GTAGGTTATTACATATACCTAAATTTATCTAGACGGGGGATGTCTACAATGCGTTAAGTA

74221  GTTGGTAATGATCATTCATTAGGTTTTCGTGGTGGCTACATTTGATATGTGAAGTACTGG
74221  CAACCATTACTAGTAAGTAATCCAAAAGCACCACCGATGTAAACTATACACTTCATGACC

74281  CTGGAAGACTGGTGCCAGTAGCTTCAGGTTTGCTGGGATTCTTTCATCAGAGATGACTAG
74281  GACCTTCTGACCACGGTCATCGAAGTCCAAACGACCCTAAGAAAGTAGTCTCTACTGATC

74341  CTTTACTTATCTTTTTATGTTGCATGTTTCTATGATGGGCCTATCCTGTCATTGTCTTCA
74341  GAAATGAATAGAAAAATACAACGTACAAAGATACTACCCGGATAGGACAGTAACAGAAGT

74401  TAGTATAATTGCAAGCTCAACTCTGTCAGTTATGTGATTTTTTTTTTTTTTTTTGGTCCTG
74401  ATCATATTAACGTTCGAGTTGAGACAGTCAATACACTAAAAAAAAAAAAAAAAACCAGGAC

74461  TCTTGCTTTTGGCTGACTTCTATATGTTTTTATTTCATGTCCTTTTCATAGTTAGATTAA
74461  AGAACGAAAACCGACTGAAGATATACAAAAATAAAGTACAGGAAAAGTATCAATCTAATT

74521  CTGGGTCTTATGTCCAAGAGATATTTTGATTTCTTTGAATGAATAAATCTATGTTAGGCT
74521  GACCCAGAATACAGGTTCTCTATAAAACTAAAGAAACTTACTTATTTAGATACAATCCGA
```

FIG. 4 (cont'd)

74581 ACTGTATTAGGTTTTATAGACACCTAGTTGATCACTTGTGTCCAGTCTCTATTCCCTGGT
74581 TGACATAATCCAAAATATCTGTGGATCAACTAGTGAACACAGGTCAGAGATAAGGGACCA

74641 ATGGTAGTTGCTGTGTTTATAGAACATTGAGGATTCTACAATGGACACATTGGTGTTGGG
74641 TACCATCAACGACACAAATATCTTGTAACTCCTAAGATGTTACCTGTGTAACCACAACCC

74701 CCCCAGCCCAGACCCAAATCGAAATTTCTAGAGCCAGGATCAGAGACTCTGCATTCAACA
74701 GGGGTCGGGTCTGGGTTTAGCTTTAAAGATCTCGGTCCTAGTCTCTGAGACGTAAGTTGT

74761 AACTCTCCAGAGATTTCATAACCACTTTTAAAGGACTCACCATCCCAAACCTTGTTAAGG
74761 TTGAGAGGTCTCTAAAGTATTGGTGAAAATTTCCTGAGTGGTAGGGTTTGGAACAATTCC

74821 AATGAAATATATGTCTGCCAGTAATTTCAGTGCTTTAAGTCATTGAAAGCTGAACTTTTA
74821 TTACTTTATATACAGACGGTCATTAAAGTCACGAAATTCAGTAACTTTCGACTTGAAAAT

74881 ATGGCACCAAAGTGGAAATATTTATATAATTGAAAGCTAAACTTCATCCTAATGGCAGTG
74881 TACCGTGGTTTCACCTTTATAAATATATTAACTTTCGATTTGAAGTAGGATTACCGTCAC

74941 TTGAGTTCACTTCCATAGGCCCTGATATAACAGTCTAATATTATTGTTTTTCACATAAAA
74941 AACTCAAGTGAAGGTATCCGGGACTATATTGTCAGATTATAATAACAAAAAGTGTATTTT

75001 TAAGATTCAGTCACTGCCATATAATTAGGGAGTGGCTCTGCTATTGGATGGACTTAAAAT
75001 ATTCTAAGTCAGTGACGGTATATTAATCCCTCACCGAGACGATAACCTACCTGAATTTTA

75061 ATTTCATTATGTTTGCCAAGCTCTGTCTCTTTACATGTTTTATAATTAACTGATCCTTCA
75061 TAAAGTAATACAAACGGTTCGAGACAGAGAAATGTACAAAATATTAATTGACTAGGAAGT

75121 TTTTTATTTTGTTTTATTTTATTTTTGAGATAGAGTCTCGCTTGGTTGCCCAGGCTGGAG
75121 AAAAATAAAACAAAATAAAATAAAAACTCTATCTCAGAGCGAACCAACGGGTCCGACCTC

75181 TGCAATGGTGCAATCTTGGCTCATTGCAACCTCTGCTTCCCAGGTTCAAGTGATTCTCCT
75181 ACGTTACCACGTTAGAACCGAGTAACGTTGGAGACGAAGGGTCCAAGTTCACTAAGAGGA

75241 GCCTCAGCCTCCTGATTAGCGGGGACTACAGGTGCGTGCCACCATGCCCAGCTAATTTTT
75241 CGGAGTCGGAGGACTAATCGCCCCTGATGTCCACGCACGGTGGTACGGGTCGATTAAAAA

75301 GTACTTTTAGTAGAGACGGGGTTTCACCATGTTGGCCAGGCTGGTCCCAAACTCCTGACC
75301 CATGAAAATCATCTCTGCCCCAAAGTGGTACAACCGGTCCGACCAGGGTTTGAGGACTGG

75361 TCAGGTGTTCTGCCCACCTCGGCCTCCCAAAGTGCTGGATTACAGGCATGAGCCACCATG
75361 AGTCCACAAGACGGGTGGAGCCGGAGGGTTTCACGACCTAATGTCCGTACTCGGTGGTAC

75421 CCCGGCCTCCTTCATTTTTAATAATCTTCATAGATACATACTTGTTGTACTAATGTTTTT
75421 GGGCCGGAGGAAGTAAAAATTATTAGAAGTATCTATGTATGAACAACATGATTACAAAAA

75481 GTGCAGTTCCTCATGATAAATAATTAAATCAATTACTAAAATCCTTATAGATTTATGATG
75481 CACGTCAAGGAGTACTATTTATTAATTTAGTTAATGATTTTAGGAATATCTAAATACTAC

75541 ATAATAAATGGAAGTGTGTATTATTGAAACATGTTTAATTAACTGTTCATATATAACCAG
75541 TATTATTTACCTTCACACATAATAACTTTGTACAAATTAATTGACAAGTATATATTGGTC

75601 TGAGTAGGGATTGGCAATTAAAAATACCAGGCTACCAGTGCATGGAAATTTGAAGAAAAC
75601 ACTCATCCCTAACCGTTAATTTTTATGGTCCGATGGTCACGTACCTTTAAACTTCTTTTG

75661 AACAACCTGAAATTCAGAATACTCCAAAATCTGAAACTTTTTGAGCACTGACATGACTAA
75661 TTGTTGGACTTTAAGTCTTATGAGGTTTTAGACTTTGAAAAACTCGTGACTGTACTGATT

75721 AAATGCTCATTGGAGCATTTCAGATTTCATTTTTTCAGATTAGGGATGCTGAATTGGTAA
75721 TTTACGAGTAACCTCGTAAAGTCTAAAGTAAAAAAGTCTAATCCCTACGACTTAACCATT

75781 GCATAATGCAGATTAATCCAAAATCTGAAAAAAATCCTAAATCAAAAACAGTTTTGGTCA
75781 CGTATTACGTCTAATTAGGTTTTAGACTTTTTTTAGGATTTAGTTTTTGTCAAAACCAGT

75841 GAAGCTTTGTGGATAAGGGATAGTCCAAGCTTTTTGGACTGAAGCTTTTTGGATAAGGTA
75841 CTTCGAAACACCTATTCCCTATCAGGTTCGAAAAACCTGACTTCGAAAAACCTATTCCAT

FIG. 4 (cont'd)

```
75901  TAGCCTATAATACATAAATACATAATACAGGATAATCACTGACCTGAATGTATAGCATCA
75901  ATCGGATATTATGTATTTATGTATTATGTCCTATTAGTGACTGGACTTACATATCGTAGT

75961  GTATGGTACACAAATATTTAAATCCATGTACTTTGTTGGATATTATGTTATATAAACTTC
75961  CATACCATGTGTTTATAAATTTAGGTACATGAAACAACCTATAATACAATATATTTGAAG

76021  TTGTAAAAAGTTTAGAGAGTAAAATCATTCACATTACCAAAAGATTTCTCATATTTATAA
76021  AACATTTTTCAAATCTCTCATTTTAGTAAGTGTAATGGTTTTCTAAAGAGTATAAATATT

76081  AAAGGATTATAGCAGCATTTTAATCAGTATCTCCTAAAGTATTTATTTATGGGTTGTTAA
76081  TTTCCTAATATCGTCGTAAAATTAGTCATAGAGGATTTCATAAATAAATACCCAACAATT

76141  ATCTAAAAGAGAAACTACAGTCTGGAGGGCTCTAAACTACTGCTGATTACATATCAGTTG
76141  TAGATTTTCTCTTTGATGTCAGACCTCCCGAGATTTGATGACGACTAATGTATAGTCAAC

76201  GGAATTAAGAGAAAATCTCAGATCATAATATTTAAATAAAAACATTTACATGAATGATTT
76201  CCTTAATTCTCTTTTAGAGTCTAGTATTATAAATTTATTTTTGTAAATGTACTTACTAAA

76261  CTAAGTTTTCACTTTACTAGACAAGAAACTAAAATTATATGACTGTCATGTTCAATATTG
76261  GATTCAAAAGTGAAATGATCTGTTCTTTGATTTTAATATACTGACAGTACAAGTTATAAC

76321  GATACTTAACAACACTACATCCAAGGAAGCCAGGTTTTGCTGATTTTAACCTCGTCCTGT
76321  CTATGAATTGTTGTGATGTAGGTTCCTTCGGTCCAAAACGACTAAAATTGGAGCAGGACA

76381  TGAGTAACTCCATGCAGGTACAGTGGTACAAACACATGTGGACACACAGACCCAGACCTT
76381  ACTCATTGAGGTACGTCCATGTCACCATGTTTGTGTACACCTGTGTGTCTGGGTCTGGAA

76441  TATTTCCTCGGGGATTCTGGTAAGTGTAGAGGTGTCTTGACCATAGTCAATAGCAGAAAT
76441  ATAAAGGAGCCCCTAAGACCATTCACATCTCCACAGAACTGGTATCAGTTATCGTCTTTA

76501  ATGCACAACCACAAGCTCTGAAATTCCATTTGATTGTTGCTCTTAGCCTTCCACTTTTTA
76501  TACGTGTTGGTGTTCGAGACTTTAAGGTAAACTAACAACGAGAATCGGAAGGTGAAAAAT

76561  GGCATATGTCAGTCCCATTTCATCCCACCCACTCTCTCCATTTGGGAGGTGGTAGAGTGA
76561  CCGTATACAGTCAGGGTAAAGTAGGGTGGGTGAGAGAGGTAAACCCTCCACCATCTCACT

76621  GACAATACTGAACTATACCAGGGCTGAGAATAAGTGTCTTTGAAAAGGGTCGAATCTGTG
76621  CTGTTATGACTTGATATGGTCCCGACTCTTATTCACAGAAACTTTTCCCAGCTTAGACAC

76681  ATGCTAGAGACAGCCCTGGAAACTGTCAGGAGTTAGCCCAACCAGGACTGTGACCAGATC
76681  TACGATCTCTGTCGGGACCTTTGACAGTCCTCAATCGGGTTGGTCCTGACACTGGTCTAG

76741  CCAGGCTGTCCACCACAGATTTGCAGGCTACCTGCAGATGTGACTTTTTCAAATGTACTC
76741  GGTCCGACAGGTGGTGTCTAAACGTCCGATGGACGTCTACACTGAAAAAGTTTACATGAG

76801  AAAGACAAGCTGACTTTGGCTAATGCAGAAATTAATTAATTCCTCTTTTTCAGTAAACTT
76801  TTTCTGTTCGACTGAAACCGATTACGTCTTTAATTAATTAAGGAGAAAAAGTCATTTGAA

76861  TATCCTCCTACACTTAGATTGTCTGTAAGTACATCTCTGGAGTTGAGCTCAACTAGAAAG
76861  ATAGGAGGATGTGAATCTAACAGACATTCATGTAGAGACCTCAACTCGAGTTGATCTTTC

76921  AAGCTGTCTGCATTTAGTTAATACCAGCATTGGATGCACACAATATAATTTGAATAATGT
76921  TTCGACAGACGTAAATCAATTATGGTCGTAACCTACGTGTGTTATATTAAACTTATTACA

76981  AGAGCAACATTTTAATCATCTCTCATAAGCAGTTTCCCCATTTGCAACTTCCTGGGAAAT
76981  TCTCGTTGTAAAATTAGTAGAGAGTATTCGTCAAAGGGGTAAACGTTGAAGGACCCTTTA

77041  CTTACATTATGAAATGTTCATTAGAACTCCCATTTTAAAACCCTGCTGCCATTTTGTGAG
77041  GAATGTAATACTTTACAAGTAATCTTGAGGGTAAAATTTTGGGACGACGGTAAAACACTC

77101  TGGGCAGAAGAAAGGCTGGAGATGAGATTTGTCTGTCTCAAATGATTCACTCCTTCATTT
77101  ACCCGTCTTCTTTCCGACCTCTACTCTAAACAGACAGAGTTTACTAAGTGAGGAAGTAAA

77161  CTGGTTCACTCCACAGGGAGCTTAAGGACATGTGCGTTTCATAGACATGCCTTTCTTTTC
77161  GACCAAGTGAGGTGTCCCTCGAATTCCTGTACACGCAAAGTATCTGTACGGAAAGAAAAG

77221  CTTTTATCACCTTGTTAAATCTTAAGATTGAACATACAATTCAGCCTGTAATCATATCAA
77221  GAAAATAGTGGAACAATTTAGAATTCTAACTTGTATGTTAAGTCGGACATTAGTATAGTT
```

FIG. 4 (cont'd)

```
77281  TTCCCATGAAAAATATTTTCCTTATTCACTGCCTCTATTTGTGCTTATACATCTGATCAT
77281  AAGGGTACTTTTTATAAAAGGAATAAGTGACGGAGATAAACACGAATATGTAGACTAGTA

77341  CTTTTTCCTTTACTTTACAATTAGTTTCTATGAACAGAAGAATCTGAAAGATTTAAAGAC
77341  GAAAAAGGAAATGAAATGTTAATCAAAGATACTTGTCTTCTTAGACTTTCTAAATTTCTG

77401  TAGTTAGCACAGCAGCAATTTATAAATCATTAATTTGGGTACTGTCTATACATTTAATGT
77401  ATCAATCGTGTCGTCGTTAAATATTTAGTAATTAAACCCATGACAGATATGTAAATTACA

77461  GTTCTTTTTCATAGTCCTATGTGAAATACATATACATATATATATATTCCACTGTTTATA
77461  CAAGAAAAAGTATCAGGATACACTTTATGTATATGTATATATATATAAGGTGACAAATAT

77521  AACAATATTCAGTTTTATTTGCATAACTCAATATATTTTATATTAACAGCTCCGTTTTTA
77521  TTGTTATAAGTCAAAATAAACGTATTGAGTTATATAAAATATAATTGTCGAGGCAAAAAT

77581  GTGTCTTAAGACATCGAGTCTGTTTTTAGAGATACAGTCTATTTGCCTTGATTTTAGCCT
77581  CACAGAATTCTGTAGCTCAGACAAAAATCTCTATGTCAGATAAACGGAACTAAAATCGGA

77641  GTTATAATCAGCTTATTATTATCTGGCCACTCTTACCAGTGAGTATCATCTTGAGGCTGT
77641  CAATATTAGTCGAATAATAATAGACCGGTGAGAATGGTCACTCATAGTAGAACTCCGACA

77701  TCTTGCTCATTTCAACTTGTCACAGGGGATGTTTTTTACTCTTTGGAGTTTAGGTACACC
77701  AGAACGAGTAAAGTTGAACAGTGTCCCCTACAAAAAATGAGAAACCTCAAATCCATGTGG

77761  AGGTTATTAATTATGCTCCTGATTCATGGTACTTCCATCATGGGGCATATAAGGTCCCTG
77761  TCCAATAATTAATACGAGGACTAAGTACCATGAAGGTAGTACCCCGTATATTCCAGGGAC

77821  TCTTTGTTTTATTCCCTTCTATCTTCATTCACCACTCTCATTTCCTCTCTCTCCACTAGA
77821  AGAAACAAAATAAGGGAAGATAGAAGTAAGTGGTGAGAGTAAAGGAGAGAGAGGTGATCT

77881  AATAATTCTCAGGAATCAAATTAATATTATTCTGGCTTATATGTGTTTTTAAAAATCTCA
77881  TTATTAAGAGTCCTTAGTTTAATTATAATAAGACCGAATATACACAAAAATTTTTAGAGT

77941  TCGCTTTTTATACATGTAATTTTAATTTATGTAAGAGACTTTGTCCTACAGATTTCATTG
77941  AGCGAAAAATATGTACATTAAAATTAAATACATTCTCTGAAACAGGATGTCTAAAGTAAC

78001  TGTTTCTTCTCTTTTTCGCCCAGCACTGTGTGTTCCATTTCTATCCAGTCTACTATGTGT
78001  ACAAAGAAGAGAAAAAGCGGGTCGTGACACACAAGGTAAAGATAGGTCAGATGATACACA

78061  ACATCAAGTCCATCATTTCTAACTGTTGCATAGTTCATGATGCGAGGCATCTTCCACATT
78061  TGTAGTTCAGGTAGTAAAGATTGACAACGTATCAAGTACTACGCTCCGTAGAAGGTGTAA

78121  GTATCCCAATTCCCTAACTGGAATCCCAGTTCCCTGCTACCTCACACAATGCTCCAGTGA
78121  CATAGGGTTAAGGGATTGACCTTAGGGTCAAGGGACGATGGAGTGTGTTACGAGGTCACT

78181  ACAGCTGGAAAATCATACAACCCAAGGAATTATTGAAAGTGATTATATCCCAGCAAAAGG
78181  TGTCGACCTTTTAGTATGTTGGGTTCCTTAATAACTTTCACTAATATAGGGTCGTTTTCC

78241  CCCAGGCCCATCTTACACTTCCACCCCAAGAAGGTACTGCTACTTTTCGGGAATGGCCTG
78241  GGGTCCGGGTAGAATGTGAAGGTGGGGTTCTTCCATGACGATGAAAAGCCCTTACCGGAC

78301  GTCTCCTTGGCGAAATTGGCATTTGATCTGTTCTCATCACTGTCGTCTGGCATCAGAAGT
78301  CAGAGGAACCGCTTTAACCGTAAACTAGACAAGAGTAGTGACAGCAGACCGTAGTCTTCA

78361  GACCCCACTTGTCAGGCACTGTACTCAGTGCTTTCCATGCACTAACTCTGATAACAATCT
78361  CTGGGGTGAACAGTCCGTGACATGAGTCACGAAAGGTACGTGATTGAGACTATTGTTAGA

78421  TTTTTTTTTCTTTTTTTGAGACAGAGTCTTGCTCTGTTGCCCAGGCTGGAGTGCAGTTGT
78421  AAAAAAAAAGAAAAAAACTCTGTCTCAGAACGAGACAACGGGTCCGACCTCACGTCAACA

78481  GTGATCTCAGCTCACTGCAACCTCCACCTCCCAAATTCAAGCGATTCTCCTGCCTCAGCC
78481  CACTAGAGTCGAGTGACGTTGGAGGTGGAGGGTTTAAGTTCGCTAAGAGGACGGAGTCGG

78541  TCCCCAGTAGCTGGGACTACAGGCGTGCACCACTACACCTGGCTAATTTTTGTATTTTTA
78541  AGGGGTCATCGACCCTGATGTCCGCACGTGGTGATGTGGACCGATTAAAAACATAAAAAT
```

FIG. 4 (cont'd)

```
78601  GTAGAGATGGGGTTTCACCATGTTGGCCAGGCTGGTCTTGAAATCCTGACCTCAGGTGAT
78601  CATCTCTACCCCAAAGTGGTACAACCGGTCCGACCAGAACTTTAGGACTGGAGTCCACTA

78661  CCACTTGACCTCCCAAAGTGCTGGAATTGCAGGCAAGAGCCACTGAGCTTGGCCTGATAA
78661  GGTGAACTGGAGGGTTTCACGACCTTAACGTCCGTTCTCGGTGACTCGAACCGGACTATT

78721  CAATCTTGTGAGCAGGTGCTTATGCAGTATTTTAGGGATGTGAAAGTAAGGTCCAAAGCG
78721  GTTAGAACACTCGTCCACGAATACGTCATAAAATCCCTACACTTTCATTCCAGGTTTCGC

78781  GTGAAATAAGAGCCTGTATTCTCTTAACCTCCATCCCGCAACATCTTTTATGTGTCAGTC
78781  CACTTTATTCTCGGACATAAGAGAATTGGAGGTAGGGCGTTGTAGAAAATACACAGTCAG

78841  CCTGCACTAAGTCTAGGGATACTGTGCTGAGCAAAAACTATCTTCTTGCTTTCACAGAGC
78841  GGACGTGATTCAGATCCCTATGACACGACTCGTTTTTGATAGAAGAACGAAAGTGTCTCG

78901  TCAGTGTCTGGCAGGGGGTCAGACTTTCATAATATAAACCCACTAAATGAGTGCATATTG
78901  AGTCACAGACCGTCCCCCAGTCTGAAAGTATTATATTTGGGTGATTTACTCACGTATAAC

78961  ATGGCGGTCACTGCTGTGAAGAAGTGGGAATGGTTAGCATGGAAACATAGCCCCAATGGG
78961  TACCGCCAGTGACGACACTTCTTCACCCTTACCAATCGTACCTTTGTATCGGGGTTACCC

79021  GGCGACTAAGTTCTTTCCCATCTCATTCTACTATGTCTACTTTCATCTCTACTTTTTTCT
79021  CCGCTGATTCAAGAAAGGGTAGAGTAAGATGATACAGATGAAAGTAGAGATGAAAAAAGA

79081  TTTCTGAGCTATCAGCTTTCTTGCTCTCAACTATATTTGATGTATTTAACCAGATTTTAT
79081  AAAGACTCGATAGTCGAAAGAACGAGAGTTGATATAAACTACATAAATTGGTCTAAAATA

79141  ATATTGTATTATGTATTTTATAACATGTATATATATCATATAACATACACATATACATAC
79141  TATAACATAATACATAAAATATTGTACATATATATAGTATATTGTATGTGTATATGTATG

79201  ATACACACAGCCAATTAAGTCTCAAGTTCAATTACAATGCTTCTAAGTTTAGGACTATTC
79201  TATGTGTGTCGGTTAATTCAGAGTTCAAGTTAATGTTACGAAGATTCAAATCCTGATAAG

79261  ATTTTCATTTTGGCAGAGAAATTATCTGGTAAAAAATTCAAGTAGAACCAAAGGTATACA
79261  TAAAAGTAAAACCGTCTCTTTAATAGACCATTTTTTAAGTTCATCTTGGTTTCCATATGT

79321  ATAGATGGGAAGTTTCCTTTTCACTCTCACACTCTCATTTCCATCCAGGGTTCTACAATT
79321  TATCTACCCTTCAAAGGAAAAGTGAGAGTGTGAGAGTAAAGGTAGGTCCCAAGATGTTAA

79381  CATCTCCTTCCAAGCAATTCCTATTGCCAGCTTTTCTTATACCCTTTCAGAAATACACAC
79381  GTAGAGGAAGGTTCGTTAAGGATAACGGTCGAAAAGAATATGGGAAAGTCTTTATGTGTG

79441  ACACACACACACACATATATACACACACACACACACACCCTTACATGTGTTTGTACATTA
79441  TGTGTGTGTGTGTGTATATATGTGTGTGTGTGTGTGTGGGAATGTACACAAACATGTAAT

79501  TCTCTCTTTTTACAAAATTGGCAGTGATTCTTTGTCCTGTTTCTGCCACTACTCAAAAAT
79501  AGAGAGAAAAATGTTTTAACCGTCACTAAGAAACAGGACAAAGACGGTGATGAGTTTTTA

79561  TTTAAAACAAATTACACACCTATAAACATACAATTTAAAGAAAAGAGTGAAAGTGAAAAT
79561  AAATTTTGTTTAATGTGTGGATATTTGTATGTTAAATTTCTTTTCTCACTTTCACTTTTA

79621  CTAAGGACCCAGCACATGGTTAAGATGAGAGCATGATGGGTTCAATGGAAAGCCTTTGTG
79621  GATTCCTGGGTCGTGTACCAATTCTACTCTCGTACTACCCAAGTTACCTTTCGGAAACAC

79681  TACCTTTCTCCTTTGCCTCCGTTCCCTCTCCAATAGAGTCAACCACGTTGGAGGTTATAG
79681  ATGGAAAGAGGAAACGGAGGCAAGGGAGAGGTTATCTCAGTTGGTGCAACCTCCAATATC

79741  CACTTCCTTCTTTATGTCCCCCCATCTCCCATCTGGTATGGTATTCTCTTTTACTGCAGA
79741  GTGAAGGAAGAAATACAGGGGGGTAGAGGGTAGACCATACCATAAGAGAAAATGACGTCT

79801  TGGACATTTTGGCAGACATATGTAGTTGCTTCTCTTTGGTATTTACCTAGGAGTTGAAGT
79801  ACCTGTAAAACCGTCTGTATACATCAACGAAGAGAAACCATAAATGGATCCTCAACTTCA

79861  GCTGGGTCACAGGGTGTATGTATATTTCACTTTAGTAGATACTGCTGTTGTAGGACTTTC
79861  CGACCCAGTGTCCCACATACATATAAAGTGAAATCATCTATGACGACAACATCCTGAAAG

79921  TCCTTAGTTTAGCTAAAGATGGGGTCCTTGTCCCAAGGCCATGAAAAATTAGGCTCGCAG
79921  AGGAATCAAATCGATTTCTACCCCAGGAACAGGGTTCCGGTACTTTTTAATCCGAGCGTC
```

FIG. 4 (cont'd)

```
79981  ACAATTTGAAAGGTGAGAATAATGGAACTTATTGGGAAAAAAGGGAAACAGGGACTCCCC
79981  TGTTAAACTTTCCACTCTTATTACCTTGAATAACCCTTTTTTCCCTTTGTCCCTGAGGGG

80041  ACAAAGCCAGGGTCCTGCTAGCATGCTTCCTGCCTTGCAGATTGAATCCCAGGTACCACC
80041  TGTTTCGGTCCCAGGACGATCGTACGAAGGACGGAACGTCTAACTTAGGGTCCATGGTGG

80101  CAGGAAGAGGAGGGGCCAGGCTCCTCCCCACTGTGAATGGTGTGACCGTCTGTGGCTCCC
80101  GTCCTTCTCCTCCCCGGTCCGAGGAGGGGTGACACTTACCACACTGGCAGACACCGAGGG

80161  CAGTGTGCACTCCTCCCAGTGTGCAGGCCGGTTGGAGTTTCTCTGGGGTCTTCTTCCCAC
80161  GTCACACGTGAGGAGGGTCACACGTCCGGCCAACCTCAAAGAGACCCCAGAAGAAGGGTG

80221  TTGGCTGTCTCACTGCCAAACTCCCAAAGTGCTTATACCAGTTTACTCTCCCATCAGTGG
80221  AACCGACAGAGTGACGGTTTGAGGGTTTCACGAATATGGTCAAATGAGAGGGTAGTCACC

80281  TGTATGTATTTGCTTCATTTCTTTGCCAATACTGATACTGTCTTATTAACTTTCCTCATT
80281  ACATACATAAACGAAGTAAAGAAACGGTTATGACTATGACAGAATAATTGAAAGGAGTAA

80341  CTAATGTATACAGTCTTGTGTTATTTGTGGTTTAATTTCCCTGAGAACCAATTATGTTGA
80341  GATTACATATGTCAGAACACAATAAACACCAAATTAAAGGGACTCTTGGTTAATACAACT

80401  GTACCTTTTCATAGGTTTACCAGCTACAGAAGTCCTCTTGTGAAGTGCCTTTGCAAGTCT
80401  CATGGAAAAGTATCCAAATGGTCGATGTCTTCAGGAGAACACTTCACGGAAACGTTCAGA

80461  TTTGTCTTTTTAATTTTTTGCATCTTTGTATATTCTAGGTATAAATCCTTTGATACATAT
80461  AAACAGAAAAATTAAAAAACGTAGAAACATATAAGATCCATATTTAGGAAACTATGTATA

80521  ATCACAAATAACTTCCTAGTCTATGGCAAATCCTATGTTGGATAAACGTACTGCAAATAG
80521  TAGTGTTTATTGAAGGATCAGATACCGTTTAGGATACAACCTATTTGCATGACGTTTATC

80581  TTTCCCAGTCTGTGGCTAGCTTCTGTGTCTGTGTCTTGCTTTGTCACTTTCTTACTGATA
80581  AAAGGGTCAGACACCGATCGAAGACACAGACACAGAACGAAACAGTGAAAGAATGACTAT

80641  TCTTTTGATGAACAGAAGTACTTAGTTTTAAAGTAGTTAAAGTTTTCTTTATGTTTTATA
80641  AGAAAACTACTTGTCTTCATGAATCAAAATTTCATCAATTTCAAAAGAAATACAAAATAT

80701  CTTTTTATGCATTTTAAAGAAATTTTTTGTTACTCCAAGGTCATACAGGTTAAATAAATT
80701  GAAAAATACGTAAAATTTCTTTAAAAAACAATGAGGTTCCAGTATGTCCAATTTATTTAA

80761  CTTACTCCAAGAACATTCTTTTAAAGTTTTGCTTTTTTTCATTTAAATGAAATCCATATG
80761  GAATGAGGTTCTTGTAAGAAAATTTCAAAACGAAAAAAAGTAAATTTACTTTAGGTATAC

80821  AAAGTGAACTTTGTTATCAAGTAACATATACAATTTCTTTTATTTTTCTGCACGGAGACC
80821  TTTCACTTGAAACAATAGTTCATTGTATATGTTAAAGAAAATAAAAAGACGTGCCTCTGG

80881  AAGTTGTCCCATCACCATTTATTGAGTGGTCTATCCTTTCCTCACTGATTACAGTGCCAG
80881  TTCAACAGGGTAGTGGTAAATAACTCACCAGATAGGAAAGGAGTGACTAATGTCACGGTC

80941  TTTTGATATGTCATGTTTCCATAGATGAAGAATATTTTGGGGCTCTCTATCTGTACCTTC
80941  AAAACTATACAGTACAAAGGTATCTACTTCTTATAAAACCCCGAGAGATAGACATGGAAG

81001  CTTTTTAAAAAATATAAATAGTGGTGATACTATGAACAATTTTGTTTGTATTATTGTTTT
81001  GAAAAATTTTTTATATTTATCACCACTATGATACTTGTTAAAACAAACATAATAACAAAA

81061  TTGCACTTAAAATTTGTCTTGGAGATCTTTTCATTTTGGCACATACGGATACACCCCTAT
81061  AACGTGAATTTTAAACAGAACCTCTAGAAAAGTAAAACCGTGTATGCCTATGTGGGGATA

81121  TTTTTTTTCCATTTTCCTAGATGTGGGGTATCCATTGGACATATGTACCGTACTGAATTT
81121  AAAAAAAAGGTAAAAGGATCTACACCCCATAGGTAACCTGTATACATGGCATGACTTAAA

81181  AATATAGAATGTCATAAATTACAAGATGTAACATTATTTTATACACTGAGATGGAGAATC
81181  TTATATCTTACAGTATTTAATGTTCTACATTGTAATAAAATATGTGACTCTACCTCTTAG

81241  AAACTGCAACGCAGTACTTCCCTGATCATCCTGAGTGATTCATGAGTTAGTTATACTAGC
81241  TTTGACGTTGCGTCATGAAGGGACTAGTAGGACTCACTAAGTACTCAATCAATATGATCG
```

FIG. 4 (cont'd)

```
81301  CTCTTATTTCTTTGAGGTGTACGTTTTCTGAGGGAATCTGCCATTTCTCCTGCCATGAGT
81301  GAGAATAAAGAAACTCCACATGCAAAAGACTCCCTTAGACGGTAAAGAGGACGGTACTCA

81361  TGCATTGCTTGGCTCGTGATAGGCATTTTTATTTTTGCATGTAATTTTGTAACAAATGCT
81361  ACGTAACGAACCGAGCACTATCCGTAAAAATAAAAACGTACATTAAAACATTGTTTACGA

81421  AACACTGCTTTATCTTCTTTTTGTTTTTGTTTATTGAGACGGAGTCTTGCTCTGTTTCCC
81421  TTGTGACGAAATAGAAGAAAAACAAAAACAAATAACTCTGCCTCAGAACGAGACAAAGGG

81481  AGGCTGGAGTGCAGTGGTGCAATCTCGGCTCACTGCAACCTCTGTCTCCCAGGTTCAAGC
81481  TCCGACCTCACGTCACCACGTTAGAGCCGAGTGACGTTGGAGACAGAGGGTCCAAGTTCG

81541  GATTCTCCTGCCTCAGCCTCCTGAGTAGCTGGGATTACAGGCATGTGCCACCATGCTCGG
81541  CTAAGAGGACGGAGTCGGAGGACTCATCGACCCTAATGTCCGTACACGGTGGTACGAGCC

81601  CTACTTTTTGTATTTTTTGTAGAGATGGGGTTTCACCATGTTGGTCAGGCTTGTCTTGAA
81601  GATGAAAAACATAAAAAACATCTCTACCCCAAAGTGGTACAACCAGTCCGAACAGAACTT

81661  CTCCTGACCTCAGGTGATCTGCCCCACTCAGCCTCCCAAAGTGCTGGGATTACAGGTGTG
81661  GAGGACTGGAGTCCACTAGACGGGGTGAGTCGGAGGGTTTCACGACCCTAATGTCCACAC

81721  AGCCACCAGCCAGCTTTATCTTTTTAAAGGTTTCTTCCTATTGTGGGTTTCATTAGAGGG
81721  TCGGTGGTCGGTCGAAATAGAAAAATTTCCAAAGAAGGATAACACCCAAAGTAATCTCCC

81781  CTTGGTTGTTGCTTTGCAAGAAAACATTGACTTGCTTTTGTTTAATAGTCTTATAAATAT
81781  GAACCAACAACGAAACGTTCTTTTGTAACTGAACGAAAACAAATTATCAGAATATTTATA

81841  TTGTTTCACTAACATCAAATACATGCCATGCTCCTGCTTTTGAGCTTTTCTGTGCAGTAA
81841  AACAAAGTGATTGTAGTTTATGTACGGTACGAGGACGAAAACTCGAAAAGACACGTCATT

81901  CTTTTCTTCTCAGTGCTAAATCATAAGTTTTTAAAGACATTTAACATGGCACACTCAACA
81901  GAAAAGAAGAGTCACGATTTAGTATTCAAAAATTTCTGTAAATTGTACCGTGTGAGTTGT

81961  TGTGTCACCAATGCCCATAGCCACTGGAAGTATCATCAGTGTCAACAGCTATGACGTTTG
81961  ACACAGTGGTTACGGGTATCGGTGACCTTCATAGTAGTCACAGTTGTCGATACTGCAAAC

82021  GCAATGACAGCTTTGCCATAACTGCTGCTTAGCCAATAACAATTGTGGAATGCTGAGTCC
82021  CGTTACTGTCGAAACGGTATTGACGACGAATCGGTTATTGTTAACACCTTACGACTCAGG

82081  AGATCTCAAACATGTTAAAGGTAAAAAAAAAAAAAAAAAAAAAGATATTTTCGAGTCTGTA
82081  TCTAGAGTTTGTACAATTTCCATTTTTTTTTTTTTTTTTTTTTCTATAAAAGCTCAGACAT

82141  AAACATGGTAGCGTATCCGGAATTGGTGGGTTCTTGGTCTCACTGACTTCAAGAATGAAG
82141  TTTGTACCATCGCATAGGCCTTAACCACCCAAGAACCAGAGTGACTGAAGTTCTTACTTC

82201  CCATGGACCCTCGCGGTAAGTGTTACAGTTCTTAAAGGTGTCGTGTCTGGAGTTTGTTCC
82201  GGTACCTGGGAGCGCCATTCACAATGTCAAGAATTTCCACAGCACAGACCTCAAACAAGG

82261  TTCTGATGTTCAGATGTGTTCGGAGTTTCTTCCTTCTGGTAGGTTCGTGGTCTCGTTGGC
82261  AAGACTACAAGTCTACACAAGCCTCAAAGAAGGAAGACCATCCAAGCACCAGAGCAACCG

82321  TCAGGAGTGAAGCTGCGGACCTTTGCGGTGAGTGTTGCAGCTCTTAAGGCGGCATGTCTG
82321  AGTCCTCACTTCGACGCCTGGAAACGCCACTCACAACGTCGAGAATTCCGCCGTACAGAC

82381  GAGTTGTTCGTTCCTTGCGGTGGGTTCGTGGTCTCGCTGGCTTCAGGAGTGAAGCTGCAG
82381  CTCAACAAGCAAGGAACGCCACCCAAGCACCAGAGCGACCGAAGTCCTCACTTCGACGTC

82441  ACCTTCCCAGTGAGTGTTACAGCTCATAAAGGCAGTGTGGACCCAAAGAGTGAGCAGCAG
82441  TGGAAGGGTCACTCACAATGTCGAGTATTTCCGTCACACCTGGGTTTCTCACTCGTCGTC

82501  CAAGATTTACTGCAAAGAGCGAGAGAACAAAGCTTCCACAGTATGGAAGGGGACCCCAGC
82501  GTTCTAAATGACGTTTCTCGCTCTCTTGTTTCGAAGGTGTCATACCTTCCCCTGGGGTCG

82561  AGGTTGCCACTGCTGGCTCAGGCAGCCTGCTTTTATTCTCTTATCTGGCCCCACCCACAT
82561  TCCAACGGTGACGACCGAGTCCGTCGGACGAAAATAAGAGAATAGACCGGGGTGGGTGTA

82621  CCTGCTGATTGGTCCATTTTACAGAGAGCTGATTGGTCTGTTTTGTCAGGGTGCTGATTG
82621  GGACGACTAACCAGGTAAAATGTCTCTCGACTAACCAGACAAAACAGTCCCACGACTAAC
```

FIG. 4 (cont'd)

```
82681  GTGCATTTACAATCCCTGAGCTAGACACAAAAGTTCTCCACCTCCCCACTGGATTAGCTA
82681  CACGTAAATGTTAGGGACTCGATCTGTGTTTTCAAGAGGTGGAGGGGTGACCTAATCGAT

82741  GATAAAGAGTGTTGATTGATGTATTTACAAACCCTGAGCTAGACACAGAGTGCTGACTGG
82741  CTATTTCTCACAACTAACTACATAAATGTTTGGGACTCGATCTGTGTCTCACGACTGACC

82801  TGCATTTACAAACCTTGAGCTAGATACAGAGCGCCGATTGGTGTATTTACAATCTCTTAG
82801  ACGTAAATGTTTGGAACTCGATCTATGTCTCGCGGCTAACCACATAAATGTTAGAGAATC

82861  CCAGACGTAAAGATTCTCCAAGTCCCCACTAGACTCAGGAGCCCAGCTGGCTTCACCCAG
82861  GGTCTGCATTTCTAAGAGGTTCAGGGGTGATCTGAGTCCTCGGGTCGACCGAAGTGGGTC

82921  TGTATCTTGCACCAGGGCTGCAGGTGGAGCTGCCTGCCAGTCCCGCGCCGTGCACCCGCA
82921  ACATAGAACGTGGTCCCGACGTCCACCTCGACGGACGGTCAGGGCGCGGCACGTGGGCGT

82981  CTCCTCAGCCCTCGGGCTGTTGATGGGACCAGGCACTGTGGAGTGGGGGTGGCACTCGTC
82981  GAGGAGTCGGGAGCCCGACAACTACCCTGGTCCGTGACACCTCACCCCCACCGTGAGCAG

83041  AGGGAGACTCAGGCCGCACAGGATCCCACAGCGGTGGCGGGGGGCGGGAGGCTCAGGCAT
83041  TCCCTCTGAGTCCGGCGTGTCCTAGGGTGTCGCCACCGCCCCCCGCCCTCCGAGTCCGTA

83101  GGCAGGCTGCAGGTCCCGAGCCCTGCCCTGCAGGGAGGCAGCTAAGGCCTGGCGAGAAAT
83101  CCGTCCGACGTCCAGGGCTCGGGACGGGACGTCCCTCCGTCGATTCCGGACCGCTCTTTA

83161  CTGGCCCGGCGAGAAATCTAGCGCGGCGCCGGTGGGCCAGCACTGCTGGGGGACCCGGTG
83161  GACCGGGCCGCTCTTTAGATCGCGCCGCGGCCACCCGGTCGTGACGACCCCCTGGGCCAC

83221  CACCCTCCGCAGCTGCTGGCCTGGGTGCTAAGCCCCTCACTGCCCGGGGCTGGCAGGGCC
83221  GTGGGAGGCGTCGACGACCGGACCCACGATTCGGGGAGTGACGGGCCCCGACCGTCCCGG

83281  AGCCGGTCGCTCCGAATGTGGGGCCTGCCAAGCCCACTCCCACCCGGAACTCCAGCTGGC
83281  TCGGCCAGCGAGGCTTACACCCCGGACGGTTCGGGTGAGGGTGGGCCTTGAGGTCGACCG

83341  CCACAAGCACCATGCGCAGCCCGGGTTCCCGCCCATGCCTCTCCCTCCACACCTCCCTGC
83341  GGTGTTCGTGGTACGCGTCGGGCCCAAGGGCGGGTACGGAGAGGGAGGTGTGGAGGGACG

83401  AAACTGAGGGAGCCAGCTCCGGCCTTGGCCAGCCCAGAGAATGGCTCCCACAGTGCAGCG
83401  TTTGACTCCCTCGGTCGAGGCCGGAACCGGTCGGGTCTCTTACCGAGGGTGTCACGTCGC

83461  GCAGGCTGAAGGGCTCCTCAAGCGCGGTCAGAATGGGCGCCGAGGCCGAGGAGGCACCGA
83461  CGTCCGACTTCCCGAGGAGTTCGCGCCAGTCTTACCCGCGGCTCCGGCTCCTCCGTGGCT

83521  GAGCGAGTGAGGGCTGGGAGGGCTGCCAGCACTGTCATCTCTCAGTAGCATAATTTATAT
83521  CTCGCTCACTCCCGACCCTCCCGACGGTCGTGACAGTAGAGAGTCATCGTATTAAATATA

83581  AACCAGTCTCTTGTTGATTAACCATTATATTATTGATACAACAAATATAAGAACTGTTAC
83581  TTGGTCAGAGAACAACTAATTGGTAATATAATAACTATGTTGTTTATATTCTTGACAATG

83641  TAGTAAATTGAGTAAAGCAGGAAAATTAAATTTGGTCTCTTACTGATCAACCATTATTAG
83641  ATCATTTAACTCATTTCGTCCTTTTAATTTAAACCAGAGAATGACTAGTTGGTAATAATC

83701  ATTGTTGATAACAACGGTTATAATGTTGATCAACCGTTATATTGTTGATACAATTATATT
83701  TAACAACTATTGTTGCCAATATTACAACTAGTTGGCAATATAACAACTATGTTAATATAA

83761  TGATGTATTTAACCAGATTTTATATATTATATTCTATATTTTATAACATGTATATGTATC
83761  ACTACATAAATTGGTCTAAAATATATAATATAAGATATAAAATATTGTACATATACATAG

83821  ATATAACATACACATATACATACACACACACAGCCAATATAATTTCACTCTCAGTTTCTT
83821  TATATTGTATGTGTATATGTATGTGTGTGTGTCGGTTATATTAAAGTGAGAGTCAAAGAA

83881  GTTAATCAACTATTATATTGTTGATACAACAAATATAAGAACTGTTACTAGTAAATTGAA
83881  CAATTAGTTGATAATATAACAACTATGTTGTTTATATTCTTGACAATGATCATTTAACTT

83941  TAAAGCAGGAAAATTACATTTGGGAGCCTTAAAGATGTAGGTTTTCTTCAAGAAATTTAT
83941  ATTTCGTCCTTTTAATGTAAACCCTCGGAATTTCTACATCCAAAAGAAGTTCTTTAAATA
```

FIG. 4 (cont'd)

```
84001  GTTATAGTTATATCCCCTGTTGCATGTGAAGACATACATTCAAGGATACTTACTGCAGCT
84001  CAATATCAATATAGGGGACAACGTACACTTCTGTATGTAAGTTCCTATGAATGACGTCGA

84061  CACACAATTTGCTGATAGGTTGGATGTGGGTGTGAGAGAAGAGATGCTGTTTTCCTTTTG
84061  GTGTGTTAAACGACTATCCAACCTACACCCACACTCTCTTCTCTACGACAAAAGGAAAAC

84121  GGCGATGGCAACTGGATAGTAATCAGTTACTAAGATGGAGAAGAATGAGAAAGAAGTCTT
84121  CCGCTACCGTTGACCTATCATTAGTCAATGATTCTACCTCTTCTTACTCTTTCTTCAGAA

84181  TTTTTGTTTGTTTGTTGGAGTGATATGGGTAGAATAAAGAGTTAAAACAGTCATGCATGT
84181  AAAAACAAACAAACAACCTCACTATACCCATCTTATTTCTCAATTTTGTCAGTACGTACA

84241  AGGTACTATAGATGTGAAAGTCTATTATTCAGGGGAGAGTTTGGAATTTAAGGGATAGAT
84241  TCCATGATATCTACACTTTCAGATAATAAGTCCCCTCTCAAACCTTAAATTCCCTATCTA

84301  TCTTGTCTTTAAGCATAAAAATGCCTTTGAAGGTGAGAAACTAGATTACATCTTTAAGGG
84301  AGAACAGAAATTCGTATTTTTACGGAAACTTCCACTCTTTGATCTAATGTAGAAATTCCC

84361  GAGAACTGTAGATAGAGATGAAAAGAAGGCAAGGACTAACCCCTGGGGCAGGTCAGCATT
84361  CTCTTGACATCTATCTCTACTTTTCTTCCGTTCCTGATTGGGGACCCCGTCCAGTCGTAA

84421  TAGAAGAAAGGGAGTTTGTAAAATGCTAAGCTGTCTGAGAAGTAGCAGCCTGCAAGGTAG
84421  ATCTTCTTTCCCTCAAACATTTTACGATTCGACAGACTCTTCATCGTCGGACGTTCCATC

84481  AAAGAAAAACAAGAGAGGTTTAGTGGACTGGAAACCAAGTGAACCTGGAAACCACAAGCA
84481  TTTCTTTTTGTTCTCTCCAAATCACCTGACCTTTGGTTCACTTGGACCTTTGGTGTTCGT

84541  GCTGTGGCAAATCCTGCCACAGTGAGATGAGGCCTGAGAACTGAGTATTGGATTTGTCAA
84541  CGACACCGTTTAGGACGGTGTCACTCTACTCCGGACTCTTGACTCATAACCTAAACAGTT

84601  TGTGGAAGGCCTTGGTGATCTTGATAAGCATGTGTTAGTAGGGTGGTGGGGTTGCAGTGT
84601  ACACCTTCCGGAACCACTAGAACTATTCGTACACAATCATCCCACCACCCCAACGTCACA

84661  TTGGGATTTGAGAGAGAATGAGAGAATGGGTAGCTGTGATGCTGAATATGTATAAATGTC
84661  AACCCTAAACTCTCTCTTACTCTCTTACCCATCGACACTACGACTTATACATATTTACAG

84721  AGGAGGAATTCTGCTGCACAGTGGGACAGAGAATGGACGCCTCCCTGGAATGGGATAGAT
84721  TCCTCCTTAAGACGACGTGTCACCCTGTCTCTTACCTGCGGAGGGACCTTACCCTATCTA

84781  GCTAAAGGGAGTGTGTGTCTTAGTTGGGAGATATTATGGCATATCTCTAAGCTAATAGTA
84781  CGATTTCCCTCACACACAGAATCAACCCTCTATAATACCGTATAGAGATTCGATTATCAT

84841  ATTAGCCAGAAGGAAGGGAAAACTGATAGTTAAAATGTTCAAAAGATTTCTCACATTCCT
84841  TAATCGGTCTTCCTTCCCTTTTGACTATCAATTTTACAAGTTTTCTAAAGAGTGTAAGGA

84901  ATCATAGTTCTCCTTCTAAGGGTGACCACGTAAGCAGGCAGGGACATGTGACTAAGTAGA
84901  TAGTATCAAGAGGAAGATTCCCACTGGTGCATTCGTCCGTCCCTGTACACTGATTCATCT

84961  GCAGCATCCAACCCCCACCTTGCACGGTCACACACATACTGCTCCATTGACACCATAGTG
84961  CGTCGTAGGTTGGGGGTGGAACGTGCCAGTGTGTGTATGACGAGGTAACTGTGGTATCAC

85021  TCTTGGTGTGAGCTCTTCATTACTTGACTCAATATCTTCTTCCTCATCTTCTCAGCTGGG
85021  AGAACCACACTCGAGAAGTAATGAACTGAGTTATAGAAGAAGGAGTAGAAGAGTCGACCC

85081  GTTGTTGGGTATATCTTCATTGCAGATATTAGCATCCTTTGTGGTCTTCTTTGTCTTTCT
85081  CAACAACCCATATAGAAGTAACGTCTATAATCGTAGGAAACACCAGAAGAAACAGAAAGA

85141  ATTCTAGGGCCAGCACAGTGGGAGGCCTAGTCAACTGAGCCAAACTGGATATAACCACAA
85141  TAAGATCCCGGTCGTGTCACCCTCCGGATCAGTTGACTCGGTTTGACCTATATTGGTGTT

85201  GGTCAAAGGCAGGAGCCAGTGAGGAGATCTTGGTTTTGAGGTCATTCCTGGTGCGATAAT
85201  CCAGTTTCCGTCCTCGGTCACTCCTCTAGAACCAAAACTCCAGTAAGGACCACGCTATTA

85261  AACCATCCTGTAGCATTTTCTTGTCACTTAGAGAAGGCATTAGCAAACTTTTTTTGTAAT
85261  TTGGTAGGACATCGTAAAAGAACAGTGAATCTCTTCCGTAATCGTTTGAAAAAAACATTA

85321  GGTCTTAATAGTAAATATTTTTGACTTTGTAGGCTATATAGCTACTCACCTCTGCTTTTA
85321  CCAGAATTATCATTTATAAAAACTGAAACATCCGATATATCGATGAGTGGAGACGAAAAT
```

FIG. 4 (cont'd)

85381 TAGTACAAAAGCAGCCATAGACAATTCATAAATAAATGAACATGTTCCAATAAAAGCAAT
85381 ATCATGTTTTCGTCGGTATCTGTTAAGTATTTATTTACTTGTACAAGGTTATTTTCGTTA

85441 AAAAACAGGCAGCAGTCTGAAGTTTGTCGACTCCTGATTTGGAATCATTCCAGAAAGTGA
85441 TTTTTGTCCGTCGTCAGACTTCAAACAGCTGAGGACTAAACCTTAGTAAGGTCTTTCACT

85501 AATAAAAGCATGGCTTCTTTTTTTTTTTTGAGACAAGGTCCTGCTCTGTCACCCAGGCTG
85501 TTATTTTCGTACCGAAGAAAAAAAAAAAACTCTGTTCCAGGACGAGACAGTGGGTCCGAC

85561 GAGTACAGTGGTGTCATCATAGCTCACTACAGCTTTGACCTGCTGGGCTCAAGTAATCCT
85561 CTCATGTCACCACAGTAGTATCGAGTGATGTCGAAACTGGACGACCCGAGTTCATTAGGA

85621 CCCACCTCAGCCTCCTGAGTGTCTAGGATTACAGGCATGTGACATCACACCTGGCTGATT
85621 GGGTGGAGTCGGAGGACTCACAGATCCTAATGTCCGTACACTGTAGTGTGGACCGACTAA

85681 TTTAAATTTTTTGTATTGATGGGGTCTTGCTATGTTGCCAAGGCTCACCTCAAACTCCTG
85681 AAATTTAAAAAACATAACTACCCCAGAACGATACAACGGTTCCGAGTGGAGTTTGAGGAC

85741 GTCTCAAGTGATTCTCCTGCCCCAGGATTCCCAAAGTGCTGGAATTAAAGGTGGGGGCCA
85741 CAGAGTTCACTAAGAGGACGGGGTCCTAAGGGTTTCACGACCTTAATTTCCACCCCCGGT

85801 CTGTGCCCAGCCAAAGCATGGCCTTTCTAAGGGTGACTCACTGTAGCACCTCCTGAGTAC
85801 GACACGGGTCGGTTTCGTACCGGAAAGATTCCCACTGAGTGACATCGTGGAGGACTCATG

85861 TTTCCTATCAAGTATCCTGGACCACTTTTTAAATAATTCATTCTAAAATCCATATTTAGG
85861 AAAGGATAGTTCATAGGACCTGGTGAAAAATTTATTAAGTAAGATTTTAGGTATAAATCC

85921 ATTGATTCCAAATTTGCCAACCTGTATTTCCCAAATAACTGGCATGATAATTCTTGTCTT
85921 TAACTAAGGTTTAAACGGTTGGACATAAAGGGTTTATTGACCGTACTATTAAGAACAGAA

85981 TTTCCCAAATGCTCATTTTCCACTCTTCAAACGTTGAGTGTTGACTGAAGTTCTGTGGTC
85981 AAAGGGTTTACGAGTAAAAGGTGAGAAGTTTGCAACTCACAACTGACTTCAAGACACCAG

86041 ATGTTTACAGTCATTTTTATGCTCTTTGTATTGTACATATGGAATGTATTTACCATTTCT
86041 TACAAATGTCAGTAAAAATACGAGAAACATAACATGTATACCTTACATAAATGGTAAAGA

86101 GTTAGCAATGATTTCTTGCAAAAACAATAACACTTGCTAGTTTTGCGTGCTTAAAAATAT
86101 CAATCGTTACTAAAGAACGTTTTTGTTATTGTGAACGATCAAAACGCACGAATTTTTATA

86161 CGAGCCCTGGCGCTCTCTACATATTATCTAATGTAATCCTTATATTAACCCTGTGAGTAG
86161 GCTCGGGACCGCGAGAGATGTATAATAGATTACATTAGGAATATAATTGGGACACTCATC

86221 TCATTATCACTTCTTTTACACAGGAGGAAGTTAGAGAAGAGTGTTAAGTGTTCTTTTAGT
86221 AGTAATAGTGAAGAAAATGTGTCCTCCTTCAATCTCTTCTCACAATTCACAAGAAAATCA

86281 CTTTTCCACTTTGTCTTTAGTTTTCTCTTAGCTGTTCTTTTAAATTCTAAGGTCATTCTT
86281 GAAAAGGTGAAACAGAAATCAAAAGAGAATCGACAAGAAAATTTAAGATTCCAGTAAGAA

86341 ATCTAAAAACTTAAAAGAGTTGATCAGCCTTTTTATCAAGTGTTAAATTTATACCATCTT
86341 TAGATTTTTGAATTTTCTCAACTAGTCGGAAAAATAGTTCACAATTTAAATATGGTAGAA

86401 TTTTCTTTGAACAGGGCTGGCAAATAAACCTGGATTTATCCCTTAGCCCTGTTACAGCAA
86401 AAAAGAAACTTGTCCCGACCGTTTATTTGGACCTAAATAGGGAATCGGGACAATGTCGTT

86461 GTCTCAGAAAATTTGGACTTCAGCTTCCCCAGTGATACATTTTCAAATGCCTATGTATGG
86461 CAGAGTCTTTTAAACCTGAAGTCGAAGGGGTCACTATGTAAAAGTTTACGGATACATACC

86521 ATTGCCCATTAGTTTATTGGCTAGAACTAAAGGAAATCAGGCAAGAGACAAAGGACATTT
86521 TAACGGGTAATCAAATAACCGATCTTGATTTCCTTTAGTCCGTTCTCTGTTTCCTGTAAA

86581 TCTCTAGGGTGTCAGTCAATGCAAAATGTTAGGACTAGCATCAGATTTTTTTTTTTTTAC
86581 AGAGATCCCACAGTCAGTTACGTTTTACAATCCTGATCGTAGTCTAAAAAAAAAAAAATG

86641 AAATGAAAATAATTGAAGTGTGGTAGAAGTTCCTCTAGTTCTGGCAGTCCTAAATATTGT
86641 TTTACTTTTATTAACTTCACACCATCTTCAAGGAGATCAAGACCGTCAGGATTTATAACA

FIG. 4 (cont'd)

```
86701  TAACTGAAGAATGATGGGGCTCATAAATTTGGAAAGGAGAGAGAGGGGAAAAGAGAACGG
86701  ATTGACTTCTTACTACCCCGAGTATTTAAACCTTTCCTCTCTCTCCCCTTTTCTCTTGCC

86761  GAATTTATGCTGAGCAGGGTGGCTAAGTATATATATTCAACAGGCTATAGGAGGAGCTAT
86761  CTTAAATACGACTCGTCCCACCGATTCATATATATAAGTTGTCCGATATCCTCCTCGATA

86821  TAGTATTCACGAAGGGGTGGCACACACATACATAGTAGGCTAACGTGTATGCAGCATGCA
86821  ATCATAAGTGCTTCCCCACCGTGTGTGTATGTATCATCCGATTGCACATACGTCGTACGT

86881  TCACAAGTCACTTTGGGGTGGAGCCTTAACATTTAATGTATTACAGTTAGGGCCTATACA
86881  AGTGTTCAGTGAAACCCCACCTCGGAATTGTAAATTACATAATGTCAATCCCGGATATGT

86941  TCAAAAGGTGAAGCAGAGGACACGAAAGCCCTCTGTGTTCAGCCTCTGTAGACTGGCCAG
86941  AGTTTTCCACTTCGTCTCCTGTGCTTTCGGGAGACACAAGTCGGAGACATCTGACCGGTC

87001  AACCACTCTGTGGTCAGAGGTCTCTTATCAGGAAAGAATTCTTGTTGTTGTGTTGAAACT
87001  TTGGTGAGACACCAGTCTCCAGAGAATAGTCCTTTCTTAAGAACAACAACACAACTTTGA

87061  GCAAAAGGGAGGGGCAGTGTCAGGCAGGTGGTTGATACCAGTCTTTCAGAAGCACTGGTT
87061  CGTTTTCCCTCCCCGTCACAGTCCGTCCACCAACTATGGTCAGAAAGTCTTCGTGACCAA

87121  TCTGTTTAACTTTTAGAGAAGAAAGCTTAATTGGAGTGTTACTGGAAAGGGATACCAGTC
87121  AGACAAATTGAAAATCTCTTCTTTCGAATTAACCTCACAATGACCTTTCCCTATGGTCAG

87181  TAGACCACAAGAGAGGATTCTTGGATCTCACACAAGAAAGAATTCAGGGTGAGTCCACAG
87181  ATCTGGTGTTCTCTCCTAAGAACCTAGAGTGTGTTCTTTCTTAAGTCCCACTCAGGTGTC

87241  AGTAAGATCAAATCAAGTTTATTAGAGAAGTAGAGAAAGAAAAGAATGGCTGCTCCATAA
87241  TCATTCTAGTTTAGTTCAAATAATCTCTTCATCTCTTTCTTTTCTTACCGACGAGGTATT

87301  GCAGAGCAGCACTGAAGGCTTCTGGTTGGCTATTTTTATGGTTATTTCTTGATTATATGC
87301  CGTCTCGTCGTGACTTCCGAAGACCAACCGATAAAAATACCAATAAAGAACTAATATACG

87361  TAAGCAAGGGGTGGATTATTCATGAATTTTCCTGGAAAGGGGTGGGGAATTCCCAGAACT
87361  ATTCGTTCCCCACCTAATAAGTACTTAAAAGGACCTTTCCCCACCCCTTAAGGGTCTTGA

87421  GAGGGTTTCTCTTTCTTTTAGACCATATAGGGTAAGTTCTGGATGTTGCCATGGCATTTG
87421  CTCCCAAAGAGAAAGAAAATCTGGTATATCCCATTCAAGACCTACAACGGTACCGTAAAC

87481  TAAACTGCCATGGCACTGGTGGGAATGTCTTTTAGCATGCTAATGCATTATAAATAGCCT
87481  ATTTGACGGTACCGTGACCACCCTTACAGAAAATCGTACGATTACGTAATATTTATCGGA

87541  AAGATAAGCTGTGAGGATGACCAGAGGTCAATTTCCTCACCATCTTAGTTTTGGCTGGCT
87541  TTCTATTCGACACTCCTACTGGTCTCCAGTTAAAGGAGTGGTAGAATCAAAACCGACCGA

87601  TCTTTACTGCTTCCTGTTTTTTCAGTGGGTTCTTTGTGACCTGTATCTGTCTTGTAATGT
87601  AGAAATGACGAAGGACAAAAAAGTCACCCAAGAAACACTGGACATAGACAGAACATTACA

87661  CCTATCTCATCCTGTAACTAAGAATGCCTGACCTCTTAGGAATGGAGCACAGGTGGTCTC
87661  GGATAGAGTAGGACATTGATTCTTACGGACTGGAGAATCCTTACCTCGTGTCCACCAGAG

87721  AGCTCATTTTATCTATCCCCTATTCAAGATGGAGTTGCTCTGGTTTAAATAGTTCTGACA
87721  TCGAGTAAAATAGATAGGGGATAAGTTCTACCTCAACGAGACCAAATTTATCAAGACTGT

87781  TATTTTCCCCAATACCCCCAAAGGGACCCTTAATCCCAAAATTTGCAGACAGATGAAGAT
87781  ATAAAAGGGGTTATGGGGGTTTCCCTGGGAATTAGGGTTTTAAACGTCTGTCTACTTCTA

87841  CCATCTTCTGTAGCTTCTTCTGGCTGAATACAGGTGATGATATTTTTGCGTAACTATTCA
87841  GGTAGAAGACATCGAAGAAGACCGACTTATGTCCACTACTATAAAAACGCATTGATAAGT

87901  GGGTAGAGAGGAGCTCAGTGAGAAAGCATCAGTATGGTGAAGGCCATTCCTAACTCCCGA
87901  CCCATCTCTCCTCGAGTCACTCTTTCGTAGTCATACCACTTCCGGTAAGGATTGAGGGCT

87961  GTTCTCACAAAAGGTGATATCTGGAAGATTAATAAGTGTTCAATTTAAGAAAACGTTGAG
87961  CAAGAGTGTTTTCCACTATAGACCTTCTAATTATTCACAAGTTAAATTCTTTTGCAACTC

88021  TAGTCTTATCCTGCATTGCTACACAAAGAGTACCACAGCAATATATTCTACAACAGTAAA
88021  ATCAGAATAGGACGTAACGATGTGTTTCTCATGGTGTCGTTATATAAGATGTTGTCATTT
```

FIG. 4 (cont'd)

```
88081  GCAAAATAAGTATAATTATCCCAACTAAACTAAATAACAAGCCTTTCCATGAACTAGGCA
88081  CGTTTTATTCATATTAATAGGGTTGATTTGATTTATTGTTCGGAAAGGTACTTGATCCGT

88141  GTTGTTGGAACCAAGCTTATATGGGGTTGCTAGCCAATTCCAACACATGTTCAGAATTAA
88141  CAACAACCTTGGTTCGAATATACCCCAACGATCGGTTAAGGTTGTGTACAAGTCTTAATT

88201  AATACTGATCCAGATATTTATGTTACCCTTCTGTTTCTTCTGAGCAGCAGCTAGAGATCA
88201  TTATGACTAGGTCTATAAATACAATGGGAAGACAAAGAAGACTCGTCGTCGATCTCTAGT

88261  CTGGTTGGTTCATAGGAACAAACAGGGTCAATCTAAATGGCAGAAAAAACTCGAAACAAT
88261  GACCAACCAAGTATCCTTGTTTGTCCCAGTTAGATTTACCGTCTTTTTTGAGCTTTGTTA

88321  GAATGGGACTAGAGTTGAATAACAAGTATACCATAGTTTCTGAAACATAATTTTTCTCTC
88321  CTTACCCTGATCTCAACTTATTGTTCATATGGTATCAAAGACTTTGTATTAAAAAGAGAG

88381  TCCAGTCTCCCATTTCTATTGAAAACAAATCATGGTAGGACTGATTTGTTTGCACAGTAA
88381  AGGTCAGAGGGTAAAGATAACTTTTGTTTAGTACCATCCTGACTAAACAAACGTGTCATT

88441  GCTTTAGTCTTATTATGCTTGGCCTGGTTATTTGTATAAAGCATAGCAATAATAATTATT
88441  CGAAATCAGAATAATACGAACCGGACCAATAAACATATTTCGTATCGTTATTATTAATAA

88501  TGCCACGTAGGCTTTTTAAAAATTGACTTTGATGTAACTTTGTTCCATAAGAAATCTCAG
88501  ACGGTGCATCCGAAAAATTTTTAACTGAAACTACATTGAAACAAGGTATTCTTTAGAGTC

88561  ATTAGACTTTCTAAAGCCTTGAGCTGAGACACAGATTTATCTGTGCCTGCAAATACTTGT
88561  TAATCTGAAAGATTTCGGAACTCGACTCTGTGTCTAAATAGACACGGACGTTTATGAACA

88621  ATGAGTTGTGTGAATTCTCCTTTTGAGATCCCAAGATAACTGGAGCTCCTAGGCCTGTCA
88621  TACTCAACACACTTAAGAGGAAAACTCTAGGGTTCTATTGACCTCGAGGATCCGGACAGT

88681  GAAAGTGACATTCTTTACTTACCACAGGTCAGGAACCCTGTAAAGGAATTGAATAGACAA
88681  CTTTCACTGTAAGAAATGAATGGTGTCCAGTCCTTGGGACATTTCCTTAACTTATCTGTT

88741  GGTATGAGGCCAGCTTTTCCCAGAGGCTTTCATCAGTTCTGTAAGTCAACTTTGATTCCT
88741  CCATACTCCGGTCGAAAAGGGTCTCCGAAAGTAGTCAAGACATTCAGTTGAAACTAAGGA

88801  TAAAGCAATCTGTTTATATTTGAAAGAATGCCATTCCAGTCAAAGCCCTGGTAAAACAGG
88801  ATTTCGTTAGACAAATATAAACTTTCTTACGGTAAGGTCAGTTTCGGGACCATTTTGTCC

88861  CAGTGTCTCTAATTGTGTCCTGTTACAAAGGAAAACAGATTTTTATTGCACATATGCAAA
88861  GTCACAGAGATTAACACAGGACAATGTTTCCTTTTGTCTAAAAATAACGTGTATACGTTT

88921  TTACTATGCTGCCATAAGTTAAGAATACTCACAAATAGTTTTCAAATTCTTGAGAAATCA
88921  AATGATACGACGGTATTCAATTCTTATGAGTGTTTATCAAAAGTTTAAGAACTCTTTAGT

88981  GGTAGAAAGAAATATGCTCCAAAGTTTTCTCATAGGAGTATAATTTACTCAATTTTTAAC
88981  CCATCTTTCTTTATACGAGGTTTCAAAAGAGTATCCTCATATTAAATGAGTTAAAAATTG

89041  AACTGTAAATAGCTCAAAAAAAAAGGTTTCTTGACTCTGAAAAATGAAACAAAGGATCAG
89041  TTGACATTTATCGAGTTTTTTTTTCCAAAGAACTGAGACTTTTTACTTTGTTTCCTAGTC

89101  CAACATTTTAAGCAAAAAGTCACTAGAAGGTTATTTTGTTCTTTTATTAGTTTAGTCCAT
89101  GTTGTAAAATTCGTTTTTCAGTGATCTTCCAATAAAACAAGAAAATAATCAAATCAGGTA

89161  GCTGTTAATTCCTGTTTGCTCAATATTTATGAACATATTGGTTTCCCAAGGGAGACTCTT
89161  CGACAATTAAGGACAAACGAGTTATAAATACTTGTATAACCAAAGGGTTCCCTCTGAGAA

89221  GAAAGTTTTTTTCCTCTCTATCTTAATGGCACACTTTACAAAATTTTTCAGAAACCTGCA
89221  CTTTCAAAAAAAGGAGAGATAGAATTACCGTGTGAAATGTTTTAAAAAGTCTTTGGACGT

89281  TTTAAGAGCCCTCTATCTGATTATAAACCATCTTTTAAAGAGGATCAAAACAAGACAACA
89281  AAATTCTCGGGAGATAGACTAATATTTGGTAGAAAATTTCTCCTAGTTTTGTTCTGTTGT

89341  ATTTTCTGTGGATAACATAAAGTCTTAGGAAAGCCGTGGTTAAAGACACAATTGACTAGA
89341  TAAAAGACACCTATTGTATTTCAGAATCCTTTCGGCACCAATTTCTGTGTTAACTGATCT
```

FIG. 4 (cont'd)

```
89401  AATTTTGGTTACTTCTGTGGCATACAACAATTTTACATAACAGTTATAATTATTACTGAT
89401  TTAAAACCAATGAAGACACCGTATGTTGTTAAAATGTATTGTCAATATTAATAATGACTA

89461  AACATAAACTAAGTCATATCAGAATTTAGGAGTTTCCCATAATTTTGGAGCACATACCAA
89461  TTGTATTTGATTCAGTATAGTCTTAAATCCTCAAAGGGTATTAAAACCTCGTGTATGGTT

89521  TAACATATTTATACAAATACAACTCAAAGAAAGCTAAACACCATTTCATATTTGACAGTG
89521  ATTGTATAAATATGTTTATGTTGAGTTTCTTTCGATTTGTGGTAAAGTATAAACTGTCAC

89581  CTTCCTGTATGATTTTAATATACCAAGTAAGCCAAATATGTCATTTTTGGACTTAAGGGG
89581  GAAGGACATACTAAAATTATATGGTTCATTCGGTTTATACAGTAAAAACCTGAATTCCCC

89641  ACCTCATATCTAAAGTATTGACCAGATCAGGAAAAGGCATAATATAGAATTTGATTTTGG
89641  TGGAGTATAGATTTCATAACTGGTCTAGTCCTTTTCCGTATTATATCTTAAACTAAAACC

89701  AAAGTTTGTCAAATATCAAAGATTTAAAACACTTGATATTATAAAATCGAATCCCAGGTC
89701  TTTCAAACAGTTTATAGTTTCTAAATTTTGTGAACTATAATATTTTAGCTTAGGGTCCAG

89761  ACTGTAAAGTCATTTATTTAGCCAAAATGATAATACAAAGATTTTCCAAAAGCAAAATCC
89761  TGACATTTCAGTAAATAAATCGGTTTTACTATTATGTTTCTAAAAGGTTTTCGTTTTAGG

89821  TTTTTTTTTTTTTTTTTTTTGAGACGAGTCTGGCTCTGTCGCCCAGCTGGAGTTCAGTG
89821  AAAAAAAAAAAAAAAAAAAAACTCTGCTCAGACCGAGACAGCGGGTCGACCTCAAGTCAC

89881  GCGCCATCTCGGCTCACTGCAAGCTCCGTCTCCCGGGTTCACACCATTCTCCTGCCTCAG
89881  CGCGGTAGAGCCGAGTGACGTTCGAGGCAGAGGGCCCAAGTGTGGTAAGAGGACGGAGTC

89941  CCTCCGGGGTAGCTGGGACTACAGGCACCCGCCACTACGCTTGGCTAATTTTTTTGTGTT
89941  GGAGGCCCCATCGACCCTGATGTCCGTGGGCGGTGATGCGAACCGATTAAAAAAACACAA

90001  TTTAGTAGAGACGGGGTTTCACCATGTTAGCCAGGATGGTCTCCATCTTCTGACCTCGTG
90001  AAATCATCTCTGCCCCAAAGTGGTACAATCGGTCCTACCAGAGGTAGAAGACTGGAGCAC

90061  ATCCACCCGCCTCAGCCTCCCAAAGTGCTGGTATTACAGGCGTGAGCCACTGCGCCCAGC
90061  TAGGTGGGCGGAGTCGGAGGGTTTCACGACCATAATGTCCGCACTCGGTGACGCGGGTCG

90121  AAGCAAAATCCTTTACTCATTGATAGAGGGAAGACAGCTTTCCAAACAATGTCTCACTTT
90121  TTCGTTTTAGGAAATGAGTAACTATCTCCCTTCTGTCGAAAGGTTTGTTACAGAGTGAAA

90181  TTCTTCTTTATTTTGTTGTTTATTCAAAAGGCAAACAAAAATCTTCCATGATCTTTTAAT
90181  AAGAAGAAATAAAACAACAAATAAGTTTTCCGTTTGTTTTTAGAAGGTACTAGAAAATTA

90241  ATTACATGAAAATTTTGTTCAAGAGAGAAAGCCAAATTTCATCTTTGCATTAATGAATGT
90241  TAATGTACTTTTAAAACAAGTTCTCTCTTTCGGTTTAAAGTAGAAACGTAATTACTTACA

90301  CAAATCCAATTCTTAAGAAAACCTTGTAGACAAATTATTCAATCTTAATCAATTTTACCA
90301  GTTTAGGTTAAGAATTCTTTTGGAACATCTGTTTAATAAGTTAGAATTAGTTAAAATGGT

90361  TGAGATAAGATTCTCATAAACCTTTTGTAGTCCTTTACAATTTTTTTTTGTTGTTGTTAA
90361  ACTCTATTCTAAGAGTATTTGGAAAACATCAGGAAATGTTAAAAAAAAACAACAACAATT

90421  AGAGCAGATTAATGCTCTAAGAAAACCCTGTTGTGCTTTTATTCCAATGTTCTATTTATG
90421  TCTCGTCTAATTACGAGATTCTTTTGGGACAACACGAAAATAAGGTTACAAGATAAATAC

90481  GAAAAACTGAATAATACCCTTTAACTTTAGCTAATATTTTAACACACAGAATTTCTTTTA
90481  CTTTTTGACTTATTATGGGAAATTGAAATCGATTATAAAATTGTGTGTCTTAAAGAAAAT

90541  CAAGATTAATTTTCACTGACCTCCCACAACTTACTCAAACCTTTAGCTTTATCCTATGTA
90541  GTTCTAATTAAAAGTGACTGGAGGGTGTTGAATGAGTTTGGAAATCGAAATAGGATACAT

90601  ACTTAAAACAGTCTTTTAACTCTGTAAACTAGGCAATAAGACCACATTCCCATGCCTTCT
90601  TGAATTTTGTCAGAAAATTGAGACATTTGATCCGTTATTCTGGTGTAAGGGTACGGAAGA

90661  TATAATCTTTTACCAAAAACACATTCTATTTTCCTTACACGCCTTGCAGGTAACACTGTT
90661  ATATTAGAAAATGGTTTTTGTGTAAGATAAAAGGAATGTGCGGAACGTCCATTGTGACAA

90721  TCTCTGGTAGCCTCAATTACATGTGCTACAATGTTAACTCTTAGCAACTTTTATATTTGG
90721  AGAGACCATCGGAGTTAATGTACACGATGTTACAATTGAGAATCGTTGAAAATATAAACC
```

FIG. 4 (cont'd)

```
90781  TGAAAAGTCTGATAAATAAGTGGTTTTAATTATGTACCAGGTGTGGAGCCTAGGACGCCA
90781  ACTTTTCAGACTATTTATTCACCAAAATTAATACATGGTCCACACCTCGGATCCTGCGGT

90841  GACAGAAGTGCAGATAAGGTCTGAGTCTTTCCAGCATAGCTAGGGGGCATGGCCAACTCC
90841  CTGTCTTCACGTCTATTCCAGACTCAGAAAGGTCGTATCGATCCCCCGTACCGGTTGAGG

90901  ACATGTCCCCAGGCCCTACCTAGAATCTAATGGCTCCAAAGCAGGTGAGTTGAACAATTA
90901  TGTACAGGGGTCCGGGATGGATCTTAGATTACCGAGGTTTCGTCCACTCAACTTGTTAAT

90961  TCAAGTTAAAGAAGCAGTTTATGGCATTGAAGCATTCAGCAAATCTAATTTAATCTGACC
90961  AGTTCAATTTCTTCGTCAAATACCGTAACTTCGTAAGTCGTTTAGATTAAATTAGACTGG

91021  TAATTTAGACCAGATGTCTAAATTTTGAAGACATTTTTATTTTACCAATATATTTGATTC
91021  ATTAAATCTGGTCTACAGATTTAAAACTTCTGTAAAAATAAAATGGTTATATAAACTAAG

91081  TCTTTATTTCCCAAAGATTATTAAAGTCCCATGAATTAAAAGGTGTTAAAGTTTTTATTT
91081  AGAAATAAAGGGTTTCTAATAATTTCAGGGTACTTAATTTTCCACAATTTCAAAAATAAA

91141  TTCTGACAAAATATTCAATTTAAGTGCTTATTTTTCAAGCCAATTAATTAGAGCTCTTTT
91141  AAGACTGTTTTATAAGTTAAATTCACGAATAAAAAGTTCGGTTAATTAATCTCGAGAAAA

91201  CTATGCATATCACACATACAACACACAAAAATACACAGACAGAAGACCCAGTAGCTGTTA
91201  GATACGTATAGTGTGTATGTTGTGTGTTTTTATGTGTCTGTCTTCTGGGTCATCGACAAT

91261  ATTTTTTCATTTGCCAGCTTTTAAGAATCTTAATTGGATTACTGGCTTCAGGGTGGAGCA
91261  TAAAAAAGTAAACGGTCGAAAATTCTTAGAATTAACCTAATGACCGAAGTCCCACCTCGT

91321  ACGTGTGGGGACAGAGCCGGGAAAACATGCAGTTTCTGGGGCCTAATAAACAGGTGCAGT
91321  TGCACACCCCTGTCTCGGCCCTTTTGTACGTCAAAGACCCCGGATTATTTGTCCACGTCA

91381  TAGAAGGCAAAACAGATTCCCCAAAATTACAGATCTCATTTTTATATTGGATTCTGGATC
91381  ATCTTCCGTTTTGTCTAAGGGGTTTTAATGTCTAGAGTAAAAATATAACCTAAGACCTAG

91441  CCAAAAAGAGGGAATCAGCCCATCCCCTCTGGGAGTTTTGGAAGGTGTAGAAGAATGTTT
91441  GGTTTTTCTCCCTTAGTCGGGTAGGGGAGACCCTCAAAACCTTCCACATCTTCTTACAAA

91501  CCATACCTTCTAGGTGGCCAAGAGCATGCTTCTCTGATCCAAACGTGCACAGAGTGGGGT
91501  GGTATGGAAGATCCACCGGTTCTCGTACGAAGAGACTAGGTTTGCACGTGTCTCACCCCA

91561  ATTCCCCTATAACTGCTATTAGCCTTCCCTTAAAGCATATTTCCTGCCTAGTTATTACAC
91561  TAAGGGGATATTGACGATAATCGGAAGGGAATTTCGTATAAAGGACGGATCAATAATGTG

91621  ACCAAGGTTAAAAGCTCTCCCATAATGCAAAGTAATTTCTGATACCCCTACAAGTAAAAA
91621  TGGTTCCAATTTTCGAGAGGGTATTACGTTTCATTAAAGACTATGGGGATGTTCATTTTT

91681  ACATTAGGTAACACAATGCAAATCAGAGCAATGCCTTGGATTTTGAGAGGGATTTGCTTG
91681  TGTAATCCATTGTGTTACGTTTAGTCTCGTTACGGAACCTAAAACTCTCCCTAAACGAAC

91741  CCTTCAATTCCTGGGGTTCCATGAGGAAAACAGATTTTTCCCAAAATGGAGCCTGTGGTG
91741  GGAAGTTAAGGACCCCAAGGTACTCCTTTTGTCTAAAAAGGGTTTTACCTCGGACACCAC

91801  CTCCCTCAGTTTTTTCTAAGGAAGCCCAGGCTGTTAGAAATGATCTTAGGTCCTCTCAAT
91801  GAGGGAGTCAAAAAAGATTCCTTCGGGTCCGACAATCTTTACTAGAATCCAGGAGAGTTA

91861  GTGGGCATCAAGAGTGGCAAGAAAACAAAATGAGAAAAACAATTCAGTTGACTGAGAAGA
91861  CACCCGTAGTTCTCACCGTTCTTTTGTTTTACTCTTTTTGTTAAGTCAACTGACTCTTCT

91921  AAAAACTTTTATCTAGAAAAAAATCAATATAAAACCTGCCAGATAGATAGATAGATAGAT
91921  TTTTTGAAAATAGATCTTTTTTTAGTTATATTTTGGACGGTCTATCTATCTATCTATCTA

91981  AATCTTGGACATCACTTTTAATTAAGCTGACTTTTAACCAAATCTCTTATTATCAGACTC
91981  TTAGAACCTGTAGTGAAAATTAATTCGACTGAAAATTGGTTTAGAGAATAATAGTCTGAG

92041  TAGCCAGGACAAACAGCTAATATTTCTGGCTTTTGAACTTTACCAAAAGTAACCTCCCAG
92041  ATCGGTCCTGTTTGTCGATTATAAAGACCGAAAACTTGAAATGGTTTTCATTGGAGGGTC
```

FIG. 4 (cont'd)

```
92101  GTGAAACCAATAAGCCTTAACTAAGGTTATGATTTAACCACAGGTGTGGGAGGTATTTTC
92101  CACTTTGGTTATTCGGAATTGATTCCAATACTAAATTGGTGTCCACACCCTCCATAAAAG

92161  AAAGAGGTGGTAAGCAGTTTTTACAAGATCTGGAACCTCCAAACATAGCTCAGAGAAAGG
92161  TTTCTCCACCATTCGTCAAAAATGTTCTAGACCTTGGAGGTTTGTATCGAGTCTCTTTCC

92221  AAGATTCAAGACAGGGAGTCAGAAGTTGTTCATGAGGGGAAGATAATTAATAAATGGCAA
92221  TTCTAAGTTCTGTCCCTCAGTCTTCAACAAGTACTCCCCTTCTATTAATTATTTACCGTT

92281  AGGTCACATAGATATCAAACCAGAAAGGACTCATTCCCGAAGCTAGGAATTGAATCCAGG
92281  TCCAGTGTATCTATAGTTTGGTCTTTCCTGAGTAAGGGCTTCGATCCTTAACTTAGGTCC

92341  CCACCACTGTGAAATAGCAAAGCCTTAGTTACTGAGCTGCAGTACTGCACAGTCTCCATT
92341  GGTGGTGACACTTTATCGTTTCGGAATCAATGACTCGACGTCATGACGTGTCAGAGGTAA

92401  GCTCCTCCGAGAAGGAGCCTAGAGCAGCCAATTTTGAGCTTGCAAAGGCTTTTAACTGCT
92401  CGAGGAGGCTCTTCCTCGGATCTCGTCGGTTAAAACTCGAACGTTTCCGAAAATTGACGA

92461  CAAGATAATTTTTAGGACTAATTGACAGGAACCCCAAAATTCACACCCTCTGGATGGCAG
92461  GTTCTATTAAAAATCCTGATTAACTGTCCTTGGGGTTTTAAGTGTGGGAGACCTACCGTC

92521  AGATCAGGAGAAAGTACCCCCACGTGGTTACAAGGTCAAGCTTTCAAGGACATAAAACAA
92521  TCTAGTCCTCTTTCATGGGGGTGCACCAATGTTCCAGTTCGAAAGTTCCTGTATTTTGTT

92581  GACGAGAGGGAAACTTCATCCAGTTTTTGTTTCAGGGACCTGCAGAAAAGTTTGTAACTG
92581  CTGCTCTCCCTTTGAAGTAGGTCAAAAACAAAGTCCCTGGACGTCTTTTCAAACATTGAC

92641  ACCAGTTTGCGGGCCAGCTTGAAGACCAGATTTGTAGGATTCCTAGGCCTGCATTCTATC
92641  TGGTCAAACGCCCGGTCGAACTTCTGGTCTAAACATCCTAAGGATCCGGACGTAAGATAG

92701  CTGTGGCTAGCTAGGGCTGCCATAATAGAATATTACAGACTAGGCAGCTTCAACCACAGG
92701  GACACCGATCGATCCCGACGGTATTATCTTATAATGTCTGATCCGTCGAAGTTGGTGTCC

92761  TGTTTATTTTCTCACTGCTCCAAAGTCTAGAAGTCCAAGATGAGGGTGCCTGTAAAGCTG
92761  ACAAATAAAAGAGTGACGAGGTTTCAGATCTTCAGGTTCTACTCCCACGGACATTTCGAC

92821  ATTTCTGGTAAGAGCTCTCCTGGCTTGTAGATGGCCACCTTCTCCCTATGTCCTCTCTGG
92821  TAAAGACCATTCTCGAGAGGACCGAACATCTACCGGTGGAAGAGGGATACAGGAGAGACC

92881  GCCTTTCCTCTATCTGGCCAAGGGAGCTATCTCTGGTGTCTTTTCCTCTTCTTATAAGGA
92881  CGGAAAGGAGATAGACCGGTTCCCTCGATAGAGACCACAGAAAAGGAGAAGAATATTCCT

92941  CAGCAGGCCTATGGATTAAGGCCTCACTTTCATGTCTTCATTTAAGTTTAATTACCTCTT
92941  GTCGTCCGGATACCTAATTCCGGAGTGAAAGTACAGAAGTAAATTCAAATTAATGGAGAA

93001  TAAAGGCCCGATGTCCAAATACAGTCACACCGTGGGTTAGGATTTCAACATAGGAATTTT
93001  ATTTCCGGGCTACAGGTTTATGTCAGTGTGGCACCCAATCCTAAAGTTGTATCCTTAAAA

93061  AGGGACACAATTCAACCCATAATAGGAGGGCATTGGAAGGAGAGTGTTCCAGGCAGAGGA
93061  TCCCTGTGTTAAGTTGGGTATTATCCTCCCGTAACCTTCCTCTCACAAGGTCCGTCTCCT

93121  AGTAGTGCAGTAGAGCATATGGAAGTAGGAAAGTGAGGAGCAATGGAAGGGGTTCAGTAT
93121  TCATCACGTCATCTCGTATACCTTCATCCTTTCACTCCTCGTTACCTTCCCCAAGTCATA

93181  GGTTTGAGCGTGGGGTGTGTAGAGGGTGAAGGCTATTTCACCCAGTGCAGTAAGCTCTAT
93181  CCAAACTCGCACCCCACACATCTCCCACTTCCGATAAAGTGGGTCACGTCATTCGAGATA

93241  CATCCACACCGGGGTTTTACAGTGGGAGAAAGGAGGGTGTTTATTTGCAGGTCAAGAAGC
93241  GTAGGTGTGGCCCCAAAATGTCACCCTCTTTCCTCCCACAAATAAACGTCCAGTTCTTCG

93301  AAACAGAATCAGGGAGCTCATGCTTAAGACCTGAACTCCACAGTGGCTTACATGTAAGGT
93301  TTTGTCTTAGTCCCTCGAGTACGAATTCTGGACTTGAGGTGTCACCGAATGTACATTCCA

93361  GCAGAGGTTACAGGCAAAGGCATCAATCAACACATGGAAGCCATATATTGGTTTGGCCTA
93361  CGTCTCCAATGTCCGTTTCCGTAGTTAGTTGTGTACCTTCGGTATATAACCAAACCGGAT

93421  AAAAGGTGGGATATCCTGAAGTAGGGGCTTACAGGTTACAGGTAAATCCAAATATTTTCT
93421  TTTTCCACCCTATAGGACTTCATCCCCGAATGTCCAATGTCCATTTAGGTTTATAAAAGA
```

FIG. 4 (cont'd)

```
93481  GATTTGCACATTGTTTAAGGAAGGGGATATTTGTCTAAAGATGGGATCAGCAGGCCAGGT
93481  CTAAACGTGTAACAAATTCCTTCCCCTATAAACAGATTTCTACCCTAGTCGTCCGGTCCA

93541  GTGGTGGCTCATGCTTGTAACCTCAGCACTTTGAAAGGCTGAAGAAGGAGGGTAACTTGA
93541  CACCACCGAGTACGAACATTGGAGTCGTGAAACTTTCCGACTTCTTCCTCCCATTGAACT

93601  GGCCAGGATTTCAAGACCAGCCTAGTCAACATGGCAAGACTCTGTCTCTAAAAAAAATAA
93601  CCGGTCCTAAAGTTCTGGTCGGATCAGTTGTACCGTTCTGAGACAGAGATTTTTTTTATT

93661  AAAAGAAAAAAAGAAAAAGAAAAAAAATAAAGATGGAATCAGCAGAAAGGAATGTTAGGT
93661  TTTTCTTTTTTTCTTTTTCTTTTTTTTATTTCTACCTTAGTCGTCTTTCCTTACAATCCA

93721  CTGGCCCATGGGCGGACTTCCTCCAGACTTCTCAGAAAGAAATTTAAGACAAAGAATGGT
93721  GACCGGGTACCCGCCTGAAGGAGGTCTGAAGAGTCTTTCTTTAAATTCTGTTTCTTACCA

93781  GCCAGGCGTGGTAGTTCACGCCTGTAATCCCAGCACTTTGGGAGGCTGAGGAGGGTGGAT
93781  CGGTCCGCACCATCAAGTGCGGACATTAGGGTCGTGAAACCCTCCGACTCCTCCCACCTA

93841  CACTTGAGGTCAGGGATTTGAGACCAGCCTGGCCAACATGGTGAAACCCCATCTCTACTA
93841  GTGAACTCCAGTCCCTAAACTCTGGTCGGACCGGTTGTACCACTTTGGGGTAGAGATGAT

93901  AAAATACAAAAACTAGCCGGGTGTGGTGGTGCACGCCTGTAATCCCAGCTCCTCAGGAGG
93901  TTTTATGTTTTTGATCGGCCCACACCACCACGTGCGGACATTAGGGTCGAGGAGTCCTCC

93961  CTGAGGCAGGAGAATCGCTTGAACCTGGGAGGTGGAGGTTGCAGTGAGCCAAGATTGCGC
93961  GACTCCGTCCTCTTAGCGAACTTGGACCCTCCACCTCCAACGTCACTCGGTTCTAACGCG

94021  CACTGCACTCCACCCTGGGCAAGAGAGCGAGACTTGAGACTCCATCTAAAAAAACAAAAT
94021  GTGACGTGAGGTGGGACCCGTTCTCTCGCTCTGAACTCTGAGGTAGATTTTTTTGTTTTA

94081  GGAAAACAAAGAATGGTGATAATTCAGTCCTCAATTCCTTTTCTTTTTTTTTTCTTTCTT
94081  CCTTTTGTTTCTTACCACTATTAAGTCAGGAGTTAAGGAAAAGAAAAAAAAAAGAAAGAA

94141  TTTTTTTTTTTTTAACTGCTCCTGCGGAGCAGGGCTACCTCATAGCCAGTATGTCCAGAG
94141  AAAAAAAAAAAAATTGACGAGGACGCCTCGTCCCGATGGAGTATCGGTCATACAGGTCTC

94201  TTGTCTCAGTTCCCTCGTTATCTGTGGTCTGGAGGATCCATATGATGGTGATCCAGGTTC
94201  AACAGAGTCAAGGGAGCAATAGACACCAGACCTCCTAGGTATACTACCACTAGGTCCAAG

94261  TGAAAAACAACTCTGGAACATCTGTTAAGATGTTATCTTTAGTTTCTATAGGAAACCAAA
94261  ACTTTTTGTTGAGACCTTGTAGACAATTCTACAATAGAAATCAAAGATATCCTTTGGTTT

94321  CATCTTCTGACTCTGACCTCCTTGGTGATTATTTTAAGCTACTGTTTCCCTTTTTGCTTA
94321  GTAGAAGACTGAGACTGGAGGAACCACTAATAAAATTCGATGACAAAGGGAAAAACGAAT

94381  TCGAGTTGCTCATTTACTTCTCAAGGCTAGCAGGATGACTGGACTTTCTCTTGAAGGAAC
94381  AGCTCAACGAGTAAATGAAGAGTTCCGATCGTCCTACTGACCTGAAAGAGAACTTCCTTG

94441  TCAAGCTGTTCCTTTATTTTTATGCTCAGGGGCGGGGGGCACTCAGCAGGTCCCTAAGAG
94441  AGTTCGACAAGGAAATAAAAATACGAGTCCCCGCCCCCCGTGAGTCGTCCAGGGATTCTC

94501  GTATCCCCGCTGTGTCTCACTATGGGTGAAGGCTCAGCGGGAAGAAAGCTAGATACCAGT
94501  CATAGGGGCGACACAGAGTGATACCCACTTCCGAGTCGCCCTTCTTTCGATCTATGGTCA

94561  TGGAACTCTCTTAAAGTAAGGAGATCTTGGGTACTTTATTAATATTTTTTTCAAGCTTTG
94561  ACCTTGAGAGAATTTCATTCCTCTAGAACCCATGAAATAATTATAAAAAAAGTTCGAAAC

94621  GTAAAGTATGAAATAACTCTGGATTAAGAGGAGAAGAACTAGAACTTAATAACCATGACA
94621  CATTTCATACTTTATTGAGACCTAATTCTCCTCTTCTTGATCTTGAATTATTGGTACTGT

94681  TTTGGGCAAATTGTTTGAAGCCTCAGTTTCCTCAACCTAAAAATAGGAATTATAACTTTT
94681  AAACCCGTTTAACAAACTTCGGAGTCAAAGGAGTTGGATTTTTATCCTTAATATTGAAAA

94741  TGAATTGTTCTGTTGTATGAGATAATGACAGTGAAATATTTTGGAGCCAAAAAGCAATGC
94741  ACTTAACAAGACAACATACTCTATTACTGTCACTTTATAAAACCTCGGTTTTTCGTTACG
```

FIG. 4 (cont'd)

```
94801  ATACTATTGGGGGTTATTATTATTTTTTGATCTTTCAGCAAGCCAGCTATAGTAGCTTTT
94801  TATGATAACCCCCAATAATAATAAAAAACTAGAAAGTCGTTCGGTCGATATCATCGAAAA

94861  CCTATATAAACACAGTATGAATTCAGTGCCCTCGCTTTCCTGACCCTCACAGCATTCAAG
94861  GGATATATTTGTGTCATACTTAAGTCACGGGAGCGAAAGGACTGGGAGTGTCGTAAGTTC

94921  CCCTGTATGGACCGCTGAGCTCTCCCTTGAAGCACCCCTTAGTCCAGTATTCTTTACTAT
94921  GGGACATACCTGGCGACTCGAGAGGGAACTTCGTGGGGAATCAGGTCATAAGAAATGATA

94981  TTTCCCCTTTAACAATTTAAACTTCTTTCAAAACAACTGGCAGTAGTTTTTTAAAAAAGA
94981  AAAGGGGAAATTGTTAAATTTGAAGAAAGTTTTGTTGACCGTCATCAAAAAATTTTTTCT

95041  AAACAGGCTACTCTTCAAATTAAAAAAAAAATTGTCTTGCTTTAGGAAAAATGTTCTTCT
95041  TTTGTCCGATGAGAAGTTTAATTTTTTTTTTAACAGAACGAAATCCTTTTTACAAGAAGA

95101  GTCTTTTCCAATTATCTTATTTCTTCTGCCTCTCATCTGCCTTGCCTAGGCAGAATTATT
95101  CAGAAAAGGTTAATAGAATAAAGAAGACGGAGAGTAGACGGAACGGATCCGTCTTAATAA

95161  CTCAAGCCTGCACATGCTGCTGTGCCTCTCTGGCTTCTAGGCCAAAACATAGGCTAATAG
95161  GAGTTCGGACGTGTACGACGACACGGAGAGACCGAAGATCCGGTTTTGTATCCGATTATC

95221  TACTCTTCTCAGCTCACTGAGCTCTTTCCTGCCGTCATTCAAATCACCTCTGAAATCCTG
95221  ATGAGAAGAGTCGAGTGACTCGAGAAAGGACGGCAGTAAGTTTAGTGGAGACTTTAGGAC

95281  CCTTTTGATAAAGTAATTTCTGACTGATCAGAGGAAAGTGATGATTTTCTCTGTGACATG
95281  GGAAAACTATTTCATTAAAGACTGACTAGTCTCCTTTCACTACTAAAAGAGACACTGTAC

95341  TCTTTTTATTTTCCATCACACTCAGTGTCTTGTCCTTCTATGCAACATATCCATGTATTT
95341  AGAAAAATAAAAGGTAGTGTGAGTCACAGAACAGGAAGATACGTTGTATAGGTACATAAA

95401  AAAAACCCTTGTATATGTATTTGCCATGTATTTGTGAGGTATAGCTCGTGAAGTAAAAAA
95401  TTTTTGGGAACATATACATAAACGGTACATAAACACTCCATATCGAGCACTTCATTTTTT

95461  AGTCTTTATTTTTTTAAACACATCATCATTTCAGCTTCAAAGTCAATGTGGTCTCTTGAG
95461  TCAGAAATAAAAAAATTTGTGTAGTAGTAAAGTCGAAGTTTCAGTTACACCAGAGAACTC

95521  AAGTTAAATATGCTGCATTTGAAATTTTATGTTTCTCATTTTTCATGTTTTTTTTTAAAG
95521  TTCAATTTATACGACGTAAACTTTAAAATACAAAGAGTAAAAAGTACAAAAAAAAATTTC

95581  CCCCTTTTAATTCCTCATGTATTTGAATATTCCAGGAAGCTAGTAGAGTAAAAAGCCAAA
95581  GGGGAAAATTAAGGAGTACATAAACTTATAAGGTCCTTCGATCATCTCATTTTTCGGTTT

95641  GTGTTAAAGTGTTTATAAGGAATGTGACTCATCGAAATTGACTCACACAATTCATCAGCT
95641  CACAATTTCACAAATATTCCTTACACTGAGTAGCTTTAACTGAGTGTGTTAAGTAGTCGA

95701  ATTGTCATCCATATGTTCTCATTATTTATGTGGCTTTTGCTTTATTTAATCAGATGACTG
95701  TAACAGTAGGTATACAAGAGTAATAAATACACCGAAAACGAAATAAATTAGTCTACTGAC

95761  AACTTATCATCGTGGGATTTTGCTTGTAGTTGTTTAATATTATATAATAAAATACTCTTG
95761  TTGAATAGTAGCACCCTAAAACGAACATCAACAAATTATAATATATTATTTTATGAGAAC

95821  TGTGAAACAAGTTAATTGACTTTTTTTAATTAAAAAAAATTTATGTGAGAGTCAGGAGTT
95821  ACACTTTGTTCAATTAACTGAAAAAAATTAATTTTTTTTAAATACACTCTCAGTCCTCAA

95881  ACATGTGCAAGTTTGTTACATGGGTATATGTTGTGATACAAAGATTTTAGCTTCTAAGGA
95881  TGTACACGTTCAAACAATGTACCCATATACAACACTATGTTTCTAAAATCGAAGATTCCT

95941  TCTCATTGCCCAAGTAGTGAACGTAGTACACTATAGGTAGTATTTCTAAACACTTTTCCC
95941  AGAGTAACGGGTTCATCACTTGCATCATGTGATATCCATCATAAAGATTTGTGAAAAGGG

96001  CTCCCCCTCTTTTGGAATCCCTAGTGTTTATTGTTCCCATCTTTGTGTCTATATGTACCT
96001  GAGGGGGAGAAAACCTTAGGGATCACAAATAACAAGGGTAGAAACACAGATATACATGGA

96061  AATGCTTAGCTCTCACTTATAAGTGCGGACGTGTGATATTTTGGTTTTCTGTTTCTGTGT
96061  TTACGAATCGAGAGTGAATATTCACGCCTGCACACTATAAAACCAAAAGACAAAGACACA

96121  TAATTCATTTAGGATAGAGAGACTCCAGCTGCAGCTGTGTTGCTACAAATGACATGAGTT
96121  ATTAAGTAAATCCTATCTCTCTGAGGTCGACGTCGACACAACGATGTTTACTGTACTCAA
```

FIG. 4 (cont'd)

```
96181  CATTCTTTTTTATGGCTGCATAGTATTCCATGGTTTATATGTATCACATTTTCTTTATTC
96181  GTAAGAAAAAATACCGACGTATCATAAGGTACCAAATATACATAGTGTAAAAGAAATAAG

96241  AGTCCACCATTGATGGTCACCTGGGTTGATTCCATGTCTTTGTTGTTGTGGACAGGGCTG
96241  TCAGGTGGTAACTACCAGTGGACCCAACTAAGGTACAGAAACAACAACACCTGTCCCGAC

96301  TGATAAACATATGAGTGCAGTTACCTTTTTTTGTATAACAGTTCATAATAAAATACTCTT
96301  ACTATTTGTATACTCACGTCAATGGAAAAAAACATATTGTCAAGTATTATTTTATGAGAA

96361  AACAGTAGCACAGAATTTAGATTGCTTTTCAGGCTAGAAGGGATAATTGAAACATAGAAA
96361  TTGTCATCGTGTCTTAAATCTAACGAAAAGTCCGATCTTCCCTATTAACTTTGTATCTTT

96421  AAAATAATGACTCCTAAGCATAGAAACAGACCCAATCATAAAGCTCTCTTCCTCTCTTTC
96421  TTTTATTACTGAGGATTCGTATCTTTGTCTGGGTTAGTATTTCGAGAGAAGGAGAGAAAG

96481  TGCCTAGTGTTAGATCTTATTCATTGTCTTAAAGCACTGTGACCATTTTCAGTGAAATCA
96481  ACGGATCACAATCTAGAATAAGTAACAGAATTTCGTGACACTGGTAAAAGTCACTTTAGT

96541  CAGTTTTATTCATGAAAAGACAATGAATTGGTGTAAGTAATCATTTGAGGATGAAGGTGA
96541  GTCAAAATAAGTACTTTTCTGTTACTTAACCACATTCATTAGTAAACTCCTACTTCCACT

96601  CTAGTCTGTGATCAACACCAGTACTTGAAGTACTTGTAAAACATGAATTGACCTTGGTTA
96601  GATCAGACACTAGTTGTGGTCATGAACTTCATGAACATTTTGTACTTAACTGGAACCAAT

96661  AATTGCAGAAAATAAAGTATTAGTATACATAAACACATTTTCTCTCAGCATTGAAAAGTT
96661  TTAACGTCTTTTATTTCATAATCATATGTATTTGTGTAAAAGAGAGTCGTAACTTTTCAA

96721  ATAGTCTATAATTTACCTGCTTGCTAAGAATAAAAATATTACTTAGAGGTTTATCAAGAC
96721  TATCAGATATTAAATGGACGAACGATTCTTATTTTTATAATGAATCTCCAAATAGTTCTG

96781  CTTTTTTCTACAAATGGATTTAATGTACAGAATTATTCCATTTTCTATCTGTGCTCTGTA
96781  GAAAAAAGATGTTTACCTAAATTACATGTCTTAATAAGGTAAAAGATAGACACGAGACAT

96841  TACTACCACCTAGTGGAATAAAATGCAAATTTACCTGTCAAAATCAGGAGAAGAAAATGA
96841  ATGATGGTGGATCACCTTATTTTACGTTTAAATGGACAGTTTTAGTCCTCTTCTTTTACT

96901  ACCAGGGGAAATTTATTTCAGGAAAAAATTTTCATAACACGTTATTGTTACTTCTTTTAG
96901  TGGTCCCCTTTAAATAAAGTCCTTTTTTAAAAGTATTGTGCAATAACAATGAAGAAAATC

96961  TATAATGTAGTTTGCATAAAATACATTAGTTTGGAGTGAAAAAAGTCCCAGCCATTTTTG
96961  ATATTACATCAAACGTATTTTATGTAATCAAACCTCACTTTTTTCAGGGTCGGTAAAAAC

97021  TGATAGCTATTAAAATGCTATTAGTTTGTCCACAAATAAGCTATTCTATTCAGAAACTTA
97021  ACTATCGATAATTTTACGATAATCAAACAGGTGTTTATTCGATAAGATAAGTCTTTGAAT

97081  GAAGCTAGGTAAATTATTGAGATGATGCCAGCATATTATATCTCTAAATTATGTTAAGAA
97081  CTTCGATCCATTTAATAACTCTACTACGGTCGTATAATATAGAGATTTAATACAATTCTT

97141  GCTTCTCTAAATTCCTCATCACTAGGGTGTATTAGTCCATTTTCACACTGCTATAAAGAA
97141  CGAAGAGATTTAAGGAGTAGTGATCCCACATAATCAGGTAAAAGTGTGACGATATTTCTT

97201  CTACCTGAGACTGGGTAATTTATGAAGAAAAGAGGTTTAATTGACTCACAGTTCTGCAGG
97201  GATGGACTCTGACCCATTAAATACTTCTTTTCTCCAAATTAACTGAGTGTCAAGACGTCC

97261  CTTAACAGGAAGCATGACTGGGAGACCTCAGGAAACATACAGTGGAAGAAGGTGAAAGGG
97261  GAATTGTCCTTCGTACTGACCCTCTGGAGTCCTTTGTATGTCACCTTCTTCCACTTTCCC

97321  AAGCAAGGACCTTCTCATGGCAGCAGGAGAGGGAGAGCACAGGGGAAGTGCCACACACTT
97321  TTCGTTCCTGGAAGAGTACCGTCGTCCTCTCCCTCTCGTGTCCCCTTCACGGTGTGTGAA

97381  TTAAACCATCAGATCTCAGGAGAACTCACTCACTCTCACAAGCACAGCAGGGAGGAAATT
97381  AATTTGGTAGTCTAGAGTCCTCTTGAGTGAGTGAGAGTGTTCGTGTCGTCCCTCCTTTAA

97441  CACCCCCACGATCCTATCATCTCACACTGGGCCCCTCCTCCAATTTGACATGAGATATGG
97441  GTGGGGGTGCTAGGATAGTAGAGTGTGACCCGGGGAGGAGGTTAAACTGTACTCTATACC
```

FIG. 4 (cont'd)

```
97501  GCAGGGACACAAATCCAAACCGTATCATAGGATTTGTTAAAAAAATCTAACATGTTCTGC
97501  CGTCCCTGTGTTTAGGTTTGGCATAGTATCCTAAACAATTTTTTTAGATTGTACAAGACG

97561  TTCAAGGCACCCATGAAATGAAGGTGTCATTTCTTAACTGAGAGGTTAAATAAAAGTGCA
97561  AAGTTCCGTGGGTACTTTACTTCCACAGTAAAGAATTGACTCTCCAATTTATTTTCACGT

97621  GAGATAAGATGGTTAAGTTTTATCGTAGCTGGGAAGAAAAGCGGGTGTGTGTATTATGCT
97621  CTCTATTCTACCAATTCAAAATAGCATCGACCCTTCTTTTCGCCCACACACATAATACGA

97681  TAGGTTTTTCCTCCCAAACAATGAAACCCAAAAAGGCAAATGAAGCTTTAAGGCGCTTTA
97681  ATCCAAAAAGGAGGGTTTGTTACTTTGGGTTTTTCCGTTTACTTCGAAATTCCGCGAAAT

97741  TCCTTTACTGGTAGGATGGTCCTCCTTTAATCTTCAGTCTCTGTTAAAGAACAAACACAA
97741  AGGAAATGACCATCCTACCAGGAGGAAATTAGAAGTCAGAGACAATTTCTTGTTTGTGTT

97801  GCTAACAATCAAAACCTGTTGTTGCTTGCTGACGGATTTCTCTAACATAGTCTTCCATCA
97801  CGATTGTTAGTTTTGGACAACAACGAACGACTGCCTAAAGAGATTGTATCAGAAGGTAGT

97861  ACCATCATAGGTTTGTTGTGGCCACCCAGGCCCTTTGGTCGTCATGTTCCCATGGAATGC
97861  TGGTAGTATCCAAACAACACCGGTGGGTCCGGGAAACCAGCAGTACAAGGGTACCTTACG

97921  TAATGAAATTACCTTCCCATTTCCTAAGGTGACATGCCTTTCAGATGGCATTGGTGTGTG
97921  ATTACTTTAATGGAAGGGTAAAGGATTCCACTGTACGGAAAGTCTACCGTAACCACACAC

97981  CTTGTGTAAACACATTTTTTTGTGCTCATGAATATTTTACCTGCCTGATTTTGGTGATCT
97981  GAACACATTTGTGTAAAAAAACACGAGTACTTATAAAATGGACGGACTAAAACCACTAGA

98041  GAGTGTTGAGCAGTGGGTGAGGGATGGTGGGGCAATGGGTAGTAAGGGGAAGTTTAATTG
98041  CTCACAACTCGTCACCCACTCCCTACCACCCCGTTACCCATCATTCCCCTTCAAATTAAC

98101  AAGTTCAGATAAAAATATCCCTCCAGAAACATTACAAAGCCACAAAATCAGCTGAAGTTG
98101  TTCAAGTCTATTTTTATAGGGAGGTCTTTGTAATGTTTCGGTGTTTTAGTCGACTTCAAC

98161  AGTCTTCTATTGTAAAGATTCTCTTTCTTCTCCTGACAGATCCCCATTCCTATCCAGGTA
98161  TCAGAAGATAACATTTCTAAGAGAAAGAAGAGGACTGTCTAGGGGTAAGGATAGGTCCAT

98221  GACCAGGCTCTAGTGAAGATTGGACACAAGTGGTTTATATCCCGAAGCTCTTAACCTAAG
98221  CTGGTCCGAGATCACTTCTAACCTGTGTTCACCAAATATAGGGCTTCGAGAATTGGATTC

98281  AGTCCTGCCTTGTTTTTTTACTTCATGTGGTCTTATATTGCTGAGGATAGCCCAGTGATC
98281  TCAGGACGGAACAAAAAAATGAAGTACACCAGAATATAACGACTCCTATCGGGTCACTAG

98341  ATTTCTACCTTAATATGTAGCCTTCAAAACGTTGGGTCTCTCAGTTTTCTTCCTTAATAA
98341  TAAAGATGGAATTATACATCGGAAGTTTTGCAACCCAGAGAGTCAAAAGAAGGAATTATT

98401  ACAATGAACCCTAATTATTTATAACTGCTCTTGTGATGGAGGAATTGGCATGATTTTGCA
98401  TGTTACTTGGGATTAATAAATATTGACGAGAACACTACCTCCTTAACCGTACTAAAACGT

98461  TTGTGGGCTTCTGGCTTTACAGTGTTTGTGGGAAAGATGGTCTTCTATCTTTGTTATTTA
98461  AACACCCGAAGACCGAAATGTCACAAACACCCTTTCTACCAGAAGATAGAAACAATAAAT

98521  TAAGTCATTCATTCCCTGTTTTTTTGAAGATATTGTTAAATAAAAAAACTTCAGCTGAAT
98521  ATTCAGTAAGTAAGGGACAAAAAAACTTCTATAACAATTTATTTTTTTGAAGTCGACTTA

98581  TAAATTTAAAAGTTTTTAATTGAGCAAAGAACCATTCTCAATTCGGGCAGCCTTCCCATC
98581  ATTTAAATTTTCAAAAATTAACTCGTTTCTTGGTAAGAGTTAAGCCCGTCGGAAGGGTAG

98641  CAGAGTAGTCCCTGTGACTTCAGTGCAGCCACATGGTGGAAGAGGATTTATGGACAGAGG
98641  GTCTCATCAGGGACACTGAAGTCACGTCGGTGTACCACCTTCTCCTAAATACCTGTCTCC

98701  AAGGAAAGTGACATACAGGAAACAGAAAAGAGATTCAGAAACAGCTGAATTGGTTATAAC
98701  TTCCTTTCACTGTATGTCCTTTGTCTTTTCTCTAAGTCTTTGTCGACTTAACCAATATTG

98761  TCAGCGTTTGCCTTATTTGAACATGGTTTGAACAGTTGGCCACGTTTGATTGGCCAAAAC
98761  AGTCGCAAACGGAATAAACTTGTACCAAACTTGTCAACCGGTGCAAACTAACCGGTTTTG
```

FIG. 4 (cont'd)

```
 98821  TCAGTAATTGGCACAAGAGTAGGCTACCATCTGTTTATAATGTCCACTTAGGTTATAGTT
 98821  AGTCATTAACCGTGTTCTCATCCGATGGTAGACAAATATTACAGGTGAATCCAATATCAA

 98881  CATGATGTGCAAAGAAACCTTTAAGCTGAGCTTAAAATGTAATGAGGCAGCTGTAGGCTA
 98881  GTACTACACGTTTCTTTGGAAATTCGACTCGAATTTTACATTACTCCGTCGACATCCGAT

 98941  AACTTGATTTAACAGTACTTATCCCTCTGTTGAAATTGCACTCTTGCTACCTGCTAGTTG
 98941  TTGAACTAAATTGTCATGAATAGGGAGACAACTTTAACGTGAGAACGATGGACGATCAAC

 99001  ATGTGGGCAGGTGTGCTAATGACACATTCGCCTGCACCTACCACCTGCTGAAGACCCTGC
 99001  TACACCCGTCCACACGATTACTGTGTAAGCGGACGTGGATGGTGGACGACTTCTGGGACG

 99061  CATGTCCTGAAGCAGTCACTTAGGCTATGAAACAGAAGGATGAGTTAGAGAAGTAAATAT
 99061  GTACAGGACTTCGTCAGTGAATCCGATACTTTGTCTTCCTACTCAATCTCTTCATTTATA

 99121  TATATTTTACCCCCCAAAGCCTAAAACCATGTCTAGGTTCTCCCCTTTCTCAATTCCCAA
 99121  ATATAAAATGGGGGGTTTCGGATTTTGGTACAGATCCAAGAGGGGAAAGAGTTAAGGGTT

 99181  TCATGCAACCTTGAAAGGTGTTATATAGATAGTTGTTAGAAATATGTCTGTCCTCCAAAA
 99181  AGTACGTTGGAACTTTCCACAATATATCTATCAACAATCTTTATACAGACAGGAGGTTTT

 99241  CCCTACTAACACGCAAAAATGGACAAATCTAGCTTTTTTGCTAAAATCCTAACAACTCAG
 99241  GGGATGATTGTGCGTTTTTACCTGTTTAGATCGAAAAAACGATTTTAGGATTGTTGAGTC

 99301  AAAGCAAAGCAAAATGAAATGTATGTACTCCATTCTCAGGATTTCCTTCTTAAAAACCAC
 99301  TTTCGTTTCGTTTTACTTTACATACATGAGGTAAGAGTCCTAAAGGAAGAATTTTTGGTG

 99361  TAGGCTTTGTGTAACTCAATTTTAAAAGTATGGTAATAGCTCCTGTAATTCGATGGCTTC
 99361  ATCCGAAACACATTGAGTTAAAATTTTCATACCATTATCGAGGACATTAAGCTACCGAAG

 99421  TTCTGGGAGACAGATATAAATCTATTCTAGACTTTAAGACTGGTGTCCACATTTTAAGTT
 99421  AAGACCCTCTGTCTATATTTAGATAAGATCTGAAATTCTGACCACAGGTGTAAAATTCAA

 99481  ACAGTTGTATGTACTTCTACTTTGTTGCAGCCTTCTCTTGGAGTCAAGAAGCCTACCAAA
 99481  TGTCAACATACATGAAGATGAAACAACGTCGGAAGAGAACCTCAGTTCTTCGGATGGTTT

 99541  GCCCTGCTCTTTGTACTCTTGAGCCCAGTGGGACCTTATTTTTCAAGTGGAACCTTTAAT
 99541  CGGGACGAGAAACATGAGAACTCGGGTCACCCTGGAATAAAAAGTTCACCTTGGAAATTA

 99601  CCAGTGTCCCTGTGGGCCAATCCCAAGTATGTAAGAGCCTGGAAAGGTGGAACTGGGGAC
 99601  GGTCACAGGGACACCCGGTTAGGGTTCATACATTCTCGGACCTTTCCACCTTGACCCCTG

 99661  TGCAAGATGGGAGGGTAAGTAAATCTGTGTCTCTGTCTAAAGGAAAGACACCTTCATGAC
 99661  ACGTTCTACCCTCCCATTCATTTAGACACAGAGACAGATTTCCTTTCTGTGGAAGTACTG

 99721  CATTTAGTTAGTGCCATTTCACTTCAGTATGAACACATATAATACTTTTCAAACTTTAAT
 99721  GTAAATCAATCACGGTAAAGTGAAGTCATACTTGTGTATATTATGAAAAGTTTGAAATTA

 99781  GCTCATTGTGTTTCATGGTTAATTTTCAGTTTAATCTTTCAGCAAGCCAGCTGTAGTAGC
 99781  CGAGTAACACAAAGTACCAATTAAAAGTCAAATTAGAAAGTCGTTCGGTCGACATCATCG

 99841  TTTTCCTATATAAACGCAGTATGAATTCAGTGCCCTCGCTTTTAGATGTGCTAGTTTAAA
 99841  AAAAGGATATATTTGCGTCATACTTAAGTCACGGGAGCGAAAATCTACACGATCAAATTT

 99901  GGATAGCCCATGGCCCTTTGTAAGGGAGAAACACTGGATATGATATCTAGGGAAGAACTG
 99901  CCTATCGGGTACCGGGAAACATTCCCTCTTTGTGACCTATACTATAGATCCCTTCTTGAC

 99961  AAGTAAGAAACTACAACAAGCATCACATCGGTGCTTTGGATAAACTTCCCCTGGGCGCTG
 99961  TTCATTCTTTGATGTTGTTCGTAGTGTAGCCACGAAACCTATTTGAAGGGGACCCGCGAC

100021  GTCTCTGGCTGCAGGCTGACGGCTGGCATTAAAAAGCATCTGGTCCTGGGACCCAGGCTC
100021  CAGAGACCGACGTCCGACTGCCGACCGTAATTTTTCGTAGACCAGGACCCTGGGTCCGAG

100081  TCAGTTGGCTCCAGGGAGTCATGTCTGGGGAAGGTGCCCGCTTCACTGAAGTGCTGTCTT
100081  AGTCAACCGAGGTCCCTCAGTACAGACCCCTTCCACGGGCGAAGTGACTTCACGACAGAA
```

FIG. 4 (cont'd)

```
100141  CATTGCCACAGATTGTGGCCACACCTGCTGCCAACTGGCTGCGGGACAGCCCTGCTTTGG
100141  GTAACGGTGTCTAACACCGGTGTGGACGACGGTTGACCGACGCCCTGTCGGGACGAAACC

100201  CTCTGTCAGGCCAGTCTCATAGGCCATATGTAGCTGGCAGGAAATAAAAGAGCATTTGAA
100201  GAGACAGTCCGGTCAGAGTATCCGGTATACATCGACCGTCCTTTATTTTCTCGTAAACTT

100261  AAGTGTTGGACGATTTCAGGGGTGGACTTGGCCATGAGTTGGGAATGCCCCTATGGGTGA
100261  TTCACAACCTGCTAAAGTCCCCACCTGAACCGGTACTCAACCCTTACGGGGATACCCACT

100321  ACGAGAATAACTGGTTTAAGCAGCATGGGTTCTTGCTTTGCATGTATCAAATGGTGCTGT
100321  TGCTCTTATTGACCAAATTCGTCGTACCCAAGAACGAAACGTACATAGTTTACCACGACA

100381  TTGCATACTCAGGGCAGCAGCTGTCCTAGAAGGTGACTCCATGGCAGTCTTGTGGGCCCT
100381  AACGTATGAGTCCCGTCGTCGACAGGATCTTCCACTGAGGTACCGTCAGAACACCCGGGA

100441  GGTAGGACATTTAGGTCCAGGAGGCAGGGGAGAGTCACATGACGTGCTGCTGGGGTATTA
100441  CCATCCTGTAAATCCAGGTCCTCCGTCCCCTCTCAGTGTACTGCACGACGACCCCATAAT

100501  GAGGCAATGACCACTGGCTTTGACCCCTCTGTAGTCTTGCTGTATTTCCTTTTTCTTTTC
100501  CTCCGTTACTGGTGACCGAAACTGGGGAGACATCAGAACGACATAAAGGAAAAAGAAAAG

100561  TCTCCTCACCTACCCAAATTAAAAAAGAACGGTTATAAAAGTCATCCCCACTGGCAACTT
100561  AGAGGAGTGGATGGGTTTAATTTTTTCTTGCCAATATTTTCAGTAGGGGTGACCGTTGAA

100621  TAGCAACTGCATTCCCTCAATGGGTAGAGAAATCCAAATGGAGTGCATTAAAACTAGGAA
100621  ATCGTTGACGTAAGGGAGTTACCCATCTCTTTAGGTTTACCTCACGTAATTTTGATCCTT

100681  GTCTATTCTCCTTCTGGCTTAGAGCACACCTTCCTGTGTCCTAGGCTAGCCAGGTTGAAA
100681  CAGATAAGAGGAAGACCGAATCTCGTGTGGAAGGACACAGGATCCGATCGGTCCAACTTT

100741  ACTCCTTTTTTTGACTCTTGATTTCTTTTTTTACTGGTTCAAACTTCTTCGCAGAGCATG
100741  TGAGGAAAAAAACTGAGAACTAAAGAAAAAAATGACCAAGTTTGAAGAAGCGTCTCGTAC

100801  TGCCTATGTACCACTGCATACCATATATATACCATATATAGAGAGTAAATAAACAGTCTT
100801  ACGGATACATGGTGACGTATGGTATATATATGGTATATATCTCTCATTTATTTGTCAGAA

100861  GATGAAAAGTAATAAGGAAAAAGTTTCCCTGTTTAAAATATTGCTTTCTAGCTCCCCGAC
100861  CTACTTTTCATTATTCCTTTTTCAAAGGGACAAATTTTATAACGAAAGATCGAGGGGCTG

100921  CTGTTTAGGAAAAAGATAACCTGGGGACACAGAAATTGCAGGGCAATCTTTATTAACCGG
100921  GACAAATCCTTTTTCTATTGGACCCCTGTGTCTTTAACGTCCCGTTAGAAATAATTGGCC

100981  TATTTGGGCAGGTTGTAATTTATTTTGTAAACAATGATTTAATGCACTATTGCAGAATAC
100981  ATAAACCCGTCCAACATTAAATAAAACATTTGTTACTAAATTACGTGATAACGTCTTATG

101041  ATGATCACTGTAGGCCAGTTAAAAATTAATGTTTTCAGTACCACACAGAGTGAACCCTAA
101041  TACTAGTGACATCCGGTCAATTTTTAATTACAAAAGTCATGGTGTGTCTCACTTGGGATT

101101  TGTAAACTGTGGACTTGTGGACCACACTAATGCAAGATGATAATAAGAAGAAAAACTGAG
101101  ACATTTGACACCTGAACACCTGGTGTGATTACGTTCTACTATTATTCTTCTTTTTGACTC

101161  AGGGTGTTCGGGAAGGGGTATAATAGGGGAATTCTGTTACCTTTTGCTCAATTTCTCTGT
101161  TCCCACAAGCCCTTCCCCATATTATCCCCTTAAGACAATGGAAAACGAGTTAAAGAGACA

101221  GAATCTAAAAGTACTCTAAAATAATAAAATCTATTATAAAAATATTTGATTCATTAGGCT
101221  CTTAGATTTTCATGAGATTTTATTATTTTAGATAATATTTTTATAAACTAAGTAATCCGA

101281  CAGGTGGACTATGATCCATGGAAATTGACTTGAAATCTCTTAGGAAAGGAAGAGACCGGA
101281  GTCCACCTGATACTAGGTACCTTTAACTGAACTTTAGAGAATCCTTTCCTTCTCTGGCCT

101341  GAAGAAAGTATTGAACTCATAAATTAAAAATGGCAAGAGGGAAGGTGGTAACCAAAAGGA
101341  CTTCTTTCATAACTTGAGTATTTAATTTTTACCGTTCTCCCTTCCACCATTGGTTTTCCT

101401  TGGGCATTTAACCTATATGCCTATCACTTCCAAAAAGTTCTAGGGCCGTCTCCTCCTATG
101401  ACCCGTAAATTGGATATACGGATAGTGAAGGTTTTTCAAGATCCCGGCAGAGGAGGATAC

101461  CTTCTGACCTGGAGAGGTACAAGGGGAACAAAATATTCCGCATTTAATATTATCCTGTTG
101461  GAAGACTGGACCTCTCCATGTTCCCCTTGTTTTATAAGGCGTAAATTATAATAGGACAAC
```

FIG. 4 (cont'd)

```
101521  AGTTGGCAAAGACATTTGGAGTCAACTTTAGTTTTGTGTATTATTACATCTGTAAACCTA
101521  TCAACCGTTTCTGTAAACCTCAGTTGAAATCAAAACACATAATAATGTAGACATTTGGAT

101581  ATTAAGTCAACAGTTACCCTTGACACCTGTAGTCAACTGGTATTATTAAATAACTATTGA
101581  TAATTCAGTTGTCAATGGGAACTGTGGACATCAGTTGACCATAATAATTTATTGATAACT

101641  GTCTCATAAAGTCAAGAACTTTCTGCTTTCTATCTAAGTGAATCTAGGGCAGAGACTGAG
101641  CAGAGTATTTCAGTTCTTGAAAGACGAAAGATAGATTCACTTAGATCCCGTCTCTGACTC

101701  CATCAGGATTCTTTAGCATGCAGCCAAGCTTGAGAAGCACTGAGCTAGAGAAAGGTCTTG
101701  GTAGTCCTAAGAAATCGTACGTCGGTTCGAACTCTTCGTGACTCGATCTCTTTCCAGAAC

101761  CACTGTAGAAACAGCTTTAGTTCCAGGTGATTCCTTGGTTAATTTGGGAGGAATAAGGCT
101761  GTGACATCTTTGTCGAAATCAAGGTCCACTAAGGAACCAATTAAACCCTCCTTATTCCGA

101821  TTCTGTCACTCTCTCTCTCTTTCTCTCTTTTTCTCTCTCTCTTGCACATGCACACGTGCA
101821  AAGACAGTGAGAGAGAGAGAAAGAGAGAAAAAGAGAGAGAGAACGTGTACGTGTGCACGT

101881  CACACACACACAAATTATCTCTCTTAGTTTTTTCTTTTTTCCTTGCATTCTGATTCTGCA
101881  GTGTGTGTGTGTTTAATAGAGAGAATCAAAAAAGAAAAAAGGAACGTAAGACTAAGACGT

101941  TTTAAGAGTACAAGCTTTGAAGTCAGAAAGACCTGGCTTAAAAACCTAACTGTCATAATG
101941  AAATTCTCATGTTCGAAACTTCAGTCTTTCTGGACCGAATTTTTGGATTGACAGTATTAC

102001  GTGCGTAAATGTCGTTATAGATTTGTCCAAACCCATAGAATGTACACCAGGAATGAACAC
102001  CACGCATTTACAGCAATATCTAAACAGGTTTGGGTATCTTACATGTGGTCCTTACTTGTG

102061  TAATGAAAACTCTAGACTTCAGGTGATAATGGTATGTCAATGTGGTTCATTAATTTCAGC
102061  ATTACTTTTGAGATCTGAAGTCCACTATTACCATACAGTTACACCAAGTAATTAAAGTCG

102121  AAATGTACCACTCTGGTGTGAGGCATTGGTAATGGTAGAAACTATTCATTTGGATGGGGA
102121  TTTACATGGTGAGACCACACTCCGTAACCATTACCATCTTTGATAAGTAAACCTACCCCT

102181  GAAAGGGATATGGGAAATCTTTGTACTTGCCTTTCAGTTTTGGTGGGAACCTAAAACTGC
102181  CTTTCCCTATACCCTTTAGAAACATGAACGGAAAGTCAAAACCACCCTTGGATTTTGACG

102241  TCTGAAAAAAACCTGAAGTCTTTAAAAACAAACCAACCTAATTGCCTTGGGCATGTTACT
102241  AGACTTTTTTTGGACTTCAGAAATTTTTGTTTGGTTGGATTAACGGAACCCGTACAATGA

102301  TAACTGCTCTATGTATCAGTTTCCTCATTTTTAAAGTTGAGGCAATAATACCTTGCACAG
102301  ATTGACGAGATACATAGTCAAAGGAGTAAAAATTTCAACTCCGTTATTATGGAACGTGTC

102361  ATTAAGTGAGATAATAGAAAGTGCCTAGGATAGTACTTGGCATATAGAAAGCTCTCAGCA
102361  TAATTCACTCTATTATCTTTCACGGATCCTATCATGAACCGTATATCTTTCGAGAGTCGT

102421  AATGCAGTATGATAACCTAATGGTTAAAAGCTTGGGTTTAGGAGTCAAATGTCTGGGAGT
102421  TTACGTCATACTATTGGATTACCAATTTTCGAACCCAAATCCTCAGTTTACAGACCCTCA

102481  TACACACTTAACTATCTGTGAGATCTTCTACAACTGAATCCTCTCTCCAAGTCTTCCAAT
102481  ATGTGTGAATTGATAGACACTCTAGAAGATGTTGACTTAGGAGAGAGGTTCAGAAGGTTA

102541  GAACAATAAAGTCTAGGGTTGTTTTTAGATGACTCAATGAAATAATGTAGTTAAGTACTT
102541  CTTGTTATTTCAGATCCCAACAAAAATCTACTGAGTTACTTTATTACATCAATTCATGAA

102601  AGCACCCAGTCTGGCAGGTATGGGTTGCATATCTCTTATCTGAAATGCTTGGGACCAGAT
102601  TCGTGGGTCAGACCGTCCATACCCAACGTATAGAGAATAGACTTTACGAACCCTGGTCTA

102661  GTGTTTTGGATTTCAAATTTTGGAGTATTTCTCTTTGGGCATCCCTAATCCAAAAAATTC
102661  CACAAAACCTAAAGTTTAAAACCTCATAAAGAGAAACCCGTAGGGATTAGGTTTTTTAAG

102721  GAAATCCAAATTGAGCATCATGTTGGCACCGAAAAAGTTTTAGATTTTAGAGCATTTCAA
102721  CTTTAGGTTTAACTCGTAGTACAACCGTGGCTTTTTCAAAATCTAAAATCTCGTAAAGTT

102781  AGTTTTAAATTAGGGATCCTCAACCTGTAGTAAACTCTCACAGTCACTGATGTTGTGAGG
102781  TCAAAATTTAATCCCTAGGAGTTGGACATCATTTGAGAGTGTCAGTGACTACAACACTCC
```

FIG. 4 (cont'd)

```
102841  TTTTCTCACTTTCTCATTTCATTTCCTGGACTCTCTTTATCTTAGAAGAAATCAGTTAAA
102841  AAAAGAGTGAAAGAGTAAAGTAAAGGACCTGAGAGAAATAGAATCTTCTTTAGTCAATTT

102901  TTTTACATAATAGAATTTATTCTTTTGGAGGGATGTATTTAATATGTCTATTCTCCCAGA
102901  AAAATGTATTATCTTAAATAAGAAAACCTCCCTACATAAATTATACAGATAAGAGGGTCT

102961  TAACCTATTTAAAACCATATTGAAATGTTTCTATGTCAACAGCTTTCTTACTTTTTCATT
102961  ATTGGATAAATTTTGGTATAACTTTACAAAGATACAGTTGTCGAAAGAATGAAAAAGTAA

103021  TTTCTGTTTCCTCCAAGAACATGTTTCTCTTATGAATATTGGCAGCACATGGGCGGGAAC
103021  AAAGACAAAGGAGGTTCTTGTACAAAGAGAATACTTATAACCGTCGTGTACCCGCCCTTG

103081  CCAACTATATTACCATGGTATCAGTTATCCTGTGGACATTAATAATACAGCTTACACCTG
103081  GGTTGATATAATGGTACCATAGTCAATAGGACACCTGTAATTATTATGTCGAATGTGGAC

103141  TGAGAGAACTCTGGGAAAATTAAAACTTGTTTGGGGGAATAAAGACCATCTACAGAATAT
103141  ACTCTCTTGAGACCCTTTTAATTTTGAACAAACCCCCTTATTTCTGGTAGATGTCTTATA

103201  AATAATACATCAATCAATCAATTAAAACTTAAACATAAAAAACCCTTTTCTTTTCAGTGC
103201  TTATTATGTAGTTAGTTAGTTAATTTTGAATTTGTATTTTTTGGGAAAAGAAAAGTCACG

103261  ATTGAAATAGTCACTGTCTTTAATCCTCTTTCCTTGCTCAGTGCTTCATGAAGCTGAGGA
103261  TAACTTTATCAGTGACAGAAATTAGGAGAAAGGAACGAGTCACGAAGTACTTCGACTCCT

103321  GCCATGGTTTTAATTCAGCTACACTTTCAGAAATGTGTATGCATTTGTATTTAGAAGCTT
103321  CGGTACCAAAATTAAGTCGATGTGAAAGTCTTTACACATACGTAAACATAAATCTTCGAA

103381  CTTTGAAAGGCTAAATATTCATCCTGTAAGAATTCTCTATGTGTTTTTTAATACAGTCTA
103381  GAAACTTTCCGATTTATAAGTAGGACATTCTTAAGAGATACACAAAAAATTATGTCAGAT

103441  AAGGGCATTTTGTATATGAAAAAATAATTTATTTTCAGGTAGGGTAAAACTTCACTGCTT
103441  TTCCCGTAAAACATATACTTTTTTATTAAATAAAAGTCCATCCCATTTTGAAGTGACGAA

103501  CACTACTTCGTAGTTGTGTCTACGAATGAGAAAAAATTCAAATAAAATAGTTATTATTAT
103501  GTGATGAAGCATCAACACAGATGCTTACTCTTTTTTAAGTTTATTTTATCAATAATAATA

103561  TAGTTTTTAGAGATGCAGTCTTGCTGTGTTGCCCAGGCTGGTCTGGGACTTCTGGCCTCA
103561  ATCAAAAATCTCTACGTCAGAACGACACAACGGGTCCGACCAGACCCTGAAGACCGGAGT

103621  AGCCATCCTCCTGCCTCGGTGTCCTGAGTCACTGGGATTACAGGCATGAGCCACCACACC
103621  TCGGTAGGAGGACGGAGCCACAGGACTCAGTGACCCTAATGTCCGTACTCGGTGGTGTGG

103681  CCACTGAAATAGTTATTTTTTAAAAAACTTAATTTCATTAGGATGTAACAGTCTCATGTA
103681  GGTGACTTTATCAATAAAAAATTTTTGAATTAAAGTAATCCTACATTGTCAGAGTACAT

103741  ACTCATCCTTTGGCTTTTATTGTTATTATTTATTTTTTCCAAGCAACCCAATGAGATATA
103741  TGAGTAGGAAACCGAAAATAACAATAATAAATAAAAAAGGTTCGTTGGGTTACTCTATAT

103801  TAAAGCAGATATTTTTATCTGCCAGATAATTAAATGAGGGAAAAATAAGGACTAACTTGC
103801  ATTTCGTCTATAAAAATAGACGGTCTATTAATTTACTCCCTTTTTATTCCTGATTGAACG

103861  TTAAGTTCACATATACCAAATAGTGGAAATGCAAGAGCTGTCCTCAGGTCTGTTAACAAC
103861  AATTCAAGTGTATATGGTTTATCACCTTTACGTTCTCGACAGGAGTCCAGACAATTGTTG

103921  AAACCTGTGGTCTTTCTACCAGACGTCCCCTGCAATCTGGTTTATACTCATTATTAAAAA
103921  TTTGGACACCAGAAAGATGGTCTGCAGGGGACGTTAGACCAAATATGAGTAATAATTTTT

103981  GCATTTGTAATTTAACTCAGTTATCTATTTACTATCAGTTATGAATAAGGATTATTTGAC
103981  CGTAAACATTAAATTGAGTCAATAGATAAATGATAGTCAATACTTATTCCTAATAAACTG

104041  TTTTTATGGTCATTAAACAATAGCTTCCTATCTGTTGTCTTTGTCTTTTTAATTTTTATT
104041  AAAAATACCAGTAATTTGTTATCGAAGGATAGACAACAGAAACAGAAAAATTAAAAATAA

104101  TATTTTATTGTTTTTTTAATAGCTTCCTATCTGTATACCAGACTTGCTTCATCTCCACAT
104101  ATAAAATAACAAAAAAATTATCGAAGGATAGACATATGGTCTGAACGAAGTAGAGGTGTA

104161  TGACCAAGAATTTATATTTTGTCATCTGTATTTAGAAGCATATGTTTTAAGCGTCTTTTA
104161  ACTGGTTCTTAAATATAAAACAGTAGACATAAATCTTCGTATACAAAATTCGCAGAAAAT
```

FIG. 4 (cont'd)

```
104221  ATGGCTCTTTTTTTTTTTTTGCTGGGAGGGGACAGTCTCGCTCTGTCTCCTAGGCTGGAG
104221  TACCGAGAAAAAAAAAAAAACGACCCTCCCCTGTCAGAGCGAGACAGAGGATCCGACCTC

104281  TGCAGTGGCACCATCTCAGCTCACTGCAACCTCCGCCTCCCTGGTGTGAGTGGTGCTCCT
104281  ACGTCACCGTGGTAGAGTCGAGTGACGTTGGAGGCGGAGGGACCACACTCACCACGAGGA

104341  GCCTCAGCCTCCCGAGTAGGTGGGATTACAGGCGTGGTCCACCAAACCCAGCTAGTTTTT
104341  CGGAGTCGGAGGGCTCATCCACCCTAATGTCCGCACCAGGTGGTTTGGGTCGATCAAAAA

104401  TATATTTTTGGTAGAGACAGGGTTTCACCATGTTAGCCAGGCTGGTCTGGAACTCCTGAC
104401  ATATAAAAACCATCTCTGTCCCAAAGTGGTACAATCGGTCCGACCAGACCTTGAGGACTG

104461  CTCAAGTAACTTGCCCACCTCAGCCTCCCAAAGTGCTGAGATTACAGGTATGAGCCACTG
104461  GAGTTCATTGAACGGGTGGAGTCGGAGGGTTTCACGACTCTAATGTCCATACTCGGTGAC

104521  TGCCTGGCCCTTTTAAGGACTCTTTTTTTTTTTTTTTTTTTTTTGAGACAGTCTCACTC
104521  ACGGACCGGGAAAATTCCTGAGAAAAAAAAAAAAAAAAAAAAAACTCTGTCAGAGTGAG

104581  TGTCGCTCAGACTGGAGTGCAGTGGCGCGATCTCGGCTCACTGCAAGCTCCACCTCCCGG
104581  ACAGCGAGTCTGACCTCACGTCACCGCGCTAGAGCCGAGTGACGTTCGAGGTGGAGGGCC

104641  GTTCACGCCATTCTCCTGCCTCAGCCTCCCGAGTAGCTGGGACTACAGGCGCCAGCCACC
104641  CAAGTGCGGTAAGAGGACGGAGTCGGAGGGCTCATCGACCCTGATGTCCGCGGTCGGTGG

104701  ACGCCCGGATAATTTTTAGTATTTTTAGTAGAGACGAGGTTTCACCGTGTTAGCCAGGAT
104701  TGCGGGCCTATTAAAAATCATAAAAATCATCTCTGCTCCAAAGTGGCACAATCGGTCCTA

104761  GGTCTCAATCTCCTGACCTCATGATCCGGCCGTCTCGCCTCCCAAAGTGCTGGGATTACA
104761  CCAGAGTTAGAGGACTGGAGTACTAGGCCGGCAGAGCGGAGGGTTTCACGACCCTAATGT

104821  GGCGTGAGCCACCGCGCCTGGCCCTTTTAAGGACTCTTAACATTACCTTGGTGTGAGTCA
104821  CCGCACTCGGTGGCGCGGACCGGGAAAATTCCTGAGAATTGTAATGGAACCACACTCAGT

104881  ACCTCATCGTGCTCCAATGGCAATCACCATAGTATGATGTCTATTTTCCACAGCTTACTG
104881  TGGAGTAGCACGAGGTTACCGTTAGTGGTATCATACTACAGATAAAAGGTGTCGAATGAC

104941  GAATATTTCAGCTATTAGTCAATATTCTTTCAGTTGCAAGTCAGAAAACCAACTTGAAAT
104941  CTTATAAAGTCGATAATCAGTTATAAGAAAGTCAACGTTCAGTCTTTTGGTTGAACTTTA

105001  TATTATTTATTTATTTATTTATTTTTTTGAGACGGAATTTTGCTCTTGTTGCCCAGGCTG
105001  ATAATAAATAAATAAATAAATAAAAAAACTCTGCCTTAAAACGAGAACAACGGGTCCGAC

105061  GAGTGCCATGGCACAATCTCGGCTCACTGCAACCTCCGCCTCCCGAGTTCAAGCAATTCT
105061  CTCACGGTACCGTGTTAGAGCCGAGTGACGTTGGAGGCGGAGGGCTCAAGTTCGTTAAGA

105121  CCTGCCTCAGCCTCCAGAGTAGCTGGGATTACAGGCATGGGCCACCACTCCCGGCTAATT
105121  GGACGGAGTCGGAGGTCTCATCGACCCTAATGTCCGTACCCGGTGGTGAGGGCCGATTAA

105181  TTTTTGTTATTTTTAGTAGAGACGGGGTTTCTCCATGTTGGTCAGGATGGTCTCAAACTC
105181  AAAAACAATAAAAATCATCTCTGCCCCAAAGAGGTACAACCAGTCCTACCAGAGTTTGAG

105241  CCAACCTCAGGTGATCTGCCCACCTCAGCCTCCCAAAGTGCTGGGATTACAGGCATGAGC
105241  GGTTGGAGTCCACTAGACGGGTGGAGTCGGAGGGTTTCACGACCCTAATGTCCGTACTCG

105301  CACCGTGCCCGGCCTGGAAATGATCTTAAGCAGACAAGGGCTTATGAAACTAGGATGCTA
105301  GTGGCACGGGCCGGACCTTTACTAGAATTCGTCTGTTCCCGAATACTTTGATCCTACGAT

105361  GGGGCTAAAGCAATTATTTCCAAGTTTCTTGTGTCCTTTGCACATCCCCCTTTTTCTTCC
105361  CCCCGATTTCGTTAATAAAGGTTCAAAGAACACAGGAAACGTGTAGGGGGAAAAAGAAGG

105421  CTTCTTCCTCTGCCTCTGGTCAGAGCTTCTGGCTCCATGTTGGCCTAGGGCTCTCCCACT
105421  GAAGAAGGAGACGGAGACCAGTCTCGAAGACCGAGGTACAACCGGATCCCGAGAGGGTGA

105481  TCAGCCGCTTTCTTCTGTGAAGTGTGGTGATCATGGACACAGCCGACCCCAGTTTTACAG
105481  AGTCGGCGAAAGAAGACACTTCACACCACTAGTACCTGTGTCGGCTGGGGTCAAAATGTC
```

FIG. 4 (cont'd)

```
105541  CATACCAAGTAAGCAACCCCAGAAGGGAGAAAATGCCTGTATTTCAGGTTATAGACATTA
105541  GTATGGTTCATTCGTTGGGGTCTTCCCTCTTTTACGGACATAAAGTCCAATATCTGTAAT

105601  AAATGAGTGAATGCACCCAAAAAAGGAATCATGTGACTGTCTTAGGTTATATGCCCACCC
105601  TTTACTCACTTACGTGGGTTTTTTCCTTAGTACACTGACAGAATCCAATATACGGGTGGG

105661  TTTAACTCAGCTGCAGCAGGGCAAGATGCTATATTGTCATCAGTTGTGGTAGGGCAAGAT
105661  AAATTGAGTCGACGTCGTCCCGTTCTACGATATAACAGTAGTCAACACCATCCCGTTCTA

105721  GCTATATTATCAGTCCAAGCAGAATGACATAGCTCTATAGAAAGACTATGTTTTTATAAG
105721  CGATATAATAGTCAGGTTCGTCTTACTGTATCGAGATATCTTTCTGATACAAAAATATTC

105781  AGTATGGAATATAGTGCAGATGAAAACAGTAGATATACACTAACATGTGGCTCTAATGTT
105781  TCATACCTTATATCACGTCTACTTTTGTCATCTATATGTGATTGTACACCGAGATTACAA

105841  TAATTTTTATTTTTTTTGAGACAGAGTCTCACTGTGTCACCCAGGCTGGAGTGCAGTGGT
105841  ATTAAAAATAAAAAAAACTCTGTCTCAGAGTGACACAGTGGGTCCGACCTCACGTCACCA

105901  GCTATCTTGGCTCACTGCAACTTTTGCCTCCCGAGTTAAGATGATTCTCCTCCCTCAGCC
105901  CGATAGAACCGAGTGACGTTGAAAACGGAGGGCTCAATTCTACTAAGAGGAGGGAGTCGG

105961  TCCCTAGCAGCTGAGATTATAGGCACCCGCCACCACGCCCAGCTAATTCTTGTATTTTCA
105961  AGGGATCGTCGACTCTAATATCCGTGGGCGGTGGTGCGGGTCGATTAAGAACATAAAAGT

106021  GTAGAGACATGGTTTCACCATGTTGGCCGGGCTGGTCTCGAACTCCTGACCTCAGTGATC
106021  CATCTCTGTACCAAAGTGGTACAACCGGCCCGACCAGAGCTTGAGGACTGGAGTCACTAG

106081  CGCCCATCTTAGGCTCCTAAAGTGCTAGGATTACAGACATAAGCCACCGCGCCTGGCCTC
106081  GCGGGTAGAATCCGAGGATTTCACGATCCTAATGTCTGTATTCGGTGGCGCGGACCGGAG

106141  ATGCTCAACTTTTATTTAGACAACAGTACAAATTGTAATTTTACCCAGATGTAAAAGAGT
106141  TACGAGTTGAAAATAAATCTGTTGTCATGTTTAACATTAAAATGGGTCTACATTTTCTCA

106201  CTAAGAGACCTAAATAGATATTTTGTGGTAGATTACATTAATGTAATGTAATGTAATGTA
106201  GATTCTCTGGATTTATCTATAAAACACCATCTAATGTAATTACATTACATTACATTACAT

106261  GGAGTTTTACATTACTACATTTGTAGTTGTTTTAGTTGTTTTTCATTGTTTGTTTCTGTG
106261  CCTCAAAATGTAATGATGTAAACATCAACAAAATCAACAAAAAGTAACAAACAAAGACAC

106321  TATTTCTGGGGATTTCATGGTGCAACAGGAGGACTAGAGTTTATTCCCGATCCCTGACTG
106321  ATAAAGACCCCTAAAGTACCACGTTGTCCTCCTGATCTCAAATAAGGGCTAGGGACTGAC

106381  TCTTACGGCAGTACTTCTCAGACCTACTGAGTTATACAACCAGGGGTGTAGGGAGGCAAG
106381  AGAATGCCGTCATGAAGAGTCTGGATGACTCAATATGTTGGTCCCCACATCCCTCCGTTC

106441  CAGTCATCACATTTATTTGAGGACTCTCATGTTTTGTCTAAAATATTCATCCTTATTTTA
106441  GTCAGTAGTGTAAATAAACTCCTGAGAGTACAAAACAGATTTTATAAGTAGGAATAAAAT

106501  TAATATACTCCATAATTTTCCCATATAAGTTTAGATAAAAGATGATACCTTAAAAGTATT
106501  ATTATATGAGGTATTAAAAGGGTATATTCAAATCTATTTTCTACTATGGAATTTTCATAA

106561  ATAACACTAAATTGTCATTCCGGGAAAATGTGCTGTGTTCCTTTCATTTTAAATAATCTG
106561  TATTGTGATTTAACAGTAAGGCCCTTTTACACGACACAAGGAAAGTAAAATTTATTAGAC

106621  AGATGAATGGTGCAGGCTGAGAAAAATAGGCTTTTGAAATACTTTTTGGTCAACATCGAG
106621  TCTACTTACCACGTCCGACTCTTTTTATCCGAAAACTTTATGAAAAACCAGTTGTAGCTC

106681  ACTTTTAACATTTGTCCTATCTTTTAGGGGAATTTAGACATTGGGCATTATGTATTCCTT
106681  TGAAAATTGTAAACAGGATAGAAAATCCCCTTAAATCTGTAACCCGTAATACATAAGGAA

106741  GGATACATTAAAAGGTGTTAGATAAGAGCGCTCACACTTGCTGCTCTTCTATTGCAACTT
106741  CCTATGTAATTTTCCACAATCTATTCTCGCGAGTGTGAACGACGAGAAGATAACGTTGAA

106801  GACAGAAGTTACTTCTCTAAACCTTAGTTTCTCATCTGAACAATGGAAATAATGATAGTG
106801  CTGTCTTCAATGAAGAGATTTGGAATCAAAGAGTAGACTTGTTACCTTTATTACTATCAC

106861  TCTATCTCATAGTATTGGTGTGAGATTTAAATGAAATAATTCATGTAAAATTGCTTGGTG
106861  AGATAGAGTATCATAACCACACTCTAAATTTACTTTATTAAGTACATTTTAACGAACCAC
```

FIG. 4 (cont'd)

```
106921  TGTGGAAACATAGTAACTTTTAACTGTTCTCATTAACTTGGCTATTTACCTGTGTTCTTC
106921  ACACCTTTGTATCATTGAAAATTGACAAGAGTAATTGAACCGATAAATGGACACAAGAAG

106981  TATCATTACATTTCAAGTTAAAATTTCAAGGTTTCACGTTGTTCTCTCTCCAATGAATGC
106981  ATAGTAATGTAAAGTTCAATTTTAAAGTTCCAAAGTGCAACAAGAGAGAGGTTACTTACG

107041  AGTTAAATCACTTAGATTTTCTAATGAGTTTTCCTTTAATGTTATGCAGTTGACTAGAGA
107041  TCAATTTAGTGAATCTAAAAGATTACTCAAAAGGAAATTACAATACGTCAACTGATCTCT

107101  GTGTATATATATTAAGAACATAATACCTTCACTATGTCCACATGTGAATTAAGAGCTTGA
107101  CACATATATATAATTCTTGTATTATGGAAGTGATACAGGTGTACACTTAATTCTCGAACT

107161  GGCTATCAGAGGGTAGAAGATGAGGGAGTGGGGATGAAGTATGTTTGTAACCTGTGTATT
107161  CCGATAGTCTCCCATCTTCTACTCCCTCACCCCTACTTCATACAAACATTGGACACATAA

107221  TTCTCTTTCTTAAAGGAATTACGGCTCATCTCTTTTTGCCCAATGTGAAGCAGTAGATAA
107221  AAGAGAAAGAATTTCCTTAATGCCGAGTAGAGAAAAACGGGTTACACTTCGTCATCTATT

107281  TGGGTGTCAGCAGGTCCTGTGGCTCTATGGAGAGGACCATCAGATCACTGAAGTGGGAAC
107281  ACCCACAGTCGTCCAGGACACCGAGATACCTCTCCTGGTAGTCTAGTGACTTCACCCTTG

107341  TATGAATCTTTTTCTTTACTGGATAAATGAAGATGGAGGTAATCCACTCAGATTTCACTG
107341  ATACTTAGAAAAAGAAATGACCTATTTACTTCTACCTCCATTAGGTGAGTCTAAAGTGAC

107401  TGTGCATTTCTCAGTCATTTTCAACAGGACCAGAAAGACAAGAGCTAGAAACTTAGTACA
107401  ACACGTAAAGAGTCAGTAAAAGTTGTCCTGGTCTTTCTGTTCTCGATCTTTGAATCATGT

107461  AGGGAGTAAGTAGCACAGTTCCAAAGGCTAAGTAAGGACTACTGTGCTTTTGCTGCCCAA
107461  TCCCTCATTCATCGTGTCAAGGTTTCCGATTCATTCCTGATGACACGAAAACGACGGGTT

107521  ATAGACACAAGTTTCTTTTTTTTCTTTCTTTCTTTTTTAAAGAGGTGGAGTCTCACTATG
107521  TATCTGTGTTCAAAGAAAAAAAAGAAAGAAAGAAAAAATTTCTCCACCTCAGAGTGATAC

107581  TCACCCAGGCTGCAGTGCAATGGTGTGATCTCAGCTCACTGCACCCTGGTTCAAGCAATT
107581  AGTGGGTCCGACGTCACGTTACCACACTAGAGTCGAGTGACGTGGGACCAAGTTCGTTAA

107641  CTCCTGCCTCAGCCTCCCGAGTAGCTGGGATTGCAGGAGCCTGCCACCATGCCCAGCTAA
107641  GAGGACGGAGTCGGAGGGCTCATCGACCCTAACGTCCTCGGACGGTGGTACGGGTCGATT

107701  TTTTTGTATTTTTTTTTTTAGTAGAGATAGGGTTTCACCATGTTGGTCAGGCTGGTCTTG
107701  AAAAACATAAAAAAAAAAATCATCTCTATCCCAAAGTGGTACAACCAGTCCGACCAGAAC

107761  AACTCCTGACCTCAGGTGATCCACCGGCCTTGGCCTCCCAAAGTGCTGGGATTACAGGTG
107761  TTGAGGACTGGAGTCCACTAGGTGGCCGGAACCGGAGGGTTTCACGACCCTAATGTCCAC

107821  TGAGCCACTGCACCCGGCCGAGTTTCGATTTAAAGAAGCTCTAGAGGTTTTTTGTTTTTC
107821  ACTCGGTGACGTGGGCCGGCTCAAAGCTAAATTTCTTCGAGATCTCCAAAAAACAAAAAG

107881  GTTTTTTGTTTTTCTGGCTCTAGATGTACTGATTATTGAGATACTGAGATGTCACATTAA
107881  CAAAAAACAAAAAGACCGAGATCTACATGACTAATAACTCTATGACTCTACAGTGTAATT

107941  GGGATTTAAGTTACCATGATTGGAAGATTTGCTTCCTTATCCCTTCTGCAGTTCCCCAAC
107941  CCCTAAATTCAATGGTACTAACCTTCTAAACGAAGGAATAGGGAAGACGTCAAGGGGTTG

108001  AATTTTCCTATCTGAACACCTTGCATTGAGACACAGGTCTCAGATCAGGTCAATGGTCAT
108001  TTAAAAGGATAGACTTGTGGAACGTAACTCTGTGTCCAGAGTCTAGTCCAGTTACCAGTA

108061  TCACCATATACCGTATATAAAATGCTAGAGTAATAAATGCAGTGTACTGATTCTACTGGA
108061  AGTGGTATATGGCATATATTTTACGATCTCATTATTTACGTCACATGACTAAGATGACCT

108121  AGGATTTTGTGTACTCTCTGGCTGTAATTGTTTTAACAATTGTTGCCTTTTCTACATATT
108121  TCCTAAAACACATGAGAGACCGACATTAACAAAATTGTTAACAACGGAAAAGATGTATAA

108181  TTGAAAATGTATCACAATCTCTCCAAATTTACTCTAGAACTCAATCTGATTAAAGAGCAC
108181  AACTTTTACATAGTGTTAGAGAGGTTTAAATGAGATCTTGAGTTAGACTAATTTCTCGTG
```

FIG. 4 (cont'd)

```
108241  CATTTTAAAAGATAAATCAATGTATCTTGGGATTGTAACTAGATCCTGGTTCATTCAAGA
108241  GTAAAATTTTCTATTTAGTTACATAGAACCCTAACATTGATCTAGGACCAAGTAAGTTCT

108301  CAATTTCATATATCCACTATAGATATCAATATTTCTCTATTATCTTTAATATCCTGAGTA
108301  GTTAAAGTATATAGGTGATATCTATAGTTATAAAGAGATAATAGAAATTATAGGACTCAT

108361  CTCATTACTTTTCTTTGCTGTTTTTTTTTATTAGTTGGCAGAGACCATAGGGGTTCAGTG
108361  GAGTAATGAAAAGAAACGACAAAAAAAAATAATCAACCGTCTCTGGTATCCCCAAGTCAC

108421  AAGTGTTGGCAACGTGTATGATATTGAATTAAATGGCCAACGGTGGGAGAAAAACAGGCA
108421  TTCACAACCGTTGCACATACTATAACTTAATTTACCGGTTGCCACCCTCTTTTTGTCCGT

108481  TTTATTTCTATTAGAATTTTGATAATCATACCAAATTTAGAAGCGTATTTTTAGACTTGT
108481  AAATAAAGATAATCTTAAAACTATTAGTATGGTTTAAATCTTCGCATAAAAATCTGAACA

108541  TTACATTCTTAGGTTGTTCATTTCACAGTAGTAATTATAGAGACTAGAAATATAAATGAT
108541  AATGTAAGAATCCAACAAGTAAAGTGTCATCATTAATATCTCTGATCTTTATATTTACTA

108601  GTTTCCAAATACTTATGAAGTCTCAGTGTTAGTAGTTTCAATTAAATTTTTTAAAATGCA
108601  CAAAGGTTTATGAATACTTCAGAGTCACAATCATCAAAGTTAATTTAAAAAATTTTACGT

108661  GTTTATATTTGAAAGTAGCTACAGTAGCCTCTCTTGCTCTAATGTTATTTGGCTACAAAA
108661  CAAATATAAACTTTCATCGATGTCATCGGAGAGAACGAGATTACAATAAACCGATGTTTT

108721  AGAGGAAAATGGTAATTTAGATGTGGCTGAATTCAGAGCTAAGTACTAATTTTAGTGTTA
108721  TCTCCTTTTACCATTAAATCTACACCGACTTAAGTCTCGATTCATGATTAAAATCACAAT

108781  GTTGCAGAGACTAACAAGATGAGTCTTATACTGCAGTCAGAGGTAGAATAAACAGAAGAT
108781  CAACGTCTCTGATTGTTCTACTCAGAATATGACGTCAGTCTCCATCTTATTTGTCTTCTA

108841  ATGGTGAGTAAGCCTTGTCCTGGGCTTGGCCATTGGTAGTCCTTGGCATATGAAAAACCA
108841  TACCACTCATTCGGAACAGGACCCGAACCGGTAACCATCAGGAACCGTATACTTTTTGGT

108901  GATACAGATCATTCTCATCCTTCCATTCCTGCTGTTTGTACTTGGCACTGTTTGAAAATA
108901  CTATGTCTAGTAAGAGTAGGAAGGTAAGGACGACAAACATGAACCGTGACAAACTTTTAT

108961  AAATTTATACAGGAATATTTATGATTTATAAATTTGAGTTACTGTATGTGACATATAACA
108961  TTTAAATATGTCCTTATAAATACTAAATATTTAAACTCAATGACATACACTGTATATTGT

109021  AAAGCTACACTTGGAAGATTGTAGCCAGTGTTGACCTCTGCACTTAGAAGATAATAGGCC
109021  TTTCGATGTGAACCTTCTAACATCGGTCACAACTGGAGACGTGAATCTTCTATTATCCGG

109081  GATTCAACCCTTCTTCCCATCTGCCCACTCTTACCCCCACCCCAAACTCCACCAAAAAAC
109081  CTAAGTTGGGAAGAAGGGTAGACGGGTGAGAATGGGGGTGGGGTTTGAGGTGGTTTTTTG

109141  CACACAGCTCAAAACAAAAACAGTTACATCATTCAGAGGTGGTACCATCATTATTTTTAT
109141  GTGTGTCGAGTTTTGTTTTTGTCAATGTAGTAAGTCTCCACCATGGTAGTAATAAAAATA

109201  GGATGGGAGATGTCAGAATTTAAGTACACTCTGAATCAGAGCTACATGATTTAACCAGAA
109201  CCTACCCTCTACAGTCTTAAATTCATGTGAGACTTAGTCTCGATGTACTAAATTGGTCTT

109261  ACACCAGAAACTGTCCTGGTGGAAAATTGTTCTTTATCCAAACAATAATCATGAAACATT
109261  TGTGGTCTTTGACAGGACCACCTTTTAACAAGAAATAGGTTTGTTATTAGTACTTTGTAA

109321  TCCACCATGGCTTTTAAAGGTCAGAATAGAAATGAGTGAGTTTGTCTTCTGCCTCTTGCA
109321  AGGTGGTACCGAAAATTTCCAGTCTTATCTTTACTCACTCAAACAGAAGACGGAGAACGT

109381  AAATATACAAGACCTTAAGACTGTTAGTTACTATTCAGATTATGGTTGCCTGGGATAACT
109381  TTTATATGTTCTGGAATTCTGACAATCAATGATAAGTCTAATACCAACGGACCCTATTGA

109441  TTAGTTTTAATATACTCCTTCACTTTGGGGATGTTCATCTAACAGAACAAATAAAATTCA
109441  AATCAAAATTATATGAGGAAGTGAAACCCCTACAAGTAGATTGTCTTGTTTATTTTAAGT

109501  GAATAAGGAGAAAGGAAATAGAATATATATTTGAAGTAAATAGAATGTTAGGAAAAACCT
109501  CTTATTCCTCTTTCCTTTATCTTATATATAAACTTCATTTATCTTACAATCCTTTTTGGA

109561  TTGGGCTAAAAAAAAAGACATGCAATTCTGAAGTAACTTTGATTTATATCATATGATTTT
109561  AACCCGATTTTTTTTTCTGTACGTTAAGACTTCATTGAAACTAAATATAGTATACTAAAA
```

FIG. 4 (cont'd)

```
109621  AAGAAAATACAATGAACAAACGAGTTGAAAATCAGCACAATACTGATTTTCACAAACGTT
109621  TTCTTTTATGTTACTTGTTTGCTCAACTTTTAGTCGTGTTATGACTAAAAGTGTTTGCAA

109681  ACCGATAGGAGGTATAAACAGAGTTCTTTCGGTAATAGCCTGCCGTCTTTTCATGAGCGC
109681  TGGCTATCCTCCATATTTGTCTCAAGAAAGCCATTATCGGACGGCAGAAAAGTACTCGCG

109741  CCACACACACTGCTCCTGTTGGTTGAGATGGCTGGTGCAGGAAGGTGGATGGGGTGGTGG
109741  GGTGTGTGTGACGAGGACAACCAACTCTACCGACCACGTCCTTCCACCTACCCCACCACC

109801  ATAGTGTGTGTTCAAAGCACAGTGCTGTGCACAGTCACTATGTGTGGCACTCAGCTTGTA
109801  TATCACACACAAGTTTCGTGTCACGACACGTGTCAGTGATACACACCGTGAGTCGAACAT

109861  ACTCATGGGAGTTTTGATTTCAGTAACAGCACCCATGGTGGCAAGATCACACATCATCAC
109861  TGAGTACCCTCAAAACTAAAGTCATTGTCGTGGGTACCACCGTTCTAGTGTGTAGTAGTG

109921  TCTGTTGATGAGTAATTTAACCCATACGCTTGCTATTCACCATTTGAACAAAGCATTGTA
109921  AGACAACTACTCATTAAATTGGGTATGCGAACGATAAGTGGTAAACTTGTTTCGTAACAT

109981  TCATATCCTGGACCCTGGAGATACCCTGAAAAATAAGACCCAGGCCTTGTGGTTGAGTTC
109981  AGTATAGGACCTGGGACCTCTATGGGACTTTTTATTCTGGGTCCGGAACACCAACTCAAG

110041  ACAGTCACTTTGGGAAAACAACCACAGCAGTGAATCTCGGTATTGCTCAGGCCACATCAT
110041  TGTCAGTGAAACCCTTTTGTTGGTGTCGTCACTTAGAGCCATAACGAGTCCGGTGTAGTA

110101  GAGTCTTCTCGGACACGTCAGGCGTGTATACGGACTCGACTTGGAGCACTCTTCCTCAGA
110101  CTCAGAAGAGCCTGTGCAGTCCGCACATATGCCTGAGCTGAACCTCGTGAGAAGGAGTCT

110161  TGTCTGTACCGCTTGCTCTTTGACATCCTCCAAATCTTTGCTTACAAATCCCATTCTCAG
110161  ACAGACATGGCGAACGAGAAACTGTAGGAGGTTTAGAAACGAATGTTTAGGGTAAGAGTC

110221  TCTGGCTTTCCTTGAGCTCTTAATCAAAATCATAAACTCCATTTCCCATTTCTCCTCAGC
110221  AGACCGAAAGGAACTCGAGAATTAGTTTTAGTATTTGAGGTAAAGGGTAAAGAGGAGTCG

110281  ATTCCAGCATTCTCCATTGCTTTTCCTTCTTTGTTTCCCCCTGTGTAGTCTAACATACTA
110281  TAAGGTCGTAAGAGGTAACGAAAAGGAAGAAACAAAGGGGGACACATCAGATTGTATGAT

110341  TCAACACAATAAATGTTTACCTGTGTCTATTAGAAAGTAAGCAGGGAGATATGTCAGTTT
110341  AGTTGTGTTATTTACAAATGGACACAGATAATCTTTCATTCGTCCCTCTATACAGTCAAA

110401  TGTTCACTGCTGTATTCATAGAGCTTAAAACGGTAAACAGCACTCAATATGTATTTGTAG
110401  ACAAGTGACGACATAAGTATCTCGAATTTTGCCATTTGTCGTGAGTTATACATAAACATC

110461  AATAAATGGCTAATTGTGCTGATGGTGTTTAGGGCACTTATGCAGACCTACATTCCTGGT
110461  TTATTTACCGATTAACACGACTACCACAAATCCCGTGAATACGTCTGGATGTAAGGACCA

110521  TTCCATTAGTGTTTGACTTTGGGAAGTCACAGATGAATCCTGCTGTTATTGCTTCTAAAT
110521  AAGGTAATCACAAACTGAAACCCTTCAGTGTCTACTTAGGACGACAATAACGAAGATTTA

110581  TCCTCATCTCCTAAAAATGACTTCTTTGTCAAAAACAAGCTGCATTTGTAGGTTCTGTTT
110581  AGGAGTAGAGGATTTTTACTGAAGAAACAGTTTTTGTTCGACGTAAACATCCAAGACAAA

110641  TCCTCATGTTGGGCAATCTGGAGTGATTTCTGGCTCTTGTAAGTATGTTTGTGGTTGCAG
110641  AGGAGTACAACCCGTTAGACCTCACTAAAGACCGAGAACATTCATACAAACACCAACGTC

110701  AGGAAAATGAATATTTCTCACCCAAATGTTGTCATGTCATCATCTCTGTCTGGCAACCAG
110701  TCCTTTTACTTATAAAGAGTGGGTTTACAACAGTACAGTAGTAGAGACAGACCGTTGGTC

110761  AGAAGCAGATGTTCTGTTCCTTGACCTCAGGCTAGTGGTTACAGTTCTGGGTGTTAAACA
110761  TCTTCGTCTACAAGACAAGGAACTGGAGTCCGATCACCAATGTCAAGACCCACAATTTGT

110821  TGTTTCACAAAACAGCACTTGCACATGCGGGGCTGCTGTTTTCATTTAACTTCATGTAGT
110821  ACAAAGTGTTTTGTCGTGAACGTGTACGCCCCGACGACAAAAGTAAATTGAAGTACATCA

110881  CTCAGGGCTCAGCAAGCTTTAGGAAAGGTCCGGTTTGGGGGCACTGGAAGTGTGTGTGTG
110881  GAGTCCCGAGTCGTTCGAAATCCTTTCCAGGCCAAACCCCCGTGACCTTCACACACACAC
```

FIG. 4 (cont'd)

```
110941  TGTGTACATATATATACACACACAAATAGATCCATACATTTATGTATCTAGTTGGCTAGC
110941  ACACATGTATATATATGTGTGTGTTTATCTAGGTATGTAAATACATAGATCAACCGATCG

111001  TATTGCAAAACACATGTTTATTTTGAGATCATCAACACTTCTAAACATGACAAAGAGTAG
111001  ATAACGTTTTGTGTACAAATAAAACTCTAGTAGTTGTGAAGATTTGTACTGTTTCTCATC

111061  CCCTAAGAACATTGCCAAGAACAAATTTTCTCCTTTCCAGAAAGCAATTTTCAGCAGATG
111061  GGGATTCTTGTAACGGTTCTTGTTTAAAAGAGGAAAGGTCTTTCGTTAAAAGTCGTCTAC

111121  ATTTTCAGAAACAAAATTCAAAAAAGCCATACTGCTGTATCCTAGCAAAGATAACTTATT
111121  TAAAAGTCTTTGTTTTAAGTTTTTTCGGTATGACGACATAGGATCGTTTCTATTGAATAA

111181  CGTTTATTTTTTACTCAAAAACATTTATTATATACACTCTGGGCTAGGCACAATGCCCAG
111181  GCAAATAAAAAATGAGTTTTTGTAAATAATATATGTGAGACCCGATCCGTGTTACGGGTC

111241  TTTTGAGGATAGAAGGATGAAGATAGAGTTTGGTATTCCAGATAGAGCTTGATTGTTGGG
111241  AAAACTCCTATCTTCCTACTTCTATCTCAAACCATAAGGTCTATCTCGAACTAACAACCC

111301  CATGTCTGATGTAACCCCAGTGGAGTGGGCGAGCCTAGAACCACCATGTATTGAGGGAGA
111301  GTACAGACTACATTGGGGTCACCTCACCCGCTCGGATCTTGGTGGTACATAACTCCCTCT

111361  GGGTGGTGGCCTCAGTGTCAGGACTCACTAGATTCAGACTCCTGGGTGTCAGAAGTGGGG
111361  CCCACCACCGGAGTCACAGTCCTGAGTGATCTAAGTCTGAGGACCCACAGTCTTCACCCC

111421  AGGAAAGGGAGATGCTGAGTGCCAGAGGGTACTGTAAGGAGAGCTTGTGCAGCTGATGGA
111421  TCCTTTCCCTCTACGACTCACGGTCTCCCATGACATTCCTCTCGAACACGTCGACTACCT

111481  TCATGCATGATGCCTGTGAACAATTGTCCTACTAGACCTCACAGTAGTTAGGGATGTCTG
111481  AGTACGTACTACGGACACTTGTTAACAGGATGATCTGGAGTGTCATCAATCCCTACAGAC

111541  CAGTCATCTCACAGTAGAGCAGTAGCTCAGCTTTGGAGTTTTGTTTCTTGAATGTCTTCT
111541  GTCAGTAGAGTGTCATCTCGTCATCGAGTCGAAACCTCAAAACAAAGAACTTACAGAAGA

111601  TTTTTAACCGTACACGTGCTTGAGCTCACTCTGATAAGCCCATTACATTTGAATCTCAGA
111601  AAAAATTGGCATGTGCACGAACTCGAGTGAGACTATTCGGGTAATGTAAACTTAGAGTCT

111661  GAGCAAAGGCAGCATCTCCATACTTGTTGCTGATGCTCCACCAGGTTTGAAAATCACTAA
111661  CTCGTTTCCGTCGTAGAGGTATGAACAACGACTACGAGGTGGTCCAAACTTTTAGTGATT

111721  AGATAGACTCTTAGGCTGGGTGCGGTGGCTCACATCTGTAATCTCAGCACTTTGGGAGGC
111721  TCTATCTGAGAATCCGACCCACGCCACCGAGTGTAGACATTAGAGTCGTGAAACCCTCCG

111781  CGAAGTGGGCAGATCATCTGAGCTCAGGAGTTCGAGACCAGCCTGACCAACATGGTGAAA
111781  GCTTCACCCGTCTAGTAGACTCGAGTCCTCAAGCTCTGGTCGGACTGGTTGTACCACTTT

111841  CCCCGTCTCTACTAAAAATACAAAAATTAGCCAGGCGTGGTGGCGCGTACCTGTAATCCC
111841  GGGGCAGAGATGATTTTTATGTTTTTAATCGGTCCGCACCACCGCGCATGGACATTAGGG

111901  AGCTACTCAGGAGGCTGAGGCAGGAGAATCACTTGACCCTGGGAGGCAGAGGGTGCAGTG
111901  TCGATGAGTCCTCCGACTCCGTCCTCTTAGTGAACTGGGACCCTCCGTCTCCCACGTCAC

111961  AGCTGAGATGGTGCCACTGCACTCCAGCCTGGGTAACCTAAAAAAAAAAAAAAAAAAAAA
111961  TCGACTCTACCACGGTGACGTGAGGTCGGACCCATTGGATTTTTTTTTTTTTTTTTTTTT

112021  AAATTAGACTTTCCAAGGGCAGCGTGGAAGCAGTGACCAGCCTGAGTAGGCACGCACACT
112021  TTTAATCTGAAAGGTTCCCGTCGCACCTTCGTCACTGGTCGGACTCATCCGTGCGTGTGA

112081  TCTTGGGGATAGCCTCCTCCATAGCATTCTTAGAAGGTTTGGTAATGACCAGTTTTTCTG
112081  AGAACCCCTATCGGAGGAGGTATCGTAAGAATCTTCCAAACCATTACTGGTCAAAAAGAC

112141  AGTAAGACCCTATCTACATTATTCTAATTAGTAACCACCTTTCATCTGCTAAGGTAAATT
112141  TCATTCTGGGATAGATGTAATAAGATTAATCATTGGTGGAAAGTAGACGATTCCATTTAA

112201  TTCACTTCAGAATATTCCTCTTAAGACCATGCAATAACTCTTACTGTTTGTTGGTGGAAA
112201  AAGTGAAGTCTTATAAGGAGAATTCTGGTACGTTATTGAGAATGACAAACAACCACCTTT
```

FIG. 4 (cont'd)

```
112261  ACCATCTCATTATTTTACTGGTTAAGGGTAAACTGAAGATGATTAGATAACTTTCCTTCC
112261  TGGTAGAGTAATAAAATGACCAATTCCCATTTGACTTCTACTAATCTATTGAAAGGAAGG

112321  TTCCCTCCCCCCTTCCTCCCTTCCTTCTCTTTCTTCCTTCCTTTCTCCCTCCCTCCCTCC
112321  AAGGGAGGGGGGAAGGAGGGAAGGAAGAGAAAGAAGGAAGGAAAGAGGGAGGGAGGGAGG

112381  CTCTCTCTTTCTTTCCTTCTCTCTTTCTTTTCTTTTCTTTTTTCTTTCTTTCTTTCTTTT
112381  GAGAGAGAAAGAAAGGAAGAGAGAAAGAAAAGAAAAGAAAAAAGAAAGAAAGAAAGAAAA

112441  TTCTTTCTTCCTTCCTTCGTTCCTTCCTCCCTCCCTCCCTCTCTCTCTTTCTTTCTTTCT
112441  AAGAAAGAAGGAAGGAAGCAAGGAAGGAGGGAGGGAGGGAGAGAGAGAAAGAAAGAAAGA

112501  CTTTTCTTTCTTTCTTTCTTTCTTTCTTTCTTTCTTTCTTTCTTTCTTTCTCTCTTTCTT
112501  GAAAAGAAAGAAAGAAAGAAAGAAAGAAAGAAAGAAAGAAAGAAAGAAAGAGAGAAAGAA

112561  TTCTTTCTTTCTTTCTTTCTCTTTCTCTTTCCTTCCTTCCTTCCTTTCTTTCTCTCTCTC
112561  AAGAAAGAAAGAAAGAAAGAGAAAGAGAAAGGAAGGAAGGAAGGAAAGAAAGAGAGAGAG

112621  TCCTTCCTTCCTTCCTTCTTTCCTTCCTTCCTTCTTTCCTTCCTTCCTTCTTTCTTCTTT
112621  AGGAAGGAAGGAAGGAAGAAAGGAAGGAAGGAAGAAAGGAAGGAAGGAAGAAAGAAGAAA

112681  TTTTAAATAAGGGTCTACCTGAAGTGTGAACTGATTTGGGAAATTTGATCATGCAGAACA
112681  AAAATTTATTCCCAGATGGACTTCACACTTGACTAAACCCTTTAAACTAGTACGTCTTGT

112741  GTAAAATTTTCTTTATGTTTGTTGCTAGCAAAATTGTGATGGTTTTTTAAAAAAATGGCT
112741  CATTTTAAAAGAAATACAAACAACGATCGTTTTAACACTACCAAAAAATTTTTTTACCGA

112801  ATTGATAATAAGGCATGCCTAATGTAGTGAAAGTTTGAAAATGTCCCAATTTCTGATTGA
112801  TAACTATTATTCCGTACGGATTACATCACTTTCAAACTTTTACAGGGTTAAAGACTAACT

112861  CAGAAGAAGAACTGGCAACTCCTCCACTAGATGGCATCATTCTTCCAGGAGTGACAAGGC
112861  GTCTTCTTCTTGACCGTTGAGGAGGTGATCTACCGTAGTAAGAAGGTCCTCACTGTTCCG

112921  GGTGCATTCTGGACCTGGCACATCAGTGGGTGGGTGCCTTTGATATGAACAACTTTTGTA
112921  CCACGTAAGACCTGGACCGTGTAGTCACCCACCCACGGAAACTATACTTGTTGAAAACAT

112981  AGCCTGAAATAAAAAATAATCAAAATAAGCCCAGCCTAGTGTTGAAATAATATCCTGTGG
112981  TCGGACTTTATTTTTTATTAGTTTTATTCGGGTCGGATCACAACTTTATTATAGGACACC

113041  TTCCAACCAATGTTATCTAATCTTTAAATTCTAACGTGAATGAAAAGTATTCTTCTAGAA
113041  AAGGTTGGTTACAATAGATTAGAAATTTAAGATTGCACTTACTTTTCATAAGAAGATCTT

113101  GGGCTTTCTTGGCAAGACTATTAAAATAAGTATTGTTGATAGCAAGGGCAGAGAGAAACC
113101  CCCGAAAGAACCGTTCTGATAATTTTATTCATAACAACTATCGTTCCCGTCTCTCTTTGG

113161  AGTTTAGCAAGATGTCATAGTGGAGAAGTATTCTAGTAGTAGTCTCAGTCTACCAGGTAT
113161  TCAAATCGTTCTACAGTATCACCTCTTCATAAGATCATCATCAGAGTCAGATGGTCCATA

113221  CTCCCACCAACTTTTGTCTGGTTCATACCTGATGTGCTTCCATCCAGACATTCCTTAACT
113221  GAGGGTGGTTGAAAACAGACCAAGTATGGACTACACGAAGGTAGGTCTGTAAGGAATTGA

113281  TCCCAAGTCTGTGTTGCTTCCAAATGGCAATGATACTTCTTCCTTTCCTTTATTTATACC
113281  AGGGTTCAGACACAACGAAGGTTTACCGTTACTATGAAGAAGGAAAGGAAATAAATATGG

113341  AGTGTAACCATGCTTGCCGTAGAAATGAAATAATTTCACTGACATATAAATGTTTACTAA
113341  TCACATTGGTACGAACGGCATCTTTACTTTATTAAAGTGACTGTATATTTACAAATGATT

113401  TATAACATTATTGGTTTGACTGCCTTCTTTTTCTCTCTGTCCTACCCCCATCCTCCAAAA
113401  ATATTGTAATAACCAAACTGACGGAAGAAAAAGAGAGACAGGATGGGGGTAGGAGGTTTT

113461  TTCATATACATGCCTATTTTAAAATCAGAACATGCAAGCAAATGTAAAGTTGTTTTCAGT
113461  AAGTATATGTACGGATAAAATTTTAGTCTTGTACGTTCGTTTACATTTCAACAAAAGTCA

113521  AGACTTTCAAATTCGTGTGACACAGGCAAGCATATTAAACAATTTGGTGGACCGGGTGCA
113521  TCTGAAAGTTTAAGCACACTGTGTCCGTTCGTATAATTTGTTAAACCACCTGGCCCACGT
```

FIG. 4 (cont'd)

113581 GTGGTTCATGCCTATAATTCTAGCATTTTGGGAGGCCAAGGCAGGAGGATCACTTAAGCC
113581 CACCAAGTACGGATATTAAGATCGTAAAACCCTCCGGTTCCGTCCTCCTAGTGAATTCGG

113641 CAGGAATTCGAGACCAGCCTGGGCAACATAGTGAGACCCCGAATCTACAAAAAAATCAAA
113641 GTCCTTAAGCTCTGGTCGGACCCGTTGTATCACTCTGGGGCTTAGATGTTTTTTTAGTTT

113701 AACATTAGCTGAACATGGTGGTACATGCCTGTAGTCCCAGCTACTTGGAGGGGCTGAGGT
113701 TTGTAATCGACTTGTACCACCATGTACGGACATCAGGGTCGATGAACCTCCCCGACTCCA

113761 GGGAGGATGGCATAAGATCTGGAGGTCAAGGTCGCAGTGAGCTATGATCAAGCCACTGCA
113761 CCCTCCTACCGTATTCTAGACCTCCAGTTCCAGCGTCACTCGATACTAGTTCGGTGACGT

113821 CTACAGCCTGAATACAGGGTGAGACCATGTCTCTAAAAGTAAATTAAATAAATAAATAAA
113821 GATGTCGGACTTATGTCCCACTCTGGTACAGAGATTTTCATTTAATTTATTTATTTATTT

113881 TAAATAAATAAATAAATAAATAAATAAAATAAAATTTAAAAAGGTTTGGTTTTGGAAATG
113881 ATTTATTTATTTATTTATTTATTTATTTTATTTTAAATTTTTCCAAACCAAAACCTTTAC

113941 ACGTAATGTATTCAAGACAAATTATTGAATGAATTGGGTGTCTGGTAAAGGTTCTTGGAT
113941 TGCATTACATAAGTTCTGTTTAATAACTTACTTAACCCACAGACCATTTCCAAGAACCTA

114001 GGAACTTTTGACCCAGGTGTTAAAATGGTCTCCAAAGAACATGAAAAGGCTTTGAGCTTA
114001 CCTTGAAAACTGGGTCCACAATTTTACCAGAGGTTTCTTGTACTTTTCCGAAACTCGAAT

114061 CTGTGGTCAAAGAGTACTAGTAGTAATAGGACAAATGTTTAGAAACACACACGTTATCTA
114061 GACACCAGTTTCTCATGATCATCATTATCCTGTTTACAAATCTTTGTGTGTGCAATAGAT

114121 GGAGCATACCAGCATGGTTTCTCTGGAAAAGACTTTCAAAATAGATGAAATGTGCTATAA
114121 CCTCGTATGGTCGTACCAAAGAGACCTTTTCTGAAAGTTTTATCTACTTTACACGATATT

114181 ATAATTCTACAAAACCCTGAAGTAGACAAGACCCAACTGCTACATGCTGGCTGGCGCATT
114181 TATTAAGATGTTTTGGGACTTCATCTGTTCTGGGTTGACGATGTACGACCGACCGCGTAA

114241 GGGCATGACATTTACAAACCGTTGGTATAATTTTCAAACAGCTTGCCCTGTCCTAAATAT
114241 CCCGTACTGTAAATGTTTGGCAACCATATTAAAAGTTTGTCGAACGGGACAGGATTTATA

114301 GTTTGCAATTGGAAAGATATTTTTGAAGCTCAGTAATTTTTGTTTTATTAAAGAAAAATA
114301 CAAACGTTAACCTTTCTATAAAAACTTCGAGTCATTAAAAACAAAATAATTTCTTTTTAT

114361 TCAACCAAGTACAGAAGGTTCGACGACAAGTTGCAAGTGGAAATACTTTCCCACACTAAT
114361 AGTTGGTTCATGTCTTCCAAGCTGCTGTTCAACGTTCACCTTTATGAAAGGGTGTGATTA

114421 GATTTGCTAGCATGAAAAATAGGTTATTATGGAGGAAATTTTTTCTTGACTTCATAGCTG
114421 CTAAACGATCGTACTTTTTATCCAATAATACCTCCTTTAAAAAAGAACTGAAGTATCGAC

114481 TAATTTATTTTAAAAGCTATTTTAAAACATGAGACGTGAAATGCCAAGAGGCATGTAGGG
114481 ATTAAATAAAATTTTCGATAAAATTTTGTACTCTGCACTTTACGGTTCTCCGTACATCCC

114541 GGTCACCACTATTTGCCAGATAGGGGAAATTGTCCAAAGATAAGTAAGGGTGAGCAGAGC
114541 CCAGTGGTGATAAACGGTCTATCCCCTTTAACAGGTTTCTATTCATTCCCACTCGTCTCG

114601 AAAAACAATTCTGCTTATTTACAAAAGAGTTTTCTTTTCTTTTCTTTTTCAGGACACAGA
114601 TTTTTGTTAAGACGAATAAATGTTTTCTCAAAAGAAAAGAAAAGAAAAAGTCCTGTGTCT

114661 ACTCAGCTTGTTTTCAATTAATTTGCCTGATTTTCTGCAGTTCATTTACTTTTGAACAAC
114661 TGAGTCGAACAAAAGTTAATTAAACGGACTAAAAGACGTCAAGTAAATGAAAACTTGTTG

114721 ATAATTGCAATTGTAGACTGAGAGAAATTGAAACTTTCAAAGAGCCATATTTCTATTGCA
114721 TATTAACGTTAACATCTGACTCTCTTTAACTTTGAAAGTTTCTCGGTATAAAGATAACGT

114781 GATATATTTTCCTGCTCTTCCAAATCTACTTACAGCATGAGTTCTTCTTTTAAATATTCA
114781 CTATATAAAAGGACGAGAAGGTTTAGATGAATGTCGTACTCAAGAAGAAAATTTATAAGT

114841 AATATTTTGAATATTGCCAAGAGCTTTGATTTCCATTTTTATCTCTTGTGGGTTTATAAA
114841 TTATAAAACTTATAACGGTTCTCGAAACTAAAGGTAAAAATAGAGAACACCCAAATATTT

114901 TTAAGAAAAAATACTCATCTTATTTTTTTAAACCTCTCTATTTTTATTGCCCTTTATTCA
114901 AATTCTTTTTTATGAGTAGAATAAAAAAATTTGGAGAGATAAAAATAACGGGAAATAAGT

FIG. 4 (cont'd)

```
114961  AATAACTTGTTGACAAACTTTGAACTTGAACCACTGAGGTAAAAGAACAAGAATTAAACA
114961  TTATTGAACAACTGTTTGAAACTTGAACTTGGTGACTCCATTTTCTTGTTCTTAATTTGT

115021  GATAGTTTAAACACATAGCTTAAAAGGATCTTTTTCCCATTTCCTATCCTTGAGCAAAGA
115021  CTATCAAATTTGTGTATCGAATTTTCCTAGAAAAAGGGTAAAGGATAGGAACTCGTTTCT

115081  ATATATTCAAACACTTTGGCAGAAGTCAATGAGGTTATACCACTAATTCCATGATGAAAA
115081  TATATAAGTTTGTGAAACCGTCTTCAGTTACTCCAATATGGTGATTAAGGTACTACTTTT

115141  TCAACTGAATGTGATACTGAAAGAGAAGGAAGAGAATTGTCACTGTAAAGTCAACTGTTA
115141  AGTTGACTTACACTATGACTTTCTCTTCCTTCTCTTAACAGTGACATTTCAGTTGACAAT

115201  GTCATATTAGGAAAAAAAATACATACAATACAATTTCTCAAATAAAGTCCAAATATACAT
115201  CAGTATAATCCTTTTTTTTATGTATGTTATGTTAAAGAGTTTATTTCAGGTTTATATGTA

115261  TCAACGTTTAAAAATAATGAGTATTTCAGATATTTGAACTCAGTCTGTTCTTTATTCCAT
115261  AGTTGCAAATTTTTATTACTCATAAAGTCTATAAACTTGAGTCAGACAAGAAATAAGGTA

115321  AAAAGATATAGGTAAGCCGTGCACAGTGGCTCACAACTATAATCCCAGCACTTTGGCACT
115321  TTTTCTATATCCATTCGGCACGTGTCACCGAGTGTTGATATTAGGGTCGTGAAACCGTGA

115381  TTGGGAGGCTGAGGTGGGAGGATCACATGAGCCCAGCCTGGGCAACATAGGGAGACCCCT
115381  AACCCTCCGACTCCACCCTCCTAGTGTACTCGGGTCGGACCCGTTGTATCCCTCTGGGGA

115441  ATCTTTACAAAATAAAATATAAAATATAAAACCTAGTTGGGCATGGCAGCATACACCTGT
115441  TAGAAATGTTTTATTTTATATTTTATATTTTGGATCAACCCGTACCGTCGTATGTGGACA

115501  AGTCCCAGGTGCTCAGGAGACTGAGACAGGAGGATCACTTGGGCCTGGGAGGTCGAGGCT
115501  TCAGGGTCCACGAGTCCTCTGACTCTGTCCTCCTAGTGAACCCGGACCCTCCAGCTCCGA

115561  GCAATGAGCCAAGATTATGCCACTGCATTCCAGCCTGGGTGACAGGGCAAGACCCTGTCT
115561  CGTTACTCGGTTCTAATACGGTGACGTAAGGTCGGACCCACTGTCCCGTTCTGGGACAGA

115621  TAAAAAAAAAAAAAAAAAGAAAGAGACAAACGTAGAAAGAGTACCAAATTTGGAGCCAATC
115621  ATTTTTTTTTTTTTTTTTCTTTCTCTGTTTGCATCTTTCTCATGGTTTAAACCTCGGTTAG

115681  AGATCAGACCTGGGTTCAAATTGAGTTTCTGTCACTTACTTCCTTTGTGGCCCTGGAGAT
115681  TCTAGTCTGGACCCAAGTTTAACTCAAAGACAGTGAATGAAGGAAACACCGGGACCTCTA

115741  GCCCTTCAACCTCCTTGAACCTTAGTTTCCTCATCTGTAAAATGGGGATGATAGTACTCA
115741  CGGGAAGTTGGAGGAACTTGGAATCAAAGGAGTAGACATTTTACCCCTACTATCATGAGT

115801  CCCTTAAAATTACAGAACTTGGCATAATAGCGGGTGCTTGATAAATGGTAGCTATAATTA
115801  GGGAATTTTAATGTCTTGAACCGTATTATCGCCCACGAACTATTTACCATCGATATTAAT

115861  TTAATATTATATAATACATTGTTCTCCTTTATGGTAAAGTAGGTTTTAAGACACTGATTT
115861  AATTATAATATATTATGTAACAAGAGGAAATACCATTTCATCCAAAATTCTGTGACTAAA

115921  TTTTGTTTTGTTTTGTTTTTGGAGACAGAGTCTCACTCCGTCACCCAGGCTGGACTGCAG
115921  AAAACAAAACAAAACAAAAACCTCTGTCTCAGAGTGAGGCAGTGGGTCCGACCTGACGTC

115981  TGACGTGATCTTGGTTCACTGCAACCTCTGCCTCCTGAGTTCAAGCGATTCTCCTGCCTC
115981  ACTGCACTAGAACCAAGTGACGTTGGAGACGGAGGACTCAAGTTCGCTAAGAGGACGGAG

116041  AGCCTCCTGAGTAGCTGGGATTACAGGCACCCGCCACCATGCCTGGCTAATTTTTGTATT
116041  TCGGAGGACTCATCGACCCTAATGTCCGTGGGCGGTGGTACGGACCGATTAAAAACATAA

116101  TTTAGTAGAGACAGGGTTTTACCAGGTTGGCCAGGCTGGTCTCAAACTCCTGACCTCAAG
116101  AAATCATCTCTGTCCCAAAATGGTCCAACCGGTCCGACCAGAGTTTGAGGACTGGAGTTC

116161  TAATCTGCCTGCCTCAGCCTCCCCAAATGCAGAGATTACAGGCATGAGCCACCGTGCCCG
116161  ATTAGACGGACGGAGTCGGAGGGGTTTACGTCTCTAATGTCCGTACTCGGTGGCACGGGC

116221  GCCTAAGACACTGTTAACACGGAGCATGCATCAAGCAGCATTTGGGATGCATCAATTTTG
116221  CGGATTCTGTGACAATTGTGCCTCGTACGTAGTTCGTCGTAAACCCTACGTAGTTAAAAC
```

FIG. 4 (cont'd)

116281 TGAGACTTTATACAAGTTAACAAATAAGAAGGCAAAAAAGAAGGCATATGTTAAAGTATA
116281 ACTCTGAAATATGTTCAATTGTTTATTCTTCCGTTTTTTCTTCCGTATACAATTTCATAT

116341 CCATGTGTCTTGTGGTGATAATCTTATATTTTATATTCTGATAATCTCATATATAAATCT
116341 GGTACACAGAACACCACTATTAGAATATAAAATATAAGACTATTAGAGTATATATTTAGA

116401 GTGACCTTGAAGTAGGTTACTTAACACCTCGATGTGTTCACCAGTAAGATGGTGTGCCAC
116401 CACTGGAACTTCATCCAATGAATTGTGGAGCTACACAAGTGGTCATTCTACCACACGGTG

116461 TTCCAGCTTTCCCTTAAAGGATGATTGTGACCTTGTCTAAGTGCAATCAGAATGTTAAGC
116461 AAGGTCGAAAGGGAATTTCCTACTAACACTGGAACAGATTCACGTTAGTCTTACAATTCG

116521 AGAACAGTAAGTATTGCAATTGTTTTGCATGCCTTTTCCTTTAAAATATACTTGTTATTT
116521 TCTTGTCATTCATAACGTTAACAAAACGTACGGAAAAGGAAATTTTATATGAACAATAAA

116581 TTTATATTCCATGCAGGGTGAATTTAAGGTGTCAGAGAGATACCTCACCATGGATGACTT
116581 AAATATAAGGTACGTCCCACTTAAATTCCACAGTCTCTCTATGGAGTGGTACCTACTGAA

116641 GACAACAGCCCTGGAGGGGAACAGAGTGAGAGAGATGTTTGGCTCTGGTACAGCCTGTGT
116641 CTGTTGTCGGGACCTCCCCTTGTCTCACTCTCTCTACAAACCGAGACCATGTCGGACACA

116701 TGTTTGCCCAGTTTCTGATATACTGTACAAAGGCGAGGTACGACAAGTATTTCCTCATTT
116701 ACAAACGGGTCAAAGACTATATGACATGTTTCCGCTCCATGCTGTTCATAAAGGAGTAAA

116761 CCTATCATTTCCAATCACATTAAATTACATTTAATTTAAGTGTATGAATAAAATTGTATC
116761 GGATAGTAAAGGTTAGTGTAATTTAATGTAAATTAAATTCACATACTTATTTTAACATAG

116821 TGGACCCAGACCCAAGATGCAAAAGTTTTGTCGTTGTTGTTGTTTTTCTTTATTTTAAAG
116821 ACCTGGGTCTGGGTTCTACGTTTTCAAAACAGCAACAACAACAAAAAGAAATAAAATTTC

116881 AGATGGAGTCTCGCTGTGTTGCCCAGGCTGGAGTGCAGTGGCTATTCACTGGTGTGATCA
116881 TCTACCTCAGAGCGACACAACGGGTCCGACCTCACGTCACCGATAAGTGACCACACTAGT

116941 TAGCTCACTGCAGCCTCAAACTCCTGGGCTCACGCAATCCTTCTGCTTCAGCCTCCTGAG
116941 ATCGAGTGACGTCGGAGTTTGAGGACCCGAGTGCGTTAGGAAGACGAAGTCGGAGGACTC

117001 TTGCTGGGATTACAGGAGTGCGCCACCGCACCATGCTAGGTCTTTTTTGTTGTTGTTTTT
117001 AACGACCCTAATGTCCTCACGCGGTGGCGTGGTACGATCCAGAAAAAACAACAACAAAAA

117061 GTTTTTTAACTTGGCACTACAAAAAAAATAACTGGGACAGTTTATCCAGATGAAACTGTA
117061 CAAAAAATTGAACCGTGATGTTTTTTTTATTGACCCTGTCAAATAGGTCTACTTTGACAT

117121 TTAGCATATATCTACTATGTTTCCAGTGATTTCATGTAAGCTTAAACATGGTGGGAAGTT
117121 AATCGTATATAGATGATACAAAGGTCACTAAAGTACATTCGAATTTGTACCACCCTTCAA

117181 AGTTTTGTCCTTGGACACGTGTAAGATCTGTCTTACCTACATGTCGGGATTGGAGCTATG
117181 TCAAAACAGGAACCTGTGCACATTCTAGACAGAATGGATGTACAGCCCTAACCTCGATAC

117241 CCGACAGTCTTCTACTCTTCTCTCTTCCTTCCTACCAGCTCACTAGGGAAGGCTCTATAG
117241 GGCTGTCAGAAGATGAGAAGAGAGAAGGAAGGATGGTCGAGTGATCCCTTCCGAGATATC

117301 GTAGTTACATTTCAGTTTCTGGTTAACCAAAAGTACTTCCAAACCACTGGATTAGGAATG
117301 CATCAATGTAAAGTCAAAGACCAATTGGTTTTCATGAAGGTTTGGTGACCTAATCCTTAC

117361 GCAAATAGTTATGGAAAATGCATTCGAGTGGTCAATCCCTTGATTTTTTTTTACTATTAA
117361 CGTTTATCAATACCTTTTACGTAAGCTCACCAGTTAGGGAACTAAAAAAAAATGATAATT

117421 TGCTGTTATCATTAATAGTAAGTAGACCACTTTACAAGAATTATTCATTGGCAAACCTGG
117421 ACGACAATAGTAATTATCATTCATCTGGTGAAATGTTCTTAATAAGTAACCGTTTGGACC

117481 TGCATTTACTAAAATCTTACAAAAGGAATTTGAGGATTTGGTTGGAAGAAATGTTCTCCT
117481 ACGTAAATGATTTTAGAATGTTTTCCTTAAACTCCTAAACCAACCTTCTTTACAAGAGGA

117541 CTTAGTAAATTAGTCTGATTTTATATGTGCCATACTTTTGTTTTCTTGTCAAATTGTTTT
117541 GAATCATTTAATCAGACTAAAATATACACGGTATGAAAACAAAAGAACAGTTTAACAAAA

117601 GCTTTTCACTTTATAACAAAGCTCCAATACTTATGATTAACATTGGCATCTAACTTTATA
117601 CGAAAAGTGAAATATTGTTTCGAGGTTATGAATACTAATTGTAACCGTAGATTGAAATAT

FIG. 4 (cont'd)

117661 ACTTAAAGGCATGTAAGTATTAGTCTTATAATGTGAACTGGCTTAAGTTATTCATATTAT
117661 TGAATTTCCGTACATTCATAATCAGAATATTACACTTGACCGAATTCAATAAGTATAATA

117721 AGCAGATCCTTGAACAACACAGGGATTAGGGGTGTCAACCCCCATGCAGTTGAAAAATCC
117721 TCGTCTAGGAACTTGTTGTGTCCCTAATCCCCACAGTTGGGGGTACGTCAACTTTTTAGG

117781 ACATACAACTTTTTTTGTTTGTTTGTTTTTTTAAACGGGGTCTTTCTCTGTCACCTGTAC
117781 TGTATGTTGAAAAAAACAAACAAACAAAAAAATTTGCCCCAGAAAGAGACAGTGGACATG

117841 TGGAGTGCAGGGGCACAATCTCGGCTCACTGCAACCTCCGCCTCCCAAGCTCAAGCGATC
117841 ACCTCACGTCCCCGTGTTAGAGCCGAGTGACGTTGGAGGCGGAGGGTTCGAGTTCGCTAG

117901 CTCTCACCTCAGTCTCCCAAGTAGCTGGGACCACAGGTGTGCACCACCACACCCAGCTAA
117901 GAGAGTGGAGTCAGAGGGTTCATCGACCCTGGTGTCCACACGTGGTGGTGTGGGTCGATT

117961 TTTTAGTATTTTTTGTAGAGACGGGGTTTCAAGATGTTTCACAGGCTGGTCTCAAACTCT
117961 AAAATCATAAAAAACATCTCTGCCCCAAAGTTCTACAAAGTGTCCGACCAGAGTTTGAGA

118021 TGAGTTCAAGTGATTCACCTGCCTTGACCTCCCAAAGTGCTGGTATTACAGGCGTGAGTC
118021 ACTCAAGTTCACTAAGTGGACGGAACTGGAGGGTTTCACGACCATAATGTCCGCACTCAG

118081 ACCATGCCCGGCCCACATATAACTTTTGACTTCCCAAAAACTTAACTACTAGTAGCCTGC
118081 TGGTACGGGCCGGGTGTATATTGAAAACTGAAGGGTTTTTGAATTGATGATCATCGGACG

118141 TGTTCACCGGAAGCCTTATCAACAACAAAAACAGTCGATTGGCACATATTTTGTATGTTA
118141 ACAAGTGGCCTTCGGAATAGTTGTTGTTTTTGTCAGCTAACCGTGTATAAAACATACAAT

118201 TGTATGTTATATATGTATTCTTACAATAAAGTAAGTTACGAAAATCATGGGGAAGGGAAA
118201 ACATACAATATATACATAAGAATGTTATTTCATTCAATGCTTTTAGTACCCCTTCCCTTT

118261 ATATATTTACTATTCATTACATGGAAGTGGATCATCATAAAGGTCTTCATCCTCATTGTC
118261 TATATAAATGATAAGTAATGTACCTTCACCTAGTAGTATTTCCAGAAGTAGGAGTAACAG

118321 CATCATGTTGAGTAGGCTGAGGAGGAGGAGGAGGAGGAGGGATTGGTCTTGCTGTTTTAG
118321 GTAGTACAACTCATCCGACTCCTCCTCCTCCTCCTCCTCCCTAACCAGAACGACAAAATC

118381 GAGTGGCAGAGGCAGAAGAAAGTCCACGTATAAGTGAACTTGTGTAGTTCAAACCCGTGT
118381 CTCACCGTCTCCGTCTTCTTTCAGGTGCATATTCACTTGAACACATCAAGTTTGGGCACA

118441 TGTTCAAGTGTCAACCGTAAATGCAAACTCCACTGGTTTTCAAATTTTACTTTAGAGTTA
118441 ACAAGTTCACAGTTGGCATTTACGTTTGAGGTGACCAAAAGTTTAAAATGAAATCTCAAT

118501 TTTTCCCTCAGCTGATTGGAGTTTTGCTCAACTCCTCTGACTTTAATAATGGCTGCTTCA
118501 AAAAGGGAGTCGACTAACCTCAAAACGAGTTGAGGAGACTGAAATTATTACCGACGAAGT

118561 TTTGTTGAGGTTTTAGAACTTGCTTTTAAGGGATTGCTCTTGACATAATTGCATCAACAG
118561 AAACAACTCCAAAATCTTGAACGAAAATTCCCTAACGAGAACTGTATTAACGTAGTTGTC

118621 ATAGACTGTTTCATGGGAGAAGAATTGTTCTGTTTCATGTCAATACTTACATTGATAAGA
118621 TATCTGACAAAGTACCCTCTTCTTAACAAGACAAAGTACAGTTATGAATGTAACTATTCT

118681 ATGCATCAAGGTAATGTGATCCATCCACTGAAGTTGTCATTAGGCCAGATTTTTTTTAAG
118681 TACGTAGTTCCATTACACTAGGTAGGTGACTTCAACAGTAATCCGGTCTAAAAAAAATTC

118741 TTGAATTATTATTTCACTTCTAGAAATAAGAAGTTTATAAAGTTTAGCATAATTTTAATG
118741 AACTTAATAATAAAGTGAAGATCTTTATTCTTCAAATATTTCAAATCGTATTAAAATTAC

118801 ATCCAGGCTTAGGAAGCATTTACAGCCAAAAAGTAAGTATATATAATTATCATATTATAC
118801 TAGGTCCGAATCCTTCGTAAATGTCGGTTTTTCATTCATATATATTAATAGTATAATATG

118861 TAAAGGGTATAATATGAAAAGTGTTTGAGAGCACAGACTATCTCCTAAAATCAAACTATC
118861 ATTTCCCATATTATACTTTTCACAAACTCTCGTGTCTGATAGAGGATTTTAGTTTGATAG

118921 AAAACCTGCAAGCCAGCAAGGCATGAGTAGGCATGACTCAGATACAAATTAGAAGCATGA
118921 TTTTGGACGTTCGGTCGTTCCGTACTCATCCGTACTGAGTCTATGTTTAATCTTCGTACT

FIG. 4 (cont'd)

```
118981  AATCTCTTTCAGCCATGCATTTAATCATGCTATCCAATATTGTGGAGGTAGTGGCCCCTG
118981  TTAGAGAAAGTCGGTACGTAAATTAGTACGATAGGTTATAACACCTCCATCACCGGGGAC

119041  GAAGTTTACCTTGGGCCAGAGATAGGTATAGAAGCCCCTTTTATGAAGTCATAGACTTGC
119041  CTTCAAATGGAACCCGGTCTCTATCCATATCTTCGGGGAAAATACTTCAGTATCTGAACG

119101  TTTAATTTATGCTCCCAGAATGACTTGCATTAAACTGTGGCAAAATATCTTTGAGTTCTC
119101  AAATTAAATACGAGGGTCTTACTGAACGTAATTTGACACCGTTTTATAGAAACTCAAGAG

119161  ATATTAGCCAGAGGGTTAATATGTAGAAGACAATCATTCATCCTTACAGATTCTCAGAAT
119161  TATAATCGGTCTCCCAATTATACATCTTCTGTTAGTAAGTAGGAATGTCTAAGAGTCTTA

119221  CTTGGAAGAGGTAGGGTTCTTTAAGTTTAGCCACTATTTTAGGTAACTGTAGCTCCTCCT
119221  GAACCTTCTCCATCCCAAGAAATTCAAATCGGTGATAAAATCCATTGACATCGAGGAGGA

119281  TGGTTCTTCAAATGATCCTGAAGGCTGGTATACAAACCAGTTATGCCCTAAAATTAATTG
119281  ACCAAGAAGTTTACTAGGACTTCCGACCATATGTTTGGTCAATACGGGATTTTAATTAAC

119341  GTAGGTAGGCAATGTATAACCTGTCATTGGCTAGTTTTTATTCAAATTTTGGATATGAAA
119341  CATCCATCCGTTACATATTGGACAGTAACCGATCAAAAATAAGTTTAAAACCTATACTTT

119401  GTCTTTGGCATAAGGTGCTAGCACTCAGAGTCAGTAGGTTTTAGTGCTATTCCTTAACTT
119401  CAGAAACCGTATTCCACGATCGTGAGTCTCAGTCATCCAAAATCACGATAAGGAATTGAA

119461  CAGTGGAATTGCCTTAGTATAGCAGAATTGCTTGAGTGTCTTATCTGTTATCACCATATA
119461  GTCACCTTAACGGAATCATATCGTCTTAACGAACTCACAGAATAGACAATAGTGGTATAT

119521  CATGAGTACCCTCAAATTATCTCATTTCCCTTTCTTTTGTAGACAATACACATTCCAACT
119521  GTACTCATGGGAGTTTAATAGAGTAAAGGGAAAGAAAACATCTGTTATGTGTAAGGTTGA

119581  ATGGAGAATGGTCCTAAGCTGGCAAGCCGCATCTTGAGCAAATTAACTGATATCCAGGTA
119581  TACCTCTTACCAGGATTCGACCGTTCGGCGTAGAACTCGTTTAATTGACTATAGGTCCAT

119641  AAGCTTTTCTTTTCTTTTCTTTTCTTTCCTTTTCTTTTCTTTTTTTTATGTCACCTTATT
119641  TTCGAAAAGAAAAGAAAAGAAAAGAAAGGAAAAGAAAAGAAAAAAAATACAGTGGAATAA

119701  TCTGTCAGAGCTTACAACTAAATTATATTTCAATGAAGAGGATTAAATAATACAATTTGA
119701  AGACAGTCTCGAATGTTGATTTAATATAAAGTTACTTCTCCTAATTTATTATGTTAAACT

119761  GATCAATAAGTTAAATTTAAGGAAGATATTCCCAACACAATGTGTGGGCATGAGCAAAGC
119761  CTAGTTATTCAATTTAAATTCCTTCTATAAGGGTTGTGTTACACACCCGTACTCGTTTCG

119821  AGAAATGGGAAAGAAGATGTATGTTTTAAAAAAAGAAAGAAAATATTGTTCAGGACTCCA
119821  TCTTTACCCTTTCTTCTACATACAAAATTTTTTTCTTTCTTTTATAACAAGTCCTGAGGT

119881  CATTACTTAACATTAAAAAATAGATGTAATTTTTGGTAACATTTAAAAATCTCATTAAGA
119881  GTAATGAATTGTAATTTTTTATCTACATTAAAAACCATTGTAAATTTTTAGAGTAATTCT

119941  AGGATAACATAACTTTTGTTAAAAAAAGGAAGAAAAAATTTGAAAGTAGAAGCAACTTCA
119941  TCCTATTGTATTGAAAACAATTTTTTTCCTTCTTTTTTAAACTTTCATCTTCGTTGAAGT

120001  GGAAGAAAATTACAGTGCATGTGATTCCAACACTGAGATATAATCACTGTTAATTTTTTA
120001  CCTTCTTTTAATGTCACGTACACTAAGGTTGTGACTCTATATTAGTGACAATTAAAAAAT

120061  TGTCTTTTTATTTTTGAGCTGGAGTTTCACTCTTGTTGCCCAGGCTGGAGTACGATGGCA
120061  ACAGAAAAATAAAAACTCGACCTCAAAGTGAGAACAACGGGTCCGACCTCATGCTACCGT

120121  CGATCTTGGCTCACTGCAACCTCTGCCTCCCGGGTTCAAGCAATTTTCCTACCTCAGCCT
120121  GCTAGAACCGAGTGACGTTGGAGACGGAGGGCCCAAGTTCGTTAAAAGGATGGAGTCGGA

120181  CCCGAGTAGCTGGGATTATAGGTGTGCGCCACCATGCCCAGCTAATTTTTGTGTTTTTAG
120181  GGGCTCATCGACCCTAATATCCACACGCGGTGGTACGGGTCGATTAAAAACACAAAAATC

120241  TAGAGATGGGATTTCACCATGTTGGCCAGGCTGGTCTTGAACTCCTGACCTAAGGTAATC
120241  ATCTCTACCCTAAAGTGGTACAACCGGTCCGACCAGAACTTGAGGACTGGATTCCATTAG

120301  CACCTGCCTTGGCCTCCTAAATTGTTGGGATTACAGGCATGAACCACTGTGCCCTGCCAT
120301  GTGGACGGAACCGGAGGATTTAACAACCCTAATGTCCGTACTTGGTGACACGGGACGGTA
```

FIG. 4 (cont'd)

```
120361  TTTTTGATGTCTTAACCTTCAATATTTTGTAAGCATTTATATACTTTATTTATTTATTTA
120361  AAAAACTACAGAATTGGAAGTTATAAAACATTCGTAAATATATGAAATAAATAAATAAAT

120421  TTTATTTATTTATTTATTTACTTATTTATTTTTGAGACTAAGTCTCGCTGTGTCACCCAG
120421  AAATAAATAAATAAATAAATGAATAAATAAAAACTCTGATTCAGAGCGACACAGTGGGTC

120481  GCTGGAGAACAGTGGCATGATCTCAGCTCACTACAACCTCCACCTCCTGGGTTCAAGCGA
120481  CGACCTCTTGTCACCGTACTAGAGTCGAGTGATGTTGGAGGTGGAGGACCCAAGTTCGCT

120541  TTCTTCTGCCTCAGCCTCCCGAGTAGCTGGGATTACAGGTCTCATGCCACCGTTCCCGGC
120541  AAGAAGACGGAGTCGGAGGGCTCATCGACCCTAATGTCCAGAGTACGGTGGCAAGGGCCG

120601  TAATTTTTGTATTTTTAGTAGAGATGAGGTTTTGCCCTGTTGGCCAGGCTGGTCTTGAAC
120601  ATTAAAAACATAAAAATCATCTCTACTCCAAAACGGGACAACCGGTCCGACCAGAACTTG

120661  TCTTGACCTCAGGTGATCCACCCGCCTTGGCTTCCCAAAGTGCTGGGATTACAGCCGTGA
120661  AGAACTGGAGTCCACTAGGTGGGCGGAACCGAAGGGTTTCACGACCCTAATGTCGGCACT

120721  GCCACCATGCCCAGCCAGTATACTTTTAGATAGTTATTTTTTCCTAACAAAATGGGATCA
120721  CGGTGGTACGGGTCGGTCATATGAAAATCTATCAATAAAAAAGGATTGTTTTACCCTAGT

120781  TATTGTACATAATTTTGTTACATGTTTTTTCACTGAATAAATGCTTTGCTTTTTTATATC
120781  ATAACATGTATTAAAACAATGTACAAAAAAGTGACTTATTTACGAAACGAAAAAATATAG

120841  AATAAGTAGTTTTCTCCAACACCATTTATAAAGTTTAATTGAATTCCATTATATTGATGT
120841  TTATTCATCAAAAGAGGTTGTGGTAAATATTTCAAATTAACTTAAGGTAATATAACTACA

120901  ACCATAATTTTTTTAAAAAATTATATTATTGAACATTTATGTTGTTGGCAATTTTTTTTT
120901  TGGTATTAAAAAAATTTTTTAATATAATAACTTGTAAATACAACAACCGTTAAAAAAAAA

120961  CACTAGTATGGACAGTACATCCTCGATTACTTCCTAAGGATAAATCTGGGATCAAAGAGT
120961  GTGATCATACCTGTCATGTAGGAGCTAATGAAGGATTCCTATTTAGACCCTAGTTTCTCA

121021  ATACACGTCTATTTTTTCATACTGCTAACTTTGTTTTGCCTATTTTTTTTCTGAGCAATA
121021  TATGTGCAGATAAAAAAGTATGACGATTGAAACAAAACGGATAAAAAAAAGACTCGTTAT

121081  ATCTACAGTAATGCCTCATCAGGCAGTTAAGCAGGCATGCTAAATACCAGATAACACTGG
121081  TAGATGTCATTACGGAGTAGTCCGTCAATTCGTCCGTACGATTTATGGTCTATTGTGACC

121141  GCTACTCAGAAAAGAGATTATCCTGTAATTTGCAAGCATTTCACAAGTTAGAAGACTTTG
121141  CGATGAGTCTTTTCTCTAATAGGACATTAAACGTTCGTAAAGTGTTCAATCTTCTGAAAC

121201  TTGAAGCCAGTTACTATCCTTGTCAATTAGTAAAAATATCCAAGAGGGCCTGAGACTTAC
121201  AACTTCGGTCAATGATAGGAACAGTTAATCATTTTTATAGGTTCTCCCGGACTCTGAATG

121261  ATTGAAAAGTAAAATAAAGTTTGATCATTTGAGTGATGTCGGATGGCATTAAGTCATGAA
121261  TAACTTTTCATTTTATTTCAAACTAGTAAACTCACTACAGCCTACCGTAATTCAGTACTT

121321  ACTAAGTGAAACTTAAAGGTGGCTGAGAATGCAACAGGCCTCCAGAGAGCAATGGAGGTC
121321  TGATTCACTTTGAATTTCCACCGACTCTTACGTTGTCCGGAGGTCTCTCGTTACCTCCAG

121381  CTTGGGTAGTGATAAAAATGGCATTTCTGGCTGGGTGCAGTGGCTCACACCTATAATCCC
121381  GAACCCATCACTATTTTTACCGTAAAGACCGACCCACGTCACCGAGTGTGGATATTAGGG

121441  AACACTATGGGAGGCCAAGACAGGAGGATCGCTTGAGGCCAGGTGTTCAAGACTAGCCTA
121441  TTGTGATACCCTCCGGTTCTGTCCTCCTAGCGAACTCCGGTCCACAAGTTCTGATCGGAT

121501  GGCAACATAGTGAGAACCTTCCTCTAAAAAAAGGGAAATAAAATAAAAATAAAAGTTTAA
121501  CCGTTGTATCACTCTTGGAAGGAGATTTTTTTCCCTTTATTTTATTTTTATTTTCAAATT

121561  AAGAGAGTTTAAAAGGCAGTTTTAAAAGAGACTTACTCAGCAAGTTTTCTGCCAAATTTA
121561  TTCTCTCAAATTTTCCGTCAAAATTTTCTCTGAATGAGTCGTTCAAAAGACGGTTTAAAT

121621  CAGTATTAAAAAGAAAGAAAGTGTGTTTTTGTTTCTGTTTGTTTTTTTGAGACAGAGTCT
121621  GTCATAATTTTTCTTTCTTTCACACAAAAACAAAGACAAACAAAAAAACTCTGTCTCAGA
```

FIG. 4 (cont'd)

```
121681  TACTCTGTTGCTCAGGCTGGGGTGCAGTGGTGCAATCTCAGCTCACTGCAACCCCTGCCT
121681  ATGAGACAACGAGTCCGACCCCACGTCACCACGTTAGAGTCGAGTGACGTTGGGGACGGA

121741  CCTGGGTTCAAGTGATTCTTGTGCCTCAGCCTCCCACACAGCAGGGATTATGGGCATGCA
121741  GGACCCAAGTTCACTAAGAACACGGAGTCGGAGGGTGTGTCGTCCCTAATACCCGTACGT

121801  CCATCATGCCTGGCTAATTTTTGTATTTTTAGTAGAGTCGAGGTTTCGCCATGTTGGCCA
121801  GGTAGTACGGACCGATTAAAAACATAAAAATCATCTCAGCTCCAAAGCGGTACAACCGGT

121861  GGCTGGTCTCAAACTCCTAGCCTCAAGTGATTTGCCCACCTTAGCCTCCCAAAGTGCTGA
121861  CCGACCAGAGTTTGAGGATCGGAGTTCACTAAACGGGTGGAATCGGAGGGTTTCACGACT

121921  GATTACAGGCATGAGCCACCGCACCCTGGCCTTGATTGTGGTTTTTTAATCAATGAGCTG
121921  CTAATGTCCGTACTCGGTGGCGTGGGACCGGAACTAACACCAAAAAATTAGTTACTCGAC

121981  CCATACTTCTGCTCTCCAGCAAAGGTTTTCTATGAGAATTTTCTGTAAGCTAAGTAAAGG
121981  GGTATGAAGACGAGAGGTCGTTTCCAAAAGATACTCTTAAAAGACATTCGATTCATTTCC

122041  AATATCTTAATATTGGAAGAAATAAAATTTAGTCAGAGTTGTTTTCTACCTTTGTACACA
122041  TTATAGAATTATAACCTTCTTTATTTTAAATCAGTCTCAACAAAAGATGGAAACATGTGT

122101  GCAACACTTACAAGTAATTTGAAGAGTAGCTAATAAAAATTTCTGCATGGATGGCTTAGG
122101  CGTTGTGAATGTTCATTAAACTTCTCATCGATTATTTTTAAAGACGTACCTACCGAATCC

122161  CATTTTAATTTTTTTAAGGTTGCCTGAGTAAATCTGAAAATAATAAATTATTACAGTTTT
122161  GTAAAATTAAAAAAATTCCAACGGACTCATTTAGACTTTTATTATTTAATAATGTCAAAA

122221  GCTCAAATAAAGAACACAAATAGAACAAAAAATACATAACTGGCTAGATTACATGAAAGC
122221  CGAGTTTATTTCTTGTGTTTATCTTGTTTTTTATGTATTGACCGATCTAATGTACTTTCG

122281  CTTTTTCCAAAACAGAGGTTTAGAGGCCAGGGCAAATAGGCAGGAAAAATAAATAAAGGG
122281  GAAAAAGGTTTTGTCTCCAAATCTCCGGTCCCGTTTATCCGTCCTTTTTATTTATTTCCC

122341  CATCCAAATTGGAAAAGAAGAAGTTAAATTAGCTTTCTTAGCAGATGACATTATCTTACA
122341  GTAGGTTTAACCTTTTCTTCTTCAATTTAATCGAAAGAATCGTCTACTGTAATAGAATGT

122401  CCTAGAAAAACCTAAAGACTCCCTCAAAAAACCTGTAGAACTGATAAATGAATTCAGTAA
122401  GGATCTTTTTGGATTTCTGAGGGAGTTTTTTGGACATCTTGACTATTTACTTAAGTCATT

122461  AGTTGCAGGATATAAAATCAACATATAAAAATCAGTAGAATTTATATATGCTAACAGTGA
122461  TCAACGTCCTATATTTTAGTTGTATATTTTTAGTCATCTTAAATATATACGATTGTCACT

122521  ACAATCTGAAAAAGAAATCAAGAAAGCAATCCCATTTATAATAGCCACAAAAAGTATAAA
122521  TGTTAGACTTTTTCTTTAGTTCTTTCGTTAGGGTAAATATTATCGGTGTTTTTCATATTT

122581  ATACCTAGGAATCAATCTAACCAAAGACATGAGAGATCTATACAAGGAAAAGTATAAAAC
122581  TATGGATCCTTAGTTAGATTGGTTTCTGTACTCTCTAGATATGTTCCTTTTCATATTTTG

122641  TATGATTTAAAAAATTGAAGAAAACACACAAAGGTGGAAAGATATTCCATATTCATGGAT
122641  ATACTAAATTTTTTAACTTCTTTTGTGTGTTTCCACCTTTCTATAAGGTATAAGTACCTA

122701  TGGAAGAATTAATTTTGTTAAAATGACTATACTACACAAAGCAATTTACAGATTCAATGC
122701  ACCTTCTTAATTAAAACAATTTTACTGATATGATGTGTTTCGTTAAATGTCTAAGTTACG

122761  AATCCCTATTAAAATACTGATGACTTTCTTCACAGAAATAGAAAAAACAATCCTAAAATG
122761  TTAGGGATAATTTTATGACTACTGAAAGAAGTGTCTTTATCTTTTTTGTTAGGATTTTAC

122821  TATATGGAGCTAAAAAGACCCCAAATAGCCAAAGCAATCTTGAGCAAAAAGAACAAAGTT
122821  ATATACCTCGATTTTTCTGGGGTTTATCGGTTTCGTTAGAACTCGTTTTTCTTGTTTCAA

122881  AGAATCACCACACTACCTTACTTCAAAATTTATTATAAAACTATAATAACCAAAACAGCA
122881  TCTTAGTGGTGTGATGGAATGAAGTTTTAAATAATATTTTGATATTATTGGTTTTGTCGT

122941  TAGTACTGATATAAAAACAGACATAGTAGACCAGTGGGACAGAATAGAGAACCCAGATAC
122941  ATCATGACTATATTTTTGTCTGTATCATCTGGTCACCCTGTCTTATCTCTTGGGTCTATG

123001  CTAAGTCCACATGTTTACAACCAACTCATCTTTGACAAAGGTGCCAAGAACTGTAACGGG
123001  GATTCAGGTGTACAAATGTTGGTTGAGTAGAAACTGTTTCCACGGTTCTTGACATTGCCC
```

FIG. 4 (cont'd)

```
123061  GAAGACAGTCTTTTCAATAAATGGTGCTGGGAAAATTGGATAATTATATGCAGAAGAATG
123061  CTTCTGTCAGAAAAGTTATTTACCACGACCCTTTTAACCTATTAATATACGTCTTCTTAC

123121  AAACTAGATTCGCTTCTCTTACCATACACAGAAATCAAATGAAAGTATATTAATGACTTG
123121  TTTGATCTAAGCGAAGAGAATGGTATGTGTCTTTAGTTTACTTTCATATAATTACTGAAC

123181  AATCTTAGACCTGAAACTATGAAATTACTTGAAGAAAACATTAAGGAAATGCTTCAGGAC
123181  TTAGAATCTGGACTTTGATACTTTAATGAACTTCTTTTGTAATTCCTTTACGAAGTCCTG

123241  ATTGGTCTAAGCAAAGATCTCATTCTGTCACTCAGGCTGGAGTGTAGTGGCATGAACCTG
123241  TAACCAGATTCGTTTCTAGAGTAAGACAGTGAGTCCGACCTCACATCACCGTACTTGGAC

123301  GCTCATTGTGGCATTGACCTCCTGGGCTCAAGCAATTCTCCCACCTTGGCTTTCCATGTA
123301  CGAGTAACACCGTAACTGGAGGACCCGAGTTCGTTAAGAGGGTGGAACCGAAAGGTACAT

123361  GCTAGAACCACAGGTGCATGCCACCACATTCCACTAATTTTTAAATTTTTTGTAGAGATG
123361  CGATCTTGGTGTCCACGTACGGTGGTGTAAGGTGATTAAAAATTTAAAAAACATCTCTAC

123421  GAGTCTCACCATCTTGCCCAGGCTGGTCTCGAACTCCTGAACTCAAGGGATCCTCCTGTC
123421  CTCAGAGTGGTAGAACGGGTCCGACCAGAGCTTGAGGACTTGAGTTCCCTAGGAGGACAG

123481  TCAGCCTCCCAAAGTGCTGAGATTACTAGCATAAGCCACTGTCCCTGGCCAGCGAAGATT
123481  AGTCGGAGGGTTTCACGACTCTAATGATCGTATTCGGTGACAGGGACCGGTCGCTTCTAA

123541  TCTTATGTAAGACCTGAAAAAGCATAGGCTATCAAAGCAAAAATAGGCAATTGGGATTAT
123541  AGAATACATTCTGGACTTTTTCGTATCCGATAGTTTCGTTTTTATCCGTTAACCCTAATA

123601  GTCAAGCTGGAAAGCTTCTCCACAGCAAAGAAAACAATCCACAAAGGGAATAGATTACCC
123601  CAGTTCGACCTTTCGAAGAGGTGTCGTTTCTTTTGTTAGGTGTTTCCCTTATCTAATGGG

123661  AAAGAATGGATGAAAATATTTGCAAACTATCAATCTGACAAGGGATTAATAACCAGAGTC
123661  TTTCTTACCTACTTTTATAAACGTTTGATAGTTAGACTGTTCCCTAATTATTGGTCTCAG

123721  TATAAGGAGCTCAAACAACTGTATAGGAAAAATCTAGTAATCTGGTTTTAAAATGGGCAT
123721  ATATTCCTCGAGTTTGTTGACATATCCTTTTTAGATCATTAGACCAAAATTTTACCCGTA

123781  GAGACCTGATTAGAAAACTCAACAGAAAAAAAAATTTGATTAAAAATGGATAAAAGATCT
123781  CTCTGGACTAATCTTTTGAGTTGTCTTTTTTTTTAAACTAATTTTTACCTATTTTCTAGA

123841  GAATGGACATTTCTCAAAAGAAGACAGACAAATGGCCAGGAGGTACATGAAAAAATGCGC
123841  CTTACCTGTAAAGAGTTTTCTTCTGTCTGTTTACCGGTCCTCCATGTACTTTTTTACGCG

123901  AACATCACTAATTATCAGAGAAATGCAAAACAAAACCACAATGTAAAATCCACTTGCCCT
123901  TTGTAGTGATTAATAGTCTCTTTACGTTTTGTTTTGGTGTTACATTTTAGGTGAACGGGA

123961  AGTTAAAATGGCTTGTATTAAAAAAAAAAAAAAAAAACAGGCAATAACAGATGCTGGGAGG
123961  TCAATTTTACCGAACATAATTTTTTTTTTTTTTTTTTGTCCGTTATTGTCTACGACCCTCC

124021  ATGTGGAGAAAGGGAACCATCATATATTGTTGGTTGAAATATAAATAGTACAGCCACTAT
124021  TACACCTCTTTCCCTTGGTAGTATATAACAACCAACTTTATATTTATCATGTCGGTGATA

124081  GGAGAACAGTATGGAGGGTCCTCCAAAAATAAAAGTAGAACTAGAACTTCCGTGTGATCC
124081  CCTCTTGTCATACCTCCCAGGAGGTTTTTATTTTCATCTTGATCTTGAAGGCACACTAGG

124141  AGCAATTCTACCACCGGGTATATATCCAAAAGAAAAAAATTAGTATATCAAAGAGATATC
124141  TCGTTAAGATGGTGGCCCATATATAGGTTTTCTTTTTTTAATCATATAGTTTCTCTATAG

124201  TGCACTCCCATGTTTATTGCAATAGTATTCACAATAGCCAAGATATGGAATTAACCTAAA
124201  ACGTGAGGGTACAAATAACGTTATCATAAGTGTTATCGGTTCTATACCTTAATTGGATTT

124261  TGTCTGTCAACAGATAAATGGATAAAGAGAATGTGGCATAAAGATATATATATATATATA
124261  ACAGACAGTTGTCTATTTACCTATTTCTCTTACACCGTATTTCTATATATATATATATAT

124321  TATACACACACACACACACACACACACAATGTGGTACTATTCAGCCATAAAAAAGAATGA
124321  ATATGTGTGTGTGTGTGTGTGTGTGTGTTACACCATGATAAGTCGGTATTTTTTCTTACT
```

FIG. 4 (cont'd)

```
124381  AATCCTGTCATTTGCAGCAACATGTATGGAACTGGAGGCCATTTTGTTAAGTGAAATAAG
124381  TTAGGACAGTAAACGTCGTTGTACATACCTTGACCTCCGGTAAAACAATTCACTTTATTC

124441  CGAGGGACCGAAAGACAAACATCACATGTTCTCATGCAGGTGCTAAAAAAGTAGATCCTA
124441  GCTCCCTGGCTTTCTGTTTGTAGTGTACAAGAGTACGTCCACGATTTTTTCATCTAGGAT

124501  TGAAGACAGAGAGTAGATTAGAGGTTACCAGAGGCCGAGAAGGGGAGTGGGAAGTAGAGG
124501  ACTTCTGTCTCTCATCTAATCTCCAATGGTCTCCGGCTCTTCCCCTCACCCTTCATCTCC

124561  ATAAAGGAAAAAAACAAGAATATAAATGTATTTATTACCATTAAACTGAACATTTAAAAA
124561  TATTTCCTTTTTTTGTTCTTATATTTACATAAATAATGGTAATTTGACTTGTAAATTTTT

124621  TTGTAAAGATGGTAAATTATATATGTGTATTTTATCTTAATTAAAATTTTAAAAATCAGG
124621  AACATTTCTACCATTTAATATATACACATAAAATAGAATTAATTTTAAAATTTTTAGTCC

124681  AGTTTAGAAATTTTTAAGAGAAGTGTGCCCATAGTGATAAGAAAGAAAGACCCTTTTGGA
124681  TCAAATCTTTAAAAATTCTCTTCACACGGGTATCACTATTCTTTCTTTCTGGGAAAACCT

124741  AAATTTTCTTGAACAAATTATACAGTATTTTCTTAAACAAATTGTACATTCTGTAGCAGT
124741  TTTAAAAGAACTTGTTTAATATGTCATAAAAGAATTTGTTTAACATGTAAGACATCGTCA

124801  TAATACACCAAATAAGATTTCAGGGTTACCTCTTGGAGATTGTATGAAATAAAAACATTT
124801  ATTATGTGGTTTATTCTAAAGTCCCAATGGAGAACCTCTAACATACTTTATTTTTGTAAA

124861  AGGTGGGCATGATGGCTCATTCCTGTAATCCTAAAACTTTGGGAGGCTGATGCAGGAACA
124861  TCCACCCGTACTACCGAGTAAGGACATTAGGATTTTGAAACCCTCCGACTACGTCCTTGT

124921  ATACTTGAGGCTAGTACTTCAAGACGAGCCTAGGCAACATAGTAAGACCCAGTCTCCACA
124921  TATGAACTCCGATCATGAAGTTCTGCTCGGATCCGTTGTATCATTCTGGGTCAGAGGTGT

124981  AAACAACCAAAAAAAATAGCAAGTGTGGTGGCACACACCTGTAGTTCCAGCTACTCAGGA
124981  TTTGTTGGTTTTTTTTATCGTTCACACCACCGTGTGTGGACATCAAGGTCGATGAGTCCT

125041  GGCTGAGGCAGGAGGAACACTTGAGGCCAGGAATGTGAGACTGCAGTGGGCTATGATTGT
125041  CCGACTCCGTCCTCCTTGTGAACTCCGGTCCTTACACTCTGACGTCACCCGATACTAACA

125101  GCCACAGCACTCCACTCCAGCCTTCACTGTAGAAAGAGACCCTGTCTCGAAAGGAAGGAG
125101  CGGTGTCGTGAGGTGAGGTCGGAAGTGACATCTTTCTCTGGGACAGAGCTTTCCTTCCTC

125161  GGAGGGAGGGAGGGAGGGAGGGAGGGAGGGAATGAAGGAAGGAAGGAAGGAAGGAAGGAA
125161  CCTCCCTCCCTCCCTCCCTCCCTCCCTCCCTTACTTCCTTCCTTCCTTCCTTCCTTCCTT

125221  GGAAGGAAATGTAAACTCATTTGATTTGGCTGTAAAGGATTAATAGAAAAGGAAAACGTA
125221  CCTTCCTTTACATTTGAGTAAACTAAACCGACATTTCCTAATTATCTTTTCCTTTTGCAT

125281  GTCACTAGGCTGAGAAAAAATTGAACTCTATTGAATTGGTATAAAGATCTAAGTGGAGGTG
125281  CAGTGATCCGACTCTTTTTAACTTGAGATAACTTAACCATATTTCTAGATTCACCTCCAC

125341  TTTGGCAGACATGATCATGAAGCTTTCACTGAGGAAGGAAACTCTAGGAGGCAAAAGCAG
125341  AAACCGTCTGTACTAGTACTTCGAAAGTGACTCCTTCCTTTGAGATCCTCCGTTTTCGTC

125401  AAATGCAACTCATCAAAATTGAAATGGTGACAAAATATGTGCATTCAAACCTGAAAGTGA
125401  TTTACGTTGAGTAGTTTTAACTTTACCACTGTTTTATACACGTAAGTTTGGACTTTCACT

125461  CTGAAAGAGAAGCCCAAACACACAATTTTGGGGTAAGATGGGAAACCATTACCAAAGTTC
125461  GACTTTCTCTTCGGGTTTGTGTGTTAAAACCCCATTCTACCCTTTGGTAATGGTTTCAAG

125521  TCAGAAAGAGCATTTTTAAAAGTAAGATTATAGAAGCCAAAAGGATATGTAGTAGTCTGT
125521  AGTCTTTCTCGTAAAAATTTTCATTCTAATATCTTCGGTTTTCCTATACATCATCAGACA

125581  TCTCACACTGCTGTAACGAACTACCTGAGACTGGGTAGTTTGTAAAGAAAAGAGGTTTTA
125581  AGAGTGTGACGACATTGCTTGATGGACTCTGACCCATCAAACATTTCTTTTCTCCAAAAT

125641  TTGACGCTCAGTTCTGCAGGCCATACAGGAGACATGGCTGGGGAGGCCTCAGGAAACTTA
125641  AACTGCGAGTCAAGACGTCCGGTATGTCCTCTGTACCGACCCCTCCGGAGTCCTTTGAAT

125701  CAGTCATGGCGGAAGGCAAAGGGGAAGCCAGTACATATTACATGGTGGGAACAGGAGGAG
125701  GTCAGTACCGCCTTCCGTTTCCCCTTCGGTCATGTATAATGTACCACCCTTGTCCTCCTC
```

FIG. 4 (cont'd)

```
125761  GAGAGGGAGGGTGGGAGGTGCCACTCACTTTTTAAAACAAACAGATCTCCTTAGAACTCA
125761  CTCTCCCTCCCACCCTCCACGGTGAGTGAAAAATTTTGTTTGTCTAGAGGAATCTTGAGT

125821  CTCACTATCATGAGAACAGCAAGGGGGAGGTTTGCTCCCATGATGCAATTACCTGACACC
125821  GAGTGATAGTACTCTTGTCGTTCCCCCTCCAAACGAGGGTACTACGTTAATGGACTGTGG

125881  AGGCCCTTCCTCCAACATGGGGGATTACAATTCCACATGAGATTTGGGTGGGGACACAAA
125881  TCCGGGAAGGAGGTTGTACCCCCTAATGTTAAGGTGTACTCTAAACCCACCCCTGTGTTT

125941  TTCAAACCATATCAGAATGTTAGTGACTAAAGTAAATGTTCTTGTTTAACTCTTTAATGT
125941  AAGTTTGGTATAGTCTTACAATCACTGATTTCATTTACAAGAACAAATTGAGAAATTACA

126001  GTATATTGAGTGCAAGCCATATGCAGGGGCTATTCTAGGTACTGGTGGTTTACTCAAGAA
126001  CATATAACTCACGTTCGGTATACGTCCCCGATAAGATCCATGACCACCAAATGAGTTCTT

126061  AAAGGGGGCAAAAAAATGAAGAAGGTGGCCAGGCATGGTGGCTTACGCCTGTAATCCCAA
126061  TTTCCCCCGTTTTTTTACTTCTTCCACCGGTCCGTACCACCGAATGCGGACATTAGGGTT

126121  CACTTTGGGAGACTGAGACGTGAGAATTGCTTGAGCCCAGGAGTTTGAGATCAGCCTGGT
126121  GTGAAACCCTCTGACTCTGCACTCTTAACGAACTCGGGTCCTCAAACTCTAGTCGGACCA

126181  AACATGGCAAATCCCTGTCTCTACAAAAAAATGCAAACAAACAAACAAACAAACAAACAA
126181  TTGTACCGTTTAGGGACAGAGATGTTTTTTTACGTTTGTTTGTTTGTTTGTTTGTTTGTT

126241  ATTAATCGGGCATGGTGTCACATGTCTGTAGTCCCAGCTACAGGTTGAGGTGGGAAGATG
126241  TAATTAGCCCGTACCACAGTGTACAGACATCAGGGTCGATGTCCAACTCCACCCTTCTAC

126301  CCTTAAGCCTAGGGAGGTTGAGGCTGCAGTCAGCCATGATAGCACCACTGCACTCCAGCC
126301  GGAATTCGGATCCCTCCAACTCCGACGTCAGTCGGTACTATCGTGGTGACGTGAGGTCGG

126361  TGGGCAACAGAGTGAGACCCCATCTGAAAAAAAAAGAAGTCAAAACAAATGAAAAAAAAA
126361  ACCCGTTGTCTCACTCTGGGGTAGACTTTTTTTTTCTTCAGTTTTGTTTACTTTTTTTTT

126421  AAAAAGTCAAAACAAATATTCAGTGTAAATGTGAGACCATGTAAAAAAGTTTAAAAGTAA
126421  TTTTTCAGTTTTGTTTATAAGTCACATTTACACTCTGGTACATTTTTTCAAATTTTCATT

126481  AATATATAGTTTAAGCAGAGGATGGGAGACGGGGAAAAAACCTTTTCTCCCTAACTTTAT
126481  TTATATATCAAATTCGTCTCCTACCCTCTGCCCCTTTTTTGGAAAAGAGGGATTGAAATA

126541  ATACTCCCTCTATAAATTAGTGCTTATGGCCAATAAGAAATGAATAATTTCTTTTTTCAC
126541  TATGAGGGAGATATTTAATCACGAATACCGGTTATTCTTTACTTATTAAAGAAAAAAGTG

126601  CGTTGGTAGTAAAGTATAATGGTAGTTAACACAAAAAACTAAATGATATATTCAGAACCT
126601  GCAACCATCATTTCATATTACCATCAATTGTGTTTTTTGATTTACTATATAAGTCTTGGA

126661  CATACTAAACAAAGAAACAAAGGCATGCAATCACAGGACAGGTGGAAACAGTGGTTCTGA
126661  GTATGATTTGTTTCTTTGTTTCCGTACGTTAGTGTCCTGTCCACCTTTGTCACCAAGACT

126721  ACTAACCACAAACCAGAACTACCAAATGTGCTACAAATTGTTTAGTAACAAAGGACCATC
126721  TGATTGGTGTTTGGTCTTGATGGTTTACACGATGTTTAACAAATCATTGTTTCCTGGTAG

126781  CCTTCAGAATTGAAGAGCACGTCTCAGTTATCTCATGCCTATGTGCATGGAACTTAAAGT
126781  GGAAGTCTTAACTTCTCGTGCAGAGTCAATAGAGTACGGATACACGTACCTTGAATTTCA

126841  CTCAAAATTACTCTTACAAGATGGCAAATTGAGGCTGTCAGCTAAGCTCCTAGATTGTCT
126841  GAGTTTTAATGAGAATGTTCTACCGTTTAACTCCGACAGTCGATTCGAGGATCTAACAGA

126901  GTTTCTCCAAGAAAAATAAATTTCAGTAATTATTAAGGAAAAAGCATAGAATTGCATCAT
126901  CAAAGAGGTTCTTTTTATTTAAAGTCATTAATAATTCCTTTTTCGTATCTTAACGTAGTA

126961  GTTTTACATTTCATTACTTTTGGCATGACATGGGAGCATGGATGTTTTCTACAAAGTGCT
126961  CAAAATGTAAAGTAATGAAAACCGTACTGTACCCTCGTACCTACAAAAGATGTTTCACGA

127021  CTGATAAATTGAAGAAGAGGCCAACAACAGCCACCGAAAAAACCTTCAAGATTCTTGCCA
127021  GACTATTTAACTTCTTCTCCGGTTGTTGTCGGTGGCTTTTTTGGAAGTTCTAAGAACGGT
```

FIG. 4 (cont'd)

```
127081  GTATGGCTCAGGGGAAAAATTCCCTCATAACCACAGATTTGACTTTTCAACTTCTGTACT
127081  CATACCGAGTCCCCTTTTTAAGGGAGTATTGGTGTCTAAACTGAAAAGTTGAAGACATGA

127141  TCTGCATATGAGTAATAATCTCTGAGGTTAAGTATTCATCCCATTTAGCTAATTGTCCAC
127141  AGACGTATACTCATTATTAGAGACTCCAATTCATAAGTAGGGTAAATCGATTAACAGGTG

127201  ATAACTCCCTGGGTCTTAGATTGCTCTATAAATACCTCCTAAGAGAAGAATTTTTCAAAT
127201  TATTGAGGGACCCAGAATCTAACGAGATATTTATGGAGGATTCTCTTCTTAAAAAGTTTA

127261  GACAGTTTCGTTTTTCCTTTTTCTTCTTTTAAAGCAACAAAGAAAAGCACGTCTGTGTTT
127261  CTGTCAAAGCAAAAAGGAAAAAGAAGAAAATTTCGTTGTTTCTTTTCGTGCAGACACAAA

127321  ATATTTAACCAAACTTAAACTTGGAGAGCATTGGCCGTGTTGTCGACGTGTTTCTTTTCT
127321  TATAAATTGGTTTGAATTTGAACCTCTCGTAACCGGCACAACAGCTGCACAAAGAAAAGA

127381  CTACTGTTAAATTCCTTACTGTTCCAGTTACTCACCATCATACTCACCTTTGCCTCTGCC
127381  GATGACAATTTAAGGAATGACAAGGTCAATGAGTGGTAGTATGAGTGGAAACGGAGACGG

127441  ACTTGGGGTCCTCTGTTCTGCAGTTGTGTTCTGCTCTCTGATGCCTCCAGGTTTTGCTGC
127441  TGAACCCCAGGAGACAAGACGTCAACACAAGACGAGAGACTACGGAGGTCCAAAACGACG

127501  ACCTTCTAGAAATTGCTCACCTGGATAAGGCCTTGGCTGTCCTTTATGACTCATCTCGTT
127501  TGGAAGATCTTTAACGAGTGGACCTATTCCGGAACCGACAGGAAATACTGAGTAGAGCAA

127561  CAGAAGCCTTTTGAATCTCTCTTGAAGAATATTCCCTTTGCTCAGTCCAAATACACATTC
127561  GTCTTCGGAAAACTTAGAGAGAACTTCTTATAAGGGAAACGAGTCAGGTTTATGTGTAAG

127621  ACTCACTTGAATGCTGCTTCTTCCTCCAGTTTCACAGTGCTGGGGATGATCCCGTAAGGC
127621  TGAGTGAACTTACGACGAAGAAGGAGGTCAAAGTGTCACGACCCCTACTAGGGCATTCCG

127681  CTTTAAATTACATTATAATTAGTCATGCACTTCTCTCTGCTCTGGGGCTGTTTGAATCGT
127681  GAAATTTAATGTAATATTAATCAGTACGTGAAGAGAGACGAGACCCCGACAAACTTAGCA

127741  TCACTCTCTTTATACCTCCAGTGTTCAGCACAGAGCCTAGGGTATAATGCGTATGCAGTA
127741  AGTGAGAGAAATATGGAGGTCACAAGTCGTGTCTCGGATCCCATATTACGCATACGTCAT

127801  ATGTTTCTTGAAGGAGTGAATGGGCAAGTGAAACACCAAACAAATACTAAAGAGCAAAAC
127801  TACAAAGAACTTCCTCACTTACCCGTTCACTTTGTGGTTTGTTTATGATTTCTCGTTTTG

127861  ATGTATTGCTCTTGTATATTAACACATTCCGAGAAGAGATGGGAGGAAGGTCTTGAATAA
127861  TACATAACGAGAACATATAATTGTGTAAGGCTCTTCTCTACCCTCCTTCCAGAACTTATT

127921  TATCAAATTATTTCTTAAGAGATCTTGATTTAGATTTTTTTCAAAATGAGATACATGTTG
127921  ATAGTTTAATAAAGAATTCTCTAGAACTAAATCTAAAAAAAGTTTTACTCTATGTACAAC

127981  ACACTGCTGTCAACAAATAATCACATAAAAGCTAGAGCCTGGCTTTTAAGTATCAGGGGG
127981  TGTGACGACAGTTGTTTATTAGTGTATTTTCGATCTCGGACCGAAAATTCATAGTCCCCC

128041  AGCATGTGTGAATAATCAGCATTGCTGCTGTTGAAGCTCCATAAAGTGGGAAGCAGCGAC
128041  TCGTACACACTTATTAGTCGTAACGACGACAACTTCGAGGTATTTCACCCTTCGTCGCTG

128101  TGCAAAGATCCAGAGATGGACATCTGAAGCATAGGAAAGGGGCAGCTTGAATGAGATAGG
128101  ACGTTTCTAGGTCTCTACCTGTAGACTTCGTATCCTTTCCCCGTCGAACTTACTCTATCC

128161  AGCAGGATCTGTATTGATTGCAGGTCACCAGATAGAATTAAAAAAATCTATGTTCTCACT
128161  TCGTCCTAGACATAACTAACGTCCAGTGGTCTATCTTAATTTTTTTAGATACAAGAGTGA

128221  AGTGGCTACAGTTTTCAAGGACAAATGACTATTAGTGGTTATTGTATTTTTCTTGTTTTC
128221  TCACCGATGTCAAAAGTTCCTGTTTACTGATAATCACCAATAACATAAAAAGAACAAAAG

128281  AATGGAGCAGCTCCATGACTTAGTTACATAAGAAGTTAAAGGCTCCACCCCCTTCCCTAC
128281  TTACCTCGTCGAGGTACTGAATCAATGTATTCTTCAATTTCCGAGGTGGGGGAAGGGATG

128341  CAATGTCTTAAGCTGTCCTCCGTGTGCATACAAACTTTGTTTCCAGACTGCCCTCGTGTG
128341  GTTACAGAATTCGACAGGAGGCACACGTATGTTTGAAACAAAGGTCTGACGGGAGCACAC

128401  ACTCAGTCCCTGGACCAGCTTCCCAGCCCCTTCTGTTTCCAGCACATCCTCCTCCACGTG
128401  TGAGTCAGGGACCTGGTCGAAGGGTCGGGGAAGACAAAGGTCGTGTAGGAGGAGGTGCAC
```

FIG. 4 (cont'd)

```
128461  TTACAGGATTACAAAGCTTTGCACAGCCTTTCAATAGGGTTTAGAGCAAGAATGACAGAT
128461  AATGTCCTAATGTTTCGAAACGTGTCGGAAAGTTATCCCAAATCTCGTTCTTACTGTCTA

128521  TGCTACCTGGTAGGCAGCACTGACTATAGTTTTATTGGCGTTGCGTAGAGTGACTGCATG
128521  ACGATGGACCATCCGTCGTGACTGATATCAAAATAACCGCAACGCATCTCACTGACGTAC

128581  ACATGCAGGTTGTGCTTTTGTTTTGCCAGGAATTTAAAGGCATTTAGCAAAGCCGTATGA
128581  TGTACGTCCAACACGAAAACAAAACGGTCCTTAAATTTCCGTAAATCGTTTCGGCATACT

128641  AATTATCTGCCTTATGTACCTCGAATGTGAGGTAATGAACTTGTCATTAGTCGTGTTTTA
128641  TTAATAGACGGAATACATGGAGCTTACACTCCATTACTTGAACAGTAATCAGCACAAAAT

128701  GTTTAGTGTTCTCGCTGGAATTTGCAAAAGATTAAAATTCTGCACATTTCATTAAGTCTT
128701  CAAATCACAAGAGCGACCTTAAACGTTTTCTAATTTTAAGACGTGTAAAGTAATTCAGAA

128761  CCACATGGGCTCAAAATACCATCCCGCAGGCTCGACCTGACTTGCCACGTTGCTTTGACA
128761  GGTGTACCCGAGTTTTATGGTAGGGCGTCCGAGCTGGACTGAACGGTGCAACGAAACTGT

128821  CCATCTCTGATTCCAGTGAACAAAACTAAGTAAGTGTGACTTACAGCCGCCCTACCAAAC
128821  GGTAGAGACTAAGGTCACTTGTTTTGATTCATTCACACTGAATGTCGGCGGGATGGTTTG

128881  ATTGAAGGTGTGAGCCTGCACTGTTGTTTTGTAATGACAATGACAAGAGTATAATGACAA
128881  TAACTTCCACACTCGGACGTGACAACAAAACATTACTGTTACTGTTCTCATATTACTGTT

128941  GAGTATAATGACATCCTAGTCCATGAAGACATGTTTTCTCTTTTCCCTCCCTCTATGTAT
128941  CTCATATTACTGTAGGATCAGGTACTTCTGTACAAAAGAGAAAAGGGAGGGAGATACATA

129001  ACTTACTTACTCTTAAGGAAATAATATAATTTCTATTTCTGCTTAAATCTGCCATCTCTA
129001  TGAATGAATGAGAATTCCTTTATTATATTAAAGATAAAGACGAATTTAGACGGTAGAGAT

129061  CTTAGAATTATTTTCCCTTGAAAAATTAAATTGCATTATCCATCAGCCAAATGGAAAATC
129061  GAATCTTAATAAAAGGGAACTTTTTAATTTAACGTAATAGGTAGTCGGTTTACCTTTTAG

129121  TGATTACTAAATGCCTACTTCTAGACATTATGAATTACCTGTAATATCACATTTCTTGGG
129121  ACTAATGATTTACGGATGAAGATCTGTAATACTTAATGGACATTATAGTGTAAAGAACCC

129181  CACTTCTCAGAATGCTATGATTTTACATAAAAGCATAAATTACAGAATGAGAAGAGTAAA
129181  GTGAAGAGTCTTACGATACTAAAATGTATTTTCGTATTTAATGTCTTACTCTTCTCATTT

129241  GCTTAGTGCATATTATGCAGGTTCGCAGAGTGATATGTGGCCTACGACTGTCATTGTAAT
129241  CGAATCACGTATAATACGTCCAAGCGTCTCACTATACACCGGATGCTGACAGTAACATTA

129301  CAAAATTGATTTTTGATCATTTATAAAACTAAAACAACTAATTGAAAGCAAATTTACTTT
129301  GTTTTAACTAAAAACTAGTAAATATTTTGATTTTGTTGATTAACTTTCGTTTAAATGAAA

129361  AACTGATGAAATTCAAGATGAAGTGACAGTAGTCATGAATCACAGTTCTGTAGATCTGCT
129361  TTGACTACTTTAAGTTCTACTTCACTGTCATCAGTACTTAGTGTCAAGACATCTAGACGA

129421  AAAATGCCAATGAACTGTTATTAATGGTGAAAGTGTTTAATATATTAATGGGAATCCAAG
129421  TTTTACGGTTACTTGACAATAATTACCACTTTCACAAATTATATAATTACCCTTAGGTTC

129481  TAAGGAAAATAAAACACATATTTTGCCCTTACCTTAAGTCATGTTGACATCATACATAAA
129481  ATTCCTTTTATTTTGTGTATAAAACGGGAATGGAATTCAGTACAACTGTAGTATGTATTT

129541  TCAGGTAGAATTTGAAGATGTTTCATCCAGCATTCATCATGAAGCAACAGAGTCAATAGC
129541  AGTCCATCTTAAACTTCTACAAAGTAGGTCGTAAGTAGTACTTCGTTGTCTCAGTTATCG

129601  GGGCAGTTACAGTCTGTAGGCAATGCTTTCTGGTGTGGATTATGCAAGAAACTTACAGTC
129601  CCCGTCAATGTCAGACATCCGTTACGAAAGACCACACCTAATACGTTCTTTGAATGTCAG

129661  ATTTGGCTTCCTTTATTCCCCTTTGCATGTAAACTACCAGGTGGTAGGTAGACCCATTCT
129661  TAAACCGAAGGAAATAAGGGGAAACGTACATTTGATGGTCCACCATCCATCTGGGTAAGA

129721  TGGCTGCCAGTATTTTTACCACTTGGATAGATTCTGCTCTCTGAGGTCTTTAAGACAAAC
129721  ACCGACGGTCATAAAAATGGTGAACCTATCTAAGACGAGAGACTCCAGAAATTCTGTTTG
```

FIG. 4 (cont'd)

```
129781 ACAGCACATGTACATTGTGATATAGGAGAAAGAACATCAGACAGAGGCAGAGAACTGGGC
129781 TGTCGTGTACATGTAACACTATATCCTCTTTCTTGTAGTCTGTCTCCGTCTCTTGACCCG

129841 TTGTCAAAATTAAGGGTGACCTAGAGCCTTAGTGTCCTTATATGTAAGATGAGAAGCTTG
129841 AACAGTTTTAATTCCCACTGGATCTCGGAATCACAGGAATATACATTCTACTCTTCGAAC

129901 GATTAAAATTCATTGCTCCTTACACTTGATTTTTATGCAGCAGAACTTTCTTCAAAAGAG
129901 CTAATTTTAAGTAACGAGGAATGTGAACTAAAAATACGTCGTCTTGAAAGAAGTTTTCTC

129961 ATCACTCCTGGAATCCCAATATACAAAATGGATAAAAGTAGGATTGTTCTGAAGTAAAGA
129961 TAGTGAGGACCTTAGGGTTATATGTTTTACCTATTTTCATCCTAACAAGACTTCATTTCT

130021 AGTAAAATCCAGAGCCCCACTTATTTGAGTCATCTCCTACCTTTTAGATGGTTATTAACA
130021 TCATTTTAGGTCTCGGGGTGAATAAACTCAGTAGAGGATGGAAAATCTACCAATAATTGT

130081 TTGTTTCTAGTTCAGAAATTCTGATGTTTTATATTAATTTAAACTAAAGTTAAATTAGGA
130081 AACAAAGATCAAGTCTTTAAGACTACAAAATATAATTAAATTTGATTTCAATTTAATCCT

130141 CTAGAAGAGCCATTTCGTGTGAAAATAGACATAGTCTGAGTGATTTAGGCAAACCCATAG
130141 GATCTTCTCGGTAAAGCACACTTTTATCTGTATCAGACTCACTAAATCCGTTTGGGTATC

130201 TGACAGATTTAGTGGCCTGATACACTGGCTTGGAAAGATCTGTTCCAAGTCAGTCTCAAT
130201 ACTGTCTAAATCACCGGACTATGTGACCGAACCTTTCTAGACAAGGTTCAGTCAGAGTTA

130261 ACACAAGGCTCGGTGAACACATGGCGAGCAGTCTTGGTGGTGGTCAAGAACATGGAATTT
130261 TGTGTTCCGAGCCACTTGTGTACCGCTCGTCAGAACCACCACCAGTTCTTGTACCTTAAA

130321 GCTGTGAGAGAGAGCTTGGTTAGGGTCTGGGCTCTTCCATCTGTTAACTGCAAACTTGAG
130321 CGACACTCTCTCTCGAACCAATCCCAGACCCGAGAAGGTAGACAATTGACGTTTGAACTC

130381 CAAGTTATTCAATCTCCCTAATATTCAGTTTTCTCATTCATAAAATGGATTGATAATGGT
130381 GTTCAATAAGTTAGAGGGATTATAAGTCAAAAGAGTAAGTATTTTACCTAACTATTACCA

130441 ACCTTCTATGTACAGTTACTGTGGGTATTAAATGAGGTAATAAGCCTGTAAAACTCCTGG
130441 TGGAAGATACATGTCAATGACACCCATAATTTACTCCATTATTCGGACATTTTGAGGACC

130501 CATGATGACATTGGCCTACATTAATTGCTCACAGAGTGAGAACTTATTATAAACACAGGC
130501 GTACTACTGTAACCGGATGTAATTAACGAGTGTCTCACTCTTGAATAATATTTGTGTCCG

130561 ATTTTTGTTGAATGACTGACTGATTGAATGAATGAATATAGAACTAGCTTTCTATTTGTG
130561 TAAAAACAACTTACTGACTGACTAACTTACTTACTTATATCTTGATCGAAAGATAAACAC

130621 ATGTATGGAATATCTCTATTTCATTTAATTTCATTTTGAATATTAAAATTCAGGCTTGCT
130621 TACATACCTTATAGAGATAAAGTAAATTAAAGTAAAACTTATAATTTTAAGTCCGAACGA

130681 TTTAAACCAAAGTATTTGCTGATGCAAAGAATGAAATTCTGACTATGATACAGTTACATA
130681 AAATTTGGTTTCATAAACGACTACGTTTCTTACTTTAAGACTGATACTATGTCAATGTAT

130741 ACTTTTGAAGAAATAAGAAAAATGCTAACACAGCATGAACAACTTTGATTTAGAGAACAG
130741 TGAAAACTTCTTTATTCTTTTTACGATTGTGTCGTACTTGTTGAAACTAAATCTCTTGTC

130801 AGTCTCTGTTAAAATCCATGGGACTTGTCAACTTCATATTTTTGTTTATGAGCATAAAAC
130801 TCAGAGACAATTTTAGGTACCCTGAACAGTTGAAGTATAAAAACAAATACTCGTATTTTG

130861 ACTCTTTAGTGCATGTCGGAATCATTTGATGCTTGCTGAATCACAGGTTGCTGGAACCCA
130861 TGAGAAATCACGTACAGCCTTAGTAAACTACGAACGACTTAGTGTCCAACGACCTTGGGT

130921 TCCCCAGATTCTGATTCAGTCTGAGATGAGGTCTGGGAATTTGCATTTTTAACTTGTTGT
130921 AGGGGTCTAAGACTAAGTCAGACTCTACTCCAGACCCTTAAACGTAAAAATTGAACAACA

130981 CTGGTGATGCTGATGCTAGTGGTCTGAGAATACACTTTGAGGATCACTTTTTCACAGTAA
130981 GACCACTACGACTACGATCACCAGACTCTTATGTGAAACTCCTAGTGAAAAAGTGTCATT

131041 AAGTCACAGTCATTAAGCAAGTTAACTCAATGAGAAATGATAATGAAAAGGCATGTACCT
131041 TTCAGTGTCAGTAATTCGTTCAATTGAGTTACTCTTTACTATTACTTTTCCGTACATGGA

131101 AAATAGATAAAGGACCTATACCAGCTATGAATTTGAGTTCAGCAATAATTGTAAAATTTG
131101 TTTATCTATTTCCTGGATATGGTCGATACTTAAACTCAAGTCGTTATTAACATTTTAAAC
```

FIG. 4 (cont'd)

```
131161  TAATTCTTTTCAGGTATTTGGTTTTTAAAAAACTCCCTATGTATGCTTTTATCTTATGTT
131161  ATTAAGAAAAGTCCATAAACCAAAAATTTTTTGAGGGATACATACGAAAATAGAATACAA

131221  TTATATGGTGTCCCTCTTTTCCTCTCTTTCTCTCTAATCCAGTTTTTAATGTGAACATGT
131221  AATATACCACAGGGAGAAAAGGAGAGAAAGAGAGATTAGGTCAAAAATTACACTTGTACA

131281  TTAATGTGAAAATGTTGTTCAAAGCAGAAGCGAACCTTTTGTGTAACCTTGGCGGTATTA
131281  AATTACACTTTTACAACAAGTTTCGTCTTCGCTTGGAAAACACATTGGAACCGCCATAAT

131341  AGTTTGTTTGTAAGCTATTTCTGCCCTGTTAGCTTCTGTACTGAAACACGTTTTCTTGCT
131341  TCAAACAAACATTCGATAAAGACGGGACAATCGAAGACATGACTTTGTGCAAAAGAACGA

131401  TTTGTTGCAGTATGGAAGAGAAGAGAGCGACTGGACAATTGTGCTATCCTGAATGGAAAA
131401  AAACAACGTCATACCTTCTCTTCTCTCGCTGACCTGTTAACACGATAGGACTTACCTTTT

131461  TAGAGGATACAATGGAAAATAGAGGATACCAACTGTATGCTACTGGGACAGACTGTTGCA
131461  ATCTCCTATGTTACCTTTTATCTCCTATGGTTGACATACGATGACCCTGTCTGACAACGT

131521  TTTGAATTGTGATAGATTTCTTTGGCTACCTGTGCATAATGTAGTTTGTAGTATCAATGT
131521  AAACTTAACACTATCTAAAGAAACCGATGGACACGTATTACATCAAACATCATAGTTACA

131581  GTTACAAGAGTGATTGTTTCTTCATGCCAGAGAAAATGAATTGCAATCATCAAATGGTGT
131581  CAATGTTCTCACTAACAAAGAAGTACGGTCTCTTTTACTTAACGTTAGTAGTTTACCACA

131641  TTCATAACTTGGTAGTAGTAACTTACCTTACCTTACCTAGAAAAACATTAATGTAAGCCA
131641  AAGTATTGAACCATCATCATTGAATGGAATGGAATGGATCTTTTTGTAATTACATTCGGT

131701  TATAACATGGGATTTTCCTCAATGATTTTAGTGCCTCCTTTTGTACTTCACTCAGATACT
131701  ATATTGTACCCTAAAAGGAGTTACTAAAATCACGGAGGAAAACATGAAGTGAGTCTATGA

131761  AAATAGTAGTTTATTCTTTAATATAAGTTACATTCTGCTCCTCAAACAAATGCAATTTTT
131761  TTTATCATCAAATAAGAAATTATATTCAATGTAAGACGAGGAGTTTGTTTACGTTAAAAA

131821  TGTGTGTGTTTGAAAGCTAATTTGAGAAAATTTCATAGGTTACATTTCCTGCAGCCTATC
131821  ACACACACAAACTTTCGATTAAACTCTTTTAAAGTATCCAATGTAAAGGACGTCGGATAG

131881  TTTATCCACAGAAAGTGTTTTCTTTTTTTTAAATCAAGACTTTTAAAACTGGATTTCCTC
131881  AAATAGGTGTCTTTCACAAAAGAAAAAAAATTTAGTTCTGAAAATTTTGACCTAAAGGAG

131941  CCATCACTGTTTTTTGAAGGTCCTCCAAGTCCGTGTTAAGGTAAATATCTGTTTTCTTCC
131941  GGTAGTGACAAAAAACTTCCAGGAGGTTCAGGCACAATTCCATTTATAGACAAAAGAAGG

132001  TGATGTCACAGCCTGAGCATACTCTGTGCATTAGGAAGACCTGAGTGCATTTCCCACCAT
132001  ACTACAGTGTCGGACTCGTATGAGACACGTAATCCTTCTGGACTCACGTAAAGGGTGGTA

132061  TGTCCTTTCCACATTATGTTGTAGCTGGCTGGCTGTCAGGCGACTACAAGACTGAGGGTC
132061  ACAGGAAAGGTGTAATACAACATCGACCGACCGACAGTCCGCTGATGTTCTGACTCCCAG

132121  TTGTGCCTTATAGATCTTTGTATCCCCCATGGCTGACATATAGTAGGTACTCAGTAAATG
132121  AACACGGAATATCTAGAAACATAGGGGGTACCGACTGTATATCATCCATGAGTCATTTAC

132181  GTTTTATAATGAATCAGTGAACATTTTGCTTCTATAGAAGTGTACCTTCTTTGTTTCTAT
132181  CAAAATATTACTTAGTCACTTGTAAAACGAAGATATCTTCACATGGAAGAAACAAAGATA

132241  ATTATGAAACCTCTTTATTAGAATTTGTGATTGATTCTGACAGTGTATAGATTTACCTTA
132241  TAATACTTTGGAGAAATAATCTTAAACACTAACTAAGACTGTCACATATCTAAATGGAAT

132301  TATTGTCTTTATTTTCCATGAGCTACTAAGTCATTAGAGATACTCTGAAGCATAGTTAGT
132301  ATAACAGAAATAAAAGGTACTCGATGATTCAGTAATCTCTATGAGACTTCGTATCAATCA

132361  TTAGGAAATCACTTCATATTGATTGTATTAGAATTATCTTGGAATTGAAGATATATCCCT
132361  AATCCTTTAGTGAAGTATAACTAACATAATCTTAATAGAACCTTAACTTCTATATAGGGA

132421  AGAGCAGGGGACCCCAACCCCCAGGCCATGGGCCACACAGCAGGAAGAGGTGAGTGGTGG
132421  TCTCGTCCCCTGGGGTTGGGGGTCCGGTACCCGGTGTGTCGTCCTTCTCCACTCACCACC
```

FIG. 4 (cont'd)

```
132481  GCCATTGAGGAGCTTCATCTGTATTTATGGCTACTTCCCATCACTCGAATTACCACCTGA
132481  CGGTAACTCCTCGAAGTAGACATAAATACCGATGAAGGGTAGTGAGCTTAATGGTGGACT

132541  ACTCCACCTCTTGTCAGCTCAGTGGCAGCATTAGATTCTCATAGGAGCACAAATCCTATT
132541  TGAGGTGGAGAACAGTCGAGTCACCGTCGTAATCTAAGAGTATCCTCGTGTTTAGGATAA

132601  GTGAACTCTGCATGCAAGGGATCTAGGCTATGCGCTCCTTATGAGAATCTAATGCTTGAT
132601  CACTTGAGACGTACGTTCCCTAGATCCGATACGCGAGGAATACTCTTAGATTACGAACTA

132661  GACCTGAGGTGTAACAGTTTCATCCTGAAACCACCCTTCACCCTGCAGTCTGTGGAAAAA
132661  CTGGACTCCACATTGTCAAAGTAGGACTTTGGTGGGAAGTGGGACGTCAGACACCTTTTT

132721  TTGTCTTCCACAAAACTGGTCCCTGGTGCCAAAAATGTTGGGGACCACTGCTCTAGAGAG
132721  AACAGAAGGTGTTTTGACCAGGGACCACGGTTTTTACAACCCCTGGTGACGAGATCTCTC

132781  AGGTCATGATATCATACCAACCAAATGGAAATGACAAATGTTTTATGTCAAGTGTTAATT
132781  TCCAGTACTATAGTATGGTTGGTTTACCTTTACTGTTTACAAAATACAGTTCACAATTAA

132841  GCAGAAATAAATCTTTTTTTTTTTTTTTTTGGTAGAAAACAAAGAGGCATACTCTGATTTT
132841  CGTCTTTATTTAGAAAAAAAAAAAAAAAAACCATCTTTTGTTTCTCCGTATGAGACTAAAA

132901  TATACTCTGTTTTTGCAGGTGCTCTTTTCTTTGAATGGAGATTTGATGAGCAAGTGGTTA
132901  ATATGAGACAAAAACGTCCACGAGAAAAGAAACTTACCTCTAAACTACTCGTTCACCAAT

132961  GGATGCAGGGAGAGCTACTATGGGTGATATTTTCCTTGTTTAGGAGCTGTGAGTTAAAAT
132961  CCTACGTCCCTCTCGATGATACCCACTATAAAAGGAACAAATCCTCGACACTCAATTTTA

133021  TGTATCCTTTGTGGTTTATCTAAGGAAAGTCAAATCTTGACAGAAAACATTTTTCCTTGG
133021  ACATAGGAAACACCAAATAGATTCCTTTCAGTTTAGAACTGTCTTTTGTAAAAAGGAACC

133081  AAGGTCAACTCTCAGACATTGTATTTTGGTTTCCCTCAGTCCTCATAACTTCCTTCTTGC
133081  TTCCAGTTGAGAGTCTGTAACATAAAACCAAAGGGAGTCAGGAGTATTGAAGGAAGAACG

133141  TGAACATATTTTATTCTCTTTTCAGAGAAGGAAAATAAAAAGGATTCTAAAAGTTTGATG
133141  ACTTGTATAAAATAAGAGAAAAGTCTCTTCCTTTTATTTTTCCTAAGATTTTCAAACTAC

133201  CATTGGAAAAATTTCCTTGAGGCATTTAGCAACACATAGAAAATGGGCTTTGATTCTTTT
133201  GTAACCTTTTTAAAGGAACTCCGTAAATCGTTGTGTATCTTTTACCCGAAACTAAGAAAA

133261  CCAAAACTTTTAGCCATAGGGTCTTTTATAGACAGGGATAGTAAAATGAAAATTGAGAAA
133261  GGTTTTGAAAATCGGTATCCCAGAAAATATCTGTCCCTATCATTTTACTTTTAACTCTTT

133321  TATAAGATGAAAAGGAATGATAAAAATATCTTTTAGGGGGCTTTTAATTGGTGATCTGAA
133321  ATATTCTACTTTTCCTTACTATTTTTATAGAAAATCCCCCGAAAATTAACCACTAGACTT

133381  ATCTTGGGAGAAGCTGTTCTTTTCAGGCCTGAGGTGCTCTTGACTGTCGCCTGCGCACTG
133381  TAGAACCCTCTTCGACAAGAAAAGTCCGGACTCCACGAGAACTGACAGCGGACGCGTGAC

133441  TGTACCCCGAGCAACATTCTAAGGGTGTGCTTTCGCCTTGGCTAACTCCTTTGACCTCAT
133441  ACATGGGGCTCGTTGTAAGATTCCCACACGAAAGCGGAACCGATTGAGGAAACTGGAGTA

133501  TCTTCATATAGTAGTCTAGGAAAAAGTTGCAGGTAATTTAAACTGTCTAGTGGTACATAG
133501  AGAAGTATATCATCAGATCCTTTTTCAACGTCCATTAAATTTGACAGATCACCATGTATC

133561  TAACTAAATTTCTATTCCTATGAGAAATGAGAATTATTTATTTGCCATCAACACATTTTA
133561  ATTGATTTAAAGATAAGGATACTCTTTACTCTTAATAAATAAACGGTAGTTGTGTAAAAT

133621  TACTTTGCATCTCCAAATTTATTGTGGCGAGACTTGTCCATTGTGAAAGTTAGAGAACAT
133621  ATGAAACGTAGAGGTTTAAATAACACCGCTCTGAACAGGTAACACTTTCAATCTCTTGTA

133681  TATGTTTGTATCATTTCTTTCATAAAACCTCAAGAGCATTTTTAAGCCCTTTTCATCAGA
133681  ATACAAACATAGTAAAGAAAGTATTTTGGAGTTCTCGTAAAAATTCGGGAAAAGTAGTCT

133741  CCCAGTGAAAACTAAGGATAGATGTTTAAAAACTGGAGGTCTCCTGATAAGGAGAACACA
133741  GGGTCACTTTTGATTCCTATCTACAAATTTTTGACCTCCAGAGGACTATTCCTCTTGTGT

133801  ATCCACCATTGTCATTTAAGTAATAAGACAGGAAATTGACCTTGACGCTTTCTTGTTAAA
133801  TAGGTGGTAACAGTAAATTCATTATTCTGTCCTTTAACTGGAACTGCGAAAGAACAATTT
```

FIG. 4 (cont'd)

133861 TAGATTTAACAGGAACATCTGCACATCTTTTTTCCTTGTGCACTATTTGTTTAATTGCAG
133861 ATCTAAATTGTCCTTGTAGACGTGTAGAAAAAAGGAACACGTGATAAACAAATTAACGTC

133921 TGGATTAATACAGCAAGAGTGCCACATTATAACTAGGCAATTATCCATTCTTCAAGACTT
133921 ACCTAATTATGTCGTTCTCACGGTGTAATATTGATCCGTTAATAGGTAAGAAGTTCTGAA

133981 AGTTATTGTCACACTAATTGATCGTTTAAGGCATAAGATGGTCTAGCATTAGGAACATGT
133981 TCAATAACAGTGTGATTAACTAGCAAATTCCGTATTCTACCAGATCGTAATCCTTGTACA

134041 GAAGCTAATCTGCTCAAAAAGATCAACAAATTAATATTGTTGCTGATATTTGCATAATTG
134041 CTTCGATTAGACGAGTTTTTCTAGTTGTTTAATTATAACAACGACTATAAACGTATTAAC

134101 GCTGCAATTATTTAATGTTTAATTGGGTTGATCAAATGAGATTCAGCAATTCACAAGTGC
134101 CGACGTTAATAAATTACAAATTAACCCAACTAGTTTACTCTAAGTCGTTAAGTGTTCACG

134161 ATTAATATAAACAGAACTGGTGGCACTTAAAATGATAATGATTAACTTATATTGCATGTT
134161 TAATTATATTTGTCTTGACCACCGTGAATTTTACTATTACTAATTGAATATAACGTACAA

134221 CTCTTCCTTTCACTTTTTTCAGTTTCTACATTTCAGACCGAGCTTGTCAGCTTTTTTGAA
134221 GAGAAGGAAAGTGAAAAAAGTCAAAGATGTAAAGTCTGGCTCGAACAGTCGAAAAAACTT

134281 AACACATCAGTAGAAACCAAGATTTTAAAATGAAGTGTCAAGACAAAGGCAAAACCTGAG
134281 TTGTGTAGTCATCTTTGGTTCTAAAATTTTACTTCACAGTTCTGTTTCCGTTTTGGACTC

134341 CAGTTCCTAAAAAGATTTGCTGTTAGAAATTTTCTTTGTGGCAGTCATTTATTAAGGATT
134341 GTCAAGGATTTTTCTAAACGACAATCTTTAAAAGAAACACCGTCAGTAAATAATTCCTAA

134401 CAACTCGTGATACACCAAAAGAAGAGTTGACTTCAGAGATGTGTTCCATGCTCTCTAGCA
134401 GTTGAGCACTATGTGGTTTTCTTCTCAACTGAAGTCTCTACACAAGGTACGAGAGATCGT

134461 CAGGAATGAATAAATTTATAACACCTGCTTTAGCCTTTGTTTTCAAAAGCACAAAGGAAA
134461 GTCCTTACTTATTTAAATATTGTGGACGAAATCGGAAACAAAAGTTTTCGTGTTTCCTTT

134521 AGTGAAAGGGAAAGAGAAACAAGTGACTGAGAAGTCTTGTTAAGGAATCAGGTTTTTTCT
134521 TCACTTTCCCTTTCTCTTTGTTCACTGACTCTTCAGAACAATTCCTTAGTCCAAAAAAGA

134581 ACCTGGTAAACATTCTCTATTCTTTTCTCAAAAGATTGCTGTAAGAAAAAATGTAAGACA
134581 TGGACCATTTGTAAGAGATAAGAAAAGAGTTTTCTAACGACATTCTTTTTTACATTCTGT

134641 AAAAAAAAAAAAAAAAACAAACAGAGGCAGAGGCAGGCAGTAGCAAGAAAGCAGAGCGTA
134641 TTTTTTTTTTTTTTTTTGTTTGTCTCCGTCTCCGTCCGTCATCGTTCTTTCGTCTCGCAT

134701 ACATCAGCTAGATGGTAACATGCAATGTCAGCTCTCTTGAAGACATGGGAAACCTAAGTT
134701 TGTAGTCGATCTACCATTGTACGTTACAGTCGAGAGAACTTCTGTACCCTTTGGATTCAA

134761 ACACCTTGGGTTAAAATTCTTCACCATATTAGTTTTGTTGCTTCATAAAATTTACCTAAG
134761 TGTGGAACCCAATTTTAAGAAGTGGTATAATCAAAACAACGAAGTATTTTAAATGGATTC

134821 CAAGTGGTCTTGCTTGCCTCAAATCCAAGCAGTCTTGAACACTTGGAGGCAATTAATGAG
134821 GTTCACCAGAACGAACGGAGTTTAGGTTCGTCAGAACTTGTGAACCTCCGTTAATTACTC

134881 TATATCTTAGTCAAAAGAATTGTTGGAGCTTTTTATTAAAGCTACAGTTTCAGTTCTGCT
134881 ATATAGAATCAGTTTTCTTAACAACCTCGAAAAATAATTTCGATGTCAAAGTCAAGACGA

134941 TTTGGGGAATTGTGCTATGAAAGCAGCTGCCAAAATAAGCTCATTTATTTTCTTCAATCC
134941 AAACCCCTTAACACGATACTTTCGTCGACGGTTTTATTCGAGTAAATAAAAGAAGTTAGG

135001 CACTCAGTGCTCAGTCACTATATTCTGTTTCCTTTTTTTTTTTCAAGTTGCATATTTGGT
135001 GTGAGTCACGAGTCAGTGATATAAGACAAAGGAAAAAAAAAAAGTTCAACGTATAAACCA

135061 TTCCCCTTATGATTGGGAAAGATGAATTTTCAGCAGAAAACATTGTTTGTTCACTTTCAA
135061 AAGGGGAATACTAACCCTTTCTACTTAAAAGTCGTCTTTTGTAACAAACAAGTGAAAGTT

135121 AGAGTGATAGTTTCTAAAACATTTAGAGCAATAAATATTCATCAGAGGTACCAAGTAAGC
135121 TCTCACTATCAAAGATTTTGTAAATCTCGTTATTTATAAGTAGTCTCCATGGTTCATTCG

FIG. 4 (cont'd)

135181 CGGCAGAAGAGTTAAGGGTTAGAGAAATCCCTTATTTCATGTCTTGACTCTAAAATTATC
135181 GCCGTCTTCTCAATTCCCAATCTCTTTAGGGAATAAAGTACAGAACTGAGATTTTAATAG

135241 AAAGTACTTTTCCTTGTAATGTGGATTTCTTCTTATGCGGATATGCAAAAACTTCAGTTA
135241 TTTCATGAAAAGGAACATTACACCTAAAGAAGAATACGCCTATACGTTTTTGAAGTCAAT

135301 TACGTAGTAATGCTAGCAGGTAATTTTAGTAGACATTTTATAACAACTGTCACTTTGTTT
135301 ATGCATCATTACGATCGTCCATTAAAATCATCTGTAAAATATTGTTGACAGTGAAACAAA

135361 CGCCACATGTAGAGTTTGTTCAGCTATTTTCCAGATATCTCCCCACAAAAGGAGGCAAAG
135361 GCGGTGTACATCTCAAACAAGTCGATAAAAGGTCTATAGAGGGGTGTTTTCCTCCGTTTC

135421 GGTACCAGCTTTTCAATGAGCATTACCTATTACTTGGCAAAGATGATGAAGACTCTATTA
135421 CCATGGTCGAAAAGTTACTCGTAATGGATAATGAACCGTTTCTACTACTTCTGAGATAAT

135481 ATAGTTCATTTGATAAATGTTGACATAACCAACAATAGAGATTAGGAAGTTAGTTTTAAG
135481 TATCAAGTAAACTATTTACAACTGTATTGGTTGTTATCTCTAATCCTTCAATCAAAATTC

135541 AAATCAATGGCATATAGACATTACCCTCATGGAGTTTGTATTCTACTACTTGAACTGATT
135541 TTTAGTTACCGTATATCTGTAATGGGAGTACCTCAAACATAAGATGATGAACTTGACTAA

135601 GTAGCTATAAAAGCATAGTTAGATAGCTGAATAGTTAGATCATAAGCAAAGAAGGCCAGA
135601 CATCGATATTTTCGTATCAATCTATCGACTTATCAATCTAGTATTCGTTTCTTCCGGTCT

135661 ACACATCTCTTATCAAGAAATCAATGAATAGTTTATCTCATTTTTAAAGCAACTTTATCC
135661 TGTGTAGAGAATAGTTCTTTAGTTACTTATCAAATAGAGTAAAAATTTCGTTGAAATAGG

135721 TTCTTTAATTCCTTCCTTTCTTCTAGTGCAAAACTACTTAATAAGGTTGGTGTTTAGGTT
135721 AAGAAATTAAGGAAGGAAAGAAGATCACGTTTTGATGAATTATTCCAACCACAAATCCAA

135781 AGTGTTCACACCATTCCTCATCTGGTGTGAATTACCTTCTCTTTCTTTACTATTTACTAC
135781 TCACAAGTGTGGTAAGGAGTAGACCACACTTAATGGAAGAGAAAGAAATGATAAATGATG

135841 CAACCTAGTACATGTGTTGACTGAATTCTTTTCAAACAATGTTGAGTTATCATGGTGCAC
135841 GTTGGATCATGTACACAACTGACTTAAGAAAAGTTTGTTACAACTCAATAGTACCACGTG

135901 CTAATAAATTAACACCACAGATTACAGCATCCTTGCTGATTTTCTCAGCAAAGCCAGATT
135901 GATTATTTAATTGTGGTGTCTAATGTCGTAGGAACGACTAAAAGAGTCGTTTCGGTCTAA

135961 AGATGGAAATAAACAAAGAAAATGATCCTAGAGTGAATTTTTCTAGAAAATATCTATTAT
135961 TCTACCTTTATTTGTTTCTTTTACTAGGATCTCACTTAAAAAGATCTTTTATAGATAATA

136021 GAACCATGCTGTTTAAAGTATTAGCTTGAAGGTGATGGATCCAGCTATTCAGAAAATAAC
136021 CTTGGTACGACAAATTTCATAATCGAACTTCCACTACCTAGGTCGATAAGTCTTTTATTG

136081 TTTCATATAACCATGATTTTGCACAGTATGAGGTCTTAAATGTGTGGAAAGAGATAAATT
136081 AAAGTATATTGGTACTAAAACGTGTCATACTCCAGAATTTACACACCTTTCTCTATTTAA

136141 TTTTATCATTACCACAAACCCCTTTTAAAGATTCAAAGGTGGAAGAAAGTGATTTATTTT
136141 AAAATAGTAATGGTGTTTGGGGAAAATTTCTAAGTTTCCACCTTCTTTCACTAAATAAAA

136201 TTCTCTTCAGCATACATATATAAAAGACTTGTCAGATGTTTAATTTGGGGAGGTTGATAA
136201 AAGAGAAGTCGTATGTATATATTTTCTGAACAGTCTACAAATTAAACCCCTCCAACTATT

136261 TGAAACATATCAACAGAGTATAGTAGTTATAGTAGTGTTTGTGGGTAAATAATTTCCTGG
136261 ACTTTGTATAGTTGTCTCATATCATCAATATCATCACAAACACCCATTTATTAAAGGACC

136321 GGTCAGACATATATAAACATATTTGCTTCAAAATGATAAAGGCATGAAATCAGTCTTAAA
136321 CCAGTCTGTATATATTTGTATAAACGAAGTTTTACTATTTCCGTACTTTAGTCAGAATTT

136381 AATTGAAATGGGGGTGATGGGGGAGAAAAAGAAGAACAAATTTGAAGTGCCCTTTCAAAT
136381 TTAACTTTACCCCCACTACCCCCTCTTTTTCTTCTTGTTTAAACTTCACGGGAAAGTTTA

136441 CTGCTGGATACAAGTATTGAAGTTTTAAGTCATCTTATTCTGTCTGAAAGTGTATTTTTC
136441 GACGACCTATGTTCATAACTTCAAAATTCAGTAGAATAAGACAGACTTTCACATAAAAAG

136501 ATTCTACAATAGACCCAATCAACAAGACGTATAACTTGAGTTGCATGATGTTCAGTTTAT
136501 TAAGATGTTATCTGGGTTAGTTGTTCTGCATATTGAACTCAACGTACTACAAGTCAAATA

FIG. 4 (cont'd)

```
136561  GTAATCTACTGTTGGGATGGTAAGAATTGATGTAGGCTGTGGTGTAAGAATGAATTAAAA
136561  CATTAGATGACAACCCTACCATTCTTAACTACATCCGACACCACATTCTTACTTAATTTT

136621  TATAGTTTCACTGGCTTTTCTCTACATATCCACTATCACAATGGCTAGGTTTCCTGTTGC
136621  ATATCAAAGTGACCGAAAAGAGATGTATAGGTGATAGTGTTACCGATCCAAAGGACAACG

136681  TCACTATTGGATTCTGGAGAAAAATTTAATGAAAGATGATATCAGAGGAAGAATAAGTGG
136681  AGTGATAACCTAAGACCTCTTTTTAAATTACTTTCTACTATAGTCTCCTTCTTATTCACC

136741  AGGTAGAGAAGAAAGGAATGATAGAGGAGGGGAAAAAAACAAAACATATTTTTGTGTTAT
136741  TCCATCTCTTCTTTCCTTACTATCTCCTCCCCTTTTTTTGTTTTGTATAAAAACACAATA

136801  CCAAAGGAGCTTTTTCCTTATTCTGTCAAGCATTGAGATCTTCTTCAGCTTTCAATGTAG
136801  GGTTTCCTCGAAAAAGGAATAAGACAGTTCGTAACTCTAGAAGAAGTCGAAAGTTACATC

136861  TTGCTAAATACAAATAATGCTACTAGGTAGTGACTAAATATAGCAAACACTTCATCAGAT
136861  AACGATTTATGTTTATTACGATGATCCATCACTGATTTATATCGTTTGTGAAGTAGTCTA

136921  ATTAGAATTAGGTCACACTATTGAGGTTATAATCTGAAGGTTGTGTTACATAGAAACCAC
136921  TAATCTTAATCCAGTGTGATAACTCCAATATTAGACTTCCAACACAATGTATCTTTGGTG

136981  TTTAGATTATTATCAACTTGGACTAGGCTTTATTTTATAATAGCATAGTAAGTAATATCT
136981  AAATCTAATAATAGTTGAACCTGATCCGAAATAAAATATTATCGTATCATTCATTATAGA

137041  ATTGTGTCATTTCTTCAACCATTTTATTCTAAGATCCATGAAGCTTCTTGAGGCCAAATA
137041  TAACACAGTAAAGAAGTTGGTAAAATAAGATTCTAGGTACTTCGAAGAACTCCGGTTTAT

137101  AAATAATAAGTTTAGACAAGAAGTAGATTGTGACTTTTTTCCCTTAGAGATACTATTTAC
137101  TTTATTATTCAAATCTGTTCTTCATCTAACACTGAAAAAAGGGAATCTCTATGATAAATG

137161  TATCTCCTATCCTGATAGGTGGAAGGTTTACTGAATTGGAAATTGGTTGACTATTAGTTT
137161  ATAGAGGATAGGACTATCCACCTTCCAAATGACTTAACCTTTAACCAACTGATAATCAAA

137221  TTAACTAAAATGTGCAATAACACATTGCAGTTTCCTCAAACTAGTTTCCTATGATCATTA
137221  AATTGATTTTACACGTTATTGTGTAACGTCAAAGGAGTTTGATCAAAGGATACTAGTAAT

137281  AACTCATTCTCAGGGTTAAGAAAGGAATGTAAATTTCTGCCTCAATTTGTACTTCATCAA
137281  TTGAGTAAGAGTCCCAATTCTTTCCTTACATTTAAAGACGGAGTTAAACATGAAGTAGTT

137341  TAAGTTTTTGAAGAGTGCAGATTTTTAGTCAGGTCTTAAAAATAAACTCACAAATCTGGA
137341  ATTCAAAAACTTCTCACGTCTAAAAATCAGTCCAGAATTTTTATTTGAGTGTTTAGACCT

137401  TGCATTTCTAAATTCTGCAAATGTTTCCTGGGGTGACTTAACAAGGAATAATCCCACAAT
137401  ACGTAAAGATTTAAGACGTTTACAAAGGACCCCACTGAATTGTTCCTTATTAGGGTGTTA

137461  ATACCTAGCTACCTAATACATGGAGCTGGGGCTCAACCCACTGTTTTTAAGGATTTGCGC
137461  TATGGATCGATGGATTATGTACCTCGACCCCGAGTTGGGTGACAAAAATTCCTAAACGCG

137521  TTACTTGTGGCTGAGGAAAAATAAGTAGTTCGAGGAAGTAGTTTTTAAATGTGAGCTTAT
137521  AATGAACACCGACTCCTTTTTATTCATCAAGCTCCTTCATCAAAAATTTACACTCGAATA

137581  AGATAGAAACAGAATATCAACTTAATTATGAAATTGTTAGAACCTGTTCTCTTGTATCTG
137581  TCTATCTTTGTCTTATAGTTGAATTAATACTTTAACAATCTTGGACAAGAGAACATAGAC

137641  AATCTGATTGCAATTACTATTGTACTGATAGACTCCAGCCATTGCAAGTCTCAGATATCT
137641  TTAGACTAACGTTAATGATAACATGACTATCTGAGGTCGGTAACGTTCAGAGTCTATAGA

137701  TAGCTGTGTAGTGATTCTTGAAATTCTTTTTAAGAAAAATTGAGTAGAAAGAAATAAACC
137701  ATCGACACATCACTAAGAACTTTAAGAAAAATTCTTTTTAACTCATCTTTCTTTATTTGG

137761  CTTTGTAAATGAGGCTTGGCTTTTGTGAAAGATCATCCGCAGGCTATGTTAAAAGGATTT
137761  GAAACATTTACTCCGAACCGAAAACACTTTCTAGTAGGCGTCCGATACAATTTTCCTAAA

137821  TAGCTCACTAAAAGTGTAATAATGGAAATGTGGAAAATATCGTAGGTAAAGGAAACTACC
137821  ATCGAGTGATTTTCACATTATTACCTTTACACCTTTTATAGCATCCATTTCCTTTGATGG
```

FIG. 4 (cont'd)

137881 TCATGCTCTGAAGGTTTTGTAGAAGCACAATTAAACATCTAAAATGGCTTTGTTACACCA
137881 AGTACGAGACTTCCAAAACATCTTCGTGTTAATTTGTAGATTTTACCGAAACAATGTGGT

137941 GAGCCATCTGGTGTGAAGAACTCTATATTTGTATGTTGAGAGGGCATGGAATAATTGTAT
137941 CTCGGTAGACCACACTTCTTGAGATATAAACATACAACTCTCCCGTACCTTATTAACATA

138001 TTTGCTGGCAATAGACACATTCTTTATTATTTGCAGATTCCTCATCAAATCTGTAATTAT
138001 AAACGACCGTTATCTGTGTAAGAAATAATAAACGTCTAAGGAGTAGTTTAGACATTAATA

138061 GCACAGTTTCTGTTATCAATAAAACAAAAGAATCCTGTTTGTGTGGTTTCATGAAATCAG
138061 CGTGTCAAAGACAATAGTTATTTTGTTTTCTTAGGACAAACACACCAAAGTACTTTAGTC

138121 CATTGTTGAATGCATGAAGTAATAATGCTAAATTAACATTTTTATGATGTCTCAAGGTTT
138121 GTAACAACTTACGTACTTCATTATTACGATTTAATTGTAAAAATACTACAGAGTTCCAAA

138181 CTGGTCAAGGGAAGTAAATGTAGGATAGTATTTTTACACCAAAATGACACAGAGAGAATT
138181 GACCAGTTCCCTTCATTTACATCCTATCATAAAAATGTGGTTTTACTGTGTCTCTCTTAA

138241 GAGCACACCAGAAAGACCAGAAACCACACCACTGGATAGAGATTCAATATGTTTCTTTTT
138241 CTCGTGTGGTCTTTCTGGTCTTTGGTGTGGTGACCTATCTCTAAGTTATACAAAGAAAAA

138301 CAAACATTTGGACAAGAAAAAAATGGGCATTTAAAAATTCTTCCTTCCCCTGGTTATGGA
138301 GTTTGTAAACCTGTTCTTTTTTTACCCGTAAATTTTTAAGAAGGAAGGGGACCAATACCT

138361 TTTATCTGTAGTAAAACTTAGCTTTGTCGTTTGAGATTTGCACAGAATGGGGGGAGTAGA
138361 AAATAGACATCATTTTGAATCGAAACAGCAAACTCTAAACGTGTCTTACCCCCCTCATCT

138421 TTACCTCTTCCCATTCATTGTCATAATGGATCTACATCACTGATAAACACCATACTTCTA
138421 AATGGAGAAGGGTAAGTAACAGTATTACCTAGATGTAGTGACTATTTGTGGTATGAAGAT

138481 TATGTGGTTAACTAGCTTTAGAATAAAAGACACTTTAAAAAGTAAAAGGCCTAGAGATCT
138481 ATACACCAATTGATCGAAATCTTATTTTCTGTGAAATTTTTCATTTTCCGGATCTCTAGA

138541 TCAATGAAGTGTCCCTTTTAGCCAAACCAGGCCTTGCAGAAATTGTCCTCAAAAGCACCA
138541 AGTTACTTCACAGGGAAAATCGGTTTGGTCCGGAACGTCTTTAACAGGAGTTTTCGTGGT

138601 AGGGAGAACAAAGCCAAGTGCAGAATTACCCAAGGGTCACACATTTTGTATTCATTTTCT
138601 TCCCTCTTGTTTCGGTTCACGTCTTAATGGGTTCCCAGTGTGTAAAACATAAGTAAAAGA

138661 TATAATTTGCCCAAATGATTTGAAGTACAGCAAAACCTGAAGTTTTGCAAAGAGTTACTG
138661 ATATTAAACGGGTTTACTAAACTTCATGTCGTTTTGGACTTCAAAACGTTTCTCAATGAC

138721 TAAACTGAACTTAAAAATGTCAGAGTGCTCGGTGACCCACTTCTCCAGACCCTGTCAACC
138721 ATTTGACTTGAATTTTTACAGTCTCACGAGCCACTGGGTGAAGAGGTCTGGGACAGTTGG

138781 TGTGAAAATATTGGCCTTTATTCAGATCTCTCAAGAAGTTACGCGCAGAGTTTGGAAGGT
138781 ACACTTTTATAACCGGAAATAAGTCTAGAGAGTTCTTCAATGCGCGTCTCAAACCTTCCA

138841 CTAGGCAAAGGTTATTAGTCAAGTGTTCTTACAGTGTCAACGCTCAATTCCCACAAGCGT
138841 GATCCGTTTCCAATAATCAGTTCACAAGAATGTCACAGTTGCGAGTTAAGGGTGTTCGCA

138901 GAGAAAGAGAGACCTGTCATTCCTGAGGGTGATGACATACATTTACTGGAGCTTATATAA
138901 CTCTTTCTCTCTGGACAGTAAGGACTCCCACTACTGTATGTAAATGACCTCGAATATATT

138961 TTTATCAGATAAGACAGCAGTTTCCTTCAGGGTAGAAAGTGTGTTTTCTACATTGATTTA
138961 AAATAGTCTATTCTGTCGTCAAAGGAAGTCCCATCTTTCACACAAAAGATGTAACTAAAT

139021 GTACAAAACAAAAAGAAAAGGGGATATTTCAAATTTTATAATTATTTTTCTGCTAAGCTG
139021 CATGTTTTGTTTTTCTTTTCCCCTATAAAGTTTAAAATATTAATAAAAAGACGATTCGAC

139081 ATTCAGTGTGATTTAAGCATATTTTTCAAATCATGAATCTGATTCCATATACATATGTGC
139081 TAAGTCACACTAAATTCGTATAAAAAGTTTAGTACTTAGACTAAGGTATATGTATACACG

139141 CTTATATTGTGATAATTTATTTTTAAGTGAAATATGCTATCATAGCCTGACTTTATGTAT
139141 GAATATAACACTATTAAATAAAAATTCACTTTATACGATAGTATCGGACTGAAATACATA

139201 AGTGGTGACAACTTGCAGGATCGCATTTCTGTAACCAAACGGCCGACAGCTGAGGTGTAG
139201 TCACCACTGTTGAACGTCCTAGCGTAAAGACATTGGTTTGCCGGCTGTCGACTCCACATC

FIG. 4 (cont'd)

```
139261  ATGCTTCCTATGGTCTGTAGAATAATCACTGGGCTTGTTCTCTAGCTATGTCTGTATGCA
139261  TACGAAGGATACCAGACATCTTATTAGTGACCCGAACAAGAGATCGATACAGACATACGT

139321  ATCGCGACAGTGTTGATCAAAACCCATGATCATTCTCTCCAAAGGTCTTTGTCACTAAGC
139321  TAGCGCTGTCACAACTAGTTTTGGGTACTAGTAAGAGAGGTTTCCAGAAACAGTGATTCG

139381  CACTAGGGATTCTGAAAAGTTCGTGAGCTGAAACAAATAAATTGAGTTGGAAGATT
139381  GTGATCCCTAAGACTTTTCAAGCACTCGACTTTGTTTATTTAACTCAACCTTCTAA
```

FIG. 5

>hg19_refGene_NM_001220776 range=chr7:50342378-50472798 5'pad=0 3'pad=0 strand=+ repeatMasking=none

Genomic Sequence of IKZF1 (SEQ ID NO: 93)

```
   1  CCTGTCTCTGGTGTGCCCTGGCCCCCGACTTGGAGGCCTCCTGGGCCAGGCCAAGACCTT
   1  GGACAGAGACCACACGGGACCGGGGGCTGAACCTCCGGAGGACCCGGTCCGGTTCTGGAA

  61  CCCCGGCAGCGATGGTCTCCAGCCACACTCAACTGCCCTGAAGGGACATTTCCTGCTTAT
  61  GGGGCCGTCGCTACCAGAGGTCGGTGTGAGTTGACGGGACTTCCCTGTAAAGGACGAATA

 121  TCCCTTGCCCGGCTGTGTCCTCCACCCGGAAGGCCTGTGCCTTCTTCGCCTGCATGTCCT
 121  AGGGAACGGGCCGACACAGGAGGTGGGCCTTCCGGACACGGAAGAAGCGGACGTACAGGA

 181  ACCCTGAGGAGGCTCCCTTGGTCTTTCATCGCTCTCCCTATGGGTCTTCACGCCTTCCCG
 181  TGGGACTCCTCCGAGGGAACCAGAAAGTAGCGAGAGGGATACCCAGAAGTGCGGAAGGGC

 241  AACCACCGCGCCCAAGCAGGAGCACGTTCTCGGCCCTCTTCACAGGGCGCTCCTCCTCAC
 241  TTGGTGGCGCGGGTTCGTCCTCGTGCAAGAGCCGGGAGAAGTGTCCCGCGAGGAGGAGTG

 301  AGGGGTGCCCGGGATTTTTATTCTGTGCCTTCCTGGTGGCTCCTACAAGTCTGGAAGGGC
 301  TCCCCACGGGCCCTAAAAATAAGACACGGAAGGACCACCGAGGATGTTCAGACCTTCCCG

 361  AGGAGGCGCATCTCACTCCTCTGGGTCCCCTCCCCTAGCGCCTGGCGGGAGCCCAGGCTG
 361  TCCTCCGCGTAGAGTGAGGAGACCCAGGGGAGGGGATCGCGGACCGCCCTCGGGTCCGAC

 421  CATTTGTGGAATTCATGACTTTTTCTCTCCTGCTCAAGCTGAACACATTGCTGGCTCCTG
 421  GTAAACACCTTAAGTACTGAAAAAGAGAGGACGAGTTCGACTTGTGTAACGACCGAGGAC

 481  CTCGGGTGGAGCCCGGCTAATTAGAGTGAGGGGCTCCCCGTAGGGCGAAGGGGTGCGCTG
 481  GAGCCCACCTCGGGCCGATTAATCTCACTCCCCGAGGGGCATCCCGCTTCCCCACGCGAC

 541  TCAGATGTGGCATTCCCGTTTTACGGAGACACACGGTGTCTTACACGCCAGGGAGAGGTC
 541  AGTCTACACCGTAAGGGCAAAATGCCTCTGTGTGCCACAGAATGTGCGGTCCCTCTCCAG

 601  TGAGACGCAAAGAGCCGTCGAGCGGGCTGCGGGATTGCTTCGCTGTCACCTCCGCCTGCA
 601  ACTCTGCGTTTCTCGGCAGCTCGCCCGACGCCCTAACGAAGCGACAGTGGAGGCGGACGT

 661  GCCACCCTTCCGCACGCACTTGTGTGTGCACCCAGGCCAACATGGAAGGCGCCATCCTAA
 661  CGGTGGGAAGGCGTGCGTGAACACACACGTGGGTCCGGTTGTACCTTCCGCGGTAGGATT

 721  CTTCTGCCGTGAGCAGGTGGGAGGGAAGAGAGACGAGAGGTATTCCATTGGTTGTCTGGG
 721  GAAGACGGCACTCGTCCACCCTCCCTTCTCTCTGCTCTCCATAAGGTAACCAACAGACCC

 781  AAAATGAATTGCACCTTCCCCTCCCTTGCGGAGGATCAACTTTTCCCACCCCCTCGGGTG
 781  TTTTACTTAACGTGGAAGGGGAGGGAACGCCTCCTAGTTGAAAAGGGTGGGGGAGCCCAC

 841  GGCACTCGCATCCTGGGGCCGGAGCCTGAACCCGGGAGCCAAGGGGCCCCAGTTCCAGGG
 841  CCGTGAGCGTAGGACCCCGGCCTCGGACTTGGGCCCTCGGTTCCCCGGGGTCAAGGTCCC

 901  ACGTGAAGCTGAGCGTACAGCGGGCGCTCCCAGACACTGGGGAAAGTGCTTTACGATGTC
 901  TGCACTTCGACTCGCATGTCGCCCGCGAGGGTCTGTGACCCCTTTCACGAAATGCTACAG

 961  CCGAGTCCCTCCAGTCTCGCCAGCGGGGCGAGCGTGAGGGTGCCCCGACCGACCAGCGGC
 961  GGCTCAGGGAGGTCAGAGCGGTCGCCCCGCTCGCACTCCCACGGGGCTGGCTGGTCGCCG

1021  CCCGGGTGCAGGGTGGCGGGCCCGGCGGCGCGCGTCCCCCTCCCCCTCCTGGCGGCCCGC
1021  GGGCCCACGTCCCACCGCCCGGGCCGCCGCGCGCAGGGGGAGGGGGAGGACCGCCGGGCG

1081  ACGTGTCGCCCGCGCCGCGCCCCCACGGGTTACGCGCGGGTCCCGCAGCGCCGCGGCCGA
1081  TGCACAGCGGGCGCGGCGCGGGGGTGCCCAATGCGCGCCCAGGGCGTCGCGGCGCCGGCT

1141  GCCGGGCTGCCCGGCCCGCGGACACAGCGCCGGCCGCCGCATCCCGTGCGGGGCCGCGGC
1141  CGGCCCGACGGGCCGGGCGCCTGTGTCGCGGCCGGCGGCGTAGGGCACGCCCCGGCGCCG
```

FIG. 5 (cont'd)

1201 GCGATGCTGCGCTGGAATGAGGAAGCGCGGCGGCGAGGGGAGGGCCCGGGCGCGGTGCGC
1201 CGCTACGACGCGACCTTACTCCTTCGCGCCGCCGCTCCCCTCCCGGGCCCGCGCCACGCG

1261 GCGGGGGTGGCGGCGGCGCGCCGAGCGGGCCCGGCGCGGGCGAGCGGGCTGCAGCCGGCG
1261 CGCCCCCACCGCCGCCGCGCGGCTCGCCCGGGCCGCGCCCGCTCGCCCGACGTCGGCCGC

1321 GCGGCGCCAGCAGGTACGGCCCGCACCCGCCGCCGCCCCGGCGGCCTTTGGGGGCTGAGC
1321 CGCCGCGGTCGTCCATGCCGGGCGTGGGCGGCGGCGGGGCCGCCGGAAACCCCCGACTCG

1381 CGGAGCCCGGCGCGATTGCAAAGTTTTCGTGCGCGGCCCCTCTGGCCCGGAGTTGCGGCT
1381 GCCTCGGGCCGCGCTAACGTTTCAAAAGCACGCGCCGGGGAGACCGGGCCTCAACGCCGA

1441 GAGACGCGCGCCGCGCGAGCCGGGGGACTCGGCGACGGGGCGGGGACGG*GACGACGCACC*
1441 CTCTGCGCGCGGCGCGCTCGGCCCCCTGAGCCGCTGCCCCGCCCCTGCCCTGCTGCGTGG

1501 *CTCTCCGTGTCCCGCTCTGCGCCCTTCTGCGCGCCCCGCTCCCTGTACCGGAGCAGCGAT*
1501 GAGAGGCACAGGGCGAGACGCGGGAAGACGCGCGGGGCGAGGGACATGGCCTCGTCGCTA

1561 *CCGGGAGGCGGCCGAGAGGTGCGCG*CGGGGCCGAGCCGGCTGCGGGGCAGGTCGAGCAGG
1561 GGCCCTCCGCCGGCTCTCCACGCGCGCCCCGGCTCGGCCGACGCCCCGTCCAGCTCGTCC

1621 GACCGCCAGCGTGCGTCACCCCAAAGTTTGCGGGGTGGCAGGGCGCGCGCTCTGGCCACC
1621 CTGGCGGTCGCACGCAGTGGGGTTTCAAACGCCCCACCGTCCCGCGCGCGAGACCGGTGG

1681 CGCCGCTCTGGGCGGCAGCTGGTGGCAACGCAAGGGCGCGGCGGGGGCGGCCGGCGCGGA
1681 GCGGCGAGACCCGCCGTCGACCACCGTTGCGTTCCCGCGCCGCCCCCGCCGGCCGCGCCT

1741 GGGGGCCAGGTACGGGGCCCGCGGGCGGCGCTGTGCGCGCGGGGCAGCCGGTCGGCCGGG
1741 CCCCCGGTCCATGCCCCGGGCGCCCGCCGCGACACGCGCGCCCCGTCGGCCAGCCGGCCC

1801 AGCGCGAAAGCCTGGTCTGAGCCGGCTGGGGGCGGGGAGTGTGGCGGAGAAATGGGGAAC
1801 TCGCGCTTTCGGACCAGACTCGGCCGACCCCCGCCCCTCACACCGCCTCTTTACCCCTTG

1861 AATGCGAGTGAGCAACTTCAGGAAGTCATTGTGAAAGAAAGCTGGGAAGAGCTCCGCGGC
1861 TTACGCTCACTCGTTGAAGTCCTTCAGTAACACTTTCTTTCGACCCTTCTCGAGGCGCCG

1921 CAAGTTAGCAGGACACTCTAACAAGTGACTGCGCGGCCCGCGCCCGGGGCGGTGACTGCG
1921 GTTCAATCGTCCTGTGAGATTGTTCACTGACGCGCCGGGCGCGGGCCCCGCCACTGACGC

1981 GCAAGCCCCCTGGGTCCCCGCGCGGCGCATCCCAGCCTGGGCGGGACGCTCGGCCGCGGC
1981 CGTTCGGGGGACCCAGGGGCGCGCCGCGTAGGGTCGGACCCGCCCTGCGAGCCGGCGCCG

2041 GAGGCGGGCAAGCCTGGCAGGGCAGAGGGAGCCCCGGCTCCGAGGTTGCTCTTCGCACCC
2041 CTCCGCCCGTTCGGACCGTCCCGTCTCCCTCGGGGCCGAGGCTCCAACGAGAAGCGTGGG

2101 GAGGATCAGTCTTGGCCCCAAAGCGCGACGCACAAATCCACGTGAGTGTTTTCAAATTGA
2101 CTCCTAGTCAGAACCGGGGTTTCGCGCTGCGTGTTTAGGTGCACTCACAAAAGTTTAACT

2161 ATTTCAATAGGAAAACTTGGGGTAACTGGTGAATTTAAAAAAAAAAAAACACAGTAAAGA
2161 TAAAGTTATCCTTTTGAACCCCATTGACCACTTAAATTTTTTTTTTTTTGTGTCATTTCT

2221 AAAGCGGTAAGGTTGGTAGACCCTGGTGTCGCTCAGGTCCGCCTCTCTTTTCTGAGGACA
2221 TTTCGCCATTCCAACCATCTGGGACCACAGCGAGTCCAGGCGGAGAGAAAAGACTCCTGT

2281 GTGAGAGAGTTCACTTCTGTCAAGCGTCTGTTGCTCTGCACTGTGCCAGCAGGTGCAGGA
2281 CACTCTCTCAAGTGAAGACAGTTCGCAGACAACGAGACGTGACACGGTCGTCCACGTCCT

2341 CCAGGCCGACATGGGACACTTCTGAGCAGCCCCGCTGTCACCAGGAGAGGAGTTCTAGCT
2341 GGTCCGGCTGTACCCTGTGAAGACTCGTCGGGGCGACAGTGGTCCTCTCCTCAAGATCGA

2401 CCCAACCATATTTAAATTTATGTAGACCTACATATACCCACGGAAGTCAGCCTTTATAAA
2401 GGGTTGGTATAAATTTAAATACATCTGGATGTATATGGGTGCCTTCAGTCGGAAATATTT

2461 GTCGTGTGTAAAGAGTTTTCCTTATATTTGAGCCGGGAGCTTTCTTTTTATACTATAAAT
2461 CAGCACACATTTCTCAAAAGGAATATAAACTCGGCCCTCGAAAGAAAAATATGATATTTA

2521 ATGATGAGATCGAGTCTGAACTTAATTTCTGCAAGAGAGGAATTATCCCGGCTTTGAAAA
2521 TACTACTCTAGCTCAGACTTGAATTAAAGACGTTCTCTCCTTAATAGGGCCGAAACTTTT

FIG. 5 (cont'd)

```
2581  GTTAGTCCTTTTGCTGACCGCAGGTTTGACGCTCAAGTCACCAAACCTTCTCAGGAAAAC
2581  CAATCAGGAAAACGACTGGCGTCCAAACTGCGAGTTCAGTGGTTTGGAAGAGTCCTTTTG

2641  CCTTAGTAATATTAAGGCATCAGGTTACTTGCGGTTATATTTGAAATGTATTTTAAATAT
2641  GGAATCATTATAATTCCGTAGTCCAATGAACGCCAATATAAACTTTACATAAAATTTATA

2701  TTGTCAAGCATCGCTGCTGATGCCTAAGGAACCTCGTGAGGGCTTGTTTTTCCTTCTAAT
2701  AACAGTTCGTAGCGACGACTACGGATTCCTTGGAGCACTCCCGAACAAAAAGGAAGATTA

2761  TTGGAGGCATCTAATGACCGAAAACCGTAGCGATTCCATAGGGTCTGACCAGGCACAGCT
2761  AACCTCCGTAGATTACTGGCTTTTGGCATCGCTAAGGTATCCCAGACTGGTCCGTGTCGA

2821  TTCAAATGCAGCTTCCCTCTCTCTAGGGACTGCAGCCCACCCAGACTGAATTTCAATGCG
2821  AAGTTTACGTCGAAGGGAGAGAGATCCCTGACGTCGGGTGGGTCTGACTTAAAGTTACGC

2881  GTGCGCTTTGCTTAGGTTACCCACTCACAATTTCCCACTGCGCCGCAGGCAGTATATTTC
2881  CACGCGAAACGAATCCAATGGGTGAGTGTTAAAGGGTGACGCGGCGTCCGTCATATAAAG

2941  AGCTTTGAGATACCTTGTTTTAAAATTCCAGACAAAATGGTGTTGAGGAAATGTCTCCTT
2941  TCGAAACTCTATGGAACAAAATTTTAAGGTCTGTTTTACCACAACTCCTTTACAGAGGAA

3001  ACTAGTCCCATCAACTTCTGTTAAAAGAGGAAAATTTATGGAATTTGAAAATACTGCGTA
3001  TGATCAGGGTAGTTGAAGACAATTTTCTCCTTTTAAATACCTTAAACTTTTATGACGCAT

3061  TGATATTTAAACTTTCATAGACATTCAAATGCTTTTAAGGCCAGGTTCAATTTGGTTATG
3061  ACTATAAATTTGAAAGTATCTGTAAGTTTACGAAAATTCCGGTCCAAGTTAAACCAATAC

3121  AGTCGAGGGGTGGGGGGGACCCACATAGAAATGTCCTGGGTCCTCTTGAGTTTATTTCTT
3121  TCAGCTCCCCACCCCCCCTGGGTGTATCTTTACAGGACCCAGGAGAACTCAAATAAAGAA

3181  TGTTTGAAGATGTTTGTTCAATGAGTTTTATTGTACTCATCTTTTATATGGAATTTTAAA
3181  ACAAACTTCTACAAACAAGTTACTCAAAATAACATGAGTAGAAAATATACCTTAAAATTT

3241  AAGTAACAATTTCAGTATTATTTATATTAGAATGTGTCAGAATTATTTCCGTGACAAATC
3241  TTCATTGTTAAAGTCATAATAAATATAATCTTACACAGTCTTAATAAAGGCACTGTTTAG

3301  AGATCATTTGGGCTATGGCTTAAAATGTACACGAGGCAAATATTCATGACAAGAAGATTC
3301  TCTAGTAAACCCGATACCGAATTTTACATGTGCTCCGTTTATAAGTACTGTTCTTCTAAG

3361  ACCTTCTTACGCTGGCATCTTGTAAAATGCAGAACAAGTTAAAGAAATAATGTGTACACA
3361  TGGAAGAATGCGACCGTAGAACATTTTACGTCTTGTTCAATTTCTTTATTACACATGTGT

3421  TACAAATAATGATGTCACATTAAAAATACTACACTATTCTTGCTTGATGGAATGTATCTG
3421  ATGTTTATTACTACAGTGTAATTTTTATGATGTGATAAGAACGAACTACCTTACATAGAC

3481  ATTTCCAATTTCACCATGAACATATTTCATACATTTTTTACATGAAAAAAAACGTGACTC
3481  TAAAGGTTAAAGTGGTACTTGTATAAAGTATGTAAAAAATGTACTTTTTTTTGCACTGAG

3541  TTAAGTCTCACAGTCAATCAGAGCTGGTGACCAGAACATTTTATTGAACTAAATGGTCAT
3541  AATTCAGAGTGTCAGTTAGTCTCGACCACTGGTCTTGTAAAATAACTTGATTTACCAGTA

3601  GTTTTCTTCCCCTTTTGTTTCACGGTGAGAGTTGAAGGAAGGAGTTTAGAAACTCTCCAG
3601  CAAAAGAAGGGGAAAACAAAGTGCCACTCTCAACTTCCTTCCTCAAATCTTTGAGAGGTC

3661  TACTTGTTTAATTCATCAGTGTTCTAATTAGAGTGGTACCTCTTGGAAAACTACACACCC
3661  ATGAACAAATTAAGTAGTCACAAGATTAATCTCACCATGGAGAACCTTTTGATGTGTGGG

3721  CCCTAATGCAGAAACATCATAGCAATAATCACCCACCCTCAGGGTCTCCAGGAGACCACA
3721  GGGATTACGTCTTTGTAGTATCGTTATTAGTGGGTGGGAGTCCCAGAGGTCCTCTGGTGT

3781  AGGGCTGCAGATAAAAGTCTGGATGTGTTAGGTTTGACCCTTTCGAAGAGTTTTACACAG
3781  TCCCGACGTCTATTTTCAGACCTACACAATCCAAACTGGGAAAGCTTCTCAAAATGTGTC

3841  GCTCCTAAAGAGAAGATCAGCTGTGGCCGTTTGTAGCCATTTCCTTTGTCGAAAAACTAA
3841  CGAGGATTTCTCTTCTAGTCGACACCGGCAAACATCGGTAAAGGAAACAGCTTTTTGATT

3901  GATCGCAGTGAATGTATTAGCCAAGAGGTCTAAAGCCCTGTTGTACTGCAGGCCACTGTC
3901  CTAGCGTCACTTACATAATCGGTTCTCCAGATTTCGGGACAACATGACGTCCGGTGACAG
```

FIG. 5 (cont'd)

```
3961  TTCCTTGTTTGACTAGAGACTTGGAGTTTGAGAACAGTGGTTCTTTGGTTTGGATACATT
3961  AAGGAACAAACTGATCTCTGAACCTCAAACTCTTGTCACCAAGAAACCAAACCTATGTAA

4021  TTTTGTTCTTGATTTGGATGTGTGTGTTTCATGCGTGGTTAATATAGCATATTTTCAATA
4021  AAAACAAGAACTAAACCTACACACACAAAGTACGCACCAATTATATCGTATAAAAGTTAT

4081  TAAATGTCAAAAATTTTGAAATAGGAAAGAACTCTCTATATATTAATGTACTTATACACA
4081  ATTTACAGTTTTTAAAACTTTATCCTTTCTTGAGAGATATATAATTACATGAATATGTGT

4141  CACTTCAAGATTATGCATTTATTAACAGATACATGAAATAAATTCCATGTGCATATGCAC
4141  GTGAAGTTCTAATACGTAAATAATTGTCTATGTACTTTATTTAAGGTACACGTATACGTG

4201  ATATGCACACAGAGCGTGCACACACACAGCATGCACACAGCGTGGAGTGAGAGGCATGGG
4201  TATACGTGTGTCTCGCACGTGTGTGTGTCGTACGTGTGTCGCACCTCACTCTCCGTACCC

4261  GCAGTGTGGAAGAGTTTTAACATCAAACAGACCTGAAATGAGTATTAAAGGCCCCCTTTA
4261  CGTCACACCTTCTCAAAATTGTAGTTTGTCTGGACTTTACTCATAATTTCCGGGGGAAAT

4321  TTTTTAAACTTTTACTAAAACAAGATGGATTTCCCTATGTTATATAATGGTGAATTTTAG
4321  AAAAATTTGAAAATGATTTTGTTCTACCTAAAGGGATACAATATATTACCACTTAAAATC

4381  GCATAAATAACGTTTTTTGAGTGTTGCATAATTGTACGTATTAATGTAATGTAACTGTGG
4381  CGTATTTATTGCAAAAAACTCACAACGTATTAACATGCATAATTACATTACATTGACACC

4441  TTAACGAAGAATTCATCAAGGATATCACTGTTTTGTGGCATTTTTTTTTTCCTCCTCTAA
4441  AATTGCTTCTTAAGTAGTTCCTATAGTGACAAAACACCGTAAAAAAAAAAGGAGGAGATT

4501  TCTTTGGACTTGTGAAATAATTTCACTATGAAATAAATGTTGGTTCTTGTCATATTCTAA
4501  AGAAACCTGAACACTTTATTAAAGTGATACTTTATTTACAACCAAGAACAGTATAAGATT

4561  GGGAGATTGATGTAAGTGGCTCCACTCCAGCTTACAGAAGGTAAACCACGACCTTTTTGC
4561  CCCTCTAACTACATTCACCGAGGTGAGGTCGAATGTCTTCCATTTGGTGCTGGAAAAACG

4621  GTTCTCTGAAAACGCTTGTCTTCCGATGCCTCTGTTTCTAAGACTGACAAGCACTCTGGG
4621  CAAGAGACTTTTGCGAACAGAAGGCTACGGAGACAAAGATTCTGACTGTTCGTGAGACCC

4681  GGCACTGTGACGCCTGCTTCTAGCGGCAGAGTTGCTGCAGCTCCTGTCCTGGCTGTGAAC
4681  CCGTGACACTGCGGACGAAGATCGCCGTCTCAACGACGTCGAGGACAGGACCGACACTTG

4741  ATTGTTCTCTCTCTGGTGTCTCTATGTTCATAACTACAGAGACTTCAGCTCTATTCCATT
4741  TAACAAGAGAGAGACCACAGAGATACAAGTATTGATGTCTCTGAAGTCGAGATAAGGTAA

4801  TCATATTTGTGCTGAATAATCATTCCATTTTATGGGAGAAAACACAAGATGTAAAAGCAA
4801  AGTATAAACACGACTTATTAGTAAGGTAAAATACCCTCTTTTGTGTTCTACATTTTCGTT

4861  CAAGTGACCCATCCTTTGAAGCTTACAAGAAGAGAAACATTAATCTATTTCACGTCTTGA
4861  GTTCACTGGGTAGGAAACTTCGAATGTTCTTCTCTTTGTAATTAGATAAAGTGCAGAACT

4921  AAACAGATCAGTTTTATTTTGCTCAAAAAGGGCACATGTACATTTTTGATCTAGGTCTTA
4921  TTTGTCTAGTCAAAATAAAACGAGTTTTTCCCGTGTACATGTAAAAACTAGATCCAGAAT

4981  GAAACGTAGAGTTTCAGAGGATCAGCATTATACACACTGTCACACACACACACACTTAAA
4981  CTTTGCATCTCAAAGTCTCCTAGTCGTAATATGTGTGACAGTGTGTGTGTGTGTGAATTT

5041  ATTCAGATGAGGAACAAGATAGGAATGAGGTTTTGTTAGGGACGCAGAGCACCTAAAACC
5041  TAAGTCTACTCCTTGTTCTATCCTTACTCCAAAACAATCCCTGCGTCTCGTGGATTTTGG

5101  AAAGGATATCGACAGTAACAAAGCTGTTTTTACTGTAGTGCTGACTGAACACTCATGCTG
5101  TTTCCTATAGCTGTCATTGTTTCGACAAAAATGACATCACGACTGACTTGTGAGTACGAC

5161  GTGTCTTCATGTGGACCATGGCTTTCTTGTATTTCTTTGCAGTTTAATAAATGACTTCAT
5161  CACAGAAGTACACCTGGTACCGAAAGAACATAAAGAAACGTCAAATTATTTACTGAAGTA

5221  ATCTCAGGTTACCTTTCCACATCTCCTGGAATATATGTTTATGTCCTTAAAGTTTCAGTG
5221  TAGAGTCCAATGGAAAGGTGTAGAGGACCTTATATACAAATACAGGAATTTCAAAGTCAC

5281  TCGTCACTTTAGTAGCTTTAGTTTGAGTTTTTAAATGTTTGGTAATATTCCAACAAATAT
5281  AGCAGTGAAATCATCGAAATCAAACTCAAAAATTTACAAACCATTATAAGGTTGTTTATA
```

FIG. 5 (cont'd)

```
5341  TTTTTAAGACATTATGAAACCTTATGAAGTGCCATATATTACAAGTGAGATAAAACAGCA
5341  AAAAATTCTGTAATACTTTGGAATACTTCACGGTATATAATGTTCACTCTATTTTGTCGT

5401  AGCAAAAGAAGGTTTGCAGAAGGTTTTTAAGTGGCGAAGTGCGGGCCTGCCCATTTTGGT
5401  TCGTTTTCTTCCAAACGTCTTCCAAAAATTCACCGCTTCACGCCCGGACGGGTAAAACCA

5461  GTCTCCTTGGTGGTTACTCCTGAGAAGGGCCTGGAGGAAGAGCAACTGAGGCCTAATCTA
5461  CAGAGGAACCACCAATGAGGACTCTTCCCGGACCTCCTTCTCGTTGACTCCGGATTAGAT

5521  CAGGCAACTGCCAAATTGTTTCAGTTGACGTTTTTCCCTCTCATGTTTGACTATAATAAA
5521  GTCCGTTGACGGTTTAACAAAGTCAACTGCAAAAAGGGAGAGTACAAACTGATATTATTT

5581  TAGGTAGTTGCCAGTGGAGCCTTCAGCCAACCACCTGGTAATAAACTGTTAAAAATGGTG
5581  ATCCATCAACGGTCACCTCGGAAGTCGGTTGGTGGACCATTATTTGACAATTTTTACCAC

5641  CAAACCCTAGGTCACAGGTGTGGGGGCCATTTGTCTTGCCTGTTAACAGGCCTGGCCTTA
5641  GTTTGGGATCCAGTGTCCACACCCCCGGTAAACAGAACGGACAATTGTCCGGACCGGAAT

5701  ATTCTTTTCTCCCATGGCCATTTCTGCCTTTGGGGAACTCACAATTCCTGTTGACTAAAA
5701  TAAGAAAAGAGGGTACCGGTAAAGACGGAAACCCCTTGAGTGTTAAGGACAACTGATTTT

5761  GAGCACCCTTTTCCACCACAAGCCTGACAAATCAGACGTCCACATAATTTCTGAACTCGT
5761  CTCGTGGGAAAAGGTGGTGTTCGGACTGTTTAGTCTGCAGGTGTATTAAAGACTTGAGCA

5821  TTTGGTTAGGACAGGAAGCACAGGCTCCCTTCCTGTCTGTGTTTTCCTAAGAGAAAACGG
5821  AAACCAATCCTGTCCTTCGTGTCCGAGGGAAGGACAGACACAAAAGGATTCTCTTTTGCC

5881  TCTTCCCTCCTTTTTTGCATATTTGGCAAGTGGTTCCACCTTTCTCTGCACCCTGGTGGA
5881  AGAAGGGAGGAAAAAACGTATAAACCGTTCACCAAGGTGGAAAGAGACGTGGGACCACCT

5941  GTGTGAAGGCAGCAGAGGAACCTTTTGGAGGAGGAAGAGGACACAGAGGCCCTGTAGCCA
5941  CACACTTCCGTCGTCTCCTTGGAAAACCTCCTCCTTCTCCTGTGTCTCCGGGACATCGGT

6001  GGCACCAAGATCCCTCCCAGGTGGCTGGGTCTGAGGGGAACTCCGAGCAGCCCTAGGTCC
6001  CCGTGGTTCTAGGGAGGGTCCACCGACCCAGACTCCCCTTGAGGCTCGTCGGGATCCAGG

6061  TCAAAGTCTGGATTTGTGTGGAAAAGGCAGCTCTCACTTGGCCTTGGCGAGGCCTCGGTT
6061  AGTTTCAGACCTAAACACACCTTTTCCGTCGAGAGTGAACCGGAACCGCTCCGGAGCCAA

6121  GGTTGGTGAGTGCCACACGGTTTCTTTGTGTGCTTGCATGGATTGGAATAGCCATTGTGT
6121  CCAACCACTCACGGTGTGCCAAAGAAACACACGAACGTACCTAACCTTATCGGTAACACA

6181  TCTTCCGTCTTCCCTGCTGGTGTTTCCACAGTGGGTGGCCTGAGCCCAGAGCAGCTCCCC
6181  AGAAGGCAGAAGGGACGACCACAAAGGTGTCACCCACCGGACTCGGGTCTCGTCGAGGGG

6241  ATATCCCTGTGCAGGCCACCTGTCTCGGGTGATGGAGAGCATCATTATGCTCCGTCTGAA
6241  TATAGGGACACGTCCGGTGGACAGAGCCCACTACCTCTCGTAGTAATACGAGGCAGACTT

6301  CGCTCTGCTTTCGGATGGCCCCATGCTCCACCTCCTGATAGCTCGTGGCGCGGGGCCACG
6301  GCGAGACGAAAGCCTACCGGGGTACGAGGTGGAGGACTATCGAGCACCGCGCCCCGGTGC

6361  GCTTAACAAATGGCTGAAAATGGGTCCTAATTAGTGGAAAAGTGCTTTCTTCATATTTTC
6361  CGAATTGTTTACCGACTTTTACCCAGGATTAATCACCTTTTCACGAAAGAAGTATAAAAG

6421  TCACTCGAGTGTGCAGTGATTCATTTTTCTTCTGCAATCAGCTCACTGCTAAAGTAAATC
6421  AGTGAGCTCACACGTCACTAAGTAAAAAGAAGACGTTAGTCGAGTGACGATTTCATTTAG

6481  TGACTCTCTTCCCGCCATTGCACACCAAAAGTTAACTCTAATGGGTAGGAGGTTAGGTTT
6481  ACTGAGAGAAGGGCGGTAACGTGTGGTTTTCAATTGAGATTACCCATCCTCCAATCCAAA

6541  GTTGAGAGAGCAATGCAGTAAAAAGAGGGGATCCAATGTGGTCTTGTCTGTCTGGTCTTC
6541  CAACTCTCTCGTTACGTCATTTTTCTCCCCTAGGTTACACCAGAACAGACAGACCAGAAG

6601  CTTTCTTCGTTTTTTCCTCCCTTGTCTTCTCTGTCATTCCCTTCCCTCCATTTGCCTTGC
6601  GAAAGAAGCAAAAAAGGAGGGAACAGAAGAGACAGTAAGGGAAGGGAGGTAAACGGAACG

6661  CTTTCCTGTCCTTCCCTTCCCTTCCTTCCCCTCTTTCTTTCTATAATTGGTGGGGGGTTT
6661  GAAAGGACAGGAAGGGAAGGGAAGGAAGGGGAGAAAGAAAGATATTAACCACCCCCCAAA
```

FIG. 5 (cont'd)

```
6721  GCACAGACTGCCAAAACACTAAGAACTGTGTAAAGTGTTTTTGAATGGCCTTACACATAT
6721  CGTGTCTGACGGTTTTGTGATTCTTGACACATTTCACAAAAACTTACCGGAATGTGTATA

6781  TGAAGTAGATTTTTATGCTCCATTTTTGAGATCACACACTAAAATCTATACCTTTAAAGC
6781  ACTTCATCTAAAAATACGAGGTAAAAACTCTAGTGTGTGATTTTAGATATGGAAATTTCG

6841  ATTTTCTGTTAGTTTGAAACTATTTGAAAATGAACAATGTGGTTTAGATTAGAGTCCTGT
6841  TAAAAGACAATCAAACTTTGATAAACTTTTACTTGTTACACCAAATCTAATCTCAGGACA

6901  TCTGAAGCTAGGAGTTCCACTATGAATATTGATTTATCAGTTTTTGACAAATTTTTGTTG
6901  AGACTTCGATCCTCAAGGTGATACTTATAACTAAATAGTCAAAAACTGTTTAAAAACAAC

6961  TTATACCAGATTTTCACTGGCAAACCTAGAGCAAATAAAATTCCACATAAGATACTTCCC
6961  AATATGGTCTAAAAGTGACCGTTTGGATCTCGTTTATTTTAAGGTGTATTCTATGAAGGG

7021  TAGACCTAATGGGAAAAATGTTTAATTTAGAGTCTTTAGGAGAAATGAGAATGAGGAATT
7021  ATCTGGATTACCCTTTTTACAAATTAAATCTCAGAAATCCTCTTTACTCTTACTCCTTAA

7081  GACCTTTTGTAAGCTTACTTCTGAGGCACTCTGAAGTGTGTTCCAGTGCTTTTAATGGAA
7081  CTGGAAAACATTCGAATGAAGACTCCGTGAGACTTCACACAAGGTCACGAAAATTACCTT

7141  ACTAGAGAGAGCCAGCAACCCCCTAGTGTGAGCCCCACTTTTAACCGGAAAAAGTGACCT
7141  TGATCTCTCTCGGTCGTTGGGGGATCACACTCGGGGTGAAAATTGGCCTTTTTCACTGGA

7201  TTTCCTCCTCCTTTGTGCTGAGTTTTGCGTAGGGCAGAAAATTAAGCTGATATTCAAAGA
7201  AAAGGAGGAGGAAACACGACTCAAAACGCATCCCGTCTTTTAATTCGACTATAAGTTTCT

7261  GATTCACTGCAAAAACATATTGATAAATCGTATATTCTATTTCATTAAATTAAAACCATA
7261  CTAAGTGACGTTTTTGTATAACTATTTAGCATATAAGATAAAGTAATTTAATTTTGGTAT

7321  CTGCTAATTATCTCAGGTTGTTAAACATAAGGCAATTAATTATCATTTTAAAAGTTGGTA
7321  GACGATTAATAGAGTCCAACAATTTGTATTCCGTTAATTAATAGTAAAATTTTCAACCAT

7381  GGAAGTTGTGAGTACTTTTGCAGTATGAGTGTTTTCCCGCTTTAGTATGAGGTTGTGTAT
7381  CCTTCAACACTCATGAAAACGTCATACTCACAAAAGGGCGAAATCATACTCCAACACATA

7441  GTTTGCTTGAATTTACAGAATTTTCACTTTAAGAGCAGACAATGTTTTGTTAAAGAAATG
7441  CAAACGAACTTAAATGTCTTAAAAGTGAAATTCTCGTCTGTTACAAAACAATTTCTTTAC

7501  AAATTTGCTAAAAAGGAGCATGTAAAGTGAAACATTAAAAATAAATAATTTCAACTTACT
7501  TTTAAACGATTTTTCCTCGTACATTTCACTTTGTAATTTTTATTTATTAAAGTTGAATGA

7561  TAAGAGCTGCAGAAAAATCTGATTGCTGTGTTTAAAATGAATTTTCCCACATTTCGCTCT
7561  ATTCTCGACGTCTTTTTAGACTAACGACACAAATTTTACTTAAAAGGGTGTAAAGCGAGA

7621  CTTATGGACAGGAGCATTTTCTGTCAGGTTATAAATAAAGACATGCCCATTTTTTGTACC
7621  GAATACCTGTCCTCGTAAAAGACAGTCCAATATTTATTTCTGTACGGGTAAAAAACATGG

7681  CCCACAAATGAGGAAGTTGTAAGCTCTCTGAGGTTTTACTGATGAGCCCCCTCCCCCTGG
7681  GGGTGTTTACTCCTTCAACATTCGAGAGACTCCAAAATGACTACTCGGGGGAGGGGGACC

7741  GTTTGCATGAAGAGATCATAGGCCACAAATAAAGGACTACAAAATGGGGTCTAAACTATC
7741  CAAACGTACTTCTCTAGTATCCGGTGTTTATTTCCTGATGTTTTACCCCAGATTTGATAG

7801  CTGGTGGGGCCTGATACCCACGTTTCGCATGGACCTTACGATGTGATGAATGGTTTTGGC
7801  GACCACCCCGGACTATGGGTGCAAAGCGTACCTGGAATGCTACACTACTTACCAAAACCG

7861  ATGAGTGTCTTAAGAATGCTTCCAGATTCGGGTTACAGGACAGCCAGCGCTGAGCTCCCT
7861  TACTCACAGAATTCTTACGAAGGTCTAAGCCCAATGTCCTGTCGGTCGCGACTCGAGGGA

7921  ATTGCAGAACAAAGTAGGAATCTAGAACTTTCTTGCTAACAGGATCCAGCTAAAACACCA
7921  TAACGTCTTGTTTCATCCTTAGATCTTGAAAGAACGATTGTCCTAGGTCGATTTTGTGGT

7981  AGTTAGATTCTTAAATGATGTTCTTTTCTGTCATTATTTGATTGTTGTCAGTAGCAGTAA
7981  TCAATCTAAGAATTTACTACAAGAAAAGACAGTAATAAACTAACAACAGTCATCGTCATT

8041  TTGTTACCAAGCCATTGATGCTTCTATTCTTCCCTTTGCCCTTCTGAGACACAGCTCATT
8041  AACAATGGTTCGGTAACTACGAAGATAAGAAGGGAAACGGGAAGACTCTGTGTCGAGTAA
```

FIG. 5 (cont'd)

```
8101  TTGACTTCAGTGGAACCCCTCGAAGGTGGGGTGATGAGCAAGGTGAATTTTCAAAGTAAA
8101  AACTGAAGTCACCTTGGGGAGCTTCCACCCCACTACTCGTTCCACTTAAAAGTTTCATTT

8161  GCTACTAAGAGACCAAACTACAATTTAAGGAACCTGATTTTTGAATCAAATTCCATATAC
8161  CGATGATTCTCTGGTTTGATGTTAAATTCCTTGGACTAAAAACTTAGTTTAAGGTATATG

8221  TGTGGGTATAGTTCAACATAGATTAATTTCTTATAGTTATTATGAAAAAAATCTCATCTT
8221  ACACCCATATCAAGTTGTATCTAATTAAAGAATATCAATAATACTTTTTTTAGAGTAGAA

8281  GATGATAGCTGATAATTTTGTGGGTGTCGTAAACAAAACAGAGGTCAGAATTCAGTCCCT
8281  CTACTATCGACTATTAAAACACCCACAGCATTTGTTTTGTCTCCAGTCTTAAGTCAGGGA

8341  TGGGGAAAATTTCCAATTAGTAGGAAACCAAGTGGCCTACCTTAGTTTGAAGACACCCAT
8341  ACCCCTTTTAAAGGTTAATCATCCTTTGGTTCACCGGATGGAATCAAACTTCTGTGGGTA

8401  CAGGATGTCTGCACCTTTTCATCCTCTCTGGAGGAAAGACTAAATACCCATTATTGTATA
8401  GTCCTACAGACGTGGAAAAGTAGGAGAGACCTCCTTTCTGATTTATGGGTAATAACATAT

8461  TAGGTCAGGCCAAAGCAGCCTTTTATATTGCAAGGAATAAGAGGTAAATAGATATATGTG
8461  ATCCAGTCCGGTTTCGTCGGAAAATATAACGTTCCTTATTCTCCATTTATCTATATACAC

8521  CAACAATGAATCCCCTAATGTGTTTACTCTAGAACACATGTTCTTTCTGTATTTATATGT
8521  GTTGTTACTTAGGGGATTACACAAATGAGATCTTGTGTACAAGAAAGACATAAATATACA

8581  AGATTTTGTAGATCTTGTCTTACCACCTGCTAATGGTAGATACTGTATCTAAATAAGTTG
8581  TCTAAAACATCTAGAACAGAATGGTGGACGATTACCATCTATGACATAGATTTATTCAAC

8641  AGGAAAATTTATAGTACCTAGGAATGTGTCCTCAGTGGGCCAATCAATCAATCATGACTT
8641  TCCTTTTAAATATCATGGATCCTTACACAGGAGTCACCCGGTTAGTTAGTTAGTACTGAA

8701  CAGGTTATTTTTAATAAATATACACGTATGGGTTCATAAACAATGGGATGTTCTTGTGAA
8701  GTCCAATAAAAATTATTTATATGTGCATACCCAAGTATTTGTTACCCTACAAGAACACTT

8761  GATCTAAATAATTTTACTTCTTTGGGACTAAATAAAATATAGCTTTTGCCAAATAAACTC
8761  CTAGATTTATTAAAATGAAGAAACCCTGATTTATTTTATATCGAAAACGGTTTATTTGAG

8821  ACACAAGCACTTATTTTAATAGAAGTCAAATGGCTTTGCAGAAACTTCAGTTTTACAGGT
8821  TGTGTTCGTGAATAAAATTATCTTCAGTTTACCGAAACGTCTTTGAAGTCAAAATGTCCA

8881  GCATTGTTTGAAATGTTACGGGTATACAAGTGGATTTCTCTATTATGTACAGTGTTAAGT
8881  CGTAACAAACTTTACAATGCCCATATGTTCACCTAAAGAGATAATACATGTCACAATTCA

8941  TTGAGTTTCAAAATGTCCACCTGAAATGATTTACTTGTACGTTAAGATAATTTAACTGCT
8941  AACTCAAAGTTTTACAGGTGGACTTTACTAAATGAACATGCAATTCTATTAAATTGACGA

9001  AAGAAGGCAAGATAAAGCATTCTTTGTGACACCATATGGCCTTGCTGAGGGAAAAACTTA
9001  TTCTTCCGTTCTATTTCGTAAGAAACACTGTGGTATACCGGAACGACTCCCTTTTTGAAT

9061  CTGTTATAAGTTTGTGTTTATCTCTCTTTTTAAAAAAAAATGAAGAAAAAAACGTTTAAA
9061  GACAATATTCAAACACAAATAGAGAGAAAAATTTTTTTTTACTTCTTTTTTTGCAAATTT

9121  ATAATGGGAACACAGCAGTTCCTGGGGTCCTCTGTCTCTTTATCTTATTATAGTAAATTA
9121  TATTACCCTTGTGTCGTCAAGGACCCCAGGAGACAGAGAAATAGAATAATATCATTTAAT

9181  CCAAAAAAATAATGACCTGGGGCATGTCTGTGTGGACCCTTCTTTTAGAGGCAGTTTCTG
9181  GGTTTTTTTATTACTGGACCCCGTACAGACACACCTGGGAAGAAAATCTCCGTCAAAGAC

9241  TGTTTTGTAAAGCTGTAGGTTCTATTTTCATTGCACTTCATATTGCTGCACAGCTCCTGA
9241  ACAAAACATTTCGACATCCAAGATAAAAGTAACGTGAAGTATAACGACGTGTCGAGGACT

9301  CCATGCATGAAGGTCCTCTGAAATCGGTAAGAGGGCAGAAGAAAATGATTCTAAACTTAG
9301  GGTACGTACTTCCAGGAGACTTTAGCCATTCTCCCGTCTTCTTTTACTAAGATTTGAATC

9361  ATTTTTTTAACTTAAGTGATGAAGTGTGAAACGCCATTTATATTTGAGGAAGCTACCTAG
9361  TAAAAAAATTGAATTCACTACTTCACACTTTGCGGTAAATATAAACTCCTTCGATGGATC

9421  GAAGTGGCTCATGTCGATGGCCCAAATCAGAAGAGGGCCTGTAAAAGCTTCTATCAATTT
9421  CTTCACCGAGTACAGCTACCGGGTTTAGTCTTCTCCCGGACATTTTCGAAGATAGTTAAA
```

FIG. 5 (cont'd)

```
9481   TGACTGTGTATGCTTCTACCATGGCGGCTCAATAAACAGCAGTATTAGTTTAAGAGTGGA
9481   ACTGACACATACGAAGATGGTACCGCCGAGTTATTTGTCGTCATAATCAAATTCTCACCT

9541   TGGTACAGTAGTATAGACGGGAAGCCTCTCCTCTCCGTGTGAACCGTGCACCCCTATGAG
9541   ACCATGTCATCATATCTGCCCTTCGGAGAGGAGAGGCACACTTGGCACGTGGGGATACTC

9601   AGGGTAGAGACAATACAATATGCCTGTAACGTCAGGACAGACAGTCATGGCCAGCTTGAA
9601   TCCCATCTCTGTTATGTTATACGGACATTGCAGTCCTGTCTGTCAGTACCGGTCGAACTT

9661   CTCCAGCCCTGGGCTTCTTGCAGCAACAAACGTGAACACAGAGGACTGTCTCCAACTCCA
9661   GAGGTCGGGACCCGAAGAACGTCGTTGTTTGCACTTGTGTCTCCTGACAGAGGTTGAGGT

9721   CTTTCTCTATTTTTAAAACAACTTTTTGAATACAGTATCTGCCATCTTTTCTTATACCTC
9721   GAAAGAGATAAAAATTTTGTTGAAAAACTTATGTCATAGACGGTAGAAAAGAATATGGAG

9781   ACTTTGAAACAGGTGGCTCCACTGTGGCATTTAAAATGTTCTGTTTCTTTTCCCTCTGTA
9781   TGAAACTTTGTCCACCGAGGTGACACCGTAAATTTTACAAGACAAAGAAAAGGGAGACAT

9841   TCAAATACCTCTTTACCAAGAAAACATTCAAACAGCATAGTTTTTAACTGTATTTTGAAA
9841   AGTTTATGGAGAAATGGTTCTTTTGTAAGTTTGTCGTATCAAAAATTGACATAAAACTTT

9901   GGTTTCCTTAGTTCCCTTTGACCCTTCCTCTTTTGCATATCAGTTCCTGGCCATAAAAAT
9901   CCAAAGGAATCAAGGGAAACTGGGAAGGAGAAAACGTATAGTCAAGGACCGGTATTTTTA

9961   AAAAAATGCTAGGACAGAATTGCACATCTGAGCTGATTTGCCCTCAAAAAGTTTCACAGT
9961   TTTTTTACGATCCTGTCTTAACGTGTAGACTCGACTAAACGGGAGTTTTTCAAAGTGTCA

10021  GGAACAAACCGCAGGAGGAGTTTTCTGTGGCTCAGTTAAATGTCGGGGGAGGGTGGTGTG
10021  CCTTGTTTGGCGTCCTCCTCAAAAGACACCGAGTCAATTTACAGCCCCCTCCCACCACAC

10081  AAAGCCAAATTGGATTCCTGCTTTCCTGTTTAAATCTTGTTTTTCATTGTTATTTGCACC
10081  TTTCGGTTTAACCTAAGGACGAAAGGACAAATTTAGAACAAAAAGTAACAATAAACGTGG

10141  AGCAATACTCTGTGGAATAATCATGAAAATGTGTAGATTGGCAGCTAATTTTTGAAAAAT
10141  TCGTTATGAGACACCTTATTAGTACTTTTACACATCTAACCGTCGATTAAAAACTTTTTA

10201  GAAAAGAATCAGAAATGAAATAAGAGTGCTCGGAAGTTTTTATGTTCTCTCAACCTGTTT
10201  CTTTTCTTAGTCTTTACTTTATTCTCACGAGCCTTCAAAAATACAAGAGAGTTGGACAAA

10261  TGTCAAATTGTTACGAAAACCTATAAGGTCTCTTTGACTAGATACAAAGACTTTGCACAT
10261  ACAGTTTAACAATGCTTTTGGATATTCCAGAGAAACTGATCTATGTTTCTGAAACGTGTA

10321  TGCCTTAGCTTTCTCTTGAAGCATTTCCTTTTTTAAAATACAGTGTAATTCACAGTGATA
10321  ACGGAATCGAAAGAGAACTTCGTAAAGGAAAAAATTTTATGTCACATTAAGTGTCACTAT

10381  TGATAGATTTGCAAAAGTAAAATCTACCAGTCTGAAGATGAAAGGACTTGTCTCTTAGCA
10381  ACTATCTAAACGTTTTCATTTTAGATGGTCAGACTTCTACTTTCCTGAACAGAGAATCGT

10441  GGAATAATGGGTTTTATTAAAGAGGTCTGTGACCTAAGGCATTTTAAATAAATTACAGGC
10441  CCTTATTACCCAAAATAATTTCTCCAGACACTGGATTCCGTAAAATTTATTTAATGTCCG

10501  TTGGTCCCTGTCTCCCCCATGTATCTACTCCCTTCAATATAAGCATCATTGAGTATTTAA
10501  AACCAGGGACAGAGGGGGTACATAGATGAGGGAAGTTATATTCGTAGTAACTCATAAATT

10561  GGAAATAACCCCAAATGTAACTCTAGTGTAGCTTCACTTGTCAGGGAGGAAAAAGTAAAT
10561  CCTTTATTGGGGTTTACATTGAGATCACATCGAAGTGAACAGTCCCTCCTTTTTCATTTA

10621  AGCATACATTTGGCCAAATAACCAGAACTTTACTGTAGAAGTTTTATGATGAAATTTGCC
10621  TCGTATGTAAACCGGTTTATTGGTCTTGAAATGACATCTTCAAAATACTACTTTAAACGG

10681  TTTAGTGCAGAGTATTACAAAGATCATGTTTAGTTTCTAGCAGTATATAAGTAGCATCCA
10681  AAATCACGTCTCATAATGTTTCTAGTACAAATCAAAGATCGTCATATATTCATCGTAGGT

10741  TCCTTATCTGTCATGCATTTGGAGTGTGCGACCCCTGCACTGGGCTGCAACATTCTGATG
10741  AGGAATAGACAGTACGTAAACCTCACACGCTGGGGACGTGACCCGACGTTGTAAGACTAC

10801  GGCAAGAGTGCTAGGGAGAAAGAGGCATCACCATCAGACTGCACGGGTTCAAGTGTCAGC
10801  CCGTTCTCACGATCCCTCTTTCTCCGTAGTGGTAGTCTGACGTGCCCAAGTTCACAGTCG
```

FIG. 5 (cont'd)

```
10861  TCTGTGGTTGATTAGCTGTGTGACCTGGGGAAAGCTATTTCTCTTAGCCTTGGTTCTCTC
10861  AGACACCAACTAATCGACACACTGGACCCCTTTCGATAAAGAGAATCGGAACCAAGAGAG

10921  ATCTATAAAATGGAGATAATGATGCAGATGCCTTGGGTTTAATTGGGAGAGTTAAAGACA
10921  TAGATATTTTACCTCTATTACTACGTCTACGGAACCCAAATTAACCCTCTCAATTTCTGT

10981  CATTTACATATTTAGCAAGTAGGTGTTGAATTCTAGCTCTACATTGGACACTATGCCAGG
10981  GTAAATGTATAAATCGTTCATCCACAACTTAAGATCGAGATGTAACCTGTGATACGGTCC

11041  TGCTCAAATAAACAAGTGGACAAGACAGACAACACCCATGGTCTTATGAGGCTTAACCAT
11041  ACGAGTTTATTTGTTCACCTGTTCTGTCTGTTGTGGGTACCAGAATACTCCGAATTGGTA

11101  TTGCCTCTTCAATGCCAGAAACTTAGTAGGTTGATTAGATAAAGCCAGTGAGTACCAGTA
11101  AACGGAGAAGTTACGGTCTTTGAATCATCCAACTAATCTATTTCGGTCACTCATGGTCAT

11161  TCCTTTTCTTTGCAGCCTTTTCCTGGCACACTAAAAATACTCAGTACATATGAAATATCA
11161  AGGAAAAGAAACGTCGGAAAAGGACCGTGTGATTTTTATGAGTCATGTATACTTTATAGT

11221  CTGGACAAAGAATCCCCCTTAGAGTACCAGTGGAGAAGGAAGGCATTTGCTTAAAAGCAA
11221  GACCTGTTTCTTAGGGGGAATCTCATGGTCACCTCTTCCTTCCGTAAACGAATTTTCGTT

11281  ACCAACAGAAAGACATTGTAAGGCAGTTGTTTAAGTCTCAGAGACCTATAATTTTTTTCT
11281  TGGTTGTCTTTCTGTAACATTCCGTCAACAAATTCAGAGTCTCTGGATATTAAAAAAAGA

11341  TTTTTCTTTTTTTTCATCTCGCTCTGTCGCCCAGGCTGGAGTGCAGTGGCACAATCTCAG
11341  AAAAAGAAAAAAAAGTAGAGCGAGACAGCGGGTCCGACCTCACGTCACCGTGTTAGAGTC

11401  CTCACTGCAAGCTCCACCTTCCGGGTTCATGCCATTCTTCTGCCTCAGCCTCCCAAGTAG
11401  GAGTGACGTTCGAGGTGGAAGGCCCAAGTACGGTAAGAAGACGGAGTCGGAGGGTTCATC

11461  CAGAGACTACAGGCGCCCGCCACCACACCTGGCTAATTTTTTGTATTTTTAGTGGAGACG
11461  GTCTCTGATGTCCGCGGGCGGTGGTGTGGACCGATTAAAAAACATAAAAATCACCTCTGC

11521  GGGTTTCGCCGTGTTAGCCAGGATGGTCTTGATCTCCTGACCTCATGATCCGCCTGCCTC
11521  CCCAAAGCGGCACAATCGGTCCTACCAGAACTAGAGGACTGGAGTACTAGGCGGACGGAG

11581  GGCCTCCCAAAGTGCTGGGATTACTGGCATGAGCCACCACGCCCGGCAACTACAATTGTT
11581  CCGGAGGGTTTCACGACCCTAATGACCGTACTCGGTGGTGCGGGCCGTTGATGTTAACAA

11641  CTTAAAGCTTGTAGAATTACTGTGTGCTACCAACAGACAGGCTAATTTTGAGTGACCCTC
11641  GAATTTCGAACATCTTAATGACACACGATGGTTGTCTGTCCGATTAAAACTCACTGGGAG

11701  AGTACTTTGTACAGTTAATTTGGCACGCTGTGTACTTAGTGGCTTTTTAACAGCTATAAA
11701  TCATGAAACATGTCAATTAAACCGTGCGACACATGAATCACCGAAAAATTGTCGATATTT

11761  TTTGGGCTGCTAGAAAAGTAGTAAAGTTGTGATTCTTGACAGGCATCTATCTGCATTTTC
11761  AAACCCGACGATCTTTTCATCATTTCAACACTAAGAACTGTCCGTAGATAGACGTAAAAG

11821  ATTTTTACTTCATTTGTCTAGACTCAGCTTGTCAGAATTATGGAAGAGACTCCTTGTGTC
11821  TAAAAATGAAGTAAACAGATCTGAGTCGAACAGTCTTAATACCTTCTCTGAGGAACACAG

11881  AGGGCAAGCACTGTGAAGAGAGGTATTCACTGTCAGAAAAGAGAGGGGAGCTGGAGGCAG
11881  TCCCGTTCGTGACACTTCTCTCCATAAGTGACAGTCTTTTCTCTCCCCTCGACCTCCGTC

11941  CTCAGAGGCCTGAGACCCGCCTCCACAGGAGCCCCAGCAGGTTCGGTGGAGCTCTGGCCA
11941  GAGTCTCCGGACTCTGGGCGGAGGTGTCCTCGGGGTCGTCCAAGCCACCTCGAGACCGGT

12001  CACTCTCCTTTGGGATGCTGAAGTCAGAATGAGTTCACTTCCCAGCCAGTCTTGCCAAGG
12001  GTGAGAGGAAACCCTACGACTTCAGTCTTACTCAAGTGAAGGGTCGGTCAGAACGGTTCC

12061  CTCCTCACCTGGAAGCAGCAACTGCCCAGGGCTGTTGGATGTTTCTCCCCAGGGGACAGC
12061  GAGGAGTGGACCTTCGTCGTTGACGGGTCCCGACAACCTACAAAGAGGGGTCCCCTGTCG

12121  CAGGTCCCAGTCCCGCCTCGGTGTGGAAGGAGGAAAGGCAGGGTCCAGGAAGCTGTTTCA
12121  GTCCAGGGTCAGGGCGGAGCCACACCTTCCTCCTTTCCGTCCCAGGTCCTTCGACAAAGT

12181  GGACAGGCCCAAGGTCCCCCAGGGATGCCTTTCAGGGTCAGCGGAGGCTGTAAATCAGCA
12181  CCTGTCCGGGTTCCAGGGGGTCCCTACGGAAAGTCCCAGTCGCCTCCGACATTTAGTCGT
```

FIG. 5 (cont'd)

12241 GGGCCCACACGGCCTGGAAGAGGCCCCTGTGCTGTCGGCTTGCCCGGCTTGCCCGGCTCC
12241 CCCGGGTGTGCCGGACCTTCTCCGGGGACACGACAGCCGAACGGGCCGAACGGGCCGAGG

12301 TAGTCCGGCTTCTGCTCCTCCTTTGTAAAGTTATGGATATGCTAATAGTTTCCAACTGAG
12301 ATCAGGCCGAAGACGAGGAGGAAACATTTCAATACCTATACGATTATCAAAGGTTGACTC

12361 ACTAGGAAAGTAAGTCCTACTTGACACTGTTTGGTCAGAAAGAGGGAGAGAAAGGAGAAG
12361 TGATCCTTTCATTCAGGATGAACTGTGACAAACCAGTCTTTCTCCCTCTCTTTCCTCTTC

12421 GACAGAGAGAGACTGAGAGAGAGACAGTCTCAGACAAAGGGAGACGGAGGGAGGGAGGGA
12421 CTGTCTCTCTCTGACTCTCTCTCTGTCAGAGTCTGTTTCCCTCTGCCTCCCTCCCTCCCT

12481 GAGACAGAGAAAGAGATGGGAGGTAGGTGTGGGAGGAGGGAGAGATGCAGAAGGCAGAGG
12481 CTCTGTCTCTTTCTCTACCCTCCATCCACACCCTCCTCCCTCTCTACGTCTTCCGTCTCC

12541 AAAGACAGACAGAGATTTAGACCTCCCAAGTCAGTGAGCAGTCCAGAGTTGGAGTGGAGG
12541 TTTCTGTCTGTCTCTAAATCTGGAGGGTTCAGTCACTCGTCAGGTCTCAACCTCACCTCC

12601 GTGCCTGGTGGCTTGTGACTGCAGACTCCACTCCCCGCTCCTAGAGGCACAGCCATGGAC
12601 CACGGACCACCGAACACTGACGTCTGAGGTGAGGGGCGAGGATCTCCGTGTCGGTACCTG

12661 AGCTTCTGTCACGTTGGCCCTGCACTTATCTCTGCATCTATTTCCCCTTGTGCAAGATTC
12661 TCGAAGACAGTGCAACCGGGACGTGAATAGAGACGTAGATAAAGGGGAACACGTTCTAAG

12721 AGAACTGCATGCTCCAAAAAAACAATAAAAGCATTCATGTTCATAAGAATTGCACAGGTA
12721 TCTTGACGTACGAGGTTTTTTTGTTATTTTCGTAAGTACAAGTATTCTTAACGTGTCCAT

12781 AAAGGTAGTTTGCTGATATTGTTGTATTTTTTACTATCGCTTCTTTTAGGTCTTGCCTGA
12781 TTTCCATCAAACGACTATAACAACATAAAAAATGATAGCGAAGAAAATCCAGAACGGACT

12841 AATTGTTTGGGTTTCCCAGGCAAAGTAGAAAACTGCGGTACGTTTCTGTGAAATAATTAT
12841 TTAACAAACCCAAAGGGTCCGTTTCATCTTTTGACGCCATGCAAAGACACTTTATTAATA

12901 TCCTTCTGGCATCTCCCTTTACAGACCTACTGATCTTGATTTTTCATTTAGGTGAAAGTT
12901 AGGAAGACCGTAGAGGGAAATGTCTGGATGACTAGAACTAAAAAGTAAATCCACTTTCAA

12961 TGTGAAAACATGCCATTAGCTTGCTTTGTGATTAACTCCTTTTACTGAATGTGAGCTCCT
12961 ACACTTTTGTACGGTAATCGAACGAAACACTAATTGAGGAAAATGACTTACACTCGAGGA

13021 TTTAAATTGAGGCCATATCAAGCTTAAATTCCATATTTTACCCGGCACTCTGCATTTCTT
13021 AAATTTAACTCCGGTATAGTTCGAATTTAAGGTATAAAATGGGCCGTGAGACGTAAAGAA

13081 CCATGTGGGAGAGGAGGGGCTCAGTAAGTGCTTTGTAAAATACACAGCCGAAGTGATGCA
13081 GGTACACCCTCTCCTCCCCGAGTCATTCACGAAACATTTTATGTGTCGGCTTCACTACGT

13141 CGTGCTAACAAAGGAGTGTGACAGGACTTAAGTGCCCTTCTAGACACTTCAGGCTCCCCT
13141 GCACGATTGTTTCCTCACACTGTCCTGAATTCACGGGAAGATCTGTGAAGTCCGAGGGGA

13201 TTGTAAGCTGTCTTGGAAGAGGCCACATTTCCTTTCCCTCAAACAGTTTCTCATTGTTTG
13201 AACATTCGACAGAACCTTCTCCGGTGTAAAGGAAAGGGAGTTTGTCAAAGAGTAACAAAC

13261 ATTATTCTTTTAGCCTTTCTCTGGAAGCAAAGCCACTTTTACGAGAAAGTCACTGCTTTT
13261 TAATAAGAAAATCGGAAAGAGACCTTCGTTTCGGTGAAAATGCTCTTTCAGTGACGAAAA

13321 TCATCTCAAGAGATGCAAGTTTGGAGTTTGGGGAAGTTTTCAGGTGCCCGTCAAGTCATC
13321 AGTAGAGTTCTCTACGTTCAAACCTCAAACCCCTTCAAAAGTCCACGGGCAGTTCAGTAG

13381 CTTTATGATGTCAGACGAGTCAGGCCACAGAATTCACAGGGCTCAGTGCAGACCGAAAAC
13381 GAAATACTACAGTCTGCTCAGTCCGGTGTCTTAAGTGTCCCGAGTCACGTCTGGCTTTTG

13441 TTGAGGCCTCTTGTTCAGAAATTATTAAAAATTTTGGTGAACATCACCCCAAGCAAAGAG
13441 AACTCCGGAGAACAAGTCTTTAATAATTTTTAAAACCACTTGTAGTGGGGTTCGTTTCTC

13501 ATCCCCTAAGCACCAGCCCCCAAGCAACTGCACTCATAAGCCCATGAAGCCCCCTGCTGT
13501 TAGGGGATTCGTGGTCGGGGGTTCGTTGACGTGAGTATTCGGGTACTTCGGGGGACGACA

13561 CAGAAACAATGTGGTTGAAATTGTGTATGCACTTGGAAGTGAGATGGATTGCAAAACACA
13561 GTCTTTGTTACACCAACTTTAACACATACGTGAACCTTCACTCTACCTAACGTTTTGTGT

FIG. 5 (cont'd)

```
13621  GGTCTCCATGCTGGGGCAGGAGTGGTGATAGGGCATGGAGTGGAAATGTCCAGCAGGCCC
13621  CCAGAGGTACGACCCCGTCCTCACCACTATCCCGTACCTCACCTTTACAGGTCGTCCGGG

13681  ACGTGCGAAAATGCAGAGCTCTCTGGCTCTTGCAGACTTGGCTGCTGACAATAGACGCGC
13681  TGCACGCTTTTACGTCTCGAGAGACCGAGAACGTCTGAACCGACGACTGTTATCTGCGCG

13741  TCCAGGAAGGTGCTCGCTGTGGTGTGATCTGCTGCCCACCCCTAGCTCCCTCCAGGAGAC
13741  AGGTCCTTCCACGAGCGACACCACACTAGACGACGGGTGGGGATCGAGGGAGGTCCTCTG

13801  TGGTGCGGGGACTGTTTGCAAATGACTGCAAAAGTAAGAAGGTTCCCACAGAGCAGAGCT
13801  ACCACGCCCCTGACAAACGTTTACTGACGTTTTCATTCTTCCAAGGGTGTCTCGTCTCGA

13861  TGATTTGGGGACCAGCCGAGGGCAGTTTGTCAGGATTCCGGCTTGAAACTGTTCTCACAT
13861  ACTAAACCCCTGGTCGGCTCCCGTCAAACAGTCCTAAGGCCGAACTTTGACAAGAGTGTA

13921  CTCACCGCCTGAAAGGACGAGTGTGTCCAGAGGACTTAGCATTGATCACCTCTGTCTCCA
13921  GAGTGGCGGACTTTCCTGCTCACACAGGTCTCCTGAATCGTAACTAGTGGAGACAGAGGT

13981  TGCAGCAAACTCAGAGGCTCAGCCCGCATTCCACTGGAAGGGCGTTTGCCAGTGGTGTTG
13981  ACGTCGTTTGAGTCTCCGAGTCGGGCGTAAGGTGACCTTCCCGCAAACGGTCACCACAAC

14041  GTTGGAAGAGCCTTGACTTTGCCTTAGGAAACATCTTTTTTTAAGAATTGAAAATAACTT
14041  CAACCTTCTCGGAACTGAAACGGAATCCTTTGTAGAAAAAAATTCTTAACTTTTATTGAA

14101  GAGTATGCAACAGTAGGGCATTTGTTATATAAATTAGTTGACTAGTGTGTAGCCAGTAAA
14101  CTCATACGTTGTCATCCCGTAAACAATATATTTAATCAACTGATCACACATCGGTCATTT

14161  ATGATGATGGTGGTGTGTATTTGTTAAATAAAAAGATATGTGTGGTATTAAATTAAAAAA
14161  TACTACTACCACCACACATAAACAATTTATTTTTCTATACACACCATAATTTAATTTTTT

14221  TATTTTAAAACAACATATTTGTAATCTGTTTAGTGTCCTCTTTTTGTAAAAAGTACAGAA
14221  ATAAAATTTTGTTGTATAAACATTAGACAAATCACAGGAGAAAAACATTTTTCATGTCTT

14281  ATAAATATACAGAAAAAATAGTAGTCCTAAGTGGTAGAAATTATGAGCATTTTCTTGCCT
14281  TATTTATATGTCTTTTTTATCATCAGGATTCACCATCTTTAATACTCGTAAAAGAACGGA

14341  TTAAAAAAAGTTGTAAAAGATTGTATCATTTATGTAGCAAAAAGTTTTAAGTCAGCATTC
14341  AATTTTTTTCAACATTTTCTAACATAGTAAATACATCGTTTTTCAAAATTCAGTCGTAAG

14401  TAAAAATTTCGTGTTGTTATAGTTGCTGTGACAAGATTTAACTTCTGTATGCTTCACCAA
14401  ATTTTTAAAGCACAACAATATCAACGACACTGTTCTAAATTGAAGACATACGAAGTGGTT

14461  TCAATACAGAGGTATTTAAGACCCGGTGTGTGATAGGCCGCGCTAAAATACTATACACAT
14461  AGTTATGTCTCCATAAATTCTGGGCCACACACTATCCGGCGCGATTTTATGATATGTGTA

14521  CTTCAGAAAACTAGAGAACTAACTTCTAACTTCCTATATTAGTGTGGCACGGCTGTTACA
14521  GAAGTCTTTTGATCTCTTGATTGAAGATTGAAGGATATAATCACACCGTGCCGACAATGT

14581  AAGATTTTTCTCATTTGAGTCTATCTTGCTTCTTTATCATTGTTTTGACAGTTTCAGAAG
14581  TTCTAAAAAGAGTAAACTCAGATAGAACGAAGAAATAGTAACAAAACTGTCAAAGTCTTC

14641  AATCGTGGCTTTTCCCCTTTTTTACAGTAAAGGTACCTGAGACTCTTGACGTATTGCTTT
14641  TTAGCACCGAAAAGGGGAAAAAATGTCATTTCCATGGACTCTGAGAACTGCATAACGAAA

14701  TTGGAAATGCTTGTGCTGGTCACATGCTTGCATCTGGGCTAGTGTGTCTGGCTTCCGTGT
14701  AACCTTTACGAACACGACCAGTGTACGAACGTAGACCCGATCACACAGACCGAAGGCACA

14761  GCTGGTGGATGCTTACTCTGTTTTCTGAAATACTTTTTCTGTACAGTGGCCACTAGCTGT
14761  CGACCACCTACGAATGAGACAAAAGACTTTATGAAAAAGACATGTCACCGGTGATCGACA

14821  ACTCCTAAGCCACACACCTACCTTGAAAATTCATGTCACTTTTAGAAATAGATAAAAGCC
14821  TGAGGATTCGGTGTGTGGATGGAACTTTTAAGTACAGTGAAAATCTTTATCTATTTTCGG

14881  CCTCCCATCCAGAAAAAGTGACTATCATGTATATCCTCATCATGACTAATACTGATATTC
14881  GGAGGGTAGGTCTTTTTCACTGATAGTACATATAGGAGTAGTACTGATTATGACTATAAG

14941  CTGAAATTGAAAATACATATTCCATATGTACCATAAAAGGTATTAAAGATATATGGAGTG
14941  GACTTTAACTTTTATGTATAAGGTATACATGGTATTTTCCATAATTTCTATATACCTCAC
```

FIG. 5 (cont'd)

```
15001  ATAGATATATTATATATAACACTTCTACCCTCACAGTTTTCAGCCTAATTGAGAGGGTAA
15001  TATCTATATAATATATATTGTGAAGATGGGAGTGTCAAAAGTCGGATTAACTCTCCCATT

15061  GATCCCTGAATCATCCATCAGTTTTTCAGGTCTCTGCTGAAAGCAGGCCACAGCTCAGAT
15061  CTAGGGACTTAGTAGGTAGTCAAAAAGTCCAGAGACGACTTTCGTCCGGTGTCGAGTCTA

15121  CCACACATCTGAACCAGAGACAGAGGTGGCCAAAAATAAAAAGGGGGACAGGGGGACAAC
15121  GGTGTGTAGACTTGGTCTCTGTCTCCACCGGTTTTTATTTTTCCCCCTGTCCCCCTGTTG

15181  CTGGTTTAGAGTCAACAAATAGACTGCATTTTCTGGTTAGTGAAGGAGCTCTCCTGAAAG
15181  GACCAAATCTCAGTTGTTTATCTGACGTAAAAGACCAATCACTTCCTCGAGAGGACTTTC

15241  TCATATACCAGAGCATAAATGAGCAGATTTCCTTGAGGTCACCTTCTGCTGGCCATAGCT
15241  AGTATATGGTCTCGTATTTACTCGTCTAAAGGAACTCCAGTGGAAGACGACCGGTATCGA

15301  TTCTTATCTGTGGAGCTGCCAGCTGTCATCCACTTTGGGGCACCTGAGACTGCCGAGCGG
15301  AAGAATAGACACCTCGACGGTCGACAGTAGGTGAAACCCCGTGGACTCTGACGGCTCGCC

15361  CAGGCCAGGACCCAAGTGCGAAAACACAGAACACCTTTTTGTTTCTACTCCACTGATGCT
15361  GTCCGGTCCTGGGTTCACGCTTTTGTGTCTTGTGGAAAAACAAAGATGAGGTGACTACGA

15421  GGGGTTCTCTCCCTGGTGTTTGTGGCTCGTAGTACACTCTGTGGAACATTCACTATGGTC
15421  CCCCAAGAGAGGGACCACAAACACCGAGCATCATGTGAGACACCTTGTAAGTGATACCAG

15481  ATCGAAGGGCAGCATCTTCCCAGTTGTTTCTTTCTTTTCTTTTTTTTTTTTAATTTAAAC
15481  TAGCTTCCCGTCGTAGAAGGGTCAACAAAGAAAGAAAAGAAAAAAAAAAAATTAAATTTG

15541  CGATCTGAGAAGCCAGCCATCTGTCAGCAAAACAGGAAGGCTCGGGCTGTCTCCTGGGCT
15541  GCTAGACTCTTCGGTCGGTAGACAGTCGTTTTGTCCTTCCGAGCCCGACAGAGGACCCGA

15601  CGTTTTGCTGCCGTAGTGAGCGTCACTTCTCCCCGTGTAAGAGTGCTGGTGAAGGCTGAG
15601  GCAAAACGACGGCATCACTCGCAGTGAAGAGGGGCACATTCTCACGACCACTTCCGACTC

15661  GCAAGGGCCCAGAAAGATTGAGGGACAAAGACAGGAGCGCCCGCATTGCCCATCTGCCAG
15661  CGTTCCCGGGTCTTTCTAACTCCCTGTTTCTGTCCTCGCGGGCGTAACGGGTAGACGGTC

15721  GCTGGAGGTGTATTCATTATTGATGGAGGTAGTGCAGTTGCTGCTCAGATATGCAGCCCT
15721  CGACCTCCACATAAGTAATAACTACCTCCATCACGTCAACGACGAGTCTATACGTCGGGA

15781  GCCTGGGTAAATGAGACATTCTTCAGCAAATTGCTTCGTTTTTTGATTGCTGATTGTACG
15781  CGGACCCATTTACTCTGTAAGAAGTCGTTTAACGAAGCAAAAAACTAACGACTAACATGC

15841  CGTGTCACCAAGCTGACTCAAGGTTCATCGATGCATGCTCAGTAAATTAGAAAGAACATA
15841  GCACAGTGGTTCGACTGAGTTCCAAGTAGCTACGTACGAGTCATTTAATCTTTCTTGTAT

15901  ACTATGGATCAGCCAAGAGAATGAATTCTGTGCCTACAATGACCCAGGGCCATTTAATTT
15901  TGATACCTAGTCGGTTCTCTTACTTAAGACACGGATGTTACTGGGTCCCGGTAAATTAAA

15961  TCTGCTTAATTTTGTTGCAGTCAGTTTGCATTTTGGGTTATTATGCAGTAGGAAATTAAC
15961  AGACGAATTAAAACAACGTCAGTCAAACGTAAAACCCAATAATACGTCATCCTTTAATTG

16021  AATAAATAACAAATTTGGTCCTCCTGTGCTTGTAATGATATTTTTATAAATCTTTGTAAT
16021  TTATTTATTGTTTAAACCAGGAGGACACGAACATTACTATAAAAATATTTAGAAACATTA

16081  GCTGTTTTTAAAAGGATCAAGGTCTGTGCCAGTCTGATACTCCAGCAAGTATGTGAGGAG
16081  CGACAAAAATTTTCCTAGTTCCAGACACGGTCAGACTATGAGGTCGTTCATACACTCCTC

16141  GAAAATGCATTATTCTTGCTAGATAACCTTGTTGTTAAATAGCATAGGGGTTCTTTATCT
16141  CTTTTACGTAATAAGAACGATCTATTGGAACAACAATTTATCGTATCCCCAAGAAATAGA

16201  CTCTCTCTTTCTCATATCTTATTAGTATTTTTGCTTTAAACTAAAATCCCTTCCTCTCTT
16201  GAGAGAGAAAGAGTATAGAATAATCATAAAAACGAAATTTGATTTTAGGGAAGGAGAGAA

16261  TCTCAGATAACCTGAGGACCATGGATGCTGATGAGGGTCAAGACATGTCCCAAGTTTCAG
16261  AGAGTCTATTGGACTCCTGGTACCTACGACTACTCCCAGTTCTGTACAGGGTTCAAAGTC

16321  GTGAGACCTTATGAGATAGCTGTGTGGGAAGTTCATGAGAAAAGCTTCCCTGGGGCCGGA
16321  CACTCTGGAATACTCTATCGACACACCCTTCAAGTACTCTTTTCGAAGGGACCCCGGCCT
```

FIG. 5 (cont'd)

```
16381  AGTCACAGTGCTTGGTATGCTCATGGGGGAGGAATAGGGGCTATTCTGCAAAAGAAAAGA
16381  TCAGTGTCACGAACCATACGAGTACCCCCTCCTTATCCCCGATAAGACGTTTTCTTTTCT

16441  CCATGATGGAATTTGCCTGAGTGTTTCCTTCACCTGTTACAAATTATCTCACTTTGAGCT
16441  GGTACTACCTTAAACGGACTCACAAAGGAAGTGGACAATGTTTAATAGAGTGAAACTCGA

16501  GAACAGAAAGCCTCCAAGATGAAATTAGTTTTACTGTTAAACTTCAGGAAAAAAAAACGG
16501  CTTGTCTTTCGGAGGTTCTACTTTAATCAAAATGACAATTTGAAGTCCTTTTTTTTTGCC

16561  GAAGAGTTAAATACATTTTTGTACTGTTGGAAGGAAAAATGGCTGATTGGTTTAAAACCC
16561  CTTCTCAATTTATGTAAAAACATGACAACCTTCCTTTTTACCGACTAACCAAATTTTGGG

16621  AAACACATGCCAATGATGGTACTTAAAGAGAGAGAGAGAGAGAAGCTTGAAAAACATAAT
16621  TTTGTGTACGGTTACTACCATGAATTTCTCTCTCTCTCTCTCTTCGAACTTTTTGTATTA

16681  TGTTGGGCACAGTCATGACTGTTTGTTCATTAAGCATGGACACAACATTGCTCCCCTTTG
16681  ACAACCCGTGTCAGTACTGACAAACAAGTAATTCGTACCTGTGTTGTAACGAGGGGAAAC

16741  CCATATATCTTTTCAAGCCGTATTGGATATAGCTCTTCTCATCCAGGAGACCCAGGAAGT
16741  GGTATATAGAAAAGTTCGGCATAACCTATATCGAGAAGAGTAGGTCCTCTGGGTCCTTCA

16801  GGAGAAGTCTGTAGTAGGAAAAGCCTAAGGGTAGGTCACAGACTGTGACCATTTGGCAGC
16801  CCTCTTCAGACATCATCCTTTTCGGATTCCCATCCAGTGTCTGACACTGGTAAACCGTCG

16861  ACTGAGGGTGGACGGCGAGCCAGTCCAACAAAACCGCACAGTTCCCCAGTGCATGGACAT
16861  TGACTCCCACCTGCCGCTCGGTCAGGTTGTTTTGGCGTGTCAAGGGGTCACGTACCTGTA

16921  AGGAAGACAGCTTTCTATCTGGCCCTGTATCCAGAGGCGTCAGCCCCAGTAGCAGCTTTC
16921  TCCTTCTGTCGAAAGATAGACCGGGACATAGGTCTCCGCAGTCGGGGTCATCGTCGAAAG

16981  ATGGACTTTGGGGTTTTCGGTATTTCATATTTTTGAGCCTCACAGACTCACAGCCAGCCC
16981  TACCTGAAACCCCAAAAGCCATAAAGTATAAAAACTCGGAGTGTCTGAGTGTCGGTCGGG

17041  CAGAGGCTGACTTATATTTGAGAAAGTTCTCAGTGGCACCTTGCCTTGGCTGAGCGCCCT
17041  GTCTCCGACTGAATATAAACTCTTTCAAGAGTCACCGTGGAACGGAACCGACTCGCGGGA

17101  CGTGTTTTGAAGTTTCTATGGGATTCTACAAGTTGGTGCTCCTGATGAAGACCAGGACCT
17101  GCACAAAACTTCAAAGATACCCTAAGATGTTCAACCACGAGGACTACTTCTGGTCCTGGA

17161  ATGTGTGGCTGCTCCCCTGCTTGGTGGTTTCCCTGGGGAAGGTGCAGGAGAGGATCTTCT
17161  TACACACCGACGAGGGGACGAACCACCAAAGGGACCCCTTCCACGTCCTCTCCTAGAAGA

17221  GAGTTCCATGGAACTGGAGATAGATCTGCCAATCACAGGCTTCCTTCTCCACCACTCCTC
17221  CTCAAGGTACCTTGACCTCTATCTAGACGGTTAGTGTCCGAAGGAAGAGGTGGTGAGGAG

17281  AGCCGCTCTATTCATGTTTCAGATTTTGGACTTAAACTCTCCCAGGTGCAAAGAACAAAC
17281  TCGGCGAGATAAGTACAAAGTCTAAAACCTGAATTTGAGAGGGTCCACGTTTCTTGTTTG

17341  AAAAGGCTAGCTTATTTTTCTTTTAGAGTGAGGCTTCGTATTTATTACAATATAATTGCC
17341  TTTTCCGATCGAATAAAAAGAAAATCTCACTCCGAAGCATAAATAATGTTATATTAACGG

17401  ACATTCTTTGTGTAATTCTCACATTTATATCTTAAATATAATTCTCATGAATGAGAATTA
17401  TGTAAGAAACACATTAAGAGTGTAAATATAGAATTTATATTAAGAGTACTTACTCTTAAT

17461  TATAATTCTCTTTTTGTATATCATTGAATATTTTCACTTAATTTTTAATTTTTTTAATCG
17461  ATATTAAGAGAAAAACATATAGTAACTTATAAAAGTGAATTAAAAATTAAAAAAATTAGC

17521  TCACAAAATAATTGTGTACATAGACACAAAATAATTGGGTACATAGTGATGTTGTGATAT
17521  AGTGTTTTATTAACACATGTATCTGTGTTTTATTAACCCATGTATCACTACAACACTATA

17581  ATACAATGTATAGTAATCGGATCAGGTAAATCAGCATATTCATCATCTCAAACATTTATC
17581  TATGTTACATATCATTAGCCTAGTCCATTTAGTCGTATAAGTAGTAGAGTTTGTAAATAG

17641  GTTTCTTTGTATTAGGAACATTCGACATCTTCCTTCTAGCTATTTGAAACTATATATTAT
17641  CAAAGAAACATAATCCTTGTAAGCTGTAGAAGGAAGATCGATAAACTTTGATATATAATA

17701  TGTTGACTACAGTCATCCTGCAATGGTGTAGAACACTAGAACTTATTCTTCCTACCTAGC
17701  ACAACTGATGTCAGTAGGACGTTACCACATCTTGTGATCTTGAATAAGAAGGATGGATCG
```

FIG. 5 (cont'd)

17761 TGTAATTTTGTCTCCTTTAACAAATCTCTCCCTATCTTCCACTCCCCCGACCTTTCCAGC
17761 ACATTAAAACAGAGGAAATTGTTTAGAGAGGGATAGAAGGTGAGGGGGCTGGAAAGGTCG

17821 CTCTATTAGCCTCTGTCCTACTTTCTACTTATAATGATGACAGCAGCATTTGTTAGTTTC
17821 GAGATAATCGGAGACAGGATGAAAGATGAATATTACTACTGTCGTCGTAAACAATCAAAG

17881 CACATGTGAGTGAGAACATGTGGCTTTTTAACTTTTAGAATGTGGTATTCAGGCACTTCA
17881 GTGTACACTCACTCTTGTACACCGAAAAATTGAAAATCTTACACCATAAGTCCGTGAAGT

17941 TGGTACAGTTGGTAAAAGTGAAAATGTGTCCAAAAGTTTGTGATTATCTATATAAACAAA
17941 ACCATGTCAACCATTTTCACTTTTACACAGGTTTTCAAACACTAATAGATATATTTGTTT

18001 AATGGTATAAATACAAATATCAATTTTGCATTGAAGAACTTACCTTAGAGGTATATTCTC
18001 TTACCATATTTATGTTTATAGTTAAAACGTAACTTCTTGAATGGAATCTCCATATAAGAG

18061 ACAAGTGCACAGAGCATTTAAGCATTTGTTCACTGCAGCATTGTTATCAGTATTTTAAAA
18061 TGTTCACGTGTCTCGTAAATTCGTAAACAAGTGACGTCGTAACAATAGTCATAAAATTTT

18121 CTATGGTACATCCATGTACTTCCACATACAGCTCTTAAAAATAAGGAGGATATGAATGAA
18121 GATACCATGTAGGTACATGAAGGTGTATGTCGAGAATTTTTATTCCTCCTATACTTACTT

18181 CTAGTATGAAAAGAAGTCCAAATACATGTGAAAGTGAGAATAGCATGGTTCTGGATGGTA
18181 GATCATACTTTTCTTCAGGTTTATGTACACTTTCACTCTTATCGTACCAAGACCTACCAT

18241 TGCAAAGTATGATCTCGTTCTTTTAAAAGAAAATAAATTACATACACATACATATTTTCT
18241 ACGTTTCATACTAGAGCAAGAAAATTTTCTTTTATTTAATGTATGTGTATGTATAAAAGA

18301 ATATGCTTGCCCATAACGTTTAGGAAAATTCTTGGGTGATATTTATTAACCTGGACTTCC
18301 TATACGAACGGGTATTGCAAATCCTTTTAAGAACCCACTATAAATAATTGGACCTGAAGG

18361 TCTTGGAAGACTGATGGTAGAAGGAAGGGGACGAGTTAGGGAAGAGGAGGAGAAGGAAAA
18361 AGAACCTTCTGACTACCATCTTCCTTCCCCTGCTCAATCCCTTCTCCTCCTCTTCCTTTT

18421 CTTTGCTTTTCATCTTCTACCTTTTAGCATTATTTGAATTTATTTTCCTTAAGCGTTTAC
18421 GAAACGAAAAGTAGAAGATGGAAAATCGTAATAAACTTAAATAAAAGGAATTCGCAAATG

18481 TTTGTTTCGTAAACAAAAAAGCACAAAAACAAAAAACGAGTTAAATGGGAAAAAAAGCAG
18481 AAACAAAGCATTTGTTTTTTCGTGTTTTTGTTTTTTGCTCAATTTACCCTTTTTTTCGTC

18541 TTTAGCTCTTTATAGCCTCTCATTTGGCTTCGCCAGCCTCTCACTGCAGCCTCAGAGAGC
18541 AAATCGAGAAATATCGGAGAGTAAACCGAAGCGGTCGGAGAGTGACGTCGGAGTCTCTCG

18601 TGGTCTGGGAAACACTGGTAGATGAGGACTGTAATCCTCACTCATGGAAGAGGATCTCAT
18601 ACCAGACCCTTTGTGACCATCTACTCCTGACATTAGGAGTGAGTACCTTCTCCTAGAGTA

18661 TCACTGGGTTTGCTGACTGTGACTAGAAGTGATTAGGGTGTCAAAAAACCCAAGCATGTT
18661 AGTGACCCAAACGACTGACACTGATCTTCACTAATCCCACAGTTTTTTGGGTTCGTACAA

18721 AAAAATTTCCAGAGGCCAAAAAGATGCTTTCATTGTTCTGCTCTTCTTTTCCTTGTCGCT
18721 TTTTTAAAGGTCTCCGGTTTTTCTACGAAAGTAACAAGACGAGAAGAAAAGGAACAGCGA

18781 TTCACTTTGGGTAGCTTCTAAATTGGTATTTTGCATGGTGCATTTAAAGAAAATGAGACC
18781 AAGTGAAACCCATCGAAGATTTAACCATAAAACGTACCACGTAAATTTCTTTTACTCTGG

18841 CCTTTGGCCAATGCAGGAGTCTACACTCTGATATTCTAGAGTCAAAGCTGAATGCTGACA
18841 GGAAACCGGTTACGTCCTCAGATGTGAGACTATAAGATCTCAGTTTCGACTTACGACTGT

18901 CCTAGGAATTCATCTCTAGAATGTTTATATAAGGAATAGCCCCTCAGTATTCCGATCTCG
18901 GGATCCTTAAGTAGAGATCTTACAAATATATTCCTTATCGGGGAGTCATAAGGCTAGAGC

18961 TATCTTAGTAACGAAACTAACAAAAGCCTGATTCTCCTCTGGTAGTTTTCTTGTCTTTAC
18961 ATAGAATCATTGCTTTGATTGTTTTCGGACTAAGAGGAGACCATCAAAAGAACAGAAATG

19021 CATAATACAAAATAAGTAATTTGTTCTGCACCCTGACTGTTCAAAGGATAGGGTAGCTGG
19021 GTATTATGTTTTATTCATTAAACAAGACGTGGGACTGACAAGTTTCCTATCCCATCGACC

19081 GGGCGGGGACAAGAATGGAGACCTTATTACATAAGACTTCCTGAAAAAGGAAACTCTGTT
19081 CCCGCCCCTGTTCTTACCTCTGGAATAATGTATTCTGAAGGACTTTTTCCTTTGAGACAA

FIG. 5 (cont'd)

```
19141  TTTGTTTGAAATGATTTGGTCTGAAATTTAGTTTGTGTACACTTACCAAAGGGATTCCTA
19141  AAACAAACTTTACTAAACCAGACTTTAAATCAAACACATGTGAATGGTTTCCCTAAGGAT

19201  TTTCTAAAACACTCATACTGCTTTTGATTCCTGTTAACCTTTGAGCACTCTACGTAATGA
19201  AAAGATTTTGTGAGTATGACGAAAACTAAGGACAATTGGAAACTCGTGAGATGCATTACT

19261  TGAGAGCACTTAAAGAGTCATGTCACTTTTAGTAAAGAATCAAAGGATACTTTTTCTACT
19261  ACTCTCGTGAATTTCTCAGTACAGTGAAAATCATTTCTTAGTTTCCTATGAAAAAGATGA

19321  TCTTCGAGTTTGATCTCTGCTTCTCCAGTTAAAACCAGTATTTGTTTTTTTCATTTCTAA
19321  AGAAGCTCAAACTAGAGACGAAGAGGTCAATTTTGGTCATAAACAAAAAAAGTAAAGATT

19381  AGTTGGAAGAAATGACAGTTAGTTATGGCATAAGGATGTACATTTAACCAAATAGGAGTT
19381  TCAACCTTCTTTACTGTCAATCAATACCGTATTCCTACATGTAAATTGGTTTATCCTCAA

19441  GACATTCTTGGTAAGAAATCTTACCAAGATTATGTTATAGATTATAAGAAATCTTAACAA
19441  CTGTAAGAACCATTCTTTAGAATGGTTCTAATACAATATCTAATATTCTTTAGAATTGTT

19501  GAATATGTTCCTAAATCATCCTCTTTTCCCATAAAATATTAAAGTATCAGCAATTTCATA
19501  CTTATACAAGGATTTAGTAGGAGAAAAGGGTATTTTATAATTTCATAGTCGTTAAAGTAT

19561  GGATTCAACCTAATGTATGCGAAATGCTAGATAAACAGATAAATACTTAATATCTGGCTT
19561  CCTAAGTTGGATTACATACGCTTTACGATCTATTTGTCTATTTATGAATTATAGACCGAA

19621  TTTTTCAAAGCACTGGGTTATTTGTTCCTTGAGATTTATCCTAAATGTGGGCTATACCCT
19621  AAAAAGTTTCGTGACCCAATAAACAAGGAACTCTAAATAGGATTTACACCCGATATGGGA

19681  GGTTTACAGTGTCTCACAGATGTGTAGTAGTAGACACTCCATAAGTGTTTACTGACTTGA
19681  CCAAATGTCACAGAGTGTCTACACATCATCATCTGTGAGGTATTCACAAATGACTGAACT

19741  ATCCACAGGGTACTGAGAAAATGCTACTGATAGACTTGGAGGAGAGCATATCTAAAGCAA
19741  TAGGTGTCCCATGACTCTTTTACGATGACTATCTGAACCTCCTCTCGTATAGATTTCGTT

19801  GCTACCCTTTCCTTTAGGGCACGTCTCACTAATTCTTTGGGTAAAGCGTATTTTTCTTCC
19801  CGATGGGAAAGGAAATCCCGTGCAGAGTGATTAAGAAACCCATTTCGCATAAAAAGAAGG

19861  TTTTGTGTTTTTGGCAGTCTTTCCAAAAATACGTGTTATACCTATGCATTATTTTTTGGT
19861  AAAACACAAAAACCGTCAGAAAGGTTTTTATGCACAATATGGATACGTAATAAAAAACCA

19921  TTGGTTTCTAAAGAAAGAGTCAGCCGGTGGGAAAGTGAAGGATGTGGGAACTGAGAGATC
19921  AACCAAAGATTTCTTTCTCAGTCGGCCACCCTTTCACTTCCTACACCCTTGACTCTCTAG

19981  TGCATCAGCATCCCACCTCTACCTCCCACGATGGGACCTGAGACAGTTATTTTTGCCTCC
19981  ACGTAGTCGTAGGGTGGAGATGGAGGGTGCTACCCTGGACTCTGTCAATAAAAACGGAGG

20041  TGGACCACTATAGTATCATCTGTAACAGGAGGGACTTGAGCCAGTTGATCTCTAAGGTTC
20041  ACCTGGTGATATCATAGTAGACATTGTCCTCCCTGAACTCGGTCAACTAGAGATTCCAAG

20101  CTCTGGCACCTGTGACCCTAAATAGATATTGGATATTGGTTTAATGCTATTTGTAGTGTG
20101  GAGACCGTGGACACTGGGATTTATCTATAACCTATAACCAAATTACGATAAACATCACAC

20161  TTTTTTTGGGGATATGGAAACCAGAAGTTTGTTTCCATAAACATAAACATAAACTGTATA
20161  AAAAAAACCCCTATACCTTTGGTCTTCAAACAAAGGTATTTGTATTTGTATTTGACATAT

20221  TATCTAAAGGATATGGAAACCTTTAGATATATATAATCTGCTTACGTAAAGAAGGTTTGT
20221  ATAGATTTCCTATACCTTTGGAAATCTATATATATTAGACGAATGCATTTCTTCCAAACA

20281  ATATATTGCAGTGTCAATGGGAATATTTTATCAAGTTAAGCATAGTAAATCACATTGATT
20281  TATATAACGTCACAGTTACCCTTATAAAATAGTTCAATTCGTATCATTTAGTGTAACTAA

20341  AAATGCTTTGTATTTACCAAACATTACCCAAAGTGTTTTCTCCTTTCAACCTCACAAGGA
20341  TTTACGAAACATAAATGGTTTGTAATGGGTTTCACAAAAGAGGAAAGTTGGAGTGTTCCT

20401  CCCACAGAAGAAAATACAGTTATCATTTCCAACCTGCAGGGAGCTGAGACACAGAGAATT
20401  GGGTGTCTTCTTTTATGTCAATAGTAAAGGTTGGACGTCCCTCGACTCTGTGTCTCTTAA

20461  TAAGCAACTGACCGGAAGTCCAACAGGGAGTCAGAGATTGCTCTGGGGTGTGATCCCCAC
20461  ATTCGTTGACTGGCCTTCAGGTTGTCCCTCAGTCTCTAACGAGACCCCACACTAGGGGTG
```

FIG. 5 (cont'd)

```
20521  TTGGACCCTAGAGTGGAAGCTTCTCCACTACTTTATAGAGTTGAGATTCTATATTTTGAG
20521  AACCTGGGATCTCACCTTCGAAGAGGTGATGAAATATCTCAACTCTAAGATATAAAACTC

20581  CTTGTATTTACCCAGAGAATTATATCCTCTTGGGCAATTGTGTATAATAAAACCTCATGC
20581  GAACATAAATGGGTCTCTTAATATAGGAGAACCCGTTAACACATATTATTTTGGAGTACG

20641  ATTTAGGAGAGGCGGGATGACAGAACTTTGTTGAGTGAATTATAATCTACTTGAGAAATT
20641  TAAATCCTCTCCGCCCTACTGTCTTGAAACAACTCACTTAATATTAGATGAACTCTTTAA

20701  ATTTGCTTACATTTTATAAGCTAATTATACCATATCTCATCCAGTTTTCCCAGAACACTT
20701  TAAACGAATGTAAAATATTCGATTAATATGGTATAGAGTAGGTCAAAAGGGTCTTGTGAA

20761  CTCATAGGTAATGCTTTATTTGAAACATAGGCCATAGGTAAGTTAAGTGTAAATGTGTAT
20761  GAGTATCCATTACGAAATAAACTTTGTATCCGGTATCCATTCAATTCACATTTACACATA

20821  TTTTATAATTTAACCAGAAGTTTATTTCATTTTTCTAAATAAGTGAAATTGTATTGCATC
20821  AAAATATTAAATTGGTCTTCAAATAAAGTAAAAAGATTTATTCACTTTAACATAACGTAG

20881  TTCTAAATTATTCTATTTAAACACTTGATGTCTTGCTGTCTCCGTCTCTGTGTGTTTGCA
20881  AAGATTTAATAAGATAAATTTGTGAACTACAGAACGACAGAGGCAGAGACACACAAACGT

20941  TGTCATTGTACATGTTCTTAGGAAAAGTGTGGGAGCTTGACGCAATATATACCTTATGTT
20941  ACAGTAACATGTACAAGAATCCTTTTCACACCCTCGAACTGCGTTATATATGGAATACAA

21001  TCTATGTGCATATAGTTTACCAAATAATACCATAAGTTTACTTAGCATATTAGAATCCAT
21001  AGATACACGTATATCAAATGGTTTATTATGGTATTCAAATGAATCGTATAATCTTAGGTA

21061  GCACATTATTTTTATTTTATCTTCACCGCAACCCTGTGGGATAGACCAAAATCATGCTTT
21061  CGTGTAATAAAAATAAAATAGAAGTGGCGTTGGGACACCCTATCTGGTTTTAGTACGAAA

21121  TCAGCCTCCTTTTTCCACTTGAGGAAAGGAGTCTTAAAAAAGGGACCAGTCTCATGTTCC
21121  AGTCGGAGGAAAAAGGTGAACTCCTTTCCTCAGAATTTTTTCCCTGGTCAGAGTACAAGG

21181  CATTCGTCTTACAACTAATTGGTCAAGCCAGAAAGCCAGAACTATGTCCTGGGTCACTAA
21181  GTAAGCAGAATGTTGATTAACCAGTTCGGTCTTTCGGTCTTGATACAGGACCCAGTGATT

21241  CTCCTAGTCACTGTGTGTTAGTATTTGAGATGCCTGTTGGCTTGATTTAGTCATTTATTT
21241  GAGGATCAGTGACACACAATCATAAACTCTACGGACAACCGAACTAAATCAGTAAATAAA

21301  TTTAGTGTTTTATAATCCTTGCATACTTTTACATTTTAAATGGTTAACCAGGCAAATTGG
21301  AAATCACAAAATATTAGGAACGTATGAAAATGTAAAATTTACCAATTGGTCCGTTTAACC

21361  TTTAAAATCAGTGCATAAAAATACTGTGCCTATCATGATGGGTTTCATGAAGTGATAACT
21361  AAATTTTAGTCACGTATTTTTATGACACGGATAGTACTACCCAAAGTACTTCACTATTGA

21421  TTTCATCATGGAGATCCTCAGCTGTCACAGAAGATGAGGGGCCCTGGGTACAGAGGCTCA
21421  AAAGTAGTACCTCTAGGAGTCGACAGTGTCTTCTACTCCCCGGGACCCATGTCTCCGAGT

21481  CGTGAGGGATGAAAGTCTCAGCAGCCCGGACTTACACTTTGGGGCTTTTAGGCAAATCAG
21481  GCACTCCCTACTTTCAGAGTCGTCGGGCCTGAATGTGAAACCCCGAAAATCCGTTTAGTC

21541  ACAACCTCTTAAGAACTATCACTGAGTTCAGGCAAGGCGAGCTTGAATTAACACAGGGCC
21541  TGTTGGAGAATTCTTGATAGTGACTCAAGTCCGTTCCGCTCGAACTTAATTGTGTCCCGG

21601  CTTGGTGGGCATGTGAATATATCTCACTTCACTACCATCCAGTTCTGACTCTTTACTAGA
21601  GAACCACCCGTACACTTATATAGAGTGAAGTGATGGTAGGTCAAGACTGAGAAATGATCT

21661  TGCCCCTGTACATACCAAGACTGATTTTTTATTCTCCCTTCTCCCCATGTGGTTTCTTCT
21661  ACGGGGACATGTATGGTTCTGACTAAAAAATAAGAGGGAAGAGGGGTACACCAAAGAAGA

21721  GCATAGAGAGTTCCTATTGATCAGTCTGACCCATGGTATTTTAGAATTGCGATCCCTACT
21721  CGTATCTCTCAAGGATAACTAGTCAGACTGGGTACCATAAAATCTTAACGCTAGGGATGA

21781  GTTTCATTATTCCTTTTTCTCCCCCATGTTGAAAAAAATAAATGTCCTGAGATGCAAGAT
21781  CAAAGTAATAAGGAAAAAGAGGGGGTACAACTTTTTTTATTTACAGGACTCTACGTTCTA

21841  CAGGGACACTGGAGCACTGACATTTAGTTCAGTGCAGGAACTGAAGGCAGATGTAATTCT
21841  GTCCCTGTGACCTCGTGACTGTAAATCAAGTCACGTCCTTGACTTCCGTCTACATTAAGA
```

FIG. 5 (cont'd)

```
21901  TAAGAAGCGTACCTGTTATTATGAACCATCCTCAACAAATTGTAGTGGATCTTGTTTTCT
21901  ATTCTTCGCATGGACAATAATACTTGGTAGGAGTTGTTTAACATCACCTAGAACAAAAGA

21961  CATAGATACAGCAGTTAAATTTTTTAATAAAAGTAACTAAGAGTTATTTGGATGTATTTT
21961  GTATCTATGTCGTCAATTTAAAAAATTATTTTCATTGATTCTCAATAAACCTACATAAAA

22021  AGCATGCACTGAGCGGAAAGTACGACATTTCTTCATTGGGTAAGTCCTGATTCTTTATGA
22021  TCGTACGTGACTCGCCTTTCATGCTGTAAAGAAGTAACCCATTCAGGACTAAGAAATACT

22081  TCCTCACTTGGTTCCAGGGCCCCATGCATCTAAGGGTGTCTCAGAGCATCCTGCAGTGCT
22081  AGGAGTGAACCAAGGTCCCGGGGTACGTAGATTCCCACAGAGTCTCGTAGGACGTCACGA

22141  CCAGCATGATCGCAGGGAAAAGCTATAGGAGGAAAAGAGTCAATAAAGTTTAGTTTCTCA
22141  GGTCGTACTAGCGTCCCTTTTCGATATCCTCCTTTTCTCAGTTATTTCAAATCAAAGAGT

22201  ACCTCCCACCTCCACCCCATAATAATGACAGCTGGTTAATCATGAGACGCGTGCACACCC
22201  TGGAGGGTGGAGGTGGGGTATTATTACTGTCGACCAATTAGTACTCTGCGCACGTGTGGG

22261  CACACGCCCTGTACATGTTTACTCATTGGGATAGCATGTCAGGCCAGAAGGCTCCATGGT
22261  GTGTGCGGGACATGTACAAATGAGTAACCCTATCGTACAGTCCGGTCTTCCGAGGTACCA

22321  CATTTCTATGAAGGTACTTTAGCAGGTCTTCAAGAAGGCAAGTGGCCTGGGTCCCTGCCT
22321  GTAAAGATACTTCCATGAAATCGTCCAGAAGTTCTTCCGTTCACCGGACCCAGGGACGGA

22381  CCCCAAATTGCAAGCTCCCTGCTTTATGTAGGAGACCTATGTGTATATTACAGTTCTGTG
22381  GGGGTTTAACGTTCGAGGGACGAAATACATCCTCTGGATACACATATAATGTCAAGACAC

22441  TAAGATTATTTTGTTATTCTTACCCCCCACACCCACCCCCCAACCCCCCGCTGCCACCAAA
22441  ATTCTAATAAAACAATAAGAATGGGGGTGTGGGTGGGGGGTTGGGGGGCGACGGTGGTTT

22501  AAAAAAAAAAAAAAATTCCTCTGACAACCTTCATAAAGTCCTGGGAGTTTGAACACCATT
22501  TTTTTTTTTTTTTTTAAGGAGACTGTTGGAAGTATTTCAGGACCCTCAAACTTGTGGTAA

22561  GCTCTAGGAAGTCATCTTATACAAAAATAAGAGTTGTGAGGTGGTTCATATACCTCCTGC
22561  CGAGATCCTTCAGTAGAATATGTTTTTATTCTCAACACTCCACCAAGTATATGGAGGACG

22621  GTTCTCCTATTTGGAGTTTTTCCCCATTTATGAAAGAGGTGAAAACGCTAAGATATTTAG
22621  CAAGAGGATAAACCTCAAAAAGGGGTAAATACTTTCTCCACTTTTGCGATTCTATAAATC

22681  CAATTATTACTTTAAACATTTTCTATTTATAGGCCGGGCGCAGTGGCTCATGCCTGTAAT
22681  GTTAATAATGAAATTTGTAAAAGATAAATATCCGGCCCGCGTCACCGAGTACGGACATTA

22741  CCCAGCGCTTGGGAGGCCAAGGCAGGCAGATCACGAGGTCAGGAGATCGAGACCATCTTG
22741  GGGTCGCGAACCCTCCGGTTCCGTCCGTCTAGTGCTCCAGTCCTCTAGCTCTGGTAGAAC

22801  GCTAACACGGTGAAACCCTGTCTCTACTAAAAAAATACAAAAATTAGTTGGGCATGGTG
22801  CGATTGTGCCACTTTGGGACAGAGATGATTTTTTTATGTTTTTAAATCAACCCGTACCAC

22861  GGGGATACCTGTGGTCCCAGCTACTCGGGAGGCTGAGACAGGAGAATGGCTTGAACCTGG
22861  CCCCTATGGACACCAGGGTCGATGAGCCCTCCGACTCTGTCCTCTTACCGAACTTGGACC

22921  GAGGCCGAGCTTGCAGTGAGCCAAGATCGCGCCACTGCACTCCAGCCTGGGTGACAGAGC
22921  CTCCGGCTCGAACGTCACTCGGTTCTAGCGCGGTGACGTGAGGTCGGACCCACTGTCTCG

22981  AAGACTCTGTCTCGAAAAAAAAAAAAAAATTCTATTTACAGCAGTGAAAATAGTAGTGACT
22981  TTCTGAGACAGAGCTTTTTTTTTTTTTAAGATAAATGTCGTCACTTTTATCATCACTGA

23041  TAATGCACATTGCCAAGGCTTTAGCATAACATGAACACTTTCACTCAATGTCTCTCTGGC
23041  ATTACGTGTAACGGTTCCGAAATCGTATTGTACTTGTGAAAGTGAGTTACAGAGAGACCG

23101  CTTTTGTTTTTCCTTGGGAAATTCTTATAATCCTGCTCCGTCTTTAACTATTCATTTTGT
23101  GAAAACAAAAAGGAACCCTTTAAGAATATTAGGACGAGGCAGAAATTGATAAGTAAAACA

23161  ATTGGCTATCCAAATATACCCAATAATGCTCTTTCTGAAAATATGCCAATTGTGGTAATT
23161  TAACCGATAGGTTTATATGGGTTATTACGAGAAAGACTTTTATACGGTTAACACCATTAA

23221  ACAGCTAAGCTGGAATATTAAATTGTGATGTCTGTTTTCCAGAGAATGAAGTAGTATTCC
23221  TGTCGATTCGACCTTATAATTTAACACTACAGACAAAAGGTCTCTTACTTCATCATAAGG
```

FIG. 5 (cont'd)

```
23281  CCAGAGCATAGGCTTGGTGCCTGTGCAGGTTCTATTTTAAATATTCCAGGAAGGGTTGTT
23281  GGTCTCGTATCCGAACCACGGACACGTCCAAGATAAAATTTATAAGGTCCTTCCCAACAA

23341  TTATATACTGAGGATGATTTTACTGGTCTTGCCAGTCGTCTGAAATGCTGGTATTACTCT
23341  AATATATGACTCCTACTAAAATGACCAGAACGGTCAGCAGACTTTACGACCATAATGAGA

23401  TGTGGAAGGTTTATTCAAACAAACAAGGACATTTCACACAATACCTAGTCATGTTTTTCA
23401  ACACCTTCCAAATAAGTTTGTTTGTTCCTGTAAAGTGTGTTATGGATCAGTACAAAAAGT

23461  GACATTTTAATGTTTGGTTCATCATTTGCACACACTCTCAAAAATCTAGGTTTGTCTATG
23461  CTGTAAAATTACAAACCAAGTAGTAAACGTGTGTGAGAGTTTTTAGATCCAAACAGATAC

23521  TGTTCATATCATTTTGCCTGTTGCCAGCTCAGTCAGCAGGCACACTCTCCCAGGCTGTTG
23521  ACAAGTATAGTAAAACGGACAACGGTCGAGTCAGTCGTCCGTGTGAGAGGGTCCGACAAC

23581  CTGTTTTGTTAGACTTCTTCAGGACCTTCATCTAAAATGGTCTTCCACACGTAGCTATAC
23581  GACAAAACAATCTGAAGAAGTCCTGGAAGTAGATTTTACCAGAAGGTGTGCATCGATATG

23641  TGCATAAGTTCACATCATCTGTTTCTTGCATGTGGGTTGTGTCTCAACTCAAGTTTAAGT
23641  ACGTATTCAAGTGTAGTAGACAAAGAACGTACACCCAACACAGAGTTGAGTTCAAATTCA

23701  TAGATTTGGAAGGGCGGAAACTATAGGAGTTGCAGCTTCAGTGGAGAAAAGAGCATTTCC
23701  ATCTAAACCTTCCCGCCTTTGATATCCTCAACGTCGAAGTCACCTCTTTTCTCGTAAAGG

23761  TACTAGTTATGGCTTCCCAAGGAAGGTTAGATTCCTCAGAGTAGGAGTGATTCCCCAATG
23761  ATGATCAATACCGAAGGGTTCCTTCCAATCTAAGGAGTCTCATCCTCACTAAGGGGTTAC

23821  CTAGAACCTTTGGTCAAATATAATTCTAATCCAGTCAAAATAAATACAGGTATTCTGTAA
23821  GATCTTGGAAACCAGTTTATATTAAGATTAGGTCAGTTTTATTTATGTCCATAAGACATT

23881  AACCCGATTTCATTTTGTAAATCCTACTTTGTATAGTATAAGCAATTTTTGTATTTGTGT
23881  TTGGGCTAAAGTAAAACATTTAGGATGAAACATATCATATTCGTTAAAAACATAAACACA

23941  GGATTATATTTTATTTTCCTATTTCAAAGAGAAGAATTTGTATTAGCAGACTCCCTTTGC
23941  CCTAATATAAAATAAAAGGATAAAGTTTCTCTTCTTAAACATAATCGTCTGAGGGAAACG

24001  ATGCGGAGAGGGGATCATTTTCCCAGTAGGCATGGGGTTCCCTTCCATTCCTTGTCCAGT
24001  TACGCCTCTCCCCTAGTAAAAGGGTCATCCGTACCCCAAGGGAAGGTAAGGAACAGGTCA

24061  CTTCTTTTCCCCACTAAGTTAAGTCAAACTAAGCAGCTGGTAAGATATTCCCTGGTTCTT
24061  GAAGAAAAGGGGTGATTCAATTCAGTTTGATTCGTCGACCATTCTATAAGGGACCAAGAA

24121  GCAAAGAAAGTGAGCAGATGGCAGAATGTATAGCTCTAAGCAGAATACCTGGTGTGGTAT
24121  CGTTTCTTTCACTCGTCTACCGTCTTACATATCGAGATTCGTCTTATGGACCACACCATA

24181  CCTCAAACACAAATTGACAGGAGGGTGTGGTGTGGCAAGCTCATTGTGGGGGTAAATTGG
24181  GGAGTTTGTGTTTAACTGTCCTCCCACACCACACCGTTCGAGTAACACCCCCATTTAACC

24241  AATAAGCTTACAGGGGGAAGAGTTGACAAAAGATAGGAAGAACCTTAAAAATATAGATGC
24241  TTATTCGAATGTCCCCCTTCTCAACTGTTTTCTATCCTTCTTGGAATTTTTATATCTACG

24301  CTTTTATGCAGTGATAAAATGTCTAGATATTTATACTGTGGTGATTATTAGGAATATGTG
24301  GAAAATACGTCACTATTTTACAGATCTATAAATATGACACCACTAATAATCCTTATACAC

24361  CAAAGATTGGCTATTAGGATGTTCATTACAGTGTTGTTTAATAATTATAAAAGGACAGAA
24361  GTTTCTAACCGATAATCCTACAAGTAATGTCACAACAAATTATTAATATTTTCCTGTCTT

24421  AGCAATGTGGACTCAAAAATAGGAAAAGAATTTAAATAAATCCTAGTGTACCCGTTATAC
24421  TCGTTACACCTGAGTTTTTATCCTTTTCTTAAATTTATTTAGGATCACATGGGCAATATG

24481  ATGAAATTATGGAAATATGACCCTGAGCATGGAAATATGTACATGAGAATGTCTAAAAGC
24481  TACTTTAATACCTTTATACTGGGACTCGTACCTTTATACATGTACTCTTACAGATTTTCG

24541  TAGTTCATTTTGAAAAACAAAATAATGTCACCTCATATTATTTATAGTATATAAAGATGA
24541  ATCAAGTAAAACTTTTTGTTTTATTACAGTGGAGTATAATAAATATCATATATTTCTACT

24601  TTTTAAGAGTGGCAGTGTCTGGGATTATAGGTGATTGTATTTCTTCCCTTTTGCACATCT
24601  AAAATTCTCACCGTCACAGACCCTAATATCCACTAACATAAAGAAGGGAAAACGTGTAGA
```

FIG. 5 (cont'd)

```
24661  ATGTTCTCTCATTTGTATTGTGTGGGGAGAAGTGACTTTTTTTATAAAAAGAAAAAGGTA
24661  TACAAGAGAGTAAACATAACACACCCCTCTTCACTGAAAAAAATATTTTTCTTTTTCCAT

24721  TATGCATCCCAGCAGAGAAGCACTGGCTCCACCCAGTACCTGCCTCCTCATGCCACCCTC
24721  ATACGTAGGGTCGTCTCTTCGTGACCGAGGTGGGTCATGGACGGAGGAGTACGGTGGGAG

24781  TCAAGCCAAAAGCCGGGGGAAGCCCAGGCACCTTGACCATGACCGCCCGAGACTCACACT
24781  AGTTCGGTTTTCGGCCCCCTTCGGGTCCGTGGAACTGGTACTGGCGGGCTCTGAGTGTGA

24841  TCTTCTTTCTCATCAGGGAAGGAAAGCCCCCCTGTAAGCGATACTCCAGATGAGGGCGAT
24841  AGAAGAAAGAGTAGTCCCTTCCTTTCGGGGGGACATTCGCTATGAGGTCTACTCCCGCTA

24901  GAGCCCATGCCGATCCCCGAGGACCTCTCCACCACCTCGGGAGGACAGCAAAGCTCCAAG
24901  CTCGGGTACGGCTAGGGGCTCCTGGAGAGGTGGTGGAGCCCTCCTGTCGTTTCGAGGTTC

24961  AGTGACAGAGTCGTGGGTAAGTGGGTCACCAGCGGCCTCTGTGCCTGTGAAACCTTTATC
24961  TCACTGTCTCAGCACCCATTCACCCAGTGGTCGCCGGAGACACGGACACTTTGGAAATAG

25021  TCTTTGTATTTTTCCAAGACAGTGATGAAGGGATGCAAGTCATTTTATCCATTGTGTTCC
25021  AGAAACATAAAAAGGTTCTGTCACTACTTCCCTACGTTCAGTAAAATAGGTAACACAAGG

25081  CTCAACTGGCATATTAAAGAAATATGGCACAAAGATCAGCAGGATGGGGGTCCTCTGGTG
25081  GAGTTGACCGTATAATTTCTTTATACCGTGTTTCTAGTCGTCCTACCCCCAGGAGACCAC

25141  TGTGGGAGGATGGACACTCACAGGCCAGCATGGCCGTGAGAGCCACACACCCCGCAAAAT
25141  ACACCCTCCTACCTGTGAGTGTCCGGTCGTACCGGCACTCTCGGTGTGTGGGGCGTTTTA

25201  GTCCAAGTTGAGGAGCAATCCTGCCCAGGGACGCGTCTCTGTCACTGTCCTCTGTCCTCA
25201  CAGGTTCAACTCCTCGTTAGGACGGGTCCCTGCGCAGAGACAGTGACAGGAGACAGGAGT

25261  CTGCACTTGCAGGAATATCAAATGTTATGGATTGTAGATCGTGAAAATTACACACTTACG
25261  GACGTGAACGTCCTTATAGTTTACAATACCTAACATCTAGCACTTTTAATGTGTGAATGC

25321  TGTTTTGGCAACAGTGCTTTTCAGTGTTTGGGGTTAGAACAAGCCACATCTGGCCATTTT
25321  ACAAAACCGTTGTCACGAAAAGTCACAAACCCCAATCTTGTTCGGTGTAGACCGGTAAAA

25381  ATGTTATCCCTCTAATCTCTAGTTCTTAAATTTCAGATTTAACTGAAAATAGAAAGTTTC
25381  TACAATAGGGAGATTAGAGATCAAGAATTTAAAGTCTAAATTGACTTTTATCTTTCAAAG

25441  ATAAATGGTAATTTTTAAATGTTAGAAAAAAATCAAAGCACACATTTACATACCTTTTCC
25441  TATTTACCATTAAAAATTTACAATCTTTTTTTAGTTTCGTGTGTAAATGTATGGAAAAGG

25501  ATAAAAAAGTGTGTGTGAAACCATCTGCAACTCCACTGGTTAACTTACACATGCGACAGT
25501  TATTTTTTCACACACACTTTGGTAGACGTTGAGGTGACCAATTGAATGTGTACGCTGTCA

25561  TTGTGTTTGGAAAACTTCACCCACCCTCTTTATTTCAAGAAACCAAAGACGGAGAGAAGT
25561  AACACAAACCTTTTGAAGTGGGTGGGAGAAATAAAGTTCTTTGGTTTCTGCCTCTCTTCA

25621  TCAGTGAATTAACCAAGGTGAAATGACAGAGTCAGAATTGAACTGAATTTCTGACTGAAA
25621  AGTCACTTAATTGGTTCCACTTTACTGTCTCAGTCTTAACTTGACTTAAAGACTGACTTT

25681  AACTAGTTCTCGCTCCATTATACCATGTTCTAATGAGCTAATGAGTCAACAGTTCCCTGG
25681  TTGATCAAGAGCGAGGTAATATGGTACAAGATTACTCGATTACTCAGTTGTCAAGGGACC

25741  AATACCTGTTTTCTTCTTTAAAAAGAGAAAGAGCTGTGATACTGAGAGCTACCTATTGGC
25741  TTATGGACAAAAGAAGAAATTTTTCTCTTTCTCGACACTATGACTCTCGATGGATAACCG

25801  ATAAAAGAATATGAAGGACATACAGGTAAAATGAGGTAGACTGGATCAATGTGGGTCAGC
25801  TATTTTCTTATACTTCCTGTATGTCCATTTTACTCCATCTGACCTAGTTACACCCAGTCG

25861  TACATAAGCCCCCATAGCCAAGGAGGGAACATGTATGTAAAATTCTCAGGCTTATGAGAA
25861  ATGTATTCGGGGGTATCGGTTCCTCCCTTGTACATACATTTTAAGAGTCCGAATACTCTT

25921  TCACAACTGTATGTCTATAGGACATCCTAATGCAATAATGGGAAAATGTGATAACTGAAT
25921  AGTGTTGACATACAGATATCCTGTAGGATTACGTTATTACCCTTTTACACTATTGACTTA

25981  TTTATCTACATGTATAGAAAACATATTTTGGGCCGGGCATGGTGGCTCAAGCTTGTAATC
25981  AAATAGATGTACATATCTTTTGTATAAAACCCGGCCCGTACCACCGAGTTCGAACATTAG
```

FIG. 5 (cont'd)

```
26041  CCAGCACTTTGGGAGGCCGAGGCTGGCGGATCACAAGGTCAGGAAATCGAGACCATCCTG
26041  GGTCGTGAAACCCTCCGGCTCCGACCGCCTAGTGTTCCAGTCCTTTAGCTCTGGTAGGAC

26101  GCTAACACGGTGAAACCCTGTCTCTACTAAAAATACAAAAAATTAGCCGGGCGTAGTGGT
26101  CGATTGTGCCACTTTGGGACAGAGATGATTTTTATGTTTTTTAATCGGCCCGCATCACCA

26161  GGGCGCCTGTAGTCCCAGCTACTCGGGAGGCTGAGGCAGGAGAATGGCGTGAACCCGGCA
26161  CCCGCGGACATCAGGGTCGATGAGCCCTCCGACTCCGTCCTCTTACCGCACTTGGGCCGT

26221  GGCGGAGCTTGCAGTGAGCCGAGATTGCGCCACTGCACTCCAGCCTGGATGACAGAGCCA
26221  CCGCCTCGAACGTCACTCGGCTCTAACGCGGTGACGTGAGGTCGGACCTACTGTCTCGGT

26281  GACTCCATCTCAAAAAAAAAAAAAAAAAAAGAAAAAGTAAAGAAAACATATTTTGTATGTT
26281  CTGAGGTAGAGTTTTTTTTTTTTTTTTTTTCTTTTTCATTTCTTTTGTATAAAACATACAA

26341  TTTTATGTGTCTTAGAAACCAAGTGGACTAGGTATAATGGTTCTTTTTTTTTTTAACTCA
26341  AAAATACACAGAATCTTTGGTTCACCTGATCCATATTACCAAGAAAAAAAAAAATTGAGT

26401  GCAGCACAGTTAATGGCACAAACAGATAAAGATGGTGGCTAAAGCCATTTGGTGTAGATG
26401  CGTCGTGTCAATTACCGTGTTTGTCTATTTCTACCACCGATTTCGGTAAACCACATCTAC

26461  AATCCAGAAAACAAGTACATTTATGAATTATTTTACCCTATTGGAAAATGGCTACTATAT
26461  TTAGGTCTTTTGTTCATGTAAATACTTAATAAAATGGGATAACCTTTTACCGATGATATA

26521  GTGGAAAGTAGAGGGGAAGAGAAATGAACTTGTGAATTATCTACTCTATTCTACCAAAGA
26521  CACCTTTCATCTCCCCTTCTCTTTACTTGAACACTTAATAGATGAGATAAGATGGTTTCT

26581  AAGATACATATATCATTTCAGGGTTTTCCAAAGTTGGGATGCAAAGGATCATGTTTCATT
26581  TTCTATGTATATAGTAAAGTCCCAAAAGGTTTCAACCCTACGTTTCCTAGTACAAAGTAA

26641  TTAATTTATGTATTTATTTTTGAGATTGTCTTCTATGTATTGCAAGTGATACTGGTTTTA
26641  AATTAAATACATAAATAAAAACTCTAACAGAAGATACATAACGTTCACTATGACCAAAAT

26701  CCATGCACTGTACCACTACGAGGGTTCCTTTCAAAACACATTCATATAAATTAAAAAATC
26701  GGTACGTGACATGGTGATGCTCCCAAGGAAAGTTTTGTGTAAGTATATTTAATTTTTTAG

26761  AGTTTAAATAAAAACATCAAGTCAATAGTAGTACATAGATATGATAAAAGTTTGCAAAAG
26761  TCAAATTTATTTTTGTAGTTCAGTTATCATCATGTATCTATACTATTTTCAAACGTTTTC

26821  TGGCACAGGAATAGTCATTGGGTGGTGATGTTCCCTGATTTTTTTAGTCCCTGAAGCACC
26821  ACCGTGTCCTTATCAGTAACCCACCACTACAAGGGACTAAAAAAATCAGGGACTTCGTGG

26881  CAGCGCCAAGGGTACTGTTCTTCCTGCTTAACACAGGAGCAAACAGATGCTCACACCCTG
26881  GTCGCGGTTCCCATGACAAGAAGGACGAATTGTGTCCTCGTTTGTCTACGAGTGTGGGAC

26941  CCCAAGAACACAGAGGCTCAGGGACTGAACCAGAAGAAATGATCCATTAACCATGTAAAT
26941  GGGTTCTTGTGTCTCCGAGTCCCTGACTTGGTCTTCTTTACTAGGTAATTGGTACATTTA

27001  GAACAGAGAGCCTGGATGTCAGAGTGAGGAGGCCAGCTCGGGTCGCTGTGGAGAAAGAGA
27001  CTTGTCTCTCGGACCTACAGTCTCACTCCTCCGGTCGAGCCCAGCGACACCTCTTTCTCT

27061  TGGGCTCTCCCTGGAATCCCTGCAGCTGCCCTTAGAGGCTGTGAGCCATCGTGGCTAGGG
27061  ACCCGAGAGGGACCTTAGGGACGTCGACGGGAATCTCCGACACTCGGTAGCACCGATCCC

27121  CATCTTTAGAGAACTGAAAGTCAGGCCGATTCCTGGAGAGTGAAGAATAGCACACGTGCC
27121  GTAGAAATCTCTTGACTTTCAGTCCGGCTAAGGACCTCTCACTTCTTATCGTGTGCACGG

27181  TTCAAAACAGTGTCAGTATCCTGTCCCTTACGGACGTCATATTGTTGGTGGGTTTTCCTG
27181  AAGTTTTGTCACAGTCATAGGACAGGGAATGCCTGCAGTATAACAACCACCCAAAAGGAC

27241  GGTGGGAGATCACCCAGTATCTGGTTGGCATTACTGATGGGTTCCCAGAGCTGTCTTTTG
27241  CCACCCTCTAGTGGGTCATAGACCAACCGTAATGACTACCCAAGGGTCTCGACAGAAAAC

27301  GTTCAAAGTCCTGCCCTCGGTCCCAGCTGCCCCCAGCACAGGTGTCACCTTGGAGTCAGG
27301  CAAGTTTCAGGACGGGAGCCAGGGTCGACGGGGGTCGTGTCCACAGTGGAACCTCAGTCC

27361  GGCGGGTTTGTCATAGCCCATGGGTCCTGGCCCTGCCCTTTATCATGTTTGACATGATTT
27361  CCGCCCAAACAGTATCGGGTACCCAGGACCGGGACGGGAAATAGTACAAACTGTACTAAA
```

FIG. 5 (cont'd)

27421 TCAGTCTACTTTTCCTTCAGGATGTAATTTAGAAAATATGATTTCAGAATTGTGAAATTT
27421 AGTCAGATGAAAAGGAAGTCCTACATTAAATCTTTTATACTAAAGTCTTAACACTTTAAA

27481 AAAAACCCTAGAAAACCTCTTTGCTTTGCTTGTAAATAGCAGTTGATGCAGCCCTGTGGA
27481 TTTTTGGGATCTTTTGGAGAAACGAAACGAACATTTATCGTCAACTACGTCGGGACACCT

27541 CAGGCGGGAACAGCCATGTGACGTGGGCACTGAGATGATTTGGGAGATTGAATGCTCCTC
27541 GTCCGCCCTTGTCGGTACACTGCACCCGTGACTCTACTAAACCCTCTAACTTACGAGGAG

27601 AGTGGGGCTAGAGGCCACAGGAGTGATAGGTTACTGTAAAGAAAGCAAAAAAGATGCAAA
27601 TCACCCCGATCTCCGGTGTCCTCACTATCCAATGACATTTCTTTCGTTTTTTCTACGTTT

27661 AGCCTACATGACAAACCAGGCACGACACAAAGGAGAGGCTTGAGAAGAGGAAGTGAAGGA
27661 TCGGATGTACTGTTTGGTCCGTGCTGTGTTTCCTCTCCGAACTCTTCTCCTTCACTTCCT

27721 GGGAGAGGATTCCACAAGACCGAAGTGCCCAAGGAGACATGGAGGGAAGAGAGGGCTCTT
27721 CCCTCTCCTAAGGTGTTCTGGCTTCACGGGTTCCTCTGTACCTCCCTTCTCTCCCGAGAA

27781 CACAGAGCTGAGTTTAGAGACCACCCTCCATGGTTCTGGAAGGAAACCAGCCAGCTTTCA
27781 GTGTCTCGACTCAAATCTCTGGTGGGAGGTACCAAGACCTTCCTTTGGTCGGTCGAAAGT

27841 TATGTGGTGACAGGCTGTTCATTAATTTGTAGTGTACAGCATTAAATAAATGAAGTATGT
27841 ATACACCACTGTCCGACAAGTAATTAAACATCACATGTCGTAATTTATTTACTTCATACA

27901 AGAGAACATTAGGAAACAATATAAAAAGGTAGGGGAATTCGTGGATAAAGGGAATAACCT
27901 TCTCTTGTAATCCTTTGTTATATTTTTCCATCCCCTTAAGCACCTATTTCCCTTATTGGA

27961 GGGTACCATATTTCATCACATTATTCCATGGGAATAAGTCATCAGTGCAAAGGACTGTAA
27961 CCCATGGTATAAAGTAGTGTAATAAGGTACCCTTATTCAGTAGTCACGTTTCCTGACATT

28021 GGAGTGCACAGCAGGAAATGAAAAGACAGAAGCAGTGGGGCCGAGAGGAGGAAATGGAGT
28021 CCTCACGTGTCGTCCTTTACTTTTCTGTCTTCGTCACCCCGGCTCTCCTCCTTTACCTCA

28081 TGCTGAAATGCAGGGTGAGCAGCAGGGGCGGAGAGTGCCCTGTGGGTAAGGCACACCTCA
28081 ACGACTTTACGTCCCACTCGTCGTCCCCGCCTCTCACGGGACACCCATTCCGTGTGGAGT

28141 GAAGGGACAGGTCCAGGCCCTCTCCTCCCTGGCCTGGAGCTTCTGGCAAGGCTTTTCTTC
28141 CTTCCCTGTCCAGGTCCGGGAGAGGAGGGACCGGACCTCGAAGACCGTTCCGAAAAGAAG

28201 TCTGAGCCTCACTTTCCTCTTTTGAAGGTGGCAATAGTAACTGAACCTGCATCANNNNNN
28201 AGACTCGGAGTGAAAGGAGAAAACTTCCACCGTTATCATTGACTTGGACGTAGTNNNNNN

28261 NNNNNNNNNNNNNNNNNNNNNNNNNNNNNNNNNNNNNNNNNNNNNNNNNNNNNNNNNNNN
28261 NNNNNNNNNNNNNNNNNNNNNNNNNNNNNNNNNNNNNNNNNNNNNNNNNNNNNNNNNNNN

28321 NNNNNNNNNNNNNNNNNNNNNNNNNNNNNNNNNNNNNNNNNNNNNNNNNNNNNNNNNNNN
28321 NNNNNNNNNNNNNNNNNNNNNNNNNNNNNNNNNNNNNNNNNNNNNNNNNNNNNNNNNNNN

28381 NNNNNNNNNNNNNNNNNNNNNNNNNNNNNNNNNNNNNNNNNNNNNNNNNNNNNNNNNNNN
28381 NNNNNNNNNNNNNNNNNNNNNNNNNNNNNNNNNNNNNNNNNNNNNNNNNNNNNNNNNNNN

28441 NNNNNNNNNNNNNNNNNNNNNNNNNNNNNNNNNNNNNNNNNNNNNNNNNNNNNNNNNNNN
28441 NNNNNNNNNNNNNNNNNNNNNNNNNNNNNNNNNNNNNNNNNNNNNNNNNNNNNNNNNNNN

28501 NNNNNNNNNNNNNNNNNNNNNNNNNNNNNNNNNNNNNNNNNNNNNNNNNNNNNNNNNNNN
28501 NNNNNNNNNNNNNNNNNNNNNNNNNNNNNNNNNNNNNNNNNNNNNNNNNNNNNNNNNNNN

28561 NNNNNNNNNNNNNNNNNNNNNNNNNNNNNNNNNNNNNNNNNNNNNNNNNNNNNNNNNNNN
28561 NNNNNNNNNNNNNNNNNNNNNNNNNNNNNNNNNNNNNNNNNNNNNNNNNNNNNNNNNNNN

28621 NNNNNNNNNNNNNNNNNNNNNNNNNNNNNNNNNNNNNNNNNNNNNNNNNNNNNNNNNNNN
28621 NNNNNNNNNNNNNNNNNNNNNNNNNNNNNNNNNNNNNNNNNNNNNNNNNNNNNNNNNNNN

28681 NNNNNNNNNNNNNNNNNNNNNNNNNNNNNNNNNNNNNNNNNNNNNNNNNNNNNNNNNNNN
28681 NNNNNNNNNNNNNNNNNNNNNNNNNNNNNNNNNNNNNNNNNNNNNNNNNNNNNNNNNNNN

28741 NNNNNNNNNNNNNNNNNNNNNNNNNNNNNNNNNNNNNNNNNNNNNNNNNNNNNNNNNNNN
28741 NNNNNNNNNNNNNNNNNNNNNNNNNNNNNNNNNNNNNNNNNNNNNNNNNNNNNNNNNNNN

FIG. 5 (cont'd)

28801 NNNNNNNNNNNNNNNNNNNNNNNNNNNNNNNNNNNNNNNNNNNNNNNNNNNNNNNNNNNN
28801 NNNNNNNNNNNNNNNNNNNNNNNNNNNNNNNNNNNNNNNNNNNNNNNNNNNNNNNNNNNN

28861 NNNNNNNNNNNNNNNNNNNNNNNNNNNNNNNNNNNNNNNNNNNNNNNNNNNNNNNNNNNN
28861 NNNNNNNNNNNNNNNNNNNNNNNNNNNNNNNNNNNNNNNNNNNNNNNNNNNNNNNNNNNN

28921 NNNNNNNNNNNNNNNNNNNNNNNNNNNNNNNNNNNNNNNNNNNNNNNNNNNNNNNNNNNN
28921 NNNNNNNNNNNNNNNNNNNNNNNNNNNNNNNNNNNNNNNNNNNNNNNNNNNNNNNNNNNN

28981 NNNNNNNNNNNNNNNNNNNNNNNNNNNNNNNNNNNNNNNNNNNNNNNNNNNNNNNNNNNN
28981 NNNNNNNNNNNNNNNNNNNNNNNNNNNNNNNNNNNNNNNNNNNNNNNNNNNNNNNNNNNN

29041 NNNNNNNNNNNNNNNNNNNNNNNNNNNNNNNNNNNNNNNNNNNNNNNNNNNNNNNNNNNN
29041 NNNNNNNNNNNNNNNNNNNNNNNNNNNNNNNNNNNNNNNNNNNNNNNNNNNNNNNNNNNN

29101 NNNNNNNNNNNNNNNNNNNNNNNNNNNNNNNNNNNNNNNNNNNNNNNNNNNNNNNNNNNN
29101 NNNNNNNNNNNNNNNNNNNNNNNNNNNNNNNNNNNNNNNNNNNNNNNNNNNNNNNNNNNN

29161 NNNNNNNNNNNNNNNNNNNNNNNNNNNNNNNNNNNNNNNNNNNNNNNNNNNNNNNNNNNN
29161 NNNNNNNNNNNNNNNNNNNNNNNNNNNNNNNNNNNNNNNNNNNNNNNNNNNNNNNNNNNN

29221 NNNNNNNNNNNNNNNNNNNNNNNNNNNNNNNNNNNNNNNNNNNNNNNNNNNNNNNNNNNN
29221 NNNNNNNNNNNNNNNNNNNNNNNNNNNNNNNNNNNNNNNNNNNNNNNNNNNNNNNNNNNN

29281 NNNNNNNNNNNNNNNNNNNNNNNNNNNNNNNNNNNNNNNNNNNNNNNNNNNNNNNNNNNN
29281 NNNNNNNNNNNNNNNNNNNNNNNNNNNNNNNNNNNNNNNNNNNNNNNNNNNNNNNNNNNN

29341 NNNNNNNNNNNNNNNNNNNNNNNNNNNNNNNNNNNNNNNNNNNNNNNNNNNNNNNNNNNN
29341 NNNNNNNNNNNNNNNNNNNNNNNNNNNNNNNNNNNNNNNNNNNNNNNNNNNNNNNNNNNN

29401 NNNNNNNNNNNNNNNNNNNNNNNNNNNNNNNNNNNNNNNNNNNNNNNNNNNNNNNNNNNN
29401 NNNNNNNNNNNNNNNNNNNNNNNNNNNNNNNNNNNNNNNNNNNNNNNNNNNNNNNNNNNN

29461 NNNNNNNNNNNNNNNNNNNNNNNNNNNNNNNNNNNNNNNNNNNNNNNNNNNNNNNNNNNN
29461 NNNNNNNNNNNNNNNNNNNNNNNNNNNNNNNNNNNNNNNNNNNNNNNNNNNNNNNNNNNN

29521 NNNNNNNNNNNNNNNNNNNNNNNNNNNNNNNNNNNNNNNNNNNNNNNNNNNNNNNNNNNN
29521 NNNNNNNNNNNNNNNNNNNNNNNNNNNNNNNNNNNNNNNNNNNNNNNNNNNNNNNNNNNN

29581 NNNNNNNNNNNNNNNNNNNNNNNNNNNNNNNNNNNNNNNNNNNNNNNNNNNNNNNNNNNN
29581 NNNNNNNNNNNNNNNNNNNNNNNNNNNNNNNNNNNNNNNNNNNNNNNNNNNNNNNNNNNN

29641 NNNNNNNNNNNNNNNNNNNNNNNNNNNNNNNNNNNNNNNNNNNNNNNNNNNNNNNNNNNN
29641 NNNNNNNNNNNNNNNNNNNNNNNNNNNNNNNNNNNNNNNNNNNNNNNNNNNNNNNNNNNN

29701 NNNNNNNNNNNNNNNNNNNNNNNNNNNNNNNNNNNNNNNNNNNNNNNNNNNNNNNNNNNN
29701 NNNNNNNNNNNNNNNNNNNNNNNNNNNNNNNNNNNNNNNNNNNNNNNNNNNNNNNNNNNN

29761 NNNNNNNNNNNNNNNNNNNNNNNNNNNNNNNNNNNNNNNNNNNNNNNNNNNNNNNNNNNN
29761 NNNNNNNNNNNNNNNNNNNNNNNNNNNNNNNNNNNNNNNNNNNNNNNNNNNNNNNNNNNN

29821 NNNNNNNNNNNNNNNNNNNNNNNNNNNNNNNNNNNNNNNNNNNNNNNNNNNNNNNNNNNN
29821 NNNNNNNNNNNNNNNNNNNNNNNNNNNNNNNNNNNNNNNNNNNNNNNNNNNNNNNNNNNN

29881 NNNNNNNNNNNNNNNNNNNNNNNNNNNNNNNNNNNNNNNNNNNNNNNNNNNNNNNNNNNN
29881 NNNNNNNNNNNNNNNNNNNNNNNNNNNNNNNNNNNNNNNNNNNNNNNNNNNNNNNNNNNN

29941 NNNNNNNNNNNNNNNNNNNNNNNNNNNNNNNNNNNNNNNNNNNNNNNNNNNNNNNNNNNN
29941 NNNNNNNNNNNNNNNNNNNNNNNNNNNNNNNNNNNNNNNNNNNNNNNNNNNNNNNNNNNN

30001 NNNNNNNNNNNNNNNNNNNNNNNNNNNNNNNNNNNNNNNNNNNNNNNNNNNNNNNNNNNN
30001 NNNNNNNNNNNNNNNNNNNNNNNNNNNNNNNNNNNNNNNNNNNNNNNNNNNNNNNNNNNN

30061 NNNNNNNNNNNNNNNNNNNNNNNNNNNNNNNNNNNNNNNNNNNNNNNNNNNNNNNNNNNN
30061 NNNNNNNNNNNNNNNNNNNNNNNNNNNNNNNNNNNNNNNNNNNNNNNNNNNNNNNNNNNN

30121 NNNNNNNNNNNNNNNNNNNNNNNNNNNNNNNNNNNNNNNNNNNNNNNNNNNNNNNNNNNN
30121 NNNNNNNNNNNNNNNNNNNNNNNNNNNNNNNNNNNNNNNNNNNNNNNNNNNNNNNNNNNN

FIG. 5 (cont'd)

```
30181  NNNNNNNNNNNNNNNNNNNNNNNNNNNNNNNNNNNNNNNNNNNNNNNNNNNNNNNNNNNN
30181  NNNNNNNNNNNNNNNNNNNNNNNNNNNNNNNNNNNNNNNNNNNNNNNNNNNNNNNNNNNN

30241  NNNNNNNNNNNNNNNNNNNNNNNNNNNNNNNNNNNNNNNNNNNNNNNNNNNNNNNNNNNN
30241  NNNNNNNNNNNNNNNNNNNNNNNNNNNNNNNNNNNNNNNNNNNNNNNNNNNNNNNNNNNN

30301  NNNNNNNNNNNNNNNNNNNNNNNNNNNNNNNNNNNNNNNNNNNNNNNNNNNNNNNNNNNN
30301  NNNNNNNNNNNNNNNNNNNNNNNNNNNNNNNNNNNNNNNNNNNNNNNNNNNNNNNNNNNN

30361  NNNNNNNNNNNNNNNNNNNNNNNNNNNNNNNNNNNNNNNNNNNNNNNNNNNNNNNNNNNN
30361  NNNNNNNNNNNNNNNNNNNNNNNNNNNNNNNNNNNNNNNNNNNNNNNNNNNNNNNNNNNN

30421  NNNNNNNNNNNNNNNNNNNNNNNNNNNNNNNNNNNNNNNNNNNNNNNNNNNNNNNNNNNN
30421  NNNNNNNNNNNNNNNNNNNNNNNNNNNNNNNNNNNNNNNNNNNNNNNNNNNNNNNNNNNN

30481  NNNNNNNNNNNNNNNNNNNNNNNNNNNNNNNNNNNNNNNNNNNNNNNNNNNNNNNNNNNN
30481  NNNNNNNNNNNNNNNNNNNNNNNNNNNNNNNNNNNNNNNNNNNNNNNNNNNNNNNNNNNN

30541  NNNNNNNNNNNNNNNNNNNNNNNNNNNNNNNNNNNNNNNNNNNNNNNNNNNNNNNNNNNN
30541  NNNNNNNNNNNNNNNNNNNNNNNNNNNNNNNNNNNNNNNNNNNNNNNNNNNNNNNNNNNN

30601  NNNNNNNNNNNNNNNNNNNNNNNNNNNNNNNNNNNNNNNNNNNNNNNNNNNNNNNNNNNN
30601  NNNNNNNNNNNNNNNNNNNNNNNNNNNNNNNNNNNNNNNNNNNNNNNNNNNNNNNNNNNN

30661  NNNNNNNNNNNNNNNNNNNNNNNNNNNNNNNNNNNNNNNNNNNNNNNNNNNNNNNNNNNN
30661  NNNNNNNNNNNNNNNNNNNNNNNNNNNNNNNNNNNNNNNNNNNNNNNNNNNNNNNNNNNN

30721  NNNNNNNNNNNNNNNNNNNNNNNNNNNNNNNNNNNNNNNNNNNNNNNNNNNNNNNNNNNN
30721  NNNNNNNNNNNNNNNNNNNNNNNNNNNNNNNNNNNNNNNNNNNNNNNNNNNNNNNNNNNN

30781  NNNNNNNNNNNNNNNNNNNNNNNNNNNNNNNNNNNNNNNNNNNNNNNNNNNNNNNNNNNN
30781  NNNNNNNNNNNNNNNNNNNNNNNNNNNNNNNNNNNNNNNNNNNNNNNNNNNNNNNNNNNN

30841  NNNNNNNNNNNNNNNNNNNNNNNNNNNNNNNNNNNNNNNNNNNNNNNNNNNNNNNNNNNN
30841  NNNNNNNNNNNNNNNNNNNNNNNNNNNNNNNNNNNNNNNNNNNNNNNNNNNNNNNNNNNN

30901  NNNNNNNNNNNNNNNNNNNNNNNNNNNNNNNNNNNNNNNNNNNNNNNNNNNNNNNNNNNN
30901  NNNNNNNNNNNNNNNNNNNNNNNNNNNNNNNNNNNNNNNNNNNNNNNNNNNNNNNNNNNN

30961  NNNNNNNNNNNNNNNNNNNNNNNNNNNNNNNNNNNNNNNNNNNNNNNNNNNNNNNNNNNN
30961  NNNNNNNNNNNNNNNNNNNNNNNNNNNNNNNNNNNNNNNNNNNNNNNNNNNNNNNNNNNN

31021  NNNNNNNNNNNNNNNNNNNNNNNNNNNNNNNNNNNNNNNNNNNNNNNNNNNNNNNNNNNN
31021  NNNNNNNNNNNNNNNNNNNNNNNNNNNNNNNNNNNNNNNNNNNNNNNNNNNNNNNNNNNN

31081  NNNNNNNNNNNNNNNNNNNNNNNNNNNNNNNNNNNNNNNNNNNNNNNNNNNNNNNNNNNN
31081  NNNNNNNNNNNNNNNNNNNNNNNNNNNNNNNNNNNNNNNNNNNNNNNNNNNNNNNNNNNN

31141  NNNNNNNNNNNNNNNNNNNNNNNNNNNNNNNNNNNNNNNNNNNNNNNNNNNNNNNNNNNN
31141  NNNNNNNNNNNNNNNNNNNNNNNNNNNNNNNNNNNNNNNNNNNNNNNNNNNNNNNNNNNN

31201  NNNNNNNNNNNNNNNNNNNNNNNNNNNNNNNNNNNNNNNNNNNNNNNNNNNNNNNNNNNN
31201  NNNNNNNNNNNNNNNNNNNNNNNNNNNNNNNNNNNNNNNNNNNNNNNNNNNNNNNNNNNN

31261  NNNNNNNNNNNNNNNNNNNNNNNNNNNNNNNNNNNNNNNNNNNNNNNNNNNNNNNNNNNN
31261  NNNNNNNNNNNNNNNNNNNNNNNNNNNNNNNNNNNNNNNNNNNNNNNNNNNNNNNNNNNN

31321  NNNNNNNNNNNNNNNNNNNNNNNNNNNNNNNNNNNNNNNNNNNNNNNNNNNNNNNNNNNN
31321  NNNNNNNNNNNNNNNNNNNNNNNNNNNNNNNNNNNNNNNNNNNNNNNNNNNNNNNNNNNN

31381  NNNNNNNNNNNNNNNNNNNNNNNNNNNNNNNNNNNNNNNNNNNNNNNNNNNNNNNNNNNN
31381  NNNNNNNNNNNNNNNNNNNNNNNNNNNNNNNNNNNNNNNNNNNNNNNNNNNNNNNNNNNN

31441  NNNNNNNNNNNNNNNNNNNNNNNNNNNNNNNNNNNNNNNNNNNNNNNNNNNNNNNNNNNN
31441  NNNNNNNNNNNNNNNNNNNNNNNNNNNNNNNNNNNNNNNNNNNNNNNNNNNNNNNNNNNN

31501  NNNNNNNNNNNNNNNNNNNNNNNNNNNNNNNNNNNNNNNNNNNNNNNNNNNNNNNNNNNN
31501  NNNNNNNNNNNNNNNNNNNNNNNNNNNNNNNNNNNNNNNNNNNNNNNNNNNNNNNNNNNN
```

FIG. 5 (cont'd)

```
31561  NNNNNNNNNNNNNNNNNNNNNNNNNNNNNNNNNNNNNNNNNNNNNNNNNNNNNNNNNNNN
31561  NNNNNNNNNNNNNNNNNNNNNNNNNNNNNNNNNNNNNNNNNNNNNNNNNNNNNNNNNNNN

31621  NNNNNNNNNNNNNNNNNNNNNNNNNNNNNNNNNNNNNNNNNNNNNNNNNNNNNNNNNNNN
31621  NNNNNNNNNNNNNNNNNNNNNNNNNNNNNNNNNNNNNNNNNNNNNNNNNNNNNNNNNNNN

31681  NNNNNNNNNNNNNNNNNNNNNNNNNNNNNNNNNNNNNNNNNNNNNNNNNNNNNNNNNNNN
31681  NNNNNNNNNNNNNNNNNNNNNNNNNNNNNNNNNNNNNNNNNNNNNNNNNNNNNNNNNNNN

31741  NNNNNNNNNNNNNNNNNNNNNNNNNNNNNNNNNNNNNNNNNNNNNNNNNNNNNNNNNNNN
31741  NNNNNNNNNNNNNNNNNNNNNNNNNNNNNNNNNNNNNNNNNNNNNNNNNNNNNNNNNNNN

31801  NNNNNNNNNNNNNNNNNNNNNNNNNNNNNNNNNNNNNNNNNNNNNNNNNNNNNNNNNNNN
31801  NNNNNNNNNNNNNNNNNNNNNNNNNNNNNNNNNNNNNNNNNNNNNNNNNNNNNNNNNNNN

31861  NNNNNNNNNNNNNNNNNNNNNNNNNNNNNNNNNNNNNNNNNNNNNNNNNNNNNNNNNNNN
31861  NNNNNNNNNNNNNNNNNNNNNNNNNNNNNNNNNNNNNNNNNNNNNNNNNNNNNNNNNNNN

31921  NNNNNNNNNNNNNNNNNNNNNNNNNNNNNNNNNNNNNNNNNNNNNNNNNNNNNNNNNNNN
31921  NNNNNNNNNNNNNNNNNNNNNNNNNNNNNNNNNNNNNNNNNNNNNNNNNNNNNNNNNNNN

31981  NNNNNNNNNNNNNNNNNNNNNNNNNNNNNNNNNNNNNNNNNNNNNNNNNNNNNNNNNNNN
31981  NNNNNNNNNNNNNNNNNNNNNNNNNNNNNNNNNNNNNNNNNNNNNNNNNNNNNNNNNNNN

32041  NNNNNNNNNNNNNNNNNNNNNNNNNNNNNNNNNNNNNNNNNNNNNNNNNNNNNNNNNNNN
32041  NNNNNNNNNNNNNNNNNNNNNNNNNNNNNNNNNNNNNNNNNNNNNNNNNNNNNNNNNNNN

32101  NNNNNNNNNNNNNNNNNNNNNNNNNNNNNNNNNNNNNNNNNNNNNNNNNNNNNNNNNNNN
32101  NNNNNNNNNNNNNNNNNNNNNNNNNNNNNNNNNNNNNNNNNNNNNNNNNNNNNNNNNNNN

32161  NNNNNNNNNNNNNNNNNNNNNNNNNNNNNNNNNNNNNNNNNNNNNNNNNNNNNNNNNNNN
32161  NNNNNNNNNNNNNNNNNNNNNNNNNNNNNNNNNNNNNNNNNNNNNNNNNNNNNNNNNNNN

32221  NNNNNNNNNNNNNNNNNNNNNNNNNNNNNNNNNNNNNNNNNNNNNNNNNNNNNNNNNNNN
32221  NNNNNNNNNNNNNNNNNNNNNNNNNNNNNNNNNNNNNNNNNNNNNNNNNNNNNNNNNNNN

32281  NNNNNNNNNNNNNNNNNNNNNNNNNNNNNNNNNNNNNNNNNNNNNNNNNNNNNNNNNNNN
32281  NNNNNNNNNNNNNNNNNNNNNNNNNNNNNNNNNNNNNNNNNNNNNNNNNNNNNNNNNNNN

32341  NNNNNNNNNNNNNNNNNNNNNNNNNNNNNNNNNNNNNNNNNNNNNNNNNNNNNNNNNNNN
32341  NNNNNNNNNNNNNNNNNNNNNNNNNNNNNNNNNNNNNNNNNNNNNNNNNNNNNNNNNNNN

32401  NNNNNNNNNNNNNNNNNNNNNNNNNNNNNNNNNNNNNNNNNNNNNNNNNNNNNNNNNNNN
32401  NNNNNNNNNNNNNNNNNNNNNNNNNNNNNNNNNNNNNNNNNNNNNNNNNNNNNNNNNNNN

32461  NNNNNNNNNNNNNNNNNNNNNNNNNNNNNNNNNNNNNNNNNNNNNNNNNNNNNNNNNNNN
32461  NNNNNNNNNNNNNNNNNNNNNNNNNNNNNNNNNNNNNNNNNNNNNNNNNNNNNNNNNNNN

32521  NNNNNNNNNNNNNNNNNNNNNNNNNNNNNNNNNNNNNNNNNNNNNNNNNNNNNNNNNNNN
32521  NNNNNNNNNNNNNNNNNNNNNNNNNNNNNNNNNNNNNNNNNNNNNNNNNNNNNNNNNNNN

32581  NNNNNNNNNNNNNNNNNNNNNNNNNNNNNNNNNNNNNNNNNNNNNNNNNNNNNNNNNNNN
32581  NNNNNNNNNNNNNNNNNNNNNNNNNNNNNNNNNNNNNNNNNNNNNNNNNNNNNNNNNNNN

32641  NNNNNNNNNNNNNNNNNNNNNNNNNNNNNNNNNNNNNNNNNNNNNNNNNNNNNNNNNNNN
32641  NNNNNNNNNNNNNNNNNNNNNNNNNNNNNNNNNNNNNNNNNNNNNNNNNNNNNNNNNNNN

32701  NNNNNNNNNNNNNNNNNNNNNNNNNNNNNNNNNNNNNNNNNNNNNNNNNNNNNNNNNNNN
32701  NNNNNNNNNNNNNNNNNNNNNNNNNNNNNNNNNNNNNNNNNNNNNNNNNNNNNNNNNNNN

32761  NNNNNNNNNNNNNNNNNNNNNNNNNNNNNNNNNNNNNNNNNNNNNNNNNNNNNNNNNNNN
32761  NNNNNNNNNNNNNNNNNNNNNNNNNNNNNNNNNNNNNNNNNNNNNNNNNNNNNNNNNNNN

32821  NNNNNNNNNNNNNNNNNNNNNNNNNNNNNNNNNNNNNNNNNNNNNNNNNNNNNNNNNNNN
32821  NNNNNNNNNNNNNNNNNNNNNNNNNNNNNNNNNNNNNNNNNNNNNNNNNNNNNNNNNNNN

32881  NNNNNNNNNNNNNNNNNNNNNNNNNNNNNNNNNNNNNNNNNNNNNNNNNNNNNNNNNNNN
32881  NNNNNNNNNNNNNNNNNNNNNNNNNNNNNNNNNNNNNNNNNNNNNNNNNNNNNNNNNNNN
```

FIG. 5 (cont'd)

32941 NNNNNNNNNNNNNNNNNNNNNNNNNNNNNNNNNNNNNNNNNNNNNNNNNNNNNNNNNNNN
32941 NNNNNNNNNNNNNNNNNNNNNNNNNNNNNNNNNNNNNNNNNNNNNNNNNNNNNNNNNNNN

33001 NNNNNNNNNNNNNNNNNNNNNNNNNNNNNNNNNNNNNNNNNNNNNNNNNNNNNNNNNNNN
33001 NNNNNNNNNNNNNNNNNNNNNNNNNNNNNNNNNNNNNNNNNNNNNNNNNNNNNNNNNNNN

33061 NNNNNNNNNNNNNNNNNNNNNNNNNNNNNNNNNNNNNNNNNNNNNNNNNNNNNNNNNNNN
33061 NNNNNNNNNNNNNNNNNNNNNNNNNNNNNNNNNNNNNNNNNNNNNNNNNNNNNNNNNNNN

33121 NNNNNNNNNNNNNNNNNNNNNNNNNNNNNNNNNNNNNNNNNNNNNNNNNNNNNNNNNNNN
33121 NNNNNNNNNNNNNNNNNNNNNNNNNNNNNNNNNNNNNNNNNNNNNNNNNNNNNNNNNNNN

33181 NNNNNNNNNNNNNNNNNNNNNNNNNNNNNNNNNNNNNNNNNNNNNNNNNNNNNNNNNNNN
33181 NNNNNNNNNNNNNNNNNNNNNNNNNNNNNNNNNNNNNNNNNNNNNNNNNNNNNNNNNNNN

33241 NNNNNNNNNNNNNNNNNNNNNNNNNNNNNNNNNNNNNNNNNNNNNNNNNNNNNNNNNNNN
33241 NNNNNNNNNNNNNNNNNNNNNNNNNNNNNNNNNNNNNNNNNNNNNNNNNNNNNNNNNNNN

33301 NNNNNNNNNNNNNNNNNNNNNNNNNNNNNNNNNNNNNNNNNNNNNNNNNNNNNNNNNNNN
33301 NNNNNNNNNNNNNNNNNNNNNNNNNNNNNNNNNNNNNNNNNNNNNNNNNNNNNNNNNNNN

33361 NNNNNNNNNNNNNNNNNNNNNNNNNNNNNNNNNNNNNNNNNNNNNNNNNNNNNNNNNNNN
33361 NNNNNNNNNNNNNNNNNNNNNNNNNNNNNNNNNNNNNNNNNNNNNNNNNNNNNNNNNNNN

33421 NNNNNNNNNNNNNNNNNNNNNNNNNNNNNNNNNNNNNNNNNNNNNNNNNNNNNNNNNNNN
33421 NNNNNNNNNNNNNNNNNNNNNNNNNNNNNNNNNNNNNNNNNNNNNNNNNNNNNNNNNNNN

33481 NNNNNNNNNNNNNNNNNNNNNNNNNNNNNNNNNNNNNNNNNNNNNNNNNNNNNNNNNNNN
33481 NNNNNNNNNNNNNNNNNNNNNNNNNNNNNNNNNNNNNNNNNNNNNNNNNNNNNNNNNNNN

33541 NNNNNNNNNNNNNNNNNNNNNNNNNNNNNNNNNNNNNNNNNNNNNNNNNNNNNNNNNNNN
33541 NNNNNNNNNNNNNNNNNNNNNNNNNNNNNNNNNNNNNNNNNNNNNNNNNNNNNNNNNNNN

33601 NNNNNNNNNNNNNNNNNNNNNNNNNNNNNNNNNNNNNNNNNNNNNNNNNNNNNNNNNNNN
33601 NNNNNNNNNNNNNNNNNNNNNNNNNNNNNNNNNNNNNNNNNNNNNNNNNNNNNNNNNNNN

33661 NNNNNNNNNNNNNNNNNNNNNNNNNNNNNNNNNNNNNNNNNNNNNNNNNNNNNNNNNNNN
33661 NNNNNNNNNNNNNNNNNNNNNNNNNNNNNNNNNNNNNNNNNNNNNNNNNNNNNNNNNNNN

33721 NNNNNNNNNNNNNNNNNNNNNNNNNNNNNNNNNNNNNNNNNNNNNNNNNNNNNNNNNNNN
33721 NNNNNNNNNNNNNNNNNNNNNNNNNNNNNNNNNNNNNNNNNNNNNNNNNNNNNNNNNNNN

33781 NNNNNNNNNNNNNNNNNNNNNNNNNNNNNNNNNNNNNNNNNNNNNNNNNNNNNNNNNNNN
33781 NNNNNNNNNNNNNNNNNNNNNNNNNNNNNNNNNNNNNNNNNNNNNNNNNNNNNNNNNNNN

33841 NNNNNNNNNNNNNNNNNNNNNNNNNNNNNNNNNNNNNNNNNNNNNNNNNNNNNNNNNNNN
33841 NNNNNNNNNNNNNNNNNNNNNNNNNNNNNNNNNNNNNNNNNNNNNNNNNNNNNNNNNNNN

33901 NNNNNNNNNNNNNNNNNNNNNNNNNNNNNNNNNNNNNNNNNNNNNNNNNNNNNNNNNNNN
33901 NNNNNNNNNNNNNNNNNNNNNNNNNNNNNNNNNNNNNNNNNNNNNNNNNNNNNNNNNNNN

33961 NNNNNNNNNNNNNNNNNNNNNNNNNNNNNNNNNNNNNNNNNNNNNNNNNNNNNNNNNNNN
33961 NNNNNNNNNNNNNNNNNNNNNNNNNNNNNNNNNNNNNNNNNNNNNNNNNNNNNNNNNNNN

34021 NNNNNNNNNNNNNNNNNNNNNNNNNNNNNNNNNNNNNNNNNNNNNNNNNNNNNNNNNNNN
34021 NNNNNNNNNNNNNNNNNNNNNNNNNNNNNNNNNNNNNNNNNNNNNNNNNNNNNNNNNNNN

34081 NNNNNNNNNNNNNNNNNNNNNNNNNNNNNNNNNNNNNNNNNNNNNNNNNNNNNNNNNNNN
34081 NNNNNNNNNNNNNNNNNNNNNNNNNNNNNNNNNNNNNNNNNNNNNNNNNNNNNNNNNNNN

34141 NNNNNNNNNNNNNNNNNNNNNNNNNNNNNNNNNNNNNNNNNNNNNNNNNNNNNNNNNNNN
34141 NNNNNNNNNNNNNNNNNNNNNNNNNNNNNNNNNNNNNNNNNNNNNNNNNNNNNNNNNNNN

34201 NNNNNNNNNNNNNNNNNNNNNNNNNNNNNNNNNNNNNNNNNNNNNNNNNNNNNNNNNNNN
34201 NNNNNNNNNNNNNNNNNNNNNNNNNNNNNNNNNNNNNNNNNNNNNNNNNNNNNNNNNNNN

34261 NNNNNNNNNNNNNNNNNNNNNNNNNNNNNNNNNNNNNNNNNNNNNNNNNNNNNNNNNNNN
34261 NNNNNNNNNNNNNNNNNNNNNNNNNNNNNNNNNNNNNNNNNNNNNNNNNNNNNNNNNNNN

FIG. 5 (cont'd)

```
34321  NNNNNNNNNNNNNNNNNNNNNNNNNNNNNNNNNNNNNNNNNNNNNNNNNNNNNNNNNNNN
34321  NNNNNNNNNNNNNNNNNNNNNNNNNNNNNNNNNNNNNNNNNNNNNNNNNNNNNNNNNNNN

34381  NNNNNNNNNNNNNNNNNNNNNNNNNNNNNNNNNNNNNNNNNNNNNNNNNNNNNNNNNNNN
34381  NNNNNNNNNNNNNNNNNNNNNNNNNNNNNNNNNNNNNNNNNNNNNNNNNNNNNNNNNNNN

34441  NNNNNNNNNNNNNNNNNNNNNNNNNNNNNNNNNNNNNNNNNNNNNNNNNNNNNNNNNNNN
34441  NNNNNNNNNNNNNNNNNNNNNNNNNNNNNNNNNNNNNNNNNNNNNNNNNNNNNNNNNNNN

34501  NNNNNNNNNNNNNNNNNNNNNNNNNNNNNNNNNNNNNNNNNNNNNNNNNNNNNNNNNNNN
34501  NNNNNNNNNNNNNNNNNNNNNNNNNNNNNNNNNNNNNNNNNNNNNNNNNNNNNNNNNNNN

34561  NNNNNNNNNNNNNNNNNNNNNNNNNNNNNNNNNNNNNNNNNNNNNNNNNNNNNNNNNNNN
34561  NNNNNNNNNNNNNNNNNNNNNNNNNNNNNNNNNNNNNNNNNNNNNNNNNNNNNNNNNNNN

34621  NNNNNNNNNNNNNNNNNNNNNNNNNNNNNNNNNNNNNNNNNNNNNNNNNNNNNNNNNNNN
34621  NNNNNNNNNNNNNNNNNNNNNNNNNNNNNNNNNNNNNNNNNNNNNNNNNNNNNNNNNNNN

34681  NNNNNNNNNNNNNNNNNNNNNNNNNNNNNNNNNNNNNNNNNNNNNNNNNNNNNNNNNNNN
34681  NNNNNNNNNNNNNNNNNNNNNNNNNNNNNNNNNNNNNNNNNNNNNNNNNNNNNNNNNNNN

34741  NNNNNNNNNNNNNNNNNNNNNNNNNNNNNNNNNNNNNNNNNNNNNNNNNNNNNNNNNNNN
34741  NNNNNNNNNNNNNNNNNNNNNNNNNNNNNNNNNNNNNNNNNNNNNNNNNNNNNNNNNNNN

34801  NNNNNNNNNNNNNNNNNNNNNNNNNNNNNNNNNNNNNNNNNNNNNNNNNNNNNNNNNNNN
34801  NNNNNNNNNNNNNNNNNNNNNNNNNNNNNNNNNNNNNNNNNNNNNNNNNNNNNNNNNNNN

34861  NNNNNNNNNNNNNNNNNNNNNNNNNNNNNNNNNNNNNNNNNNNNNNNNNNNNNNNNNNNN
34861  NNNNNNNNNNNNNNNNNNNNNNNNNNNNNNNNNNNNNNNNNNNNNNNNNNNNNNNNNNNN

34921  NNNNNNNNNNNNNNNNNNNNNNNNNNNNNNNNNNNNNNNNNNNNNNNNNNNNNNNNNNNN
34921  NNNNNNNNNNNNNNNNNNNNNNNNNNNNNNNNNNNNNNNNNNNNNNNNNNNNNNNNNNNN

34981  NNNNNNNNNNNNNNNNNNNNNNNNNNNNNNNNNNNNNNNNNNNNNNNNNNNNNNNNNNNN
34981  NNNNNNNNNNNNNNNNNNNNNNNNNNNNNNNNNNNNNNNNNNNNNNNNNNNNNNNNNNNN

35041  NNNNNNNNNNNNNNNNNNNNNNNNNNNNNNNNNNNNNNNNNNNNNNNNNNNNNNNNNNNN
35041  NNNNNNNNNNNNNNNNNNNNNNNNNNNNNNNNNNNNNNNNNNNNNNNNNNNNNNNNNNNN

35101  NNNNNNNNNNNNNNNNNNNNNNNNNNNNNNNNNNNNNNNNNNNNNNNNNNNNNNNNNNNN
35101  NNNNNNNNNNNNNNNNNNNNNNNNNNNNNNNNNNNNNNNNNNNNNNNNNNNNNNNNNNNN

35161  NNNNNNNNNNNNNNNNNNNNNNNNNNNNNNNNNNNNNNNNNNNNNNNNNNNNNNNNNNNN
35161  NNNNNNNNNNNNNNNNNNNNNNNNNNNNNNNNNNNNNNNNNNNNNNNNNNNNNNNNNNNN

35221  NNNNNNNNNNNNNNNNNNNNNNNNNNNNNNNNNNNNNNNNNNNNNNNNNNNNNNNNNNNN
35221  NNNNNNNNNNNNNNNNNNNNNNNNNNNNNNNNNNNNNNNNNNNNNNNNNNNNNNNNNNNN

35281  NNNNNNNNNNNNNNNNNNNNNNNNNNNNNNNNNNNNNNNNNNNNNNNNNNNNNNNNNNNN
35281  NNNNNNNNNNNNNNNNNNNNNNNNNNNNNNNNNNNNNNNNNNNNNNNNNNNNNNNNNNNN

35341  NNNNNNNNNNNNNNNNNNNNNNNNNNNNNNNNNNNNNNNNNNNNNNNNNNNNNNNNNNNN
35341  NNNNNNNNNNNNNNNNNNNNNNNNNNNNNNNNNNNNNNNNNNNNNNNNNNNNNNNNNNNN

35401  NNNNNNNNNNNNNNNNNNNNNNNNNNNNNNNNNNNNNNNNNNNNNNNNNNNNNNNNNNNN
35401  NNNNNNNNNNNNNNNNNNNNNNNNNNNNNNNNNNNNNNNNNNNNNNNNNNNNNNNNNNNN

35461  NNNNNNNNNNNNNNNNNNNNNNNNNNNNNNNNNNNNNNNNNNNNNNNNNNNNNNNNNNNN
35461  NNNNNNNNNNNNNNNNNNNNNNNNNNNNNNNNNNNNNNNNNNNNNNNNNNNNNNNNNNNN

35521  NNNNNNNNNNNNNNNNNNNNNNNNNNNNNNNNNNNNNNNNNNNNNNNNNNNNNNNNNNNN
35521  NNNNNNNNNNNNNNNNNNNNNNNNNNNNNNNNNNNNNNNNNNNNNNNNNNNNNNNNNNNN

35581  NNNNNNNNNNNNNNNNNNNNNNNNNNNNNNNNNNNNNNNNNNNNNNNNNNNNNNNNNNNN
35581  NNNNNNNNNNNNNNNNNNNNNNNNNNNNNNNNNNNNNNNNNNNNNNNNNNNNNNNNNNNN

35641  NNNNNNNNNNNNNNNNNNNNNNNNNNNNNNNNNNNNNNNNNNNNNNNNNNNNNNNNNNNN
35641  NNNNNNNNNNNNNNNNNNNNNNNNNNNNNNNNNNNNNNNNNNNNNNNNNNNNNNNNNNNN
```

FIG. 5 (cont'd)

```
35701  NNNNNNNNNNNNNNNNNNNNNNNNNNNNNNNNNNNNNNNNNNNNNNNNNNNNNNNNNNNN
35701  NNNNNNNNNNNNNNNNNNNNNNNNNNNNNNNNNNNNNNNNNNNNNNNNNNNNNNNNNNNN

35761  NNNNNNNNNNNNNNNNNNNNNNNNNNNNNNNNNNNNNNNNNNNNNNNNNNNNNNNNNNNN
35761  NNNNNNNNNNNNNNNNNNNNNNNNNNNNNNNNNNNNNNNNNNNNNNNNNNNNNNNNNNNN

35821  NNNNNNNNNNNNNNNNNNNNNNNNNNNNNNNNNNNNNNNNNNNNNNNNNNNNNNNNNNNN
35821  NNNNNNNNNNNNNNNNNNNNNNNNNNNNNNNNNNNNNNNNNNNNNNNNNNNNNNNNNNNN

35881  NNNNNNNNNNNNNNNNNNNNNNNNNNNNNNNNNNNNNNNNNNNNNNNNNNNNNNNNNNNN
35881  NNNNNNNNNNNNNNNNNNNNNNNNNNNNNNNNNNNNNNNNNNNNNNNNNNNNNNNNNNNN

35941  NNNNNNNNNNNNNNNNNNNNNNNNNNNNNNNNNNNNNNNNNNNNNNNNNNNNNNNNNNNN
35941  NNNNNNNNNNNNNNNNNNNNNNNNNNNNNNNNNNNNNNNNNNNNNNNNNNNNNNNNNNNN

36001  NNNNNNNNNNNNNNNNNNNNNNNNNNNNNNNNNNNNNNNNNNNNNNNNNNNNNNNNNNNN
36001  NNNNNNNNNNNNNNNNNNNNNNNNNNNNNNNNNNNNNNNNNNNNNNNNNNNNNNNNNNNN

36061  NNNNNNNNNNNNNNNNNNNNNNNNNNNNNNNNNNNNNNNNNNNNNNNNNNNNNNNNNNNN
36061  NNNNNNNNNNNNNNNNNNNNNNNNNNNNNNNNNNNNNNNNNNNNNNNNNNNNNNNNNNNN

36121  NNNNNNNNNNNNNNNNNNNNNNNNNNNNNNNNNNNNNNNNNNNNNNNNNNNNNNNNNNNN
36121  NNNNNNNNNNNNNNNNNNNNNNNNNNNNNNNNNNNNNNNNNNNNNNNNNNNNNNNNNNNN

36181  NNNNNNNNNNNNNNNNNNNNNNNNNNNNNNNNNNNNNNNNNNNNNNNNNNNNNNNNNNNN
36181  NNNNNNNNNNNNNNNNNNNNNNNNNNNNNNNNNNNNNNNNNNNNNNNNNNNNNNNNNNNN

36241  NNNNNNNNNNNNNNNNNNNNNNNNNNNNNNNNNNNNNNNNNNNNNNNNNNNNNNNNNNNN
36241  NNNNNNNNNNNNNNNNNNNNNNNNNNNNNNNNNNNNNNNNNNNNNNNNNNNNNNNNNNNN

36301  NNNNNNNNNNNNNNNNNNNNNNNNNNNNNNNNNNNNNNNNNNNNNNNNNNNNNNNNNNNN
36301  NNNNNNNNNNNNNNNNNNNNNNNNNNNNNNNNNNNNNNNNNNNNNNNNNNNNNNNNNNNN

36361  NNNNNNNNNNNNNNNNNNNNNNNNNNNNNNNNNNNNNNNNNNNNNNNNNNNNNNNNNNNN
36361  NNNNNNNNNNNNNNNNNNNNNNNNNNNNNNNNNNNNNNNNNNNNNNNNNNNNNNNNNNNN

36421  NNNNNNNNNNNNNNNNNNNNNNNNNNNNNNNNNNNNNNNNNNNNNNNNNNNNNNNNNNNN
36421  NNNNNNNNNNNNNNNNNNNNNNNNNNNNNNNNNNNNNNNNNNNNNNNNNNNNNNNNNNNN

36481  NNNNNNNNNNNNNNNNNNNNNNNNNNNNNNNNNNNNNNNNNNNNNNNNNNNNNNNNNNNN
36481  NNNNNNNNNNNNNNNNNNNNNNNNNNNNNNNNNNNNNNNNNNNNNNNNNNNNNNNNNNNN

36541  NNNNNNNNNNNNNNNNNNNNNNNNNNNNNNNNNNNNNNNNNNNNNNNNNNNNNNNNNNNN
36541  NNNNNNNNNNNNNNNNNNNNNNNNNNNNNNNNNNNNNNNNNNNNNNNNNNNNNNNNNNNN

36601  NNNNNNNNNNNNNNNNNNNNNNNNNNNNNNNNNNNNNNNNNNNNNNNNNNNNNNNNNNNN
36601  NNNNNNNNNNNNNNNNNNNNNNNNNNNNNNNNNNNNNNNNNNNNNNNNNNNNNNNNNNNN

36661  NNNNNNNNNNNNNNNNNNNNNNNNNNNNNNNNNNNNNNNNNNNNNNNNNNNNNNNNNNNN
36661  NNNNNNNNNNNNNNNNNNNNNNNNNNNNNNNNNNNNNNNNNNNNNNNNNNNNNNNNNNNN

36721  NNNNNNNNNNNNNNNNNNNNNNNNNNNNNNNNNNNNNNNNNNNNNNNNNNNNNNNNNNNN
36721  NNNNNNNNNNNNNNNNNNNNNNNNNNNNNNNNNNNNNNNNNNNNNNNNNNNNNNNNNNNN

36781  NNNNNNNNNNNNNNNNNNNNNNNNNNNNNNNNNNNNNNNNNNNNNNNNNNNNNNNNNNNN
36781  NNNNNNNNNNNNNNNNNNNNNNNNNNNNNNNNNNNNNNNNNNNNNNNNNNNNNNNNNNNN

36841  NNNNNNNNNNNNNNNNNNNNNNNNNNNNNNNNNNNNNNNNNNNNNNNNNNNNNNNNNNNN
36841  NNNNNNNNNNNNNNNNNNNNNNNNNNNNNNNNNNNNNNNNNNNNNNNNNNNNNNNNNNNN

36901  NNNNNNNNNNNNNNNNNNNNNNNNNNNNNNNNNNNNNNNNNNNNNNNNNNNNNNNNNNNN
36901  NNNNNNNNNNNNNNNNNNNNNNNNNNNNNNNNNNNNNNNNNNNNNNNNNNNNNNNNNNNN

36961  NNNNNNNNNNNNNNNNNNNNNNNNNNNNNNNNNNNNNNNNNNNNNNNNNNNNNNNNNNNN
36961  NNNNNNNNNNNNNNNNNNNNNNNNNNNNNNNNNNNNNNNNNNNNNNNNNNNNNNNNNNNN

37021  NNNNNNNNNNNNNNNNNNNNNNNNNNNNNNNNNNNNNNNNNNNNNNNNNNNNNNNNNNNN
37021  NNNNNNNNNNNNNNNNNNNNNNNNNNNNNNNNNNNNNNNNNNNNNNNNNNNNNNNNNNNN
```

FIG. 5 (cont'd)

```
37081  NNNNNNNNNNNNNNNNNNNNNNNNNNNNNNNNNNNNNNNNNNNNNNNNNNNNNNNNNNNN
37081  NNNNNNNNNNNNNNNNNNNNNNNNNNNNNNNNNNNNNNNNNNNNNNNNNNNNNNNNNNNN

37141  NNNNNNNNNNNNNNNNNNNNNNNNNNNNNNNNNNNNNNNNNNNNNNNNNNNNNNNNNNNN
37141  NNNNNNNNNNNNNNNNNNNNNNNNNNNNNNNNNNNNNNNNNNNNNNNNNNNNNNNNNNNN

37201  NNNNNNNNNNNNNNNNNNNNNNNNNNNNNNNNNNNNNNNNNNNNNNNNNNNNNNNNNNNN
37201  NNNNNNNNNNNNNNNNNNNNNNNNNNNNNNNNNNNNNNNNNNNNNNNNNNNNNNNNNNNN

37261  NNNNNNNNNNNNNNNNNNNNNNNNNNNNNNNNNNNNNNNNNNNNNNNNNNNNNNNNNNNN
37261  NNNNNNNNNNNNNNNNNNNNNNNNNNNNNNNNNNNNNNNNNNNNNNNNNNNNNNNNNNNN

37321  NNNNNNNNNNNNNNNNNNNNNNNNNNNNNNNNNNNNNNNNNNNNNNNNNNNNNNNNNNNN
37321  NNNNNNNNNNNNNNNNNNNNNNNNNNNNNNNNNNNNNNNNNNNNNNNNNNNNNNNNNNNN

37381  NNNNNNNNNNNNNNNNNNNNNNNNNNNNNNNNNNNNNNNNNNNNNNNNNNNNNNNNNNNN
37381  NNNNNNNNNNNNNNNNNNNNNNNNNNNNNNNNNNNNNNNNNNNNNNNNNNNNNNNNNNNN

37441  NNNNNNNNNNNNNNNNNNNNNNNNNNNNNNNNNNNNNNNNNNNNNNNNNNNNNNNNNNNN
37441  NNNNNNNNNNNNNNNNNNNNNNNNNNNNNNNNNNNNNNNNNNNNNNNNNNNNNNNNNNNN

37501  NNNNNNNNNNNNNNNNNNNNNNNNNNNNNNNNNNNNNNNNNNNNNNNNNNNNNNNNNNNN
37501  NNNNNNNNNNNNNNNNNNNNNNNNNNNNNNNNNNNNNNNNNNNNNNNNNNNNNNNNNNNN

37561  NNNNNNNNNNNNNNNNNNNNNNNNNNNNNNNNNNNNNNNNNNNNNNNNNNNNNNNNNNNN
37561  NNNNNNNNNNNNNNNNNNNNNNNNNNNNNNNNNNNNNNNNNNNNNNNNNNNNNNNNNNNN

37621  NNNNNNNNNNNNNNNNNNNNNNNNNNNNNNNNNNNNNNNNNNNNNNNNNNNNNNNNNNNN
37621  NNNNNNNNNNNNNNNNNNNNNNNNNNNNNNNNNNNNNNNNNNNNNNNNNNNNNNNNNNNN

37681  NNNNNNNNNNNNNNNNNNNNNNNNNNNNNNNNNNNNNNNNNNNNNNNNNNNNNNNNNNNN
37681  NNNNNNNNNNNNNNNNNNNNNNNNNNNNNNNNNNNNNNNNNNNNNNNNNNNNNNNNNNNN

37741  NNNNNNNNNNNNNNNNNNNNNNNNNNNNNNNNNNNNNNNNNNNNNNNNNNNNNNNNNNNN
37741  NNNNNNNNNNNNNNNNNNNNNNNNNNNNNNNNNNNNNNNNNNNNNNNNNNNNNNNNNNNN

37801  NNNNNNNNNNNNNNNNNNNNNNNNNNNNNNNNNNNNNNNNNNNNNNNNNNNNNNNNNNNN
37801  NNNNNNNNNNNNNNNNNNNNNNNNNNNNNNNNNNNNNNNNNNNNNNNNNNNNNNNNNNNN

37861  NNNNNNNNNNNNNNNNNNNNNNNNNNNNNNNNNNNNNNNNNNNNNNNNNNNNNNNNNNNN
37861  NNNNNNNNNNNNNNNNNNNNNNNNNNNNNNNNNNNNNNNNNNNNNNNNNNNNNNNNNNNN

37921  NNNNNNNNNNNNNNNNNNNNNNNNNNNNNNNNNNNNNNNNNNNNNNNNNNNNNNNNNNNN
37921  NNNNNNNNNNNNNNNNNNNNNNNNNNNNNNNNNNNNNNNNNNNNNNNNNNNNNNNNNNNN

37981  NNNNNNNNNNNNNNNNNNNNNNNNNNNNNNNNNNNNNNNNNNNNNNNNNNNNNNNNNNNN
37981  NNNNNNNNNNNNNNNNNNNNNNNNNNNNNNNNNNNNNNNNNNNNNNNNNNNNNNNNNNNN

38041  NNNNNNNNNNNNNNNNNNNNNNNNNNNNNNNNNNNNNNNNNNNNNNNNNNNNNNNNNNNN
38041  NNNNNNNNNNNNNNNNNNNNNNNNNNNNNNNNNNNNNNNNNNNNNNNNNNNNNNNNNNNN

38101  NNNNNNNNNNNNNNNNNNNNNNNNNNNNNNNNNNNNNNNNNNNNNNNNNNNNNNNNNNNN
38101  NNNNNNNNNNNNNNNNNNNNNNNNNNNNNNNNNNNNNNNNNNNNNNNNNNNNNNNNNNNN

38161  NNNNNNNNNNNNNNNNNNNNNNNNNNNNNNNNNNNNNNNNNNNNNNNNNNNNNNNNNNNN
38161  NNNNNNNNNNNNNNNNNNNNNNNNNNNNNNNNNNNNNNNNNNNNNNNNNNNNNNNNNNNN

38221  NNNNNNNNNNNNNNNNNNNNNNNNNNNNNNNNNNNNNNNNNNNNNNNNNNNNNNNNNNNN
38221  NNNNNNNNNNNNNNNNNNNNNNNNNNNNNNNNNNNNNNNNNNNNNNNNNNNNNNNNNNNN

38281  NNNNNNNNNNNNNNNNNNNNNNNNNNNNNNNNNNNNNNNNNNNNNNNNNNNNNNNNNNNN
38281  NNNNNNNNNNNNNNNNNNNNNNNNNNNNNNNNNNNNNNNNNNNNNNNNNNNNNNNNNNNN

38341  NNNNNNNNNNNNNNNNNNNNNNNNNNNNNNNNNNNNNNNNNNNNNNNNNNNNNNNNNNNN
38341  NNNNNNNNNNNNNNNNNNNNNNNNNNNNNNNNNNNNNNNNNNNNNNNNNNNNNNNNNNNN

38401  NNNNNNNNNNNNNNNNNNNNNNNNNNNNNNNNNNNNNNNNNNNNNNNNNNNNNNNNNNNN
38401  NNNNNNNNNNNNNNNNNNNNNNNNNNNNNNNNNNNNNNNNNNNNNNNNNNNNNNNNNNNN
```

FIG. 5 (cont'd)

```
38461  NNNNNNNNNNNNNNNNNNNNNNNNNNNNNNNNNNNNNNNNNNNNNNNNNNNNNNNNNNNN
38461  NNNNNNNNNNNNNNNNNNNNNNNNNNNNNNNNNNNNNNNNNNNNNNNNNNNNNNNNNNNN

38521  NNNNNNNNNNNNNNNNNNNNNNNNNNNNNNNNNNNNNNNNNNNNNNNNNNNNNNNNNNNN
38521  NNNNNNNNNNNNNNNNNNNNNNNNNNNNNNNNNNNNNNNNNNNNNNNNNNNNNNNNNNNN

38581  NNNNNNNNNNNNNNNNNNNNNNNNNNNNNNNNNNNNNNNNNNNNNNNNNNNNNNNNNNNN
38581  NNNNNNNNNNNNNNNNNNNNNNNNNNNNNNNNNNNNNNNNNNNNNNNNNNNNNNNNNNNN

38641  NNNNNNNNNNNNNNNNNNNNNNNNNNNNNNNNNNNNNNNNNNNNNNNNNNNNNNNNNNNN
38641  NNNNNNNNNNNNNNNNNNNNNNNNNNNNNNNNNNNNNNNNNNNNNNNNNNNNNNNNNNNN

38701  NNNNNNNNNNNNNNNNNNNNNNNNNNNNNNNNNNNNNNNNNNNNNNNNNNNNNNNNNNNN
38701  NNNNNNNNNNNNNNNNNNNNNNNNNNNNNNNNNNNNNNNNNNNNNNNNNNNNNNNNNNNN

38761  NNNNNNNNNNNNNNNNNNNNNNNNNNNNNNNNNNNNNNNNNNNNNNNNNNNNNNNNNNNN
38761  NNNNNNNNNNNNNNNNNNNNNNNNNNNNNNNNNNNNNNNNNNNNNNNNNNNNNNNNNNNN

38821  NNNNNNNNNNNNNNNNNNNNNNNNNNNNNNNNNNNNNNNNNNNNNNNNNNNNNNNNNNNN
38821  NNNNNNNNNNNNNNNNNNNNNNNNNNNNNNNNNNNNNNNNNNNNNNNNNNNNNNNNNNNN

38881  NNNNNNNNNNNNNNNNNNNNNNNNNNNNNNNNNNNNNNNNNNNNNNNNNNNNNNNNNNNN
38881  NNNNNNNNNNNNNNNNNNNNNNNNNNNNNNNNNNNNNNNNNNNNNNNNNNNNNNNNNNNN

38941  NNNNNNNNNNNNNNNNNNNNNNNNNNNNNNNNNNNNNNNNNNNNNNNNNNNNNNNNNNNN
38941  NNNNNNNNNNNNNNNNNNNNNNNNNNNNNNNNNNNNNNNNNNNNNNNNNNNNNNNNNNNN

39001  NNNNNNNNNNNNNNNNNNNNNNNNNNNNNNNNNNNNNNNNNNNNNNNNNNNNNNNNNNNN
39001  NNNNNNNNNNNNNNNNNNNNNNNNNNNNNNNNNNNNNNNNNNNNNNNNNNNNNNNNNNNN

39061  NNNNNNNNNNNNNNNNNNNNNNNNNNNNNNNNNNNNNNNNNNNNNNNNNNNNNNNNNNNN
39061  NNNNNNNNNNNNNNNNNNNNNNNNNNNNNNNNNNNNNNNNNNNNNNNNNNNNNNNNNNNN

39121  NNNNNNNNNNNNNNNNNNNNNNNNNNNNNNNNNNNNNNNNNNNNNNNNNNNNNNNNNNNN
39121  NNNNNNNNNNNNNNNNNNNNNNNNNNNNNNNNNNNNNNNNNNNNNNNNNNNNNNNNNNNN

39181  NNNNNNNNNNNNNNNNNNNNNNNNNNNNNNNNNNNNNNNNNNNNNNNNNNNNNNNNNNNN
39181  NNNNNNNNNNNNNNNNNNNNNNNNNNNNNNNNNNNNNNNNNNNNNNNNNNNNNNNNNNNN

39241  NNNNNNNNNNNNNNNNNNNNNNNNNNNNNNNNNNNNNNNNNNNNNNNNNNNNNNNNNNNN
39241  NNNNNNNNNNNNNNNNNNNNNNNNNNNNNNNNNNNNNNNNNNNNNNNNNNNNNNNNNNNN

39301  NNNNNNNNNNNNNNNNNNNNNNNNNNNNNNNNNNNNNNNNNNNNNNNNNNNNNNNNNNNN
39301  NNNNNNNNNNNNNNNNNNNNNNNNNNNNNNNNNNNNNNNNNNNNNNNNNNNNNNNNNNNN

39361  NNNNNNNNNNNNNNNNNNNNNNNNNNNNNNNNNNNNNNNNNNNNNNNNNNNNNNNNNNNN
39361  NNNNNNNNNNNNNNNNNNNNNNNNNNNNNNNNNNNNNNNNNNNNNNNNNNNNNNNNNNNN

39421  NNNNNNNNNNNNNNNNNNNNNNNNNNNNNNNNNNNNNNNNNNNNNNNNNNNNNNNNNNNN
39421  NNNNNNNNNNNNNNNNNNNNNNNNNNNNNNNNNNNNNNNNNNNNNNNNNNNNNNNNNNNN

39481  NNNNNNNNNNNNNNNNNNNNNNNNNNNNNNNNNNNNNNNNNNNNNNNNNNNNNNNNNNNN
39481  NNNNNNNNNNNNNNNNNNNNNNNNNNNNNNNNNNNNNNNNNNNNNNNNNNNNNNNNNNNN

39541  NNNNNNNNNNNNNNNNNNNNNNNNNNNNNNNNNNNNNNNNNNNNNNNNNNNNNNNNNNNN
39541  NNNNNNNNNNNNNNNNNNNNNNNNNNNNNNNNNNNNNNNNNNNNNNNNNNNNNNNNNNNN

39601  NNNNNNNNNNNNNNNNNNNNNNNNNNNNNNNNNNNNNNNNNNNNNNNNNNNNNNNNNNNN
39601  NNNNNNNNNNNNNNNNNNNNNNNNNNNNNNNNNNNNNNNNNNNNNNNNNNNNNNNNNNNN

39661  NNNNNNNNNNNNNNNNNNNNNNNNNNNNNNNNNNNNNNNNNNNNNNNNNNNNNNNNNNNN
39661  NNNNNNNNNNNNNNNNNNNNNNNNNNNNNNNNNNNNNNNNNNNNNNNNNNNNNNNNNNNN

39721  NNNNNNNNNNNNNNNNNNNNNNNNNNNNNNNNNNNNNNNNNNNNNNNNNNNNNNNNNNNN
39721  NNNNNNNNNNNNNNNNNNNNNNNNNNNNNNNNNNNNNNNNNNNNNNNNNNNNNNNNNNNN

39781  NNNNNNNNNNNNNNNNNNNNNNNNNNNNNNNNNNNNNNNNNNNNNNNNNNNNNNNNNNNN
39781  NNNNNNNNNNNNNNNNNNNNNNNNNNNNNNNNNNNNNNNNNNNNNNNNNNNNNNNNNNNN
```

FIG. 5 (cont'd)

```
39841  NNNNNNNNNNNNNNNNNNNNNNNNNNNNNNNNNNNNNNNNNNNNNNNNNNNNNNNNNNNN
39841  NNNNNNNNNNNNNNNNNNNNNNNNNNNNNNNNNNNNNNNNNNNNNNNNNNNNNNNNNNNN

39901  NNNNNNNNNNNNNNNNNNNNNNNNNNNNNNNNNNNNNNNNNNNNNNNNNNNNNNNNNNNN
39901  NNNNNNNNNNNNNNNNNNNNNNNNNNNNNNNNNNNNNNNNNNNNNNNNNNNNNNNNNNNN

39961  NNNNNNNNNNNNNNNNNNNNNNNNNNNNNNNNNNNNNNNNNNNNNNNNNNNNNNNNNNNN
39961  NNNNNNNNNNNNNNNNNNNNNNNNNNNNNNNNNNNNNNNNNNNNNNNNNNNNNNNNNNNN

40021  NNNNNNNNNNNNNNNNNNNNNNNNNNNNNNNNNNNNNNNNNNNNNNNNNNNNNNNNNNNN
40021  NNNNNNNNNNNNNNNNNNNNNNNNNNNNNNNNNNNNNNNNNNNNNNNNNNNNNNNNNNNN

40081  NNNNNNNNNNNNNNNNNNNNNNNNNNNNNNNNNNNNNNNNNNNNNNNNNNNNNNNNNNNN
40081  NNNNNNNNNNNNNNNNNNNNNNNNNNNNNNNNNNNNNNNNNNNNNNNNNNNNNNNNNNNN

40141  NNNNNNNNNNNNNNNNNNNNNNNNNNNNNNNNNNNNNNNNNNNNNNNNNNNNNNNNNNNN
40141  NNNNNNNNNNNNNNNNNNNNNNNNNNNNNNNNNNNNNNNNNNNNNNNNNNNNNNNNNNNN

40201  NNNNNNNNNNNNNNNNNNNNNNNNNNNNNNNNNNNNNNNNNNNNNNNNNNNNNNNNNNNN
40201  NNNNNNNNNNNNNNNNNNNNNNNNNNNNNNNNNNNNNNNNNNNNNNNNNNNNNNNNNNNN

40261  NNNNNNNNNNNNNNNNNNNNNNNNNNNNNNNNNNNNNNNNNNNNNNNNNNNNNNNNNNNN
40261  NNNNNNNNNNNNNNNNNNNNNNNNNNNNNNNNNNNNNNNNNNNNNNNNNNNNNNNNNNNN

40321  NNNNNNNNNNNNNNNNNNNNNNNNNNNNNNNNNNNNNNNNNNNNNNNNNNNNNNNNNNNN
40321  NNNNNNNNNNNNNNNNNNNNNNNNNNNNNNNNNNNNNNNNNNNNNNNNNNNNNNNNNNNN

40381  NNNNNNNNNNNNNNNNNNNNNNNNNNNNNNNNNNNNNNNNNNNNNNNNNNNNNNNNNNNN
40381  NNNNNNNNNNNNNNNNNNNNNNNNNNNNNNNNNNNNNNNNNNNNNNNNNNNNNNNNNNNN

40441  NNNNNNNNNNNNNNNNNNNNNNNNNNNNNNNNNNNNNNNNNNNNNNNNNNNNNNNNNNNN
40441  NNNNNNNNNNNNNNNNNNNNNNNNNNNNNNNNNNNNNNNNNNNNNNNNNNNNNNNNNNNN

40501  NNNNNNNNNNNNNNNNNNNNNNNNNNNNNNNNNNNNNNNNNNNNNNNNNNNNNNNNNNNN
40501  NNNNNNNNNNNNNNNNNNNNNNNNNNNNNNNNNNNNNNNNNNNNNNNNNNNNNNNNNNNN

40561  NNNNNNNNNNNNNNNNNNNNNNNNNNNNNNNNNNNNNNNNNNNNNNNNNNNNNNNNNNNN
40561  NNNNNNNNNNNNNNNNNNNNNNNNNNNNNNNNNNNNNNNNNNNNNNNNNNNNNNNNNNNN

40621  NNNNNNNNNNNNNNNNNNNNNNNNNNNNNNNNNNNNNNNNNNNNNNNNNNNNNNNNNNNN
40621  NNNNNNNNNNNNNNNNNNNNNNNNNNNNNNNNNNNNNNNNNNNNNNNNNNNNNNNNNNNN

40681  NNNNNNNNNNNNNNNNNNNNNNNNNNNNNNNNNNNNNNNNNNNNNNNNNNNNNNNNNNNN
40681  NNNNNNNNNNNNNNNNNNNNNNNNNNNNNNNNNNNNNNNNNNNNNNNNNNNNNNNNNNNN

40741  NNNNNNNNNNNNNNNNNNNNNNNNNNNNNNNNNNNNNNNNNNNNNNNNNNNNNNNNNNNN
40741  NNNNNNNNNNNNNNNNNNNNNNNNNNNNNNNNNNNNNNNNNNNNNNNNNNNNNNNNNNNN

40801  NNNNNNNNNNNNNNNNNNNNNNNNNNNNNNNNNNNNNNNNNNNNNNNNNNNNNNNNNNNN
40801  NNNNNNNNNNNNNNNNNNNNNNNNNNNNNNNNNNNNNNNNNNNNNNNNNNNNNNNNNNNN

40861  NNNNNNNNNNNNNNNNNNNNNNNNNNNNNNNNNNNNNNNNNNNNNNNNNNNNNNNNNNNN
40861  NNNNNNNNNNNNNNNNNNNNNNNNNNNNNNNNNNNNNNNNNNNNNNNNNNNNNNNNNNNN

40921  NNNNNNNNNNNNNNNNNNNNNNNNNNNNNNNNNNNNNNNNNNNNNNNNNNNNNNNNNNNN
40921  NNNNNNNNNNNNNNNNNNNNNNNNNNNNNNNNNNNNNNNNNNNNNNNNNNNNNNNNNNNN

40981  NNNNNNNNNNNNNNNNNNNNNNNNNNNNNNNNNNNNNNNNNNNNNNNNNNNNNNNNNNNN
40981  NNNNNNNNNNNNNNNNNNNNNNNNNNNNNNNNNNNNNNNNNNNNNNNNNNNNNNNNNNNN

41041  NNNNNNNNNNNNNNNNNNNNNNNNNNNNNNNNNNNNNNNNNNNNNNNNNNNNNNNNNNNN
41041  NNNNNNNNNNNNNNNNNNNNNNNNNNNNNNNNNNNNNNNNNNNNNNNNNNNNNNNNNNNN

41101  NNNNNNNNNNNNNNNNNNNNNNNNNNNNNNNNNNNNNNNNNNNNNNNNNNNNNNNNNNNN
41101  NNNNNNNNNNNNNNNNNNNNNNNNNNNNNNNNNNNNNNNNNNNNNNNNNNNNNNNNNNNN

41161  NNNNNNNNNNNNNNNNNNNNNNNNNNNNNNNNNNNNNNNNNNNNNNNNNNNNNNNNNNNN
41161  NNNNNNNNNNNNNNNNNNNNNNNNNNNNNNNNNNNNNNNNNNNNNNNNNNNNNNNNNNNN
```

FIG. 5 (cont'd)

```
41221 NNNNNNNNNNNNNNNNNNNNNNNNNNNNNNNNNNNNNNNNNNNNNNNNNNNNNNNNNNNN
41221 NNNNNNNNNNNNNNNNNNNNNNNNNNNNNNNNNNNNNNNNNNNNNNNNNNNNNNNNNNNN

41281 NNNNNNNNNNNNNNNNNNNNNNNNNNNNNNNNNNNNNNNNNNNNNNNNNNNNNNNNNNNN
41281 NNNNNNNNNNNNNNNNNNNNNNNNNNNNNNNNNNNNNNNNNNNNNNNNNNNNNNNNNNNN

41341 NNNNNNNNNNNNNNNNNNNNNNNNNNNNNNNNNNNNNNNNNNNNNNNNNNNNNNNNNNNN
41341 NNNNNNNNNNNNNNNNNNNNNNNNNNNNNNNNNNNNNNNNNNNNNNNNNNNNNNNNNNNN

41401 NNNNNNNNNNNNNNNNNNNNNNNNNNNNNNNNNNNNNNNNNNNNNNNNNNNNNNNNNNNN
41401 NNNNNNNNNNNNNNNNNNNNNNNNNNNNNNNNNNNNNNNNNNNNNNNNNNNNNNNNNNNN

41461 NNNNNNNNNNNNNNNNNNNNNNNNNNNNNNNNNNNNNNNNNNNNNNNNNNNNNNNNNNNN
41461 NNNNNNNNNNNNNNNNNNNNNNNNNNNNNNNNNNNNNNNNNNNNNNNNNNNNNNNNNNNN

41521 NNNNNNNNNNNNNNNNNNNNNNNNNNNNNNNNNNNNNNNNNNNNNNNNNNNNNNNNNNNN
41521 NNNNNNNNNNNNNNNNNNNNNNNNNNNNNNNNNNNNNNNNNNNNNNNNNNNNNNNNNNNN

41581 NNNNNNNNNNNNNNNNNNNNNNNNNNNNNNNNNNNNNNNNNNNNNNNNNNNNNNNNNNNN
41581 NNNNNNNNNNNNNNNNNNNNNNNNNNNNNNNNNNNNNNNNNNNNNNNNNNNNNNNNNNNN

41641 NNNNNNNNNNNNNNNNNNNNNNNNNNNNNNNNNNNNNNNNNNNNNNNNNNNNNNNNNNNN
41641 NNNNNNNNNNNNNNNNNNNNNNNNNNNNNNNNNNNNNNNNNNNNNNNNNNNNNNNNNNNN

41701 NNNNNNNNNNNNNNNNNNNNNNNNNNNNNNNNNNNNNNNNNNNNNNNNNNNNNNNNNNNN
41701 NNNNNNNNNNNNNNNNNNNNNNNNNNNNNNNNNNNNNNNNNNNNNNNNNNNNNNNNNNNN

41761 NNNNNNNNNNNNNNNNNNNNNNNNNNNNNNNNNNNNNNNNNNNNNNNNNNNNNNNNNNNN
41761 NNNNNNNNNNNNNNNNNNNNNNNNNNNNNNNNNNNNNNNNNNNNNNNNNNNNNNNNNNNN

41821 NNNNNNNNNNNNNNNNNNNNNNNNNNNNNNNNNNNNNNNNNNNNNNNNNNNNNNNNNNNN
41821 NNNNNNNNNNNNNNNNNNNNNNNNNNNNNNNNNNNNNNNNNNNNNNNNNNNNNNNNNNNN

41881 NNNNNNNNNNNNNNNNNNNNNNNNNNNNNNNNNNNNNNNNNNNNNNNNNNNNNNNNNNNN
41881 NNNNNNNNNNNNNNNNNNNNNNNNNNNNNNNNNNNNNNNNNNNNNNNNNNNNNNNNNNNN

41941 NNNNNNNNNNNNNNNNNNNNNNNNNNNNNNNNNNNNNNNNNNNNNNNNNNNNNNNNNNNN
41941 NNNNNNNNNNNNNNNNNNNNNNNNNNNNNNNNNNNNNNNNNNNNNNNNNNNNNNNNNNNN

42001 NNNNNNNNNNNNNNNNNNNNNNNNNNNNNNNNNNNNNNNNNNNNNNNNNNNNNNNNNNNN
42001 NNNNNNNNNNNNNNNNNNNNNNNNNNNNNNNNNNNNNNNNNNNNNNNNNNNNNNNNNNNN

42061 NNNNNNNNNNNNNNNNNNNNNNNNNNNNNNNNNNNNNNNNNNNNNNNNNNNNNNNNNNNN
42061 NNNNNNNNNNNNNNNNNNNNNNNNNNNNNNNNNNNNNNNNNNNNNNNNNNNNNNNNNNNN

42121 NNNNNNNNNNNNNNNNNNNNNNNNNNNNNNNNNNNNNNNNNNNNNNNNNNNNNNNNNNNN
42121 NNNNNNNNNNNNNNNNNNNNNNNNNNNNNNNNNNNNNNNNNNNNNNNNNNNNNNNNNNNN

42181 NNNNNNNNNNNNNNNNNNNNNNNNNNNNNNNNNNNNNNNNNNNNNNNNNNNNNNNNNNNN
42181 NNNNNNNNNNNNNNNNNNNNNNNNNNNNNNNNNNNNNNNNNNNNNNNNNNNNNNNNNNNN

42241 NNNNNNNNNNNNNNNNNNNNNNNNNNNNNNNNNNNNNNNNNNNNNNNNNNNNNNNNNNNN
42241 NNNNNNNNNNNNNNNNNNNNNNNNNNNNNNNNNNNNNNNNNNNNNNNNNNNNNNNNNNNN

42301 NNNNNNNNNNNNNNNNNNNNNNNNNNNNNNNNNNNNNNNNNNNNNNNNNNNNNNNNNNNN
42301 NNNNNNNNNNNNNNNNNNNNNNNNNNNNNNNNNNNNNNNNNNNNNNNNNNNNNNNNNNNN

42361 NNNNNNNNNNNNNNNNNNNNNNNNNNNNNNNNNNNNNNNNNNNNNNNNNNNNNNNNNNNN
42361 NNNNNNNNNNNNNNNNNNNNNNNNNNNNNNNNNNNNNNNNNNNNNNNNNNNNNNNNNNNN

42421 NNNNNNNNNNNNNNNNNNNNNNNNNNNNNNNNNNNNNNNNNNNNNNNNNNNNNNNNNNNN
42421 NNNNNNNNNNNNNNNNNNNNNNNNNNNNNNNNNNNNNNNNNNNNNNNNNNNNNNNNNNNN

42481 NNNNNNNNNNNNNNNNNNNNNNNNNNNNNNNNNNNNNNNNNNNNNNNNNNNNNNNNNNNN
42481 NNNNNNNNNNNNNNNNNNNNNNNNNNNNNNNNNNNNNNNNNNNNNNNNNNNNNNNNNNNN

42541 NNNNNNNNNNNNNNNNNNNNNNNNNNNNNNNNNNNNNNNNNNNNNNNNNNNNNNNNNNNN
42541 NNNNNNNNNNNNNNNNNNNNNNNNNNNNNNNNNNNNNNNNNNNNNNNNNNNNNNNNNNNN
```

FIG. 5 (cont'd)

42601 NNNNNNNNNNNNNNNNNNNNNNNNNNNNNNNNNNNNNNNNNNNNNNNNNNNNNNNNNNNN
42601 NNNNNNNNNNNNNNNNNNNNNNNNNNNNNNNNNNNNNNNNNNNNNNNNNNNNNNNNNNNN

42661 NNNNNNNNNNNNNNNNNNNNNNNNNNNNNNNNNNNNNNNNNNNNNNNNNNNNNNNNNNNN
42661 NNNNNNNNNNNNNNNNNNNNNNNNNNNNNNNNNNNNNNNNNNNNNNNNNNNNNNNNNNNN

42721 NNNNNNNNNNNNNNNNNNNNNNNNNNNNNNNNNNNNNNNNNNNNNNNNNNNNNNNNNNNN
42721 NNNNNNNNNNNNNNNNNNNNNNNNNNNNNNNNNNNNNNNNNNNNNNNNNNNNNNNNNNNN

42781 NNNNNNNNNNNNNNNNNNNNNNNNNNNNNNNNNNNNNNNNNNNNNNNNNNNNNNNNNNNN
42781 NNNNNNNNNNNNNNNNNNNNNNNNNNNNNNNNNNNNNNNNNNNNNNNNNNNNNNNNNNNN

42841 NNNNNNNNNNNNNNNNNNNNNNNNNNNNNNNNNNNNNNNNNNNNNNNNNNNNNNNNNNNN
42841 NNNNNNNNNNNNNNNNNNNNNNNNNNNNNNNNNNNNNNNNNNNNNNNNNNNNNNNNNNNN

42901 NNNNNNNNNNNNNNNNNNNNNNNNNNNNNNNNNNNNNNNNNNNNNNNNNNNNNNNNNNNN
42901 NNNNNNNNNNNNNNNNNNNNNNNNNNNNNNNNNNNNNNNNNNNNNNNNNNNNNNNNNNNN

42961 NNNNNNNNNNNNNNNNNNNNNNNNNNNNNNNNNNNNNNNNNNNNNNNNNNNNNNNNNNNN
42961 NNNNNNNNNNNNNNNNNNNNNNNNNNNNNNNNNNNNNNNNNNNNNNNNNNNNNNNNNNNN

43021 NNNNNNNNNNNNNNNNNNNNNNNNNNNNNNNNNNNNNNNNNNNNNNNNNNNNNNNNNNNN
43021 NNNNNNNNNNNNNNNNNNNNNNNNNNNNNNNNNNNNNNNNNNNNNNNNNNNNNNNNNNNN

43081 NNNNNNNNNNNNNNNNNNNNNNNNNNNNNNNNNNNNNNNNNNNNNNNNNNNNNNNNNNNN
43081 NNNNNNNNNNNNNNNNNNNNNNNNNNNNNNNNNNNNNNNNNNNNNNNNNNNNNNNNNNNN

43141 NNNNNNNNNNNNNNNNNNNNNNNNNNNNNNNNNNNNNNNNNNNNNNNNNNNNNNNNNNNN
43141 NNNNNNNNNNNNNNNNNNNNNNNNNNNNNNNNNNNNNNNNNNNNNNNNNNNNNNNNNNNN

43201 NNNNNNNNNNNNNNNNNNNNNNNNNNNNNNNNNNNNNNNNNNNNNNNNNNNNNNNNNNNN
43201 NNNNNNNNNNNNNNNNNNNNNNNNNNNNNNNNNNNNNNNNNNNNNNNNNNNNNNNNNNNN

43261 NNNNNNNNNNNNNNNNNNNNNNNNNNNNNNNNNNNNNNNNNNNNNNNNNNNNNNNNNNNN
43261 NNNNNNNNNNNNNNNNNNNNNNNNNNNNNNNNNNNNNNNNNNNNNNNNNNNNNNNNNNNN

43321 NNNNNNNNNNNNNNNNNNNNNNNNNNNNNNNNNNNNNNNNNNNNNNNNNNNNNNNNNNNN
43321 NNNNNNNNNNNNNNNNNNNNNNNNNNNNNNNNNNNNNNNNNNNNNNNNNNNNNNNNNNNN

43381 NNNNNNNNNNNNNNNNNNNNNNNNNNNNNNNNNNNNNNNNNNNNNNNNNNNNNNNNNNNN
43381 NNNNNNNNNNNNNNNNNNNNNNNNNNNNNNNNNNNNNNNNNNNNNNNNNNNNNNNNNNNN

43441 NNNNNNNNNNNNNNNNNNNNNNNNNNNNNNNNNNNNNNNNNNNNNNNNNNNNNNNNNNNN
43441 NNNNNNNNNNNNNNNNNNNNNNNNNNNNNNNNNNNNNNNNNNNNNNNNNNNNNNNNNNNN

43501 NNNNNNNNNNNNNNNNNNNNNNNNNNNNNNNNNNNNNNNNNNNNNNNNNNNNNNNNNNNN
43501 NNNNNNNNNNNNNNNNNNNNNNNNNNNNNNNNNNNNNNNNNNNNNNNNNNNNNNNNNNNN

43561 NNNNNNNNNNNNNNNNNNNNNNNNNNNNNNNNNNNNNNNNNNNNNNNNNNNNNNNNNNNN
43561 NNNNNNNNNNNNNNNNNNNNNNNNNNNNNNNNNNNNNNNNNNNNNNNNNNNNNNNNNNNN

43621 NNNNNNNNNNNNNNNNNNNNNNNNNNNNNNNNNNNNNNNNNNNNNNNNNNNNNNNNNNNN
43621 NNNNNNNNNNNNNNNNNNNNNNNNNNNNNNNNNNNNNNNNNNNNNNNNNNNNNNNNNNNN

43681 NNNNNNNNNNNNNNNNNNNNNNNNNNNNNNNNNNNNNNNNNNNNNNNNNNNNNNNNNNNN
43681 NNNNNNNNNNNNNNNNNNNNNNNNNNNNNNNNNNNNNNNNNNNNNNNNNNNNNNNNNNNN

43741 NNNNNNNNNNNNNNNNNNNNNNNNNNNNNNNNNNNNNNNNNNNNNNNNNNNNNNNNNNNN
43741 NNNNNNNNNNNNNNNNNNNNNNNNNNNNNNNNNNNNNNNNNNNNNNNNNNNNNNNNNNNN

43801 NNNNNNNNNNNNNNNNNNNNNNNNNNNNNNNNNNNNNNNNNNNNNNNNNNNNNNNNNNNN
43801 NNNNNNNNNNNNNNNNNNNNNNNNNNNNNNNNNNNNNNNNNNNNNNNNNNNNNNNNNNNN

43861 NNNNNNNNNNNNNNNNNNNNNNNNNNNNNNNNNNNNNNNNNNNNNNNNNNNNNNNNNNNN
43861 NNNNNNNNNNNNNNNNNNNNNNNNNNNNNNNNNNNNNNNNNNNNNNNNNNNNNNNNNNNN

43921 NNNNNNNNNNNNNNNNNNNNNNNNNNNNNNNNNNNNNNNNNNNNNNNNNNNNNNNNNNNN
43921 NNNNNNNNNNNNNNNNNNNNNNNNNNNNNNNNNNNNNNNNNNNNNNNNNNNNNNNNNNNN

FIG. 5 (cont'd)

```
43981  NNNNNNNNNNNNNNNNNNNNNNNNNNNNNNNNNNNNNNNNNNNNNNNNNNNNNNNNNNNN
43981  NNNNNNNNNNNNNNNNNNNNNNNNNNNNNNNNNNNNNNNNNNNNNNNNNNNNNNNNNNNN

44041  NNNNNNNNNNNNNNNNNNNNNNNNNNNNNNNNNNNNNNNNNNNNNNNNNNNNNNNNNNNN
44041  NNNNNNNNNNNNNNNNNNNNNNNNNNNNNNNNNNNNNNNNNNNNNNNNNNNNNNNNNNNN

44101  NNNNNNNNNNNNNNNNNNNNNNNNNNNNNNNNNNNNNNNNNNNNNNNNNNNNNNNNNNNN
44101  NNNNNNNNNNNNNNNNNNNNNNNNNNNNNNNNNNNNNNNNNNNNNNNNNNNNNNNNNNNN

44161  NNNNNNNNNNNNNNNNNNNNNNNNNNNNNNNNNNNNNNNNNNNNNNNNNNNNNNNNNNNN
44161  NNNNNNNNNNNNNNNNNNNNNNNNNNNNNNNNNNNNNNNNNNNNNNNNNNNNNNNNNNNN

44221  NNNNNNNNNNNNNNNNNNNNNNNNNNNNNNNNNNNNNNNNNNNNNNNNNNNNNNNNNNNN
44221  NNNNNNNNNNNNNNNNNNNNNNNNNNNNNNNNNNNNNNNNNNNNNNNNNNNNNNNNNNNN

44281  NNNNNNNNNNNNNNNNNNNNNNNNNNNNNNNNNNNNNNNNNNNNNNNNNNNNNNNNNNNN
44281  NNNNNNNNNNNNNNNNNNNNNNNNNNNNNNNNNNNNNNNNNNNNNNNNNNNNNNNNNNNN

44341  NNNNNNNNNNNNNNNNNNNNNNNNNNNNNNNNNNNNNNNNNNNNNNNNNNNNNNNNNNNN
44341  NNNNNNNNNNNNNNNNNNNNNNNNNNNNNNNNNNNNNNNNNNNNNNNNNNNNNNNNNNNN

44401  NNNNNNNNNNNNNNNNNNNNNNNNNNNNNNNNNNNNNNNNNNNNNNNNNNNNNNNNNNNN
44401  NNNNNNNNNNNNNNNNNNNNNNNNNNNNNNNNNNNNNNNNNNNNNNNNNNNNNNNNNNNN

44461  NNNNNNNNNNNNNNNNNNNNNNNNNNNNNNNNNNNNNNNNNNNNNNNNNNNNNNNNNNNN
44461  NNNNNNNNNNNNNNNNNNNNNNNNNNNNNNNNNNNNNNNNNNNNNNNNNNNNNNNNNNNN

44521  NNNNNNNNNNNNNNNNNNNNNNNNNNNNNNNNNNNNNNNNNNNNNNNNNNNNNNNNNNNN
44521  NNNNNNNNNNNNNNNNNNNNNNNNNNNNNNNNNNNNNNNNNNNNNNNNNNNNNNNNNNNN

44581  NNNNNNNNNNNNNNNNNNNNNNNNNNNNNNNNNNNNNNNNNNNNNNNNNNNNNNNNNNNN
44581  NNNNNNNNNNNNNNNNNNNNNNNNNNNNNNNNNNNNNNNNNNNNNNNNNNNNNNNNNNNN

44641  NNNNNNNNNNNNNNNNNNNNNNNNNNNNNNNNNNNNNNNNNNNNNNNNNNNNNNNNNNNN
44641  NNNNNNNNNNNNNNNNNNNNNNNNNNNNNNNNNNNNNNNNNNNNNNNNNNNNNNNNNNNN

44701  NNNNNNNNNNNNNNNNNNNNNNNNNNNNNNNNNNNNNNNNNNNNNNNNNNNNNNNNNNNN
44701  NNNNNNNNNNNNNNNNNNNNNNNNNNNNNNNNNNNNNNNNNNNNNNNNNNNNNNNNNNNN

44761  NNNNNNNNNNNNNNNNNNNNNNNNNNNNNNNNNNNNNNNNNNNNNNNNNNNNNNNNNNNN
44761  NNNNNNNNNNNNNNNNNNNNNNNNNNNNNNNNNNNNNNNNNNNNNNNNNNNNNNNNNNNN

44821  NNNNNNNNNNNNNNNNNNNNNNNNNNNNNNNNNNNNNNNNNNNNNNNNNNNNNNNNNNNN
44821  NNNNNNNNNNNNNNNNNNNNNNNNNNNNNNNNNNNNNNNNNNNNNNNNNNNNNNNNNNNN

44881  NNNNNNNNNNNNNNNNNNNNNNNNNNNNNNNNNNNNNNNNNNNNNNNNNNNNNNNNNNNN
44881  NNNNNNNNNNNNNNNNNNNNNNNNNNNNNNNNNNNNNNNNNNNNNNNNNNNNNNNNNNNN

44941  NNNNNNNNNNNNNNNNNNNNNNNNNNNNNNNNNNNNNNNNNNNNNNNNNNNNNNNNNNNN
44941  NNNNNNNNNNNNNNNNNNNNNNNNNNNNNNNNNNNNNNNNNNNNNNNNNNNNNNNNNNNN

45001  NNNNNNNNNNNNNNNNNNNNNNNNNNNNNNNNNNNNNNNNNNNNNNNNNNNNNNNNNNNN
45001  NNNNNNNNNNNNNNNNNNNNNNNNNNNNNNNNNNNNNNNNNNNNNNNNNNNNNNNNNNNN

45061  NNNNNNNNNNNNNNNNNNNNNNNNNNNNNNNNNNNNNNNNNNNNNNNNNNNNNNNNNNNN
45061  NNNNNNNNNNNNNNNNNNNNNNNNNNNNNNNNNNNNNNNNNNNNNNNNNNNNNNNNNNNN

45121  NNNNNNNNNNNNNNNNNNNNNNNNNNNNNNNNNNNNNNNNNNNNNNNNNNNNNNNNNNNN
45121  NNNNNNNNNNNNNNNNNNNNNNNNNNNNNNNNNNNNNNNNNNNNNNNNNNNNNNNNNNNN

45181  NNNNNNNNNNNNNNNNNNNNNNNNNNNNNNNNNNNNNNNNNNNNNNNNNNNNNNNNNNNN
45181  NNNNNNNNNNNNNNNNNNNNNNNNNNNNNNNNNNNNNNNNNNNNNNNNNNNNNNNNNNNN

45241  NNNNNNNNNNNNNNNNNNNNNNNNNNNNNNNNNNNNNNNNNNNNNNNNNNNNNNNNNNNN
45241  NNNNNNNNNNNNNNNNNNNNNNNNNNNNNNNNNNNNNNNNNNNNNNNNNNNNNNNNNNNN

45301  NNNNNNNNNNNNNNNNNNNNNNNNNNNNNNNNNNNNNNNNNNNNNNNNNNNNNNNNNNNN
45301  NNNNNNNNNNNNNNNNNNNNNNNNNNNNNNNNNNNNNNNNNNNNNNNNNNNNNNNNNNNN
```

FIG. 5 (cont'd)

```
45361 NNNNNNNNNNNNNNNNNNNNNNNNNNNNNNNNNNNNNNNNNNNNNNNNNNNNNNNNNNNN
45361 NNNNNNNNNNNNNNNNNNNNNNNNNNNNNNNNNNNNNNNNNNNNNNNNNNNNNNNNNNNN

45421 NNNNNNNNNNNNNNNNNNNNNNNNNNNNNNNNNNNNNNNNNNNNNNNNNNNNNNNNNNNN
45421 NNNNNNNNNNNNNNNNNNNNNNNNNNNNNNNNNNNNNNNNNNNNNNNNNNNNNNNNNNNN

45481 NNNNNNNNNNNNNNNNNNNNNNNNNNNNNNNNNNNNNNNNNNNNNNNNNNNNNNNNNNNN
45481 NNNNNNNNNNNNNNNNNNNNNNNNNNNNNNNNNNNNNNNNNNNNNNNNNNNNNNNNNNNN

45541 NNNNNNNNNNNNNNNNNNNNNNNNNNNNNNNNNNNNNNNNNNNNNNNNNNNNNNNNNNNN
45541 NNNNNNNNNNNNNNNNNNNNNNNNNNNNNNNNNNNNNNNNNNNNNNNNNNNNNNNNNNNN

45601 NNNNNNNNNNNNNNNNNNNNNNNNNNNNNNNNNNNNNNNNNNNNNNNNNNNNNNNNNNNN
45601 NNNNNNNNNNNNNNNNNNNNNNNNNNNNNNNNNNNNNNNNNNNNNNNNNNNNNNNNNNNN

45661 NNNNNNNNNNNNNNNNNNNNNNNNNNNNNNNNNNNNNNNNNNNNNNNNNNNNNNNNNNNN
45661 NNNNNNNNNNNNNNNNNNNNNNNNNNNNNNNNNNNNNNNNNNNNNNNNNNNNNNNNNNNN

45721 NNNNNNNNNNNNNNNNNNNNNNNNNNNNNNNNNNNNNNNNNNNNNNNNNNNNNNNNNNNN
45721 NNNNNNNNNNNNNNNNNNNNNNNNNNNNNNNNNNNNNNNNNNNNNNNNNNNNNNNNNNNN

45781 NNNNNNNNNNNNNNNNNNNNNNNNNNNNNNNNNNNNNNNNNNNNNNNNNNNNNNNNNNNN
45781 NNNNNNNNNNNNNNNNNNNNNNNNNNNNNNNNNNNNNNNNNNNNNNNNNNNNNNNNNNNN

45841 NNNNNNNNNNNNNNNNNNNNNNNNNNNNNNNNNNNNNNNNNNNNNNNNNNNNNNNNNNNN
45841 NNNNNNNNNNNNNNNNNNNNNNNNNNNNNNNNNNNNNNNNNNNNNNNNNNNNNNNNNNNN

45901 NNNNNNNNNNNNNNNNNNNNNNNNNNNNNNNNNNNNNNNNNNNNNNNNNNNNNNNNNNNN
45901 NNNNNNNNNNNNNNNNNNNNNNNNNNNNNNNNNNNNNNNNNNNNNNNNNNNNNNNNNNNN

45961 NNNNNNNNNNNNNNNNNNNNNNNNNNNNNNNNNNNNNNNNNNNNNNNNNNNNNNNNNNNN
45961 NNNNNNNNNNNNNNNNNNNNNNNNNNNNNNNNNNNNNNNNNNNNNNNNNNNNNNNNNNNN

46021 NNNNNNNNNNNNNNNNNNNNNNNNNNNNNNNNNNNNNNNNNNNNNNNNNNNNNNNNNNNN
46021 NNNNNNNNNNNNNNNNNNNNNNNNNNNNNNNNNNNNNNNNNNNNNNNNNNNNNNNNNNNN

46081 NNNNNNNNNNNNNNNNNNNNNNNNNNNNNNNNNNNNNNNNNNNNNNNNNNNNNNNNNNNN
46081 NNNNNNNNNNNNNNNNNNNNNNNNNNNNNNNNNNNNNNNNNNNNNNNNNNNNNNNNNNNN

46141 NNNNNNNNNNNNNNNNNNNNNNNNNNNNNNNNNNNNNNNNNNNNNNNNNNNNNNNNNNNN
46141 NNNNNNNNNNNNNNNNNNNNNNNNNNNNNNNNNNNNNNNNNNNNNNNNNNNNNNNNNNNN

46201 NNNNNNNNNNNNNNNNNNNNNNNNNNNNNNNNNNNNNNNNNNNNNNNNNNNNNNNNNNNN
46201 NNNNNNNNNNNNNNNNNNNNNNNNNNNNNNNNNNNNNNNNNNNNNNNNNNNNNNNNNNNN

46261 NNNNNNNNNNNNNNNNNNNNNNNNNNNNNNNNNNNNNNNNNNNNNNNNNNNNNNNNNNNN
46261 NNNNNNNNNNNNNNNNNNNNNNNNNNNNNNNNNNNNNNNNNNNNNNNNNNNNNNNNNNNN

46321 NNNNNNNNNNNNNNNNNNNNNNNNNNNNNNNNNNNNNNNNNNNNNNNNNNNNNNNNNNNN
46321 NNNNNNNNNNNNNNNNNNNNNNNNNNNNNNNNNNNNNNNNNNNNNNNNNNNNNNNNNNNN

46381 NNNNNNNNNNNNNNNNNNNNNNNNNNNNNNNNNNNNNNNNNNNNNNNNNNNNNNNNNNNN
46381 NNNNNNNNNNNNNNNNNNNNNNNNNNNNNNNNNNNNNNNNNNNNNNNNNNNNNNNNNNNN

46441 NNNNNNNNNNNNNNNNNNNNNNNNNNNNNNNNNNNNNNNNNNNNNNNNNNNNNNNNNNNN
46441 NNNNNNNNNNNNNNNNNNNNNNNNNNNNNNNNNNNNNNNNNNNNNNNNNNNNNNNNNNNN

46501 NNNNNNNNNNNNNNNNNNNNNNNNNNNNNNNNNNNNNNNNNNNNNNNNNNNNNNNNNNNN
46501 NNNNNNNNNNNNNNNNNNNNNNNNNNNNNNNNNNNNNNNNNNNNNNNNNNNNNNNNNNNN

46561 NNNNNNNNNNNNNNNNNNNNNNNNNNNNNNNNNNNNNNNNNNNNNNNNNNNNNNNNNNNN
46561 NNNNNNNNNNNNNNNNNNNNNNNNNNNNNNNNNNNNNNNNNNNNNNNNNNNNNNNNNNNN

46621 NNNNNNNNNNNNNNNNNNNNNNNNNNNNNNNNNNNNNNNNNNNNNNNNNNNNNNNNNNNN
46621 NNNNNNNNNNNNNNNNNNNNNNNNNNNNNNNNNNNNNNNNNNNNNNNNNNNNNNNNNNNN

46681 NNNNNNNNNNNNNNNNNNNNNNNNNNNNNNNNNNNNNNNNNNNNNNNNNNNNNNNNNNNN
46681 NNNNNNNNNNNNNNNNNNNNNNNNNNNNNNNNNNNNNNNNNNNNNNNNNNNNNNNNNNNN
```

FIG. 5 (cont'd)

```
46741  NNNNNNNNNNNNNNNNNNNNNNNNNNNNNNNNNNNNNNNNNNNNNNNNNNNNNNNNNNNN
46741  NNNNNNNNNNNNNNNNNNNNNNNNNNNNNNNNNNNNNNNNNNNNNNNNNNNNNNNNNNNN

46801  NNNNNNNNNNNNNNNNNNNNNNNNNNNNNNNNNNNNNNNNNNNNNNNNNNNNNNNNNNNN
46801  NNNNNNNNNNNNNNNNNNNNNNNNNNNNNNNNNNNNNNNNNNNNNNNNNNNNNNNNNNNN

46861  NNNNNNNNNNNNNNNNNNNNNNNNNNNNNNNNNNNNNNNNNNNNNNNNNNNNNNNNNNNN
46861  NNNNNNNNNNNNNNNNNNNNNNNNNNNNNNNNNNNNNNNNNNNNNNNNNNNNNNNNNNNN

46921  NNNNNNNNNNNNNNNNNNNNNNNNNNNNNNNNNNNNNNNNNNNNNNNNNNNNNNNNNNNN
46921  NNNNNNNNNNNNNNNNNNNNNNNNNNNNNNNNNNNNNNNNNNNNNNNNNNNNNNNNNNNN

46981  NNNNNNNNNNNNNNNNNNNNNNNNNNNNNNNNNNNNNNNNNNNNNNNNNNNNNNNNNNNN
46981  NNNNNNNNNNNNNNNNNNNNNNNNNNNNNNNNNNNNNNNNNNNNNNNNNNNNNNNNNNNN

47041  NNNNNNNNNNNNNNNNNNNNNNNNNNNNNNNNNNNNNNNNNNNNNNNNNNNNNNNNNNNN
47041  NNNNNNNNNNNNNNNNNNNNNNNNNNNNNNNNNNNNNNNNNNNNNNNNNNNNNNNNNNNN

47101  NNNNNNNNNNNNNNNNNNNNNNNNNNNNNNNNNNNNNNNNNNNNNNNNNNNNNNNNNNNN
47101  NNNNNNNNNNNNNNNNNNNNNNNNNNNNNNNNNNNNNNNNNNNNNNNNNNNNNNNNNNNN

47161  NNNNNNNNNNNNNNNNNNNNNNNNNNNNNNNNNNNNNNNNNNNNNNNNNNNNNNNNNNNN
47161  NNNNNNNNNNNNNNNNNNNNNNNNNNNNNNNNNNNNNNNNNNNNNNNNNNNNNNNNNNNN

47221  NNNNNNNNNNNNNNNNNNNNNNNNNNNNNNNNNNNNNNNNNNNNNNNNNNNNNNNNNNNN
47221  NNNNNNNNNNNNNNNNNNNNNNNNNNNNNNNNNNNNNNNNNNNNNNNNNNNNNNNNNNNN

47281  NNNNNNNNNNNNNNNNNNNNNNNNNNNNNNNNNNNNNNNNNNNNNNNNNNNNNNNNNNNN
47281  NNNNNNNNNNNNNNNNNNNNNNNNNNNNNNNNNNNNNNNNNNNNNNNNNNNNNNNNNNNN

47341  NNNNNNNNNNNNNNNNNNNNNNNNNNNNNNNNNNNNNNNNNNNNNNNNNNNNNNNNNNNN
47341  NNNNNNNNNNNNNNNNNNNNNNNNNNNNNNNNNNNNNNNNNNNNNNNNNNNNNNNNNNNN

47401  NNNNNNNNNNNNNNNNNNNNNNNNNNNNNNNNNNNNNNNNNNNNNNNNNNNNNNNNNNNN
47401  NNNNNNNNNNNNNNNNNNNNNNNNNNNNNNNNNNNNNNNNNNNNNNNNNNNNNNNNNNNN

47461  NNNNNNNNNNNNNNNNNNNNNNNNNNNNNNNNNNNNNNNNNNNNNNNNNNNNNNNNNNNN
47461  NNNNNNNNNNNNNNNNNNNNNNNNNNNNNNNNNNNNNNNNNNNNNNNNNNNNNNNNNNNN

47521  NNNNNNNNNNNNNNNNNNNNNNNNNNNNNNNNNNNNNNNNNNNNNNNNNNNNNNNNNNNN
47521  NNNNNNNNNNNNNNNNNNNNNNNNNNNNNNNNNNNNNNNNNNNNNNNNNNNNNNNNNNNN

47581  NNNNNNNNNNNNNNNNNNNNNNNNNNNNNNNNNNNNNNNNNNNNNNNNNNNNNNNNNNNN
47581  NNNNNNNNNNNNNNNNNNNNNNNNNNNNNNNNNNNNNNNNNNNNNNNNNNNNNNNNNNNN

47641  NNNNNNNNNNNNNNNNNNNNNNNNNNNNNNNNNNNNNNNNNNNNNNNNNNNNNNNNNNNN
47641  NNNNNNNNNNNNNNNNNNNNNNNNNNNNNNNNNNNNNNNNNNNNNNNNNNNNNNNNNNNN

47701  NNNNNNNNNNNNNNNNNNNNNNNNNNNNNNNNNNNNNNNNNNNNNNNNNNNNNNNNNNNN
47701  NNNNNNNNNNNNNNNNNNNNNNNNNNNNNNNNNNNNNNNNNNNNNNNNNNNNNNNNNNNN

47761  NNNNNNNNNNNNNNNNNNNNNNNNNNNNNNNNNNNNNNNNNNNNNNNNNNNNNNNNNNNN
47761  NNNNNNNNNNNNNNNNNNNNNNNNNNNNNNNNNNNNNNNNNNNNNNNNNNNNNNNNNNNN

47821  NNNNNNNNNNNNNNNNNNNNNNNNNNNNNNNNNNNNNNNNNNNNNNNNNNNNNNNNNNNN
47821  NNNNNNNNNNNNNNNNNNNNNNNNNNNNNNNNNNNNNNNNNNNNNNNNNNNNNNNNNNNN

47881  NNNNNNNNNNNNNNNNNNNNNNNNNNNNNNNNNNNNNNNNNNNNNNNNNNNNNNNNNNNN
47881  NNNNNNNNNNNNNNNNNNNNNNNNNNNNNNNNNNNNNNNNNNNNNNNNNNNNNNNNNNNN

47941  NNNNNNNNNNNNNNNNNNNNNNNNNNNNNNNNNNNNNNNNNNNNNNNNNNNNNNNNNNNN
47941  NNNNNNNNNNNNNNNNNNNNNNNNNNNNNNNNNNNNNNNNNNNNNNNNNNNNNNNNNNNN

48001  NNNNNNNNNNNNNNNNNNNNNNNNNNNNNNNNNNNNNNNNNNNNNNNNNNNNNNNNNNNN
48001  NNNNNNNNNNNNNNNNNNNNNNNNNNNNNNNNNNNNNNNNNNNNNNNNNNNNNNNNNNNN

48061  NNNNNNNNNNNNNNNNNNNNNNNNNNNNNNNNNNNNNNNNNNNNNNNNNNNNNNNNNNNN
48061  NNNNNNNNNNNNNNNNNNNNNNNNNNNNNNNNNNNNNNNNNNNNNNNNNNNNNNNNNNNN
```

FIG. 5 (cont'd)

```
48121  NNNNNNNNNNNNNNNNNNNNNNNNNNNNNNNNNNNNNNNNNNNNNNNNNNNNNNNNNNNN
48121  NNNNNNNNNNNNNNNNNNNNNNNNNNNNNNNNNNNNNNNNNNNNNNNNNNNNNNNNNNNN

48181  NNNNNNNNNNNNNNNNNNNNNNNNNNNNNNNNNNNNNNNNNNNNNNNNNNNNNNNNNNNN
48181  NNNNNNNNNNNNNNNNNNNNNNNNNNNNNNNNNNNNNNNNNNNNNNNNNNNNNNNNNNNN

48241  NNNNNNNNNNNNNNNNNNNNNNNNNNNNNNNNNNNNNNNNNNNNNNNNNNNNNNNNNNNN
48241  NNNNNNNNNNNNNNNNNNNNNNNNNNNNNNNNNNNNNNNNNNNNNNNNNNNNNNNNNNNN

48301  NNNNNNNNNNNNNNNNNNNNNNNNNNNNNNNNNNNNNNNNNNNNNNNNNNNNNNNNNNNN
48301  NNNNNNNNNNNNNNNNNNNNNNNNNNNNNNNNNNNNNNNNNNNNNNNNNNNNNNNNNNNN

48361  NNNNNNNNNNNNNNNNNNNNNNNNNNNNNNNNNNNNNNNNNNNNNNNNNNNNNNNNNNNN
48361  NNNNNNNNNNNNNNNNNNNNNNNNNNNNNNNNNNNNNNNNNNNNNNNNNNNNNNNNNNNN

48421  NNNNNNNNNNNNNNNNNNNNNNNNNNNNNNNNNNNNNNNNNNNNNNNNNNNNNNNNNNNN
48421  NNNNNNNNNNNNNNNNNNNNNNNNNNNNNNNNNNNNNNNNNNNNNNNNNNNNNNNNNNNN

48481  NNNNNNNNNNNNNNNNNNNNNNNNNNNNNNNNNNNNNNNNNNNNNNNNNNNNNNNNNNNN
48481  NNNNNNNNNNNNNNNNNNNNNNNNNNNNNNNNNNNNNNNNNNNNNNNNNNNNNNNNNNNN

48541  NNNNNNNNNNNNNNNNNNNNNNNNNNNNNNNNNNNNNNNNNNNNNNNNNNNNNNNNNNNN
48541  NNNNNNNNNNNNNNNNNNNNNNNNNNNNNNNNNNNNNNNNNNNNNNNNNNNNNNNNNNNN

48601  NNNNNNNNNNNNNNNNNNNNNNNNNNNNNNNNNNNNNNNNNNNNNNNNNNNNNNNNNNNN
48601  NNNNNNNNNNNNNNNNNNNNNNNNNNNNNNNNNNNNNNNNNNNNNNNNNNNNNNNNNNNN

48661  NNNNNNNNNNNNNNNNNNNNNNNNNNNNNNNNNNNNNNNNNNNNNNNNNNNNNNNNNNNN
48661  NNNNNNNNNNNNNNNNNNNNNNNNNNNNNNNNNNNNNNNNNNNNNNNNNNNNNNNNNNNN

48721  NNNNNNNNNNNNNNNNNNNNNNNNNNNNNNNNNNNNNNNNNNNNNNNNNNNNNNNNNNNN
48721  NNNNNNNNNNNNNNNNNNNNNNNNNNNNNNNNNNNNNNNNNNNNNNNNNNNNNNNNNNNN

48781  NNNNNNNNNNNNNNNNNNNNNNNNNNNNNNNNNNNNNNNNNNNNNNNNNNNNNNNNNNNN
48781  NNNNNNNNNNNNNNNNNNNNNNNNNNNNNNNNNNNNNNNNNNNNNNNNNNNNNNNNNNNN

48841  NNNNNNNNNNNNNNNNNNNNNNNNNNNNNNNNNNNNNNNNNNNNNNNNNNNNNNNNNNNN
48841  NNNNNNNNNNNNNNNNNNNNNNNNNNNNNNNNNNNNNNNNNNNNNNNNNNNNNNNNNNNN

48901  NNNNNNNNNNNNNNNNNNNNNNNNNNNNNNNNNNNNNNNNNNNNNNNNNNNNNNNNNNNN
48901  NNNNNNNNNNNNNNNNNNNNNNNNNNNNNNNNNNNNNNNNNNNNNNNNNNNNNNNNNNNN

48961  NNNNNNNNNNNNNNNNNNNNNNNNNNNNNNNNNNNNNNNNNNNNNNNNNNNNNNNNNNNN
48961  NNNNNNNNNNNNNNNNNNNNNNNNNNNNNNNNNNNNNNNNNNNNNNNNNNNNNNNNNNNN

49021  NNNNNNNNNNNNNNNNNNNNNNNNNNNNNNNNNNNNNNNNNNNNNNNNNNNNNNNNNNNN
49021  NNNNNNNNNNNNNNNNNNNNNNNNNNNNNNNNNNNNNNNNNNNNNNNNNNNNNNNNNNNN

49081  NNNNNNNNNNNNNNNNNNNNNNNNNNNNNNNNNNNNNNNNNNNNNNNNNNNNNNNNNNNN
49081  NNNNNNNNNNNNNNNNNNNNNNNNNNNNNNNNNNNNNNNNNNNNNNNNNNNNNNNNNNNN

49141  NNNNNNNNNNNNNNNNNNNNNNNNNNNNNNNNNNNNNNNNNNNNNNNNNNNNNNNNNNNN
49141  NNNNNNNNNNNNNNNNNNNNNNNNNNNNNNNNNNNNNNNNNNNNNNNNNNNNNNNNNNNN

49201  NNNNNNNNNNNNNNNNNNNNNNNNNNNNNNNNNNNNNNNNNNNNNNNNNNNNNNNNNNNN
49201  NNNNNNNNNNNNNNNNNNNNNNNNNNNNNNNNNNNNNNNNNNNNNNNNNNNNNNNNNNNN

49261  NNNNNNNNNNNNNNNNNNNNNNNNNNNNNNNNNNNNNNNNNNNNNNNNNNNNNNNNNNNN
49261  NNNNNNNNNNNNNNNNNNNNNNNNNNNNNNNNNNNNNNNNNNNNNNNNNNNNNNNNNNNN

49321  NNNNNNNNNNNNNNNNNNNNNNNNNNNNNNNNNNNNNNNNNNNNNNNNNNNNNNNNNNNN
49321  NNNNNNNNNNNNNNNNNNNNNNNNNNNNNNNNNNNNNNNNNNNNNNNNNNNNNNNNNNNN

49381  NNNNNNNNNNNNNNNNNNNNNNNNNNNNNNNNNNNNNNNNNNNNNNNNNNNNNNNNNNNN
49381  NNNNNNNNNNNNNNNNNNNNNNNNNNNNNNNNNNNNNNNNNNNNNNNNNNNNNNNNNNNN

49441  NNNNNNNNNNNNNNNNNNNNNNNNNNNNNNNNNNNNNNNNNNNNNNNNNNNNNNNNNNNN
49441  NNNNNNNNNNNNNNNNNNNNNNNNNNNNNNNNNNNNNNNNNNNNNNNNNNNNNNNNNNNN
```

FIG. 5 (cont'd)

```
49501  NNNNNNNNNNNNNNNNNNNNNNNNNNNNNNNNNNNNNNNNNNNNNNNNNNNNNNNNNNNN
49501  NNNNNNNNNNNNNNNNNNNNNNNNNNNNNNNNNNNNNNNNNNNNNNNNNNNNNNNNNNNN

49561  NNNNNNNNNNNNNNNNNNNNNNNNNNNNNNNNNNNNNNNNNNNNNNNNNNNNNNNNNNNN
49561  NNNNNNNNNNNNNNNNNNNNNNNNNNNNNNNNNNNNNNNNNNNNNNNNNNNNNNNNNNNN

49621  NNNNNNNNNNNNNNNNNNNNNNNNNNNNNNNNNNNNNNNNNNNNNNNNNNNNNNNNNNNN
49621  NNNNNNNNNNNNNNNNNNNNNNNNNNNNNNNNNNNNNNNNNNNNNNNNNNNNNNNNNNNN

49681  NNNNNNNNNNNNNNNNNNNNNNNNNNNNNNNNNNNNNNNNNNNNNNNNNNNNNNNNNNNN
49681  NNNNNNNNNNNNNNNNNNNNNNNNNNNNNNNNNNNNNNNNNNNNNNNNNNNNNNNNNNNN

49741  NNNNNNNNNNNNNNNNNNNNNNNNNNNNNNNNNNNNNNNNNNNNNNNNNNNNNNNNNNNN
49741  NNNNNNNNNNNNNNNNNNNNNNNNNNNNNNNNNNNNNNNNNNNNNNNNNNNNNNNNNNNN

49801  NNNNNNNNNNNNNNNNNNNNNNNNNNNNNNNNNNNNNNNNNNNNNNNNNNNNNNNNNNNN
49801  NNNNNNNNNNNNNNNNNNNNNNNNNNNNNNNNNNNNNNNNNNNNNNNNNNNNNNNNNNNN

49861  NNNNNNNNNNNNNNNNNNNNNNNNNNNNNNNNNNNNNNNNNNNNNNNNNNNNNNNNNNNN
49861  NNNNNNNNNNNNNNNNNNNNNNNNNNNNNNNNNNNNNNNNNNNNNNNNNNNNNNNNNNNN

49921  NNNNNNNNNNNNNNNNNNNNNNNNNNNNNNNNNNNNNNNNNNNNNNNNNNNNNNNNNNNN
49921  NNNNNNNNNNNNNNNNNNNNNNNNNNNNNNNNNNNNNNNNNNNNNNNNNNNNNNNNNNNN

49981  NNNNNNNNNNNNNNNNNNNNNNNNNNNNNNNNNNNNNNNNNNNNNNNNNNNNNNNNNNNN
49981  NNNNNNNNNNNNNNNNNNNNNNNNNNNNNNNNNNNNNNNNNNNNNNNNNNNNNNNNNNNN

50041  NNNNNNNNNNNNNNNNNNNNNNNNNNNNNNNNNNNNNNNNNNNNNNNNNNNNNNNNNNNN
50041  NNNNNNNNNNNNNNNNNNNNNNNNNNNNNNNNNNNNNNNNNNNNNNNNNNNNNNNNNNNN

50101  NNNNNNNNNNNNNNNNNNNNNNNNNNNNNNNNNNNNNNNNNNNNNNNNNNNNNNNNNNNN
50101  NNNNNNNNNNNNNNNNNNNNNNNNNNNNNNNNNNNNNNNNNNNNNNNNNNNNNNNNNNNN

50161  NNNNNNNNNNNNNNNNNNNNNNNNNNNNNNNNNNNNNNNNNNNNNNNNNNNNNNNNNNNN
50161  NNNNNNNNNNNNNNNNNNNNNNNNNNNNNNNNNNNNNNNNNNNNNNNNNNNNNNNNNNNN

50221  NNNNNNNNNNNNNNNNNNNNNNNNNNNNNNNNNNNNNNNNNNNNNNNNNNNNNNNNNNNN
50221  NNNNNNNNNNNNNNNNNNNNNNNNNNNNNNNNNNNNNNNNNNNNNNNNNNNNNNNNNNNN

50281  NNNNNNNNNNNNNNNNNNNNNNNNNNNNNNNNNNNNNNNNNNNNNNNNNNNNNNNNNNNN
50281  NNNNNNNNNNNNNNNNNNNNNNNNNNNNNNNNNNNNNNNNNNNNNNNNNNNNNNNNNNNN

50341  NNNNNNNNNNNNNNNNNNNNNNNNNNNNNNNNNNNNNNNNNNNNNNNNNNNNNNNNNNNN
50341  NNNNNNNNNNNNNNNNNNNNNNNNNNNNNNNNNNNNNNNNNNNNNNNNNNNNNNNNNNNN

50401  NNNNNNNNNNNNNNNNNNNNNNNNNNNNNNNNNNNNNNNNNNNNNNNNNNNNNNNNNNNN
50401  NNNNNNNNNNNNNNNNNNNNNNNNNNNNNNNNNNNNNNNNNNNNNNNNNNNNNNNNNNNN

50461  NNNNNNNNNNNNNNNNNNNNNNNNNNNNNNNNNNNNNNNNNNNNNNNNNNNNNNNNNNNN
50461  NNNNNNNNNNNNNNNNNNNNNNNNNNNNNNNNNNNNNNNNNNNNNNNNNNNNNNNNNNNN

50521  NNNNNNNNNNNNNNNNNNNNNNNNNNNNNNNNNNNNNNNNNNNNNNNNNNNNNNNNNNNN
50521  NNNNNNNNNNNNNNNNNNNNNNNNNNNNNNNNNNNNNNNNNNNNNNNNNNNNNNNNNNNN

50581  NNNNNNNNNNNNNNNNNNNNNNNNNNNNNNNNNNNNNNNNNNNNNNNNNNNNNNNNNNNN
50581  NNNNNNNNNNNNNNNNNNNNNNNNNNNNNNNNNNNNNNNNNNNNNNNNNNNNNNNNNNNN

50641  NNNNNNNNNNNNNNNNNNNNNNNNNNNNNNNNNNNNNNNNNNNNNNNNNNNNNNNNNNNN
50641  NNNNNNNNNNNNNNNNNNNNNNNNNNNNNNNNNNNNNNNNNNNNNNNNNNNNNNNNNNNN

50701  NNNNNNNNNNNNNNNNNNNNNNNNNNNNNNNNNNNNNNNNNNNNNNNNNNNNNNNNNNNN
50701  NNNNNNNNNNNNNNNNNNNNNNNNNNNNNNNNNNNNNNNNNNNNNNNNNNNNNNNNNNNN

50761  NNNNNNNNNNNNNNNNNNNNNNNNNNNNNNNNNNNNNNNNNNNNNNNNNNNNNNNNNNNN
50761  NNNNNNNNNNNNNNNNNNNNNNNNNNNNNNNNNNNNNNNNNNNNNNNNNNNNNNNNNNNN

50821  NNNNNNNNNNNNNNNNNNNNNNNNNNNNNNNNNNNNNNNNNNNNNNNNNNNNNNNNNNNN
50821  NNNNNNNNNNNNNNNNNNNNNNNNNNNNNNNNNNNNNNNNNNNNNNNNNNNNNNNNNNNN
```

FIG. 5 (cont'd)

50881 NNNNNNNNNNNNNNNNNNNNNNNNNNNNNNNNNNNNNNNNNNNNNNNNNNNNNNNNNNNN
50881 NNNNNNNNNNNNNNNNNNNNNNNNNNNNNNNNNNNNNNNNNNNNNNNNNNNNNNNNNNNN

50941 NNNNNNNNNNNNNNNNNNNNNNNNNNNNNNNNNNNNNNNNNNNNNNNNNNNNNNNNNNNN
50941 NNNNNNNNNNNNNNNNNNNNNNNNNNNNNNNNNNNNNNNNNNNNNNNNNNNNNNNNNNNN

51001 NNNNNNNNNNNNNNNNNNNNNNNNNNNNNNNNNNNNNNNNNNNNNNNNNNNNNNNNNNNN
51001 NNNNNNNNNNNNNNNNNNNNNNNNNNNNNNNNNNNNNNNNNNNNNNNNNNNNNNNNNNNN

51061 NNNNNNNNNNNNNNNNNNNNNNNNNNNNNNNNNNNNNNNNNNNNNNNNNNNNNNNNNNNN
51061 NNNNNNNNNNNNNNNNNNNNNNNNNNNNNNNNNNNNNNNNNNNNNNNNNNNNNNNNNNNN

51121 NNNNNNNNNNNNNNNNNNNNNNNNNNNNNNNNNNNNNNNNNNNNNNNNNNNNNNNNNNNN
51121 NNNNNNNNNNNNNNNNNNNNNNNNNNNNNNNNNNNNNNNNNNNNNNNNNNNNNNNNNNNN

51181 NNNNNNNNNNNNNNNNNNNNNNNNNNNNNNNNNNNNNNNNNNNNNNNNNNNNNNNNNNNN
51181 NNNNNNNNNNNNNNNNNNNNNNNNNNNNNNNNNNNNNNNNNNNNNNNNNNNNNNNNNNNN

51241 NNNNNNNNNNNNNNNNNNNNNNNNNNNNNNNNNNNNNNNNNNNNNNNNNNNNNNNNNNNN
51241 NNNNNNNNNNNNNNNNNNNNNNNNNNNNNNNNNNNNNNNNNNNNNNNNNNNNNNNNNNNN

51301 NNNNNNNNNNNNNNNNNNNNNNNNNNNNNNNNNNNNNNNNNNNNNNNNNNNNNNNNNNNN
51301 NNNNNNNNNNNNNNNNNNNNNNNNNNNNNNNNNNNNNNNNNNNNNNNNNNNNNNNNNNNN

51361 NNNNNNNNNNNNNNNNNNNNNNNNNNNNNNNNNNNNNNNNNNNNNNNNNNNNNNNNNNNN
51361 NNNNNNNNNNNNNNNNNNNNNNNNNNNNNNNNNNNNNNNNNNNNNNNNNNNNNNNNNNNN

51421 NNNNNNNNNNNNNNNNNNNNNNNNNNNNNNNNNNNNNNNNNNNNNNNNNNNNNNNNNNNN
51421 NNNNNNNNNNNNNNNNNNNNNNNNNNNNNNNNNNNNNNNNNNNNNNNNNNNNNNNNNNNN

51481 NNNNNNNNNNNNNNNNNNNNNNNNNNNNNNNNNNNNNNNNNNNNNNNNNNNNNNNNNNNN
51481 NNNNNNNNNNNNNNNNNNNNNNNNNNNNNNNNNNNNNNNNNNNNNNNNNNNNNNNNNNNN

51541 NNNNNNNNNNNNNNNNNNNNNNNNNNNNNNNNNNNNNNNNNNNNNNNNNNNNNNNNNNNN
51541 NNNNNNNNNNNNNNNNNNNNNNNNNNNNNNNNNNNNNNNNNNNNNNNNNNNNNNNNNNNN

51601 NNNNNNNNNNNNNNNNNNNNNNNNNNNNNNNNNNNNNNNNNNNNNNNNNNNNNNNNNNNN
51601 NNNNNNNNNNNNNNNNNNNNNNNNNNNNNNNNNNNNNNNNNNNNNNNNNNNNNNNNNNNN

51661 NNNNNNNNNNNNNNNNNNNNNNNNNNNNNNNNNNNNNNNNNNNNNNNNNNNNNNNNNNNN
51661 NNNNNNNNNNNNNNNNNNNNNNNNNNNNNNNNNNNNNNNNNNNNNNNNNNNNNNNNNNNN

51721 NNNNNNNNNNNNNNNNNNNNNNNNNNNNNNNNNNNNNNNNNNNNNNNNNNNNNNNNNNNN
51721 NNNNNNNNNNNNNNNNNNNNNNNNNNNNNNNNNNNNNNNNNNNNNNNNNNNNNNNNNNNN

51781 NNNNNNNNNNNNNNNNNNNNNNNNNNNNNNNNNNNNNNNNNNNNNNNNNNNNNNNNNNNN
51781 NNNNNNNNNNNNNNNNNNNNNNNNNNNNNNNNNNNNNNNNNNNNNNNNNNNNNNNNNNNN

51841 NNNNNNNNNNNNNNNNNNNNNNNNNNNNNNNNNNNNNNNNNNNNNNNNNNNNNNNNNNNN
51841 NNNNNNNNNNNNNNNNNNNNNNNNNNNNNNNNNNNNNNNNNNNNNNNNNNNNNNNNNNNN

51901 NNNNNNNNNNNNNNNNNNNNNNNNNNNNNNNNNNNNNNNNNNNNNNNNNNNNNNNNNNNN
51901 NNNNNNNNNNNNNNNNNNNNNNNNNNNNNNNNNNNNNNNNNNNNNNNNNNNNNNNNNNNN

51961 NNNNNNNNNNNNNNNNNNNNNNNNNNNNNNNNNNNNNNNNNNNNNNNNNNNNNNNNNNNN
51961 NNNNNNNNNNNNNNNNNNNNNNNNNNNNNNNNNNNNNNNNNNNNNNNNNNNNNNNNNNNN

52021 NNNNNNNNNNNNNNNNNNNNNNNNNNNNNNNNNNNNNNNNNNNNNNNNNNNNNNNNNNNN
52021 NNNNNNNNNNNNNNNNNNNNNNNNNNNNNNNNNNNNNNNNNNNNNNNNNNNNNNNNNNNN

52081 NNNNNNNNNNNNNNNNNNNNNNNNNNNNNNNNNNNNNNNNNNNNNNNNNNNNNNNNNNNN
52081 NNNNNNNNNNNNNNNNNNNNNNNNNNNNNNNNNNNNNNNNNNNNNNNNNNNNNNNNNNNN

52141 NNNNNNNNNNNNNNNNNNNNNNNNNNNNNNNNNNNNNNNNNNNNNNNNNNNNNNNNNNNN
52141 NNNNNNNNNNNNNNNNNNNNNNNNNNNNNNNNNNNNNNNNNNNNNNNNNNNNNNNNNNNN

52201 NNNNNNNNNNNNNNNNNNNNNNNNNNNNNNNNNNNNNNNNNNNNNNNNNNNNNNNNNNNN
52201 NNNNNNNNNNNNNNNNNNNNNNNNNNNNNNNNNNNNNNNNNNNNNNNNNNNNNNNNNNNN

FIG. 5 (cont'd)

```
52261  NNNNNNNNNNNNNNNNNNNNNNNNNNNNNNNNNNNNNNNNNNNNNNNNNNNNNNNNNNNN
52261  NNNNNNNNNNNNNNNNNNNNNNNNNNNNNNNNNNNNNNNNNNNNNNNNNNNNNNNNNNNN

52321  NNNNNNNNNNNNNNNNNNNNNNNNNNNNNNNNNNNNNNNNNNNNNNNNNNNNNNNNNNNN
52321  NNNNNNNNNNNNNNNNNNNNNNNNNNNNNNNNNNNNNNNNNNNNNNNNNNNNNNNNNNNN

52381  NNNNNNNNNNNNNNNNNNNNNNNNNNNNNNNNNNNNNNNNNNNNNNNNNNNNNNNNNNNN
52381  NNNNNNNNNNNNNNNNNNNNNNNNNNNNNNNNNNNNNNNNNNNNNNNNNNNNNNNNNNNN

52441  NNNNNNNNNNNNNNNNNNNNNNNNNNNNNNNNNNNNNNNNNNNNNNNNNNNNNNNNNNNN
52441  NNNNNNNNNNNNNNNNNNNNNNNNNNNNNNNNNNNNNNNNNNNNNNNNNNNNNNNNNNNN

52501  NNNNNNNNNNNNNNNNNNNNNNNNNNNNNNNNNNNNNNNNNNNNNNNNNNNNNNNNNNNN
52501  NNNNNNNNNNNNNNNNNNNNNNNNNNNNNNNNNNNNNNNNNNNNNNNNNNNNNNNNNNNN

52561  NNNNNNNNNNNNNNNNNNNNNNNNNNNNNNNNNNNNNNNNNNNNNNNNNNNNNNNNNNNN
52561  NNNNNNNNNNNNNNNNNNNNNNNNNNNNNNNNNNNNNNNNNNNNNNNNNNNNNNNNNNNN

52621  NNNNNNNNNNNNNNNNNNNNNNNNNNNNNNNNNNNNNNNNNNNNNNNNNNNNNNNNNNNN
52621  NNNNNNNNNNNNNNNNNNNNNNNNNNNNNNNNNNNNNNNNNNNNNNNNNNNNNNNNNNNN

52681  NNNNNNNNNNNNNNNNNNNNNNNNNNNNNNNNNNNNNNNNNNNNNNNNNNNNNNNNNNNN
52681  NNNNNNNNNNNNNNNNNNNNNNNNNNNNNNNNNNNNNNNNNNNNNNNNNNNNNNNNNNNN

52741  NNNNNNNNNNNNNNNNNNNNNNNNNNNNNNNNNNNNNNNNNNNNNNNNNNNNNNNNNNNN
52741  NNNNNNNNNNNNNNNNNNNNNNNNNNNNNNNNNNNNNNNNNNNNNNNNNNNNNNNNNNNN

52801  NNNNNNNNNNNNNNNNNNNNNNNNNNNNNNNNNNNNNNNNNNNNNNNNNNNNNNNNNNNN
52801  NNNNNNNNNNNNNNNNNNNNNNNNNNNNNNNNNNNNNNNNNNNNNNNNNNNNNNNNNNNN

52861  NNNNNNNNNNNNNNNNNNNNNNNNNNNNNNNNNNNNNNNNNNNNNNNNNNNNNNNNNNNN
52861  NNNNNNNNNNNNNNNNNNNNNNNNNNNNNNNNNNNNNNNNNNNNNNNNNNNNNNNNNNNN

52921  NNNNNNNNNNNNNNNNNNNNNNNNNNNNNNNNNNNNNNNNNNNNNNNNNNNNNNNNNNNN
52921  NNNNNNNNNNNNNNNNNNNNNNNNNNNNNNNNNNNNNNNNNNNNNNNNNNNNNNNNNNNN

52981  NNNNNNNNNNNNNNNNNNNNNNNNNNNNNNNNNNNNNNNNNNNNNNNNNNNNNNNNNNNN
52981  NNNNNNNNNNNNNNNNNNNNNNNNNNNNNNNNNNNNNNNNNNNNNNNNNNNNNNNNNNNN

53041  NNNNNNNNNNNNNNNNNNNNNNNNNNNNNNNNNNNNNNNNNNNNNNNNNNNNNNNNNNNN
53041  NNNNNNNNNNNNNNNNNNNNNNNNNNNNNNNNNNNNNNNNNNNNNNNNNNNNNNNNNNNN

53101  NNNNNNNNNNNNNNNNNNNNNNNNNNNNNNNNNNNNNNNNNNNNNNNNNNNNNNNNNNNN
53101  NNNNNNNNNNNNNNNNNNNNNNNNNNNNNNNNNNNNNNNNNNNNNNNNNNNNNNNNNNNN

53161  NNNNNNNNNNNNNNNNNNNNNNNNNNNNNNNNNNNNNNNNNNNNNNNNNNNNNNNNNNNN
53161  NNNNNNNNNNNNNNNNNNNNNNNNNNNNNNNNNNNNNNNNNNNNNNNNNNNNNNNNNNNN

53221  NNNNNNNNNNNNNNNNNNNNNNNNNNNNNNNNNNNNNNNNNNNNNNNNNNNNNNNNNNNN
53221  NNNNNNNNNNNNNNNNNNNNNNNNNNNNNNNNNNNNNNNNNNNNNNNNNNNNNNNNNNNN

53281  NNNNNNNNNNNNNNNNNNNNNNNNNNNNNNNNNNNNNNNNNNNNNNNNNNNNNNNNNNNN
53281  NNNNNNNNNNNNNNNNNNNNNNNNNNNNNNNNNNNNNNNNNNNNNNNNNNNNNNNNNNNN

53341  NNNNNNNNNNNNNNNNNNNNNNNNNNNNNNNNNNNNNNNNNNNNNNNNNNNNNNNNNNNN
53341  NNNNNNNNNNNNNNNNNNNNNNNNNNNNNNNNNNNNNNNNNNNNNNNNNNNNNNNNNNNN

53401  NNNNNNNNNNNNNNNNNNNNNNNNNNNNNNNNNNNNNNNNNNNNNNNNNNNNNNNNNNNN
53401  NNNNNNNNNNNNNNNNNNNNNNNNNNNNNNNNNNNNNNNNNNNNNNNNNNNNNNNNNNNN

53461  NNNNNNNNNNNNNNNNNNNNNNNNNNNNNNNNNNNNNNNNNNNNNNNNNNNNNNNNNNNN
53461  NNNNNNNNNNNNNNNNNNNNNNNNNNNNNNNNNNNNNNNNNNNNNNNNNNNNNNNNNNNN

53521  NNNNNNNNNNNNNNNNNNNNNNNNNNNNNNNNNNNNNNNNNNNNNNNNNNNNNNNNNNNN
53521  NNNNNNNNNNNNNNNNNNNNNNNNNNNNNNNNNNNNNNNNNNNNNNNNNNNNNNNNNNNN

53581  NNNNNNNNNNNNNNNNNNNNNNNNNNNNNNNNNNNNNNNNNNNNNNNNNNNNNNNNNNNN
53581  NNNNNNNNNNNNNNNNNNNNNNNNNNNNNNNNNNNNNNNNNNNNNNNNNNNNNNNNNNNN
```

FIG. 5 (cont'd)

53641 NNNNNNNNNNNNNNNNNNNNNNNNNNNNNNNNNNNNNNNNNNNNNNNNNNNNNNNNNNNN
53641 NNNNNNNNNNNNNNNNNNNNNNNNNNNNNNNNNNNNNNNNNNNNNNNNNNNNNNNNNNNN

53701 NNNNNNNNNNNNNNNNNNNNNNNNNNNNNNNNNNNNNNNNNNNNNNNNNNNNNNNNNNNN
53701 NNNNNNNNNNNNNNNNNNNNNNNNNNNNNNNNNNNNNNNNNNNNNNNNNNNNNNNNNNNN

53761 NNNNNNNNNNNNNNNNNNNNNNNNNNNNNNNNNNNNNNNNNNNNNNNNNNNNNNNNNNNN
53761 NNNNNNNNNNNNNNNNNNNNNNNNNNNNNNNNNNNNNNNNNNNNNNNNNNNNNNNNNNNN

53821 NNNNNNNNNNNNNNNNNNNNNNNNNNNNNNNNNNNNNNNNNNNNNNNNNNNNNNNNNNNN
53821 NNNNNNNNNNNNNNNNNNNNNNNNNNNNNNNNNNNNNNNNNNNNNNNNNNNNNNNNNNNN

53881 NNNNNNNNNNNNNNNNNNNNNNNNNNNNNNNNNNNNNNNNNNNNNNNNNNNNNNNNNNNN
53881 NNNNNNNNNNNNNNNNNNNNNNNNNNNNNNNNNNNNNNNNNNNNNNNNNNNNNNNNNNNN

53941 NNNNNNNNNNNNNNNNNNNNNNNNNNNNNNNNNNNNNNNNNNNNNNNNNNNNNNNNNNNN
53941 NNNNNNNNNNNNNNNNNNNNNNNNNNNNNNNNNNNNNNNNNNNNNNNNNNNNNNNNNNNN

54001 NNNNNNNNNNNNNNNNNNNNNNNNNNNNNNNNNNNNNNNNNNNNNNNNNNNNNNNNNNNN
54001 NNNNNNNNNNNNNNNNNNNNNNNNNNNNNNNNNNNNNNNNNNNNNNNNNNNNNNNNNNNN

54061 NNNNNNNNNNNNNNNNNNNNNNNNNNNNNNNNNNNNNNNNNNNNNNNNNNNNNNNNNNNN
54061 NNNNNNNNNNNNNNNNNNNNNNNNNNNNNNNNNNNNNNNNNNNNNNNNNNNNNNNNNNNN

54121 NNNNNNNNNNNNNNNNNNNNNNNNNNNNNNNNNNNNNNNNNNNNNNNNNNNNNNNNNNNN
54121 NNNNNNNNNNNNNNNNNNNNNNNNNNNNNNNNNNNNNNNNNNNNNNNNNNNNNNNNNNNN

54181 NNNNNNNNNNNNNNNNNNNNNNNNNNNNNNNNNNNNNNNNNNNNNNNNNNNNNNNNNNNN
54181 NNNNNNNNNNNNNNNNNNNNNNNNNNNNNNNNNNNNNNNNNNNNNNNNNNNNNNNNNNNN

54241 NNNNNNNNNNNNNNNNNNNNNNNNNNNNNNNNNNNNNNNNNNNNNNNNNNNNNNNNNNNN
54241 NNNNNNNNNNNNNNNNNNNNNNNNNNNNNNNNNNNNNNNNNNNNNNNNNNNNNNNNNNNN

54301 NNNNNNNNNNNNNNNNNNNNNNNNNNNNNNNNNNNNNNNNNNNNNNNNNNNNNNNNNNNN
54301 NNNNNNNNNNNNNNNNNNNNNNNNNNNNNNNNNNNNNNNNNNNNNNNNNNNNNNNNNNNN

54361 NNNNNNNNNNNNNNNNNNNNNNNNNNNNNNNNNNNNNNNNNNNNNNNNNNNNNNNNNNNN
54361 NNNNNNNNNNNNNNNNNNNNNNNNNNNNNNNNNNNNNNNNNNNNNNNNNNNNNNNNNNNN

54421 NNNNNNNNNNNNNNNNNNNNNNNNNNNNNNNNNNNNNNNNNNNNNNNNNNNNNNNNNNNN
54421 NNNNNNNNNNNNNNNNNNNNNNNNNNNNNNNNNNNNNNNNNNNNNNNNNNNNNNNNNNNN

54481 NNNNNNNNNNNNNNNNNNNNNNNNNNNNNNNNNNNNNNNNNNNNNNNNNNNNNNNNNNNN
54481 NNNNNNNNNNNNNNNNNNNNNNNNNNNNNNNNNNNNNNNNNNNNNNNNNNNNNNNNNNNN

54541 NNNNNNNNNNNNNNNNNNNNNNNNNNNNNNNNNNNNNNNNNNNNNNNNNNNNNNNNNNNN
54541 NNNNNNNNNNNNNNNNNNNNNNNNNNNNNNNNNNNNNNNNNNNNNNNNNNNNNNNNNNNN

54601 NNNNNNNNNNNNNNNNNNNNNNNNNNNNNNNNNNNNNNNNNNNNNNNNNNNNNNNNNNNN
54601 NNNNNNNNNNNNNNNNNNNNNNNNNNNNNNNNNNNNNNNNNNNNNNNNNNNNNNNNNNNN

54661 NNNNNNNNNNNNNNNNNNNNNNNNNNNNNNNNNNNNNNNNNNNNNNNNNNNNNNNNNNNN
54661 NNNNNNNNNNNNNNNNNNNNNNNNNNNNNNNNNNNNNNNNNNNNNNNNNNNNNNNNNNNN

54721 NNNNNNNNNNNNNNNNNNNNNNNNNNNNNNNNNNNNNNNNNNNNNNNNNNNNNNNNNNNN
54721 NNNNNNNNNNNNNNNNNNNNNNNNNNNNNNNNNNNNNNNNNNNNNNNNNNNNNNNNNNNN

54781 NNNNNNNNNNNNNNNNNNNNNNNNNNNNNNNNNNNNNNNNNNNNNNNNNNNNNNNNNNNN
54781 NNNNNNNNNNNNNNNNNNNNNNNNNNNNNNNNNNNNNNNNNNNNNNNNNNNNNNNNNNNN

54841 NNNNNNNNNNNNNNNNNNNNNNNNNNNNNNNNNNNNNNNNNNNNNNNNNNNNNNNNNNNN
54841 NNNNNNNNNNNNNNNNNNNNNNNNNNNNNNNNNNNNNNNNNNNNNNNNNNNNNNNNNNNN

54901 NNNNNNNNNNNNNNNNNNNNNNNNNNNNNNNNNNNNNNNNNNNNNNNNNNNNNNNNNNNN
54901 NNNNNNNNNNNNNNNNNNNNNNNNNNNNNNNNNNNNNNNNNNNNNNNNNNNNNNNNNNNN

54961 NNNNNNNNNNNNNNNNNNNNNNNNNNNNNNNNNNNNNNNNNNNNNNNNNNNNNNNNNNNN
54961 NNNNNNNNNNNNNNNNNNNNNNNNNNNNNNNNNNNNNNNNNNNNNNNNNNNNNNNNNNNN

FIG. 5 (cont'd)

```
55021  NNNNNNNNNNNNNNNNNNNNNNNNNNNNNNNNNNNNNNNNNNNNNNNNNNNNNNNNNNNN
55021  NNNNNNNNNNNNNNNNNNNNNNNNNNNNNNNNNNNNNNNNNNNNNNNNNNNNNNNNNNNN

55081  NNNNNNNNNNNNNNNNNNNNNNNNNNNNNNNNNNNNNNNNNNNNNNNNNNNNNNNNNNNN
55081  NNNNNNNNNNNNNNNNNNNNNNNNNNNNNNNNNNNNNNNNNNNNNNNNNNNNNNNNNNNN

55141  NNNNNNNNNNNNNNNNNNNNNNNNNNNNNNNNNNNNNNNNNNNNNNNNNNNNNNNNNNNN
55141  NNNNNNNNNNNNNNNNNNNNNNNNNNNNNNNNNNNNNNNNNNNNNNNNNNNNNNNNNNNN

55201  NNNNNNNNNNNNNNNNNNNNNNNNNNNNNNNNNNNNNNNNNNNNNNNNNNNNNNNNNNNN
55201  NNNNNNNNNNNNNNNNNNNNNNNNNNNNNNNNNNNNNNNNNNNNNNNNNNNNNNNNNNNN

55261  NNNNNNNNNNNNNNNNNNNNNNNNNNNNNNNNNNNNNNNNNNNNNNNNNNNNNNNNNNNN
55261  NNNNNNNNNNNNNNNNNNNNNNNNNNNNNNNNNNNNNNNNNNNNNNNNNNNNNNNNNNNN

55321  NNNNNNNNNNNNNNNNNNNNNNNNNNNNNNNNNNNNNNNNNNNNNNNNNNNNNNNNNNNN
55321  NNNNNNNNNNNNNNNNNNNNNNNNNNNNNNNNNNNNNNNNNNNNNNNNNNNNNNNNNNNN

55381  NNNNNNNNNNNNNNNNNNNNNNNNNNNNNNNNNNNNNNNNNNNNNNNNNNNNNNNNNNNN
55381  NNNNNNNNNNNNNNNNNNNNNNNNNNNNNNNNNNNNNNNNNNNNNNNNNNNNNNNNNNNN

55441  NNNNNNNNNNNNNNNNNNNNNNNNNNNNNNNNNNNNNNNNNNNNNNNNNNNNNNNNNNNN
55441  NNNNNNNNNNNNNNNNNNNNNNNNNNNNNNNNNNNNNNNNNNNNNNNNNNNNNNNNNNNN

55501  NNNNNNNNNNNNNNNNNNNNNNNNNNNNNNNNNNNNNNNNNNNNNNNNNNNNNNNNNNNN
55501  NNNNNNNNNNNNNNNNNNNNNNNNNNNNNNNNNNNNNNNNNNNNNNNNNNNNNNNNNNNN

55561  NNNNNNNNNNNNNNNNNNNNNNNNNNNNNNNNNNNNNNNNNNNNNNNNNNNNNNNNNNNN
55561  NNNNNNNNNNNNNNNNNNNNNNNNNNNNNNNNNNNNNNNNNNNNNNNNNNNNNNNNNNNN

55621  NNNNNNNNNNNNNNNNNNNNNNNNNNNNNNNNNNNNNNNNNNNNNNNNNNNNNNNNNNNN
55621  NNNNNNNNNNNNNNNNNNNNNNNNNNNNNNNNNNNNNNNNNNNNNNNNNNNNNNNNNNNN

55681  NNNNNNNNNNNNNNNNNNNNNNNNNNNNNNNNNNNNNNNNNNNNNNNNNNNNNNNNNNNN
55681  NNNNNNNNNNNNNNNNNNNNNNNNNNNNNNNNNNNNNNNNNNNNNNNNNNNNNNNNNNNN

55741  NNNNNNNNNNNNNNNNNNNNNNNNNNNNNNNNNNNNNNNNNNNNNNNNNNNNNNNNNNNN
55741  NNNNNNNNNNNNNNNNNNNNNNNNNNNNNNNNNNNNNNNNNNNNNNNNNNNNNNNNNNNN

55801  NNNNNNNNNNNNNNNNNNNNNNNNNNNNNNNNNNNNNNNNNNNNNNNNNNNNNNNNNNNN
55801  NNNNNNNNNNNNNNNNNNNNNNNNNNNNNNNNNNNNNNNNNNNNNNNNNNNNNNNNNNNN

55861  NNNNNNNNNNNNNNNNNNNNNNNNNNNNNNNNNNNNNNNNNNNNNNNNNNNNNNNNNNNN
55861  NNNNNNNNNNNNNNNNNNNNNNNNNNNNNNNNNNNNNNNNNNNNNNNNNNNNNNNNNNNN

55921  NNNNNNNNNNNNNNNNNNNNNNNNNNNNNNNNNNNNNNNNNNNNNNNNNNNNNNNNNNNN
55921  NNNNNNNNNNNNNNNNNNNNNNNNNNNNNNNNNNNNNNNNNNNNNNNNNNNNNNNNNNNN

55981  NNNNNNNNNNNNNNNNNNNNNNNNNNNNNNNNNNNNNNNNNNNNNNNNNNNNNNNNNNNN
55981  NNNNNNNNNNNNNNNNNNNNNNNNNNNNNNNNNNNNNNNNNNNNNNNNNNNNNNNNNNNN

56041  NNNNNNNNNNNNNNNNNNNNNNNNNNNNNNNNNNNNNNNNNNNNNNNNNNNNNNNNNNNN
56041  NNNNNNNNNNNNNNNNNNNNNNNNNNNNNNNNNNNNNNNNNNNNNNNNNNNNNNNNNNNN

56101  NNNNNNNNNNNNNNNNNNNNNNNNNNNNNNNNNNNNNNNNNNNNNNNNNNNNNNNNNNNN
56101  NNNNNNNNNNNNNNNNNNNNNNNNNNNNNNNNNNNNNNNNNNNNNNNNNNNNNNNNNNNN

56161  NNNNNNNNNNNNNNNNNNNNNNNNNNNNNNNNNNNNNNNNNNNNNNNNNNNNNNNNNNNN
56161  NNNNNNNNNNNNNNNNNNNNNNNNNNNNNNNNNNNNNNNNNNNNNNNNNNNNNNNNNNNN

56221  NNNNNNNNNNNNNNNNNNNNNNNNNNNNNNNNNNNNNNNNNNNNNNNNNNNNNNNNNNNN
56221  NNNNNNNNNNNNNNNNNNNNNNNNNNNNNNNNNNNNNNNNNNNNNNNNNNNNNNNNNNNN

56281  NNNNNNNNNNNNNNNNNNNNNNNNNNNNNNNNNNNNNNNNNNNNNNNNNNNNNNNNNNNN
56281  NNNNNNNNNNNNNNNNNNNNNNNNNNNNNNNNNNNNNNNNNNNNNNNNNNNNNNNNNNNN

56341  NNNNNNNNNNNNNNNNNNNNNNNNNNNNNNNNNNNNNNNNNNNNNNNNNNNNNNNNNNNN
56341  NNNNNNNNNNNNNNNNNNNNNNNNNNNNNNNNNNNNNNNNNNNNNNNNNNNNNNNNNNNN
```

FIG. 5 (cont'd)

```
56401  NNNNNNNNNNNNNNNNNNNNNNNNNNNNNNNNNNNNNNNNNNNNNNNNNNNNNNNNNNNN
56401  NNNNNNNNNNNNNNNNNNNNNNNNNNNNNNNNNNNNNNNNNNNNNNNNNNNNNNNNNNNN

56461  NNNNNNNNNNNNNNNNNNNNNNNNNNNNNNNNNNNNNNNNNNNNNNNNNNNNNNNNNNNN
56461  NNNNNNNNNNNNNNNNNNNNNNNNNNNNNNNNNNNNNNNNNNNNNNNNNNNNNNNNNNNN

56521  NNNNNNNNNNNNNNNNNNNNNNNNNNNNNNNNNNNNNNNNNNNNNNNNNNNNNNNNNNNN
56521  NNNNNNNNNNNNNNNNNNNNNNNNNNNNNNNNNNNNNNNNNNNNNNNNNNNNNNNNNNNN

56581  NNNNNNNNNNNNNNNNNNNNNNNNNNNNNNNNNNNNNNNNNNNNNNNNNNNNNNNNNNNN
56581  NNNNNNNNNNNNNNNNNNNNNNNNNNNNNNNNNNNNNNNNNNNNNNNNNNNNNNNNNNNN

56641  NNNNNNNNNNNNNNNNNNNNNNNNNNNNNNNNNNNNNNNNNNNNNNNNNNNNNNNNNNNN
56641  NNNNNNNNNNNNNNNNNNNNNNNNNNNNNNNNNNNNNNNNNNNNNNNNNNNNNNNNNNNN

56701  NNNNNNNNNNNNNNNNNNNNNNNNNNNNNNNNNNNNNNNNNNNNNNNNNNNNNNNNNNNN
56701  NNNNNNNNNNNNNNNNNNNNNNNNNNNNNNNNNNNNNNNNNNNNNNNNNNNNNNNNNNNN

56761  NNNNNNNNNNNNNNNNNNNNNNNNNNNNNNNNNNNNNNNNNNNNNNNNNNNNNNNNNNNN
56761  NNNNNNNNNNNNNNNNNNNNNNNNNNNNNNNNNNNNNNNNNNNNNNNNNNNNNNNNNNNN

56821  NNNNNNNNNNNNNNNNNNNNNNNNNNNNNNNNNNNNNNNNNNNNNNNNNNNNNNNNNNNN
56821  NNNNNNNNNNNNNNNNNNNNNNNNNNNNNNNNNNNNNNNNNNNNNNNNNNNNNNNNNNNN

56881  NNNNNNNNNNNNNNNNNNNNNNNNNNNNNNNNNNNNNNNNNNNNNNNNNNNNNNNNNNNN
56881  NNNNNNNNNNNNNNNNNNNNNNNNNNNNNNNNNNNNNNNNNNNNNNNNNNNNNNNNNNNN

56941  NNNNNNNNNNNNNNNNNNNNNNNNNNNNNNNNNNNNNNNNNNNNNNNNNNNNNNNNNNNN
56941  NNNNNNNNNNNNNNNNNNNNNNNNNNNNNNNNNNNNNNNNNNNNNNNNNNNNNNNNNNNN

57001  NNNNNNNNNNNNNNNNNNNNNNNNNNNNNNNNNNNNNNNNNNNNNNNNNNNNNNNNNNNN
57001  NNNNNNNNNNNNNNNNNNNNNNNNNNNNNNNNNNNNNNNNNNNNNNNNNNNNNNNNNNNN

57061  NNNNNNNNNNNNNNNNNNNNNNNNNNNNNNNNNNNNNNNNNNNNNNNNNNNNNNNNNNNN
57061  NNNNNNNNNNNNNNNNNNNNNNNNNNNNNNNNNNNNNNNNNNNNNNNNNNNNNNNNNNNN

57121  NNNNNNNNNNNNNNNNNNNNNNNNNNNNNNNNNNNNNNNNNNNNNNNNNNNNNNNNNNNN
57121  NNNNNNNNNNNNNNNNNNNNNNNNNNNNNNNNNNNNNNNNNNNNNNNNNNNNNNNNNNNN

57181  NNNNNNNNNNNNNNNNNNNNNNNNNNNNNNNNNNNNNNNNNNNNNNNNNNNNNNNNNNNN
57181  NNNNNNNNNNNNNNNNNNNNNNNNNNNNNNNNNNNNNNNNNNNNNNNNNNNNNNNNNNNN

57241  NNNNNNNNNNNNNNNNNNNNNNNNNNNNNNNNNNNNNNNNNNNNNNNNNNNNNNNNNNNN
57241  NNNNNNNNNNNNNNNNNNNNNNNNNNNNNNNNNNNNNNNNNNNNNNNNNNNNNNNNNNNN

57301  NNNNNNNNNNNNNNNNNNNNNNNNNNNNNNNNNNNNNNNNNNNNNNNNNNNNNNNNNNNN
57301  NNNNNNNNNNNNNNNNNNNNNNNNNNNNNNNNNNNNNNNNNNNNNNNNNNNNNNNNNNNN

57361  NNNNNNNNNNNNNNNNNNNNNNNNNNNNNNNNNNNNNNNNNNNNNNNNNNNNNNNNNNNN
57361  NNNNNNNNNNNNNNNNNNNNNNNNNNNNNNNNNNNNNNNNNNNNNNNNNNNNNNNNNNNN

57421  NNNNNNNNNNNNNNNNNNNNNNNNNNNNNNNNNNNNNNNNNNNNNNNNNNNNNNNNNNNN
57421  NNNNNNNNNNNNNNNNNNNNNNNNNNNNNNNNNNNNNNNNNNNNNNNNNNNNNNNNNNNN

57481  NNNNNNNNNNNNNNNNNNNNNNNNNNNNNNNNNNNNNNNNNNNNNNNNNNNNNNNNNNNN
57481  NNNNNNNNNNNNNNNNNNNNNNNNNNNNNNNNNNNNNNNNNNNNNNNNNNNNNNNNNNNN

57541  NNNNNNNNNNNNNNNNNNNNNNNNNNNNNNNNNNNNNNNNNNNNNNNNNNNNNNNNNNNN
57541  NNNNNNNNNNNNNNNNNNNNNNNNNNNNNNNNNNNNNNNNNNNNNNNNNNNNNNNNNNNN

57601  NNNNNNNNNNNNNNNNNNNNNNNNNNNNNNNNNNNNNNNNNNNNNNNNNNNNNNNNNNNN
57601  NNNNNNNNNNNNNNNNNNNNNNNNNNNNNNNNNNNNNNNNNNNNNNNNNNNNNNNNNNNN

57661  NNNNNNNNNNNNNNNNNNNNNNNNNNNNNNNNNNNNNNNNNNNNNNNNNNNNNNNNNNNN
57661  NNNNNNNNNNNNNNNNNNNNNNNNNNNNNNNNNNNNNNNNNNNNNNNNNNNNNNNNNNNN

57721  NNNNNNNNNNNNNNNNNNNNNNNNNNNNNNNNNNNNNNNNNNNNNNNNNNNNNNNNNNNN
57721  NNNNNNNNNNNNNNNNNNNNNNNNNNNNNNNNNNNNNNNNNNNNNNNNNNNNNNNNNNNN
```

FIG. 5 (cont'd)

57781 NNNNNNNNNNNNNNNNNNNNNNNNNNNNNNNNNNNNNNNNNNNNNNNNNNNNNNNNNNNN
57781 NNNNNNNNNNNNNNNNNNNNNNNNNNNNNNNNNNNNNNNNNNNNNNNNNNNNNNNNNNNN

57841 NNNNNNNNNNNNNNNNNNNNNNNNNNNNNNNNNNNNNNNNNNNNNNNNNNNNNNNNNNNN
57841 NNNNNNNNNNNNNNNNNNNNNNNNNNNNNNNNNNNNNNNNNNNNNNNNNNNNNNNNNNNN

57901 NNNNNNNNNNNNNNNNNNNNNNNNNNNNNNNNNNNNNNNNNNNNNNNNNNNNNNNNNNNN
57901 NNNNNNNNNNNNNNNNNNNNNNNNNNNNNNNNNNNNNNNNNNNNNNNNNNNNNNNNNNNN

57961 NNNNNNNNNNNNNNNNNNNNNNNNNNNNNNNNNNNNNNNNNNNNNNNNNNNNNNNNNNNN
57961 NNNNNNNNNNNNNNNNNNNNNNNNNNNNNNNNNNNNNNNNNNNNNNNNNNNNNNNNNNNN

58021 NNNNNNNNNNNNNNNNNNNNNNNNNNNNNNNNNNNNNNNNNNNNNNNNNNNNNNNNNNNN
58021 NNNNNNNNNNNNNNNNNNNNNNNNNNNNNNNNNNNNNNNNNNNNNNNNNNNNNNNNNNNN

58081 NNNNNNNNNNNNNNNNNNNNNNNNNNNNNNNNNNNNNNNNNNNNNNNNNNNNNNNNNNNN
58081 NNNNNNNNNNNNNNNNNNNNNNNNNNNNNNNNNNNNNNNNNNNNNNNNNNNNNNNNNNNN

58141 NNNNNNNNNNNNNNNNNNNNNNNNNNNNNNNNNNNNNNNNNNNNNNNNNNNNNNNNNNNN
58141 NNNNNNNNNNNNNNNNNNNNNNNNNNNNNNNNNNNNNNNNNNNNNNNNNNNNNNNNNNNN

58201 NNNNNNNNNNNNNNNNNNNNNNNNNNNNNNNNNNNNNNNNNNNNNNNNNNNNNNNNNNNN
58201 NNNNNNNNNNNNNNNNNNNNNNNNNNNNNNNNNNNNNNNNNNNNNNNNNNNNNNNNNNNN

58261 NNNNNNNNNNNNNNNNNNNNNNNNNNNNNNNNNNNNNNNNNNNNNNNNNNNNNNNNNNNN
58261 NNNNNNNNNNNNNNNNNNNNNNNNNNNNNNNNNNNNNNNNNNNNNNNNNNNNNNNNNNNN

58321 NNNNNNNNNNNNNNNNNNNNNNNNNNNNNNNNNNNNNNNNNNNNNNNNNNNNNNNNNNNN
58321 NNNNNNNNNNNNNNNNNNNNNNNNNNNNNNNNNNNNNNNNNNNNNNNNNNNNNNNNNNNN

58381 NNNNNNNNNNNNNNNNNNNNNNNNNNNNNNNNNNNNNNNNNNNNNNNNNNNNNNNNNNNN
58381 NNNNNNNNNNNNNNNNNNNNNNNNNNNNNNNNNNNNNNNNNNNNNNNNNNNNNNNNNNNN

58441 NNNNNNNNNNNNNNNNNNNNNNNNNNNNNNNNNNNNNNNNNNNNNNNNNNNNNNNNNNNN
58441 NNNNNNNNNNNNNNNNNNNNNNNNNNNNNNNNNNNNNNNNNNNNNNNNNNNNNNNNNNNN

58501 NNNNNNNNNNNNNNNNNNNNNNNNNNNNNNNNNNNNNNNNNNNNNNNNNNNNNNNNNNNN
58501 NNNNNNNNNNNNNNNNNNNNNNNNNNNNNNNNNNNNNNNNNNNNNNNNNNNNNNNNNNNN

58561 NNNNNNNNNNNNNNNNNNNNNNNNNNNNNNNNNNNNNNNNNNNNNNNNNNNNNNNNNNNN
58561 NNNNNNNNNNNNNNNNNNNNNNNNNNNNNNNNNNNNNNNNNNNNNNNNNNNNNNNNNNNN

58621 NNNNNNNNNNNNNNNNNNNNNNNNNNNNNNNNNNNNNNNNNNNNNNNNNNNNNNNNNNNN
58621 NNNNNNNNNNNNNNNNNNNNNNNNNNNNNNNNNNNNNNNNNNNNNNNNNNNNNNNNNNNN

58681 NNNNNNNNNNNNNNNNNNNNNNNNNNNNNNNNNNNNNNNNNNNNNNNNNNNNNNNNNNNN
58681 NNNNNNNNNNNNNNNNNNNNNNNNNNNNNNNNNNNNNNNNNNNNNNNNNNNNNNNNNNNN

58741 NNNNNNNNNNNNNNNNNNNNNNNNNNNNNNNNNNNNNNNNNNNNNNNNNNNNNNNNNNNN
58741 NNNNNNNNNNNNNNNNNNNNNNNNNNNNNNNNNNNNNNNNNNNNNNNNNNNNNNNNNNNN

58801 NNNNNNNNNNNNNNNNNNNNNNNNNNNNNNNNNNNNNNNNNNNNNNNNNNNNNNNNNNNN
58801 NNNNNNNNNNNNNNNNNNNNNNNNNNNNNNNNNNNNNNNNNNNNNNNNNNNNNNNNNNNN

58861 NNNNNNNNNNNNNNNNNNNNNNNNNNNNNNNNNNNNNNNNNNNNNNNNNNNNNNNNNNNN
58861 NNNNNNNNNNNNNNNNNNNNNNNNNNNNNNNNNNNNNNNNNNNNNNNNNNNNNNNNNNNN

58921 NNNNNNNNNNNNNNNNNNNNNNNNNNNNNNNNNNNNNNNNNNNNNNNNNNNNNNNNNNNN
58921 NNNNNNNNNNNNNNNNNNNNNNNNNNNNNNNNNNNNNNNNNNNNNNNNNNNNNNNNNNNN

58981 NNNNNNNNNNNNNNNNNNNNNNNNNNNNNNNNNNNNNNNNNNNNNNNNNNNNNNNNNNNN
58981 NNNNNNNNNNNNNNNNNNNNNNNNNNNNNNNNNNNNNNNNNNNNNNNNNNNNNNNNNNNN

59041 NNNNNNNNNNNNNNNNNNNNNNNNNNNNNNNNNNNNNNNNNNNNNNNNNNNNNNNNNNNN
59041 NNNNNNNNNNNNNNNNNNNNNNNNNNNNNNNNNNNNNNNNNNNNNNNNNNNNNNNNNNNN

59101 NNNNNNNNNNNNNNNNNNNNNNNNNNNNNNNNNNNNNNNNNNNNNNNNNNNNNNNNNNNN
59101 NNNNNNNNNNNNNNNNNNNNNNNNNNNNNNNNNNNNNNNNNNNNNNNNNNNNNNNNNNNN

FIG. 5 (cont'd)

```
59161  NNNNNNNNNNNNNNNNNNNNNNNNNNNNNNNNNNNNNNNNNNNNNNNNNNNNNNNNNNNN
59161  NNNNNNNNNNNNNNNNNNNNNNNNNNNNNNNNNNNNNNNNNNNNNNNNNNNNNNNNNNNN

59221  NNNNNNNNNNNNNNNNNNNNNNNNNNNNNNNNNNNNNNNNNNNNNNNNNNNNNNNNNNNN
59221  NNNNNNNNNNNNNNNNNNNNNNNNNNNNNNNNNNNNNNNNNNNNNNNNNNNNNNNNNNNN

59281  NNNNNNNNNNNNNNNNNNNNNNNNNNNNNNNNNNNNNNNNNNNNNNNNNNNNNNNNNNNN
59281  NNNNNNNNNNNNNNNNNNNNNNNNNNNNNNNNNNNNNNNNNNNNNNNNNNNNNNNNNNNN

59341  NNNNNNNNNNNNNNNNNNNNNNNNNNNNNNNNNNNNNNNNNNNNNNNNNNNNNNNNNNNN
59341  NNNNNNNNNNNNNNNNNNNNNNNNNNNNNNNNNNNNNNNNNNNNNNNNNNNNNNNNNNNN

59401  NNNNNNNNNNNNNNNNNNNNNNNNNNNNNNNNNNNNNNNNNNNNNNNNNNNNNNNNNNNN
59401  NNNNNNNNNNNNNNNNNNNNNNNNNNNNNNNNNNNNNNNNNNNNNNNNNNNNNNNNNNNN

59461  NNNNNNNNNNNNNNNNNNNNNNNNNNNNNNNNNNNNNNNNNNNNNNNNNNNNNNNNNNNN
59461  NNNNNNNNNNNNNNNNNNNNNNNNNNNNNNNNNNNNNNNNNNNNNNNNNNNNNNNNNNNN

59521  NNNNNNNNNNNNNNNNNNNNNNNNNNNNNNNNNNNNNNNNNNNNNNNNNNNNNNNNNNNN
59521  NNNNNNNNNNNNNNNNNNNNNNNNNNNNNNNNNNNNNNNNNNNNNNNNNNNNNNNNNNNN

59581  NNNNNNNNNNNNNNNNNNNNNNNNNNNNNNNNNNNNNNNNNNNNNNNNNNNNNNNNNNNN
59581  NNNNNNNNNNNNNNNNNNNNNNNNNNNNNNNNNNNNNNNNNNNNNNNNNNNNNNNNNNNN

59641  NNNNNNNNNNNNNNNNNNNNNNNNNNNNNNNNNNNNNNNNNNNNNNNNNNNNNNNNNNNN
59641  NNNNNNNNNNNNNNNNNNNNNNNNNNNNNNNNNNNNNNNNNNNNNNNNNNNNNNNNNNNN

59701  NNNNNNNNNNNNNNNNNNNNNNNNNNNNNNNNNNNNNNNNNNNNNNNNNNNNNNNNNNNN
59701  NNNNNNNNNNNNNNNNNNNNNNNNNNNNNNNNNNNNNNNNNNNNNNNNNNNNNNNNNNNN

59761  NNNNNNNNNNNNNNNNNNNNNNNNNNNNNNNNNNNNNNNNNNNNNNNNNNNNNNNNNNNN
59761  NNNNNNNNNNNNNNNNNNNNNNNNNNNNNNNNNNNNNNNNNNNNNNNNNNNNNNNNNNNN

59821  NNNNNNNNNNNNNNNNNNNNNNNNNNNNNNNNNNNNNNNNNNNNNNNNNNNNNNNNNNNN
59821  NNNNNNNNNNNNNNNNNNNNNNNNNNNNNNNNNNNNNNNNNNNNNNNNNNNNNNNNNNNN

59881  NNNNNNNNNNNNNNNNNNNNNNNNNNNNNNNNNNNNNNNNNNNNNNNNNNNNNNNNNNNN
59881  NNNNNNNNNNNNNNNNNNNNNNNNNNNNNNNNNNNNNNNNNNNNNNNNNNNNNNNNNNNN

59941  NNNNNNNNNNNNNNNNNNNNNNNNNNNNNNNNNNNNNNNNNNNNNNNNNNNNNNNNNNNN
59941  NNNNNNNNNNNNNNNNNNNNNNNNNNNNNNNNNNNNNNNNNNNNNNNNNNNNNNNNNNNN

60001  NNNNNNNNNNNNNNNNNNNNNNNNNNNNNNNNNNNNNNNNNNNNNNNNNNNNNNNNNNNN
60001  NNNNNNNNNNNNNNNNNNNNNNNNNNNNNNNNNNNNNNNNNNNNNNNNNNNNNNNNNNNN

60061  NNNNNNNNNNNNNNNNNNNNNNNNNNNNNNNNNNNNNNNNNNNNNNNNNNNNNNNNNNNN
60061  NNNNNNNNNNNNNNNNNNNNNNNNNNNNNNNNNNNNNNNNNNNNNNNNNNNNNNNNNNNN

60121  NNNNNNNNNNNNNNNNNNNNNNNNNNNNNNNNNNNNNNNNNNNNNNNNNNNNNNNNNNNN
60121  NNNNNNNNNNNNNNNNNNNNNNNNNNNNNNNNNNNNNNNNNNNNNNNNNNNNNNNNNNNN

60181  NNNNNNNNNNNNNNNNNNNNNNNNNNNNNNNNNNNNNNNNNNNNNNNNNNNNNNNNNNNN
60181  NNNNNNNNNNNNNNNNNNNNNNNNNNNNNNNNNNNNNNNNNNNNNNNNNNNNNNNNNNNN

60241  NNNNNNNNNNNNNNNNNNNNNNNNNNNNNNNNNNNNNNNNNNNNNNNNNNNNNNNNNNNN
60241  NNNNNNNNNNNNNNNNNNNNNNNNNNNNNNNNNNNNNNNNNNNNNNNNNNNNNNNNNNNN

60301  NNNNNNNNNNNNNNNNNNNNNNNNNNNNNNNNNNNNNNNNNNNNNNNNNNNNNNNNNNNN
60301  NNNNNNNNNNNNNNNNNNNNNNNNNNNNNNNNNNNNNNNNNNNNNNNNNNNNNNNNNNNN

60361  NNNNNNNNNNNNNNNNNNNNNNNNNNNNNNNNNNNNNNNNNNNNNNNNNNNNNNNNNNNN
60361  NNNNNNNNNNNNNNNNNNNNNNNNNNNNNNNNNNNNNNNNNNNNNNNNNNNNNNNNNNNN

60421  NNNNNNNNNNNNNNNNNNNNNNNNNNNNNNNNNNNNNNNNNNNNNNNNNNNNNNNNNNNN
60421  NNNNNNNNNNNNNNNNNNNNNNNNNNNNNNNNNNNNNNNNNNNNNNNNNNNNNNNNNNNN

60481  NNNNNNNNNNNNNNNNNNNNNNNNNNNNNNNNNNNNNNNNNNNNNNNNNNNNNNNNNNNN
60481  NNNNNNNNNNNNNNNNNNNNNNNNNNNNNNNNNNNNNNNNNNNNNNNNNNNNNNNNNNNN
```

FIG. 5 (cont'd)

```
60541  NNNNNNNNNNNNNNNNNNNNNNNNNNNNNNNNNNNNNNNNNNNNNNNNNNNNNNNNNNNN
60541  NNNNNNNNNNNNNNNNNNNNNNNNNNNNNNNNNNNNNNNNNNNNNNNNNNNNNNNNNNNN

60601  NNNNNNNNNNNNNNNNNNNNNNNNNNNNNNNNNNNNNNNNNNNNNNNNNNNNNNNNNNNN
60601  NNNNNNNNNNNNNNNNNNNNNNNNNNNNNNNNNNNNNNNNNNNNNNNNNNNNNNNNNNNN

60661  NNNNNNNNNNNNNNNNNNNNNNNNNNNNNNNNNNNNNNNNNNNNNNNNNNNNNNNNNNNN
60661  NNNNNNNNNNNNNNNNNNNNNNNNNNNNNNNNNNNNNNNNNNNNNNNNNNNNNNNNNNNN

60721  NNNNNNNNNNNNNNNNNNNNNNNNNNNNNNNNNNNNNNNNNNNNNNNNNNNNNNNNNNNN
60721  NNNNNNNNNNNNNNNNNNNNNNNNNNNNNNNNNNNNNNNNNNNNNNNNNNNNNNNNNNNN

60781  NNNNNNNNNNNNNNNNNNNNNNNNNNNNNNNNNNNNNNNNNNNNNNNNNNNNNNNNNNNN
60781  NNNNNNNNNNNNNNNNNNNNNNNNNNNNNNNNNNNNNNNNNNNNNNNNNNNNNNNNNNNN

60841  NNNNNNNNNNNNNNNNNNNNNNNNNNNNNNNNNNNNNNNNNNNNNNNNNNNNNNNNNNNN
60841  NNNNNNNNNNNNNNNNNNNNNNNNNNNNNNNNNNNNNNNNNNNNNNNNNNNNNNNNNNNN

60901  NNNNNNNNNNNNNNNNNNNNNNNNNNNNNNNNNNNNNNNNNNNNNNNNNNNNNNNNNNNN
60901  NNNNNNNNNNNNNNNNNNNNNNNNNNNNNNNNNNNNNNNNNNNNNNNNNNNNNNNNNNNN

60961  NNNNNNNNNNNNNNNNNNNNNNNNNNNNNNNNNNNNNNNNNNNNNNNNNNNNNNNNNNNN
60961  NNNNNNNNNNNNNNNNNNNNNNNNNNNNNNNNNNNNNNNNNNNNNNNNNNNNNNNNNNNN

61021  NNNNNNNNNNNNNNNNNNNNNNNNNNNNNNNNNNNNNNNNNNNNNNNNNNNNNNNNNNNN
61021  NNNNNNNNNNNNNNNNNNNNNNNNNNNNNNNNNNNNNNNNNNNNNNNNNNNNNNNNNNNN

61081  NNNNNNNNNNNNNNNNNNNNNNNNNNNNNNNNNNNNNNNNNNNNNNNNNNNNNNNNNNNN
61081  NNNNNNNNNNNNNNNNNNNNNNNNNNNNNNNNNNNNNNNNNNNNNNNNNNNNNNNNNNNN

61141  NNNNNNNNNNNNNNNNNNNNNNNNNNNNNNNNNNNNNNNNNNNNNNNNNNNNNNNNNNNN
61141  NNNNNNNNNNNNNNNNNNNNNNNNNNNNNNNNNNNNNNNNNNNNNNNNNNNNNNNNNNNN

61201  NNNNNNNNNNNNNNNNNNNNNNNNNNNNNNNNNNNNNNNNNNNNNNNNNNNNNNNNNNNN
61201  NNNNNNNNNNNNNNNNNNNNNNNNNNNNNNNNNNNNNNNNNNNNNNNNNNNNNNNNNNNN

61261  NNNNNNNNNNNNNNNNNNNNNNNNNNNNNNNNNNNNNNNNNNNNNNNNNNNNNNNNNNNN
61261  NNNNNNNNNNNNNNNNNNNNNNNNNNNNNNNNNNNNNNNNNNNNNNNNNNNNNNNNNNNN

61321  NNNNNNNNNNNNNNNNNNNNNNNNNNNNNNNNNNNNNNNNNNNNNNNNNNNNNNNNNNNN
61321  NNNNNNNNNNNNNNNNNNNNNNNNNNNNNNNNNNNNNNNNNNNNNNNNNNNNNNNNNNNN

61381  NNNNNNNNNNNNNNNNNNNNNNNNNNNNNNNNNNNNNNNNNNNNNNNNNNNNNNNNNNNN
61381  NNNNNNNNNNNNNNNNNNNNNNNNNNNNNNNNNNNNNNNNNNNNNNNNNNNNNNNNNNNN

61441  NNNNNNNNNNNNNNNNNNNNNNNNNNNNNNNNNNNNNNNNNNNNNNNNNNNNNNNNNNNN
61441  NNNNNNNNNNNNNNNNNNNNNNNNNNNNNNNNNNNNNNNNNNNNNNNNNNNNNNNNNNNN

61501  NNNNNNNNNNNNNNNNNNNNNNNNNNNNNNNNNNNNNNNNNNNNNNNNNNNNNNNNNNNN
61501  NNNNNNNNNNNNNNNNNNNNNNNNNNNNNNNNNNNNNNNNNNNNNNNNNNNNNNNNNNNN

61561  NNNNNNNNNNNNNNNNNNNNNNNNNNNNNNNNNNNNNNNNNNNNNNNNNNNNNNNNNNNN
61561  NNNNNNNNNNNNNNNNNNNNNNNNNNNNNNNNNNNNNNNNNNNNNNNNNNNNNNNNNNNN

61621  NNNNNNNNNNNNNNNNNNNNNNNNNNNNNNNNNNNNNNNNNNNNNNNNNNNNNNNNNNNN
61621  NNNNNNNNNNNNNNNNNNNNNNNNNNNNNNNNNNNNNNNNNNNNNNNNNNNNNNNNNNNN

61681  NNNNNNNNNNNNNNNNNNNNNNNNNNNNNNNNNNNNNNNNNNNNNNNNNNNNNNNNNNNN
61681  NNNNNNNNNNNNNNNNNNNNNNNNNNNNNNNNNNNNNNNNNNNNNNNNNNNNNNNNNNNN

61741  NNNNNNNNNNNNNNNNNNNNNNNNNNNNNNNNNNNNNNNNNNNNNNNNNNNNNNNNNNNN
61741  NNNNNNNNNNNNNNNNNNNNNNNNNNNNNNNNNNNNNNNNNNNNNNNNNNNNNNNNNNNN

61801  NNNNNNNNNNNNNNNNNNNNNNNNNNNNNNNNNNNNNNNNNNNNNNNNNNNNNNNNNNNN
61801  NNNNNNNNNNNNNNNNNNNNNNNNNNNNNNNNNNNNNNNNNNNNNNNNNNNNNNNNNNNN

61861  NNNNNNNNNNNNNNNNNNNNNNNNNNNNNNNNNNNNNNNNNNNNNNNNNNNNNNNNNNNN
61861  NNNNNNNNNNNNNNNNNNNNNNNNNNNNNNNNNNNNNNNNNNNNNNNNNNNNNNNNNNNN
```

FIG. 5 (cont'd)

```
61921  NNNNNNNNNNNNNNNNNNNNNNNNNNNNNNNNNNNNNNNNNNNNNNNNNNNNNNNNNNNN
61921  NNNNNNNNNNNNNNNNNNNNNNNNNNNNNNNNNNNNNNNNNNNNNNNNNNNNNNNNNNNN

61981  NNNNNNNNNNNNNNNNNNNNNNNNNNNNNNNNNNNNNNNNNNNNNNNNNNNNNNNNNNNN
61981  NNNNNNNNNNNNNNNNNNNNNNNNNNNNNNNNNNNNNNNNNNNNNNNNNNNNNNNNNNNN

62041  NNNNNNNNNNNNNNNNNNNNNNNNNNNNNNNNNNNNNNNNNNNNNNNNNNNNNNNNNNNN
62041  NNNNNNNNNNNNNNNNNNNNNNNNNNNNNNNNNNNNNNNNNNNNNNNNNNNNNNNNNNNN

62101  NNNNNNNNNNNNNNNNNNNNNNNNNNNNNNNNNNNNNNNNNNNNNNNNNNNNNNNNNNNN
62101  NNNNNNNNNNNNNNNNNNNNNNNNNNNNNNNNNNNNNNNNNNNNNNNNNNNNNNNNNNNN

62161  NNNNNNNNNNNNNNNNNNNNNNNNNNNNNNNNNNNNNNNNNNNNNNNNNNNNNNNNNNNN
62161  NNNNNNNNNNNNNNNNNNNNNNNNNNNNNNNNNNNNNNNNNNNNNNNNNNNNNNNNNNNN

62221  NNNNNNNNNNNNNNNNNNNNNNNNNNNNNNNNNNNNNNNNNNNNNNNNNNNNNNNNNNNN
62221  NNNNNNNNNNNNNNNNNNNNNNNNNNNNNNNNNNNNNNNNNNNNNNNNNNNNNNNNNNNN

62281  NNNNNNNNNNNNNNNNNNNNNNNNNNNNNNNNNNNNNNNNNNNNNNNNNNNNNNNNNNNN
62281  NNNNNNNNNNNNNNNNNNNNNNNNNNNNNNNNNNNNNNNNNNNNNNNNNNNNNNNNNNNN

62341  NNNNNNNNNNNNNNNNNNNNNNNNNNNNNNNNNNNNNNNNNNNNNNNNNNNNNNNNNNNN
62341  NNNNNNNNNNNNNNNNNNNNNNNNNNNNNNNNNNNNNNNNNNNNNNNNNNNNNNNNNNNN

62401  NNNNNNNNNNNNNNNNNNNNNNNNNNNNNNNNNNNNNNNNNNNNNNNNNNNNNNNNNNNN
62401  NNNNNNNNNNNNNNNNNNNNNNNNNNNNNNNNNNNNNNNNNNNNNNNNNNNNNNNNNNNN

62461  NNNNNNNNNNNNNNNNNNNNNNNNNNNNNNNNNNNNNNNNNNNNNNNNNNNNNNNNNNNN
62461  NNNNNNNNNNNNNNNNNNNNNNNNNNNNNNNNNNNNNNNNNNNNNNNNNNNNNNNNNNNN

62521  NNNNNNNNNNNNNNNNNNNNNNNNNNNNNNNNNNNNNNNNNNNNNNNNNNNNNNNNNNNN
62521  NNNNNNNNNNNNNNNNNNNNNNNNNNNNNNNNNNNNNNNNNNNNNNNNNNNNNNNNNNNN

62581  NNNNNNNNNNNNNNNNNNNNNNNNNNNNNNNNNNNNNNNNNNNNNNNNNNNNNNNNNNNN
62581  NNNNNNNNNNNNNNNNNNNNNNNNNNNNNNNNNNNNNNNNNNNNNNNNNNNNNNNNNNNN

62641  NNNNNNNNNNNNNNNNNNNNNNNNNNNNNNNNNNNNNNNNNNNNNNNNNNNNNNNNNNNN
62641  NNNNNNNNNNNNNNNNNNNNNNNNNNNNNNNNNNNNNNNNNNNNNNNNNNNNNNNNNNNN

62701  NNNNNNNNNNNNNNNNNNNNNNNNNNNNNNNNNNNNNNNNNNNNNNNNNNNNNNNNNNNN
62701  NNNNNNNNNNNNNNNNNNNNNNNNNNNNNNNNNNNNNNNNNNNNNNNNNNNNNNNNNNNN

62761  NNNNNNNNNNNNNNNNNNNNNNNNNNNNNNNNNNNNNNNNNNNNNNNNNNNNNNNNNNNN
62761  NNNNNNNNNNNNNNNNNNNNNNNNNNNNNNNNNNNNNNNNNNNNNNNNNNNNNNNNNNNN

62821  NNNNNNNNNNNNNNNNNNNNNNNNNNNNNNNNNNNNNNNNNNNNNNNNNNNNNNNNNNNN
62821  NNNNNNNNNNNNNNNNNNNNNNNNNNNNNNNNNNNNNNNNNNNNNNNNNNNNNNNNNNNN

62881  NNNNNNNNNNNNNNNNNNNNNNNNNNNNNNNNNNNNNNNNNNNNNNNNNNNNNNNNNNNN
62881  NNNNNNNNNNNNNNNNNNNNNNNNNNNNNNNNNNNNNNNNNNNNNNNNNNNNNNNNNNNN

62941  NNNNNNNNNNNNNNNNNNNNNNNNNNNNNNNNNNNNNNNNNNNNNNNNNNNNNNNNNNNN
62941  NNNNNNNNNNNNNNNNNNNNNNNNNNNNNNNNNNNNNNNNNNNNNNNNNNNNNNNNNNNN

63001  NNNNNNNNNNNNNNNNNNNNNNNNNNNNNNNNNNNNNNNNNNNNNNNNNNNNNNNNNNNN
63001  NNNNNNNNNNNNNNNNNNNNNNNNNNNNNNNNNNNNNNNNNNNNNNNNNNNNNNNNNNNN

63061  NNNNNNNNNNNNNNNNNNNNNNNNNNNNNNNNNNNNNNNNNNNNNNNNNNNNNNNNNNNN
63061  NNNNNNNNNNNNNNNNNNNNNNNNNNNNNNNNNNNNNNNNNNNNNNNNNNNNNNNNNNNN

63121  NNNNNNNNNNNNNNNNNNNNNNNNNNNNNNNNNNNNNNNNNNNNNNNNNNNNNNNNNNNN
63121  NNNNNNNNNNNNNNNNNNNNNNNNNNNNNNNNNNNNNNNNNNNNNNNNNNNNNNNNNNNN

63181  NNNNNNNNNNNNNNNNNNNNNNNNNNNNNNNNNNNNNNNNNNNNNNNNNNNNNNNNNNNN
63181  NNNNNNNNNNNNNNNNNNNNNNNNNNNNNNNNNNNNNNNNNNNNNNNNNNNNNNNNNNNN

63241  NNNNNNNNNNNNNNNNNNNNNNNNNNNNNNNNNNNNNNNNNNNNNNNNNNNNNNNNNNNN
63241  NNNNNNNNNNNNNNNNNNNNNNNNNNNNNNNNNNNNNNNNNNNNNNNNNNNNNNNNNNNN
```

FIG. 5 (cont'd)

63301 NNNNNNNNNNNNNNNNNNNNNNNNNNNNNNNNNNNNNNNNNNNNNNNNNNNNNNNNNNNN
63301 NNNNNNNNNNNNNNNNNNNNNNNNNNNNNNNNNNNNNNNNNNNNNNNNNNNNNNNNNNNN

63361 NNNNNNNNNNNNNNNNNNNNNNNNNNNNNNNNNNNNNNNNNNNNNNNNNNNNNNNNNNNN
63361 NNNNNNNNNNNNNNNNNNNNNNNNNNNNNNNNNNNNNNNNNNNNNNNNNNNNNNNNNNNN

63421 NNNNNNNNNNNNNNNNNNNNNNNNNNNNNNNNNNNNNNNNNNNNNNNNNNNNNNNNNNNN
63421 NNNNNNNNNNNNNNNNNNNNNNNNNNNNNNNNNNNNNNNNNNNNNNNNNNNNNNNNNNNN

63481 NNNNNNNNNNNNNNNNNNNNNNNNNNNNNNNNNNNNNNNNNNNNNNNNNNNNNNNNNNNN
63481 NNNNNNNNNNNNNNNNNNNNNNNNNNNNNNNNNNNNNNNNNNNNNNNNNNNNNNNNNNNN

63541 NNNNNNNNNNNNNNNNNNNNNNNNNNNNNNNNNNNNNNNNNNNNNNNNNNNNNNNNNNNN
63541 NNNNNNNNNNNNNNNNNNNNNNNNNNNNNNNNNNNNNNNNNNNNNNNNNNNNNNNNNNNN

63601 NNNNNNNNNNNNNNNNNNNNNNNNNNNNNNNNNNNNNNNNNNNNNNNNNNNNNNNNNNNN
63601 NNNNNNNNNNNNNNNNNNNNNNNNNNNNNNNNNNNNNNNNNNNNNNNNNNNNNNNNNNNN

63661 NNNNNNNNNNNNNNNNNNNNNNNNNNNNNNNNNNNNNNNNNNNNNNNNNNNNNNNNNNNN
63661 NNNNNNNNNNNNNNNNNNNNNNNNNNNNNNNNNNNNNNNNNNNNNNNNNNNNNNNNNNNN

63721 NNNNNNNNNNNNNNNNNNNNNNNNNNNNNNNNNNNNNNNNNNNNNNNNNNNNNNNNNNNN
63721 NNNNNNNNNNNNNNNNNNNNNNNNNNNNNNNNNNNNNNNNNNNNNNNNNNNNNNNNNNNN

63781 NNNNNNNNNNNNNNNNNNNNNNNNNNNNNNNNNNNNNNNNNNNNNNNNNNNNNNNNNNNN
63781 NNNNNNNNNNNNNNNNNNNNNNNNNNNNNNNNNNNNNNNNNNNNNNNNNNNNNNNNNNNN

63841 NNNNNNNNNNNNNNNNNNNNNNNNNNNNNNNNNNNNNNNNNNNNNNNNNNNNNNNNNNNN
63841 NNNNNNNNNNNNNNNNNNNNNNNNNNNNNNNNNNNNNNNNNNNNNNNNNNNNNNNNNNNN

63901 NNNNNNNNNNNNNNNNNNNNNNNNNNNNNNNNNNNNNNNNNNNNNNNNNNNNNNNNNNNN
63901 NNNNNNNNNNNNNNNNNNNNNNNNNNNNNNNNNNNNNNNNNNNNNNNNNNNNNNNNNNNN

63961 NNNNNNNNNNNNNNNNNNNNNNNNNNNNNNNNNNNNNNNNNNNNNNNNNNNNNNNNNNNN
63961 NNNNNNNNNNNNNNNNNNNNNNNNNNNNNNNNNNNNNNNNNNNNNNNNNNNNNNNNNNNN

64021 NNNNNNNNNNNNNNNNNNNNNNNNNNNNNNNNNNNNNNNNNNNNNNNNNNNNNNNNNNNN
64021 NNNNNNNNNNNNNNNNNNNNNNNNNNNNNNNNNNNNNNNNNNNNNNNNNNNNNNNNNNNN

64081 NNNNNNNNNNNNNNNNNNNNNNNNNNNNNNNNNNNNNNNNNNNNNNNNNNNNNNNNNNNN
64081 NNNNNNNNNNNNNNNNNNNNNNNNNNNNNNNNNNNNNNNNNNNNNNNNNNNNNNNNNNNN

64141 NNNNNNNNNNNNNNNNNNNNNNNNNNNNNNNNNNNNNNNNNNNNNNNNNNNNNNNNNNNN
64141 NNNNNNNNNNNNNNNNNNNNNNNNNNNNNNNNNNNNNNNNNNNNNNNNNNNNNNNNNNNN

64201 NNNNNNNNNNNNNNNNNNNNNNNNNNNNNNNNNNNNNNNNNNNNNNNNNNNNNNNNNNNN
64201 NNNNNNNNNNNNNNNNNNNNNNNNNNNNNNNNNNNNNNNNNNNNNNNNNNNNNNNNNNNN

64261 NNNNNNNNNNNNNNNNNNNNNNNNNNNNNNNNNNNNNNNNNNNNNNNNNNNNNNNNNNNN
64261 NNNNNNNNNNNNNNNNNNNNNNNNNNNNNNNNNNNNNNNNNNNNNNNNNNNNNNNNNNNN

64321 NNNNNNNNNNNNNNNNNNNNNNNNNNNNNNNNNNNNNNNNNNNNNNNNNNNNNNNNNNNN
64321 NNNNNNNNNNNNNNNNNNNNNNNNNNNNNNNNNNNNNNNNNNNNNNNNNNNNNNNNNNNN

64381 NNNNNNNNNNNNNNNNNNNNNNNNNNNNNNNNNNNNNNNNNNNNNNNNNNNNNNNNNNNN
64381 NNNNNNNNNNNNNNNNNNNNNNNNNNNNNNNNNNNNNNNNNNNNNNNNNNNNNNNNNNNN

64441 NNNNNNNNNNNNNNNNNNNNNNNNNNNNNNNNNNNNNNNNNNNNNNNNNNNNNNNNNNNN
64441 NNNNNNNNNNNNNNNNNNNNNNNNNNNNNNNNNNNNNNNNNNNNNNNNNNNNNNNNNNNN

64501 NNNNNNNNNNNNNNNNNNNNNNNNNNNNNNNNNNNNNNNNNNNNNNNNNNNNNNNNNNNN
64501 NNNNNNNNNNNNNNNNNNNNNNNNNNNNNNNNNNNNNNNNNNNNNNNNNNNNNNNNNNNN

64561 NNNNNNNNNNNNNNNNNNNNNNNNNNNNNNNNNNNNNNNNNNNNNNNNNNNNNNNNNNNN
64561 NNNNNNNNNNNNNNNNNNNNNNNNNNNNNNNNNNNNNNNNNNNNNNNNNNNNNNNNNNNN

64621 NNNNNNNNNNNNNNNNNNNNNNNNNNNNNNNNNNNNNNNNNNNNNNNNNNNNNNNNNNNN
64621 NNNNNNNNNNNNNNNNNNNNNNNNNNNNNNNNNNNNNNNNNNNNNNNNNNNNNNNNNNNN

FIG. 5 (cont'd)

64681 NNNNNNNNNNNNNNNNNNNNNNNNNNNNNNNNNNNNNNNNNNNNNNNNNNNNNNNNNNNN
64681 NNNNNNNNNNNNNNNNNNNNNNNNNNNNNNNNNNNNNNNNNNNNNNNNNNNNNNNNNNNN

64741 NNNNNNNNNNNNNNNNNNNNNNNNNNNNNNNNNNNNNNNNNNNNNNNNNNNNNNNNNNNN
64741 NNNNNNNNNNNNNNNNNNNNNNNNNNNNNNNNNNNNNNNNNNNNNNNNNNNNNNNNNNNN

64801 NNNNNNNNNNNNNNNNNNNNNNNNNNNNNNNNNNNNNNNNNNNNNNNNNNNNNNNNNNNN
64801 NNNNNNNNNNNNNNNNNNNNNNNNNNNNNNNNNNNNNNNNNNNNNNNNNNNNNNNNNNNN

64861 NNNNNNNNNNNNNNNNNNNNNNNNNNNNNNNNNNNNNNNNNNNNNNNNNNNNNNNNNNNN
64861 NNNNNNNNNNNNNNNNNNNNNNNNNNNNNNNNNNNNNNNNNNNNNNNNNNNNNNNNNNNN

64921 NNNNNNNNNNNNNNNNNNNNNNNNNNNNNNNNNNNNNNNNNNNNNNNNNNNNNNNNNNNN
64921 NNNNNNNNNNNNNNNNNNNNNNNNNNNNNNNNNNNNNNNNNNNNNNNNNNNNNNNNNNNN

64981 NNNNNNNNNNNNNNNNNNNNNNNNNNNNNNNNNNNNNNNNNNNNNNNNNNNNNNNNNNNN
64981 NNNNNNNNNNNNNNNNNNNNNNNNNNNNNNNNNNNNNNNNNNNNNNNNNNNNNNNNNNNN

65041 NNNNNNNNNNNNNNNNNNNNNNNNNNNNNNNNNNNNNNNNNNNNNNNNNNNNNNNNNNNN
65041 NNNNNNNNNNNNNNNNNNNNNNNNNNNNNNNNNNNNNNNNNNNNNNNNNNNNNNNNNNNN

65101 NNNNNNNNNNNNNNNNNNNNNNNNNNNNNNNNNNNNNNNNNNNNNNNNNNNNNNNNNNNN
65101 NNNNNNNNNNNNNNNNNNNNNNNNNNNNNNNNNNNNNNNNNNNNNNNNNNNNNNNNNNNN

65161 NNNNNNNNNNNNNNNNNNNNNNNNNNNNNNNNNNNNNNNNNNNNNNNNNNNNNNNNNNNN
65161 NNNNNNNNNNNNNNNNNNNNNNNNNNNNNNNNNNNNNNNNNNNNNNNNNNNNNNNNNNNN

65221 NNNNNNNNNNNNNNNNNNNNNNNNNNNNNNNNNNNNNNNNNNNNNNNNNNNNNNNNNNNN
65221 NNNNNNNNNNNNNNNNNNNNNNNNNNNNNNNNNNNNNNNNNNNNNNNNNNNNNNNNNNNN

65281 NNNNNNNNNNNNNNNNNNNNNNNNNNNNNNNNNNNNNNNNNNNNNNNNNNNNNNNNNNNN
65281 NNNNNNNNNNNNNNNNNNNNNNNNNNNNNNNNNNNNNNNNNNNNNNNNNNNNNNNNNNNN

65341 NNNNNNNNNNNNNNNNNNNNNNNNNNNNNNNNNNNNNNNNNNNNNNNNNNNNNNNNNNNN
65341 NNNNNNNNNNNNNNNNNNNNNNNNNNNNNNNNNNNNNNNNNNNNNNNNNNNNNNNNNNNN

65401 NNNNNNNNNNNNNNNNNNNNNNNNNNNNNNNNNNNNNNNNNNNNNNNNNNNNNNNNNNNN
65401 NNNNNNNNNNNNNNNNNNNNNNNNNNNNNNNNNNNNNNNNNNNNNNNNNNNNNNNNNNNN

65461 NNNNNNNNNNNNNNNNNNNNNNNNNNNNNNNNNNNNNNNNNNNNNNNNNNNNNNNNNNNN
65461 NNNNNNNNNNNNNNNNNNNNNNNNNNNNNNNNNNNNNNNNNNNNNNNNNNNNNNNNNNNN

65521 NNNNNNNNNNNNNNNNNNNNNNNNNNNNNNNNNNNNNNNNNNNNNNNNNNNNNNNNNNNN
65521 NNNNNNNNNNNNNNNNNNNNNNNNNNNNNNNNNNNNNNNNNNNNNNNNNNNNNNNNNNNN

65581 NNNNNNNNNNNNNNNNNNNNNNNNNNNNNNNNNNNNNNNNNNNNNNNNNNNNNNNNNNNN
65581 NNNNNNNNNNNNNNNNNNNNNNNNNNNNNNNNNNNNNNNNNNNNNNNNNNNNNNNNNNNN

65641 NNNNNNNNNNNNNNNNNNNNNNNNNNNNNNNNNNNNNNNNNNNNNNNNNNNNNNNNNNNN
65641 NNNNNNNNNNNNNNNNNNNNNNNNNNNNNNNNNNNNNNNNNNNNNNNNNNNNNNNNNNNN

65701 NNNNNNNNNNNNNNNNNNNNNNNNNNNNNNNNNNNNNNNNNNNNNNNNNNNNNNNNNNNN
65701 NNNNNNNNNNNNNNNNNNNNNNNNNNNNNNNNNNNNNNNNNNNNNNNNNNNNNNNNNNNN

65761 NNNNNNNNNNNNNNNNNNNNNNNNNNNNNNNNNNNNNNNNNNNNNNNNNNNNNNNNNNNN
65761 NNNNNNNNNNNNNNNNNNNNNNNNNNNNNNNNNNNNNNNNNNNNNNNNNNNNNNNNNNNN

65821 NNNNNNNNNNNNNNNNNNNNNNNNNNNNNNNNNNNNNNNNNNNNNNNNNNNNNNNNNNNN
65821 NNNNNNNNNNNNNNNNNNNNNNNNNNNNNNNNNNNNNNNNNNNNNNNNNNNNNNNNNNNN

65881 NNNNNNNNNNNNNNNNNNNNNNNNNNNNNNNNNNNNNNNNNNNNNNNNNNNNNNNNNNNN
65881 NNNNNNNNNNNNNNNNNNNNNNNNNNNNNNNNNNNNNNNNNNNNNNNNNNNNNNNNNNNN

65941 NNNNNNNNNNNNNNNNNNNNNNNNNNNNNNNNNNNNNNNNNNNNNNNNNNNNNNNNNNNN
65941 NNNNNNNNNNNNNNNNNNNNNNNNNNNNNNNNNNNNNNNNNNNNNNNNNNNNNNNNNNNN

66001 NNNNNNNNNNNNNNNNNNNNNNNNNNNNNNNNNNNNNNNNNNNNNNNNNNNNNNNNNNNN
66001 NNNNNNNNNNNNNNNNNNNNNNNNNNNNNNNNNNNNNNNNNNNNNNNNNNNNNNNNNNNN

FIG. 5 (cont'd)

```
66061  NNNNNNNNNNNNNNNNNNNNNNNNNNNNNNNNNNNNNNNNNNNNNNNNNNNNNNNNNNNN
66061  NNNNNNNNNNNNNNNNNNNNNNNNNNNNNNNNNNNNNNNNNNNNNNNNNNNNNNNNNNNN

66121  NNNNNNNNNNNNNNNNNNNNNNNNNNNNNNNNNNNNNNNNNNNNNNNNNNNNNNNNNNNN
66121  NNNNNNNNNNNNNNNNNNNNNNNNNNNNNNNNNNNNNNNNNNNNNNNNNNNNNNNNNNNN

66181  NNNNNNNNNNNNNNNNNNNNNNNNNNNNNNNNNNNNNNNNNNNNNNNNNNNNNNNNNNNN
66181  NNNNNNNNNNNNNNNNNNNNNNNNNNNNNNNNNNNNNNNNNNNNNNNNNNNNNNNNNNNN

66241  NNNNNNNNNNNNNNNNNNNNNNNNNNNNNNNNNNNNNNNNNNNNNNNNNNNNNNNNNNNN
66241  NNNNNNNNNNNNNNNNNNNNNNNNNNNNNNNNNNNNNNNNNNNNNNNNNNNNNNNNNNNN

66301  NNNNNNNNNNNNNNNNNNNNNNNNNNNNNNNNNNNNNNNNNNNNNNNNNNNNNNNNNNNN
66301  NNNNNNNNNNNNNNNNNNNNNNNNNNNNNNNNNNNNNNNNNNNNNNNNNNNNNNNNNNNN

66361  NNNNNNNNNNNNNNNNNNNNNNNNNNNNNNNNNNNNNNNNNNNNNNNNNNNNNNNNNNNN
66361  NNNNNNNNNNNNNNNNNNNNNNNNNNNNNNNNNNNNNNNNNNNNNNNNNNNNNNNNNNNN

66421  NNNNNNNNNNNNNNNNNNNNNNNNNNNNNNNNNNNNNNNNNNNNNNNNNNNNNNNNNNNN
66421  NNNNNNNNNNNNNNNNNNNNNNNNNNNNNNNNNNNNNNNNNNNNNNNNNNNNNNNNNNNN

66481  NNNNNNNNNNNNNNNNNNNNNNNNNNNNNNNNNNNNNNNNNNNNNNNNNNNNNNNNNNNN
66481  NNNNNNNNNNNNNNNNNNNNNNNNNNNNNNNNNNNNNNNNNNNNNNNNNNNNNNNNNNNN

66541  NNNNNNNNNNNNNNNNNNNNNNNNNNNNNNNNNNNNNNNNNNNNNNNNNNNNNNNNNNNN
66541  NNNNNNNNNNNNNNNNNNNNNNNNNNNNNNNNNNNNNNNNNNNNNNNNNNNNNNNNNNNN

66601  NNNNNNNNNNNNNNNNNNNNNNNNNNNNNNNNNNNNNNNNNNNNNNNNNNNNNNNNNNNN
66601  NNNNNNNNNNNNNNNNNNNNNNNNNNNNNNNNNNNNNNNNNNNNNNNNNNNNNNNNNNNN

66661  NNNNNNNNNNNNNNNNNNNNNNNNNNNNNNNNNNNNNNNNNNNNNNNNNNNNNNNNNNNN
66661  NNNNNNNNNNNNNNNNNNNNNNNNNNNNNNNNNNNNNNNNNNNNNNNNNNNNNNNNNNNN

66721  NNNNNNNNNNNNNNNNNNNNNNNNNNNNNNNNNNNNNNNNNNNNNNNNNNNNNNNNNNNN
66721  NNNNNNNNNNNNNNNNNNNNNNNNNNNNNNNNNNNNNNNNNNNNNNNNNNNNNNNNNNNN

66781  NNNNNNNNNNNNNNNNNNNNNNNNNNNNNNNNNNNNNNNNNNNNNNNNNNNNNNNNNNNN
66781  NNNNNNNNNNNNNNNNNNNNNNNNNNNNNNNNNNNNNNNNNNNNNNNNNNNNNNNNNNNN

66841  NNNNNNNNNNNNNNNNNNNNNNNNNNNNNNNNNNNNNNNNNNNNNNNNNNNNNNNNNNNN
66841  NNNNNNNNNNNNNNNNNNNNNNNNNNNNNNNNNNNNNNNNNNNNNNNNNNNNNNNNNNNN

66901  NNNNNNNNNNNNNNNNNNNNNNNNNNNNNNNNNNNNNNNNNNNNNNNNNNNNNNNNNNNN
66901  NNNNNNNNNNNNNNNNNNNNNNNNNNNNNNNNNNNNNNNNNNNNNNNNNNNNNNNNNNNN

66961  NNNNNNNNNNNNNNNNNNNNNNNNNNNNNNNNNNNNNNNNNNNNNNNNNNNNNNNNNNNN
66961  NNNNNNNNNNNNNNNNNNNNNNNNNNNNNNNNNNNNNNNNNNNNNNNNNNNNNNNNNNNN

67021  NNNNNNNNNNNNNNNNNNNNNNNNNNNNNNNNNNNNNNNNNNNNNNNNNNNNNNNNNNNN
67021  NNNNNNNNNNNNNNNNNNNNNNNNNNNNNNNNNNNNNNNNNNNNNNNNNNNNNNNNNNNN

67081  NNNNNNNNNNNNNNNNNNNNNNNNNNNNNNNNNNNNNNNNNNNNNNNNNNNNNNNNNNNN
67081  NNNNNNNNNNNNNNNNNNNNNNNNNNNNNNNNNNNNNNNNNNNNNNNNNNNNNNNNNNNN

67141  NNNNNNNNNNNNNNNNNNNNNNNNNNNNNNNNNNNNNNNNNNNNNNNNNNNNNNNNNNNN
67141  NNNNNNNNNNNNNNNNNNNNNNNNNNNNNNNNNNNNNNNNNNNNNNNNNNNNNNNNNNNN

67201  NNNNNNNNNNNNNNNNNNNNNNNNNNNNNNNNNNNNNNNNNNNNNNNNNNNNNNNNNNNN
67201  NNNNNNNNNNNNNNNNNNNNNNNNNNNNNNNNNNNNNNNNNNNNNNNNNNNNNNNNNNNN

67261  NNNNNNNNNNNNNNNNNNNNNNNNNNNNNNNNNNNNNNNNNNNNNNNNNNNNNNNNNNNN
67261  NNNNNNNNNNNNNNNNNNNNNNNNNNNNNNNNNNNNNNNNNNNNNNNNNNNNNNNNNNNN

67321  NNNNNNNNNNNNNNNNNNNNNNNNNNNNNNNNNNNNNNNNNNNNNNNNNNNNNNNNNNNN
67321  NNNNNNNNNNNNNNNNNNNNNNNNNNNNNNNNNNNNNNNNNNNNNNNNNNNNNNNNNNNN

67381  NNNNNNNNNNNNNNNNNNNNNNNNNNNNNNNNNNNNNNNNNNNNNNNNNNNNNNNNNNNN
67381  NNNNNNNNNNNNNNNNNNNNNNNNNNNNNNNNNNNNNNNNNNNNNNNNNNNNNNNNNNNN
```

FIG. 5 (cont'd)

```
67441  NNNNNNNNNNNNNNNNNNNNNNNNNNNNNNNNNNNNNNNNNNNNNNNNNNNNNNNNNNNN
67441  NNNNNNNNNNNNNNNNNNNNNNNNNNNNNNNNNNNNNNNNNNNNNNNNNNNNNNNNNNNN

67501  NNNNNNNNNNNNNNNNNNNNNNNNNNNNNNNNNNNNNNNNNNNNNNNNNNNNNNNNNNNN
67501  NNNNNNNNNNNNNNNNNNNNNNNNNNNNNNNNNNNNNNNNNNNNNNNNNNNNNNNNNNNN

67561  NNNNNNNNNNNNNNNNNNNNNNNNNNNNNNNNNNNNNNNNNNNNNNNNNNNNNNNNNNNN
67561  NNNNNNNNNNNNNNNNNNNNNNNNNNNNNNNNNNNNNNNNNNNNNNNNNNNNNNNNNNNN

67621  NNNNNNNNNNNNNNNNNNNNNNNNNNNNNNNNNNNNNNNNNNNNNNNNNNNNNNNNNNNN
67621  NNNNNNNNNNNNNNNNNNNNNNNNNNNNNNNNNNNNNNNNNNNNNNNNNNNNNNNNNNNN

67681  NNNNNNNNNNNNNNNNNNNNNNNNNNNNNNNNNNNNNNNNNNNNNNNNNNNNNNNNNNNN
67681  NNNNNNNNNNNNNNNNNNNNNNNNNNNNNNNNNNNNNNNNNNNNNNNNNNNNNNNNNNNN

67741  NNNNNNNNNNNNNNNNNNNNNNNNNNNNNNNNNNNNNNNNNNNNNNNNNNNNNNNNNNNN
67741  NNNNNNNNNNNNNNNNNNNNNNNNNNNNNNNNNNNNNNNNNNNNNNNNNNNNNNNNNNNN

67801  NNNNNNNNNNNNNNNNNNNNNNNNNNNNNNNNNNNNNNNNNNNNNNNNNNNNNNNNNNNN
67801  NNNNNNNNNNNNNNNNNNNNNNNNNNNNNNNNNNNNNNNNNNNNNNNNNNNNNNNNNNNN

67861  NNNNNNNNNNNNNNNNNNNNNNNNNNNNNNNNNNNNNNNNNNNNNNNNNNNNNNNNNNNN
67861  NNNNNNNNNNNNNNNNNNNNNNNNNNNNNNNNNNNNNNNNNNNNNNNNNNNNNNNNNNNN

67921  NNNNNNNNNNNNNNNNNNNNNNNNNNNNNNNNNNNNNNNNNNNNNNNNNNNNNNNNNNNN
67921  NNNNNNNNNNNNNNNNNNNNNNNNNNNNNNNNNNNNNNNNNNNNNNNNNNNNNNNNNNNN

67981  NNNNNNNNNNNNNNNNNNNNNNNNNNNNNNNNNNNNNNNNNNNNNNNNNNNNNNNNNNNN
67981  NNNNNNNNNNNNNNNNNNNNNNNNNNNNNNNNNNNNNNNNNNNNNNNNNNNNNNNNNNNN

68041  NNNNNNNNNNNNNNNNNNNNNNNNNNNNNNNNNNNNNNNNNNNNNNNNNNNNNNNNNNNN
68041  NNNNNNNNNNNNNNNNNNNNNNNNNNNNNNNNNNNNNNNNNNNNNNNNNNNNNNNNNNNN

68101  NNNNNNNNNNNNNNNNNNNNNNNNNNNNNNNNNNNNNNNNNNNNNNNNNNNNNNNNNNNN
68101  NNNNNNNNNNNNNNNNNNNNNNNNNNNNNNNNNNNNNNNNNNNNNNNNNNNNNNNNNNNN

68161  NNNNNNNNNNNNNNNNNNNNNNNNNNNNNNNNNNNNNNNNNNNNNNNNNNNNNNNNNNNN
68161  NNNNNNNNNNNNNNNNNNNNNNNNNNNNNNNNNNNNNNNNNNNNNNNNNNNNNNNNNNNN

68221  NNNNNNNNNNNNNNNNNNNNNNNNNNNNNNNNNNAAGCTTTGATTGGGCCGTTACTGTCT
68221  NNNNNNNNNNNNNNNNNNNNNNNNNNNNNNNNNNTTCGAAACTAACCCGGCAATGACAGA

68281  TTTGACCTTTCTTGTTTGCTTGCCCTTTTGTTTCTTTCCTCCTTTTTCCTTCCTTCCTGT
68281  AAACTGGAAAGAACAAACGAACGGGAAAACAAAGAAAGGAGGAAAAAGGAAGGAAGGACA

68341  CTTTCTTCTTCCTTCCTTCCTTTCTTCCTTTTTCTTTTTAATTTTCCTCCTTTCTCTTTC
68341  GAAAGAAGAAGGAAGGAAGGAAAGAAGGAAAAAGAAAAATTAAAAGGAGGAAAGAGAAAG

68401  TCCTTTCTTTCCTTCCTTCTTTCCTCTTTTTTTCTTTCCTCCCTCCCTCCCTTTCTTTCT
68401  AGGAAAGAAAGGAAGGAAGAAAGGAGAAAAAAAGAAAGGAGGGAGGGAGGGAAAGAAAGA

68461  TCCTTCCTTTCTTTCTTCCCTCCTTCCCTCCCCACCCTCCCTCCCTTCCCCTCGTCTCCC
68461  AGGAAGGAAAGAAAGAAGGGAGGAAGGGAGGGGTGGGAGGGAGGGAAGGGGAGCAGAGGG

68521  TTCCCCTCGTCTCCCTTCCCCTCCCCTCCCTCCCTCCCTTCCTCCTTTTTCTTTCCCTTT
68521  AAGGGGAGCAGAGGGAAGGGGAGGGGAGGGAGGGAGGGAAGGAGGAAAAAGAAAGGGAAA

68581  CCTCCTTCCTTCCTTCCTCTCTTCTTTTCTCCATCCCTTTCTTCCTTTTAACATTTGATC
68581  GGAGGAAGGAAGGAAGGAGAGAAGAAAAGAGGTAGGGAAAGAAGGAAAATTGTAAACTAG

68641  ATGGGTACCATTTCATCAAGATTCTGTTACTTAGGTCCAAGGACTAGTGACCAAATTGTT
68641  TACCCATGGTAAAGTAGTTCTAAGACAATGAATCCAGGTTCCTGATCACTGGTTTAACAA

68701  TTTCCCAGGAGTAAACTTTTCTACAAGACATAGAGAAATGACTGCCAGTGCCATCAGGCA
68701  AAAGGGTCCTCATTTGAAAAGATGTTCTGTATCTCTTTACTGACGGTCACGGTAGTCCGT

68761  CACCATCCTGTGTGATAGGTAACCTAAAATAATGGTACAGCGGGGAGTAACTGGAAGAGT
68761  GTGGTAGGACACACTATCCATTGGATTTTATTACCATGTCGCCCCTCATTGACCTTCTCA
```

FIG. 5 (cont'd)

68821 CACAACTACACAAATCTCTTGCATTTTCCTGATCATTAAATGAATTAGGGATTTCCTGGT
68821 GTGTTGATGTGTTTAGAGAACGTAAAAGGACTAGTAATTTACTTAATCCCTAAAGGACCA

68881 TTGAGATTTGTGGACAAGGAGAACTACTTCTTTGTACAAGAGGCTTGTGCCAGGAGAAGA
68881 AACTCTAAACACCTGTTCCTCTTGATGAAGAAACATGTTCTCCGAACACGGTCCTCTTCT

68941 CACGCTGTGGTTACAATGTTACTGTCTCTAGCTATGGTCATTTCATGTCTTTAACTGAGT
68941 GTGCGACACCAATGTTACAATGACAGAGATCGATACCAGTAAAGTACAGAAATTGACTCA

69001 GTACCTAGAGTGTAATACAGTGCAGCAGTGATGGGCTGAAGGCCTAATGCACCAGCACAC
69001 CATGGATCTCACATTATGTCACGTCGTCACTACCCGACTTCCGGATTACGTGGTCGTGTG

69061 ATGCCTGGAAGACCTAACGTTGAGAATCCGCATTTTTTTCATCACTCACATTTATTTTGC
69061 TACGGACCTTCTGGATTGCAACTCTTAGGCGTAAAAAAAGTAGTGAGTGTAAATAAAACG

69121 ATCTCCCTGTTTTGATTACCTTCAGAGACCCAAGCACTTGCTTTTGTATATTTGAGTCTG
69121 TAGAGGGACAAAACTAATGGAAGTCTCTGGGTTCGTGAACGAAAACATATAAACTCAGAC

69181 GGTTTTATTTTCCTTTTAGAAATAGTCCAAAATCCTTTTAGAGCCTAGACCTTTGAATAA
69181 CCAAAATAAAAGGAAAATCTTTATCAGGTTTTAGGAAAATCTCGGATCTGGAAACTTATT

69241 AGTGCTAACTTAACCTGAGGAATGCTGTTTTTTTGTTCACAAATAAGGCTTAATTGTGAA
69241 TCACGATTGAATTGGACTCCTTACGACAAAAAAACAAGTGTTTATTCCGAATTAACACTT

69301 GTCGTGAGAATTGCTTTCTGAGCTGACTTATAAATTTACCCACCTCTTTTTCCCCAAACC
69301 CAGCACTCTTAACGAAAGACTCGACTGAATATTTAAATGGGTGGAGAAAAAGGGGTTTGG

69361 CCCAAAAAAATCCTCCAGAAGGTGAGCCCAGCTTGTTGTAAAAGATTTTGAAGCAGAAGTC
69361 GGGTTTTTTAGGAGGTCTTCCACTCGGGTCGAACAACATTTTCTAAAACTTCGTCTTCAG

69421 CTGGGTTTAAGCTTCAGTTCTCTGCCTTACCAGAATCGGGATGTGTGGGGCAGGCCTACC
69421 GACCCAAATTCGAAGTCAAGAGACGGAATGGTCTTAGCCCTACACACCCCGTCCGGATGG

69481 TCCTCTTTCTTCATCTGCAAAATACATTGAATGAAATCATATTTTTTCCTAAGTATATGA
69481 AGGAGAAAGAAGTAGACGTTTTATGTAACTTACTTTAGTATAAAAAAGGATTCATATACT

69541 CATGTAAAGTGGTATTTCAAAAACTCATTAATCTGCATGACCAGGTCAGAAAAGACACAC
69541 GTACATTTCACCATAAAGTTTTTGAGTAATTAGACGTACTGGTCCAGTCTTTTCTGTGTG

69601 CTTTTGCCTTGTGTCTAGTGTGTGACTGTCCTCACATGTAGATGACCCAGGCCACATCCG
69601 GAAAACGGAACACAGATCACACACTGACAGGAGTGTACATCTACTGGGTCCGGTGTAGGC

69661 CTGATGTTGTCTTCCTTTACTTCTTTGTCCCTTCCAATGACTCCTTTATGAAGTCAATCA
69661 GACTACAACAGAAGGAAATGAAGAAACAGGGAAGGTTACTGAGGAAATACTTCAGTTAGT

69721 GCAGTGTTTCTAAGCCAGGTTCCTTCTCTTCACACATCCCCAACCCACAGGGCAAGTCAT
69721 CGTCACAAAGATTCGGTCCAAGGAAGAGAAGTGTGTAGGGGTTGGGTGTCCCGTTCAGTA

69781 CCACATTTTGCCTCTCTATTTTTTGTGCTTTGGGAAACACATTTTACAACTTCCAAACTA
69781 GGTGTAAAACGGAGAGATAAAAAACACGAAACCCTTTGTGTAAAATGTTGAAGGTTTGAT

69841 TTTGCCTAAGTTCATCTGAGCACATCTAGAATTATTCCACTCCTCTGCATCAGTGCTAAA
69841 AAACGGATTCAAGTAGACTCGTGTAGATCTTAATAAGGTGAGGAGACGTAGTCACGATTT

69901 AGTACAATCATGTATAAGCTGTTATACTCCCGTTATTTTGTACCTCATGTGCAGGTAGAT
69901 TCATGTTAGTACATATTCGACAATATGAGGGCAATAAAACATGGAGTACACGTCCATCTA

69961 TGCAAGTTCCTTGCAGGCAGGTACTACATCTACTTGAATTGCTTCACGATCACATAACAC
69961 ACGTTCAAGGAACGTCCGTCCATGATGTAGATGAACTTAACGAAGTGCTAGTGTATTGTG

70021 AATGCAGTGTTAAAAGTAGAAAAGTAATTGACATCTTGACTAACAGAAACACTAAATTCA
70021 TTACGTCACAATTTTCATCTTTTCATTAACTGTAGAACTGATTGTCTTTGTGATTTAAGT

70081 GTGTATTGTGATGATACCTTTTTAAGAGATAGGCTATAGAAATAGAAAATCATCTTAGTT
70081 CACATAACACTACTATGGAAAAATTCTCTATCCGATATCTTTATCTTTTAGTAGAATCAA

70141 GGAATTGAAAGTCAAGAAGCAACATTTTAAGTAAGAGATGAAAATACTTAAAAGGGAAAG
70141 CCTTAACTTTCAGTTCTTCGTTGTAAAATTCATTCTCTACTTTTATGAATTTTCCCTTTC

FIG. 5 (cont'd)

```
70201  GAGCAGTGCTTACACAGATGAGGGGAAAAAATAAAATGTATCATCTAAAAATTTAAATCA
70201  CTCGTCACGAATGTGTCTACTCCCCTTTTTTATTTTACATAGTAGATTTTTAAATTTAGT

70261  AATATATTAGGTTGGTGCAAAAGTAACTGCGATTTTTGCCATTAAAAGTAATAGCAAAAA
70261  TTATATAATCCAACCACGTTTTCATTGACGCTAAAAACGGTAATTTTCATTATCGTTTTT

70321  CCACGGTTACTTTTGCACCAACCTAATAGATGGGAAAAATAAGAGGAATGAATATTTTAA
70321  GGTGCCAATGAAAACGTGGTTGGATTATCTACCCTTTTTATTCTCCTTACTTATAAAATT

70381  GCTTTGCTATATAATTAAAATATTCTTAGAAGTCTGGAGTCTGTGAAGGTCACACCCTCT
70381  CGAAACGATATATTAATTTTATAAGAATCTTCAGACCTCAGACACTTCCAGTGTGGGAGA

70441  GGTCTTCTCCCAGCCCATAGGGTATAAATAATCTGAATTGACGGCATCCAGGGATCTCAG
70441  CCAGAAGAGGGTCGGGTATCCCATATTTATTAGACTTAACTGCCGTAGGTCCCTAGAGTC

70501  AAATTATTAGTACATCCCACAGTGAATTACCACCTTACTAAAATATTCATGGGTATATAC
70501  TTTAATAATCATGTAGGGTGTCACTTAATGGTGGAATGATTTTATAAGTACCCATATATG

70561  TATGGATTTGTTTTATCCTATTTAGTCTTAAAAACTATAAAGAAATCTGCAGGCTTATTA
70561  ATACCTAAACAAAATAGGATAAATCAGAATTTTTGATATTTCTTTAGACGTCCGAATAAT

70621  ACATATTACTCAGAATCATATTGTCTCCAAAGCACAAACTGAATCAGTTACAAGATATTG
70621  TGTATAATGAGTCTTAGTATAACAGAGGTTTCGTGTTTGACTTAGTCAATGTTCTATAAC

70681  GACTAGAGATCATGGCAAATCAGAGGTACATAAGACCTAGTTCCGTTGTGGAGCTAAACA
70681  CTGATCTCTAGTACCGTTTAGTCTCCATGTATTCTGGATCAAGGCAACACCTCGATTTGT

70741  AACTGCAGAGACCTAAAGGGAAGCCTTGCACCACACTCTAGGTTTGGAGCTCAGGTTTTG
70741  TTGACGTCTCTGGATTTCCCTTCGGAACGTGGTGTGAGATCCAAACCTCGAGTCCAAAAC

70801  AGTGGTGTCAGCACTCCAGAACACATGGGATCCCCGGGAGGTGGAAATTGAGCCGTCTTT
70801  TCACCACAGTCGTGAGGTCTTGTGTACCCTAGGGGCCCTCCACCTTTAACTCGGCAGAAA

70861  GGAGAATCAGCTAATGAGACAGATGCATGTTAAATGTCTGTTGTGGCCCAGGCACTCTGC
70861  CCTCTTAGTCGATTACTCTGTCTACGTACAATTTACAGACAACACCGGGTCCGTGAGACG

70921  TAGGCAGAGGGGTGAACCAGAAGAATGAGATTCATGGGGCCAAAGAATTTGCCTTCTGGT
70921  ATCCGTCTCCCCACTTGGTCTTCTTACTCTAAGTACCCCGGTTTCTTAAACGGAAGACCA

70981  GTAAGAAAAGATGGAGGCAGCTTGGCAGAAAGAAAAAAAAGGTAAAAGATAGAAATGAAA
70981  CATTCTTTTCTACCTCCGTCGAACCGTCTTTCTTTTTTTTCCATTTTCTATCTTTACTTT

71041  TACAGAATAATCTATCTCCTCATCCCACAAGCAATTCTGCCTGGTTTGTGGCTCACGCCT
71041  ATGTCTTATTAGATAGAGGAGTAGGGTGTTCGTTAAGACGGACCAAACACCGAGTGCGGA

71101  GTAATCCCAGCACTTTGGGAGGCCGAGGCAGGAGGATCACTTGAGGTCAGGAGTTCGAGA
71101  CATTAGGGTCGTGAAACCCTCCGGCTCCGTCCTCCTAGTGAACTCCAGTCCTCAAGCTCT

71161  CTAGCCTGGACCACAAGGTGAAACCTCATCTCTACTAAAAATGCAAAAAAATTTAGGGCC
71161  GATCGGACCTGGTGTTCCACTTTGGAGTAGAGATGATTTTTACGTTTTTTTAAATCCCGG

71221  GGGTGCAGTGGCAGTTCTGCCTGGTTTGAACATCTGGTTCAGTTAAAATACTTCATGAAA
71221  CCCACGTCACCGTCAAGACGGACCAAACTTGTAGACCAAGTCAATTTTATGAAGTACTTT

71281  ATATTTAGCTTGATGCACTGAAATCCATCACTGCTTTTGTGGGATGCACTGACTGCAGTC
71281  TATAAATCGAACTACGTGACTTTAGGTAGTGACGAAAACACCCTACGTGACTGACGTCAG

71341  TGACTGTTCTCCTAGTGGAAAGGGGAGCAATAGCTTCTGTCTGCATGTGCATGAAACAGA
71341  ACTGACAAGAGGATCACCTTTCCCCTCGTTATCGAAGACAGACGTACACGTACTTTGTCT

71401  TGGAAATTTAGAAGAGATTCTAGTGCAGACAACTTCATCCCACCCCCGCTGCCCACAGAG
71401  ACCTTTAAATCTTCTCTAAGATCACGTCTGTTGAAGTAGGGTGGGGGCGACGGGTGTCTC

71461  CTAGCCATGTGCACGGTGTGTTTGAACAATGTTATGTTGCTGCTGTGCACAGAGATCCCC
71461  GATCGGTACACGTGCCACACAAACTTGTTACAATACAACGACGACACGTGTCTCTAGGGG

71521  AGTCTCATAAAACATACTGGATGGAAGGCTGTCGAGAGATCATCAGGCCCCAGTGCATAA
71521  TCAGAGTATTTTGTATGACCTACCTTCCGACAGCTCTCTAGTAGTCCGGGGTCACGTATT
```

FIG. 5 (cont'd)

```
71581  GTTCTTCCTAAGCATCCTTAACAGGTGATCACCTCGCCTATTGAGAACCCTCAGGAGGCA
71581  CAAGAAGGATTCGTAGGAATTGTCCACTAGTGGAGCGGATAACTCTTGGGAGTCCTCCGT

71641  GCCCACTTACGGAAGCACTGATTGTTACAAAAGCCCTGAACTAAATCTGCTTGTCTCTAA
71641  CGGGTGAATGCCTTCGTGACTAACAATGTTTTCGGGACTTGATTTAGACGAACAGAGATT

71701  AGCCAGCCCTGCAGATGTCTGCAGTGTAACTACTTTCTCTTCTCTCAAGCAGTTCAGCCC
71701  TCGGTCGGGACGTCTACAGACGTCACATTGATGAAAGAGAAGAGAGTTCGTCAAGTCGGG

71761  TTCAAATCATTGACAACAGCTCTACAAAGCCCTCTAAATAGCCCGTTCTCCTGGCTAAAG
71761  AAGTTTAGTAACTGTTGTCGAGATGTTTCGGGAGATTTATCGGGCAAGAGGACCGATTTC

71821  TGTGTTGGTTTCCTCAGCATATGATGAAATAAACACCATGATGCCTTTGCCTTGCTTTTT
71821  ACACAACCAAAGGAGTCGTATACTACTTTATTTGTGGTACTACGGAAACGGAACGAAAAA

71881  CTTGCTGGTCTCACTCTTCCCTGGCATTCTTCAATGTGCCCAAGTCCTTCCTAGAACATT
71881  GAACGACCAGAGTGAGAAGGGACCGTAAGAAGTTACACGGGTTCAGGAAGGATCTTGTAA

71941  GCACCCAAAGGGCCTTCCTGGTCTTTCCAGGGAATGCAGAATGAAAAAGAAATCCCATCC
71941  CGTGGGTTTCCCGGAAGGACCAGAAAGGTCCCTTACGTCTTACTTTTTCTTTAGGGTAGG

72001  CCTGCCTCGAAAGGAGCTCTTCTGTGTGTAAGTGTACCTTCCCCCTCAGGGCATAATGGG
72001  GGACGGAGCTTTCCTCGAGAAGACACACATTCACATGGAAGGGGGAGTCCCGTATTACCC

72061  AAACAGTTTGCCAAAGCTAACTGTGTAATTTCACATGACTCACTGCCGTTAGTCTGAGAA
72061  TTTGTCAAACGGTTTCGATTGACACATTAAAGTGTACTGAGTGACGGCAATCAGACTCTT

72121  AGCATGGCATATTAAACTCATTTTCCATGCTTCCCAACTTTATTTACTATTCCATTTCTG
72121  TCGTACCGTATAATTTGAGTAAAAGGTACGAAGGGTTGAAATAAATGATAAGGTAAAGAC

72181  AGGGGCAGAGAGCTGAGCAGGAATAACACCTTCCTTGCTCCTCCTAATGGGGCACATGTG
72181  TCCCCGTCTCTCGACTCGTCCTTATTGTGGAAGGAACGAGGAGGATTACCCCGTGTACAC

72241  CACATATAAAATTGTGTTCGATCTTTGCAGCCACGACCCATGTTAACTGTCAACTGAGAA
72241  GTGTATATTTTAACACAAGCTAGAAACGTCGGTGCTGGGTACAATTGACAGTTGACTCTT

72301  CTCATGAGTCAGTTTCTCAGGAACAGCCCTGAAGACATTATCTCCTGCATCTTGTATTTG
72301  GAGTACTCAGTCAAAGAGTCCTTGTCGGGACTTCTGTAATAGAGGACGTAGAACATAAAC

72361  TGCCTTTGATATTTGGAGGGAAGGGTAGGATCTGGCAATTATCGTTATCTCATTTGGTTC
72361  ACGGAAACTATAAACCTCCCTTCCCATCCTAGACCGTTAATAGCAATAGAGTAAACCAAG

72421  AGTGTATTTCATTTCAGCCTGTTAAGATCTTTTGGAAATACTGTATGTGCTAGTTACAGG
72421  TCACATAAAGTAAAGTCGGACAATTCTAGAAAACCTTTATGACATACACGATCAATGTCC

72481  GACAGTGATAAATAAGACAGCATTCCTGTCCTTGAGATGCTATTTCCACAGCTCCATGAG
72481  CTGTCACTATTTATTCTGTCGTAAGGACAGGAACTCTACGATAAAGGTGTCGAGGTACTC

72541  ATGCCTAGTTAAAAACAGAGCCTTTTTTGGAAACAGCCTACTAATCTGTTAAAATAATAA
72541  TACGGATCAATTTTTGTCTCGGAAAAAACCTTTGTCGGATGATTAGACAATTTTATTATT

72601  TGGAAAAAGATAAAGTTAGCATACCTGAGCTGCAAGGGCTGCCTCCTGGTCTGATCTCTG
72601  ACCTTTTTCTATTTCAATCGTATGGACTCGACGTTCCCGACGGAGGACCAGACTAGAGAC

72661  ATAAGGATCAGATCCTAGAGCCTCTGAGATCCCTGTCCTCCCTGTCTGCACAAGCACTCG
72661  TATTCCTAGTCTAGGATCTCGGAGACTCTAGGGACAGGAGGGACAGACGTGTTCGTGAGC

72721  CAGAAGGAGAAACAGTTTACGGTGGTTCATCATGACTTTGAACCAAGCTTAAAGTCAAAG
72721  GTCTTCCTCTTTGTCAAATGCCACCAAGTAGTACTGAAACTTGGTTCGAATTTCAGTTTC

72781  TCATACTCTTTAAACCATTGGAAACCAAGTTTTTGCGAGTTGCCTAAAGTGGGCAAAAAT
72781  AGTATGAGAAATTTGGTAACCTTTGGTTCAAAAACGCTCAACGGATTTCACCCGTTTTTA

72841  CCCACAATGCACCTGAGCACAAGCAGGAAAACATGCCATTGTCTCCCCAGGAGCCCTCCT
72841  GGGTGTTACGTGGACTCGTGTTCGTCCTTTTGTACGGTAACAGAGGGGTCCTCGGGAGGA

72901  TGACTTCTACTTTACTTTATCCATTGACACTAGTCTTATAAGTAGCTTTGTCTGTCCAAT
72901  ACTGAAGATGAAATGAAATAGGTAACTGTGATCAGAATATTCATCGAAACAGACAGGTTA
```

FIG. 5 (cont'd)

```
72961  TTTTAATTGAATTTCGTTTTTATTTTCGTGAGTGGAAATATCACTTTGAAAGAAATCAGT
72961  AAAATTAACTTAAAGCAAAAATAAAAGCACTCACCTTTATAGTGAAACTTTCTTTAGTCA

73021  CCTCTCCTGAAATCCAGAATTCCTGGAGCTCAGTTTACATGTTTGACGCGTGTCACATGA
73021  GGAGAGGACTTTAGGTCTTAAGGACCTCGAGTCAAATGTACAAACTGCGCACAGTGTACT

73081  TTCCACAAGTCACTCAAGGGCAGGAGGATTACCATCGATACGGAAAGATTTCTTAGAAAG
73081  AAGGTGTTCAGTGAGTTCCCGTCCTCCTAATGGTAGCTATGCCTTTCTAAAGAATCTTTC

73141  CTTAAGTGAAAGGGAAACCAGGGAGAAAGTGTGCTTCGTGAGAATAGGTATGCGGACGGC
73141  GAATTCACTTTCCCTTTGGTCCCTCTTTCACACGAAGCACTCTTATCCATACGCCTGCCG

73201  TCTTTGTGACGCTCTGTGCAACCCTCGTGTTTGCATTGAACCAAGCTGTGCTGCAGATGG
73201  AGAAACACTGCGAGACACGTTGGGAGCACAAACGTAACTTGGTTCGACACGACGTCTACC

73261  ACACCCATCCCATTTCCCCGACTCATACCAGGGAGGCCCACTTTGCAAGGTACACAGAGG
73261  TGTGGGTAGGGTAAAGGGGCTGAGTATGGTCCCTCCGGGTGAAACGTTCCATGTGTCTCC

73321  GGACCACAGAGCAGGGGGCCATGCAGGGGACCAAGGGACATTTTAGTGTAACCAAAGTGT
73321  CCTGGTGTCTCGTCCCCCGGTACGTCCCCTGGTTCCCTGTAAAATCACATTGGTTTCACA

73381  GAAGTATGCCCTTTATTTCAAAAGAATAAAGAAAATCACAGGTTTTCCCGCTGATATGCC
73381  CTTCATACGGGAAATAAAGTTTTCTTATTTCTTTTAGTGTCCAAAAGGGCGACTATACGG

73441  AGGGACATTTCCAAGAGAATTCCTTTTTTGAGAGAAATCTCCTTTGATATCCCATCAGTC
73441  TCCCTGTAAAGGTTCTCTTAAGGAAAAAACTCTCTTTAGAGGAAACTATAGGGTAGTCAG

73501  AGCCATACTGCATAATTGTTAGATAGTGAAAGAAATTCATTTTTTAAGTTTGTCAGAAAA
73501  TCGGTATGACGTATTAACAATCTATCACTTTCTTTAAGTAAAAAATTCAAACAGTCTTTT

73561  ATAAATTCTTTGAAGTCTTAAATTGTTGCCTCCGGACATGACATATCTGGCTCTTCCAGA
73561  TATTTAAGAAACTTCAGAATTTAACAACGGAGGCCTGTACTGTATAGACCGAGAAGGTCT

73621  ATCCATGTTAGTCCTAGCTGAGGAAGAAGGAGAAGGAGAGGGGCGTTTGTTGATTATTGA
73621  TAGGTACAATCAGGATCGACTCCTTCTTCCTCTTCCTCTCCCCGCAAACAACTAATAACT

73681  TTTTGTAAGATGCCCCACACGTTGGCTATTAGCAGAATTCTCACTTCTAAAAGGAAAATG
73681  AAAACATTCTACGGGGTGTGCAACCGATAATCGTCTTAAGAGTGAAGATTTTCCTTTTAC

73741  AGTGTGAGCTATGTTCAATGAGAAACAGTTATTTTTGGGACATTCTTTGAGGTAAAACAC
73741  TCACACTCGATACAAGTTACTCTTTGTCAATAAAAACCCTGTAAGAAACTCCATTTTGTG

73801  CTCCTTAAGATGCTGCTTCCTTATTGCTATGGGACCAAGATTAGAGCAAGAACATAGTGG
73801  GAGGAATTCTACGACGAAGGAATAACGATACCCTGGTTCTAATCTCGTTCTTGTATCACC

73861  TTTTCAGACCCTGGACATCATCCACAGCCGCAGCAGAGGCCCTGCCCACTTGAACAATGA
73861  AAAAGTCTGGGACCTGTAGTAGGTGTCGGCGTCGTCTCCGGGACGGGTGAACTTGTTACT

73921  GACAGGCCACCATTTTGTTTCGAGAATGAGCAAAGTGAACCACCATGCCAGATATTGTTA
73921  CTGTCCGGTGGTAAAACAAAGCTCTTACTCGTTTCACTTGGTGGTACGGTCTATAACAAT

73981  AGTCAGCAACTCTTCTGAAGATGGACATAGTAAAAAATAAACAAACAAGGCAGCACTTGA
73981  TCAGTCGTTGAGAAGACTTCTACCTGTATCATTTTTTATTTGTTTGTTCCGTCGTGAACT

74041  GATGGTCATGGCAGAGCAATCTCAACAAGCGATTTGTTATTTTGCACAGTGATGTACCCA
74041  CTACCAGTACCGTCTCGTTAGAGTTGTTCGCTAAACAATAAAACGTGTCACTACATGGGT

74101  CTCATTGAATAAAATGCACCAGAACCATGCACTACAGATGCTAAGGAGAGTTGTCCTTCA
74101  GAGTAACTTATTTTACGTGGTCTTGGTACGTGATGTCTACGATTCCTCTCAACAGGAAGT

74161  ACAAAGGAGATAGGCCCCACTGGCCGTGGGGCAGTTTATGTTATTTGGTCCTTGTCATGG
74161  TGTTTCCTCTATCCGGGGTGACCGGCACCCCGTCAAATACAATAAACCAGGAACAGTACC

74221  GCAGGCATGGCCCTTTCTATGCTTCACAGATGAGGAAGGTCCCTGGCACAGGTCCAGTCT
74221  CGTCCGTACCGGGAAAGATACGAAGTGTCTACTCCTTCCAGGGACCGTGTCCAGGTCAGA

74281  CCAGCATGGCCTAGAGGTGGCAGGTGCTACTTAGCATCGCCAGCCTCCTGCTTGGTCATG
74281  GGTCGTACCGGATCTCCACCGTCCACGATGAATCGTAGCGGTCGGAGGACGAACCAGTAC
```

FIG. 5 (cont'd)

```
74341  GGGTCAGCCAGTTTATAACACGAACGGAGGTTAATGAACTGATCTTCCCATCGCACAACT
74341  CCCAGTCGGTCAAATATTGTGCTTGCCTCCAATTACTTGACTAGAAGGGTAGCGTGTTGA

74401  GGTATGAACCCACATCTTCTGATTATAAATCTTTTGCTCTTTAACTCTTAGTCATTACCA
74401  CCATACTTGGGTGTAGAAGACTAATATTTAGAAAACGAGAAATTGAGAATCAGTAATGGT

74461  CTGTCTAGTGTAGGCCTGTGTGTTCATGGCCTTTGTTGCCACCAAAAGATCAACTATTAG
74461  GACAGATCACATCCGGACACACAAGTACCGGAAACAACGGTGGTTTTCTAGTTGATAATC

74521  CTGAATAACATACTGAGACATGTTGGTGTTGTGTTCTAAATAGCACTAGTAAACTGTTAG
74521  GACTTATTGTATGACTCTGTACAACCACAACACAAGATTTATCGTGATCATTTGACAATC

74581  GGAAATCTGACTATATAGCTACTATCCAGTCTAGTTTTTCTTGCGAAGTGTTTGTTGAGT
74581  CCTTTAGACTGATATATCGATGATAGGTCAGATCAAAAAGAACGCTTCACAAACAACTCA

74641  GTGTAATGAGGAGTAAGGAAGGTGAATAAGAAATGGCCTGAGTCTTTATAAAATAAGCAA
74641  CACATTACTCCTCATTCCTTCCACTTATTCTTTACCGGACTCAGAAATATTTTATTCGTT

74701  GGAGAGAAAACAGTTTTGATGAGAAGCGCATGGAATTTTTAGAAGATAGGACGTGTATTA
74701  CCTCTCTTTTGTCAAAACTACTCTTCGCGTACCTTAAAAATCTTCTATCCTGCACATAAT

74761  TGTACCTATAAGAATGGGTAGGATTTTAGAAGAGATGGATGGGGAAAAGGAACAGGGAGT
74761  ACATGGATATTCTTACCCATCCTAAAATCTTCTCTACCTACCCCTTTTCCTTGTCCCTCA

74821  GGGAACAAAACGTGGACCAAGGAAGAGCAGGTTTAGCCATGGAAGCCTCACCGCCGGCTT
74821  CCCTTGTTTTGCACCTGGTTCCTTCTCGTCCAAATCGGTACCTTCGGAGTGGCGGCCGAA

74881  TGGTTTATCGTGGGCCAAGGGGACAGACCCTGTGGGGAGGGCTGGCAGCAGGGAGGTCTT
74881  ACCAAATAGCACCCGGTTCCCCTGTCTGGGACACCCCTCCCGACCGTCGTCCCTCCAGAA

74941  CCAGAAGTCTATCCTGCAGGCAGTAACAGCCACCCAGTCTATAAGCTGAGTGGGCATGGG
74941  GGTCTTCAGATAGGACGTCCGTCATTGTCGGTGGGTCAGATATTCGACTCACCCGTACCC

75001  GGTGATGGGGAATGGGTGGGGAGTTATTGGGGTAACTTACCCCAAAATGATAGCTAGCTG
75001  CCACTACCCCTTACCCACCCCTCAATAACCCCATTGAATGGGGTTTTACTATCGATCGAC

75061  GAACCATTTATTCTATTGCATTTTATCAATAAATCTTATAGGAAGTACCATCCTAGTGAA
75061  CTTGGTAAATAAGATAACGTAAAATAGTTATTTAGAATATCCTTCATGGTAGGATCACTT

75121  AACCCTGTCACATTGAGGGCATTCATGCTTATGTTTTAAAACATGTTATTGGGTCTATGA
75121  TTGGGACAGTGTAACTCCCGTAAGTACGAATACAAAATTTTGTACAATAACCCAGATACT

75181  AAAATAAGGCTGAAACCTATGAGCACCCTCCATGCAAAGTTTCAGTCAAGACTTTGGAAA
75181  TTTTATTCCGACTTTGGATACTCGTGGGAGGTACGTTTCAAAGTCAGTTCTGAAACCTTT

75241  CAAGACAGTGTCTTACTCACTTTATAAATTCATTCAGAAAGCCGTAGGTTTGAAAATTCC
75241  GTTCTGTCACAGAATGAGTGAAATATTTAAGTAAGTCTTTCGGCATCCAAACTTTTAAGG

75301  AAACTTAGATGTAAGAAGCTCTGAGAAACACATGAAATCACCCCCACATCAGTAGAGATG
75301  TTTGAATCTACATTCTTCGAGACTCTTTGTGTACTTTAGTGGGGGTGTAGTCATCTCTAC

75361  TCTCAGCAGACATGGGAAGAGGGGCAGCAGGGTGTAGGGAGGTGGGGCAGCCCCGGGGTG
75361  AGAGTCGTCTGTACCCTTCTCCCCGTCGTCCCACATCCCTCCACCCCGTCGGGGCCCCAC

75421  GGCCTTGCAGGCTGGGCTTGAATCCCATGGCCACCACCGTCCGCTGGGAGGCCTGGAGCC
75421  CCGGAACGTCCGACCCGAACTTAGGGTACCGGTGGTGGCAGGCGACCCTCCGGACCTCGG

75481  GGCTGCCCACTCTCTGACCAGCACATGTTGATGCTGTATCCTTGAAGGGACCGTGGTCTG
75481  CCGACGGGTGAGAGACTGGTCGTGTACAACTACGACATAGGAACTTCCCTGGCACCAGAC

75541  ACATCCTGTGATGCAGACCTGAATCCAGCACCCACAGGGTCTGCACATTCCCTCTTTGAG
75541  TGTAGGACACTACGTCTGGACTTAGGTCGTGGGTGTCCCAGACGTGTAAGGGAGAAACTC

75601  GTGGAGCCCAGCTCCAGAGGCTGGTCCCTGACTCTGTTTCTCAAGAAGCCTGTACAGATG
75601  CACCTCGGGTCGAGGTCTCCGACCAGGGACTGAGACAAAGAGTTCTTCGGACATGTCTAC

75661  TTCCCCTCACCACTGTTTCCAGTCACCTTTGGCTTTCACGGTGCAGATGCTAAGTTTGAT
75661  AAGGGGAGTGGTGACAAAGGTCAGTGGAAACCGAAAGTGCCACGTCTACGATTCAAACTA
```

FIG. 5 (cont'd)

75721 TTTCAGAGCCCATCTGGGAATTTAGTGAACTGAACAGGTAGCATTTCTGAACCCACCCAT
75721 AAAGTCTCGGGTAGACCCTTAAATCACTTGACTTGTCCATCGTAAAGACTTGGGTGGGTA

75781 AACCCATGCCCTCCCCACTGATTTTGAAAGAGAGTTTGCTGCAGGTGACTTTGCAGCTGG
75781 TTGGGTACGGGAGGGGTGACTAAAACTTTCTCTCAAACGACGTCCACTGAAACGTCGACC

75841 GTAGAGAATCTTGGGGCAGGATTCCGAGGCAGGCAGATGAGTGAGGATAAATTGGGTTCT
75841 CATCTCTTAGAACCCCGTCCTAAGGCTCCGTCCGTCTACTCACTCCTATTTAACCCAAGA

75901 GACGGCACGTTACACCAGTGGACTCTAACGACGACCTCACCTCGTGCACAGATAATTCTG
75901 CTGCCGTGCAATGTGGTCACCTGAGATTGCTGCTGGAGTGGAGCACGTGTCTATTAAGAC

75961 CCTTGTGCTTAACCGTTAGAAATGTGTCACTGAAGTGTGAACATATTATGCTGTTAGATT
75961 GGAACACGAATTGGCAATCTTTACACAGTGACTTCACACTTGTATAATACGACAATCTAA

76021 TCCCATCATTTCTGTTCTTTCATTCCCTCTCATTTGCATTGGTTACTCATAAATGTAGAT
76021 AGGGTAGTAAAGACAAGAAAGTAAGGGAGAGTAAACGTAACCAATGAGTATTTACATCTA

76081 CTTTGGTATGATTTGTACAACTGCCGGGTGTCAATCTGTGAAAGAAATAGCAGAGCAAGC
76081 GAAACCATACTAAACATGTTGACGGCCCACAGTTAGACACTTTCTTTATCGTCTCGTTCG

76141 TGGGCTCTGGTAGCGCTTTATCCCTGCGTGCTGGCTTGCCCGGGTTGACTCAGAGGCAGT
76141 ACCCGAGACCATCGCGAAATAGGGACGCACGACCGAACGGGCCCAACTGAGTCTCCGTCA

76201 CTCACATTCAGCTGCGCTGGGGCCAAGGACCCAGGGAGCCAAGTGTGTTTCTGTTTTCTG
76201 GAGTGTAAGTCGACGCGACCCCGGTTCCTGGGTCCCTCGGTTCACACAAAGACAAAAGAC

76261 TATTTAGCAATTTAAGACCTGCGTTTAAATACTAGCTATGCATTCTAGCAAAAGAGGTTT
76261 ATAAATCGTTAAATTCTGGACGCAAATTTATGATCGATACGTAAGATCGTTTTCTCCAAA

76321 ATATTTTAACACAGTAACTCTTAATTGTTTAATTCAGTTCGTGTGTTACCTCTCGGAATA
76321 TATAAAATTGTGTCATTGAGAATTAACAAATTAAGTCAAGCACACAATGGAGAGCCTTAT

76381 AAATAGTGGAAGCCAATTAACTATAGACTTCATTAGTTTGGATTTAAGATCACCAAAACA
76381 TTTATCACCTTCGGTTAATTGATATCTGAAGTAATCAAACCTAAATTCTAGTGGTTTTGT

76441 TTTACCACATCTCAATTGTTCATTACATGCTCTCTCTTTTTTAATGCAGTTTTTATAATA
76441 AAATGGTGTAGAGTTAACAAGTAATGTACGAGAGAGAAAAAATTACGTCAAAAATATTAT

76501 TGGGGAGTGGGGGTGTGGATTTAACCATTATATTTTTATGATATTGGGAGTAGATTTAAC
76501 ACCCCTCACCCCCACACCTAAATTGGTAATATAAAAATACTATAACCCTCATCTAAATTG

76561 CATTATGTAAATTGGATTTTTTAATTTTAAAAAGTCACTTATCTTGATGTAAAATCATGT
76561 GTAATACATTTAACCTAAAAAATTAAAATTTTTCAGTGAATAGAACTACATTTTAGTACA

76621 CTTAGTAACCTTGATAAACTAAGTTTTGCATGATTACACCTTAAGGTTAAAACATATTTC
76621 GAATCATTGGAACTATTTGATTCAAAACGTACTAATGTGGAATTCCAATTTTGTATAAAG

76681 ATTTCATCATTTCCCAGAAGGGGCACTGAATTCACCCATTTCCTGTTTTTCATCTCAGAA
76681 TAAAGTAGTAAAGGGTCTTCCCCGTGACTTAAGTGGGTAAAGGACAAAAAGTAGAGTCTT

76741 TGTTCTGTGTTTCCTCCATATCTACTTTCCCGGCAGCAGGACCCTGGAAGCAGTCACACC
76741 ACAAGACACAAAGGAGGTATAGATGAAAGGGCCGTCGTCCTGGGACCTTCGTCAGTGTGG

76801 AACCTCATTTACCCCACCTGAGATTTGTGCGCTTTGAACATAGTTGCAATCAAATCAACA
76801 TTGGAGTAAATGGGGTGGACTCTAAACACGCGAAACTTGTATCAACGTTAGTTTAGTTGT

76861 ATATCTTTGCTCAGAAATGGATATGTGAAGTAAAATGTGCTGCCCTGTTCATGTATGAAA
76861 TATAGAAACGAGTCTTTACCTATACACTTCATTTTACACGACGGGACAAGTACATACTTT

76921 TCATTCAGCTAGCTGGCCAGTGAGCCCTTCATTGCAACAAAGATTTTTCTAGAGCCCCTG
76921 AGTAAGTCGATCGACCGGTCACTCGGGAAGTAACGTTGTTTCTAAAAAGATCTCGGGGAC

76981 CACTATCTGGGGCTATGTCAGGCCTCACACTCCTGCTCACACGTTTGGAGGCTACCTTGG
76981 GTGATAGACCCCGATACAGTCCGGAGTGTGAGGACGAGTGTGCAAACCTCCGATGGAACC

77041 CCAGTATTACCTTAATCCAGCATTTAGGGGAAGGAGCATTTCAAGACTAAATTTTCTAAA
77041 GGTCATAATGGAATTAGGTCGTAAATCCCCTTCCTCGTAAAGTTCTGATTTAAAAGATTT

FIG. 5 (cont'd)

```
77101  CTGCTCAAGCCTACCTCATTTTATTTCTTGTGTATTTTAACACTTTTGGATGAGGACTCT
77101  GACGAGTTCGGATGGAGTAAAATAAAGAACACATAAAATTGTGAAAACCTACTCCTGAGA

77161  TCCTAGAACCTACTAACAATTCCCCCCCGCCCCCATGCCAAGATTCTTTAAAGACTTTCT
77161  AGGATCTTGGATGATTGTTAAGGGGGGGCGGGGGTACGGTTCTAAGAAATTTCTGAAAGA

77221  TGAAAACGCTTCAGTCTTTTCTTCTTAGCTCAAAAGTACTATCCTAAATACTAGCTCTGG
77221  ACTTTTGCGAAGTCAGAAAAGAAGAATCGAGTTTTCATGATAGGATTTATGATCGAGACC

77281  CATTACAGGGAGTTAATTTGTGGGCACACACAGTAAATTATAAACCCCTTAAGCAGAGAA
77281  GTAATGTCCCTCAATTAAACACCCGTGTGTGTCATTTAATATTTGGGGAATTCGTCTCTT

77341  GATTGTATTATCAGTTTATTAGTTTTCTTATTCATTCCTTCAGCACACATTTCTGTTGCC
77341  CTAACATAATAGTCAAATAATCAAAAGAATAAGTAAGGAAGTCGTGTGTAAAGACAACGG

77401  TCCAATGCAGCAGAGAAATTGACTTCTACAGTTTCCACAACAGTCCAGATTTCAACTGTG
77401  AGGTTACGTCGTCTCTTTAACTGAAGATGTCAAAGGTGTTGTCAGGTCTAAAGTTGACAC

77461  TAGTGCTCTTTCAGCCAGAAAGTACACTTGTGTTTCCCTGGCCATAGGTCCTGAACCTCA
77461  ATCACGAGAAAGTCGGTCTTTCATGTGAACACAAAGGGACCGGTATCCAGGACTTGGAGT

77521  CTTCTGAAAAGTCATTGTGCATAGAGAGCTAATAGCTGTACCCTAAATGATCCTGGCTTT
77521  GAAGACTTTTCAGTAACACGTATCTCTCGATTATCGACATGGGATTTACTAGGACCGAAA

77581  GAATTCTCTTATCTGCTTGGATAGTATTATCTGTCTCTTCCTCTGCATTCTAATTTGCTA
77581  CTTAAGAGAATAGACGAACCTATCATAATAGACAGAGAAGGAGACGTAAGATTAAACGAT

77641  CTTCTAATCTGCTGGGAATTACAATAAGAAAGAACCATTTAATCATTTTTACAACTGTGC
77641  GAAGATTAGACGACCCTTAATGTTATTCTTTCTTGGTAAATTAGTAAAAATGTTGACACG

77701  CTAAAGAGAGTGTGTGTAAGTGCCGAGAGAGTGTATGAGGGACTTGCCCATGAGTAAATG
77701  GATTTCTCTCACACACATTCACGGCTCTCTCACATACTCCCTGAACGGGTACTCATTTAC

77761  CATGAATTTTAGGTCAAGGGTTTTTTGCTTCTCTTTTGGTTGATTACCTCAGAGATCAGT
77761  GTACTTAAAATCCAGTTCCCAAAAAACGAAGAGAAAACCAACTAATGGAGTCTCTAGTCA

77821  TTTACTTTCTTTCTCATTCTTGACCTATCATCACTAGCTGATATGGATGATGTGTACAAC
77821  AAATGAAAGAAAGAGTAAGAACTGGATAGTAGTGATCGACTATACCTACTACACATGTTG

77881  TTCTGAGTAAGAATAATGTCAATGGGACGGGATGGGATTGGCTGGTGATTCTGTTGATCT
77881  AAGACTCATTCTTATTACAGTTACCCTGCCCTACCCTAACCGACCACTAAGACAACTAGA

77941  TAAAGTTTATATATTTTAAGTTTAGTGTTTCAGAATGAGACCAAAGCGGTGACATTTTCA
77941  ATTTCAAATATATAAAATTCAAATCACAAAGTCTTACTCTGGTTTCGCCACTGTAAAAGT

78001  ACCTCTTCGGTCTCTCTTCAGTTTTTTCATTTTAAGTTTTTGTTGTGCTTCTATCACTTA
78001  TGGAGAAGCCAGAGAGAAGTCAAAAAAGTAAAATTCAAAAACAACACGAAGATAGTGAAT

78061  AAGGAAGCCTCCAAGTTGAAATCAAATACTAATGACATTTTTATCTAATGTATAAATGTG
78061  TTCCTTCGGAGGTTCAACTTTAGTTTATGATTACTGTAAAAATAGATTACATATTTACAC

78121  TTTTTATTATTTATTAGGAAATTTATTTTACTTGGCCCTCAGCCATGACATATCATGGCA
78121  AAAAATAATAAATAATCCTTTAAATAAAATGAACCGGGAGTCGGTACTGTATAGTACCGT

78181  TAATCACTATCCTAAATTTGTATATCTTATCCTTGCATAAGGTAAGACTTTCTATGAATT
78181  ATTAGTGATAGGATTTAAACATATAGAATAGGAACGTATTCCATTCTGAAAGATACTTAA

78241  ACACATATTTGTATTTTCCTCTCTTACATATTTTAAGAATTTTTTTATACTTTGTTTTCT
78241  TGTGTATAAACATAAAAGGAGAGAATGTATAAAATTCTTAAAAAAATATGAAACAAAAGA

78301  GCAAATGAAATATTGCTCATAAGCCAGGTGATGGCTGTCCACGCCTCTTTTCCCCTGCTT
78301  CGTTTACTTTATAACGAGTATTCGGTCCACTACCGACAGGTGCGGAGAAAAGGGGACGAA

78361  ACCCTTGCTTAGATCTTATGGTAGAATCTTTTCATAGAAGACACAGAAAGACATGAAAGA
78361  TGGGAACGAATCTAGAATACCATCTTAGAAAAGTATCTTCTGTGTCTTTCTGTACTTTCT

78421  AAGAGCTGGAGAAGCCTGAGGGGCTGCCCAGTGAGTGGTCTGCTAGGATGCTGTGCCACA
78421  TTCTCGACCTCTTCGGACTCCCCGACGGGTCACTCACCAGACGATCCTACGACACGGTGT
```

FIG. 5 (cont'd)

78481 GCCCAGGCACAGGAGGCAGGGAGAGCAATGGGGCCCTTCCCTTCCACCAACATTCAGCAG
78481 CGGGTCCGTGTCCTCCGTCCCTCTCGTTACCCCGGGAAGGGAAGGTGGTTGTAAGTCGTC

78541 AATTTGCAGCTCCATGTTTCCAAAGCTTCCAGGGCACTTGCATTTAGAGAGAGAGAGCAA
78541 TTAAACGTCGAGGTACAAAGGTTTCGAAGGTCCCGTGAACGTAAATCTCTCTCTCTCGTT

78601 GCAAGCTGCCTTTCCTCTTCCTCAGTTCTGCCAGCCACACTCTTGCCATGATGAGCAGTT
78601 CGTTCGACGGAAAGGAGAAGGAGTCAAGACGGTCGGTGTGAGAACGGTACTACTCGTCAA

78661 TCAGCCAAAAGCTCCTTCCCCTGCCCTAACACCTCCTGCAAGGCCTGAGGTCTGGAAGCC
78661 AGTCGGTTTTCGAGGAAGGGGACGGGATTGTGGAGGACGTTCCGGACTCCAGACCTTCGG

78721 ACCTGCGCCTGCTGGCCCCTCCTTTCTTGTTTCTGCAATGGATGTTGTGGCCCTGTGAGG
78721 TGGACGCGGACGACCGGGGAGGAAAGAACAAAGACGTTACCTACAACACCGGGACACTCC

78781 GAGAAGAGAAAAAGAAGTTGCCCTCCTCCCTCTATCCTCACCTCCTGCCATGCTGTCACC
78781 CTCTTCTCTTTTTCTTCAACGGGAGGAGGGAGATAGGAGTGGAGGACGGTACGACAGTGG

78841 CTTATAAGAGAGAAGGGCTAACCATCCAGGCTAATCCTCCAGTGATGCAGGAGAGGACAT
78841 GAATATTCTCTCTTCCCGATTGGTAGGTCCGATTAGGAGGTCACTACGTCCTCTCCTGTA

78901 CCTGGCCGGAAGAGTCAGAGCTTCCAGGTGAGCTCAGGTGGGTCAGCCCCCGAGGCTGTG
78901 GGACCGGCCTTCTCAGTCTCGAAGGTCCACTCGAGTCCACCCAGTCGGGGGCTCCGACAC

78961 AAGAGCCCAGGGGCCAGTAGATGCCACTTTTGCTCCAGGAAGAATCTTCAACTGTGTCCT
78961 TTCTCGGGTCCCCGGTCATCTACGGTGAAAACGAGGTCCTTCTTAGAAGTTGACACAGGA

79021 TTTTATTCAAGGGGCTCTCTTTTCAGCGAATCTCTAGATGTACTAGTCACAAACACTCGC
79021 AAAATAAGTTCCCCGAGAGAAAAGTCGCTTAGAGATCTACATGATCAGTGTTTGTGAGCG

79081 ATTTATTAAAATGTATCCATGATCCCACAATCCTTTTACATATTTCTCTCCAGGAGTATC
79081 TAAATAATTTTACATAGGTACTAGGGTGTTAGGAAAATGTATAAAGAGAGGTCCTCATAG

79141 ACATTTCTGAGGGCCCTGTGCCTGTTTTCTGCAGGAAGTTGCTGTTGTCCCGGGTCCCCC
79141 TGTAAAGACTCCCGGGACACGGACAAAAGACGTCCTTCAACGACAACAGGGCCCAGGGGG

79201 TGCCCCCAGCACCTCTGTTACAAGAAGCAGACCCTTCATGCCACACTGGGACCCAGGGAG
79201 ACGGGGGTCGTGGAGACAATGTTCTTCGTCTGGGAAGTACGGTGTGACCCTGGGTCCCTC

79261 GCCCCAAGCCAGGATGCTGGGATCTTAGTAAAGGTTGGAATGATGTCAGAACATAGAGGA
79261 CGGGGTTCGGTCCTACGACCCTAGAATCATTTCCAACCTTACTACAGTCTTGTATCTCCT

79321 GGCAGAATTCCCCCCATAGCATCATCCTGGAGGGCGCTGATTTGTGTGCTCTGCCAGGTT
79321 CCGTCTTAAGGGGGGTATCGTAGTAGGACCTCCCGCGACTAAACACACGAGACGGTCCAA

79381 CATCTGTGACTCAGGATTTAAAAGCCCCAGGTGTGGTGTCCCTTCTGTGCCTGCAAGGTG
79381 GTAGACACTGAGTCCTAAATTTTCGGGGTCCACACCACAGGGAAGACACGGACGTTCCAC

79441 CGTCTTTAGCAGTTCTCCCTGGTGTGGAAGGATCAGTGGTTCTTGCAGCCTAGGCACCCT
79441 GCAGAAATCGTCAAGAGGGACCACACCTTCCTAGTCACCAAGAACGTCGGATCCGTGGGA

79501 CCACAGCAAGCCCAACACAGGTGCTGTGAGCAGCTGGTTCATGAACGGTGATCCTGGGGA
79501 GGTGTCGTTCGGGTTGTGTCCACGACACTCGTCGACCAAGTACTTGCCACTAGGACCCCT

79561 GAAGAGGAGGATGAAAATGGAAAACCAGTGCAAAGGTGTGTCATCCAGTTGGTTACTGCT
79561 CTTCTCCTCCTACTTTTACCTTTTGGTCACGTTTCCACACAGTAGGTCAACCAATGACGA

79621 GTGGGTGCCCGGGCTTCCATCCCACCAGAGCCCCCACTAGCCAGGGCAGCCTGGCGGAGG
79621 CACCCACGGGCCCGAAGGTAGGGTGGTCTCGGGGGTGATCGGTCCCGTCGGACCGCCTCC

79681 TGAGCATCATTCTGCTTTCTGGCTGCACCTGTGTGGACAGAGCCCGTTCCAAAGCCTCCC
79681 ACTCGTAGTAAGACGAAAGACCGACGTGGACACACCTGTCTCGGGCAAGGTTTCGGAGGG

79741 AGGCACAGGGCAGACATCAAGCAAGGGGCAGAGCTGGGGCGAGGGCTCTGGGTGCCCCCG
79741 TCCGTGTCCCGTCTGTAGTTCGTTCCCCGTCTCGACCCCGCTCCCGAGACCCACGGGGGC

79801 TTATTGAACACAGGCCTGAAGGGAGCCTAAGAGGTGGCTGGCAGGAGATACTACAAGGCA
79801 AATAACTTGTGTCCGGACTTCCCTCGGATTCTCCACCGACCGTCCTCTATGATGTTCCGT

FIG. 5 (cont'd)

```
79861  GAAAGACAGGGCAGCAGTCTTTGTACTGTACGTTTTTGTTTTTTAAGAGAGAACAAAAAG
79861  CTTTCTGTCCCGTCGTCAGAAACATGACATGCAAAAACAAAAAATTCTCTCTTGTTTTTC

79921  TCAAGGTTGAGAGATGAGAAATACTCTTGCCAAAAAGAGAACACCAAAATCCTGGAGTCA
79921  AGTTCCAACTCTCTACTCTTTATGAGAACGGTTTTTCTCTTGTGGTTTTAGGACCTCAGT

79981  CGGGTCTTCCATTACCCTCTCTAGCATTTCTGCTTGTCTTTTCCCTAGTATTGGTGAAGA
79981  GCCCAGAAGGTAATGGGAGAGATCGTAAAGACGAACAGAAAAGGGATCATAACCACTTCT

80041  ATTTTTAAAGTAACCAACCCATACCGTTGGTTACAGGCCCTGTGGTCACCAGGCTGTCTC
80041  TAAAAATTTCATTGGTTGGGTATGGCAACCAATGTCCGGGACACCAGTGGTCCGACAGAG

80101  CCCATGATGGGGATGGAGAGTGGTTAGTGCAGAAACTTAGACCTCCCCTCCAGCTTGTTG
80101  GGGTACTACCCCTACCTCTCACCAATCACGTCTTTGAATCTGGAGGGGAGGTCGAACAAC

80161  AATGCCCTGAAGTTTATCTAGAAGGGAAGATACTCAAGCGTAGGATTTCAGTGATGCATT
80161  TTACGGGACTTCAAATAGATCTTCCCTTCTATGAGTTCGCATCCTAAAGTCACTACGTAA

80221  TGGACAGCATCAGTACTATGCTTCAGCGTCAAAAACGTCACTTTGGGTAGGAACAATACA
80221  ACCTGTCGTAGTCATGATACGAAGTCGCAGTTTTTGCAGTGAAACCCATCCTTGTTATGT

80281  TAATGCGTGGCAATGCCTTTTGTGACACCTGTTCAGGAGATTCCCATAGGAAGCTTCTGA
80281  ATTACGCACCGTTACGGAAAACACTGTGGACAAGTCCTCTAAGGGTATCCTTCGAAGACT

80341  GGCAGAGTCCTCAGGTGAGGAGGGGGACAGGCCTGGGTCTTGGGGGAAGGTGGAGATGAC
80341  CCGTCTCAGGAGTCCACTCCTCCCCCTGTCCGGACCCAGAACCCCCTTCCACCTCTACTG

80401  CAGCCTCATGCCTCTCTCCCCAGTGGCCTCAGTCTCCATCAGGCAAATCTTGAGAAGCCT
80401  GTCGGAGTACGGAGAGAGGGGTCACCGGAGTCAGAGGTAGTCCGTTTAGAACTCTTCGGA

80461  CCTCCATTCTGCAGGCAAATGACTGAGATGTGTGAGCTCTGCTTCCCAACAGGCGGAAAT
80461  GGAGGTAAGACGTCCGTTTACTGACTCTACACACTCGAGACGAAGGGTTGTCCGCCTTTA

80521  TCACATGGGGAAGGGCACCTGTGAATGGCCTTCTAGAACTATCAGGAAGTTCTGGATTTA
80521  AGTGTACCCCTTCCCGTGGACACTTACCGGAAGATCTTGATAGTCCTTCAAGACCTAAAT

80581  GTACCCTGTGAGAGCAGATGGTCCTGGGTGCACTCGGATGATCCTGCCTAGCCAGCTGGA
80581  CATGGGACACTCTCGTCTACCAGGACCCACGTGAGCCTACTAGGACGGATCGGTCGACCT

80641  TTGCAGAGTGGTCATCATTATCAGTGAGCTATTGAGGGGTTGAGAGCAGTCAGTGTCATG
80641  AACGTCTCACCAGTAGTAATAGTCACTCGATAACTCCCCAACTCTCGTCAGTCACAGTAC

80701  TATAAGGATGGGTTGGGGTACCGGCCAACGCCCGCCTTGAGGCCTGGCCGCCGGATGGGA
80701  ATATTCCTACCCAACCCCATGGCCGGTTGCGGGCGGAACTCCGGACCGGCGGCCTACCCT

80761  GGCGAGAGCACAAGAGAGTCCTGGCTAGGTGTGCCCCGCTCTGCAGGGCCACACCATCCA
80761  CCGCTCTCGTGTTCTCTCAGGACCGATCCACACGGGGCGAGACGTCCCGGTGTGGTAGGT

80821  CTGGAAACCCTGTGCCCACTGGGCTGCGTGCTAAGAGGCTGTGGCCAATGCTCTTGTCCA
80821  GACCTTTGGGACACGGGTGACCCGACGCACGATTCTCCGACACCGGTTACGAGAACAGGT

80881  AATTTTACTGAATCTGCAGTCTCTCTTAATTCACTCCAAAGTTTAATGTGTTAGCTTGCG
80881  TTAAAATGACTTAGACGTCAGAGAGAATTAAGTGAGGTTTCAAATTACACAATCGAACGC

80941  AATAAATAAATAAATAAATAAATAAATAAATAAATGGAAAGAAACAGTCCTCAGAAAGTC
80941  TTATTTATTTATTTATTTATTTATTTATTTATTTACCTTTCTTTGTCAGGAGTCTTTCAG

81001  CCAGTCAAATTTTAATTCCAACAGATATTCAGCAGTTTCCTCTAAGAACAATGAGAGTTC
81001  GGTCAGTTTAAAATTAAGGTTGTCTATAAGTCGTCAAAGGAGATTCTTGTTACTCTCAAG

81061  TGGGGCTAGCCAGTGTTTCTCTTGGAAAATAAGGAAGAGGGAAAGCGGTGCATTCATTTA
81061  ACCCCGATCGGTCACAAAGAGAACCTTTTATTCCTTCTCCCTTTCGCCACGTAAGTAAAT

81121  AAAACCTGCCCTAGGGAGGCAGCGTTCCCTGTGAACTCCGAGGCCACAGTGAGCAGAGCA
81121  TTTTGGACGGGATCCCTCCGTCGCAAGGGACACTTGAGGCTCCGGTGTCACTCGTCTCGT

81181  GGCTGGAGGCCTCCCGGCTGTCCTGCCCCTCCTGCCACATGCCTGTGAAAATGCTAGATA
81181  CCGACCTCCGGAGGGCCGACAGGACGGGGAGGACGGTGTACGGACACTTTTACGATCTAT
```

FIG. 5 (cont'd)

```
81241  AGGACTTTTTCTCAGCAACTTCCACGCTCCTTCAGTGGGGATGTCTTTGACTCAGAGCTC
81241  TCCTGAAAAAGAGTCGTTGAAGGTGCGAGGAAGTCACCCCTACAGAAACTGAGTCTCGAG

81301  TGCCACTGGTTATCTCCACGAACAGAAAATGCCACAGATGGGTTAATTCACTGTGTTGTT
81301  ACGGTGACCAATAGAGGTGCTTGTCTTTTACGGTGTCTACCCAATTAAGTGACACAACAA

81361  CTCATTTTCCCTCAGTTTCAGGCTTTTCTCTCCTTGCCTGTTTTCCTCGCTTAAAAAATG
81361  GAGTAAAAGGGAGTCAAAGTCCGAAAAGAGAGGAACGGACAAAAGGAGCGAATTTTTTAC

81421  ATGTGGGGGTCCCTAAACGCATCTACCCCGATAGATTTATGTTTTCTTTTCCATTAGTCC
81421  TACACCCCCAGGGATTTGCGTAGATGGGGCTATCTAAATACAAAAGAAAAGGTAATCAGG

81481  ACTTTGCGTCTCAGCCCTAAAATTAAGTTTTTGATTATAATGTAAGGAAGTTTTACCATA
81481  TGAAACGCAGAGTCGGGATTTTAATTCAAAAACTAATATTACATTCCTTCAAAATGGTAT

81541  TTTTAACTCTGGCTTTTTAAATACAAAAGAAAAATAACAGAATGGCCTTCTAGAACTATC
81541  AAAATTGAGACCGAAAAATTTATGTTTTCTTTTTATTGTCTTACCGGAAGATCTTGATAG

81601  AGGAACTTCTGGATCTAGTACCCTGTGGGGACAGATGGTCTGGAGCCAGCGCACTTGGAT
81601  TCCTTGAAGACCTAGATCATGGGACACCCCTGTCTACCAGACCTCGGTCGCGTGAACCTA

81661  GATCTCTCTCAGCCATCTGGACCATAGAGTGAACTTGTTACTGTCCCTCCAAGGCTGACA
81661  CTAGAGAGAGTCGGTAGACCTGGTATCTCACTTGAACAATGACAGGGAGGTTCCGACTGT

81721  ACTATGAGCTCATACTCTTCTAGCAGTTTAATTTAGACCCAAGAAAGGCTGTGTGTGTGT
81721  TGATACTCGAGTATGAGAAGATCGTCAAATTAAATCTGGGTTCTTTCCGACACACACACA

81781  GAATTTGTGAGAGTGTGTGAGTGTGTCTTTGTGCCTGTGTTTCTGTGTGTGTCTGTGTGT
81781  CTTAAACACTCTCACACACTCACACAGAAACACGGACACAAAGACACACACAGACACACA

81841  ACATGTGTGTCTGTGGGGTGTGTCTGTGTGTGCACGGCTGTGTGTCTGTGCGTGTGCATG
81841  TGTACACACAGACACCCCACACAGACACACACGTGCCGACACACAGACACGCACACGTAC

81901  GCTTTGTCTGTGTGTGTGCGCACGCACTCTGCTAAGCTACTCAATGCAATTCCTTACTCT
81901  CGAAACAGACACACACACGCGTGCGTGAGACGATTCGATGAGTTACGTTAAGGAATGAGA

81961  TACTTCCCTTTCTGTCACTTCTCCATAATTCTTTGTATTTCGGTTGGGCTGGTATCTCGC
81961  ATGAAGGGAAAGACAGTGAAGAGGTATTAAGAAACATAAAGCCAACCCGACCATAGAGCG

82021  GGCGGCTTCCTCTTTTCCTGCATTCCTATATTTCATTATTTGCTCTTGTTCCTCTTCTAG
82021  CCGCCGAAGGAGAAAAGGACGTAAGGATATAAAGTAATAAACGAGAACAAGGAGAAGATC

82081  GGCTTTTACAATATAGCCAGGAGGATGTGGAAACCCAGTTACAAGATGACACACAAGCAC
82081  CCGAAAATGTTATATCGGTCCTCCTACACCTTTGGGTCAATGTTCTACTGTGTGTTCGTG

82141  AGTGTCACAATCGCTGTGCTTGGGCCCTACCTCCTGGAGACCAGGGTGGGACGGTGTCTC
82141  TCACAGTGTTAGCGACACGAACCCGGGATGGAGGACCTCTGGTCCCACCCTGCCACAGAG

82201  TGGATATGGAGGGAAGGGCGGAAGATCACGGGGTGGCAGAAGGCCCGACTGTCCGGTCTT
82201  ACCTATACCTCCCTTCCCGCCTTCTAGTGCCCCACCGTCTTCCGGGCTGACAGGCCAGAA

82261  CTGGAAGCTGGGGTCTCGTGGTCGCTGGGCTGGTGGTGCTCTAAAACCTAGAGTAACCGA
82261  GACCTTCGACCCCAGAGCACCAGCGACCCGACCACCACGAGATTTTGGATCTCATTGGCT

82321  GAGCAGGATGACTGCACCCCTGACTGCCGACTCACCGGGCTTCGGAGGGCCATGGGTGTG
82321  CTCGTCCTACTGACGTGGGGACTGACGGCTGAGTGGCCCGAAGCCTCCCGGTACCCACAC

82381  TGATTCCACTTGTGATCCTCCTACTTCCCCAGCCCACCCTGGTGGTCTCCCACTTCTCTC
82381  ACTAAGGTGAACACTAGGAGGATGAAGGGGTCGGGTGGGACCACCAGAGGGTGAAGAGAG

82441  TCTCTGCCTGTGGAGTGTTATAACCGACTCCTTCTTCTAGGCATCTCCATCCCAACCCCA
82441  AGAGACGGACACCTCACAATATTGGCTGAGGAAGAAGATCCGTAGAGGTAGGGTTGGGGT

82501  GACCAGTTCCCTTAAACCACCTCCCACCACAGGACCCCCACAAGCAGGGACCTCTCACAG
82501  CTGGTCAAGGGAATTTGGTGGAGGGTGGTGTCCTGGGGGTGTTCGTCCCTGGAGAGTGTC

82561  TTCCTGTTGCCTGGGGACTTCATCTCAGCTTCCAAGGCCTCTGGAACCAGGCCCTGCATC
82561  AAGGACAACGGACCCCTGAAGTAGAGTCGAAGGTTCCGGAGACCTTGGTCCGGGACGTAG
```

FIG. 5 (cont'd)

```
82621  CTGGGCATGACTGTCCCCATGATTCTCTGAGCCAGCCACCACCCCACCACCCCCCCACCG
82621  GACCCGTACTGACAGGGGTACTAAGAGACTCGGTCGGTGGTGGGGTGGTGGGGGGGTGGC

82681  CCAAGTCCACTGCTGACCCTGCTGTAGCCCCCCACCTCCACTTGTTGAGATTCCCTCTTC
82681  GGTTCAGGTGACGACTGGGACGACATCGGGGGGTGGAGGTGAACAACTCTAAGGGAGAAG

82741  CTGCTTCTCATTTTGAATGTCACCCTTCTGTGACTTCTCACAACCCCCCTGCCACCCCTC
82741  GACGAAGAGTAAAACTTACAGTGGGAAGACACTGAAGAGTGTTGGGGGGACGGTGGGGAG

82801  CCTCCAGTTGGCATGGCTTAGTCTTCCTAAGAACATGTGCTGCTTCCCAGTACCCAGGGC
82801  GGAGGTCAACCGTACCGAATCAGAAGGATTCTTGTACACGACGAAGGGTCATGGGTCCCG

82861  TGCTGTGCACCGTGGCACGTGAGTTTCGGTGCATCTTCCTCCTGCTGTTTATAAATTGCA
82861  ACGACACGTGGCACCGTGCACTCAAAGCCACGTAGAAGGAGGACGACAAATATTTAACGT

82921  ACATCCCTGGACAGATCTTGGATTTTCCCTCTATAATTTCTCTGGAGACTCCCTCGGGGT
82921  TGTAGGGACCTGTCTAGAACCTAAAAGGGAGATATTAAAGAGACCTCTGAGGGAGCCCCA

82981  TTGCACACACATCTGTGGAATGCCCAAGTTGGAGATGGTCCTCCCTGATGTGTAGTGTGG
82981  AACGTGTGTGTAGACACCTTACGGGTTCAACCTCTACCAGGAGGGACTACACATCACACC

83041  GCTATTCAGAGGGCCTCATTTCATAAACTCATTAACAGCTAGGACGCGAAGACTTGGAGA
83041  CGATAAGTCTCCCGGAGTAAAGTATTTGAGTAATTGTCGATCCTGCGCTTCTGAACCTCT

83101  AGTTAGCTCAGGACACACGGAGTGGGAGGGAGGCAACGAGTTAAGAAATGGGCTTTGGAG
83101  TCAATCGAGTCCTGTGTGCCTCACCCTCCCTCCGTTGCTCAATTCTTTACCCGAAACCTC

83161  TGCCTCGAATTTGGCCTCCACTTTTCTTTTCTACTGTCTTACCTGGTCTTAGGCAGGTCG
83161  ACGGAGCTTAAACCGGAGGTGAAAAGAAAAGATGACAGAATGGACCAGAATCCGTCCAGC

83221  GGTGACCATCTGGAGTCGGAGTTTCTCTCATTTGTAAAGCGGGGGTGATATTTTTCTCAC
83221  CCACTGGTAGACCTCAGCCTCAAAGAGAGTAAACATTTCGCCCCCACTATAAAAAGAGTG

83281  AGGGCTGCTTCAAGGGTTAACAAAGTTAATGTCTAGGAAGGACATAGCATAGCACCTTCA
83281  TCCCGACGAAGTTCCCAATTGTTTCAATTACAGATCCTTCCTGTATCGTATCGTGGAAGT

83341  CCTGGTTGCAAGCCCCTGGAGTCACATGGCAACAGCTGTGGAACCAGGTAAATGACTTGA
83341  GGACCAACGTTCGGGGACCTCAGTGTACCGTTGTCGACACCTTGGTCCATTTACTGAACT

83401  CTTACATGTTACACGCTCTTAGTTGTTCGATTTGTAAATGGGAAGAGTGTGTGACCCAAA
83401  GAATGTACAATGTGCGAGAATCAACAAGCTAAACATTTACCCTTCTCACACACTGGGTTT

83461  TTAGTCGTTTCCAGATATTTCCTGGTAAATGGTTGTTGAATCATAAAACTAGAAAGATGG
83461  AATCAGCAAAGGTCTATAAAGGACCATTTACCAACAACTTAGTATTTTGATCTTTCTACC

83521  GAAAGAAAGGGAGGAACCCCCCTTACTTCGAAGAAGTGTTGTTGATGTGAAGGACAGGAC
83521  CTTTCTTTCCCTCCTTGGGGGGAATGAAGCTTCTTCACAACAACTACACTTCCTGTCCTG

83581  TTTTTGAGACACTCTCATCCTAAGAAACAGCTGATATCTACTAGGAAAAAACATGACATT
83581  AAAAACTCTGTGAGAGTAGGATTCTTTGTCGACTATAGATGATCCTTTTTTGTACTGTAA

83641  TGAAGTTTCTTCCTAAGAGATGTGAGGTTTTGACAGAAGTGCCAGGAAGCCAGAGGTGTG
83641  ACTTCAAAGAAGGATTCTCTACACTCCAAAACTGTCTTCACGGTCCTTCGGTCTCCACAC

83701  TGAGTAGTGGGCCAATCTCGCGTGAAGGCTGTGGGACGGGGCAGGAGAGGGGCAGCCAGC
83701  ACTCATCACCCGGTTAGAGCGCACTTCCGACACCCTGCCCCGTCCTCTCCCCGTCGGTCG

83761  ATTTCCTGAGCGCCAGCTAATGGCGGGGACCTGGCACCTTTGCTCTGTGACTCTCCAGCT
83761  TAAAGGACTCGCGGTCGATTACCGCCCCTGGACCGTGGAAACGAGACACTGAGAGGTCGA

83821  GTATGGTGACATGAGGCTGGCGTTTTCTTTGGTTTCATACGTGAGGAAGCTGAGGCTTGG
83821  CATACCACTGTACTCCGACCGCAAAAGAAACCAAAGTATGCACTCCTTCGACTCCGAACC

83881  TGATGTCCTGTGCATGGCTCGGACTCCAGAGCTACTCAGAGGCAGAGGCCGTCTGTAAAC
83881  ACTACAGGACACGTACCGAGCCTGAGGTCTCGATGAGTCTCCGTCTCCGGCAGACATTTG

83941  ACCTTCAGGTGGTTGGAGGCAGGGTGCTGCAGCCAATGCTGATCACTCACAAGCCAAGGC
83941  TGGAAGTCCACCAACCTCCGTCCCACGACGTCGGTTACGACTAGTGAGTGTTCGGTTCCG
```

FIG. 5 (cont'd)

84001 TTTATTGTAAGGGCTAAATAAAATAACATATGCCTAGCATTTATACAGCACGGGGCTTTT
84001 AAATAACATTCCCGATTTATTTTATTGTATACGGATCGTAAATATGTCGTGCCCCGAAAA

84061 TAGGAAATAGTGAGACGACCATGGAGAGGTGGAGGAAGAGAGAAGGGAAAGAAGAAAAAG
84061 ATCCTTTATCACTCTGCTGGTACCTCTCCACCTCCTTCTCTCTTCCCTTTCTTCTTTTTC

84121 AAAAAAAAAGCCTTAAAGAGTTTCTTAAGAGAACTATATATTACAAAGTCCTTGGAGTTT
84121 TTTTTTTTTCGGAATTTCTCAAAGAATTCTCTTGATATATAATGTTTCAGGAACCTCAAA

84181 TTTTTCCCTGGTTAGACATAAGTTTACATGAAACGTTAAACGGCTTAAAGTAGCCACATC
84181 AAAAAGGGACCAATCTGTATTCAAATGTACTTTGCAATTTGCCGAATTTCATCGGTGTAG

84241 TCCTTCCTTATGTCTTCTCACAGCCACTTGTGAGTTTCTTATCAAGATACAGAATTATGG
84241 AGGAAGGAATACAGAAGAGTGTCGGTGAACACTCAAAGAATAGTTCTATGTCTTAATACC

84301 CCAAGTGCGGTAGCTCACACGTGTAATCCCAGCACTTTGAGAGACTGAGGTGGAAGGATC
84301 GGTTCACGCCATCGAGTGTGCACATTAGGGTCGTGAAACTCTCTGACTCCACCTTCCTAG

84361 ATGTGTGCTCAGGAGTTTCAGACCAACCTAGGCAATATGGTAAAACCCTGTCTCTACAAA
84361 TACACACGAGTCCTCAAAGTCTGGTTGGATCCGTTATACCATTTTGGGACAGAGATGTTT

84421 AAAATACAAAAATTAGCTGGGCATGGTGGCATATTCCAATAGTTCCAGGCACTCGGGAGG
84421 TTTTATGTTTTTAATCGACCCGTACCACCGTATAAGGTTATCAAGGTCCGTGAGCCCTCC

84481 CTGAGACAGGAGGATTGCTTGAGCCCAAGAGGTCAAGACTGCAGTGAGCTGTGATCGAGC
84481 GACTCTGTCCTCCTAACGAACTCGGGTTCTCCAGTTCTGACGTCACTCGACACTAGCTCG

84541 CACTGCACTACAGCCTGGGCCACAGAGCAAGATCCTGTCTCAAAAAATAAAATAAAATAA
84541 GTGACGTGATGTCGGACCCGGTGTCTCGTTCTAGGACAGAGTTTTTTATTTTATTTTATT

84601 AATAAATTCTGCAACAAGTCACAATTCCTTGCTCAGAAATCTCTACAGGTGTGCTTCTTT
84601 TTATTTAAGACGTTGTTCAGTGTTAAGGAACGAGTCTTTAGAGATGTCCACACGAAGAAA

84661 GTTAAGAAATGGAGGAAACATGAATTTCATCCTGACTTCTGAGTCTTGTAGAGACCAGAT
84661 CAATTCTTTACCTCCTTTGTACTTAAAGTAGGACTGAAGACTCAGAACATCTCTGGTCTA

84721 CTGACTCCTGCAGCCTTCTGCCCACAGAGCTGGCAGGCGGGGGAATGTGCGCAGAGTGAG
84721 GACTGAGGACGTCGGAAGACGGGTGTCTCGACCGTCCGCCCCCTTACACGCGTCTCACTC

84781 GAGGAGCTGATCTGACATTCCGAACAGTGGAGACTGCTGCCTATTTGGCCGCACCACTGT
84781 CTCCTCGACTAGACTGTAAGGCTTGTCACCTCTGACGACGGATAAACCGGCGTGGTGACA

84841 CCTTCTGCATGGAAAAGTCACAGTAAATAATGGACTCTCTACCTGTGAGTCGATTTTACT
84841 GGAAGACGTACCTTTTCAGTGTCATTTATTACCTGAGAGATGGACACTCAGCTAAAATGA

84901 GAGCTGCCTTTTTAAATATATGTGTAGAAAGGGCGATCTCTGTGTGTCATTTGCACATGT
84901 CTCGACGGAAAAATTTATATACACATCTTTCCCGCTAGAGACACACAGTAAACGTGTACA

84961 ACATACACATGTACACACGTGCACACGTGGTCACTCATGTACACATGTGTGTGCACCAGT
84961 TGTATGTGTACATGTGTGCACGTGTGCACCAGTGAGTACATGTGTACACACACGTGGTCA

85021 GCACCAGACCAGATGCACCCACCCAATTCCACGCTCCTCAGCCCCTTGCTTTCCTCTGCA
85021 CGTGGTCTGGTCTACGTGGGTGGGTTAAGGTGCGAGGAGTCGGGGAACGAAAGGAGACGT

85081 GACAGCCAGTTCAGCTACAGTTATGCCAGATTGCCTGCACTCTGATCTTTACCATCACCA
85081 CTGTCGGTCAAGTCGATGTCAATACGGTCTAACGGACGTGAGACTAGAAATGGTAGTGGT

85141 GACTCTCAGCTTGAGCTCATGCCTGAGAAATCCACTTTCTGGGAGGAAGGCAGAAGAAAC
85141 CTGAGAGTCGAACTCGAGTACGGACTCTTTAGGTGAAAGACCCTCCTTCCGTCTTCTTTG

85201 TGCCAAGGCAGGACTGAAGACTTGACCTCCACCTGTAGTGGGGTCAGGTCACCAGAGGCT
85201 ACGGTTCCGTCCTGACTTCTGAACTGGAGGTGGACATCACCCCAGTCCAGTGGTCTCCGA

85261 GGCTGACTCCCCAGGATTTCTCAGCAGAGTATTACACAAATACCCCTTCCTTAAAGATTA
85261 CCGACTGAGGGGTCCTAAAGAGTCGTCTCATAATGTGTTTATGGGGAAGGAATTTCTAAT

85321 GCAACCACTTAAAGACACAAAGTGTGCAGGACTGTACCCATGGCCGAGAGCGGCGGGATT
85321 CGTTGGTGAATTTCTGTGTTTCACACGTCCTGACATGGGTACCGGCTCTCGCCGCCCTAA

FIG. 5 (cont'd)

```
85381  AAGAGGGCAACTGAGTTGTTCTTCCCATCCCTCCTCCTCTGTGCTGAGTCACCTTCTGCT
85381  TTCTCCCGTTGACTCAACAAGAAGGGTAGGGAGGAGGAGACACGACTCAGTGGAAGACGA

85441  TGGAATTCTGACAGGGACCCGTTGGGCTTCTGGAAGGGAGGGACAGCAGAGGATCCACCC
85441  ACCTTAAGACTGTCCCTGGGCAACCCGAAGACCTTCCCTCCCTGTCGTCTCCTAGGTGGG

85501  TCTGTGTGTCCTGGGGGAGATTACTTATCTCTGGCCTCCCTGAAGCAGGGCCTGGGCTTC
85501  AGACACACAGGACCCCCTCTAATGAATAGAGACCGGAGGGACTTCGTCCCGGACCCGAAG

85561  TGGAATCTTTGAGGCTGACACCCTGCCAGCCCTGGGGATGAGAGGGAATGGCCGTGTCTG
85561  ACCTTAGAAACTCCGACTGTGGGACGGTCGGGACCCCTACTCTCCCTTACCGGCACAGAC

85621  TCTGCAGAGCCTGAGGAGGAGCTGAGCACAGCCTCCAGAGTTCTCTTCAGTTGATCGCTT
85621  AGACGTCTCGGACTCCTCCTCGACTCGTGTCGGAGGTCTCAAGAGAAGTCAACTAGCGAA

85681  AGGTGGACAAAGGCCACAGAAATGGATTTAAACTCCTCAGCCCTTTCTTTGCATGTTTGT
85681  TCCACCTGTTTCCGGTGTCTTTACCTAAATTTGAGGAGTCGGGAAAGAAACGTACAAACA

85741  TCTCATTTGAAGTCAGAAGTGATATGTCCTACACCTCAAGAACGTGTGAAATGCACATAC
85741  AGAGTAAACTTCAGTCTTCACTATACAGGATGTGGAGTTCTTGCACACTTTACGTGTATG

85801  AATAACCCCATTTCAGGAAGCCAAGTCCAGCTTAACAGTCAAAACATTTCCTTCAGTCTT
85801  TTATTGGGGTAAAGTCCTTCGGTTCAGGTCGAATTGTCAGTTTTGTAAAGGAAGTCAGAA

85861  TAGTCCTTCACTTTGCCGAACTCCCTTTTACACCGGCAGCAACAGTTTAACCTGTTGCTT
85861  ATCAGGAAGTGAAACGGCTTGAGGGAAAATGTGGCCGTCGTTGTCAAATTGGACAACGAA

85921  CTGTAAGAGTGTGCTACTGGGAAAACCACATCTAAAACACGTGTGCAGTTACATCAGCTA
85921  GACATTCTCACACGATGACCCTTTTGGTGTAGATTTTGTGCACACGTCAATGTAGTCGAT

85981  GAGCACATGCTAAACAGTTGATCAAAGGCTCTTGCCTTGTGGCCCACGCTGCAGACACTC
85981  CTCGTGTACGATTTGTCAACTAGTTTCCGAGAACGGAACACCGGGTGCGACGTCTGTGAG

86041  TGACGACTGCCGAGCTCCGCAGCCCCATGTCGTCCCTTCCGCACTGCCTGCTGTGCCTCT
86041  ACTGCTGACGGCTCGAGGCGTCGGGGTACAGCAGGGAAGGCGTGACGGACGACACGGAGA

86101  CCTCTCCATGTGGCAGGGAACACAGCCAGTCATCACCATGTGGCTCTGCCCGGCGCTGCC
86101  GGAGAGGTACACCGTCCCTTGTGTCGGTCAGTAGTGGTACACCGAGACGGGCCGCGACGG

86161  CCAGCATGTCCTGACAGGGCCTAGATATGGAAAGGTGGCTCTCCATGCACACACCCCAAG
86161  GGTCGTACAGGACTGTCCCGGATCTATACCTTTCCACCGAGAGGTACGTGTGTGGGGTTC

86221  CCCCTCCTGCCCGCCGTGTGACCCACACTCTTATGGGCAGCCCAGTTATTTTGTAGCATT
86221  GGGGAGGACGGGCGGCACACTGGGTGTGAGAATACCCGTCGGGTCAATAAAACATCGTAA

86281  TCCCTTCCTTATCATTTTGGCCCAGTGATCCAGCACAAATCTCCCTTATTAGAATAAAAT
86281  AGGGAAGGAATAGTAAAACCGGGTCACTAGGTCGTGTTTAGAGGGAATAATCTTATTTTA

86341  TTGGAATGACAAAATTAAATTTCATTTTTCACTTATATTGAGGACCTCACACTCTTCACC
86341  AACCTTACTGTTTTAATTTAAAGTAAAAAGTGAATATAACTCCTGGAGTGTGAGAAGTGG

86401  CCTGCCACGATCCCTGACAAGAGCCTTCCTATCTAATCATTGTTCCTCCAGCCCTCTTAG
86401  GGACGGTGCTAGGGACTGTTCTCGGAAGGATAGATTAGTAACAAGGAGGTCGGGAGAATC

86461  TTTTCTTCAGCCTTTCTTGATTGCCTGAATGTCCCTTTCCCTTCTCCTTTTAAAGCATGA
86461  AAAAGAAGTCGGAAAGAACTAACGGACTTACAGGGAAAGGGAAGAGGAAAATTTCGTACT

86521  ACCAAGCTTTCTTACCCCGTTCTCATTATCATTTTTGCATTTTCTTCTTTGCATATGATT
86521  TGGTTCGAAAGAATGGGGCAAGAGTAATAGTAAAAACGTAAAAGAAGAAACGTATACTAA

86581  CTCCTTAAATTATAAAACTTGGGGGTAATTTCTAGAGGTGCCATCATAGTGCTTCTGTCT
86581  GAGGAATTTAATATTTTGAACCCCCATTAAAGATCTCCACGGTAGTATCACGAAGACAGA

86641  ACTCAGTGTCTTTAGAATCAGCAAATATCATTTTTACAAAAAAGTAGTATTTCTTCCAAA
86641  TGAGTCACAGAAATCTTAGTCGTTTATAGTAAAAATGTTTTTTCATCATAAAGAAGGTTT

86701  AAAGAGTAAGCAAGAAGGTTACAACACTGGGAAAATATCCCTAAGCCTGTTCTTCAACCT
86701  TTTCTCATTCGTTCTTCCAATGTTGTGACCCTTTTATAGGGATTCGGACAAGAAGTTGGA
```

FIG. 5 (cont'd)

```
86761  GTTGAATGTTTTCCCCTAAATTGTTATATGGAGATCCTGGACCCGGAAGTTGGCTGACAT
86761  CAACTTACAAAAGGGGATTTAACAATATACCTCTAGGACCTGGGCCTTCAACCGACTGTA

86821  GAAACAGGCCTAGCAGGGCAGCTGAGGAAATGCTCCAACCTCAGGATCCAGGAAGATTGC
86821  CTTTGTCCGGATCGTCCCGTCGACTCCTTTACGAGGTTGGAGTCCTAGGTCCTTCTAACG

86881  ACATGGCACCAAAACAATCATTTAAAAGCTAATCCTGGCCAGGCACAGTGGCTCACGCCT
86881  TGTACCGTGGTTTTGTTAGTAAATTTTCGATTAGGACCGGTCCGTGTCACCGAGTGCGGA

86941  GTAATCCCAGCACTTTGGGAGGCCGAGGTGGGCTGATCACAAGGTCAAGAGATCGAGACC
86941  CATTAGGGTCGTGAAACCCTCCGGCTCCACCCGACTAGTGTTCCAGTTCTCTAGCTCTGG

87001  ATCCTGACCAACATGGTGAAACCCCATCTCTACCAAAAGTACAAATATTAGCTGGGCATG
87001  TAGGACTGGTTGTACCACTTTGGGGTAGAGATGGTTTTCATGTTTATAATCGACCCGTAC

87061  GTGGTGCGCGCCTGTAGTCCCAGCTACCCGGGAGGCTGAGGCAGGAGAATCACTTGAACC
87061  CACCACGCGCGGACATCAGGGTCGATGGGCCCTCCGACTCCGTCCTCTTAGTGAACTTGG

87121  CGGGAGGAGGAGGTTGCAGTGAGCCAAGATCATGCCACTGCACTCCAGCCTGGTGACAGA
87121  GCCCTCCTCCTCCAACGTCACTCGGTTCTAGTACGGTGACGTGAGGTCGGACCACTGTCT

87181  GCAAGACTCCATCTCAAAAAAGAAAAAAAAAGCTAATCCCATAAAAGAACCATCATTTTG
87181  CGTTCTGAGGTAGAGTTTTTTCTTTTTTTTTCGATTAGGGTATTTTCTTGGTAGTAAAAC

87241  AACCTGCTGTTTCCTTTCTTGTACTCTTTAGAAGTACCCATTTCTCCCTTTCTAAGCCAT
87241  TTGGACGACAAAGGAAAGAACATGAGAAATCTTCATGGGTAAAGAGGGAAAGATTCGGTA

87301  AGGTGTATTAATTGGAGCTTTTTCTATCTTAATTAGTTCACTGTGAACAATTAAAATTGT
87301  TCCACATAATTAACCTCGAAAAAGATAGAATTAATCAAGTGACACTTGTTAATTTTAACA

87361  GTTAATAAAACAAAAACAAAAATAGGACTGGTGCCTAGTTGTACTACATGAAGAGAGAAA
87361  CAATTATTTTGTTTTTGTTTTTATCCTGACCACGGATCAACATGATGTACTTCTCTCTTT

87421  GGGCCAGACATTGGTTTTTCCTAATCTTCTGTCAAGTTCTCCAAATCATCTGCTCTGGAA
87421  CCCGGTCTGTAACCAAAAAGGATTAGAAGACAGTTCAAGAGGTTTAGTAGACGAGACCTT

87481  GGTAGCTCCAACAGCTGGGATTTGAAGTAAAGCATAGTGACTTTGGCCATCACTGACATG
87481  CCATCGAGGTTGTCGACCCTAAACTTCATTTCGTATCACTGAAACCGGTAGTGACTGTAC

87541  TCCCATTTGAAGCAACCAAAACTGTCCCTCGACCTGACACTCATCCCTGAAACACCATGA
87541  AGGGTAAACTTCGTTGGTTTTGACAGGGAGCTGGACTGTGAGTAGGGACTTTGTGGTACT

87601  GGGTAAGTGAGGCGCTTCGGAAGGTCCACTCAACCCCATTGCCAGATAGAGTAAGTGTCT
87601  CCCATTCACTCCGCGAAGCCTTCCAGGTGAGTTGGGGTAACGGTCTATCTCATTCACAGA

87661  GCCAGGGGCATTTGGAGCTGAAGGGAAGACTGTACAGACTCACGGTTTGCAGGCACTGAA
87661  CGGTCCCCGTAAACCTCGACTTCCCTTCTGACATGTCTGAGTGCCAAACGTCCGTGACTT

87721  GGCGTTTTCCTGCCTTCTTTTTCACCTTCAGTGGACTTGCAAAGCACTAGCCCTATTGTT
87721  CCGCAAAAGGACGGAAGAAAAAGTGGAAGTCACCTGAACGTTTCGTGATCGGGATAACAA

87781  TTTCCCATCTGGGAAACATGGTGAATGTTGGTTGGTTGTAGCTAATCCTATGGGTCTTGA
87781  AAAGGGTAGACCCTTTGTACCACTTACAACCAACCAACATCGATTAGGATACCCAGAACT

87841  GGTCTTTGTTGACAAGAAGGTAGATGTTATCTTTATCTGCGTGTGGCTTTCTACTAAAAC
87841  CCAGAAACAACTGTTCTTCCATCTACAATAGAAATAGACGCACACCGAAAGATGATTTTG

87901  ATGAGCTACAGGGCTCTCTTTTTTGTTTTAAAGCATTTTTCCATAAGGTTCACCCTTACT
87901  TACTCGATGTCCCGAGAGAAAAAACAAAATTTCGTAAAAAGGTATTCCAAGTGGGAATGA

87961  ATTGCTTATCTGAATAATATTACCTGCTGAGAAGTTTATTCATTGCTCACCAGTTGTAGG
87961  TAACGAATAGACTTATTATAATGGACGACTCTTCAAATAAGTAACGAGTGGTCAACATCC

88021  GAGATTTTGACACAGGACTGGAGGATTTTTTTCTCATCGTAACAGTGCAGACCCATGGAA
88021  CTCTAAAACTGTGTCCTGACCTCCTAAAAAAAGAGTAGCATTGTCACGTCTGGGTACCTT

88081  AGCTTGGAAGCAGTTGTGACCGGATAAGAGCAGGTTGAGGATGATAATCTTAGGGCAATG
88081  TCGAACCTTCGTCAACACTGGCCTATTCTCGTCCAACTCCTACTATTAGAATCCCGTTAC
```

FIG. 5 (cont'd)

```
88141  AGCAGGTTGATTGAGAGGGGTGCCTGAAAGCAAGGTCCCCATGATGCAAGCAAACAAACT
88141  TCGTCCAACTAACTCTCCCCACGGACTTTCGTTCCAGGGGTACTACGTTCGTTTGTTTGA

88201  CACATGCCAGACGGTGGACAGGAAACACAGGCAGGATGTGGTGCAGGCTGGGCTGCCTTG
88201  GTGTACGGTCTGCCACCTGTCCTTTGTGTCCGTCCTACACCACGTCCGACCCGACGGAAC

88261  GCTGGGCAAAGGCAGGGGCTTCATGGCCATGCTGGGATGTGACGTGGTTGGAAAACAATA
88261  CGACCCGTTTCCGTCCCCGAAGTACCGGTACGACCCTACACTGCACCAACCTTTTGTTAT

88321  AGAATGGAGACCTCTCCAAAGACCTCAGACATAATTTGGCCATGAGAGGCAAGGGTAGAG
88321  TCTTACCTCTGGAGAGGTTTCTGGAGTCTGTATTAAACCGGTACTCTCCGTTCCCATCTC

88381  GCGAGCCCCCTGTGGGTTGGAATGTATGGAATCCAGATGAAGCACCATCAACATGCATGG
88381  CGCTCGGGGGACACCCAACCTTACATACCTTAGGTCTACTTCGTGGTAGTTGTACGTACC

88441  GCTACATAGGAGAGCTGGGTCTGGGGGAAAAGATGGGATTTGGGTTTGGGTGTGCATGTT
88441  CGATGTATCCTCTCGACCCAGACCCCCTTTTCTACCCTAAACCCAAACCCACACGTACAA

88501  CCAGGCATGGAGGGAAGAATGGGCAGAATGACGAGGATCAAGCCCTGGTGGAGCCCCCAG
88501  GGTCCGTACCTCCCTTCTTACCCGTCTTACTGCTCCTAGTTCGGGACCACCTCGGGGGTC

88561  ACCAGGGCCCTGGGCATATTTCCACTTGCCTTCTTCTGCAAACTTTTGTGTGCCTGTTGG
88561  TGGTCCCGGGACCCGTATAAAGGTGAACGGAAGAAGACGTTTGAAAACACACGGACAACC

88621  GTGGAAGGTACTATGCTGGGGCCATCCAGGATCCGGAGCAGTGTAAGACATCATGGCCTG
88621  CACCTTCCATGATACGACCCCGGTAGGTCCTAGGCCTCGTCACATTCTGTAGTACCGGAC

88681  CATGGTGTGACCCTTGACATCTGAAAAGAACGAGCTGGTGGAGTGGGAAGGAGACAAGTG
88681  GTACCACACTGGGAACTGTAGACTTTTCTTGCTCGACCACCTCACCCTTCCTCTGTTCAC

88741  GCAGCAGAGTTGACATCATCAGGACTGACTGCAGGACAGGCGGTGAAACGAGCCACTGAG
88741  CGTCGTCTCAACTGTAGTAGTCCTGACTGACGTCCTGTCCGCCACTTTGCTCGGTGACTC

88801  GAGTTACCCAGTGCCCTGGGGAGCTTAGATGTGAGACTTACACCACCCAGCACTCCCCAG
88801  CTCAATGGGTCACGGGACCCCTCGAATCTACACTCTGAATGTGGTGGGTCGTGAGGGGTC

88861  CTCTGTGTCCCTGGGTCCCACTGAACTTGATTGTATTTTAGTTGCCTCTTTTCTAAGACC
88861  GAGACACAGGGACCCAGGGTGACTTGAACTAACATAAAATCAACGGAGAAAAGATTCTGG

88921  GGAGCAACAATACCTTCCTTGAGTGTGCATGTGCAGTCCATAGATGGCAGCCAGTGTTCT
88921  CCTCGTTGTTATGGAAGGAACTCACACGTACACGTCAGGTATCTACCGTCGGTCACAAGA

88981  CTTCCCATGAGAAGACTCTGAGCCTCCTCACTAGAGGGTGGTCTAAAAACAAATGGATCC
88981  GAAGGGTACTCTTCTGAGACTCGGAGGAGTGATCTCCCACCAGATTTTTGTTTACCTAGG

89041  ATCCACAGAAGGTCTGAAAGGTTTTCATAGAATCTTGACTTGGTAGCACTTCAGGATCTA
89041  TAGGTGTCTTCCAGACTTTCCAAAAGTATCTTAGAACTGAACCATCGTGAAGTCCTAGAT

89101  ACTCGTGCTTTCCAGAAGTGTGGCCTGTGGTGTTCTGTCTGGAGTATTTGGTCCTCCCAT
89101  TGAGCACGAAAGGTCTTCACACCGGACACCACAAGACAGACCTCATAAACCAGGAGGGTA

89161  CCACCTCCACCTTGCTGTCCTGTCCTGTGACTCTCACTAGCTCAGTCACCGGGTCAGGAA
89161  GGTGGAGGTGGAACGACAGGACAGGACACTGAGAGTGATCGAGTCAGTGGCCCAGTCCTT

89221  GCCCTGCCATGAAATGCTAGATTTGGAGGCATTGCCAAGGTACCACAAACCATACTCAAA
89221  CGGGACGGTACTTTACGATCTAAACCTCCGTAACGGTTCCATGGTGTTTGGTATGAGTTT

89281  CAAGGTCATAATAGACTAGTGATCTCACTGTGGCTAACAGGTTCATGTGATTTAAAGAAT
89281  GTTCCAGTATTATCTGATCACTAGAGTGACACCGATTGTCCAAGTACACTAAATTTCTTA

89341  GACAGCATTTTTTCTAAATTTTATAAATTTTATAAATTTCTCCTAAATACAAATCTGAAT
89341  CTGTCGTAAAAAAGATTTAAAATATTTAAAATATTTAAAGAGGATTTATGTTTAGACTTA

89401  GTGTTTACCTTTAGACAGATTTTCCCAGAAAATTGTCAGTGTTCTCGAATTTGAAAGTAG
89401  CACAAATGGAAATCTGTCTAAAAGGGTCTTTTAACAGTCACAAGAGCTTAAACTTTCATC

89461  ATCAGATCTCCTCCCTCTAGTTTTGAAAATCTCAAGTAGGTTTAGCCTCTCCCCAGAGTG
89461  TAGTCTAGAGGAGGGAGATCAAAACTTTTAGAGTTCATCCAAATCGGAGAGGGGTCTCAC
```

FIG. 5 (cont'd)

```
89521  ACAACGGCACAAGAAGTTTATAATTTTATGCACAGCTAAATGCAAACTGAAAAGTGTGGT
89521  TGTTGCCGTGTTCTTCAAATATTAAAATACGTGTCGATTTACGTTTGACTTTTCACACCA

89581  TTGTGGGTATTTCATTTTTCCCATAATGTTCATCAATTTGGCAATTCAAATAGGATTCAG
89581  AACACCCATAAAGTAAAAAGGGTATTACAAGTAGTTAAACCGTTAAGTTTATCCTAAGTC

89641  AATCCAAGGTGTTCGCAGCATTTTATATGAAAATGTGCCTGAGAGTTTGGGGAATAGAAA
89641  TTAGGTTCCACAAGCGTCGTAAAATATACTTTTACACGGACTCTCAAACCCCTTATCTTT

89701  TTCTTACCAAATAAGTTAAATTTGCTCTTGATAAGAATATATTTTGTAAAATGTAGAAAA
89701  AAGAATGGTTTATTCAATTTAAACGAGAACTATTCTTATATAAAACATTTTACATCTTTT

89761  CTGAGAAAAAAAGTTTGACACCTGTTTTATCTGCATCCTTTTATTAAACAGTGGCCTGAA
89761  GACTCTTTTTTTCAAACTGTGGACAAAATAGACGTAGGAAAATAATTTGTCACCGGACTT

89821  TTTACTAAAGGACAGAGAACAGGGTTGAGAGGTAATCACTGAATAATAGCTTCGCTAATC
89821  AAATGATTTCCTGTCTCTTGTCCCAACTCTCCATTAGTGACTTATTATCGAAGCGATTAG

89881  CCACAGTGACTGCTTCTTATGACAAGCAAGAGGGTCAACTTAGAGGCAGGACTGTCTTCA
89881  GGTGTCACTGACGAAGAATACTGTTCGTTCTCCCAGTTGAATCTCCGTCCTGACAGAAGT

89941  GGGGCAAAAGCAAGTCAGCACCTACAAACCTCTCCAAGAGAGTGAGAAAAAGCAGGTTGT
89941  CCCCGTTTTCGTTCAGTCGTGGATGTTTGGAGAGGTTCTCTCACTCTTTTTCGTCCAACA

90001  ATGGCTCATTTTGCAGCTTGCCAGAAGCAATGTGGGAATATTGTCAGACTGCACAGACCT
90001  TACCGAGTAAAACGTCGAACGGTCTTCGTTACACCCTTATAACAGTCTGACGTGTCTGGA

90061  GGGGCCAGCTGGCTCCTAGAGTGCGAGGAGCTCTCAGTGACTGCTGTGCATACTCACCTG
90061  CCCCGGTCGACCGAGGATCTCACGCTCCTCGAGAGTCACTGACGACACGTATGAGTGGAC

90121  CTCTGTGACTTTGTTCAGTCCCTACCCTGGATGTGTGGTGAAGGGTGCCAGGCTTAGCTG
90121  GAGACACTGAAACAAGTCAGGGATGGGACCTACACACCACTTCCCACGGTCCGAATCGAC

90181  CTGGACCAGTGAGGTCCCTGAGGGGGCAGGGCTAAGAGGTGTAGCAGTCGCACTTGACCA
90181  GACCTGGTCACTCCAGGGACTCCCCCGTCCCGATTCTCCACATCGTCAGCGTGAACTGGT

90241  GTCATTGATTCACTGGTTGGGAATTTGTTCATTGAGGGGACACCATTACTCCCCATGCCT
90241  CAGTAACTAAGTGACCAACCCTTAAACAAGTAACTCCCCTGTGGTAATGAGGGGTACGGA

90301  CACGTGCAGGTGAGTGTGTGTATATTTGCATTAACACACAAACACACTTATGTGTGTCCC
90301  GTGCACGTCCACTCACACACATATAAACGTAATTGTGTGTTTGTGTGAATACACACAGGG

90361  TGTATGTGCAGCTGCAGTACCTTACACATCTTCCAGTGCCTCTCAAGCATCATAAAAACA
90361  ACATACACGTCGACGTCATGGAATGTGTAGAAGGTCACGGAGAGTTCGTAGTATTTTTGT

90421  GCTTCCACAAAACCTCTACTACCCACCTGGCATCCACAGAGCTCCCAGTGATTGGCTCCC
90421  CGAAGGTGTTTTGGAGATGATGGGTGGACCGTAGGTGTCTCGAGGGTCACTAACCGAGGG

90481  AAAAGATACTGAACTTTGGCATGGAACAGAGTGAGTTTCCACATTTGCTGTTGTACATAA
90481  TTTTCTATGACTTGAAACCGTACCTTGTCTCACTCAAAGGTGTAAACGACAACATGTATT

90541  TTACCTGTCCAGCTAGAATAGTACACACTTCTTTTACTGAGCCCAGAAGTTTATGTGCCT
90541  AATGGACAGGTCGATCTTATCATGTGTGAAGAAAATGACTCGGGTCTTCAAATACACGGA

90601  GAACACGGATGGTACAGGAACAAGGGTGAGCGCTTATCAATTCAGCATTACTCTGGAGAC
90601  CTTGTGCCTACCATGTCCTTGTTCCCACTCGCGAATAGTTAAGTCGTAATGAGACCTCTG

90661  ATGAAACAAACTAATAGGTACAGCTATATTTTGTTTTTTAAACAATTTTGTGAACCACAT
90661  TACTTTGTTTGATTATCCATGTCGATATAAAACAAAAAATTTGTTAAAACACTTGGTGTA

90721  ATTTGGGACAAAAATCAACAAGTAAATTTGAATTACACTAGGCAAAGGACTGATTCTTTT
90721  TAAACCCTGTTTTTAGTTGTTCATTTAAACTTAATGTGATCCGTTTCCTGACTAAGAAAA

90781  GAAACGTGATTGACATTCAACGTCTAACTTTCCAAAAGAAGACATACATGTGGCCCACAA
90781  CTTTGCACTAACTGTAAGTTGCAGATTGAAAGGTTTTCTTCTGTATGTACACCGGGTGTT

90841  TCATATGAAATAAAGTTCATCATCATTGATCATTAGAGAAATGCAAATCAAAACCACAAT
90841  AGTATACTTTATTTCAAGTAGTAGTAACTAGTAATCTCTTTACGTTTAGTTTTGGTGTTA
```

FIG. 5 (cont'd)

```
90901  GAGATACCATCTCACACCAGTCAGAATGGTTATTAATAAAAAGTCAAAGAATGACAGTTG
90901  CTCTATGGTAGAGTGTGGTCAGTCTTACCAATAATTATTTTTCAGTTTCTTACTGTCAAC

90961  CTGGTGAGGTTGTAGAGAAAAAGGAACGCTTATACACTGTTGAGGGGATTGTAAATTAGT
90961  GACCACTCCAACATCTCTTTTTCCTTGCGAATATGTGACAACTCCCCTAACATTTAATCA

91021  TCAACCATGTGGAAGACAGTGTGGCAATTCCTCAAAGACCTATATACCATTTGACCCAGC
91021  AGTTGGTACACCTTCTGTCACACCGTTAAGGAGTTTCTGGATATATGGTAAACTGGGTCG

91081  AATCCCATTACTGCATATATACCCAAAGGAATATGAGTCATTCTACCGTAAGACACATGC
91081  TTAGGGTAATGACGTATATATGGGTTTCCTTATACTCAGTAAGATGGCATTCTGTGTACG

91141  ACGCATTTGTTTGTTGCAGCACTATTCACGATAGCAAAAACATGGAATCAACCTACATGC
91141  TGCGTAAACAAACAACGTCGTGATAAGTGCTATCGTTTTTGTACCTTAGTTGGATGTACG

91201  CCATCAATGATAGACTGGATAAAGAAAATGTGGTACATATACCCCATGGAATACTATGCA
91201  GGTAGTTACTATCTGACCTATTTCTTTTACACCATGTATATGGGGTACCTTATGATACGT

91261  GCCATAAGAAAAAGAATGAGATCATGCCCTTTGCAGGAACATGGATGGAGCTGGAGGCCA
91261  CGGTATTCTTTTTCTTACTCTAGTACGGGAAACGTCCTTGTACCTACCTCGACCTCCGGT

91321  TTATCCTTAGCAAACTAACCCAGGAACAGAAAACCAAGTGCAGATGTTCTCACTTTTAAG
91321  AATAGGAATCGTTTGATTGGGTCCTTGTCTTTTGGTTCACGTCTACAAGAGTGAAAATTC

91381  TGTGAGCTGAATGAGGAGAATACATGGGCACATAGAGGGGCCTATCAGAGGGTGGAGGGT
91381  ACACTCGACTTACTCCTCTTATGTACCCGTGTATCTCCCCGGATAGTCTCCCACCTCCCA

91441  GGGAGAAGGAAGAGTATCAGAAAAAATAACAGGTAGTAGATTTAATACCGGATGACAAAA
91441  CCCTCTTCCTTCTCATAGTCTTTTTTATTGTCCATCATCTAAATTATGGCCTACTGTTTT

91501  CAATCTGTATAACAAACCCCCATGACATGAGTTTACCTATATAACAAACCCGCACATGTA
91501  GTTAGACATATTGTTTGGGGGTACTGTACTCAAATGGATATATTGTTTGGGCGTGTACAT

91561  CTCCTGAACTTAAAAGTTAAATTAAAAAAAAATTAATGTCTAATAATATATTACAGTATT
91561  GAGGACTTGAATTTTCAATTTAATTTTTTTTTAATTACAGATTATTATATAATGTCATAA

91621  CTTCATATTCAATGGCAATGTGTGAAGTGGGAAGTGTCTTGACAGAATTCGGTGTTTCAA
91621  GAAGTATAAGTTACCGTTACACACTTCACCCTTCACAGAACTGTCTTAAGCCACAAAGTT

91681  GGCTTACACTTTGATGCCCAAGACTGCACAAGGCTACATTTTCTACTGGTGAGACAAATT
91681  CCGAATGTGAAACTACGGGTTCTGACGTGTTCCGATGTAAAAGATGACCACTCTGTTTAA

91741  CCAGACGCATTGCATTCAGATCTAATCTCTTAGCTCCTTAATCTTCAGGGTACTGGTAAA
91741  GGTCTGCGTAACGTAAGTCTAGATTAGAGAATCGAGGAATTAGAAGTCCCATGACCATTT

91801  CATGAAGACCTCCCCAGTGCTGTAGTCATCATGATATGTACAGCAGGTGGCTGAGCTCTG
91801  GTACTTCTGGAGGGGTCACGACATCAGTAGTACTATACATGTCGTCCACCGACTCGAGAC

91861  GATGTAGACTGCAGGGATATATTAGGAAGTTAATTCTCAAGGCAAGTCATCTTCAAGCAC
91861  CTACATCTGACGTCCCTATATAATCCTTCAATTAAGAGTTCCGTTCAGTAGAAGTTCGTG

91921  CATATCAGCATGATCAGCAATATAAGTAGTATCTCAGTGCTTTGTTGTTTAGTCAGAGTT
91921  GTATAGTCGTACTAGTCGTTATATTCATCATAGAGTCACGAAACAACAAATCAGTCTCAA

91981  TTGTACTCTATCACCCATTGTAATGTTCCTATTTGCAAAAGGTAATACATACCCTTTAAA
91981  AACATGAGATAGTGGGTAACATTACAAGGATAAACGTTTTCCATTATGTATGGGAAATTT

92041  ACATCTTTGCTTTTTCTCCCATTATCGAGATGCTAGCAGCTTCATAAAGCAGAATAACTA
92041  TGTAGAAACGAAAAAGAGGGTAATAGCTCTACGATCGTCGAAGTATTTCGTCTTATTGAT

92101  AGGGCAAACAGATTATATAAAGGGTTGGAGCTCAATGAAGACAACAAGAACAGCAAAGGT
92101  TCCCGTTTGTCTAATATATTTCCCAACCTCGAGTTACTTCTGTTGTTCTTGTCGTTTCCA

92161  TATTGTAAAACTGGCTGCTTGCAGGCCAACAAGCACATCCATATGGAGGCAATCAGTTTA
92161  ATAACATTTTGACCGACGAACGTCCGGTTGTTCGTGTAGGTATACCTCCGTTAGTCAAAT

92221  TGCTACCTCTGTCTGTTTGATGGGATTCATAATATTGACTTTATCCATTAGATTTGGACT
92221  ACGATGGAGACAGACAAACTACCCTAAGTATTATAACTGAAATAGGTAATCTAAACCTGA
```

FIG. 5 (cont'd)

```
92281  ACCAGGGAATAAAATAAGCAGATGGAGAGTAAGGATTTGCTAGGAAATAATTCAGCCAGT
92281  TGGTCCCTTATTTTATTCGTCTACCTCTCATTCCTAAACGATCCTTTATTAAGTCGGTCA

92341  CACTTTGAAAGCTGTTCAAGAAACAGCTTTCAAAGTGTCTCTCAAACTATGTTTGCCCAT
92341  GTGAAACTTTCGACAAGTTCTTTGTCGAAAGTTTCACAGAGAGTTTGATACAAACGGGTA

92401  TATCCCAATAATTTATTTCCCAATAATTTCATGGGAAAAGAAGGAAGTTCTGTGGTCAGA
92401  ATAGGGTTATTAAATAAAGGGTTATTAAAGTACCCTTTTCTTCCTTCAAGACACCAGTCT

92461  TAAATCTGGAAAACACTGGTTTAAGCAAAGTTCAGTAGGTCTGCTTCCCTGCAGGTCACC
92461  ATTTAGACCTTTTGTGACCAAATTCGTTTCAAGTCATCCAGACGAAGGGACGTCCAGTGG

92521  TCAGAGTCTTTACTCTGCTAACCTAGGAACTCATCCAACAAGTTTAATTTAACAGCTACA
92521  AGTCTCAGAAATGAGACGATTGGATCCTTGAGTAGGTTGTTCAAATTAAATTGTCGATGT

92581  CTGTGTACGTCACTTTAACAGTCACTGAGCTGTGACTCTTGGGGGAAAGATTGTGCGTGT
92581  GACACATGCAGTGAAATTGTCAGTGACTCGACACTGAGAACCCCCTTTCTAACACGCACA

92641  GTGTGTGTGTGTGTACACATGTGTGCACATGTGCAGAATCTACCAAATCTTAAGAGAAAG
92641  CACACACACACACATGTGTACACACGTGTACACGTCTTAGATGGTTTAGAATTCTCTTTC

92701  GAACATGCTGGGAAACTGTCCTGTGAAAGAGAATAGAAACCTGAAGATTTGAGGCAGTGA
92701  CTTGTACGACCCTTTGACAGGACACTTTCTCTTATCTTTGGACTTCTAAACTCCGTCACT

92761  TAGCATTTATGAAAGCAGCAGATAAGGACTAATCACCAAAAGGGGTAGCTCTTTTGTTGG
92761  ATCGTAAATACTTTCGTCGTCTATTCCTGATTAGTGGTTTTCCCCATCGAGAAAACAACC

92821  TTGGGGAAAACAGGAATTTTTCCCCCACCCAATGTGCTGCATTTTCTAATTTTCTATGAA
92821  AACCCCTTTTGTCCTTAAAAAGGGGGTGGGTTACACGACGTAAAAGATTAAAAGATACTT

92881  CACTTCCTAAGAAAAAGCTGAATGAAGAACATTTGCGATGCAATCAGCTCATTAAGAAAC
92881  GTGAAGGATTCTTTTTCGACTTACTTCTTGTAAACGCTACGTTAGTCGAGTAATTCTTTG

92941  ACGCACTTTTGTGGAGATACGTGCTGTCCCAGGAGATGCTCTGCGAGGAGCCGAGTGTTT
92941  TGCGTGAAAACACCTCTATGCACGACAGGGTCCTCTACGAGACGCTCCTCGGCTCACAAA

93001  GGACTGGAGCTGCTGAATGGTTTCTCACAGTTCTAGAATGTTTGGGGCTGCACCCCTCTAA
93001  CCTGACCTCGACGACTTACCAAAGAGTGTCAAGATCTTACAAACCCCGACGTGGGAGATT

93061  GATGTTGAACCCATCAGTAATTGCTCCAAACCACTTTATGGGATATAATGCTGTGAGTTG
93061  CTACAACTTGGGTAGTCATTAACGAGGTTTGGTGAAATACCCTATATTACGACACTCAAC

93121  ACACCTGAGGGGATTGTGGTCCTGTTCATGAGTAATTACTTTTCTGTTGCCTATAGAAGG
93121  TGTGGACTCCCCTAACACCAGGACAAGTACTCATTAATGAAAAGACAACGGATATCTTCC

93181  GCCAGCAATAGCAGATGAGTAGCTGAACAGTGGTTTTGAGTAATAAAACGTTCTTTTTTA
93181  CGGTCGTTATCGTCTACTCATCGACTTGTCACCAAAACTCATTATTTTGCAAGAAAAAAT

93241  AAAAAAAGTAATGCTTTCTGTTAAACTCTGACTATACTCTCTCCTGGTATCACAACCCAG
93241  TTTTTTTCATTACGAAAGACAATTTGAGACTGATATGAGAGAGGACCATAGTGTTGGGTC

93301  CTTTCTTTTTGCCTTCTTTATTGCAGTTACATATGGGGCTGATGACTTTAGGGATTTCCA
93301  GAAAGAAAAACGGAAGAAATAACGTCAATGTATACCCCGACTACTGAAATCCCTAAAGGT

93361  TGCAATAATTCCCAAATCTTTCTCTCGTAAGTATATGCCTTGCTTCTGGAAAACAAAAGC
93361  ACGTTATTAAGGGTTTAGAAAGAGAGCATTCATATACGGAACGAAGACCTTTTGTTTTCG

93421  ATGCCTTCATCTCCTATCATGTAAATATCGTACGTGCATGTTCCTTCATCAACCCCCGAG
93421  TACGGAAGTAGAGGATAGTACATTTATAGCATGCACGTACAAGGAAGTAGTTGGGGGCTC

93481  ATACATTAAATATTCACTGTTCTATTCGTTAGACACCTACCATATCATTTTTGGGTATTT
93481  TATGTAATTTATAAGTGACAAGATAAGCAATCTGTGGATGGTATAGTAAAAACCCATAAA

93541  ATACCATAAAGTGCAAAACGAAGGTCTAGGCAGTTGTGCGGTGTCCTGGGAGCATGGCAG
93541  TATGGTATTTCACGTTTTGCTTCCAGATCCGTCAACACGCCACAGGACCCTCGTACCGTC

93601  TGGAGTAACAGTAAGGGTTGGAGTCACAGTAGCACTGATGGGATTGTTACTTCGCAGATG
93601  ACCTCATTGTCATTCCCAACCTCAGTGTCATCGTGACTACCCTAACAATGAAGCGTCTAC
```

FIG. 5 (cont'd)

```
93661  CTGCTGGACAGCTTTGAGATTACTCCTGTAATCCTTTTTATTGAGTGTGAGGATAAAATG
93661  GACGACCTGTCGAAACTCTAATGAGGACATTAGGAAAAATAACTCACACTCCTATTTTAC

93721  GCCATATTTTCTGTCACCAACAAAGAACTGAACATGGTTTCAAGATAATTTTTACAATTT
93721  CGGTATAAAAGACAGTGGTTGTTTCTTGACTTGTACCAAAGTTCTATTAAAAATGTTAAA

93781  TGTGGGACAGGAGAAGGAGATATGCTCTTCATCTGTGGTTCTGGAGTATTAATTTCAGAA
93781  ACACCCTGTCCTCTTCCTCTATACGAGAAGTAGACACCAAGACCTCATAATTAAAGTCTT

93841  CTGAGAAGAGAAAATTGCAGGCCTCCAGGCCGTTATTCTGTGGTGCATCGCTGCTGGAGC
93841  GACTCTTCTCTTTTAACGTCCGGAGGTCCGGCAATAAGACACCACGTAGCGACGACCTCG

93901  CAACGTACTGTTCCTGCTTGGTGCCCGCAGGACCTTCTCTGATCTGAGCTGTTAAACCAA
93901  GTTGCATGACAAGGACGAACCACGGGCGTCCTGGAAGAGACTAGACTCGACAATTTGGTT

93961  AAACAGATGTGAATTTCATTTTTCTTTTTAGATATTGAGCTGATAAATGATAAATATAT
93961  TTTGTCTACACTTAAAGTAAAAAGAAAAAATCTATAACTCGACTATTTACTATTTATATA

94021  TTGGGTAACATCCTCAAATGAGTACTTTAAAGAACAGAGAGTGCTTTTGAAAATGTATAG
94021  AACCCATTGTAGGAGTTTACTCATGAAATTTCTTGTCTCTCACGAAAACTTTTACATATC

94081  AGAGCTGAATATTTAAAGCCATACAAGTTGATAATCCCCTTAGGACCTGTATTAGTAAAT
94081  TCTCGACTTATAAATTTCGGTATGTTCAACTATTAGGGGAATCCTGGACATAATCATTTA

94141  CCTCTAATACTATAAAGCAACATCAGAAAACAGGTCGCATTTGTTAACACTGTGACAATT
94141  GGAGATTATGATATTTCGTTGTAGTCTTTTGTCCAGCGTAAACAATTGTGACACTGTTAA

94201  ATAATTATAGGCTCTAATTTGAACAGTGCCAGTAACAGTTAAAGACAGGTGTCTGACATC
94201  TATTAATATCCGAGATTAAACTTGTCACGGTCATTGTCAATTTCTGTCCACAGACTGTAG

94261  CTGGTTATCAAAAACTATCTGGTGTCTAAGGAATTTAACAGTATCAAAGTACATCTTTTT
94261  GACCAATAGTTTTTGATAGACCACAGATTCCTTAAATTGTCATAGTTTCATGTAGAAAAA

94321  GCTCACAAACTAGATTGGCTACTTTTCCAGCCTATAGAAGTTACAGAAATCTTTCTTTTA
94321  CGAGTGTTTGATCTAACCGATGAAAAGGTCGGATATCTTCAATGTCTTTAGAAAGAAAAT

94381  CTGATATTCCTTTGATTCCACTTTAAAGCAATAGCTTGATACCTACTTTTTGAGATGTAT
94381  GACTATAAGGAAACTAAGGTGAAATTTCGTTATCGAACTATGGATGAAAAACTCTACATA

94441  ATGTATGTACTTGTAAATGCTTATATATGTGTATTTGTTTACACGTGAGCTTATATGAAC
94441  TACATACATGAACATTTACGAATATATACACATAAACAAATGTGCACTCGAATATACTTG

94501  ATATAAAACATTATGGTATTGGACAGAGAAATGATATTGATTTGAAGAATCATATTGTTG
94501  TATATTTTGTAATACCATAACCTGTCTCTTTACTATAACTAAACTTCTTAGTATAACAAC

94561  AAGTATTTTGAGAAGTCAAATGCACTTGAGAGTAAGCTAATGCATCCTAAAACATGTTTC
94561  TTCATAAAACTCTTCAGTTTACGTGAACTCTCATTCGATTACGTAGGATTTTGTACAAAG

94621  TGTGAAGTCTGAGGAAGGTGTCAGCCAGAGCATATGTTGAAGCAGACCCTTCAGTGAAGC
94621  ACACTTCAGACTCCTTCCACAGTCGGTCTCGTATACAACTTCGTCTGGGAAGTCACTTCG

94681  CTTCAGTCTGTAAGAATCGCTGCATGTGAAGATGTGTTAATGTTATGATAGTTACAGTTT
94681  GAAGTCAGACATTCTTAGCGACGTACACTTCTACACAATTACAATACTATCAATGTCAAA

94741  TTATAAAAGAGATGATATACACTTGGATATGCTTTCTGTCTATATTTATGCAAATGTGTC
94741  AATATTTTCTCTACTATATGTGAACCTATACGAAAGACAGATATAAATACGTTTACACAG

94801  CATAAGGTATTGGTGTCTCTCTTTCTCTCCCACTCTCCCCAGTGTTGGAATTGTGACTAT
94801  GTATTCCATAACCACAGAGAGAAAGAGAGGGTGAGAGGGGTCACAACCTTAACACTGATA

94861  CTTCTCACACAAGCGGCTACTTGGTCTTGATGCCTTCCCCCGCAAAACAGCAACCAAACT
94861  GAAGAGTGTGTTCGCCGATGAACCAGAACTACGGAAGGGGGCGTTTTGTCGTTGGTTTGA

94921  GTTCTGGGCCAATATCACCACCTTGTGGTCATGATGAAGAATTGCCCCCTTTGCCCTCAA
94921  CAAGACCCGGTTATAGTGGTGGAACACCAGTACTACTTCTTAACGGGGGAAACGGGAGTT

94981  CACCTCTTTTCTTCTTGAAAATTAAAAACAACCCCTTTCACCCCCTCTACTGTCCTTATT
94981  GTGGAGAAAAGAAGAACTTTTAATTTTTGTTGGGGAAAGTGGGGGAGATGACAGGAATAA
```

FIG. 5 (cont'd)

```
95041  CCAGTTTGTGTCCGTAGTTGCTGGAGGAAAGAAAATGCCTATTGCTCTTTTTTTTATTCT
95041  GGTCAAACACAGGCATCAACGACCTCCTTTCTTTTACGGATAACGAGAAAAAAAATAAGA

95101  CTTTATCTGTTTACTCTTCTGCCTTTCTTTTCTCTCCCTGACTTCATTCCATTTAAAGGC
95101  GAAATAGACAAATGAGAAGACGGAAAGAAAAGAGAGGGACTGAAGTAAGGTAAATTTCCG

95161  CTTAAATTGCAAATAACGAAAAAAGTATTTTCTAATAATATACCCTAGTGGGACGAAAAC
95161  GAATTTAACGTTTATTGCTTTTTTCATAAAAGATTATTATATGGGATCACCCTGCTTTTG

95221  AACCTTCTACATTTTAAATGATATTAAGTTATAATAAATGGTTCCATGAACTTTAAAACG
95221  TTGGAAGATGTAAAATTTACTATAATTCAATATTATTTACCAAGGTACTTGAAATTTTGC

95281  CTTAAAAGTTTTATAAATCTCTTTTAGAGGCAACACAAAAATATCTATATATATATCTTC
95281  GAATTTTCAAAATATTTAGAGAAAATCTCCGTTGTGTTTTTATAGATATATATATAGAAG

95341  TCTTCACCTCAAATTTTCATTTAATTACCGTGATTCAAGATATATCTTAAATATTTCCAT
95341  AGAAGTGGAGTTTAAAAGTAAATTAATGGCACTAAGTTCTATATAGAATTTATAAAGGTA

95401  TTCATTTGATTTTTACTTGCTAGTCACCAGTGTTGCAAGAATATTTCTGTACCATTTTTC
95401  AAGTAAACTAAAAATGAACGATCAGTGGTCACAACGTTCTTATAAAGACATGGTAAAAAG

95461  AAGTAAAATATTGAGCATTTCAAGCTTACATGGCCTAAACTCACACTAGAGTGACTACTT
95461  TTCATTTTATAACTCGTAAAGTTCGAATGTACCGGATTTGAGTGTGATCTCACTGATGAA

95521  CGGACTATCTTTTCAATGGAAAAATGCGTTCTGAGTACCAAACATTTACTTTTTCAGTAA
95521  GCCTGATAGAAAAGTTACCTTTTTACGCAAGACTCATGGTTTGTAAATGAAAAAGTCATT

95581  ATATGAAGACACATTCTAAAAAGGAAAGGGAAATGAAGAGGAAGCTTAATTCATTGGTCA
95581  TATACTTCTGTGTAAGATTTTTCCTTTCCCTTTACTTCTCCTTCGAATTAAGTAACCAGT

95641  GGTGGGGACTAACAGTGTACATTATACCTATGCATTAAAAAATGTTTAATTATCCATGAG
95641  CCACCCCTGATTGTCACATGTAATATGGATACGTAATTTTTTACAAATTAATAGGTACTC

95701  CACATACAGTGCCTGGCACAGATTCAGGCCTCTTGGCTCCTCTTGGCATCTGAGTTCCTT
95701  GTGTATGTCACGGACCGTGTCTAAGTCCGGAGAACCGAGGAGAACCGTAGACTCAAGGAA

95761  GGATTCTCCAGATTCTTCAATCCAAACTTGTCTATCTACCAAAGTCCACCTTCCATACAG
95761  CCTAAGAGGTCTAAGAAGTTAGGTTTGAACAGATAGATGGTTTCAGGTGGAAGGTATGTC

95821  GGGTGTGGGGTCTCTCTTAGTACTGTTGGGTGCCAATAACATAGAAGCCCTCCAAGATAG
95821  CCCACACCCCAGAGAGAATCATGACAACCCACGGTTATTGTATCTTCGGGAGGTTCTATC

95881  GTCAATGAGATTTTAATTTTTCCCAACTTTAAATAGCATCTGGGAAGGAAAGCAGCTTTT
95881  CAGTTACTCTAAAATTAAAAAGGGTTGAAATTTATCGTAGACCCTTCCTTTCGTCGAAAA

95941  GACTAGGAGTTTGAAAACATCCACTCTTCATATTTATTGTCACATTTATTGAGTAATAAA
95941  CTGATCCTCAAACTTTTGTAGGTGAGAAGTATAAATAACAGTGTAAATAACTCATTATTT

96001  ATTGGGCTCTTGTCCATTATCTCTCAGTCAATGAAAGAGCCCACGGTGGGCATGAGCCAG
96001  TAACCCGAGAACAGGTAATAGAGAGTCAGTTACTTTCTCGGGTGCCACCCGTACTCGGTC

96061  AGTGTTCCGGAGAAAGAGAGGACCAGTCTCCATTTCATGTTCTATATTTAATCAGTTCAA
96061  TCACAAGGCCTCTTTCTCTCCTGGTCAGAGGTAAAGTACAAGATATAAATTAGTCAAGTT

96121  TTCAGCACCTTACTGAGTTTGACATTTTTCTAAGTAATGGGGTGGGGGGTTACAAAATAT
96121  AAGTCGTGGAATGACTCAAACTGTAAAAAGATTCATTACCCCACCCCCCAATGTTTTATA

96181  TTATAACTATCTTTCCTATCTTCAGGGAGATGTACCATTTCACTGAAGCAATACCACAGC
96181  AATATTGATAGAAAGGATAGAAGTCCCTCTACATGGTAAAGTGACTTCGTTATGGTGTCG

96241  TAAGCAGTTCCAGCTCCGAGTAACAGAGGAAGGAGTGAGCGATTTAGGAACTCACAGAAG
96241  ATTCGTCAAGGTCGAGGCTCATTGTCTCCTTCCTCACTCGCTAAATCCTTGAGTGTCTTC

96301  GGCACGGCCAGGCAACTCGGGCCCTGGCAAATGTTCCATAGAGACAGCATCCATGGGGTT
96301  CCGTGCCGGTCCGTTGAGCCCGGGACCGTTTACAAGGTATCTCTGTCGTAGGTACCCCAA

96361  GAACCAAGCACAATGCCTGCAAATCGGGCAGGCGGGTTCATGGAATTGATTCTAGGGCAG
96361  CTTGGTTCGTGTTACGGACGTTTAGCCCGTCCGCCCAAGTACCTTAACTAAGATCCCGTC
```

FIG. 5 (cont'd)

```
96421  GTATGATCAGCACCATTTAAGGAGTGGCAGTTGTTAAGAAACTGAAGGGATTTCTCATAT
96421  CATACTAGTCGTGGTAAATTCCTCACCGTCAACAATTCTTTGACTTCCCTAAAGAGTATA

96481  GGCATTTTCAACAGAATTCAGCAGGAGCCTTGCATATCCCTTGGGATGGGTTCCGGGGTA
96481  CCGTAAAAGTTGTCTTAAGTCGTCCTCGGAACGTATAGGGAACCCTACCCAAGGCCCCAT

96541  TTATGGAGCTGCCAGGAGGTGCTCAGCTTCAGTAAGTGCCAGTCATTCCTTCCCAACCTC
96541  AATACCTCGACGGTCCTCCACGAGTCGAAGTCATTCACGGTCAGTAAGGAAGGGTTGGAG

96601  CTCCTTCATTAGTGGAAGTATCAGCTGGTGTCATTGCCTTCTTCAGGAGGATGGATTTCA
96601  GAGGAAGTAATCACCTTCATAGTCGACCACAGTAACGGAAGAAGTCCTCCTACCTAAAGT

96661  AAATGAAGGGCCAACAAAACTCACATTCTCGCAGAGCCTCCGTCACAACTGCATGTGTTC
96661  TTTACTTCCCGGTTGTTTTGAGTGTAAGAGCGTCTCGGAGGCAGTGTTGACGTACACAAG

96721  ACTGCCATCAACAGGCCAACACCCACTTGTTCTTTTCTTCTAGGTAAAGGAAAAGGTCTG
96721  TGACGGTAGTTGTCCGGTTGTGGGTGAACAAGAAAAGAAGATCCATTTCCTTTTCCAGAC

96781  TGGGACAAAGGCCCTGAACTCCTCACTCCTTGAATGGGAGGCATATTGGTGGAGGCTGTC
96781  ACCCTGTTTCCGGGACTTGAGGAGTGAGGAACTTACCCTCCGTATAACCACCTCCGACAG

96841  ACACAACTACAGGTGGCAGGAACCTGCCATCAGGGTTCCCATCAGCCTCCAGGGCTTGCT
96841  TGTGTTGATGTCCACCGTCCTTGGACGGTAGTCCCAAGGGTAGTCGGAGGTCCCGAACGA

96901  TCTCTGCCCTGTGTGTGGACACCTTCCATCACTGGAAACCCCTCTCTCAGAAGAACCACT
96901  AGAGACGGGACACACACCTGTGGAAGGTAGTGACCTTTGGGGAGAGAGTCTTCTTGGTGA

96961  TCTTGCCCTCATCTCCCACTTGCCTCTCCTCGGCACCTTCTCCACCCTCAGGGGCCAAGC
96961  AGAACGGGAGTAGAGGGTGAACGGAGAGGAGCCGTGGAAGAGGTGGGAGTCCCCGGTTCG

97021  TGAGGAAGTGTGCATCCTGTGCCACCAACCTTGCTCGCAGGAATTAGTTTCAGTCCCCAG
97021  ACTCCTTCACACGTAGGACACGGTGGTTGGAACGAGCGTCCTTAATCAAAGTCAGGGGTC

97081  TGACTGACTCTTCCAAACCTGCACCAGCCTATGCTGCCCTTTTGAAAGGAGGCGTGCGTA
97081  ACTGACTGAGAAGGTTTGGACGTGGTCGGATACGACGGGAAAACTTTCCTCCGCACGCAT

97141  CAGCCTGGCTGGTACAGAAGATTCCAGATTTCAGTGACTACAGGACGCTGTCACCCCTTC
97141  GTCGGACCGACCATGTCTTCTAAGGTCTAAAGTCACTGATGTCCTGCGACAGTGGGGAAG

97201  TGTTTTTCTTTTTTCTGTCCACATCTCTGATTGAGCATACCTTCAGGGAAAACCCCAGAA
97201  ACAAAAAGAAAAAAGACAGGTGTAGAGACTAACTCGTATGGAAGTCCCTTTTGGGGTCTT

97261  ACCTTTTTCACACTTACATGGGAAGCCAAGACACTCTCATCCTGGGCTTGTGTTTTTAAA
97261  TGGAAAAAGTGTGAATGTACCCTTCGGTTCTGTGAGAGTAGGACCCGAACACAAAAATTT

97321  ATCTATATTTTAATTTCACAGGTCCTTACATTTATGACTAATAGATTTCAGATTTTGAGA
97321  TAGATATAAAATTAAAGTGTCCAGGAATGTAAATACTGATTATCTAAAGTCTAAAACTCT

97381  TACAATCTGTAGTTGCAACTTATGAAGATAGTTTCAAGCCCTGATTTCTGTCATCTATGA
97381  ATGTTAGACATCAACGTTGAATACTTCTATCAAAGTTCGGGACTAAAGACAGTAGATACT

97441  AAACAGTAAGCAAGTTGCTTGTATTCTCCTCCTAGCTGGATAAGAGACCCCCGTTTTCAT
97441  TTTGTCATTCGTTCAACGAACATAAGAGGAGGATCGACCTATTCTCTGGGGGCAAAAGTA

97501  GGACAGCCTCCTTGGGTGGACAGAAGTCTCCTGATCTTGTCTATGTAACCAGCACCCACT
97501  CCTGTCGGAGGAACCCACCTGTCTTCAGAGGACTAGAACAGATACATTGGTCGTGGGTGA

97561  TTGCATTTTTCCGCAAAGAAAAGAGGAGCTTAACCCCATTTACGGGAAATCCACGCACTG
97561  AACGTAAAAAGGCGTTTCTTTTCTCCTCGAATTGGGGTAAATGCCCTTTAGGTGCGTGAC

97621  CTTGAATCTTACGCGCCCCGTGGTGACGGTGTTGCCCACTCTGTTCCCTTCCCACCAAAT
97621  GAACTTAGAATGCGCGGGGCACCACTGCCACAACGGGTGAGACAAGGGAAGGGTGGTTTA

97681  CCTGCCAGCACCTGGCAGTCATCCAGTCCTTGTCTTAGACTTCACCAACCTTTCCCGTCA
97681  GGACGGTCGTGGACCGTCAGTAGGTCAGGAACAGAATCTGAAGTGGTTGGAAAGGGCAGT

97741  TAACATGGCTTAGAAGTTGTCCGAATAGTGCTAGAAGCTTTCAGCCCTGGAATGCTCAGC
97741  ATTGTACCGAATCTTCAACAGGCTTATCACGATCTTCGAAAGTCGGGACCTTACGAGTCG
```

FIG. 5 (cont'd)

```
97801  ATCTGCCATCTAACTTCCATTTAAAACGTTTTGAGCATTTGCTGATACAGGTTCCTCTGT
97801  TAGACGGTAGATTGAAGGTAAATTTTGCAAAACTCGTAAACGACTATGTCCAAGGAGACA

97861  CCTTTCCCCATTATTTTCAGTTCCTTGGCCTTGCCCATAGTGATCTGTGGATATTGTCTG
97861  GGAAAGGGGTAATAAAAGTCAAGGAACCGGAACGGGTATCACTAGACACCTATAACAGAC

97921  CATACTCTTTTTTAGAAACCTAGAGCATCGCAGTGTCCTTAATTTTCCTCTTCAAACTCT
97921  GTATGAGAAAAAATCTTTGGATCTCGTAGCGTCACAGGAATTAAAAGGAGAAGTTTGAGA

97981  ATATATTCCTGAGCTGATCATCCCTACTGCTGTTCCTACAGAACTGTGTGACTAATCTTC
97981  TATATAAGGACTCGACTAGTAGGGATGACGACAAGGATGTCTTGACACACTGATTAGAAG

98041  TATATATGTCCCTACATCTAGCCATCTAGGTGGAGATCTAGGTACCTATCTCCCTAAAAT
98041  ATATATACAGGGATGTAGATCGGTAGATCCACCTCTAGATCCATGGATAGAGGGATTTTA

98101  TGTACTTGGTATCCACATTGACCTCAGGACAGTATGTGATAGGCTCTTGTGCCTTTTCGA
98101  ACATGAACCATAGGTGTAACTGGAGTCCTGTCATACACTATCCGAGAACACGGAAAAGCT

98161  CTAGGAGTTTGAAAACATCCACTCTTCATATTTATTGTCACATTTGTTGAATAATAAAAT
98161  GATCCTCAAACTTTTGTAGGTGAGAAGTATAAATAACAGTGTAAACAACTTATTATTTTA

98221  TGGGCTCTTGTCCATTATGTCTCAGTCAGTGAAAGAGCCCAGGGTGGGCCTGAGCCAGAG
98221  ACCCGAGAACAGGTAATACAGAGTCAGTCACTTTCTCGGGTCCCACCCGGACTCGGTCTC

98281  TGTTTGTGTCCCTAGTTCTCTTTTGGTTCTGTTACAGCTCTCAGTGACAGTGTCATTGAG
98281  ACAAACACAGGGATCAAGAGAAAACCAAGACAATGTCGAGAGTCACTGTCACAGTAACTC

98341  GCTAACAAGGACAGAGTACTGCTTTCAGCCACCATTTGTCCAATGAGTGGCTGATCTCCA
98341  CGATTGTTCCTGTCTCATGACGAAAGTCGGTGGTAAACAGGTTACTCACCGACTAGAGGT

98401  GGCCTCTGGCTTTGAGAACATCTGTGATATCTAAGGCAGCATCCATTGTGGGCTTTCCCC
98401  CCGGAGACCGAAACTCTTGTAGACACTATAGATTCCGTCGTAGGTAACACCCGAAAGGGG

98461  CATGCTTCTGTTTCCTTCCTGTCACATAGCTTTGCCTCCTCCTGCAAGCAGCCTGCTGTA
98461  GTACGAAGACAAAGGAAGGACAGTGTATCGAAACGGAGGAGGACGTTCGTCGGACGACAT

98521  GCAGAACCGGTGTTCCTGAAGCCAGAAACCCAAAGGTCGTGTCCAATGCTTCCCTGCTGT
98521  CGTCTTGGCCACAAGGACTTCGGTCTTTGGGTTTCCAGCACAGGTTACGAAGGGACGACA

98581  TCTGCTCCCCACCTGCAAGCGCCCACACACTGATCAACAGCACACGCCATAGAGCATGCC
98581  AGACGAGGGGTGGACGTTCGCGGGTGTGTGACTAGTTGTCGTGTGCGGTATCTCGTACGG

98641  AAAGAATCCCAGAAATACTCATTCTTAATGATCCAGAAGAACAAGTGATAGCTTCTGGCA
98641  TTTCTTAGGGTCTTTATGAGTAAGAATTACTAGGTCTTCTTGTTCACTATCGAAGACCGT

98701  AGTTCTAATAGGCCATATGTGCCCATGGGAAAGCAAGAGTCAATTCTCTCTAGCTGGTTG
98701  TCAAGATTATCCGGTATACACGGGTACCCTTTCGTTCTCAGTTAAGAGAGATCGACCAAC

98761  CCTCTGAATTTATGAAGTCAAGCCGCGTAGGGGAACATGCCAAGAGGATTATCCCAATGC
98761  GGAGACTTAAATACTTCAGTTCGGCGCATCCCCTTGTACGGTTCTCCTAATAGGGTTACG

98821  CTGTTCTGCGTGGTGTCCTTTTTCTAGCCTCGGAAGCACTAGGCCTACACCTTCGCTATA
98821  GACAAGACGCACCACAGGAAAAAGATCGGAGCCTTCGTGATCCGGATGTGGAAGCGATAT

98881  GCCCTCGTCTTAGCGCCTGTATTTGAAAAACTTGCCACACCAATCTTAATTTGCTCCATT
98881  CGGGAGCAGAATCGCGGACATAAACTTTTTGAACGGTGTGGTTAGAATTAAACGAGGTAA

98941  GTGTTCTAATCTCATTTTAAAAACCACAAGGTAAATGATTAAAAATAATCTTAGATTAAG
98941  CACAAGATTAGAGTAAAATTTTTGGTGTTCCATTTACTAATTTTTATTAGAATCTAATTC

99001  GAGTACACAGATCTTTGCAGCCTCATTGTGTTTCCAGAGCGGGCTAGTGTAGACACTGGT
99001  CTCATGTGTCTAGAAACGTCGGAGTAACACAAAGGTCTCGCCCGATCACATCTGTGACCA

99061  GAACAAGGAGGGCCTAGAGAATTAGCTTTCTCCCAGAAAGATGCACAGCCTCTACCTGAG
99061  CTTGTTCCTCCCGGATCTCTTAATCGAAAGAGGGTCTTTCTACGTGTCGGAGATGGACTC

99121  AGTACCAATTCCAGAGAACTCAATGGTCATTAAGCACCATTGCCTCGACAGCCAGCCAGC
99121  TCATGGTTAAGGTCTCTTGAGTTACCAGTAATTCGTGGTAACGGAGCTGTCGGTCGGTCG
```

FIG. 5 (cont'd)

```
99181   CTCACTTGCCTGCCTATCTCCTTTATTTTCCAAGTATCTTGTCCCTGGCAGTGGGGAGAG
99181   GAGTGAACGGACGGATAGAGGAAATAAAAGGTTCATAGAACAGGGACCGTCACCCCTCTC

99241   GTTAGCAGGAGGCTGCTCAGATGCTCTCGGTCTCTGATCTTCAGGATCTGAAGGGGAGAG
99241   CAATCGTCCTCCGACGAGTCTACGAGAGCCAGAGACTAGAAGTCCTAGACTTCCCCTCTC

99301   CATTTGAAGAATCCCCATTGCTGGATTTCTCAGGACAATCCTGCATAATGCCAGGATCTG
99301   GTAAACTTCTTAGGGGTAACGACCTAAAGAGTCCTGTTAGGACGTATTACGGTCCTAGAC

99361   ATGGAGGAGACAGGCAGCTCTGTTAATCCTCTGGTGCATCCTCACTTCTGTGGTCTCCAA
99361   TACCTCCTCTGTCCGTCGAGACAATTAGGAGACCACGTAGGAGTGAAGACACCAGAGGTT

99421   GTCCACCATGTCCCAGTTAATTCATTTCATTATTCATCTGTAAGTCATTTCCCTAAAGAG
99421   CAGGTGGTACAGGGTCAATTAAGTAAAGTAATAAGTAGACATTCAGTAAAGGGATTTCTC

99481   CTAATAAGAAAACACTGGCAGTACAATCAGCCCTCCATATCCATGGGTTCAGCCTCTGGA
99481   GATTATTCTTTTGTGACCGTCATGTTAGTCGGGAGGTATAGGTACCCAAGTCGGAGACCT

99541   AATTCAACCCACTGTGGCTTGAAAATACAGTATTCAAGAGACATGGAACCTGTGGATATA
99541   TTAAGTTGGGTGACACCGAACTTTTATGTCATAAGTTCTCTGTACCTTGGACACCTATAT

99601   GAAGGCAGATTTTTCGTATCCATAGGTTCTATAGGGCCATTTTAGGGACTTGCACATCTA
99601   CTTCCGTCTAAAAAGCATAGGTATCCAAGATATCCCGGTAAAATCCCTGAACGTGTAGAT

99661   CAGACCTTCAGGAGTCTCAGAACTGATGCACTGCAGATACCAAGAGATGACTGTAAGTGG
99661   GTCTGGAAGTCCTCAGAGTCTTGACTACGTGACGTCTATGGTTCTCTACTGACATTCACC

99721   TTAGGAATTTGGATGCTGGGGCCAGGCTGCCTGCAGTTACCTTCCAGCTCTGCCACTTGC
99721   AATCCTTAAACCTACGACCCCGGTCCGACGGACGTCAATGGAAGGTCGAGACGGTGAACG

99781   CAGCTATGTGACCTTAGCAAGTTGTTCAACCTCTCTGTGCCTTGGCTTCTTCAACTGTAA
99781   GTCGATACACTGGAATCGTTCAACAAGTTGGAGAGACACGGAACCGAAGAAGTTGACATT

99841   AATAGGATAATGATAGCACTTCCCTTATGGAGTCCTTGTGAAGGTTAAATGGCAGAGTAC
99841   TTATCCTATTACTATCGTGAAGGGAATACCTCAGGAACACTTCCAATTTACCGTCTCATG

99901   AATTAATGTGCTGTGTGCCCAGCGTGTGGTATTGGGGTTAGGTGAAAGACTGTACTGGGA
99901   TTAATTACACGACACACGGGTCGCACACCATAACCCCAATCCACTTTCTGACATGACCCT

99961   TCACTGGGGGTGAGCCTCCATGTGCCATGCCCCAACCACTATCCTCAGCTAACTTCTTGT
99961   AGTGACCCCCACTCGGAGGTACACGGTACGGGGTTGGTGATAGGAGTCGATTGAAGAACA

100021  CTGTCAGTGTTAGGCTGGTGCTATAATAATTTCCATTTTCATGGATGAGGAAATCAAGGC
100021  GACAGTCACAATCCGACCACGATATTATTAAAGGTAAAAGTACCTACTCCTTTAGTTCCG

100081  ACAGAGAAGTTACATGACTTGCCTAAGATCTCAGTGCTTTTAAATAGTGCAGCTAAGATT
100081  TGTCTCTTCAATGTACTGAACGGATTCTAGAGTCACGAAAATTTATCACGTCGATTCTAA

100141  CCAGACCAGGTATTTTTATTTCAGTGTCTGGACTGTAGATCTCTAAATCGAGAGGAACTC
100141  GGTCTGGTCCATAAAAATAAAGTCACAGACCTGACATCTAGAGATTTAGCTCTCCTTGAG

100201  CCTGAATAAAATAAGCTTGGAGTGCTGTTAACTAAGTTGGTTATTTAAGACAGTTGTTCT
100201  GGACTTATTTTATTCGAACCTCACGACAATTGATTCAACCAATAAATTCTGTCAACAAGA

100261  CAGTCCTCAGTGTACATTAGAATCTTCTGGAGGGTATGTTAAAACAGACTGCTGGGCCCA
100261  GTCAGGAGTCACATGTAATCTTAGAAGACCTCCCATACAATTTTGTCTGACGACCCGGGT

100321  CCGAGAGTTCCTGAGCCTGCAACTCTGGGTTGAGCCTGAGAGTCTGTGCTTCTAGTAAGT
100321  GGCTCTCAAGGACTCGGACGTTGAGACCCAACTCGGACTCTCAGACACGAAGATCATTCA

100381  TCTCAGGTGATGCTTATGCTGCTTCTCCCAAATTTTGAGAACCATTGATTGAAAATGTTG
100381  AGAGTCCACTACGAATACGACGAAGAGGGTTTAAAACTCTTGGTAACTAACTTTTACAAC

100441  ATCAAAAATTATGTGGTCTAGGCTGAGCACAGTGGCTCACAACTGTAATCTCAACACTTT
100441  TAGTTTTTAATACACCAGATCCGACTCGTGTCACCGAGTGTTGACATTAGAGTTGTGAAA

100501  GGGAGGCCAAGTCAGGTGGATCACTGAGCTCAGGAGTTCGAGAGCAGCCTGGTCAACATG
100501  CCCTCCGGTTCAGTCCACCTAGTGACTCGAGTCCTCAAGCTCTCGTCGGACCAGTTGTAC
```

FIG. 5 (cont'd)

```
100561  ACAAGACCCATCTCTACAAAAAACACCAAAAAAAAATGGCTGGATGTGGTGGTGCACACC
100561  TGTTCTGGGTAGAGATGTTTTTTGTGGTTTTTTTTTACCGACCTACACCACCACGTGTGG

100621  TGTAGTCACAACTACTGGGGAGGCTGAGGTGGGAGGATCACTTGAGCCCGGGAGACAGAG
100621  ACATCAGTGTTGATGACCCCTCCGACTCCACCCTCCTAGTGAACTCGGGCCCTCTGTCTC

100681  CAAGACCCTGTCTCAAAAAAGAAACATTTAGTCTTGATTGTCATCTATCTCATTGATCAT
100681  GTTCTGGGACAGAGTTTTTTCTTTGTAAATCAGAACTAACAGTAGATAGAGTAACTAGTA

100741  TTTACTTGGCAAAATTTACCTACTTACTCTTATTAGTCTGTAAAAATGGTTATTAAAATG
100741  AAATGAACCGTTTTAAATGGATGAATGAGAATAATCAGACATTTTTACCAATAATTTTAC

100801  GTGGCTTTCAGTGTAACTACAAATTCTCTTAGTCATTATAGTGTTGGATTCACCAATGTA
100801  CACCGAAAGTCACATTGATGTTTAAGAGAATCAGTAATATCACAACCTAAGTGGTTACAT

100861  TCATCAGTCAGTGTTTCTGAAGTGTGTAAATGAAATAACTCCTACTTTCTTTAGGAAGAA
100861  AGTAGTCAGTCACAAAGACTTCACACATTTACTTTATTGAGGATGAAAGAAATCCTTCTT

100921  AAATATTCAAATGACATAATTACCTTGTGATGTGTGACTTAAAGGTAACAGTAATGCAGA
100921  TTTATAAGTTTACTGTATTAATGGAACACTACACACTGAATTTCCATTGTCATTACGTCT

100981  GTCAATAGTGGTCATTGTATTCAAGACACTAAAAGTTCACCTCCCACCCCCCCCCCCCAC
100981  CAGTTATCACCAGTAACATAAGTTCTGTGATTTTCAAGTGGAGGGTGGGGGGGGGGGGTG

101041  CCACCACCCAACAAACACACAAGCTTCTTTCCCTTTGGAAAAAAAAGCTCTTCCAGATAC
101041  GGTGGTGGGTTGTTTGTGTGTTCGAAGAAAGGGAAACCTTTTTTTTCGAGAAGGTCTATG

101101  CTACATTCATAAACTATCCCAATTAACCCTTCAGCAAGTGGAAGAAGTGTAAGAAAGGAT
101101  GATGTAAGTATTTGATAGGGTTAATTGGGAAGTCGTTCACCTTCTTCACATTCTTTCCTA

101161  ACCTCTTCTTTAGAACACAGGGTTTGTTTTTATGTTATTTAAGATAAACAGGAATTCAAA
101161  TGGAGAAGAAATCTTGTGTCCCAAACAAAAATACAATAAATTCTATTTGTCCTTAAGTTT

101221  TGGTCATGTACCAAAGCAACACAAAGAACTTCCGGAAATCTGAAAGGGAACTGTGGTCAG
101221  ACCAGTACATGGTTTCGTTGTGTTTCTTGAAGGCCTTTAGACTTTCCCTTGACACCAGTC

101281  AACTCTGAGCATTTTTATGTTTACTGAGTTTTGTCCCAAAGTTTATTAATGTTTACATGC
101281  TTGAGACTCGTAAAAATACAAATGACTCAAAACAGGGTTTCAAATAATTACAAATGTACG

101341  CACAAGGAAAGGTAGCATCACAATAAGAGACGTTTTTCAGGCTTGATAACCACTTATTAG
101341  GTGTTCCTTTCCATCGTAGTGTTATTCTCTGCAAAAAGTCCGAACTATTGGTGAATAATC

101401  GTATTTTGCCAAACAAGTTCACACATCCTAGAGAGCTGGATTGTGTGACCCAGAACCCAC
101401  CATAAAACGGTTTGTTCAAGTGTGTAGGATCTCTCGACCTAACACACTGGGTCTTGGGTG

101461  CCTCTAGGGCAAGGTGCCCATCTGATGGGTAGGGTGTAGGAGTAGGCCTCAGACCACTCC
101461  GGAGATCCCGTTCCACGGGTAGACTACCCATCCCACATCCTCATCCGGAGTCTGGTGAGG

101521  TGACGTGAACCTGCTTAAAGTGAGGGCCCAATTCTAAAGTGGGAACTATGTAAATACCTT
101521  ACTGCACTTGGACGAATTTCACTCCCGGGTTAAGATTTCACCCTTGATACATTTATGGAA

101581  TCTAGTGCATTTTCAGATAATCGCCACTGGGCCTATGGATGGAGAGGGCTGGCAGATCTC
101581  AGATCACGTAAAAGTCTATTAGCGGTGACCCGGATACCTACCTCTCCCGACCGTCTAGAG

101641  CCTGTAACCCCAGGTGCATCCCGAGGCCTGCCACCGAAGCCCACTCAAGGCTGAATGCAC
101641  GGACATTGGGGTCCACGTAGGGCTCCGGACGGTGGCTTCGGGTGAGTTCCGACTTACGTG

101701  GGCGAGCTCAGGCTGCTCTCCCCTTGGTATTTGCTAAGAACTTCTGTTTAGTAGCTCTCC
101701  CCGCTCGAGTCCGACGAGAGGGGAACCATAAACGATTCTTGAAGACAAATCATCGAGAGG

101761  ACACCTATTTGATTGTCTTTTTGCTGCTGTGTTGTTTTGTTGAGTTTTTTTTTTGCAATG
101761  TGTGGATAAACTAACAGAAAAACGACGACACAACAAAACAACTCAAAAAAAAAACGTTAC

101821  ACACTGAGTGGCCTCCTGTATTGTTTCTTTCAGCCAGTAATGTTAAAGTAGAGACTCAGA
101821  TGTGACTCACCGGAGGACATAACAAAGAAAGTCGGTCATTACAATTTCATCTCTGAGTCT

101881  GTGATGAAGAGAATGGGCGTGCCTGTGAAATGAATGGGGAAGAATGTGCGGAGGATTTAC
101881  CACTACTTCTCTTACCCGCACGGACACTTTACTTACCCCTTCTTACACGCCTCCTAAATG
```

FIG. 5 (cont'd)

```
101941  GAATGCTTGATGCCTCGGGAGAGAAAATGAATGGCTCCCACAGGGACCAAGGCAGCTCGG
101941  CTTACGAACTACGGAGCCCTCTCTTTTACTTACCGAGGGTGTCCCTGGTTCCGTCGAGCC

102001  CTTTGTCGGGAGTTGGAGGCATTCGACTTCCTAACGGAAAACTAAAGTGTGATATCTGTG
102001  GAAACAGCCCTCAACCTCCGTAAGCTGAAGGATTGCCTTTTGATTTCACACTATAGACAC

102061  GGATCATTTGCATCGGGCCCAATGTGCTCATGGTTCACAAAAGAAGCCACACTGGTAAGG
102061  CCTAGTAAACGTAGCCCGGGTTACACGAGTACCAAGTGTTTTCTTCGGTGTGACCATTCC

102121  CCTGGCTCAGTTTTTCCTTTAGTGGCCTGGAGAAGGTGCATGGGGTTTGAAGGAGGAAAG
102121  GGACCGAGTCAAAAAGGAAATCACCGGACCTCTTCCACGTACCCCAAACTTCCTCCTTTC

102181  CATCCTGTCTTCCTTGTGTTCTGAGCATGTTTCTAATTGACTGGTAGCTCAGTTGTTGCA
102181  GTAGGACAGAAGGAACACAAGACTCGTACAAAGATTAACTGACCATCGAGTCAACAACGT

102241  AGCGATTGGTTCCAAGTGGTACCGAGTCATAGAGTCCTTGTTCTGGTACAGCCTTGTAAA
102241  TCGCTAACCAAGGTTCACCATGGCTCAGTATCTCAGGAACAAGACCATGTCGGAACATTT

102301  GGACTTCTCAACACGTACCAATTCCACCCTATAAATAAAACAAGGGAAAAGTGAACAGCA
102301  CCTGAAGAGTTGTGCATGGTTAAGGTGGGATATTTATTTTGTTCCCTTTTCACTTGTCGT

102361  TCACATGAGAGGCTTGGCGAGGGCTGCTATTATAGTAACACATACTAAGTAGTCTCAGCT
102361  AGTGTACTCTCCGAACCGCTCCCGACGATAATATCATTGTGTATGATTCATCAGAGTCGA

102421  GAGCCCTCAGGGTACGTGTGCTGAGTGGTCACCCTCCACAAAACAAAAAATCCTGATACA
102421  CTCGGGAGTCCCATGCACACGACTCACCAGTGGGAGGTGTTTTGTTTTTTAGGACTATGT

102481  CCAAAACTTACTCCTCAAAGTTTCCACTGAGAAACCATGAGTAAAATGTGTGTTTAAATT
102481  GGTTTTGAATGAGGAGTTTCAAAGGTGACTCTTTGGTACTCATTTTACACACAAATTTAA

102541  GTATCCAAACTAACAGGGTTTGATGTTTAGAAACAATAATCAATGATGGAATAGCAGCAA
102541  CATAGGTTTGATTGTCCCAAACTACAAATCTTTGTTATTAGTTACTACCTTATCGTCGTT

102601  AATCGAGTTTTCAGAAAGACCTCAGATGAGCTTTCAAATGGCTTGCCCTCTAACAGGAAA
102601  TTAGCTCAAAAGTCTTTCTGGAGTCTACTCGAAAGTTTACCGAACGGGAGATTGTCCTTT

102661  GACTTTGAATCAGATGCTTCTATTGCCACTGGTTATCAGCTCAAATTCCTAAAGAACTTC
102661  CTGAAACTTAGTCTACGAAGATAACGGTGACCAATAGTCGAGTTTAAGGATTTCTTGAAG

102721  ATCCCAAATACCCTGTCTTGCTGAAAGGTTTACTGGAAGTATAAGAGAATGTCATGTTCT
102721  TAGGGTTTATGGGACAGAACGACTTTCCAAATGACCTTCATATTCTCTTACAGTACAAGA

102781  GTGTCCAGAAAGGAAGGAACACGGGCACCCTAGTGTCAGCGAGTTGTGCTCAGGCTCACA
102781  CACAGGTCTTTCCTTCCTTGTGCCCGTGGGATCACAGTCGCTCAACACGAGTCCGAGTGT

102841  GGATGCCCCCTCACCAGAGGCGTGGGAACACGGCGAGCCCCAGCTGGCCGCGCTCTGCCA
102841  CCTACGGGGGAGTGGTCTCCGCACCCTTGTGCCGCTCGGGGTCGACCGGCGCGAGACGGT

102901  CTGTTTCTAATAGCCGGTCACGTTGATGGAAGTGTCACAGAGTTGTCCAACAGAACTGTC
102901  GACAAAGATTATCGGCCAGTGCAACTACCTTCACAGTGTCTCAACAGGTTGTCTTGACAG

102961  CAGTCAGAAAACCACCACTCATGGTGCTGGAGTGTCTTAGAAGTAAAATATGAATAACAC
102961  GTCAGTCTTTTGGTGGTGAGTACCACGACCTCACAGAATCTTCATTTTATACTTATTGTG

103021  ACACTTATTTAACTATAGGCAGGAGGTTTCTTATGAATTGAAGAGAAACTTTTCTTTGCG
103021  TGTGAATAAATTGATATCCGTCCTCCAAAGAATACTTAACTTCTCTTTGAAAAGAAACGC

103081  TGGGAAGCTGTTCTAAAGTTGGGTAAAACACAATAGATCCACCACCTCTAGCAGCCACTG
103081  ACCCTTCGACAAGATTTCAACCCATTTTGTGTTATCTAGGTGGTGGAGATCGTCGGTGAC

103141  ATAGCTGAAACGTGAAACATAGAGACCCTAAGCTATCACTGCCTCTGAGCTGGCATTGTT
103141  TATCGACTTTGCACTTTGTATCTCTGGGATTCGATAGTGACGGAGACTCGACCGTAACAA

103201  AGGTCATCATAAAGCTAGCGTCTCCCACTGCAAAACCCAAGAGGAAAAAAATAGTTGAAA
103201  TCCAGTAGTATTTCGATCGCAGAGGGTGACGTTTTGGGTTCTCCTTTTTTTATCAACTTT

103261  ATCCTATTTTAAAGGCCTAGCAGATTCTATAAGATACCTTGGGAAAATGATGACGATGAC
103261  TAGGATAAAATTTCCGGATCGTCTAAGATATTCTATGGAACCCTTTTACTACTGCTACTG
```

FIG. 5 (cont'd)

```
103321  TTGAAATCAGACCCTCGTATGCTGCTTCCGTGGGGGCGAACAAAAATATGTTCATCAAAA
103321  AACTTTAGTCTGGGAGCATACGACGAAGGCACCCCCGCTTGTTTTTATACAAGTAGTTTT

103381  ATTAAGCAGAAATGCAGAAAATTTTGTGAGCCAAAAAAGCTGTGTTATCAGGAAATGCAG
103381  TAATTCGTCTTTACGTCTTTTAAAACACTCGGTTTTTTCGACACAATAGTCCTTTACGTC

103441  ATATTTGTGGGGTTGTAATTTTTTATATTTGAATCGGGCGGTTTTCAAAATGATCTATTC
103441  TATAAACACCCCAACATTAAAAAATATAAACTTAGCCCGCCAAAAGTTTTACTAGATAAG

103501  CATTTGTAGTGTATCTGAAAACCTATAAAAATAAGTTGATATCAATAGATATCCATCTTC
103501  GTAAACATCACATAGACTTTTGGATATTTTTATTCAACTATAGTTATCTATAGGTAGAAG

103561  CATAAAAATTCAACTTCTAAAATTAAGCAAACTTTGCTTTTTCTAATGGCCCCTTTATCC
103561  GTATTTTTAAGTTGAAGATTTTAATTCGTTTGAAACGAAAAAGATTACCGGGGAAATAGG

103621  TCAAATTACCCACTGAAATAGACGGATCACACTCAGCCCTAAGTGAAGCAAGCGTGCATG
103621  AGTTTAATGGGTGACTTTATCTGCCTAGTGTGAGTCGGGATTCACTTCGTTCGCACGTAC

103681  AGAGTAGTCCCAGCCTCGCCTTTGTAATGAGGTGGAAATTAACATGAAGGTAGGCTACCC
103681  TCTCATCAGGGTCGGAGCGGAAACATTACTCCACCTTTAATTGTACTTCCATCCGATGGG

103741  TGTGATAGACACTTAACAGGATACTCGGGGACCCATGGTAATACATCCCTGATAAGGAAT
103741  ACACTATCTGTGAATTGTCCTATGAGCCCCTGGGTACCATTATGTAGGGACTATTCCTTA

103801  AGACCTCACAAATGAACTACTTGCCTGTTAATTCATTTAAAGCCTGACTGTACAGTGAAA
103801  TCTGGAGTGTTTACTTGATGAACGGACAATTAAGTAAATTTCGGACTGACATGTCACTTT

103861  ATTCTCTTAAATAAATATTTGATAAGTGAATCAAATTCTGGCTTACTAAATTGCCAAAAT
103861  TAAGAGAATTTATTTATAAACTATTCACTTAGTTTAAGACCGAATGATTTAACGGTTTTA

103921  ATAATGACTGCCTGCCTTGATAAAAAGAATAATTACATTTAATGAATAAACCTGCCAAGT
103921  TATTACTGACGGACGGAACTATTTTTCTTATTAATGTAAATTACTTATTTGGACGGTTCA

103981  ACAGATATGCCAGGTGGCACCTGCTGTTTGCTGCTCACTTCTCCCAACAAATAGCAGCTA
103981  TGTCTATACGGTCCACCGTGGACGACAAACGACGAGTGAAGAGGGTTGTTTATCGTCGAT

104041  GGTGCCACCTGCACACCAATAAGCTGAGTTTTTCACTTACGGAACAAATAACTTTCAGAA
104041  CCACGGTGGACGTGTGGTTATTCGACTCAAAAAGTGAATGCCTTGTTTATTGAAAGTCTT

104101  GTCAATTTTATAGTTTCTGCCTTGCCCTTTGTTAAAAAAATACACACACTTGAAGCAATG
104101  CAGTTAAAATATCAAAGACGGAACGGGAAACAATTTTTTTATGTGTGTGAACTTCGTTAC

104161  AACTCATGAATTGTTTTCATCATGCATTTCCACTTGCCTAAATATAAAGGGTCCCAGGTA
104161  TTGAGTACTTAACAAAAGTAGTACGTAAAGGTGAACGGATTTATATTTCCCAGGGTCCAT

104221  GATACAGAAATACCTGGTTTGGCCAAACTTGGTTTGAATAACTAGACATGCTAGAAAAGG
104221  CTATGTCTTTATGGACCAAACCGGTTTGAACCAAACTTATTGATCTGTACGATCTTTTCC

104281  TTTTCATTTTCCTGGGATCTGAGTGGAATATGTTAGAAAAGGCATGCTTTCTGAATTCTC
104281  AAAAGTAAAAGGACCCTAGACTCACCTTATACAATCTTTTCCGTACGAAAGACTTAAGAG

104341  TATGCTTAAAACATTTCTAGAGCAGTGCTTCTCAAACTTGAAAGAGCATGTAAATCACCT
104341  ATACGAATTTTGTAAAGATCTCGTCACGAAGAGTTTGAACTTTCTCGTACATTTAGTGGA

104401  GAGATCTCGTGAACATACAACTCTGCTTCAGACCTGGGGGGAGGCAGGAGAGCAAGCATT
104401  CTCTAGAGCACTTGTATGTTGAGACGAAGTCTGGACCCCCCTCCGTCCTCTCGTTCGTAA

104461  CCTAACAAGCTCCCAGCTTGTGGAGCACAGAGCCGCCTCAGGCAGCAGGGCAGTGCAGCT
104461  GGATTGTTCGAGGGTCGAACACCTCGTGTCTCGGCGGAGTCCGTCGTCCCGTCACGTCGA

104521  GAGCAGTGACAGTGAACAGGGCCATTCAGAGGGCTCTCCACCTGGGGCTTAGGTACGACG
104521  CTCGTCACTGTCACTTGTCCCGGTAAGTCTCCCGAGAGGTGGACCCCGAATCCATGCTGC

104581  GGAATCCCCACTGGACAGGCTAGGACTTGCACTGTGGCCATTGTTCCTCCTCCTGCCCAT
104581  CCTTAGGGGTGACCTGTCCGATCCTGAACGTGACACCGGTAACAAGGAGGAGGACGGGTA

104641  GGCTGAGTCAGCTTCTCAGTCCCTTCCAGGATACACTGAGAGGATTCAGGGGCGGTCTCG
104641  CCGACTCAGTCGAAGAGTCAGGGAAGGTCCTATGTGACTCTCCTAAGTCCCCGCCAGAGC
```

FIG. 5 (cont'd)

```
104701  CCTCTGCCCATATCCCCACGTTGGTGAAGTACCACTGGCGCCATTTTCTAATCAGCTCAT
104701  GGAGACGGGTATAGGGGTGCAACCACTTCATGGTGACCGCGGTAAAAGATTAGTCGAGTA

104761  CGGCACCAGCACGTCACTTCCCCTGTTGTGCAGCTCAGTTTTATATTTCTGACTCGGGTG
104761  GCCGTGGTCGTGCAGTGAAGGGGACAACACGTCGAGTCAAAATATAAAGACTGAGCCCAC

104821  TAATAGTAACATCTTCCCCACCAATGTCTCAGGGTTATTGTGAGAACCAGAGAGGAGAGA
104821  ATTATCATTGTAGAAGGGGTGGTTACAGAGTCCCAATAACACTCTTGGTCTCTCCTCTCT

104881  GGTAGGAAGGAAGCAGGAAATGCAGGGTGCAAATACACCACATTATTATTCTAAATAATG
104881  CCATCCTTCCTTCGTCCTTTACGTCCCACGTTTATGTGGTGTAATAATAAGATTTATTAC

104941  GGATTTTTAATAACAAAGACCAAGAAGATTGTCTGTGCCTATCTAGTTCCCATCTGTAAG
104941  CCTAAAAATTATTGTTTCTGGTTCTTCTAACAGACACGGATAGATCAAGGGTAGACATTC

105001  ATAAAAAGGTGCAGTCCCTGAGCCTCCTAAAAACAGCACCCTAATGGCACTGCTCCTCCC
105001  TATTTTTCCACGTCAGGGACTCGGAGGATTTTTGTCGTGGGATTACCGTGACGAGGAGGG

105061  AGGTATGATTGCAGTAGACCTACGTCAGTTCTTGCAGTTCAAACACATTTTTTCACTTTC
105061  TCCATACTAACGTCATCTGGATGCAGTCAAGAACGTCAAGTTTGTGTAAAAAAGTGAAAG

105121  TTCTGAAATGCCCTCAAATTCTATGACATAGTATCCATGAAGACTTCCCTTTTTACCCAG
105121  AAGACTTTACGGGAGTTTAAGATACTGTATCATAGGTACTTCTGAAGGGAAAAATGGGTC

105181  TGAAGTTACTAGAGGGGGTTCAAACCTTCTTACAGAGGGTTCCTAAAATGGGAGATCTGT
105181  ACTTCAATGATCTCCCCCAAGTTTGGAAGAATGTCTCCCAAGGATTTTACCCTCTAGACA

105241  GGAGTCATTGGGATTAAAAATTAAATTTCAAATTCATGACATCAATGTCCTCATCCCAGT
105241  CCTCAGTAACCCTAATTTTTAATTTAAAGTTTAAGTACTGTAGTTACAGGAGTAGGGTCA

105301  TAAATAAAAGTAAATACAACCTTGAAGAAATTTGACCTACTCAGCTGCAATAGCTGTTGA
105301  ATTTATTTTCATTTATGTTGGAACTTCTTTAAACTGGATGAGTCGACGTTATCGACAACT

105361  CCTGCAGAAGGCAAATGATGGACCCCGGCCACGCAAGAACACACATGGCGTGGGCTGCGT
105361  GGACGTCTTCCGTTTACTACCTGGGGCCGGTGCGTTCTTGTGTGTACCGCACCCGACGCA

105421  TCTTGTGCCCCAGCTCCATGGACGTGTCTTCTTAGCTGTGGACCCCTCCAAAGGAAACTG
105421  AGAACACGGGGTCGAGGTACCTGCACAGAAGAATCGACACCTGGGGAGGTTTCCTTTGAC

105481  CTTGAGTGGAGTGCTCTGTATTGTCACTCCTGGGAATGCTCTCTTAACACCCCCATGCCT
105481  GAACTCACCTCACGAGACATAACAGTGAGGACCCTTACGAGAGAATTGTGGGGGTACGGA

105541  TGTGCTATGTGTTCATACCAGCATAGGCACTCAGAAGCAAAAAAGGTTTCCAGTGAAATT
105541  ACACGATACACAAGTATGGTCGTATCCGTGAGTCTTCGTTTTTTCCAAAGGTCACTTTAA

105601  TGTTTGCAGGCAGGTATTAAGACATCAGACACTGCAGGATCCAAGTGAACCCCTGCCCGC
105601  ACAAACGTCCGTCCATAATTCTGTAGTCTGTGACGTCCTAGGTTCACTTGGGGACGGGCG

105661  CTGCCTGCCTGCCCTGCTCTGCTCTGCAGAAGGGCATGTGTCTGTAGCAATCTGCCCTTT
105661  GACGGACGGACGGGACGAGACGAGACGTCTTCCCGTACACAGACATCGTTAGACGGGAAA

105721  CTGTCTGCGATGGGCAGAGACCCTGGCTCTGCCTCCTGTTTTCCCTGTAGCCCTCCAGAC
105721  GACAGACGCTACCCGTCTCTGGGACCGAGACGGAGGACAAAAGGGACATCGGGAGGTCTG

105781  CTGGGGAGAGACATGGGACTCCAGCACCTGCCCAGCACGGAAGGGGGTCTTTCCCAGGTG
105781  GACCCCTCTCTGTACCCTGAGGTCGTGGACGGGTCGTGCCTTCCCCCAGAAAGGGTCCAC

105841  TAAGTGTAGGGCTGCATTCACTAATTTAGGGTCATACCACAAACACTGTTGTGTCACCAG
105841  ATTCACATCCCGACGTAAGTGATTAAATCCCAGTATGGTGTTTGTGACAACACAGTGGTC

105901  GATGTTGTCACATGCTTATTGTGAGCATTTTTGTGACATGAGCTTTCTCCTGAGAGGCCA
105901  CTACAACAGTGTACGAATAACACTCGTAAAAACACTGTACTCGAAAGAGGACTCTCCGGT

105961  CCCTGTCCAAATGAGAGCTGTAGTTGGAGGCACATCCGTCTCATGCTGCCTGGGTCTCCC
105961  GGGACAGGTTTACTCTCGACATCAACCTCCGTGTAGGCAGAGTACGACGGACCCAGAGGG

106021  TGCACCAGCTCACTCTACTTTTCCTTTTTATCCACTTGGAGTTAAATGCACACATTTATG
106021  ACGTGGTCGAGTGAGATGAAAAGGAAAAATAGGTGAACCTCAATTTACGTGTGTAAATAC
```

FIG. 5 (cont'd)

```
106081  CACAAGTGCACAGAAGGCCCAGAACTGTTCCTAATAGATAATTAAATGATCTCTCTCCAG
106081  GTGTTCACGTGTCTTCCGGGTCTTGACAAGGATTATCTATTAATTTACTAGAGAGAGGTC

106141  TGGAAACTCTCCTGGGCTACCTGGCTGCTAGCTGTTTTAGCCTCTTCATCCAGTATTGAT
106141  ACCTTTGAGAGGACCCGATGGACCGACGATCGACAAAATCGGAGAAGTAGGTCATAACTA

106201  TTACATGCATCGGTTTGTAACTCAGACAGTATAGTTAGTTAGTTTGTTTCACCATCACCT
106201  AATGTACGTAGCCAAACATTGAGTCTGTCATATCAATCAATCAAACAAAGTGGTAGTGGA

106261  TCCAACCTGCTTACGTTTAAACTCCTTCTCTCTGCTTAGCTAATACAGATTTCTGTAAGG
106261  AGGTTGGACGAATGCAAATTTGAGGAAGAGAGACGAATCGATTATGTCTAAAGACATTCC

106321  ATTTGGAGAAATACCAGATACCTCCTGGTTAGTATCAGGACCTCTCCATTGGCCTATAAT
106321  TAAACCTCTTTATGGTCTATGGAGGACCAATCATAGTCCTGGAGAGGTAACCGGATATTA

106381  TGAACATCACTGTAAATTAGTTTCAGCTTTTATAGTAATGCATCTAACCCGCCAGCTTAA
106381  ACTTGTAGTGACATTTAATCAAAGTCGAAAATATCATTACGTAGATTGGGCGGTCGAATT

106441  AAAAAAAGTGATGATAATCATGAAATTCAAGTGTCAATATAGACTTTTAAATCTGGTGTG
106441  TTTTTTTCACTACTATTAGTACTTTAAGTTCACAGTTATATCTGAAAATTTAGACCACAC

106501  GATGTTAATAGTGCCAGATATGCTTCTGTGTAATCATTTTTGAGAAGTGCTGTCTTCTTT
106501  CTACAATTATCACGGTCTATACGAAGACACATTAGTAAAAACTCTTCACGACAGAAGAAA

106561  ACCATAATCACATTAATCAATCGGGAAATGGTTAAATAGACATTTTAATACATTGTTTTT
106561  TGGTATTAGTGTAATTAGTTAGCCCTTTACCAATTTATCTGTAAAATTATGTAACAAAAA

106621  TCCTGAGAAAAAAAGTGACTCCAGGAAATATGTTGTTACAATATCTCAACACCAGGAATT
106621  AGGACTCTTTTTTTCACTGAGGTCCTTTATACAACAATGTTATAGAGTTGTGGTCCTTAA

106681  GTGGTCACATAGCATTCTTCTTCTAAATAAAGCATTTGTTTTACAAAAGAGTTTCATGTT
106681  CACCAGTGTATCGTAAGAAGAAGATTTATTTCGTAAACAAAATGTTTTCTCAAAGTACAA

106741  TACTTAAACGTGACAAATGTATCACTCTTCGAAGTGAGAGTTAAATGAAATGTTCCCTGA
106741  ATGAATTTGCACTGTTTACATAGTGAGAAGCTTCACTCTCAATTTACTTTACAAGGGACT

106801  TTTAGATTCCAAGACCTGTGACTACTCAGTAGGACAATAGCATATTTCTTTTACTCAGAT
106801  AAATCTAAGGTTCTGGACACTGATGAGTCATCCTGTTATCGTATAAAGAAAATGAGTCTA

106861  ACCTGTTTATCCCTTTGTCAGCTCCAGAATGGAGACACAGGTGCTGCCACACAGAGGAGA
106861  TGGACAAATAGGGAAACAGTCGAGGTCTTACCTCTGTGTCCACGACGGTGTGTCTCCTCT

106921  GGGTCAGGTGTTTTCTTAGTCACAAATGCAGCAGTCTCACCCCTGAAAGAATTCCTTCAT
106921  CCCAGTCCACAAAAGAATCAGTGTTTACGTCGTCAGAGTGGGGACTTTCTTAAGGAAGTA

106981  AACAACTAAATTGCACCTCTTAGAATACCTGTACTTAAAATATAATTTGTCTTCTATGGA
106981  TTGTTGATTTAACGTGGAGAATCTTATGGACATGAATTTTATATTAAACAGAAGATACCT

107041  TATAGACAAATAATAGCTTAAATGTTTTAGGATTTGTAAAGAAAGAAAAAGCTAGAAATC
107041  ATATCTGTTTATTATCGAATTTACAAAATCCTAAACATTTCTTTCTTTTTCGATCTTTAG

107101  TCAATGCAACTCTGACTTGTATGTCCTGCCATAGGAAGGTTTGGGACTTTTCTTTGGAAG
107101  AGTTACGTTGAGACTGAACATACAGGACGGTATCCTTCCAAACCCTGAAAAGAAACCTTC

107161  ATGGGAGGCTTCCTTCACAGTTTCTTAACTTCTCATTTTATTCAATCTTTCTCCATCTCT
107161  TACCCTCCGAAGGAAGTGTCAAAGAATTGAAGAGTAAAATAAGTTAGAAAGAGGTAGAGA

107221  CTCTCTCTTTCTCTCATCCTCACGCTCTCTGTCTGTCTCTCTCCTGATTTGTCTGCTTAG
107221  GAGAGAGAAAGAGAGTAGGAGTGCGAGAGACAGACAGAGAGAGGACTAAACAGACGAATC

107281  GGACAGACAGGTAATGGAGAAGAAATTGAAAGGGAAAATACAGGGAAAATGTAAATGAAA
107281  CCTGTCTGTCCATTACCTCTTCTTTAACTTTCCCTTTTATGTCCCTTTTACATTTACTTT

107341  AGAAGTTATTATAACTGTTATAATGAAGTGCCTTTCATTTAAATATAAGAATGTAACGCT
107341  TCTTCAATAATATTGACAATATTACTTCACGGAAAGTAAATTTATATTCTTACATTGCGA

107401  GAAATGAACTTGTGATCCTGAAATGCATTTTTAATGAGTTTCCTTTTTATTTTGCTGCTT
107401  CTTTACTTGAACACTAGGACTTTACGTAAAAATTACTCAAAGGAAAAATAAAACGACGAA
```

FIG. 5 (cont'd)

```
107461  CAGTGGCATATTTTAAAGACCCTTTGAAAAAAGCCACATTAAAAAACCCCACCAAATGCC
107461  GTCACCGTATAAAATTTCTGGGAAACTTTTTTCGGTGTAATTTTTTGGGGTGGTTTACGG

107521  ACAACACGCAAAATTGGATATTGGTTTATTCCAAAACTGCTGATCAGGAAGAGTGGCTCT
107521  TGTTGTGCGTTTTAACCTATAACCAAATAAGGTTTTGACGACTAGTCCTTCTCACCGAGA

107581  TCATCACAAAATGTTGCAGTCACTTTATTTAAATGAGTTTGAATTTGCATTGTGATGTGC
107581  AGTAGTGTTTTACAACGTCAGTGAAATAAATTTACTCAAACTTAAACGTAACACTACACG

107641  CATTCTGATTTAGGGAAAAAAAATTAGATTTTCAGATCAAATTGACCCAGCCAGTGAAGC
107641  GTAAGACTAAATCCCTTTTTTTTAATCTAAAAGTCTAGTTTAACTGGGTCGGTCACTTCG

107701  GTTAAGGAGCTGGCAGGTTTAGTCTGAAAGCCTCATGTTCTATCAAACCTGCAGCCGGTG
107701  CAATTCCTCGACCGTCCAAATCAGACTTTCGGAGTACAAGATAGTTTGGACGTCGGCCAC

107761  GAAGTCACCAGGCCCCCGTGGGAAACAACTTTCTCGTAGCATCGTCCTCATGTCCCCACG
107761  CTTCAGTGGTCCGGGGGCACCCTTTGTTGAAAGAGCATCGTAGCAGGAGTACAGGGGTGC

107821  CTGAGTTTAGTTCTCACCAGCTCTCCTCTCTCCGTCCCAGGAGAACGGCCCTTCCAGTGC
107821  GACTCAAATCAAGAGTGGTCGAGAGGAGAGAGGCAGGGTCCTCTTGCCGGGAAGGTCACG

107881  AATCAGTGCGGGGCCTCATTCACCCAGAAGGGCAACCTGCTCCGGCACATCAAGCTGCAT
107881  TTAGTCACGCCCCGGAGTAAGTGGGTCTTCCCGTTGGACGAGGCCGTGTAGTTCGACGTA

107941  TCCGGGGAGAAGCCCTTCAAATGCCACCTCTGCAACTACGCCTGCCGCCGGAGGGACGCC
107941  AGGCCCCTCTTCGGGAAGTTTACGGTGGAGACGTTGATGCGGACGGCGGCCTCCCTGCGG

108001  CTCACTGGCCACCTGAGGACGCACTCCGGTAGGTCCCCTGGATGCAGTCCGGGGCTGTCT
108001  GAGTGACCGGTGGACTCCTGCGTGAGGCCATCCAGGGGACCTACGTCAGGCCCCGACAGA

108061  GGGTGTCCCGGGATTCCTCCACTCTGCCCGCCTGGGTCCCGGATTGTGTCCTTGCTGGCT
108061  CCCACAGGGCCCTAAGGAGGTGAGACGGGCGGACCCAGGGCCTAACACAGGAACGACCGA

108121  AACCCTGAGTCCCTCCCAGCTCGCAGTCCTGCATCGGGTGTGAGCTGTTGCTTCTTTGAC
108121  TTGGGACTCAGGGAGGGTCGAGCGTCAGGACGTAGCCCACACTCGACAACGAAGAAACTG

108181  ATTGCCCCATCCCCCCTCCCCATATTCTCCTTTTCCCACTGCACCAGGGAGATTGGGCGC
108181  TAACGGGGTAGGGGGGAGGGGTATAAGAGGAAAAGGGTGACGTGGTCCCTCTAACCCGCG

108241  AGGACCCCCATGCACATACACACACAGAAGTCTCACCTTAGGTAGCATGTTTCAGAACAG
108241  TCCTGGGGGTACGTGTATGTGTGTGTCTTCAGAGTGGAATCCATCGTACAAAGTCTTGTC

108301  GCCTCCTCATCCCGTTTGTCAGGCTGGTATGGTTTCCCTAAAGGATTTTGCGGGAAATGT
108301  CGGAGGAGTAGGGCAAACAGTCCGACCATACCAAAGGGATTTCCTAAAACGCCCTTTACA

108361  TTTCACCAAGTGTACTGCTAAGACCCAAAACGTTTTCAAGTACAATTCTTTCTGTTGTTA
108361  AAAGTGGTTCACATGACGATTCTGGGTTTTGCAAAAGTTCATGTTAAGAAAGACAACAAT

108421  AGTCCCGCTTTGGAGTGTTTTACACAGGTGTAATGGATAGCTTTTTTGCAGAGCTGGTAG
108421  TCAGGGCGAAACCTCACAAAATGTGTCCACATTACCTATCGAAAAAACGTCTCGACCATC

108481  AGAAGGGTGATTTAGGGCGCACCCACCCAGACTGAGCCCCGTGTGGCTCTCACACCAAAA
108481  TCTTCCCACTAAATCCCGCGTGGGTGGGTCTGACTCGGGGCACACCGAGAGTGTGGTTTT

108541  ACCAGCCAAGGCCACAGTTACAGAGGCCAGTCTGGGGCTGTTACCAGATTTTAGACAGCA
108541  TGGTCGGTTCCGGTGTCAATGTCTCCGGTCAGACCCCGACAATGGTCTAAAATCTGTCGT

108601  GCCTTTCTCTTTGAATTAGACAGTTAAAGTACAACCCACATAATCTGGAGTCTTGACAAG
108601  CGGAAAGAGAAACTTAATCTGTCAATTTCATGTTGGGTGTATTAGACCTCAGAACTGTTC

108661  ATCATCATAGGCATAAACGCTCTATCATTCTCAAAACAGTCTCAGCCTGCAAAGTTCAAA
108661  TAGTAGTATCCGTATTTGCGAGATAGTAAGAGTTTTGTCAGAGTCGGACGTTTCAAGTTT

108721  TCCACTAAAGTTTGGTTAGATCCTCTGCCTCCTGAGAAATGGTCCTGGGTGTTTCATTAT
108721  AGGTGATTTCAAACCAATCTAGGAGACGGAGGACTCTTTACCAGGACCCACAAAGTAATA

108781  CCAGCAGTCCCATAATTCTACAGGGCAGAGGAAGAGAGGGCTCTTGGCCGGCCTGTCATG
108781  GGTCGTCAGGGTATTAAGATGTCCCGTCTCCTTCTCTCCCGAGAACCGGCCGGACAGTAC
```

FIG. 5 (cont'd)

```
108841  GATCATGTTTGCCTACAGTGTGGTCTATACAACATGACATGGCACAGGTCTCCTTCATAC
108841  CTAGTACAAACGGATGTCACACCAGATATGTTGTACTGTACCGTGTCCAGAGGAAGTATG

108901  CGTCCAGTTGGGGATATTTGCTGTAGCATACTGCATGAGACTTCGGAGGCGAAAGGTTGA
108901  GCAGGTCAACCCCTATAAACGACATCGTATGACGTACTCTGAAGCCTCCGCTTTCCAACT

108961  TGGCTTTTGTCCTTCCCCTCAAGGAGCTTCCTGCCCCAGCCAGCCACCAGCCAGGGCCCT
108961  ACCGAAAACAGGAAGGGGAGTTCCTCGAAGGACGGGGTCGGTCGGTGGTCGGTCCCGGGA

109021  TCTCCAAGCAGCAGCCTCTCTAAGCCGGTGCCCTGGGGGATGGCAATGCCTCAGACCAGC
109021  AGAGGTTCGTCGTCGGAGAGATTCGGCCACGGGACCCCCTACCGTTACGGAGTCTGGTCG

109081  TACTCCTCACCCACCCTGGGTAGCAGGATAAGGAGGAGCCTCCCTCAGGGAGGCAGACGT
109081  ATGAGGAGTGGGTGGGACCCATCGTCCTATTCCTCCTCGGAGGGAGTCCCTCCGTCTGCA

109141  GTGTTCTTTGTGAAATATCTGCAGCGGCCCAGGCCATCTCTTCCCAAATGTGATGCGTGT
109141  CACAAGAAACACTTTATAGACGTCGCCGGGTCCGGTAGAGAAGGGTTTACACTACGCACA

109201  ATTTGATGGTTGAGGGTTTTAGAGGCTGCTCATTGTGTCCATCTCTTTATCACACATTTA
109201  TAAACTACCAACTCCCAAAATCTCCGACGAGTAACACAGGTAGAGAAATAGTGTGTAAAT

109261  CTGAGCACCCCTGGGTGCCCATTCTGCACAGAAGACCTCAGGTGCACACAAGGAAAGCAC
109261  GACTCGTGGGGACCCACGGGTAAGACGTGTCTTCTGGAGTCCACGTGTGTTCCTTTCGTG

109321  CAATGTGTTACAGGAGGCATGACAGAGTGTCTGAGGGGACAGTGGGAGCATAAGGAAGGG
109321  GTTACACAATGTCCTCCGTACTGTCTCACAGACTCCCCTGTCACCCTCGTATTCCTTCCC

109381  GACAGTGGGTCCTGGGGTGGAAAGTCAGGAGAGACTTCCCATAGAAGGGAGGGGCTTCTG
109381  CTGTCACCCAGGACCCCACCTTTCAGTCCTCTCTGAAGGGTATCTTCCCTCCCCGAAGAC

109441  AAGTACATGCTGGAAGGCGAGTGTCTGAGGTTTGCTTTAGAGACATTCTAAACTAGTGTG
109441  TTCATGTACGACCTTCCGCTCACAGACTCCAAACGAAATCTCTGTAAGATTTGATCACAC

109501  TGAGTCGGCAGTAATCCCAGAGAGGGGTGCGGCACCCATGTTGGCAAGAACTCGGTCTCA
109501  ACTCAGCCGTCATTAGGGTCTCTCCCCACGCCGTGGGTACAACCGTTCTTGAGCCAGAGT

109561  CTCCTGGCAGGTGGTCCCTGCAGTAGTTCACCCAGTTGGCTGGAGACAAAAAGGAGAGGA
109561  GAGGACCGTCCACCAGGGACGTCATCAAGTGGGTCAACCGACCTCTGTTTTTCCTCTCCT

109621  GTCACAGGGGCTGGTGCATCACCTCCTCTCCATCCTGACCTCCTTCCTGGCGGTGCACAT
109621  CAGTGTCCCCGACCACGTAGTGGAGGAGAGGTAGGACTGGAGGAAGGACCGCCACGTGTA

109681  GGAGAAGGATCCCCACATGCTCGCCATCAGAAAATTGTCATGATTTGGGTGATTTGACTT
109681  CCTCTTCCTAGGGGTGTACGAGCGGTAGTCTTTTAACAGTACTAAACCCACTAAACTGAA

109741  CCTAAAAACTTCCAAGAAAGGAGCTATACCAAGCTGAGGAGTTGCTTGCCCGAGAGGGCG
109741  GGATTTTTGAAGGTTCTTTCCTCGATATGGTTCGACTCCTCAACGAACGGGCTCTCCCGC

109801  GGCAGATCAGCAGGGGGGCCATGGAGTGGGACACTTGCCTTGTTACAGAGGGACAGGGAG
109801  CCGTCTAGTCGTCCCCCCGGTACCTCACCCTGTGAACGGAACAATGTCTCCCTGTCCCTC

109861  AACAGGTGGTTCCCCTGAGATAGGAAGACAGTAGCATGACGGTGAGCATCTTTAAATGTT
109861  TTGTCCACCAAGGGGACTCTATCCTTCTGTCATCGTACTGCCACTCGTAGAAATTTACAA

109921  CACATGGGTGATGAGCATGTATGGTGGTCCCACCTGGAGACAAAGGTGGTACCTGGGCCT
109921  GTGTACCCACTACTCGTACATACCACCAGGGTGGACCTCTGTTTCCACCATGGACCCGGA

109981  GATAAGCAAGGCCCATGGAGGCCTCAGCTAAGAGAACTGTGCAGTCTGTCTGCCATGCTA
109981  CTATTCGTTCCGGGTACCTCCGGAGTCGATTCTCTTGACACGTCAGACAGACGGTACGAT

110041  ACCAGTGGTCTAGGAAGAAGCTTCACATCTGTTGTTTCTAAGGAGCCATGTAGACATAGA
110041  TGGTCACCAGATCCTTCTTCGAAGTGTAGACAACAAAGATTCCTCGGTACATCTGTATCT

110101  CACAGTTGGCAGCAATATTGCCTTGGGTTAGTGGGAAGCACCACTTCCCATGTCAGTGGA
110101  GTGTCAACCGTCGTTATAACGGAACCCAATCACCCTTCGTGGTGAAGGGTACAGTCACCT

110161  AAACACAGACACTCGTTCTTAGGTTGACACCAACCATAGGTCATCATCACTCCTAGATTA
110161  TTTGTGTCTGTGAGCAAGAATCCAACTGTGGTTGGTATCCAGTAGTAGTGAGGATCTAAT
```

FIG. 5 (cont'd)

110221 CTCTGATTGCAATGGAATCTCTCATGCCCATCAGTCCTTAAAAGCAGAGCTGCTCTCTTT
110221 GAGACTAACGTTACCTTAGAGAGTACGGGTAGTCAGGAATTTTCGTCTCGACGAGAGAAA

110281 CCTTTCTTGTTGTGGAGTTAGGAACATGTAGTGGAGTATTTTATGTTATTCTGGCTCCAG
110281 GGAAAGAACAACACCTCAATCCTTGTACATCACCTCATAAAATACAATAAGACCGAGGTC

110341 GCCTATGTATTTCATTTGAGGCATGATGGTTTCCTATTCTAAGTACCACTAAGTATTGAG
110341 CGGATACATAAAGTAAACTCCGTACTACCAAAGGATAAGATTCATGGTGATTCATAACTC

110401 TAGTTATAAAATGGTGGTAGACTTTGGACTGTGTATTTCTATTCTGGATCCACGGATGAG
110401 ATCAATATTTTACCACCATCTGAAACCTGACACATAAAGATAAGACCTAGGTGCCTACTC

110461 CAAGTGGAGAAAACCCATCATGGATGCAGGGCTGCTGGGGATCTGTCTGTCCGAAAATGC
110461 GTTCACCTCTTTTGGGTAGTACCTACGTCCCGACGACCCCTAGACAGACAGGCTTTTACG

110521 TATAGAGACACACACTGCTCTTGGGGAAAAAAACAGTGATGATTTCTTCAAAATGATTTC
110521 ATATCTCTGTGTGTGACGAGAACCCCTTTTTTTGTCACTACTAAAGAAGTTTTACTAAAG

110581 ACTGAAGTGAAATAAGGACTTTGGCCTTGCTCTGGCAAATTCAAATGTGGCCACACTCTA
110581 TGACTTCACTTTATTCCTGAAACCGGAACGAGACCGTTTAAGTTTACACCGGTGTGAGAT

110641 CTCCATTGTGGAATGGTGACTCCCCTGTCCCATGAAAAACCAGGATCAACATCACAGCTT
110641 GAGGTAACACCTTACCACTGAGGGGACAGGGTACTTTTTGGTCCTAGTTGTAGTGTCGAA

110701 TCTCTAGCAACTGGTGGTGGCCTGAGGTCTTATGAACTAGCATGTTAGCAGGGATAGAGT
110701 AGAGATCGTTGACCACCACCGGACTCCAGAATACTTGATCGTACAATCGTCCCTATCTCA

110761 TAGGGAATTTGTCCGATGCTGACAGCAAGAGGGTGCTGGGGGAGCTGGAGGGGTGGAGAA
110761 ATCCCTTAAACAGGCTACGACTGTCGTTCTCCCACGACCCCCTCGACCTCCCCACCTCTT

110821 GTGATCTCCCTTCCTGCCTCATGGCTTCCTTTGGAAGTTGCAAGCTTAGAATTTCTTTCC
110821 CACTAGAGGGAAGGACGGAGTACCGAAGGAAACCTTCAACGTTCGAATCTTAAAGAAAGG

110881 CAAAGAATATTGGACTATGCTTCAAGAGACACTTGAGTTCAGTTGCTTACAGTGAACATA
110881 GTTTCTTATAACCTGATACGAAGTTCTCTGTGAACTCAAGTCAACGAATGTCACTTGTAT

110941 CTTCTTATGTTCCAGAGTTAAACTCAATCATATTTTCAGAAAAATAGATATTCAGACATC
110941 GAAGAATACAAGGTCTCAATTTGAGTTAGTATAAAAGTCTTTTTATCTATAAGTCTGTAG

111001 ATGTCATATTTACAGGAAGCTATTTGATCATGGAATTTACTGAAGTGACAGCTTTTTCAG
111001 TACAGTATAAATGTCCTTCGATAAACTAGTACCTTAAATGACTTCACTGTCGAAAAAGTC

111061 GAAAGGGTATCGAGTGGTTATCTATATCCTATTAATTTCTAAAAGCAATGCTCAATAAAA
111061 CTTTCCCATAGCTCACCAATAGATATAGGATAATTAAAGATTTTCGTTACGAGTTATTTT

111121 TGTGCAATTTTAGGCAATATTCTGTGTTTCAACATTATTTCCTTATGTTGGGGGTACATC
111121 ACACGTTAAAATCCGTTATAAGACACAAAGTTGTAATAAAGGAATACAACCCCCATGTAG

111181 ACTTTATATAGATAAAGAAAGATCCTTTTCATTCTCTATTAAATGGTCGAGAAGTCAAAT
111181 TGAAATATATCTATTTCTTTCTAGGAAAAGTAAGAGATAATTTACCAGCTCTTCAGTTTA

111241 TTTGGCTTTCATGTTGGTCTTCTTACTGTAGCTTCTGTTCACCTAAGAAAGAGATTTAAC
111241 AAACCGAAAGTACAACCAGAAGAATGACATCGAAGACAAGTGGATTCTTTCTCTAAATTG

111301 CAACATAAGCTTTGGCTAAACCATTGTACCAAACATTTCTATTTGGATGCTCTTAACTTT
111301 GTTGTATTCGAAACCGATTTGGTAACATGGTTTGTAAAGATAAACCTACGAGAATTGAAA

111361 TATACAATACTTTGAAATGTGTTCAATAAAACAACATGAGAAAGAAGTAGAAGATTCTGC
111361 ATATGTTATGAAACTTTACACAAGTTATTTTGTTGTACTCTTTCTTCATCTTCTAAGACG

111421 TATTAGGTTGGAAATTGATATTCCTTACATAAGTGATTAAAGATACTTTATTCAGTTTAT
111421 ATAATCCAACCTTTAACTATAAGGAATGTATTCACTAATTTCTATGAAATAAGTCAAATA

111481 CCCTTAAAATGGTATCTACTGAAGTCCTTAAACTTAGGCATGATATTAATTCCTGGCTAG
111481 GGGAATTTTACCATAGATGACTTCAGGAATTTGAATCCGTACTATAATTAAGGACCGATC

111541 TCTTTCTTTTTCCTAAAATATCACTCAATAAAATCCAAGAAGGACTAAAACTCATTATAT
111541 AGAAAGAAAAAGGATTTTATAGTGAGTTATTTTAGGTTCTTCCTGATTTTGAGTAATATA

FIG. 5 (cont'd)

```
111601  AGAACTGCACTGCCCAATACAGCAGCCACTAGCCACATGCAGTATTTTTAATTATAATAA
111601  TCTTGACGTGACGGGTTATGTCGTCGGTGATCGGTGTACGTCATAAAAATTAATATTATT

111661  GTTAAAATTAAACAAAATTAAAACTTCAGCCCTCAGTGGCACTAGCCACACTTTTTGTGT
111661  CAATTTTAATTTGTTTTAATTTTGAAGTCGGGAGTCACCGTGATCGGTGTGAAAAACACA

111721  CCAACAGCTACATATGGCTGGTGGCTGCCATATTGGACAGCACTAATAGAGAGCATTTCT
111721  GGTTGTCGATGTATACCGACCACCGACGGTATAACCTGTCGTGATTATCTCTCGTAAAGA

111781  ATCATCATAGGAAGTTCTGTTGAACAAGGCTGATCTGGAAGCTACACCATCCTAAAGCTC
111781  TAGTAGTATCCTTCAAGACAACTTGTTCCGACTAGACCTTCGATGTGGTAGGATTTCGAG

111841  TTTGGCAAGAAAGCAGAGCTTTTCCATAAGCTCAGTTTATGAACAATATATTTTGTATTT
111841  AAACCGTTCTTTCGTCTCGAAAAGGTATTCGAGTCAAATACTTGTTATATAAAACATAAA

111901  TCTATGTATATGTATATGAGAATACGTATACATAGAAATATATGAAAATACATATACATA
111901  AGATACATATACATATACTCTTATGCATATGTATCTTTATATACTTTTATGTATATGTAT

111961  TAAATATACATATACATAAAATAGAAATACATATACATAGAAAATACAAAATATTTTGTA
111961  ATTTATATGTATATGTATTTTATCTTTATGTATATGTATCTTTTATGTTTTATAAAACAT

112021  TTACATATACATATGCATGGAAATACAAAATATTTTGTATTATATAATGCAAATGTAAGA
112021  AATGTATATGTATACGTACCTTTATGTTTTATAAAACATAATATATTACGTTTACATTCT

112081  TATATTTATATTATGTAAGAAAATACATTTGTGCAATAAAACGCTTATTTCATTCAAGCA
112081  ATATAAATATAATACATTCTTTTATGTAAACACGTTATTTTGCGAATAAAGTAAGTTCGT

112141  TATTTGTCCAGCATGGTTTCTTAGAGACTGAAGTTACCCAGTTTAGCACCTGGAACTGAA
112141  ATAAACAGGTCGTACCAAAGAATCTCTGACTTCAATGGGTCAAATCGTGGACCTTGACTT

112201  TTCACTCTGGCTGTGTTAGATGTAGCACCAGCGTCATGACAGATCCAGCCCACAGCATAG
112201  AAGTGAGACCGACACAATCTACATCGTGGTCGCAGTACTGTCTAGGTCGGGTGTCGTATC

112261  ACTGAGGCCTACTCTGGAGGCAAATCTGCAGACAATGTGGCCAACACATGGGCCTTCCTC
112261  TGACTCCGGATGAGACCTCCGTTTAGACGTCTGTTACACCGGTTGTGTACCCGGAAGGAG

112321  ACATCTCTGTCCAGTCGCTGGCATCCACGTTATAACACAGCAGTGGCTCGTTTTCTCCAG
112321  TGTAGAGACAGGTCAGCGACCGTAGGTGCAATATTGTGTCGTCACCGAGCAAAAGAGGTC

112381  TTAAAGGCTAGGCTTCCGTGATTGAAGCAGGAGAGAATTTGGTAGTCAGTAAAGTAGACA
112381  AATTTCCGATCCGAAGGCACTAACTTCGTCCTCTCTTAAACCATCAGTCATTTCATCTGT

112441  AACTAAGACAAAACAAGAGTCGCATGAGTTCTTGGTACAATTAAAGAAACCCTTGGCCAC
112441  TTGATTCTGTTTTGTTCTCAGCGTACTCAAGAACCATGTTAATTTCTTTGGGAACCGGTG

112501  CAACGTTTTTAAATTCAGGAATTTCACCAAGTCCGTAACAGTTTTAGCTCTCAAGGGTAG
112501  GTTGCAAAAATTTAAGTCCTTAAAGTGGTTCAGGCATTGTCAAAATCGAGAGTTCCCATC

112561  AATTTTTTTTTTAACTTTTTTGGTAATAATTGTATTGCATGCATTCCCCTTACACAGAAG
112561  TTAAAAAAAAAATTGAAAAAACCATTATTAACATAACGTACGTAAGGGGAATGTGTCTTC

112621  GCTGGCATTTAATTGGGGTCTTGAACTCAATTGTGTTTTCTGCAGTTGGTAAACCTCACA
112621  CGACCGTAAATTAACCCCAGAACTTGAGTTAACACAAAAGACGTCAACCATTTGGAGTGT

112681  AATGTGGATATTGTGGCCGAAGCTATAAACAGCGAAGCTCTTTAGAGGAACATAAAGAGC
112681  TTACACCTATAACACCGGCTTCGATATTTGTCGCTTCGAGAAATCTCCTTGTATTTCTCG

112741  GCTGCCACAACTACTTGGAAAGCATGGGCCTTCCGGGCACACTGTACCCAGGTAAGCGCT
112741  CGACGGTGTTGATGAACCTTTCGTACCCGGAAGGCCCGTGTGACATGGGTCCATTCGCGA

112801  GCTGCTCGGAGGCCAGCCTGGTGGGCTCTCCCCCCAGCACGGTGGGGAAGGAGGGCGCTC
112801  CGACGAGCCTCCGGTCGGACCACCCGAGAGGGGGGTCGTGCCACCCCTTCCTCCCGCGAG

112861  TGCATGCAGCCTTAGGAGCAGAGCCTTGGGCCTGCTTCCTGCCGGGGCTAGGAGGGAGGG
112861  ACGTACGTCGGAATCCTCGTCTCGGAACCCGGACGAAGGACGGCCCCGATCCTCCCTCCC

112921  AAGTTTTTGGCCAATAGCATCAGTTTCACCAGAAGCACGTTGTGCTTCCCAGCTTTCTAG
112921  TTCAAAAACCGGTTATCGTAGTCAAAGTGGTCTTCGTGCAACACGAAGGGTCGAAAGATC
```

FIG. 5 (cont'd)

```
112981  GTCCTCATCTGACCAGAGAGAGCTTGATTTTAAAACCCTTCCCACTTCCAATCGGGAGAA
112981  CAGGAGTAGACTGGTCTCTCTCGAACTAAAATTTTGGGAAGGGTGAAGGTTAGCCCTCTT

113041  ACTCCTAGGATAGCAGTGACCTTGAAAGTTTTGGGGTTGTTTTTTGGATGTTGGTGATTT
113041  TGAGGATCCTATCGTCACTGGAACTTTCAAAACCCCAACAAAAAACCTACAACCACTAAA

113101  TAAAACAACAACAAAAAAAACACCTCAAGTAGTGATATTTCTTTGTAAACAAAATAAAAT
113101  ATTTTGTTGTTGTTTTTTTTGTGGAGTTCATCACTATAAAGAAACATTTGTTTTATTTTA

113161  GTAAAATATTGTTTTGAAACAATTTTTTAACAAAGTTGATCAAATAAGAACTTTCAGGCT
113161  CATTTTATAACAAAACTTTGTTAAAAAATTGTTTCAACTAGTTTATTCTTGAAAGTCCGA

113221  GTGATTTTAAGCATCAGTTCAGACTGAGGGCAGGGTATCCACTCCTGCATGGAGTGTGAG
113221  CACTAAAATTCGTAGTCAAGTCTGACTCCCGTCCCATAGGTGAGGACGTACCTCACACTC

113281  GTTGAAGTTTGTTGGAAGCCCCTGGTAGTTGATAATATTGAGGTTGTTGAAGGATGAGAG
113281  CAACTTCAAACAACCTTCGGGGACCATCAACTATTATAACTCCAACAACTTCCTACTCTC

113341  GAAAGGTCGCTTCTTTCTTAGGAGCTGTGATGCTCCACTGTATTGCATAACGAGATAGCA
113341  CTTTCCAGCGAAGAAAGAATCCTCGACACTACGAGGTGACATAACGTATTGCTCTATCGT

113401  CTTGATTCAGACCCCAGAGCCTGTAGAATAAATGATGTGGAGAGAGTATTGAAAAAGGCT
113401  GAACTAAGTCTGGGGTCTCGGACATCTTATTTACTACACCTCTCTCATAACTTTTTCCGA

113461  GGATTTATCTGGGGGAATGGCAATGTTATAAAAGGTTCTTCCCTAATTTTTTAAGAGATA
113461  CCTAAATAGACCCCCTTACCGTTACAATATTTTCCAAGAAGGGATTAAAAAATTCTCTAT

113521  AGCAATTTATAAAGAGATCAAATAAAACTAATCTCTTTCAAAACAGTATTCATTTAGCAC
113521  TCGTTAAATATTTCTCTAGTTTATTTTGATTAGAGAAAGTTTTGTCATAAGTAAATCGTG

113581  TACCCCTGGAAAAATCATCACTAGACTGTGAGTCGAAATTTAACGAATGGAGGAAAATTT
113581  ATGGGGACCTTTTTAGTAGTGATCTGACACTCAGCTTTAAATTGCTTACCTCCTTTTAAA

113641  ATTAAGCCTCATTCACCTTTCGGACTTTAACAAATGGTTCAAAAGGGAAAATTCACCAGA
113641  TAATTCGGAGTAAGTGGAAAGCCTGAAATTGTTTACCAAGTTTTCCCTTTTAAGTGGTCT

113701  GTACCCTCAGATTATTAATGGCAGATGAGAGCAGGAAAAAAGAATGTTGAGAATGGCTAA
113701  CATGGGAGTCTAATAATTACCGTCTACTCTCGTCCTTTTTTCTTACAACTCTTACCGATT

113761  AAATTGATTCCAATTAGTCTTGGCATGGAGAGGCAACATCTCACCTGGCCAGAGCCCTGC
113761  TTTAACTAAGGTTAATCAGAACCGTACCTCTCCGTTGTAGAGTGGACCGGTCTCGGGACG

113821  AGCCAGAGTGCTGTCTCCTCTGCCAGTCAGCCAGGGATCTGGGGCTTACAGGCGATTCCT
113821  TCGGTCTCACGACAGAGGAGACGGTCAGTCGGTCCCTAGACCCCGAATGTCCGCTAAGGA

113881  CCAGGCCTCAATCTTCTCACCTGTGAAATGGGAAGATACCATTAAATTGTCATTTGGCTT
113881  GGTCCGGAGTTAGAAGAGTGGACACTTTACCCTTCTATGGTAATTTAACAGTAAACCGAA

113941  CTTTCAAAATCTCAGGTCTAGAATGGAAAGGCATTGAAGGTGAGTGGAAGAGAAGAAACT
113941  GAAAGTTTTAGAGTCCAGATCTTACCTTTCCGTAACTTCCACTCACCTTCTCTTCTTTGA

114001  GGATGTTAAAATAATAATAATGTAACAGTTATTAATTCACATGGCCAGACCCCAGGGCAG
114001  CCTACAATTTTATTATTATTACATTGTCAATAATTAAGTGTACCGGTCTGGGGTCCCGTC

114061  AAGACTAATGGACGAGAGGATGATTATGTTCCTTTGAAATAAAATGTCAACATTCAAATA
114061  TTCTGATTACCTGCTCTCCTACTAATACAAGGAAACTTTATTTTACAGTTGTAAGTTTAT

114121  TTGTTTTTTTCTGTAAAAAATAAGTGAATGGGTCTTGGAAGGAAGTGCTCCTAATGATGT
114121  AACAAAAAAAGACATTTTTTATTCACTTACCCAGAACCTTCCTTCACGAGGATTACTACA

114181  AGTTTACATATTAATGCTTAATAAACCATTTTATTTACTCAACAAATATTCACTGAGGAC
114181  TCAAATGTATAATTACGAATTATTTGGTAAAATAAATGAGTTGTTTATAAGTGACTCCTG

114241  TTATAATCAATAATACCAAGCCCTATTGAATACAGTAATCTAATATACACATAGAATTGA
114241  AATATTAGTTATTATGGTTCGGGATAACTTATGTCATTAGATTATATGTGTATCTTAACT

114301  AAAGACAAAATGAACAAAAGAAACAGACAGTATATCATTTCTGTTTCCTCCACTGTTTTC
114301  TTTCTGTTTTACTTGTTTTCTTTGTCTGTCATATAGTAAAGACAAAGGAGGTGACAAAAG
```

FIG. 5 (cont'd)

```
114361  ATTACTAAAGAAACAAGCTGCAGTACACAGCCGGCTGAGAGCTGCTTCCGGGGGAGCAGG
114361  TAATGATTTCTTTGTTCGACGTCATGTGTCGGCCGACTCTCGACGAAGGCCCCCTCGTCC

114421  AGAAGCAGCACTCATTTCACTGAGACCTGGGTTTGAGTTCTCTGTTTTTGAATGTGACCC
114421  TCTTCGTCGTGAGTAAAGTGACTCTGGACCCAAACTCAAGAGACAAAAACTTACACTGGG

114481  AGAGCTCATCGCTTAAATGCGACTGATAATTCGTGCCTGGCCACCCTCATAGCAGCGCTC
114481  TCTCGAGTAGCGAATTTACGCTGACTATTAAGCACGGACCGGTGGGAGTATCGTCGCGAG

114541  TGAAAGAAACATAAAGGAGTGGATACACGTGTGAGCAGGAGCCTAGACATGTGTCAGGTA
114541  ACTTTCTTTGTATTTCCTCACCTATGTGCACACTCGTCCTCGGATCTGTACACAGTCCAT

114601  CTTACCTAAACATGGATGTTTAGGTCACTGACATACTGACACCATCAAGCTAATTCTTCT
114601  GAATGGATTTGTACCTACAAATCCAGTGACTGTATGACTGTGGTAGTTCGATTAAGAAGA

114661  CTATTGGTCTCTATGTCAGTAAGGCTACGTGCCAGTAATGTGTATTAAATATTACCCTGT
114661  GATAACCAGAGATACAGTCATTCCGATGCACGGTCATTACACATAATTTATAATGGGACA

114721  GGTGAGTATCAATTTCACCCTAAAATGTTCATTTATTCCCTTTGGTGGTTAAGTTACTTG
114721  CCACTCATAGTTAAAGTGGGATTTTACAAGTAAATAAGGGAAACCACCAATTCAATGAAC

114781  GACTACCACAGTGATGCCTCTATGTCCCCACACTCAGGAGGTATGAAAGCGTCTCTAGGA
114781  CTGATGGTGTCACTACGGAGATACAGGGGTGTGAGTCCTCCATACTTTCGCAGAGATCCT

114841  AGGAGCAGTGGTCTGGTCTCAGTGTGGCAGCAGACAAAGCCAGGCTCGCACTTAATTACA
114841  TCCTCGTCACCAGACCAGAGTCACACCGTCGTCTGTTTCGGTCCGAGCGTGAATTAATGT

114901  TTGAATTATTTCTGTCTGGTATGGCCTCAAAAGGTGCAAAATGATCATAAATATCTTTCG
114901  AACTTAATAAAGACAGACCATACCGGAGTTTTCCACGTTTTACTAGTATTTATAGAAAGC

114961  ACAGTCACCTTTGGTTTTTGCCCTTGCCAGCACCTGGCCCTTGTAGGTGCTGCTGGTTTA
114961  TGTCAGTGGAAACCAAAAACGGGAACGGTCGTGGACCGGGAACATCCACGACGACCAAAT

115021  AGGAACTTGGAGTATTAAGGGGATCCATAAAAGGACTTTGACAGAAGTCTTCCTGAACTG
115021  TCCTTGAACCTCATAATTCCCCTAGGTATTTTCCTGAAACTGTCTTCAGAAGGACTTGAC

115081  TGCTTAGGGCCAGGAAGGCAGGCAGGGGCTTGGTCATTTCAGCTGTGCTGTACCCGGATG
115081  ACGAATCCCGGTCCTTCCGTCCGTCCCCGAACCAGTAAAGTCGACACGACATGGGCCTAC

115141  AGTGGAAACTGTGCCTTCTGATGCATCTCTCCTCCTCTGTTCCCCTCTAAGAACCCCTTG
115141  TCACCTTTGACACGGAAGACTACGTAGAGAGGAGGAGACAAGGGGAGATTCTTGGGGAAC

115201  TCTGTGCTCAGATGGATGAGCAAGTAGTCTCTTCTCCCACCCCAAAAACCTCCTTAGATG
115201  AGACACGAGTCTACCTACTCGTTCATCAGAGAAGAGGGTGGGGTTTTTGGAGGAATCTAC

115261  GGGTGGATTCAGTAAAATCAAAGCCTCAGTTAGGCAATATAGGAAAAGATGAATTTTTGT
115261  CCCACCTAAGTCATTTTAGTTTCGGAGTCAATCCGTTATATCCTTTTCTACTTAAAAACA

115321  GAATATAATTTTCTTTAGTAAAAGGCTTTTGGTCACCTCTTATAATTTCTCAATGTCTTT
115321  CTTATATTAAAAGAAATCATTTTCCGAAAACCAGTGGAGAATATTAAAGAGTTACAGAAA

115381  ATGGAAAAAATAAGTTTCTCTTGAGCCTTTGGTGCACAAACAGAGTCACCAGCCCTTGGA
115381  TACCTTTTTTATTCAAAGAGAACTCGGAAACCACGTGTTTGTCTCAGTGGTCGGGAACCT

115441  GGTGCATGCATCTAATGACAGAGCAGCCTGTGACTCGCGAGCATCAGGCTCACTTGTTCC
115441  CCACGTACGTAGATTACTGTCTCGTCGGACACTGAGCGCTCGTAGTCCGAGTGAACAAGG

115501  TTGCTGTGATTGACTCTGGGGGGTGGAGGCTTTTGGGAGGCCCTGCGCCATGGTGCAGAG
115501  AACGACACTAACTGAGACCCCCCACCTCCGAAAACCCTCCGGGACGCGGTACCACGTCTC

115561  GAAGACCCCTGACCTCTGGGAGCCCTGGGCAGGCTGTGGGTGTGGCTTGGCAGAGAAGGA
115561  CTTCTGGGGACTGGAGACCCTCGGGACCCGTCCGACACCCACACCGAACCGTCTCTTCCT

115621  TGGACATGTCAGGAAGCATATTAGCTTAATAGATGAAGTGTGTGACCAGTGTAATTGGGT
115621  ACCTGTACAGTCCTTCGTATAATCGAATTATCTACTTCACACACTGGTCACATTAACCCA

115681  TTTATGGATTTATATTTATCTTGCATATAAATCAGGGTGTGGCCTATATATGTTTGCCCA
115681  AAATACCTAAATATAAATAGAACGTATATTTAGTCCCACACCGGATATATACAAACGGGT
```

FIG. 5 (cont'd)

115741 TTTAATAAAAAACACATATTCCAAATGTTAAAATATAAAATATACCAGCAACAATAGCCA
115741 AAATTATTTTTTGTGTATAAGGTTTACAATTTTATATTTTATATGGTCGTTGTTATCGGT

115801 ATTTGAAATATATGTTTTCAAAGTAACATTCATAATAGCAATGAAGACATAAATACTTAG
115801 TAAACTTTATATACAAAAGTTTCATTGTAAGTATTATCGTTACTTCTGTATTTATGAATC

115861 AAATGAAGAAAACCAGCAAGCCATAGTGAGGCAAGAAAGAAAACATGGGAGATTGGAGAG
115861 TTTACTTCTTTTGGTCGTTCGGTATCACTCCGTTCTTTCTTTTGTACCCTCTAACCTCTC

115921 GTAGAGAGGTCTGGATGCCGTCCATGGGCCTCTGCCCAAATTAGTGTATCATTTCAACAT
115921 CATCTCTCCAGACCTACGGCAGGTACCCGGAGACGGGTTTAATCACATAGTAAAGTTGTA

115981 AAAACTGGCTTGTAAATTTTACTGGAATCTGGTAACCATGTATCATAAAGTATCTGGATA
115981 TTTTGACCGAACATTTAAAATGACCTTAGACCATTGGTACATAGTATTTCATAGACCTAT

116041 TATACATGAGATAATTGGCAACTTTTTAGAAGAAGAATAATGTCAAGTGATGTATGAAAA
116041 ATATGTACTCTATTAACCGTTGAAAAATCTTCTTCTTATTACAGTTCACTACATACTTTT

116101 TGTAGCTGAAATGGATGGAACTCTTTGAAGAATAGACAAACAAATCAATAATAGAGATGG
116101 ACATCGACTTTACCTACCTTGAGAAACTTCTTATCTGTTTGTTTAGTTATTATCTCTACC

116161 ATACCCTACTGAAGACCCCATGATAAATCAGCATGAAATATCCGAGGCAGGAGGAAGCAT
116161 TATGGGATGACTTCTGGGGTACTATTTAGTCGTACTTTATAGGCTCCGTCCTCCTTCGTA

116221 AAGGCAGGAACGGTATTGGAAGAATTGATCAGGCATTTAAGATAATCAGTTTACATTATC
116221 TTCCGTCCTTGCCATAACCTTCTTAACTAGTCCGTAAATTCTATTAGTCAAATGTAATAG

116281 ATCTCCTTATACACTAGGATAAATTGCCGGGAAATGAAAGAGTTATATTTTTATAACTCC
116281 TAGAGGAATATGTGATCCTATTTAACGGCCCTTTACTTTCTCAATATAAAAATATTGAGG

116341 AACCACAATAACTGATGTAAATATAGATCCAGCTATGCAGGATACAAAGTTGTATCTTCA
116341 TTGGTGTTATTGACTACATTTATATCTAGGTCGATACGTCCTATGTTTCAACATAGAAGT

116401 ATTATGGAAAGAGATGACATAGAACAATTGAGAATGACTAGAAATGGCCCACACATCAGC
116401 TAATACCTTTCTCTACTGTATCTTGTTAACTCTTACTGATCTTTACCGGGTGTGTAGTCG

116461 ATTTACCTCCATAATTTCTAAATTTTCTACAGCAGTCAGGGGTGCTTTGATTTTCAGGAG
116461 TAAATGGAGGTATTAAAGATTTAAAAGATGTCGTCAGTCCCCACGAAACTAAAAGTCCTC

116521 TTTGTTGTATGCTCAGGGATAAGGGGCTCTGGGTTTTTCCTCCACATTGCCCAGATCTGC
116521 AAACAACATACGAGTCCCTATTCCCCGAGACCCAAAAAGGAGGTGTAACGGGTCTAGACG

116581 TGTAGGCTCTTGGGGGCCACATTTTTGTATCTCCGTTCACTGTGCTGGTCCATGAAGTCA
116581 ACATCCGAGAACCCCCGGTGTAAAAACATAGAGGCAAGTGACACGACCAGGTACTTCAGT

116641 GATGTTAGATCACACAGTTCTTTGCGTCTCAGAGGGCTGCTGTTAGGGACTGACTGAGGT
116641 CTACAATCTAGTGTGTCAAGAAACGCAGAGTCTCCCGACGACAATCCCTGACTGACTCCA

116701 AGCAGATTTGGGAGTATTATGAAAAGTTAAAAGGACTTGTCAAAGGGACATCAATACTTA
116701 TCGTCTAAACCCTCATAATACTTTTCAATTTTCCTGAACAGTTTCCCTGTAGTTATGAAT

116761 ATCCCAGTCCAGCCTCTGGTGATGGTGGTGGTGCCTGTGCATTTGGACTTAAAGAGGATG
116761 TAGGGTCAGGTCGGAGACCACTACCACCACCACGGACACGTAAACCTGAATTTCTCCTAC

116821 ATGTGTGGTGAGCAGCTGTTGGAGGAAGAAGCATTTGCAGGTGGCTGGTCATTGGCATTG
116821 TACACACCACTCGTCGACAACCTCCTTCTTCGTAAACGTCCACCGACCAGTAACCGTAAC

116881 CTCCGGCTGCCTCTGCCTGTCTGGAAGTGTTGCTGGGAAGATTAGAATTAATCTCTAGGA
116881 GAGGCCGACGGAGACGGACAGACCTTCACAACGACCCTTCTAATCTTAATTAGAGATCCT

116941 AGGGCCTGGCTCTTGTAGGCACTTAACAAATGTCAGATTTAACATTGGACGCGACTGAAC
116941 TCCCGGACCGAGAACATCCGTGAATTGTTTACAGTCTAAATTGTAACCTGCGCTGACTTG

117001 CCTTTAAACATAAGCCTTTCTAAACTGGCCTCTCTGTCTTTGACTTTAGTCATTAAAGAA
117001 GGAAATTTGTATTCGGAAAGATTTGACCGGAGAGACAGAAACTGAAATCAGTAATTTCTT

117061 GAAACTAATCACAGTGAAATGGCAGAAGACCTGTGCAAGATAGGATCAGAGAGATCTCTC
117061 CTTTGATTAGTGTCACTTTACCGTCTTCTGGACACGTTCTATCCTAGTCTCTCTAGAGAG

FIG. 5 (cont'd)

```
117121  GTGCTGGACAGACTAGCAAGTAACGTCGCCAAACGTAAGAGCTCTATGCCTCAGAAATTT
117121  CACGACCTGTCTGATCGTTCATTGCAGCGGTTTGCATTCTCGAGATACGGAGTCTTTAAA

117181  CTTGGTAAGAGTTAAATGTTTGCTGTCTCTTAAAAAAAAACTATGTGGGTGTTTTAGATG
117181  GAACCATTCTCAATTTACAAACGACAGAGAATTTTTTTTTGATACACCCACAAAATCTAC

117241  CAAGTAGAAATGAGTTGAGGGTGGAAGAAAGGGAAAAAAATCTTATTTTTTCAAAAGGAA
117241  GTTCATCTTTACTCAACTCCCACCTTCTTTCCCTTTTTTTAGAATAAAAAAGTTTTCCTT

117301  AAATTGGTAAGCTTAACATTCCTTAAATATCTTAGAATTTTTTCCAATAAGTATCTTAAA
117301  TTTAACCATTCGAATTGTAAGGAATTTATAGAATCTTAAAAAAGGTTATTCATAGAATTT

117361  AATAACAAACCTCCCATCAGTTTTTCCTAGATTTGATTTTGCAGCATCTGGGGCCTGCCC
117361  TTATTGTTTGGAGGGTAGTCAAAAAGGATCTAAACTAAAACGTCGTAGACCCCGGACGGG

117421  TGTGATCTGCCTGTGGACATCGCTCTTAGGGGCGGCTGCACCAGCGTGCACAGGGTGGAG
117421  ACACTAGACGGACACCTGTAGCGAGAATCCCCGCCGACGTGGTCGCACGTGTCCCACCTC

117481  AGTTTGGGCCTGGCTCGTCCGGGGGACACCACACTGCAGGACACTCCAGGCCTGGCCGGC
117481  TCAAACCCGGACCGAGCAGGCCCCCTGTGGTGTGACGTCCTGTGAGGTCCGGACCGGCCG

117541  TTCTCAGAGCTTCAGATCCTCATTTTTCATATGAAGCTCCTAATGCTCCCCTTATGGGGG
117541  AAGAGTCTCGAAGTCTAGGAGTAAAAAGTATACTTCGAGGATTACGAGGGGAATACCCCC

117601  ACTCTGAAGGGTTAATGGGAGGAATCATACAGTGACTGACCCCTGAGAAGTGTCCAGTGA
117601  TGAGACTTCCCAATTACCCTCCTTAGTATGTCACTGACTGGGGACTCTTCACAGGTCACT

117661  AGACAGGGCTTAGCTAGGATTGCTGTTTTGCCTAATGCTCTGCGGGATTAAAAAAAAAGA
117661  TCTGTCCCGAATCGATCCTAACGACAAAACGGATTACGAGACGCCCTAATTTTTTTTTCT

117721  AGAAGAAGAACAAGACCATTCGTCTCTCTAGGAGCATTGCCCAGAGTAGGTATTAGACAC
117721  TCTTCTTCTTGTTCTGGTAAGCAGAGAGATCCTCGTAACGGGTCTCATCCATAATCTGTG

117781  ACCAACACCACCATCCAGCCAGACGCTGCAGGGACAGTGAGCCAGGGTCCGAGTGGAAAG
117781  TGGTTGTGGTGGTAGGTCGGTCTGCGACGTCCCTGTCACTCGGTCCCAGGCTCACCTTTC

117841  GCGCTAGGCTTGGGAACCAGCTCAGAGTCAATACAGAGCCACCGCCACTCACCAACTCTG
117841  CGCGATCCGAACCCTTGGTCGAGTCTCAGTTATGTCTCGGTGGCGGTGAGTGGTTGAGAC

117901  TCAGCTTAGTAAAATGGCTCTGCCCCTAGAGCCCTGGTTCCATCCTTTAGTATCTCACAG
117901  AGTCGAATCATTTTACCGAGACGGGGATCTCGGGACCAAGGTAGGAAATCATAGAGTGTC

117961  GGTGATTGTGAATATCCCATGACTCCAAGATTGAGAAAACGTTTAGAATCCCTCGGTGTG
117961  CCACTAACACTTATAGGGTACTGAGGTTCTAACTCTTTTGCAAATCTTAGGGAGCCACAC

118021  AAGGTTAACTCTGTCCGGAAAGAGGACCAGTAAAAGCTTCATGAGGCTGAGATGCACTTT
118021  TTCCAATTGAGACAGGCCTTTCTCCTGGTCATTTTCGAAGTACTCCGACTCTACGTGAAA

118081  GGAAGAGGAATAGAGTTTCAGCACATTCTAGGTGTTGGAGGAATGGGGGAATCTAGGCAG
118081  CCTTCTCCTTATCTCAAAGTCGTGTAAGATCCACAACCTCCTTACCCCCTTAGATCCGTC

118141  ATGTTTAAAATCAATGAGAAACCAGAATGCTGACCATGAGGGTTGGAGTGGGGGCCTAAG
118141  TACAAATTTTAGTTACTCTTTGGTCTTACGACTGGTACTCCCAACCTCACCCCCGGATTC

118201  GACATGACGGAGGAGCAGGGTGTGTTCCCAGCTTAACTCAGGTACCCATGGGGAAGCAGG
118201  CTGTACTGCCTCCTCGTCCCACACAAGGGTCGAATTGAGTCCATGGGTACCCCTTCGTCC

118261  AAAAGTGAAGGTGTCCTAGGCAGCTCTGCCACAGGATGAATGGCTTCAGATGCCAGGTGA
118261  TTTTCACTTCCACAGGATCCGTCGAGACGGTGTCCTACTTACCGAAGTCTACGGTCCACT

118321  GCGAGGGACCCTTCATTCAGTCAGCAGGAAAGAAGCACTGGCATATTTTTTATGAGAACA
118321  CGCTCCCTGGGAAGTAAGTCAGTCGTCCTTTCTTCGTGACCGTATAAAAAATACTCTTGT

118381  AAGGCTAGGATAGTAAAGACAGCAAGTACCAAAAAATGACTGGAAAAGGGAGACTGTGGA
118381  TTCCGATCCTATCATTTCTGTCGTTCATGGTTTTTTACTGACCTTTTCCCTCTGACACCT

118441  GGCAGTGGCAGCAGGCATGGAAAGAAGGGCTTGTGAAGGGGAAGGGGTGGTGTCAGAGGA
118441  CCGTCACCGTCGTCCGTACCTTTCTTCCCGAACACTTCCCCTTCCCCACCACAGTCTCCT
```

FIG. 5 (cont'd)

```
118501  ACATAGGGCTGGGGGCAGGGATTAGGTGAGGGAAACCATGAGTCACACTGATTCTAGAGT
118501  TGTATCCCGACCCCCGTCCCTAATCCACTCCCTTTGGTACTCAGTGTGACTAAGATCTCA

118561  AGTGTGCCCTTGATGAAAAGGATAACACCAGGTTCTAGGAAAAGATGGGGTTCTGTTTTT
118561  TCACACGGGAACTACTTTTCCTATTGTGGTCCAAGATCCTTTTCTACCCCAAGACAAAAA

118621  GACGTGTTGATTTTCAAGGACTTCTGGTGTTTGTGACACATGGGGAAATTGTGGTGGGAG
118621  CTGCACAACTAAAAGTTCCTGAAGACCACAAACACTGTGTACCCCTTTAACACCACCCTC

118681  AGAGGTGGGGCCAGAACAGGGGCTGGTGAGGCCAAGGGTCCCAGAGGGCACCTGTTGACC
118681  TCTCCACCCCGGTCTTGTCCCCGACCACTCCGGTTCCCAGGGTCTCCCGTGGACAACTGG

118741  TGCAGGATGACATGAAGGGGGAAGGACAGAGGCAAGGCCAAGTCCTGGGCACCAGCCTCC
118741  ACGTCCTACTGTACTTCCCCCTTCCTGTCTCCGTTCCGGTTCAGGACCCGTGGTCGGAGG

118801  CTCTTGCAGCTTCAAATAGGGCTCCATTTTGACCTTTTGATTAATTAGAGGTTTGTCATA
118801  GAGAACGTCGAAGTTTATCCCGAGGTAAAACTGGAAAACTAATTAATCTCCAAACAGTAT

118861  GGTTGGGGGTTGAGAGGAGCAAGGGAGAGAAGGATTCAGTGTACAAAAAGAATGAAAGCC
118861  CCAACCCCCAACTCTCCTCGTTCCCTCTCTTCCTAAGTCACATGTTTTTCTTACTTTCGG

118921  ACTGGCTGAGCCAGTGGGGAGTTGTCCACACACACATGAGCCTTTGGACCATGAGAACGA
118921  TGACCGACTCGGTCACCCCTCAACAGGTGTGTGTGTACTCGGAAACCTGGTACTCTTGCT

118981  GGGAGGCCTTGCCTTCCTGAACGGAGTAGGAGTGAGGTCCTGTGCTGAGCGTAAGCAGTG
118981  CCCTCCGGAACGGAAGGACTTGCCTCATCCTCACTCCAGGACACGACTCGCATTCGTCAC

119041  GGATTCCCACAGCACTGGGCACAGAGCCCACGGGCTGCCTCCTGAGCAGCCAGCATCTGC
119041  CCTAAGGGTGTCGTGACCCGTGTCTCGGGTGCCCGACGGAGGACTCGTCGGTCGTAGACG

119101  CTGGGGTGGACACAGTGACAGAGAGATGGGTGGTGACTGGGGTATGGGCAGAGATAAGGC
119101  GACCCCACCTGTGTCACTGTCTCTCTACCCACCACTGACCCCATACCCGTCTCTATTCCG

119161  AGCAAGTGTGTGCAAGGGGAGTGAAGGGTTACTGACCTTAAGAAGCAGGGATGGCGTCCT
119161  TCGTTCACACACGTTCCCCTCACTTCCCAATGACTGGAATTCTTCGTCCCTACCGCAGGA

119221  CTGTCAGGTGAGGAGCCTGGAGAATGCTTTGGTGAATGAACGTTTGCAGCCCCTTTTAGC
119221  GACAGTCCACTCCTCGGACCTCTTACGAAACCACTTACTTGCAAACGTCGGGGAAAATCG

119281  TTTTGGAGACTTGAAACCAAAGGAGAGATTCATCTGTGAAACTCTACTGGAGCCACTCCC
119281  AAAACCTCTGAACTTTGGTTTCCTCTCTAAGTAGACACTTTGAGATGACCTCGGTGAGGG

119341  CAACCCCCACCCTTGTGAGACCACAATGTGGGCGTTGGCTTGAGATGCTTCTGTGTTAGT
119341  GTTGGGGGTGGGAACACTCTGGTGTTACACCCGCAACCGAACTCTACGAAGACACAATCA

119401  AGAAGAAATAAACAACACAGTGCTCTGATGAGGCAAAGCGAAGATGAAAAAGGAGTTCCC
119401  TCTTCTTTATTTGTTGTGTCACGAGACTACTCCGTTTCGCTTCTACTTTTTCCTCAAGGG

119461  AGGGGACATAGTAGGAACAGTGGACGAGGGTAGCAGAAGAGGAGTTTGGAGCAAAAGACT
119461  TCCCCTGTATCATCCTTGTCACCTGCTCCCATCGTCTTCTCCTCAAACCTCGTTTTCTGA

119521  CACAAGCAGCTGCATAATCTGTTGGTGCTTGGCAGTTCATTTGTAAAAATGATGCCTCTT
119521  GTGTTCGTCGACGTATTAGACAACCACGAACCGTCAAGTAAACATTTTTACTACGGAGAA

119581  CCTGCCCTAAAATACCTACCTTACCCCCGCTTCAACTTGATGAGATTTCCATCAGTCACT
119581  GGACGGGATTTTATGGATGGAATGGGGGCGAAGTTGAACTACTCTAAAGGTAGTCAGTGA

119641  CCCAATGTGTCACAGCTTCTGCAGCCCTAAAATTAAAAGGTGAGTGAGTCTCTGAGGCCC
119641  GGGTTACACAGTGTCGAAGACGTCGGGATTTTAATTTTCCACTCACTCAGAGACTCCGGG

119701  CTCTCCACTTCTCGGATGCTGAGTTTAGCCTTCATGTGAATGTGGAAAGACTAGGAATAC
119701  GAGAGGTGAAGAGCCTACGACTCAAATCGGAAGTACACTTACACCTTTCTGATCCTTATG

119761  AGCTGTTATCACACAAGCTGGCCCAATAGTGGTTCAGTTGAGAGAGCCCCATCCTTCAGA
119761  TCGACAATAGTGTGTTCGACCGGGTTATCACCAAGTCAACTCTCTCGGGGTAGGAAGTCT

119821  GTCAGCTCCAGCTAGGAGTGACTGGTGGCCTTGAGCATGGTGCTGGGCTTAGTGTTGCCA
119821  CAGTCGAGGTCGATCCTCACTGACCACCGGAACTCGTACCACGACCCGAATCACAACGGT
```

FIG. 5 (cont'd)

```
119881  TCTGTGGAATGGGTGTGGGTCTGTTGCCCTGCCTCCTCCCAGAGCTATTCTGAGGCTCAG
119881  AGACACCTTACCCACACCCAGACAACGGGACGGAGGAGGGTCTCGATAAGACTCCGAGTC

119941  AAGGGGTGATGGATGTGATGGTGCTCCCAACACTAGAAAGCATCTTAAGAATGTAAGATT
119941  TTCCCCACTACCTACACTACCACGAGGGTTGTGATCTTTCGTAGAATTCTTACATTCTAA

120001  TTCATGATGACTGTTGCTCAGAGTGGCTATTATAGTTTTGCTTTATTGTTCTATAACCTA
120001  AAGTACTACTGACAACGAGTCTCACCGATAATATCAAAACGAAATAACAAGATATTGGAT

120061  TGATTAAAATTTTTACCTTAAACTTTGACGTGAGTGTGAATAAGTATTTGTTTTGCCAGC
120061  ACTAATTTTAAAAATGGAATTTGAAACTGCACTCACACTTATTCATAAACAAAACGGTCG

120121  AACATTCCTCACCACTGGGGCCATTAAAGATCTCCCCCTCTGAGACCATCAAATACAGGT
120121  TTGTAAGGAGTGGTGACCCCGGTAATTTCTAGAGGGGGAGACTCTGGTAGTTTATGTCCA

120181  CAACAGGACTGATTAATCTAATTAGAAAAGGGCTTGTATTAAATAGCAATGATAATTGTT
120181  GTTGTCCTGACTAATTAGATTAATCTTTTCCCGAACATAATTTATCGTTACTATTAACAA

120241  GTTTTTAGTCTGTCTGGTGTTTGACTTGGGAACGTTTTTAAAATAGAGAAAAGCACAAAG
120241  CAAAAATCAGACAGACCACAAACTGAACCCTTGCAAAAATTTTATCTCTTTTCGTGTTTC

120301  AGGAAAACAACAATTACCAATATTCCTGCTACCCATTATAATTATCTAGGTATATTTTCT
120301  TCCTTTTGTTGTTAATGGTTATAAGGACGATGGGTAATATTAATAGATCCATATAAAAGA

120361  TCTTTTGTAAGAAAAAGAAACCCTGTTATATTGTTAAAATAACACAAAGTTAATATAAAG
120361  AGAAAACATTCTTTTTCTTTGGGACAATATAACAATTTTATTGTGTTTCAATTATATTTC

120421  AATTTTAATGCAAAGATTAATGTTTTCAAATCACCACAAAACCCAACATCCAGAAATTAC
120421  TTAAAATTACGTTTCTAATTACAAAAGTTTAGTGGTGTTTTGGGTTGTAGGTCTTTAATG

120481  CAATATTAAAAGTAGAAAAGTATCATTCTAAATATTTTCTGTTGCATATGTATGTGAGTG
120481  GTTATAATTTTCATCTTTTCATAGTAAGATTTATAAAAGACAACGTATACATACACTCAC

120541  GATAGGCTGATGAATTAGGTGGATTGATGGATAGGTAAATATGAAATAAATACTTTCATA
120541  CTATCCGACTACTTAATCCACCTAACTACCTATCCATTTATACTTTATTTATGAAAGTAT

120601  AATATTCCAACTTATCATACATGCCTTAAATTCAAGAGGTGAAAAAAGACCCAAACAAAA
120601  TTATAAGGTTGAATAGTATGTACGGAATTTAAGTTCTCCACTTTTTTCTGGGTTTGTTTT

120661  CTAGAGAAGCGGCTTATTTTAAATATCCTCTGACATAAAGGAATATTATATTTAAAGGAT
120661  GATCTCTTCGCCGAATAAAATTTATAGGAGACTGTATTTCCTTATAATATAAATTTCCTA

120721  CCTCTAAGATTAAAAATATGTACTATGAAAAACATTAAGAAATTTGAATTTTTTTTAATC
120721  GGAGATTCTAATTTTTATACATGATACTTTTTGTAATTCTTTAAACTTAAAAAAAATTAG

120781  CATTTGTTTCAATTTAAGCAGCATCTACTGGCTCACTGCTTTGAAAAATAAGGACAGTAT
120781  GTAAACAAAGTTAAATTCGTCGTAGATGACCGAGTGACGAAACTTTTTATTCCTGTCATA

120841  TCCAGTTCACATTCAGTGTTCCAGTGTTCACATTATCTTATTATTTTTACATTGTCCAGC
120841  AGGTCAAGTGTAAGTCACAAGGTCACAAGTGTAATAGAATAATAAAAATGTAACAGGTCG

120901  TTTGTAATATTCACATTCTATTCTGTAATCATAATTCATAGTAGTTTAGTTATTTATTAC
120901  AAACATTATAAGTGTAAGATAAGACATTAGTATTAAGTATCATCAAATCAATAAATAATG

120961  TAACTCTATTTAAATAGATTCAAGGATCAGACCCTGCCCTTTTCTTCTTATTTATGTTTA
120961  ATTGAGATAAATTTATCTAAGTTCCTAGTCTGGGACGGGAAAAGAAGAATAAATACAAAT

121021  TTTTGATTAATCTCTTAATTGATTGGACTTTACATTCAAGCAACTTTTTTAAAAAAAAGT
121021  AAAACTAATTAGAGAATTAACTAACCTGAAATGTAAGTTCGTTGAAAAAATTTTTTTTCA

121081  TTCTATAGATGTTCTATTTCTATCATTGTATTGTTTTTGAGGATGTTGGCCTGTTGCCTT
121081  AAGATATCTACAAGATAAAGATAGTAACATAACAAAAACTCCTACAACCGGACAACGGAA

121141  TGTATTTGATGAGCATTTTGACAGAGTCTATGGTCTTGGGCCACTCTTTCTTTTTCTCCC
121141  ACATAAACTACTCGTAAAACTGTCTCAGATACCAGAACCCGGTGAGAAAGAAAAAGAGGG

121201  TTGAGAACTTTTTAGATTTTGCTGATGGCATTGCTTGTTGAATGTTGCTGTGGAAACATC
121201  AACTCTTGAAAAATCTAAAACGACTACCGTAACGAACAACTTACAACGACACCTTTGTAG
```

FIG. 5 (cont'd)

```
121261  AAGTCTAGTGTAACTGTTTCTTCTTCAAGGTGATTTGCATTTTATTCCTGAATGCCTGAG
121261  TTCAGATCACATTGACAAAGAAGAAGTTCCACTAAACGTAAAATAAGGACTTACGGACTC

121321  GGTTCTTTATTTAACCTTGAAGTTAAATACCCTAATTAGGATGTATCTTGGTCTATTCAT
121321  CCAAGAAATAAATTGGAACTTCAATTTATGGGATTAATCCTACATAGAACCAGATAAGTA

121381  TCGGAATAAAAAATTCCTGCCATTTTGTCTAGAGAGTCCCTTTTTTTTCTCTTTATTTCT
121381  AGCCTTATTTTTTAAGGACGGTAAAACAGATCTCTCAGGGAAAAAAAAGAGAAATAAAGA

121441  GGGAAATTCTCTTTTATATAAATATGTTTTGTTCCATCTATTGTGATCTCTGTTGAGGGA
121441  CCCTTTAAGAGAAAATATATTTATACAAAACAAGGTAGATAACACTAGAGACAACTCCCT

121501  TACCAGTTGTCCATATGTTAGATAATTTGTCTTCCATATCTGTTAACAGTTCTTAAAGTT
121501  ATGGTCAACAGGTATACAATCTATTAAACAGAAGGTATAGACAATTGTCAAGAATTTCAA

121561  TTTTGTTTATTTCTTTGTCTATTTTTACATTTACTCACTGTTCTCTTGTGGTTTTCCTCT
121561  AAAACAAATAAAGAAACAGATAAAAATGTAAATGAGTGACAAGAGAACACCAAAAGGAGA

121621  GTCAGTAATTTAATTTTTAGTAGTTCCTGTTCTATTACTTGCTATTTTTAATCCATGCAT
121621  CAGTCATTAAATTAAAAATCATCAAGGACAAGATAATGAACGATAAAAATTAGGTACGTA

121681  TAATTTTATAATAATATTATTTTGCTCCTTATTTTGTCTCCTGAGACCCGAAATCTCTTT
121681  ATTAAAATATTATTATAATAAAACGAGGAATAAAACAGAGGACTCTGGGCTTTAGAGAAA

121741  TTTCCTCTTACTCTGTTGCTTTTGCATTTTATTTTGAATACTTTTAAAATTGATTCCATG
121741  AAAGGAGAATGAGACAACGAAAACGTAAAATAAAACTTATGAAAATTTTAACTAAGGTAC

121801  TTATGAAGCAATTATGAGGCATTTCCTCTCTTGTTGGAATTAACGATTTTTTCCCCTAGG
121801  AATACTTCGTTAATACTCCGTAAAGGAGAGAACAACCTTAATTGCTAAAAAAGGGGATCC

121861  AGGGACTCTATGGTCTGTGTTTTACTTCCTTTCTTCCCCTGTATTTCTAGAAAATATTTT
121861  TCCCTGAGATACCAGACACAAAATGAAGGAAAGAAGGGGACATAAAGATCTTTTATAAAA

121921  CCTAGTAACCCTGACATTTCTTTTCATCTTGCTTATTCTAGTTGGTCTGATATAGCTTGA
121921  GGATCATTGGGACTGTAAAGAAAAGTAGAACGAATAAGATCAACCAGACTATATCGAACT

121981  TTGACATTTCAGCCTTCTTCCCACTATATTTTTTTTTCCTGTGAGAGCTATTGGGTTTTC
121981  AACTGTAAAGTCGGAAGAAGGGTGATATAAAAAAAAAGGACACTCTCGATAACCCAAAAG

122041  TAAATCCTGAAAGAATGCCAAAGATGGGGTTGGAGGAGTTTGGTGAGGCAAAGTGCAGCC
122041  ATTTAGGACTTTCTTACGGTTTCTACCCCAACCTCCTCAAACCACTCCGTTTCACGTCGG

122101  TTTGTTAAAATACTTTTCCTTTGCTCTCTCTCCCTCATCTGAAATTTAGTTAAATACCCT
122101  AAACAATTTTATGAAAAGGAAACGAGAGAGAGGGAGTAGACTTTAAATCAATTTATGGGA

122161  AAGCCATCAGCACTGTACCTAGTTGGGGAATGCTTTCATCCCCACAGGAGATTCTCTGGG
122161  TTCGGTAGTCGTGACATGGATCAACCCCTTACGAAAGTAGGGGTGTCCTCTAAGAGACCC

122221  GCTTTGGGCCATCTTCCCCTTCAGTGTAGACCACAGAGGACTTTGCTTCTGTCCCAGGGA
122221  CGAAACCCGGTAGAAGGGGAAGTCACATCTGGTGTCTCCTGAAACGAAGACAGGGTCCCT

122281  GCCCGCAGGGGCTCACTTCTCCATGTTCATCTGATTCTTGTCAGCCAAGGTTTCAAATGC
122281  CGGGCGTCCCCGAGTGAAGAGGTACAAGTAGACTAAGAACAGTCGGTTCCAAAGTTTACG

122341  TTTTCTGATCAGAACAGGGAAAAGATACCTATCTGAATCATGTCTTTATAGATATGAGGC
122341  AAAAGACTAGTCTTGTCCCTTTTCTATGGATAGACTTAGTACAGAAATATCTATACTCCG

122401  TATGAGGGAAAATTCTGAGGTTATTCTTGACTCACACCTAAAGATTTGGAAATGAGATTA
122401  ATACTCCCTTTTAAGACTCCAATAAGAACTGAGTGTGGATTTCTAAACCTTTACTCTAAT

122461  GCAGCAAAGCTTTGCCCTACATCTCATGTCAGAATTTTCTGTTTCTTTCTAGTCTTTGAG
122461  CGTCGTTTCGAAACGGGATGTAGAGTACAGTCTTAAAAGACAAAGAAAGATCAGAAACTC

122521  TGTATGTGTGTTCTCACACACGCCATAATGAAATGCATATTATATATAATTATGTGTATA
122521  ACATACACACAAGAGTGTGTGCGGTATTACTTTACGTATAATATATATTAATACACATAT

122581  TATAATATTCTATGACTATACATGACATGTTCCTTTAGCTGATTGCTGTTAAGAGAAATT
122581  ATATTATAAGATACTGATATGTACTGTACAAGGAAATCGACTAACGACAATTCTCTTTAA
```

FIG. 5 (cont'd)

```
122641  TATAGGTTTTTATTTTTCTTGTTTTGTTGGGTATTAAGGAAGAGAAATTCTATGGTAATT
122641  ATATCCAAAAATAAAAAGAACAAAACAACCCATAATTCCTTCTCTTTAAGATACCATTAA

122701  TTCATGTGGCACAGTAATCTGGCATATATGTTGATTTTTTTCCTACACCCATTTGTTGTG
122701  AAGTACACCGTGTCATTAGACCGTATATACAACTAAAAAAAGGATGTGGGTAAACAACAC

122761  ATACCAAGTTTGAAAACAACAGATTTCAGTGGTTGCTTGGGAAACCACAGAACCATGACT
122761  TATGGTTCAAACTTTTGTTGTCTAAAGTCACCAACGAACCCTTTGGTGTCTTGGTACTGA

122821  TGGGGAGAGACAGGATGATTAGGTGGGAAAGCACCCTTTTGGTGGGGCTGTAAAGACTTT
122821  ACCCCTCTCTGTCCTACTAATCCACCCTTTCGTGGGAAAACCACCCCGACATTTCTGAAA

122881  TATATTTAGCAAAATTGGCTACAAAGTCCATTCCCCTCCTTTTCTTGCCTTGATTTGGTA
122881  ATATAAATCGTTTTAACCGATGTTTCAGGTAAGGGGAGGAAAAGAACGGAACTAAACCAT

122941  GAGGGATAGACTTGGATACAAACTAGAATGGATTCATTCTTCTCTGGAGTTAGTGTAACA
122941  CTCCCTATCTGAACCTATGTTTGATCTTACCTAAGTAAGAAGAGACCTCAATCACATTGT

123001  AGACATTTAGCTGCTCAACACAAAAACAGAAACAAAAAAATTGTGTGGTTTCAGCAGTGC
123001  TCTGTAAATCGACGAGTTGTGTTTTTGTCTTTGTTTTTTTAACACACCAAAGTCGTCACG

123061  TATACAATTACTTTTTCTGACCTTTAATGGAGAGAAACACCACTTCTTTGGTCCCTACCA
123061  ATATGTTAATGAAAAAGACTGGAAATTACCTCTCTTTGTGGTGAAGAAACCAGGGATGGT

123121  TCAGCTTCATAGGGTTTTCATCCTGTTCTGTTTCTGGGAGGGCGTAACTGGCCATGCACA
123121  AGTCGAAGTATCCCAAAAGTAGGACAAGACAAAGACCCTCCCGCATTGACCGGTACGTGT

123181  AGTTTTTTTTCTCTAATCAGAGTATGTGCCACTTCTGACCACCAGTAGATGAAAACGAAT
123181  TCAAAAAAAAGAGATTAGTCTCATACACGGTGAAGACTGGTGGTCATCTACTTTTGCTTA

123241  GGAAACCAGGCTATTATATGATACATATCCATTACAAAATAAGACATGAAACTCAAAGGT
123241  CCTTTGGTCCGATAATATACTATGTATAGGTAATGTTTTATTCTGTACTTTGAGTTTCCA

123301  ACTTTATGGTATAATGGGGCATATATTCCTGGACAATTCTTAATGGTCACAGATTTTATA
123301  TGAAATACCATATTACCCCGTATATAAGGACCTGTTAAGAATTACCAGTGTCTAAAATAT

123361  AAAGGACTATTAGTAAATGTATGAATTACAGAGTAATTTATCCTTCTGTTAGTAAGAACC
123361  TTTCCTGATAATCATTTACATACTTAATGTCTCATTAAATAGGAAGACAATCATTCTTGG

123421  AGCTGATGACCTCAGTGTCAGGTGCATCGTGGAAGGTGTTGGGACCTTCCCTTGCCACCA
123421  TCGACTACTGGAGTCACAGTCCACGTAGCACCTTCCACAACCCTGGAAGGGAACGGTGGT

123481  CCCTCACCAGCCATCATCAGCCATAACCTGCACATTGGGGAAGTTTTGACTTATCCCTCA
123481  GGGAGTGGTCGGTAGTAGTCGGTATTGGACGTGTAACCCCTTCAAAACTGAATAGGGAGT

123541  CTTTTGCCCCTCTTCAAGCTGTTCTTTCCACAGTGAATGAGAAGGCCACTTCTTCCTTCA
123541  GAAAACGGGGAGAAGTTCGACAAGAAAGGTGTCACTTACTCTTCCGGTGAAGAAGGAAGT

123601  AACCTTTCAGTGGTTTCCATTTTCCTTTAGACAAAGTCTCTGCCTAGCTGGCCTCTGCCT
123601  TTGGAAAGTCACCAAAGGTAAAAGGAAATCTGTTTCAGAGACGGATCGACCGGAGACGGA

123661  GCCCCTCCTGCCTACCTCTCGAGCACTGCCCCCACCTAGGGCTCTGGTTCCCCAACCTTC
123661  CGGGGAGGACGGATGGAGAGCTCGTGACGGGGGTGGATCCCGAGACCAAGGGGTTGGAAG

123721  ACTCGGTCCTGCCACACCTCCCAGCCCCTTCTCCCTTCAGAACTTTCCTTCTTGTTGTCC
123721  TGAGCCAGGACGGTGTGGAGGGTCGGGGAAGAGGGAAGTCTTGAAAGGAAGAACAACAGG

123781  CCAACACTGGGACACAAAACCCTCCTTATCAACCCTCCTTATCTGGCTGACTCTTACAAG
123781  GGTTGTGACCCTGTGTTTTGGGAGGAATAGTTGGGAGGAATAGACCGACTGAGAATGTTC

123841  ATCAGAAACCTGTGTAATGCTCTCATGGCACGCTCCCCTTGTCTTCGTGGATTTCTCAGA
123841  TAGTCTTTGGACACATTACGAGAGTACCGTGCGAGGGGAACAGAAGCACCTAAAGAGTCT

123901  TGGGAAGGAATTATCCATGCAATCACACATAAACTTCTACCTACCCTCCCCTAGTAGCTG
123901  ACCCTTCCTTAATAGGTACGTTAGTGTGTATTTGAAGATGGATGGGAGGGGATCATCGAC

123961  TCTGCTGCTAAGGATGGGGACCATTCTCACTTACTCACTGTTCTGTCCCTCTGCCCAGTC
123961  AGACGACGATTCCTACCCCTGGTAAGAGTGAATGAGTGACAAGACAGGGAGACGGGTCAG
```

FIG. 5 (cont'd)

```
124021  CAGATGTGTTGAAGGATGGAAATATACAGAGTAGTGGTAAAATATAAACCGTTCAGACAT
124021  GTCTACACAACTTCCTACCTTTATATGTCTCATCACCATTTTATATTTGGCAAGTCTGTA

124081  TCCAAGGATGGGCTCATGTGCTTTGACTCATTAATGTACCACTGCTGAAAACAGAACACA
124081  AGGTTCCTACCCGAGTACACGAAACTGAGTAATTACATGGTGACGACTTTTGTCTTGTGT

124141  GCCGCAGTCTTGCCAGTAAGAGTGCAGTTACTGTAATTAATGAATTTGCTAATTAAGCCA
124141  CGGCGTCAGAACGGTCATTCTCACGTCAATGACATTAATTACTTAAACGATTAATTCGGT

124201  TGATTTCATACTGAACTTATGACCAACATATTGAGAAGGTGTGTCTTCAAGAAAATTTAT
124201  ACTAAAGTATGACTTGAATACTGGTTGTATAACTCTTCCACACAGAAGTTCTTTTAAATA

124261  TTTTTGTATTAAGATATTTACTCCAAAGCTAATTGAAGAAGCCAAATCTAGGCTCTGGTT
124261  AAAAACATAATTCTATAAATGAGGTTTCGATTAACTTCTTCGGTTTAGATCCGAGACCAA

124321  TCACCATTGCCAGGGAAATGAGCTCATGGACTCCTATGAACTGATGATGTTAGATCAGAA
124321  AGTGGTAACGGTCCCTTTACTCGAGTACCTGAGGATACTTGACTACTACAATCTAGTCTT

124381  GTTTCTCAAGGCCAGGGCCCAATCACTGCTGAGGCGTCAACAGTAGTTCCTTGTACATCA
124381  CAAAGAGTTCCGGTCCCGGGTTAGTGACGACTCCGCAGTTGTCATCAAGGAACATGTAGT

124441  ATAATTCTCATTACTTTTAAAAAATAACAGATGAATAGCAACTATTTTCCCTGTAGCTCC
124441  TATTAAGAGTAATGAAAATTTTTTATTGTCTACTTATCGTTGATAAAAGGGACATCGAGG

124501  CTTGCTGTGCCTCCTACCCTCCACCACATGTTTCTGGGGAGCCCTGCTTCGGGCCTGCCA
124501  GAACGACACGGAGGATGGGAGGTGGTGTACAAAGACCCCTCGGGACGAAGCCCGGACGGT

124561  ACTACAGAGAATTACTTTTGAGTATCCCTTCCACTCTCATCTCAAGACAGAGTTCATCTA
124561  TGATGTCTCTTAATGAAAACTCATAGGGAAGGTGAGAGTAGAGTTCTGTCTCAAGTAGAT

124621  CCTTTGGGTTATTTGTCAAAAATGTGTCATTTTATTACAAAAAATATACAATCATCATGT
124621  GGAAACCCAATAAACAGTTTTTACACAGTAAAATAATGTTTTTTATATGTTAGTAGTACA

124681  ATTTTGATTAAATTTTACACTAGATTATTAAAATTATTAAATACAATTATTAAAATTAAT
124681  TAAAACTAATTTAAAATGTGATCTAATAATTTTAATAATTTATGTTAATAATTTTAATTA

124741  AATTTAACATATCACATATTTTAAATATATTGTATATAATGAATAATAATATAATTATTG
124741  TTAAATTGTATAGTGTATAAAATTTATATAACATATATTACTTATTATTATATTAATAAC

124801  TCTATTTTAATTCAATAAATGTATAGTAAGTTAGCCAGTTGTAAATTACTGAGAACACTC
124801  AGATAAAATTAAGTTATTTACATATCATTCAATCGGTCAACATTTAATGACTCTTGTGAG

124861  TACTGAAAAAGCATCATTTCAAATACACTATTTAAAATATTAAATGAAATACAATAACAT
124861  ATGACTTTTTCGTAGTAAAGTTTATGTGATAAATTTTATAATTTACTTTATGTTATTGTA

124921  AATTAAACTAATCTTTGGTTCCCCTATTTATGTATTCATTTATCCAACAAAATCTCCTTA
124921  TTAATTTGATTAGAAACCAAGGGGATAAATACATAAGTAAATAGGTTGTTTTAGAGGAAT

124981  AGTGCTTATAATGGGTAGGTCCTGGCTCGGTGTCCCCTAGACAGACGCATGGGCCTTCCC
124981  TCACGAATATTACCCATCCAGGACCGAGCCACAGGGGATCTGTCTGCGTACCCGGAAGGG

125041  CCAGCCCGTCAGTATGGTGCAGGTGTGATGTGTCCGCAGGTGTGTGTGTATGTGTGCAGG
125041  GGTCGGGCAGTCATACCACGTCCACACTACACAGGCGTCCACACACACATACACACGTCC

125101  TGTGGGGTCCGCAGGCGTGCTGGGCCCCCAGGCCGTGTTCCCCTTCCCCTCCCCGGTTGT
125101  ACACCCCAGGCGTCCGCACGACCCGGGGGTCCGGCACAAGGGGAAGGGGAGGGGCCAACA

125161  AGATTTCAGCTGTTGCTGCCAGACCTGACCGGTTCCGGAGGTGGCCGCGCCCCACTCACT
125161  TCTAAAGTCGACAACGACGGTCTGGACTGGCCAAGGCCTCCACCGGCGCGGGGTGAGTGA

125221  GTCGCCTGCTTTCCACAGGGGACAAGGGCCTGTCCGACACGCCCTACGACAGCAGCGCCA
125221  CAGCGGACGAAAGGTGTCCCCTGTTCCCGGACAGGCTGTGCGGGATGCTGTCGTCGCGGT

125281  GCTACGAGAAGGAGAACGAAATGATGAAGTCCCACGTGATGGACCAAGCCATCAACAACG
125281  CGATGCTCTTCCTCTTGCTTTACTACTTCAGGGTGCACTACCTGGTTCGGTAGTTGTTGC

125341  CCATCAACTACCTGGGGGCCGAGTCCCTGCGCCCGCTGGTGCAGACGCCCCCGGGCGGTT
125341  GGTAGTTGATGGACCCCCGGCTCAGGGACGCGGGCGACCACGTCTGCGGGGGCCCGCCAA
```

FIG. 5 (cont'd)

```
125401  CCGAGGTGGTCCCGGTCATCAGCCCGATGTACCAGCTGCACAAGCCGCTCGCGGAGGGCA
125401  GGCTCCACCAGGGCCAGTAGTCGGGCTACATGGTCGACGTGTTCGGCGAGCGCCTCCCGT

125461  CCCCGCGCTCCAACCACTCGGCCCAGGACAGCGCCGTGGAGAACCTGCTGCTGCTCTCCA
125461  GGGGCGCGAGGTTGGTGAGCCGGGTCCTGTCGCGGCACCTCTTGGACGACGACGAGAGGT

125521  AGGCCAAGTTGGTGCCCTCGGAGCGCGAGGCGTCCCCGAGCAACAGCTGCCAAGACTCCA
125521  TCCGGTTCAACCACGGGAGCCTCGCGCTCCGCAGGGGCTCGTTGTCGACGGTTCTGAGGT

125581  CGGACACCGAGAGCAACAACGAGGAGCAGCGCAGCGGTCTCATCTACCTGACCAACCACA
125581  GCCTGTGGCTCTCGTTGTTGCTCCTCGTCGCGTCGCCAGAGTAGATGGACTGGTTGGTGT

125641  TCGCCCCGCACGCGCGCAACGGGCTGTCGCTCAAGGAGGAGCACCGCGCCTACGACCTGC
125641  AGCGGGGCGTGCGCGCGTTGCCCGACAGCGAGTTCCTCCTCGTGGCGCGGATGCTGGACG

125701  TGCGCGCCGCCTCCGAGAACTCGCAGGACGCGCTCCGCGTGGTCAGCACCAGCGGGGAGC
125701  ACGCGCGGCGGAGGCTCTTGAGCGTCCTGCGCGAGGCGCACCAGTCGTGGTCGCCCCTCG

125761  AGATGAAGGTGTACAAGTGCGAACACTGCCGGGTGCTCTTCCTGGATCACGTCATGTACA
125761  TCTACTTCCACATGTTCACGCTTGTGACGGCCCACGAGAAGGACCTAGTGCAGTACATGT

125821  CCATCCACATGGGCTGCCACGGCTTCCGTGATCCTTTTGAGTGCAACATGTGCGGCTACC
125821  GGTAGGTGTACCCGACGGTGCCGAAGGCACTAGGAAAACTCACGTTGTACACGCCGATGG

125881  ACAGCCAGGACCGGTACGAGTTCTCGTCGCACATAACGCGAGGGGAGCACCGCTTCCACA
125881  TGTCGGTCCTGGCCATGCTCAAGAGCAGCGTGTATTGCGCTCCCCTCGTGGCGAAGGTGT

125941  TGAGCTAAAGCCCTCCCGCGCCCCCACCCCAGACCCCGAGCCACCCCAGGAAAAGCACAA
125941  ACTCGATTTCGGGAGGGCGCGGGGGTGGGGTCTGGGGCTCGGTGGGGTCCTTTTCGTGTT

126001  GGACTGCCGCCTTCTCGCTCCCGCCAGCAGCATAGACTGGACTGGACCAGACAATGTTGT
126001  CCTGACGGCGGAAGAGCGAGGGCGGTCGTCGTATCTGACCTGACCTGGTCTGTTACAACA

126061  GTTTGGATTTGTAACTGTTTTTTGTTTTTTGTTTGAGTTGGTTGATTGGGGTTTGATTTG
126061  CAAACCTAAACATTGACAAAAAACAAAAAACAAACTCAACCAACTAACCCCAAACTAAAC

126121  CTTTTGAAAAGATTTTTATTTTTAGAGGCAGGGCTGCATTGGGAGCATCCAGAACTGCTA
126121  GAAAACTTTTCTAAAAATAAAAATCTCCGTCCCGACGTAACCCTCGTAGGTCTTGACGAT

126181  CCTTCCTAGATGTTTCCCCAGACCGCTGGCTGAGATTCCCTCACCTGTCGCTTCCTAGAA
126181  GGAAGGATCTACAAAGGGGTCTGGCGACCGACTCTAAGGGAGTGGACAGCGAAGGATCTT

126241  TCCCCTTCTCCAAACGATTAGTCTAAATTTTCAGAGAGAAATAGATAAAACACGCCACAG
126241  AGGGGAAGAGGTTTGCTAATCAGATTTAAAAGTCTCTCTTTATCTATTTTGTGCGGTGTC

126301  CCTGGGAAGGAGCGTGCTCTACCCTGTGCTAAGCACGGGGTTCGCGCACCAGGTGTCTTT
126301  GGACCCTTCCTCGCACGAGATGGGACACGATTCGTGCCCCAAGCGCGTGGTCCACAGAAA

126361  TTCCAGTCCCCAGAAGCAGAGAGCACAGCCCCTGCTGTGTGGGTCTGCAGGTGAGCAGAC
126361  AAGGTCAGGGGTCTTCGTCTCTCGTGTCGGGGACGACACACCCAGACGTCCACTCGTCTG

126421  AGGACAGGTGTGCCGCCACCCAAGTGCCAAGACACAGCAGGGCCAACAACCTGTGCCCAG
126421  TCCTGTCCACACGGCGGTGGGTTCACGGTTCTGTGTCGTCCCGGTTGTTGGACACGGGTC

126481  GCCAGCTTCGAGCTACATGCATCTAGGGCGGAGAGGCTGCACTTGTGAGAGAAAATACTA
126481  CGGTCGAAGCTCGATGTACGTAGATCCCGCCTCTCCGACGTGAACACTCTCTTTTATGAT

126541  TTTCAAGTCATATTCTGCGTAGGAAAATGAATTGGTTGGGGAAAGTCGTGTCTGTCAGAC
126541  AAAGTTCAGTATAAGACGCATCCTTTTACTTAACCAACCCCTTTCAGCACAGACAGTCTG

126601  TGCCCTGGGTGGAGGGAGACGCCGGGCTAGAGCCTTTGGGATCGTCCTGGATTCACTGGC
126601  ACGGGACCCACCTCCCTCTGCGGCCCGATCTCGGAAACCCTAGCAGGACCTAAGTGACCG

126661  TTTGCGGAGGCTGCTCAGATGGCCTGAGCCTCCCGAGGCTTGCTGCCCCGTAGGAGGAGA
126661  AAACGCCTCCGACGAGTCTACCGGACTCGGAGGGCTCCGAACGACGGGGCATCCTCCTCT

126721  CTGTCTTCCCGTGGGCATATCTGGGGAGCCCTGTTCCCCGCTTTTTCACTCCCATACCTT
126721  GACAGAAGGGCACCCGTATAGACCCCTCGGGACAAGGGGCGAAAAAGTGAGGGTATGGAA
```

FIG. 5 (cont'd)

```
126781  TAATGGCCCCCAAAATCTGTCACTACAATTTAAACACCAGTCCCGAAATTTGGATCTTCT
126781  ATTACCGGGGGTTTTAGACAGTGATGTTAAATTTGTGGTCAGGGCTTTAAACCTAGAAGA

126841  TTCTTTTTGAATCTCTCAAACGGCAACATTCCTCAGAAACCAAAGCTTTATTTCAAATCT
126841  AAGAAAAACTTAGAGAGTTTGCCGTTGTAAGGAGTCTTTGGTTTCGAAATAAAGTTTAGA

126901  CTTCCTTCCCTGGCTGGTTCCATCTAGTACCAGAGGCCTCTTTTCCTGAAGAAATCCAAT
126901  GAAGGAAGGGACCGACCAAGGTAGATCATGGTCTCCGGAGAAAAGGACTTCTTTAGGTTA

126961  CCTAGCCCTCATTTTAATTATGTACATCTGTTTGTAGCCACAAGCCTGAATTTCTCAGTG
126961  GGATCGGGAGTAAAATTAATACATGTAGACAAACATCGGTGTTCGGACTTAAAGAGTCAC

127021  TTGGTAAGTTTCTTTACCTACCCTCACTATATATTATTCTCGTTTTAAAACCCATAAAGG
127021  AACCATTCAAAGAAATGGATGGGAGTGATATATAATAAGAGCAAAATTTTGGGTATTTCC

127081  AGTGATTTAGAACAGTCATTAATTTTCAACTCAATGAAATATGTGAAGCCCAGCATCTCT
127081  TCACTAAATCTTGTCAGTAATTAAAAGTTGAGTTACTTTATACACTTCGGGTCGTAGAGA

127141  GTTGCTAACACACAGAGCTCACCTGTTTGAAACCAAGCTTTCAAACATGTTGAAGCTCTT
127141  CAACGATTGTGTGTCTCGAGTGGACAAACTTTGGTTCGAAAGTTTGTACAACTTCGAGAA

127201  TACTGTAAAGGCAAGCCAGCATGTGTGTCCACACATACATAGGATGGCTGGCTCTGCACC
127201  ATGACATTTCCGTTCGGTCGTACACACAGGTGTGTATGTATCCTACCGACCGAGACGTGG

127261  TGTAGGATATTGGAATGCACAGGGCAATTGAGGGACTGAGCCAGACCTTCGGAGAGTAAT
127261  ACATCCTATAACCTTACGTGTCCCGTTAACTCCCTGACTCGGTCTGGAAGCCTCTCATTA

127321  GCCACCAGATCCCCTAGGAAAGAGGAGGCAAATGGCACTGCAGGTGAGAACCCCGCCCAT
127321  CGGTGGTCTAGGGGATCCTTTCTCCTCCGTTTACCGTGACGTCCACTCTTGGGGCGGGTA

127381  CCGTGCTATGACATGGAGGCACTGAAGCCCGAGGAAGGTGTGTGGAGATTCTAATCCCAA
127381  GGCACGATACTGTACCTCCGTGACTTCGGGCTCCTTCCACACACCTCTAAGATTAGGGTT

127441  CAAGCAAGGGTCTCCTTCAAGATTAATGCTATCAATCATTAAGGTCATTACTCTCAACCA
127441  GTTCGTTCCCAGAGGAAGTTCTAATTACGATAGTTAGTAATTCCAGTAATGAGAGTTGGT

127501  CCTAGGCAATGAAGAATATACCATTTCAAATATTTACAGTACTTGTCTTCACCAACACTG
127501  GGATCCGTTACTTCTTATATGGTAAAGTTTATAAATGTCATGAACAGAAGTGGTTGTGAC

127561  TCCCAAGGTGAAATGAAGCAACAGAGAGGAAATTGTACATAAGTACCTCAGCATTTAATC
127561  AGGGTTCCACTTTACTTCGTTGTCTCTCCTTTAACATGTATTCATGGAGTCGTAAATTAG

127621  CAAACAGGGGTTCTTAGTCTCAGCACTATGACATTTTGGGCTGACTACTTATTTGTTAGG
127621  GTTTGTCCCCAAGAATCAGAGTCGTGATACTGTAAAACCCGACTGATGAATAAACAATCC

127681  CGGGAGCTCTCCTGTGCATTGTAGGATAATTAGCAGTATCCCTGGTGGCTACCCAATAGA
127681  GCCCTCGAGAGGACACGTAACATCCTATTAATCGTCATAGGGACCACCGATGGGTTATCT

127741  CGCCAGTAGCACCCCGAATTGACAACCCAAACTCTCCAGACATCACCAACTGTCCCCTGC
127741  GCGGTCATCGTGGGGCTTAACTGTTGGGTTTGAGAGGTCTGTAGTGGTTGACAGGGGACG

127801  GAGGAGAAATCACTCCTGGGGGAGAACCACTGACCCAAATGAATTCTAAACCAATCAAAT
127801  CTCCTCTTTAGTGAGGACCCCCTCTTGGTGACTGGGTTTACTTAAGATTTGGTTAGTTTA

127861  GTCTGGGAAGCCCTCCAAGAAAAAAAATAGAAAAGCACTTGAAGAATATTCCCAATATTC
127861  CAGACCCTTCGGGAGGTTCTTTTTTTTATCTTTTCGTGAACTTCTTATAAGGGTTATAAG

127921  CCGGTCAGCAGTATCAAGGCTGACTTGTGTTCATGTGGAGTCATTATAAATTCTATAAAT
127921  GGCCAGTCGTCATAGTTCCGACTGAACACAAGTACACCTCAGTAATATTTAAGATATTTA

127981  CAATTATTCCCCTTCGGTCTTAAAAATATATTTCCTCATAAACATTTGAGTTTTGTTGAA
127981  GTTAATAAGGGGAAGCCAGAATTTTTATATAAAGGAGTATTTGTAAACTCAAAACAACTT

128041  AAGATGGAGTTTACAAAGATACCATTCTTGAGTCATGGATTTCTCTGCTCACAGAAGGGT
128041  TTCTACCTCAAATGTTTCTATGGTAAGAACTCAGTACCTAAAGAGACGAGTGTCTTCCCA

128101  GTGGCATTTGGAAACGGGAATAAACAAAATTGCTGCACCAATGCACTGAGTGAAGGAAGA
128101  CACCGTAAACCTTTGCCCTTATTTGTTTTAACGACGTGGTTACGTGACTCACTTCCTTCT
```

FIG. 5 (cont'd)

```
128161  GAGACAGAGGATCAAGGGCTTTAGACAGCACTCCTTCAATATGCAATCACAGAGAAAGAT
128161  CTCTGTCTCCTAGTTCCCGAAATCTGTCGTGAGGAAGTTATACGTTAGTGTCTCTTTCTA

128221  GCGCCTTATCCAAGTTAATATCTCTAAGGTGAGAGCCTTCTTAGAGTCAGTTTGTTGCAA
128221  CGCGGAATAGGTTCAATTATAGAGATTCCACTCTCGGAAGAATCTCAGTCAAACAACGTT

128281  ATTTCACCTACTCTGTTCTTTTCCATCCATCCCCCTGAGTCAGTTGGTTGAAGGGAGTTA
128281  TAAAGTGGATGAGACAAGAAAAGGTAGGTAGGGGGACTCAGTCAACCAACTTCCCTCAAT

128341  TTTTTTCAAGTGGAATTCAAACAAAGCTCAAACCAGAACTGTAAATAGTGATTGCAGGAA
128341  AAAAAAGTTCACCTTAAGTTTGTTTCGAGTTTGGTCTTGACATTTATCACTAACGTCCTT

128401  TTCTTTTCTAAACTGCTTTGCCCTTTCCTCTCACTGCCTTTTATAGCCAATATAAATGTC
128401  AAGAAAAGATTTGACGAAACGGGAAAGGAGAGTGACGGAAAATATCGGTTATATTTACAG

128461  TCTTTGCACACCTTTTGTTGTGGTTTTATATTGTAACACCATTTTTCTTTGAAACTATTG
128461  AGAAACGTGTGGAAAACAACACCAAAATATAACATTGTGGTAAAAAGAAACTTTGATAAC

128521  TATTTAAAGTAAGGTTTCATATTATGTCAGCAAGTAATTAACTTATGTTTAAAAGGTGGC
128521  ATAAATTTCATTCCAAAGTATAATACAGTCGTTCATTAATTGAATACAAATTTTCCACCG

128581  CATATCATGTACCAAAAGTTGCTGAAGTTTCTCTTCTAGCTGGTAAAGTAGGAGTTTGCA
128581  GTATAGTACATGGTTTTCAACGACTTCAAAGAGAAGATCGACCATTTCATCCTCAAACGT

128641  TGACTTCACACTTTTTTTGCGTAGTTTCTTCTGTTGTATGATGGCGTGAGTGTGTGTCTT
128641  ACTGAAGTGTGAAAAAAACGCATCAAAGAAGACAACATACTACCGCACTCACACACAGAA

128701  GGGTACCGCTGTGTACTACTGTGTGCCTAGATTCCATGCACTCTCGTTGTGTTTGAAGTA
128701  CCCATGGCGACACATGATGACACACGGATCTAAGGTACGTGAGAGCAACACAAACTTCAT

128761  AATATTGGAGACCGGAGGGTAACAGGTTGGCCTGTTGATTACAGCTAGTAATCGCTGTGT
128761  TTATAACCTCTGGCCTCCCATTGTCCAACCGGACAACTAATGTCGATCATTAGCGACACA

128821  CTTGTTCCGCCCCCTCCCTGACACCCCAGCTTCCCAGGATGTGGAAAGCCTGGATCTCAG
128821  GAACAAGGCGGGGGAGGGACTGTGGGGTCGAAGGGTCCTACACCTTTCGGACCTAGAGTC

128881  CTCCTTGCCCCATATCCCTTCTGTAATTTGTACCTAAAGAGTGTGATTATCCTAATTCAA
128881  GAGGAACGGGGTATAGGGAAGACATTAAACATGGATTTCTCACACTAATAGGATTAAGTT

128941  GAGTCACTAAAACTCATCACATTATCATTGCATATCAGCAAAGGGTAAAGTCCTAGCACC
128941  CTCAGTGATTTTGAGTAGTGTAATAGTAACGTATAGTCGTTTCCCATTTCAGGATCGTGG

129001  AATTGCTTCACATACCAGCATGTTCCATTTCCAATTTAGAATTAGCCACATAATAAAATC
129001  TTAACGAAGTGTATGGTCGTACAAGGTAAAGGTTAAATCTTAATCGGTGTATTATTTTAG

129061  TTAGAATCTTCCTTGAGAAAGAGCTGCCTGAGATGTAGTTTTGTTATATGGTTCCCCACC
129061  AATCTTAGAAGGAACTCTTTCTCGACGGACTCTACATCAAAACAATATACCAAGGGGTGG

129121  GACCATTTTTGTGCTTTTTTCTTGTTTTGTTTTGTTTTGACTGCACTGTGAGTTTTGTAG
129121  CTGGTAAAAACACGAAAAAAGAACAAAACAAAACAAAACTGACGTGACACTCAAAACATC

129181  TGTCCTCTTCTTGCCAAAACAAACGCGAGATGAACTGGACTTATGTAGACAAATCGTGAT
129181  ACAGGAGAAGAACGGTTTTGTTTGCGCTCTACTTGACCTGAATACATCTGTTTAGCACTA

129241  GCCAGTGTATCCTTCCTTTCTTCAGTTCCAGCAATAATGAATGGTCAACTTTTTTAAAAT
129241  CGGTCACATAGGAAGGAAAGAAGTCAAGGTCGTTATTACTTACCAGTTGAAAAAATTTTA

129301  CTAGATCTCTCTCATTCATTTCAATGTATTTTTACTTTAAGATGAACCAAAATTATTAGA
129301  GATCTAGAGAGAGTAAGTAAAGTTACATAAAAATGAAATTCTACTTGGTTTTAATAATCT

129361  CTTATTTAAGATGTACAGGCATCAGAAAAAAGAAGCACATAATGCTTTTGGTGCGATGGC
129361  GAATAAATTCTACATGTCCGTAGTCTTTTTTCTTCGTGTATTACGAAAACCACGCTACCG

129421  ACTCACTGTGAACATGTGTAACCACATATTAATATGCAATATTGTTTCCAATACTTTCTA
129421  TGAGTGACACTTGTACACATTGGTGTATAATTATACGTTATAACAAAGGTTATGAAAGAT

129481  ATACAGTTTTTTATAATGTTGTGTGTGGTGATTGTTCAGGTCGAATCTGTTGTATCCAGT
129481  TATGTCAAAAAATATTACAACACACACCACTAACAAGTCCAGCTTAGACAACATAGGTCA
```

FIG. 5 (cont'd)

```
129541  ACAGCTTTAGGTCTTCAGCTGCCCTTCTGGCGAGTACATGCACAGGATTGTAAATGAGAA
129541  TGTCGAAATCCAGAAGTCGACGGGAAGACCGCTCATGTACGTGTCCTAACATTTACTCTT

129601  ATGCAGTCATATTTCCAGTCTGCCTCTATGATGATGTTAAATTATTGCTGTTTAGCTGTG
129601  TACGTCAGTATAAAGGTCAGACGGAGATACTACTACAATTTAATAACGACAAATCGACAC

129661  AACAAGGGATGTACCACTGGAGGAATAGAGTATCCTTTTGTACACATTTTGAAATGCTTC
129661  TTGTTCCCTACATGGTGACCTCCTTATCTCATAGGAAAACATGTGTAAAACTTTACGAAG

129721  TTCTGTAGTGATAGAACAAATAAATGCAACGAATACTCTGTCTGCCCTATCCCGTGAAGT
129721  AAGACATCACTATCTTGTTTATTTACGTTGCTTATGAGACAGACGGGATAGGGCACTTCA

129781  CCACACTGGCGTAAGAGAAGGCCCAGCAGAGCAGGAATCTGCCTAGACTTTCTCCCAATG
129781  GGTGTGACCGCATTCTCTTCCGGGTCGTCTCGTCCTTAGACGGATCTGAAAGAGGGTTAC

129841  AGATCCCAATATGAGAGGGAGAAGAGATGGGCCTCAGGACAGCTGCAATACCACTTGGGA
129841  TCTAGGGTTATACTCTCCCTCTTCTCTACCCGGAGTCCTGTCGACGTTATGGTGAACCCT

129901  ACACATGTGGTGTCTTGATGTGGCCAGCGCAGCAGTTCAGCACAACGTACCTCCCATCTA
129901  TGTGTACACCACAGAACTACACCGGTCGCGTCGTCAAGTCGTGTTGCATGGAGGGTAGAT

129961  CAACAGTGCTGGACGTGGGAATTCTAAGTCCCAGTCTTGAGGGTGGGTGGAGATGGAGGG
129961  GTTGTCACGACCTGCACCCTTAAGATTCAGGGTCAGAACTCCCACCCACCTCTACCTCCC

130021  CAACAAGAGATACATTTCCAGTTCTCCACTGCAGCATGCTTCAGTCATTCTGTGAGTGGC
130021  GTTGTTCTCTATGTAAAGGTCAAGAGGTGACGTCGTACGAAGTCAGTAAGACACTCACCG

130081  CGGGCCCAGGGCCCTCACAATTTCACTACCTTGTCTTTTACATAGTCATAAGAATTATCC
130081  GCCCGGGTCCCGGGAGTGTTAAAGTGATGGAACAGAAAATGTATCAGTATTCTTAATAGG

130141  TCAACATAGCCTTTTGACGCTGTAAATCTTGAGTATTCATTTACCCTTTTCTGATCTCCT
130141  AGTTGTATCGGAAAACTGCGACATTTAGAACTCATAAGTAAATGGGAAAAGACTAGAGGA

130201  GGAAACAGCTGCCTGCCTGCATTGCACTTCTCTTCCCGAGGAGTGGGGTAAATTTAAAAG
130201  CCTTTGTCGACGGACGGACGTAACGTGAAGAGAAGGGCTCCTCACCCCATTTAAATTTTC

130261  TCAAGTTATAGTTTGGATGTTAGTATAGAATTTTGAAATTGGGAATTAAAAATCAGGACT
130261  AGTTCAATATCAAACCTACAATCATATCTTAAAACTTTAACCCTTAATTTTTAGTCCTGA

130321  GGGGACTGGGAGACCAAAAATTTCTGATCCCATTTCTGATGGATGTGTCACACCTTTTCT
130321  CCCCTGACCCTCTGGTTTTTAAAGACTAGGGTAAAGACTACCTACACAGTGTGGAAAAGA

130381  GTCAAAATAAAATGTCTTGGAGGTTATGACTCCTTGGTGAA
130381  CAGTTTTATTTTACAGAACCTCCAATACTGAGGAACCACTT
```

DIAGNOSTIC GENE MARKER PANEL FOR COLORECTAL CANCER

CROSS-REFERENCE TO RELATED APPLICATIONS

This application is a U.S. National Stage application of PCT/AU2013/000481, filed May 10, 2013, which claims priority from U.S. provisional application 61/646,174, filed May 11, 2012.

SEQUENCE LISTING

The instant application contains a Sequence Listing which has been submitted electronically in ASCII format and is hereby incorporated by reference in its entirety. Said ASCII copy, created on Sep. 20, 2017, is named 117215-0102_SL.txt and is 421,502 bytes in size.

FIELD OF THE INVENTION

The present invention relates generally to a method of screening for the onset, predisposition to the onset and/or progression of a neoplasm. More particularly, the present invention relates to a method of screening for the onset, predisposition to the onset and/or progression of a neoplasm by screening for changes to the methylation levels of a panel of gene markers. The method of the present invention is useful in a range of applications including, but not limited to, those relating to the diagnosis and/or monitoring of colorectal neoplasms, such as colorectal adenocarcinosis.

BACKGROUND OF THE INVENTION

Colorectal cancer includes cancerous growths in the colon, rectum and appendix. With 655,000 deaths worldwide per year, it is the fourth most common form of cancer in the United States and the third leading cause of cancer-related death in the Western world. Colorectal cancers arise from adenomatous polyps in the colon. These mushroom-shaped growths are usually benign, but some develop into cancer over time. Localized colon cancer is usually diagnosed through colonoscopy.

Invasive cancers that are confined within the wall of the colon (stages I and II) are curable with surgery. If untreated, they spread to regional lymph nodes (stage III), where up to 73% are curable by surgery and chemotherapy. Cancer that metastasizes to distant sites (stage IV) is usually not curable, although chemotherapy can extend survival, and in rare cases, surgery and chemotherapy together have seen patients through to a cure (Markowitz and Bertagnolli, 2009, *N Engl. J. Med.* 361(25): 2449-60). Radiation is used with rectal cancer.

Colorectal cancer is preceded by adenomas. Adenomas are benign tumours, or neoplasms, of epithelial origin which are derived from glandular tissue or exhibit clearly defined glandular structures. Some adenomas show recognisable tissue elements, such as fibrous tissue (fibroadenomas) and epithelial structure, while others, such as bronchial adenomas, produce active compounds that might give rise to clinical syndromes.

Adenomas may progress to become an invasive neoplasm and are then termed adenocarcinomas. Accordingly, adenocarcinomas are defined as malignant epithelial tumours arising from glandular structures, which are constituent parts of many organs of the body. The term adenocarcinoma is also applied to tumours showing a glandular growth pattern.

These tumours may be sub-classified according to the substances that they produce, for example mucus secreting and serous adenocarcinomas, or to the microscopic arrangement of their cells into patterns, for example papillary and follicular adenocarcinomas. These carcinomas may be solid or cystic (cystadenocarcinomas). Each organ may produce tumours showing a variety of histological types, for example the ovary may produce both mucinous and cystadenocarcinoma.

Adenomas in different organs behave differently. In general, the overall chance of carcinoma being present within an adenoma (i.e. a focus of cancer having developed within a benign lesion) is approximately 5%. However, this is related to size of an adenoma. For instance, in the large bowel (colon and rectum specifically) occurrence of a cancer within an adenoma is rare in adenomas of less than 1 centimetre. Such a development is estimated at 40 to 50% in adenomas which are greater than 4 centimetres and show certain histopathological change such as villous change, or high grade dysplasia. Adenomas with higher degrees of dysplasia have a higher incidence of carcinoma. In any given colorectal adenoma, the predictors of the presence of cancer now or the future occurrence of cancer in the organ include size (especially greater than 9 mm) degree of change from tubular to villous morphology, presence of high grade dysplasia and the morphological change described as “serrated adenoma”. In any given individual, the additional features of increasing age, familial occurrence of colorectal adenoma or cancer, male gender or multiplicity of adenomas, predict a future increased risk for cancer in the organ—so-called risk factors for cancer. Except for the presence of adenomas and its size, none of these is objectively defined and all those other than number and size are subject to observer error and to confusion as to precise definition of the feature in question. Because such factors can be difficult to assess and define, their value as predictors of current or future risk for cancer is imprecise.

Once a sporadic adenoma has developed, the chance of a new adenoma occurring is approximately 30% within 26 months.

The symptoms of colorectal cancer depend on the location of tumor in the bowel, and whether is has metastasised. Unfortunately, many of the symptoms may occur in other diseases as well, and hence symptoms may not be conclusively diagnostic of colorectal cancer.

Local symptoms are more likely if the tumor is located closer to the anus. There may be a change in bowel habit (new-onset constipation or diarrhea in the absence of another cause), a feeling of incomplete defecation and reduction in diameter of stools. Tenesmus and change in stool shape are both characteristic of rectal cancer. Lower gastrointestinal bleeding, including the passage of bright red blood in the stool, may indicate colorectal cancer, as may the increased presence of mucus. Melena, black stool with a tarry appearance, normally occurs in upper gastrointestinal bleeding (such as from a duodenal ulcer), but is sometimes encountered in colorectal cancer when the disease is located in the beginning of the large bowl.

A tumor that is large enough to fill the entire lumen of the bowel may cause bowel obstruction. This situation is characterized by constipation, abdominal pain, abdominal distension and vomiting. This occasionally leads to the obstructed and distended bowel perforating and causing peritonitis.

Certain local effects of colorectal cancer occur when the disease has become more advanced. A large tumor is more likely to be noticed on feeling the abdomen, and it may be noticed by a doctor on physical examination. The disease may invade other organs, and may cause blood or air in the urine or vaginal discharge.

If a tumor has caused chronic occult bleeding, iron deficiency anaemia may occur. This may be experienced as fatigue, palpitations and noticed as pallor. Colorectal cancer may also lead to weight loss, generally due to a decreased appetite.

More unusual constitutional symptoms are an unexplained fever and one of several paraneoplastic syndromes. The most common paraneoplastic syndrome is thrombosis, usually deep vein thrombosis.

Colorectal cancer most commonly spreads to the liver. This may go unnoticed, but large deposits in the liver may cause jaundice and abdominal pain (due to stretching of the capsule). If the tumor deposit obstructs the bile duct, the jaundice may be accompanied by other features of biliary obstruction, such as pale stools.

Colorectal cancer can take many years to develop and early detection of colorectal cancer greatly improves the prognosis. Even modest efforts to implement colorectal cancer screening methods can result in a drop in cancer deaths. Despite this, colorectal cancer screening rates remain low. There are currently several different tests available for this purpose:

- Digital rectal exam: The doctor inserts a lubricated, gloved finger into the rectum to feel for abnormal areas. It only detects tumors large enough to be felt in the distal part of the rectum but is useful as an initial screening test.
- Faecal occult blood test: a test for blood in the stool. Two types of tests can be used for detecting occult blood in stools i.e. guaiac based (chemical test) and immunochemical. The sensitivity of immunochemical testing is superior to that of chemical testing without an unacceptable reduction in specificity (Weitzel J N (December 1999). "Genetic cancer risk assessment. Putting it all together". *Cancer* 86 (11 Suppl): 2483-92).
- Endoscopy:
  - Sigmoidoscopy: A lit probe (sigmoidoscope) is inserted into the rectum and lower colon to check for polyps and other abnormalities.
  - Colonoscopy: A lit probe called a colonoscope is inserted into the rectum and the entire colon to look for polyps and other abnormalities that may be caused by cancer. A colonoscopy has the advantage that if polyps are found during the procedure they can be removed immediately. Tissue can also be taken for biopsy.
- Double contrast barium enema (DCBE): First, an overnight preparation is taken to cleanse the colon. An enema containing barium sulfate is administered, then air is insufflated into the colon, distending it. The result is a thin layer of barium over the inner lining of the colon which is visible on X-ray films. A cancer or a precancerous polyp can be detected this way. This technique can miss the (less common) flat polyp.
- Virtual colonoscopy replaces X-ray films in the double contrast barium enema (above) with a special computed tomography scan and requires special workstation software in order for the radiologist to interpret. This technique is approaching colonoscopy in sensitivity for polyps. However, any polyps found must still be removed by standard colonoscopy.
- Standard computed axial tomography is an x-ray method that can be used to determine the degree of spread of cancer, but is not sensitive enough to use for screening. Some cancers are found in CAT scans performed for other reasons.
- Blood tests: Measurement of the patient's blood for elevated levels of certain proteins can give an indication of tumor load. In particular, high levels of carcinoembryonic antigen (CEA) in the blood can indicate metastasis of adenocarcinoma. While these tests are frequently false positive or false negative, and are not recommended for screening, they can be useful to assess disease recurrence. CA19-9 and CA 242 biomarkers can indicate e-selectin related metastatic risks, help follow therapeutic progress, and assess disease recurrence. Recently, an assay for detection in plasma of methylated sequences of the Septin 9 gene has also become available to assist in diagnosis of colorectal cancer.
- Positron emission tomography (PET) is a 3-dimensional scanning technology where a radioactive sugar is injected into the patient, the sugar collects in tissues with high metabolic activity, and an image is formed by measuring the emission of radiation from the sugar. Because cancer cells often have very high metabolic rates, this can be used to differentiate benign and malignant tumors. PET is not used for screening and does not (yet) have a place in routine workup of colorectal cancer cases.
- Stool DNA testing is an emerging technology in screening for colorectal cancer. Premalignant adenomas and cancers shed DNA markers from their cells which are not degraded during the digestive process and remain stable in the stool. Capture, followed by PCR amplifies the DNA to detectable levels for assay.
- High C-Reactive Protein levels as risk marker Despite the existence of these tests, diagnosis remains problematic. Most of the more sensitive tests are quite invasive and expensive and therefore uptake by patients is low. There is therefore an ongoing need to develop simpler and more informative diagnostic protocols or aids to diagnosis that enable one to direct colonoscopy at people more likely to have developed adenomas or carcinomas. A simple and accurate screening test would enable much more widely applicable screening systems to be set up.

To this end, more recently there have been identified genetic markers which are modulated, in terms of their expression levels, in individuals who have developed a neoplasm of the large intestine. Some of these markers are upregulated in terms of their level of expression, while others are downregulated. However, a feature common to most of these markers, and the use of genetic marker expression levels in general as a diagnostic, is that they often exhibit only moderate levels of sensitivity and specificity. The development of diagnostic protocols which provide high levels of sensitivity and specificity is highly sought after.

In work leading up to the present invention, it has been unexpectedly determined that the gene markers BCAT1, IKZF1 IRF4, GRASP and CAHM, although each individually being one of a number of gene markers known to exhibit utility in terms of diagnosing colorectal neoplasia development, have in fact been determined to collectively enable a significantly higher level of sensitivity or specificity to be achieved than where any one of these gene markers is analysed either alone or together with other unrelated gene markers. More specifically, screening for an increase in the level of methylation of any two or more of these five specific markers can be designed so as to achieve a level of specificity or sensitivity not previously achievable.

Bearing in mind the large number of gene markers which, in differential gene expression analysis studies, have been shown to exhibit modulated expression levels in neoplasia, the identification that five specific markers can in fact collectively provide improved diagnostic outcomes relative either to these markers individually or to other groups of markers is both unexpected and unpredictable.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

The subject specification contains nucleotide sequence information prepared using the programme PatentIn Version 3.5, presented herein after the bibliography. Each nucleotide sequence is identified in the sequence listing by the numeric indicator <210> followed by the sequence identifier (e.g. <210>1, <210>2, etc). The length, type of sequence (DNA, etc) and source organism for each sequence is indicated by information provided in the numeric indicator fields <211>, <212> and <213>, respectively. Nucleotide sequences referred to in the specification are identified by the indicator SEQ ID NO: followed by the sequence identifier (e.g. SEQ ID NO:1, SEQ ID NO:2, etc.). The sequence identifier referred to in the specification correlates to the information provided in numeric indicator field <400> in the sequence listing, which is followed by the sequence identifier (e.g. <400>1, <400>2, etc). That is SEQ ID NO:1 as detailed in the specification correlates to the sequence indicated as <400>1 in the sequence listing.

One aspect of the present invention is directed to a method of screening for the onset or predisposition to the onset of or monitoring a large intestine neoplasm in an individual, said method comprising assessing the methylation status of a DNA region selected from:

(i) the region, including 2 kb upstream of the transcription start site, defined by any two or more of Hg19 coordinates:
  (1) chr12:24962958 . . . 25102393
  (2) chr7:50344378 . . . 50472798
  (3) chr6:391739 . . . 411443;
  (4) chr12:52400748 . . . 52409671; and
  (5) chr6:163834097 . . . 163834982; or
(ii) the gene region, including 2 kb upstream of any two or more of:
  (1) BCAT1 (2) IKZF1 (3) IRF4 (4) GRASP and (5) CAHM in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In another aspect said method is directed to identifying biological samples in which any one of said DNA regions exhibits a higher level of methylation.

In still another aspect said method is directed to identifying biological samples in which two or more of said DNA regions exhibit a higher level of methylation.

In yet another aspect there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:
  (1) chr12:24962958 . . . 25102393; and
  (2) chr7:50344378 . . . 50472798;
  and optionally one or more of (3) chr6:391739 . . . 411443, (4) chr12:52400748 . . . 52409671 and (5) chr6:163834097 . . . 163834982; or
(ii) the gene region, including 2 kb upstream of:
  (1) BCAT1; and
  (2) IKZF1;
  and optionally one or more of (3) IRF4, (4) GRASP and (5) CAHM in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In one embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798; and
  (3) chr6:391739 . . . 411443; or
(ii) the gene region, including 2 kb upstream of:
  (1) BCAT1, (2) IKZF1 and (3) IRF4.

In another embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798 and
  (4) chr12:52400748 . . . 52409671; or
(ii) the gene region, including 2 kb upstream of:
  (1) BCAT1, (2) IKZF1; and (4) GRASP.

In still another embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798 and
  (5) chr6:163834097 . . . 163834982; or
(ii) the gene region, including 2 kb upstream of:
  (1) BCAT1, (2) IKZF1 and (5) CAHM In still yet another embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798
  (3) chr6:391739 . . . 411443; and
  (4) chr12:52400748 . . . 52409671; or
(ii) the gene region, including 2 kb upstream of:
  (1) BCAT1, (2) IKZF1, (3) IRF4 and (4) GRASP.

In yet still another embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798
  (3) chr6:391739 . . . 411443; and
  (5) chr6:163834097 . . . 163834982; or
(ii) the gene region, including 2 kb upstream of:
  (1) BCAT1, (2) IKZF1, (3) IRF4 and (5) CAHM.

In a further embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798
  (4) chr12:52400748 . . . 52409671 and
  (5) chr6:163834097 . . . 163834982; or
(ii) the gene region, including 2 kb upstream of:
  (1) BCAT1, (2) IKZF1, (4) GRASP and (5) CAHM.

In yet another further embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798
  (3) chr6:391739 . . . 411443
  (4) chr12:52400748 . . . 52409671 and
  (5) chr6:163834097 . . . 163834982; or
(ii) the gene region, including 2 kb upstream of:
  (1) BCAT1, (2) IKZF1, (3) IRF4, (4) GRASP and (5) CAHM.

In another embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:
  (1) chr12:24962958 . . . 25102393; and
  (5) chr6:163834097 . . . 163834982;
  and optionally one or more of (2) chr7:50344378 . . . 50472798, (3) chr6:391739 . . . 411443; and (4) chr12:52400748 . . . 52409671; or
(ii) the gene region, including 2 kb upstream of:
  (1) BCAT1; and
  (5) CAHM;
  and optionally one or more of (2) IKZF1, (3) IRF4 and (4) GRASP in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In still another embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:
  (2) chr7:50344378 . . . 50472798; and
  (5) chr6:163834097 . . . 163834982;
  and optionally one or more of (1) chr12:24962958 . . . 25102393, (3) chr6:391739 . . . 411443 and (4) chr12:52400748 . . . 52409671; or
(ii) the gene region, including 2 kb upstream of:
  (2) IKZF1; and
  (5) CAHM;
  and optionally one or more of (1) BCAT1, (3) IRF4 and (4) GRASP in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In a further embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:
  (1) chr12:24962958 . . . 25102393; and
  (3) chr6:391739 . . . 411443;
  and optionally one or more of (2) chr7:50344378 . . . 50472798, (4) chr12:52400748 . . . 52409671 and (5) chr6:163834097 . . . 163834982; or
(ii) the gene region, including 2 kb upstream of:
  (1) BCAT1; and
  (3) IRF4;
  and optionally one or more of (2) IKZF1, (4) GRASP and (5) CAHM in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In yet another further embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:
  (1) chr12:24962958 . . . 25102393; and
  (4) chr12:52400748 . . . 52409671;
  and optionally one or more of (2) chr7:50344378 . . . 50472798, (3) chr6:391739 . . . 411443 and (5) chr6:163834097 . . . 163834982; or
(ii) the gene region, including 2 kb upstream of:
  (1) BCAT1; and
  (4) GRASP;
  and optionally one or more of (2) IKZF1, (3) IRF4 and (5) CAHM in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In still another further embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:
  (2) chr7:50344378 . . . 50472798; and
  (3) chr6:391739 . . . 411443;
  and optionally one or more of (1) chr12:24962958 . . . 25102393, (4) chr12:52400748 . . . 52409671 and (5) chr6:163834097 . . . 163834982; or
(ii) the gene region, including 2 kb upstream of:
  (2) IKZF1; and
  (3) IRF4;

and optionally one or more of (1) BCAT1, (4) GRASP and (5) CAHM in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In yet still another embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:
  (2) chr7:50344378 . . . 50472798; and
  (4) chr12:52400748 . . . 52409671;
  and optionally one or more of (1) chr12:24962958 . . . 25102393, (3) chr6:391739 . . . 411443 and (5) chr6:163834097 . . . 163834982; or
(ii) the gene region, including 2 kb upstream of:
  (2) IKZF1; and
  (4) GRASP;
  and optionally one or more of (1) BCAT1, (3) IRF4 and (5) CAHM in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In still yet another embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:
  (3) chr6:391739 . . . 411443; and
  (4) chr12:52400748 . . . 52409671;
  and optionally one or more of (1) chr12:24962958 . . . 25102393, (2) chr7:50344378 . . . 50472798 and (5) chr6:163834097 . . . 163834982; or
(ii) the gene region, including 2 kb upstream of:
  (3) IRF4; and
  (4) GRASP;
  and optionally one or more of (1) BCAT1, (2) IKZF1 and (5) CAHM in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In another embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:
  (3) chr6:391739 . . . 411443; and
  (5) chr6:163834097 . . . 163834982;
  and optionally one or more of (1) chr12:24962958 . . . 25102393, (2) chr7:50344378 . . . 50472798 and (4) chr12:52400748 . . . 52409671; or
(ii) the gene region, including 2 kb upstream of:
  (3) IRF4; and
  (5) CAHM;
  and optionally one or more of (1) BCAT1, (2) IKZF1 and (4) GRASP in a biological sample from said individual wherein a higher level of methylation of at least one of the DNA regions of group (i) and/or (ii) relative to control levels is indicative of a large intestine neoplasm or a predisposition to the onset of a large intestine neoplastic state.

The subregions which have been determined to exhibit particular utility are listed below with reference to the gene and chromosomal region within which they are found:

(1) BCAT subregions chr12:25101992-25102093 (SEQ ID NO:1 or corresponding minus strand) and chr12:25101909-25101995 (SEQ ID NO:2 or corresponding minus strand)
(2) IKZF1 subregions: chr7:50343867-50343961 (SEQ ID NO:3 or corresponding minus strand) and chr7:50343804-5033895 (SEQ ID NO:4 or corresponding minus strand)
(3) IRF4 subregions chr6:392036-392145 (SEQ ID NO:5 or corresponding minus strand)
(4) GRASP subregions: chr12:52399672-52399922, chr12:52400821-52401051 (SEQ ID NO:6 or corresponding minus strand), chr12:52401407-52401664 (SEQ ID NO:7 or corresponding minus strand) chr12:52400866-52400973 and Chr12:52401107-52401664.
(5) CAHM subregions: chr6:163834295-163834500 (SEQ ID NO:8 or corresponding minus strand), chr6:163834621-163834906, chr6:163834393-163834455 and chr6:163834393-163834519.

To the extent that the method of the present invention includes analysing the methylation of GRASP, the subject residues are:

| | | | |
|---|---|---|---|
| chr12:52399713 | chr12:52399731 | chr12:52399749 | chr12:52399783 |
| chr12:52399796 | chr12:52399808 | chr12:52399823 | chr12:52399835 |
| chr12:52399891 | | | |
| chr12:52400847 | chr12:52400850 | chr12:52400859 | chr12:52400866 |
| chr12:52400869 | chr12:52400873 | chr12:52400881 | chr12:52400886 |
| chr12:52400893 | chr12:52400895 | chr12:52400899 | chr12:52400902 |
| chr12:52400907 | chr12:52400913 | chr12:52400919 | chr12:52400932 |
| chr12:52400938 | chr12:52400958 | chr12:52400962 | chr12:52400971 |
| chr12:52400973 | chr12:52400976 | chr12:52400998 | chr12:52401008 |
| chr12:52401010 | chr12:52401012 | chr12:52401016 | chr12:52401019 |
| chr12:52401025 | chr12:52401041 | chr12:52401044 | chr12:52401053 |
| chr12:52401060 | chr12:52401064 | chr12:52401092 | chr12:52401118 |
| chr12:52401438 | chr12:52401448 | chr12:52401460 | chr12:52401465 |
| chr12:52401474 | chr12:52401477 | chr12:52401479 | chr12:52401483 |
| chr12:52401504 | chr12:52401514 | chr12:52401523 | chr12:52401540 |
| chr12:52401553 | chr12:52401576 | chr12:52401588 | chr12:52401595 |
| chr12:52401599 | chr12:52401604 | chr12:52401606 | chr12:52401634 |
| chr12:52401640 | chr12:52401644 | chr12:52401659 | |
| chr12:52401160 | chr12:52401165 | chr12:52401174 | chr12:52401177 |

-continued

| | | | |
|---|---|---|---|
| chr12:52401179 | chr12:52401183 | chr12:52401204 | chr12:52401215 |
| chr12:52401223 | chr12:52401240 | chr12:52401253 | chr12:52401288 |
| chr12:52401295 | chr12:52401299 | chr12:52401304 | chr12:52401334 |
| chr12:52401340 | chr12:52401344 | chr12:52401359 | |

or a corresponding cytosine at position n+1 on the opposite DNA strand.

To the extent that the method of the present invention includes analysing CAHM, the subject residues are:

| | | |
|---|---|---|
| chr6:163834330 | chr6:163834332 | chr6:163834357 |
| chr6:163834373 | chr6:163834384 | chr6:163834390 |
| chr6:163834392 | chr6:163834406 | chr6:163834412 |
| chr6:163834419 | chr6:163834443 | chr6:163834448 |
| chr6:163834452 | chr6:163834464 | chr6:163834483 |
| chr6:163834653 | chr6:163834660 | chr6:163834672 |
| chr6:163834675 | chr6:163834678 | chr6:163834681 |
| chr6:163834815 | chr6:163834824 | chr6:163834835 |
| chr6:163834840 | chr6:163834853 | chr6:163834855 |
| chr6:163834858 | chr6:163834863 | chr6:163834869 |
| chr6:163834872 | | |

or a corresponding cytosine at position n+1 on the opposite DNA strand.

To the extent that the method of the present invention includes analysing IKZF1, the subject residues are:

| | | |
|---|---|---|
| chr7:50343869 | chr7:50343872 | chr7:50343883 |
| chr7:50343889 | chr7:50343890 | chr7:50343897 |
| chr7:50343907 | chr7:50343909 | chr7:50343914 |
| chr7:50343934 | chr7:50343939 | chr7:50343950 |
| chr7:50343959 | chr7:50343805 | chr7:50343822 |
| chr7:50343824 | chr7:50343826 | chr7:50343829 |
| chr7:50343831 | chr7:50343833 | chr7:50343838 |
| chr7:50343847 | chr7:50343850 | chr7:50343858 |
| chr7:50343864 | chr7:50343869 | chr7:50343872 |
| chr7:50343890 | | |

or a corresponding cytosine at position n+1 on the opposite DNA strand.

To the extent that the method of the present invention includes analysing IRF4, the subject residues are:

| | | |
|---|---|---|
| chr6:392036 | chr6:392047 | chr6:392049 |
| chr6:392057 | chr6:392060 | chr6:392066 |
| chr6:392080 | chr6:392094 | chr6:392102 |
| chr6:392131 | | |

or a corresponding cytosine at position n+1 on the opposite DNA strand.

Another aspect of the present invention is directed to a method of screening for the onset or predisposition to the onset of or monitoring a large intestine neoplasm in an individual, said method comprising assessing the level of expression of a DNA region selected from:

(i) the region, including 2 kb upstream of the transcription start site, defined by any two or more of Hg19 coordinates:

(1) chr12:24962958 . . . 25102393

(2) chr7:50344378 . . . 50472798

(3) chr6:391739 . . . 411443; or (4) chr12:52400748 . . . 52409671; and (5) chr6:163834097 . . . 163834982; or (ii) the gene region, including 2 kb upstream of any two or more of:

(1) BCAT1 (2) IKZF1 (3) IRF4 (4) GRASP and (5) CAHM in a biological sample from said individual wherein a lower level of expression of at least one of the DNA regions of group (i) and/or (ii) relative to control levels is indicative of a large intestine neoplasm or a predisposition to the onset of a neoplastic state.

BRIEF DESCRIPTION OF THE DRAWINGS

FIG. 1 depicts the genomic sequence of GRASP as defined by the Hg19 coordinates chr12:52398748-52409671, which has the forward strand sequence of SEQ ID NO: 89. The coding strand for GRASP resides on the forward (plus) strand, corresponding to the top strand (5'-3') of the double stranded sequence depicted in FIG. 1. Examples of GRASP sub-regions that can be used in bisulfite conversion and methylation specific assays are marked in bold and italicized font with a dashed underline. An example of a GRASP sub-region of interest generated by HHaI/HBaII digestion of genomic DNA is marked in bold font with a thick underline.

FIG. 2 depicts the genomic sequence of CAHM as defined by Hg19 coordinates chr6:163834097-163836982, which has the forward strand sequence of SEQ ID NO: 90. The coding strand for CAHM resides on the reverse (minus) strand, corresponding to the bottom strand (3'-5') of the double stranded sequence depicted in FIG. 2. Examples of CAHM sub-regions that can be used in the bisulfite conversion and methylation specific assay are marked in FIG. 2 in bold and italicized font with a dashed underline. Note this is also an example on assays running on opposite strands.

FIG. 3 depicts the genomic sequence of IRF4 as defined by Hg19 coordinates chr6:389739-411443, which has the forward strand sequence of SEQ ID NO: 91. The coding strand for IRF4 resides on the forward (plus) strand, corresponding to the top strand (5'-3') of the double stranded sequence depicted in FIG. 3. An example of an IRF4 sub-region that can be used in the bisulfite conversion and methylation specific assay is marked in FIG. 3 in bold and italicized font with a dashed underline.

FIG. 4 depicts the genomic sequence of BCAT1 as defined by Hg19 coordinates chr12:24962958-25102393, which has the forward strand sequence of SEQ ID NO: 92. The coding strand for BCAT1 resides on the reverse (minus) strand, corresponding to the bottom strand (3'-5') of the sequence depicted in FIG. 4. An example of a BCAT1 sub-region that can be used in the bisulfite conversion and methylation specific assay is marked in FIG. 4 in bold and italicized font with a dashed underline. An example of a BCAT1 sub-region of interest generated by HHaI/HBaII digestion of genomic DNA is marked in FIG. 4 in bold font with a thick underline. A BCAT1 sub-region that can be used in the bisulfite conversion and methylation specific assay that is generated by HHaI/HBaII digestion of genomic DNA is marked in FIG. 4 in bold and italicized font with a squiggly underline.

FIG. 5 depicts the genomic sequence of IKZF1 as defined by the Hg19 coordinates chr7:50342378-50472798, which has the forward strand sequence of SEQ ID NO: 93. The coding strand for IKZF1 resides on the forward (plus) strand, corresponding to the top strand (5'-3') of the double stranded sequence depicted in FIG. 5. Examples of IKZF1 sub-regions that can be used in the bisulfite conversion and methylation specific assay are marked in FIG. 5 in bold and italicized font with a dashed underline.

DETAILED DESCRIPTION OF THE INVENTION

The present invention is predicated, in part, on the determination that the change in methylation pattern of a panel of gene markers can provide a higher level of either diagnostic specificity or diagnostic sensitivity when tested collectively than if any one of these markers is tested either in isolation or together with markers other than those specified herein. This finding has therefore now facilitated the development of an improved test for diagnosing, prognosing or monitoring neoplasms of the large intestine based on assessing the methylation of two or more of the gene markers BCAT1, IKZF1, CAHM, GRASP and IRF4.

In accordance with the present invention, it has been determined that certain specific panels of genes are modulated, in terms of differential changes to their levels of methylation, depending on whether or not the cell in issue is neoplastic or not. It should be understood that the genes in issue are described herein both by reference to their name and their chromosomal coordinates. The chromosomal coordinates are consistent with the human genome database version Hg19 which was released in February 2009 (herein referred to as "Hg19 coordinates").

Accordingly, one aspect of the present invention is directed to a method of screening for the onset or predisposition to the onset of or monitoring a large intestine neoplasm in an individual, said method comprising assessing the methylation status of a DNA region selected from:

(i) the region, including 2 kb upstream of the transcription start site, defined by any two or more of Hg19 coordinates:
  (1) chr12:24962958 . . . 25102393
  (2) chr7:50344378 . . . 50472798
  (3) chr6:391739 . . . 411443;
  (4) chr12:52400748 . . . 52409671; and
  (5) chr6:163834097 . . . 163834982; or
(ii) the gene region, including 2 kb upstream of any two or more of:
  (1) BCAT1 (2) IKZF1 (3) IRF4 (4) GRASP and (5) CAHM in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In one embodiment, said method is directed to identifying biological samples in which any one of said DNA regions exhibits a higher level of methylation.

In another embodiment, said method is directed to identifying biological samples in which two or more of said DNA regions exhibit a higher level of methylation.

Without limiting the present invention to any one theory or mode of action, the panel of DNA regions (markers) specified herein provide not only an improved diagnostic outcome relative to prior art methods but, in addition, enable the development of a screening method which can be designed to focus on providing either a high level of diagnostic specificity or a high level of diagnostic sensitivity. As would be understood by the person of skill in the art, in the context of diagnostics "sensitivity" defines the proportion of positive results which are correctly identified, that is, the percentage of individuals correctly identified as having the disease in issue. "Specificity", however, defines the proportion of negative results which are correctly identified, that is, the percentage of individuals correctly identified as not having the disease in issue.

In the context of the present invention it has been determined that screening a patient sample for the methylation status of the specified panel of markers can be designed to provide either a diagnostic result which exhibits a high level of specificity or a diagnostic result which exhibits a high level of sensitivity.

Where a high level of sensitivity is sought, the screening method is designed to identify samples in which any one of the markers of the panel exhibits increased methylation relative to control levels. That is, not all of the markers are required to exhibit hypermethylation in order to define the result as positive. Where a higher level of sensitivity is sought, the level of specificity is inherently reduced. However, if it is desired to pursue a higher level of specificity (which may reduce the level of sensitivity) then the method is designed to identify samples in which two or more of the panel of DNA regions exhibit increased methylation.

Accordingly, to the extent that the present invention is directed to embodiments of the method in which "any one of" the DNA regions (markers) of the specified panel exhibits a higher level of methylation, these embodiments are designed to achieve results exhibiting increased sensitivity based on any one of the markers in the panel being hypermethylated. It should be understood that it need not be the same marker which is hypermethylated in each sample. Rather, it is simply that one of the markers which forms part of the panel is hypermethylated. It should also be understood that in relation to some samples, two or more of the markers of the panel may be hypermethylated. These samples should be understood to nevertheless fall within the scope of this embodiment of the invention since this embodiment is not excluding the situation where multiple markers are hypermethylated but is merely including within its scope all those samples where as few as one marker are hypermethylated. Overall these data will provide increased sensitivity but reduced specificity.

To the extent that the present invention is directed to embodiments of the method in which "two or more" of the DNA regions (markers) of the specified panel exhibit a higher level of methylation, these embodiments are designed to achieve a higher level of specificity. This is achieved by virtue of the fact that at least two, if not more, of the specified panel of markers are determined to be hypermethylated.

Reference to "large intestine" should be understood as a reference to a cell derived from one of the eight anatomical regions of the large intestine, which regions commence after the terminal region of the ileum, these being:

(i) the cecum;
(ii) the ascending colon;
(iii) the transverse colon;
(iv) the descending colon;
(v) the sigmoid colon;
(vi) the rectum;
(vii) the splenic flexure; and
(viii) the hepatic flexure.

Reference to "neoplasm" should be understood as a reference to a lesion, tumour or other encapsulated or unencapsulated mass or other form of growth which comprises neoplastic cells. A "neoplastic cell" should be understood as a reference to a cell exhibiting abnormal growth. The term "growth" should be understood in its broadest sense and includes reference to proliferation. In this regard, an example of abnormal cell growth is the uncontrolled proliferation of a cell. Another example is failed apoptosis in a cell, thus prolonging its usual life span. The neoplastic cell may be a benign cell or a malignant cell. In a preferred embodiment, the subject neoplasm is an adenoma or an adenocarcinoma. Without limiting the present invention to any one theory or mode of action, an adenoma is generally a benign tumour of epithelial origin which is either derived from epithelial tissue or exhibits clearly defined epithelial structures. These structures may take on a glandular appearance. It can comprise a malignant cell population within the adenoma, such as occurs with the progression of a benign adenoma or benign neoplastic legion to a malignant adenocarcinoma.

Preferably, said neoplastic cell is an adenoma or adenocarcinoma and even more preferably a colorectal adenoma or adenocarcinoma.

Reference to "DNA region" should be understood as a reference to a specific section of genomic DNA. These DNA regions are specified either by reference to a gene name or a set of chromosomal coordinates. Both the gene names and the chromosomal coordinates would be well known to, and understood by, the person of skill in the art. As detailed hereinbefore, the chromosomal coordinates correspond to the Hg19 version of the genome. In general, a gene can be routinely identified by reference to its name, via which both its sequences and chromosomal location can be routinely obtained, or by reference to its chromosomal coordinates, via which both the gene name and its sequence can also be routinely obtained.

Reference to each of the genes/DNA regions detailed above should be understood as a reference to all forms of these molecules and to fragments or variants thereof. As would be appreciated by the person of skill in the art, some genes are known to exhibit allelic variation between individuals or single nucleotide polymorphisms. SNPs encompass insertions and deletions of varying size and simple sequence repeats, such as dinucleotide and trinucleotide repeats. Variants include nucleic acid sequences from the same region sharing at least 90%, 95%, 98%, 99% sequence identity i.e. having one or more deletions, additions, substitutions, inverted sequences etc. relative to the DNA regions described herein. Accordingly, the present invention should be understood to extend to such variants which, in terms of the present diagnostic applications, achieve the same outcome despite the fact that minor genetic variations between the actual nucleic acid sequences may exist between individuals. The present invention should therefore be understood to extend to all forms of DNA which arise from any other mutation, polymorphic or allelic variation.

It should be understood that the "individual" who is the subject of testing may be any human or non-human mammal. Examples of non-human mammals includes primates, livestock animals (e.g. horses, cattle, sheep, pigs, donkeys), laboratory test animals (e.g. mice, rats, rabbits, guinea pigs), companion animals (e.g. dogs, cats) and captive wild animals (e.g. deer, foxes).

Preferably the mammal is a human.

The panel of genes which has been identified demonstrates increased methylation in large intestine neoplastic cells relative to corresponding non-neoplastic cells. This increased methylation is, in some cases, localised to a few specific CpG sites within the DNA region while in other cases it is observed across a wide range of CpG sites.

However, although specific regions from all genes exhibit increased methylation and are therefore useful diagnostic markers, it is the analysis of these specific markers as a panel which has provided an independent and very significant improvement over the sensitivity and specificity could be obtainable over these markers are analysed individually. This improvement is also significant even when considered against the sensitivity and specificity obtainable using other markers known to exhibit increased methylation as a marker of the onset of a large intestine neoplasm. Accordingly, the method of the present invention has now provided a means of achieving a higher level of sensitivity and specificity than has been achievable to date.

In one aspect there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:
  (1) chr12:24962958 . . . 25102393; and
  (2) chr7:50344378 . . . 50472798;
  and optionally one or more of (3) chr6:391739 . . . 411443, (4) chr12:52400748 . . . 52409671 and (5) chr6:163834097 . . . 163834982; or
(ii) the gene region, including 2 kb upstream of:
  (1) BCAT1; and
  (2) IKZF1;

and optionally one or more of (3) IRF4, (4) GRASP and (5) CAHM in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In one embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798; and
  (3) chr6:391739 . . . 411443; or
(ii) the gene region, including 2 kb upstream of:
  (1) BCAT1, (2) IKZF1 and (3) IRF4.

In another embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798 and
  (4) chr12:52400748 . . . 52409671; or
(ii) the gene region, including 2 kb upstream of:
  (1) BCAT1, (2) IKZF1; and (4) GRASP.

In still another embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798 and
  (5) chr6:163834097 . . . 163834982; or
(ii) the gene region, including 2 kb upstream of:
  (1) BCAT1, (2) IKZF1 and (5) CAHM In still yet another embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798
  (3) chr6:391739 . . . 411443; and (4) chr12:52400748 . . . 52409671; or (ii) the gene region, including 2 kb upstream of:

(1) BCAT1, (2) IKZF1, (3) IRF4 and (4) GRASP.

In yet still another embodiment of this aspect, the gene marker panel which is screened for is:

(i) the DNA regions, including 2 kb upstream of the transcription start site, defined by Hg19 coordinates:

(1) chr12:24962958 . . . 25102393

(2) chr7:50344378 . . . 50472798

(3) chr6:391739 . . . 411443; and (5) chr6:163834097 . . . 163834982; or (ii) the gene region, including 2 kb upstream of:

(1) BCAT1, (2) IKZF1, (3) IRF4 and (5) CAHM.

In a further embodiment of this aspect, the gene marker panel which is screened for is:

(i) the DNA regions, including 2 kb upstream of the transcription start site, defined by Hg19 coordinates:

(1) chr12:24962958 . . . 25102393

(2) chr7:50344378 . . . 50472798

(4) chr12:52400748 . . . 52409671 and (5) chr6:163834097 . . . 163834982; or (ii) the gene region, including 2 kb upstream of:

(1) BCAT1, (2) IKZF1, (4) GRASP and (5) CAHM.

In yet another further embodiment of this aspect, the gene marker panel which is screened for is:

(i) the DNA regions, including 2 kb upstream of the transcription start site, defined by Hg19 coordinates:

(1) chr12:24962958 . . . 25102393

(2) chr7:50344378 . . . 50472798

(3) chr6:391739 . . . 411443

(4) chr12:52400748 . . . 52409671 and (5) chr6:163834097 . . . 163834982; or (ii) the gene region, including 2 kb upstream of:

(1) BCAT1, (2) IKZF1, (3) IRF4, (4) GRASP and (5) CAHM.

In another embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:

(1) chr12:24962958 . . . 25102393; and (5) chr6:163834097 . . . 163834982;

and optionally one or more of (2) chr7:50344378 . . . 50472798, (3) chr6:391739 . . . 411443; and (4) chr12:52400748 . . . 52409671; or (ii) the gene region, including 2 kb upstream of:

(1) BCAT1; and (5) CAHM;

and optionally one or more of (2) IKZF1, (3) IRF4 and (4) GRASP in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In still another embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:

(2) chr7:50344378 . . . 50472798; and (5) chr6:163834097 . . . 163834982;

and optionally one or more of (1) chr12:24962958 . . . 25102393, (3) chr6:391739 . . . 411443 and (4) chr12:52400748 . . . 52409671; or (ii) the gene region, including 2 kb upstream of:

(2) IKZF1; and (5) CAHM;

and optionally one or more of (1) BCAT1, (3) IRF4 and (4) GRASP in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In a further embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:

(1) chr12:24962958 . . . 25102393; and (3) chr6:391739 . . . 411443;

and optionally one or more of (2) chr7:50344378 . . . 50472798, (4) chr12:52400748 . . . 52409671 and (5) chr6:163834097 . . . 163834982; or (ii) the gene region, including 2 kb upstream of:

(1) BCAT1; and (3) IRF4;

and optionally one or more of (2) IKZF1, (4) GRASP and (5) CAHM in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In yet another further embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:

(1) chr12:24962958 . . . 25102393; and (4) chr12:52400748 . . . 52409671;

and optionally one or more of (2) chr7:50344378 . . . 50472798, (3) chr6:391739 . . . 411443 and (5) chr6:163834097 . . . 163834982; or (ii) the gene region, including 2 kb upstream of:

(1) BCAT1; and (4) GRASP;

and optionally one or more of (2) IKZF1, (3) IRF4 and (5) CAHM in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In still another further embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:

(2) chr7:50344378 . . . 50472798; and (3) chr6:391739 . . . 411443;

and optionally one or more of (1) chr12:24962958 . . . 25102393, (4) chr12:52400748 . . . 52409671 and (5) chr6:163834097 . . . 163834982; or (ii) the gene region, including 2 kb upstream of:

(2) IKZF1; and (3) IRF4;

and optionally one or more of (1) BCAT1, (4) GRASP and (5) CAHM in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In yet still another embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:
  (2) chr7:50344378 . . . 50472798; and
  (4) chr12:52400748 . . . 52409671;
  and optionally one or more of (1) chr12:24962958 . . . 25102393, (3) chr6:391739 . . . 411443 and (5) chr6:163834097 . . . 163834982; or
(ii) the gene region, including 2 kb upstream of:
  (2) IKZF1; and
  (4) GRASP;
  and optionally one or more of (1) BCAT1, (3) IRF4 and (5) CAHM in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In still yet another embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:
  (3) chr6:391739 . . . 411443; and
  (4) chr12:52400748 . . . 52409671;
  and optionally one or more of (1) chr12:24962958 . . . 25102393, (2) chr7:50344378 . . . 50472798 and (5) chr6:163834097 . . . 163834982; or
(ii) the gene region, including 2 kb upstream of:
  (3) IRF4; and
  (4) GRASP;
  and optionally one or more of (1) BCAT1, (2) IKZF1 and (5) CAHM in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In another embodiment there is provided a method of screening for the onset or predisposition to the onset of or monitoring a large intestine neoplasm in an individual, said method comprising assessing the methylation status of:

(i) the DNA regions, including 2 kb upstream of the transcription start site, defined by Hg19 coordinates:
  (3) chr6:391739 . . . 411443; and
  (5) chr6:163834097 . . . 163834982;
  and optionally one or more of (1) chr12:24962958 . . . 25102393, (2) chr7:50344378 . . . 50472798 and (4) chr12:52400748 . . . 52409671; or
(ii) the gene region, including 2 kb upstream of:
  (3) IRF4; and
  (5) CAHM;
  and optionally one or more of (1) BCAT1, (2) IKZF1 and (4) GRASP in a biological sample from said individual wherein a higher level of methylation of at least one of the DNA regions of group (i) and/or (ii) relative to control levels is indicative of a large intestine neoplasm or a predisposition to the onset of a large intestine neoplastic state.

In accordance with these aspects and embodiments, in yet another embodiment said control level is a non-neoplastic level.

In one embodiment, said method is directed to identifying biological samples in which any one of said DNA regions exhibits a higher level of methylation.

In another embodiment, said method is directed to identifying biological samples in which two or more of said DNA regions exhibits a higher level of methylation.

Still further, in another embodiment, said large intestine tissue is preferably colorectal tissue.

In still another embodiment, the neoplasm is malignant, such as a carcinoma.

In a further embodiment, the neoplasm is non-malignant, such as an adenoma.

In terms of screening for the methylation of these gene regions, it should be understood that the assays can be designed to screen either the specific regions listed herein (which correspond to the "plus" strand of the gene) or the complementary "minus" strand. It is well within the skill of the person in the art to choose which strand to analyse and to target that strand based on the chromosomal coordinates provided herein. In some circumstances, assays may be established to screen both strands.

It should be understood that one may screen for the specified panel of markers exclusively or one may elect to additionally screen for other markers, such as other DNA hypermethylation markers, other RNA expression level markers or other protein markers. These other markers may, for example, provide additional information in relation to the health status of the patient in issue.

Without limiting the present invention to any one theory or mode of action, although measuring the methylation levels across these DNA regions is diagnostic of a large intestine neoplastic condition, it has been determined that discrete subregions are particularly useful in this regard since these subregions contain a high density of CpG dinucleotides which are frequently hypermethylated in large intestine neoplasias, such as colorectal cancers. This finding renders these subregions a particularly useful target for analysis since it both simplifies the screening process due to a shorter more clearly defined region of DNA requiring analysis and, further, the fact that the results from these regions will provide a significantly more definitive result in relation to the presence, or not, of hypermethylation than would be obtained if analysis was performed across the DNA region as a whole. This finding therefore both simplifies the screening process and increases the sensitivity and specificity of large intestine neoplasia diagnosis.

The subregions which have been determined to exhibit particular utility are listed below with reference to the gene and chromosomal region within which they are found:

(1) BCAT subregions chr12:25101992-25102093 (SEQ ID NO:1 or corresponding minus strand) and chr12:25101909-25101995 (SEQ ID NO:2 or corresponding minus strand)
(2) IKZF1 subregions: chr7:50343867-50343961 (SEQ ID NO:3 or corresponding minus strand) and chr7:50343804-5033895 (SEQ ID NO:4 or corresponding minus strand)
(3) IRF4 subregions chr6:392036-392145 (SEQ ID NO:5 or corresponding minus strand)

(4) GRASP subregions: chr12:52399672-52399922, chr12:52400821-52401051 (SEQ ID NO:6 or corresponding minus strand), chr12:52401407-52401664 (SEQ ID NO:7 or corresponding minus strand) chr12:52400866-52400973 and Chr12:52401107-52401664.

(5) CAHM subregions: chr6:163834295-163834500 (SEQ ID NO:8), chr6:163834621-163834906, chr6:163834393-163834455 and chr6:163834393-163834519.

Without limiting the present invention to any one theory or mode of action, the skilled person may screen one or more subregions for each gene marker.

In one embodiment, the methylation marker subregions tested for each selected gene marker are:

(1) The BCAT subregion defined by SEQ ID NO:1 or SEQ ID NO:2 or corresponding minus strand;

(2) The IKZF1 subregion defined by SEQ ID NO:3 or SEQ ID NO:4 or corresponding minus strand;

(3) The IRF4 subregion defined by SEQ ID NO:5 or corresponding minus strand;

(4) The GRASP subregion defined by SEQ ID NO:6 or 7 or corresponding minus strands; and (5) The CAHM subregion defined by SEQ ID NO:8 or corresponding minus strand.

Without limiting the present invention to any one theory or mode of action, DNA methylation is universal in bacteria, plants, and animals. DNA methylation is a type of chemical modification of DNA that is stable over rounds of cell division but does not involve changes in the underlying DNA sequence of the organism. Chromatin and DNA modifications are two important features of epigenetics and play a role in the process of cellular differentiation, allowing cells to stably maintain different characteristics despite containing the same genomic material. In eukaryotic organisms DNA methylation occurs only at the number 5 carbon of the cytosine pyrimidine ring. In mammals, DNA methylation occurs mostly at the number 5 carbon of the cytosine of a CpG dinucleotide. CpG dinucleotides comprise approximately 1% human genome.

70-80% of all CpGs are methylated. CpGs may be grouped in clusters called "CpG islands" that are present in the 5' regulatory regions of many genes and are frequently unmethylated. In many disease processes such as cancer, gene promoters and/or CpG islands acquire abnormal hypermethylation, which is associated with heritable transcriptional silencing. DNA methylation may impact the transcription of genes in two ways. First, the methylation of DNA may itself physically impede the binding of transcriptional proteins to the gene, thus blocking transcription. Second, methylated DNA may be bound by proteins known as Methyl-CpG-binding domain proteins (MBDs). MBD proteins then recruit additional proteins to the locus, such as histone deacetylases and other chromatin remodelling proteins that can modify histones, thereby forming compact, inactive chromatin termed silent chromatin. This link between DNA methylation and chromatin structure is very important. In particular, loss of Methyl-CpG-binding Protein 2 (MeCP2) has been implicated in Rett syndrome and Methyl-CpG binding domain protein 2 (MBD2) mediates the transcriptional silencing of hypermethylated genes in cancer.

In humans, the process of DNA methylation is carried out by three enzymes, DNA methyltransferase 1, 3a and 3b (DNMT1, DNMT3a, DNMT3b). It is thought that DNMT3a and DNMT3b are the de novo methyltransferases that set up DNA methylation patterns early in development. DNMT1 is the proposed maintenance methyltransferase that is responsible for copying DNA methylation patterns to the daughter strands during DNA replication. DNMT3L is a protein that is homologous to the other DNMT3s but has no catalytic activity. Instead, DNMT3L assists the de novo methyltransferases by increasing their ability to bind to DNA and stimulating their activity. Finally, DNMT2 has been identified as an "enigmatic" DNA methylstransferase homolog, containing all 10 sequence motifs common to all DNA methyltransferases; however, DNMT2 may not methylate DNA but instead has been shown to methylate a small RNA.

"Methylation status" should therefore be understood as a reference to the presence, absence and/or quantity of methylation at a particular nucleotide, or nucleotides, within a DNA region. The methylation status of a particular DNA sequence (e.g. DNA region as described herein) can indicate the methylation state of every base in the sequence or can indicate the methylation state of a subset of the base pairs (e.g., of cytosines or the methylation state of one or more specific restriction enzyme recognition sequences) within the sequence, or can indicate information regarding regional methylation density within the sequence without providing precise information of where in the sequence the methylation occurs. The methylation status can optionally be represented or indicated by a "methylation value." A methylation value can be generated, for example, by quantifying the amount of intact DNA present following restriction digestion with a methylation dependent restriction enzyme. In this example, if a particular sequence in the DNA is quantified using quantitative PCR, an amount of template DNA approximately equal to a mock treated control indicates the sequence is not highly methylated whereas an amount of template substantially less than occurs in the mock treated sample indicates the presence of methylated DNA at the sequence. Accordingly, a value, i.e., a methylation value, for example from the above described example, represents the methylation status and can thus be used as a quantitative indicator of the methylation status. This is of particular use when it is desirable to compare the methylation status of a sequence in a sample to a threshold value.

The method of the present invention is predicated on the comparison of the level of methylation of specific DNA regions of a biological sample with the control methylation levels of these DNA regions. The "control level" is the "normal level", which is the level of methylation of the DNA region of a corresponding large intestine cell or cellular population which is not neoplastic or in another biological sample from which DNA may be isolated for assay.

The normal (or "non-neoplastic") methylation level may be determined using non-neoplastic tissues derived from the same individual who is the subject of testing. However, it would be appreciated that this may be quite invasive for the individual concerned and it is therefore likely to be more convenient to analyse the test results relative to a standard result which reflects individual or collective results obtained from individuals other than the patient in issue. This latter form of analysis is in fact the preferred method of analysis since it enables the design of kits which require the collection and analysis of a single biological sample, being a test sample of interest. The standard results which provide the normal methylation level may be calculated by any suitable means which would be well known to the person of skill in the art. For example, a population of normal tissues can be assessed in terms of the level of methylation of the genes of the present invention, thereby providing a standard value or range of values against which all future test samples are analysed. It should also be understood that the normal level may be determined from the subjects of a specific cohort and for use with respect to test samples derived from that cohort. Accordingly, there may be determined a number of standard values or ranges which correspond to cohorts which differ in respect of characteristics such as age, gender, ethnicity or health status. Said "normal level" may be a discrete level or a range of levels. An increase in the methylation level of the subject genes relative to normal levels is indicative of the tissue being neoplastic.

The term "methylation" shall be taken to mean the presence of a methyl group added by the action of a DNA methyl transferase enzyme to a cytosine base or bases in a region of nucleic acid, e.g. genomic DNA. As described herein, there are several methods known to those skilled in the art for determining the level or degree of methylation of nucleic acid.

By "higher level" is meant that there are a higher number of methylated CpG dinucleotides in the subject diagnosed than in a control sample, that is, either the proportion of DNA molecules methylated at a particular CpG site is higher or there are a higher number of separate CpG sites methylated in the subject. It should be understood that the terms "enhanced" and "increased" are used interchangeably with the term "higher".

In relation to detecting a "higher level" of methylation, it should be understood that in some situations the normal/control level will in fact correspond to the absence of any detectable methylation while the neoplastic level will correspond to the presence of methylation, per se. In this situation the diagnostic method is relatively simple since one need only screen for the mere presence of methylation (i.e. a qualitative assessment only), rather than assessing the methylation levels relative to a control level of methylation, which analysis necessarily involves a measure of quantification. Without limiting the present invention in any way, it is observed in blood-derived samples, for example, that in the context of some markers the change in methylation of that marker upon the onset of neoplasia is a shift from undetectable levels of methylation to the presence of detectable methylation. In these situations a relatively simple qualitative assessment is enabled where one need only screen a test sample to determine the presence or not of methylation. In the context of the definitions provided herein, reference to "higher level" encompasses both a relative increase in the level of methylation of a marker or the onset of methylation where previously none was evident. As detailed hereinbefore, the control level may be newly assessed for each patient or there may be a standard result against which all test samples are assessed. Where it is known that methylation is not present on the marker of interest, one need only screen for the presence or not of methylation since the control level is the absence of methylation and the "higher level" is thereby the presence of any amount of methylation.

The present invention is not to be limited by a precise number of methylated residues that are considered to be diagnostic of neoplasia in a subject, because some variation between patient samples will occur. The present invention is also not limited by positioning of the methylated residue.

Nevertheless, a number of specific cytosine residues which undergo hypermethylation within these subregions have also been identified. In another embodiment, therefore, a screening method can be employed which is specifically directed to assessing the methylation status of one or more of either these residues or the corresponding cytosine at position n+1 on the opposite DNA strand.

To this end, detailed in Table 1 are the cytosine residues which have been identified in this regard. It should be appreciated by the person of skill in the art that these individual residues are numbered by reference to Hg19, which also corresponds to the numbering of the specific subregions listed hereinbefore and which can be further identified when the coordinate numbering for each subregion is applied to the corresponding subregion sequences which are provided in the sequence listing. It should be understood that these residues have been identified in the context of the subregion DNA. However, there are other residues which are hypermethylated outside the subregions themselves but within the larger DNA region from which the subregions derive. Accordingly, these specified residues represent a particularly useful subset of individual cytosine residues which undergo hypermethylation within the context of the DNA regions and subregions herein disclosed. These individual residues are grouped below according to the DNA region within which they occur. These DNA regions are identified by reference to both the Hg19 chromosomal coordinates and the gene region name.

To the extent that the method of the present invention includes analysing the methylation of GRASP, the subject residues are:

| | | | |
|---|---|---|---|
| chr12:52399713 | chr12:52399731 | chr12:52399749 | chr12:52399783 |
| chr12:52399796 | chr12:52399808 | chr12:52399823 | chr12:52399835 |
| chr12:52399891 | | | |
| chr12:52400847 | chr12:52400850 | chr12:52400859 | chr12:52400866 |
| chr12:52400869 | chr12:52400873 | chr12:52400881 | chr12:52400886 |
| chr12:52400893 | chr12:52400895 | chr12:52400899 | chr12:52400902 |
| chr12:52400907 | chr12:52400913 | chr12:52400919 | chr12:52400932 |
| chr12:52400938 | chr12:52400958 | chr12:52400962 | chr12:52400971 |
| chr12:52400973 | chr12:52400976 | chr12:52400998 | chr12:52401008 |
| chr12:52401010 | chr12:52401012 | chr12:52401016 | chr12:52401019 |
| chr12:52401025 | chr12:52401041 | chr12:52401044 | chr12:52401053 |
| chr12:52401060 | chr12:52401064 | chr12:52401092 | chr12:52401118 |
| chr12:52401438 | chr12:52401448 | chr12:52401460 | chr12:52401465 |
| chr12:52401474 | chr12:52401477 | chr12:52401479 | chr12:52401483 |
| chr12:52401504 | chr12:52401514 | chr12:52401523 | chr12:52401540 |
| chr12:52401553 | chr12:52401576 | chr12:52401588 | chr12:52401595 |
| chr12:52401599 | chr12:52401604 | chr12:52401606 | chr12:52401634 |
| chr12:52401640 | chr12:52401644 | chr12:52401659 | |
| chr12:52401160 | chr12:52401165 | chr12:52401174 | chr12:52401177 |
| chr12:52401179 | chr12:52401183 | chr12:52401204 | chr12:52401215 |
| chr12:52401223 | chr12:52401240 | chr12:52401253 | chr12:52401288 |
| chr12:52401295 | chr12:52401299 | chr12:52401304 | chr12:52401334 |
| chr12:52401340 | chr12:52401344 | chr12:52401359 | |

or a corresponding cytosine at position n+1 on the opposite DNA strand.

To the extent that the method of the present invention includes analysing CAHM, the subject residues are:

| | | |
|---|---|---|
| chr6:163834330 | chr6:163834332 | chr6:163834357 |
| chr6:163834373 | chr6:163834384 | chr6:163834390 |
| chr6:163834392 | chr6:163834406 | chr6:163834412 |
| chr6:163834419 | chr6:163834443 | chr6:163834448 |
| chr6:163834452 | chr6:163834464 | chr6:163834483 |
| chr6:163834653 | chr6:163834660 | chr6:163834672 |
| chr6:163834675 | chr6:163834678 | chr6:163834681 |
| chr6:163834815 | chr6:163834824 | chr6:163834835 |
| chr6:163834840 | chr6:163834853 | chr6:163834855 |
| chr6:163834858 | chr6:163834863 | chr6:163834869 |
| chr6:163834872 | | |

or a corresponding cytosine at position n+1 on the opposite DNA strand.

To the extent that the method of the present invention includes analysing IKZF1, the subject residues are:

| | | |
|---|---|---|
| chr7:50343869 | chr7:50343872 | chr7:50343883 |
| chr7:50343889 | chr7:50343890 | chr7:50343897 |
| chr7:50343907 | chr7:50343909 | chr7:50343914 |
| chr7:50343934 | chr7:50343939 | chr7:50343950 |
| chr7:50343959 | chr7:50343805 | chr7:50343822 |
| chr7:50343824 | chr7:50343826 | chr7:50343829 |
| chr7:50343831 | chr7:50343833 | chr7:50343838 |
| chr7:50343847 | chr7:50343850 | chr7:50343858 |
| chr7:50343864 | chr7:50343869 | chr7:50343872 |
| chr7:50343890 | | |

or a corresponding cytosine at position n+1 on the opposite DNA strand.

To the extent that the method of the present invention includes analysing IRF4, the subject residues are:

| | | |
|---|---|---|
| chr6:392036 | chr6:392047 | chr6:392049 |
| chr6:392057 | chr6:392060 | chr6:392066 |
| chr6:392080 | chr6:392094 | chr6:392102 |
| chr6:392131 | | |

or a corresponding cytosine at position n+1 on the opposite DNA strand.

The detection method of the present invention can be performed on any suitable biological sample. To this end, reference to a "biological sample" should be understood as a reference to any sample of biological material derived from an animal such as, but not limited to, cellular material, biofluids (e.g. blood), faeces, tissue biopsy specimens, surgical specimens or fluid which has been introduced into the body of an animal and subsequently removed (such as, for example, the solution retrieved from an enema wash). The biological sample which is tested according to the method of the present invention may be tested directly or may require some form of treatment prior to testing. For example, a biopsy or surgical sample may require homogenisation prior to testing or it may require sectioning for in situ testing of the qualitative expression levels of individual genes. Alternatively, a cell sample may require permeabilisation prior to testing. Further, to the extent that the biological sample is not in liquid form, (if such form is required for testing) it may require the addition of a reagent, such as a buffer, to mobilise the sample.

To the extent that the DNA region of interest is present in a biological sample, the biological sample may be directly tested or else all or some of the nucleic acid present in the biological sample may be isolated prior to testing. In yet another example, the sample may be partially purified or otherwise enriched prior to analysis. For example, to the extent that a biological sample comprises a very diverse cell population, it may be desirable to enrich for a sub-population of particular interest. It is within the scope of the present invention for the target cell population or molecules derived therefrom to be treated prior to testing, for example, inactivation of live virus. It should also be understood that the biological sample may be freshly harvested or it may have been stored (for example by freezing) prior to testing or otherwise treated prior to testing (such as by undergoing culturing).

The choice of what type of sample is most suitable for testing in accordance with the method disclosed herein will be dependent on the nature of the situation. Preferably, said sample is a faecal (stool) sample, enema wash, surgical resection, tissue biopsy or blood sample (e.g. whole blood, serum or plasma).

More preferably, said biological sample is a blood sample, biopsy sample or stool sample.

As detailed hereinbefore, the present invention is designed to screen for a neoplastic cell or cellular population, which is located in the large intestine. Accordingly, reference to "cell or cellular population" should be understood as a reference to an individual cell or a group of cells. Said group of cells may be a diffuse population of cells, a cell suspension, an encapsulated population of cells or a population of cells which take the form of tissue.

Reference to the "onset" of a neoplasm, such as adenoma or adenocarcinoma, should be understood as a reference to one or more cells of that individual exhibiting dysplasia. In this regard, the adenoma or adenocarcinoma may be well developed in that a mass of dysplastic cells has developed. Alternatively, the adenoma or adenocarcinoma may be at a very early stage in that only relatively few abnormal cell divisions have occurred at the time of diagnosis. The present invention also extends to the assessment of an individual's predisposition to the development of a neoplasm, such as an adenoma or adenocarcinoma. Without limiting the present invention in any way, changed methylation levels may be indicative of that individual's predisposition to developing a neoplasia, such as the future development of an adenoma or adenocarcinoma or another adenoma or adenocarcinoma.

Although the preferred method is to assess methylation levels for the purpose of diagnosing neoplasia development or predisposition thereto, the detection of converse changes in the levels of said methylation may be desired under certain circumstances, for example, to monitor the effectiveness of therapeutic or prophylactic treatment directed to modulating a neoplastic condition, such as adenoma or adenocarcinoma development. For example, where elevated levels of methylation indicate that an individual has developed a condition characterised by adenoma or adenocarcinoma development, screening for a decrease in the levels of methylation subsequently to the onset of a therapeutic treatment regime may be utilised to indicate successful clearance of the neoplastic cells. In another example, one can use this method to test the tissue at the margins of a tumour resection in order to determine whether the full margin of the tumour has been removed.

The present method can therefore be used in the diagnosis, prognosis, classification, prediction of disease risk, detection of recurrence of disease, selection of treatment of a number of types of neoplasias and monitoring of neoplasias. A cancer at any stage of progression can be detected, such as primary, metastatic, and recurrent cancers.

The present invention provides methods for determining whether a mammal (e.g., a human) has a neoplasia of the large intestine, whether a biological sample taken from a mammal contains neoplastic cells or DNA derived from neoplastic cells, estimating the risk or likelihood of a mammal developing a neoplasm, monitoring the efficacy of anti-cancer treatment, or selecting the appropriate anti-cancer treatment in a mammal with cancer. Such methods are based on the determination that neoplastic cells have a different methylation status than normal cells in the DNA regions described herein. Accordingly, by determining whether or not a cell contains differentially methylated sequences in the DNA regions as described herein, it is possible to determine that a cell is neoplastic.

The method of the invention can be used to evaluate individuals known or suspected to have a neoplasia or as a routine clinical test, i.e., in an individual not necessarily suspected to have a neoplasia. Further diagnostic assays can be performed to confirm the status of neoplasia in the individual.

Further, the present methods may be used to assess the efficacy of a course of treatment. For example, the efficacy of an anti-cancer treatment can be assessed by monitoring DNA methylation of the sequences described herein over time in a mammal having cancer. For example, a reduction or absence of methylation in any of the diagnostic sequences of the invention in a biological sample taken from a mammal following a treatment, compared to a level in a sample taken from the mammal before, or earlier in, the treatment, indicates efficacious treatment.

The method of the present invention is therefore useful as a one-time test or as an on-going monitor of those individuals thought to be at risk of neoplasia development or as a monitor of the effectiveness of therapeutic or prophylactic treatment regimes directed to inhibiting or otherwise slowing neoplasia development. In these situations, mapping the modulation of methylation levels in any one or more classes of biological samples is a valuable indicator of the status of an individual or the effectiveness of a therapeutic or prophylactic regime which is currently in use. Accordingly, the method of the present invention should be understood to extend to monitoring for increases or decreases in methylation levels in an individual relative to their normal level (as hereinbefore defined), or relative to one or more earlier methylation levels determined from a biological sample of said individual.

The methods for detecting neoplasia can comprise the detection of one or more other cancer-associated polynucleotide or polypeptides sequences. Accordingly, detection of methylation by the method of the invention can be used either alone, or in combination with other screening methods for the diagnosis or prognosis of neoplasia.

Any method for detecting DNA methylation can be used in the methods of the present invention. A number of methods are available for detection of differentially methylated DNA at specific loci in either primary tissue samples or in patient samples such as blood, urine, stool or saliva (reviewed in Kristensen and Hansen *Clin Chem.* 55:1471-83, 2009; Ammerpohl et al. *Biochim Biophys Acta.* 1790:847-62, 2009; Shames et al. *Cancer Lett.* 251:187-98, 2007; Clark et al. *Nat Protoc.* 1:2353-64, 2006). For analysis of the proportion or extent of DNA methylation in a target gene, DNA is normally treated with sodium bisulfite and regions of interest amplified using primers and PCR conditions that will amplify independently of the methylation status of the DNA. The methylation of the overall amplicon or individual CpG sites can then be assessed by sequencing, including pyrosequencing, restriction enzyme digestion (COBRA) or by melting curve analysis. Alternatively ligation-based methods for analysis of methylation at specific CpG sites may be used. Detection of aberrantly methylated DNA released from tumours and into bodily fluids is being developed as a means of cancer diagnosis. Here, in the case of hypermethylated sequences, it is necessary to use sensitive methods that allow the selective amplification of the methylated DNA sequence from a background of normal cellular DNA that is unmethylated. Such methods based on bisulfite-treated DNA, for example; include methylation selective PCR (MSP), Heavymethyl PCR, Headloop PCR and Helper-dependent chain reaction (PCT/AU2008/001475).

Briefly, in some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. patent application Ser. Nos. 10/971,986; 11/071,013; and Ser. No. 10/971,339. In some embodiments, amplification can be performed using primers that are gene specific. Alternatively, adaptors can be added to the ends of the randomly fragmented DNA, the DNA can be digested with a methylation-dependent or methylation-sensitive restriction enzyme, intact DNA can be amplified using primers that hybridize to the adaptor sequences. In this case, a second step can be performed to determine the presence, absence or quantity of a particular gene in an amplified pool of DNA. In some embodiments, the DNA is amplified using real-time, quantitative PCR.

In some embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. A methylation-sensitive enzyme is one which cuts DNA if its recognition sequence is unmethylated while a methylation-dependent enzyme cuts DNA if its recognition sequence is methylated. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. patent application Ser. No. 10/971,986.

Kits for the above methods can include, e.g., one or more of methylation-dependent restriction enzymes, methylation-sensitive restriction enzymes, amplification (e.g., PCR) reagents, probes and/or primers.

Quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol. Biotechnol.* 20(2):163-79 (2002). Amplifications may be monitored in "real time."

Additional methods for detecting DNA methylation can involve genomic sequencing before and after treatment of the DNA with bisulfite. See, e.g., Frommer et al., *Proc. Natl. Acad. Sci. USA* 89:1827-1831 (1992). When sodium bisulfite is contacted to DNA, unmethylated cytosine is converted to uracil, while methylated cytosine is not modified.

In some embodiments, restriction enzyme digestion of PCR products amplified from bisulfite-converted DNA is used to detect DNA methylation. See, e.g., Sadri & Hornsby, *Nucl. Acids Res.* 24:5058-5059 (1996); Xiong & Laird, *Nucleic Acids Res.* 25:2532-2534 (1997).

In some embodiments, a methylation-specific PCR ("MSP") reaction is used alone or in combination with other methods to detect DNA methylation. An MSP assay entails initial modification of DNA by sodium bisulfite, converting all unmethylated, but not methylated, cytosines to uracil, and subsequent amplification with primers specific for methylated verses unmethylated DNA. See, Herman et al. *Proc. Natl. Acad. Sci. USA* 93:9821-9826 (1996); U.S. Pat. No. 5,786,146.

In some embodiments, a MethyLight assay is used alone or in combination with other methods to detect DNA methylation (see, Eads et al., *Cancer Res.* 59:2302-2306 (1999)). Briefly, in the MethyLight process genomic DNA is converted in a sodium bisulfite reaction (the bisulfite process converts unmethylated cytosine residues to uracil). Amplification of a DNA sequence of interest is then performed using PCR primers that hybridize to CpG dinucleotides. By using primers that hybridize only to sequences resulting from bisulfite conversion of methylated DNA, (or alternatively to unmethylated sequences) amplification can indicate methylation status of sequences where the primers hybridize. Furthermore, the amplification product can be detected with a probe that specifically binds to a sequence resulting from bisulfite treatment of a unmethylated DNA. If desired, both primers and probes can be used to detect methylation status. Thus, kits for use with MethyLight can include sodium bisulfite as well as primers or detectably-labelled probes (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In some embodiments, a Ms-SNuPE (Methylation-sensitive Single Nucleotide Primer Extension) reaction is used alone or in combination with other methods to detect DNA methylation (see, Gonzalgo & Jones, *Nucleic Acids Res.* 25:2529-2531 (1997)). The Ms-SNuPE technique is a quantitative method for assessing methylation differences at specific CpG sites based on bisulfite treatment of DNA, followed by single-nucleotide primer extension (Gonzalgo & Jones, supra). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest.

Typical reagents (e.g., as might be found in a typical Ms-SNuPE-based kit) for Ms-SNuPE analysis can include, but are not limited to: PCR primers for specific gene (or methylation-altered DNA sequence or CpG island); optimized PCR buffers and deoxynucleotides; gel extraction kit; positive control primers; Ms-SNuPE primers for a specific gene; reaction buffer (for the Ms-SNuPE reaction); and detectably-labelled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

Additional methylation detection methods include, but are not limited to, methylated CpG island amplification (see, Toyota et al., *Cancer Res.* 59:2307-12 (1999)) and those described in, e.g., U.S. Patent Publication 2005/0069879; Rein, et al. *Nucleic Acids Res.* 26 (10): 2255-64 (1998); Olek, et al. Nat. *Genet.* 17(3): 275-6 (1997); and PCT Publication No. WO 00/70090.

More detailed information in relation to several of these generally described methods is provided below:

(a) Probe or Primer Design and/or Production

Several methods described herein for the diagnosis of a neoplasia use one or more probes and/or primers. Methods for designing probes and/or primers for use in, for example, PCR or hybridization are known in the art and described, for example, in Dieffenbach and Dveksler (Eds) (In: PCR Primer: A Laboratory Manual, Cold Spring Harbor Laboratories, N Y, 1995). Furthermore, several software packages are publicly available that design optimal probes and/or primers for a variety of assays, e.g. Primer 3 available from the Center for Genome Research, Cambridge, Mass., USA.

Clearly, the potential use of the probe or primer should be considered during its design. For example, should the probe or primer be produced for use in a methylation specific PCR or ligase chain reaction (LCR) assay the nucleotide at the 3' end (or 5' end in the case of LCR) should preferably correspond to a methylated nucleotide in a nucleic acid.

Probes and/or primers useful for detection of a sequence associated with a neoplasia are assessed, for example, to determine those that do not form hairpins, self-prime or form primer dimers (e.g. with another probe or primer used in a detection assay). Furthermore, a probe or primer (or the sequence thereof) is often assessed to determine the temperature at which it denatures from a target nucleic acid (i.e. the melting temperature of the probe or primer, or Tm). Methods for estimating Tm are known in the art and described, for example, in Santa Lucia, *Proc. Natl. Acad. Sci. USA,* 95: 1460-1465, 1995 or Bresslauer et al., *Proc. Natl. Acad. Sci. USA,* 83: 3746-3750, 1986.

Methods for producing/synthesizing a probe or primer of the present invention are known in the art. For example, oligonucleotide synthesis is described, in Gait (Ed) (In: Oligonucleotide Synthesis: A Practical Approach, IRL Press, Oxford, 1984). For example, a probe or primer may be obtained by biological synthesis (e.g. by digestion of a nucleic acid with a restriction endonuclease) or by chemical synthesis. For short sequences (up to about 100 nucleotides) chemical synthesis is preferable.

For longer sequences standard replication methods employed in molecular biology are useful, such as, for example, the use of M13 for single stranded DNA as described by Messing, *Methods Enzymol,* 101, 20-78, 1983. Other methods for oligonucleotide synthesis include, for example, phosphotriester and phosphodiester methods (Narang, et al. *Meth. Enzymol* 68: 90, 1979) and synthesis on a support (Beaucage, et al. *Tetrahedron Letters* 22:1859-1862, 1981) as well as phosphoramidate technique, Caruthers, M. H., et al., *Methods in Enzymology*, Vol. 154, pp. 287-314 (1988), and others described in "Synthesis and Applications of DNA and RNA," S. A. Narang, editor, Academic Press, New York, 1987, and the references cited therein. Probes comprising locked nucleic acid (LNA) are synthesized as described, for example, in Nielsen et al. *J. Chem. Soc. Perkin Trans.,* 1:3423, 1997; Singh and Wengel, *Chem. Commun.* 1247, 1998. While, probes comprising peptide-nucleic acid (PNA) are synthesized as described, for example, in Egholm et al., *Am. Chem. Soc.,* 114:1895, 1992; Egholm et al., *Nature,* 365:566, 1993; and Orum et al., *Nucl. Acids Res.,* 21:5332, 1993.

(b) Methylation-Sensitive Endonuclease Digestion of DNA

In one example, the increased methylation in a sample is determined using a process comprising treating the nucleic acid with an amount of a methylation-sensitive restriction endonuclease enzyme under conditions sufficient for nucleic acid to be digested and then detecting the fragments produced. Exemplary methylation-sensitive endonucleases include, for example, HhaI or HpaII. Preferably, assays include internal controls that are digested with a methylation-insensitive enzyme having the same specificity as the methylation-sensitive enzyme employed. For example, the methylation-insensitive enzyme MspI is an isoschizomer of the methylation-sensitive enzyme HpaII.

Hybridization Assay Formats

In one example, the digestion of nucleic acid is detected by selective hybridization of a probe or primer to the undigested nucleic acid. Alternatively, the probe selectively hybridizes to both digested and undigested nucleic acid but facilitates differentiation between both forms, e.g., by electrophoresis. Suitable detection methods for achieving selective hybridization to a hybridization probe include, for example, Southern or other nucleic acid hybridization (Kawai et al., *Mol. Cell. Biol.* 14:7421-7427, 1994; Gonzalgo et al., *Cancer Res.* 57:594-599, 1997).

Suitable hybridization conditions are determined based on the melting temperature (Tm) of a nucleic acid duplex comprising the probe. The skilled artisan will be aware that optimum hybridization reaction conditions should be determined empirically for each probe, although some generalities can be applied. Preferably, hybridizations employing short oligonucleotide probes are performed at low to medium stringency. In the case of a GC rich probe or primer or a longer probe or primer a high stringency hybridization and/or wash is preferred. A high stringency is defined herein as being a hybridization and/or wash carried out in about 0.1×SSC buffer and/or about 0.1% (w/v) SDS, or lower salt concentration, and/or at a temperature of at least 65° C., or equivalent conditions. Reference herein to a particular level of stringency encompasses equivalent conditions using wash/hybridization solutions other than SSC known to those skilled in the art.

In accordance with the present example, a difference in the fragments produced for the test sample and a negative control sample is indicative of the subject having a neoplasia. Similarly, in cases where the control sample comprises data from a tumor, cancer tissue or a cancerous cell or pre-cancerous cell, similarity, albeit not necessarily absolute identity, between the test sample and the control sample is indicative of a positive diagnosis (i.e. cancer).

Amplification Assay Formats

In an alternative example, the fragments produced by the restriction enzyme are detected using an amplification system, such as, for example, polymerase chain reaction (PCR), rolling circle amplification (RCA), inverse polymerase chain reaction (iPCR), in situ PCR (Singer-Sam et al., *Nucl. Acids Res.* 18:687, 1990), strand displacement amplification (SDA) or cycling probe technology.

Methods of PCR are known in the art and described, for example, by McPherson et al., PCR: A Practical Approach. (series eds, D. Rickwood and B. D. Hames), IRL Press Limited, Oxford. pp 1-253, 1991 and by Dieffenbach (ed) and Dveksler (ed) (In: PCR Primer: A Laboratory Manual, Cold Spring Harbour Laboratories, N Y, 1995), the contents of which are each incorporated in their entirety by way of reference. Generally, for PCR two non-complementary nucleic acid primer molecules comprising at least about 18 nucleotides in length, and more preferably at least 20-30 nucleotides in length are hybridized to different strands of a nucleic acid template molecule at their respective annealing sites, and specific nucleic acid molecule copies of the template that intervene the annealing sites are amplified enzymatically. Amplification products may be detected, for example, using electrophoresis and detection with a detectable marker that binds nucleic acids. Alternatively, one or more of the oligonucleotides are labelled with a detectable marker (e.g. a fluorophore) and the amplification product detected using, for example, a lightcycler (Perkin Elmer, Wellesley, Mass., USA, Roche Applied Science, Indianapolis, Ind., USA).

Strand displacement amplification (SDA) utilizes oligonucleotide primers, a DNA polymerase and a restriction endonuclease to amplify a target sequence. The oligonucleotides are hybridized to a target nucleic acid and the polymerase is used to produce a copy of the region intervening the primer annealing sites. The duplexes of copied nucleic acid and target nucleic acid are then nicked with an endonuclease that specifically recognizes a sequence at the beginning of the copied nucleic acid. The DNA polymerase recognizes the nicked DNA and produces another copy of the target region at the same time displacing the previously generated nucleic acid. The advantage of SDA is that it occurs in an isothermal format, thereby facilitating high-throughput automated analysis.

Cycling Probe Technology uses a chimeric synthetic primer that comprises DNA-RNA-DNA that is capable of hybridizing to a target sequence. Upon hybridization to a target sequence the RNA-DNA duplex formed is a target for RNaseH thereby cleaving the primer. The cleaved primer is then detected, for example, using mass spectrometry or electrophoresis.

For primers that flank or are adjacent to a methylation-sensitive endonuclease recognition site, it is preferred that such primers flank only those sites that are hypermethylated in neoplasia to ensure that a diagnostic amplification product is produced. In this regard, an amplification product will only be produced when the restriction site is not cleaved, i.e., when it is methylated. Accordingly, detection of an amplification product indicates that the CpG dinucleotide/s of interest is/are methylated.

As will be known to the skilled artisan, the precise length of the amplified product will vary depending upon the distance between the primers. Clearly this form of analysis may be used to determine the methylation status of a plurality of CpG dinucleotides provided that each dinucleotide is within a methylation sensitive restriction endonuclease site. In these methods, one or more of the primers may be labelled with a detectable marker to facilitate rapid detection of amplified nucleic acid, for example, a fluorescent label (e.g. Cy5 or Cy3) or a radioisotope (e.g. $^{32}P$).

The amplified nucleic acids are generally analyzed using, for example, non-denaturing agarose gel electrophoresis, non-denaturing polyacrylamide gel electrophoresis, mass spectrometry, liquid chromatography (e.g. HPLC or dHPLC), or capillary electrophoresis. (e.g. MALDI-TOF). High throughput detection methods, such as, for example, matrix-assisted laser desorption/ionization time of flight (MALDI-TOF), electrospray ionization (ESI), mass spectrometry (including tandem mass spectrometry, e.g. LC MS/MS), biosensor technology, evanescent fiber-optics technology or DNA chip technology (e.g., WO98/49557; WO 96/17958; Fodor et al., *Science* 767-773, 1991; U.S. Pat. Nos. 5,143,854; and 5,837,832, the contents of which are all incorporated herein by reference), are especially preferred for all assay formats described herein. Alternatively, amplification of a nucleic acid may be continuously monitored using a melting curve analysis method as described herein and/or in, for example, U.S. Pat. No. 6,174,670, which is incorporated herein by reference.

(c) Other Assay Formats

In an alternative example, the increased methylation in a sample is determined by performing a process comprising treating chromatin containing the nucleic acid with an amount of DNaseI under conditions sufficient for nucleic acid to be digested and then detecting the fragments produced. This assay format is predicated on the understanding that chromatin containing methylated DNA, e.g., hyper methylated DNA, has a more tightly-closed conformation than non-hyper methylated DNA and, as a consequence, is less susceptible to endonuclease digestion by DNase I.

In accordance with this method, DNA fragments of different lengths are produced by DNase I digestion of methylated compared to non-methylated DNA. Such different DNA fragments are detected, for example, using an assay described earlier. Alternatively, the DNA fragments are detected using PCR-SSCP essentially as described, for example, in Gregory and Feil, *Nucleic Acids Res.,* 27, e32i-e32iv, 1999. In adapting PCR-SSCP to the present invention, amplification primers flanking or comprising one or more CpG dinucleotides in a nucleic acid that are resistant to DNase I digestion in a neoplasia sample but not resistant to DNase I digestion in a healthy/normal control or healthy/normal test sample are used to amplify the DNase I-generated fragments. In this case, the production of a specific nucleic acid fragment using DNase I is diagnostic of neoplasia, because the DNA is not efficiently degraded. In contrast, template DNA from a healthy/normal subject sample is degraded by the action of DNase I and, as a consequence, amplification fails to produce a discrete amplification product. Alternative methods to PCR-SSCP, such as for example, PCR-dHPLC are also known in the art and contemplated by the present invention.

(d) Selective Mutagenesis of Non-Methylated DNA

In an alternative method the increased methylation in a sample is determined using a process comprising treating the nucleic acid with an amount of a compound that selectively mutates a non-methylated cytosine residue within a CpG dinucleotide under conditions sufficient to induce mutagenesis.

Preferred compounds mutate cytosine to uracil or thymidine, such as, for example, a salt of bisulfite, e.g., sodium bisulfite or potassium bisulfite (Frommer et al., 1992, supra). Bisulfite treatment of DNA is known to distinguish methylated from non-methylated cytosine residues, by mutating cytosine residues that are not protected by methylation, including cytosine residues that are not within a CpG dinucleotide or that are positioned within a CpG dinucleotide that is not subject to methylation.

Sequence Based Detection

In one example, the presence of one or more mutated nucleotides or the number of mutated sequences is determined by sequencing mutated DNA. One form of analysis comprises amplifying mutated nucleic acid using an amplification reaction described herein, for example, PCR. The amplified product is then directly sequenced or cloned and the cloned product sequenced. Methods for sequencing DNA are known in the art and include for example, the dideoxy chain termination method or the Maxam-Gilbert method (see Sambrook et al., Molecular Cloning, A Laboratory Manual (2nd Ed., CSHP, New York 1989) or Zyskind et al., Recombinant DNA Laboratory Manual, (Acad. Press, 1988)).

As the treatment of nucleic acid with a compound, such as, for example, bisulfite results in non-methylated cytosines being mutated to uracil (and hence thymidine after an amplification process), analysis of the sequence determines the presence or absence of a methylated nucleotide. For example, by comparing the sequence obtained using a control sample or a sample that has not been treated with bisulfite, or the known nucleotide sequence of the region of interest with a treated sample facilitates the detection of differences in the nucleotide sequence. Any thymine residue detected at the site of a cytosine in the treated sample compared to a control or untreated sample may be considered to be caused by mutation as a result of bisulfite treatment. Suitable methods for the detection of methylation using sequencing of bisulfite treated nucleic acid are described, for example, in Frommer et al., 1992, supra or Clark et al., *Nucl. Acids Res.* 22:2990-2997, 1994.

In another method, the presence of a mutated or non-mutated nucleotide in a bisulfite treated sample is detected using pyrosequencing, such as, for example, as described in Uhlmann et al., *Electrophoresis,* 23: 4072-4079, 2002. Essentially this method is a form of real-time sequencing that uses a primer that hybridizes to a site adjacent or close to the site of a cytosine that is methylated. Following hybridization of the primer and template in the presence of a DNA polymerase each of four modified deoxynucleotide triphosphates are added separately according to a predetermined dispensation order. Only an added nucleotide that is complementary to the bisulfite treated sample is incorporated and inorganic pyrophosphate (PPi) is liberated. The PPi then drives a reaction resulting in production of detectable levels of light. Such a method allows determination of the identity of a specific nucleotide adjacent to the site of hybridization of the primer.

Methods of solid phase pyrosequencing are known in the art and reviewed in, for example, Landegren et al., *Genome Res.,* 8(8): 769-776, 1998. Such methods enable the high-throughput detection of methylation of a number of CpG dinucleotides.

A related method for determining the sequence of a bisulfite treated nucleotide is methylation-sensitive single nucleotide primer extension (Me-SnuPE) or SNaPmeth. Suitable methods are described, for example, in Gonzalgo and Jones, 1997, supra, or Uhlmann et al., *Electrophoresis,* 23:4072-4079, 2002. An oligonucleotide is used that hybridizes to the region of a nucleic acid adjacent to the site of a cytosine that is methylated. This oligonucleotide is then used in a primer extension protocol with a polymerase and a free nucleotide diphosphate or dideoxynucleotide triphosphate that corresponds to either or any of the possible bases that occur at this site following bisulfite treatment (i.e., thymine or cytosine). Preferably, the nucleotide-diphosphate is labelled with a detectable marker (e.g. a fluorophore). Following primer extension, unbound labelled nucleotide diphosphates are removed, e.g. using size exclusion chromatography or electrophoresis, or hydrolyzed, using for example, alkaline phosphatase, and the incorporation of the labelled nucleotide to the oligonucleotide is detected, indicating the base that is present at the site.

Clearly other high throughput sequencing methods are encompassed by the present invention. Such methods include, for example, solid phase minisequencing (as described, for example, in Southern et al., Genomics, 13:1008-1017, 1992), or minisequencing with FRET (as described, for example, in Chen and Kwok, *Nucleic Acids Res.* 25:347-353, 1997).

Restriction Endonuclease-Based Assay Format

In one method, the presence of a non-mutated sequence is detected using combined bisulfite restriction analysis (COBRA) essentially as described in Xiong and Laird, 2001, supra. This method exploits the differences in restriction enzyme recognition sites between methylated and unmethylated nucleic acid after treatment with a compound that selectively mutates a non-methylated cytosine residue, e.g., bisulfite.

Following bisulfite treatment a region of interest comprising one or more CpG dinucleotides that are methylated and are included in a restriction endonuclease recognition sequence is amplified using an amplification reaction described herein, e.g., PCR. The amplified product is then contacted with the restriction enzyme that cleaves at the site of the CpG dinucleotide for a time and under conditions sufficient for cleavage to occur. A restriction site may be selected to indicate the presence or absence of methylation. For example, the restriction endonuclease TaqI cleaves the sequence TCGA, following bisulfite treatment of a non-methylated nucleic acid the sequence will be TTGA and, as a consequence, will not be cleaved. The digested and/or non-digested nucleic acid is then detected using a detection means known in the art, such as, for example, electrophoresis and/or mass spectrometry. The cleavage or non-cleavage of the nucleic acid is indicative of cancer in a subject. Clearly, this method may be employed in either a positive read-out or negative read-out system for the diagnosis of a cancer.

Positive Read-Out Assay Format

In one embodiment, the assay format of the invention comprises a positive read-out system in which DNA from a sample that has been treated, for example, with bisulfite is detected as a positive signal. Preferably, the non-hypermethylated DNA from a healthy or normal control subject is not detected or only weakly detected.

In a preferred embodiment, the increased methylation in a subject sample is determined using a process comprising:

(i) treating the nucleic acid with an amount of a compound that selectively mutates a non-methylated cytosine residue under conditions sufficient to induce mutagenesis thereby producing a mutated nucleic acid;

(ii) hybridizing a nucleic acid to a probe or primer comprising a nucleotide sequence that is complementary to a sequence comprising a methylated cytosine residue under conditions such that selective hybridization to the non-mutated nucleic acid occurs; and (iii) detecting the selective hybridization.

In this context, the term "selective hybridization" means that hybridization of a probe or primer to the non-mutated nucleic acid occurs at a higher frequency or rate, or has a higher maximum reaction velocity, than hybridization of the same probe or primer to the corresponding mutated sequence. Preferably, the probe or primer does not hybridize to the non-methylated sequence carrying the mutation(s) under the reaction conditions used.

Hybridization-Based Assay Format

In one embodiment, the hybridization is detected using Southern, dot blot, slot blot or other nucleic acid hybridization means (Kawai et al., 1994, supra; Gonzalgo et al., 1997, supra). Subject to appropriate probe selection, such assay formats are generally described herein above and apply mutatis mutandis to the presently described selective mutagenesis approach.

Preferably, a ligase chain reaction format is employed to distinguish between a mutated and non-mutated nucleic acid. Ligase chain reaction (described in EP 320,308 and U.S. Pat. No. 4,883,750) uses at least two oligonucleotide probes that anneal to a target nucleic acid in such a way that they are juxtaposed on the target nucleic acid. In a ligase chain reaction assay, the target nucleic acid is hybridized to a first probe that is complementary to a diagnostic portion of the target sequence (the diagnostic probe) e.g., a nucleic acid comprising one or more methylated CpG dinucleotide(s), and with a second probe that is complementary to a nucleotide sequence contiguous with the diagnostic portion (the contiguous probe), under conditions wherein the diagnostic probe remains bound substantially only to the target nucleic acid. The diagnostic and contiguous probes can be of different lengths and/or have different melting temperatures such that the stringency of the hybridization can be adjusted to permit their selective hybridization to the target, wherein the probe having the higher melting temperature is hybridized at higher stringency and, following washing to remove unbound and/or non-selectively bound probe, the other probe having the lower melting temperature is hybridized at lower stringency. The diagnostic probe and contiguous probe are then covalently ligated such as, for example, using T4 DNA ligase, to thereby produce a larger target probe that is complementary to the target sequence, and the probes that are not ligated are removed by modifying the hybridization stringency. In this respect, probes that have not been ligated will selectively hybridize under lower stringency hybridization conditions than probes that have been ligated. Accordingly, the stringency of the hybridization can be increased to a stringency that is at least as high as the stringency used to hybridize the longer probe, and preferably at a higher stringency due to the increased length contributed by the shorter probe following ligation.

In another example, one or both of the probes is labelled such that the presence or absence of the target sequence can be tested by melting the target-probe duplex, eluting the dissociated probe, and testing for the label(s). Where both probes are labelled, different ligands are used to permit distinction between the ligated and unligated probes, in which case the presence of both labels in the same eluate fraction confirms the ligation event. If the target nucleic acid is bound to a solid matrix e.g., in a Southern hybridization, slot blot, dot blot, or microchip assay format, the presence of both the diagnostic and contiguous probes can be determined directly.

Methylation specific microarrays (MSO) are also useful for differentiating between a mutated and non-mutated sequence. A suitable method is described, for example, in Adorjan et al. *Nucl. Acids Res.,* 30: e21, 2002. MSO uses nucleic acid that has been treated with a compound that selectively mutates a non-methylated cytosine residue (e.g., bisulfite) as template for an amplification reaction that amplifies both mutant and non-mutated nucleic acid. The amplification is performed with at least one primer that comprises a detectable label, such as, for example, a fluorophore, e.g., Cy3 or Cy5.

To produce a microarray for detection of mutated nucleic acid oligonucleotides are spotted onto, for example, a glass slide, preferably, with a degree of redundancy (for example, as described in Golub et al., *Science,* 286:531-537, 1999). Preferably, for each CpG dinucleotide analyzed two different oligonucleotides are used. Each oligonucleotide comprises a sequence $N_2$-16CG$N_2$-16 or $N_2$-16TG$N_2$-16 (wherein N is a number of nucleotides adjacent or juxtaposed to the CpG dinucleotide of interest) reflecting the methylated or non-methylated status of the CpG dinucleotides.

The labelled amplification products are then hybridized to the oligonucleotides on the microarray under conditions that enable detection of single nucleotide differences. Following washing to remove unbound amplification product, hybridization is detected using, for example, a microarray scanner. Not only does this method allow for determination of the methylation status of a large number of CpG dinucleotides, it is also semi-quantitative, enabling determination of the degree of methylation at each CpG dinucleotide analyzed. As there may be some degree of heterogeneity of methylation in a single sample, such quantification may assist in the diagnosis of cancer.

Amplification-Based Assay Format

In an alternative example, the hybridization is detected using an amplification system. In methylation-specific PCR formats (MSP; Herman et al. Proc. Natl. Acad. Sci. USA 93:9821-9826, 1992), the hybridization is detected using a process comprising amplifying the bisulfite-treated DNA. Accordingly, by using one or more probe or primer that anneals specifically to the unmutated sequence under moderate and/or high stringency conditions an amplification product is only produced using a sample comprising a methylated nucleotide. Alternate assays that provide for selective amplification of either the methylated or the unmethylated component from a mixture of bisulfite-treated DNA are provided by Cottrell et al., *Nucl. Acids Res.* 32: e10, 2003 (HeavyMethyl PCR), Rand et al. *Nucl. Acids Res.* 33:e127, 2005 (Headloop PCR), Rand et al. *Epigenetics* 1:94-100, 2006 (Bisulfite Differential Denaturation PCR) and PCT/AU07/000389 (End-specific PCR).

Any amplification assay format described herein can be used, such as, for example, polymerase chain reaction (PCR), rolling circle amplification (RCA), inverse polymerase chain reaction (iPCR), in situ PCR (Singer-Sam et al., 1990, supra), strand displacement amplification, or cycling probe technology. PCR techniques have been developed for detection of gene mutations (Kuppuswamy et al., *Proc. Natl. Acad. Sci. USA* 88:1143-1147, 1991) and quantitation of allelic-specific expression (Szabo and Mann, *Genes Dev.* 9: 3097-3108, 1995; and Singer-Sam et al., *PCR Methods Appl.* 1: 160-163, 1992). Such techniques use internal primers, which anneal to a PCR-generated template and terminate immediately 5' of the single nucleotide to be assayed. Such as format is readily combined with ligase chain reaction as described herein above. The use of a real-time quantitative assay format is also useful. Subject to the selection of appropriate primers, such assay formats are generally described herein above and apply mutatis mutandis to the presently described selective mutagenesis approach.

Methylation-specific melting-curve analysis (essentially as described in Worm et al., *Clin. Chem.,* 47:1183-1189, 2001) is also contemplated by the present invention. This process exploits the difference in melting temperature in amplification products produced using bisulfite treated methylated or unmethylated nucleic acid. In essence, non-discriminatory amplification of a bisulfite treated sample is performed in the presence of a fluorescent dye that specifically binds to double stranded DNA (e.g., SYBR Green I). By increasing the temperature of the amplification product while monitoring fluorescence the melting properties and thus the sequence of the amplification product is determined. A decrease in the fluorescence reflects melting of at least a domain in the amplification product. The temperature at which the fluorescence decreases is indicative of the nucleotide sequence of the amplified nucleic acid, thereby permitting the nucleotide at the site of one or more CpG dinucleotides to be determined. As the sequence of the nucleic acids amplified using the present invention The present invention also encompasses the use of real-time quantitative forms of PCR, such as, for example, TaqMan (Holland et al., *Proc. Natl. Acad. Sci. USA,* 88:7276-7280, 1991; Lee et al., *Nucleic Acid Res.* 21:3761-3766, 1993) to perform this embodiment. For example, the MethylLight method of Eads et al., *Nucl. Acids Res.* 28: E32, 2000 uses a modified TaqMan assay to detect methylation of a CpG dinucleotide. Essentially, this method comprises treating a nucleic acid sample with bisulfite and amplifying nucleic acid comprising one or more CpG dinucleotides that are methylated in a neoplastic cell and not in a control sample using an amplification reaction, e.g., PCR. The amplification reaction is performed in the presence of three oligonucleotides, a forward and reverse primer that flank the region of interest and a probe that hybridizes between the two primers to the site of the one or more methylated CpG dinucleotides. The probe is dual labelled with a 5' fluorescent reporter and a 3' quencher (or vice versa). When the probe is intact, the quencher dye absorbs the fluorescence of the reporter due to their proximity. Following annealing of to the PCR product the probe is cleaved by 5' to 3' exonuclease activity of, for example, Taq DNA polymerase. This cleavage releases the reporter from the quencher thereby resulting in an increased fluorescence signal that can be used to estimate the initial template methylation level. By using a probe or primer that selectively hybridizes to unmutated nucleic acid (i.e. methylated nucleic acid) the level of methylation is determined, e.g., using a standard curve.

Alternatively, rather than using a labelled probe that requires cleavage, a probe, such as, for example, a Molecular Beacon is used (see, for example, Mhlanga and Malmberg, *Methods* 25:463-471, 2001). Molecular beacons are single stranded nucleic acid molecules with a stem-and-loop structure. The loop structure is complementary to the region surrounding the one or more CpG dinucleotides that are methylated in a neoplastic sample and not in a control sample. The stem structure is formed by annealing two "arms" complementary to each other, which are on either side of the probe (loop). A fluorescent moiety is bound to one arm and a quenching moiety that suppresses any detectable fluorescence when the molecular beacon is not bound to a target sequence is bound to the other arm. Upon binding of the loop region to its target nucleic acid the arms are separated and fluorescence is detectable. However, even a single base mismatch significantly alters the level of fluorescence detected in a sample. Accordingly, the presence or absence of a particular base is determined by the level of fluorescence detected. Such an assay facilitates detection of one or more unmutated sites (i.e. methylated nucleotides) in a nucleic acid.

Fluorescently labelled locked nucleic acid (LNA) molecules or fluorescently labelled protein-nucleic acid (PNA) molecules are useful for the detection of nucleotide differences (e.g., as described in Simeonov and Nikiforov, *Nucleic Acids Research,* 30(17):1-5, 2002). LNA and PNA molecules bind, with high affinity, to nucleic acid, in particular, DNA. Fluorophores (in particular, rhodomine or hexachlorofluorescein) conjugated to the LNA or PNA probe fluoresce at a significantly greater level upon hybridization of the probe to target nucleic acid. However, the level of increase of fluorescence is not enhanced to the same level when even a single nucleotide mismatch occurs. Accordingly, the degree of fluorescence detected in a sample is indicative of the presence of a mismatch between the LNA or PNA probe and the target nucleic acid, such as, in the presence of a mutated cytosine in a methylated CpG dinucleotide. Preferably, fluorescently labelled LNA or PNA technology is used to detect at least a single base change in a nucleic acid that has been previously amplified using, for example, an amplification method known in the art and/or described herein.

As will be apparent to the skilled artisan, LNA or PNA detection technology is amenable to a high-throughput detection of one or more markers by immobilizing an LNA or PNA probe to a solid support, as described in Orum et al., *Clin. Chem.* 45:1898-1905, 1999.

Alternatively, a real-time assay, such as, for example, the so-called HeavyMethyl assay (Cottrell et al., 2003, supra) is used to determine the presence or level of methylation of nucleic acid in a test sample. Essentially, this method uses one or more non-extendible nucleic acid (e.g., oligonucleotide) blockers that bind to bisulfite-treated nucleic acid in a methylation specific manner (i.e., the blocker/s bind specifically to unmutated DNA under moderate to high stringency conditions). An amplification reaction is performed using one or more primers that may optionally be methylation specific but that flank the one or more blockers. In the presence of unmethylated nucleic acid (i.e., non-mutated DNA) the blocker/s bind and no PCR product is produced. Using a TaqMan assay essentially as described supra the level of methylation of nucleic acid in a sample is determined.

Other amplification based methods for detecting methylated nucleic acid following treatment with a compound that selectively mutates a non-methylated cytosine residue include, for example, methylation-specific single stranded conformation analysis (MS-SSCA) (Bianco et al., *Hum. Mutat.,* 14:289-293, 1999), methylation-specific denaturing gradient gel electrophoresis (MS-DGGE) (Abrams and Stanton, *Methods Enzymol.,* 212:71-74, 1992) and methylation-specific denaturing high-performance liquid chromatography (MS-DHPLC) (Deng et al. *Chin. J. Cancer Res.,* 12:171-191, 2000). Each of these methods use different techniques for detecting nucleic acid differences in an amplification product based on differences in nucleotide sequence and/or secondary structure. Such methods are clearly contemplated by the present invention.

As with other amplification-based assay formats, the amplification product is analyzed using a range of procedures, including gel electrophoresis, gel filtration, mass spectrometry, and in the case of labelled primers, by identifying the label in the amplification product. In an alternative embodiment, restriction enzyme digestion of PCR products amplified from bisulfite-converted DNA is performed essentially as described by Sadri and Hornsby, *Nucl. Acids Res.* 24:5058-5059, 1996; and Xiong and Laird, *Nucl. Acids Res.* 25:2532-2534, 1997), to analyze the product formed.

High throughput detection methods, such as, for example, matrix-assisted laser desorption/ionization time of flight (MALDI-TOF), electrospray ionization (ESI), Mass spectrometry (including tandem mass spectrometry, e.g. LC MS/MS), biosensor technology, evanescent fiber-optics technology or DNA chip technology, can also be employed.

As with the other assay formats described herein that utilize hybridization and/or amplification detection systems, combinations of such processes as described herein above are particularly contemplated by the selective mutagenesis-based assay formats of the present invention. In one example, the increased methylation is detected by performing a process comprising:

(i) treating the nucleic acid with an amount of a compound that selectively mutates a non-methylated cytosine residue within a CpG dinucleotide under conditions sufficient to induce mutagenesis thereby producing a mutated nucleic acid;
(ii) hybridizing the nucleic acid to two non-overlapping and non-complementary primers each of which comprises a nucleotide sequence that is complementary to a sequence in the DNA comprising a methylated cytosine residue under conditions such that hybridization to the non-mutated nucleic acid occurs;
(iii) amplifying nucleic acid intervening the hybridized primers thereby producing a DNA fragment consisting of a sequence that comprises a primer sequence;
(iv) hybridizing the amplified DNA fragment to a probe comprising a nucleotide sequence that corresponds or is complementary to a sequence comprising a methylated cytosine residue under conditions such that hybridization to the non-mutated nucleic acid occurs; and detecting the hybridization.

Negative Read-Out Assays

In another example, the assay format comprises a negative read-out system in which reduced methylation of DNA from a healthy/normal control sample is detected as a positive signal and preferably, methylated DNA from a neoplastic sample is not detected or is only weakly detected.

In a preferred embodiment, the reduced methylation is determined using a process comprising:

(i) treating the nucleic acid with an amount of a compound that selectively mutates a non-methylated cytosine residue within a CpG island under conditions sufficient to induce mutagenesis thereby producing a mutated nucleic acid;
(ii) hybridizing the nucleic acid to a probe or primer comprising a nucleotide sequence that is complementary to a sequence comprising the mutated cytosine residue under conditions such that selective hybridization to the mutated nucleic acid occurs; and
(iii) detecting the selective hybridization.

In this context, the term "selective hybridization" means that hybridization of a probe or primer to the mutated nucleic acid occurs at a higher frequency or rate, or has a higher maximum reaction velocity, than hybridization of the same probe or primer to the corresponding non-mutated sequence. Preferably, the probe or primer does not hybridize to the methylated sequence (or non-mutated sequence) under the reaction conditions used.

Hybridization-Based Assay Format

In one embodiment the hybridization is detected using Southern, dot blot, slot blot or other nucleic acid hybridization means (Kawai et al., 1994, supra; Gonzalgo et al., 1997, supra). Subject to appropriate probe selection, such assay formats are generally described herein above and apply mutatis mutandis to the presently described selective mutagenesis approach. Preferably, a ligase chain reaction format is employed to distinguish between a non-mutated and mutated nucleic acid. In this respect, the assay requirements and conditions are as described herein above for positive read-out assays and apply mutatis mutandis to the present format. However the selection of probes will differ. For negative read-out assays, one or more probes are selected that selectively hybridize to the mutated sequence rather than the non-mutated sequence.

Preferably, the ligase chain reaction probe(s) have 3'-terminal and/or 5'-terminal sequences that comprise a CpG dinucleotide that is not methylated in a healthy control sample, but is hypermethylated in cancer, such that the diagnostic probe and contiguous probe are capable of being ligated only when the cytosine of the CpG dinucleotide is mutated to thymidine e.g., in the case of a non-methylated cytosine residue.

As will be apparent to the skilled artisan the MSO method described supra is amenable to either or both positive and/or negative readout assays. This is because the assay described detects both mutated and non-mutated sequences thereby facilitating determining the level of methylation. However, an assay detecting only methylated or non-methylated sequences is contemplated by the invention.

Amplification-Based Assay Format

In an alternative example, the hybridization is detected using an amplification system using any amplification assay format as described herein above for positive read-out assay albeit using primers (and probes where applicable) selectively hybridize to a mutated nucleic acid.

In adapting the HeavyMethyl assay described supra to a negative read-out format, the blockers that bind to bisulfite-treated nucleic acid in a methylation specific manner bind specifically to mutated DNA under moderate to high stringency conditions. An amplification reaction is performed using one or more primers that may optionally be methylation specific (i.e. only bind to mutated nucleic acid) but that flank the one or more blockers. In the presence of methylated nucleic acid (i.e., mutated DNA) the blocker/s bind and no PCR product is produced.

In one example, the reduced methylation in the normal/healthy control subject is detected by performing a process comprising:

(i) treating the nucleic acid with an amount of a compound that selectively mutates non-methylated cytosine residues under conditions sufficient to induce mutagenesis thereby producing a mutated nucleic acid;
(ii) hybridizing the nucleic acid to two non-overlapping and non-complementary primers each of which comprises a nucleotide sequence that is complementary to a sequence in the DNA comprising a mutated cytosine residue under conditions such that hybridization to the mutated nucleic acid occurs;
(iii) amplifying nucleic acid intervening the hybridized primers thereby producing a DNA fragment consisting of a sequence that comprises a primer sequence;
(iv) hybridizing the amplified DNA fragment to a probe comprising a nucleotide sequence that corresponds or is complementary to a sequence comprising a mutated cytosine residue under conditions such that hybridization to the mutated nucleic acid occurs; and
(v) detecting the hybridization.

As will be apparent to the skilled artisan a negative read-out assay preferably includes a suitable control sample to ensure that the negative result is caused by methylated nucleic acid rather than a reaction failing.

This invention also provides kits for the detection and/or quantification of the diagnostic sequences of the invention, or expression or methylation thereof using the methods described herein.

For kits for detection of methylation, the kits of the invention can comprise at least one polynucleotide that hybridizes to at least one of the diagnostic sequences of the invention and at least one reagent for detection of gene methylation. Reagents for detection of methylation include, e.g., sodium bisulfite, polynucleotides designed to hybridize to sequence that is the product of a biomarker sequence of the invention if the biomarker sequence is not methylated (e.g., containing at least one C→U conversion), and/or a methylation-sensitive or methylation-dependent restriction enzyme. The kits may also include control natural or synthetic DNA sequences representing methylated or unmethylated forms of the sequence. The kits can provide solid supports in the form of an assay apparatus that is adapted to use in the assay. The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein.

As detailed hereinbefore, hypermethylation is associated with transcriptional silencing. Accordingly, in addition to the increased level of methylation of these genes providing a basis upon which to screen for the predisposition to or onset of a large intestine neoplasm, the downregulation in the level of expression of these genes is also diagnostically valuable.

In accordance with this aspect of the present invention, reference to a gene "expression product" or "expression of a gene" is a reference to either a transcription product (such as primary RNA or mRNA) or a translation product such as protein. In this regard, one can assess changes to the level of expression of a gene either by screening for changes to the level of expression product which is produced (i.e. RNA or protein), changes to the chromatin proteins with which the gene is associated, for example the presence of histone H3 methylated on lysine at amino acid position number 9 or 27 (repressive modifications) or changes to the DNA itself which acts to downregulate expression, such as changes to the methylation of the DNA. These genes and their gene expression products, whether they be RNA transcripts, changes to the DNA which act to downregulate expression or encoded proteins, are collectively referred to as "neoplastic markers".

Accordingly, another aspect of the present invention is directed to a method of screening for the onset or predisposition to the onset of or monitoring a large intestine neoplasm in an individual, said method comprising assessing the level of expression of a DNA region selected from:

(i) the region, including 2 kb upstream of the transcription start site, defined by any two or more of Hg19 coordinates:
  (1) chr12:24962958 . . . 25102393
  (2) chr7:50344378 . . . 50472798
  (3) chr6:391739 . . . 411443; or
  (4) chr12:52400748 . . . 52409671; and
  (5) chr6:163834097 . . . 163834982; or
(ii) the gene region, including 2 kb upstream of any two or more of:
  (1) BCAT1 (2) IKZF1 (3) IRF4 (4) GRASP and (5) CAHM in a biological sample from said individual wherein a lower level of expression of at least one of the DNA regions of group (i) and/or (ii) relative to control levels is indicative of a large intestine neoplasm or a predisposition to the onset of a neoplastic state.

In one embodiment, said method is directed to identifying biological samples in which any one of said DNA regions exhibits a higher level of methylation.

In another embodiment, said method is directed to identifying biological samples in which two or more of said DNA regions exhibits a higher level of methylation.

The method of this aspect of the present invention is predicated on the comparison of the level of the neoplastic markers of a biological sample with the control levels of these markers. The "control level" may be either a "normal level", which is the level of marker expressed by a corresponding large intestine cell or cellular population which is not neoplastic.

As detailed hereinbefore, the normal (or "non-neoplastic") level may be determined using tissues derived from the same individual who is the subject of testing. However, it would be appreciated that this may be quite invasive for the individual concerned and it is therefore likely to be more convenient to analyse the test results relative to a standard result which reflects individual or collective results obtained from individuals other than the patient in issue.

There is more particularly provided a method of screening for the onset or predisposition to the onset of or monitoring a large intestine neoplasm in an individual, said method comprising assessing the level of expression of one or more genes or transcripts selected from:

(i) the DNA regions, including 2 kb upstream of the transcription start site, defined by Hg19 coordinates:
  (1) chr12:24962958 . . . 25102393; and
  (2) chr7:50344378 . . . 50472798;
  and optionally one or more of (3) chr6:391739 . . . 411443, (4) chr12:52400748 . . . 52409671 and (5) chr6:163834097 . . . 163834982; or
(ii) the gene region, including 2 kb upstream or:
  (1) BCAT1; and
  (2) IKZF1;
  and optionally one or more of (3) IRF4, (4) GRASP and (5) CAHM in a biological sample from said individual wherein a lower level of expression of at least one of the DNA regions of group (i) and/or group (ii) relative to control levels is indicative of a neoplastic large intestine neoplasm or a predisposition to the onset of a neoplastic state.

Preferably, said control level is a non-neoplastic level.

In one embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798; and
  (3) chr6:391739 . . . 411443; or
(ii) the gene region, including 2 kb upstream of:
  (1) BCAT1 (2) IKZF1 and (3) IRF4.

In another embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798; and
  (4) chr12:52400748 . . . 52409671; or
(ii) the gene region, including 2 kb upstream of:
  (1) BCAT1 (2) IKZF1 and (4) GRASP.

In still another embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798; and
  (5) chr6:163834097 . . . 163834982; or
(ii) the gene region, including 2 kb upstream of:
  (1) BCAT1 (2) IKZF1 and (5) CAHM In still yet another embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798
  (3) chr6:391739 . . . 411443; and
  (4) chr12:52400748 . . . 52409671; or
(ii) the gene region, including 2 kb upstream of:
  (1) BCAT1 (2) IKZF1 (3) IRF4 and (4) GRASP.

In yet still another embodiment of this aspect, the gene marker panel which is screened for is:

(i) the DNA regions, including 2 kb upstream of the transcription start site, defined by Hg19 coordinates:
  (1) chr12:24962958 . . . 25102393
  (2) chr7:50344378 . . . 50472798
  (3) chr6:391739 . . . 411443; and
  (5) chr6:163834097 . . . 163834982; or
(ii) the gene region, including 2 kb upstream of:
  (1) BCAT1 (2) IKZF1 (3) IRF4 and (5) CAHM.

In a further embodiment of this aspect, the gene marker panel which is screened for is:

(i) the DNA regions, including 2 kb upstream of the transcription start site, defined by Hg19 coordinates:
   (1) chr12:24962958 . . . 25102393
   (2) chr7:50344378 . . . 50472798
   (4) chr12:52400748 . . . 52409671; and
   (5) chr6:163834097 . . . 163834982; or
(ii) the gene region, including 2 kb upstream of any one or more of:
   (1) BCAT1 (2) IKZF1 (4) GRASP and (5) CAHM.

In yet another further embodiment of this aspect, the gene marker panel which is screened for is:

(i) the DNA regions, including 2 kb upstream of the transcription start site, defined by Hg19 coordinates:
   (1) chr12:24962958 . . . 25102393
   (2) chr7:50344378 . . . 50472798
   (3) chr6:391739 . . . 411443; or
   (4) chr12:52400748 . . . 52409671; and
   (5) chr6:163834097 . . . 163834982; or
(ii) the gene region, including 2 kb upstream of any one or more of:
   (1) BCAT1 (2) IKZF1 (3) IRF4 (4) GRASP and (5) CAHM.

In one embodiment, said method is directed to identifying biological samples in which any one of said DNA regions exhibits a higher level of methylation.

In another embodiment, said method is directed to identifying biological samples in which two or more of said DNA regions exhibits a higher level of methylation.

As detailed hereinbefore, the present invention is designed to screen for a neoplastic cell or cellular population, which is located in the large intestine. Accordingly, reference to "cell or cellular population" should be understood as a reference to an individual cell or a group of cells. Said group of cells may be a diffuse population of cells, a cell suspension, an encapsulated population of cells or a population of cells which take the form of tissue.

Reference to "expression" should be understood as a reference to the transcription and/or translation of a nucleic acid molecule. Reference to "RNA" should be understood to encompass reference to any form of RNA, such as primary RNA or mRNA or non-translated RNA (e.g. miRNAs etc.). Without limiting the present invention in any way, the modulation of gene transcription leading to increased or decreased RNA synthesis may also correlate with the translation of some of these RNA transcripts (such as mRNA) to produce a protein product. Accordingly, the present invention also extends to detection methodology which is directed to screening for modulated levels or patterns of the neoplastic marker protein products as an indicator of the neoplastic state of a cell or cellular population. Although one method is to screen for mRNA transcripts and/or the corresponding protein product, it should be understood that the present invention is not limited in this regard and extends to screening for any other form of neoplastic marker expression product such as, for example, a primary RNA transcript.

In terms of screening for the downregulation of expression of a marker it would also be well known to the person of skill in the art that changes which are detectable at the DNA level are indicative of changes to gene expression activity and therefore changes to expression product levels. Such changes include but are not limited to, changes to DNA methylation. Accordingly, reference herein to "screening the level of expression" and comparison of these "levels of expression" to control "levels of expression" should be understood as a reference to assessing DNA factors which are related to transcription, such as gene/DNA methylation patterns. These have, in part, been described in detail hereinbefore.

It would also be known to a person skilled in the art that changes in the structure of chromatin are indicative of changes in gene expression. Silencing of gene expression is often associated with modification of chromatin proteins, methylation of lysines at either or both positions 9 and 27 of histone H3 being well studied examples, while active chromatin is marked by acetylation of lysine 9 of histone H3. Thus association of gene sequences with chromatin carrying repressive or active modifications can be used to make an assessment of the expression level of a gene.

Reference to "nucleic acid molecule" should be understood as a reference to both deoxyribonucleic acid molecules and ribonucleic acid molecules and fragments thereof. The present invention therefore extends to both directly screening for mRNA levels in a biological sample or screening for the complementary cDNA which has been reverse-transcribed from an mRNA population of interest. It is well within the skill of the person of skill in the art to design methodology directed to screening for either DNA or RNA. As detailed above, the method of the present invention also extends to screening for the protein product translated from the subject mRNA or the genomic DNA itself.

In one preferred embodiment, the level of gene expression is measured by reference to genes which encode a protein product and, more particularly, said level of expression is measured at the protein level.

In another particularly preferred embodiment, said gene expression is assessed by the association of DNA with chromatin proteins carrying repressive modifications, for example, methylation of lysines 9 or 27 of histone H3.

The present invention should be understood to encompass methods of detection based on identifying both proteins and/or nucleic acid molecules in one or more biological samples. This may be of particular significance to the extent that some of the neoplastic markers of interest may correspond to genes or gene fragments which do not encode a protein product. Accordingly, to the extent that this occurs it would not be possible to test for a protein and the subject marker would have to be assessed on the basis of transcription expression profiles or changes to genomic DNA.

The term "protein" should be understood to encompass peptides, polypeptides and proteins (including protein fragments). The protein may be glycosylated or unglycosylated and/or may contain a range of other molecules fused, linked, bound or otherwise associated to the protein such as amino acids, lipids, carbohydrates or other peptides, polypeptides or proteins. Reference herein to a "protein" includes a protein comprising a sequence of amino acids as well as a protein associated with other molecules such as amino acids, lipids, carbohydrates or other peptides, polypeptides or proteins.

The proteins encoded by the neoplastic markers of the present invention may be in multimeric form meaning that two or more molecules are associated together. Where the same protein molecules are associated together, the complex is a homomultimer. An example of a homomultimer is a homodimer. Where at least one marker protein is associated with at least one non-marker protein, then the complex is a heteromultimer such as a heterodimer.

Reference to a "fragment" should be understood as a reference to a portion of the subject nucleic acid molecule or protein. This is particularly relevant with respect to screening for modulated RNA levels in stool samples since the subject RNA is likely to have been degraded or otherwise fragmented due to the environment of the gut. One may therefore actually be detecting fragments of the subject RNA molecule, which fragments are identified by virtue of the use of a suitably specific probe.

Although the preferred method is to detect the expression product or DNA changes of the neoplastic markers for the purpose of diagnosing neoplasia development or predisposition thereto, the detection of converse changes in the levels of said markers may be desired under certain circumstances, for example, to monitor the effectiveness of therapeutic or prophylactic treatment directed to modulating a neoplastic condition, such as adenoma or adenocarcinoma development. For example, where reduced expression of the subject markers indicates that an individual has developed a condition characterised by adenoma or adenocarcinoma development, for example, screening for an increase in the levels of these markers subsequently to the onset of a therapeutic regime may be utilised to indicate reversal or other form of improvement of the subject individual's condition. The method of the present invention is therefore useful as a one off test or as an on-going monitor of those individuals thought to be at risk of neoplasia development or as a monitor of the effectiveness of therapeutic or prophylactic treatment regimes directed to inhibiting or otherwise slowing neoplasia development.

Means of assessing the subject expressed neoplasm markers in a biological sample can be achieved by any suitable method, which would be well known to the person of skill in the art. To this end, it would be appreciated that to the extent that one is examining either a homogeneous cellular population (such as a tumour biopsy or a cellular population which has been enriched from a heterogeneous starting population) or a tissue section, one may utilise a wide range of techniques such as in situ hybridisation, assessment of expression profiles by microassays, immunoassays and the like (hereinafter described in more detail) to detect the absence of or downregulation of the level of expression of one or more markers of interest. However, to the extent that one is screening a heterogenous cellular population or a bodily fluid in which heterogeneous populations of cells are found, such as a blood sample, the absence of or reduction in level of expression of a particular marker may be undetectable due to the inherent expression of the marker by non-neoplastic cells which are present in the sample. That is, a decrease in the level of expression of a subgroup of cells may not be detectable. In this situation, a more appropriate mechanism of detecting a reduction in a neoplastic subpopulation of the expression levels of one or more markers of the present invention is via indirect means, such as the detection of epigenetic changes.

Methods of detecting changes to gene expression levels (in addition to the methylation analyses hereinbefore described in detail), particularly where the subject biological sample is not contaminated with high numbers of non-neoplastic cells, include but are not limited to:

(i) In vivo detection.

Molecular Imaging may be used following administration of imaging probes or reagents capable of disclosing altered expression of the markers in the intestinal tissues.

Molecular imaging (Moore et al., *BBA,* 1402:239-249, 1988; Weissleder et al., *Nature Medicine* 6:351-355, 2000) is the in vivo imaging of molecular expression that correlates with the macro-features currently visualized using "classical" diagnostic imaging techniques such as X-Ray, computed tomography (CT), MRI, Positron Emission Tomography (PET) or endoscopy.

(ii) Detection of downregulation of RNA expression in the cells by Fluorescent In Situ Hybridization (FISH), or in extracts from the cells by technologies such as Quantitative Reverse Transcriptase Polymerase Chain Reaction (QRTPCR) or Flow cytometric qualification of competitive RT-PCR products (Wedemeyer et al., *Clinical Chemistry* 48:9 1398-1405, 2002).

(iii) Assessment of expression profiles of RNA, for example by array technologies (Alon et al., *Proc. Natl. Acad. Sci. USA:* 96:6745-6750, June 1999).

A "microarray" is a linear or multi-dimensional array of preferably discrete regions, each having a defined area, formed on the surface of a solid support. The density of the discrete regions on a microarray is determined by the total numbers of target polynucleotides to be detected on the surface of a single solid phase support. As used herein, a DNA microarray is an array of oligonucleotide probes placed onto a chip or other surfaces used to amplify or clone target polynucleotides. Since the position of each particular group of probes in the array is known, the identities of the target polynucleotides can be determined based on their binding to a particular position in the microarray.

DNA microarray technology make it possible to conduct a large scale assay of a plurality of target nucleic acid molecules on a single solid phase support. U.S. Pat. No. 5,837,832 (Chee et al.) and related patent applications describe immobilizing an array of oligonucleotide probes for hybridization and detection of specific nucleic acid sequences in a sample. Target polynucleotides of interest isolated from a tissue of interest are hybridized to the DNA chip and the specific sequences detected based on the target polynucleotides' preference and degree of hybridization at discrete probe locations. One important use of arrays is in the analysis of differential gene expression, where the profile of expression of genes in different cells or tissues, often a tissue of interest and a control tissue, is compared and any differences in gene expression among the respective tissues are identified. Such information is useful for the identification of the types of genes expressed in a particular tissue type and diagnosis of conditions based on the expression profile.

(iv) Measurement of altered neoplastic marker protein levels in cell extracts, for example by immunoassay.

Testing for proteinaceous neoplastic marker expression product in a biological sample can be performed by any one of a number of suitable methods which are well known to those skilled in the art. Examples of suitable methods include, but are not limited to, antibody screening of tissue sections, biopsy specimens or bodily fluid samples. To the extent that antibody based methods of diagnosis are used, the presence of the marker protein may be determined in a number of ways such as by Western blotting, ELISA or flow cytometry procedures. These, of course, include both single-site and two-site or "sandwich" assays of the non-competitive types, as well as in the traditional competitive binding assays. These assays also include direct binding of a labelled antibody to a target.

(v) Determining altered expression of protein neoplastic markers on the cell surface, for example by immunohistochemistry.

(vi) Determining altered protein expression based on any suitable functional test, enzymatic test or immunological test in addition to those detailed in points (iv) and (v) above.

A person of ordinary skill in the art could determine, as a matter of routine procedure, the appropriateness of applying a given method to a particular type of biological sample.

A related aspect of the present invention provides a molecular array, which array comprises a plurality of:

(i) nucleic acid molecules comprising a nucleotide sequence corresponding to any two or more of the neoplastic marker DNA hereinbefore described or a sequence exhibiting at least 80% identity thereto or a functional derivative, fragment, variant or homologue of said nucleic acid molecule; or (ii) nucleic acid molecules comprising a nucleotide sequence capable of hybridising to any one or more of the sequences of (i) under medium stringency conditions or a functional derivative, fragment, variant or homologue of said nucleic acid molecules; or (iii) nucleic acid probes or oligonucleotides comprising a nucleotide sequence capable of hybridising to any two or more of the sequences of (i) under medium stringency conditions or a functional derivative, fragment, variant or homologue of said nucleic acid molecule; or (iv) probes capable of binding to any two or more of the proteins encoded by the nucleic acid molecules of (i) or a derivative, fragment or, homologue thereof.

wherein the level of expression of said marker genes of (i)-(iii) or proteins of (iv) is indicative of the neoplastic state of a cell or cellular subpopulation derived from the large intestine.

Preferably, said percent identity is at least 85%, 90%, 91%, 92%, 93%, 94%, 95%, 96%, 97%, 98% or 99%.

"Hybridization" refers to the process by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low), as set forth herein.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m$=69.3+0.41 (G+C) % (Marmur and Doty, *J. Mol. Biol.* 5:109, 1962). However, the $T_m$ of a duplex DNA decreases by 1° C. with every increase of 1% in the number of mismatch base pairs (Bonner and Laskey, *Eur. J Biochem.* 46:83, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

Where nucleic acids of the invention are defined by their ability to hybridize under high stringency, these conditions comprise about 50% formamide at about 37° C. to 42° C. In one aspect, nucleic acids of the invention are defined by their ability to hybridize under reduced stringency comprising conditions in about 35% to 25% formamide at about 30° C. to 35° C. Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 n/ml sheared and denatured salmon sperm DNA). In one aspect, nucleic acids of the invention are defined by their ability to hybridize under reduced stringency conditions comprising 35% formamide at a reduced temperature of 35° C.

Preferably, the subject probes are designed to bind to the nucleic acid or protein to which they are directed with a level of specificity which minimises the incidence of non-specific reactivity. However, it would be appreciated that it may not be possible to eliminate all potential cross-reactivity or non-specific reactivity, this being an inherent limitation of any probe based system.

In terms of the probes which are used to detect the subject proteins, they may take any suitable form including antibodies and aptamers.

A library or array of nucleic acid or protein probes provides rich and highly valuable information. Further, two or more arrays or profiles (information obtained from use of an array) of such sequences are useful tools for comparing a test set of results with a reference, such as another sample or stored calibrator. In using an array, individual probes typically are immobilized at separate locations and allowed to react for binding reactions. Primers associated with assembled sets of markers are useful for either preparing libraries of sequences or directly detecting markers from other biological samples.

A library (or array, when referring to physically separated nucleic acids corresponding to at least some sequences in a library) of gene markers exhibits highly desirable properties. These properties are associated with specific conditions, and may be characterized as regulatory profiles. A profile, as termed here refers to a set of members that provides diagnostic information of the tissue from which the markers were originally derived. A profile in many instances comprises a series of spots on an array made from deposited sequences.

A characteristic patient profile is generally prepared by use of an array. An array profile may be compared with one or more other array profiles or other reference profiles. The comparative results can provide rich information pertaining to disease states, developmental state, receptiveness to therapy and other information about the patient.

Another aspect of the present invention provides a diagnostic kit for assaying biological samples comprising one or more agents for detecting one or more neoplastic markers and reagents useful for facilitating the detection by said agents. Further means may also be included, for example, to receive a biological sample. The agent may be any suitable detecting molecule.

The present invention is further described by reference to the following non-limiting examples.

EXAMPLE 1

CAHM: Colorectal Adenocarcinoma HyperMethylated
Single-Plex Performance:

74 normals: 0.8 pg hypermethylated/mL plasma (95% CI: 0.2; 1.4)

73 adenomas: 9.1 pg hypermethylated/mL plasma (95% CI: −8; 27)

73 cancers: 1788 pg hypermethylated/mL plasma (95% CI: 231; 3344).

The CAHM assay (threshold cut of 3 pg/mL plasma) is 55% sensitive for colorectal cancer with a 93% specificity (FIG. 1).

GRASP: General Receptor for Phosphoinositides 1-Associated Scaffold Protein.
Single Plex Performance:

34 normals: 1.3 pg hypermethylated/mL plasma (95% CI: 0.2; 2.5)

33 adenomas: 0.1 pg hypermethylated/mL plasma (95% CI: −0.1; 0.4)

33 cancers: 670.8 pg hypermethylated/mL plasma (95% CI: −470.7; 1812)

The GRASP assay is 58% sensitive for colorectal cancer with a 100% specificity using a threshold cut of 20 pg methylated/mL plasma (FIG. 2).

IRF4: Interferon Regulatory Factor 4
Single Plex Performance:

24 normals: 6 pg hypermethylated/mL plasma (95% CI: 2.9; 9.0)

23 adenomas: 3.7 pg hypermethylated/mL plasma (95% CI: −0.4; 8.0)

33 cancers: 5340 pg hypermethylated/mL plasma (95% CI: −5369; 16049)

The IRF4 assay is 57% sensitive for colorectal cancer with a 96% specificity using a threshold cut of 20 pg methylated/mL plasma (FIG. 3).

BCAT1: Branched Chain Amino Acid Transaminase 1, Cytosolic
Single Plex Performance Summary 14 normals: 0 pg hypermethylated/mL plasma (95% CI: na)

13 adenomas: 0.4 pg hypermethylated/mL plasma (95% CI: −0.4; 1.3)

13 cancers: 4088 pg hypermethylated/mL plasma (95% CI: −4459; 10539)

The BCAT1 assay is 62% sensitive for colorectal cancer with a 100% specificity using a threshold cut of 3 pg methylated/mL plasma (FIG. 4).

IKZF1: IKAROS Family Zinc Finger 1

Single Plex Performance Summary 14 normals: 0 pg hypermethylated/mL plasma (95% CI: na)

13 adenomas: 0 pg hypermethylated/mL plasma (95% CI: na)

13 cancers: 113 pg hypermethylated/mL plasma (95% CI: −43; 270)

The IKZF1 assay is 54% sensitive for colorectal cancer with a 100% specificity using a threshold cut of 3 pg methylated/mL plasma (FIG. 4).

The methylation levels of the five genes were measured in the same 14 normals, 13 adenomas and 13 cancers. The table below demonstrates the improvement in clinical utility when measuring the methylation in TWO of the genes:

| (% sens; % spec) | CAHM>$_{6\ pg/ml}$ | GRASP$_{>20\ pg/ml}$ | IRF4$_{>20\ pg/ml}$ | BCAT$_{>3\ pg/ml}$ | IKZF1$_{>3\ pg/ml}$ |
|---|---|---|---|---|---|
| CAHM>$_{6\ pg/ml}$ | 54%; 100% | 62%; 100% | 69%; 100% | 69%; 100% | 69%; 100% |
| GRASP$_{>20\ pg/ml}$ | — | 54%; 100% | 69%; 100% | 77%; 100% | 77%; 100% |
| IRF4$_{>20\ pg/ml}$ | — | — | 54%; 100% | 85%; 100% | 69%; 100% |
| BCAT$_{>3\ pg/ml}$ | — | — | — | 62%; 100% | 77%; 100% |
| IKZF1$_{>3\ pg/ml}$ | — | — | — | — | 54%; 100% |

Combining the methylation levels measured in any three of the five genes resulted in:

CAHM$_{6pg/mL}$—GRASP$_{20pg/mL}$—IRF4$_{20pg/mL}$: 77% sensitivity and 100% specificity CAHM$_{6pg/mL}$—GRASP$_{20pg/mL}$—BCAT$_{3pg/mL}$: 77% sensitivity and 100% specificity CAHM$_{6pg/mL}$ GRASP$_{20pg/mL}$—IKZF1$_{3pg/mL}$: 77% sensitivity and 100% specificity CAHM$_{6pg/mL}$—IKZF1$_{3pg/mL}$—BCAT$_{3pg/mL}$: 77% sensitivity and 100% specificity GRASP$_{20pg/mL}$—IKZF1$_{3pg/mL}$—BCAT$_{3pg/mL}$: 85% sensitivity and 100% specificity Combining the methylation levels from all five genes results in a 92% sensitivity and 100% specificity:

Targeted Amplicon Sequences for GRASP, CAW IRF4, IKZF1 and BCAT1

The wild-type DNA sequence of the CAHM MSP amplicon is located on Chromosome 6, plus strand; 163,834,393⇒163,834,455 (Hg19)

```
GAAGGAAGCA TTTCGAGCAC GACTGACGCT CCCCTTATTA

TTTGCTAAGC CGCTGCGCTC GGG
```

The wild-type DNA sequence of the GRASP MSP amplicon is located on Chromosome 12, plus strand; 52,400,886⇒52,400,973 (Hg19)

```
cggaagtcgc gcccgccgct ccggtcccga ccccgggacc

ccctgccgca gccgccaccc ctgggccccc agcggacgag

ctgtacgc
```

The wild-type DNA sequence of the IKZF1 MSP amplicon is located on Chromosome 7, plus strand; 50,343,867⇒50,343,961 (Hg19)

gacgacgcac cctctccgtg tcccgctctg cgcccttctg cgcgccccgc tccctgtacc ggagcagcga tccgggaggc ggccgagagg tg The wild-type DNA sequence of the BCAT1 MSP amplicon is located on Chromosome 12, minus strand; 25,101,992⇒25,102,093 (Hg19)

gtcttcctgc tgatgcaatc CGctaggtcg cgagtctccg ccgcgagagg gccggtctgc aatccagccc gccacgtgta ctcgccgccg cctcg The wild-type DNA sequence of the IRF4 MSP amplicon is located on Chromosome 6, minus strand; 392,036⇒392,145 (Hg19)

tgggtgcctt ggacggcccc gcctcagcca ctcctggggc cccgacagtc cggttagctc atcccgtcca gcttgtggcg accccgtcgc aggagcgcgg agggcaggcg PCR Protocols Used to Measure the Methylation Levels Across GRASP, CAHM, IRF4, IKZF1 and BCAT1 in Plasma Specimens Real-Time PCR Protocols GRASP, CAHM, IRF4, BCAT1, IKZF1

| | CAHM | GRASP | IRF4 | BCAT1 | IKZF1 |
|---|---|---|---|---|---|
| FWD Primer | 5'GAAGGAA GTATTTCGA GTACGATTG AC 200 nM final | 5'CGGAAGT CGCGTTCGT C 200 nM final | 5'TGGGTGT TTTGGACG GTTTC 400 nM final | 5'GTTTTTTT GTTGATGTA ATTCGTTAG GTC 200 nM final | 5'GACGACG TATTTTTTT CGTGTTTC 200 nM final |
| REV primer | 5'CCCGAACG CAACGACTT AA 200 nM final | 5'GCGTACA ACTCGTCCG CTAA 200 nM final | 5'CGCCTAC CCTCCGCG 400 nM final | 5'CAATACC CGAAACGA CGACG 200 nM final | 5'GCGCACC TCTCGACCG 200 nM final |
| Probe | na | [HEX] TTCGATTTC GGGATTTTT TGTCGTAGT C [BHQ1] 100 nM final | [HEX] TCGTTTAGT TTGTGGCG ATTTCGTCG [BHQ1] 200 nM final | [HEX] TTCGTCGCG AGAGGGTC GGTT [BHQ] 200 nM final | na |
| 1x PCR | Platinum Taq DNA polymerase (Invitrogen) | Platinum Taq DNA polymerase (Invitrogen) | Platinum Taq DNA polymerase (Invitrogen) | Platinum Taq DNA polymerase (1nvitrogen) | GoTaq Hot Start buffer. 1x buffer contains 2 mM MgCl2 (Promega) |
| Final $MgCL_2$ conc. [mM] | 4.0 | 4.0 | 3.0 | 4.0 | +1.0 |
| dNTPs | 0.2 mM | 0.2 mM | 0.2 mM | 0.2 mM | — |
| SYBR | 1/120,000 | na | na | na | 1/120,000 |
| | | | LC480 cycling conditions | | |
| 1x<br>3x<br><br><br>47x | 95° C.; 2 min<br>92° C.; 15 sec<br>62° C.; 15 sec<br>72° C.; 20 sec<br>82° C.; 15 sec<br>62° C.; 15 sec<br>72° C.; 20 sec<br>(w/quant) | 95° C.; 2 min<br>92° C.; 15 sec<br>64° C.; 15 sec<br>72° C.; 20 sec<br>85° C.; 15 sec<br>64° C.; 15 sec<br>72° C.; 20 sec<br>(w/quant) | 95° C.; 2 min<br>50 cycles:<br>95° C.; 10 sec<br>61° C.; 20 sec<br>(w/quant) | 95° C.; 2 min<br>50 cycles:<br>95° C.; 15 sec<br>62° C.; 30 sec<br>72° C.; 30 sec<br>(w/quant) | 95° C.; 2 min<br>50 cycles:<br>95° C.; 15 sec<br>62° C.; 30 sec<br>72° C.; 30 sec<br>(w/quant) |
| melt curve analysis | 95° C.; 5 sec 65° C.; 1 min 97° C. continuous 0.11 deg/sec | na | na | na | 95° C.; 5 sec 65° C.; 1 min 97° C. continuous 0.11 deg/sec |

-continued

| | CAHM | GRASP | IRF4 | BCAT1 | IKZF1 |
|---|---|---|---|---|---|
| Correct Melt Temp (° C.) | <80° C. | na | na | na | 82.9-83.2° C. |

TABLE 1

| Gene | Genomic Strand | Current sub-region(s) of interest (genomic sequence) | Coordinates of sub-region(s) | Resulting bisulphite converted sequence (strands no longer complementary) | Oligonucleotide sequences for measurement of methylation levels |
|---|---|---|---|---|---|
| BCATI | top strand | 5'-cagtgccCGaggCGgCG gCGagtacaCGtggC GggctggattgcagacCGgcc ctctCGCGgCGgagactCGCGa cctagCGgattgcatcagcaggaagac (SEQ ID NO. 1) | 25,101,992-25,102,093 | 5'-tagtgttCGaggCGgCGgCG agtataCGtggCGggttgga ttgtagatCGgtttttttCGCGgC GgagattCGCGatttagCGgatt gtattagtaggaagat (SEQ ID NO: 27) | |
| | minus strand | 3'-gtcacggGCtccGCcGC cGCtcatgtGCaccGCc cgacctaacgtctgGCcggga gaGCGCcGCctctgaGCGCt ggatcGCctaacgtagtcgtccttctg (SEQ ID NO. 28) | | 3'-gttatggGCtttGCtGCtGC ttatgtGCattGCttgatttaatg tttgGCtgggagaGCGCtGCtttt gaGCGCtggattGCttaatgt agttgtttttttg (SEQ ID NO. 29) | 5'-gtttttttgttga tgtaattcgttaggtc (SEQ ID NO. 30) 5'-caatacccgaaac gacgacg (SEQ ID NO. 31) 5'-ttcgtcgcgagag ggtcggtt (SEQ ID NO. 32) 5'-tttttgttgatgt aattcgttaggtc (SEQ ID NO. 33) 5'-attacaaaccgac cctctcg (SEQ ID NO. 34) |
| | top strand | 5'-agatcccaagggtCGt agcccctggcCGtgtggacCGg gtctgCGgctgcagagCGCGg tcccCGgctgcagcaagacctgg ggcagt (SEQ ID NO. 2) | 25,101,909-25,101,995 | This sequence is for measuring CpG methylation levels using methylation sensitive restriction enzymes (e.g. HbaII, HhaI (underlined) | 5'-agatcccaaggg tcgtagc (SEQ ID NO. 35) 5'-actgccccaggt cttgct (SEQ ID NO. 36) |
| | minus strand | 3'-tctagggttcccaGCatc ggggaccgGCacacctgGCc cagacGCcgacgtctcGCGCca ggGCcgacgtcgttctggacc ccgtca(SEQ ID NO. 37) | | | |
| IKZF1 | top strand | 5'-gaCGaCGcaccctctcCG tgtccCGctctgCGccctt ctgCGCGcccCGctccctgtac CGgagcagCGatcCGggag gCGgcCGagaggtgCGc (SEQ ID NO. 3) | 50,343,867-50,343,961 | 5'-gaCGaCGtatttttttCGtgt ttCGttttgCGtttttttgCGCG tttCGtttttttgtatCGgagtag CGattCGggaggCGgtCGagagg tgCGt (SEQ ID NO. 38) | 5'-gacgacgtattttt ttcgtgtttc (SEQ ID NO. 39) 5'-gcgcacctctcgac cg (SEQ ID NO. 40) 5'-tttgtatcggagta gcgattcgggag (SEQ ID NO. 41) |
| | minus strand | 3'-ctGCtGCgtgggagag GCacaggGCgagacGCgg gaagacGCGCgggGCgaggg acatgGCctcgtcGCtagGC cctccGCcgGCtctccacGCg (SEQ ID NO. 42) | | 3'-ttGCtGCgtgggagagGC ataggGCgagatGCgggaa gatGCGCgggGCgagggatatg GCtttgttGCtagGCtttttGCt gGCtttttatGCg (SEQ ID NO. 43) | |
| | top strand | 5'-cCGgagttgCGgctga gaCGCGCGcCGCGCG agcCGggggactCGgCGaCG gggCGgggaCGggaCGa | 50,343,804-50,343,895 | This sequence is for measuring CpG methylation levels using | 5'-ggagttgcggct gagac (SEQ ID NO. 44) 5'-agagcgggacac |

TABLE 1-continued

| Gene | Genomic Strand | Current sub-region(s) of interest (genomic sequence) | Coordinates of sub-region(s) | Resulting bisulphite converted sequence (strands no longer complementary) | Oligonucleotide sequences for measurement of methylation levels |
|---|---|---|---|---|---|
| | | CGcaccctctcCGtgtccCGctct (SEQ ID NO. 4) | | methylation sensitive restriction enzymes (e.g. HbaII, HhaI (underlined) | ggaga (SEQ ID NO. 45) |
| | minus strand | 3'-gGCctcaacGCcgact ctGCGCGCgGCGCGC tcgGCcccctgaGCcGCt GCcccGCccctGCcctGCtGC gtgggagagGCacaggGCgaga (SEQ ID NO. 46) | | | |
| IRF4 | top strand | 5'-CGcctgccctcCGCG ctcctgCGaCGgggtCGcc acaagctggaCGgatgagcta acCGgactgtCGgggccccag gagtggctgaggCGgggcCGt ccaaggcaccca (SEQ ID NO. 5) | 392,036-392,145 | 5'-CGtttgtttttCGCGttttt gCGaCGgggtCGttataagttg gaCGgatgagttaatCGgattgt CGgggttttaggagtggttgagg CGgggtCGtttaaggtattta (SEQ ID NO. 47) | 5'-gtttttgcgacg gggtc (SEQ ID NO. 48) 5'-taaaaccccgac aatccg (SEQ ID NO. 49) |
| | minus strand | 3'-GCggacgggagGCGC gaggacGCtGCcccaGC ggtgttcgacctGCcctactcga ttgGCctgacaGCcccggggtc ctcaccgactccGCcccgGCa ggttccgtgggt (SEQ ID NO. 50) | | 3'-GCggatgggagGCGCgaggat GCtGCtttaGCggtgtttg atttGCtttatttgattgGCttga taGCtttggggttttattgattt tGCtttgGCaggttttgtgggt (SEQ ID NO. 51) | 5'-tgggtgttttgga cggtttc (SEQ ID NO. 52) 5'-tagttatttttgg ggtttcgatagttc (SEQ ID NO. 53) 5'-cgcctaccctccg cg (SEQ ID NO. 54) 5'-tcgtttagtttgt ggcgatttcgtcg (SEQ ID NO. 55) |
| GRASP | top strand | 5'-caggaagctgcagcag aaggaggaggCGgCGgcca cccCGgacccCGcCGccCGg actccCGactCGgaagtCG CGccCGcCGctcCGgtccCG acccCGggaccccctgcCG cagcCGccacccctgggccc ccagCGgaCGagctgtaCGCG gCGctggaggactatcaccctg cCGagctgtacCGCGCGctC GcCGtgtcCGggggcaccctg cccCGcCGaaaggtgCGtcc ccCGccCGccttcaggatctgct cagcccctctcCGactccctaca gggcctgctgactcCG (SEQ ID NO. 6) | 52,400,821-52,401,051 | 5'-taggaagttgtagtagaag gaggaggCGgCGgttatttCGga tttGCtCGttCGgattttCGatt CGgaagtCGCGttCGtCGttt CGgtttCGatttCGggatttttttgtC GtagtCGttatttttgggtttttag CGgaCGagttgtaCGCGgCGttgga ggattattattttgtCGagtt gtatCGCGCGttCGtCGtgttCGg gggtattttgtttCGtCGaaa ggtgCGtttttCGttCGtttttag gatttgtttagttttttttCGattt tttatagggttgttgatttCG (SEQ ID NO. 56) | 5'-cggaagtcgcgtt cgtc (SEQ ID NO. 57) 5'-gcgtacaactcgt ccgctaa (SEQ ID NO. 58) 5'-ttcgatttcggga tttttgtcgtagtc (SEQ ID NO. 59) 5'-cggattttcgatt cggaagt (SEQ ID NO. 60) |
| | minus strand | 3'-gtccttcgacgtcgtcttc ctcctccGCcGCcggtgggG CctgggGCgGCggGCctgagg GCtgaGCctcaGCGCgg GCgGCgagGCcaggGCtgggG Ccctgggggacgg GCgtcg GCggtggggacccgggggtc GCctGCtcgacatGCGCcGC gacctcctgatagtgggacg GCtcgacatgGCGCGCgaGCg GCacagGCccccgtgggacgg gGCgGCtttccacGCagggg GCggGCggaagtcctagacga gtcggggagagGCtgagggatg tcccggacgactgagGC (SEQ ID NO. 61) | | 3'-gtttttgatgttgtttttttt tttGCtGCtggtgggGCttgggGC gGCggGCttgaggGCtgaGCttta GCGCggGCgGCgagG CtaggGCtgggGCtttgggggatg GCgttgGCggtggggatttgg gggttGCttGCttgatatGCGCtG CgatttttgatagtgggatgGC ttgatatgGCGCGCgaGCgGCata gGCttttgtgggatgggGC gGCtttttatGCaggggGCggGC ggaagttttagatgagttgggga gagGCtgagggatgttttggatg attgagGC (SEQ ID NO. 62) | 5'-ggtagggtgtttt cggatac (SEQ ID NO. 63) 5'-aacgaacgaacta tacgcgac (SEQ ID NO. 64) |
| | top strand | 5'-gacagagacagccccaggc aagttgaaggtcCGagagc cccCGgtgggagaagCGggc CGgtggctgCGcCGCGtgC GttctcactctgaggaagtgCG tggggagcCGctgactcCGgata gcacacccttcCGaggggactcc | 52,401,407-52,401,664 | 5'-gatagagatagttttaggtaag ttgaaggttCGagagttttCGgtgg gagaagCGggtCGgtggttgCGtC GCGtgCGtttttattttgagg aagtgCGtggggagtCGttgattt CGgatagtatatttttttCGagggg atttttCGatttttgggttgggggtt | |

TABLE 1-continued

| Gene | Genomic Strand | Current sub-region(s) of interest (genomic sequence) | Coordinates of sub-region(s) | Resulting bisulphite converted sequence (strands no longer complementary) | Oligonucleotide sequences for measurement of methylation levels |
|---|---|---|---|---|---|
| | | cCGattcctgggctgggggcct<br>gcCGcctggccccaCGtctga<br>CGtaCGgggCGCGagggcc<br>actgctccctggacttctgtCGg<br>aacCGgaCGcagtgggaggggt<br>CGcagg<br>(SEQ ID NO. 7) | | tgtCGtttggttttaCGtttgaCGta<br>CGgggCGCGagggttattgtttttg<br>gattttgtCGgaatCGgaC<br>GtagtgggaggggtCGtagg<br>(SEQ ID NO. 65) | |
| | minus strand | 3'-ctgtctctgtcggggtccg<br>ttcaacttccagGCtctcgggg<br>GCcaccctcttcGCccgGCca<br>ccgacGCgGCGCacGCaa<br>gagtgagactccttcacGCaccc<br>ctcgGCgactgagGCctatcgt<br>gtgggaagGCtcccctgagggGC<br>taaggacccgacccccggacg<br>GCggaccggggtGCagactGC<br>atGCcccGCGCtcccggtg<br>acgagggacctgaagacaGCct<br>tgGCctGCgtcaccctccccaG<br>Cgtcc (SEQ ID NO. 66) | | 3'-ttgtttttgttggggtttgtttaat<br>ttttagGCttttggggGCtattttttt<br>tGCttgGCtattgatGCgGCGCatGCa<br>agagtgagatttttttatG<br>CatttttttgGCgattgagGCttattg<br>tgtgggaagGCtttttttgagggG<br>CtaaggatttgattttggatgGCgg<br>attggggtGCagattGCatGCt<br>ttGCGCttttggtgatgagggattt<br>gaagataGCtttgGCttGCgttat<br>tttttttaGCgttt<br>(SEQ ID NO. 67) | 5'-cggagttagcggt<br>tttttacg<br>(SEQ ID NO. 68)<br>5'-cgataaaaaaaac<br>gaaccga<br>(SEQ ID NO. 69)<br>5'-agagtgagaacgt<br>acgcggc<br>(SEQ ID NO. 70) |
| | top strand | 5'-gacagagacagccccag<br>gcaagttgaaggtcCGagag<br>ccccCGgtgggagaagCGgg<br>cCGgtggctgCGcCGCGtg<br>CGttctcactctgaggaagtgCG<br>tggggagcCGctgactcCGga<br>tagcacacccttcCGaggggact<br>ccccCGattcctgggctgggggcc<br>tgcCGcctggccccaCGtctg<br>aCGtaCGgggCGCGagggc<br>cactgctccctggacttctgtCG<br>gaacCGgaCGcagtgggaggg<br>gtCGcagg (SEQ ID NO. 71) | | This sequence is for measuring CpG methylation levels using methylation sensitive restriction enzymes (e.g. HbaII, HhaI (underlined) | 5'-caagttgaaggtc<br>cgagagc<br>(SEQ ID NO. 72)<br>5'-cgcacttcctcag<br>agtgaga<br>(SEQ ID NO. 73) |
| | minus strand | 3'-ctgtctctgtcggggtccgt<br>tcaacttccagGCtctcgggg<br>GCcaccctcttcGCccgGCc<br>accgacGCgGCGCacGCaa<br>gagtgagactccttcacGCaccc<br>ctcgGCgactgagGCctatcgt<br>gtgggaagGCtcccctgagggGC<br>taaggacccgacccccggacg<br>GCggaccggggtGCagactGC<br>atGCcccGCGCtcccggtg<br>acgagggacctgaagacaGCct<br>tgGCctGCgtcaccctccccaG<br>Cgtcc (SEQ ID NO. 74) | | | |
| CAHM | top strand | 5'-atctgtaaaaatgttgactt<br>ctgcttttcagactaCGCGcac<br>agcctctttatttcctactgCGgc<br>ttcattccctcaCGgaacactgaC<br>GccatCGCGaaggaagcattt<br>CGagcaCGactgaCGctcccc<br>ttattatttgctaagcCGctgCGc<br>tCGggtctggctaCGatttgcttt<br>cagaataaCGggaaggtgcaacaaga<br>(SEQ ID NO. 8) | 163,834,295-<br>163,834,500 | 5'-atttgtaaaaatgttgatttttgtt<br>ttttagattaCGCGtatagtttttttatt<br>ttttattgCGgttttatttttttaCGg<br>aatattgaCGttatCGCGaagga<br>agtatttCGagtaCGattgaCGtttt<br>ttttattatttgttaagtCGttgCGt<br>tCGggtttggttaCGatttgtttttag<br>aataaCGggaaggtgtaataaga<br>(SEQ ID NO. 75) | 5'-gaaggaagtattt<br>cgagtacgattgacc<br>(SEQ ID NO. 76)<br>5'-cccgaacgcaacg<br>acttaa<br>(SEQ ID NO. 77)<br>5'-gcctctaaaaaaa<br>cgatcttattacacc<br>(SEQ ID NO. 78) |
| | minus strand | 3'-tagacatttttacaactg<br>aagacgaaaagtctgatGCGCg<br>tgtcggagaaataaaggatgacG<br>CcgaagtaagggagtGCcttgtg<br>actGCggtaGCGCttccttcg<br>taaaGCtcgtGCtgactGCgag<br>gggaataataaacgattcgGC<br>gacGCgaGCccagaccgatGCt<br>aaacgaaagtcttattGCc<br>cttccacgttgttct<br>(SEQ ID NO. 79) | | 3'-tagatatttttataattgaagat<br>gaaaagtttgatGCGCgtgttggag<br>aaataaaggatgatGCtgaagtaagg<br>gagtGCtttgtgattGCggta<br>GCGCtttttttgtaaaGCttgtGC<br>tgattGCgaggggaataataaatg<br>atttgGCgatGCgaGCttagattga<br>tGCtaaatgaaagttttattGCtt<br>ttttatgttgtttt<br>(SEQ ID NO. 80) | 5'-gaaacactaacg<br>ccatcg<br>(SEQ ID NO. 81)<br>5'-cgtagttagatt<br>cgagcgtag<br>(SEQ ID NO. 82)<br>5'-aggggagcgtta<br>gtcgtgttcgaaa<br>(SEQ ID NO. 83) |

TABLE 1-continued

| Gene | Genomic Strand | Current sub-region(s) of interest (genomic sequence) | Coordinates of sub-region(s) | Resulting bisulphite converted sequence (strands no longer complementary) | Oligonucleotide sequences for measurement of methylation levels |
|---|---|---|---|---|---|
| | minus strand | 3'-cgGCacgacgaaaggtcg gagagtcgtttagtGCttgt gGCtttcttcggtGCcGCc GCtGCcctccccGCaGCGCG CacgaagggaGCcGCtgtt tcGCcctcgGCccGCGCgGC cgGCtcccGCggGCcGCgtc tcaggGCgtctccGCctGCg GCGCcgtGCGCggaGCttttc ggagtttgagaataggaGCcg agaggGCggggtggagGCgg gGCgtcggttctggGCGCgG CaccGCccggGCtGCcggtt cctttcgggtggtcgggagGC tgGCac (SEQ ID NO. 84) | 163,834,621-163,834,906 | tgGCatgatgaaaggttggagagttg tttagtGCttgtgGCtttttttggt GCtGCtGCtGCtttttttGCaGGGC GCatgaagggaGCtGC tgttttGCttttgGCttGCGCgGCt gGCttttGCggGCtGCgttt taggGCgtttttGCttGCgGCGCtg tGCGCggaGCtttttggag tttgagaataggaGCtgagaggGC ggggtggagGCgggGCgttg gttttggGCGCgGCattGCttggGC tGCtggttttttttgggtggttg ggagGC tgGCat (SEQ ID NO. 85) | 5'-gtttttttcgg cgataaagc (SEQ ID NO. 86) 5'-cgcctctacga aactctacg (SEQ ID NO. 87) 5'-cgtcggtcgag ggcgttc (SEQ ID NO. 88) |

BIBLIOGRAPHY

Abrams and Stanton, *Methods Enzymol.,* 212:71-74, 1992

Adorjan et al. *Nucl. Acids Res.,* 30: e21, 2002

Alon et al., *Proc. Natl. Acad. Sci. USA:* 96:6745-6750, June 1999

Ammerpohl et al. *Biochim Biophys Acta.* 1790:847-62, 2009

Beaucage, et al. *Tetrahedron Letters* 22:1859-1862, 1981

Bianco et al., *Hum. Mutat.,* 14:289-293, 1999

Bonner and Laskey, *Eur. J Biochem.* 46:83, 1974

Bresslauer et al., *Proc. Natl. Acad. Sci. USA,* 83: 3746-3750, 1986

Caruthers, M. H., et al., *Methods in Enzymology,* Vol. 154, pp. 287-314 (1988)

Chen and Kwok, *Nucleic Acids Res.* 25:347-353, 1997

Clark et al. *Nat Protoc.* 1:2353-64, 2006

Clark et al., *Nucl. Acids Res.* 22:2990-2997, 1994

Cottrell et al., *Nucl. Acids Res.* 32: e10, 2003

DeGraves, et al., *Biotechniques* 34(1):106-10, 112-5 (2003)

Deiman B, et al., *Mol. Biotechnol.* 20(2):163-79 (2002)

Deng et al. *Chin. J. Cancer Res.,* 12:171-191, 2000

Dieffenbach (ed) and Dveksler (ed) (In: PCR Primer: A Laboratory Manual, Cold Spring Harbour Laboratories, N Y, 1995

Eads et al., *Nucl. Acids Res.* 28: E32, 2000

Egholm et al., *Am. Chem. Soc.,* 114:1895, 1992

Egholm et al., *Nature,* 365:566, 1993

Fodor et al., *Science* 767-773, 1991

Frommer et al., *Proc. Natl. Acad. Sci. USA* 89:1827-1831 (1992)

Gibson et al., *Genome Research* 6:995-1001 (1996)

Golub et al., *Science,* 286:531-537, 1999

Gonzalgo & Jones, *Nucleic Acids Res.* 25:2529-2531 (1997)

Gonzalgo et al., *Cancer Res.* 57:594-599, 1997

Gregory and Feil, *Nucleic Acids Res.,* 27, e32i-e32iv, 1999

Havelange et al., *Blood* 2011, 118:2827

Herman et al. *Proc. Natl. Acad. Sci. USA* 93:9821-9826 (1996)

Holland et al., *Proc. Natl. Acad. Sci. USA,* 88:7276-7280, 1991

Javierre et al., *Mol. Cancer Res.* 9(8):1139-51, 2011

Kawai et al., *Mol. Cell. Biol.* 14:7421-7427, 1994

Kibriya et al., *BMC* 2011, 4:50

Kristensen and Hansen *Clin Chem.* 55:1471-83, 2009

Kuppuswamy et al., *Proc. Natl. Acad. Sci. USA* 88:1143-1147, 1991

Landegren et al., *Genome Res.,* 8(8): 769-776, 1998

Lee et al., *Nucleic Acid Res.* 21:3761-3766, 1993

Markowitz and Bertagnolli, 2009, *N Engl. J. Med.* 361(25): 2449-60

Marmur and Doty, *J. Mol. Biol.* 5:109, 1962

Martinez et al., *Am. J. Surg Pathol.* 2012, 36:296

McPherson et al., PCR: A Practical Approach. (series eds, D. Rickwood and B. D. Hames), IRL Press Limited, Oxford. pp 1-253, 1991

Messing, *Methods Enzymol,* 101, 20-78, 1983

Mhlanga and Malmberg, *Methods* 25:463-471, 2001

Moore et al., *BBA,* 1402:239-249, 1988

Narang, et al. *Meth. Enzymol* 68: 90, 1979

Nevrivy et al. *JBC* 2000, 275(22):16827-36

Nielsen et al. *J. Chem. Soc. Perkin Trans.,* 1:3423, 1997

Olek, et al. *Nat. Genet.* 17(3): 275-6 (1997)

Orum et al., *Clin. Chem.* 45:1898-1905, 1999

Orum et al., *Nucl. Acids Res.,* 21:5332, 1993

Oster et al., *Int. J. Cancer* 2011, 129:2855

Pathak et al. *PLoS One* 2011, 6:e22628

Rand et al. *Epigenetics* 1:94-100, 2006

Rand et al. *Nucl. Acids Res.* 33:e127, 2005

Rein, et al. *Nucleic Acids Res.* 26 (10): 2255-64 (1998)

Sadri & Hornsby, *Nucl. Acids Res.* 24:5058-5059 (1996)

Sambrook et al., *Molecular Cloning, A Laboratory Manual* (2nd Ed., CSHP, New York 1989)

Santa Lucia, *Proc. Natl. Acad. Sci. USA,* 95: 1460-1465, 1995

Shames et al. *Cancer Lett.* 251:187-98, 2007

Simeonov and Nikiforov, *Nucleic Acids Research,* 30(17): 1-5, 2002

Singer-Sam et al., *Nucl. Acids Res.* 18:687, 1990

Singer-Sam et al., *PCR Methods Appl.* 1: 160-163, 1992

Singh and Wengel, *Chem. Commun.* 1247, 1998

Slattery et al., *Carcinogenesis* 2011, 32:160

Southern et al., *Genomics,* 13:1008-1017, 1992

Szabo and Mann, *Genes Dev.* 9: 3097-3108, 1995

Toyota et al., *Cancer Res.* 59:2307-12 (1999)

Uhlmann et al., *Electrophoresis,* 23:4072-4079, 2002

Wedemeyer et al., *Clinical Chemistry* 48:9 1398-1405, 2002

Weissleder et al., *Nature Medicine* 6:351-355, 2000

Weitzel J N (December 1999), *Cancer* 86 (11 Suppl): 2483-92

Worm et al., *Clin. Chem.,* 47:1183-1189, 2001

Xiong & Laird, *Nucleic Acids Res.* 25:2532-2534 (1997)

Yamashita et al. (*Cancer Sci.* 2010, 101:1708

Zyskind et al., Recombinant DNA Laboratory Manual, (Acad. Press, 1988)

The invention claimed is:

1. A method of assessing the methylation status of DNA present in a biological sample obtained from a human individual at risk of developing or of recurrence of, or suffering from, a large intestine neoplasm, consisting of:

assessing the methylation status of a BCAT1 gene by detecting the methylation status of one or more DNA subregions located within the BCAT1 gene, wherein the subregions are SEQ ID NO: 1 or SEQ ID NO: 2 or the complements thereof, by performing a bisulfite conversion of the one or more DNA subregions, amplifying the converted BCAT1 DNA subregions or the complement thereof with primers comprising a nucleic acid sequence that is complementary to the converted BCAT1 DNA subregions under selective hybridization conditions, and detecting the methylation status of one or more cytosines in the one or more DNA subregions; and assessing the methylation status of an IKZF1 gene by detecting the methylation status of one or more DNA subregions located within the IKZF1 gene, wherein the subregions are SEQ ID NO: 3 or SEQ ID NO: 4 or the complements thereof, by performing a bisulfite conversion of the one or more DNA subregions, amplifying the converted IKZF1 DNA subregions or the complement thereof with primers comprising a nucleic acid sequence that is complementary to the converted IKZF1 DNA subregions under selective hybridization conditions, and detecting the methylation status of one or more cytosines in the one or more DNA subregions.

2. The method of claim 1, wherein the one or more DNA subregions located within the BCAT1 gene is within a nucleic acid sequence as set forth in SEQ ID NO:1; and the one or more DNA subregions located within the IKZF1 gene is within a nucleic acid sequence as set forth in SEQ ID NO:3.

3. The method of claim 1, wherein detecting the methylation status of the one or more DNA subregions located within the BCAT1 gene comprises detecting the methylation of one or more cytosine residues in the gene region encompassing BCAT1; and detecting the methylation status of the one or more DNA subregions located within the IKZF1 gene comprises detecting the methylation of one or more cytosine residues in the gene region encompassing IKZF1.

4. The method of claim 1, wherein detecting the methylation status of the one or more DNA subregions located within the IKZF1 gene consists of detecting the methylation of one or more cytosine residues on the plus strand selected from chr7:50343869 chr7:50343872 chr7:50343883 chr7:50343889 chr7:50343890 chr7:50343897 chr7:50343907 chr7:50343909 chr7:50343914 chr7:50343934 chr7:50343939 chr7:50343950 chr7:50343959 chr7:50343805 chr7:50343822 chr7:50343824 chr7:50343826 chr7:50343829 chr7:50343831 chr7:50343833 chr7:50343838 chr7:50343847 chr7:50343850 chr7:50343858 and chr7:50343864 or a corresponding cytosine residue at position n+1 on the opposite strand.

5. The method of claim 1, wherein the large intestine neoplasm is an adenoma or an adenocarcinoma.

6. The method of claim 1, wherein the large intestine neoplasm is a colorectal neoplasia.

7. The method of claim 1, wherein the biological sample is selected from a faecal sample, enema wash, surgical resection, tissue biopsy, and blood sample.

8. The method of claim 1, wherein the biological sample is a plasma sample.

9. The method of claim 1, further comprising administering a cancer treatment to the individual when methylation is detected at one or more cytosines in at least one of the DNA subregions.

10. The method of claim 1, wherein the primers comprising a nucleic acid sequence that is complementary to the converted BCAT1 DNA subregions comprise a sequence as set forth in SEQ ID NO: 17 and SEQ ID NO: 22.

11. The method of claim 1, wherein the primers comprising a nucleic acid sequence that is complementary to the converted IKZF1 DNA subregions comprise a sequence as set forth in SEQ ID NO: 18 and SEQ ID NO: 23.

12. A method of treating a human individual suffering from or at risk of developing or of recurrence of a large intestine neoplasm, comprising:

assessing the methylation status of DNA present in a biological sample obtained from the human individual by a process consisting of:

assessing the methylation status of a BCAT1 gene by detecting the methylation status of one or more DNA subregions located within the BCAT1 gene, wherein the subregions are SEQ ID NO: 1 or SEQ ID NO: 2 or the complements thereof, by performing a bisulfite conversion of the one or more DNA subregions, amplifying the converted BCAT1 DNA subregions or the complement thereof with primers comprising a nucleic acid sequence that is complementary to the converted BCAT1 DNA subregions under selective hybridization conditions, and detecting the methylation status of one or more cytosines in the one or more DNA subregions; and assessing the methylation status of an IKZF1 gene by detecting the methylation status of one or more DNA subregions located within the IKZF1 gene, wherein the subregions are SEQ ID NO: 3 or SEQ ID NO: 4 or the complements thereof, by performing a bisulfite conversion of the one or more DNA subregions, amplifying the converted IKZF1 DNA subregions or the complement thereof with primers comprising a nucleic acid sequence that is complementary to the converted IKZF1 DNA subregions under selective hybridization conditions, and detecting the methylation status of one or more cytosines in the one or more DNA subregions; and administering a cancer treatment to the human individual, wherein the human individual has:

(i) a methylated BCAT1 DNA subregion that is SEQ ID NO: 1 and/or 2; and or (ii) a methylated IKZF1 DNA subregion that is SEQ ID NO: 3 and/or 4.

13. The method of claim 12, further comprising assessing a post-treatment methylation status of DNA present in a biological sample obtained from the individual at a time point subsequent to said administering, comprising:

(i) detecting a methylation status of a BCAT1 DNA subregion that is SEQ ID NO: 1 by performing a bisulfite conversion of the DNA subregion, amplifying the converted BCAT1 DNA subregion with primers that are SEQ ID NO: 17 and SEQ ID NO: 2, and detecting the methylation status of one or more cytosines in the DNA subregion; and (ii) detecting a methylation status of an IKZF1 DNA subregion that is SEQ ID NO: 3 by performing a bisulfite conversion of the DNA subregion, amplifying the converted IKZF1 DNA subregion with primers that are SEQ ID NO: 18 and SEQ ID NO: 23, and detecting the methylation status of one or more cytosines in the DNA subregion.

14. A method of monitoring the methylation status of a human individual suffering from or at risk of developing or of recurrence of a large intestine neoplasm, comprising (a) assessing a first methylation status of DNA present in a first biological sample obtained at a first time point from a human individual suffering from or at risk of developing a large intestine neoplasm, comprising:

(i) detecting a first methylation status of a DNA subregion located within the BCAT1 gene, wherein the subregion is SEQ ID NO: 1 or SEQ ID NO: 2 or the complement thereof, by performing a bisulfite conversion of the DNA subregion, amplifying the converted BCAT1 DNA subregion or the complement thereof with primers comprising a nucleic acid sequence that is complementary to the converted BCAT1 DNA subregion under selective hybridization conditions, and detecting the methylation status of one or more cytosines in the DNA subregion; and (ii) detecting a first methylation status of a DNA subregion located within the IKZF1, wherein the subregion is SEQ ID NO: 3 or SEQ ID NO: 4 or the complement thereof, by performing a bisulfite conversion of the DNA subregion, amplifying the converted IKZF1 DNA subregion or the complement thereof with primers comprising a nucleic acid sequence that is complementary to the converted IKZF1 DNA subregion under selective hybridization conditions, and detecting the methylation status of one or more cytosines in the DNA subregion; and (b) assessing a second methylation status of DNA present in a second biological sample obtained from the individual at a second time point subsequent to the first time point, comprising:

(i) detecting a second methylation status of a BCAT1 DNA subregion that is SEQ ID NO: 1 or SEQ ID NO: 2 or the complement thereof, by performing a bisulfite conversion of the DNA subregion and detecting the methylation status of one or more cytosines in the DNA subregion; and (ii) detecting a second methylation status of an IKZF1 DNA subregion that is SEQ ID NO: 3 or SEQ ID NO: 4 or the complement thereof, by performing a bisulfite conversion of the DNA subregion and detecting the methylation status of one or more cytosines in the DNA subregion.

* * * * *

SEQUENCE LISTING

<160> NUMBER OF SEQ ID NOS: 93

<210> SEQ ID NO 1
<211> LENGTH: 102
<212> TYPE: DNA
<213> ORGANISM: Homo sapiens

<400> SEQUENCE: 1
cagtgcccga ggcggcggcg agtacacgtg gcgggctgga ttgcagaccg gccctctcgc 60
ggcggagact cgcgacctag cggattgcat cagcaggaag ac 102

<210> SEQ ID NO 2
<211> LENGTH: 87
<212> TYPE: DNA
<213> ORGANISM: Homo sapiens

<400> SEQUENCE: 2
agatcccaag ggtcgtagcc cctggccgtg tggaccgggt ctgcggctgc agagcgcggt 60
cccggctgca gcaagacctg gggcagt 87

<210> SEQ ID NO 3
<211> LENGTH: 95
<212> TYPE: DNA
<213> ORGANISM: Homo sapiens

<400> SEQUENCE: 3
gacgacgcac cctctccgtg tcccgctctg cgcccttctg cgcgccccgc tccctgtacc 60
ggagcagcga tccgggaggc ggccgagagg tgcgc 95

<210> SEQ ID NO 4
<211> LENGTH: 92
<212> TYPE: DNA
<213> ORGANISM: Homo sapiens

<400> SEQUENCE: 4
ccggagttgc ggctgagacg cgcgccgcgc gagccggggg actcggcgac ggggcgggga 60
cgggacgacg caccctctcc gtgtcccgct ct 92

<210> SEQ ID NO 5
<211> LENGTH: 110
<212> TYPE: DNA
<213> ORGANISM: Homo sapiens

<400> SEQUENCE: 5
cgcctgccct ccgcgctcct gcgacggggt cgccacaagc tggacgggat gagctaaccg 60
gactgtcggg gccccaggag tggctgaggc ggggccgtcc aaggcaccca 110

<210> SEQ ID NO 6
<211> LENGTH: 299
<212> TYPE: DNA
<213> ORGANISM: Homo sapiens

<400> SEQUENCE: 6
caggaagctg cagcagaagg aggaggcggc ggccaccccg gaccccgccg cccggactcc 60
cgactcggaa gtcgcgcccg ccgctccggt cccgaccccg ggaccccctg ccgcagccgc 120
cacccctggg cccccagcgg acgagctgta cgcggcgctg gaggactatc accctgccga 180
gctgtaccgc gcgctcgccg tgtccggggg caccctgccc cgccgaaagg tgcgtccccc 240
gcccgccttc aggatctgct cagcccctct ccgactccct acagggcctg ctgactccg 299

-continued

<210> SEQ ID NO 7
<211> LENGTH: 258
<212> TYPE: DNA
<213> ORGANISM: Homo sapiens

<400> SEQUENCE: 7
gacagagaca gccccaggca agttgaaggt ccgagagccc ccggtgggag aagcgggccg 60
gtggctgcgc cgcgtgcgtt ctcactctga ggaagtgcgt ggggagccgc tgactccgga 120
tagcacaccc ttccgagggg actccccgat tcctgggctg ggggcctgcc gcctggcccc 180
acgtctgacg tacggggcgc gagggccact gctccctgga cttctgtcgg aaccggacgc 240
agtgggaggg gtcgcagg 258

<210> SEQ ID NO 8
<211> LENGTH: 206
<212> TYPE: DNA
<213> ORGANISM: Homo sapiens

<400> SEQUENCE: 8
atctgtaaaa atgttgactt ctgcttttca gactacgcgc acagcctctt tatttcctac 60
tgcggcttca ttccctcacg gaacactgac gccatcgcga aggaagcatt tcgagcacga 120
ctgacgctcc ccttattatt tgctaagccg ctgcgctcgg gtctggctac gatttgcttt 180
cagaataacg ggaaggtgca acaaga 206

<210> SEQ ID NO 9
<211> LENGTH: 63
<212> TYPE: DNA
<213> ORGANISM: Homo sapiens

<400> SEQUENCE: 9
gaaggaagca tttcgagcac gactgacgct ccccttatta tttgctaagc cgctgcgctc 60
ggg 63

<210> SEQ ID NO 10
<211> LENGTH: 88
<212> TYPE: DNA
<213> ORGANISM: Homo sapiens

<400> SEQUENCE: 10
cggaagtcgc gcccgccgct ccggtcccga ccccgggacc ccctgccgca gccgccaccc 60
ctgggccccc agcggacgag ctgtacgc 88

<210> SEQ ID NO 11
<211> LENGTH: 92
<212> TYPE: DNA
<213> ORGANISM: Homo sapiens

<400> SEQUENCE: 11
gacgacgcac cctctccgtg tcccgctctg cgcccttctg cgcgccccgc tccctgtacc 60
ggagcagcga tccgggaggc ggccgagagg tg 92

<210> SEQ ID NO 12
<211> LENGTH: 95
<212> TYPE: DNA
<213> ORGANISM: Homo sapiens

<400> SEQUENCE: 12

-continued gtcttcctgc tgatgcaatc cgctaggtcg cgagtctccg ccgcgagagg gccggtctgc 60
aatccagccc gccacgtgta ctcgccgccg cctcg 95

<210> SEQ ID NO 13
<211> LENGTH: 110
<212> TYPE: DNA
<213> ORGANISM: Homo sapiens

<400> SEQUENCE: 13
tgggtgcctt ggacggcccc gcctcagcca ctcctggggc cccgacagtc cggttagctc 60
atcccgtcca gcttgtggcg accccgtcgc aggagcgcgg agggcaggcg 110

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gaaggaagta tttcgagtac gattgac 27

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
cggaagtcgc gttcgtc 17

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
tgggtgtttt ggacggtttc 20

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 17 gttttttgt tgatgtaatt cgttaggtc 29

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
gacgacgtat ttttttcgtg tttc 24

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
cccgaacgca acgacttaa 19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gcgtacaact cgtccgctaa 20

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
cgcctaccct ccgcg 15

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
caatacccga aacgacgacg 20

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gcgcacctct cgaccg 16

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic probe

<400> SEQUENCE: 24
ttcgatttcg ggatttttttg tcgtagtc 28

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 25
tcgtttagtt tgtggcgatt tcgtcg 26

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic probe

<400> SEQUENCE: 26
ttcgtcgcga gagggtcggt t 21

<210> SEQ ID NO 27
<211> LENGTH: 102
<212> TYPE: DNA
<213> ORGANISM: Homo sapiens

<400> SEQUENCE: 27
tagtgttcga ggcggcggcg agtatacgtg gcgggttgga ttgtagatcg gttttttcgc 60
ggcggagatt cgcgatttag cggattgtat tagtaggaag at 102

<210> SEQ ID NO 28
<211> LENGTH: 102
<212> TYPE: DNA
<213> ORGANISM: Homo sapiens

<400> SEQUENCE: 28
gtcttcctgc tgatgcaatc cgctaggtcg cgagtctccg ccgcgagagg gccggtctgc 60
aatccagccc gccacgtgta ctcgccgccg cctcgggcac tg 102

<210> SEQ ID NO 29
<211> LENGTH: 102
<212> TYPE: DNA
<213> ORGANISM: Homo sapiens

<400> SEQUENCE: 29
gtttttttgt tgatgtaatt cgttaggtcg cgagttttcg tcgcgagagg gtcggtttgt 60
aatttagttc gttacgtgta ttcgtcgtcg tttcgggtat tg 102

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
gtttttttgt tgatgtaatt cgttaggtc 29

<210> SEQ ID NO 31
<211> LENGTH: 20

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
caatacccga aacgacgacg 20

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ttcgtcgcga gagggtcggt t 21

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tttttgttga tgtaattcgt taggtc 26

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
attacaaacc gaccctctcg 20

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
agatcccaag ggtcgtagc 19

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
actgccccag gtcttgct 18

<210> SEQ ID NO 37
<211> LENGTH: 87
<212> TYPE: DNA

<213> ORGANISM: Homo sapiens

<400> SEQUENCE: 37
actgccccag gtcttgctgc agccgggacc gcgctctgca gccgcagacc cggtccacac 60
ggccaggggc tacgaccctt gggatct 87

<210> SEQ ID NO 38
<211> LENGTH: 95
<212> TYPE: DNA
<213> ORGANISM: Homo sapiens

<400> SEQUENCE: 38
gacgacgtat ttttttcgtg tttcgttttg cgtttttttg cgcgtttcgt tttttgtatc 60
ggagtagcga ttcgggaggc ggtcgagagg tgcgt 95

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
gacgacgtat ttttttcgtg tttc 24

<210> SEQ ID NO 40
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
gcgcacctct cgaccg 16

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
tttgtatcgg agtagcgatt cgggag 26

<210> SEQ ID NO 42
<211> LENGTH: 95
<212> TYPE: DNA
<213> ORGANISM: Homo sapiens

<400> SEQUENCE: 42
gcgcacctct cggccgcctc ccggatcgct gctccggtac agggagcggg gcgcgcagaa 60
gggcgcagag cgggacacgg agagggtgcg tcgtc 95

<210> SEQ ID NO 43
<211> LENGTH: 95
<212> TYPE: DNA
<213> ORGANISM: Homo sapiens

<400> SEQUENCE: 43

-continued gcgtattttt cggtcgtttt tcggatcgtt gtttcggtat agggagcggg gcgcgtagaa 60
gggcgtagag cgggatacgg agagggtgcg tcgtt 95

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
ggagttgcgg ctgagac 17

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
agagcgggac acggaga 17

<210> SEQ ID NO 46
<211> LENGTH: 92
<212> TYPE: DNA
<213> ORGANISM: Homo sapiens

<400> SEQUENCE: 46
agagcgggac acggagaggg tgcgtcgtcc cgtccccgcc ccgtcgccga gtcccccggc 60
tcgcgcggcg cgcgtctcag ccgcaactcc gg 92

<210> SEQ ID NO 47
<211> LENGTH: 110
<212> TYPE: DNA
<213> ORGANISM: Homo sapiens

<400> SEQUENCE: 47
cgtttgtttt tcgcgttttt gcgacggggt cgttataagt tggacgggat gagttaatcg 60
gattgtcggg gttttaggag tggttgaggc ggggtcgttt aaggtattta 110

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
gtttttgcga cggggtc 17

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
taaaaccccg acaatccg 18

<210> SEQ ID NO 50
<211> LENGTH: 110
<212> TYPE: DNA
<213> ORGANISM: Homo sapiens

<400> SEQUENCE: 50
tgggtgcctt ggacggcccc gcctcagcca ctcctggggc cccgacagtc cggttagctc 60
atcccgtcca gcttgtggcg accccgtcgc aggagcgcgg agggcaggcg 110

<210> SEQ ID NO 51
<211> LENGTH: 110
<212> TYPE: DNA
<213> ORGANISM: Homo sapiens

<400> SEQUENCE: 51
tgggtgtttt ggacggtttc gttttagtta tttttggggt ttcgatagtt cggttagttt 60
atttcgttta gtttgtggcg atttcgtcgt aggagcgcgg agggtaggcg 110

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 52
tgggtgtttt ggacggtttc 20

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 53
tagttatttt tggggtttcg atagttc 27

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 54
cgcctaccct ccgcg 15

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 55
tcgtttagtt tgtggcgatt tcgtcg 26

<210> SEQ ID NO 56

<211> LENGTH: 299
<212> TYPE: DNA
<213> ORGANISM: Homo sapiens

<400> SEQUENCE: 56
taggaagttg tagtagaagg aggaggcggc ggttatttcg gatttcgtcg ttcggatttt 60
cgattcggaa gtcgcgttcg tcgtttcggt ttcgatttcg ggatttttg tcgtagtcgt 120 tatttttggg tttttagcgg acgagttgta cgcggcgttg gaggattatt attttgtcga 180
gttgtatcgc gcgttcgtcg tgttcggggg tattttgttt cgtcgaaagg tgcgtttttc 240
gttcgttttt aggatttgtt tagttttttt tcgatttttt atagggtttg ttgatttcg 299

<210> SEQ ID NO 57
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 57
cggaagtcgc gttcgtc 17

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 58
gcgtacaact cgtccgctaa 20

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 59
ttcgatttcg ggatttttg tcgtagtc 28

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 60
cggattttcg attcggaagt 20

<210> SEQ ID NO 61
<211> LENGTH: 298
<212> TYPE: DNA
<213> ORGANISM: Homo sapiens

<400> SEQUENCE: 61
cggagtcagc aggccctgta gggagtcgga gaggggctga gcagatcctg aaggcgggcg 60
ggggacgcac ctttcggcgg ggcagggtgc ccccggacac ggcgagcgcg cggtacagct 120
cggcagggtg atagtcctcc agcgccgcgt acagctcgtc cgctgggggc ccaggggtgg 180
cggctgcggc agggggtccc ggggtcggga ccggagcggc gggcgcgact ccgagtcggg 240
agtccgggcg gcggggtccg gggtggccgc cgcctcctcc ttctgctgca gcttcctg 298

<210> SEQ ID NO 62
<211> LENGTH: 298
<212> TYPE: DNA
<213> ORGANISM: Homo sapiens

<400> SEQUENCE: 62
cggagttagt aggttttgta gggagtcgga gaggggttga gtagattttg aaggcgggcg 60
ggggacgtat ttttcggcgg ggtagggtgt tttcggatac ggcgagcgcg cggtatagtt 120
cggtagggtg atagtttttt agcgtcgcgt atagttcgtt cgttgggggt ttaggggtgg 180
cggttgcggt agggggtttc ggggtcggga tcggagcggc gggcgcgatt tcgagtcggg 240
agttcgggcg gcggggttcg gggtggtcgt cgtttttttt ttttgttgta gttttttg 298

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 63
ggtagggtgt tttcggatac 20

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 64
aacgaacgaa ctatacgcga c 21

<210> SEQ ID NO 65
<211> LENGTH: 258
<212> TYPE: DNA
<213> ORGANISM: Homo sapiens

<400> SEQUENCE: 65
gatagagata gttttaggta agttgaaggt tcgagagttt tcggtgggag aagcgggtcg 60
gtggttgcgt cgcgtgcgtt tttattttga ggaagtgcgt ggggagtcgt tgatttcgga 120
tagtatattt tttcgagggg atttttcgat ttttgggttg ggggtttgtc gtttggtttt 180
acgtttgacg tacggggcgc gagggttatt gtttttttgga tttttgtcgg aatcggacgt 240
agtgggaggg gtcgtagg 258

<210> SEQ ID NO 66
<211> LENGTH: 258
<212> TYPE: DNA
<213> ORGANISM: Homo sapiens

<400> SEQUENCE: 66
cctgcgaccc ctcccactgc gtccggttcc gacagaagtc cagggagcag tggccctcgc 60
gccccgtacg tcagacgtgg ggccaggcgg caggccccca gcccaggaat cggggagtcc 120
cctcggaagg gtgtgctatc cggagtcagc ggctccccac gcacttcctc agagtgagaa 180
cgcacgcggc gcagccaccg gcccgcttct cccaccgggg gctctcggac cttcaacttg 240
cctggggctg tctctgtc 258

<210> SEQ ID NO 67
<211> LENGTH: 258
<212> TYPE: DNA
<213> ORGANISM: Homo sapiens

<400> SEQUENCE: 67
tttgcgattt tttttattgc gttcggtttc gatagaagtt tagggagtag tggttttcgc 60
gtttcgtacg ttagacgtgg ggttaggcgg taggttttta gtttaggaat cggggagttt 120
tttcggaagg gtgtgttatt cggagttagc ggttttttac gtattttttt agagtgagaa 180
cgtacgcggc gtagttatcg gttcgttttt tttatcgggg gttttcggat ttttaatttg 240
tttggggttg tttttgtt 258

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 68
cggagttagc ggttttttac g 21

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 69
cgataaaaaa aacgaaccga 20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 70
agagtgagaa cgtacgcggc 20

<210> SEQ ID NO 71
<211> LENGTH: 258
<212> TYPE: DNA
<213> ORGANISM: Homo sapiens

<400> SEQUENCE: 71
gacagagaca gccccaggca agttgaaggt ccgagagccc ccggtgggag aagcgggccg 60
gtggctgcgc cgcgtgcgtt ctcactctga ggaagtgcgt ggggagccgc tgactccgga 120
tagcacaccc ttccgagggg actccccgat tcctgggctg ggggcctgcc gcctggcccc 180

-continued acgtctgacg tacggggcgc gagggccact gctccctgga cttctgtcgg aaccggacgc 240
agtgggaggg gtcgcagg 258

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 72
caagttgaag gtccgagagc 20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
cgcacttcct cagagtgaga 20

<210> SEQ ID NO 74
<211> LENGTH: 258
<212> TYPE: DNA
<213> ORGANISM: Homo sapiens

<400> SEQUENCE: 74
cctgcgaccc ctcccactgc gtccggttcc gacagaagtc cagggagcag tggccctcgc 60
gccccgtacg tcagacgtgg ggccaggcgg caggccccca gcccaggaat cggggagtcc 120
cctcggaagg gtgtgctatc cggagtcagc ggctccccac gcacttcctc agagtgagaa 180
cgcacgcggc gcagccaccg gcccgcttct cccaccgggg gctctcggac cttcaacttg 240
cctggggctg tctctgtc 258

<210> SEQ ID NO 75
<211> LENGTH: 206
<212> TYPE: DNA
<213> ORGANISM: Homo sapiens

<400> SEQUENCE: 75
atttgtaaaa atgttgattt ttgtttttta gattacgcgt atagtttttt tatttttat 60 tgcggtttta tttttttacg gaatattgac gttatcgcga aggaagtatt tcgagtacga 120
ttgacgtttt ttttattatt tgttaagtcg ttgcgttcgg gtttggttac gatttgtttt 180
tagaataacg ggaaggtgta ataaga 206

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 76
gaaggaagta tttcgagtac gattgacc 28

<210> SEQ ID NO 77

<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 77
cccgaacgca acgacttaa 19

<210> SEQ ID NO 78
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 78
gcctctaaaa aaacgatctt attacacc 28

<210> SEQ ID NO 79
<211> LENGTH: 206
<212> TYPE: DNA
<213> ORGANISM: Homo sapiens

<400> SEQUENCE: 79
tcttgttgca ccttcccgtt attctgaaag caaatcgtag ccagacccga gcgcagcggc 60
ttagcaaata ataaggggag cgtcagtcgt gctcgaaatg cttccttcgc gatggcgtca 120
gtgttccgtg agggaatgaa gccgcagtag gaaataaaga ggctgtgcgc gtagtctgaa 180
aagcagaagt caacattttt acagat 206

<210> SEQ ID NO 80
<211> LENGTH: 206
<212> TYPE: DNA
<213> ORGANISM: Homo sapiens

<400> SEQUENCE: 80
ttttgttgta ttttttcgtt attttgaaag taaatcgtag ttagattcga gcgtagcggt 60
ttagtaaata ataaggggag cgttagtcgt gttcgaaatg tttttttcgc gatggcgtta 120
gtgtttcgtg agggaatgaa gtcgtagtag gaaataaaga ggttgtgcgc gtagtttgaa 180
aagtagaagt taatattttt atagat 206

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
gaaacactaa cgccatcg 18

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 82

```
cgtagttaga ttcgagcgta g                                              21


<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83

aggggagcgt tagtcgtgtt cgaaa                                          25


<210> SEQ ID NO 84
<211> LENGTH: 285
<212> TYPE: DNA
<213> ORGANISM: Homo sapiens

<400> SEQUENCE: 84

cacggtcgga gggctggtgg gctttccttg gccgtcgggc ccgccacggc gcgggtcttg     60

gctgcggggc ggaggtgggg cgggagagcc gaggataaga gtttgaggct tttcgaggcg    120

cgtgccgcgg cgtccgcctc tgcgggactc tgcgccgggc gccctcggcc ggcgcgcccg    180

gctcccgctt tgtcgccgag ggaagcacgc gcgacgcccc tcccgtcgcc gccgtggctt    240

ctttcggtgt tcgtgatttg ctgagaggct ggaaagcagc acggc                    285


<210> SEQ ID NO 85
<211> LENGTH: 285
<212> TYPE: DNA
<213> ORGANISM: Homo sapiens

<400> SEQUENCE: 85

tacggtcgga gggttggtgg gtttttttg gtcgtcgggt tcgttacggc gcgggttttg      60

gttgcggggc ggaggtgggg cgggagagtc gaggataaga gtttgaggtt tttcgaggcg    120

cgtgtcgcgg cgttcgtttt tgcgggattt tgcgtcgggc gttttcggtc ggcgcgttcg    180

gttttcgttt tgtcgtcgag ggaagtacgc gcgacgtttt tttcgtcgtc gtcgtggttt    240

ttttcggtgt tcgtgatttg ttgagaggtt ggaaagtagt acggt                    285


<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86

gtttttttcg gcgataaagc                                                20


<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87

cgcctctacg aaactctacg                                                20
```

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
cgtcggtcga gggcgttc 18

<210> SEQ ID NO 89
<211> LENGTH: 10924
<212> TYPE: DNA
<213> ORGANISM: Homo sapiens

<400> SEQUENCE: 89 cccaccccc acagatgctg tctgtcagga gcaggcaaca gacggtcctg gggtccatct 60
gtgctaatgc ttcacaatag agtcccatgt ttccccactg acaccccctc ggcccctcag 120
ctgatggcca cttggtggtg ccaaggcggg aggtgggagg agggagaaga aggcactaag 180
agagctacct cttagctcct ggcagtcctc aatccacccc ggccccccac ccaacaagca 240
tcctgccatc tggacttgtg caatcactga ggggcggaaa agcaccctct tccacccaca 300
cctcttgtag gggatggggg cctagaggac tgggggtggg gaggagaaca cagagtcaag 360
gagactagag aagaagactg agccaggcgc aagaactgag acaggcagga ggcagaaagt 420
ctttcctggc ctcgcaggtg gacgtggcca ttgcccctct gtgctcctta tgccacgtgt 480
ctaacacagc acatgtgcaa ggtaccactc cctaccaggc caagagcctc tgtaacccca 540
gtgcccagcc agtacctggc acacagcagg gcttaaatgt tggacaacat cacagagtgg 600
ttagattgca ggctctggaa ccaggctgcc tggctttgaa tctcagctct gccgctgagt 660
gacttagggc aaattactta tcttctctgg gcctcagttt cctcatctgt aagggaggat 720
aatggtgctt atttcgtagg gttgttatga agaccaagtg agttaatgca tgtatgtaaa 780
aggacacaca gaacaaacag tgtgcatagc acatgctaag tgctcaataa atgttaactg 840
tgaaggcata acagatttgg gaagactggg ggaggaggga ggggacagac aagggcaccg 900
cattgccgcc tctgcttctt ggccgatggg tgttgggaca tggagtcccc agcctgtgct 960
gctgacgccc tgtggtggct agccgctctt tagacaccag acgctgcctt ccacttcctc 1020
ctctcacttc ttattcgggc accactgacg acagagactt cggctgggcc attcccgcct 1080
ctcctaccgc ctggcagcca tggtaacagc ctgggggatg gtccctaaga tggggtcaga 1140
gaacggctga gcatggccat ccccccagcc ctgaactccc actcagcctg ggctcatccc 1200
aacctcctga gtcaagtcca cagtaagcgt ctgtctcctg ggaaggggga tctgaccccg 1260
gcatcaggag ctgaggaaag gtgttgccag cagggatcac tcaagcccct tggaggggac 1320
aggccagaac taagcctact gctttcaggg tttccacctc ttcccttctt cctagacgtg 1380
cgaacagggg gcagcctctt tcagctcttc tggggcagct gcgtcaaggg aaaatcctgg 1440
gccctctccc tccctggggg cttctgcgca gtgagttcag ggagtctcct ccctcctcca 1500
tcgggcctcc acccctactc ctgcgcagcc ccgctgccgc tctccctgcc ctggagtctc 1560
ctgcagcccc ttggatctcc gtgactctcc ctacctcccc gactccccag gcttcttaca 1620
gtgacctctt accgtgcccc actccatgaa tcgccagagc tattcgtccc taaatttcaa 1680
accttgcgca atgtcccttc acagacccct ccaggtatca cgcagccccg agccccgagc 1740
cccgccccgg gggcctcatc ccgccccttc gcgtccgcgg ctcgttttcc cccactgagc 1800

-continued

```
gcccagctcc cgcagtttcc ccggccgtcg agcgccgtgg gcggggctcc agggcggcgg   1860
cgcctcgcgg ggagggtcct ccgtgctggg ggcgaggcca cccgaggcag ctccccgccc   1920
gcccccaacc ccgccccgct ctcggagcct ataaagggag gcgacccgcg gcccgcccgg   1980
ctggcatccc ccagccgccg ccagccccgc cgaggggagc cagcgccgtc tctgaggggc   2040
gtccggcgcc ggagccatga ccctccgccg actcaggaag ctgcagcaga aggaggaggc   2100
ggcggccacc ccggaccccg ccgcccggac tcccgactcg gaagtcgcgc ccgccgctcc   2160
ggtcccgacc ccgggacccc ctgccgcagc cgccacccct gggcccccag cggacgagct   2220
gtacgcggcg ctggaggact atcaccctgc cgagctgtac cgcgcgctcg ccgtgtccgg   2280
gggcaccctg ccccgccgaa aggtgcgtcc cccgcccgcc ttcaggatct gctcagcccc   2340
tctccgactc cctacagggc ctgctgactc cgcagtgccc tctcctcggc gtccgcggag   2400
tcccccacct tcttccccgg cccgctgggt gcctcgactc cccgcgttcc ccgctgctgc   2460
gaaggccgtg gccctcgcct gcacaccgcg cccaggctcg gtggctctta actccgcgcc   2520
ccatgcacgc cccctctctc cctccttgac tcctcccagc accccccttc tcctacccgc   2580
tccatctggc tttctgcccc ccatgccccg cctccccgtg gccaggtgtc ctgggtcccc   2640
aggagcccct cgcccgaggg acagagacag ccccaggcaa gttgaaggtc cgagagcccc   2700
cggtgggaga agcgggccgg tggctgcgcc gcgtgcgttc tcactctgag gaagtgcgtg   2760
gggagccgct gactccggat agcacaccct tccgagggga ctccccgatt cctgggctgg   2820
gggcctgccg cctggcccca cgtctgacgt acggggcgcg agggccactg ctccctggac   2880
ttctgtcgga accggacgca gtgggagggg tcgcagggcg cccgcggggc aggaaggatg   2940
cgggccgcgc ccacctctga gtcccctctg ccagcctctt cctctggccc caggagacct   3000
gaggctcaga acctacacaa caccaggtta agaagagggg cctggtggcc tttcctcacc   3060
cagccgccct ccttcgcccc ggcccccagc tagcccccac acaatgaaca gcttgttgag   3120
aatttgcatt ttatgaaaat catgttgaaa gacaaagggg tctctctgtg ctgcccagtc   3180
cttcctccct ggccgtttgg gaactgtccc cacccctgag gccaatctgg ttctgaacct   3240
tctcttcctt gccttgggca gctttggggg agggttagca aaggcacaga acagaaaggc   3300
cctgggctgt gcaggctcca aagaaaaggg ctgctctggg actggacctc ctcccaggac   3360
caaaaagtta gggagggtga gagactactt tagtttatca aggaccctga agagacagga   3420
accttcatct ctcatccttc ctccacaccc cccaccacca cccctaaaga actcccagtc   3480
tcggtccttt agtgagactt gctgacaagt ttgacatcta agatgttttg tcccagaaag   3540
cacaaaatat atggcaatgg agagagagac ccaggtatag ctgggcacag ctggtcacct   3600
gcagctggga tccacaactg gtccttgaaa cggcctgtac cttaggagac ctggcacctc   3660
tgaccccaca ttctggctgg gattgccagc ccttcgggac agggtccctg accccagccc   3720
tcccaagcca ctgtctgtag ctgagaaatt agatggagag acccaactgg cagaaggtcc   3780
tcggagcacc ttgataggtg agcccagggg acacctatcc tctgaatccc actggggaag   3840
agcccctgcc tcagctttgg gagtctggat ggcctgagcc tctacagaca tgggccctag   3900
gggtggagac cattttagaa taatgatctc cccacctgct gccagtgtgg aaaccagcaa   3960
gggcttagag gttcatggat ctggaaccca ggaggatggt tgtgtccctg cagtcccagg   4020
tatgaaggta aggcctgtag agaaagttga ggagtggtgc cagtagtggc acttggcaaa   4080
tagttccacc agcaccaaaa caggtgtgga tgtggagctg ggaaggggca gacaggaagt   4140
```

-continued

```
gggtcgctgt gtccagggta acctctcagt gtctgctcaa ggacagtccc gccttacctg   4200
ctccttctga ccatcttact gcccagggct caggattccg ctggaagaat ctcagccaga   4260
gtcctgaaca gcagcggtga gtcaccaaca cccagcccct gccatggtcc aaaggggtga   4320
ggtgctgggt tggggggtgc caggacagca tctcagccta gcgagggtag tcattctcct   4380
agcctttaaa catggctccc ccgctgggag tgagggcagg tgggggtgag ggctgtgtga   4440
agggggtggc agagaaagga ggtagggact tttgagtcat taggtgctct tcaacacacc   4500
cccagtccct gccagttacc cctccctggg gagatctgga tgaacggatg tgggagttgg   4560
gagggggtgt aggcaaagtc tatggggaac gtcctaaccc aggcctcctg ggctcccctg   4620
agccctccta gccttggcaa accccacggg cccagacctt agccaggctg tgtccagctg   4680
cttggggctg gctgcccctg cctccagaat gtcagtcctc ttctggtccc agcctgtggc   4740
agccctctta ggagggatct gagcgtgggc agaagtaggt gctgactcca ggccctggga   4800
ccccacagtt tcccttctct actcatgtcc catccctgat ttgggcttga ctttctctaa   4860
aatggatcag caaactgacc tgctagccag attggcctgt ttggcccttg agctaataat   4920
ttttaaagag ttgtaaaaat aaaaacaaat aacaatatat gacagagatc ataaggggcc   4980
tgcaaagaaa gcctaaagta tttaccattt ggccctttgc agaaaaagtt tgctgaccct   5040
tccaaaaaac cctagaacat tggggtagac gcggaactcc cagccaccct gctccctgcc   5100
ccaatagtac agagagggga aaggcctgct gttcagagtg agaggggctc gagctggagt   5160
ggggaggtgc tgctcagcat ttgggggaat ctctgggtca ggctggaagc ggagaagcct   5220
ggtctccagg gcctttccga ggctgagcta cttgaagggg cctttggagg ctgctttaac   5280
tgtgcctctg gctgggcggg aaggaagggg gtgggagtgg gcagaggaaa ctctgggctc   5340
ccccagcagg cgaggatctg gagcagctcc agaccattgt gtccagcggg caggccttca   5400
gtgcgggaag ggcggcctc gaggctcccc tcccccagcc cccacatctg gtgggctggc   5460
cccagcatag ctgggaggag cagctgtggt cttgctgagc ctcgtgactg gcctctgggg   5520
gtggggccag tcctctctcc aaagctgtgg aacagaggag gctccaggct gtggctgaat   5580
ttcgggcctt agctagtcag taagtggtac tgtagggctc actggaaagc tgggatgggg   5640
ctaaaaaact cagccggctc atccttcagg ggaccggccc ttctctgtgc ttccctccca   5700
ccactagagg ctggattggt tctctgtggc tccatgaggc tgatttcaat tgggtatggg   5760
aaagacattc caataatctg tgatgagact gagctgtcac tggagacaga gtcctgctgg   5820
aatgttctag accagttgcc aatatccagg gaggcccaag ctatgggact tctacacctt   5880
ttaatcctaa ttgtcttgac ccctgtgtct cttgcaggaa agtgctgacg ttggagaagg   5940
aggataacca gaccttcggc tttgagatcc aggtgggaga agctgcacac aggggtcagg   6000
ggggttggat gaccagcctg agggatgaac ggacttgtcc caaccctggg ctgagggtcc   6060
ccttgtccat tacagactta tggccttcac caccgggagg agcagcgtgt ggaaatggtg   6120
acctttgtct gccgagttca tgagtctagc cctgcccagc tggctgggct cacaccaggt   6180
ggggcctgag cccaggacac ccaggtctgg gaaggggata tgaccttact cccaagcaaa   6240
gggggtgagc aatctctcct gaaatcaatt cctcttcctt ttccttcttt gagaaggcca   6300
gaaagaagaa tggatagaat ctgggctttg gatctaggca aatttgccat gtactgtgtg   6360
atcttgcaca gccccatcta caaaatgagg gtaataatgc atccaaacat cacagtgcgg   6420
caaggggatt ccctgggcac actgccaggg cctaattaat ggtggatgat gctgctgctg   6480
ctctgattcc tcccagcaac cctggcagtc agcatgggca ggagccaggg aagaagcaac   6540
```

attccattaa gtctgtttga tattggggat caggccaatc ctgccccaaa atgggcccag 6600
tgctgaggaa ccgatgttac tcccttttaa aaaattagaa actttttttt tttttaagag 6660
acagggcctc agtctgtcac ccaggctaga gtgcagtggc gtaatcataa ctcactataa 6720
ccttgaactc ctgggctcaa gcgatcctcc tcttgcctct gcctcccaaa gcaatatgtt 6780
acttcctcta acaaggaaat tatgcttcag caggagatcc ctggattgag cagatctaga 6840
gtccccaggt tccaggaagg gcagcctgaa actgtatgaa tcaatccccc ctccaccatc 6900
tttgccccta agcccctacc tccttcccac ttaccagcag cccgtgctag ctatcttagt 6960
ccattttctg ttaccataac agaatacctg atactgggta attataaaga aaagaggttt 7020
atttagctca tggttctgga ggctgggaag ttcaagactg ggtggccgca tcaggtgagg 7080
gcctcatgct gcgttctgac atgatggatg gcatctcatg gcaggaacgc ctgcaagagt 7140
ggtgagtagg cacacgcaaa agagacaaaa catgggtgat cttgctttat agcaacccac 7200
tcgccaggta actaaaccag tcctaccaga gcaagaactc actccccaaa aacagcatgg 7260
atcccttcac tgggcagatc cttcatggcc caaatgccac tttttttgag atggagtttc 7320
gctcttgttg cccaggctgg agtgcaatgg catgatctca gctcactgca gcctctgcct 7380
cccagattca agcaattctc ctgcctcagc ctcccgagta gctgggatta caggcactgg 7440
ccaccaagcc cagctcattt ttgtattttt agtagagatg ggttttgcc ttgttggcca 7500
ggctggtctc gaactcctga cctcaggtga tccacccgcc tcggcctccc aaagtgctgg 7560
gattacaggt gtgagccacg gcgctcggcc ccaaatgcct cttaaaggtc ctaccatctc 7620
tcagcactgt tacgttgggg atgaagcctc aacatgagtt ttggggacaa acaatattta 7680
aatggtagca gtagccaagt ggtatactac aacttctcaa agtagtttca aatccactct 7740
ccctccccat catccctgaa gcatccacag cagggatcca taccccttt tacagatagg 7800
aatggggccc tgacatgggg cacactgtgc ttgaggtcag gaagctctcc agtggtgcag 7860
ggtagcagaa ctatccctct gggggccagt cattccctgt gcttctctcc caccaccaga 7920
ggctggactg attatctgtg gatccatgag gccatgccat gcctggggcc agggtcggtt 7980
cccagctggg tgctgctcac ctgctcttcc ctgaattgac tgggtcttat ggccagcgtg 8040
gactggacag aaataaccaa atctgagggt agcccagggt cctgggtggg cttagctttg 8100
ggacagaact tctttttttt tttttttttt ttgagacgga gtctcgctct gtcgcccagg 8160
ctggagtgca gtggcgcgat ctcggctcac tgcaagctcc gcctcccggg ttcacgccat 8220
tctcctgcct cagcctcccg agtagctggg actacaggcg cctgctacca cgcccggcta 8280
attttttgta tttttagtag agacggggtt tcaccgtgtt agccaggatg gtctcgatct 8340
cctgacctcg tgatccgccc gcctcggcct cccaaagtgc tgggattaca ggcgtgagcc 8400
accgcgcccg gccggacaga acttcttgag ggcagagtga gggtgttggg tgtgtgaggt 8460
ccccaccctt tggctggggt gctgggcgtg gacaacctgg tagtcactac aggcccacaa 8520
gaatggctgt ggttctgtgt gtttggatcg agtatgagag atgtcagagg agatctacag 8580
agaaccatga ggagttggag gagggagttc aggagtattc cctggagtta ctacccaccc 8640
ttctcccctt tctggctaag gtaggaggct ggtattctag catgccccat ggagcaaatc 8700
taaccccctt gtctgcctgg caggggacac catcgccagc gtcaatggcc tgaatgtgga 8760
aggcatccgg catcgagaga ttgtggacat cattaaggcg tcaggcaatg ttctcaggta 8820
tgtctgggag ccgaggtgcc tgaattcctg agctcagcct cttggtattt cctcagcctg 8880

-continued tggctcactc aggctttgat tctccaacct cagactggaa actctatatg ggacatcaat 8940
tcggaaggca gaactggagg ctcgtctgca gtacctgaag gtaggggaac ctagataacg 9000
tccagcctcc accctcctct tcccaagcct ctgccctgtg gggggtcact tacagctgaa 9060
tctcctgtaa ctgaagattt cttttgtcta ctccctgatc cctcgtctgt acccacgtcc 9120
tgctagtttc ctgctagctt gtgacagtgg ggtggggact gtctcttgca gcaaaccctg 9180
tatgagaagt ggggagagta caggtcccta atggtgcagg agcagcggct ggtgcatggt 9240
gagtagatcc cggggtgtga ggggccactt gttctgctac agacacccca tctgcgcttc 9300
cccctcagaa ctggcgggtt ctagtaaaga acggtttact agtaaacctc cacagtaaag 9360
caaggtttgt tgagctacta ctactttggg tactgccgca gccacatttc tggttattct 9420
cacactagcc ctctgcaggt aagtaacaga tagtgtcatc ttcactttac agaggggaac 9480
accagggctc aaagagtttg tgtcaattat ttccgaggcc cgtttgtgct aagcggcccc 9540
cataaggatc tgagtgataa ttcctgattt gcgggtgagg gaagtagggt ctcaggtttg 9600
tgcctggcca gggccacaga gatggtcagc aggacggagc ggggacgccc cgcccatgcc 9660
ctccgaccct ttgcagaggc caccacggtc caggcctgac ccgcccccta cctctcccgt 9720
ctctgcgcag gcctggtggt gaaggacccc agcatctacg acacgctgga gtcggtgcgc 9780
tcctgcctct acggcgcggg cctgctcccg ggctcgctgc ccttcgggcc tctgctcgcc 9840
gtgcccgggc gtccccgcgg aggcgcccga cgggccaggg gcgacgccga cgacgccgtc 9900
taccacacgt gcttcttcgg ggactccgag ccgccggcgc tgccgccccc gccgcccccg 9960
gcccgcgcct tcggcccggg ccccgccgag acccctgccg tggggccggg ccctgggccg 10020
cgggccgcgc tgagccgcag cgccagtgtg cggtgcgcgg gccctggcgg gggcggaggc 10080
gggggcgcgc cgggcgcgct ctggactgag gctcgcgagc aggccctatg cggcccccggc 10140 ctgcgcaaaa ccaagtaccg cagcttccgc cggcggctgc tcaagttcat ccccggactc 10200
aaccgctccc tggaggagga ggagagccag ctgtaggggc gggggcgggc agggaggtat 10260
ttatttattt attcgcaaca gccagcgcta aaagaggggg aggccgagcc aagaggaccc 10320
caggagccca gagcagcggg agagggtcct tcctagcctc ggcccgccgg gtcggttcct 10380
ggctggtgtc tgctgaggga gtggggggcc cagccccttc tcttctcccc cgccaaacca 10440
cagtgggagc tggggcaggg ggagagccag gcaatcgggg gccaaagatg gggtgctcg 10500 cctacagtct gcatctgtag tgccttgtgg ggtatccagg aacaccctcc cagcagggga 10560
tgggaaccct gtcccatgaa gccctctcct cagctttact tgctccccg cccttagcct 10620 tggggagaaa tggcccgtgg tgggctgacc ccccaccctc cacacacaca gttccatgac 10680
ccagcgggcc cccaggggca tcaggtgctg gtcctcctcc ctcctggcct cgaccccctaa 10740 gggcttcgcc cctcccaggg gcctgtaact aagtcgggtc ctgccaggca gggggcctgt 10800
gttctgtgcc ccttgggaga caggaactgg cgagttcagg tggggtgggg acagcacaga 10860
ctgttccacc gttgtgcata ttgttgcttc tgaaccacaa actgtataaa tggatggttt 10920
tttg 10924

<210> SEQ ID NO 90
<211> LENGTH: 2886
<212> TYPE: DNA
<213> ORGANISM: Homo sapiens

<400> SEQUENCE: 90
agcataattt cggtctccta cggaatttct ttaaactaac gagccccaca ctgacttcca 60

-continued

```
cttagtattg aacagctgca ccaactcccc aaccacgaaa ccccgcttta gtcctcacgg    120
gaggggagag ctcccgaacg cggggcggtg ggggtccgcg cagagcaggc tcgggaggcc    180
gagcggagga gcggggcccg cgccgggcac acgcgtcctc caggccggcg gcgcggcgtg    240
ggcctgctct cgggagggct cggcgaggac caccgagtcc gcgcagcccc cgccgacctc    300
tcggaaatgt gaccgccgaa gctagagggg ccgcagggct caccccgcag ccctccgcaa    360
cgcgccaact tggacgccag cggcgcgggg tcccggccgg gcagggggcg tccggcaccg    420
gcgggtccac cccggcccgc ccgcccgccg caagcccggc ccggcacctc ctttgtgcgc    480
cctcctggcc tcccagtccc cccggcgctc ggtcccgccc ggccgtgacc ttcccgccct    540
ccccaccatc ccaagcgggg aaaggggccg ccccggcggg ggtcgggccg gggccggggc    600
cctggagacg ctcaccttcg tccagcagcc gctcgaggtg gttgaagatc ccgcagaagt    660
tgggcaggct gctcatgagc ttcttgtcgt tcatcagctg catcaggtaa tctggggtgg    720
gcttcggctt ctccttcgtt tccatttccc cgaccatatt ccaggctccg cagctcactc    780
cgcccgccgc cgccgccgcc gccgccggag aggagggagg ggcgggggcg agccccggcc    840
gcgggccgct cgggacccgg cgtcccgctc cgcgccggct cccgctctgg ctcccgcgcc    900
gagccccggg gcggccggca ccgcgcgctc gcccgccccc cgcaggcact ttccgcccgg    960
gcccgacgcg ctcccagccg ccgccgctct cggccgcccg gctcggcgcg tccctcacga   1020
ggccggcggg cgggcgggag gcgggtctcg gctggccgag tgcgggcgcg gggcgcgggc   1080
tgctggcgcc ggacgaggag gagccggggc cgccgctcgc tcggctggtc gagcccgctc   1140
agcgccgccg ccgcctgtgc cgcgggctcg gggggtctct ctgggctggt ccccgccgcg   1200
gcgcctctgc cgctgccgcc gcgctccgac tgcgctcctc ctcttcctcc tcctccttct   1260
cctcctcctc ctcctcactc acttggcggc ggagttcgcc tcagttcagg cggcgctgcc   1320
agcggcggcg gcagcagcgg cggcggcggg gggaggggca gcggcgcggg gagggccggg   1380
ggcgggcggc gggcggggcc gcgcagggcg gccgttagcg ggtcccggcc ggcgcgctcc   1440
cgctgcctgc tgcccgccgc cccgcgaccg gggcagccgc cggcgccgcg ccccctcctc   1500
cctgcctccc cggcggggcg ggcgacgggg gcaacgggag tgtgacggac tgcggcgctc   1560
ggcgggcctg ggcgcaagga ctgggtcgcc gccgtgcggg gcgcccgggg cgggtgggtg   1620
tgggctgcgg ggccgacggc cgcggggggg gcgcggggct ttccacggca cggggcgggt   1680
ggggctgcgg gcgcggtcgg ggctggcgcg gcaggcgaga ggaattccag cgggacgcgc   1740
cagcgctgcc tccgcctcgc ctcccgttac tatagttttt tcagaacctc ttatccaccc   1800
cgcagaagag aaattttttt ttaacgtcct gttgcttcac gggggacttt cggggtgggc   1860
atcacgtggc ccgacacgta gccgtggggc tccagagcgc gtgcgcgcgt cgagcccggt   1920
cgccacgccc cttccgaggg tcgctccgcc ccccgtcgggc cccgcgagcg cgcggtgggg   1980
gaggggaggg ccccggagcg cgcctgcgtg gggcgggggc ggcagccgac taggggctgg   2040
gtctggccgt ttagggccgg gtcttggccc gtcgcccacg gtgcggaggg ctggtgggct   2100
ttccttggcc gtcgggcccg ccacggcgcg ggtcttggct gcggggcgga ggtggggcgg   2160
gagagccgag gataagagtt tgaggctttt cgaggcgcgt gccgcggcgt ccgcctctgc   2220
gggactctgc gccgggcgcc ctcggccggc gcgcccggct cccgctttgt cgccgaggga   2280
agcacgcgcg acgcccctcc cgtcgccgcc gtggcttctt tcggtgttcg tgatttgctg   2340
agaggctgga aagcagcacg gcggagagga gccttgcact cgccaggcgg gaagcctgcg   2400
```

-continued

```
cggacacgcg tgcgcaccca cggggcggcg ggcgggcgtg gggggtccgg gccacgcggg   2460

cgacgcgcct ctagggaagc gatcttgttg caccttcccg ttattctgaa agcaaatcgt   2520

agccagaccc gagcgcagcg gcttagcaaa taataagggg agcgtcagtc gtgctcgaaa   2580

tgcttccttc gcgatggcgt cagtgttccg tgagggaatg aagccgcagt aggaaataaa   2640

gaggctgtgc gcgtagtctg aaaagcagaa gtcaacattt ttacagatga agaaagaata   2700

cggaggcaag aggtctttct ctgcagtttg gtggatttcc aacatttaga cttgtttgga   2760

agaatttcct cagctgcacc aatgaagtcc ttgatctata gaagtcggca gtccctaaat   2820

ctacgtctgc attttgttgc aaatccttta taacattcca ttaaaataat gcagagttat   2880

ttaata                                                              2886
```

<210> SEQ ID NO 91
<211> LENGTH: 21705
<212> TYPE: DNA
<213> ORGANISM: Homo sapiens

<400> SEQUENCE: 91

```
agattagcaa ttacatttaa aaacaaggta gtggtgtgaa ggctcagagt ttcacacaac     60

gactgttgtt ctgaactaaa agcagaggat gtggatgagt gaggggaggg tatgttgaaa    120

atgactaaac ccggtgcaga ggacacgtat acgaaagtgc aaaaagctct catttgccat    180

tttttgtcct cagcaaactc ctctctggta tgtttgtgaa cgtttgaggg aaaggtaaca    240

ctgattaaaa tataatgcaa caagaaggca acgatctttg ctttgttcac tgatgtgttc    300

caagtgccta ggacggttcc tgacaagtag caggtgctca aaatacattt gtcaagtgaa    360

taaatctgtg aaaggaaagg aagaaaaaca ggttgtgacc agaacttttt gtgaacaaaa    420

ccctgttgtt tattacatag actttggtaa tggaaaactt acttgggtga aataaaaaat    480

ggcatcctgt taatttctga gaacgtctgt tggttttagg aaaagcatac ctatccatac    540

ctcactacct gttttgctct agcctaaaca tagattcttc tttggttagg agacattgac    600

ccaatatata agattaaaac aaaaactgag aaataagtga aatcaaaagc ttttcaaaag    660

ttgcaggttg acctacggtg gtggtggtct aaaatcatat agaaaccaga gatctgatgg    720

tttacctgaa aatgcgaagt aaatgcacat actcagcatc tcagacgatc gaaagctcaa    780

cgggtgaaag ctcagggggt taattttgcg attaaggaca tcttggaaaa gtatgtaaaa    840

tccctggtcc acttaagtat tattcctatt ttgggctttt atttatttat tttgagatgg    900

agtcttgctc tgtcgcccac ctcggctcac tgcaacttca gcctcccggg ttcaagcgat    960

tctcgtggct cgtcctctca agtagctggg gccacgcccg gctaattttt gtatttttag   1020

tagagatggg gtttcaccgt gttggccagg ctggtctcga actcctgacc tcaggcgatc   1080

caccgcctcg gcctcccaaa gtgctgggat tacaggcttg agccacagcg cctggcctat   1140

tttgggcttt tataccccac tggtaaactg ctttcctcca ggttgaggtt aaaacgacat   1200

cattttaagg tgaactgaag tctggaagtg attaagcact tggatcctta gggagcctct   1260

ccccgccccc atctctttca tgctaagata attaaaactt cggggccggg gcattgtctg   1320

agtcacttca attcaccagc ctaatagatg caaaaggatg taagcatgtc agacacgcag   1380

agacagtatt tgaatcaagc ttaatagctc aagggagctg ggccatttcc tatttttcttt   1440

ttagtgagtg cgatgttctc taaacaccgc ggagaggcag ggttcccggt gatggccttg   1500

ccgagggtgc tcccgcaacc tccacctcca gttctctttg gaccattcct ccgtcttccg   1560

ttacacgctc tgcaaagcga agtccccttc gcaccagatt cccgctacta cacgcccccc   1620
```

-continued

```
atttcccgcc ctggccacat cgctgcagtt tagtgattga ctggcctcct gaggtcctgg   1680
cgcaaaggcg agattcgcat ttcgcacctc gcccttcgcg ggaaacggcc ccagtgacag   1740
tccccgaagc ggcgcgcgcc cggctggagg tgcgctctcc gggcgcggcg cgcggagggt   1800
cgccaagggc gcgggaaccc caccccggcc gcggcagccc ccagccttca cgccggccct   1860
gaggctcgcc cgcccggccg gccccggctc tcggcttgca aagtccctct ccccagtcca   1920
acccccggcc cccacaggcc tcggcgcccc gccccgcccc aggccccgcc ccagagagtt   1980
ctataaagtt cctctttccc acctcgcact ctcagtttca ccgctcgatc ttgggaccca   2040
ccgctgccct cagctccgag tccagggcga ggtaagggct ggagtcgggc aggaggaggg   2100
gtgtgaggct gataccagag aggacccgga gcgcgaacca gaggttcgac ctccagggca   2160
gcgcagggta ccccggcttc ggagcgggaa gggagcgcgc cccgtcctgg agctccgact   2220
cccaccccat ctgcgctgag ccggaggcgc tggtttgggc tccaaggccc gcctccttgg   2280
ctctgcccga gcctccccgc ctgccctccg cgctcctgcg acggggtcgc cacaagctgg   2340
acgggatgag ctaaccggac tgtcggggcc ccaggagtgg ctgaggcggg gccgtccaag   2400
gcacccacac aagacggcac aactgcctgc gagaaacagg cccggccctg tggaccccaa   2460
tccgaggctc cttcccctgc tcttcgttcc taaggggccc aagctcacgg cggcctccgg   2520
cgcggtgctc acccgctggc gcaggaggag gaggagctcc acatttgggt cgctccgagc   2580
cttgcgtgcg gtggcctagc cggcctggcg cggtccctgc ctcccaggct ccgcagctgt   2640
cgtcgccctc tcccgcgccc tccccgcctc cgctctcccg ggcctgctcc ggggtccggc   2700
ggacgctctg cgcgcggaat cccccgtact ggggctgcag cccccgcgtc tgcgccactt   2760
gtcgtttgca gagcccactt agtgcgcgct agctgggcag ggataggggt cctattcggg   2820
gcgaagggtc tggatgcgag cagagaaagc ggagggtgga ggaacccggg gctgcgcccc   2880
tggaacgccc ggccgcaggc gaggtcctcc gcgcgtggag gccgccaggg gagtggaaac   2940
tgacagagtc gcggggaagg ggcgagaagc gggttgggag tgagcgaagg caagcgagag   3000
ctgcgagtga gtgcggaagg agggccagga ggggtggcgg ctgggtgggg agagagggtg   3060
caagacgagc ggcgcgtgtc gggagccttt gggctgcggg tgcgttacag gagagcaggc   3120
gggtaggagc cttcgcgggg gccgagctcg gaaggcggac ggctgtgccc gcccagggga   3180
tgcgcccggg ccggccgcga aggtgccttc ttccgggggc ccggacgacc ctgacacggc   3240
acgcgcgcgc ttcgcagcct caaagactcc ggggcctcgt ggtcactggc gcaggggatc   3300
ggggcggggt gcccggagtg cggtgcctcg tggctgaagg gcagctcttc tccccgcagt   3360
gcagagcaga gcgggcggag gaccccgggc gcgggcgcgg acggcacgcg gggcatgaac   3420
ctggagggcg gcggccgagg cggagagttc ggcatgagcg cggtgagctg cggcaacggg   3480
aagctccgcc agtggctgat cgaccagatc gacagcggca agtaccccgg gctggtgtgg   3540
gagaacgagg agaagagcat cttccgcatc ccctggaagc acgcgggcaa gcaggactac   3600
aaccgcgagg aggacgccgc gctcttcaag gtctccggcc tcgggagccg gcgggggcgc   3660
gccggggagg gcccagagac agagcccggg gtccccggcg ccgcctccga ggcgagccca   3720
ggggaccgcg cggggcggac gggcgggcgg cggaggcatc aggtggcgtc gccggagccg   3780
caggaggagg aaaggaggcc tcggctctca gcgggaccgc gggggccggg agccgggtcc   3840
tgggcgcgtg gaggctgcag ggaaaccgct gaaggcccgg ccgggcccgg ggaagggcgg   3900
ccaaaggctt gaggggtttt gcgcgttcgt ccgtgcgttc tcgtttccac gcaagcctcc   3960
```

-continued

```
cgcccttcct ccgggctccc gtctgccgcc tccgtccgtg ggtccccctc gccctctccg   4020
tgcgtccgcg cctgtgccgg cggctgtttt cgtctctcac cgcgtctctg tttctctttt   4080
cgctgctttt ctctctgagt ctctctctct ccatgttttt cctgaggtca gcctctcttc   4140
tcgctcctgc tagctctctg cgggtactcc cacctctgtc tttctctttg tgtgtctctg   4200
tctctctctt tcccccatcg cagtggaact cagggcctct gtctagagct gtctcccttg   4260
ccctttgcgc gagtgcacac acgtgtgtcg ttgttacgat tgttctcccc taaggcagtt   4320
tacccagaga actacgtgtc tgggcccagc cccccacctgt gggcagagca ggggaagggg   4380
acttcctccg ggaatttggt ctcaatttgc tctcagagtg cctcagctgt gctgccatcc   4440
agatgtctcc tgtgggtgac agctcacacc acagctgtcc ttagtcctag gcaagctcac   4500
tcagacactg ggtgggtaga gccccctcaa ggaacctccg catctcactc taccggttat   4560
aaatacccag aaaatgtgtc ttcaacttgg cagtgatagg gtccaagatg gaaaatcatt   4620
ttcctagagc atagctgggg tctttcagtt tacgttctga gcaacggtgt aaatctgaag   4680
gacctatgcg ccattctttc ttttagaaat acaatttcaa gattccttat aaaatatctg   4740
tattttgggt ttagcatggt ggctcacacc tgtaatccca gcactttggg aagatgaggt   4800
ggaaggatgc ctatgcaaca tagtgagacc ctgcctctgc aaaaaataat aattaaaaaa   4860
attagccagg catggtggtg aacacctgta ggccgagggc ccagctactc tagaggctga   4920
gataggagga ccctagaact caggagttcg atgctgcggt gagctatcat cgtgccactg   4980
tactctagcc tgggcagcag agcaggactc tgattccaaa aagaaagcta ataaaccaga   5040
catgtatttt gacttttcgt tctcttcatt ctttcccacc aggcttgggc actgtttaaa   5100
ggaaagttcc gagaaggcat cgacaagccg gaccctccca cctggaagac gcgcctgcgg   5160
tgcgctttga acaagagcaa tgactttgag gaactggttg agcggagcca gctggacatc   5220
tcagacccgt acaaagtgta caggattgtt cctgagggag ccaaaaaagg taggggctct   5280
cctgaatttg ggtcacctaa cagaggcagc cagatccttg aggcacctta acttcattct   5340
gagcatcact ttctagcttt ccttttgtat tgcctgcctg cctgccttct gcctcacagt   5400
gaagcccagc ctccttgcct gagttatgtg ggtcacaagt tgaaattcct gtggggttca   5460
gcataggaga attaatcaca ctgtatgcct caatgtatat gggggggggt gcattgaata   5520
tgtgttttcc agttagtctt tcaaaaaaaa aaagaaaaaa gaaaactgga taacttgtta   5580
aaatttactt atctaatagt ctttagtgag tgactatttt gcagaaaagg agtaatgaga   5640
ggaatatctc atcactatgc atggtaataa aactgtcaac ttttaaagtg taacatggtc   5700
agctgaggtg tttattaaaa gtcagattcc tggacccctc ttttcaagat tctgaccagt   5760
gtgtctggaa gagagctcag gaatctgcat ctggaacaaa tccttcaggt gacctcactt   5820
gggaaacatc tggctggcgg ggtcctttat gtcacaaggc acattcgcat gccatctgtc   5880
atgtatttct ttacctgtcc tgtacaactc agaccttgta gaaaaaaatc agtttaatag   5940
catgaaaaaa taacttccca agggagttgc tgaaaaatac cttatttgtc aacaccgtgt   6000
tatgcattct aagaattaaa tgctcaggta tttttacaag atttgacatt tagttaggtc   6060
agttcctgtt tttacgttgt gccatttccc ttttccccaa acatgtagga gccaagcagc   6120
tcaccctgga ggacccgcag atgtccatga gccaccccta caccatgaca acgccttacc   6180
cttcgctccc agcccaggta tggtggaggg cactgggctc cctgagggcg aggctgtgtg   6240
ggccagctgc ccacatggcc agagaaccac agcagcccag acagcagaac ttgccatttg   6300
ctatggctgc tccaacagcc cagaaaaacc ccaggtcact gaacgaatgt ctcactttcc   6360
```

acacggtgct gccattggtg tggattttaa gttggggagg gtcgggcgtg tccgcctgtt 6420
ggaatatgct tctcaggtct tctgggaaac agatgttttg tggaagtgga agattttgga 6480
agtagtgcct tatcatgtga aaccacaggg cagctgatct cttcaggctt tcttgatgtg 6540
aatgacagct ttgtttcatc cactttggtg ggtaaaagaa ggcaaattcc cctgtggtac 6600
ttttggtgcc aggtttagcc atatgacgaa gctttacata aaacagtaca agtatctcca 6660
ttgtccttta tgatcctcca tgagtgtttt cacttagtct gatgaagggt tcactccagt 6720
cttttcggat gataaaatgc ttcggctgtc agtctaataa gggattccct gaggagtttg 6780
gaggctgtaa gagcaccccc cgtctcaatg ccagtgcttc ttatctcagc ctctcctgca 6840
ctcctttacc cccgtctcga tgccagtgct tcctatctca gcctctcctg cactccttta 6900
cccccgtctc gatgccagtg cttcctatct cagcctctcc tgcactcctt tacccccgtc 6960
tcgatgccag tgcttcttat ctcagcctct cctgcactcc tttacccccg tctcaatgcc 7020
agtgcttcct atctcagcct ctcctgcact cctttaaccc cgtctcgatg ccagtgcttc 7080
ttatctcagc ctctcctgca ctcctttacc cccgtctcaa tgccagtgct tcctatctca 7140
gcctctcctg cactccttta cccccgtctc aatgccagtg cttcctatct cagcctctcc 7200
tgcactcctt tacccccgtc tcgatgccag tgcttcttat ctcagcctct cctgcactcc 7260
tttacccccg tctcgatgcc agtgcttcct atctcagcct ctcctgcact cctttacccc 7320
cgtctcaatg ccagtgcttc ttatctcagc ctctcctgca ctcctttagc aggttcacaa 7380
ctacatgatg ccacccctcg accgaagctg gagggactac gtcccggatc agccacaccc 7440
ggaaatcccg taccaatgtc ccatgacgtt tggacccccgc ggccaccact ggcaaggccc 7500
agcttgtgaa aatggtaagg aggataccag tgcaggaaat agaagagcta attgctaatg 7560
tggccatggg ccatggcgaa tcctggtctg tcctgggcag caccaaagct ctttcccctt 7620
cttagaggct gcgtgtgcag ctcggggaga ggggggtttt ctcactcctg tgggatggtg 7680
gcatcccaca gccaagttta ctctcaggat ccatgctagg cactgccctt cgtgggatct 7740
tatttaaaca ccacagagat cactccaggc agtggaaaac agccccccac tttttatata 7800
gagaggagat tgtggaagct cataaataat aagtagggat gctgggagat tattgagctg 7860
gtatatttct ctcgaatagt ggtgtgttca ttgttgctat tgttggaatt agaggtgata 7920
ctaaaaaagg aacggaaaaa taccatggca aacacataaa acgtctctac aggtgcctac 7980
ctaccactgg gtcccagaaa gacttgctga ttgtggatta gatgtggtcc cctgccctcg 8040
ggagttcccc agacatcaaa atgagctccc tcagcagaag ctctcattag ctgggtgcag 8100
ggagaatcta gcaatgcggt aactcaggcc ttcaggactt ttgagttagt tacttaaatg 8160
gaagtcctga gacaggtcaa cacactgaac cctttggatg ttttaggaat atttgttcct 8220
ttgcaatttg gccttttttt ccccagtcat gttcaggtta tccttggctg caggtagtga 8280
agaggtgtac cactctttaa tgtttgtact gagtggcatg ttcacaaaaa agctcagaat 8340
tcagttgcat tggcttttca agagggattt gcagcaaggg ctggtttcca atatggtagt 8400
ggaggaattg gctaacataa aactagctcc tgaaattcag acttgcgttt actgctctgg 8460
ctctatggaa ttagtaacca tgggaaagag gcaatgctta gaactgtgta aagtgatgga 8520
gtaggtagag acctgtcttg aagcatcggt aacagtaaat gaagcagcag caagatcagg 8580
tgttctgtgc cacattcttt ttccattcat gtttcataca acattgtctt caggaacatg 8640
gttcagtgtt ctcccaaccc acaagagaca agcaaaataa aaatggacta aataatttgc 8700

```
tagtttttaa ttgggctctt tggcacagac tcaagtagac ctgaactctc agctctgttg   8760
tgaacccgct ttgtgaacaa ggacaaagca tgtcatctgt ctctgagcct cagtctccct   8820
gttagtcagt tacagagaga gcgctccaag tttccttcca aagctgtgca ctggctcgtt   8880
tctccatcag ctttggtttt ccagttggtc tccagctcat ctttgcctca caagagcgtg   8940
ccctgctagt tgctggtgct gggagtgggt gggaaggtga ttgggcgcca gccccttcct   9000
tcccaggctt cacacacaca ccccaggaag ccccgcggtg cgtcggactc tctgtctaga   9060
catcatctga tttttatttg caaatgcagg ttgccaggtg acaggaacct tttatgcttg   9120
tgccccacct gagtcccagg ctcccggagt ccccacagag ccaagcataa ggtctgccga   9180
agccttggcg ttctcaggtg agtgcagggt ttgctcctgg aggcaccgca ggaggccagc   9240
ctctgctgcc agctctgtca tctttgggca gattcgatgg gactttagac acttgctttg   9300
ctccctctgg ggtctggagt agatgtagac acatcctgtg tgtgaggtga ccagggtgat   9360
ttaggagcac cattagaaaa cctgacatca ctgcttgtgg ttctgctgac cgtttcagcc   9420
actggcttga atggagtcat tttggcttct tcactggcac ctctctgaat ttctaggaat   9480
gtgcctttac ctttaccgag ggcccctctt cagccaacat tctcacgatg tggaataatt   9540
gcttggaagt gtagaagggc ttctcatttt gagaagctga tcatccttcc aggttgagcc   9600
acaaataagt cctcctcctc tactccctgg ggacattagt tctggtccct catctctaaa   9660
acattgatgt gcctaagagt aatacacatt ttggtcttcc tctgaacttt aatatagctt   9720
gcaaacaaat atggattcaa tctgattttt aaagttttat ttctaaaaaa aaaaaaaaaa   9780
tccctgcacc atggagatct tacctactat aaagaaggca cctctaggct tggcaagcac   9840
acgtgctata tgtatattta tttttcagat aatattttgg attgttttta aatgggattt   9900
gtttttatat taaaaccaaa tagcttaagg tttggaattc tcatcttgcc ctctggcatc   9960
tttaaaaatc agtgatgaaa aatactaact aaattctgaa ggtttcaggg aggcgagagt  10020
tgtggcactt ttgctgctca gaggggagct ggagtttgac ctaccagctc tttctagttg  10080
tgaatgaggc ttgcaccttt ttttctgagg tgctcgtgag taactgagga tgccctttgg  10140
gaggaggtgc ttctgagcag gaaggcttgt gtttgttttt agaaactttc aaacccttgt  10200
cttgaacacc taagacttgt gtgggtgcct gaagagtagg aaataaacag ctatttatat  10260
ctcggcaacc tcgtgatttc tgatgacatt aaatgaaatg aaacctgccc cgagaatcac  10320
ctcgaatggc caacacccac tctctttggg gcgcactgtc tgactcgctt tcagacagtg  10380
tgttgaagca gagaattgag acagtgatgt gggttaagtc tcaaaacctg ctgttgagga  10440
ataagatagt tttgtgggtt tctttttttg gtatgcatga tacagattaa ttatcagcca  10500
tgagcacatt tattagataa ctgtgattcc cattgatttt ggggttccat acagttacca  10560
gtggcagctg cctcctgtct gtgccactcc cctgcggtct ggctgaggag cttgtgcaaa  10620
cccagcttgg ttctttcaac tcatgggcga tattttaaag aggcttctga aatcagcaaa  10680
acgtttgtaa atggattcat cttgtttaaa gtttcagaga gcgcagtttt agagttcttt  10740
tcaaacttaa acacaaagcc cagtgggaat ttcagcagac tttacatgaa cttttagagt  10800
atttttctca ttaatttctt tcttttcaca agaattaatt ttgtgataaa aacaccacat  10860
atccagtgtg gaaaactaat ttaaaaatca gaaaaacaaa aatggaaaat aaaaatatca  10920
cattctacca cccagaaatc accattaagg cctcagtgct taccctttaa tgtgtgtatg  10980
tgagtgtgtt tatatataaa ttatatagac ataaataatt aagcacctaa ttctatatat  11040
aatttatata tgtacacaca cacacacaca cacacacatt tgctttttac ctaaatgatg  11100
```

-continued

```
tcatgttatt attttgggga cgtttcaggt atgtggaccg acttgcttct ttctgaaaca  11160
ccgttatatt ttttgctagt ataaattaaa cttagggttc atttcctcca aagtaaaaat  11220
tgatttgctt aaagatgaat tttcattcag tgacacatga cttaaatgac atcaccacta  11280
tcatcatcat aattcacaaa taagacttag caagttctta atagtgatgc tctataatag  11340
gaattcaact tacatttcca gaaaattaat gaaagataca cttgttcctt aaaaaaagag  11400
tcggtggcca catacgtttg taatatgctg gtttagacag attaaatggg tttctttcca  11460
cgggacttct ccaagtgttg accgagctca tgctgtctgt ggatctctgg gggagacaag  11520
ggcacgctgt gtttcccagg cctccttgac gcgggaacct tttgttcccc cacgggacat  11580
gtgggacact agagttccac cacaggtgct tggctctgtg gagtcgttgg cctcgaggtg  11640
gtgtccttgg cccccagcac tgactccgga gctctgtgtt tgcagactgc cggctgcaca  11700
tctgcctgta ctaccgggaa atcctcgtga aggagctgac cacgtccagc cccgagggct  11760
gccggatctc ccatggacat acgtatgacg ccagcaacct ggaccaggtc ctgttcccct  11820
acccagagga caatggccag aggaaaaaca ttgagaagct gctgagccac ctggagaggg  11880
gcgtggtcct ctggatggcc cccgacgggc tctatgcgaa aagactgtgc cagagcagga  11940
tctactggga cgggcccctg gcgctgtgca acgaccggcc caacaaactg gagagagacc  12000
agacctgcaa gctctttgac acacagcagt tcttgtcagg taaggcacct cgttatctgt  12060
tagaatggag gtggtgatgg cctgcctgcc acaggggtca gaaaccacag ggtccctccc  12120
accccaggct gaggtcttcc tcctgttgac ttcggcgccc actgggcttg gggcttgact  12180
ccagtagaga tcttctgtct ggctctgttg tgggcagaga gtccggatca gatggtccag  12240
gtggaccatg gctcaggctg ttctcttgca attctggttt tcagcagtcg cctcttaaaa  12300
cagttccatt tcattgcact atgatctcga caaatacgtc tgctgatgtg gcggctcttt  12360
tcaggttccc agaaaaatca taaaggttgg aagcatattg ttaacattct tggttgtcag  12420
gtgtgtcacc ctcatgcaga tgctggccca cgagtgagac ggagggtgga gtggactgta  12480
ctggttttgc acaggagaag ttataggaga gtgctataag ttggctctgt gatatgaaca  12540
tttctaagca tatttttcag aaccagtgag ttttgttttt ctaccttgga tttcatgaca  12600
attcagcgaa cctctggctg gcttctgtga agcccctcgc cctgtcatgc tgggcttcct  12660
cactggcttt gtggggctgt ccaggtggag ggagcctccc gcgtgggagg gagctgctct  12720
acccgccact cgccacccca ccgccaactc ttcctctgcc ttttcccagt cctgtccctt  12780
cctgagcccc ttcagaaact cctgtgtctt tgatttctca tgtgcctccc cttttcttga  12840
atgtgcttct tcattcaact tatttaaaat aaaaatatga cacgtctgtg tgctctggca  12900
ctgttgacat gtgctcgtac ttctgggtgt aagtgaccca agtttttgta agctcatcca  12960
gattttcttt tggtgcccaa agcaaatatg tccccagata actaagcttc aggccaggtg  13020
tggtggccca tgcctgtaat cccagcactt taggaggctg aggtgggcag atcacttgag  13080
gccaggagtt caagaccagc ctggccaaca tggcaaaacc ccgtctctac taaagataca  13140
aaaattagct gggcgtgatg gtgggcgcct gtaatcccag ctactcagga ggatgaggca  13200
caagaatcgc ttgaacctgt gggaggcgga ggttgcagtg agctgagatc gcaccacggt  13260
gctgcagttt gcaggacaga gcgagactcc attgcccccc gcaccacaaa aaaataacta  13320
agctcacaca gaggctgacc ataggaagag ggagaactgt gctggttccc cgaggcggcg  13380
gcaagtgagg aagtcacctg ggctggaca cctctcattc taagggcaga accatcccca  13440
```

-continued

```
agccctggcc agggcggtcc catccttctt ggggttgggc atggtgttca tgggggacca  13500
aggaaattga agggcaactg gggggacccc ccctcccctg tcagcatctc ctgtgtctgc  13560
cttgggatct ggaagagctc acatgggcca ggaaggctaa ggcccactgg gcctggattt  13620
ctgaagactc tggaccttgg tgccagtgga ttcagaagat accacaaggt gagggctttc  13680
taatgaaagt gtcacaagga actggcactg gcttttctga gtgcctcttg ctgggcgttt  13740
ttagggaggt agagcccccg tggtgactaa gctggaaggt gcacattgag tcacaggtgc  13800
actgcgtgag agacagcaca ggcagggggt ggacgcctgt gagtgtcctg gggctgtaga  13860
cttgcgcgac tagaacttac tattaatctg tgagcaagag ctggtcttgg ctttcattcc  13920
ttcctctgta accaagggct gtgctctttg cccactgcag cctctcacct caaagtgttc  13980
actgaggttc aaggaggatg ctgtgaacgt aaaaactgca gctgtgccaa ccagcttctg  14040
cataattaag gattcccacc aaacactctc atgttatcta gggttggagc catgctttct  14100
cagagaattg tgccaactcg ccattctgat tagcctgtgt aggtgtagtc tcagatcacg  14160
gcagtgtgaa tgtattttac agattctgac taagtcattt gggtttgatt tgaattctgg  14220
aaaaaaaaaa aagcaggaag tcaaatagtc ctgtaagtta gctagaaact tctgttcagt  14280
tgaagagaac agtggagatc tttgatatct tcctattcag gtctgcacag cactagggac  14340
agcccccagg gcccggcccg agggtgtgta tctgataagg acgcgtctgt tctgcagaag  14400
ctgtagcggc tcctgtgtca actcgtttct tttgcgggcg tgacatttta ttgtagctac  14460
aggcagaaga tttgtcttgt gtacagggga gggagcatgg gctaaagtca ggggatgggc  14520
acttgtcttt ccaacaatgt tccagtccgt tttgtatctt ttgggtaggt gtggtggctt  14580
caggatgtac atgtgtatat ccacaagcgg gaggccaggg gggctgcccc actcctgttc  14640
tcaagtcaag ttactgttcc atccctggag acaggcaaga agtctactca gagttacaca  14700
gttcaggcat agtgacagtg ggactcagct gccgatggct ggtgctcagt caccacgttg  14760
acgttacata ttttctgtgg tgcctgagtt acgtggatgt ccgcagtagc acagatactg  14820
gattatgtgg gctctgtagt gaggggatga ggttttaaaa tgatcctggg atgtcgaaac  14880
attctgattt tttaaatgaa aacttgtcca tggcataaat tggtcttttg ccattgcgtg  14940
actacgtttc ttgttcttta tctcccgact tcactgtggt ctactacctt ttgaatcttc  15000
gtgggtccaa tgctgcaaag cagtgttctt tagctgtcga ctagttcctc ttgaagaatc  15060
gagggagacc gagggccctg gggggaaagc acccaaagga atgcatacat gctattttgt  15120
atctgagatg ttcacatcaa gagccccact cagcggagta agagtgctca ttcctcttgc  15180
agtgttcaga atcacagtaa gctcttgctt cctgtttaac ctggtgtgtt cggtgatgag  15240
ggtttctgaa catggtctct ttcttgtggg cttctacaga gctgcaagcg tttgctcacc  15300
acggccgctc cctgccaaga ttccaggtga ctctatgctt tggagaggag tttccagacc  15360
ctcagaggca aagaaagctc atcacagctc acgtgagtcc tcagttacac tcctaccata  15420
gtggcttcct gttctttgta aaggccagag tttcatttag aaaagtccca aatgaaaagt  15480
aaatgtcaaa tgacctggaa aaataagcgt aacccttaaa ctagtgaggg aggaagcatg  15540
gtccaacgag cagcacagtc tgaggactca cgtgctcctc ccagacttga gatctgctca  15600
tcaaagaacc agggaggaca gcctcaaagg agggtgcctc tttccccatc tttttttattt  15660
ttcaggaaag ttgtcgtatt tccattttat agggattgaa aaagattgat ggttaaagtt  15720
gccctttaaa attctccagg ttaagattgc tgtaagaatg ctatctagct agtggatctt  15780
cattcaatgg aaaagctttt cccaaatgag aaactatcca ttccctggag gcattttgta  15840
```

-continued ggtctctgca gctgtgtcct agcacctctt ttatttctgg aattttagaa attatttaat 15900
tattgggcat atgatatttg aaagaggctg aatctttcaa ggaattcaag caaatcagac 15960
cctctcgtaa tgttctctag catagctcaa gatgggttca actgtggcaa gtaacactaa 16020
aagggtaggg ttaggattag ggttagagtt ttcttttta tgagaaaagg tttccataga 16080
taacatgaag cattaatttg ccatgggaaa cagaatcttg aacccttaag acttttgaat 16140
ttgaaaactt cacattgcta catacttgca agcattatta acgggcttgc atgctgagca 16200
ataccaggta aaagttacac cccctaacat caaagttctc atcatgttct agctctgatg 16260
ctatttctca ttgagaactg aaatgaaaca tggtttaatc ttgaacatac aaccccccctt 16320
cttgatttta aaaacaaaga ccagccaacc aaccagtata taatcccata gactcaggag 16380
ttttctcatg agttctctcc agtgattgac ttaataattg atatgattgt tgaaataata 16440
actgatacat tgttaacaac aggaattgct aaatgactaa ataaacttgg cattgataag 16500
cagcatttaa gaagttgatg atcggccggg cacagtggct cacgcctgta atcccggcac 16560
tttgggaggc tgaggcgggc agatcatgtg gtcaggagtt cgagaccagc ctgaccaaca 16620
tggtgaaacc ccctctctac taaaaataca aaaattagcc gggcgtggtg gtgcgcacct 16680
gtaatcccag ctactcggga ggctgaagca agggagtcac ttgaacccag gagtcagagc 16740
ttgcagtgag ccgagattgc accactgcac tccagcctgg gtgacagagt gagactctgt 16800
ctcaaaaaaa aaacaaaaaa agaagttgat gatcagctca gctatcacat caatccagtt 16860
ttaaagttga catggatgca agtcactgtc ctctaagtca gggaaagatg gatccccaga 16920
tgaccccctc atgctgaaga cgaggctgcg tggtccataa aatgaataaa cacacgtgta 16980
cacctatgag ttccactttt aaaaattatt aatttaattc atttcaggta cttaggagtt 17040
tagcttaagt cgtcatatat aaaatacagt ctctaatatc atgattgatg gagagcattc 17100
agcttgcctt agatgctgta aattcaggaa aagctgaaca ttaaggcgtt tttgtttttt 17160
ggtgagtgtg atccacgcta ataaccagac agtataaatt tgaggccagt tagcttctct 17220
ttttccacaa tagtagtttt gttgttgttt aactttactt tttatttctt ttacctctgg 17280
ttgagaacta tacagattac ctagaaatca aatcattcag gatgagctcc ttgtttcttt 17340
caaactgcag ttgtggaaaa acaaaatcat tggcctaaat taccctgcag attccctcag 17400
acttcctttt aatttgatca ctttacttga tttgatgcag ttttagttaa atgtacattt 17460
taagtggcag tcgatttgaa agtaacatct ttaacccaga attaagtcac tttggctgtt 17520
tttttacatg ttgatctatg gaaggactaa ccaaaaaatt gcttctttag atggctccaa 17580
atatgaaatg ttttgatgtg ttctaggatg taactttggg ctttacgtta ctgtctcctt 17640
agaatctgag tgctgtttaa tagtgagcca gttgcaggat atctcagtaa tgtcttttta 17700
aaatctctta ttaaaggtag aacctctgct agccagacaa ctatattatt ttgctcaaca 17760
aaacagtgga catttcctga ggggctacga tttaccagaa cacatcagca atccagaaga 17820
ttaccacaga tctatccgcc attcctctat tcaagaatga aaaatgtcaa gatgagtggt 17880
tttctttttc cttttttttt ttttttttt gatacgggga tacggggtct tgctctgtct 17940
cccaggctgg agtgcagtga cacaatctca gctcactgtg acctccgcct cctgggttca 18000
agagactctc ctgcctcagc ctccctggta gctgggatta caggtgtgag ccactgcacc 18060
cacccaagac aagtgatttt cattgtaaat atttgacttt agtgaaagcg tccaattgac 18120
tgccctctta ctgttttgag gaattcagaa gtggagattt cagttcagcg gttgaggaga 18180
attgcggcga gacaagcatg gaaaatcagt gacatctgat tggcagatga gcttatttca 18240
aaaggaaggg tggctttgca tttcttgtgt tctgtagact gccatcattg atgatcactg 18300
tgaaaattga ccaagtgatg tgtttacatt tactgaaatg cgctctttaa tttgttgtag 18360
attaggtctt gctggaagac agagaaaact tgcctttcag tattgacact gactagagtg 18420
atgactgctt gtaggtatgt ctgtgccatt tctcagggaa gtaagatgta aattgaagaa 18480
gcctcacacg taaaagaaat gtattaatgt atgtaggagc tgcagttctt gtggaagaca 18540
cttgctgagt gaaggaaatg aatctttgac tgaagccgtg cctgtagcct tggggaggcc 18600
catcccccac ctgccagcgg tttcctggtg tgggtccctc tgccccgccc tccttcccat 18660
tggctttctc tccttggcct ttcctggaag ccagttagta aacttcctat tttcttgagt 18720
caaaaaacat gagcgctact cttggatggg acatttttgt ctgtcctaca atctagtaat 18780
gtctaagtaa tggttaagtt ttcttgtttc tgcatctttt tgaccctcat tctttagaga 18840
tgctaaaatt cttcgcataa agaagaagaa attaaggaac ataaatctta atacttgaac 18900
tgttgccctt ctgtccaagt acttaactat ctgttccctt cctctgtgcc acgctcctct 18960
gtttgtttgg ctgtccagcg atcagccatg gcgacactaa aggaggagga gccggggact 19020
cccaggctgg agagcactgc caggacccac cactggaagc aggatggagc tgactacgga 19080
actgcacact cagtgggctg tttctgctta tttcatctgt tctatgcttc ctcgtgccaa 19140
ttatagtttg acagggcctt aaaattactt ggctttttcc aaatgcttct atttatagaa 19200
tcccaaagac ctccacttgc ttaagtatac ctatcactta catttttgtg gttttgagaa 19260
agtacagcag tagactgggg cgtcacctcc aggccgtttc tcatactaca ggatatttac 19320
tattactccc aggatcagca gaagattgcg tagctctcaa atgtgtgttc ctgcttttct 19380
aatggatatt ttaaattcat tcaacaagca cctagtaagt gcctgctgta tccctacatt 19440
acacagttca gcctttatca agcttagtga gcagtgagca ctgaaacatt attttttaat 19500
gtttaaaaag tttctaatat taaagtcaga atattaatac aattaatatt aatattaact 19560
acagaaaaga caaacagtag agaacagcaa aaaaataaaa aggatctcct tttttcccag 19620
cccaaattct cctctctaaa agtgtccaca agaaggggtg tttattcttc caacacattt 19680
cacttttctg taaatataca taaacttaaa aagaaaacct catggagtca tcttgcacac 19740
actttcatgc agtgctcttt gtagctaaca gtgaagattt acctcgttct gctcagaggc 19800
cttgctgtgg agctccactg ccatgtaccc agtagggttt gacatttcat tagccatgca 19860
acatggatat gtattgggca gcagactgtg tttcgtgaac tgcagtgatg tatacatctt 19920
atagatgcaa agtattttgg ggtatattat cctaagggaa gataaagatg atattaagaa 19980
ctgctgtttc acggggccct tacctgtgac cctctttgct gaagaatatt taaccccaca 20040
cagcacttca aagaagctgt cttggaagtc tgtctcagga gcaccctgtc ttcttaattc 20100
tccaagcgga tgctccattt caattgcttt gtgacttctt cttctttgtt tttttaaata 20160
ttatgctgct ttaacagtgg agctgaattt tctggaaaat gcttcttggc tggggccact 20220
acctcctttc ctatctttac atctatgtgt atgttgactt tttaaaattc tgagtgatcc 20280
agggtatgac ctagggaatg aactagctat gaaatactca gggttaggaa tcctagcact 20340
tgtctcagga ctctgaaaag gaacggcttc ctcattcctt gtcttgataa agtggaattg 20400
gcaaactaga atttagtttg tactcagtgg acagtgctgt tgaagatttg aggacttgtt 20460
aaagagcact gggtcatatg gaaaaaatgt atgtgtctcc caggtgcatt tcttggttta 20520
tgtcttgttc ttgagatttt gtatatttag gaaaacctca agcagtaatt aatatctcct 20580

```
ggaacactat agagaaccaa gtgaccgact catttacaac tgaaacctag gaagcccctg  20640
agtcctgagc gaaaacagga gagttagtcg ccctacagaa aacccagcta gactattggg  20700
tatgaactaa aaagagactg tgccatggtg agaaaaatgt aaaatcctac agtgaaatga  20760
gcagccctta cagtattgtt accaccaagg gcaggtaggt attagtgttt gaaaaagctg  20820
gtctttgagc gagggcataa atacagctag ccccaggggt ggaacaactc tgggagtctt  20880
gggtactcgc acctcttggc tttgttgatg ctccgccagg aaggccactt gtgtgtgcgt  20940
gtcagttact tttttagtaa caattcagat ccagtgtaaa cttccgttca ttgctctcca  21000
gtcacatgcc cccacttccc cacaggtgaa agtttttctg aaagtgttgg gattggttaa  21060
ggtctttatt tgtattacgt atctcccgaa gtcctctgtg gccagctgca tctgtctgaa  21120
tggtgcgtga aggctctcag accttacaca ccattttgta agttatgttt tacatgcccc  21180
gtttttgaga ctgatctcga tgcaggtgga tctccttgag atcctgatag cctgttacag  21240
gaatgaagta aaggtcagtt tttttttgta ttgattttca cagctttgag gaacatgcat  21300
aagaaatgta gctgaagtag aggggacgtg agagaagggc caggccggca ggccaaccct  21360
cctccaatgg aaattcccgt gttgcttcaa actgagacag atgggactta acaggcaatg  21420
gggtccactt ccccctcttc agcatccccc gtaccccact ttctgctgaa agaactgcca  21480
gcaggtagga ccccagaggc cccaaatga aagcttgaat ttcccctact ggctctgcgt  21540
tttgctgaga tctgtaggaa aggatgcttc acaaactgag gtagataatg ctatgctgtc  21600
gttggtatac atcatgaatt tttatgtaaa ttgctctgca aagcaaattg atatgtttga  21660
taaatttatg tttttaggta aataaaaact tttaaaaatt tgtta                  21705
```

<210> SEQ ID NO 92
<211> LENGTH: 139436
<212> TYPE: DNA
<213> ORGANISM: Homo sapiens

<400> SEQUENCE: 92

```
agtagggagg tgggcaggag ccagtgatga cggaatggca atcacatttg acctctgatc     60
tgtttatttc ctcctccttg acgtctccat ataaatgtta cacgggcatc cccacactcg    120
gatacgcacc cacagtggct gattcggggg taaccgtgtc atttgcttgc aacactggca    180
cctctgccct gcaccccggg agtgagcagt gagtgaggct cgggtctggg cgctggctcc    240
gaatcttcgg gctgggagag actccaccat ctgggggcgg cctgggggag cagccttagt    300
gtcttcctgc tgatgcaatc cgctaggtcg cgagtctccg ccgcgagagg gccggtctgc    360
aatccagccc gccacgtgta ctcgccgccg cctcgggcac tgccccaggt cttgctgcag    420
ccgggaccgc gctctgcagc cgcagacccg gtccacacgg ccaggggcta cgacccttgg    480
gatctgccct ccgctcagct cgagcttccc tcgtggccga cggaacaatg aaggtaacta    540
cttatggttt tgtccgtgtt ttacaaaaat gtgtgcgtga atcgaaccgg cgatttctcc    600
aagaaacata gttggcaggg aggggaggaa ggcgagacaa ccatggctta tatccccccgc   660
aaacgtctca gtatcttctt tatcaatcgt agtttgcggg gaccgtgcat tctgttcaga    720
tttcggttta acctccactc gcaggacgtg ccttctcgga ctttttcaca ttcgcttttg    780
ggaacggagg tgaaagtctg ctacagctcc ctcccctgct tgtgaagttt ggaaaggaag    840
tgagggcttc tctcagtttc tcctatgcac aggaggtggg gaattttgga gaggaggtct    900
ggggatgtcc cgggctgtaa atgcgctttc ctgcagcgtg tgttcgtgat gcaggaggga    960
```

-continued gcggctggaa gagttgaccc gggtggagag gggagggaga acgatctttt cactgttaaa 1020
agcagaaggc ccctcttatt ttgtttcttg tggaaattaa agcttctagg agttacaaat 1080
gatagacgcc taagggcatt catttgttaa accagtgagc accctaatgg ctctgatctt 1140
gctaatcaag gataattagc ctagctgcct attatttctg actatttagg tgtagggatg 1200
tacaccgttg agtgttttgt tttcctagtt tcacacactg gaaaactgca atcgcatata 1260
aaacccgaag agcaactttt tccaaggaaa gtgaaggatg ggcagatatt cttgccatct 1320
aacattttgg aattgagatg accataatgc aatctgaact tctggtagga ataaagcctc 1380
gtttcagagt ttctaaggag ggagatgaag cgtggttctc aactgctctt atctacaacc 1440
catcccagac catagtttca cttagaagaa ataatatgta aatagcgcct ttgttgccaa 1500
acaaaaactt tcactacaat taaacagtaa ccgagtggaa actatgcgtt tttgtattca 1560
acagagatca cacaactttt cttctatagt tagaggttct atttctggct tcctcatgct 1620
tgtttcattt cagatgaaaa acacacttta gttgattata gctttagtaa gtaaaaggag 1680
aaaactaaga atgaacagtc ttgcttttcc agctttttcc tgtccatgtg cagttgtggt 1740
taattacgcg tttttgtagg tccaaaaacc cctgtccctt ccacaagata cttttataac 1800
atggggaact aggtaagata tctacaagta gtctcttttc tgtttcctga tatttcctaa 1860
gattaagaaa gaaatgattg tattctaggt atgatcgaag aagtatggaa ggttccatta 1920
agttagtttt atcacaatat ttcaaacatc tttccactta tctcttaaat atgtattgct 1980
atcacaagct tgattttta aaaaaatgtt atttgcacat ggcatcttga ttgcctttgt 2040
cctcagcaaa ttctccgggc ttaagtcatg catgagcttg tattttaaga cagacacatg 2100
cagaatgggc aacttggata agaaacatag gatatacact gagtagcatg tgtacaaaaa 2160
tggtaagtga gtattatgac ttaataaatt tagatgggga tttaaaaatg atacacatgt 2220
aaatgggatt ggaggcaagg gaagtccgtg tgtgtgtgtg tgtgtgtgtg tgtgtgtgtg 2280
tgtgtgtgtg tggagggaag acgggaggcc tagtggggag agaggtttta cattccagac 2340
acaggatgtg gcccctcagg ctaggctcag agatgtaaag ctagttaagc tggcctaaca 2400
aaagggtggt ggttagaaaa aggaaaaaaa gaggtggggg ttggggagga aaagaattta 2460
atgctggcca atattttcat ctgataagtt tcagtaatga gtaatttcac tggatttcag 2520
aactacagag agaaaagggg aaaaatattt ttcctttttt acgcaagaat ttctcttgct 2580
tttcagctca ttagaaccag atctaattat ttgaaatgag tttaaaacct tattatgaaa 2640
ggaagttgaa aacattcgat cacaattgag ttttgtacta tggactaaaa ccaagatgtg 2700
ctttctgtca gtagctgtgc aactccctga aaaaagaaaa atagcgcaga gcgatctgag 2760
ctttgtgaag gctacacaat ttatcaggcc cagagagata ggagtgtgag acttcagtca 2820
cgtccccccg tacgcatgcg caggagtaat tatttaaaga cattttgttc ctgactaact 2880
gcctcactca ttatgttcct ggaatttgtg atacaaaaaa acaatgttta gcctatcaat 2940
agtttatata gtttatgtta ttttaatata aattcttctc aacttagaaa ctgcctcttt 3000
tttcttttaa aaacccactt gtaactgctg tatatattca gggcaacttg atttggtgtt 3060
tcgttggttg cagtcctcaa atttgacctc aatatactct ctacttatat aaattttgtc 3120
tcagttttgt ccgtaggctg acattccaat tgttttccta attatatatt ttgttcctta 3180
tttctcatgt ctagaaataa agctagggaa gtaaacagct ggaaaactga tagtggtgtt 3240
attaacctaa ctgagagggc tgggcttatg agtaaattat tcctgtgcat aaatgaaaga 3300
ttgtttctaa atggcagcta tgttgagcct ttgtattagt tacatctttt ggggtttcag 3360
gttgccagct tctttaaatg gcctcttctc aactggtata ggaagttgga aaataaagaa 3420
ctttctttat ttccctttag tgttggtaac cacagtttct ttaaataaca gatgcccacc 3480
ccagggaaac ccagtggcat gatcagcctt atgctcagga aggtttggtt gctatactgg 3540
agagtgagaa tctgggacct tccatgatag acataattgt gccagctatc ctctactttc 3600
tatatgatgc tatcattctt ttttcttttc tttttttga cagaatctca ctgtgttgtt 3660
caggctggag tgccgcagag tgatctctac tcactgcaac ctctgcctcc taggttcaag 3720
caattcttgt gcctcagcct cctgagaagc tgggattacc accatgccca gctaattttc 3780
gtattttttt gtaaagacgg agttttgcca tgttggccag gctggtctgg aactcctggc 3840
ctcaagcgat ctgcccatct cggcctccca aagtgctggg attacaggca tgtgctatca 3900
ttctttttga gcacaggagg aaactatggc tgatctgctc attttactgt caaaaatata 3960
ggcagctttt gtattgtaac attatcccct taacagctgt ccaactggtc tatacatttc 4020
acctaacata tggtaaatgt tcctactgtt ggcctttcct gagcctctgt ccattcaact 4080
aaggccactg caatgggatt gtatgcagtt cagccaagaa ataaatgtga ggtgcaactc 4140
acattttta aatgtttcaa aattaagcat ttaggtgctt ttattcataa acatgacttt 4200
gcaaatattg gtaaacagtt tcatcataag accttgtcag tgactcacaa tgtcaatggt 4260
gaacgcaaag gagaatctgt cttttctgga acaccaggtt caggtatcag tttcaactat 4320
gcttataatt tgtgctctaa agtccacaaa gctaaattat ctttccccta aaaattgagt 4380
actcatatcc ttaaaatagc ttggaaatta gattacctta tgaatacagc atagcatgtc 4440
acataaacgt ttttctactg ttataccttt ttggtgggaa agactatttt gcaaaacatt 4500
tttcttgtgt tcagtaatta atgggaaaaa caaactctaa aagaaagaga cagttatgtc 4560
ccaaaaatac aggaaaatgg aagaatggaa acagggaaga ccaataaaga aaaaaataga 4620
ggaaattaca agtaataaac tgaagtcata ctgaaaaaca tatggctctt tcttattgaa 4680
agttgtgaaa tacttgcaaa actcagctag ttccattaag aatagtcttt aatctaaaaa 4740
gaacaaattc atttgtcagt tctttatttc ggtgtgtaga tttgaatgtt tcatcaattg 4800
catttacggt ttatccctca gtgtgagaac tgtttttgct gttttgacta taaatggata 4860
tctgctttag gaagacttag gaagcctggg acataggatt acagatcaaa ttctatttga 4920
ctccatagaa gttgagacgg aaggagcacc tgttgggata ttctagacca aacattccac 4980
agctgtctct taacgtgact gacaaagaga cacagttgag acgaagtttg ggtatatcct 5040
gggatgaggc caagggtgga tttgcacagg atggtcacag ggcagttgtt agcattccac 5100
cactacataa aagggtgatt ttgccaagtg catttcattt catttcagtt gatttagata 5160
ccaagttata ttgttttgac tttaggacta gatgtgagtt caggaatttg aaatcataat 5220
aaatgtttcc ttgaactttg aagataaaag gtagagttaa aagacagctg cgaagtctac 5280
atggggaagc ataatacatg actcagggtt ccatggtttt cagtgtcggt gagtgctctg 5340
tacacttata agaatagtgc tggtgtttat agaagaaaca catgcaggtt tgaggcaaga 5400
cttccttgct taattggtgc ttttgctttc cattttctaa atgccatgca aactactttt 5460
tttttttct tttgttgaga cggagtcttg ctctgtcacc caggctggag tacagtggtg 5520
cgatctcggc tcactgcaag ctccgcctcc tgggttcacg ccattctcct gcctcagctt 5580
cctgagtagc tgggactaca ggcgcccgcc accacgcccg gctaattttt tgtatttttt 5640
gtagagacgg ggtttcacca tgttagccag gaaggtcttg atctcctgac ctcgtgatct 5700

-continued gcccgcctcg gccacccaag gtgctgggat tacaggcgtg agccaccgct cccggcctca 5760
aactacttta actgaaaaca ttcttctaag gaaagcatca gaaaacttac tagaattgct 5820
taagaataaa taaataatac aaataaaaga gcaaaatgag aaagtagaca gactcctagt 5880
ctattgtgct attgatctct ccaggttcta ggctttcttg ggtctgacac cactttgtaa 5940
attttttttt tttttttttt ttttttccag atagggtctc attctgtcac ctaggctgga 6000
gtgcagtggt acaatcatgg ctcacttcag cttcaacctc ctgggctcaa gtgatcttcc 6060
tgcctcagct ccctgagtag ctgggaccac aggcatgtgc caccacgccc ggtgaatttt 6120
tgtatttttt gtagagatgg ggtttctcca tgttgcactg gctggtcttg aactcctggg 6180
ctccagtgat ccacccacct tggcctccaa agtgctggga ttacaggcat ccgtcactgc 6240
actgggccag tttgtaaatc ttatgaaaag tatggccaat cttttgcaaa atgtgcaaac 6300
acatatagac acaaagtttt atatctaaat tattggttat taaagccagg acaatagagt 6360
gcatatagca tggaagacag gtagaaaaga ctgaaatggt ttagttattc agagcagtgg 6420
agggctattg gctcttgcct ttgcagtcag ctgagatatg aaactatata agcagaagct 6480
tcacgctgcc atttgaatat tgaaaatctc cacttttagt tcaagagata aacaaccaat 6540
ggtttgtttg ttcacagcac ataagttatc actttcttct ctgtttcatc ccatcaagat 6600
ctaaggtgta tagttacaga atagaactcg gttcatacca tatgcaccct aatttcttcg 6660
atcttcaact agtttggaag tgtgtgtggg tgttttctta gccaaggtta atatgcaatt 6720
tcttagtgga gtgtaggagt ttggggtgcc tagccttcct acttcccact tagataactt 6780
cccctacctg ttgtacctgt caaaggagaa ggccagtatg gccatgttct ttgcaggtga 6840
ctccacctta gccacagctg attgtaacaa gggtgtatat ttggcccaag tccagccatc 6900
tttttttttt ttttttgagg cggagtcttg ttctgtcacc cacgctggag tgcagtggtg 6960
tgattttggc tcactgcaac ctctgcctcc cgggttcaag caattctcct gcctcagcct 7020
cctgagtagc tgggattaca gacacccacg accacgcttg gctttgtatt tttgtatttt 7080
tagtagagac ggggtttctc catgttggcc aggctggtct agaactcttg acctcaagtg 7140
atccgcccgc cttggcctcc caaactactg ggattacatg cccagccagc catcttttac 7200
ttctttctta ttctcttatt ccacatattc aagcaggtac cacgtcctgt ggactctgtc 7260
ttctctgaat ctataggttc tctctttccc attgccctgc atactggttt atgctctcat 7320
tacttctcgc ttgaattatt ccaaaagtct cccaactggt ctgaagctta attttcatta 7380
tgtgctgttc gatgtcattc caccacgcaa aatctatggc ttctccattg tctcctgagt 7440
ttagtttagt gcatgagacc gtttaaaatc tacctacacc tcttctatgt gcatgcattt 7500
ctctagtcat aagagaggat ttgatctatc tcaaaatgtg ttcttatatt tgcatttact 7560
ggtttttaac tccctccatc ctatctataa tttgcaccat gttgctcacc atgcagccca 7620
ctccccagac accttgtgag aacagtgatc atgtttttgc agtggaatga acatgggcga 7680
aaggtgggaa ggtatgcata gatttacatt ttgaagtcag gaaataagat actgatcaat 7740
gctttaattc gactgtgctt tttacctttt cctctgttgt agcatgaacc ttgccccaaa 7800
aagatattga tcatatgctg caactcctct gcacttacct tttcttctac catggcagga 7860
accttgcacc attgttggtg ctttacagat attggttgag ttaaatcgag agcctatttc 7920
tggactttca agattcagat taattgattc tgttttatac ttctctgttt ttgaatggca 7980
catacatctt tccacacttg gatttctttg aagttaaagc tttaattgac ttccaaaaga 8040
cagaggatta taaaaacaca gagaacagta aagtatttac acggtcttaa tgcctattgc 8100
caaacacata tagctgctat taatgcctat tgccagactc atatagctgc aaactcatgt 8160
agcttaatgc ccattgccaa actcatatag ctgctatata tgtctactgg aaaactcaca 8220
tagctggttg attttaaatt gattgtagga aaattcatac aaaaagatgc tacataggaa 8280
tataaactga acaccacaaa aatcgtaatg aacaaactca gtaatgccag cctgttcaat 8340
cactagtttt cagattaagg cagtatgcaa agggaaacat ccttggaatg gtcttagaat 8400
atagaacaaa gtcatgtgtt tgggaatctt aaccaattcc aatactgttc aacatgtttt 8460
tctttgttgc aaacaatgca gtttttaagc aaactaatga atgcataccc tgacaaacaa 8520
atccaacaaa agaggtactt agagcagtgt tcattgaatc ctagaatttt gaaagaaaaa 8580
atctattagg tcattttggg cttttacttc tgctgaagaa ggattgttct tttgagttta 8640
tttttctagc tttcagttct attccattta aatgcctcga gaaataggac ttctcaaatt 8700
ccctgtggag agttctggca cctactatat tcacttttga aagtctcctg ataactgatt 8760
tccttttctt tttggttata cacatcaact attcatggtt ggctctgctg atagttttcc 8820
atgattcttt atgcttattt aaaagaaatc atataacatt aatcatataa catataacca 8880
ttacttggtt ataaagcatg atattaacta aactggcttt taaaaattca ataacattag 8940
agcaaatatt ttattaatat tgtcagtagt tccatgaata tatagatgta ggatgtcaat 9000
aaagtttatg ccccttaata actgagtgtg ttaatgttgt atttgctggt taactggcac 9060
cttccctcct tttgatcaat gttcttagaa cagtatgtac aggagtactt tagtctacca 9120
cttgatattc aaggacaaca cttcgaagct tgaaatgagg gattgtttta accatattaa 9180
cgtaactgca tagtttgcaa tagatttaat gattcaacat cattgttaat atttagttta 9240
attaaaagtg ccttatatta acttgtacac atgtgaaatg acttatcaac aagattattt 9300
attgcagcat tgtttgtgat tacaaagagt ggaagtcatt tgcatagtca ttaggcgtaa 9360
aaaataatga cattaaaaga aaacaattga ggaaagaacc agtaagctct caggtagaga 9420
taaaaagaaa gttaccgtga gccttttcac tgtatatatt tatatatttg atttttgaca 9480
cgtgagttta ttataatcaa gattgaatga aaaaaattga agccttttaa tgaaattagc 9540
ttgacaccag agtcattatc aagaaaatct gaaatactgg tacctatgca catttgattt 9600
tattattttt agttttatta ttttttgaga cagagtcttg ctctgtcgcc cagactggag 9660
tgaagtggtg tgatctcagc tcactgcaat ctccagcctc ccaggttcaa gcgattctcc 9720
tcagcctccc gagtagctgg gattacagat gcctgccacc atgcttggct agtttttgta 9780
tttttagtag tgacggagtt ttgccatgct ggccaggctg atctcaaact cctgacctca 9840
ggtggtccac ctgcctcagc ctcccaaagt gttgggatta caggcgtgag ccactgcacc 9900
cggccattta agcaaatttt agttaagacc agtaacatat ttttgacagt atttccgaag 9960
tgttgtattt aatttaacta attgaaaatt atctattaag aaagcaagtt aaatgtaatg 10020
tgtatacttc atagtataca cattataatg attcatagta accattatat gaagagtgtc 10080
taaacttttc ttcaaatcta ccatttatat agtacaataa tgaccagcaa acaatggcta 10140
agttttactt aattagacat ttgtgtagct cctaccaagg ctaccagact ttgtacccag 10200
taacaggaaa acagaaataa ttcaagcatt attctcactc ttgagaaaca attctattta 10260
gggagatata cataaaaagc aaaggtggct gggtgcagtg gctcatgcct gtaatcccag 10320
cactttggga ggccaaggca ggcagatcac ttgaggccag gagttcgaga ctagcctgac 10380
caacatggtg aaaccctgtt tctactaaac atacaaaaat tagctgggtg tggtggcatg 10440

-continued

```
cacctgcaat cccagctact gggcaggctg aggcagataa ttgcttgaac ctgggaggtg  10500
gaggctacag tgagctgaga ttgcaccact gtactccagc ctgggtgaca gagcgagact  10560
ccatctcaat gaataaataa ataaataaat aaatagcaaa ggcaataatg tgcatatagt  10620
aggtgctaca gtagaagtct gcacaaggtt ctgtgtatgt ggaaaagaca agtcagaaaa  10680
attaggaaag gctttattgg gaggtgacat ttaagcagaa tcacgaaaga agacctgatg  10740
aacatggggg taagagcact tgtacacaac cccatactcc tgggctcaga ctcacttgct  10800
cattccctaa tcatagaaga ccttgaggaa aagcatgctg gggttccctt ccagcccact  10860
ggtaaataca gagaggccta agcacccaac atcccccagg gaatacacca ctgggactta  10920
aagcattggc aacccagcac ccagttaaat tccccttgtc actgtttcca cattgtcccc  10980
atcaccttca ctctcttgat gctctgcatt ttctctctta actcgaccca cagtagaccc  11040
tcccactcaa atctgccccc aataaccttt gcaaccaata ttaccgcact acactttatc  11100
ttccctaagg gtttcctgct cctcctggtc ttaggtgagg tcatttctct gccagccttt  11160
aaagtggaag ctgctcattt tctctgtccc tcatccaggg ctggagtggg actgatgccc  11220
ttcaccctgc ccagtactgt ttccacatga gactccttgc atagcatctg ctctctgcta  11280
ctcagaccag gagtctgtgc tctctcttcc tctaaccatc attggaagac accccagtcc  11340
ctctggcccc attatccact gtagatttta gcacttacct cctctcttcc ctcccatgtg  11400
ctgttttccc atttatttta aggtgcatgt ggatggccca ttccccttcc tggcatctta  11460
atccctttaa tttctcattt ccattaattt gctacattcc tcatatgcca gctacccta  11520
tggccatatc ccagaccttt gaatcacaca ccaaattcca tcaagtccta tgagtcattt  11580
ttggtccaag acctatctta catctatgca gtgctatcta ttttaacaac catgtgccca  11640
gtttaggcca ctgtcttctc ttcactgaat atatgtgttc ctgtttttttc tcatccccat  11700
ttgtttccca gacacaattt gttctccaga gcagagtgat cacatcagtc acctgctata  11760
aaaactcctc aacccggtgg ggcatggtga ctcacagccc cagcactgta atcccagcac  11820
tttgggaggc tgaggtggga ggatcacttg agcacaggag gagctgaagt gatctgtgat  11880
cacgtcactg cactccagcc tgggctacag agtgacaccc tatctcaaaa acaagcaaac  11940
aaacaaacaa acaaaaacca acaaaaaatt ttttattaag caaaaaacct cttcaacctc  12000
ttcctgttat gttttgaata aaagctaaag tccccaccat gctccagaag ttcccaaggg  12060
atctggtcct tctcatcttt acagcctcat cttgttttgc cgtttccacc tccctcatcc  12120
cccaaactct ttttcttcag ggcctttgca cttgctgatg cctctgcctg gaaggtcttc  12180
ttctgattcc ccatccaggg gtgccttatc accctgccct gccaacctca gattggatgc  12240
tacttcctca aagagaccct tgggactccc atgtttccca ggctttcagt gccctcatct  12300
caacttgtaa tgattgtatt ggggtgatta tttgtatgac tttgggattg atatctgact  12360
cttccactag accatacatt tcttgagagc agagagcata tccagttttt ttaccactgt  12420
gcaaccatat gtcgtccaat gcttggccca taatagggg ttggtgaatg tggtaggctg  12480
agtcatagcc cccaaggatg cccatagcct catccccaga agctttcatg gtaaaaggga  12540
ttttgcagat tgtgattaag ttatggatct tgagatggag agattatcct tgattatcta  12600
aataggtcca atataatcag tagcgtcttt ataagagaga ggcagagggt caaaagcaga  12660
atcagagaag gagatgccac agtggaagca aaggggtgtg tgtgtatgtg tgtgtgtatg  12720
tgtgtgtgtg tgtgtgagag agagagattg agatttaaag agctccatta cttgatctga  12780
ggataaggat gagccaaaga atgcaggtgg cttgtagaag ctggagaagc caagaaaaca  12840
```

-continued

```
ttctcactct agagcctcca gaaggaatgc agctctgctg acaccttgat ttggaacttc  12900
cagaaccata agataataat tttgtgtagt tttgaggctg ggctcatgcc tgtaattcca  12960
gcactttggg aggccaaggt gggtggatca cttgaggtca ggagtttgag actagcctgg  13020
ccaacatggt gaaaccctgt atgtactaaa tatacaaaaa ttagccaggt gtggtggtgc  13080
acgcctatag acccaactac ttgggaagct ggggcaggag aatcacttga acccgggagg  13140
tagagattgc agtaagctaa gattgtgcca ctgcactcca gcctgggcta cagcgtgaga  13200
cttcgtcaga aaaaaagaat aattttgtat aatttcaggc cacaaagtct gcagtcatct  13260
gttacaacag cagtagtaca cgaatacaga ttttggtacc tggaaatggt gtgctactgt  13320
aacagatacc taaacaatgt ggaagtggct tttgaattgg gtgttgggca gcatgtggaa  13380
gaattttgag aagcatgata ggaaaagcct agcttgcctt agaaagactg ttagtagaag  13440
tagggatgtt aaaggcgctg ctggtgagga cttggaagtg aagagcatgg taaagaaaat  13500
gtgtttcatt ttagagaata tcaaagtcat tgtagaaggt tggcagaagt gtaggttttc  13560
ataatgtgtt gttggtgagg gctgagaaag aaatgaggac catgtttagg gaaactggag  13620
gaaaaagatc cttgtcatac agtggaatga aactgtggaa ttgtgtctta cagttatatg  13680
ggaagcagaa tttgtttgaa cttggatatt tggcttagct ttccaagtaa agtattgaag  13740
gtgtagcctg gttttctctt gctgttttat agtaaaatgc ccgagaaaaa gggataaatt  13800
gaggtaggaa ctgttaagaa aaaggaacaa agacatgatg acttgggaaa ttctcaggat  13860
acctggtttg taaaagatgc tagaattaga agattcattg tcaggaaagt gtgctctgga  13920
gaggaagcca agggtgagtt ccttgtggcg taggttaggg gctgtggcag ggatgcaggg  13980
aagagatgat ggtgacttgg actaggggtc tgacggggta tgggaaaata gagaggaatg  14040
agttgattct gttgggactt tgtattgagt tccttgattc cataagtgga aacacatgta  14100
gagctctctt tcctggccac ctaagctctc tgaccatatc cctgactctc tccagaatgc  14160
cttggcttca tgtccacgtg aggacaaatc atatttttct gcattttgcg tgctggattc  14220
ctctctggac taaagatcca atgagaggtg gtttctagct ttctgctctt tcccacaaca  14280
ctccgtcagt gagtcttctg gatgtcctat aggcaactca ctggatccac ttggtctgtg  14340
gaagaatcac taccacatcc atttcacctt gggcacagac tagaaggtga ggcagtcatg  14400
tcctgcagtc actgggtagc ttacaagtgc taatacagca atagcttaat tagagagaga  14460
gagaagaaga agaatgttat ggagcctgtt tctagagagg aaaccacaat atcttgatca  14520
agagacccta aaactggaag aaccagagca gctggtatca aaatgtggaa aaaactgaga  14580
tgtggcaagt ggtacaactg atagccaagg aggaaaaatt tgtatccccc tgtaatccca  14640
gcactttggg aggctgaaac aggtggatca cctgaggtca ggagttcgag accagcctgg  14700
ccaatatggt gaaaccctgt ctctactaaa aatacaaaaa ttagctgggc gtggtggtgt  14760
gcacctatag tcccagctac ttgggaggct gaggcaggaa aattgcttga acctgggagc  14820
agaggttgca gtgagccaag atcgcaccac tgcactccag cctgggtgac aagagttaaa  14880
ctctgtctca aaaaaataaa aagaaaagtt tgtaccctct tcttttctct tgcctcagga  14940
taactgagat tcttataatg catttattga acaaatattt gaggagtact cattatgtaa  15000
gcatcagaca ctgctcaagg tcttgaggct gtgagggtgt attagtccgt tttcacactg  15060
ctataaagaa ctacctgaga ctgggtgatt tataaagaaa agaggtttaa ctgaattaca  15120
gttcatcatg gccagaaagg cctcaggaaa cttacaatca tggcagaagg tgaagaggaa  15180
```

-continued gcaaggcaca tcttacatgg tggcaggaga cacagtgaga agggagaagt gccacacttt 15240
taaaccatca gatcttatga tgatatagga gttaagaaga aatcacttag gtagatagtg 15300
agggtacggg agtccttggt aaggcttttc ttttaaatga aaagcagccc cacacataga 15360
caagcaagct gggagcttgc acgggtgaat gccggcagaa actaggaacc agacacgtta 15420
agatggcggc tccattttcc cttctctgcc agccaagtgt acagtaagga gcagacaagc 15480
tggtgccggc caagaggaga attcatgtgc ataataagat tagggtgggg tgaccagcct 15540
tcccagtgcg ctatgtgaac atcatacctg attgaaccaa tctgtgagcc ctatgtaaat 15600
cagacaccac ctcctcaagc ctgactataa aatctggtgc attcgccacc cgccggtgtt 15660
tcctctcaga agtcccctct ctctcattag agagagggct gttttccttt ctccttcttc 15720
tgcctattaa cctgtgctcc taaactccct gtgtgtgtct gttctgaatt ttcccggcat 15780
gagaggatga acctggggta tataccccag aaaacatagc cacttaagtg agaactcact 15840
cactattcac ccccaagatc caatcacctt cgaccaggtt cctcccctgg cgtgagggga 15900
ttaaaattcc acatgaggtt tgagtaggga cacagagcca aaccaaacca tatcagaggg 15960
tgaagagcag gtaaagttgc agctctcctg caacttgcag ggaaaggcca tataacacat 16020
ggttatgagc acaaactggg actggactgc aggtgtgtga gccccagctt tgctattgag 16080
tgaccaccag caagttatta aactgtgcct cagttttttt gtttatgaaa tggtggtatt 16140
agtacaaccc acctctcatg gatgatgtga ggattaaata aaataacatg ttgccaggca 16200
cagtggtgca cacctgtaat ctcggcacat tgggaggctg aggcccgagg gttacttgag 16260
gttagaagcc tgagacctgc ctggccaaca tagcgaaacc tcatctctgc ttaaaataca 16320
aaaaaaaaaa aaaaaaaaaa aaaaaaaaaa ggccaggcgt ggtggctcat gcttgtaatc 16380
ccagcacttt gggaggccga ggcgggtgga tcacaaggtc aggagtttga gaccagcctg 16440
gccaatatgg tgaatccccg tctctactaa aaatacaaaa attagccaag tgtggtggtg 16500
ggcacctgta gtcccagcta ctcgggaggc tgaggcagga gaatcacttg aacctgggag 16560
gcagaagttg cagtgagccg aggttgcgcc actgcactcc agcctgggcg acggagcgag 16620
actccatctc aaaacaaaac aaaaaaacca aaaaaattaa ccaggcatgg tggcacacac 16680
ctgtaatccc agctactcag gaggctgagg caggagaatc acttgaaccc aggaggtgga 16740
ggttgcagtg agttaagatt gtgccactgc actccagcct gtgcgataga aggagacagt 16800
ctgcaacaaa gatccaaaaa caaatataaa gcacttataa cagggtctgg tctgaaataa 16860
gtactatgta agtactgtaa gtattaacta atattattac aatttatcct catatagtaa 16920
catatcaaat attttcagtc agtgatgcaa tatgaataaa atgaaatgat gcagtagtga 16980
cagaactgag agaaagctgg tacaaattta tactgactgg tcagggaaag cttcacagaa 17040
aaggtgaact ttcagctgac acctgagtac catggtctgg aggtaagagt gtcccatgca 17100
tatggaacag caaatgaaac ttcccagagc ataatctgag aggggagatt tcaggagtgg 17160
agccacatca ttgaagttcc ttagtcctgg taagtgtgga ttttattcta agtgtggtga 17220
aatgcccctg agaggttttg agtagtagat ggaattccat ttttaaaagt cactggtgag 17280
tcaagtagtg tactatggtt acattttttt cccctttatac ctcattttgt ttttcctgca 17340
gttaattctt gcattatttc cttttattta cttaccttac tatatattta ttatgaattc 17400
tttccaattc ccaacttcct gacagcctct caatgtaatt ttacttaggt taaatgtatc 17460
tgacagttca ttttcttttt tgtctctgta ctctttctgc taccattctc attcttgcac 17520
taatttgtgc tggtttctct ctgagccagc tgcacagctg cctgcctaag acttcctctt 17580

```
ggcatctttt accctctctc tgtgttacat ccccggtttt ctgaatcgtg tggcgttctc  17640
ctttttactt tacttcctca tttgtgttgc acgtatgctc tagttgtttt tagataaaga  17700
gtgcatcaga ggtagatgtt ttgattcctt acatgcctga ctttttgttc tacttttgct  17760
ctaggttaat acttgatttt gaataatatc ctaggttaga aatgattttt cgtcagaatt  17820
ttaagggaat tgcttttctg ttgtctagtt tcctgtgtta ctgataggaa gtccaaaggg  17880
gctcgtattt caggtccttt ttatgtgtaa cctgtttttt gttccttgag gtattcaggg  17940
tctcttttta ttgctaattt ggggagcttt atcataacat gggtccttag tcattcatcc  18000
tagaaaattt tcctttccta tatctttgat gatttcgtct cctctgcttt ccctcttttc  18060
tcattcttaa acttctattt gtttgacatt agacctcctt gtttgatctt ctaatttaat  18120
ttttctctcc tagtgtccaa tttttgaggt gggagaaaga tctcatcaat gttatctttc  18180
agcctttccc ctgaatttta aaattttact cttcatattt cttctgatta atcctttaaa  18240
aaaatagcat cctgggccag gtgcagtggc tcacacctgt aatcccagca ctttggaagg  18300
ctgagcgggg agtggatcac ctgaggtcag gagctcaaga ccagtctggc caacatgatg  18360
aaaccctgtc tctactaaaa atacaaaaac ttagccaggc gtggtggtgg gctcctgtag  18420
tcccagctac ttgggaggct gagacaggag aatcaccaga acctgggagg tggaggttgt  18480
agtgagctga gattgtgtgc cattgtactc caacctgggt gacagagcaa gactctatct  18540
caaaaaaaaa aaaaaaaaaa aaagggccct gttccactga ggcttcagtg cggagcatgg  18600
agggatacta cctccaaatt ccaaacacgt ttgacacatc taaagaacct tctaaaggat  18660
gactaaacta attctgcaag ctttagcctc taacttatct ccaatttata tttaatagaa  18720
ggctggaaat tgaacagaaa ggaaataaga ttatttggaa ataaaaaatt gtcagccaag  18780
caaggagagc ttggcatttc tggaaacttc tttaccctgg aagaggtaaa aaagtgattc  18840
tcccattccc ccaacagggc attcactaaa aattaagtga gaaatgcttt gcctagagga  18900
tctgtagctt gcgaacactt gacttgtgcc actggtgtac ggaacatagc agtgtcagct  18960
ctgccctggg acagtcaagg ctggctggtg ctgcctgtgg ttagagtcaa gagaggggtc  19020
ttcagtgggt gcagtttgca gttccagagt ttagtagagc aaagacgtca tgaactatgt  19080
gaactctgag gaaaggtgtc atagaaacac ctcaaaagga cactgtctaa gaaggctact  19140
tgctggggca aggagacccc aggggtcaga ggctgtgtag ggaataatgc cagagctggg  19200
gttgaaggag aatccttaga ggtgagacag aatgtgcatc attgcagtgg ggctgtgcaa  19260
ggcagtggtc tccacaggag gtgaggacaa gggggagggg aggttgtgaa gaatccgtaa  19320
gtgaccatga tgcaatagaa agccagaatt tgggcatttg ccataggaga gggcccccag  19380
tgccagatta taatggtcac agacaaatga gatttttaac catttcctct aattcatggt  19440
ccacacttaa ccccgtgggt cctggaaaca gcagctggag aatggagagg aaagtgatgt  19500
gggagagaga aaactttctt taccctttc ataactgagt ttatgaagta aactgacagt  19560
agaaagataa ataggagaaa agacataaat ttattttgtg cgtacacatg ggagtcccat  19620
aaaatatgag actcaaagaa aggccagatg attgaagttt atatagtatt cctgagctac  19680
agaaaaggaa tcagggcttg gggcttattg aggggaggtg gtgacaggtt ataagagggt  19740
gaggagagga agtgtatagc aagcataggt tgtcttgtta tgcagataaa aagtctctca  19800
ggtgataaaa gttgtctcag agtcccccat cagaagaata ggtaatagcc tgtgacaagg  19860
tctacctgtc caatcttctc cctggtgata aaatcttccc tggttgatga gattcttatc  19920
```

aaagtttttt tctttataga tataaatttt gtttacaaaa agacagtttt tcagagctac 19980
tcctgtgtct acagtgtctc agaataacta actggaaata catcaaataa gcatatcctg 20040
atgtggcata ttctggtcat attttgggat ggtgcgtcct gagctccaat gctgaaaaaa 20100
caggaacccc atttctgttg gatgtgccaa cctaaaataa tcaaaagggt cagaatctag 20160
tttaaagata ctttattcaa gtgcaaagtt taaggacagt gctagggaaa cacggatccc 20220
aaagaatgga agtcagcgtt ctgaacttta gaagtttggg attgtttata gagagagagt 20280
ttagggaagc ttaacagaat ttcaacatct ttctgtgtaa ggcttaatgc ctagttacaa 20340
tgatctgatt agtcaaggtg gtcactttca tttgagaaag gcatatttaa catttcacgg 20400
gctgggagcg gtggttcatg cctgtaatct cagcactttg ggaggccgag gcgggcagat 20460
catctgaggt caggagttcg aggccagcct ggccaatatg gggaaacccc ttctctacta 20520
aaaatacaat acaataaaat aaaataaaat aaaaaaaatt agccgggcat ggtgcacgtg 20580
cctgtaatcc cagctacttg ggaagctgag gcaggagaat tgcttgaacc tgggaggcag 20640
aggttgtggt gagctgagat tgcaccattg cactccagcc tggcaacaa gaatgaaact 20700 ccatctcaaa caacaacaac aacaacaaca acaacaacaa caacaacaac aacaaacatt 20760
tcacactgaa ggtgtaacag tcatgggttt gtattttcgt ttttcttggt tttttttttt 20820 ttttttgag actgtctcgc tctgtattgc aggctggcat ggcacaatca cagctcgctg 20880
cagcttcgat tttgtgggct caagtgatcc taccacctca gtctcccgac tagctgggac 20940
cacagtcatg tgccaccaca cccggctaat ttattttta tttcttatag agaccagatc 21000 cccctttgc ccaggctggt ctcaaactcc tggactcaaa caattctcct gcctcagcct 21060
cccaaagtgc ctggattaca ggcatgggct actgtgctca tcccatgggg tcttttgtgc 21120
caactggtgt gagttaggta caggacaata aaggaggcag ttaatccatt aatccataac 21180
aaagatcagt gaagggggaa ggtctggtct ctggtctctc ctagtcattt acagaactag 21240
aacgatgaga agagagtgaa tctataacct aagaagcaga attgcaaaca tgctatgtga 21300
ctcagtttcc agtacttaac ttctcccttg gcataataaa taattttaga gagttttaag 21360
aattttgttt tcttttacag atgttaacaa cctcagcttg ctgggggctg gtggtggtgg 21420
ctgctcagac agtaaagcat tgaatgcaat gtgaggtcaa agttttatta cagatcatac 21480
cggtctttta agtacttgca gcaagatttt cctaatactt aaaagtgact ggaaactcaa 21540
taggatcagt gtgatcttct ccagataggg atggtagatt tttgaaagtg ggtgtgaagg 21600
gcagtaatga gagaaaaata aaactatttc tggttgtact ctcccaagtc aaggtcattc 21660
aatgaatggt tatatagatt tgcatcaaaa gtccctgttt tcagcctcac ctttggaaac 21720
acctggattc tctattctga gactttctga gatgagggaa aggtggcttc tcatcagtat 21780
ctccttcttt gtgcaataca gtttcagttc tttctaatct acagagttag ttccttctct 21840
actgtcagct ttctaccttc caaaatgtgt taatgtcact cattatcatg tttcccattc 21900
tctttccctt atggtttaaa ctttaaaaga caatggtatt tgtttaagtg aatatctaaa 21960
aagatgtgga gaaagattca tgtgttcagt ctaccatgtt taattggagt cactggtaga 22020
tttttaagga aaaataacat tctaggtttt tccagtattg ctatgtagct tgtctatgta 22080
gatcaccttg cattcttctg tttctctctt ataacttgat ttttttcttt tcttttcttt 22140 tcttttttttt tcgagacaga gtctcacttt gtcacccagg ctggagtaca gtggcacaat 22200
ctcgtctcat tgctgcctcc atctcctggg ttcaagtgat tctcccacct caccttccca 22260
aatagccggg attacagaca tcttataact tgatttttac tcatttcatt atcatccaag 22320
agatgaaatt taactcaaag caaatgacta ttgtttcaaa tacaaatctt aatcagggag 22380
aaaagattat aacttatagt tgaactgggg tttggagatt atatgtgttt tttaaaatta 22440
ttctgtccca catgtaacat acaagtgagg attttaaaaa tttgtctgca gttttttttt 22500
ttttaattga tcattcttgg gtgtttctcg cagaggggga tttggcaggg tcataggaca 22560
atagtggagg gaaggtcagc agataaacga gtgaacaaag gtctctggtt ttcctaggca 22620
gaggaccctg cggccttccg cagtgtttgt gtccctgggt acttgagatt agggagtggt 22680
gatgactctt aaagagcatg ctgccttcaa gcatctgttt aacaaagcac atcttgcacc 22740
gcccttaatc catttaaccc tgagtggaca cagcacatgt ttcagagagc accgggttgg 22800
gggtaaggtc atagatcaac agcatcccaa ggcagaagaa tttttcttag tacagaacaa 22860
aatggagtct cctatgtcta cttctttcta cacagacaca gcaacaatct gatttctcta 22920
tcttttcccc acatttcccc cttttctatt ccacaaaacc gccattgtca tcatggcccg 22980
ttctcaatga gctgttgggt acacctccca gacggggtgg cggccgggca gaggggctcc 23040
tcacttccca gaaggggtgg cctggcagag gcaccccccaa cctccctccc ggacggggcg 23100
gctggccagg cgggggctgc ccccaacttc ccagacgggg tggctgctgg gcggaggggc 23160
tctttacttc tcagatgggg cggctgccgg gtggaggggc tcctcacttc tcagacgggg 23220
cggccgggca gaggcgctcc tcacctccca gacggggcag cagggcagag gcgctcccca 23280
catctcagac gatgggcggc cgggcagaga cgctcctcac ttcctagacg ggatggcagc 23340
cgggaagagg cgctcctcac ttcccagact gggcagccag gcagaggggc tcctcacatc 23400
ccagacgatg ggcagccagg cagagaagct cctcacttcc cagatggggt ggcggccggg 23460
cagaggctgc aatctcggca ctttgggagg ccaaggcagg cggctgggag gtggaggttg 23520
tagcgagccg agatcacgcc actacactcc agcttgggca acattgagca ctgagtgaac 23580
gagactccgt ctgcaatccc ggcacctcgg gaggccgagg ctggcagatc actcccggtt 23640
aggagctgga gaccagcccg gccaacacag cgaaaccccg tctccaccaa aaaaatacga 23700
aaaccagtca ggcatggtgg cgcgcgcctg caatcacagg cactcggcag gctgaggcag 23760
gacaatcagg cagggaggtt gcagtgagca gagatggcag cagtacagtc cagcttcggc 23820
ttggcatcag agggagaccg tggaaagaga gggagaggga gaccgtgggg agagggagag 23880
ggggaggggg agctgcaatt ttttatttag caatttccaa acctattgtg ttaggcaggg 23940
ttctccaggg aaacagaacc aatagggcat atctatatct atatttatat ctttatctat 24000
atctatatct ataatctttc tatctatcta tcaagagatc gagagagaga gatttatttt 24060
aaggaattgg ttcatgtgat tgtgggagct ggcaagtctg aaatccatag ggcaagttgg 24120
tcagctggaa attctggtaa gagttgatgt tgcagtcgtg agtctgaaat ttgcagggca 24180
ggtcaggtac agtatctatt gcaattgcag tcctgaggcc aaattccttc ttcaggaaac 24240
ctccgtcttt tttgctgtta aggccttcaa ctaattggat gaagccctcc cacattgagg 24300
gcaatctgct ttactcaaag tctgctgatt taaatggtaa tcacatctaa aaaatacttt 24360
cacagcaaca tttgaacttg tgttgtctaa gcaattgggc actatagctt agccaagcag 24420
acacatgaaa ttaaccatca ctctgtagag atgaaagaac tactgtttca aaaaacaact 24480
gtttttgaat ccgtcattta tcaacggatt cacccaatgg ttaacctttc tatatgcttt 24540
ctctttctcc caagtactga atcatatgaa aataaattat ggttgtgata tttcctatct 24600
aaatacttca tatgggacat tctcctacat agcacaccta agaagattag tattaattca 24660
gagagatcat gtcatatctg gttcatatat aattttccct agctgacctc aaaatgtgtt 24720
tgttttgttt acatattact ctttatagtt atgtttcttt taatacggat caatatttgt 24780
gtgtttttgc tgctattttt tttaatgaca ttgttttgaa taattcaggc tcattggcta 24840
tttcacatcc tgaatttctc taattttatc tttatgatta gagccaggct ctaattcttg 24900
gcaagaataa cactgaagtg aggttgtgta ctcctaattg ccctgcatca aagacacatg 24960
atatgcattg gttcctgcat tagtcatgtt aagtttgatt agctggtgaa ggtggtcgcc 25020
accatttctc actcttgtaa agggacattt tctcctttta aattaatatg taatttgtgg 25080
cacaagactt tgagactgtg taaatatccc attctctgac aacctttctt ctgatgactt 25140
tagcattaac tgatctaatt atatcattct tggcattgag tagcattctt gtgtaaagaa 25200
ggggttctct ttctctccct cctctcatta taatttgtta ctgttatttt cttacaagtt 25260
actaagaatt actcaaaggc agtatttttc aataaatcat tggtaattta tggtcttctc 25320
actctagaaa agggaggatg ggtcagaaag ctgaggggaa aaaaagggag gaaacgagaa 25380
tgtatattat cgacataatc ggttgaaaat gtctagtgct gtaattatgc catcatgcag 25440
attaaaaagc cacctgtgaa aaatcaactt gtattgtttt gttttgtttg atttttaata 25500
aatccttata gtgtatgaat aaaaattaaa ttaattgatc agtatcttca ctaatggcag 25560
agaaggggat ggactgagca gattctgctt ttcactctga tatttgttaa ttgccctgtg 25620
tggtctgaag acctgggttc tagtaccagc tctccctctg cagacaggtg tgttactttg 25680
gtcaaggcaa tcaatcttct tgatactcag tttggttctc tctgatttga gcataagaaa 25740
tatacttgaa ggccgggcat ggtggcttat gcctgtaatt ccagcactat gggaagccga 25800
ggtgggagga tcgcttgggc tcaggagttt gagaccaggc tggcaacat ggcaaaacct 25860 caactctaca aaaaacaaac aaaaaattag ccaggcatgg tggtgcacgc ctgtagtccc 25920
agctactcag gaggttgagg caggagaatc ctgggaggca gaggttgcag tgatctgaga 25980
ttgtgccact gcactccagc ctgggagcct gggtgacaga gagagaccct gtctaaaata 26040
tatatataca cacacttgaa tgcttcatgt cccttgctca gtgacagccc cgtcctctgc 26100
ttctgcacag ttgaccaagg cttctcagtc tactcctgtg tagaaaagaa ttaaagcagg 26160
cctgaggctg ctagtcttag aaaggcttgc aaagttggcc cttgtctggt gtctgggaac 26220
ttgaatttct ggagggttct caccattccc tgaaaagaat ggctcacgat gcctaaaata 26280
tttgtacaaa caatgaagtt tctgctgaac atctgcttcc ttctgggagt ctggaatttt 26340
aggatgtgct aggtaggggt gtttacatga cagccccaca taaaaacctt gggcactgag 26400
tgtctaatga gattccctag taagtaatat tttacacata ttatcacaac tcattgctgg 26460
aggagttaag tgcatcctgt gtgactccac tgggagagga ctctgggaag cacatgtctg 26520
atttcctttg tcccatgtgc cttttccttt tgctgatttt tgccttgtaa attttttttt 26580
ttttttttga gagacagagt cttactctgt tgcccagact ggagttcagt ggccccatgt 26640
cggctcactg cagcctctgc ctcctggatt caagcaattc tcctgcctca gcctcccgag 26700
tagctgggac tacaggcgcg cgctgccaca ccggctaatt tttgtatttt tagtagagac 26760
ggggtttcac catgttggcc aggatggtct tgatctcctg acctcgtgat ccgcctgcct 26820
cggcctccca aagtgctgga attataggcc tgggccactg tgcctggcca taatttttat 26880
cctgtaataa attatagtcg aaagtattga gtcctgtgaa tcaacttaga gaatcaccaa 26940
actgcttcca attttctcat atgtaaaatg ggttgctata ataatgatga tatctacctt 27000
atagggttgt tttaagtatg aaaaatatgg tgaaatatgt gtgaaactag gggccggatg 27060

```
taggatgagt catacagtgg gtggttatta ttacggatca tattaactct tcaggtaaaa  27120
accatcttgt agctgggcaa ggtggcacat gcctgtagtc ccagctactt gggggactga  27180
ggcaggtgga tcgcttgagc ctaggagttc aaggctgtag tacgctatga tcacgtctat  27240
caatagccac tggactccag cctggacaat gtaatgagag tctgtctcaa aaaaaaggaa  27300
caatcttgtg tttgcgtgtg tgctcatgtc tttgttggaa taatactgac acagtcactc  27360
aaattaactc tcaaatcttt gattattcat ttgatgggaa caacaggttt atgtgccagc  27420
ttatcaggac ccctagttct ttcattaaag tgtgtatgtg tgtgtgtatg tgtgtatgtg  27480
tgcacatgtg tgctagtttt cttatctaac gacgaagtcc tttgggaggt ttactttttc  27540
attactattt ttttcatgct ttcctttgat gtgcacctgg caatttatag agccaatgtg  27600
tactacatat tctgctgcag aaaatgacag aggtgaggaa ggagcaggaa gcagatttag  27660
aaaggaatgt tacagtttat caagttgtga ctaatggaag ctattaaaac aaaaggtacc  27720
aacccatctt aaatattcac tgcctctaca actatttttc tataactgtt gttccttgtc  27780
agctctgggg tggagggaat attcctgaat gttttattaa gtaattcaaa gatcttccta  27840
ggtatgtgta tcaaagatcc tatgatgtat ctgtcttgta aattgagact ggcatatatt  27900
gggcttacat tactgggaaa aatgtatgtc atcatcattg gtgaaaaaga gtttccatag  27960
cagtttttc taagtagaga gataaatgaa tcagactttt ggaggaggta tgttttaact  28020
cactggagga tcacaccaag tctgaacatc taaggaaccc tagtggaaaa ctggttttcc  28080
tgtatgctgc tctagcgatc tgaggaaagg cctaaaaaaa gccagtgtcc ctgtgatatt  28140
gtgaaataca tatatgtggt ctttgttcct gtttcctggc atacaagtac taaaaatcct  28200
tggaatctcc aaagtgctgt ctttttgtat attagtgttg actgatagct tcagagtggg  28260
gctggtcaag ttgatcacca atggccagtg gtttaatcag tcatgcctat gtaatgaagc  28320
ctccatgaaa atccaaaggg aatggactgg ggagcttcta agaagtgttt tttaccttcc  28380
cgtgagcctc ctgtgctgaa cacgtggagg gtcacgggaa ggtaagcaaa aattcattca  28440
catgctggga gggtggcaca tcccaactcc acgaggacaa aagctcctgt gctcagaacc  28500
cttccagact tggaccttgt atctcttcat tggcttttat ttgtatttta aaaaatatcc  28560
tgagtgataa actggtagat gtaagtgtct tcctcagttc tgtgaaccac gctagcaaat  28620
taatcaaacc ggaagagggg gtcatggcaa ccccaacttg aaacctgttg gtcagcagtt  28680
ccagagacct gaacttatga ctggttggaa ggacggggtg ctcttgtggg actgagccct  28740
caacttgtgg atctgatgct atctctgggt agacagtgtt ggagctgaat tggaggacac  28800
ctagcttgtg tccactgcag aactgattgc ttgcttcctg ctggggagaa atccctatat  28860
attttggggt ccagaagtct tccgtgttga ttgtttttgt gtgagagcag aggaaaaatg  28920
gtttgagagt ttttcgggaa acagcccctc ttagtatagt ggtagaaaca ctccaaaaat  28980
aaaatatgct accccaaaaa taaaaaatga aaataaaaat aaaaatctgg agtggtcagt  29040
ttgccaagag gatttatgga gcatctaagg tcaagcatta cttctcagcc ctgcagcagg  29100
cctctaatta agccatgcca cagagtgcgg tttgcagaga ggtggagttc ctgtggattc  29160
attcttctct ctaaaattat aaataacgca gcttccaaac atgccatatt acctcacaag  29220
gtctaaagac tcaatatgaa tcttcaactt aacaattata actgacacag attgagatct  29280
tcctggatgc tgaaataggc tttacatgat ttatctcatt tagttctcat aaaactctat  29340
tattaatatt attttacaga tagagaaatg gaagcacaga gagggtaagt gtattagtcc  29400
```

atttttatgc tgctaataaa gacataccca agacagggta atttatacag aaaaagaggt 29460
ttaatggact cacatttcca catggctggg aggcctcaca atcatggcag aaggcaaaag 29520
gcacttctta cctggtggtg gcaagacaga aaatgagaac caagcgaaag gggtttcccc 29580
ttataaaacc atcaggtaac atgagacaat tattcactac cacagaaact atatggggga 29640
aaccgccccc atgattcagt tatcttccat tgggtccctc ccacaacacg tggagctaca 29700
attcaagatg agatttgtgt ggagacatag ctaacccata tcagtaagta attagacaaa 29760
ccttgcaaag ctagtaagtg gtattgctgg aattaaatct gccaatgtca ctccagagtc 29820
tatgtgattt actggtatat tatagggtct acctataagc ttgataacct tatgttagaa 29880
caaataacca tgacatattc tgttcagtag tttgcatttc cttttgactc ctacagggga 29940
ggaggccgag gttcagggac attaaagtgg ggtttagaga cattaggtgg tttacccaag 30000
ctttatctac tagatactag ataattgtct atctgacaat aaagctagaa cttacaccca 30060
gctggacaat ggagctacag cttaaaacaa aatcttctaa tgagctcaga actcatggct 30120
taataagatt tgggaaaagt cctgcggaca tttcactgtc tatccagaaa tgcgaggaag 30180
ttaggagaaa aggcaaagta tctcatagac agataaaggc agttcagtaa gtagcctgaa 30240
taaatagcca tatttaaaat ctaatttggt tcttttgtgc ctaacacaat tgactttatg 30300
ctggtatcta ttttctgctc tgtctctctt tctgtctcta cttatgtgtg tatgcatgtg 30360
ttataaaata tatcagccca ttgatcaatt tttaatttaa gcaaaaacat ggtagattaa 30420
tatattcaat caatttattg agtagatatt tatcgaggct cacacattta tctgactgtg 30480
tactaagcac tggaaaccca aagagaatga agtcactgcc tagacagttg gaggctgaca 30540
cataaacaag cagggtaata atcaagtgtc ataactagtc tattacatgc aatgttaaac 30600
tagcatctct accatgcaaa acttgtgctc ttggggatac aggaagactt tccagagaag 30660
tacacaggac aggaatgtgt taggaaacca gtcagttccc aggtcctcga tcaggtcaca 30720
gtgacttgcg attctatttt gaacataggt cttaaatctt tattttgata gcaagggttt 30780
taaacttttg atatatgata tacttctgaa aatcaaattt catattctaa aattaagtat 30840
ttttgccctt aactaacttg aacataatac tataatacat taacatatat tattaataat 30900
aaataggacc cctggaagtc caagagagac atgaggctta tttggtatgt taaaatcata 30960
caggaagtgt tgttaaataa gaaatggtgt tacactttct ttgagttata tttatatgga 31020
tatgttgtta atatgtgttc caacattgta tgagattcct aaaaatctga tatggacatc 31080
cagtgtggtt gttgggtcct ctatgagcct agggagcact ggccggttac cttgcatcca 31140
ttcatgtcag cgttggtagt gtcaggcacc cgatggttct tagaagagta cttagctcta 31200
ctctgcagtg tctgaagttg ctggatatat acctgctgta taaactgctg actagggcgc 31260
tgcagtttac ttactgtctt ctcatgggga ccttcccctt caactctttc ctcttgggtt 31320
tcacatcttg ggtggggagt ttcatcctag tagtttgcct gagaatacag gtgaacccac 31380
agaacaaagt ggacttcgaa agcatctcct tggagtgaga ctttgcttct ttctctttgc 31440
tagcaccatc ttgtacctta tcgtcatgaa ctttgttggc tgaatcattc ccatttactt 31500
aattgaagag taagagactg gaacaatgct cactttgatt ttcctggata agagttaaga 31560
gttcttgaga tggcagcttg tttgacacat gaattttctt caaatttgtg cttactacca 31620
actgatttgg tgtggaggag agcccagaga agttccctct ctctgtcaga acaactttgt 31680
aacatttatt aacctgactt ctgccttcaa ttaactgtaa ccttttgcct tccaaattaa 31740
aaagttccac attactccaa aaataaaaag tgaaaataaa aataaaaggc tgatatgtca 31800

-continued tggtatatgc agtaaattgc tttattctga ttttttttttc taaaagcctt ttgcaaatcc 31860
tgaagtgctg tgtattcaag gaaattcatg aaagggacct tgacaagtag tcttaaatac 31920
aggtttctga taactttgga gatcacacct ttggactagg taaaaacatc caaaactcgt 31980
ctgggcgcag tggctcacgc ctgtaatccc agcactttgg gaggccaagg caggcggatc 32040
acgaggtcag gagatcgaga ccatcctggc taacacggtg aaaccccatc tctactaaaa 32100
acacaaaaac aaaattagcc gggcgtggtg gcgggcgcct gtagttccag ctacccggca 32160
ggctgaggcg gaagaatggc gcgaagcggc aagacggagc ttgcagtgag ccgagatcgc 32220
gccactgcac tccagcctca aaaaaaaaaa aaaaaaaaaa aaaagtccaa agctctaatg 32280
aaaaactgat gcattcatgc agattgctaa cccaacatca aggagaacga gaattacatg 32340
ggactgagtg aatgaaggat tgaaattact attttaaagg gtttttgttt gaaacattac 32400
tgattttttt tatgttttgt tttccagact caagaaaata ttttttttct tttgagctat 32460
ttatagctta cagcattggg gtaaagtata cttctgtgag caaaatggaa acatttacct 32520
ttctttctac ctgaattctt cagaatttgg aaactattca ttagtgttct tattttctgg 32580
caatatagtt atttgcataa gttcaataag aacctatttt cggctgtgca tggtggctca 32640
tgcctgtaat cccagcacct tgggagggcg aggccggtgg atcacaaggt caggagtttg 32700
agaacagcct ggccaagatg gtgaaacccc gtctctacta aaactacaaa gattaaccag 32760
gcgcggtggc aggcgcctgt aatcccagct actcgggagg ctgaggcagg agaatagctt 32820
gaaccttggg tggcagaggt tgcagtgagc cgagatcgca ccactgcgct ccagcctagg 32880
ggacaagagc gagactctat ctcaaaacaa acaaacaaaa aaacaaaaag caaacaaaca 32940
aaaaaagagc ttattttctt ttgtaactgg acacatggaa acagtggtta ttttaccaag 33000
gctttgactg gaatgtcttt tttttgagtg caaccggact gcttcgaggg attgaggttg 33060
actttataca gccagtagac ttggaaaaag acacacctgg taccttgccc acacaattcc 33120
tttatagcgt ttctaacttt gcaataagta aagaatgtca ctttctgaca ggcccaggga 33180
cctcaagata ttttggagac gttgaaaaga gagcaattca cccaattcat acaggtttta 33240
caggcacagt ctgatggcga atctttggct tggcttcatt gcttcaagag tttgtttttt 33300
tgacacggaa tctcactctg tcacccattc tggagtgcag tggtgagatc ttggctcact 33360
gaaacctctg cttcctggat tcaagtgatt ctcctgcttc agcctcccga gtagctggga 33420
ttacaggcat gtgttgctac tcccagctaa tttttttgtat ttttggtaga gatgaggttt 33480
caccatgttg cccagggtgg tcttgaactc ctgacctcag gtgatccacc cacctcagcc 33540
tcccaaagtg ctgggattac aggcgtgagc cactgtgccc agcccttgag aggtttcaaa 33600
agtcttaatc tgagattcct tatgaaaaaa ttccaacaaa gccaacttaa gagccatccc 33660
tgtagaaaat atatctattt aaatatcgtc tgttttatgc cacaatgttt gttttgcgtt 33720
gcaagccgtt atctcctagg catgggtaat ccactttgag aggaaaatcc agacatcatt 33780
gtgcctaatt tgctgccacc tgtgtctgtg ctggatctta ccagggttag ctttattttc 33840
tttcaactgg caaaattctg ataaagcatg tagcttcacg gtagagcaaa aagtgtaact 33900
taattgaaag tcatgacttt caggagtcta atgatgctaa tatattttct tctagagagg 33960
tgtctttatt gtatgtaatt ccctgaagaa atgtaaagat ttatctaatt cctattgctc 34020
tgacaggcgt gctcaataga agcattgaag taaaataaaa ataacctttt taatctgtgt 34080
atttctcttg cccaccaaga tatttaattt ttttcttgat ctttgctttt gtttatgtga 34140

-continued agatatttat gtctatatca tttctgtata tatcacagaa aagttttcac ttgcttgaca 34200
ttttattcta caatgatttt tagtttaagt ttaaagaatg gctacattca gatttatttt 34260
cacaactata gtcctgctaa actgcctttg ttgaaaactc agtttttata ataaataaaa 34320
aatatcaaag caaaaaaaaa agagccttca tgataaatca ccattcttac tgcactttaa 34380
gcagataatc atgccagaga ctaaactgac tttgcaaata aattagtttt attattatta 34440
tctttgtggg taaaagttgg gatgactgta gaagagaaaa ttatatttca gaagaaaatt 34500
ataccatact tgttattaga ttctagtctt gataattgtt tttttgagtt tttgttattt 34560
gcctacaatt tgggctgaat cctgaattcc ttcctgggta caagtctcca aactaatgtt 34620
tcctaatttt tctaccattt ttctgtcttg gaatcaccaa gccctgcagg ctttagctag 34680
acaacttgat ataaactttg gaagaaataa tgacagcaac ttaatatatg agcagtgttc 34740
atgtcagctg atgtatggat tactcagaag gtttacttga acacctgatt caaactataa 34800
tccagaaata tctgtaagat tgccactgca atctgaagct acttcagaga ctctaggaaa 34860
attagtttat agacaactcc agatgttaat ctttgttttt cttttgtttt catggaaatg 34920
ccttttatta aacatctgat tgcttgattc atagaggcct gactttggtg gaagcaacac 34980
cactgcctga aatgagatat aactgttaac cgtttaattg gagcggcctg ttctcacgac 35040
tgcaagacta gttcaatggc ttataaaata atccacccgc tgggcacagt agttcacacc 35100
tgtaatctca gcactttggg aggctgaggt gggcaaattg cttgagctca ggagttcgag 35160
accagccaga gcaacatggt gaaaccctgt ctctaccaaa aatataaaaa attagccggg 35220
catagtagca tgtgcctgtg gtcccagctc ctcgggaggt ggatgtggga ggattgcctg 35280
agcctgggag gcagagcttg cagtgagctg agattatgac actgcactct agcctgggca 35340
atacagtgag accccatctc aaaaaaaaaa aaaaaagata atctaccaac ccaatttctc 35400
aactggggaa tgttgggctc ctgctctcct gtctctgacc tttcattctc ccttgaggct 35460
agccatcaag actacaaccc ctcttcccca aagtgggcca tagaaacaaa accccttttc 35520
cccaaagcca accataaaac ctaaaaatag tactctaact tccaccaccc ccagcctgtc 35580
tgtgtaaggc cataaagaaa ttatctgact cactttgttt gactgaaggt tataagaccc 35640
ccattccaga gagggtccag caccacaccc agaaggaaga aatgcatgct cagagaggca 35700
agaagggtcc agacagacag gctgtgctgg atttccctgc tcagtctatt agcattagac 35760
catacctttt ttgtccaatc atatttctac gtggctctcc atactttgtt taacctaacc 35820
taagggggct cagggtttg gcctgggcat tgtctgttgg ggaatagagt gagtcatccc 35880
cagctcatgg gtttgcatcc agttcttgtt gtaaaaggcc caaagcctgt tggatggcaa 35940
ccctgagcca tcgtggaagg ggggttccag tttcacaaat agatactcag acagccaaac 36000
taccatctac ttggtgccaa cgtttgcact gtggtcaaag acttacctag cacagactga 36060
acaaatcttc ccatctgtca cataaatgtc cccaagcaat gttgaagcac atgccaggat 36120
cggccttgct aggtcctgct tggtagataa gcaaatggct tccttgtggt gtttttattc 36180
tattttgtct cattaacact acaactttgt gttatctact tgataatctg taattgtaaa 36240
tacatacagg attatgtaat ttgtgtaaat acataatgac agacttctga aaactggtat 36300
tttttacttg gtgtccattt gaagctgttt taggttctgt ggcacatgaa ccaatggcat 36360
ttaaaaagca tactctcctt gctcttaaaa aaacaaacaa aacaaaacaa aaactgtcca 36420
ttaaaatttt tgtatttttg taaagacagg gtttcaccat aaaaatggac agtttccctt 36480
atatctttgg gtcttcgttc tgtaggctct cgtgtcacat aaaattatga tcaaataaat 36540
ttgtatgact tttctcctat taatctgccc cttgtcaatg attttgagca accttctgaa 36600
gaaagtgatg gggaagtatt ccctttgctg ccacaaggta tatatcagat aagtcagtct 36660
attttcttga acatatatca cattcatagg aaaaacactt tttccaaaag attactgtct 36720
tcccaaatac ccacgttctc cattttttttt ttttttttt agagatgggg tctcactgtg 36780
ttgtccaggc tagtctcaag cttctggact caagcaatcc tctcacctca gcttcccaaa 36840
gtgctgtgat tacagacata agccatcacg cccggcccca ttttctcctt tgggtgtatg 36900
tatattgctc attgtcaggc atcaaccatt tctcttctct gagatggagt ctcactctgt 36960
cacccaggct ggagtgcagt ggcgcaatct tggctcactg caagctctgc ctccctggtt 37020
cacgccattc tcctgcctca gcctcccgag tagctgggac tacaggtgcc caccactacg 37080
cccggctaat ttttttgtat ttcttttttg gtagagacgg ggtttcaccg tgttagacag 37140
gatggtctca atctcctgac ctcgtgatcc gcccgcctcg gcctcccaaa gtgctgggat 37200
tacaggtgtg agccactgcg cccagccctc ttctaatttt ttatatttat catgtattta 37260
ctagaactgg tttattttcg tgagcatatg ttgtggattc tactataaat aatgcactta 37320
ataatcatta ataaaactta aatcctttcc gtcttgattg tggcctttttc tttttgctat 37380
taatttcctc agcataggtt aacctgaact cttaaaagct atttaggtac tggtataaaa 37440
caaaattttc tccaaagcaa tccagtatat aatatctgga ttttaaaaaa gcagcctcat 37500
ttaattagga ttaatttctc ctttcagaag ttaagtgatt ctgtttctgt aaaacgcaaa 37560
attataagct taattgtttt ccacacagga aatgaaattc ctaatctttt tatccagaat 37620
cttcatgtgt ttgtctctct gtccatctgt cactcctttt taaggtacct ggagatgacc 37680
tagaggcttg ccacgcttag ggtttcctcc ctgtgcagaa gaagatggga agtgcaaatg 37740
aggacgaggg gtggggaggg aagagggagt caggtgattc agcaagtgca ggagcccaca 37800
gactaagctc aggaatttgc actttgtctg ctcgcagagt gagtttcatc gtggtgtgta 37860
tatattgaga tatgcaacag actccactgg aatgtcagaa gaacttatgt ttatttttcc 37920
tctaacatgt gggaaagatt aaactgtatt tgtatttaac tcacatagat tggcacgtgc 37980
tcattctgtg tgtcaccctg ccacgctgtc acaaacttcg agcagggtcc tgaggggaga 38040
ggagggcata gctcctgctc ccagggggtt gcctgtgtag ccctgcgcat tcattctctt 38100
ccagagggtt gtgatttgtg gcggtctgtg tgagcctggt taaggagagt tacagattat 38160
gtcatctggt gttaactgat aatctttgca aaagggacat tggctttaag agatgtctgc 38220
aaaaaaaact ctaaacaaac ataaataaaa atttaaaagg ataaagccag aataataatg 38280
aaaatattag taatgtaaaa caaggaaatg tgtcatgttt ttcatgataa ctaatatttt 38340
ttcaattttt tttttttttt aagacagtct cactctgtca ccaggctgga gtcagtagtg 38400
cgatcttggc tcactgcaac ctccacctcc caggttcaca caattctcat gtctcagcct 38460
cctgagtagc tgggtttaca ggcactcgcc accatgccca gctaattttt gtatttttag 38520
taaagacagg gttttaccat gttggccagg ctggtctcaa actcctgacc tcaggtgatc 38580
ggccgccttg gcctcccaaa gtgctgggat tacaggcgtg tgccactgtg cctggcccca 38640
gttcttatta taagttctcc attaaccata tcatgagatt aaaaaaacaa caatgatttc 38700
atcggaactg acaaatagtg ggtgacacaa ttttgatcat caagaagact ttaaaagaag 38760
gatttgtatc actgtcatta ctgattactt ggcccttgtg tatactgggc ctttagctag 38820
ggctggtaca ataaaataac catagttaga aagatatttt aaaggattac ttatttcatg 38880

-continued

```
tttatctcac ccttttatcc ctatttttgg gcatgattta ttattattag gtttttaaat  38940
aaataatgaa ataagcatgt taggtttgca tgctgctttg gttaacattg ctatataacc  39000
aaccacccca aactttgtgg ccttaaaaca ataatttatt tatttattta tttatttatt  39060
tatttattta tttatttatt tttgagacag agtctcgcta tgtcacccag gctggagtgc  39120
agcggcatga tctcggctca ctgcaacctc cacctcctgg gttcaagtga tcctcctgcc  39180
tcagcctccc gtagagctgg gattacaggc acccgccatc aagcccagct aatttttcct  39240
ttatttttag tagagacggg gtttcaccat gttggccagg ttggtctcga actcctgatc  39300
tcaggtgata tgcctgcttt ggcctcccaa agtgctggga ttacaggtgt gagccactgt  39360
gcatggccaa caataattta tttttatctc tcatggtctc tagattgcct gggcccggct  39420
gagcagtctg agtcagcctt atggtctctc atgtgttttt aatcagtcat gaggggccgg  39480
catcatctga aggcttgact gggctggatg tttaagacag ccactcacag ggctgacagt  39540
gatgctggat gttgcactgt tgactaatga gcctgcacgt ggctcctcca tgtgatttgg  39600
gctatttata gctggggtga ctgggttcta ggtggggtag ttccaagatc cttccaagag  39660
gaagaaagca gaaactgcct ggccagttag tgtatatgct tagtcttaga acagtgtcac  39720
ttccatattt ctccatagtc cattaatcaa agcagttaca ggaagcagac agacaggaag  39780
ggaaaacaca atgcaacaga aggagagatt gaagtgttgg cagctgcaag ccaagaaaca  39840
cctgggttac cagaagctag aagaagaaag gtaggattct cccctacagg ttccaaagga  39900
agctgggcct gtccacacct cacctctgga actatgagac aatcactttc tgtgggttta  39960
agctacccag tttgtggcac tttgttacta ccgtcctagg caaatgatac agtaactaca  40020
tacacagtac atagaattgc tcattttact tcgttgaatg ggacttggca ttgaataagc  40080
ccaaatgaga attcttttgt caagattttt ttatggctca cttttccaga gacgtgacat  40140
ggcaggagta aggggagggt ttggcaggta ggaattatac tcatctgtca ttgtcttccc  40200
aataccaacc aggaagcatg taaataatag ctgtgcagtt tgttttctga accaaactgg  40260
gccttatttt ttttaaagaa actttattaa acaaacaaaa acctagaaac actagatgta  40320
tatttttaag gtttctctca cataatatcc taatcatcag tataccgtaa tccaagggct  40380
acatataact gaaaaataaa tgggtcttaa aaaaattaaa acatggtata taacactagc  40440
taacatgtac tgagcagtta ctaagtgcta agtactgcta agtcctttat agatatcttc  40500
atgttgagtg tcgtcactgc ccattactta ctctgagttt aaatatgaga ctcaaaagag  40560
gttagtaatt tgccaaaagt catagggctt ataagtgata gaaccaggat aacgaatctc  40620
aaccaaggga cttcaatgcc caaaccggtg ctcagactgt agccccatgt agttagctat  40680
ttacatttga aaaaattttt aatgtttatt atttttttta agacagggtc ttgctctgtc  40740
acctaggctg gagtggagtg gtgtgatctt ggctcactgc aacctccacc tcctgggctc  40800
aagtgatcct ctcatctcag cctcccaagt agctgggacc acaggtgtat ggcaccacgc  40860
ccaactaatt tgttgtgttc ttggtagagg tgagtttcac catgttgccc aggctggtct  40920
tgaactcctg agctcaagtg acctgcccac ttgcctcacc ctcctaaagt ggggggatta  40980
caggtgtgag ccaccatgcc cggcccagct atttacattt aaatataaat taaaatgaaa  41040
caagattaaa aattcggttt ctcaatcaca ctaaccacac ttgaagtgct cagtagctac  41100
atgtggctta gtggctacct ggcagatata gaacgtttcc atcagcacag aaagttctac  41160
tggaaagcat tgatccaatc tctttgaaca gtcacaatgc atataaagtc cttattatga  41220
ctgtacaagg gaagacaacg agtagaggaa ggcagaaaat aggaaaaaag gaagaagaaa  41280
```

-continued

```
gatttagggt gagggagagc agttctatga agaaaagaag ctcatatcta ggagtggagt  41340
ggaccctgag aacatgttag tctattatat tctaaacttt ggcagttaaa attccaaagt  41400
atattaagta catgctttct aaaatattag agagctgcag ttcaacagat ttttaactct  41460
ccacagcatg tccggcactg ggtgaggtgg gatggctagg tgaataatat aggcattgtc  41520
atgtgtgttc gtgtgaagag accaccaaac aggctttgtg tgagcaataa agctttttaa  41580
tcacctgggt acaggcgggc cgagtctgaa aagagagtca gcaaagggtg gtgggattat  41640
aattagttct tagaggtttg ggataggcgg tggagtagga acaatttttt gtgggcaggg  41700
gatggatctt acaaagtaca ttctcaaggg cgaggagaat attacaaagt accttaaggg  41760
cagggaagga tattacaaag taccttctca agggtgggga gggtgtatca tacaaagtgc  41820
attcacaagg gtggggaaat atcacaaagt acattatcgc aagggcaggg agggtgtatt  41880
gtcacaaagt caattgatcg gttagggtgg ggcaggaaca aatcacaaca gtggaatgtc  41940
atcagttaag gcaggaacct gctattttca cttttgttga tcttcagttg cttcaggcca  42000
tctggatgta tacgtgcagg tcacagggga tatgatggat tagcttgggc tcagaggcct  42060
gacagacatg aacttcccat cataaaatta gaagagcatt aatcaaatga ttagaataaa  42120
atattaccat tattttgaaa tggcaagcat tgtatgtaaa taaacagcag aggaacccac  42180
tgtagcctag acagggttca gagacgttcc tgccaaggac atggcacagg gactgaacaa  42240
ggaaggatga cagtgcctgg caaaggcagg gaatgttaca ggtatttggg cacctgtgag  42300
aaggcctgat gtccgaaagg actgaaataa attaaatgtg tggggggaga gagaaagaaa  42360
gagcctagca aaaggtgagc tggagagtca gaggcagaag gcagaatctg ggatgggctg  42420
ggagcttgcc aatcattttg tcaaatgggt gatgtgaagc cttgaaggtt ttttgaccaa  42480
gaggagatgt cttcagattt gcgtttgaga cattttcact ggttgtcatg ctaagaatgg  42540
cttaaagaga agcaaggctg gggtcagagg agctgcttgg aagctgtttg gtactaggat  42600
gcggataaca tggttggaga aatggcaact gtcagggtat ttggagcaag aatggataga  42660
cattggtgat catcacttgg atgcatttga gggacaactg ctatgtttct actagagcaa  42720
ctacatagag caggagtaag caacttacag tccacagacc acatttgctc tgtcccgttt  42780
ttcaaataca gtttaatgga aacagagcca tgcccgttct ttcacctatt ctgcatggct  42840
gacatcaggc atggttctaa gtaatataca taagtttcat atattaatgc tcatctatcc  42900
cagttgacaa acatgaagtg ttgctattgt ctcattttac agcggagaaa actgacatag  42960
agattctctt tcgcacccat agcttcagtt accacctcta tgccaatgat tcaataatac  43020
ctctaatcca gacctcttct ctgagcttca gacaggcaga tctctcacag ccagtcttgg  43080
agacacttca gaaatcatag gtcccaaacc agactcctcc tcatcccctc aaacacattc  43140
tttttcaaca ttcctttttt cttagtgaac atcaccaaat agataagcaa gtcagatcca  43200
aggaggcctc cttggcactt ctctcatcct tgtcccacct tatatcatct atttttcttt  43260
ttcttttttt ttgagatggt gtctcactgt gtcacccagg caagtgcagt ggtgtgatcc  43320
tggcccactg cagcctcaac ctcaccaagt tcaggtaatc ctctcacctt aatcccgtga  43380
gtagctggga ctacaggcac atgccaccga gcccggctaa tttttgtatt tttaccagag  43440
acagggtttt gccatgttgc ccaggctgcc accttatctc cattcttgct gaaatctggc  43500
tgtttctctc cacttctatt accaaccacc agccaaatct gacttattaa aaggatcatc  43560
tcgtatgtgg gttctgtaat agcttcttca aaatccattc ctctccaccc agaccctctt  43620
```

-continued ccaatctcca aactgcagcc aataccttca attctgtcac cgctcctgca tactccacct 43680
aatccttaac ctttcaatgg tttctcttgc ccctaggtta agctaaattg aaaactgcta 43740
aagctacagc ttcttagtgt aactagtaag tacagtgact actatgtctg gtttacttca 43800
gctgttgctg actaatagca cttcttgaat gaagaaatta tattaccgta ctgtagggaa 43860
aaatttgtac ttcaatggaa aactgaatta tttagagcaa acctttaagg ttatctgatt 43920
ctgattccat gggccctttc attgggtctt acattgtttc attgtttttg agttatttta 43980
cagatgactg atagaaatgc aaaataatta ttgcatgcag tcatgcaagt aaaatctgaa 44040
ggtcagggtt caattaactt ctctccccta ctgtggaaga agccaatttc atttgcatat 44100
tcatttcaat atttctgacc tataaacatg cctgttcttt gaaccagttt ttatatctgc 44160
ctggtaactt cattaaatga tttaaataaa ctctataatt tagtttattt tatacctgta 44220
tgacagtcag gcttttacct tatttttgct ttttaaaatt attctttagc tctccctaag 44280
gcactacttg gctggccctt tggctactca ctagcccaag ctccatcctc ttctgtctac 44340
cgcagcccca ggctctcttt tggccctttg ttccagccct cctcagagaa gttcttttgt 44400
cctggaactc actttcatac caggtgctct tcatcccttc ttcctttagt aaatttcttt 44460
aatctttcag atttctgctc aaggatcact tgctgaaagc ctttccaggc ctttctgagt 44520
caatacaatc cattattaga ggctcttaga gcacaggcag cacttgttat aattttacat 44580
ctgtctgtgg gattccttaa cactttctaa cacaattaac acttttctct ctggctgggg 44640
gcaatgcatg ataacaggat gatggtatgc tctcaaccct cccccagcaa ctagcccagt 44700
gcttcgaaca tggtggatag atacaccgtt tttattttag acagattttt gagtagcaag 44760
tacctactgc tcaggagaca gatggactga aaaaatatat ttgggagtca tcagcacata 44820
ggtgcagcca tgaaaatgca cgagaagcaa aaccattggc aggaacaaaa tgaaggctat 44880
tagagacctt atttaggtgg aataattgga cagaagccct taatggggag gaaatagaag 44940
cagttaatac agatggaggc cgggcgccgt ggctcacgcc tgtaatccta gcactttggg 45000
aggctgagat aggtgggtgg cttgagtcca ggagtttgag agcagcctgg gcaacatagc 45060
aaaacccggt ctctacaaaa aatacaaaaa ttagcccggc gtggtggcgc aggcctgtag 45120
tcccggctac tggggaggct gagatgggag aattgcttga accggggagg cggatgttgc 45180
aattagacga gatcgcgcca ctgcactcca gcctgggcga cagagcgaga ctccgtctca 45240
aaacaacaag gacaaaactt atcttataag cgaccctgga cttccaggga cactcgccgc 45300
tctatggtgg tacgtgacct gcctggactc tgtggtcttt ggagcttggg accccacccc 45360
agcgtaagag gcctttctgt gccttgtata aaggagagga aaagtgtagg ttttctgagt 45420
tgataagatt agagctacag tatattatca gtagcgttgt atgaaaccat ttaaaaaacc 45480
aaaccggatt taaccgcttt cacccagaat aaactgccct ccccctcttt ccaagatcaa 45540
gtcagcccca gttaccactt cctattaatt taaaaaccag gaaggctcat aatttaggct 45600
gacgttgccc caggcgaaca ctgcatataa gacaatagct attccaatcc tcctttccct 45660
ttctaaaccg aatagtactt ctaacatcac ttttccagtc ctctttctaa atattgcgat 45720
cacgagccta catcggaaaa ctatgaaaac agtatgattg gagctcttga tggtctgctt 45780
tgcctgaaaa cgatgaaagg cattgagatc tttgggcaga aatggccctt agggaatgcg 45840
agcctggtag ccccataaca ccccgagtta caaattcggt ttgggtaggt ggcgcaggga 45900
aatctaaaag ctggattcac gttctccccc ttcagtttgc acatagcggt cagtggcaga 45960
caagagcaga cgcacaaatg tcaatccccg cccgcaaact ctcgagggca gaaactgctt 46020
tttgtcagtt ggatttggag tcggtggaaa agctgcccta atgtagtttc tccgaggttt 46080
ccttagcctt gaccgagggg cgcttcccgg ccattcacct agaggttgtt taataaacaa 46140
ggatgctcgc gaaatatctg cgcttggaaa ggcgctcgtt cgtggcgcgc attctcgggc 46200
ctccgcaagc gaccccggtg acagggacaa ccgcttcggt tttagcgact gcagacagac 46260
tgggacgaga cggttggagg ctcctcccca agggatgctg gaggggttgc gtcgtaccct 46320
gcgcctggcc ctggcgcgcg gccccaggtc gtggtaccca gcgccctatg ggccgtgcgc 46380
cggggcttgg ccacaccgcc tgctttcgct tccagccgcg cgctccgtgc cactgccgct 46440
ctctgcagcc ccgcgtcccc gcagcctccc catggccagc ccgcttcgct ccgctgcggc 46500
ccttgcccgc caggtacctc gaacccgggc gtttgcggaa ggggggagga ttggaacccg 46560
ggtctcggta gctcgcgggc ctggccgggc gccttgtcgc cgtttcctgc accatcctcc 46620
ttcgccttgc cctccattcc gcctccagcg aggcgtcttc ccttccccgc atccctgccc 46680
gaaatctgga gtcccagcct gcaatctcca cctcttcgag gttcccgctg cccaggtcta 46740
gcaccctcat gggtaacccg ctccggagcg tggcgaggac cgccacgggg gacgtgaggg 46800
tagctatgga ctcgctctga gggaggaggc gggagctgaa tctctgggct gccagaaccc 46860
acagccacat cctacgtgac tctgccaccc caaaatattt tgaccgcagc cttctgcctc 46920
cttggatctc ttccttcccc acccccaccc ccgtagttat ttagcagatt acgcattaaa 46980
acaaatgtct gcaggttttc ccaattagtc ccgcttccct gtgtctttat cttttaaatt 47040
gcccactaat accatgaggt ttaaggtgtg gggtggatgc tgcggcatcg gaggaccctg 47100
ctggtggagg aaatggttca cgcccgtccc cgttcccttt gcaggcttgc tattgtgcgt 47160
ctgtgattga caagaccacg aggctgagcg cgccctggag atttttctat aaatggctta 47220
acaccccagt ctagactatt tgctcggata taagggagac aattgttttt ttgttctttg 47280
ccggcgaacc ctggctctgt agggctgacc tggaatttaa ccagtcttcc ctgagccggc 47340
ggaggaggac aaaaaccgcc gcgaccccgg cagggtggga agtgcagggc agcgctccca 47400
agacacgctt gttggaggtt cgggcctggg tgcttggttg tctgagcctc ctttttttgtg 47460
tttgcctggg tcctggagag gagcgcacgg tatcatggtg agcgtcacgt aggttacccc 47520
gggtcccgct tacccacctg catttactta atggtggttt aattcttctt taaggattgc 47580
agtaacggat gctccgcaga gtgtaccgga gaaggaggat caaaagaggt ggtggggact 47640
tttaaggtaa gttgcttgcc agaggcttag tgtctaaagc aacgttcaac tgaataaatc 47700
catttcttgt tgagattcgg ggaaattttc actgtgtggg ttacccagtt cctaggttgt 47760
gttgccagac ttttaaaatt ccactcttag aggaaaaaaa gccatttaga gagtgacagt 47820
acattcatca caacaaaaat tatctagcag ctaattgctg attttatttt gagtcatata 47880
tttttcttga aaaatagtca atgcgtaaat attaaactag ttgtttatca gattccataa 47940
tacgtacaaa ccttcagtct acttgtagaa aaagttaaac tgtgattttt ctctttcagt 48000
agcacataac actctacagt gaaagtgttg cattttcttc ttttctatct gaattgcggg 48060
gtttatatag taaatagctc atacttcaaa cagtgagaaa caaagcacgt tgaaaactgt 48120
acaaatacaa atgtaagatg taatattatt ttttctataa gtctatctcc taccctccct 48180
cctcgtggag gttttagctt cttcttttta tgcctagtgc tgctcttctg cctgtttgag 48240
tcactgtcaa ttgtcatcag acaattgaca cagagtgtcc taatgatctc acatcctggc 48300
ggttcagaga gggaaggaaa cttgactcat cagtttctca cacattgagc tctctcacag 48360

-continued

```
tgtgctggag actgtgccat gcattggaca tccaaaggtg aattcaagat taggtctcta  48420
cttgcaagga atttttattt tatttttctt tttccttctc ttgctgtcat cttagcaagg  48480
attttttaaa aagcaaaatt agaatattgc aatttctttt ctgtttttttg agacagggtc  48540
tcgctctgtc acccaggctg gagtgcagtg gcacgatctc agctcactgc aatctctgcc  48600
tcccaggttc aagtgattct cctgcctcag cctcctgagt agctgagatt acaggcatgt  48660
gccatcacgc ccagctaatt ttgtattttt agtagagatg gggttatcac catgttagcc  48720
aggctggtct cgaactcctg gcctcatgca atccacctcc caaagtgctg ggattgcagg  48780
cgtgagccac caagcctagc ctgaagaatt ctttgcaaag aaaaatatca actcaaattt  48840
aaataatctt ttcctttctt tttctttttt ttgagacaga gtcttgttct gttgcccaga  48900
ctgaagtgca gtggcaccat caattaggta tcactttcag ccttgatctc tcagactcaa  48960
gtgatcctct tagcctctca agtacctgag actatcggct tgcatgccat caggcccaac  49020
taatttcgtc atttttgta gagatgggat ctccctgtgt tgcccagact gatctccaac  49080
tcctgggctt gtgcaaccct cccacctcgg cctcccaaaa tgctgggtca caggcataag  49140
ccacaatgcc tggccataaa taatcttttt tatttgttaa tttagatttc tgtatattag  49200
gttttattta ggggaattgc ctgtttacac tcatgtattt acacatcaaa acatgagtta  49260
tggtggatgt attcacagca catatgtaat aaggcatgtg taaaaatgat attgataatt  49320
tagggaataa aaatggtaga ttttatagac catctttgtt tttgatatac ttttctctgt  49380
ctcaaaaaac aaaaacaaaa acaaacaaac aaacaaaata tatatatata gcctacattg  49440
ttgttaacta taatcaccct actctgctat gaacagtaga ctttatcgct tctatctaac  49500
tgtatgtttg tactcattaa ccaacctctc ttcctccacc tacacccttc ccaccccctg  49560
ccatcttctg atatctatca ttctatgagt actctcttcc tccatgagat caactttttt  49620
ttttagctct cacgtatgag tgagaacatg caatatttgt ttttctgggt tttttttttt  49680
ttctgtgttt ggcttatttc gcttaccata atgacttcca gttccatcca tgttgctaca  49740
aatgacacga ttttactctt ttttaatggc tgagtagtat tccattgtgt atatgcacca  49800
cattttattt gttcattgat ggacacttag gtgattccat gtcttgacta ttgtgaatag  49860
tgctgtaata aacatgggac tgcagatatc cctttgatat actgatttcc tttcctttgg  49920
aaaataccca gtagtaggat tgttggttta tatggtcatt ctacttttag tttttttttt  49980
ggaaagcttc ataccatttt ccacagtaga taaactaatt tacattctta ccaacagtgt  50040
ataagcgttc tcttttctct gtatcctcat cagcatctgt tattttttgt ctttctaata  50100
ataaccattc taactgtggt tgcttttgac atatttctct acctttttgt taatctacat  50160
catttataac atttcatatg gccttttggg tctctcttgg gtagttttcg tatttcttct  50220
cccctcccca tttatgatgc agtcatatta catgaggatg cagttttgca gcagggccta  50280
gcaatgagat acgttgttac acatcctggc gaatctttct gtggactcta ggatcctctt  50340
catttgcaag aggtcagcca tctatttctt ccaattcctc cagcttcaca tatctccaca  50400
gaatgcaaca ctgcaaatct gcagttctct tcatgatcct ctttattaga ttttaaaaga  50460
gtatctccaa aagatgaaca tagtgcctaa ggctttccaa atggagtaag aataatgcac  50520
aagaacctag aataaagtta ttaaatgtct gatacagttg taatacagac ttgatttttg  50580
aaaaatgtgg ccaatgaaga gaagagcaaa tgtgctatac gatggtgagc aaaaggtgtt  50640
gacaggcctg gcatggtgac tcacccctgt aatcccagca ctttgggagg ctgaggtggg  50700
tggatcattt gaggtcagga gtttgagact agcctggcca acatggtgaa accctgtttg  50760
```

tattaaaaat acaaaaatta gccaggtgcg atgacacatg cctgtaatcc cagctacctg 50820
ggaggctgag gcttgagact tgcttgaacc ggggaggcgg aggttgcagc gagccgagat 50880
tgtgccactg cactccagcc tgggcaacag agcaaaaaaa aaaaaaaaaa aaaaaaaaag 50940
tgttgactga accctggctg aaacagtttt caggtgcttt caacaaattt acacttccct 51000
gccctgagcc tccctatttc agaacaaatg attacccaac tgcaaacttt gaattaggaa 51060
gttgtttttta atatgccctg tttttctcaa tatttcttgc catttcacaa tcagttattg 51120
tggcattcca attcttccac aaacatatga tgtgaaacat cctgacttcg atgtcatcag 51180
ggaatgtgga gcattggaaa gagacagatt aattatgcag aagaaagtat catttgacaa 51240
aatattattt ttatttatct ttggaaagga aatctagaaa aagaaaatac tttttaaaga 51300
acactgataa aaattgttta taaaatttgt ttcctttagg aaacaaatcg ttcccttaaa 51360
actacatttc atatctgccc caaacgagtc acatgtcttc agctaatatt gcttgtttac 51420
gtttgaactt tattcaattc tatcacctag taatttagta ttcttaggta atttctcttt 51480
gagctcaggt taaaagttgt tatttttagt tttcagagtt gcagaatttt tttttcaagt 51540
agagaaaagt tcatgatgag attctgaagc cacctaatcg tatattactt tgaaaaactg 51600
gatatatgcc gggcgcggta gctcacacct gtaatcccag cactttcaga ggccgaggtg 51660
ggtgggtcac ctgaggtcag gagttcgaga ccagcctggt caacatggtg aaaccccatc 51720
tctaccaaaa atacaaaact tagccgggtg ttgtggcaca tgcctgtagt cccagctact 51780
caggaggctg aagcaggaga atcacttgaa cctgggaggc ggaggttgca gtgagcccag 51840
atcacatcac tgctcttccg cctgggtgac agagtgagac tccatctaaa agaaaaagca 51900
aaacaaaaca aaactggata cagggcagtg cttaggtaca aatcagaaag ttagaggttg 51960
ctattcatat cattaagaaa taatgtgtct tacgaaagaa tgtagcagtt tactgaaata 52020
gaagtcatac ctagaaatgt aataatttat ctttaattgt cagaaattta actgatatta 52080
tgaagttcta attataagaa cacttatttg aggttaaaaa ttaccttatt ctatccctgc 52140
tttgccgcta atttgatctc tctggattag tgggttattg tgggtcctat gggtatttta 52200
aggagaggtc tcagaaaact aaaaattata tatactggat cataatcatt cttgtcaccc 52260
actctcatct ttctgttttt gttttgtgtt ttactaccct tccccttttta ctaagtagtc 52320
ttagtagaag aaaatttgca ttaagtttgt cgtactgtat tgatatggct ccaaatgttt 52380
cttagcccag ggtcctcccc attcactgat aaaagctaac taaggtaaat cacaggtgtt 52440
tattgtgcaa gaatactgtg aaactattca tgtaataaaa agtttgtgtt agaatttcac 52500
tctctttaaa tcctggacat cttctgtgag tgtatctgaa agcagccaga catcttcagt 52560
atttaagaaa ccctttacta ttctgtgtgc taggcactgt gttagctttg gaattcaact 52620
gtgaatactc tagccagact tcttgtctaa atagtccaga ataggggttg ctaaactttc 52680
tttctttttt tttgagatgg agttccactc ttattgccca ggctggagtg cactggtgtg 52740
tctctgctga ctgcaacctc tgcctcccag gttcaagcag ttctcctgcc tcagcctccc 52800
aagtagctgg gattacaggc gcccaccact acactcagtt aatttttgta tttttagtag 52860
agacagggtt gtgctgtttg ccaggttgat ctcaaactcc tgacctttgg tgatccaccc 52920
gcctcggcct cccaaagtgt tgggattcag ggtgtgccac tgtgcccggc ctgctaaact 52980
ttcttaaatg gctagatgat aaatatttta ggcttgaggg ccatcaggtt tctgttacaa 53040
ctagttggct gtgctgccac tgaagataca agaatggcgt gactatgttc caataacatt 53100
ttaatttcaa aacaggccag ctggctgcat ttggtctgca agtaaagtct gcctgacccc 53160
ctacctagtc cagaggacaa cgggagagaa aagggattca aagataaaaa taatttagct 53220
ggaatatatt tctttaaata aacttattat acttagtaaa aagtcttaaa ttaacgtttt 53280
tacttgaatt aaatagtggt aaaacaggct gggcacagtg gctcatgcct gtaatcttag 53340
aactttggga ggtcgaggca ggcagattgc ttaagcccag gagttcgaga ccagcctggg 53400
caacatagtg agtccctatc tctaaaaaaa atacaaaata ataataataa tggtagaaca 53460
aagtcaattt tttattgaaa cttggcattt tattggcata ttacaaagta gcattactag 53520
actagcctga acattacagt aatattctgt ccttaatgcc ttttgtgtca ctgtaatatg 53580
agctttctgt ttgttttgga atatgttttc agcctgaata ttattctaaa aatacaattt 53640
actatcattc ataatatatc aaatgactca cgtagctgca aggcagtgaa ttaaacagaa 53700
ttagatcatt ttaaaaataa tgataagagc tgatgatgta aagtgaaggt ctgtatttaa 53760
tttgggaggg aaaagacttt ttttgtatat tcaaagagat ggagtttgac atcccttcac 53820
aacctgttac aggttgaact tgcccctgtt tttttaactg atcaaaaagt tccttctctt 53880
gtgtttcttt ttttcttctc ttttctcttc ttttcttttc tttttttttt ttctgagaca 53940
gagtcttgct ctgtctccca ggctggagtg cagtggtgcg atcttgactc tctgcaacct 54000
ccgcctcccg ggttcaagtg attttcctgc ctcagcctcc tgagtagctg cgactacagg 54060
tgcatgccac cacgcctggc taatttttag tatttttagt agagacgggg tttcaccatg 54120
ttagctagga tggtctcaat ctccaaacct tgtgatctgc atgcctcggc ttcccaaagt 54180
gctggtctcc tgtgtttttg tcagcattcc acagatgcta taaagttagt ggtggtatcg 54240
catgcaattt gtacgcttaa tgtttggcca tttgcagtgg gcaaactggc tatgtcggga 54300
gctggtgaga tgctgcttgt ggggagttgt ttcctattac tctgatttat ctttgtttaa 54360
ataagagttc ctttgttcac tgtttcctcc acacagaaca gaggatttat atcttagtgt 54420
tcattctcaa ctttcctgtt ttcaaagagg aaaacatttg cttcactttg ctcatttctt 54480
ctccagtgca cccagaggat tttgaaggct tatgccaaca attctttggg gcagttggag 54540
tgtaaccatt gctaaatagc agttcagtac ttaatgacat tcattttagt ttaacaaatc 54600
attgtgagtg ttgccatttt ttattaggga aaacatctct ttcatctttc ccaaatactc 54660
aacatgagtc ctatggtgag agtgaaaaag ggttgtattc tttttttgca tcatcttacc 54720
ccatctgcta ttttgtccct cttctatata tcactgaaat ttggttctga tattctatta 54780
ggcagtgtac attgcagaga ttatgaataa ctggccgaat tctgaatgca ggcatgattt 54840
gttcagctca gagtgttaaa tttctgtgtt agctgctaac ctttaaaagt caattgattt 54900
cctttttttt tttcccctct gtataatcta gccagcgaat gctcagtagc ttttctgtaa 54960
atagtgatga tttttcttcc ccaggctaaa gacctaatag tcacaccagc taccatttta 55020
aaggaaaaac cagaccccaa taatctggtt tttggaactg tgttcacgga tcatatgctg 55080
acggtggagt ggtcctcaga gtttggatgg gagaaacctc atatcaagcc tcttcagaac 55140
ctgtcattgc accctggctc atcagctttg cactatgcag tggaagtaag tacatgggaa 55200
ttaaagagag tgacatgctt gcacttcact gtgggtacta agtagcttct cctgctaaaa 55260
tagctcttgg gcagtatggg ctttatcata tttaccagag gaagccgaaa atgtctttaa 55320
aagttttcct atagacagtt ggattgaaga taaatcttag cagctaattt ttcagataat 55380
cttgcatttt ctgtgacgtc aataaaaaaa ttatttaaag caaatagaaa ggacagctgg 55440
tgggaaaatt ggcaattaaa aagccagcac tgttgataat ttaataagtc acctttcttc 55500
ttagatcttc taataattga gaaagggtca ttgagaacaa tattatgatt tgattttaat 55560
gctaactcca catttttatg accagtaata atgtctagtt atgcatgtta agggacatgt 55620
aattaaatgt cctccttcag ccatgagttg aaataatttt aagcataaaa tgtttaaaga 55680
attctttctc tggtcctttt cagggtgcac aattaaccag atgcacagta tacttcccat 55740
tgtcttgatt ctcattgtat tttacttttg aatgatttgg acatctttcc cagaataata 55800
ggggtgctgg aaataataat agtcttccta ttaagtgcta aaatatggta atagtaaaat 55860
attaatagat taatgataaa ataacaactt ttgtttactg aattcctgca atacgttctg 55920
tattatgttc catatatgaa tcatctcatt taattacctt aagtgagaag gcatgtgatt 55980
aagcattcag gctttgaagt cagacatcct gggctcaaat tcggtctcat ttgctccata 56040
ggaaccttta tgacttgagg aatttaatca tttgtgcttt aatttcttta tctataaaat 56100
tggggtagtt ataatatcta tcttacagtg atctcataag tataaaataa agtaatttat 56160
ctaagcatat agagtcatat ctggtgcata gcgagagccc agttgttagc aataataatt 56220
aactcttgaa gcagtggtct catccattat aaaaggaggc tcagaagagt tgtttcttga 56280
ctaatattac acagcagtaa gggtggagct aaggttccaa tgagaagctt ctttctgtta 56340
tatagcccct acatgtatac accaaaatta ctaggatgct tttgcaatta actccttcaa 56400
aattataaat tcatataatt ttggaaagat attcactgtc catatgtatc cacaaaatgt 56460
tgaatttagg aatctaagtt tctgttccca gctcttcctg ttatgtcaat ttgaatgagt 56520
tctttcatta tttgccacaa gccctcacca tgtcataagg tataataaag aacaggtgaa 56580
atgaagtgct tttatttatt tatttttcag acagattctt gctctgtcac ccaggctgga 56640
gtgcagtggc acgatcgtgg ctcactgcag cctcaaactc ctgggctcaa gcaaacctcg 56700
tacctcagcc tcctgagtag ctgggaccac agacacatgt caccatgtct ggctaatttt 56760
tacatatttt gttgagactg ggttttgcca tgttgcccag gctggtctca aactcctggg 56820
ctcaagcaat cctcttgcct tggcttcttc aagtgctggg atgacagcca tgagccactg 56880
ctcctggcta tgtgctttta aatttgaaag gaataatatg cccaagccca ggtcactggt 56940
tctcaaactt aatgtgcatc agaatcagct ggctacatct ccagagtttc tcatttctaa 57000
caagtgtcca gatcatgtta attttgtcgc tccagggacc acattttggg aattgctggc 57060
ctatgggaag taaatgagaa atgatttaat gtcatttttg gaagttaaaa aagattttgg 57120
tggtcactgg tttttgaaaa ctctttgaag gctgggtggg gtggttcaca tctgtaattt 57180
cagcagtttc ggggagatgg ggttcttggg aaatgagccc tccacccatg ggatctgatg 57240
ctatttccac gtagataatg tcagagtcgt tcaaaccaga gtgactccat cctgaatagg 57300
ggctgggtaa aataaggctg agacctactg ggctgcaaca tgatgagacc ctgactctat 57360
tgaaacaaaa caaaacaaaa caaaacaaaa caaaacaaaa aacggccagg cgaggtggct 57420
cacgcctgta ataccagcac tttgggaggc caaggcgggc ggatcacgag gtcaggagat 57480
cgagaccatc ctggctaaca tggtgaaacc ccatctctac taaaaataga aaaaaaaaaa 57540
aaaattagcc gggcgtggtg gcaggcgcct gtagtccaag ctacttagga ggctgaggca 57600
ggaaaatgac gtgaacccag gaggcggagt ttgcagtgag ccgagatcac gccgctgcac 57660
tccacactgg gtgacagagc aagactccat ctcaaaaaaa aaaaacaaaa acctctttgg 57720
ccatctattt agatgagttg gaatgctact ttgattggtt ttgccaattt agatttttgt 57780
aattagggta gtttaaaaaa actctcaaat tactgttatc ctttgttaaa aaccaaaatc 57840

-continued

```
ttttattatt agtcttctgc ttacaatata agtaaaataa atgttttgta ttaataactg  57900
gattgtatat tgcatggtta ccactatgta acaaaattaa tagcttaaaa ttacaagcgt  57960
cattttaaaa ttatttttca tgtttctggg gttgactagg atggctaagt ggtttttgct  58020
tggggtccgt cacacggttg ctgtcagtgg ctggggttag agtcagctca caggcttcct  58080
aactcatatg gtgctggagg gagtgtctct tagcatgcta atgcttcata atttgtgtat  58140
aatgaacagt gaggatgacc agaggtcact ttcattgcca tctgggctgc aaaactcaag  58200
gagttgaagg ctcttccggc attacttgtt ctccatgtgg tctcctcagg atggcagtca  58260
cagagtaggc agccttctta tgtgctgacc tagggcccaa aatctgtatg tgtcagttga  58320
ctgagcccag atggaagctc tattgctgtt tacgccctag cctcaaaact actctttcaa  58380
gaaaaattct ccaaccgagt tttcctcta ctctcacacc accacaacaa tagtcaacat  58440
aggagacttc tatgatcaaa ggtgtaggga tttctcccca ccaccaagca gtgaacccca  58500
gctgggtgtc ctccaattca attctcacac tgttattacg ggaaaggtgt cccaatccag  58560
tccccaagag gttcttggat gttgcacaag aaagaatttg gggagagtcc acaaagtaaa  58620
ataaaattta ttaagaaagt aaaggaaaaa aagaatggct actccgtaga cagaggagct  58680
ccgagggctg ctggttggct attttaatgg ttatttcttg atcatttgct aaagaagggg  58740
tagattattc ataaatttc cagaaaaggg atgggcaatt cctggaactg agggttcctc  58800
cccttttag accttgtagg ttaacttccc accattgcca tggcctctgt aaattgtcgt  58860
gacactggta ggagtgtctg ttagcatgct aatgcattat aattagctta taatgagcag  58920
cgaggacggc cagacatccc tttcattgcc atatgggatt tggcaggttt tggctggctt  58980
ctttaccaca tcttgttta tcagtggggt ctttgtaacc tgtatgttgt gccgacctcc  59040
tatctcatcc tgtgacctag aatactaacc tcctgagaat gcagcccagt aggtttcagc  59100
cttattttac ccagccccta atcaggatgg agtcgctctg gtccaaacac ctctgacatt  59160
atccacctgg aaatagtgtc agatcccatg ggttaagggc tcattcccca agaccctaac  59220
caccctcacc tggcccagac acaagtcaca agtcctgtcc tctggaatgt ctgactgaga  59280
ggcatcaagt tggagttccc atgacccct cttctggttt gattaattta ctggagcagc  59340
tcacaaaact cagggaaaca cttaggttta gtggtttatt ataaaggata ctgcaaagtg  59400
tatagatgaa gcgatgtgta gggtgaggta tcgggggata gagtgcaggg cttccatgcc  59460
ctcccggggt gtgccaccct ttaggaacct tcatgtgttc tgctatccgg aagctcactg  59520
aactcattct tttgggtttt tatggaagct tcacgtcaat attccttccc ctggggtatg  59580
aggcaggacc ttcaccggag agggtctttt attttatttc attattttta aaatataaga  59640
tggggtcttg ctatgtagcc tagggtggta ttgaattcct gggcccaagt aagcctcccg  59700
cctctgcctc cgaaagtgct gggactacag gcatgagcca cccagcccct ttggagagga  59760
tcttaagact cacagttaga aaggagggca ggagaaggtc agagagattc tgcttcctgc  59820
ccctgaggcc taacacaccc agcattataa caaaagactg taacaagggc tatgggagtt  59880
accagccagg aactgtaaat cacacagtat tatttctgcc ttactcttat cagtcatgat  59940
ggttacaaag gcctgtccaa gttcaaaagg aggaaaaaag cactccactt cttgatgagg  60000
aaggtcaggg ttctggaaga gcatggggga ctggaaatat tgttcggcca tttcatggaa  60060
aatacagtct gtaatagaca tcagtgataa atggggagat atggtggatg tattgttttc  60120
ctctgagtgc caaattgggt tctaagattt cacaggccag atattattga agtggctacg  60180
ttgtctgggg tatatacctt ggggttcgtc attttgtgcc aggaaaattt aggacaagga  60240
```

ctcacacgag gagtttagga gtggaggttt aataggcaga agagaaacag aaacagttct 60300
ttctgtaggg agagagggat cttcgaggga aaagaccatc cagcagcaga tgagctggat 60360
tttatagtca ggtttgagga ggaagtgtct gatttactta gggctaacag gttggtttga 60420
tcaggtatga cgtttacata gcacaccggg aagtctggtt gccccaccct aatcctttta 60480
tgcaaatgga ctttcctagt tgattggagc tatcttgtct gctccttact gtacaggtgg 60540
ctgacaaaga gaagggaaga tggagccgcc atcttgaaca tgattgacgc agctgtggat 60600
atctatgtct gcagcttgat tttacaggct gctcttcttt agaaaggggc tgcttttcat 60660
taaaacaaaa accttactga ggactcttgt accctcacta tctgcaggtg atttcttaac 60720
tcctgtatca ttattatagt gtcataggaa tctaggaagt gtgattgcct tctggagaga 60780
acttcagggt ccctggattt tctcactaat catattcatt tcattccctg tttacctgtt 60840
taataaatgt tgagtggcta ctatgtgccc agggctgtgc aaggtgcctg gaataggatg 60900
gcaagcaaac caaccatgac cttgctctca aagaattgtt ttctttcttt cttttttttc 60960
tgagacaagg tcttgctctg tcgcccaggc tggagtgcag tggcctgatc tcagctcact 61020
gcaacttcca cctcctggct tcaacagatt ctcctccctc agcctcccag gtagctggga 61080
ttataggtgc ccaccaccat gcccggctaa tttttgtatt tttagtagag acagggtttc 61140
atcatgttgg ccaggctagt ctcaaactcc tgacctcaag tgatccgcct gcctcagtgc 61200
cgagattaca ggcatgagcc actgcacctg gcctgttttc tgtctttttt ttttaacccc 61260
cacatggaaa gttaggcagg gatttaattt caaagagttt cttcccaaat attgtggtga 61320
aacatctagt ccatttatgt ttcaggcttt ttcatagata ttactgtttc tcttagactg 61380
acagacttag gacatcacat gattgaatgt caacctgact tttaagttca ataatagttt 61440
catttttttaa atgcaaaatt aaataggagt aatatccttg aacatgtttc tccttcactc 61500
atcggaccta ttgagtctag aatccatttt attttgagag ctccaactac atgtggtttc 61560
tgttaatatc tgaaagtaat ttttaatatc tgaaagtttc aaatagtgat aatatttgaa 61620
ggtttcaaat agtggaggag agacgcaaac tgcgagtagg gaacgcggat tgaaggaaat 61680
gaaaagttga taataggcac ttcattttca gattataaca aatatttagt gaaataaagc 61740
ataattttaa aaaatggata agacatgtat gtactattta atgtgtacta ataaatgaat 61800
gctcatattt gccatccaga taaagaaata gaacagttga acatcacaga agccctcgcg 61860
tgtcccattc agatcacaaa ctctatcttt ctactggtaa ccattattct tacttttgtg 61920
ataacctttc tttgctttcc tttatggagt gtgtagattc ttaacactat agttttgcct 61980
ctttttgaac ttcatgtaaa tgaaaaaatg tatatatttt gtgtttgtgt gcatgtgtgt 62040
gtgtgtgctt gcacacgtgt gaatacccct tattgtttga gcttagtatt atgtaagatc 62100
taaccaggaa ggaccaacct aacatttgtg gggcctggga cctaagtata gacagagatg 62160
acatggtcca ctccatatct gttcccatcc cagttctgcc ctgtgctaca aggggtcttc 62220
cagacactgc ataggtaccc ataccacctg caggcagatg acctttgcct gtcctttgga 62280
gttaggcctg ggtaccctac tagtggtgtc tgctcttggg atgataaacc cgaggggctt 62340
atcagcttta tatatatata tatatatata tatatatatt tttttttttt ttttttttag 62400
ctagcatctc tctcgttctt ccaggctgga gagcagtggt gtgatcttgg ctcactgtaa 62460
tctccacctc ctgggttcaa gcgattctcc tgcctcagcc tcccaagtag ctgagattac 62520
aggcacgtgc cactatgcct ggctaatttt tgtattttta gtagagactg ggtttcacca 62580

-continued

```
tgttggcatg tgagccacta tgcccggcct cttttttttt ttttttaag agacagggtc  62640

ttactatgtt gcccaggctg gtgttgaact cctggcctca atagatcctc tgtccttggt  62700

ctcccaaagt gctggctcag tcattatgtt ctttactgcc atccattgca gtataaaaag  62760

aataacagtt ttccctcaga atattcttgg tgaaacagta acaattatta attttattaa  62820

atcttggctc ttgagcaaat gtcattttaa tattctgtgt gataaaatag caatgtcaca  62880

taaagtgctt ttacatactt aagtactatg gttgtctgaa gaaaaaggag ttgtgtgatt  62940

gtcttgagtt tgtaagtgga actacttttt tcatcgagca ccgtttttac ttgaaataac  63000

aaagtatgaa tatgaatgca gatttggcca tttggcagat ttttatttat ttatttgaga  63060

caaggtcttg ctgtgtcacc cagactgggg tgcagctcac tgcagccttt acctcctggg  63120

ctcaagtgat cctcctgcct cagcctcctt agttgctggg accacaggtg tgcagcacca  63180

tgctcagcta atttttaaat tttttgtgga gacaaggtct gaccatgttg cccaggctgg  63240

tctcgaactc ctgggctcca gcaatcctct cgcttcagct tctcaaagtg ctggaattac  63300

aggcgtgagc cacggttccc agctcgcctt ttcatatgtt tattgggttg ctaaatatgt  63360

tcttatttga agtgcccact tgttcaagtt ttttgttcac tttttattg ctgtctttat  63420

aatttttga tgacaagaaa tatgtttaaa ttaaaggcag ttttgtcaat ctgccttatg  63480

tttggaattt gttgtgtctt taaagactct tttcctgccc ttatattata aagatatctt  63540

atagtattga tattgtcatt cacagttagg tctttaatcc tagaagttga tttttgtatg  63600

aagtaagggc ccaatttatt tttttccacc tatgtatacc cagttttccc agcaccattt  63660

aaacgggcgg tactttcccc tctgatatgt catgatgaca cctttgtcat gtacacatga  63720

gtttgcttct ggatctctat ttgtgttcag ttgttttact tgtctgcata aatgccacag  63780

tcttggtttc tcagtcatta taatgagcct tgcctgctag gaagggtcct tctactttgt  63840

tctccaagag tgccttggat attcttggtc attttctttc catataattt ttagatttgg  63900

tttatcaagt cgataaactt ttgtcatgca gttttttaaa agaaaataaa gtgccctaat  63960

gtgatttttt ttaatttgga ttacattgaa tacataaatc agtttgggga aaatcaacat  64020

ctttataata ttgaggcttt ttatccatga gcatgaaatt gctttctaca ttaataactt  64080

ggtaaagttt tatattttcc ttatggatct ttcacttctt ttgttagatt tttctccacc  64140

taagtactgt atcttttaat tctactgtaa atagtgtttt tattttttaa ctgctgctat  64200

tacataggaa tataattttg catctggcca gcttgcctaa acagatgatt tcaaaatatt  64260

atctgtcaga ttttctgtgt tctctatctc tgtaatcata tcatctatgt tttatgatct  64320

atgacagtta tatttttca tctccaagct gatattttaa atttcattat tcttgcttta  64380

tactggttgt acatattcag ttagagtgat tgcagtaggc aatttgcgat gttcccaatt  64440

tgataaggaa agcttttaca ttttaccatt aagtataacg tttgcgagct tattatagct  64500

atcctttgtc acttagggaa gttatctttg ttttttagtt atctaggaaa ctaaaaaatc  64560

agaaaagtta gtttgatttt atcagataca tctgctacat ctaatgagat gatcatatag  64620

tttttttcct cccataaact gtgaatataa tgaatcacat taattgattt ttttaaatgt  64680

taaaccaatc tccatttctg ggataaattc aacttagtca tgttgtatta gccttttgta  64740

tatcttatat ctataatact gaatgagatt atcatactct ttacatgtat ttgaagccat  64800

gtcattaagt gcatacaatt tttattaaat ttttaattga caaataattg tatttattta  64860

tggggtacga tgtagtgttt tgatatatgt ttacattgta gagtgactaa atcaagctaa  64920

ttagcatact catcactgaa catatttatc atttcttgtg gtgagaacat ttgaaattta  64980
```

-continued atctcttagc aattttgaaa tatatgatac attattatta actacagtca ccatgctgtg 65040
cgataggtct caaaaactta ttcctcctaa ttgaaatttt gttccctttg accaacatct 65100
tccaattccc caacccctag cctcctctgg taaccaccat tctactctct acttccatta 65160
gtttgacttt ttcagtccac atatgagtga aatcgtgcag tatttgtctt tctgtacttg 65220
tcttgtttca cttagcataa tgtccaacgg gttccccatg tcattgtaaa tgatggaatt 65280
ttcttttta tagctaaata acattccatc atgtatacat accacatttt ctttatcgat 65340
tcatctgttg atggacagtt aggttgcttc tgtatcctgg ctattgtgaa taatgctaca 65400
ataaacatga gagcacagat acctcatgct gatttcaatt cctttggata agggtcccca 65460
aaccccaggc tatggaacag cagtggtatg tgtggcctgt taggtactgg atcgcactgt 65520
aggaggtgag cagctgcgag tgagcattac cacctgagct ccatctcatc tcagatcagt 65580
ggcagcatta ggttctcata ggagtgtgaa ccctattgtg aactgtgcat tgcaggaatc 65640
taggtggtgc actttttatg agaatctaat gcttgatgat ctgaggtaga atgattgcac 65700
tctgcaagac tccccacgct catccctgtg gaaaaattat cttccacaaa actggtccct 65760
ggtgccaaaa aggttgggga ctgctgcttt tggatatata cccagaagtg ggattgctga 65820
agcatatggt agtttaattt taattttaat ttaatttagt ttaattaatt tatttttagc 65880
acctaggctg gaatgcagca gtgcaatcat agctcactgc agcttccaat tcctgacctc 65940
aagccatcct cccaactcag cctcccaaat ttctggaact acaggaatga gccatctcac 66000
tcagccctat ttttagtgtt gggaagaatc tcaaaaagta atgactgtac taatttacac 66060
cgctaccctc agtatacaag ggttccatat cctcactaat acttatcttt tatctttttg 66120
atagtagcca ttctaagtat gtatagtttt aaaattatga agtttaaatt gaaccttagg 66180
aagttgctac tctgtcacca ggctggagtg cagcagcgtg atcttggttc accacaatct 66240
ccgcctcctg ggtttaagca attctcctgg ctcagcctcc caagtagctg ggactacagg 66300
cacatgctac catgcctggc tcatttttat atttttggta gagatgggtt tcaccatgtt 66360
gtccaggctg gtctcgaact cctgacctca agtgatccaa cagccttggc ctcccaacgt 66420
gttgggatta cagacgtgag ccatcacacc cagccttgaa gttgcctttt ttatcttcag 66480
tagtgcttct tggcttaaat tcttttgttt tataaatagt aatggaagct tgccagtttt 66540
attttagaaa gtatttgcag gccaggtgca gtggctcatg cctgtaatcc cagcactttg 66600
ggaggccgag gcaggcacat cacttgagcc caggagttcg agaccagcct aggcaacatg 66660
gcaaaacctc gtctctacaa aaaatacaaa aaattaactt gggcgtggtg gtgcgcgcct 66720
gtagtcccag ctactctgga ggctgaggtg ggaggattgc ttgaacccag ggggtagagg 66780
ttgcagtgag ccaagatctt gccactgaac ttcattcagc ctgggtgaca gagaaaaaca 66840
actctgtctc aaaaaaaaaa aataaataat aaaaaataaa gtatttgcat gatatatctt 66900
tttctgtctt tttgattcag atattgtcag ctgagtccaa tctaacaaac ttatatttta 66960
accgaagctt tagtactgtt atatttaata aactaataat atatttgcac ttaaatacaa 67020
catctaattt tatgcttttt aattatacat gatttgtatt tctttttttc ccatgtaagt 67080
ttttagggta tacatcttta aaggccttac ttttcattat cgttcagttt aacttatttt 67140
ctaatttcca tttttcttct gtgacctatg gtttagttag tggtggattt attttccaaa 67200
atatggatgg tgtccagtca aacttttggt attgatttct ggcttatctt gtgtttggaa 67260
aatatgtgaa ttctacagct ggtctgtgta agagttctct gtatcagtta gggaagtttg 67320
ttcttcctgt tgttcatatc ttgcatatct ttactaaggt ttagcctgtt tgttctataa 67380
attacttaga gaagctgtgt taaattttcc cactaaaatt attgattttt gtctttctct 67440
gtatttatca gtatgtatct actgaagtct tttcaaatcc ctgatcagtg gtttgttcag 67500
gacagcactt tgattgaggg aggtgacgtg gcttaacata gtatggtctt gagctgcctg 67560
gtttctgtga tttagggact gaaccagctc tggtcacatc tggattatct actatccagc 67620
attcaaatga accagattac atgaaaggat atgggggtac tctttggggg ccacggtgcc 67680
acaaggcctt tggtttcgat ctccattgcc tagggaatta acctgtgctg tgtgattcta 67740
gatgttttct tcctgctccc ttaaataaca cctaaatgtg ttattcagca gtgtggctcc 67800
tgctaagcag aggagaactc ggaattccta ccaaattctg ataataaaat aactttcctc 67860
cacctcaacc attgttttta ccagtcctgt caactgttag ctttcctgga tttaatgatc 67920
tcaagttgag gtcaatgtca acagctttat gggatgaata agatgaacgc ccataggaaa 67980
gtcagtctct tgaacacggg ttgttttctt ttggttaccc tctaagattt tttctctttg 68040
atctccagtt atttgaagga ttgaaggcat ttcgaggagt agataataaa attcgactgt 68100
ttcagccaaa cctcaacatg gatagaatgt atcgctctgc tgtgagggca actctgccgg 68160
tatgtaagtg taggagtttc ttttgtgttt cttttaatgt aacgggtcac ggtgttgacc 68220
accaaataaa taatttctga atagttagat aaatattcag tacaaaccat atgaacatta 68280
acattatttc tgatctactt tagttaggta aaaatacaag aaaatggccg ggcacggtgg 68340
ttcactccta taatcccagc actctgggag actgaggtgg gtggatcact tgaaaccagg 68400
aattggagac aagcctggcc aacatggtga aacaccatct ctgcaaaaaa tacaaaaatt 68460
agccgggttt ggtggcacat gcctgtggtc ccatcggtgt ggctgaggca tgagaattgc 68520
ttgaacctgg caggtggagg ctgcagtgag ccaagataat cacatcactg ccctccagcc 68580
taagccgcaa agtgagactc tgtaaaaaaa aaaaacaaaa aacaaaaaac ccaagaaaat 68640
aatatcattt ggcaattcca caatttttta aaatcagtgt ctgtggggga ttcatatgca 68700
agtgagagat gaaagagtaa ggaagaaaaa tgtatctcaa cctaaaataa tatttgaaga 68760
ccacatgaaa ttaatattga aaatggaaaa tatggtgtgc agcacaggta ttttgcggat 68820
attttgccta attgctttag atgctagcaa gatatagtaa cttaattatt ttgatatttt 68880
atcttaagta atgttttgag ataaaaagat atcaaaatgg tttctcatgg ccattgaatc 68940
gtggctgtca caatgtttct tatggagcag aaatcattgt aagatgggtt agattttttt 69000
tttgagagag agtctcactc tgtcacccaa gctatagtgc agtggcacaa tcttggctca 69060
ctacaacctc cacctccggg gttcaagtga ttcttgtgcc tcagcctcct tagtatctgg 69120
gattacaagt gcacgcagcc atgcccagct taattttttt aaaaattatt tttagtggag 69180
acatgatttc accatgttag ccaggctgga cttgaacttc tggcctcaag tgatctgcct 69240
gcctcagcct cccaaagttc tgggattaca ggcatgagcc accgtgccca gcttcaggga 69300
tttagcccaa cctatgcatt caggaagcct gaggacggct aaatccaagt gttcttcatt 69360
cctctgccta tttttgtaac ccgcatttca cccatctcct ttggaggcca taatatagta 69420
gcagagggga aattaaggta aattctttgg actagggcat agtttcgctc ttcttctcat 69480
tacagctaga tcactgggga aaagtcttta aaatggggct ggaaggaaag ggaagtaata 69540
tttgttagac atcaattttg ctaccaaact gtgttatgta gtttcacatt ccttatctgt 69600
gtaatcacag cagtaaggcg ttgctaagaa gattatttgt tgtacagttt attagtgcct 69660
ttgtacagag aagaaaactt gagtccagag agattaaatg acttgtctga agtcacaaag 69720
agcaaaagga cagggcaaga aattagatcc aggtgttttt attcctggtc aagttctctt 69780
ctcactgaat tctgtctcta gacagcaata ccaggggctg aggcaggtgc tacagggttc 69840
acctatatga ttggcagtcc caatttctat aacattacta cattattatt gctgttacag 69900
gtcaatattt aaatagacaa attctgactt catgagcttt actcagatgc ttatgactga 69960
ctcatttcta ccttaggtga cccatcacat ctctgaaagt atgtttctct actttgcaag 70020
tgagcagaga ctaaattatt ttatgaagta tcacccatct agtagatgta attttttttt 70080
ctttagaaat aaagtgctct ttgcttttgc ccattttcct attgggttat ctatctcttc 70140
attgactttg gggatatcca aatatatata ccagttaaaa ttctttgttg atcatgctac 70200
caataacttc acccagtttg ttgctttaca tcttttgaag aacggaagtc tttaagtttc 70260
aaatagtcac attttatcca tttttttcct tcatgatttg tgttttacat ctcctactta 70320
agaatccttt cctaccttaa ggtcacagag atattttgta ctttttaaat aaagtcttag 70380
tattttgtca catttaagta tatcatctaa ttagaattga ttggggggta tggtaagatg 70440
tagggatcta atcttatctt tcacatgtgg atagctcgtc atcccatcac aatttttggg 70500
gggaaaatca gaaaaaattg tttggtttta ttattacttt aaaatttttt ttattggtac 70560
cataaattat acatatttat gaggtacact gatgttttca tgcatgcata taatgtgtaa 70620
tgattaggac aaataagaaa gaaataaata aaaattagga taattaggat atccatcacc 70680
tcaaacattt cttatttttt tgtgttggga ttattaattt tttaacagtt taaatgcttc 70740
agtgaggatc atttattatt gccacattgt gagaaaattc tgtcatttat tatgtttttc 70800
attctttcag gtatttgaca aagaagagct cttagagtgt attcaacagc ttgtgaaatt 70860
ggatcaagaa tgggtcccat attcaacatc tgctagtctg tatattcgtc ctacattcat 70920
tggaactgag gtgcaaactg actctttatt ttggggtact ttgctgggca agttattatt 70980
gtttattgtt gtttgaaact tctagcatat agtttgcagt agccccccag tagcatcatt 71040
aatgacttct tccttctgat tgtcaagatt agaggtagca aacattttct gtgaagcgcc 71100
aatcagtaaa tattttttgg ctttgtggcc atatagtttc taataagaaa ttagatccct 71160
acctcttacc ataccccaaa atcaattata attcgattat atacttaaat gtgacaaaat 71220
actaagacgt ttattaagaa atacaaaata tctctgtgac cttaggtagg aaatgatttt 71280
ttttttttga ggtctctctc tggttttttt tttttgccca cgttgtcgct taggctgggg 71340
tgcagtgatg caatcacggc tgactgcagc tttgacctcc tgggctcaag tgatcctcct 71400
gcctcagctt cccaagtagc tagtactaca ggcatgtgct accatgccta gctaattttt 71460
aaatttttttg tagagatgat gtctcactct gttgtcctgg ctggtctcaa actcctggcc 71520
tctagcaatc ctcccacctt ggcctcccaa agtcctggga ttacaggcat gagccacttc 71580
acctgaccgg agaggattct taaactctgc cattttagta ctaaagcagc catagacagc 71640
acataaatga gtaaatgcag tgctgtttgc cttgcccaat taagactagt cattattttc 71700
taagtttaca agtgcagtgc ctcccattgt ggcagtactt ctctgaggta gaaatggttt 71760
taaaatttag gggagggaga gctgctaatt ttcattttca tgaggtcttg ggattacttg 71820
gcatggagtg agaatggagg ttccccttcc cacatagaaa aatggtgaaa ataaagttca 71880
cagtgggagt taaggaagga aattgaagag ctgggatggt aggtttaaat aacatgacct 71940
tatgatttcc tggtgggtca cagtctcttg gttgggtgcc cttgtgaata aaggcatgga 72000
ttgggcatgc ctggaggggc caaggccttt tgagcggacg agtatgttta tatgaagacc 72060

-continued

```
ctgtcacctg tctctggtat ctgctaggca gctgtggctt gagagtgtga tattgaggga  72120
taattgatgg aaggagattg aatgtggctg gcaggtaaag agatagggaa catatggaga  72180
tatttagaat aagagagtgt gagatagagc gcttttgcta tagcctagcc attctgttct  72240
ctactaagtg ttgcggggtt accaggtttt ctactaggct gtatgaatgc aaaaggtaga  72300
gagatatata gggccatgga ataaataccg aagtgttttc tttggtatcc ttgatacctt  72360
tcgaaagccg tgtaaggatc tagataatga atttcgtgaa ttgcagtctc tctgacaagt  72420
tttaaagaat aggaacaatt ttaaaaagtc atctacttcc ataagttttt tgacatttta  72480
agataattga attttttttt ttcagctttt aagttccagg gtacatgtgc aggtaggtgt  72540
gttatatagg taaatgtaag ccatggtggt ttgctgtaca aatcaaccca tcacctaggt  72600
attaagccca gcatccatta gctattcttc ctgatgctct tcctcctccc gccccttccg  72660
acagacccta gtatgtgctg ctccctgcat gtgcccatgt gttctcattg ttcagctccc  72720
acttataaga gaacatgcag tgtttggttt tcttttaata ttatttttaa ctttatgata  72780
ggaaggagta ctttttaaag ttggttgaaa cattgttact gatctcaaag cactaccttc  72840
cagttattct gagatacttt ttcagtctaa gatctgatac tcctattcct ggtttgttga  72900
gagtttttgt catgaatgga tgttggattt tgtcaattgc ttttttgaa tctcttgaca  72960
tgattatgtg gttttgtact ttattacatt attaatgaat gaattatatc aatttatttt  73020
tggatgttaa atcaacctta ttttcctaag ctaaatccta cttggtcatt gtgaataatc  73080
catttttta tcttgctata ttcagtttgc taatatttta agaatttttg tttcactgtt  73140
catgaaatat attgatctag ttttcatttt tcttttcttt cttttttttt ttttttttta  73200
catctccctc ctcttcctct tgatctagtt ttctaataca gctgcactcc aacttacgat  73260
ggtcctactt aggagttttt gactgtatga tgtttgaaaa caatatgagt ttagtagaaa  73320
cttactttga gtacacatac cattctgttt ttttgctttt agtacagtat tcaataaatt  73380
atgtgagata accaatactt tattataaaa taatacactt ttagatgatt ctgccctacc  73440
ataggctaat gtaattgttc tgagcacatt taagatagga taagctaaga tacgatggat  73500
gtttggtagg ttaggtatat taaatgcatt ttcaccttaa ggatattttc aacttaggat  73560
gagtttattg agttgtaacc ccatcacaag ttgaggaaca tctatgtatc taattccatg  73620
attcagtaaa ttctttagac tgccaaaatc ctgtaatcta gagttagaca agatcttaaa  73680
tcaggttttg tggtccatct tgtagtcatg atcattctca ctattaggga attcttaact  73740
ttttgcattt gaatcaccga ggtgttattt aaaatacaca tatggaatcc aagctccaga  73800
gactctgagt agatctggtg agtgattgtg atgcctgccc acattcaaga accttagtac  73860
aaaagccctg ctgaatggtt ctctttcact atacactcta tcaacttatg tacttgatca  73920
cactttggac ctcaaaatca ataattttta aaaatctact tcctaagttg tgaggtacga  73980
attgaaggaa ataatgaata ctatttgggg agtcaacatt atttattaac gaataccatt  74040
tggggagccg acattattta tatttggttg gtatatttgt atcaactatc attttctaat  74100
taatggtata ggcagaataa accatcactt gtgattcaga aaggaacatg atacaaataa  74160
catccaataa tgtatatgga tttaaataga tctgcccccct acagatgtta cgcaattcat  74220
gttggtaatg atcattcatt aggttttcgt ggtggctaca tttgatatgt gaagtactgg  74280
ctggaagact ggtgccagta gcttcaggtt tgctgggatt ctttcatcag agatgactag  74340
ctttacttat ctttttatgt tgcatgtttc tatgatgggc ctatcctgtc attgtcttca  74400
tagtataatt gcaagctcaa ctctgtcagt tatgtgattt tttttttttt tttggtcctg  74460
```

tcttgctttt ggctgacttc tatatgtttt tatttcatgt ccttttcata gttagattaa 74520
ctgggtctta tgtccaagag atattttgat ttctttgaat gaataaatct atgttaggct 74580
actgtattag gttttataga cacctagttg atcacttgtg tccagtctct attccctggt 74640
atggtagttg ctgtgtttat agaacattga ggattctaca atggacacat tggtgttggg 74700
ccccagccca gacccaaatc gaaatttcta gagccaggat cagagactct gcattcaaca 74760
aactctccag agatttcata accactttta aaggactcac catcccaaac cttgttaagg 74820
aatgaaatat atgtctgcca gtaatttcag tgctttaagt cattgaaagc tgaactttta 74880
atggcaccaa agtggaaata tttatataat tgaaagctaa acttcatcct aatggcagtg 74940
ttgagttcac ttccataggc cctgatataa cagtctaata ttattgtttt tcacataaaa 75000
taagattcag tcactgccat ataattaggg agtggctctg ctattggatg gacttaaaat 75060
atttcattat gtttgccaag ctctgtctct ttacatgttt tataattaac tgatccttca 75120
tttttatttt gttttatttt atttttgaga tagagtctcg cttggttgcc caggctggag 75180
tgcaatggtg caatcttggc tcattgcaac ctctgcttcc caggttcaag tgattctcct 75240
gcctcagcct cctgattagc ggggactaca ggtgcgtgcc accatgccca gctaattttt 75300
gtacttttag tagagacggg gtttcaccat gttggccagg ctggtcccaa actcctgacc 75360
tcaggtgttc tgcccacctc ggcctcccaa agtgctggat tacaggcatg agccaccatg 75420
cccggcctcc ttcattttta ataatcttca tagatacata cttgttgtac taatgttttt 75480
gtgcagttcc tcatgataaa taattaaatc aattactaaa atccttatag atttatgatg 75540
ataataaatg gaagtgtgta ttattgaaac atgtttaatt aactgttcat atataaccag 75600
tgagtaggga ttggcaatta aaaataccag gctaccagtg catggaaatt tgaagaaaac 75660
aacaacctga aattcagaat actccaaaat ctgaaacttt ttgagcactg acatgactaa 75720
aaatgctcat tggagcattt cagatttcat tttttcagat tagggatgct gaattggtaa 75780
gcataatgca gattaatcca aaatctgaaa aaaatcctaa atcaaaaaca gttttggtca 75840
gaagctttgt ggataaggga tagtccaagc tttttggact gaagcttttt ggataaggta 75900
tagcctataa tacataaata cataatacag gataatcact gacctgaatg tatagcatca 75960
gtatggtaca caaatattta aatccatgta ctttgttgga tattatgtta tataaacttc 76020
ttgtaaaaag tttagagagt aaaatcattc acattaccaa aagatttctc atatttataa 76080
aaaggattat agcagcattt taatcagtat ctcctaaagt atttatttat gggttgttaa 76140
atctaaaaga gaaactacag tctggagggc tctaaactac tgctgattac atatcagttg 76200
ggaattaaga gaaaatctca gatcataata tttaaataaa aacatttaca tgaatgattt 76260 ctaagtttc actttactag acaagaaact aaaattatat gactgtcatg ttcaatattg 76320
gatacttaac aacactacat ccaaggaagc caggttttgc tgattttaac ctcgtcctgt 76380
tgagtaactc catgcaggta cagtggtaca aacacatgtg gacacacaga cccagacctt 76440
tatttcctcg gggattctgg taagtgtaga ggtgtcttga ccatagtcaa tagcagaaat 76500
atgcacaacc acaagctctg aaattccatt tgattgttgc tcttagcctt ccacttttta 76560
ggcatatgtc agtcccattt catcccaccc actctctcca tttgggaggt ggtagagtga 76620
gacaatactg aactatacca gggctgagaa taagtgtctt tgaaaagggt cgaatctgtg 76680
atgctagaga cagccctgga aactgtcagg agttagccca accaggactg tgaccagatc 76740
ccaggctgtc caccacagat ttgcaggcta cctgcagatg tgactttttc aaatgtactc 76800

```
aaagacaagc tgactttggc taatgcagaa attaattaat tcctcttttt cagtaaactt  76860
tatcctccta cacttagatt gtctgtaagt acatctctgg agttgagctc aactagaaag  76920
aagctgtctg catttagtta ataccagcat tggatgcaca caatataatt tgaataatgt  76980
agagcaacat tttaatcatc tctcataagc agtttcccca tttgcaactt cctgggaaat  77040
cttacattat gaaatgttca ttagaactcc cattttaaaa ccctgctgcc attttgtgag  77100
tgggcagaag aaaggctgga gatgagattt gtctgtctca aatgattcac tccttcattt  77160
ctggttcact ccacagggag cttaaggaca tgtgcgtttc atagacatgc ctttcttttc  77220
cttttatcac cttgttaaat cttaagattg aacatacaat tcagcctgta atcatatcaa  77280
ttcccatgaa aaatattttc cttattcact gcctctattt gtgcttatac atctgatcat  77340
ctttttcctt tactttacaa ttagtttcta tgaacagaag aatctgaaag atttaaagac  77400
tagttagcac agcagcaatt tataaatcat taatttgggt actgtctata catttaatgt  77460
gttctttttc atagtcctat gtgaaataca tatacatata tatatattcc actgtttata  77520
aacaatattc agttttattt gcataactca atatatttta tattaacagc tccgttttta  77580
gtgtcttaag acatcgagtc tgtttttaga gatacagtct atttgccttg attttagcct  77640
gttataatca gcttattatt atctggccac tcttaccagt gagtatcatc ttgaggctgt  77700
tcttgctcat ttcaacttgt cacaggggat gtttttttact ctttggagtt taggtacacc  77760
aggttattaa ttatgctcct gattcatggt acttccatca tggggcatat aaggtccctg  77820
tctttgtttt attcccttct atcttcattc accactctca tttcctctct ctccactaga  77880
aataattctc aggaatcaaa ttaatattat tctggcttat atgtgttttt aaaaatctca  77940
tcgcttttta tacatgtaat tttaatttat gtaagagact ttgtcctaca gatttcattg  78000
tgtttcttct ctttttcgcc cagcactgtg tgttccattt ctatccagtc tactatgtgt  78060
acatcaagtc catcatttct aactgttgca tagttcatga tgcgaggcat cttccacatt  78120
gtatcccaat tccctaactg gaatcccagt tccctgctac ctcacacaat gctccagtga  78180
acagctggaa aatcatacaa cccaaggaat tattgaaagt gattatatcc cagcaaaagg  78240
cccaggccca tcttacactt ccaccccaag aaggtactgc tacttttcgg gaatggcctg  78300
gtctccttgg cgaaattggc atttgatctg ttctcatcac tgtcgtctgg catcagaagt  78360
gaccccactt gtcaggcact gtactcagtg ctttccatgc actaactctg ataacaatct  78420
tttttttttc ttttttgag acagagtctt gctctgttgc ccaggctgga gtgcagttgt  78480
gtgatctcag ctcactgcaa cctccacctc ccaaattcaa gcgattctcc tgcctcagcc  78540
tccccagtag ctgggactac aggcgtgcac cactacacct ggctaatttt tgtattttta  78600
gtagagatgg ggtttcacca tgttggccag gctggtcttg aaatcctgac ctcaggtgat  78660
ccacttgacc tcccaaagtg ctggaattgc aggcaagagc cactgagctt ggcctgataa  78720
caatcttgtg agcaggtgct tatgcagtat tttagggatg tgaaagtaag gtccaaagcg  78780
gtgaaataag agcctgtatt ctcttaacct ccatcccgca acatctttta tgtgtcagtc  78840
cctgcactaa gtctagggat actgtgctga gcaaaaacta tcttcttgct ttcacagagc  78900
tcagtgtctg gcagggggtc agactttcat aatataaacc cactaaatga gtgcatattg  78960
atggcggtca ctgctgtgaa gaagtgggaa tggttagcat ggaaacatag ccccaatggg  79020
ggcgactaag ttctttccca tctcattcta ctatgtctac tttcatctct actttttttct  79080
tttctgagct atcagctttc ttgctctcaa ctatatttga tgtatttaac cagattttat  79140
atattgtatt atgtatttta taacatgtat atatatcata taacatacac atatacatac  79200
```

atacacacag ccaattaagt ctcaagttca attacaatgc ttctaagttt aggactattc 79260
attttcattt tggcagagaa attatctggt aaaaaattca agtagaacca aaggtataca 79320
atagatggga agtttccttt tcactctcac actctcattt ccatccaggg ttctacaatt 79380
catctccttc caagcaattc ctattgccag cttttcttat accctttcag aaatacacac 79440
acacacacac acacatatat acacacacac acacacaccc ttacatgtgt ttgtacatta 79500
tctctctttt tacaaaattg gcagtgattc tttgtcctgt ttctgccact actcaaaaat 79560
tttaaaacaa attacacacc tataaacata caatttaaag aaaagagtga aagtgaaaat 79620
ctaaggaccc agcacatggt taagatgaga gcatgatggg ttcaatggaa agcctttgtg 79680
tacctttctc ctttgcctcc gttccctctc caatagagtc aaccacgttg gaggttatag 79740
cacttccttc tttatgtccc cccatctccc atctggtatg gtattctctt ttactgcaga 79800
tggacatttt ggcagacata tgtagttgct tctctttggt atttacctag gagttgaagt 79860
gctgggtcac agggtgtatg tatatttcac tttagtagat actgctgttg taggactttc 79920
tccttagttt agctaaagat ggggtccttg tcccaaggcc atgaaaaatt aggctcgcag 79980
acaatttgaa aggtgagaat aatggaactt attgggaaaa aagggaaaca gggactcccc 80040
acaaagccag ggtcctgcta gcatgcttcc tgccttgcag attgaatccc aggtaccacc 80100
caggaagagg aggggccagg ctcctcccca ctgtgaatgg tgtgaccgtc tgtggctccc 80160
cagtgtgcac tcctcccagt gtgcaggccg gttggagttt ctctggggtc ttcttcccac 80220
ttggctgtct cactgccaaa ctcccaaagt gcttatacca gtttactctc ccatcagtgg 80280
tgtatgtatt tgcttcattt ctttgccaat actgatactg tcttattaac tttcctcatt 80340
ctaatgtata cagtcttgtg ttatttgtgg tttaatttcc ctgagaacca attatgttga 80400
gtaccttttc ataggtttac cagctacaga agtcctcttg tgaagtgcct ttgcaagtct 80460
tttgtctttt taatttttg catctttgta tattctaggt ataaatcctt tgatacatat 80520
atcacaaata acttcctagt ctatggcaaa tcctatgttg gataaacgta ctgcaaatag 80580
tttcccagtc tgtggctagc ttctgtgtct gtgtcttgct ttgtcacttt cttactgata 80640
tcttttgatg aacagaagta cttagtttta aagtagttaa agttttcttt atgttttata 80700
ctttttatgc attttaaaga aatttttgt tactccaagg tcatacaggt taaataaatt 80760
cttactccaa gaacattctt ttaaagtttt gctttttttc atttaaatga aatccatatg 80820
aaagtgaact ttgttatcaa gtaacatata caatttcttt tatttttctg cacggagacc 80880
aagttgtccc atcaccattt attgagtggt ctatcctttc ctcactgatt acagtgccag 80940
ttttgatatg tcatgtttcc atagatgaag aatattttgg ggctctctat ctgtaccttc 81000
ctttttaaaa aatataaata gtggtgatac tatgaacaat tttgtttgta ttattgtttt 81060
ttgcacttaa aatttgtctt ggagatcttt tcattttggc acatacggat acacccctat 81120
ttttttttcc attttcctag atgtggggta tccattggac atatgtaccg tactgaattt 81180
aatatagaat gtcataaatt acaagatgta acattatttt atacactgag atggagaatc 81240
aaactgcaac gcagtacttc cctgatcatc ctgagtgatt catgagttag ttatactagc 81300
ctcttatttc tttgaggtgt acgttttctg agggaatctg ccatttctcc tgccatgagt 81360
tgcattgctt ggctcgtgat aggcattttt atttttgcat gtaattttgt aacaaatgct 81420
aacactgctt tatcttcttt ttgtttttgt ttattgagac ggagtcttgc tctgtttccc 81480
aggctggagt gcagtggtgc aatctcggct cactgcaacc tctgtctccc aggttcaagc 81540

-continued

```
gattctcctg cctcagcctc ctgagtagct gggattacag gcatgtgcca ccatgctcgg  81600
ctactttttg tattttttgt agagatgggg tttcaccatg ttggtcaggc ttgtcttgaa  81660
ctcctgacct caggtgatct gccccactca gcctcccaaa gtgctgggat tacaggtgtg  81720
agccaccagc cagctttatc tttttaaagg tttcttccta ttgtgggttt cattagaggg  81780
cttggttgtt gctttgcaag aaaacattga cttgcttttg tttaatagtc ttataaatat  81840
ttgtttcact aacatcaaat acatgccatg ctcctgcttt tgagcttttc tgtgcagtaa  81900
cttttcttct cagtgctaaa tcataagttt ttaaagacat ttaacatggc acactcaaca  81960
tgtgtcacca atgcccatag ccactggaag tatcatcagt gtcaacagct atgacgtttg  82020
gcaatgacag ctttgccata actgctgctt agccaataac aattgtggaa tgctgagtcc  82080
agatctcaaa catgttaaag gtaaaaaaaa aaaaaaaaaa aagatatttt cgagtctgta  82140
aaacatggta gcgtatccgg aattggtggg ttcttggtct cactgacttc aagaatgaag  82200
ccatggaccc tcgcggtaag tgttacagtt cttaaaggtg tcgtgtctgg agtttgttcc  82260
ttctgatgtt cagatgtgtt cggagtttct tccttctggt aggttcgtgg tctcgttggc  82320
tcaggagtga agctgcggac ctttgcggtg agtgttgcag ctcttaaggc ggcatgtctg  82380
gagttgttcg ttccttgcgg tgggttcgtg gtctcgctgg cttcaggagt gaagctgcag  82440
accttcccag tgagtgttac agctcataaa ggcagtgtgg acccaaagag tgagcagcag  82500
caagatttac tgcaaagagc gagagaacaa agcttccaca gtatggaagg ggaccccagc  82560
aggttgccac tgctggctca ggcagcctgc ttttattctc ttatctggcc ccacccacat  82620
cctgctgatt ggtccatttt acagagagct gattggtctg ttttgtcagg gtgctgattg  82680
gtgcatttac aatccctgag ctagacacaa aagttctcca cctccccact ggattagcta  82740
gataaagagt gttgattgat gtatttacaa accctgagct agacacagag tgctgactgg  82800
tgcatttaca aaccttgagc tagatacaga gcgccgattg gtgtatttac aatctcttag  82860
ccagacgtaa agattctcca agtccccact agactcagga gcccagctgg cttcacccag  82920
tgtatcttgc accagggctg caggtggagc tgcctgccag tcccgcgccg tgcacccgca  82980
ctcctcagcc ctcgggctgt tgatgggacc aggcactgtg gagtgggggt ggcactcgtc  83040
agggagactc aggccgcaca ggatcccaca gcggtggcgg ggggcgggag gctcaggcat  83100
ggcaggctgc aggtcccgag ccctgccctg cagggaggca gctaaggcct ggcgagaaat  83160
ctggcccggc gagaaatcta gcgcggcgcc ggtgggccag cactgctggg ggacccggtg  83220
caccctccgc agctgctggc ctgggtgcta agcccctcac tgcccggggc tggcagggcc  83280
agccggtcgc tccgaatgtg gggcctgcca agcccactcc cacccggaac tccagctggc  83340
ccacaagcac catgcgcagc ccgggttccc gcccatgcct ctccctccac acctccctgc  83400
aaactgaggg agccagctcc ggccttggcc agcccagaga atggctccca cagtgcagcg  83460
gcaggctgaa gggctcctca agcgcggtca gaatgggcgc cgaggccgag gaggcaccga  83520
gagcgagtga gggctgggag ggctgccagc actgtcatct ctcagtagca taatttatat  83580
aaccagtctc ttgttgatta accattatat tattgataca acaaatataa gaactgttac  83640
tagtaaattg agtaaagcag gaaaattaaa tttggtctct tactgatcaa ccattattag  83700
attgttgata acaacggtta taatgttgat caaccgttat attgttgata caattatatt  83760
tgatgtattt aaccagattt tatatattat attctatatt ttataacatg tatatgtatc  83820
atataacata cacatataca tacacacaca cagccaatat aatttcactc tcagtttctt  83880
gttaatcaac tattatattg ttgatacaac aaatataaga actgttacta gtaaattgaa  83940
```

taaagcagga aaattacatt tgggagcctt aaagatgtag gttttcttca agaaatttat 84000
gttatagtta tatcccctgt tgcatgtgaa gacatacatt caaggatact tactgcagct 84060
cacacaattt gctgataggt tggatgtggg tgtgagagaa gagatgctgt tttccttttg 84120
ggcgatggca actggatagt aatcagttac taagatggag aagaatgaga aagaagtctt 84180
tttttgtttg tttgttggag tgatatgggt agaataaaga gttaaaacag tcatgcatgt 84240
aggtactata gatgtgaaag tctattattc aggggagagt ttggaattta agggatagat 84300
tcttgtcttt aagcataaaa atgcctttga aggtgagaaa ctagattaca tctttaaggg 84360
gagaactgta gatagagatg aaaagaaggc aaggactaac ccctggggca ggtcagcatt 84420
tagaagaaag ggagtttgta aaatgctaag ctgtctgaga agtagcagcc tgcaaggtag 84480
aaagaaaaac aagagaggtt tagtggactg gaaaccaagt gaacctggaa accacaagca 84540
gctgtggcaa atcctgccac agtgagatga ggcctgagaa ctgagtattg gatttgtcaa 84600
tgtggaaggc cttggtgatc ttgataagca tgtgttagta gggtggtggg gttgcagtgt 84660
ttgggatttg agagagaatg agagaatggg tagctgtgat gctgaatatg tataaatgtc 84720
aggaggaatt ctgctgcaca gtgggacaga gaatggacgc ctccctggaa tgggatagat 84780
gctaaaggga gtgtgtgtct tagttgggag atattatggc atatctctaa gctaatagta 84840
attagccaga aggaagggaa aactgatagt taaaatgttc aaaagatttc tcacattcct 84900
atcatagttc tccttctaag ggtgaccacg taagcaggca gggacatgtg actaagtaga 84960
gcagcatcca accccccacct tgcacggtca cacacatact gctccattga caccatagtg 85020
tcttggtgtg agctcttcat tacttgactc aatatcttct tcctcatctt ctcagctggg 85080
gttgttgggt atatcttcat tgcagatatt agcatccttt gtggtcttct ttgtctttct 85140
attctagggc cagcacagtg ggaggcctag tcaactgagc caaactggat ataaccacaa 85200
ggtcaaaggc aggagccagt gaggagatct tggttttgag gtcattcctg gtgcgataat 85260
aaccatcctg tagcattttc ttgtcactta gagaaggcat tagcaaactt tttttgtaat 85320
ggtcttaata gtaaatattt ttgactttgt aggctatata gctactcacc tctgctttta 85380
tagtacaaaa gcagccatag acaattcata aataaatgaa catgttccaa taaaagcaat 85440
aaaaacaggc agcagtctga agtttgtcga ctcctgattt ggaatcattc cagaaagtga 85500
aataaaagca tggcttcttt tttttttttg agacaaggtc ctgctctgtc acccaggctg 85560
gagtacagtg gtgtcatcat agctcactac agctttgacc tgctgggctc aagtaatcct 85620
cccacctcag cctcctgagt gtctaggatt acaggcatgt gacatcacac ctggctgatt 85680
tttaaatttt ttgtattgat ggggtcttgc tatgttgcca aggctcacct caaactcctg 85740
gtctcaagtg attctcctgc cccaggattc ccaaagtgct ggaattaaag gtgggggcca 85800
ctgtgcccag ccaaagcatg gcctttctaa gggtgactca ctgtagcacc tcctgagtac 85860
tttcctatca agtatcctgg accacttttt aaataattca ttctaaaatc catatttagg 85920
attgattcca aatttgccaa cctgtatttc ccaaataact ggcatgataa ttcttgtctt 85980
tttcccaaat gctcattttc cactcttcaa acgttgagtg ttgactgaag ttctgtggtc 86040
atgtttacag tcatttttat gctctttgta ttgtacatat ggaatgtatt taccatttct 86100
gttagcaatg atttcttgca aaaacaataa cacttgctag ttttgcgtgc ttaaaaaatat 86160
cgagccctgg cgctctctac atattatcta atgtaatcct tatattaacc ctgtgagtag 86220
tcattatcac ttcttttaca caggaggaag ttagagaaga gtgttaagtg ttcttttagt 86280
cttttccact ttgtctttag ttttctctta gctgttcttt taaattctaa ggtcattctt 86340
atctaaaaac ttaaaagagt tgatcagcct ttttatcaag tgttaaattt ataccatctt 86400
ttttctttga acagggctgg caaataaacc tggatttatc ccttagccct gttacagcaa 86460
gtctcagaaa atttggactt cagcttcccc agtgatacat tttcaaatgc ctatgtatgg 86520
attgcccatt agtttattgg ctagaactaa aggaaatcag gcaagagaca aaggacattt 86580
tctctagggt gtcagtcaat gcaaaatgtt aggactagca tcagattttt ttttttttac 86640
aaatgaaaat aattgaagtg tggtagaagt tcctctagtt ctggcagtcc taaatattgt 86700
taactgaaga atgatggggc tcataaattt ggaaaggaga gagaggggaa aagagaacgg 86760
gaatttatgc tgagcagggt ggctaagtat atatattcaa caggctatag gaggagctat 86820
tagtattcac gaaggggtgg cacacacata catagtaggc taacgtgtat gcagcatgca 86880
tcacaagtca ctttggggtg gagccttaac atttaatgta ttacagttag ggcctataca 86940
tcaaaaggtg aagcagagga cacgaaagcc ctctgtgttc agcctctgta gactggccag 87000
aaccactctg tggtcagagg tctcttatca ggaaagaatt cttgttgttg tgttgaaact 87060
gcaaaaggga ggggcagtgt caggcaggtg gttgatacca gtctttcaga agcactggtt 87120
tctgtttaac ttttagagaa gaaagcttaa ttggagtgtt actggaaagg gataccagtc 87180
tagaccacaa gagaggattc ttggatctca cacaagaaag aattcagggt gagtccacag 87240
agtaagatca aatcaagttt attagagaag tagagaaaga aaagaatggc tgctccataa 87300
gcagagcagc actgaaggct tctggttggc tatttttatg gttatttctt gattatatgc 87360
taagcaaggg gtggattatt catgaatttt cctggaaagg ggtggggaat tcccagaact 87420
gagggtttct ctttctttta gaccatatag ggtaagttct ggatgttgcc atggcatttg 87480
taaactgcca tggcactggt gggaatgtct tttagcatgc taatgcatta taaatagcct 87540
aagataagct gtgaggatga ccagaggtca atttcctcac catcttagtt ttggctggct 87600
tctttactgc ttcctgtttt ttcagtgggt tctttgtgac ctgtatctgt cttgtaatgt 87660
cctatctcat cctgtaacta agaatgcctg acctcttagg aatggagcac aggtggtctc 87720
agctcatttt atctatcccc tattcaagat ggagttgctc tggtttaaat agttctgaca 87780
tattttcccc aataccccca aagggaccct taatcccaaa atttgcagac agatgaagat 87840
ccatcttctg tagcttcttc tggctgaata caggtgatga tatttttgcg taactattca 87900
gggtagagag gagctcagtg agaaagcatc agtatggtga aggccattcc taactcccga 87960
gttctcacaa aaggtgatat ctggaagatt aataagtgtt caatttaaga aaacgttgag 88020
tagtcttatc ctgcattgct acacaaagag taccacagca atatattcta caacagtaaa 88080
gcaaaataag tataattatc ccaactaaac taaataacaa gcctttccat gaactaggca 88140
gttgttggaa ccaagcttat atggggttgc tagccaattc caacacatgt tcagaattaa 88200
aatactgatc cagatattta tgttaccctt ctgtttcttc tgagcagcag ctagagatca 88260
ctggttggtt catagggaaca aacagggtca atctaaatgg cagaaaaaac tcgaaacaat 88320
gaatgggact agagttgaat aacaagtata ccatagtttc tgaaacataa tttttctctc 88380
tccagtctcc catttctatt gaaaacaaat catggtagga ctgatttgtt tgcacagtaa 88440
gctttagtct tattatgctt ggcctggtta tttgtataaa gcatagcaat aataattatt 88500
tgccacgtag gctttttaaa aattgacttt gatgtaactt tgttccataa gaaatctcag 88560
attagacttt ctaaagcctt gagctgagac acagatttat ctgtgcctgc aaatacttgt 88620
atgagttgtg tgaattctcc ttttgagatc ccaagataac tggagctcct aggcctgtca 88680
gaaagtgaca ttctttactt accacaggtc aggaaccctg taaaggaatt gaatagacaa 88740
ggtatgaggc cagcttttcc cagaggcttt catcagttct gtaagtcaac tttgattcct 88800
taaagcaatc tgtttatatt tgaaagaatg ccattccagt caaagccctg gtaaaacagg 88860
cagtgtctct aattgtgtcc tgttacaaag gaaaacagat ttttattgca catatgcaaa 88920
ttactatgct gccataagtt aagaatactc acaaatagtt ttcaaattct tgagaaatca 88980
ggtagaaaga aatatgctcc aaagttttct cataggagta taatttactc aatttttaac 89040
aactgtaaat agctcaaaaa aaaaggtttc ttgactctga aaaatgaaac aaaggatcag 89100
caacatttta agcaaaaagt cactagaagg ttattttgtt cttttattag tttagtccat 89160
gctgttaatt cctgtttgct caatatttat gaacatattg gtttcccaag ggagactctt 89220
gaaagttttt ttcctctcta tcttaatggc acactttaca aaatttttca gaaacctgca 89280
tttaagagcc ctctatctga ttataaacca tcttttaaag aggatcaaaa caagacaaca 89340
attttctgtg gataacataa agtcttagga aagccgtggt taaagacaca attgactaga 89400
aattttggtt acttctgtgg catacaacaa ttttacataa cagttataat tattactgat 89460
aacataaact aagtcatatc agaatttagg agtttcccat aattttggag cacataccaa 89520
taacatattt atacaaatac aactcaaaga aagctaaaca ccatttcata tttgacagtg 89580
cttcctgtat gattttaata taccaagtaa gccaaatatg tcatttttgg acttaagggg 89640
acctcatatc taaagtattg accagatcag gaaaaggcat aatatagaat ttgattttgg 89700
aaagtttgtc aaatatcaaa gatttaaaac acttgatatt ataaaatcga atcccaggtc 89760
actgtaaagt catttattta gccaaaatga taatacaaag attttccaaa agcaaaatcc 89820
ttttttttt ttttttttt tgagacgagt ctggctctgt cgcccagctg gagttcagtg 89880
gcgccatctc ggctcactgc aagctccgtc tcccgggttc acaccattct cctgcctcag 89940
cctccggggt agctgggact acaggcaccc gccactacgc ttggctaatt tttttgtgtt 90000
tttagtagag acggggtttc accatgttag ccaggatggt ctccatcttc tgacctcgtg 90060
atccacccgc ctcagcctcc caaagtgctg gtattacagg cgtgagccac tgcgcccagc 90120
aagcaaaatc ctttactcat tgatagaggg aagacagctt tccaaacaat gtctcacttt 90180
ttcttcttta ttttgttgtt tattcaaaag gcaaacaaaa atcttccatg atcttttaat 90240
attacatgaa aattttgttc aagagagaaa gccaaatttc atctttgcat taatgaatgt 90300
caaatccaat tcttaagaaa accttgtaga caaattattc aatcttaatc aattttacca 90360
tgagataaga ttctcataaa ccttttgtag tcctttacaa ttttttttg ttgttgttaa 90420
agagcagatt aatgctctaa gaaaaccctg ttgtgctttt attccaatgt tctatttatg 90480
gaaaaactga ataataccct ttaactttag ctaatatttt aacacacaga atttctttta 90540
caagattaat tttcactgac ctcccacaac ttactcaaac ctttagcttt atcctatgta 90600
acttaaaaca gtcttttaac tctgtaaact aggcaataag accacattcc catgccttct 90660
tataatcttt taccaaaaac acattctatt ttccttacac gccttgcagg taacactgtt 90720
tctctggtag cctcaattac atgtgctaca atgttaactc ttagcaactt ttatatttgg 90780
tgaaaagtct gataaataag tggttttaat tatgtaccag gtgtggagcc taggacgcca 90840
gacagaagtg cagataaggt ctgagtcttt ccagcatagc tagggggcat ggccaactcc 90900
acatgtcccc aggccctacc tagaatctaa tggctccaaa gcaggtgagt tgaacaatta 90960
tcaagttaaa gaagcagttt atggcattga agcattcagc aaatctaatt taatctgacc 91020

-continued

```
taatttagac cagatgtcta aattttgaag acatttttat tttaccaata tatttgattc  91080
tctttatttc ccaaagatta ttaaagtccc atgaattaaa aggtgttaaa gtttttattt  91140
ttctgacaaa atattcaatt taagtgctta tttttcaagc caattaatta gagctctttt  91200
ctatgcatat cacacataca acacacaaaa atacacagac agaagaccca gtagctgtta  91260
attttttcat ttgccagctt ttaagaatct taattggatt actggcttca gggtggagca  91320
acgtgtgggg acagagccgg gaaaacatgc agtttctggg gcctaataaa caggtgcagt  91380
tagaaggcaa aacagattcc ccaaaattac agatctcatt tttatattgg attctggatc  91440
ccaaaaagag ggaatcagcc catcccctct gggagttttg gaaggtgtag aagaatgttt  91500
ccataccttc taggtggcca agagcatgct tctctgatcc aaacgtgcac agagtggggt  91560
attcccctat aactgctatt agccttccct taaagcatat ttcctgccta gttattacac  91620
accaaggtta aaagctctcc cataatgcaa agtaatttct gataccccta caagtaaaaa  91680
acattaggta acacaatgca aatcagagca atgccttgga ttttgagagg gatttgcttg  91740
ccttcaattc ctggggttcc atgaggaaaa cagatttttc ccaaaatgga gcctgtggtg  91800
ctccctcagt tttttctaag gaagcccagg ctgttagaaa tgatcttagg tcctctcaat  91860
gtgggcatca agagtggcaa gaaaacaaaa tgagaaaaac aattcagttg actgagaaga  91920
aaaaactttt atctagaaaa aaatcaatat aaaacctgcc agatagatag atagatagat  91980
aatcttggac atcactttta attaagctga cttttaacca aatctcttat tatcagactc  92040
tagccaggac aaacagctaa tatttctggc ttttgaactt taccaaaagt aacctcccag  92100
gtgaaaccaa taagccttaa ctaaggttat gatttaacca caggtgtggg aggtattttc  92160
aaagaggtgg taagcagttt ttacaagatc tggaacctcc aaacatagct cagagaaagg  92220
aagattcaag acagggagtc agaagttgtt catgagggga agataattaa taaatggcaa  92280
aggtcacata gatatcaaac cagaaaggac tcattcccga agctaggaat tgaatccagg  92340
ccaccactgt gaaatagcaa agccttagtt actgagctgc agtactgcac agtctccatt  92400
gctcctccga gaaggagcct agagcagcca attttgagct tgcaaaggct tttaactgct  92460
caagataatt tttaggacta attgacagga accccaaaat tcacaccctc tggatggcag  92520
agatcaggag aaagtacccc cacgtggtta caaggtcaag ctttcaagga cataaaacaa  92580
gacgagaggg aaacttcatc cagtttttgt ttcagggacc tgcagaaaag tttgtaactg  92640
accagtttgc gggccagctt gaagaccaga tttgtaggat tcctaggcct gcattctatc  92700
ctgtggctag ctagggctgc cataatagaa tattacagac taggcagctt caaccacagg  92760
tgtttatttt ctcactgctc caaagtctag aagtccaaga tgagggtgcc tgtaaagctg  92820
atttctggta agagctctcc tggcttgtag atggccacct tctccctatg tcctctctgg  92880
gcctttcctc tatctggcca agggagctat ctctggtgtc ttttcctctt cttataagga  92940
cagcaggcct atggattaag gcctcacttt catgtcttca tttaagttta attacctctt  93000
taaaggcccg atgtccaaat acagtcacac cgtgggttag gatttcaaca taggaatttt  93060
agggacacaa ttcaacccat aataggaggg cattggaagg agagtgttcc aggcagagga  93120
agtagtgcag tagagcatat ggaagtagga aagtgaggag caatggaagg ggttcagtat  93180
ggtttgagcg tggggtgtgt agagggtgaa ggctatttca cccagtgcag taagctctat  93240
catccacacc ggggttttac agtgggagaa aggagggtgt ttatttgcag gtcaagaagc  93300
aaacagaatc agggagctca tgcttaagac ctgaactcca cagtggctta catgtaaggt  93360
gcagaggtta caggcaaagg catcaatcaa cacatggaag ccatatattg gtttggccta  93420
```

aaaaggtggg atatcctgaa gtaggggctt acaggttaca ggtaaatcca aatattttct 93480
gatttgcaca ttgtttaagg aaggggatat ttgtctaaag atgggatcag caggccaggt 93540
gtggtggctc atgcttgtaa cctcagcact ttgaaaggct gaagaaggag ggtaacttga 93600
ggccaggatt tcaagaccag cctagtcaac atggcaagac tctgtctcta aaaaaaataa 93660
aaaagaaaaa aagaaaaaga aaaaaaataa agatggaatc agcagaaagg aatgttaggt 93720
ctggcccatg ggcggacttc ctccagactt ctcagaaaga aatttaagac aaagaatggt 93780
gccaggcgtg gtagttcacg cctgtaatcc cagcactttg ggaggctgag gagggtggat 93840
cacttgaggt cagggatttg agaccagcct ggccaacatg gtgaaacccc atctctacta 93900
aaaatacaaa aactagccgg gtgtggtggt gcacgcctgt aatcccagct cctcaggagg 93960
ctgaggcagg agaatcgctt gaacctggga ggtggaggtt gcagtgagcc aagattgcgc 94020
cactgcactc caccctgggc aagagagcga gacttgagac tccatctaaa aaaacaaaat 94080
ggaaaacaaa gaatggtgat aattcagtcc tcaattcctt ttcttttttt tttctttctt 94140
tttttttttt tttaactgct cctgcggagc agggctacct catagccagt atgtccagag 94200
ttgtctcagt tccctcgtta tctgtggtct ggaggatcca tatgatggtg atccaggttc 94260
tgaaaaacaa ctctggaaca tctgttaaga tgttatcttt agtttctata ggaaaccaaa 94320
catcttctga ctctgacctc cttggtgatt attttaagct actgtttccc tttttgctta 94380
tcgagttgct catttacttc tcaaggctag caggatgact ggactttctc ttgaaggaac 94440
tcaagctgtt cctttatttt tatgctcagg ggcgggggc actcagcagg tccctaagag 94500
gtatccccgc tgtgtctcac tatgggtgaa ggctcagcgg gaagaaagct agataccagt 94560
tggaactctc ttaaagtaag gagatcttgg gtactttatt aatatttttt tcaagctttg 94620
gtaaagtatg aaataactct ggattaagag gagaagaact agaacttaat aaccatgaca 94680
tttgggcaaa ttgtttgaag cctcagtttc ctcaacctaa aaataggaat tataactttt 94740
tgaattgttc tgttgtatga gataatgaca gtgaaatatt ttggagccaa aaagcaatgc 94800
atactattgg gggttattat tattttttga tctttcagca agccagctat agtagctttt 94860
cctatataaa cacagtatga attcagtgcc ctcgctttcc tgaccctcac agcattcaag 94920
ccctgtatgg accgctgagc tctcccttga agcacccctt agtccagtat tctttactat 94980
tttccccttt aacaatttaa acttctttca aaacaactgg cagtagtttt ttaaaaaaga 95040
aaacaggcta ctcttcaaat taaaaaaaaa attgtcttgc tttaggaaaa atgttcttct 95100
gtcttttcca attatcttat ttcttctgcc tctcatctgc cttgcctagg cagaattatt 95160
ctcaagcctg cacatgctgc tgtgcctctc tggcttctag gccaaaacat aggctaatag 95220
tactcttctc agctcactga gctctttcct gccgtcattc aaatcacctc tgaaatcctg 95280
ccttttgata aagtaatttc tgactgatca gaggaaagtg atgattttct ctgtgacatg 95340
tctttttatt ttccatcaca ctcagtgtct tgtccttcta tgcaacatat ccatgtattt 95400
aaaaaccctt gtatatgtat ttgccatgta tttgtgaggt atagctcgtg aagtaaaaaa 95460
agtctttatt tttttaaaca catcatcatt tcagcttcaa agtcaatgtg gtctcttgag 95520
aagttaaata tgctgcattt gaaattttat gtttctcatt tttcatgttt ttttttaaag 95580
ccccttttaa ttcctcatgt atttgaatat tccaggaagc tagtagagta aaaagccaaa 95640
gtgttaaagt gtttataagg aatgtgactc atcgaaattg actcacacaa ttcatcagct 95700
attgtcatcc atatgttctc attatttatg tggcttttgc tttatttaat cagatgactg 95760
aacttatcat cgtgggattt tgcttgtagt tgtttaatat tatataataa aatactcttg 95820
tgtgaaacaa gttaattgac ttttttttaat taaaaaaaat ttatgtgaga gtcaggagtt 95880
acatgtgcaa gtttgttaca tgggtatatg ttgtgataca aagattttag cttctaagga 95940
tctcattgcc caagtagtga acgtagtaca ctataggtag tatttctaaa cacttttccc 96000
ctccccctct tttggaatcc ctagtgttta ttgttcccat ctttgtgtct atatgtacct 96060
aatgcttagc tctcacttat aagtgcggac gtgtgatatt ttggttttct gtttctgtgt 96120
taattcattt aggatagaga gactccagct gcagctgtgt tgctacaaat gacatgagtt 96180
cattcttttt tatggctgca tagtattcca tggtttatat gtatcacatt ttctttattc 96240
agtccaccat tgatggtcac ctgggttgat tccatgtctt tgttgttgtg gacagggctg 96300
tgataaacat atgagtgcag ttaccttttt ttgtataaca gttcataata aaatactctt 96360
aacagtagca cagaatttag attgcttttc aggctagaag ggataattga aacatagaaa 96420
aaaataatga ctcctaagca tagaaacaga cccaatcata aagctctctt cctctctttc 96480
tgcctagtgt tagatcttat tcattgtctt aaagcactgt gaccattttc agtgaaatca 96540
cagttttatt catgaaaaga caatgaattg gtgtaagtaa tcatttgagg atgaaggtga 96600
ctagtctgtg atcaacacca gtacttgaag tacttgtaaa acatgaattg accttggtta 96660
aattgcagaa aataaagtat tagtatacat aaacacattt tctctcagca ttgaaaagtt 96720
atagtctata atttacctgc ttgctaagaa taaaaatatt acttagaggt ttatcaagac 96780
ctttttttcta caaatggatt taatgtacag aattattcca ttttctatct gtgctctgta 96840
tactaccacc tagtggaata aaatgcaaat ttacctgtca aaatcaggag aagaaaatga 96900
accaggggaa atttatttca ggaaaaaatt ttcataacac gttattgtta cttcttttag 96960
tataatgtag tttgcataaa atacattagt ttggagtgaa aaaagtccca gccatttttg 97020
tgatagctat taaaatgcta ttagtttgtc cacaaataag ctattctatt cagaaactta 97080
gaagctaggt aaattattga gatgatgcca gcatattata tctctaaatt atgttaagaa 97140
gcttctctaa attcctcatc actagggtgt attagtccat tttcacactg ctataaagaa 97200
ctacctgaga ctgggtaatt tatgaagaaa agaggtttaa ttgactcaca gttctgcagg 97260
cttaacagga agcatgactg ggagacctca ggaaacatac agtggaagaa ggtgaaaggg 97320
aagcaaggac cttctcatgg cagcaggaga gggagagcac aggggaagtg ccacacactt 97380
ttaaaccatc agatctcagg agaactcact cactctcaca agcacagcag ggaggaaatt 97440
cacccccacg atcctatcat ctcacactgg gcccctcctc caatttgaca tgagatatgg 97500
gcagggacac aaatccaaac cgtatcatag gatttgttaa aaaaatctaa catgttctgc 97560
ttcaaggcac ccatgaaatg aaggtgtcat ttcttaactg agaggttaaa taaaagtgca 97620
gagataagat ggttaagttt tatcgtagct gggaagaaaa gcgggtgtgt gtattatgct 97680
taggtttttc ctcccaaaca atgaaaccca aaaaggcaaa tgaagcttta aggcgcttta 97740
tcctttactg gtaggatggt cctcctttaa tcttcagtct ctgttaaaga acaaacacaa 97800
gctaacaatc aaaacctgtt gttgcttgct gacggatttc tctaacatag tcttccatca 97860
accatcatag gtttgttgtg gccacccagg ccctttggtc gtcatgttcc catggaatgc 97920
taatgaaatt accttcccat ttcctaaggt gacatgcctt tcagatggca ttggtgtgtg 97980
cttgtgtaaa cacatttttt tgtgctcatg aatattttac ctgcctgatt ttggtgatct 98040
gagtgttgag cagtgggtga gggatggtgg ggcaatgggt agtaagggga agtttaattg 98100
aagttcagat aaaaatatcc ctccagaaac attacaaagc cacaaaatca gctgaagttg 98160
agtcttctat tgtaaagatt ctctttcttc tcctgacaga tccccattcc tatccaggta 98220
gaccaggctc tagtgaagat tggacacaag tggtttatat cccgaagctc ttaacctaag 98280
agtcctgcct tgttttttta cttcatgtgg tcttatattg ctgaggatag cccagtgatc 98340
atttctacct taatatgtag ccttcaaaac gttgggtctc tcagttttct tccttaataa 98400
acaatgaacc ctaattattt ataactgctc ttgtgatgga ggaattggca tgattttgca 98460
ttgtgggctt ctggctttac agtgtttgtg ggaaagatgg tcttctatct ttgttattta 98520
taagtcattc attccctgtt tttttgaaga tattgttaaa taaaaaaact tcagctgaat 98580
taaatttaaa agtttttaat tgagcaaaga accattctca attcgggcag ccttcccatc 98640
cagagtagtc cctgtgactt cagtgcagcc acatggtgga agaggattta tggacagagg 98700
aaggaaagtg acatacagga aacagaaaag agattcagaa acagctgaat tggttataac 98760
tcagcgtttg ccttatttga acatggtttg aacagttggc cacgtttgat tggccaaaac 98820
tcagtaattg gcacaagagt aggctaccat ctgtttataa tgtccactta ggttatagtt 98880
catgatgtgc aaagaaacct ttaagctgag cttaaaatgt aatgaggcag ctgtaggcta 98940
aacttgattt aacagtactt atccctctgt tgaaattgca ctcttgctac ctgctagttg 99000
atgtgggcag gtgtgctaat gacacattcg cctgcaccta ccacctgctg aagaccctgc 99060
catgtcctga agcagtcact taggctatga aacagaagga tgagttagag aagtaaatat 99120
tatattttac cccccaaagc ctaaaaccat gtctaggttc tccccttttct caattcccaa 99180 tcatgcaacc ttgaaaggtg ttatatagat agttgttaga aatatgtctg tcctccaaaa 99240
ccctactaac acgcaaaaat ggacaaatct agctttttttg ctaaaatcct aacaactcag 99300
aaagcaaagc aaaatgaaat gtatgtactc cattctcagg atttccttct taaaaaccac 99360
taggctttgt gtaactcaat tttaaaagta tggtaatagc tcctgtaatt cgatggcttc 99420
ttctgggaga cagatataaa tctattctag actttaagac tggtgtccac attttaagtt 99480
acagttgtat gtacttctac tttgttgcag ccttctcttg gagtcaagaa gcctaccaaa 99540
gccctgctct ttgtactctt gagcccagtg ggaccttatt tttcaagtgg aacctttaat 99600
ccagtgtccc tgtgggccaa tcccaagtat gtaagagcct ggaaaggtgg aactggggac 99660
tgcaagatgg gagggtaagt aaatctgtgt ctctgtctaa aggaaagaca ccttcatgac 99720
catttagtta gtgccatttc acttcagtat gaacacatat aatacttttc aaactttaat 99780
gctcattgtg tttcatggtt aattttcagt ttaatctttc agcaagccag ctgtagtagc 99840
ttttcctata taaacgcagt atgaattcag tgccctcgct tttagatgtg ctagtttaaa 99900
ggatagccca tggccctttg taagggagaa acactggata tgatatctag ggaagaactg 99960
aagtaagaaa ctacaacaag catcacatcg gtgctttgga taaacttccc ctgggcgctg 100020
gtctctggct gcaggctgac ggctggcatt aaaaagcatc tggtcctggg acccaggctc 100080
tcagttggct ccagggagtc atgtctgggg aaggtgcccg cttcactgaa gtgctgtctt 100140
cattgccaca gattgtggcc acacctgctg ccaactggct gcgggacagc cctgctttgg 100200
ctctgtcagg ccagtctcat aggccatatg tagctggcag gaaataaaag agcatttgaa 100260
aagtgttgga cgatttcagg ggtggacttg gccatgagtt gggaatgccc ctatgggtga 100320
acgagaataa ctggtttaag cagcatgggt tcttgctttg catgtatcaa atggtgctgt 100380
ttgcatactc agggcagcag ctgtcctaga aggtgactcc atggcagtct tgtgggccct 100440
ggtaggacat ttaggtccag gaggcagggg agagtcacat gacgtgctgc tggggtatta 100500

-continued gaggcaatga ccactggctt tgacccctct gtagtcttgc tgtatttcct ttttcttttc 100560
tctcctcacc tacccaaatt aaaaaagaac ggttataaaa gtcatcccca ctggcaactt 100620
tagcaactgc attccctcaa tgggtagaga aatccaaatg gagtgcatta aaactaggaa 100680
gtctattctc cttctggctt agagcacacc ttcctgtgtc ctaggctagc caggttgaaa 100740
actccttttt ttgactcttg atttcttttt ttactggttc aaacttcttc gcagagcatg 100800
tgcctatgta ccactgcata ccatatatat accatatata gagagtaaat aaacagtctt 100860
gatgaaaagt aataaggaaa aagtttccct gtttaaaata ttgctttcta gctccccgac 100920
ctgtttagga aaaagataac ctggggacac agaaattgca gggcaatctt tattaaccgg 100980
tatttgggca ggttgtaatt tattttgtaa acaatgattt aatgcactat tgcagaatac 101040
atgatcactg taggccagtt aaaaattaat gttttcagta ccacacagag tgaaccctaa 101100
tgtaaactgt ggacttgtgg accacactaa tgcaagatga taataagaag aaaaactgag 101160
agggtgttcg ggaaggggta taataggga attctgttac cttttgctca atttctctgt 101220
gaatctaaaa gtactctaaa ataataaaat ctattataaa aatatttgat tcattaggct 101280
caggtggact atgatccatg gaaattgact tgaaatctct taggaaagga agagaccgga 101340
gaagaaagta ttgaactcat aaattaaaaa tggcaagagg gaaggtggta accaaaagga 101400
tgggcattta acctatatgc ctatcacttc caaaaagttc tagggccgtc tcctcctatg 101460
cttctgacct ggagaggtac aaggggaaca aaatattccg catttaatat tatcctgttg 101520
agttggcaaa gacatttgga gtcaacttta gttttgtgta ttattacatc tgtaaaccta 101580
attaagtcaa cagttaccct tgacacctgt agtcaactgg tattattaaa taactattga 101640
gtctcataaa gtcaagaact ttctgctttc tatctaagtg aatctagggc agagactgag 101700
catcaggatt ctttagcatg cagccaagct tgagaagcac tgagctagag aaaggtcttg 101760
cactgtagaa acagctttag ttccaggtga ttccttggtt aatttgggag gaataaggct 101820
ttctgtcact ctctctctct ttctctcttt ttctctctct cttgcacatg cacacgtgca 101880
cacacacaca caaattatct ctcttagttt tttcttttt ccttgcattc tgattctgca 101940
tttaagagta caagctttga agtcagaaag acctggctta aaaacctaac tgtcataatg 102000
gtgcgtaaat gtcgttatag atttgtccaa acccatagaa tgtacaccag gaatgaacac 102060
taatgaaaac tctagacttc aggtgataat ggtatgtcaa tgtggttcat taatttcagc 102120
aaatgtacca ctctggtgtg aggcattggt aatggtagaa actattcatt tggatgggga 102180
gaaagggata tgggaaatct ttgtacttgc ctttcagttt tggtgggaac ctaaaactgc 102240
tctgaaaaaa acctgaagtc tttaaaaaca aaccaaccta attgccttgg gcatgttact 102300
taactgctct atgtatcagt ttcctcattt ttaaagttga ggcaataata ccttgcacag 102360
attaagtgag ataatagaaa gtgcctagga tagtacttgg catatagaaa gctctcagca 102420
aatgcagtat gataacctaa tggttaaaag cttgggttta ggagtcaaat gtctgggagt 102480
tacacactta actatctgtg agatcttcta caactgaatc ctctctccaa gtcttccaat 102540
gaacaataaa gtctagggtt gtttttagat gactcaatga aataatgtag ttaagtactt 102600
agcacccagt ctggcaggta tgggttgcat atctcttatc tgaaatgctt gggaccagat 102660
gtgttttgga tttcaaattt tggagtattt ctctttgggc atccctaatc caaaaaattc 102720
gaaatccaaa ttgagcatca tgttggcacc gaaaaagttt tagattttag agcatttcaa 102780
agttttaaat tagggatcct caacctgtag taaactctca cagtcactga tgttgtgagg 102840
ttttctcact ttctcatttc atttcctgga ctctctttat cttagaagaa atcagttaaa 102900
ttttacataa tagaatttat tcttttggag ggatgtattt aatatgtcta ttctcccaga 102960
taacctattt aaaaccatat tgaaatgttt ctatgtcaac agctttctta ctttttcatt 103020
tttctgtttc ctccaagaac atgtttctct tatgaatatt ggcagcacat gggcgggaac 103080
ccaactatat taccatggta tcagttatcc tgtggacatt aataatacag cttacacctg 103140
tgagagaact ctgggaaaat taaaacttgt ttgggggaat aaagaccatc tacagaatat 103200
aataatacat caatcaatca attaaaactt aaacataaaa aaccctttc ttttcagtgc 103260
attgaaatag tcactgtctt taatcctctt tccttgctca gtgcttcatg aagctgagga 103320
gccatggttt taattcagct acactttcag aaatgtgtat gcatttgtat ttagaagctt 103380
ctttgaaagg ctaaatattc atcctgtaag aattctctat gtgtttttta atacagtcta 103440
aagggcattt tgtatatgaa aaaataattt attttcaggt agggtaaaac ttcactgctt 103500
cactacttcg tagttgtgtc tacgaatgag aaaaaattca aataaaatag ttattattat 103560
tagtttttag agatgcagtc ttgctgtgtt gcccaggctg gtctgggact tctggcctca 103620
agccatcctc ctgcctcggt gtcctgagtc actgggatta caggcatgag ccaccacacc 103680
ccactgaaat agttattttt taaaaaactt aatttcatta ggatgtaaca gtctcatgta 103740
actcatcctt tggcttttat tgttattatt tattttttcc aagcaaccca atgagatata 103800
taaagcagat atttttatct gccagataat taaatgaggg aaaaataagg actaacttgc 103860
ttaagttcac atataccaaa tagtggaaat gcaagagctg tcctcaggtc tgttaacaac 103920
aaacctgtgg tctttctacc agacgtcccc tgcaatctgg tttatactca ttattaaaaa 103980
gcatttgtaa tttaactcag ttatctattt actatcagtt atgaataagg attatttgac 104040
tttttatggt cattaaacaa tagcttccta tctgttgtct ttgtcttttt aatttttatt 104100
tattttattg tttttttaat agcttcctat ctgtatacca gacttgcttc atctccacat 104160
tgaccaagaa tttatatttt gtcatctgta tttagaagca tatgttttaa gcgtctttta 104220
atggctcttt tttttttttt gctgggaggg gacagtctcg ctctgtctcc taggctggag 104280
tgcagtggca ccatctcagc tcactgcaac ctccgcctcc ctggtgtgag tggtgctcct 104340
gcctcagcct cccgagtagg tgggattaca ggcgtggtcc accaaaccca gctagttttt 104400
tatatttttg gtagagacag ggtttcacca tgttagccag gctggtctgg aactcctgac 104460
ctcaagtaac ttgcccacct cagcctccca aagtgctgag attacaggta tgagccactg 104520
tgcctggccc ttttaaggac tctttttttt tttttttttt tttttgagac agtctcactc 104580
tgtcgctcag actggagtgc agtggcgcga tctcggctca ctgcaagctc cacctcccgg 104640
gttcacgcca ttctcctgcc tcagcctccc gagtagctgg gactacaggc gccagccacc 104700
acgcccggat aatttttagt atttttagta gagacgaggt ttcaccgtgt tagccaggat 104760
ggtctcaatc tcctgacctc atgatccggc cgtctcgcct cccaaagtgc tgggattaca 104820
ggcgtgagcc accgcgcctg gccctttttaa ggactcttaa cattaccttg gtgtgagtca 104880
acctcatcgt gctccaatgg caatcaccat agtatgatgt ctattttcca cagcttactg 104940
gaatatttca gctattagtc aatattcttt cagttgcaag tcagaaaacc aacttgaaat 105000
tattatttat ttatttattt atttttttga gacggaattt tgctcttgtt gcccaggctg 105060
gagtgccatg gcacaatctc ggctcactgc aacctccgcc tcccgagttc aagcaattct 105120
cctgcctcag cctccagagt agctgggatt acaggcatgg gccaccactc ccggctaatt 105180
tttttgttat ttttagtaga gacggggttt ctccatgttg gtcaggatgg tctcaaactc 105240

-continued ccaacctcag gtgatctgcc cacctcagcc tcccaaagtg ctgggattac aggcatgagc 105300
caccgtgccc ggcctggaaa tgatcttaag cagacaaggg cttatgaaac taggatgcta 105360
ggggctaaag caattatttc caagtttctt gtgtcctttg cacatccccc tttttcttcc 105420
cttcttcctc tgcctctggt cagagcttct ggctccatgt tggcctaggg ctctcccact 105480
tcagccgctt tcttctgtga agtgtggtga tcatggacac agccgacccc agttttacag 105540
cataccaagt aagcaacccc agaagggaga aaatgcctgt atttcaggtt atagacatta 105600
aaatgagtga atgcacccaa aaaaggaatc atgtgactgt cttaggttat atgcccaccc 105660
tttaactcag ctgcagcagg gcaagatgct atattgtcat cagttgtggt agggcaagat 105720
gctatattat cagtccaagc agaatgacat agctctatag aaagactatg tttttataag 105780
agtatggaat atagtgcaga tgaaaacagt agatatacac taacatgtgg ctctaatgtt 105840
taatttttat tttttttgag acagagtctc actgtgtcac ccaggctgga gtgcagtggt 105900
gctatcttgg ctcactgcaa cttttgcctc ccgagttaag atgattctcc tccctcagcc 105960
tccctagcag ctgagattat aggcacccgc caccacgccc agctaattct tgtattttca 106020
gtagagacat ggtttcacca tgttggccgg gctggtctcg aactcctgac ctcagtgatc 106080
cgcccatctt aggctcctaa agtgctagga ttacagacat aagccaccgc gcctggcctc 106140
atgctcaact tttatttaga caacagtaca aattgtaatt ttacccagat gtaaaagagt 106200
ctaagagacc taaatagata ttttgtggta gattacatta atgtaatgta atgtaatgta 106260
ggagttttac attactacat ttgtagttgt tttagttgtt tttcattgtt tgtttctgtg 106320
tatttctggg gatttcatgg tgcaacagga ggactagagt ttattcccga tccctgactg 106380
tcttacggca gtacttctca gacctactga gttatacaac caggggtgta gggaggcaag 106440
cagtcatcac atttatttga ggactctcat gttttgtcta aaatattcat ccttatttta 106500
taatatactc cataattttc ccatataagt ttagataaaa gatgatacct taaaagtatt 106560
ataacactaa attgtcattc cgggaaaatg tgctgtgttc ctttcatttt aaataatctg 106620
agatgaatgg tgcaggctga gaaaaatagg cttttgaaat actttttggt caacatcgag 106680
acttttaaca tttgtcctat cttttagggg aatttagaca ttgggcatta tgtattcctt 106740
ggatacatta aaaggtgtta gataagagcg ctcacacttg ctgctcttct attgcaactt 106800
gacagaagtt acttctctaa accttagttt ctcatctgaa caatggaaat aatgatagtg 106860
tctatctcat agtattggtg tgagatttaa atgaaataat tcatgtaaaa ttgcttggtg 106920
tgtggaaaca tagtaacttt taactgttct cattaacttg gctatttacc tgtgttcttc 106980
tatcattaca tttcaagtta aaatttcaag gtttcacgtt gttctctctc caatgaatgc 107040
agttaaatca cttagatttt ctaatgagtt ttcctttaat gttatgcagt tgactagaga 107100
gtgtatatat attaagaaca taataccttc actatgtcca catgtgaatt aagagcttga 107160
ggctatcaga gggtagaaga tgagggagtg gggatgaagt atgtttgtaa cctgtgtatt 107220
ttctctttct taaaggaatt acggctcatc tctttttgcc caatgtgaag cagtagataa 107280
tgggtgtcag caggtcctgt ggctctatgg agaggaccat cagatcactg aagtgggaac 107340
tatgaatctt tttctttact ggataaatga agatggaggt aatccactca gatttcactg 107400
tgtgcatttc tcagtcattt tcaacaggac cagaaagaca agagctagaa acttagtaca 107460
agggagtaag tagcacagtt ccaaaggcta agtaaggact actgtgcttt tgctgcccaa 107520
atagacacaa gtttcttttt tttctttctt tctttttaa agaggtggag tctcactatg 107580
tcacccaggc tgcagtgcaa tggtgtgatc tcagctcact gcaccctggt tcaagcaatt 107640

-continued ctcctgcctc agcctcccga gtagctggga ttgcaggagc ctgccaccat gcccagctaa 107700
tttttgtatt ttttttttta gtagagatag ggtttcacca tgttggtcag gctggtcttg 107760
aactcctgac ctcaggtgat ccaccggcct tggcctccca aagtgctggg attacaggtg 107820
tgagccactg cacccggccg agtttcgatt taaagaagct ctagaggttt tttgtttttc 107880 gtttttttgtt tttctggctc tagatgtact gattattgag atactgagat gtcacattaa 107940
gggatttaag ttaccatgat tggaagattt gcttccttat cccttctgca gttccccaac 108000
aattttccta tctgaacacc ttgcattgag acacaggtct cagatcaggt caatggtcat 108060
tcaccatata ccgtatataa aatgctagag taataaatgc agtgtactga ttctactgga 108120
aggattttgt gtactctctg gctgtaattg ttttaacaat tgttgccttt tctacatatt 108180
ttgaaaatgt atcacaatct ctccaaattt actctagaac tcaatctgat taaagagcac 108240
cattttaaaa gataaatcaa tgtatcttgg gattgtaact agatcctggt tcattcaaga 108300
caatttcata tatccactat agatatcaat atttctctat tatctttaat atcctgagta 108360
ctcattactt ttctttgctg ttttttttta ttagttggca gagaccatag gggttcagtg 108420
aagtgttggc aacgtgtatg atattgaatt aaatggccaa cggtgggaga aaaacaggca 108480
tttatttcta ttagaatttt gataatcata ccaaatttag aagcgtattt ttagacttgt 108540
ttacattctt aggttgttca tttcacagta gtaattatag agactagaaa tataaatgat 108600
gtttccaaat acttatgaag tctcagtgtt agtagtttca attaaatttt ttaaaatgca 108660
gtttatattt gaaagtagct acagtagcct ctcttgctct aatgttattt ggctacaaaa 108720
agaggaaaat ggtaatttag atgtggctga attcagagct aagtactaat tttagtgtta 108780
gttgcagaga ctaacaagat gagtcttata ctgcagtcag aggtagaata aacagaagat 108840
atggtgagta agccttgtcc tggcttggc cattggtagt ccttggcata tgaaaaacca 108900
gatacagatc attctcatcc ttccattcct gctgtttgta cttggcactg tttgaaaata 108960
aaatttatac aggaatattt atgatttata aatttgagtt actgtatgtg acatataaca 109020
aaagctacac ttggaagatt gtagccagtg ttgacctctg cacttagaag ataataggcc 109080
gattcaaccc ttcttcccat ctgcccactc ttacccccac cccaaactcc accaaaaaac 109140
cacacagctc aaaacaaaaa cagttacatc attcagaggt ggtaccatca ttatttttat 109200
ggatgggaga tgtcagaatt taagtacact ctgaatcaga gctacatgat ttaaccagaa 109260
acaccagaaa ctgtcctggt ggaaaattgt tctttatcca aacaataatc atgaaacatt 109320
tccaccatgg cttttaaagg tcagaataga aatgagtgag tttgtcttct gcctcttgca 109380
aaatatacaa gaccttaaga ctgttagtta ctattcagat tatggttgcc tgggataact 109440
ttagttttaa tatactcctt cactttgggg atgttcatct aacagaacaa ataaaattca 109500
gaataaggag aaaggaaata gaatatatat ttgaagtaaa tagaatgtta ggaaaaacct 109560
ttgggctaaa aaaaaagaca tgcaattctg aagtaacttt gatttatatc atatgatttt 109620
aagaaaatac aatgaacaaa cgagttgaaa atcagcacaa tactgatttt cacaaacgtt 109680
accgatagga ggtataaaca gagttctttc ggtaatagcc tgccgtcttt tcatgagcgc 109740
ccacacacac tgctcctgtt ggttgagatg gctggtgcag gaaggtggat ggggtggtgg 109800
atagtgtgtg ttcaaagcac agtgctgtgc acagtcacta tgtgtggcac tcagcttgta 109860
actcatggga gttttgattt cagtaacagc acccatggtg gcaagatcac acatcatcac 109920
tctgttgatg agtaatttaa cccatacgct tgctattcac catttgaaca aagcattgta 109980

-continued tcatatcctg gaccctggag ataccctgaa aaataagacc caggccttgt ggttgagttc 110040
acagtcactt tgggaaaaca accacagcag tgaatctcgg tattgctcag gccacatcat 110100
gagtcttctc ggacacgtca ggcgtgtata cggactcgac ttggagcact cttcctcaga 110160
tgtctgtacc gcttgctctt tgacatcctc caaatctttg cttacaaatc ccattctcag 110220
tctggctttc cttgagctct taatcaaaat cataaactcc atttcccatt tctcctcagc 110280
attccagcat tctccattgc ttttccttct ttgtttcccc ctgtgtagtc taacatacta 110340
tcaacacaat aaatgtttac ctgtgtctat tagaaagtaa gcagggagat atgtcagttt 110400
tgttcactgc tgtattcata gagcttaaaa cggtaaacag cactcaatat gtatttgtag 110460
aataaatggc taattgtgct gatggtgttt agggcactta tgcagaccta cattcctggt 110520
ttccattagt gtttgacttt gggaagtcac agatgaatcc tgctgttatt gcttctaaat 110580
tcctcatctc ctaaaaatga cttctttgtc aaaaacaagc tgcatttgta ggttctgttt 110640
tcctcatgtt gggcaatctg gagtgatttc tggctcttgt aagtatgttt gtggttgcag 110700
aggaaaatga atatttctca cccaaatgtt gtcatgtcat catctctgtc tggcaaccag 110760
agaagcagat gttctgttcc ttgacctcag gctagtggtt acagttctgg gtgttaaaca 110820
tgtttcacaa aacagcactt gcacatgcgg ggctgctgtt ttcatttaac ttcatgtagt 110880
ctcagggctc agcaagcttt aggaaaggtc cggtttgggg gcactggaag tgtgtgtgtg 110940
tgtgtacata tatatacaca cacaaataga tccatacatt tatgtatcta gttggctagc 111000
tattgcaaaa cacatgttta ttttgagatc atcaacactt ctaaacatga caaagagtag 111060
ccctaagaac attgccaaga acaaattttc tcctttccag aaagcaattt tcagcagatg 111120
attttcagaa acaaaattca aaaaagccat actgctgtat cctagcaaag ataacttatt 111180
cgtttatttt ttactcaaaa acatttatta tatacactct gggctaggca caatgcccag 111240
ttttgaggat agaaggatga agatagagtt tggtattcca gatagagctt gattgttggg 111300
catgtctgat gtaaccccag tggagtgggc gagcctagaa ccaccatgta ttgagggaga 111360
gggtggtggc ctcagtgtca ggactcacta gattcagact cctgggtgtc agaagtgggg 111420
aggaaaggga gatgctgagt gccagagggt actgtaagga gagcttgtgc agctgatgga 111480
tcatgcatga tgcctgtgaa caattgtcct actagacctc acagtagtta gggatgtctg 111540
cagtcatctc acagtagagc agtagctcag ctttggagtt ttgtttcttg aatgtcttct 111600
tttttaaccg tacacgtgct tgagctcact ctgataagcc cattacattt gaatctcaga 111660
gagcaaaggc agcatctcca tacttgttgc tgatgctcca ccaggtttga aaatcactaa 111720
agatagactc ttaggctggg tgcggtggct cacatctgta atctcagcac tttgggaggc 111780
cgaagtgggc agatcatctg agctcaggag ttcgagacca gcctgaccaa catggtgaaa 111840
ccccgtctct actaaaaata caaaaattag ccaggcgtgg tggcgcgtac ctgtaatccc 111900
agctactcag gaggctgagg caggagaatc acttgaccct gggaggcaga gggtgcagtg 111960
agctgagatg gtgccactgc actccagcct gggtaaccta aaaaaaaaaa aaaaaaaaaa 112020
aaattagact ttccaagggc agcgtggaag cagtgaccag cctgagtagg cacgcacact 112080
tcttggggat agcctcctcc atagcattct tagaaggttt ggtaatgacc agtttttctg 112140
agtaagaccc tatctacatt attctaatta gtaaccacct ttcatctgct aaggtaaatt 112200
ttcacttcag aatattcctc ttaagaccat gcaataactc ttactgtttg ttggtggaaa 112260
accatctcat tattttactg gttaagggta aactgaagat gattagataa ctttccttcc 112320
ttccctcccc ccttcctccc ttccttctct ttcttccttc ctttctccct ccctccctcc 112380

-continued ctctctcttt ctttccttct ctctttcttt tcttttcttt tttctttctt tctttctttt 112440
ttctttcttc cttccttcgt tccttcctcc ctccctccct ctctctcttt ctttctttct 112500
cttttctttc tttctttctt tctttctttc tttctttctt tctttctttc tctctttctt 112560
ttctttcttt ctttctttct ctttctcttt ccttccttcc ttcctttctt tctctctctc 112620
tccttccttc cttccttctt tccttccttc cttctttcct tccttccttc tttcttcttt 112680
ttttaaataa gggtctacct gaagtgtgaa ctgatttggg aaatttgatc atgcagaaca 112740
gtaaaatttt ctttatgttt gttgctagca aaattgtgat ggttttttaa aaaaatggct 112800
attgataata aggcatgcct aatgtagtga aagtttgaaa atgtcccaat ttctgattga 112860
cagaagaaga actggcaact cctccactag atggcatcat tcttccagga gtgacaaggc 112920
ggtgcattct ggacctggca catcagtggg tgggtgcctt tgatatgaac aacttttgta 112980
agcctgaaat aaaaaataat caaaataagc ccagcctagt gttgaaataa tatcctgtgg 113040
ttccaaccaa tgttatctaa tctttaaatt ctaacgtgaa tgaaaagtat tcttctagaa 113100
gggctttctt ggcaagacta ttaaaataag tattgttgat agcaagggca gagagaaacc 113160
agtttagcaa gatgtcatag tggagaagta ttctagtagt agtctcagtc taccaggtat 113220
ctcccaccaa cttttgtctg gttcatacct gatgtgcttc catccagaca ttccttaact 113280
tcccaagtct gtgttgcttc caaatggcaa tgatacttct tcctttcctt tatttatacc 113340
agtgtaacca tgcttgccgt agaaatgaaa taatttcact gacatataaa tgtttactaa 113400
tataacatta ttggtttgac tgccttcttt ttctctctgt cctacccccca tcctccaaaa 113460
ttcatataca tgcctatttt aaaatcagaa catgcaagca aatgtaaagt tgttttcagt 113520
agactttcaa attcgtgtga cacaggcaag catattaaac aatttggtgg accgggtgca 113580
gtggttcatg cctataattc tagcattttg ggaggccaag gcaggaggat cacttaagcc 113640
caggaattcg agaccagcct gggcaacata gtgagacccc gaatctacaa aaaaatcaaa 113700
aacattagct gaacatggtg gtacatgcct gtagtcccag ctacttggag gggctgaggt 113760
gggaggatgg cataagatct ggaggtcaag gtcgcagtga gctatgatca agccactgca 113820
ctacagcctg aatacagggt gagaccatgt ctctaaaagt aaattaaata aataaataaa 113880
taaataaata aataaataaa taaataaaat aaaatttaaa aaggtttggt tttggaaatg 113940
acgtaatgta ttcaagacaa attattgaat gaattgggtg tctggtaaag gttcttggat 114000
ggaacttttg acccaggtgt taaaatggtc tccaaagaac atgaaaaggc tttgagctta 114060
ctgtggtcaa agagtactag tagtaatagg acaaatgttt agaaacacac acgttatcta 114120
ggagcatacc agcatggttt ctctggaaaa gactttcaaa atagatgaaa tgtgctataa 114180
ataattctac aaaaccctga agtagacaag acccaactgc tacatgctgg ctggcgcatt 114240
gggcatgaca tttacaaacc gttggtataa ttttcaaaca gcttgccctg tcctaaatat 114300
gtttgcaatt ggaaagatat ttttgaagct cagtaatttt tgttttatta aagaaaaata 114360
tcaaccaagt acagaaggtt cgacgacaag ttgcaagtgg aaatactttc ccacactaat 114420
gatttgctag catgaaaaat aggttattat ggaggaaatt ttttcttgac ttcatagctg 114480
taatttattt taaaagctat tttaaaacat gagacgtgaa atgccaagag gcatgtaggg 114540
ggtcaccact atttgccaga taggggaaat tgtccaaaga taagtaaggg tgagcagagc 114600
aaaaacaatt ctgcttattt acaaaagagt tttcttttct tttctttttc aggacacaga 114660
actcagcttg ttttcaatta atttgcctga ttttctgcag ttcatttact tttgaacaac 114720
ataattgcaa ttgtagactg agagaaattg aaactttcaa agagccatat ttctattgca 114780
gatatatttt cctgctcttc caaatctact tacagcatga gttcttcttt taaatattca 114840
aatattttga atattgccaa gagctttgat ttccattttt atctcttgtg ggtttataaa 114900
ttaagaaaaa atactcatct tattttttta aacctctcta tttttattgc cctttattca 114960
aataacttgt tgacaaactt tgaacttgaa ccactgaggt aaaagaacaa gaattaaaca 115020
gatagtttaa acacatagct taaaaggatc tttttcccat ttcctatcct tgagcaaaga 115080
atatattcaa acactttggc agaagtcaat gaggttatac cactaattcc atgatgaaaa 115140
tcaactgaat gtgatactga aagagaagga agagaattgt cactgtaaag tcaactgtta 115200
gtcatattag gaaaaaaaat acatacaata caatttctca aataaagtcc aaatatacat 115260
tcaacgttta aaaataatga gtatttcaga tatttgaact cagtctgttc tttattccat 115320
aaaagatata ggtaagccgt gcacagtggc tcacaactat aatcccagca ctttggcact 115380
ttgggaggct gaggtgggag gatcacatga gcccagcctg ggcaacatag ggagacccct 115440
atctttacaa aataaaatat aaaatataaa acctagttgg gcatggcagc atacacctgt 115500
agtcccaggt gctcaggaga ctgagacagg aggatcactt gggcctggga ggtcgaggct 115560
gcaatgagcc aagattatgc cactgcattc cagcctgggt gacagggcaa gaccctgtct 115620
taaaaaaaaa aaaaaaagaa agagacaaac gtagaaagag taccaaattt ggagccaatc 115680
agatcagacc tgggttcaaa ttgagtttct gtcacttact tcctttgtgg ccctggagat 115740
gcccttcaac ctccttgaac cttagtttcc tcatctgtaa aatggggatg atagtactca 115800
cccttaaaat tacagaactt ggcataatag cgggtgcttg ataaatggta gctataatta 115860
ttaatattat ataatacatt gttctccttt atggtaaagt aggttttaag acactgattt 115920
ttttgttttg ttttgttttt ggagacagag tctcactccg tcacccaggc tggactgcag 115980
tgacgtgatc ttggttcact gcaacctctg cctcctgagt tcaagcgatt ctcctgcctc 116040
agcctcctga gtagctggga ttacaggcac ccgccaccat gcctggctaa tttttgtatt 116100
tttagtagag acagggtttt accaggttgg ccaggctggt ctcaaactcc tgacctcaag 116160
taatctgcct gcctcagcct ccccaaatgc agagattaca ggcatgagcc accgtgcccg 116220
gcctaagaca ctgttaacac ggagcatgca tcaagcagca tttgggatgc atcaattttg 116280
tgagacttta tacaagttaa caaataagaa ggcaaaaaag aaggcatatg ttaaagtata 116340
ccatgtgtct tgtggtgata atcttatatt ttatattctg ataatctcat atataaatct 116400
gtgaccttga agtaggttac ttaacacctc gatgtgttca ccagtaagat ggtgtgccac 116460
ttccagcttt cccttaaagg atgattgtga ccttgtctaa gtgcaatcag aatgttaagc 116520
agaacagtaa gtattgcaat tgttttgcat gccttttcct ttaaaatata cttgttattt 116580
tttatattcc atgcagggtg aatttaaggt gtcagagaga tacctcacca tggatgactt 116640
gacaacagcc ctggagggga acagagtgag agagatgttt ggctctggta cagcctgtgt 116700
tgtttgccca gtttctgata tactgtacaa aggcgaggta cgacaagtat ttcctcattt 116760
cctatcattt ccaatcacat taaattacat ttaatttaag tgtatgaata aaattgtatc 116820
tggacccaga cccaagatgc aaaagttttg tcgttgttgt tgtttttctt tattttaaag 116880
agatggagtc tcgctgtgtt gcccaggctg gagtgcagtg gctattcact ggtgtgatca 116940
tagctcactg cagcctcaaa ctcctgggct cacgcaatcc ttctgcttca gcctcctgag 117000
ttgctgggat tacaggagtg cgccaccgca ccatgctagg tctttttttgt tgttgttttt 117060 gttttttaac ttggcactac aaaaaaaaata actgggacag tttatccaga tgaaactgta 117120
ttagcatata tctactatgt ttccagtgat ttcatgtaag cttaaacatg gtgggaagtt 117180
agttttgtcc ttggacacgt gtaagatctg tcttacctac atgtcgggat tggagctatg 117240
ccgacagtct tctactcttc tctcttcctt cctaccagct cactagggaa ggctctatag 117300
gtagttacat ttcagtttct ggttaaccaa aagtacttcc aaaccactgg attaggaatg 117360
gcaaatagtt atggaaaatg cattcgagtg gtcaatccct tgattttttt ttactattaa 117420
tgctgttatc attaatagta agtagaccac tttacaagaa ttattcattg gcaaacctgg 117480
tgcatttact aaaatcttac aaaaggaatt tgaggatttg gttggaagaa atgttctcct 117540
cttagtaaat tagtctgatt ttatatgtgc catacttttg ttttcttgtc aaattgtttt 117600
gcttttcact ttataacaaa gctccaatac ttatgattaa cattggcatc taactttata 117660
acttaaaggc atgtaagtat tagtcttata atgtgaactg gcttaagtta ttcatattat 117720
agcagatcct tgaacaacac agggattagg ggtgtcaacc cccatgcagt tgaaaaatcc 117780
acatacaact tttttgttt gtttgttttt ttaaacgggg tctttctctg tcacctgtac 117840
tggagtgcag gggcacaatc tcggctcact gcaacctccg cctcccaagc tcaagcgatc 117900
ctctcacctc agtctcccaa gtagctggga ccacaggtgt gcaccaccac acccagctaa 117960
ttttagtatt ttttgtagag acggggtttc aagatgtttc acaggctggt ctcaaactct 118020
tgagttcaag tgattcacct gccttgacct cccaaagtgc tggtattaca ggcgtgagtc 118080
accatgcccg gcccacatat aactttttgac ttcccaaaaa cttaactact agtagcctgc 118140
tgttcaccgg aagccttatc aacaacaaaa acagtcgatt ggcacatatt ttgtatgtta 118200
tgtatgttat atatgtattc ttacaataaa gtaagttacg aaaatcatgg ggaagggaaa 118260
atatatttac tattcattac atggaagtgg atcatcataa aggtcttcat cctcattgtc 118320
catcatgttg agtaggctga ggaggaggag gaggaggagg gattggtctt gctgttttag 118380
gagtggcaga ggcagaagaa agtccacgta taagtgaact tgtgtagttc aaacccgtgt 118440
tgttcaagtg tcaaccgtaa atgcaaactc cactggtttt caaattttac tttagagtta 118500
ttttccctca gctgattgga gttttgctca actcctctga ctttaataat ggctgcttca 118560
tttgttgagg ttttagaact tgcttttaag ggattgctct tgacataatt gcatcaacag 118620
atagactgtt tcatgggaga agaattgttc tgtttcatgt caatacttac attgataaga 118680
atgcatcaag gtaatgtgat ccatccactg aagttgtcat taggccagat ttttttaag 118740
ttgaattatt atttcacttc tagaaataag aagtttataa agtttagcat aattttaatg 118800
atccaggctt aggaagcatt tacagccaaa aagtaagtat atataattat catattatac 118860
taaagggtat aatatgaaaa gtgtttgaga gcacagacta tctcctaaaa tcaaactatc 118920
aaaacctgca agccagcaag gcatgagtag gcatgactca gatacaaatt agaagcatga 118980
aatctctttc agccatgcat ttaatcatgc tatccaatat tgtggaggta gtggcccctg 119040
gaagtttacc ttgggccaga gataggtata gaagcccctt ttatgaagtc atagacttgc 119100
tttaatttat gctcccagaa tgacttgcat taaactgtgg caaaatatct ttgagttctc 119160
atattagcca gagggttaat atgtagaaga caatcattca tccttacaga ttctcagaat 119220
cttggaagag gtagggttct ttaagtttag ccactatttt aggtaactgt agctcctcct 119280
tggttcttca aatgatcctg aaggctggta tacaaaccag ttatgcccta aaattaattg 119340
gtaggtaggc aatgtataac ctgtcattgg ctagttttta ttcaaatttt ggatatgaaa 119400
gtctttggca taaggtgcta gcactcagag tcagtaggtt ttagtgctat tccttaactt 119460

-continued cagtggaatt gccttagtat agcagaattg cttgagtgtc ttatctgtta tcaccatata 119520
catgagtacc ctcaaattat ctcatttccc tttcttttgt agacaataca cattccaact 119580
atggagaatg gtcctaagct ggcaagccgc atcttgagca aattaactga tatccaggta 119640
aagcttttct tttcttttct tttctttcct tttcttttct tttttttatg tcaccttatt 119700
tctgtcagag cttacaacta aattatattt caatgaagag gattaaataa tacaatttga 119760
gatcaataag ttaaatttaa ggaagatatt cccaacacaa tgtgtgggca tgagcaaagc 119820
agaaatggga aagaagatgt atgttttaaa aaaagaaaga aaatattgtt caggactcca 119880
cattacttaa cattaaaaaa tagatgtaat ttttggtaac atttaaaaat ctcattaaga 119940
aggataacat aacttttgtt aaaaaaagga agaaaaaatt tgaaagtaga agcaacttca 120000
ggaagaaaat tacagtgcat gtgattccaa cactgagata taatcactgt taattttttta 120060 tgtcttttta tttttgagct ggagtttcac tcttgttgcc caggctggag tacgatggca 120120
cgatcttggc tcactgcaac ctctgcctcc cgggttcaag caattttcct acctcagcct 120180
cccgagtagc tgggattata ggtgtgcgcc accatgccca gctaattttt gtgtttttag 120240
tagagatggg atttcaccat gttggccagg ctggtcttga actcctgacc taaggtaatc 120300
cacctgcctt ggcctcctaa attgttggga ttacaggcat gaaccactgt gccctgccat 120360
tttttgatgt cttaaccttc aatattttgt aagcatttat atactttatt tatttattta 120420
tttatttatt tatttattta cttatttatt tttgagacta agtctcgctg tgtcacccag 120480
gctggagaac agtggcatga tctcagctca ctacaacctc cacctcctgg gttcaagcga 120540
ttcttctgcc tcagcctccc gagtagctgg gattacaggt ctcatgccac cgttcccggc 120600
taatttttgt atttttagta gagatgaggt tttgccctgt tggccaggct ggtcttgaac 120660
tcttgacctc aggtgatcca cccgccttgg cttcccaaag tgctgggatt acagccgtga 120720
gccaccatgc ccagccagta tacttttaga tagttatttt ttcctaacaa aatgggatca 120780
tattgtacat aattttgtta catgtttttt cactgaataa atgctttgct tttttatatc 120840
aataagtagt tttctccaac accatttata aagtttaatt gaattccatt atattgatgt 120900
accataattt ttttaaaaaa ttatattatt gaacatttat gttgttggca attttttttt 120960
cactagtatg gacagtacat cctcgattac ttcctaagga taaatctggg atcaaagagt 121020
atacacgtct atttttttcat actgctaact ttgttttgcc tatttttttt ctgagcaata 121080
atctacagta atgcctcatc aggcagttaa gcaggcatgc taaataccag ataacactgg 121140
gctactcaga aaagagatta tcctgtaatt tgcaagcatt tcacaagtta gaagactttg 121200
ttgaagccag ttactatcct tgtcaattag taaaaatatc caagagggcc tgagacttac 121260
attgaaaagt aaaataaagt ttgatcattt gagtgatgtc ggatggcatt aagtcatgaa 121320
actaagtgaa acttaaaggt ggctgagaat gcaacaggcc tccagagagc aatggaggtc 121380
cttgggtagt gataaaaatg gcatttctgg ctgggtgcag tggctcacac ctataatccc 121440
aacactatgg gaggccaaga caggaggatc gcttgaggcc aggtgttcaa gactagccta 121500
ggcaacatag tgagaacctt cctctaaaaa aagggaaata aaataaaaat aaaagtttaa 121560
aagagagttt aaaaggcagt tttaaaagag acttactcag caagttttct gccaaattta 121620
cagtattaaa aagaaagaaa gtgtgttttt gtttctgttt gtttttttga gacagagtct 121680
tactctgttg ctcaggctgg ggtgcagtgg tgcaatctca gctcactgca acccctgcct 121740
cctgggttca agtgattctt gtgcctcagc ctcccacaca gcagggatta tgggcatgca 121800
ccatcatgcc tggctaattt ttgtattttt agtagagtcg aggtttcgcc atgttggcca 121860
ggctggtctc aaactcctag cctcaagtga tttgcccacc ttagcctccc aaagtgctga 121920
gattacaggc atgagccacc gcaccctggc cttgattgtg gtttttttaat caatgagctg 121980 ccatacttct gctctccagc aaaggttttc tatgagaatt ttctgtaagc taagtaaagg 122040
aatatcttaa tattggaaga aataaaattt agtcagagtt gttttctacc tttgtacaca 122100
gcaacactta caagtaattt gaagagtagc taataaaaat ttctgcatgg atggcttagg 122160
cattttaatt tttttaaggt tgcctgagta aatctgaaaa taataaatta ttacagtttt 122220
gctcaaataa agaacacaaa tagaacaaaa aatacataac tggctagatt acatgaaagc 122280
ctttttccaa aacagaggtt tagaggccag ggcaaatagg caggaaaaat aaataaaggg 122340
catccaaatt ggaaaagaag aagttaaatt agctttctta gcagatgaca ttatcttaca 122400
cctagaaaaa cctaaagact ccctcaaaaa acctgtagaa ctgataaatg aattcagtaa 122460
agttgcagga tataaaatca acatataaaa atcagtagaa tttatatatg ctaacagtga 122520
acaatctgaa aaagaaatca agaaagcaat cccatttata atagccacaa aaagtataaa 122580
atacctagga atcaatctaa ccaaagacat gagagatcta tacaaggaaa agtataaaac 122640
tatgatttaa aaaattgaag aaaacacaca aaggtggaaa gatattccat attcatggat 122700
tggaagaatt aattttgtta aaatgactat actacacaaa gcaatttaca gattcaatgc 122760
aatccctatt aaaatactga tgactttctt cacagaaata gaaaaaacaa tcctaaaatg 122820
tatatggagc taaaaagacc ccaaatagcc aaagcaatct tgagcaaaaa gaacaaagtt 122880
agaatcacca cactacctta cttcaaaatt tattataaaa ctataataac caaaacagca 122940
tagtactgat ataaaaacag acatagtaga ccagtgggac agaatagaga acccagatac 123000
ctaagtccac atgtttacaa ccaactcatc tttgacaaag gtgccaagaa ctgtaacggg 123060
gaagacagtc ttttcaataa atggtgctgg gaaaattgga taattatatg cagaagaatg 123120
aaactagatt cgcttctctt accatacaca gaaatcaaat gaaagtatat taatgacttg 123180
aatcttagac ctgaaactat gaaattactt gaagaaaaca ttaaggaaat gcttcaggac 123240
attggtctaa gcaaagatct cattctgtca ctcaggctgg agtgtagtgg catgaacctg 123300
gctcattgtg gcattgacct cctgggctca agcaattctc ccaccttggc tttccatgta 123360
gctagaacca caggtgcatg ccaccacatt ccactaattt ttaaattttt tgtagagatg 123420
gagtctcacc atcttgccca ggctggtctc gaactcctga actcaaggga tcctcctgtc 123480
tcagcctccc aaagtgctga gattactagc ataagccact gtccctggcc agcgaagatt 123540
tcttatgtaa gacctgaaaa agcataggct atcaaagcaa aaataggcaa ttgggattat 123600
gtcaagctgg aaagcttctc cacagcaaag aaaacaatcc acaaagggaa tagattaccc 123660
aaagaatgga tgaaaatatt tgcaaactat caatctgaca agggattaat aaccagagtc 123720
tataaggagc tcaaacaact gtataggaaa aatctagtaa tctggtttta aaatgggcat 123780
gagacctgat tagaaaactc aacagaaaaa aaaatttgat taaaaatgga taaaagatct 123840
gaatggacat ttctcaaaag aagacagaca aatggccagg aggtacatga aaaaatgcgc 123900
aacatcacta attatcagag aaatgcaaaa caaaaccaca atgtaaaatc cacttgccct 123960
agttaaaatg gcttgtatta aaaaaaaaaa aaaaaaacagg caataacaga tgctgggagg 124020
atgtggagaa agggaaccat catatattgt tggttgaaat ataaatagta cagccactat 124080
ggagaacagt atggagggtc ctccaaaaat aaaagtagaa ctagaacttc cgtgtgatcc 124140
agcaattcta ccaccgggta tatatccaaa agaaaaaaat tagtatatca aagagatatc 124200
tgcactccca tgtttattgc aatagtattc acaatagcca agatatggaa ttaacctaaa 124260
tgtctgtcaa cagataaatg gataaagaga atgtggcata aagatatata tatatatata 124320
tatacacaca cacacacaca cacacacaat gtggtactat tcagccataa aaaagaatga 124380
aatcctgtca tttgcagcaa catgtatgga actggaggcc attttgttaa gtgaaataag 124440
cgagggaccg aaagacaaac atcacatgtt ctcatgcagg tgctaaaaaa gtagatccta 124500
tgaagacaga gagtagatta gaggttacca gaggccgaga aggggagtgg gaagtagagg 124560
ataaaggaaa aaaacaagaa tataaatgta tttattacca ttaaactgaa catttaaaaa 124620
ttgtaaagat ggtaaattat atatgtgtat tttatcttaa ttaaaatttt aaaaatcagg 124680
agtttagaaa tttttaagag aagtgtgccc atagtgataa gaaagaaaga ccctttttgga 124740
aaattttctt gaacaaatta tacagtattt tcttaaacaa attgtacatt ctgtagcagt 124800
taatacacca aataagattt cagggttacc tcttggagat tgtatgaaat aaaaacattt 124860
aggtgggcat gatggctcat tcctgtaatc ctaaaacttt gggaggctga tgcaggaaca 124920
atacttgagg ctagtacttc aagacgagcc taggcaacat agtaagaccc agtctccaca 124980
aaacaaccaa aaaaaatagc aagtgtggtg gcacacacct gtagttccag ctactcagga 125040
ggctgaggca ggaggaacac ttgaggccag gaatgtgaga ctgcagtggg ctatgattgt 125100
gccacagcac tccactccag ccttcactgt agaaagagac cctgtctcga aaggaaggag 125160
ggagggaggg agggagggag ggagggaggg aatgaaggaa ggaaggaagg aaggaaggaa 125220
ggaaggaaat gtaaactcat ttgatttggc tgtaaaggat taatagaaaa ggaaaacgta 125280
gtcactaggc tgagaaaaat tgaactctat tgaattggta taaagatcta agtggaggtg 125340
tttggcagac atgatcatga agctttcact gaggaaggaa actctaggag gcaaaagcag 125400
aaatgcaact catcaaaatt gaaatggtga caaaatatgt gcattcaaac ctgaaagtga 125460
ctgaaagaga agcccaaaca cacaattttg gggtaagatg ggaaaccatt accaaagttc 125520
tcagaaagag catttttaaa agtaagatta tagaagccaa aaggatatgt agtagtctgt 125580
tctcacactg ctgtaacgaa ctacctgaga ctgggtagtt tgtaaagaaa agaggtttta 125640
ttgacgctca gttctgcagg ccatacagga gacatggctg gggaggcctc aggaaactta 125700
cagtcatggc ggaaggcaaa ggggaagcca gtacatatta catggtggga acaggaggag 125760
gagagggagg gtgggaggtg ccactcactt tttaaaacaa acagatctcc ttagaactca 125820
ctcactatca tgagaacagc aagggggagg tttgctccca tgatgcaatt acctgacacc 125880
aggcccttcc tccaacatgg gggattacaa ttccacatga gatttgggtg gggacacaaa 125940
ttcaaaccat atcagaatgt tagtgactaa agtaaatgtt cttgtttaac tctttaatgt 126000
gtatattgag tgcaagccat atgcaggggc tattctaggt actggtggtt tactcaagaa 126060
aaagggggca aaaaaatgaa gaaggtggcc aggcatggtg gcttacgcct gtaatcccaa 126120
cactttggga gactgagacg tgagaattgc ttgagcccag gagtttgaga tcagcctggt 126180
aacatggcaa atccctgtct ctacaaaaaa atgcaaacaa acaaacaaac aaacaaacaa 126240
attaatcggg catggtgtca catgtctgta gtcccagcta caggttgagg tgggaagatg 126300
ccttaagcct agggaggttg aggctgcagt cagccatgat agcaccactg cactccagcc 126360
tgggcaacag agtgagaccc catctgaaaa aaaaagaagt caaaacaaat gaaaaaaaaa 126420
aaaaagtcaa aacaaatatt cagtgtaaat gtgagaccat gtaaaaaagt ttaaaagtaa 126480
aatatatagt ttaagcagag gatgggagac ggggaaaaaa ccttttctcc ctaactttat 126540
atactccctc tataaattag tgcttatggc caataagaaa tgaataattt ctttttcac 126600 cgttggtagt aaagtataat ggtagttaac acaaaaaact aaatgatata ttcagaacct 126660
catactaaac aaagaaacaa aggcatgcaa tcacaggaca ggtggaaaca gtggttctga 126720
actaaccaca aaccagaact accaaatgtg ctacaaattg tttagtaaca aaggaccatc 126780
ccttcagaat tgaagagcac gtctcagtta tctcatgcct atgtgcatgg aacttaaagt 126840
ctcaaaatta ctcttacaag atggcaaatt gaggctgtca gctaagctcc tagattgtct 126900
gtttctccaa gaaaaataaa tttcagtaat tattaaggaa aaagcataga attgcatcat 126960
gttttacatt tcattacttt tggcatgaca tgggagcatg gatgttttct acaaagtgct 127020
ctgataaatt gaagaagagg ccaacaacag ccaccgaaaa aaccttcaag attcttgcca 127080
gtatggctca ggggaaaaat tccctcataa ccacagattt gacttttcaa cttctgtact 127140
tctgcatatg agtaataatc tctgaggtta agtattcatc ccatttagct aattgtccac 127200
ataactccct gggtcttaga ttgctctata aatacctcct aagagaagaa tttttcaaat 127260
gacagtttcg tttttccttt ttcttctttt aaagcaacaa agaaaagcac gtctgtgttt 127320
atatttaacc aaacttaaac ttggagagca ttggccgtgt tgtcgacgtg tttcttttct 127380
ctactgttaa attccttact gttccagtta ctcaccatca tactcacctt tgcctctgcc 127440
acttggggtc ctctgttctg cagttgtgtt ctgctctctg atgcctccag gttttgctgc 127500
accttctaga aattgctcac ctggataagg ccttggctgt cctttatgac tcatctcgtt 127560
cagaagcctt ttgaatctct cttgaagaat attccctttg ctcagtccaa atacacattc 127620
actcacttga atgctgcttc ttcctccagt ttcacagtgc tggggatgat cccgtaaggc 127680
ctttaaatta cattataatt agtcatgcac ttctctctgc tctggggctg tttgaatcgt 127740
tcactctctt tatacctcca gtgttcagca cagagcctag ggtataatgc gtatgcagta 127800
atgtttcttg aaggagtgaa tggcaagtg aaacaccaaa caaatactaa agagcaaaac 127860
atgtattgct cttgtatatt aacacattcc gagaagagat gggaggaagg tcttgaataa 127920
tatcaaatta tttcttaaga gatcttgatt tagattttt tcaaaatgag atacatgttg 127980
acactgctgt caacaaataa tcacataaaa gctagagcct ggcttttaag tatcaggggg 128040
agcatgtgtg aataatcagc attgctgctg ttgaagctcc ataaagtggg aagcagcgac 128100
tgcaaagatc cagagatgga catctgaagc ataggaaagg ggcagcttga atgagatagg 128160
agcaggatct gtattgattg caggtcacca gatagaatta aaaaaatcta tgttctcact 128220
agtggctaca gttttcaagg acaaatgact attagtggtt attgtatttt tcttgttttc 128280
aatggagcag ctccatgact tagttacata agaagttaaa ggctccaccc ccttccctac 128340
caatgtctta agctgtcctc cgtgtgcata caaactttgt ttccagactg ccctcgtgtg 128400
actcagtccc tggaccagct tcccagcccc ttctgtttcc agcacatcct cctccacgtg 128460
ttacaggatt acaaagcttt gcacagcctt tcaatagggt ttagagcaag aatgacagat 128520
tgctacctgg taggcagcac tgactatagt tttattggcg ttgcgtagag tgactgcatg 128580
acatgcaggt tgtgcttttg ttttgccagg aatttaaagg catttagcaa agccgtatga 128640
aattatctgc cttatgtacc tcgaatgtga ggtaatgaac ttgtcattag tcgtgtttta 128700
gtttagtgtt ctcgctggaa tttgcaaaag attaaaattc tgcacatttc attaagtctt 128760
ccacatgggc tcaaaatacc atcccgcagg ctcgacctga cttgccacgt tgctttgaca 128820
ccatctctga ttccagtgaa caaaactaag taagtgtgac ttacagccgc cctaccaaac 128880
attgaaggtg tgagcctgca ctgttgtttt gtaatgacaa tgacaagagt ataatgacaa 128940
gagtataatg acatcctagt ccatgaagac atgttttctc ttttccctcc ctctatgtat 129000
acttacttac tcttaaggaa ataatataat ttctatttct gcttaaatct gccatctcta 129060
cttagaatta ttttcccttg aaaaattaaa ttgcattatc catcagccaa atggaaaatc 129120
tgattactaa atgcctactt ctagacatta tgaattacct gtaatatcac atttcttggg 129180
cacttctcag aatgctatga ttttacataa aagcataaat tacagaatga gaagagtaaa 129240
gcttagtgca tattatgcag gttcgcagag tgatatgtgg cctacgactg tcattgtaat 129300
caaaattgat ttttgatcat ttataaaact aaaacaacta attgaaagca aatttacttt 129360
aactgatgaa attcaagatg aagtgacagt agtcatgaat cacagttctg tagatctgct 129420
aaaatgccaa tgaactgtta ttaatggtga aagtgtttaa tatattaatg ggaatccaag 129480
taaggaaaat aaaacacata ttttgccctt accttaagtc atgttgacat catacataaa 129540
tcaggtagaa tttgaagatg tttcatccag cattcatcat gaagcaacag agtcaatagc 129600
gggcagttac agtctgtagg caatgctttc tggtgtggat tatgcaagaa acttacagtc 129660
atttggcttc ctttattccc ctttgcatgt aaactaccag gtggtaggta gacccattct 129720
tggctgccag tatttttacc acttggatag attctgctct ctgaggtctt taagacaaac 129780
acagcacatg tacattgtga tataggagaa agaacatcag acagaggcag agaactgggc 129840
ttgtcaaaat taagggtgac ctagagcctt agtgtcctta tatgtaagat gagaagcttg 129900
gattaaaatt cattgctcct tacacttgat ttttatgcag cagaactttc ttcaaaagag 129960
atcactcctg gaatcccaat atacaaaatg gataaaagta ggattgttct gaagtaaaga 130020
agtaaaatcc agagccccac ttatttgagt catctcctac cttttagatg gttattaaca 130080
ttgtttctag ttcagaaatt ctgatgtttt atattaattt aaactaaagt taaattagga 130140
ctagaagagc catttcgtgt gaaaatagac atagtctgag tgatttaggc aaacccatag 130200
tgacagattt agtggcctga tacactggct tggaaagatc tgttccaagt cagtctcaat 130260
acacaaggct cggtgaacac atggcgagca gtcttggtgg tggtcaagaa catggaattt 130320
gctgtgagag agagcttggt tagggtctgg gctcttccat ctgttaactg caaacttgag 130380
caagttattc aatctcccta atattcagtt ttctcattca taaaatggat tgataatggt 130440
accttctatg tacagttact gtgggtatta aatgaggtaa taagcctgta aaactcctgg 130500
catgatgaca ttggcctaca ttaattgctc acagagtgag aacttattat aaacacaggc 130560
atttttgttg aatgactgac tgattgaatg aatgaatata gaactagctt tctatttgtg 130620
atgtatggaa tatctctatt tcatttaatt tcattttgaa tattaaaatt caggcttgct 130680
tttaaaccaa agtatttgct gatgcaaaga atgaaattct gactatgata cagttacata 130740
acttttgaag aaataagaaa aatgctaaca cagcatgaac aactttgatt tagagaacag 130800
agtctctgtt aaaatccatg ggacttgtca acttcatatt tttgtttatg agcataaaac 130860
actctttagt gcatgtcgga atcatttgat gcttgctgaa tcacaggttg ctggaaccca 130920
tccccagatt ctgattcagt ctgagatgag gtctgggaat ttgcattttt aacttgttgt 130980
ctggtgatgc tgatgctagt ggtctgagaa tacactttga ggatcacttt ttcacagtaa 131040
aagtcacagt cattaagcaa gttaactcaa tgagaaatga taatgaaaag gcatgtacct 131100
aaatagataa aggacctata ccagctatga atttgagttc agcaataatt gtaaaatttg 131160
taattctttt caggtatttg gtttttaaaa aactccctat gtatgctttt atcttatgtt 131220
ttatatggtg tccctctttt cctctctttc tctctaatcc agtttttaat gtgaacatgt 131280
ttaatgtgaa aatgttgttc aaagcagaag cgaacctttt gtgtaacctt ggcggtatta 131340

-continued agtttgtttg taagctattt ctgccctgtt agcttctgta ctgaaacacg ttttcttgct 131400
tttgttgcag tatggaagag aagagagcga ctggacaatt gtgctatcct gaatggaaaa 131460
tagaggatac aatggaaaat agaggatacc aactgtatgc tactgggaca gactgttgca 131520
tttgaattgt gatagatttc tttggctacc tgtgcataat gtagtttgta gtatcaatgt 131580
gttacaagag tgattgtttc ttcatgccag agaaaatgaa ttgcaatcat caaatggtgt 131640
ttcataactt ggtagtagta acttacctta ccttacctag aaaaacatta atgtaagcca 131700
tataacatgg gattttcctc aatgatttta gtgcctcctt ttgtacttca ctcagatact 131760
aaatagtagt ttattcttta atataagtta cattctgctc ctcaaacaaa tgcaattttt 131820
tgtgtgtgtt tgaaagctaa tttgagaaaa tttcataggt tacatttcct gcagcctatc 131880
tttatccaca gaaagtgttt tctttttttt aaatcaagac ttttaaaact ggatttcctc 131940
ccatcactgt tttttgaagg tcctccaagt ccgtgttaag gtaaatatct gttttcttcc 132000
tgatgtcaca gcctgagcat actctgtgca ttaggaagac ctgagtgcat ttcccaccat 132060
tgtcctttcc acattatgtt gtagctggct ggctgtcagg cgactacaag actgagggtc 132120
ttgtgcctta tagatctttg tatcccccat ggctgacata tagtaggtac tcagtaaatg 132180
gttttataat gaatcagtga acattttgct tctatagaag tgtaccttct ttgtttctat 132240
attatgaaac ctctttatta gaatttgtga ttgattctga cagtgtatag atttacctta 132300
tattgtcttt attttccatg agctactaag tcattagaga tactctgaag catagttagt 132360
ttaggaaatc acttcatatt gattgtatta gaattatctt ggaattgaag atatatccct 132420
agagcagggg accccaaccc ccaggccatg ggccacacag caggaagagg tgagtggtgg 132480
gccattgagg agcttcatct gtatttatgg ctacttccca tcactcgaat taccacctga 132540
actccacctc ttgtcagctc agtggcagca ttagattctc ataggagcac aaatcctatt 132600
gtgaactctg catgcaaggg atctaggcta tgcgctcctt atgagaatct aatgcttgat 132660
gacctgaggt gtaacagttt catcctgaaa ccacccttca ccctgcagtc tgtggaaaaa 132720
ttgtcttcca caaaactggt ccctggtgcc aaaaatgttg gggaccactg ctctagagag 132780
aggtcatgat atcataccaa ccaaatggaa atgacaaatg ttttatgtca agtgttaatt 132840
gcagaaataa atcttttttt tttttttttg gtagaaaaca aagaggcata ctctgatttt 132900
tatactctgt ttttgcaggt gctcttttct ttgaatggag atttgatgag caagtggtta 132960
ggatgcaggg agagctacta tgggtgatat tttccttgtt taggagctgt gagttaaaat 133020
tgtatccttt gtggtttatc taaggaaagt caaatcttga cagaaaacat ttttccttgg 133080
aaggtcaact ctcagacatt gtattttggt ttccctcagt cctcataact tccttcttgc 133140
tgaacatatt ttattctctt ttcagagaag gaaaataaaa aggattctaa aagtttgatg 133200
cattggaaaa atttccttga ggcatttagc aacacataga aaatgggctt tgattctttt 133260
ccaaaacttt tagccatagg gtcttttata gacagggata gtaaaatgaa aattgagaaa 133320
tataagatga aaaggaatga taaaaatatc ttttaggggg cttttaattg gtgatctgaa 133380
atcttgggag aagctgttct tttcaggcct gaggtgctct tgactgtcgc ctgcgcactg 133440
tgtaccccga gcaacattct aagggtgtgc tttcgccttg gctaactcct ttgacctcat 133500
tcttcatata gtagtctagg aaaaagttgc aggtaattta aactgtctag tggtacatag 133560
taactaaatt tctattccta tgagaaatga gaattattta tttgccatca acacatttta 133620
tactttgcat ctccaaattt attgtggcga gacttgtcca ttgtgaaagt tagagaacat 133680

-continued tatgtttgta tcatttcttt cataaaacct caagagcatt tttaagccct tttcatcaga 133740
cccagtgaaa actaaggata gatgtttaaa aactggaggt ctcctgataa ggagaacaca 133800
atccaccatt gtcatttaag taataagaca ggaaattgac cttgacgctt tcttgttaaa 133860
tagatttaac aggaacatct gcacatcttt tttccttgtg cactatttgt ttaattgcag 133920
tggattaata cagcaagagt gccacattat aactaggcaa ttatccattc ttcaagactt 133980
agttattgtc acactaattg atcgtttaag gcataagatg gtctagcatt aggaacatgt 134040
gaagctaatc tgctcaaaaa gatcaacaaa ttaatattgt tgctgatatt tgcataattg 134100
gctgcaatta tttaatgttt aattgggttg atcaaatgag attcagcaat tcacaagtgc 134160
attaatataa acagaactgg tggcacttaa aatgataatg attaacttat attgcatgtt 134220
ctcttccttt cactttttc agtttctaca tttcagaccg agcttgtcag ctttttgaa 134280 aacacatcag tagaaaccaa gattttaaaa tgaagtgtca agacaaaggc aaaacctgag 134340
cagttcctaa aaagatttgc tgttagaaat tttctttgtg gcagtcattt attaaggatt 134400
caactcgtga tacaccaaaa gaagagttga cttcagagat gtgttccatg ctctctagca 134460
caggaatgaa taaatttata acacctgctt tagcctttgt tttcaaaagc acaaaggaaa 134520
agtgaaaggg aaagagaaac aagtgactga gaagtcttgt taaggaatca ggtttttct 134580 acctggtaaa cattctctat tcttttctca aaagattgct gtaagaaaaa atgtaagaca 134640
aaaaaaaaaa aaaaaaacaa acagaggcag aggcaggcag tagcaagaaa gcagagcgta 134700
acatcagcta gatggtaaca tgcaatgtca gctctcttga agacatggga aacctaagtt 134760
acaccttggg ttaaaattct tcaccatatt agttttgttg cttcataaaa tttacctaag 134820
caagtggtct tgcttgcctc aaatccaagc agtcttgaac acttggaggc aattaatgag 134880
tatatcttag tcaaaagaat tgttggagct ttttattaaa gctacagttt cagttctgct 134940
tttggggaat tgtgctatga aagcagctgc caaaataagc tcatttattt tcttcaatcc 135000
cactcagtgc tcagtcacta tattctgttt cctttttttt tttcaagttg catatttggt 135060
ttccccttat gattgggaaa gatgaatttt cagcagaaaa cattgtttgt tcactttcaa 135120
agagtgatag tttctaaaac atttagagca ataaatattc atcagaggta ccaagtaagc 135180
cggcagaaga gttaagggtt agagaaatcc cttatttcat gtcttgactc taaaattatc 135240
aaagtacttt tccttgtaat gtggatttct tcttatgcgg atatgcaaaa acttcagtta 135300
tacgtagtaa tgctagcagg taattttagt agacatttta taacaactgt cactttgttt 135360
cgccacatgt agagtttgtt cagctatttt ccagatatct ccccacaaaa ggaggcaaag 135420
ggtaccagct tttcaatgag cattacctat tacttggcaa agatgatgaa gactctatta 135480
atagttcatt tgataaatgt tgacataacc aacaatagag attaggaagt tagttttaag 135540
aaatcaatgg catatagaca ttaccctcat ggagtttgta ttctactact tgaactgatt 135600
gtagctataa aagcatagtt agatagctga atagttagat cataagcaaa gaaggccaga 135660
acacatctct tatcaagaaa tcaatgaata gtttatctca tttttaaagc aactttatcc 135720
ttctttaatt ccttcctttc ttctagtgca aaactactta ataaggttgg tgtttaggtt 135780
agtgttcaca ccattcctca tctggtgtga attaccttct ctttctttac tatttactac 135840
caacctagta catgtgttga ctgaattctt ttcaaacaat gttgagttat catggtgcac 135900
ctaataaatt aacaccacag attacagcat ccttgctgat tttctcagca aagccagatt 135960
agatggaaat aaacaaagaa aatgatccta gagtgaattt ttctagaaaa tatctattat 136020
gaaccatgct gtttaaagta ttagcttgaa ggtgatggat ccagctattc agaaaataac 136080
tttcatataa ccatgatttt gcacagtatg aggtcttaaa tgtgtggaaa gagataaatt 136140
ttttatcatt accacaaacc ccttttaaag attcaaaggt ggaagaaagt gatttatttt 136200
ttctcttcag catacatata taaaagactt gtcagatgtt taatttgggg aggttgataa 136260
tgaaacatat caacagagta tagtagttat agtagtgttt gtgggtaaat aatttcctgg 136320
ggtcagacat atataaacat atttgcttca aaatgataaa ggcatgaaat cagtcttaaa 136380
aattgaaatg ggggtgatgg gggagaaaaa gaagaacaaa tttgaagtgc cctttcaaat 136440
ctgctggata caagtattga agttttaagt catcttattc tgtctgaaag tgtatttttc 136500
attctacaat agacccaatc aacaagacgt ataacttgag ttgcatgatg ttcagtttat 136560
gtaatctact gttgggatgg taagaattga tgtaggctgt ggtgtaagaa tgaattaaaa 136620
tatagtttca ctggcttttc tctacatatc cactatcaca atggctaggt ttcctgttgc 136680
tcactattgg attctggaga aaaatttaat gaaagatgat atcagaggaa gaataagtgg 136740
aggtagagaa gaaaggaatg atagaggagg ggaaaaaaac aaaacatatt tttgtgttat 136800
ccaaaggagc tttttcctta ttctgtcaag cattgagatc ttcttcagct ttcaatgtag 136860
ttgctaaata caaataatgc tactaggtag tgactaaata tagcaaacac ttcatcagat 136920
attagaatta ggtcacacta ttgaggttat aatctgaagg ttgtgttaca tagaaaccac 136980
tttagattat tatcaacttg gactaggctt tattttataa tagcatagta agtaatatct 137040
attgtgtcat ttcttcaacc attttattct aagatccatg aagcttcttg aggccaaata 137100
aaataataag tttagacaag aagtagattg tgactttttt cccttagaga tactatttac 137160
tatctcctat cctgataggt ggaaggttta ctgaattgga aattggttga ctattagttt 137220
ttaactaaaa tgtgcaataa cacattgcag tttcctcaaa ctagtttcct atgatcatta 137280
aactcattct cagggttaag aaaggaatgt aaatttctgc ctcaatttgt acttcatcaa 137340
taagtttttg aagagtgcag atttttagtc aggtcttaaa aataaactca caaatctgga 137400
tgcatttcta aattctgcaa atgtttcctg ggtgacttta acaaggaata atcccacaat 137460
atacctagct acctaataca tggagctggg gctcaaccca ctgtttttaa ggatttgcgc 137520
ttacttgtgg ctgaggaaaa ataagtagtt cgaggaagta gtttttaaat gtgagcttat 137580
agatagaaac agaatatcaa cttaattatg aaattgttag aacctgttct cttgtatctg 137640
aatctgattg caattactat tgtactgata gactccagcc attgcaagtc tcagatatct 137700
tagctgtgta gtgattcttg aaattctttt taagaaaaat tgagtagaaa gaaataaacc 137760
ctttgtaaat gaggcttggc ttttgtgaaa gatcatccgc aggctatgtt aaaaggattt 137820
tagctcacta aaagtgtaat aatggaaatg tggaaaatat cgtaggtaaa ggaaactacc 137880
tcatgctctg aaggttttgt agaagcacaa ttaaacatct aaaatggctt tgttacacca 137940
gagccatctg gtgtgaagaa ctctatattt gtatgttgag agggcatgga ataattgtat 138000
tttgctggca atagacacat tctttattat ttgcagattc ctcatcaaat ctgtaattat 138060
gcacagtttc tgttatcaat aaaacaaaag aatcctgttt gtgtggtttc atgaaatcag 138120
cattgttgaa tgcatgaagt aataatgcta aattaacatt tttatgatgt ctcaaggttt 138180
ctggtcaagg gaagtaaatg taggatagta tttttacacc aaaatgacac agagagaatt 138240
gagcacacca gaaagaccag aaaccacacc actggataga gattcaatat gtttcttttt 138300
caaacatttg gacaagaaaa aaatgggcat ttaaaaattc ttccttcccc tggttatgga 138360
tttatctgta gtaaaactta gctttgtcgt ttgagatttg cacagaatgg ggggagtaga 138420

-continued ttacctcttc ccattcattg tcataatgga tctacatcac tgataaacac catacttcta 138480
tatgtggtta actagcttta gaataaaaga cactttaaaa agtaaaaggc ctagagatct 138540
tcaatgaagt gtccctttta gccaaaccag gccttgcaga aattgtcctc aaaagcacca 138600
agggagaaca aagccaagtg cagaattacc caagggtcac acattttgta ttcattttct 138660
tataatttgc ccaaatgatt tgaagtacag caaaacctga agttttgcaa agagttactg 138720
taaactgaac ttaaaaatgt cagagtgctc ggtgacccac ttctccagac cctgtcaacc 138780
tgtgaaaata ttggccttta ttcagatctc tcaagaagtt acgcgcagag tttggaaggt 138840
ctaggcaaag gttattagtc aagtgttctt acagtgtcaa cgctcaattc ccacaagcgt 138900
gagaaagaga gacctgtcat tcctgagggt gatgacatac atttactgga gcttatataa 138960
tttatcagat aagacagcag tttccttcag ggtagaaagt gtgttttcta cattgattta 139020
gtacaaaaca aaaagaaaag gggatatttc aaattttata attatttttc tgctaagctg 139080
attcagtgtg atttaagcat atttttcaaa tcatgaatct gattccatat acatatgtgc 139140
cttatattgt gataatttat ttttaagtga aatatgctat catagcctga ctttatgtat 139200
agtggtgaca acttgcagga tcgcatttct gtaaccaaac ggccgacagc tgaggtgtag 139260
atgcttccta tggtctgtag aataatcact gggcttgttc tctagctatg tctgtatgca 139320
atcgcgacag tgttgatcaa aacccatgat cattctctcc aaaggtcttt gtcactaagc 139380
cactagggat tctgaaaagt tcgtgagctg aaacaaataa attgagttgg aagatt 139436

<210> SEQ ID NO 93
<211> LENGTH: 130421
<212> TYPE: DNA
<213> ORGANISM: Homo sapiens
<220> FEATURE:
<221> NAME/KEY: modified_base
<222> LOCATION: (28255)..(68254)
<223> OTHER INFORMATION: a, c, t, g, unknown or other

<400> SEQUENCE: 93
cctgtctctg gtgtgccctg gcccccgact tggaggcctc ctgggccagg ccaagacctt 60
ccccggcagc gatggtctcc agccacactc aactgccctg aagggacatt tcctgcttat 120
tcccttgccc ggctgtgtcc tccacccgga aggcctgtgc cttcttcgcc tgcatgtcct 180
accctgagga ggctcccttg gtctttcatc gctctcccta tgggtcttca cgccttcccg 240
aaccaccgcg cccaagcagg agcacgttct cggccctctt cacagggcgc tcctcctcac 300
aggggtgccc gggattttta ttctgtgcct tcctggtggc tcctacaagt ctggaagggc 360
aggaggcgca tctcactcct ctgggtcccc tcccctagcg cctggcggga gcccaggctg 420
catttgtgga attcatgact ttttctctcc tgctcaagct gaacacattg ctggctcctg 480
ctcgggtgga gcccggctaa ttagagtgag gggctccccg tagggcgaag gggtgcgctg 540
tcagatgtgg cattcccgtt ttacggagac acacggtgtc ttacacgcca gggagaggtc 600
tgagacgcaa agagccgtcg agcgggctgc gggattgctt cgctgtcacc tccgcctgca 660
gccacccttc cgcacgcact tgtgtgtgca cccaggccaa catggaaggc gccatcctaa 720
cttctgccgt gagcaggtgg gagggaagag agacgagagg tattccattg gttgtctggg 780
aaaatgaatt gcaccttccc ctcccttgcg gaggatcaac ttttcccacc ccctcgggtg 840
ggcactcgca tcctggggcc ggagcctgaa cccgggagcc aaggggcccc agttccaggg 900
acgtgaagct gagcgtacag cgggcgctcc cagacactgg ggaaagtgct ttacgatgtc 960
ccgagtccct ccagtctcgc cagcggggcg agcgtgaggg tgccccgacc gaccagcggc 1020

-continued

```
cccgggtgca gggtggcggg cccggcggcg cgcgtccccc tccccctcct ggcggcccgc   1080
acgtgtcgcc cgcgccgcgc ccccacgggt tacgcgcggg tcccgcagcg ccgcggccga   1140
gccgggctgc ccggcccgcg gacacagcgc cggccgccgc atcccgtgcg gggccgcggc   1200
gcgatgctgc gctggaatga ggaagcgcgg cggcgagggg agggcccggg cgcggtgcgc   1260
gcgggggtgg cggcggcgcg ccgagcgggc ccggcgcggg cgagcgggct gcagccggcg   1320
gcggcgccag caggtacggc ccgcacccgc cgccgccccg gcggcctttg ggggctgagc   1380
cggagcccgg cgcgattgca aagttttcgt gcgcggcccc tctggcccgg agttgcggct   1440
gagacgcgcg ccgcgcgagc cgggggactc ggcgacgggg cggggacggg acgacgcacc   1500
ctctccgtgt cccgctctgc gcccttctgc gcgccccgct ccctgtaccg gagcagcgat   1560
ccgggaggcg gccgagaggt gcgcgcgggg ccgagccggc tgcggggcag gtcgagcagg   1620
gaccgccagc gtgcgtcacc ccaaagtttg cggggtggca gggcgcgcgc tctggccacc   1680
cgccgctctg ggcggcagct ggtggcaacg caagggcgcg gcgggggcgg ccggcgcgga   1740
gggggccagg tacggggccc gcgggcggcg ctgtgcgcgc ggggcagccg gtcggccggg   1800
agcgcgaaag cctggtctga gccggctggg ggcggggagt gtggcggaga aatggggaac   1860
aatgcgagtg agcaacttca ggaagtcatt gtgaaagaaa gctgggaaga gctccgcggc   1920
caagttagca ggacactcta acaagtgact gcgcggcccg cgcccggggc ggtgactgcg   1980
gcaagccccc tgggtccccg cgcggcgcat cccagcctgg gcgggacgct cggccgcggc   2040
gaggcgggca agcctggcag ggcagaggga gccccggctc cgaggttgct cttcgcaccc   2100
gaggatcagt cttggcccca aagcgcgacg cacaaatcca cgtgagtgtt ttcaaattga   2160
atttcaatag gaaaacttgg ggtaactggt gaatttaaaa aaaaaaaaac acagtaaaga   2220
aaagcggtaa ggttggtaga ccctggtgtc gctcaggtcc gcctctcttt tctgaggaca   2280
gtgagagagt tcacttctgt caagcgtctg ttgctctgca ctgtgccagc aggtgcagga   2340
ccaggccgac atgggacact tctgagcagc cccgctgtca ccaggagagg agttctagct   2400
cccaaccata tttaaattta tgtagaccta catataccca cggaagtcag cctttataaa   2460
gtcgtgtgta aagagttttc cttatatttg agccgggagc tttcttttta tactataaat   2520
atgatgagat cgagtctgaa cttaatttct gcaagagagg aattatcccg gctttgaaaa   2580
gttagtcctt ttgctgaccg caggtttgac gctcaagtca ccaaaccttc tcaggaaaac   2640
ccttagtaat attaaggcat caggttactt gcggttatat ttgaaatgta ttttaaatat   2700
ttgtcaagca tcgctgctga tgcctaagga acctcgtgag ggcttgtttt tccttctaat   2760
ttggaggcat ctaatgaccg aaaaccgtag cgattccata gggtctgacc aggcacagct   2820
ttcaaatgca gcttccctct ctctagggac tgcagcccac ccagactgaa tttcaatgcg   2880
gtgcgctttg cttaggttac ccactcacaa tttcccactg cgccgcaggc agtatatttc   2940
agctttgaga taccttgttt taaaattcca gacaaaatgg tgttgaggaa atgtctcctt   3000
actagtccca tcaacttctg ttaaaagagg aaaatttatg gaatttgaaa atactgcgta   3060
tgatatttaa actttcatag acattcaaat gcttttaagg ccaggttcaa tttggttatg   3120
agtcgagggg tggggggggac ccacatagaa atgtcctggg tcctcttgag tttatttctt   3180
tgtttgaaga tgtttgttca atgagtttta ttgtactcat cttttatatg gaattttaaa   3240
aagtaacaat ttcagtatta tttatattag aatgtgtcag aattatttcc gtgacaaatc   3300
agatcatttg ggctatggct taaaatgtac acgaggcaaa tattcatgac aagaagattc   3360
```

-continued

```
accttcttac gctggcatct tgtaaaatgc agaacaagtt aaagaaataa tgtgtacaca   3420
tacaaataat gatgtcacat taaaaatact acactattct tgcttgatgg aatgtatctg   3480
atttccaatt tcaccatgaa catatttcat acatttttta catgaaaaaa aacgtgactc   3540
ttaagtctca cagtcaatca gagctggtga ccagaacatt ttattgaact aaatggtcat   3600
gttttcttcc ccttttgttt cacggtgaga gttgaaggaa ggagtttaga aactctccag   3660
tacttgttta attcatcagt gttctaatta gagtggtacc tcttggaaaa ctacacaccc   3720
ccctaatgca gaaacatcat agcaataatc acccaccctc agggtctcca ggagaccaca   3780
agggctgcag ataaaagtct ggatgtgtta ggtttgaccc tttcgaagag ttttacacag   3840
gctcctaaag agaagatcag ctgtggccgt ttgtagccat ttcctttgtc gaaaaactaa   3900
gatcgcagtg aatgtattag ccaagaggtc taaagccctg ttgtactgca ggccactgtc   3960
ttccttgttt gactagagac ttggagtttg agaacagtgg ttctttggtt tggatacatt   4020
ttttgttctt gatttggatg tgtgtgtttc atgcgtggtt aatatagcat attttcaata   4080
taaatgtcaa aaattttgaa ataggaaaga actctctata tattaatgta cttatacaca   4140
cacttcaaga ttatgcattt attaacagat acatgaaata aattccatgt gcatatgcac   4200
atatgcacac agagcgtgca cacacacagc atgcacacag cgtggagtga gaggcatggg   4260
gcagtgtgga agagttttaa catcaaacag acctgaaatg agtattaaag gcccccttta   4320
tttttaaact tttactaaaa caagatggat ttccctatgt tatataatgg tgaattttag   4380
gcataaataa cgtttttga gtgttgcata attgtacgta ttaatgtaat gtaactgtgg   4440
ttaacgaaga attcatcaag gatatcactg ttttgtggca ttttttttt cctcctctaa   4500
tctttggact tgtgaaataa tttcactatg aaataaatgt tggttcttgt catattctaa   4560
gggagattga tgtaagtggc tccactccag cttacagaag gtaaaccacg accttttgc   4620
gttctctgaa aacgcttgtc ttccgatgcc tctgtttcta agactgacaa gcactctggg   4680
ggcactgtga cgcctgcttc tagcggcaga gttgctgcag ctcctgtcct ggctgtgaac   4740
attgttctct ctctggtgtc tctatgttca taactacaga gacttcagct ctattccatt   4800
tcatatttgt gctgaataat cattccattt tatgggagaa aacacaagat gtaaaagcaa   4860
caagtgaccc atcctttgaa gcttacaaga agagaaacat taatctattt cacgtcttga   4920
aaacagatca gttttatttt gctcaaaaag ggcacatgta catttttgat ctaggtctta   4980
gaaacgtaga gtttcagagg atcagcatta tacacactgt cacacacaca cacacttaaa   5040
attcagatga ggaacaagat aggaatgagg ttttgttagg gacgcagagc acctaaaacc   5100
aaaggatatc gacagtaaca aagctgtttt tactgtagtg ctgactgaac actcatgctg   5160
gtgtcttcat gtggaccatg gctttcttgt atttctttgc agtttaataa atgacttcat   5220
atctcaggtt acctttccac atctcctgga atatatgttt atgtccttaa agtttcagtg   5280
tcgtcacttt agtagcttta gtttgagttt ttaaatgttt ggtaatattc caacaaatat   5340
tttttaagac attatgaaac cttatgaagt gccatatatt acaagtgaga taaaacagca   5400
agcaaaagaa ggtttgcaga aggtttttaa gtggcgaagt gcgggcctgc ccattttggt   5460
gtctccttgg tggttactcc tgagaagggc ctggaggaag agcaactgag gcctaatcta   5520
caggcaactg ccaaattgtt tcagttgacg tttttccctc tcatgtttga ctataataaa   5580
taggtagttg ccagtggagc cttcagccaa ccacctggta ataaactgtt aaaaatggtg   5640
caaaccctag gtcacaggtg tgggggccat ttgtcttgcc tgttaacagg cctggcctta   5700
attcttttct cccatggcca tttctgcctt tggggaactc acaattcctg ttgactaaaa   5760
```

-continued

```
gagcaccctt ttccaccaca agcctgacaa atcagacgtc cacataattt ctgaactcgt   5820
tttggttagg acaggaagca caggctccct tcctgtctgt gttttcctaa gagaaaacgg   5880
tcttccctcc tttttgcat atttggcaag tggttccacc tttctctgca ccctggtgga   5940
gtgtgaaggc agcagaggaa ccttttggag gaggaagagg acacagaggc cctgtagcca   6000
ggcaccaaga tccctcccag gtggctgggt ctgaggggaa ctccgagcag ccctaggtcc   6060
tcaaagtctg gatttgtgtg gaaaaggcag ctctcacttg gccttggcga ggcctcggtt   6120
ggttggtgag tgccacacgg tttctttgtg tgcttgcatg gattggaata gccattgtgt   6180
tcttccgtct tccctgctgg tgtttccaca gtgggtggcc tgagcccaga gcagctcccc   6240
atatccctgt gcaggccacc tgtctcgggt gatggagagc atcattatgc tccgtctgaa   6300
cgctctgctt tcggatggcc ccatgctcca cctcctgata gctcgtggcg cggggccacg   6360
gcttaacaaa tggctgaaaa tgggtcctaa ttagtggaaa agtgctttct tcatattttc   6420
tcactcgagt gtgcagtgat tcatttttct tctgcaatca gctcactgct aaagtaaatc   6480
tgactctctt cccgccattg cacaccaaaa gttaactcta atgggtagga ggttaggttt   6540
gttgagagag caatgcagta aaaagagggg atccaatgtg gtcttgtctg tctggtcttc   6600
ctttcttcgt tttttcctcc cttgtcttct ctgtcattcc cttccctcca tttgccttgc   6660
ctttcctgtc cttcccttcc cttccttccc ctctttcttt ctataattgg tggggggttt   6720
gcacagactg ccaaaacact aagaactgtg taaagtgttt ttgaatggcc ttacacatat   6780
tgaagtagat ttttatgctc catttttgag atcacacact aaaatctata cctttaaagc   6840
attttctgtt agtttgaaac tatttgaaaa tgaacaatgt ggtttagatt agagtcctgt   6900
tctgaagcta ggagttccac tatgaatatt gatttatcag tttttgacaa atttttgttg   6960
ttataccaga ttttcactgg caaacctaga gcaaataaaa ttccacataa gatacttccc   7020
tagacctaat gggaaaaatg tttaatttag agtctttagg agaaatgaga atgaggaatt   7080
gacctttttgt aagcttactt ctgaggcact ctgaagtgtg ttccagtgct tttaatggaa   7140
actagagaga gccagcaacc ccctagtgtg agccccactt ttaaccggaa aaagtgacct   7200
tttcctcctc ctttgtgctg agttttgcgt agggcagaaa attaagctga tattcaaaga   7260
gattcactgc aaaaacatat tgataaatcg tatattctat ttcattaaat taaaaccata   7320
ctgctaatta tctcaggttg ttaaacataa ggcaattaat tatcatttta aaagttggta   7380
ggaagttgtg agtacttttg cagtatgagt gttttcccgc tttagtatga ggttgtgtat   7440
gtttgcttga atttacagaa ttttcacttt aagagcagac aatgttttgt taaagaaatg   7500
aaatttgcta aaaaggagca tgtaaagtga aacattaaaa ataaataatt tcaacttact   7560
taagagctgc agaaaaatct gattgctgtg tttaaaatga attttcccac atttcgctct   7620
cttatggaca ggagcatttt ctgtcaggtt ataaataaag acatgcccat tttttgtacc   7680
cccacaaatg aggaagttgt aagctctctg aggttttact gatgagcccc ctccccctgg   7740
gtttgcatga agagatcata ggccacaaat aaaggactac aaaatggggt ctaaactatc   7800
ctggtggggc ctgataccca cgtttcgcat ggaccttacg atgtgatgaa tggttttggc   7860
atgagtgtct taagaatgct tccagattcg ggttacagga cagccagcgc tgagctccct   7920
attgcagaac aaagtaggaa tctagaactt tcttgctaac aggatccagc taaaacacca   7980
agttagattc ttaaatgatg ttcttttctg tcattatttg attgttgtca gtagcagtaa   8040
ttgttaccaa gccattgatg cttctattct tccctttgcc cttctgagac acagctcatt   8100
```

ttgacttcag tggaacccct cgaaggtggg gtgatgagca aggtgaattt tcaaagtaaa 8160
gctactaaga gaccaaacta caatttaagg aacctgattt ttgaatcaaa ttccatatac 8220
tgtgggtata gttcaacata gattaatttc ttatagttat tatgaaaaaa atctcatctt 8280
gatgatagct gataattttg tgggtgtcgt aaacaaaaca gaggtcagaa ttcagtccct 8340
tggggaaaat ttccaattag taggaaacca agtggcctac cttagtttga agacacccat 8400
caggatgtct gcaccttttc atcctctctg gaggaaagac taaataccca ttattgtata 8460
taggtcaggc caaagcagcc ttttatattg caaggaataa gaggtaaata gatatatgtg 8520
caacaatgaa tcccctaatg tgtttactct agaacacatg ttctttctgt atttatatgt 8580
agattttgta gatcttgtct taccacctgc taatggtaga tactgtatct aaataagttg 8640
aggaaaattt atagtaccta ggaatgtgtc ctcagtgggc caatcaatca atcatgactt 8700
caggttattt ttaataaata tacacgtatg ggttcataaa caatgggatg ttcttgtgaa 8760
gatctaaata attttacttc tttgggacta aataaaatat agcttttgcc aaataaactc 8820
acacaagcac ttattttaat agaagtcaaa tggctttgca gaaacttcag ttttacaggt 8880
gcattgtttg aaatgttacg ggtatacaag tggatttctc tattatgtac agtgttaagt 8940
ttgagtttca aaatgtccac ctgaaatgat ttacttgtac gttaagataa tttaactgct 9000
aagaaggcaa gataaagcat tctttgtgac accatatggc cttgctgagg gaaaaactta 9060
ctgttataag tttgtgttta tctctctttt taaaaaaaaa tgaagaaaaa aacgtttaaa 9120
ataatgggaa cacagcagtt cctggggtcc tctgtctctt tatcttatta tagtaaatta 9180
ccaaaaaaat aatgacctgg ggcatgtctg tgtggaccct tcttttagag gcagtttctg 9240
tgttttgtaa agctgtaggt tctattttca ttgcacttca tattgctgca cagctcctga 9300
ccatgcatga aggtcctctg aaatcggtaa gagggcagaa gaaaatgatt ctaaacttag 9360
attttttttaa cttaagtgat gaagtgtgaa acgccattta tatttgagga agctacctag 9420
gaagtggctc atgtcgatgg cccaaatcag aagagggcct gtaaaagctt ctatcaattt 9480
tgactgtgta tgcttctacc atggcggctc aataaacagc agtattagtt taagagtgga 9540
tggtacagta gtatagacgg gaagcctctc ctctccgtgt gaaccgtgca cccctatgag 9600
agggtagaga caatacaata tgcctgtaac gtcaggacag acagtcatgg ccagcttgaa 9660
ctccagccct gggcttcttg cagcaacaaa cgtgaacaca gaggactgtc tccaactcca 9720
ctttctctat ttttaaaaca actttttgaa tacagtatct gccatctttt cttatacctc 9780
actttgaaac aggtggctcc actgtggcat ttaaaatgtt ctgtttcttt tccctctgta 9840
tcaaatacct ctttaccaag aaaacattca aacagcatag tttttaactg tattttgaaa 9900
ggtttcctta gttccctttg acccttcctc ttttgcatat cagttcctgg ccataaaaat 9960
aaaaaatgct aggacagaat tgcacatctg agctgatttg ccctcaaaaa gtttcacagt 10020
ggaacaaacc gcaggaggag ttttctgtgg ctcagttaaa tgtcgggggga gggtggtgtg 10080
aaagccaaat tggattcctg ctttcctgtt taaatcttgt ttttcattgt tatttgcacc 10140
agcaatactc tgtggaataa tcatgaaaat gtgtagattg gcagctaatt tttgaaaaat 10200
gaaaagaatc agaaatgaaa taagagtgct cggaagtttt tatgttctct caacctgttt 10260
tgtcaaattg ttacgaaaac ctataaggtc tctttgacta gatacaaaga ctttgcacat 10320
tgccttagct ttctcttgaa gcatttcctt ttttaaaata cagtgtaatt cacagtgata 10380
tgatagattt gcaaaagtaa aatctaccag tctgaagatg aaaggacttg tctcttagca 10440
ggaataatgg gttttattaa agaggtctgt gacctaaggc attttaaata aattacaggc 10500
ttggtccctg tctcccccat gtatctactc ccttcaatat aagcatcatt gagtatttaa 10560
ggaaataacc ccaaatgtaa ctctagtgta gcttcacttg tcagggagga aaaagtaaat 10620
agcatacatt tggccaaata accagaactt tactgtagaa gttttatgat gaaatttgcc 10680
tttagtgcag agtattacaa agatcatgtt tagtttctag cagtatataa gtagcatcca 10740
tccttatctg tcatgcattt ggagtgtgcg acccctgcac tgggctgcaa cattctgatg 10800
ggcaagagtg ctagggagaa agaggcatca ccatcagact gcacgggttc aagtgtcagc 10860
tctgtggttg attagctgtg tgacctgggg aaagctattt ctcttagcct tggttctctc 10920
atctataaaa tggagataat gatgcagatg ccttgggttt aattgggaga gttaaagaca 10980
catttacata tttagcaagt aggtgttgaa ttctagctct acattggaca ctatgccagg 11040
tgctcaaata aacaagtgga caagacagac aacacccatg gtcttatgag gcttaaccat 11100
ttgcctcttc aatgccagaa acttagtagg ttgattagat aaagccagtg agtaccagta 11160
tccttttctt tgcagccttt tcctggcaca ctaaaaatac tcagtacata tgaaatatca 11220
ctggacaaag aatccccctt agagtaccag tggagaagga aggcatttgc ttaaaagcaa 11280
accaacagaa agacattgta aggcagttgt ttaagtctca gagacctata atttttttct 11340
tttttctttt ttttcatctc gctctgtcgc ccaggctgga gtgcagtggc acaatctcag 11400
ctcactgcaa gctccacctt ccgggttcat gccattcttc tgcctcagcc tcccaagtag 11460
cagagactac aggcgcccgc caccacacct ggctaatttt ttgtattttt agtggagacg 11520
gggtttcgcc gtgttagcca ggatggtctt gatctcctga cctcatgatc cgcctgcctc 11580
ggcctcccaa agtgctggga ttactggcat gagccaccac gcccggcaac tacaattgtt 11640
cttaaagctt gtagaattac tgtgtgctac caacagacag gctaattttg agtgaccctc 11700
agtactttgt acagttaatt tggcacgctg tgtacttagt ggctttttaa cagctataaa 11760
tttgggctgc tagaaaagta gtaaagttgt gattcttgac aggcatctat ctgcattttc 11820
atttttactt catttgtcta gactcagctt gtcagaatta tggaagagac tccttgtgtc 11880
agggcaagca ctgtgaagag aggtattcac tgtcagaaaa gagaggggag ctggaggcag 11940
ctcagaggcc tgagacccgc ctccacagga gccccagcag gttcggtgga gctctggcca 12000
cactctcctt tgggatgctg aagtcagaat gagttcactt cccagccagt cttgccaagg 12060
ctcctcacct ggaagcagca actgcccagg gctgttggat gtttctcccc aggggacagc 12120
caggtcccag tcccgcctcg gtgtggaagg aggaaaggca gggtccagga agctgtttca 12180
ggacaggccc aaggtccccc agggatgcct ttcagggtca gcggaggctg taaatcagca 12240
gggcccacac ggcctggaag aggcccctgt gctgtcggct tgcccggctt gcccggctcc 12300
tagtccggct tctgctcctc ctttgtaaag ttatggatat gctaatagtt tccaactgag 12360
actaggaaag taagtcctac ttgacactgt ttggtcagaa agagggagag aaaggagaag 12420
gacagagaga gactgagaga gagacagtct cagacaaagg gagacggagg gagggaggga 12480
gagacagaga aagagatggg aggtaggtgt gggaggaggg agagatgcag aaggcagagg 12540
aaagacagac agagatttag acctcccaag tcagtgagca gtccagagtt ggagtggagg 12600
gtgcctggtg gcttgtgact gcagactcca ctccccgctc ctagaggcac agccatggac 12660
agcttctgtc acgttggccc tgcacttatc tctgcatcta tttccccttg tgcaagattc 12720
agaactgcat gctccaaaaa aacaataaaa gcattcatgt tcataagaat tgcacaggta 12780
aaaggtagtt tgctgatatt gttgtatttt ttactatcgc ttcttttagg tcttgcctga 12840

-continued

```
aattgtttgg gtttcccagg caaagtagaa aactgcggta cgtttctgtg aaataattat  12900
tccttctggc atctcccttt acagacctac tgatcttgat ttttcattta ggtgaaagtt  12960
tgtgaaaaca tgccattagc ttgctttgtg attaactcct tttactgaat gtgagctcct  13020
tttaaattga ggccatatca agcttaaatt ccatatttta cccggcactc tgcatttctt  13080
ccatgtggga gaggaggggc tcagtaagtg ctttgtaaaa tacacagccg aagtgatgca  13140
cgtgctaaca aaggagtgtg acaggactta agtgcccttc tagacacttc aggctcccct  13200
ttgtaagctg tcttggaaga ggccacattt cctttccctc aaacagtttc tcattgtttg  13260
attattcttt tagcctttct ctggaagcaa agccactttt acgagaaagt cactgctttt  13320
tcatctcaag agatgcaagt ttggagtttg gggaagtttt caggtgcccg tcaagtcatc  13380
ctttatgatg tcagacgagt caggccacag aattcacagg gctcagtgca gaccgaaaac  13440
ttgaggcctc ttgttcagaa attattaaaa attttggtga acatcacccc aagcaaagag  13500
atcccctaag caccagcccc caagcaactg cactcataag cccatgaagc cccctgctgt  13560
cagaaacaat gtggttgaaa ttgtgtatgc acttggaagt gagatggatt gcaaaacaca  13620
ggtctccatg ctggggcagg agtggtgata gggcatggag tggaaatgtc cagcaggccc  13680
acgtgcgaaa atgcagagct ctctggctct tgcagacttg gctgctgaca atagacgcgc  13740
tccaggaagg tgctcgctgt ggtgtgatct gctgcccacc cctagctccc tccaggagac  13800
tggtgcgggg actgtttgca aatgactgca aaagtaagaa ggttcccaca gagcagagct  13860
tgatttgggg accagccgag ggcagtttgt caggattccg gcttgaaact gttctcacat  13920
ctcaccgcct gaaaggacga gtgtgtccag aggacttagc attgatcacc tctgtctcca  13980
tgcagcaaac tcagaggctc agcccgcatt ccactggaag ggcgtttgcc agtggtgttg  14040
gttggaagag ccttgacttt gccttaggaa acatcttttt ttaagaattg aaaataactt  14100
gagtatgcaa cagtagggca tttgttatat aaattagttg actagtgtgt agccagtaaa  14160
atgatgatgg tggtgtgtat ttgttaaata aaaagatatg tgtggtatta aattaaaaaa  14220
tattttaaaa caacatattt gtaatctgtt tagtgtcctc tttttgtaaa aagtacagaa  14280
ataaatatac agaaaaaata gtagtcctaa gtggtagaaa ttatgagcat tttcttgcct  14340
ttaaaaaaag ttgtaaaaga ttgtatcatt tatgtagcaa aaagttttaa gtcagcattc  14400
taaaaatttc gtgttgttat agttgctgtg acaagattta acttctgtat gcttcaccaa  14460
tcaatacaga ggtatttaag acccggtgtg tgataggccg cgctaaaata ctatacacat  14520
cttcagaaaa ctagagaact aacttctaac ttcctatatt agtgtggcac ggctgttaca  14580
aagatttttc tcatttgagt ctatcttgct tctttatcat tgttttgaca gtttcagaag  14640
aatcgtggct tttccccttt tttacagtaa aggtacctga gactcttgac gtattgcttt  14700
ttggaaatgc ttgtgctggt cacatgcttg catctgggct agtgtgtctg gcttccgtgt  14760
gctggtggat gcttactctg ttttctgaaa tacttttttct gtacagtggc cactagctgt  14820
actcctaagc cacacaccta ccttgaaaat tcatgtcact tttagaaata gataaaagcc  14880
cctcccatcc agaaaaagtg actatcatgt atatcctcat catgactaat actgatattc  14940
ctgaaattga aaatacatat tccatatgta ccataaaagg tattaaagat atatggagtg  15000
atagatatat tatatataac acttctaccc tcacagtttt cagcctaatt gagagggtaa  15060
gatccctgaa tcatccatca gtttttcagg tctctgctga aagcaggcca cagctcagat  15120
ccacacatct gaaccagaga cagaggtggc caaaaataaa aagggggaca gggggacaac  15180
ctggtttaga gtcaacaaat agactgcatt ttctggttag tgaaggagct ctcctgaaag  15240
```

```
tcatatacca gagcataaat gagcagattt ccttgaggtc accttctgct ggccatagct  15300
ttcttatctg tggagctgcc agctgtcatc cactttgggg cacctgagac tgccgagcgg  15360
caggccagga cccaagtgcg aaaacacaga acaccttttt gtttctactc cactgatgct  15420
ggggttctct ccctggtgtt tgtggctcgt agtacactct gtggaacatt cactatggtc  15480
atcgaagggc agcatcttcc cagttgtttc tttcttttct tttttttttt taatttaaac  15540
cgatctgaga agccagccat ctgtcagcaa aacaggaagg ctcgggctgt ctcctgggct  15600
cgttttgctg ccgtagtgag cgtcacttct ccccgtgtaa gagtgctggt gaaggctgag  15660
gcaagggccc agaaagattg agggacaaag acaggagcgc ccgcattgcc catctgccag  15720
gctggaggtg tattcattat tgatggaggt agtgcagttg ctgctcagat atgcagccct  15780
gcctgggtaa atgagacatt cttcagcaaa ttgcttcgtt ttttgattgc tgattgtacg  15840
cgtgtcacca agctgactca aggttcatcg atgcatgctc agtaaattag aaagaacata  15900
actatggatc agccaagaga atgaattctg tgcctacaat gacccagggc catttaattt  15960
tctgcttaat tttgttgcag tcagtttgca ttttgggtta ttatgcagta ggaaattaac  16020
aataaataac aaatttggtc ctcctgtgct tgtaatgata tttttataaa tctttgtaat  16080
gctgtttttta aaaggatcaa ggtctgtgcc agtctgatac tccagcaagt atgtgaggag  16140
gaaaatgcat tattcttgct agataacctt gttgttaaat agcatagggg ttctttatct  16200
ctctctcttt ctcatatctt attagtattt ttgctttaaa ctaaaatccc ttcctctctt  16260
tctcagataa cctgaggacc atggatgctg atgagggtca agacatgtcc caagtttcag  16320
gtgagacctt atgagatagc tgtgtgggaa gttcatgaga aaagcttccc tggggccgga  16380
agtcacagtg cttggtatgc tcatgggggga ggaatagggg ctattctgca aaagaaaaga  16440
ccatgatgga atttgcctga gtgtttcctt cacctgttac aaattatctc actttgagct  16500
gaacagaaag cctccaagat gaaattagtt ttactgttaa acttcaggaa aaaaaaacgg  16560
gaagagttaa atacattttt gtactgttgg aaggaaaaat ggctgattgg tttaaaaccc  16620
aaacacatgc caatgatggt acttaaagag agagagagag agaagcttga aaaacataat  16680
tgttgggcac agtcatgact gtttgttcat taagcatgga cacaacattg ctcccctttg  16740
ccatatatct tttcaagccg tattggatat agctcttctc atccaggaga cccaggaagt  16800
ggagaagtct gtagtaggaa aagcctaagg gtaggtcaca gactgtgacc atttggcagc  16860
actgagggtg gacggcgagc cagtccaaca aaaccgcaca gttccccagt gcatggacat  16920
aggaagacag ctttctatct ggccctgtat ccagaggcgt cagccccagt agcagctttc  16980
atggactttg gggttttcgg tatttcatat ttttgagcct cacagactca cagccagccc  17040
cagaggctga cttatatttg agaaagttct cagtggcacc ttgccttggc tgagcgccct  17100
cgtgttttga agtttctatg ggattctaca agttggtgct cctgatgaag accaggacct  17160
atgtgtggct gctcccctgc ttggtggttt ccctggggaa ggtgcaggag aggatcttct  17220
gagttccatg gaactggaga tagatctgcc aatcacaggc ttccttctcc accactcctc  17280
agccgctcta ttcatgtttc agattttgga cttaaactct cccaggtgca aagaacaaac  17340
aaaaggctag cttatttttc ttttagagtg aggcttcgta tttattacaa tataattgcc  17400
acattctttg tgtaattctc acatttatat cttaaatata attctcatga atgagaatta  17460
tataattctc tttttgtata tcattgaata ttttcactta atttttaatt tttttaatcg  17520
tcacaaaata attgtgtaca tagacacaaa ataattgggt acatagtgat gttgtgatat  17580
```

atacaatgta tagtaatcgg atcaggtaaa tcagcatatt catcatctca aacatttatc 17640
gtttctttgt attaggaaca ttcgacatct tccttctagc tatttgaaac tatatattat 17700
tgttgactac agtcatcctg caatggtgta gaacactaga acttattctt cctacctagc 17760
tgtaattttg tctcctttaa caaatctctc cctatcttcc actcccccga cctttccagc 17820
ctctattagc ctctgtccta ctttctactt ataatgatga cagcagcatt tgttagtttc 17880
cacatgtgag tgagaacatg tggcttttta acttttagaa tgtggtattc aggcacttca 17940
tggtacagtt ggtaaaagtg aaaatgtgtc caaaagtttg tgattatcta tataaacaaa 18000
aatggtataa atacaaatat caattttgca ttgaagaact taccttagag gtatattctc 18060
acaagtgcac agagcattta agcatttgtt cactgcagca ttgttatcag tattttaaaa 18120
ctatggtaca tccatgtact tccacataca gctcttaaaa ataaggagga tatgaatgaa 18180
ctagtatgaa aagaagtcca aatacatgtg aaagtgagaa tagcatggtt ctggatggta 18240
tgcaaagtat gatctcgttc ttttaaaaga aaataaatta catacacata catattttct 18300
atatgcttgc ccataacgtt taggaaaatt cttgggtgat atttattaac ctggacttcc 18360
tcttggaaga ctgatggtag aaggaagggg acgagttagg gaagaggagg agaaggaaaa 18420
ctttgctttt catcttctac cttttagcat tatttgaatt tattttcctt aagcgtttac 18480
tttgtttcgt aaacaaaaaa gcacaaaaac aaaaaacgag ttaaatggga aaaaaagcag 18540
tttagctctt tatagcctct catttggctt cgccagcctc tcactgcagc ctcagagagc 18600
tggtctggga aacactggta gatgaggact gtaatcctca ctcatggaag aggatctcat 18660
tcactgggtt tgctgactgt gactagaagt gattagggtg tcaaaaaacc caagcatgtt 18720
aaaaatttcc agaggccaaa aagatgcttt cattgttctg ctcttctttt ccttgtcgct 18780
ttcactttgg gtagcttcta aattggtatt ttgcatggtg catttaaaga aaatgagacc 18840
cctttggcca atgcaggagt ctacactctg atattctaga gtcaaagctg aatgctgaca 18900
cctaggaatt catctctaga atgtttatat aaggaatagc ccctcagtat tccgatctcg 18960
tatcttagta acgaaactaa caaaagcctg attctcctct ggtagttttc ttgtctttac 19020
cataatacaa aataagtaat ttgttctgca ccctgactgt tcaaaggata gggtagctgg 19080
gggcggggac aagaatggag accttattac ataagacttc ctgaaaaagg aaactctgtt 19140
tttgtttgaa atgatttggt ctgaaattta gtttgtgtac acttaccaaa gggattccta 19200
tttctaaaac actcatactg cttttgattc ctgttaacct ttgagcactc tacgtaatga 19260
tgagagcact taaagagtca tgtcactttt agtaaagaat caaaggatac tttttctact 19320
tcttcgagtt tgatctctgc ttctccagtt aaaaccagta tttgtttttt tcatttctaa 19380
agttggaaga aatgacagtt agttatggca taaggatgta catttaacca aataggagtt 19440
gacattcttg gtaagaaatc ttaccaagat tatgttatag attataagaa atcttaacaa 19500
gaatatgttc ctaaatcatc ctcttttccc ataaaatatt aaagtatcag caatttcata 19560
ggattcaacc taatgtatgc gaaatgctag ataaacagat aaatacttaa tatctggctt 19620
tttttcaaag cactgggtta tttgttcctt gagatttatc ctaaatgtgg gctataccct 19680
ggtttacagt gtctcacaga tgtgtagtag tagacactcc ataagtgttt actgacttga 19740
atccacaggg tactgagaaa atgctactga tagacttgga ggagagcata tctaaagcaa 19800
gctacccttt cctttagggc acgtctcact aattctttgg gtaaagcgta tttttcttcc 19860
ttttgtgttt ttggcagtct ttccaaaaat acgtgttata cctatgcatt attttttggt 19920
ttggtttcta aagaaagagt cagccggtgg gaaagtgaag gatgtgggaa ctgagagatc 19980
tgcatcagca tcccacctct acctcccacg atgggacctg agacagttat ttttgcctcc 20040
tggaccacta tagtatcatc tgtaacagga gggacttgag ccagttgatc tctaaggttc 20100
ctctggcacc tgtgacccta aatagatatt ggatattggt ttaatgctat ttgtagtgtg 20160
tttttttggg gatatggaaa ccagaagttt gtttccataa acataaacat aaactgtata 20220
tatctaaagg atatggaaac ctttagatat atataatctg cttacgtaaa gaaggtttgt 20280
atatattgca gtgtcaatgg gaatatttta tcaagttaag catagtaaat cacattgatt 20340
aaatgctttg tatttaccaa acattaccca aagtgttttc tcctttcaac ctcacaagga 20400
cccacagaag aaaatacagt tatcatttcc aacctgcagg gagctgagac acagagaatt 20460
taagcaactg accggaagtc caacagggag tcagagattg ctctggggtg tgatccccac 20520
ttggacccta gagtggaagc ttctccacta ctttatagag ttgagattct atattttgag 20580
cttgtattta cccagagaat tatatcctct tgggcaattg tgtataataa aacctcatgc 20640
atttaggaga ggcgggatga cagaactttg ttgagtgaat tataatctac ttgagaaatt 20700
atttgcttac attttataag ctaattatac catatctcat ccagttttcc cagaacactt 20760
ctcataggta atgctttatt tgaaacatag gccataggta agttaagtgt aaatgtgtat 20820
ttttataatt taaccagaag tttatttcat ttttctaaat aagtgaaatt gtattgcatc 20880
ttctaaatta ttctatttaa acacttgatg tcttgctgtc tccgtctctg tgtgtttgca 20940
tgtcattgta catgttctta ggaaaagtgt gggagcttga cgcaatatat accttatgtt 21000
tctatgtgca tatagtttac caaataatac cataagttta cttagcatat tagaatccat 21060
gcacattatt tttattttat cttcaccgca accctgtggg atagaccaaa atcatgcttt 21120
tcagcctcct ttttccactt gaggaaagga gtcttaaaaa agggaccagt ctcatgttcc 21180
cattcgtctt acaactaatt ggtcaagcca gaaagccaga actatgtcct gggtcactaa 21240
ctcctagtca ctgtgtgtta gtatttgaga tgcctgttgg cttgatttag tcatttattt 21300
tttagtgttt tataatcctt gcatactttt acattttaaa tggttaacca ggcaaattgg 21360
tttaaaatca gtgcataaaa atactgtgcc tatcatgatg ggtttcatga agtgataact 21420
tttcatcatg gagatcctca gctgtcacag aagatgaggg gccctgggta cagaggctca 21480
cgtgagggat gaaagtctca gcagcccgga cttacacttt ggggctttta ggcaaatcag 21540
acaacctctt aagaactatc actgagttca ggcaaggcga gcttgaatta acacagggcc 21600
cttggtgggc atgtgaatat atctcacttc actaccatcc agttctgact ctttactaga 21660
tgcccctgta cataccaaga ctgatttttt attctccctt ctccccatgt ggtttcttct 21720
gcatagagag ttcctattga tcagtctgac ccatggtatt ttagaattgc gatccctact 21780
gtttcattat tcctttttct cccccatgtt gaaaaaaata aatgtcctga gatgcaagat 21840
cagggacact ggagcactga catttagttc agtgcaggaa ctgaaggcag atgtaattct 21900
taagaagcgt acctgttatt atgaaccatc ctcaacaaat tgtagtggat cttgttttct 21960
catagataca gcagttaaat tttttaataa aagtaactaa gagttatttg gatgtatttt 22020
agcatgcact gagcggaaag tacgacattt cttcattggg taagtcctga ttctttatga 22080
tcctcacttg gttccagggc cccatgcatc taagggtgtc tcagagcatc ctgcagtgct 22140
ccagcatgat cgcagggaaa agctatagga ggaaaagagt caataaagtt tagtttctca 22200
acctcccacc tccaccccat aataatgaca gctggttaat catgagacgc gtgcacaccc 22260
cacacgccct gtacatgttt actcattggg atagcatgtc aggccagaag gctccatggt 22320

-continued catttctatg aaggtacttt agcaggtctt caagaaggca agtggcctgg gtccctgcct 22380
ccccaaattg caagctccct gctttatgta ggagacctat gtgtatatta cagttctgtg 22440
taagattatt ttgttattct tacccccaca cccacccccc aacccccgc tgccaccaaa 22500 aaaaaaaaaa aaaaattcct ctgacaacct tcataaagtc ctgggagttt gaacaccatt 22560
gctctaggaa gtcatcttat acaaaaataa gagttgtgag gtggttcata tacctcctgc 22620
gttctcctat ttggagtttt tccccattta tgaaagaggt gaaaacgcta agatatttag 22680
caattattac tttaaacatt ttctatttat aggccgggcg cagtggctca tgcctgtaat 22740
cccagcgctt gggaggccaa ggcaggcaga tcacgaggtc aggagatcga gaccatcttg 22800
gctaacacgg tgaaaccctg tctctactaa aaaaatacaa aaatttagtt gggcatggtg 22860
ggggatacct gtggtcccag ctactcggga ggctgagaca ggagaatggc ttgaacctgg 22920
gaggccgagc ttgcagtgag ccaagatcgc gccactgcac tccagcctgg gtgacagagc 22980
aagactctgt ctcgaaaaaa aaaaaaaatt ctatttacag cagtgaaaat agtagtgact 23040
taatgcacat tgccaaggct ttagcataac atgaacactt tcactcaatg tctctctggc 23100
cttttgtttt tccttgggaa attcttataa tcctgctccg tctttaacta ttcattttgt 23160
attggctatc caaatatacc caataatgct ctttctgaaa atatgccaat tgtggtaatt 23220
acagctaagc tggaatatta aattgtgatg tctgttttcc agagaatgaa gtagtattcc 23280
ccagagcata ggcttggtgc ctgtgcaggt tctattttaa atattccagg aagggttgtt 23340
ttatatactg aggatgattt tactggtctt gccagtcgtc tgaaatgctg gtattactct 23400
tgtggaaggt ttattcaaac aaacaaggac atttcacaca atacctagtc atgtttttca 23460
gacattttaa tgtttggttc atcatttgca cacactctca aaaatctagg tttgtctatg 23520
tgttcatatc attttgcctg ttgccagctc agtcagcagg cacactctcc caggctgttg 23580
ctgttttgtt agacttcttc aggaccttca tctaaaatgg tcttccacac gtagctatac 23640
tgcataagtt cacatcatct gtttcttgca tgtgggttgt gtctcaactc aagtttaagt 23700
tagatttgga agggcggaaa ctataggagt tgcagcttca gtggagaaaa gagcatttcc 23760
tactagttat ggcttcccaa ggaaggttag attcctcaga gtaggagtga ttccccaatg 23820
ctagaacctt tggtcaaata taattctaat ccagtcaaaa taaatacagg tattctgtaa 23880
aacccgattt cattttgtaa atcctacttt gtatagtata agcaattttt gtatttgtgt 23940
ggattatatt ttattttcct atttcaaaga gaagaatttg tattagcaga ctccctttgc 24000
atgcggagag gggatcattt tcccagtagg catggggttc ccttccattc cttgtccagt 24060
cttcttttcc ccactaagtt aagtcaaact aagcagctgg taagatattc cctggttctt 24120
gcaaagaaag tgagcagatg gcagaatgta tagctctaag cagaatacct ggtgtggtat 24180
cctcaaacac aaattgacag gagggtgtgg tgtggcaagc tcattgtggg ggtaaattgg 24240
aataagctta caggggggaag agttgacaaa agataggaag aaccttaaaa atatagatgc 24300
cttttatgca gtgataaaat gtctagatat ttatactgtg gtgattatta ggaatatgtg 24360
caaagattgg ctattaggat gttcattaca gtgttgttta ataattataa aaggacagaa 24420
agcaatgtgg actcaaaaat aggaaaagaa tttaaataaa tcctagtgta cccgttatac 24480
atgaaattat ggaaatatga ccctgagcat ggaaatatgt acatgagaat gtctaaaagc 24540
tagttcattt tgaaaaacaa aataatgtca cctcatatta tttatagtat ataaagatga 24600
ttttaagagt ggcagtgtct gggattatag gtgattgtat ttcttccctt ttgcacatct 24660
atgttctctc atttgtattg tgtggggaga agtgactttt tttataaaaa gaaaaaggta 24720

```
tatgcatccc agcagagaag cactggctcc acccagtacc tgcctcctca tgccaccctc  24780
tcaagccaaa agccggggga agcccaggca ccttgaccat gaccgcccga gactcacact  24840
tcttctttct catcagggaa ggaaagcccc cctgtaagcg atactccaga tgagggcgat  24900
gagcccatgc cgatccccga ggacctctcc accacctcgg gaggacagca aagctccaag  24960
agtgacagag tcgtgggtaa gtgggtcacc agcggcctct gtgcctgtga aacctttatc  25020
tctttgtatt tttccaagac agtgatgaag ggatgcaagt cattttatcc attgtgttcc  25080
ctcaactggc atattaaaga aatatggcac aaagatcagc aggatggggg tcctctggtg  25140
tgtgggagga tggacactca caggccagca tggccgtgag agccacacac cccgcaaaat  25200
gtccaagttg aggagcaatc ctgcccaggg acgcgtctct gtcactgtcc tctgtcctca  25260
ctgcacttgc aggaatatca aatgttatgg attgtagatc gtgaaaatta cacacttacg  25320
tgttttggca acagtgcttt tcagtgtttg gggttagaac aagccacatc tggccatttt  25380
atgttatccc tctaatctct agttcttaaa tttcagattt aactgaaaat agaaagtttc  25440
ataaatggta atttttaaat gttagaaaaa aatcaaagca cacatttaca taccttttcc  25500
ataaaaaagt gtgtgtgaaa ccatctgcaa ctccactggt taacttacac atgcgacagt  25560
ttgtgtttgg aaaacttcac ccaccctctt tatttcaaga aaccaaagac ggagagaagt  25620
tcagtgaatt aaccaaggtg aaatgacaga gtcagaattg aactgaattt ctgactgaaa  25680
aactagttct cgctccatta taccatgttc taatgagcta atgagtcaac agttccctgg  25740
aatacctgtt ttcttcttta aaaagagaaa gagctgtgat actgagagct acctattggc  25800
ataaaagaat atgaaggaca tacaggtaaa atgaggtaga ctggatcaat gtgggtcagc  25860
tacataagcc cccatagcca aggagggaac atgtatgtaa aattctcagg cttatgagaa  25920
tcacaactgt atgtctatag gacatcctaa tgcaataatg ggaaaatgtg ataactgaat  25980
tttatctaca tgtatagaaa acatattttg ggccgggcat ggtggctcaa gcttgtaatc  26040
ccagcacttt gggaggccga ggctggcgga tcacaaggtc aggaaatcga gaccatcctg  26100
gctaacacgg tgaaaccctg tctctactaa aaatacaaaa aattagccgg gcgtagtggt  26160
gggcgcctgt agtcccagct actcgggagg ctgaggcagg agaatggcgt gaacccggca  26220
ggcggagctt gcagtgagcc gagattgcgc cactgcactc cagcctggat gacagagcca  26280
gactccatct caaaaaaaaa aaaaaaaaag aaaaagtaaa gaaaacatat tttgtatgtt  26340
ttttatgtgt cttagaaacc aagtggacta ggtataatgg ttcttttttt ttttaactca  26400
gcagcacagt taatggcaca aacagataaa gatggtggct aaagccattt ggtgtagatg  26460
aatccagaaa acaagtacat ttatgaatta ttttacccta ttggaaaatg gctactatat  26520
gtggaaagta gaggggaaga gaaatgaact tgtgaattat ctactctatt ctaccaaaga  26580
aagatacata tatcatttca gggttttcca aagttgggat gcaaaggatc atgtttcatt  26640
ttaatttatg tatttatttt tgagattgtc ttctatgtat tgcaagtgat actggtttta  26700
ccatgcactg taccactacg agggttcctt tcaaaacaca ttcatataaa ttaaaaaatc  26760
agtttaaata aaaacatcaa gtcaatagta gtacatagat atgataaaag tttgcaaaag  26820
tggcacagga atagtcattg ggtggtgatg ttccctgatt tttttagtcc ctgaagcacc  26880
cagcgccaag ggtactgttc ttcctgctta acacaggagc aaacagatgc tcacaccctg  26940
cccaagaaca cagaggctca gggactgaac cagaagaaat gatccattaa ccatgtaaat  27000
gaacagagag cctggatgtc agagtgagga ggccagctcg ggtcgctgtg gagaaagaga  27060
```

-continued

```
tgggctctcc ctggaatccc tgcagctgcc cttagaggct gtgagccatc gtggctaggg  27120
catctttaga gaactgaaag tcaggccgat tcctggagag tgaagaatag cacacgtgcc  27180
ttcaaaacag tgtcagtatc ctgtccctta cggacgtcat attgttggtg ggttttcctg  27240
ggtgggagat cacccagtat ctggttggca ttactgatgg gttcccagag ctgtcttttg  27300
gttcaaagtc ctgccctcgg tcccagctgc ccccagcaca ggtgtcacct tggagtcagg  27360
ggcgggtttg tcatagccca tgggtcctgg ccctgccctt tatcatgttt gacatgattt  27420
tcagtctact tttccttcag gatgtaattt agaaaatatg atttcagaat tgtgaaattt  27480
aaaaacccta gaaaacctct ttgctttgct tgtaaatagc agttgatgca gccctgtgga  27540
caggcgggaa cagccatgtg acgtgggcac tgagatgatt tgggagattg aatgctcctc  27600
agtggggcta gaggccacag gagtgatagg ttactgtaaa gaaagcaaaa aagatgcaaa  27660
agcctacatg acaaaccagg cacgacacaa aggagaggct tgagaagagg aagtgaagga  27720
gggagaggat tccacaagac cgaagtgccc aaggagacat ggagggaaga gagggctctt  27780
cacagagctg agtttagaga ccaccctcca tggttctgga aggaaaccag ccagctttca  27840
tatgtggtga caggctgttc attaatttgt agtgtacagc attaaataaa tgaagtatgt  27900
agagaacatt aggaaacaat ataaaaaggt aggggaattc gtggataaag ggaataacct  27960
gggtaccata tttcatcaca ttattccatg ggaataagtc atcagtgcaa aggactgtaa  28020
ggagtgcaca gcaggaaatg aaaagacaga agcagtgggg ccgagaggag gaaatggagt  28080
tgctgaaatg cagggtgagc agcaggggcg gagagtgccc tgtgggtaag gcacacctca  28140
gaagggacag gtccaggccc tctcctccct ggcctggagc ttctggcaag gcttttcttc  28200
tctgagcctc actttcctct tttgaaggtg gcaatagtaa ctgaacctgc atcannnnnn  28260
nnnnnnnnnn nnnnnnnnnn nnnnnnnnnn nnnnnnnnnn nnnnnnnnnn nnnnnnnnnn  28320
nnnnnnnnnn nnnnnnnnnn nnnnnnnnnn nnnnnnnnnn nnnnnnnnnn nnnnnnnnnn  28380
nnnnnnnnnn nnnnnnnnnn nnnnnnnnnn nnnnnnnnnn nnnnnnnnnn nnnnnnnnnn  28440
nnnnnnnnnn nnnnnnnnnn nnnnnnnnnn nnnnnnnnnn nnnnnnnnnn nnnnnnnnnn  28500
nnnnnnnnnn nnnnnnnnnn nnnnnnnnnn nnnnnnnnnn nnnnnnnnnn nnnnnnnnnn  28560
nnnnnnnnnn nnnnnnnnnn nnnnnnnnnn nnnnnnnnnn nnnnnnnnnn nnnnnnnnnn  28620
nnnnnnnnnn nnnnnnnnnn nnnnnnnnnn nnnnnnnnnn nnnnnnnnnn nnnnnnnnnn  28680
nnnnnnnnnn nnnnnnnnnn nnnnnnnnnn nnnnnnnnnn nnnnnnnnnn nnnnnnnnnn  28740
nnnnnnnnnn nnnnnnnnnn nnnnnnnnnn nnnnnnnnnn nnnnnnnnnn nnnnnnnnnn  28800
nnnnnnnnnn nnnnnnnnnn nnnnnnnnnn nnnnnnnnnn nnnnnnnnnn nnnnnnnnnn  28860
nnnnnnnnnn nnnnnnnnnn nnnnnnnnnn nnnnnnnnnn nnnnnnnnnn nnnnnnnnnn  28920
nnnnnnnnnn nnnnnnnnnn nnnnnnnnnn nnnnnnnnnn nnnnnnnnnn nnnnnnnnnn  28980
nnnnnnnnnn nnnnnnnnnn nnnnnnnnnn nnnnnnnnnn nnnnnnnnnn nnnnnnnnnn  29040
nnnnnnnnnn nnnnnnnnnn nnnnnnnnnn nnnnnnnnnn nnnnnnnnnn nnnnnnnnnn  29100
nnnnnnnnnn nnnnnnnnnn nnnnnnnnnn nnnnnnnnnn nnnnnnnnnn nnnnnnnnnn  29160
nnnnnnnnnn nnnnnnnnnn nnnnnnnnnn nnnnnnnnnn nnnnnnnnnn nnnnnnnnnn  29220
nnnnnnnnnn nnnnnnnnnn nnnnnnnnnn nnnnnnnnnn nnnnnnnnnn nnnnnnnnnn  29280
nnnnnnnnnn nnnnnnnnnn nnnnnnnnnn nnnnnnnnnn nnnnnnnnnn nnnnnnnnnn  29340
nnnnnnnnnn nnnnnnnnnn nnnnnnnnnn nnnnnnnnnn nnnnnnnnnn nnnnnnnnnn  29400
nnnnnnnnnn nnnnnnnnnn nnnnnnnnnn nnnnnnnnnn nnnnnnnnnn nnnnnnnnnn  29460
```

-continued

```
nnnnnnnnnn nnnnnnnnnn nnnnnnnnnn nnnnnnnnnn nnnnnnnnnn nnnnnnnnnn  29520
nnnnnnnnnn nnnnnnnnnn nnnnnnnnnn nnnnnnnnnn nnnnnnnnnn nnnnnnnnnn  29580
nnnnnnnnnn nnnnnnnnnn nnnnnnnnnn nnnnnnnnnn nnnnnnnnnn nnnnnnnnnn  29640
nnnnnnnnnn nnnnnnnnnn nnnnnnnnnn nnnnnnnnnn nnnnnnnnnn nnnnnnnnnn  29700
nnnnnnnnnn nnnnnnnnnn nnnnnnnnnn nnnnnnnnnn nnnnnnnnnn nnnnnnnnnn  29760
nnnnnnnnnn nnnnnnnnnn nnnnnnnnnn nnnnnnnnnn nnnnnnnnnn nnnnnnnnnn  29820
nnnnnnnnnn nnnnnnnnnn nnnnnnnnnn nnnnnnnnnn nnnnnnnnnn nnnnnnnnnn  29880
nnnnnnnnnn nnnnnnnnnn nnnnnnnnnn nnnnnnnnnn nnnnnnnnnn nnnnnnnnnn  29940
nnnnnnnnnn nnnnnnnnnn nnnnnnnnnn nnnnnnnnnn nnnnnnnnnn nnnnnnnnnn  30000
nnnnnnnnnn nnnnnnnnnn nnnnnnnnnn nnnnnnnnnn nnnnnnnnnn nnnnnnnnnn  30060
nnnnnnnnnn nnnnnnnnnn nnnnnnnnnn nnnnnnnnnn nnnnnnnnnn nnnnnnnnnn  30120
nnnnnnnnnn nnnnnnnnnn nnnnnnnnnn nnnnnnnnnn nnnnnnnnnn nnnnnnnnnn  30180
nnnnnnnnnn nnnnnnnnnn nnnnnnnnnn nnnnnnnnnn nnnnnnnnnn nnnnnnnnnn  30240
nnnnnnnnnn nnnnnnnnnn nnnnnnnnnn nnnnnnnnnn nnnnnnnnnn nnnnnnnnnn  30300
nnnnnnnnnn nnnnnnnnnn nnnnnnnnnn nnnnnnnnnn nnnnnnnnnn nnnnnnnnnn  30360
nnnnnnnnnn nnnnnnnnnn nnnnnnnnnn nnnnnnnnnn nnnnnnnnnn nnnnnnnnnn  30420
nnnnnnnnnn nnnnnnnnnn nnnnnnnnnn nnnnnnnnnn nnnnnnnnnn nnnnnnnnnn  30480
nnnnnnnnnn nnnnnnnnnn nnnnnnnnnn nnnnnnnnnn nnnnnnnnnn nnnnnnnnnn  30540
nnnnnnnnnn nnnnnnnnnn nnnnnnnnnn nnnnnnnnnn nnnnnnnnnn nnnnnnnnnn  30600
nnnnnnnnnn nnnnnnnnnn nnnnnnnnnn nnnnnnnnnn nnnnnnnnnn nnnnnnnnnn  30660
nnnnnnnnnn nnnnnnnnnn nnnnnnnnnn nnnnnnnnnn nnnnnnnnnn nnnnnnnnnn  30720
nnnnnnnnnn nnnnnnnnnn nnnnnnnnnn nnnnnnnnnn nnnnnnnnnn nnnnnnnnnn  30780
nnnnnnnnnn nnnnnnnnnn nnnnnnnnnn nnnnnnnnnn nnnnnnnnnn nnnnnnnnnn  30840
nnnnnnnnnn nnnnnnnnnn nnnnnnnnnn nnnnnnnnnn nnnnnnnnnn nnnnnnnnnn  30900
nnnnnnnnnn nnnnnnnnnn nnnnnnnnnn nnnnnnnnnn nnnnnnnnnn nnnnnnnnnn  30960
nnnnnnnnnn nnnnnnnnnn nnnnnnnnnn nnnnnnnnnn nnnnnnnnnn nnnnnnnnnn  31020
nnnnnnnnnn nnnnnnnnnn nnnnnnnnnn nnnnnnnnnn nnnnnnnnnn nnnnnnnnnn  31080
nnnnnnnnnn nnnnnnnnnn nnnnnnnnnn nnnnnnnnnn nnnnnnnnnn nnnnnnnnnn  31140
nnnnnnnnnn nnnnnnnnnn nnnnnnnnnn nnnnnnnnnn nnnnnnnnnn nnnnnnnnnn  31200
nnnnnnnnnn nnnnnnnnnn nnnnnnnnnn nnnnnnnnnn nnnnnnnnnn nnnnnnnnnn  31260
nnnnnnnnnn nnnnnnnnnn nnnnnnnnnn nnnnnnnnnn nnnnnnnnnn nnnnnnnnnn  31320
nnnnnnnnnn nnnnnnnnnn nnnnnnnnnn nnnnnnnnnn nnnnnnnnnn nnnnnnnnnn  31380
nnnnnnnnnn nnnnnnnnnn nnnnnnnnnn nnnnnnnnnn nnnnnnnnnn nnnnnnnnnn  31440
nnnnnnnnnn nnnnnnnnnn nnnnnnnnnn nnnnnnnnnn nnnnnnnnnn nnnnnnnnnn  31500
nnnnnnnnnn nnnnnnnnnn nnnnnnnnnn nnnnnnnnnn nnnnnnnnnn nnnnnnnnnn  31560
nnnnnnnnnn nnnnnnnnnn nnnnnnnnnn nnnnnnnnnn nnnnnnnnnn nnnnnnnnnn  31620
nnnnnnnnnn nnnnnnnnnn nnnnnnnnnn nnnnnnnnnn nnnnnnnnnn nnnnnnnnnn  31680
nnnnnnnnnn nnnnnnnnnn nnnnnnnnnn nnnnnnnnnn nnnnnnnnnn nnnnnnnnnn  31740
nnnnnnnnnn nnnnnnnnnn nnnnnnnnnn nnnnnnnnnn nnnnnnnnnn nnnnnnnnnn  31800
```

-continued nnnnnnnnnn nnnnnnnnnn nnnnnnnnnn nnnnnnnnnn nnnnnnnnnn nnnnnnnnnn 31860
nnnnnnnnnn nnnnnnnnnn nnnnnnnnnn nnnnnnnnnn nnnnnnnnnn nnnnnnnnnn 31920
nnnnnnnnnn nnnnnnnnnn nnnnnnnnnn nnnnnnnnnn nnnnnnnnnn nnnnnnnnnn 31980
nnnnnnnnnn nnnnnnnnnn nnnnnnnnnn nnnnnnnnnn nnnnnnnnnn nnnnnnnnnn 32040
nnnnnnnnnn nnnnnnnnnn nnnnnnnnnn nnnnnnnnnn nnnnnnnnnn nnnnnnnnnn 32100
nnnnnnnnnn nnnnnnnnnn nnnnnnnnnn nnnnnnnnnn nnnnnnnnnn nnnnnnnnnn 32160
nnnnnnnnnn nnnnnnnnnn nnnnnnnnnn nnnnnnnnnn nnnnnnnnnn nnnnnnnnnn 32220
nnnnnnnnnn nnnnnnnnnn nnnnnnnnnn nnnnnnnnnn nnnnnnnnnn nnnnnnnnnn 32280
nnnnnnnnnn nnnnnnnnnn nnnnnnnnnn nnnnnnnnnn nnnnnnnnnn nnnnnnnnnn 32340
nnnnnnnnnn nnnnnnnnnn nnnnnnnnnn nnnnnnnnnn nnnnnnnnnn nnnnnnnnnn 32400
nnnnnnnnnn nnnnnnnnnn nnnnnnnnnn nnnnnnnnnn nnnnnnnnnn nnnnnnnnnn 32460
nnnnnnnnnn nnnnnnnnnn nnnnnnnnnn nnnnnnnnnn nnnnnnnnnn nnnnnnnnnn 32520
nnnnnnnnnn nnnnnnnnnn nnnnnnnnnn nnnnnnnnnn nnnnnnnnnn nnnnnnnnnn 32580
nnnnnnnnnn nnnnnnnnnn nnnnnnnnnn nnnnnnnnnn nnnnnnnnnn nnnnnnnnnn 32640
nnnnnnnnnn nnnnnnnnnn nnnnnnnnnn nnnnnnnnnn nnnnnnnnnn nnnnnnnnnn 32700
nnnnnnnnnn nnnnnnnnnn nnnnnnnnnn nnnnnnnnnn nnnnnnnnnn nnnnnnnnnn 32760
nnnnnnnnnn nnnnnnnnnn nnnnnnnnnn nnnnnnnnnn nnnnnnnnnn nnnnnnnnnn 32820
nnnnnnnnnn nnnnnnnnnn nnnnnnnnnn nnnnnnnnnn nnnnnnnnnn nnnnnnnnnn 32880
nnnnnnnnnn nnnnnnnnnn nnnnnnnnnn nnnnnnnnnn nnnnnnnnnn nnnnnnnnnn 32940
nnnnnnnnnn nnnnnnnnnn nnnnnnnnnn nnnnnnnnnn nnnnnnnnnn nnnnnnnnnn 33000
nnnnnnnnnn nnnnnnnnnn nnnnnnnnnn nnnnnnnnnn nnnnnnnnnn nnnnnnnnnn 33060
nnnnnnnnnn nnnnnnnnnn nnnnnnnnnn nnnnnnnnnn nnnnnnnnnn nnnnnnnnnn 33120
nnnnnnnnnn nnnnnnnnnn nnnnnnnnnn nnnnnnnnnn nnnnnnnnnn nnnnnnnnnn 33180
nnnnnnnnnn nnnnnnnnnn nnnnnnnnnn nnnnnnnnnn nnnnnnnnnn nnnnnnnnnn 33240
nnnnnnnnnn nnnnnnnnnn nnnnnnnnnn nnnnnnnnnn nnnnnnnnnn nnnnnnnnnn 33300
nnnnnnnnnn nnnnnnnnnn nnnnnnnnnn nnnnnnnnnn nnnnnnnnnn nnnnnnnnnn 33360
nnnnnnnnnn nnnnnnnnnn nnnnnnnnnn nnnnnnnnnn nnnnnnnnnn nnnnnnnnnn 33420
nnnnnnnnnn nnnnnnnnnn nnnnnnnnnn nnnnnnnnnn nnnnnnnnnn nnnnnnnnnn 33480
nnnnnnnnnn nnnnnnnnnn nnnnnnnnnn nnnnnnnnnn nnnnnnnnnn nnnnnnnnnn 33540
nnnnnnnnnn nnnnnnnnnn nnnnnnnnnn nnnnnnnnnn nnnnnnnnnn nnnnnnnnnn 33600
nnnnnnnnnn nnnnnnnnnn nnnnnnnnnn nnnnnnnnnn nnnnnnnnnn nnnnnnnnnn 33660
nnnnnnnnnn nnnnnnnnnn nnnnnnnnnn nnnnnnnnnn nnnnnnnnnn nnnnnnnnnn 33720
nnnnnnnnnn nnnnnnnnnn nnnnnnnnnn nnnnnnnnnn nnnnnnnnnn nnnnnnnnnn 33780
nnnnnnnnnn nnnnnnnnnn nnnnnnnnnn nnnnnnnnnn nnnnnnnnnn nnnnnnnnnn 33840
nnnnnnnnnn nnnnnnnnnn nnnnnnnnnn nnnnnnnnnn nnnnnnnnnn nnnnnnnnnn 33900
nnnnnnnnnn nnnnnnnnnn nnnnnnnnnn nnnnnnnnnn nnnnnnnnnn nnnnnnnnnn 33960
nnnnnnnnnn nnnnnnnnnn nnnnnnnnnn nnnnnnnnnn nnnnnnnnnn nnnnnnnnnn 34020
nnnnnnnnnn nnnnnnnnnn nnnnnnnnnn nnnnnnnnnn nnnnnnnnnn nnnnnnnnnn 34080
nnnnnnnnnn nnnnnnnnnn nnnnnnnnnn nnnnnnnnnn nnnnnnnnnn nnnnnnnnnn 34140
nnnnnnnnnn nnnnnnnnnn nnnnnnnnnn nnnnnnnnnn nnnnnnnnnn nnnnnnnnnn 34200

-continued

```
nnnnnnnnnn nnnnnnnnnn nnnnnnnnnn nnnnnnnnnn nnnnnnnnnn nnnnnnnnnn  34260
nnnnnnnnnn nnnnnnnnnn nnnnnnnnnn nnnnnnnnnn nnnnnnnnnn nnnnnnnnnn  34320
nnnnnnnnnn nnnnnnnnnn nnnnnnnnnn nnnnnnnnnn nnnnnnnnnn nnnnnnnnnn  34380
nnnnnnnnnn nnnnnnnnnn nnnnnnnnnn nnnnnnnnnn nnnnnnnnnn nnnnnnnnnn  34440
nnnnnnnnnn nnnnnnnnnn nnnnnnnnnn nnnnnnnnnn nnnnnnnnnn nnnnnnnnnn  34500
nnnnnnnnnn nnnnnnnnnn nnnnnnnnnn nnnnnnnnnn nnnnnnnnnn nnnnnnnnnn  34560
nnnnnnnnnn nnnnnnnnnn nnnnnnnnnn nnnnnnnnnn nnnnnnnnnn nnnnnnnnnn  34620
nnnnnnnnnn nnnnnnnnnn nnnnnnnnnn nnnnnnnnnn nnnnnnnnnn nnnnnnnnnn  34680
nnnnnnnnnn nnnnnnnnnn nnnnnnnnnn nnnnnnnnnn nnnnnnnnnn nnnnnnnnnn  34740
nnnnnnnnnn nnnnnnnnnn nnnnnnnnnn nnnnnnnnnn nnnnnnnnnn nnnnnnnnnn  34800
nnnnnnnnnn nnnnnnnnnn nnnnnnnnnn nnnnnnnnnn nnnnnnnnnn nnnnnnnnnn  34860
nnnnnnnnnn nnnnnnnnnn nnnnnnnnnn nnnnnnnnnn nnnnnnnnnn nnnnnnnnnn  34920
nnnnnnnnnn nnnnnnnnnn nnnnnnnnnn nnnnnnnnnn nnnnnnnnnn nnnnnnnnnn  34980
nnnnnnnnnn nnnnnnnnnn nnnnnnnnnn nnnnnnnnnn nnnnnnnnnn nnnnnnnnnn  35040
nnnnnnnnnn nnnnnnnnnn nnnnnnnnnn nnnnnnnnnn nnnnnnnnnn nnnnnnnnnn  35100
nnnnnnnnnn nnnnnnnnnn nnnnnnnnnn nnnnnnnnnn nnnnnnnnnn nnnnnnnnnn  35160
nnnnnnnnnn nnnnnnnnnn nnnnnnnnnn nnnnnnnnnn nnnnnnnnnn nnnnnnnnnn  35220
nnnnnnnnnn nnnnnnnnnn nnnnnnnnnn nnnnnnnnnn nnnnnnnnnn nnnnnnnnnn  35280
nnnnnnnnnn nnnnnnnnnn nnnnnnnnnn nnnnnnnnnn nnnnnnnnnn nnnnnnnnnn  35340
nnnnnnnnnn nnnnnnnnnn nnnnnnnnnn nnnnnnnnnn nnnnnnnnnn nnnnnnnnnn  35400
nnnnnnnnnn nnnnnnnnnn nnnnnnnnnn nnnnnnnnnn nnnnnnnnnn nnnnnnnnnn  35460
nnnnnnnnnn nnnnnnnnnn nnnnnnnnnn nnnnnnnnnn nnnnnnnnnn nnnnnnnnnn  35520
nnnnnnnnnn nnnnnnnnnn nnnnnnnnnn nnnnnnnnnn nnnnnnnnnn nnnnnnnnnn  35580
nnnnnnnnnn nnnnnnnnnn nnnnnnnnnn nnnnnnnnnn nnnnnnnnnn nnnnnnnnnn  35640
nnnnnnnnnn nnnnnnnnnn nnnnnnnnnn nnnnnnnnnn nnnnnnnnnn nnnnnnnnnn  35700
nnnnnnnnnn nnnnnnnnnn nnnnnnnnnn nnnnnnnnnn nnnnnnnnnn nnnnnnnnnn  35760
nnnnnnnnnn nnnnnnnnnn nnnnnnnnnn nnnnnnnnnn nnnnnnnnnn nnnnnnnnnn  35820
nnnnnnnnnn nnnnnnnnnn nnnnnnnnnn nnnnnnnnnn nnnnnnnnnn nnnnnnnnnn  35880
nnnnnnnnnn nnnnnnnnnn nnnnnnnnnn nnnnnnnnnn nnnnnnnnnn nnnnnnnnnn  35940
nnnnnnnnnn nnnnnnnnnn nnnnnnnnnn nnnnnnnnnn nnnnnnnnnn nnnnnnnnnn  36000
nnnnnnnnnn nnnnnnnnnn nnnnnnnnnn nnnnnnnnnn nnnnnnnnnn nnnnnnnnnn  36060
nnnnnnnnnn nnnnnnnnnn nnnnnnnnnn nnnnnnnnnn nnnnnnnnnn nnnnnnnnnn  36120
nnnnnnnnnn nnnnnnnnnn nnnnnnnnnn nnnnnnnnnn nnnnnnnnnn nnnnnnnnnn  36180
nnnnnnnnnn nnnnnnnnnn nnnnnnnnnn nnnnnnnnnn nnnnnnnnnn nnnnnnnnnn  36240
nnnnnnnnnn nnnnnnnnnn nnnnnnnnnn nnnnnnnnnn nnnnnnnnnn nnnnnnnnnn  36300
nnnnnnnnnn nnnnnnnnnn nnnnnnnnnn nnnnnnnnnn nnnnnnnnnn nnnnnnnnnn  36360
nnnnnnnnnn nnnnnnnnnn nnnnnnnnnn nnnnnnnnnn nnnnnnnnnn nnnnnnnnnn  36420
nnnnnnnnnn nnnnnnnnnn nnnnnnnnnn nnnnnnnnnn nnnnnnnnnn nnnnnnnnnn  36480
nnnnnnnnnn nnnnnnnnnn nnnnnnnnnn nnnnnnnnnn nnnnnnnnnn nnnnnnnnnn  36540
```

-continued nnnnnnnnnn nnnnnnnnnn nnnnnnnnnn nnnnnnnnnn nnnnnnnnnn nnnnnnnnnn 36600
nnnnnnnnnn nnnnnnnnnn nnnnnnnnnn nnnnnnnnnn nnnnnnnnnn nnnnnnnnnn 36660
nnnnnnnnnn nnnnnnnnnn nnnnnnnnnn nnnnnnnnnn nnnnnnnnnn nnnnnnnnnn 36720
nnnnnnnnnn nnnnnnnnnn nnnnnnnnnn nnnnnnnnnn nnnnnnnnnn nnnnnnnnnn 36780
nnnnnnnnnn nnnnnnnnnn nnnnnnnnnn nnnnnnnnnn nnnnnnnnnn nnnnnnnnnn 36840
nnnnnnnnnn nnnnnnnnnn nnnnnnnnnn nnnnnnnnnn nnnnnnnnnn nnnnnnnnnn 36900
nnnnnnnnnn nnnnnnnnnn nnnnnnnnnn nnnnnnnnnn nnnnnnnnnn nnnnnnnnnn 36960
nnnnnnnnnn nnnnnnnnnn nnnnnnnnnn nnnnnnnnnn nnnnnnnnnn nnnnnnnnnn 37020
nnnnnnnnnn nnnnnnnnnn nnnnnnnnnn nnnnnnnnnn nnnnnnnnnn nnnnnnnnnn 37080
nnnnnnnnnn nnnnnnnnnn nnnnnnnnnn nnnnnnnnnn nnnnnnnnnn nnnnnnnnnn 37140
nnnnnnnnnn nnnnnnnnnn nnnnnnnnnn nnnnnnnnnn nnnnnnnnnn nnnnnnnnnn 37200
nnnnnnnnnn nnnnnnnnnn nnnnnnnnnn nnnnnnnnnn nnnnnnnnnn nnnnnnnnnn 37260
nnnnnnnnnn nnnnnnnnnn nnnnnnnnnn nnnnnnnnnn nnnnnnnnnn nnnnnnnnnn 37320
nnnnnnnnnn nnnnnnnnnn nnnnnnnnnn nnnnnnnnnn nnnnnnnnnn nnnnnnnnnn 37380
nnnnnnnnnn nnnnnnnnnn nnnnnnnnnn nnnnnnnnnn nnnnnnnnnn nnnnnnnnnn 37440
nnnnnnnnnn nnnnnnnnnn nnnnnnnnnn nnnnnnnnnn nnnnnnnnnn nnnnnnnnnn 37500
nnnnnnnnnn nnnnnnnnnn nnnnnnnnnn nnnnnnnnnn nnnnnnnnnn nnnnnnnnnn 37560
nnnnnnnnnn nnnnnnnnnn nnnnnnnnnn nnnnnnnnnn nnnnnnnnnn nnnnnnnnnn 37620
nnnnnnnnnn nnnnnnnnnn nnnnnnnnnn nnnnnnnnnn nnnnnnnnnn nnnnnnnnnn 37680
nnnnnnnnnn nnnnnnnnnn nnnnnnnnnn nnnnnnnnnn nnnnnnnnnn nnnnnnnnnn 37740
nnnnnnnnnn nnnnnnnnnn nnnnnnnnnn nnnnnnnnnn nnnnnnnnnn nnnnnnnnnn 37800
nnnnnnnnnn nnnnnnnnnn nnnnnnnnnn nnnnnnnnnn nnnnnnnnnn nnnnnnnnnn 37860
nnnnnnnnnn nnnnnnnnnn nnnnnnnnnn nnnnnnnnnn nnnnnnnnnn nnnnnnnnnn 37920
nnnnnnnnnn nnnnnnnnnn nnnnnnnnnn nnnnnnnnnn nnnnnnnnnn nnnnnnnnnn 37980
nnnnnnnnnn nnnnnnnnnn nnnnnnnnnn nnnnnnnnnn nnnnnnnnnn nnnnnnnnnn 38040
nnnnnnnnnn nnnnnnnnnn nnnnnnnnnn nnnnnnnnnn nnnnnnnnnn nnnnnnnnnn 38100
nnnnnnnnnn nnnnnnnnnn nnnnnnnnnn nnnnnnnnnn nnnnnnnnnn nnnnnnnnnn 38160
nnnnnnnnnn nnnnnnnnnn nnnnnnnnnn nnnnnnnnnn nnnnnnnnnn nnnnnnnnnn 38220
nnnnnnnnnn nnnnnnnnnn nnnnnnnnnn nnnnnnnnnn nnnnnnnnnn nnnnnnnnnn 38280
nnnnnnnnnn nnnnnnnnnn nnnnnnnnnn nnnnnnnnnn nnnnnnnnnn nnnnnnnnnn 38340
nnnnnnnnnn nnnnnnnnnn nnnnnnnnnn nnnnnnnnnn nnnnnnnnnn nnnnnnnnnn 38400
nnnnnnnnnn nnnnnnnnnn nnnnnnnnnn nnnnnnnnnn nnnnnnnnnn nnnnnnnnnn 38460
nnnnnnnnnn nnnnnnnnnn nnnnnnnnnn nnnnnnnnnn nnnnnnnnnn nnnnnnnnnn 38520
nnnnnnnnnn nnnnnnnnnn nnnnnnnnnn nnnnnnnnnn nnnnnnnnnn nnnnnnnnnn 38580
nnnnnnnnnn nnnnnnnnnn nnnnnnnnnn nnnnnnnnnn nnnnnnnnnn nnnnnnnnnn 38640
nnnnnnnnnn nnnnnnnnnn nnnnnnnnnn nnnnnnnnnn nnnnnnnnnn nnnnnnnnnn 38700
nnnnnnnnnn nnnnnnnnnn nnnnnnnnnn nnnnnnnnnn nnnnnnnnnn nnnnnnnnnn 38760
nnnnnnnnnn nnnnnnnnnn nnnnnnnnnn nnnnnnnnnn nnnnnnnnnn nnnnnnnnnn 38820
nnnnnnnnnn nnnnnnnnnn nnnnnnnnnn nnnnnnnnnn nnnnnnnnnn nnnnnnnnnn 38880
nnnnnnnnnn nnnnnnnnnn nnnnnnnnnn nnnnnnnnnn nnnnnnnnnn nnnnnnnnnn 38940

-continued nnnnnnnnnn nnnnnnnnnn nnnnnnnnnn nnnnnnnnnn nnnnnnnnnn nnnnnnnnnn 39000
nnnnnnnnnn nnnnnnnnnn nnnnnnnnnn nnnnnnnnnn nnnnnnnnnn nnnnnnnnnn 39060
nnnnnnnnnn nnnnnnnnnn nnnnnnnnnn nnnnnnnnnn nnnnnnnnnn nnnnnnnnnn 39120
nnnnnnnnnn nnnnnnnnnn nnnnnnnnnn nnnnnnnnnn nnnnnnnnnn nnnnnnnnnn 39180
nnnnnnnnnn nnnnnnnnnn nnnnnnnnnn nnnnnnnnnn nnnnnnnnnn nnnnnnnnnn 39240
nnnnnnnnnn nnnnnnnnnn nnnnnnnnnn nnnnnnnnnn nnnnnnnnnn nnnnnnnnnn 39300
nnnnnnnnnn nnnnnnnnnn nnnnnnnnnn nnnnnnnnnn nnnnnnnnnn nnnnnnnnnn 39360
nnnnnnnnnn nnnnnnnnnn nnnnnnnnnn nnnnnnnnnn nnnnnnnnnn nnnnnnnnnn 39420
nnnnnnnnnn nnnnnnnnnn nnnnnnnnnn nnnnnnnnnn nnnnnnnnnn nnnnnnnnnn 39480
nnnnnnnnnn nnnnnnnnnn nnnnnnnnnn nnnnnnnnnn nnnnnnnnnn nnnnnnnnnn 39540
nnnnnnnnnn nnnnnnnnnn nnnnnnnnnn nnnnnnnnnn nnnnnnnnnn nnnnnnnnnn 39600
nnnnnnnnnn nnnnnnnnnn nnnnnnnnnn nnnnnnnnnn nnnnnnnnnn nnnnnnnnnn 39660
nnnnnnnnnn nnnnnnnnnn nnnnnnnnnn nnnnnnnnnn nnnnnnnnnn nnnnnnnnnn 39720
nnnnnnnnnn nnnnnnnnnn nnnnnnnnnn nnnnnnnnnn nnnnnnnnnn nnnnnnnnnn 39780
nnnnnnnnnn nnnnnnnnnn nnnnnnnnnn nnnnnnnnnn nnnnnnnnnn nnnnnnnnnn 39840
nnnnnnnnnn nnnnnnnnnn nnnnnnnnnn nnnnnnnnnn nnnnnnnnnn nnnnnnnnnn 39900
nnnnnnnnnn nnnnnnnnnn nnnnnnnnnn nnnnnnnnnn nnnnnnnnnn nnnnnnnnnn 39960
nnnnnnnnnn nnnnnnnnnn nnnnnnnnnn nnnnnnnnnn nnnnnnnnnn nnnnnnnnnn 40020
nnnnnnnnnn nnnnnnnnnn nnnnnnnnnn nnnnnnnnnn nnnnnnnnnn nnnnnnnnnn 40080
nnnnnnnnnn nnnnnnnnnn nnnnnnnnnn nnnnnnnnnn nnnnnnnnnn nnnnnnnnnn 40140
nnnnnnnnnn nnnnnnnnnn nnnnnnnnnn nnnnnnnnnn nnnnnnnnnn nnnnnnnnnn 40200
nnnnnnnnnn nnnnnnnnnn nnnnnnnnnn nnnnnnnnnn nnnnnnnnnn nnnnnnnnnn 40260
nnnnnnnnnn nnnnnnnnnn nnnnnnnnnn nnnnnnnnnn nnnnnnnnnn nnnnnnnnnn 40320
nnnnnnnnnn nnnnnnnnnn nnnnnnnnnn nnnnnnnnnn nnnnnnnnnn nnnnnnnnnn 40380
nnnnnnnnnn nnnnnnnnnn nnnnnnnnnn nnnnnnnnnn nnnnnnnnnn nnnnnnnnnn 40440
nnnnnnnnnn nnnnnnnnnn nnnnnnnnnn nnnnnnnnnn nnnnnnnnnn nnnnnnnnnn 40500
nnnnnnnnnn nnnnnnnnnn nnnnnnnnnn nnnnnnnnnn nnnnnnnnnn nnnnnnnnnn 40560
nnnnnnnnnn nnnnnnnnnn nnnnnnnnnn nnnnnnnnnn nnnnnnnnnn nnnnnnnnnn 40620
nnnnnnnnnn nnnnnnnnnn nnnnnnnnnn nnnnnnnnnn nnnnnnnnnn nnnnnnnnnn 40680
nnnnnnnnnn nnnnnnnnnn nnnnnnnnnn nnnnnnnnnn nnnnnnnnnn nnnnnnnnnn 40740
nnnnnnnnnn nnnnnnnnnn nnnnnnnnnn nnnnnnnnnn nnnnnnnnnn nnnnnnnnnn 40800
nnnnnnnnnn nnnnnnnnnn nnnnnnnnnn nnnnnnnnnn nnnnnnnnnn nnnnnnnnnn 40860
nnnnnnnnnn nnnnnnnnnn nnnnnnnnnn nnnnnnnnnn nnnnnnnnnn nnnnnnnnnn 40920
nnnnnnnnnn nnnnnnnnnn nnnnnnnnnn nnnnnnnnnn nnnnnnnnnn nnnnnnnnnn 40980
nnnnnnnnnn nnnnnnnnnn nnnnnnnnnn nnnnnnnnnn nnnnnnnnnn nnnnnnnnnn 41040
nnnnnnnnnn nnnnnnnnnn nnnnnnnnnn nnnnnnnnnn nnnnnnnnnn nnnnnnnnnn 41100
nnnnnnnnnn nnnnnnnnnn nnnnnnnnnn nnnnnnnnnn nnnnnnnnnn nnnnnnnnnn 41160
nnnnnnnnnn nnnnnnnnnn nnnnnnnnnn nnnnnnnnnn nnnnnnnnnn nnnnnnnnnn 41220
nnnnnnnnnn nnnnnnnnnn nnnnnnnnnn nnnnnnnnnn nnnnnnnnnn nnnnnnnnnn 41280

-continued nnnnnnnnnn nnnnnnnnnn nnnnnnnnnn nnnnnnnnnn nnnnnnnnnn nnnnnnnnnn 41340
nnnnnnnnnn nnnnnnnnnn nnnnnnnnnn nnnnnnnnnn nnnnnnnnnn nnnnnnnnnn 41400
nnnnnnnnnn nnnnnnnnnn nnnnnnnnnn nnnnnnnnnn nnnnnnnnnn nnnnnnnnnn 41460
nnnnnnnnnn nnnnnnnnnn nnnnnnnnnn nnnnnnnnnn nnnnnnnnnn nnnnnnnnnn 41520
nnnnnnnnnn nnnnnnnnnn nnnnnnnnnn nnnnnnnnnn nnnnnnnnnn nnnnnnnnnn 41580
nnnnnnnnnn nnnnnnnnnn nnnnnnnnnn nnnnnnnnnn nnnnnnnnnn nnnnnnnnnn 41640
nnnnnnnnnn nnnnnnnnnn nnnnnnnnnn nnnnnnnnnn nnnnnnnnnn nnnnnnnnnn 41700
nnnnnnnnnn nnnnnnnnnn nnnnnnnnnn nnnnnnnnnn nnnnnnnnnn nnnnnnnnnn 41760
nnnnnnnnnn nnnnnnnnnn nnnnnnnnnn nnnnnnnnnn nnnnnnnnnn nnnnnnnnnn 41820
nnnnnnnnnn nnnnnnnnnn nnnnnnnnnn nnnnnnnnnn nnnnnnnnnn nnnnnnnnnn 41880
nnnnnnnnnn nnnnnnnnnn nnnnnnnnnn nnnnnnnnnn nnnnnnnnnn nnnnnnnnnn 41940
nnnnnnnnnn nnnnnnnnnn nnnnnnnnnn nnnnnnnnnn nnnnnnnnnn nnnnnnnnnn 42000
nnnnnnnnnn nnnnnnnnnn nnnnnnnnnn nnnnnnnnnn nnnnnnnnnn nnnnnnnnnn 42060
nnnnnnnnnn nnnnnnnnnn nnnnnnnnnn nnnnnnnnnn nnnnnnnnnn nnnnnnnnnn 42120
nnnnnnnnnn nnnnnnnnnn nnnnnnnnnn nnnnnnnnnn nnnnnnnnnn nnnnnnnnnn 42180
nnnnnnnnnn nnnnnnnnnn nnnnnnnnnn nnnnnnnnnn nnnnnnnnnn nnnnnnnnnn 42240
nnnnnnnnnn nnnnnnnnnn nnnnnnnnnn nnnnnnnnnn nnnnnnnnnn nnnnnnnnnn 42300
nnnnnnnnnn nnnnnnnnnn nnnnnnnnnn nnnnnnnnnn nnnnnnnnnn nnnnnnnnnn 42360
nnnnnnnnnn nnnnnnnnnn nnnnnnnnnn nnnnnnnnnn nnnnnnnnnn nnnnnnnnnn 42420
nnnnnnnnnn nnnnnnnnnn nnnnnnnnnn nnnnnnnnnn nnnnnnnnnn nnnnnnnnnn 42480
nnnnnnnnnn nnnnnnnnnn nnnnnnnnnn nnnnnnnnnn nnnnnnnnnn nnnnnnnnnn 42540
nnnnnnnnnn nnnnnnnnnn nnnnnnnnnn nnnnnnnnnn nnnnnnnnnn nnnnnnnnnn 42600
nnnnnnnnnn nnnnnnnnnn nnnnnnnnnn nnnnnnnnnn nnnnnnnnnn nnnnnnnnnn 42660
nnnnnnnnnn nnnnnnnnnn nnnnnnnnnn nnnnnnnnnn nnnnnnnnnn nnnnnnnnnn 42720
nnnnnnnnnn nnnnnnnnnn nnnnnnnnnn nnnnnnnnnn nnnnnnnnnn nnnnnnnnnn 42780
nnnnnnnnnn nnnnnnnnnn nnnnnnnnnn nnnnnnnnnn nnnnnnnnnn nnnnnnnnnn 42840
nnnnnnnnnn nnnnnnnnnn nnnnnnnnnn nnnnnnnnnn nnnnnnnnnn nnnnnnnnnn 42900
nnnnnnnnnn nnnnnnnnnn nnnnnnnnnn nnnnnnnnnn nnnnnnnnnn nnnnnnnnnn 42960
nnnnnnnnnn nnnnnnnnnn nnnnnnnnnn nnnnnnnnnn nnnnnnnnnn nnnnnnnnnn 43020
nnnnnnnnnn nnnnnnnnnn nnnnnnnnnn nnnnnnnnnn nnnnnnnnnn nnnnnnnnnn 43080
nnnnnnnnnn nnnnnnnnnn nnnnnnnnnn nnnnnnnnnn nnnnnnnnnn nnnnnnnnnn 43140
nnnnnnnnnn nnnnnnnnnn nnnnnnnnnn nnnnnnnnnn nnnnnnnnnn nnnnnnnnnn 43200
nnnnnnnnnn nnnnnnnnnn nnnnnnnnnn nnnnnnnnnn nnnnnnnnnn nnnnnnnnnn 43260
nnnnnnnnnn nnnnnnnnnn nnnnnnnnnn nnnnnnnnnn nnnnnnnnnn nnnnnnnnnn 43320
nnnnnnnnnn nnnnnnnnnn nnnnnnnnnn nnnnnnnnnn nnnnnnnnnn nnnnnnnnnn 43380
nnnnnnnnnn nnnnnnnnnn nnnnnnnnnn nnnnnnnnnn nnnnnnnnnn nnnnnnnnnn 43440
nnnnnnnnnn nnnnnnnnnn nnnnnnnnnn nnnnnnnnnn nnnnnnnnnn nnnnnnnnnn 43500
nnnnnnnnnn nnnnnnnnnn nnnnnnnnnn nnnnnnnnnn nnnnnnnnnn nnnnnnnnnn 43560
nnnnnnnnnn nnnnnnnnnn nnnnnnnnnn nnnnnnnnnn nnnnnnnnnn nnnnnnnnnn 43620
nnnnnnnnnn nnnnnnnnnn nnnnnnnnnn nnnnnnnnnn nnnnnnnnnn nnnnnnnnnn 43680

-continued

```
nnnnnnnnnn nnnnnnnnnn nnnnnnnnnn nnnnnnnnnn nnnnnnnnnn nnnnnnnnnn  43740
nnnnnnnnnn nnnnnnnnnn nnnnnnnnnn nnnnnnnnnn nnnnnnnnnn nnnnnnnnnn  43800
nnnnnnnnnn nnnnnnnnnn nnnnnnnnnn nnnnnnnnnn nnnnnnnnnn nnnnnnnnnn  43860
nnnnnnnnnn nnnnnnnnnn nnnnnnnnnn nnnnnnnnnn nnnnnnnnnn nnnnnnnnnn  43920
nnnnnnnnnn nnnnnnnnnn nnnnnnnnnn nnnnnnnnnn nnnnnnnnnn nnnnnnnnnn  43980
nnnnnnnnnn nnnnnnnnnn nnnnnnnnnn nnnnnnnnnn nnnnnnnnnn nnnnnnnnnn  44040
nnnnnnnnnn nnnnnnnnnn nnnnnnnnnn nnnnnnnnnn nnnnnnnnnn nnnnnnnnnn  44100
nnnnnnnnnn nnnnnnnnnn nnnnnnnnnn nnnnnnnnnn nnnnnnnnnn nnnnnnnnnn  44160
nnnnnnnnnn nnnnnnnnnn nnnnnnnnnn nnnnnnnnnn nnnnnnnnnn nnnnnnnnnn  44220
nnnnnnnnnn nnnnnnnnnn nnnnnnnnnn nnnnnnnnnn nnnnnnnnnn nnnnnnnnnn  44280
nnnnnnnnnn nnnnnnnnnn nnnnnnnnnn nnnnnnnnnn nnnnnnnnnn nnnnnnnnnn  44340
nnnnnnnnnn nnnnnnnnnn nnnnnnnnnn nnnnnnnnnn nnnnnnnnnn nnnnnnnnnn  44400
nnnnnnnnnn nnnnnnnnnn nnnnnnnnnn nnnnnnnnnn nnnnnnnnnn nnnnnnnnnn  44460
nnnnnnnnnn nnnnnnnnnn nnnnnnnnnn nnnnnnnnnn nnnnnnnnnn nnnnnnnnnn  44520
nnnnnnnnnn nnnnnnnnnn nnnnnnnnnn nnnnnnnnnn nnnnnnnnnn nnnnnnnnnn  44580
nnnnnnnnnn nnnnnnnnnn nnnnnnnnnn nnnnnnnnnn nnnnnnnnnn nnnnnnnnnn  44640
nnnnnnnnnn nnnnnnnnnn nnnnnnnnnn nnnnnnnnnn nnnnnnnnnn nnnnnnnnnn  44700
nnnnnnnnnn nnnnnnnnnn nnnnnnnnnn nnnnnnnnnn nnnnnnnnnn nnnnnnnnnn  44760
nnnnnnnnnn nnnnnnnnnn nnnnnnnnnn nnnnnnnnnn nnnnnnnnnn nnnnnnnnnn  44820
nnnnnnnnnn nnnnnnnnnn nnnnnnnnnn nnnnnnnnnn nnnnnnnnnn nnnnnnnnnn  44880
nnnnnnnnnn nnnnnnnnnn nnnnnnnnnn nnnnnnnnnn nnnnnnnnnn nnnnnnnnnn  44940
nnnnnnnnnn nnnnnnnnnn nnnnnnnnnn nnnnnnnnnn nnnnnnnnnn nnnnnnnnnn  45000
nnnnnnnnnn nnnnnnnnnn nnnnnnnnnn nnnnnnnnnn nnnnnnnnnn nnnnnnnnnn  45060
nnnnnnnnnn nnnnnnnnnn nnnnnnnnnn nnnnnnnnnn nnnnnnnnnn nnnnnnnnnn  45120
nnnnnnnnnn nnnnnnnnnn nnnnnnnnnn nnnnnnnnnn nnnnnnnnnn nnnnnnnnnn  45180
nnnnnnnnnn nnnnnnnnnn nnnnnnnnnn nnnnnnnnnn nnnnnnnnnn nnnnnnnnnn  45240
nnnnnnnnnn nnnnnnnnnn nnnnnnnnnn nnnnnnnnnn nnnnnnnnnn nnnnnnnnnn  45300
nnnnnnnnnn nnnnnnnnnn nnnnnnnnnn nnnnnnnnnn nnnnnnnnnn nnnnnnnnnn  45360
nnnnnnnnnn nnnnnnnnnn nnnnnnnnnn nnnnnnnnnn nnnnnnnnnn nnnnnnnnnn  45420
nnnnnnnnnn nnnnnnnnnn nnnnnnnnnn nnnnnnnnnn nnnnnnnnnn nnnnnnnnnn  45480
nnnnnnnnnn nnnnnnnnnn nnnnnnnnnn nnnnnnnnnn nnnnnnnnnn nnnnnnnnnn  45540
nnnnnnnnnn nnnnnnnnnn nnnnnnnnnn nnnnnnnnnn nnnnnnnnnn nnnnnnnnnn  45600
nnnnnnnnnn nnnnnnnnnn nnnnnnnnnn nnnnnnnnnn nnnnnnnnnn nnnnnnnnnn  45660
nnnnnnnnnn nnnnnnnnnn nnnnnnnnnn nnnnnnnnnn nnnnnnnnnn nnnnnnnnnn  45720
nnnnnnnnnn nnnnnnnnnn nnnnnnnnnn nnnnnnnnnn nnnnnnnnnn nnnnnnnnnn  45780
nnnnnnnnnn nnnnnnnnnn nnnnnnnnnn nnnnnnnnnn nnnnnnnnnn nnnnnnnnnn  45840
nnnnnnnnnn nnnnnnnnnn nnnnnnnnnn nnnnnnnnnn nnnnnnnnnn nnnnnnnnnn  45900
nnnnnnnnnn nnnnnnnnnn nnnnnnnnnn nnnnnnnnnn nnnnnnnnnn nnnnnnnnnn  45960
nnnnnnnnnn nnnnnnnnnn nnnnnnnnnn nnnnnnnnnn nnnnnnnnnn nnnnnnnnnn  46020
```

-continued nnnnnnnnnn nnnnnnnnnn nnnnnnnnnn nnnnnnnnnn nnnnnnnnnn nnnnnnnnnn 46080
nnnnnnnnnn nnnnnnnnnn nnnnnnnnnn nnnnnnnnnn nnnnnnnnnn nnnnnnnnnn 46140
nnnnnnnnnn nnnnnnnnnn nnnnnnnnnn nnnnnnnnnn nnnnnnnnnn nnnnnnnnnn 46200
nnnnnnnnnn nnnnnnnnnn nnnnnnnnnn nnnnnnnnnn nnnnnnnnnn nnnnnnnnnn 46260
nnnnnnnnnn nnnnnnnnnn nnnnnnnnnn nnnnnnnnnn nnnnnnnnnn nnnnnnnnnn 46320
nnnnnnnnnn nnnnnnnnnn nnnnnnnnnn nnnnnnnnnn nnnnnnnnnn nnnnnnnnnn 46380
nnnnnnnnnn nnnnnnnnnn nnnnnnnnnn nnnnnnnnnn nnnnnnnnnn nnnnnnnnnn 46440
nnnnnnnnnn nnnnnnnnnn nnnnnnnnnn nnnnnnnnnn nnnnnnnnnn nnnnnnnnnn 46500
nnnnnnnnnn nnnnnnnnnn nnnnnnnnnn nnnnnnnnnn nnnnnnnnnn nnnnnnnnnn 46560
nnnnnnnnnn nnnnnnnnnn nnnnnnnnnn nnnnnnnnnn nnnnnnnnnn nnnnnnnnnn 46620
nnnnnnnnnn nnnnnnnnnn nnnnnnnnnn nnnnnnnnnn nnnnnnnnnn nnnnnnnnnn 46680
nnnnnnnnnn nnnnnnnnnn nnnnnnnnnn nnnnnnnnnn nnnnnnnnnn nnnnnnnnnn 46740
nnnnnnnnnn nnnnnnnnnn nnnnnnnnnn nnnnnnnnnn nnnnnnnnnn nnnnnnnnnn 46800
nnnnnnnnnn nnnnnnnnnn nnnnnnnnnn nnnnnnnnnn nnnnnnnnnn nnnnnnnnnn 46860
nnnnnnnnnn nnnnnnnnnn nnnnnnnnnn nnnnnnnnnn nnnnnnnnnn nnnnnnnnnn 46920
nnnnnnnnnn nnnnnnnnnn nnnnnnnnnn nnnnnnnnnn nnnnnnnnnn nnnnnnnnnn 46980
nnnnnnnnnn nnnnnnnnnn nnnnnnnnnn nnnnnnnnnn nnnnnnnnnn nnnnnnnnnn 47040
nnnnnnnnnn nnnnnnnnnn nnnnnnnnnn nnnnnnnnnn nnnnnnnnnn nnnnnnnnnn 47100
nnnnnnnnnn nnnnnnnnnn nnnnnnnnnn nnnnnnnnnn nnnnnnnnnn nnnnnnnnnn 47160
nnnnnnnnnn nnnnnnnnnn nnnnnnnnnn nnnnnnnnnn nnnnnnnnnn nnnnnnnnnn 47220
nnnnnnnnnn nnnnnnnnnn nnnnnnnnnn nnnnnnnnnn nnnnnnnnnn nnnnnnnnnn 47280
nnnnnnnnnn nnnnnnnnnn nnnnnnnnnn nnnnnnnnnn nnnnnnnnnn nnnnnnnnnn 47340
nnnnnnnnnn nnnnnnnnnn nnnnnnnnnn nnnnnnnnnn nnnnnnnnnn nnnnnnnnnn 47400
nnnnnnnnnn nnnnnnnnnn nnnnnnnnnn nnnnnnnnnn nnnnnnnnnn nnnnnnnnnn 47460
nnnnnnnnnn nnnnnnnnnn nnnnnnnnnn nnnnnnnnnn nnnnnnnnnn nnnnnnnnnn 47520
nnnnnnnnnn nnnnnnnnnn nnnnnnnnnn nnnnnnnnnn nnnnnnnnnn nnnnnnnnnn 47580
nnnnnnnnnn nnnnnnnnnn nnnnnnnnnn nnnnnnnnnn nnnnnnnnnn nnnnnnnnnn 47640
nnnnnnnnnn nnnnnnnnnn nnnnnnnnnn nnnnnnnnnn nnnnnnnnnn nnnnnnnnnn 47700
nnnnnnnnnn nnnnnnnnnn nnnnnnnnnn nnnnnnnnnn nnnnnnnnnn nnnnnnnnnn 47760
nnnnnnnnnn nnnnnnnnnn nnnnnnnnnn nnnnnnnnnn nnnnnnnnnn nnnnnnnnnn 47820
nnnnnnnnnn nnnnnnnnnn nnnnnnnnnn nnnnnnnnnn nnnnnnnnnn nnnnnnnnnn 47880
nnnnnnnnnn nnnnnnnnnn nnnnnnnnnn nnnnnnnnnn nnnnnnnnnn nnnnnnnnnn 47940
nnnnnnnnnn nnnnnnnnnn nnnnnnnnnn nnnnnnnnnn nnnnnnnnnn nnnnnnnnnn 48000
nnnnnnnnnn nnnnnnnnnn nnnnnnnnnn nnnnnnnnnn nnnnnnnnnn nnnnnnnnnn 48060
nnnnnnnnnn nnnnnnnnnn nnnnnnnnnn nnnnnnnnnn nnnnnnnnnn nnnnnnnnnn 48120
nnnnnnnnnn nnnnnnnnnn nnnnnnnnnn nnnnnnnnnn nnnnnnnnnn nnnnnnnnnn 48180
nnnnnnnnnn nnnnnnnnnn nnnnnnnnnn nnnnnnnnnn nnnnnnnnnn nnnnnnnnnn 48240
nnnnnnnnnn nnnnnnnnnn nnnnnnnnnn nnnnnnnnnn nnnnnnnnnn nnnnnnnnnn 48300
nnnnnnnnnn nnnnnnnnnn nnnnnnnnnn nnnnnnnnnn nnnnnnnnnn nnnnnnnnnn 48360
nnnnnnnnnn nnnnnnnnnn nnnnnnnnnn nnnnnnnnnn nnnnnnnnnn nnnnnnnnnn 48420

-continued nnnnnnnnnn nnnnnnnnnn nnnnnnnnnn nnnnnnnnnn nnnnnnnnnn nnnnnnnnnn 48480
nnnnnnnnnn nnnnnnnnnn nnnnnnnnnn nnnnnnnnnn nnnnnnnnnn nnnnnnnnnn 48540
nnnnnnnnnn nnnnnnnnnn nnnnnnnnnn nnnnnnnnnn nnnnnnnnnn nnnnnnnnnn 48600
nnnnnnnnnn nnnnnnnnnn nnnnnnnnnn nnnnnnnnnn nnnnnnnnnn nnnnnnnnnn 48660
nnnnnnnnnn nnnnnnnnnn nnnnnnnnnn nnnnnnnnnn nnnnnnnnnn nnnnnnnnnn 48720
nnnnnnnnnn nnnnnnnnnn nnnnnnnnnn nnnnnnnnnn nnnnnnnnnn nnnnnnnnnn 48780
nnnnnnnnnn nnnnnnnnnn nnnnnnnnnn nnnnnnnnnn nnnnnnnnnn nnnnnnnnnn 48840
nnnnnnnnnn nnnnnnnnnn nnnnnnnnnn nnnnnnnnnn nnnnnnnnnn nnnnnnnnnn 48900
nnnnnnnnnn nnnnnnnnnn nnnnnnnnnn nnnnnnnnnn nnnnnnnnnn nnnnnnnnnn 48960
nnnnnnnnnn nnnnnnnnnn nnnnnnnnnn nnnnnnnnnn nnnnnnnnnn nnnnnnnnnn 49020
nnnnnnnnnn nnnnnnnnnn nnnnnnnnnn nnnnnnnnnn nnnnnnnnnn nnnnnnnnnn 49080
nnnnnnnnnn nnnnnnnnnn nnnnnnnnnn nnnnnnnnnn nnnnnnnnnn nnnnnnnnnn 49140
nnnnnnnnnn nnnnnnnnnn nnnnnnnnnn nnnnnnnnnn nnnnnnnnnn nnnnnnnnnn 49200
nnnnnnnnnn nnnnnnnnnn nnnnnnnnnn nnnnnnnnnn nnnnnnnnnn nnnnnnnnnn 49260
nnnnnnnnnn nnnnnnnnnn nnnnnnnnnn nnnnnnnnnn nnnnnnnnnn nnnnnnnnnn 49320
nnnnnnnnnn nnnnnnnnnn nnnnnnnnnn nnnnnnnnnn nnnnnnnnnn nnnnnnnnnn 49380
nnnnnnnnnn nnnnnnnnnn nnnnnnnnnn nnnnnnnnnn nnnnnnnnnn nnnnnnnnnn 49440
nnnnnnnnnn nnnnnnnnnn nnnnnnnnnn nnnnnnnnnn nnnnnnnnnn nnnnnnnnnn 49500
nnnnnnnnnn nnnnnnnnnn nnnnnnnnnn nnnnnnnnnn nnnnnnnnnn nnnnnnnnnn 49560
nnnnnnnnnn nnnnnnnnnn nnnnnnnnnn nnnnnnnnnn nnnnnnnnnn nnnnnnnnnn 49620
nnnnnnnnnn nnnnnnnnnn nnnnnnnnnn nnnnnnnnnn nnnnnnnnnn nnnnnnnnnn 49680
nnnnnnnnnn nnnnnnnnnn nnnnnnnnnn nnnnnnnnnn nnnnnnnnnn nnnnnnnnnn 49740
nnnnnnnnnn nnnnnnnnnn nnnnnnnnnn nnnnnnnnnn nnnnnnnnnn nnnnnnnnnn 49800
nnnnnnnnnn nnnnnnnnnn nnnnnnnnnn nnnnnnnnnn nnnnnnnnnn nnnnnnnnnn 49860
nnnnnnnnnn nnnnnnnnnn nnnnnnnnnn nnnnnnnnnn nnnnnnnnnn nnnnnnnnnn 49920
nnnnnnnnnn nnnnnnnnnn nnnnnnnnnn nnnnnnnnnn nnnnnnnnnn nnnnnnnnnn 49980
nnnnnnnnnn nnnnnnnnnn nnnnnnnnnn nnnnnnnnnn nnnnnnnnnn nnnnnnnnnn 50040
nnnnnnnnnn nnnnnnnnnn nnnnnnnnnn nnnnnnnnnn nnnnnnnnnn nnnnnnnnnn 50100
nnnnnnnnnn nnnnnnnnnn nnnnnnnnnn nnnnnnnnnn nnnnnnnnnn nnnnnnnnnn 50160
nnnnnnnnnn nnnnnnnnnn nnnnnnnnnn nnnnnnnnnn nnnnnnnnnn nnnnnnnnnn 50220
nnnnnnnnnn nnnnnnnnnn nnnnnnnnnn nnnnnnnnnn nnnnnnnnnn nnnnnnnnnn 50280
nnnnnnnnnn nnnnnnnnnn nnnnnnnnnn nnnnnnnnnn nnnnnnnnnn nnnnnnnnnn 50340
nnnnnnnnnn nnnnnnnnnn nnnnnnnnnn nnnnnnnnnn nnnnnnnnnn nnnnnnnnnn 50400
nnnnnnnnnn nnnnnnnnnn nnnnnnnnnn nnnnnnnnnn nnnnnnnnnn nnnnnnnnnn 50460
nnnnnnnnnn nnnnnnnnnn nnnnnnnnnn nnnnnnnnnn nnnnnnnnnn nnnnnnnnnn 50520
nnnnnnnnnn nnnnnnnnnn nnnnnnnnnn nnnnnnnnnn nnnnnnnnnn nnnnnnnnnn 50580
nnnnnnnnnn nnnnnnnnnn nnnnnnnnnn nnnnnnnnnn nnnnnnnnnn nnnnnnnnnn 50640
nnnnnnnnnn nnnnnnnnnn nnnnnnnnnn nnnnnnnnnn nnnnnnnnnn nnnnnnnnnn 50700
nnnnnnnnnn nnnnnnnnnn nnnnnnnnnn nnnnnnnnnn nnnnnnnnnn nnnnnnnnnn 50760

-continued nnnnnnnnnn nnnnnnnnnn nnnnnnnnnn nnnnnnnnnn nnnnnnnnnn nnnnnnnnnn 50820
nnnnnnnnnn nnnnnnnnnn nnnnnnnnnn nnnnnnnnnn nnnnnnnnnn nnnnnnnnnn 50880
nnnnnnnnnn nnnnnnnnnn nnnnnnnnnn nnnnnnnnnn nnnnnnnnnn nnnnnnnnnn 50940
nnnnnnnnnn nnnnnnnnnn nnnnnnnnnn nnnnnnnnnn nnnnnnnnnn nnnnnnnnnn 51000
nnnnnnnnnn nnnnnnnnnn nnnnnnnnnn nnnnnnnnnn nnnnnnnnnn nnnnnnnnnn 51060
nnnnnnnnnn nnnnnnnnnn nnnnnnnnnn nnnnnnnnnn nnnnnnnnnn nnnnnnnnnn 51120
nnnnnnnnnn nnnnnnnnnn nnnnnnnnnn nnnnnnnnnn nnnnnnnnnn nnnnnnnnnn 51180
nnnnnnnnnn nnnnnnnnnn nnnnnnnnnn nnnnnnnnnn nnnnnnnnnn nnnnnnnnnn 51240
nnnnnnnnnn nnnnnnnnnn nnnnnnnnnn nnnnnnnnnn nnnnnnnnnn nnnnnnnnnn 51300
nnnnnnnnnn nnnnnnnnnn nnnnnnnnnn nnnnnnnnnn nnnnnnnnnn nnnnnnnnnn 51360
nnnnnnnnnn nnnnnnnnnn nnnnnnnnnn nnnnnnnnnn nnnnnnnnnn nnnnnnnnnn 51420
nnnnnnnnnn nnnnnnnnnn nnnnnnnnnn nnnnnnnnnn nnnnnnnnnn nnnnnnnnnn 51480
nnnnnnnnnn nnnnnnnnnn nnnnnnnnnn nnnnnnnnnn nnnnnnnnnn nnnnnnnnnn 51540
nnnnnnnnnn nnnnnnnnnn nnnnnnnnnn nnnnnnnnnn nnnnnnnnnn nnnnnnnnnn 51600
nnnnnnnnnn nnnnnnnnnn nnnnnnnnnn nnnnnnnnnn nnnnnnnnnn nnnnnnnnnn 51660
nnnnnnnnnn nnnnnnnnnn nnnnnnnnnn nnnnnnnnnn nnnnnnnnnn nnnnnnnnnn 51720
nnnnnnnnnn nnnnnnnnnn nnnnnnnnnn nnnnnnnnnn nnnnnnnnnn nnnnnnnnnn 51780
nnnnnnnnnn nnnnnnnnnn nnnnnnnnnn nnnnnnnnnn nnnnnnnnnn nnnnnnnnnn 51840
nnnnnnnnnn nnnnnnnnnn nnnnnnnnnn nnnnnnnnnn nnnnnnnnnn nnnnnnnnnn 51900
nnnnnnnnnn nnnnnnnnnn nnnnnnnnnn nnnnnnnnnn nnnnnnnnnn nnnnnnnnnn 51960
nnnnnnnnnn nnnnnnnnnn nnnnnnnnnn nnnnnnnnnn nnnnnnnnnn nnnnnnnnnn 52020
nnnnnnnnnn nnnnnnnnnn nnnnnnnnnn nnnnnnnnnn nnnnnnnnnn nnnnnnnnnn 52080
nnnnnnnnnn nnnnnnnnnn nnnnnnnnnn nnnnnnnnnn nnnnnnnnnn nnnnnnnnnn 52140
nnnnnnnnnn nnnnnnnnnn nnnnnnnnnn nnnnnnnnnn nnnnnnnnnn nnnnnnnnnn 52200
nnnnnnnnnn nnnnnnnnnn nnnnnnnnnn nnnnnnnnnn nnnnnnnnnn nnnnnnnnnn 52260
nnnnnnnnnn nnnnnnnnnn nnnnnnnnnn nnnnnnnnnn nnnnnnnnnn nnnnnnnnnn 52320
nnnnnnnnnn nnnnnnnnnn nnnnnnnnnn nnnnnnnnnn nnnnnnnnnn nnnnnnnnnn 52380
nnnnnnnnnn nnnnnnnnnn nnnnnnnnnn nnnnnnnnnn nnnnnnnnnn nnnnnnnnnn 52440
nnnnnnnnnn nnnnnnnnnn nnnnnnnnnn nnnnnnnnnn nnnnnnnnnn nnnnnnnnnn 52500
nnnnnnnnnn nnnnnnnnnn nnnnnnnnnn nnnnnnnnnn nnnnnnnnnn nnnnnnnnnn 52560
nnnnnnnnnn nnnnnnnnnn nnnnnnnnnn nnnnnnnnnn nnnnnnnnnn nnnnnnnnnn 52620
nnnnnnnnnn nnnnnnnnnn nnnnnnnnnn nnnnnnnnnn nnnnnnnnnn nnnnnnnnnn 52680
nnnnnnnnnn nnnnnnnnnn nnnnnnnnnn nnnnnnnnnn nnnnnnnnnn nnnnnnnnnn 52740
nnnnnnnnnn nnnnnnnnnn nnnnnnnnnn nnnnnnnnnn nnnnnnnnnn nnnnnnnnnn 52800
nnnnnnnnnn nnnnnnnnnn nnnnnnnnnn nnnnnnnnnn nnnnnnnnnn nnnnnnnnnn 52860
nnnnnnnnnn nnnnnnnnnn nnnnnnnnnn nnnnnnnnnn nnnnnnnnnn nnnnnnnnnn 52920
nnnnnnnnnn nnnnnnnnnn nnnnnnnnnn nnnnnnnnnn nnnnnnnnnn nnnnnnnnnn 52980
nnnnnnnnnn nnnnnnnnnn nnnnnnnnnn nnnnnnnnnn nnnnnnnnnn nnnnnnnnnn 53040
nnnnnnnnnn nnnnnnnnnn nnnnnnnnnn nnnnnnnnnn nnnnnnnnnn nnnnnnnnnn 53100
nnnnnnnnnn nnnnnnnnnn nnnnnnnnnn nnnnnnnnnn nnnnnnnnnn nnnnnnnnnn 53160

-continued nnnnnnnnnn nnnnnnnnnn nnnnnnnnnn nnnnnnnnnn nnnnnnnnnn nnnnnnnnnn 53220
nnnnnnnnnn nnnnnnnnnn nnnnnnnnnn nnnnnnnnnn nnnnnnnnnn nnnnnnnnnn 53280
nnnnnnnnnn nnnnnnnnnn nnnnnnnnnn nnnnnnnnnn nnnnnnnnnn nnnnnnnnnn 53340
nnnnnnnnnn nnnnnnnnnn nnnnnnnnnn nnnnnnnnnn nnnnnnnnnn nnnnnnnnnn 53400
nnnnnnnnnn nnnnnnnnnn nnnnnnnnnn nnnnnnnnnn nnnnnnnnnn nnnnnnnnnn 53460
nnnnnnnnnn nnnnnnnnnn nnnnnnnnnn nnnnnnnnnn nnnnnnnnnn nnnnnnnnnn 53520
nnnnnnnnnn nnnnnnnnnn nnnnnnnnnn nnnnnnnnnn nnnnnnnnnn nnnnnnnnnn 53580
nnnnnnnnnn nnnnnnnnnn nnnnnnnnnn nnnnnnnnnn nnnnnnnnnn nnnnnnnnnn 53640
nnnnnnnnnn nnnnnnnnnn nnnnnnnnnn nnnnnnnnnn nnnnnnnnnn nnnnnnnnnn 53700
nnnnnnnnnn nnnnnnnnnn nnnnnnnnnn nnnnnnnnnn nnnnnnnnnn nnnnnnnnnn 53760
nnnnnnnnnn nnnnnnnnnn nnnnnnnnnn nnnnnnnnnn nnnnnnnnnn nnnnnnnnnn 53820
nnnnnnnnnn nnnnnnnnnn nnnnnnnnnn nnnnnnnnnn nnnnnnnnnn nnnnnnnnnn 53880
nnnnnnnnnn nnnnnnnnnn nnnnnnnnnn nnnnnnnnnn nnnnnnnnnn nnnnnnnnnn 53940
nnnnnnnnnn nnnnnnnnnn nnnnnnnnnn nnnnnnnnnn nnnnnnnnnn nnnnnnnnnn 54000
nnnnnnnnnn nnnnnnnnnn nnnnnnnnnn nnnnnnnnnn nnnnnnnnnn nnnnnnnnnn 54060
nnnnnnnnnn nnnnnnnnnn nnnnnnnnnn nnnnnnnnnn nnnnnnnnnn nnnnnnnnnn 54120
nnnnnnnnnn nnnnnnnnnn nnnnnnnnnn nnnnnnnnnn nnnnnnnnnn nnnnnnnnnn 54180
nnnnnnnnnn nnnnnnnnnn nnnnnnnnnn nnnnnnnnnn nnnnnnnnnn nnnnnnnnnn 54240
nnnnnnnnnn nnnnnnnnnn nnnnnnnnnn nnnnnnnnnn nnnnnnnnnn nnnnnnnnnn 54300
nnnnnnnnnn nnnnnnnnnn nnnnnnnnnn nnnnnnnnnn nnnnnnnnnn nnnnnnnnnn 54360
nnnnnnnnnn nnnnnnnnnn nnnnnnnnnn nnnnnnnnnn nnnnnnnnnn nnnnnnnnnn 54420
nnnnnnnnnn nnnnnnnnnn nnnnnnnnnn nnnnnnnnnn nnnnnnnnnn nnnnnnnnnn 54480
nnnnnnnnnn nnnnnnnnnn nnnnnnnnnn nnnnnnnnnn nnnnnnnnnn nnnnnnnnnn 54540
nnnnnnnnnn nnnnnnnnnn nnnnnnnnnn nnnnnnnnnn nnnnnnnnnn nnnnnnnnnn 54600
nnnnnnnnnn nnnnnnnnnn nnnnnnnnnn nnnnnnnnnn nnnnnnnnnn nnnnnnnnnn 54660
nnnnnnnnnn nnnnnnnnnn nnnnnnnnnn nnnnnnnnnn nnnnnnnnnn nnnnnnnnnn 54720
nnnnnnnnnn nnnnnnnnnn nnnnnnnnnn nnnnnnnnnn nnnnnnnnnn nnnnnnnnnn 54780
nnnnnnnnnn nnnnnnnnnn nnnnnnnnnn nnnnnnnnnn nnnnnnnnnn nnnnnnnnnn 54840
nnnnnnnnnn nnnnnnnnnn nnnnnnnnnn nnnnnnnnnn nnnnnnnnnn nnnnnnnnnn 54900
nnnnnnnnnn nnnnnnnnnn nnnnnnnnnn nnnnnnnnnn nnnnnnnnnn nnnnnnnnnn 54960
nnnnnnnnnn nnnnnnnnnn nnnnnnnnnn nnnnnnnnnn nnnnnnnnnn nnnnnnnnnn 55020
nnnnnnnnnn nnnnnnnnnn nnnnnnnnnn nnnnnnnnnn nnnnnnnnnn nnnnnnnnnn 55080
nnnnnnnnnn nnnnnnnnnn nnnnnnnnnn nnnnnnnnnn nnnnnnnnnn nnnnnnnnnn 55140
nnnnnnnnnn nnnnnnnnnn nnnnnnnnnn nnnnnnnnnn nnnnnnnnnn nnnnnnnnnn 55200
nnnnnnnnnn nnnnnnnnnn nnnnnnnnnn nnnnnnnnnn nnnnnnnnnn nnnnnnnnnn 55260
nnnnnnnnnn nnnnnnnnnn nnnnnnnnnn nnnnnnnnnn nnnnnnnnnn nnnnnnnnnn 55320
nnnnnnnnnn nnnnnnnnnn nnnnnnnnnn nnnnnnnnnn nnnnnnnnnn nnnnnnnnnn 55380
nnnnnnnnnn nnnnnnnnnn nnnnnnnnnn nnnnnnnnnn nnnnnnnnnn nnnnnnnnnn 55440
nnnnnnnnnn nnnnnnnnnn nnnnnnnnnn nnnnnnnnnn nnnnnnnnnn nnnnnnnnnn 55500

-continued nnnnnnnnnn nnnnnnnnnn nnnnnnnnnn nnnnnnnnnn nnnnnnnnnn nnnnnnnnnn 55560
nnnnnnnnnn nnnnnnnnnn nnnnnnnnnn nnnnnnnnnn nnnnnnnnnn nnnnnnnnnn 55620
nnnnnnnnnn nnnnnnnnnn nnnnnnnnnn nnnnnnnnnn nnnnnnnnnn nnnnnnnnnn 55680
nnnnnnnnnn nnnnnnnnnn nnnnnnnnnn nnnnnnnnnn nnnnnnnnnn nnnnnnnnnn 55740
nnnnnnnnnn nnnnnnnnnn nnnnnnnnnn nnnnnnnnnn nnnnnnnnnn nnnnnnnnnn 55800
nnnnnnnnnn nnnnnnnnnn nnnnnnnnnn nnnnnnnnnn nnnnnnnnnn nnnnnnnnnn 55860
nnnnnnnnnn nnnnnnnnnn nnnnnnnnnn nnnnnnnnnn nnnnnnnnnn nnnnnnnnnn 55920
nnnnnnnnnn nnnnnnnnnn nnnnnnnnnn nnnnnnnnnn nnnnnnnnnn nnnnnnnnnn 55980
nnnnnnnnnn nnnnnnnnnn nnnnnnnnnn nnnnnnnnnn nnnnnnnnnn nnnnnnnnnn 56040
nnnnnnnnnn nnnnnnnnnn nnnnnnnnnn nnnnnnnnnn nnnnnnnnnn nnnnnnnnnn 56100
nnnnnnnnnn nnnnnnnnnn nnnnnnnnnn nnnnnnnnnn nnnnnnnnnn nnnnnnnnnn 56160
nnnnnnnnnn nnnnnnnnnn nnnnnnnnnn nnnnnnnnnn nnnnnnnnnn nnnnnnnnnn 56220
nnnnnnnnnn nnnnnnnnnn nnnnnnnnnn nnnnnnnnnn nnnnnnnnnn nnnnnnnnnn 56280
nnnnnnnnnn nnnnnnnnnn nnnnnnnnnn nnnnnnnnnn nnnnnnnnnn nnnnnnnnnn 56340
nnnnnnnnnn nnnnnnnnnn nnnnnnnnnn nnnnnnnnnn nnnnnnnnnn nnnnnnnnnn 56400
nnnnnnnnnn nnnnnnnnnn nnnnnnnnnn nnnnnnnnnn nnnnnnnnnn nnnnnnnnnn 56460
nnnnnnnnnn nnnnnnnnnn nnnnnnnnnn nnnnnnnnnn nnnnnnnnnn nnnnnnnnnn 56520
nnnnnnnnnn nnnnnnnnnn nnnnnnnnnn nnnnnnnnnn nnnnnnnnnn nnnnnnnnnn 56580
nnnnnnnnnn nnnnnnnnnn nnnnnnnnnn nnnnnnnnnn nnnnnnnnnn nnnnnnnnnn 56640
nnnnnnnnnn nnnnnnnnnn nnnnnnnnnn nnnnnnnnnn nnnnnnnnnn nnnnnnnnnn 56700
nnnnnnnnnn nnnnnnnnnn nnnnnnnnnn nnnnnnnnnn nnnnnnnnnn nnnnnnnnnn 56760
nnnnnnnnnn nnnnnnnnnn nnnnnnnnnn nnnnnnnnnn nnnnnnnnnn nnnnnnnnnn 56820
nnnnnnnnnn nnnnnnnnnn nnnnnnnnnn nnnnnnnnnn nnnnnnnnnn nnnnnnnnnn 56880
nnnnnnnnnn nnnnnnnnnn nnnnnnnnnn nnnnnnnnnn nnnnnnnnnn nnnnnnnnnn 56940
nnnnnnnnnn nnnnnnnnnn nnnnnnnnnn nnnnnnnnnn nnnnnnnnnn nnnnnnnnnn 57000
nnnnnnnnnn nnnnnnnnnn nnnnnnnnnn nnnnnnnnnn nnnnnnnnnn nnnnnnnnnn 57060
nnnnnnnnnn nnnnnnnnnn nnnnnnnnnn nnnnnnnnnn nnnnnnnnnn nnnnnnnnnn 57120
nnnnnnnnnn nnnnnnnnnn nnnnnnnnnn nnnnnnnnnn nnnnnnnnnn nnnnnnnnnn 57180
nnnnnnnnnn nnnnnnnnnn nnnnnnnnnn nnnnnnnnnn nnnnnnnnnn nnnnnnnnnn 57240
nnnnnnnnnn nnnnnnnnnn nnnnnnnnnn nnnnnnnnnn nnnnnnnnnn nnnnnnnnnn 57300
nnnnnnnnnn nnnnnnnnnn nnnnnnnnnn nnnnnnnnnn nnnnnnnnnn nnnnnnnnnn 57360
nnnnnnnnnn nnnnnnnnnn nnnnnnnnnn nnnnnnnnnn nnnnnnnnnn nnnnnnnnnn 57420
nnnnnnnnnn nnnnnnnnnn nnnnnnnnnn nnnnnnnnnn nnnnnnnnnn nnnnnnnnnn 57480
nnnnnnnnnn nnnnnnnnnn nnnnnnnnnn nnnnnnnnnn nnnnnnnnnn nnnnnnnnnn 57540
nnnnnnnnnn nnnnnnnnnn nnnnnnnnnn nnnnnnnnnn nnnnnnnnnn nnnnnnnnnn 57600
nnnnnnnnnn nnnnnnnnnn nnnnnnnnnn nnnnnnnnnn nnnnnnnnnn nnnnnnnnnn 57660
nnnnnnnnnn nnnnnnnnnn nnnnnnnnnn nnnnnnnnnn nnnnnnnnnn nnnnnnnnnn 57720
nnnnnnnnnn nnnnnnnnnn nnnnnnnnnn nnnnnnnnnn nnnnnnnnnn nnnnnnnnnn 57780
nnnnnnnnnn nnnnnnnnnn nnnnnnnnnn nnnnnnnnnn nnnnnnnnnn nnnnnnnnnn 57840
nnnnnnnnnn nnnnnnnnnn nnnnnnnnnn nnnnnnnnnn nnnnnnnnnn nnnnnnnnnn 57900

-continued

```
nnnnnnnnnn nnnnnnnnnn nnnnnnnnnn nnnnnnnnnn nnnnnnnnnn nnnnnnnnnn  57960
nnnnnnnnnn nnnnnnnnnn nnnnnnnnnn nnnnnnnnnn nnnnnnnnnn nnnnnnnnnn  58020
nnnnnnnnnn nnnnnnnnnn nnnnnnnnnn nnnnnnnnnn nnnnnnnnnn nnnnnnnnnn  58080
nnnnnnnnnn nnnnnnnnnn nnnnnnnnnn nnnnnnnnnn nnnnnnnnnn nnnnnnnnnn  58140
nnnnnnnnnn nnnnnnnnnn nnnnnnnnnn nnnnnnnnnn nnnnnnnnnn nnnnnnnnnn  58200
nnnnnnnnnn nnnnnnnnnn nnnnnnnnnn nnnnnnnnnn nnnnnnnnnn nnnnnnnnnn  58260
nnnnnnnnnn nnnnnnnnnn nnnnnnnnnn nnnnnnnnnn nnnnnnnnnn nnnnnnnnnn  58320
nnnnnnnnnn nnnnnnnnnn nnnnnnnnnn nnnnnnnnnn nnnnnnnnnn nnnnnnnnnn  58380
nnnnnnnnnn nnnnnnnnnn nnnnnnnnnn nnnnnnnnnn nnnnnnnnnn nnnnnnnnnn  58440
nnnnnnnnnn nnnnnnnnnn nnnnnnnnnn nnnnnnnnnn nnnnnnnnnn nnnnnnnnnn  58500
nnnnnnnnnn nnnnnnnnnn nnnnnnnnnn nnnnnnnnnn nnnnnnnnnn nnnnnnnnnn  58560
nnnnnnnnnn nnnnnnnnnn nnnnnnnnnn nnnnnnnnnn nnnnnnnnnn nnnnnnnnnn  58620
nnnnnnnnnn nnnnnnnnnn nnnnnnnnnn nnnnnnnnnn nnnnnnnnnn nnnnnnnnnn  58680
nnnnnnnnnn nnnnnnnnnn nnnnnnnnnn nnnnnnnnnn nnnnnnnnnn nnnnnnnnnn  58740
nnnnnnnnnn nnnnnnnnnn nnnnnnnnnn nnnnnnnnnn nnnnnnnnnn nnnnnnnnnn  58800
nnnnnnnnnn nnnnnnnnnn nnnnnnnnnn nnnnnnnnnn nnnnnnnnnn nnnnnnnnnn  58860
nnnnnnnnnn nnnnnnnnnn nnnnnnnnnn nnnnnnnnnn nnnnnnnnnn nnnnnnnnnn  58920
nnnnnnnnnn nnnnnnnnnn nnnnnnnnnn nnnnnnnnnn nnnnnnnnnn nnnnnnnnnn  58980
nnnnnnnnnn nnnnnnnnnn nnnnnnnnnn nnnnnnnnnn nnnnnnnnnn nnnnnnnnnn  59040
nnnnnnnnnn nnnnnnnnnn nnnnnnnnnn nnnnnnnnnn nnnnnnnnnn nnnnnnnnnn  59100
nnnnnnnnnn nnnnnnnnnn nnnnnnnnnn nnnnnnnnnn nnnnnnnnnn nnnnnnnnnn  59160
nnnnnnnnnn nnnnnnnnnn nnnnnnnnnn nnnnnnnnnn nnnnnnnnnn nnnnnnnnnn  59220
nnnnnnnnnn nnnnnnnnnn nnnnnnnnnn nnnnnnnnnn nnnnnnnnnn nnnnnnnnnn  59280
nnnnnnnnnn nnnnnnnnnn nnnnnnnnnn nnnnnnnnnn nnnnnnnnnn nnnnnnnnnn  59340
nnnnnnnnnn nnnnnnnnnn nnnnnnnnnn nnnnnnnnnn nnnnnnnnnn nnnnnnnnnn  59400
nnnnnnnnnn nnnnnnnnnn nnnnnnnnnn nnnnnnnnnn nnnnnnnnnn nnnnnnnnnn  59460
nnnnnnnnnn nnnnnnnnnn nnnnnnnnnn nnnnnnnnnn nnnnnnnnnn nnnnnnnnnn  59520
nnnnnnnnnn nnnnnnnnnn nnnnnnnnnn nnnnnnnnnn nnnnnnnnnn nnnnnnnnnn  59580
nnnnnnnnnn nnnnnnnnnn nnnnnnnnnn nnnnnnnnnn nnnnnnnnnn nnnnnnnnnn  59640
nnnnnnnnnn nnnnnnnnnn nnnnnnnnnn nnnnnnnnnn nnnnnnnnnn nnnnnnnnnn  59700
nnnnnnnnnn nnnnnnnnnn nnnnnnnnnn nnnnnnnnnn nnnnnnnnnn nnnnnnnnnn  59760
nnnnnnnnnn nnnnnnnnnn nnnnnnnnnn nnnnnnnnnn nnnnnnnnnn nnnnnnnnnn  59820
nnnnnnnnnn nnnnnnnnnn nnnnnnnnnn nnnnnnnnnn nnnnnnnnnn nnnnnnnnnn  59880
nnnnnnnnnn nnnnnnnnnn nnnnnnnnnn nnnnnnnnnn nnnnnnnnnn nnnnnnnnnn  59940
nnnnnnnnnn nnnnnnnnnn nnnnnnnnnn nnnnnnnnnn nnnnnnnnnn nnnnnnnnnn  60000
nnnnnnnnnn nnnnnnnnnn nnnnnnnnnn nnnnnnnnnn nnnnnnnnnn nnnnnnnnnn  60060
nnnnnnnnnn nnnnnnnnnn nnnnnnnnnn nnnnnnnnnn nnnnnnnnnn nnnnnnnnnn  60120
nnnnnnnnnn nnnnnnnnnn nnnnnnnnnn nnnnnnnnnn nnnnnnnnnn nnnnnnnnnn  60180
nnnnnnnnnn nnnnnnnnnn nnnnnnnnnn nnnnnnnnnn nnnnnnnnnn nnnnnnnnnn  60240
```

-continued nnnnnnnnnn nnnnnnnnnn nnnnnnnnnn nnnnnnnnnn nnnnnnnnnn nnnnnnnnnn 60300
nnnnnnnnnn nnnnnnnnnn nnnnnnnnnn nnnnnnnnnn nnnnnnnnnn nnnnnnnnnn 60360
nnnnnnnnnn nnnnnnnnnn nnnnnnnnnn nnnnnnnnnn nnnnnnnnnn nnnnnnnnnn 60420
nnnnnnnnnn nnnnnnnnnn nnnnnnnnnn nnnnnnnnnn nnnnnnnnnn nnnnnnnnnn 60480
nnnnnnnnnn nnnnnnnnnn nnnnnnnnnn nnnnnnnnnn nnnnnnnnnn nnnnnnnnnn 60540
nnnnnnnnnn nnnnnnnnnn nnnnnnnnnn nnnnnnnnnn nnnnnnnnnn nnnnnnnnnn 60600
nnnnnnnnnn nnnnnnnnnn nnnnnnnnnn nnnnnnnnnn nnnnnnnnnn nnnnnnnnnn 60660
nnnnnnnnnn nnnnnnnnnn nnnnnnnnnn nnnnnnnnnn nnnnnnnnnn nnnnnnnnnn 60720
nnnnnnnnnn nnnnnnnnnn nnnnnnnnnn nnnnnnnnnn nnnnnnnnnn nnnnnnnnnn 60780
nnnnnnnnnn nnnnnnnnnn nnnnnnnnnn nnnnnnnnnn nnnnnnnnnn nnnnnnnnnn 60840
nnnnnnnnnn nnnnnnnnnn nnnnnnnnnn nnnnnnnnnn nnnnnnnnnn nnnnnnnnnn 60900
nnnnnnnnnn nnnnnnnnnn nnnnnnnnnn nnnnnnnnnn nnnnnnnnnn nnnnnnnnnn 60960
nnnnnnnnnn nnnnnnnnnn nnnnnnnnnn nnnnnnnnnn nnnnnnnnnn nnnnnnnnnn 61020
nnnnnnnnnn nnnnnnnnnn nnnnnnnnnn nnnnnnnnnn nnnnnnnnnn nnnnnnnnnn 61080
nnnnnnnnnn nnnnnnnnnn nnnnnnnnnn nnnnnnnnnn nnnnnnnnnn nnnnnnnnnn 61140
nnnnnnnnnn nnnnnnnnnn nnnnnnnnnn nnnnnnnnnn nnnnnnnnnn nnnnnnnnnn 61200
nnnnnnnnnn nnnnnnnnnn nnnnnnnnnn nnnnnnnnnn nnnnnnnnnn nnnnnnnnnn 61260
nnnnnnnnnn nnnnnnnnnn nnnnnnnnnn nnnnnnnnnn nnnnnnnnnn nnnnnnnnnn 61320
nnnnnnnnnn nnnnnnnnnn nnnnnnnnnn nnnnnnnnnn nnnnnnnnnn nnnnnnnnnn 61380
nnnnnnnnnn nnnnnnnnnn nnnnnnnnnn nnnnnnnnnn nnnnnnnnnn nnnnnnnnnn 61440
nnnnnnnnnn nnnnnnnnnn nnnnnnnnnn nnnnnnnnnn nnnnnnnnnn nnnnnnnnnn 61500
nnnnnnnnnn nnnnnnnnnn nnnnnnnnnn nnnnnnnnnn nnnnnnnnnn nnnnnnnnnn 61560
nnnnnnnnnn nnnnnnnnnn nnnnnnnnnn nnnnnnnnnn nnnnnnnnnn nnnnnnnnnn 61620
nnnnnnnnnn nnnnnnnnnn nnnnnnnnnn nnnnnnnnnn nnnnnnnnnn nnnnnnnnnn 61680
nnnnnnnnnn nnnnnnnnnn nnnnnnnnnn nnnnnnnnnn nnnnnnnnnn nnnnnnnnnn 61740
nnnnnnnnnn nnnnnnnnnn nnnnnnnnnn nnnnnnnnnn nnnnnnnnnn nnnnnnnnnn 61800
nnnnnnnnnn nnnnnnnnnn nnnnnnnnnn nnnnnnnnnn nnnnnnnnnn nnnnnnnnnn 61860
nnnnnnnnnn nnnnnnnnnn nnnnnnnnnn nnnnnnnnnn nnnnnnnnnn nnnnnnnnnn 61920
nnnnnnnnnn nnnnnnnnnn nnnnnnnnnn nnnnnnnnnn nnnnnnnnnn nnnnnnnnnn 61980
nnnnnnnnnn nnnnnnnnnn nnnnnnnnnn nnnnnnnnnn nnnnnnnnnn nnnnnnnnnn 62040
nnnnnnnnnn nnnnnnnnnn nnnnnnnnnn nnnnnnnnnn nnnnnnnnnn nnnnnnnnnn 62100
nnnnnnnnnn nnnnnnnnnn nnnnnnnnnn nnnnnnnnnn nnnnnnnnnn nnnnnnnnnn 62160
nnnnnnnnnn nnnnnnnnnn nnnnnnnnnn nnnnnnnnnn nnnnnnnnnn nnnnnnnnnn 62220
nnnnnnnnnn nnnnnnnnnn nnnnnnnnnn nnnnnnnnnn nnnnnnnnnn nnnnnnnnnn 62280
nnnnnnnnnn nnnnnnnnnn nnnnnnnnnn nnnnnnnnnn nnnnnnnnnn nnnnnnnnnn 62340
nnnnnnnnnn nnnnnnnnnn nnnnnnnnnn nnnnnnnnnn nnnnnnnnnn nnnnnnnnnn 62400
nnnnnnnnnn nnnnnnnnnn nnnnnnnnnn nnnnnnnnnn nnnnnnnnnn nnnnnnnnnn 62460
nnnnnnnnnn nnnnnnnnnn nnnnnnnnnn nnnnnnnnnn nnnnnnnnnn nnnnnnnnnn 62520
nnnnnnnnnn nnnnnnnnnn nnnnnnnnnn nnnnnnnnnn nnnnnnnnnn nnnnnnnnnn 62580
nnnnnnnnnn nnnnnnnnnn nnnnnnnnnn nnnnnnnnnn nnnnnnnnnn nnnnnnnnnn 62640

-continued nnnnnnnnnn nnnnnnnnnn nnnnnnnnnn nnnnnnnnnn nnnnnnnnnn nnnnnnnnnn 62700
nnnnnnnnnn nnnnnnnnnn nnnnnnnnnn nnnnnnnnnn nnnnnnnnnn nnnnnnnnnn 62760
nnnnnnnnnn nnnnnnnnnn nnnnnnnnnn nnnnnnnnnn nnnnnnnnnn nnnnnnnnnn 62820
nnnnnnnnnn nnnnnnnnnn nnnnnnnnnn nnnnnnnnnn nnnnnnnnnn nnnnnnnnnn 62880
nnnnnnnnnn nnnnnnnnnn nnnnnnnnnn nnnnnnnnnn nnnnnnnnnn nnnnnnnnnn 62940
nnnnnnnnnn nnnnnnnnnn nnnnnnnnnn nnnnnnnnnn nnnnnnnnnn nnnnnnnnnn 63000
nnnnnnnnnn nnnnnnnnnn nnnnnnnnnn nnnnnnnnnn nnnnnnnnnn nnnnnnnnnn 63060
nnnnnnnnnn nnnnnnnnnn nnnnnnnnnn nnnnnnnnnn nnnnnnnnnn nnnnnnnnnn 63120
nnnnnnnnnn nnnnnnnnnn nnnnnnnnnn nnnnnnnnnn nnnnnnnnnn nnnnnnnnnn 63180
nnnnnnnnnn nnnnnnnnnn nnnnnnnnnn nnnnnnnnnn nnnnnnnnnn nnnnnnnnnn 63240
nnnnnnnnnn nnnnnnnnnn nnnnnnnnnn nnnnnnnnnn nnnnnnnnnn nnnnnnnnnn 63300
nnnnnnnnnn nnnnnnnnnn nnnnnnnnnn nnnnnnnnnn nnnnnnnnnn nnnnnnnnnn 63360
nnnnnnnnnn nnnnnnnnnn nnnnnnnnnn nnnnnnnnnn nnnnnnnnnn nnnnnnnnnn 63420
nnnnnnnnnn nnnnnnnnnn nnnnnnnnnn nnnnnnnnnn nnnnnnnnnn nnnnnnnnnn 63480
nnnnnnnnnn nnnnnnnnnn nnnnnnnnnn nnnnnnnnnn nnnnnnnnnn nnnnnnnnnn 63540
nnnnnnnnnn nnnnnnnnnn nnnnnnnnnn nnnnnnnnnn nnnnnnnnnn nnnnnnnnnn 63600
nnnnnnnnnn nnnnnnnnnn nnnnnnnnnn nnnnnnnnnn nnnnnnnnnn nnnnnnnnnn 63660
nnnnnnnnnn nnnnnnnnnn nnnnnnnnnn nnnnnnnnnn nnnnnnnnnn nnnnnnnnnn 63720
nnnnnnnnnn nnnnnnnnnn nnnnnnnnnn nnnnnnnnnn nnnnnnnnnn nnnnnnnnnn 63780
nnnnnnnnnn nnnnnnnnnn nnnnnnnnnn nnnnnnnnnn nnnnnnnnnn nnnnnnnnnn 63840
nnnnnnnnnn nnnnnnnnnn nnnnnnnnnn nnnnnnnnnn nnnnnnnnnn nnnnnnnnnn 63900
nnnnnnnnnn nnnnnnnnnn nnnnnnnnnn nnnnnnnnnn nnnnnnnnnn nnnnnnnnnn 63960
nnnnnnnnnn nnnnnnnnnn nnnnnnnnnn nnnnnnnnnn nnnnnnnnnn nnnnnnnnnn 64020
nnnnnnnnnn nnnnnnnnnn nnnnnnnnnn nnnnnnnnnn nnnnnnnnnn nnnnnnnnnn 64080
nnnnnnnnnn nnnnnnnnnn nnnnnnnnnn nnnnnnnnnn nnnnnnnnnn nnnnnnnnnn 64140
nnnnnnnnnn nnnnnnnnnn nnnnnnnnnn nnnnnnnnnn nnnnnnnnnn nnnnnnnnnn 64200
nnnnnnnnnn nnnnnnnnnn nnnnnnnnnn nnnnnnnnnn nnnnnnnnnn nnnnnnnnnn 64260
nnnnnnnnnn nnnnnnnnnn nnnnnnnnnn nnnnnnnnnn nnnnnnnnnn nnnnnnnnnn 64320
nnnnnnnnnn nnnnnnnnnn nnnnnnnnnn nnnnnnnnnn nnnnnnnnnn nnnnnnnnnn 64380
nnnnnnnnnn nnnnnnnnnn nnnnnnnnnn nnnnnnnnnn nnnnnnnnnn nnnnnnnnnn 64440
nnnnnnnnnn nnnnnnnnnn nnnnnnnnnn nnnnnnnnnn nnnnnnnnnn nnnnnnnnnn 64500
nnnnnnnnnn nnnnnnnnnn nnnnnnnnnn nnnnnnnnnn nnnnnnnnnn nnnnnnnnnn 64560
nnnnnnnnnn nnnnnnnnnn nnnnnnnnnn nnnnnnnnnn nnnnnnnnnn nnnnnnnnnn 64620
nnnnnnnnnn nnnnnnnnnn nnnnnnnnnn nnnnnnnnnn nnnnnnnnnn nnnnnnnnnn 64680
nnnnnnnnnn nnnnnnnnnn nnnnnnnnnn nnnnnnnnnn nnnnnnnnnn nnnnnnnnnn 64740
nnnnnnnnnn nnnnnnnnnn nnnnnnnnnn nnnnnnnnnn nnnnnnnnnn nnnnnnnnnn 64800
nnnnnnnnnn nnnnnnnnnn nnnnnnnnnn nnnnnnnnnn nnnnnnnnnn nnnnnnnnnn 64860
nnnnnnnnnn nnnnnnnnnn nnnnnnnnnn nnnnnnnnnn nnnnnnnnnn nnnnnnnnnn 64920
nnnnnnnnnn nnnnnnnnnn nnnnnnnnnn nnnnnnnnnn nnnnnnnnnn nnnnnnnnnn 64980

-continued nnnnnnnnnn nnnnnnnnnn nnnnnnnnnn nnnnnnnnnn nnnnnnnnnn nnnnnnnnnn 65040
nnnnnnnnnn nnnnnnnnnn nnnnnnnnnn nnnnnnnnnn nnnnnnnnnn nnnnnnnnnn 65100
nnnnnnnnnn nnnnnnnnnn nnnnnnnnnn nnnnnnnnnn nnnnnnnnnn nnnnnnnnnn 65160
nnnnnnnnnn nnnnnnnnnn nnnnnnnnnn nnnnnnnnnn nnnnnnnnnn nnnnnnnnnn 65220
nnnnnnnnnn nnnnnnnnnn nnnnnnnnnn nnnnnnnnnn nnnnnnnnnn nnnnnnnnnn 65280
nnnnnnnnnn nnnnnnnnnn nnnnnnnnnn nnnnnnnnnn nnnnnnnnnn nnnnnnnnnn 65340
nnnnnnnnnn nnnnnnnnnn nnnnnnnnnn nnnnnnnnnn nnnnnnnnnn nnnnnnnnnn 65400
nnnnnnnnnn nnnnnnnnnn nnnnnnnnnn nnnnnnnnnn nnnnnnnnnn nnnnnnnnnn 65460
nnnnnnnnnn nnnnnnnnnn nnnnnnnnnn nnnnnnnnnn nnnnnnnnnn nnnnnnnnnn 65520
nnnnnnnnnn nnnnnnnnnn nnnnnnnnnn nnnnnnnnnn nnnnnnnnnn nnnnnnnnnn 65580
nnnnnnnnnn nnnnnnnnnn nnnnnnnnnn nnnnnnnnnn nnnnnnnnnn nnnnnnnnnn 65640
nnnnnnnnnn nnnnnnnnnn nnnnnnnnnn nnnnnnnnnn nnnnnnnnnn nnnnnnnnnn 65700
nnnnnnnnnn nnnnnnnnnn nnnnnnnnnn nnnnnnnnnn nnnnnnnnnn nnnnnnnnnn 65760
nnnnnnnnnn nnnnnnnnnn nnnnnnnnnn nnnnnnnnnn nnnnnnnnnn nnnnnnnnnn 65820
nnnnnnnnnn nnnnnnnnnn nnnnnnnnnn nnnnnnnnnn nnnnnnnnnn nnnnnnnnnn 65880
nnnnnnnnnn nnnnnnnnnn nnnnnnnnnn nnnnnnnnnn nnnnnnnnnn nnnnnnnnnn 65940
nnnnnnnnnn nnnnnnnnnn nnnnnnnnnn nnnnnnnnnn nnnnnnnnnn nnnnnnnnnn 66000
nnnnnnnnnn nnnnnnnnnn nnnnnnnnnn nnnnnnnnnn nnnnnnnnnn nnnnnnnnnn 66060
nnnnnnnnnn nnnnnnnnnn nnnnnnnnnn nnnnnnnnnn nnnnnnnnnn nnnnnnnnnn 66120
nnnnnnnnnn nnnnnnnnnn nnnnnnnnnn nnnnnnnnnn nnnnnnnnnn nnnnnnnnnn 66180
nnnnnnnnnn nnnnnnnnnn nnnnnnnnnn nnnnnnnnnn nnnnnnnnnn nnnnnnnnnn 66240
nnnnnnnnnn nnnnnnnnnn nnnnnnnnnn nnnnnnnnnn nnnnnnnnnn nnnnnnnnnn 66300
nnnnnnnnnn nnnnnnnnnn nnnnnnnnnn nnnnnnnnnn nnnnnnnnnn nnnnnnnnnn 66360
nnnnnnnnnn nnnnnnnnnn nnnnnnnnnn nnnnnnnnnn nnnnnnnnnn nnnnnnnnnn 66420
nnnnnnnnnn nnnnnnnnnn nnnnnnnnnn nnnnnnnnnn nnnnnnnnnn nnnnnnnnnn 66480
nnnnnnnnnn nnnnnnnnnn nnnnnnnnnn nnnnnnnnnn nnnnnnnnnn nnnnnnnnnn 66540
nnnnnnnnnn nnnnnnnnnn nnnnnnnnnn nnnnnnnnnn nnnnnnnnnn nnnnnnnnnn 66600
nnnnnnnnnn nnnnnnnnnn nnnnnnnnnn nnnnnnnnnn nnnnnnnnnn nnnnnnnnnn 66660
nnnnnnnnnn nnnnnnnnnn nnnnnnnnnn nnnnnnnnnn nnnnnnnnnn nnnnnnnnnn 66720
nnnnnnnnnn nnnnnnnnnn nnnnnnnnnn nnnnnnnnnn nnnnnnnnnn nnnnnnnnnn 66780
nnnnnnnnnn nnnnnnnnnn nnnnnnnnnn nnnnnnnnnn nnnnnnnnnn nnnnnnnnnn 66840
nnnnnnnnnn nnnnnnnnnn nnnnnnnnnn nnnnnnnnnn nnnnnnnnnn nnnnnnnnnn 66900
nnnnnnnnnn nnnnnnnnnn nnnnnnnnnn nnnnnnnnnn nnnnnnnnnn nnnnnnnnnn 66960
nnnnnnnnnn nnnnnnnnnn nnnnnnnnnn nnnnnnnnnn nnnnnnnnnn nnnnnnnnnn 67020
nnnnnnnnnn nnnnnnnnnn nnnnnnnnnn nnnnnnnnnn nnnnnnnnnn nnnnnnnnnn 67080
nnnnnnnnnn nnnnnnnnnn nnnnnnnnnn nnnnnnnnnn nnnnnnnnnn nnnnnnnnnn 67140
nnnnnnnnnn nnnnnnnnnn nnnnnnnnnn nnnnnnnnnn nnnnnnnnnn nnnnnnnnnn 67200
nnnnnnnnnn nnnnnnnnnn nnnnnnnnnn nnnnnnnnnn nnnnnnnnnn nnnnnnnnnn 67260
nnnnnnnnnn nnnnnnnnnn nnnnnnnnnn nnnnnnnnnn nnnnnnnnnn nnnnnnnnnn 67320
nnnnnnnnnn nnnnnnnnnn nnnnnnnnnn nnnnnnnnnn nnnnnnnnnn nnnnnnnnnn 67380

```
nnnnnnnnnn nnnnnnnnnn nnnnnnnnnn nnnnnnnnnn nnnnnnnnnn nnnnnnnnnn  67440
nnnnnnnnnn nnnnnnnnnn nnnnnnnnnn nnnnnnnnnn nnnnnnnnnn nnnnnnnnnn  67500
nnnnnnnnnn nnnnnnnnnn nnnnnnnnnn nnnnnnnnnn nnnnnnnnnn nnnnnnnnnn  67560
nnnnnnnnnn nnnnnnnnnn nnnnnnnnnn nnnnnnnnnn nnnnnnnnnn nnnnnnnnnn  67620
nnnnnnnnnn nnnnnnnnnn nnnnnnnnnn nnnnnnnnnn nnnnnnnnnn nnnnnnnnnn  67680
nnnnnnnnnn nnnnnnnnnn nnnnnnnnnn nnnnnnnnnn nnnnnnnnnn nnnnnnnnnn  67740
nnnnnnnnnn nnnnnnnnnn nnnnnnnnnn nnnnnnnnnn nnnnnnnnnn nnnnnnnnnn  67800
nnnnnnnnnn nnnnnnnnnn nnnnnnnnnn nnnnnnnnnn nnnnnnnnnn nnnnnnnnnn  67860
nnnnnnnnnn nnnnnnnnnn nnnnnnnnnn nnnnnnnnnn nnnnnnnnnn nnnnnnnnnn  67920
nnnnnnnnnn nnnnnnnnnn nnnnnnnnnn nnnnnnnnnn nnnnnnnnnn nnnnnnnnnn  67980
nnnnnnnnnn nnnnnnnnnn nnnnnnnnnn nnnnnnnnnn nnnnnnnnnn nnnnnnnnnn  68040
nnnnnnnnnn nnnnnnnnnn nnnnnnnnnn nnnnnnnnnn nnnnnnnnnn nnnnnnnnnn  68100
nnnnnnnnnn nnnnnnnnnn nnnnnnnnnn nnnnnnnnnn nnnnnnnnnn nnnnnnnnnn  68160
nnnnnnnnnn nnnnnnnnnn nnnnnnnnnn nnnnnnnnnn nnnnnnnnnn nnnnnnnnnn  68220
nnnnnnnnnn nnnnnnnnnn nnnnnnnnnn nnnnaagctt tgattgggcc gttactgtct  68280
tttgaccttt cttgtttgct tgccctttttg tttctttcct cctttttcct tccttcctgt  68340
ctttcttctt ccttccttcc tttcttcctt tttcttttta attttcctcc tttctctttc  68400
tcctttcttt ccttccttct ttcctctttt tttctttcct ccctccctcc ctttctttct  68460
tccttccttt ctttcttccc tccttccctc cccaccctcc ctcccttccc ctcgtctccc  68520
ttcccctcgt ctcccttccc ctcccctccc tccctccctt cctccttttt ctttcccttt  68580
cctccttcct tccttcctct cttcttttct ccatcccttt cttcctttta acatttgatc  68640
atgggtacca tttcatcaag attctgttac ttaggtccaa ggactagtga ccaaattgtt  68700
tttcccagga gtaaactttt ctacaagaca tagagaaatg actgccagtg ccatcaggca  68760
caccatcctg tgtgataggt aacctaaaat aatggtacag cggggagtaa ctggaagagt  68820
cacaactaca caaatctctt gcattttcct gatcattaaa tgaattaggg atttcctggt  68880
ttgagatttg tggacaagga gaactacttc tttgtacaag aggcttgtgc caggagaaga  68940
cacgctgtgg ttacaatgtt actgtctcta gctatggtca tttcatgtct ttaactgagt  69000
gtacctagag tgtaatacag tgcagcagtg atgggctgaa ggcctaatgc accagcacac  69060
atgcctggaa gacctaacgt tgagaatccg catttttttc atcactcaca tttattttgc  69120
atctccctgt tttgattacc ttcagagacc caagcacttg cttttgtata tttgagtctg  69180
ggttttattt tccttttaga aatagtccaa aatcctttta gagcctagac ctttgaataa  69240
agtgctaact taacctgagg aatgctgttt ttttgttcac aaataaggct taattgtgaa  69300
gtcgtgagaa ttgctttctg agctgactta taaatttacc cacctctttt tccccaaacc  69360
cccaaaaaat cctccagaag gtgagcccag cttgttgtaa aagattttga agcagaagtc  69420
ctgggtttaa gcttcagttc tctgccttac cagaatcggg atgtgtgggg caggcctacc  69480
tcctctttct tcatctgcaa aatacattga atgaaatcat attttttcct aagtatatga  69540
catgtaaagt ggtatttcaa aaactcatta atctgcatga ccaggtcaga aaagacacac  69600
cttttgcctt gtgtctagtg tgtgactgtc ctcacatgta gatgacccag gccacatccg  69660
ctgatgttgt cttcctttac ttctttgtcc cttccaatga ctcctttatg aagtcaatca  69720
```

gcagtgtttc taagccaggt tccttctctt cacacatccc caacccacag ggcaagtcat 69780
ccacattttg cctctctatt ttttgtgctt tgggaaacac attttacaac ttccaaacta 69840
tttgcctaag ttcatctgag cacatctaga attattccac tcctctgcat cagtgctaaa 69900
agtacaatca tgtataagct gttatactcc cgttattttg tacctcatgt gcaggtagat 69960
tgcaagttcc ttgcaggcag gtactacatc tacttgaatt gcttcacgat cacataacac 70020
aatgcagtgt taaaagtaga aaagtaattg acatcttgac taacagaaac actaaattca 70080
gtgtattgtg atgatacctt tttaagagat aggctataga aatagaaaat catcttagtt 70140
ggaattgaaa gtcaagaagc aacattttaa gtaagagatg aaaatactta aaagggaaag 70200
gagcagtgct tacacagatg aggggaaaaa ataaaatgta tcatctaaaa atttaaatca 70260
aatatattag gttggtgcaa aagtaactgc gatttttgcc attaaaagta atagcaaaaa 70320
ccacggttac ttttgcacca acctaataga tgggaaaaat aagaggaatg aatattttaa 70380
gctttgctat ataattaaaa tattcttaga agtctggagt ctgtgaaggt cacaccctct 70440
ggtcttctcc cagcccatag ggtataaata atctgaattg acggcatcca gggatctcag 70500
aaattattag tacatcccac agtgaattac caccttacta aaatattcat gggtatatac 70560
tatggatttg ttttatccta tttagtctta aaaactataa agaaatctgc aggcttatta 70620
acatattact cagaatcata ttgtctccaa agcacaaact gaatcagtta caagatattg 70680
gactagagat catggcaaat cagaggtaca taagacctag ttccgttgtg gagctaaaca 70740
aactgcagag acctaaaggg aagccttgca ccacactcta ggtttggagc tcaggttttg 70800
agtggtgtca gcactccaga acacatggga tccccgggag gtggaaattg agccgtcttt 70860
ggagaatcag ctaatgagac agatgcatgt taaatgtctg ttgtggccca ggcactctgc 70920
taggcagagg ggtgaaccag aagaatgaga ttcatggggc caaagaattt gccttctggt 70980
gtaagaaaag atggaggcag cttggcagaa agaaaaaaaa ggtaaaagat agaaatgaaa 71040
tacagaataa tctatctcct catcccacaa gcaattctgc ctggtttgtg gctcacgcct 71100
gtaatcccag cactttggga ggccgaggca ggaggatcac ttgaggtcag gagttcgaga 71160
ctagcctgga ccacaaggtg aaacctcatc tctactaaaa atgcaaaaaa atttagggcc 71220
gggtgcagtg gcagttctgc ctggtttgaa catctggttc agttaaaata cttcatgaaa 71280
atatttagct tgatgcactg aaatccatca ctgcttttgt gggatgcact gactgcagtc 71340
tgactgttct cctagtggaa aggggagcaa tagcttctgt ctgcatgtgc atgaaacaga 71400
tggaaattta gaagagattc tagtgcagac aacttcatcc cacccccgct gcccacagag 71460
ctagccatgt gcacggtgtg tttgaacaat gttatgttgc tgctgtgcac agagatcccc 71520
agtctcataa aacatactgg atggaaggct gtcgagagat catcaggccc cagtgcataa 71580
gttcttccta agcatcctta acaggtgatc acctcgccta ttgagaaccc tcaggaggca 71640
gcccacttac ggaagcactg attgttacaa aagccctgaa ctaaatctgc ttgtctctaa 71700
agccagccct gcagatgtct gcagtgtaac tactttctct tctctcaagc agttcagccc 71760
ttcaaatcat tgacaacagc tctacaaagc cctctaaata gcccgttctc ctggctaaag 71820
tgtgttggtt tcctcagcat atgatgaaat aaacaccatg atgcctttgc cttgcttttt 71880
cttgctggtc tcactcttcc ctggcattct tcaatgtgcc caagtccttc ctagaacatt 71940
gcacccaaag ggccttcctg gtctttccag ggaatgcaga atgaaaaaga aatcccatcc 72000
cctgcctcga aaggagctct tctgtgtgta agtgtacctt ccccctcagg gcataatggg 72060
aaacagtttg ccaaagctaa ctgtgtaatt tcacatgact cactgccgtt agtctgagaa 72120
agcatggcat attaaactca ttttccatgc ttcccaactt tatttactat tccatttctg 72180
aggggcagag agctgagcag gaataacacc ttccttgctc ctcctaatgg ggcacatgtg 72240
cacatataaa attgtgttcg atctttgcag ccacgaccca tgttaactgt caactgagaa 72300
ctcatgagtc agtttctcag gaacagccct gaagacatta tctcctgcat cttgtatttg 72360
tgcctttgat atttggaggg aagggtagga tctggcaatt atcgttatct catttggttc 72420
agtgtatttc atttcagcct gttaagatct tttggaaata ctgtatgtgc tagttacagg 72480
gacagtgata aataagacag cattcctgtc cttgagatgc tatttccaca gctccatgag 72540
atgcctagtt aaaaacagag ccttttttgg aaacagccta ctaatctgtt aaaataataa 72600
tggaaaaaga taaagttagc atacctgagc tgcaagggct gcctcctggt ctgatctctg 72660
ataaggatca gatcctagag cctctgagat ccctgtcctc cctgtctgca caagcactcg 72720
cagaaggaga aacagtttac ggtggttcat catgactttg aaccaagctt aaagtcaaag 72780
tcatactctt taaaccattg gaaaccaagt ttttgcgagt tgcctaaagt gggcaaaaat 72840
cccacaatgc acctgagcac aagcaggaaa acatgccatt gtctccccag gagccctcct 72900
tgacttctac tttactttat ccattgacac tagtcttata agtagctttg tctgtccaat 72960
ttttaattga atttcgtttt tattttcgtg agtggaaata tcactttgaa agaaatcagt 73020
cctctcctga aatccagaat tcctggagct cagtttacat gtttgacgcg tgtcacatga 73080
ttccacaagt cactcaaggg caggaggatt accatcgata cggaaagatt tcttagaaag 73140
cttaagtgaa agggaaacca gggagaaagt gtgcttcgtg agaataggta tgcggacggc 73200
tctttgtgac gctctgtgca accctcgtgt ttgcattgaa ccaagctgtg ctgcagatgg 73260
acacccatcc catttccccg actcatacca gggaggccca ctttgcaagg tacacagagg 73320
ggaccacaga gcaggggggcc atgcagggga ccaagggaca ttttagtgta accaaagtgt 73380
gaagtatgcc ctttatttca aaagaataaa gaaaatcaca ggttttcccg ctgatatgcc 73440
agggacattt ccaagagaat tccttttttg agagaaatct cctttgatat cccatcagtc 73500
agccatactg cataattgtt agatagtgaa agaaattcat tttttaagtt tgtcagaaaa 73560
ataaattctt tgaagtctta aattgttgcc tccggacatg acatatctgg ctcttccaga 73620
atccatgtta gtcctagctg aggaagaagg agaaggagag gggcgtttgt tgattattga 73680
ttttgtaaga tgccccacac gttggctatt agcagaattc tcacttctaa aaggaaaatg 73740
agtgtgagct atgttcaatg agaaacagtt atttttggga cattctttga ggtaaaacac 73800
ctccttaaga tgctgcttcc ttattgctat gggaccaaga ttagagcaag aacatagtgg 73860
ttttcagacc ctggacatca tccacagccg cagcagaggc cctgccccact tgaacaatga 73920
gacaggccac cattttgttt cgagaatgag caaagtgaac caccatgcca gatattgtta 73980
agtcagcaac tcttctgaag atggacatag taaaaaaataa acaaacaagg cagcacttga 74040
gatggtcatg gcagagcaat ctcaacaagc gatttgttat tttgcacagt gatgtaccca 74100
ctcattgaat aaaatgcacc agaaccatgc actacagatg ctaaggagag ttgtccttca 74160
acaaaggaga taggccccac tggccgtggg gcagtttatg ttatttggtc cttgtcatgg 74220
gcaggcatgg ccctttctat gcttcacaga tgaggaaggt ccctggcaca ggtccagtct 74280
ccagcatggc ctagaggtgg caggtgctac ttagcatcgc cagcctcctg cttggtcatg 74340
gggtcagcca gtttataaca cgaacggagg ttaatgaact gatcttccca tcgcacaact 74400
ggtatgaacc cacatcttct gattataaat cttttgctct ttaactctta gtcattacca 74460
ctgtctagtg taggcctgtg tgttcatggc ctttgttgcc accaaaagat caactattag 74520
ctgaataaca tactgagaca tgttggtgtt gtgttctaaa tagcactagt aaactgttag 74580
ggaaatctga ctatatagct actatccagt ctagtttttc ttgcgaagtg tttgttgagt 74640
gtgtaatgag gagtaaggaa ggtgaataag aaatggcctg agtctttata aaataagcaa 74700
ggagagaaaa cagttttgat gagaagcgca tggaattttt agaagatagg acgtgtatta 74760
tgtacctata agaatgggta ggattttaga agagatggat ggggaaaagg aacagggagt 74820
gggaacaaaa cgtggaccaa ggaagagcag gtttagccat ggaagcctca ccgccggctt 74880
tggtttatcg tgggccaagg ggacagaccc tgtggggagg gctggcagca gggaggtctt 74940
ccagaagtct atcctgcagg cagtaacagc cacccagtct ataagctgag tgggcatggg 75000
ggtgatgggg aatgggtggg gagttattgg ggtaacttac cccaaaatga tagctagctg 75060
gaaccattta ttctattgca ttttatcaat aaatcttata ggaagtacca tcctagtgaa 75120
aaccctgtca cattgagggc attcatgctt atgttttaaa acatgttatt gggtctatga 75180
aaaataaggc tgaaacctat gagcaccctc catgcaaagt ttcagtcaag actttggaaa 75240
caagacagtg tcttactcac tttataaatt cattcagaaa gccgtaggtt tgaaaattcc 75300
aaacttagat gtaagaagct ctgagaaaca catgaaatca cccccacatc agtagagatg 75360
tctcagcaga catgggaaga ggggcagcag ggtgtaggga ggtggggcag ccccggggtg 75420
ggccttgcag gctgggcttg aatcccatgg ccaccaccgt ccgctgggag gcctggagcc 75480
ggctgcccac tctctgacca gcacatgttg atgctgtatc cttgaaggga ccgtggtctg 75540
acatcctgtg atgcagacct gaatccagca cccacagggt ctgcacattc cctctttgag 75600
gtggagccca gctccagagg ctggtccctg actctgtttc tcaagaagcc tgtacagatg 75660
ttcccctcac cactgtttcc agtcaccttt ggctttcacg gtgcagatgc taagtttgat 75720
tttcagagcc catctgggaa tttagtgaac tgaacaggta gcatttctga acccacccat 75780
aacccatgcc ctccccactg attttgaaag agagtttgct gcaggtgact ttgcagctgg 75840
gtagagaatc ttggggcagg attccgaggc aggcagatga gtgaggataa attgggttct 75900
gacggcacgt tacaccagtg gactctaacg acgacctcac ctcgtgcaca gataattctg 75960
ccttgtgctt aaccgttaga aatgtgtcac tgaagtgtga acatattatg ctgttagatt 76020
tcccatcatt tctgttcttt cattccctct catttgcatt ggttactcat aaatgtagat 76080
ctttggtatg atttgtacaa ctgccgggtg tcaatctgtg aaagaaatag cagagcaagc 76140
tgggctctgg tagcgcttta tccctgcgtg ctggcttgcc cgggttgact cagaggcagt 76200
ctcacattca gctgcgctgg ggccaaggac ccagggagcc aagtgtgttt ctgttttctg 76260
tatttagcaa tttaagacct gcgtttaaat actagctatg cattctagca aaagaggttt 76320
atattttaac acagtaactc ttaattgttt aattcagttc gtgtgttacc tctcggaata 76380
aaatagtgga agccaattaa ctatagactt cattagtttg gatttaagat caccaaaaca 76440
tttaccacat ctcaattgtt cattacatgc tctctctttt ttaatgcagt ttttataata 76500
tggggagtgg gggtgtggat ttaaccatta tatttttatg atattgggag tagatttaac 76560
cattatgtaa attggatttt ttaattttaa aaagtcactt atcttgatgt aaaatcatgt 76620
cttagtaacc ttgataaact aagttttgca tgattacacc ttaaggttaa aacatatttc 76680
atttcatcat ttcccagaag gggcactgaa ttcacccatt tcctgttttt catctcagaa 76740
tgttctgtgt ttcctccata tctactttcc cggcagcagg accctggaag cagtcacacc 76800
aacctcattt accccacctg agatttgtgc gctttgaaca tagttgcaat caaatcaaca 76860
atatctttgc tcagaaatgg atatgtgaag taaaatgtgc tgccctgttc atgtatgaaa 76920
tcattcagct agctggccag tgagcccttc attgcaacaa agatttttct agagcccctg 76980
cactatctgg ggctatgtca ggcctcacac tcctgctcac acgtttggag gctaccttgg 77040
ccagtattac cttaatccag catttagggg aaggagcatt tcaagactaa attttctaaa 77100
ctgctcaagc ctacctcatt ttatttcttg tgtattttaa cacttttgga tgaggactct 77160
tcctagaacc tactaacaat tcccccccgc ccccatgcca agattcttta aagactttct 77220
tgaaaacgct tcagtctttt cttcttagct caaaagtact atcctaaata ctagctctgg 77280
cattacaggg agttaatttg tgggcacaca cagtaaatta taaacccctt aagcagagaa 77340
gattgtatta tcagtttatt agttttctta ttcattcctt cagcacacat ttctgttgcc 77400
tccaatgcag cagagaaatt gacttctaca gtttccacaa cagtccagat ttcaactgtg 77460
tagtgctctt tcagccagaa agtacacttg tgtttccctg gccataggtc ctgaacctca 77520
cttctgaaaa gtcattgtgc atagagagct aatagctgta ccctaaatga tcctggcttt 77580
gaattctctt atctgcttgg atagtattat ctgtctcttc ctctgcattc taatttgcta 77640
cttctaatct gctgggaatt acaataagaa agaaccattt aatcattttt acaactgtgc 77700
ctaaagagag tgtgtgtaag tgccgagaga gtgtatgagg gacttgccca tgagtaaatg 77760
catgaatttt aggtcaaggg ttttttgctt ctcttttggt tgattacctc agagatcagt 77820
tttactttct ttctcattct tgacctatca tcactagctg atatggatga tgtgtacaac 77880
ttctgagtaa gaataatgtc aatgggacgg gatgggattg gctggtgatt ctgttgatct 77940
taaagtttat atattttaag tttagtgttt cagaatgaga ccaaagcggt gacattttca 78000
acctcttcgg tctctcttca gttttttcat tttaagtttt tgttgtgctt ctatcactta 78060
aaggaagcct ccaagttgaa atcaaatact aatgacattt ttatctaatg tataaatgtg 78120
tttttattat ttattaggaa atttatttta cttggccctc agccatgaca tatcatggca 78180
taatcactat cctaaatttg tatatcttat ccttgcataa ggtaagactt tctatgaatt 78240
acacatattt gtattttcct ctcttacata ttttaagaat ttttttatac tttgttttct 78300
gcaaatgaaa tattgctcat aagccaggtg atggctgtcc acgcctcttt tcccctgctt 78360
acccttgctt agatcttatg gtagaatctt ttcatagaag acacagaaag acatgaaaga 78420
aagagctgga gaagcctgag gggctgccca gtgagtggtc tgctaggatg ctgtgccaca 78480
gcccaggcac aggaggcagg gagagcaatg gggcccttcc cttccaccaa cattcagcag 78540
aatttgcagc tccatgtttc caaagcttcc agggcacttg catttagaga gagagagcaa 78600
gcaagctgcc tttcctcttc ctcagttctg ccagccacac tcttgccatg atgagcagtt 78660
tcagccaaaa gctccttccc ctgccctaac acctcctgca aggcctgagg tctggaagcc 78720
acctgcgcct gctggcccct cctttcttgt ttctgcaatg gatgttgtgg ccctgtgagg 78780
gagaagagaa aaagaagttg ccctcctccc tctatcctca cctcctgcca tgctgtcacc 78840
cttataagag agaagggcta accatccagg ctaatcctcc agtgatgcag gagaggacat 78900
cctggccgga agagtcagag cttccaggtg agctcaggtg ggtcagcccc cgaggctgtg 78960
aagagcccag gggccagtag atgccacttt tgctccagga agaatcttca actgtgtcct 79020
ttttattcaa ggggctctct tttcagcgaa tctctagatg tactagtcac aaacactcgc 79080
atttattaaa atgtatccat gatcccacaa tccttttaca tatttctctc caggagtatc 79140
acatttctga gggccctgtg cctgttttct gcaggaagtt gctgttgtcc cgggtccccc 79200

-continued

```
tgcccccagc acctctgtta caagaagcag acccttcatg ccacactggg acccagggag  79260
gccccaagcc aggatgctgg gatcttagta aaggttggaa tgatgtcaga acatagagga  79320
ggcagaattc cccccatagc atcatcctgg agggcgctga tttgtgtgct ctgccaggtt  79380
catctgtgac tcaggattta aaagccccag gtgtggtgtc ccttctgtgc ctgcaaggtg  79440
cgtctttagc agttctccct ggtgtggaag gatcagtggt tcttgcagcc taggcaccct  79500
ccacagcaag cccaacacag gtgctgtgag cagctggttc atgaacggtg atcctgggga  79560
gaagaggagg atgaaaatgg aaaaccagtg caaaggtgtg tcatccagtt ggttactgct  79620
gtgggtgccc gggcttccat cccaccagag cccccactag ccagggcagc ctggcggagg  79680
tgagcatcat tctgctttct ggctgcacct gtgtggacag agcccgttcc aaagcctccc  79740
aggcacaggg cagacatcaa gcaaggggca gagctggggc gagggctctg ggtgcccccg  79800
ttattgaaca caggcctgaa gggagcctaa gaggtggctg gcaggagata ctacaaggca  79860
gaaagacagg gcagcagtct ttgtactgta cgtttttgtt ttttaagaga gaacaaaaag  79920
tcaaggttga gagatgagaa atactcttgc caaaaagaga acaccaaaat cctggagtca  79980
cgggtcttcc attaccctct ctagcatttc tgcttgtctt ttccctagta ttggtgaaga  80040
atttttaaag taaccaaccc ataccgttgg ttacaggccc tgtggtcacc aggctgtctc  80100
cccatgatgg ggatggagag tggttagtgc agaaacttag acctcccctc cagcttgttg  80160
aatgccctga agtttatcta gaagggaaga tactcaagcg taggatttca gtgatgcatt  80220
tggacagcat cagtactatg cttcagcgtc aaaaacgtca ctttgggtag gaacaataca  80280
taatgcgtgg caatgccttt tgtgacacct gttcaggaga ttcccatagg aagcttctga  80340
ggcagagtcc tcaggtgagg agggggacag gcctgggtct tgggggaagg tggagatgac  80400
cagcctcatg cctctctccc cagtggcctc agtctccatc aggcaaatct tgagaagcct  80460
cctccattct gcaggcaaat gactgagatg tgtgagctct gcttcccaac aggcggaaat  80520
tcacatgggg aagggcacct gtgaatggcc ttctagaact atcaggaagt tctggattta  80580
gtaccctgtg agagcagatg gtcctgggtg cactcggatg atcctgccta gccagctgga  80640
ttgcagagtg gtcatcatta tcagtgagct attgaggggt tgagagcagt cagtgtcatg  80700
tataaggatg ggttggggta ccggccaacg cccgccttga ggcctggccg ccggatggga  80760
ggcgagagca caagagagtc ctggctaggt gtgccccgct ctgcagggcc acaccatcca  80820
ctggaaaccc tgtgcccact gggctgcgtg ctaagaggct gtggccaatg ctcttgtcca  80880
aattttactg aatctgcagt ctctcttaat tcactccaaa gtttaatgtg ttagcttgcg  80940
aataaataaa taaataaata aataaataaa taaatggaaa gaaacagtcc tcagaaagtc  81000
ccagtcaaat tttaattcca acagatattc agcagtttcc tctaagaaca atgagagttc  81060
tggggctagc cagtgtttct cttggaaaat aaggaagagg gaaagcggtg cattcattta  81120
aaaacctgcc ctagggaggc agcgttccct gtgaactccg aggccacagt gagcagagca  81180
ggctggaggc ctcccggctg tcctgcccct cctgccacat gcctgtgaaa atgctagata  81240
aggacttttt ctcagcaact tccacgctcc ttcagtgggg atgtctttga ctcagagctc  81300
tgccactggt tatctccacg aacagaaaat gccacagatg ggttaattca ctgtgttgtt  81360
ctcattttcc ctcagtttca ggcttttctc tccttgcctg ttttcctcgc ttaaaaaatg  81420
atgtgggggt ccctaaacgc atctaccccg atagatttat gttttctttt ccattagtcc  81480
actttgcgtc tcagccctaa aattaagttt ttgattataa tgtaaggaag ttttaccata  81540
ttttaactct ggctttttaa atacaaaaga aaaataacag aatggccttc tagaactatc  81600
```

-continued aggaacttct ggatctagta ccctgtgggg acagatggtc tggagccagc gcacttggat 81660
gatctctctc agccatctgg accatagagt gaacttgtta ctgtccctcc aaggctgaca 81720
actatgagct catactcttc tagcagttta atttagaccc aagaaaggct gtgtgtgtgt 81780
gaatttgtga gagtgtgtga gtgtgtcttt gtgcctgtgt ttctgtgtgt gtctgtgtgt 81840
acatgtgtgt ctgtggggtg tgtctgtgtg tgcacggctg tgtgtctgtg cgtgtgcatg 81900
gctttgtctg tgtgtgtgcg cacgcactct gctaagctac tcaatgcaat tccttactct 81960
tacttccctt tctgtcactt ctccataatt ctttgtattt cggttgggct ggtatctcgc 82020
ggcggcttcc tcttttcctg cattcctata tttcattatt tgctcttgtt cctcttctag 82080
ggcttttaca atatagccag gaggatgtgg aaacccagtt acaagatgac acacaagcac 82140
agtgtcacaa tcgctgtgct tgggccctac ctcctggaga ccagggtggg acggtgtctc 82200
tggatatgga gggaagggcg gaagatcacg gggtggcaga aggcccgact gtccggtctt 82260
ctggaagctg gggtctcgtg gtcgctgggc tggtggtgct ctaaaaccta gagtaaccga 82320
gagcaggatg actgcacccc tgactgccga ctcaccgggc ttcggagggc catgggtgtg 82380
tgattccact tgtgatcctc ctacttcccc agcccaccct ggtggtctcc cacttctctc 82440
tctctgcctg tggagtgtta taaccgactc cttcttctag gcatctccat cccaacccca 82500
gaccagttcc cttaaaccac ctcccaccac aggaccccca caagcaggga cctctcacag 82560
ttcctgttgc ctggggactt catctcagct tccaaggcct ctggaaccag gccctgcatc 82620
ctgggcatga ctgtccccat gattctctga gccagccacc accccaccac ccccccaccg 82680
ccaagtccac tgctgaccct gctgtagccc cccacctcca cttgttgaga ttccctcttc 82740
ctgcttctca ttttgaatgt cacccttctg tgacttctca caaccccccct gccacccctc 82800 cctccagttg gcatggctta gtcttcctaa gaacatgtgc tgcttcccag tacccagggc 82860
tgctgtgcac cgtggcacgt gagtttcggt gcatcttcct cctgctgttt ataaattgca 82920
acatccctgg acagatcttg gattttccct ctataatttc tctggagact ccctcggggt 82980
ttgcacacac atctgtggaa tgcccaagtt ggagatggtc ctccctgatg tgtagtgtgg 83040
gctattcaga gggcctcatt tcataaactc attaacagct aggacgcgaa gacttggaga 83100
agttagctca ggacacacgg agtgggaggg aggcaacgag ttaagaaatg ggctttggag 83160
tgcctcgaat ttggcctcca cttttctttt ctactgtctt acctggtctt aggcaggtcg 83220
ggtgaccatc tggagtcgga gtttctctca tttgtaaagc gggggtgata tttttctcac 83280
agggctgctt caagggttaa caaagttaat gtctaggaag gacatagcat agcaccttca 83340
cctggttgca agcccctgga gtcacatggc aacagctgtg gaaccaggta aatgacttga 83400
cttacatgtt acacgctctt agttgttcga tttgtaaatg ggaagagtgt gtgacccaaa 83460
ttagtcgttt ccagatattt cctggtaaat ggttgttgaa tcataaaact agaaagatgg 83520
gaaagaaagg gaggaacccc ccttacttcg aagaagtgtt gttgatgtga aggacaggac 83580
tttttgagac actctcatcc taagaaacag ctgatatcta ctaggaaaaa acatgacatt 83640
tgaagtttct tcctaagaga tgtgaggttt tgacagaagt gccaggaagc cagaggtgtg 83700
tgagtagtgg gccaatctcg cgtgaaggct gtgggacggg gcaggagagg ggcagccagc 83760
atttcctgag cgccagctaa tggcggggac ctggcacctt tgctctgtga ctctccagct 83820
gtatggtgac atgaggctgg cgttttcttt ggtttcatac gtgaggaagc tgaggcttgg 83880
tgatgtcctg tgcatggctc ggactccaga gctactcaga ggcagaggcc gtctgtaaac 83940

```
accttcaggt ggttggaggc agggtgctgc agccaatgct gatcactcac aagccaaggc  84000
tttattgtaa gggctaaata aaataacata tgcctagcat ttatacagca cggggctttt  84060
taggaaatag tgagacgacc atggagaggt ggaggaagag agaagggaaa gaagaaaaag  84120
aaaaaaaaag ccttaaagag tttcttaaga gaactatata ttacaaagtc cttggagttt  84180
tttttccctg gttagacata agtttacatg aaacgttaaa cggcttaaag tagccacatc  84240
tccttcctta tgtcttctca cagccacttg tgagtttctt atcaagatac agaattatgg  84300
ccaagtgcgg tagctcacac gtgtaatccc agcactttga gagactgagg tggaaggatc  84360
atgtgtgctc aggagtttca gaccaaccta ggcaatatgg taaaaccctg tctctacaaa  84420
aaaatacaaa aattagctgg gcatggtggc atattccaat agttccaggc actcgggagg  84480
ctgagacagg aggattgctt gagcccaaga ggtcaagact gcagtgagct gtgatcgagc  84540
cactgcacta cagcctgggc cacagagcaa gatcctgtct caaaaaaataa aataaaataa  84600
aataaattct gcaacaagtc acaattcctt gctcagaaat ctctacaggt gtgcttcttt  84660
gttaagaaat ggaggaaaca tgaatttcat cctgacttct gagtcttgta gagaccagat  84720
ctgactcctg cagccttctg cccacagagc tggcaggcgg gggaatgtgc gcagagtgag  84780
gaggagctga tctgacattc cgaacagtgg agactgctgc ctatttggcc gcaccactgt  84840
ccttctgcat ggaaaagtca cagtaaataa tggactctct acctgtgagt cgattttact  84900
gagctgcctt tttaaatata tgtgtagaaa gggcgatctc tgtgtgtcat ttgcacatgt  84960
acatacacat gtacacacgt gcacacgtgg tcactcatgt acacatgtgt gtgcaccagt  85020
gcaccagacc agatgcaccc acccaattcc acgctcctca gccccttgct ttcctctgca  85080
gacagccagt tcagctacag ttatgccaga ttgcctgcac tctgatcttt accatcacca  85140
gactctcagc ttgagctcat gcctgagaaa tccactttct gggaggaagg cagaagaaac  85200
tgccaaggca ggactgaaga cttgacctcc acctgtagtg gggtcaggtc accagaggct  85260
ggctgactcc ccaggatttc tcagcagagt attacacaaa taccccttcc ttaaagatta  85320
gcaaccactt aaagacacaa agtgtgcagg actgtaccca tggccgagag cggcgggatt  85380
aagagggcaa ctgagttgtt cttcccatcc ctcctcctct gtgctgagtc accttctgct  85440
tggaattctg acagggaccc gttgggcttc tggaagggag ggacagcaga ggatccaccc  85500
tctgtgtgtc ctgggggaga ttacttatct ctggcctccc tgaagcaggg cctgggcttc  85560
tggaatcttt gaggctgaca ccctgccagc cctggggatg agagggaatg gccgtgtctg  85620
tctgcagagc ctgaggagga gctgagcaca gcctccagag ttctcttcag ttgatcgctt  85680
aggtggacaa aggccacaga aatggattta aactcctcag ccctttcttt gcatgtttgt  85740
tctcatttga agtcagaagt gatatgtcct acacctcaag aacgtgtgaa atgcacatac  85800
aataacccca tttcaggaag ccaagtccag cttaacagtc aaaacatttc cttcagtctt  85860
tagtccttca ctttgccgaa ctccctttta caccggcagc aacagtttaa cctgttgctt  85920
ctgtaagagt gtgctactgg gaaaaccaca tctaaaacac gtgtgcagtt acatcagcta  85980
gagcacatgc taaacagttg atcaaaggct cttgccttgt ggcccacgct gcagacactc  86040
tgacgactgc cgagctccgc agccccatgt cgtcccttcc gcactgcctg ctgtgcctct  86100
cctctccatg tggcagggaa cacagccagt catcaccatg tggctctgcc cggcgctgcc  86160
ccagcatgtc ctgacagggc ctagatatgg aaaggtggct ctccatgcac acaccccaag  86220
cccctcctgc ccgccgtgtg acccacactc ttatgggcag cccagttatt ttgtagcatt  86280
tcccttcctt atcattttgg cccagtgatc cagcacaaat ctcccttatt agaataaaat  86340
```

ttggaatgac aaaattaaat ttcatttttc acttatattg aggacctcac actcttcacc 86400
cctgccacga tccctgacaa gagccttcct atctaatcat tgttcctcca gccctcttag 86460
ttttcttcag cctttcttga ttgcctgaat gtccctttcc cttctccttt taaagcatga 86520
accaagcttt cttaccccgt tctcattatc atttttgcat tttcttcttt gcatatgatt 86580
ctccttaaat tataaaactt gggggtaatt tctagaggtg ccatcatagt gcttctgtct 86640
actcagtgtc tttagaatca gcaaatatca tttttacaaa aaagtagtat ttcttccaaa 86700
aaagagtaag caagaaggtt acaacactgg gaaaatatcc ctaagcctgt tcttcaacct 86760
gttgaatgtt ttcccctaaa ttgttatatg gagatcctgg acccggaagt tggctgacat 86820
gaaacaggcc tagcagggca gctgaggaaa tgctccaacc tcaggatcca ggaagattgc 86880
acatggcacc aaaacaatca tttaaaagct aatcctggcc aggcacagtg gctcacgcct 86940
gtaatcccag cactttggga ggccgaggtg ggctgatcac aaggtcaaga gatcgagacc 87000
atcctgacca acatggtgaa accccatctc taccaaaagt acaaatatta gctgggcatg 87060
gtggtgcgcg cctgtagtcc cagctacccg ggaggctgag gcaggagaat cacttgaacc 87120
cgggaggagg aggttgcagt gagccaagat catgccactg cactccagcc tggtgacaga 87180
gcaagactcc atctcaaaaa agaaaaaaaa agctaatccc ataaaagaac catcattttg 87240
aacctgctgt ttcctttctt gtactcttta gaagtaccca tttctccctt tctaagccat 87300
aggtgtatta attggagctt tttctatctt aattagttca ctgtgaacaa ttaaaattgt 87360
gttaataaaa caaaaacaaa aataggactg gtgcctagtt gtactacatg aagagagaaa 87420
gggccagaca ttggtttttc ctaatcttct gtcaagttct ccaaatcatc tgctctggaa 87480
ggtagctcca acagctggga tttgaagtaa agcatagtga ctttggccat cactgacatg 87540
tcccatttga agcaaccaaa actgtccctc gacctgacac tcatccctga aacaccatga 87600
gggtaagtga ggcgcttcgg aaggtccact caaccccatt gccagataga gtaagtgtct 87660
gccaggggca tttggagctg aagggaagac tgtacagact cacggtttgc aggcactgaa 87720
ggcgttttcc tgccttcttt ttcaccttca gtggacttgc aaagcactag ccctattgtt 87780
tttcccatct gggaaacatg gtgaatgttg gttggttgta gctaatccta tgggtcttga 87840
ggtctttgtt gacaagaagg tagatgttat ctttatctgc gtgtggcttt ctactaaaac 87900
atgagctaca gggctctctt ttttgtttta aagcattttt ccataaggtt caccccttact 87960
attgcttatc tgaataatat tacctgctga gaagtttatt cattgctcac cagttgtagg 88020
gagattttga cacaggactg gaggattttt ttctcatcgt aacagtgcag acccatggaa 88080
agcttggaag cagttgtgac cggataagag caggttgagg atgataatct tagggcaatg 88140
agcaggttga ttgagagggg tgcctgaaag caaggtcccc atgatgcaag caaacaaact 88200
cacatgccag acggtggaca ggaaacacag gcaggatgtg gtgcaggctg ggctgccttg 88260
gctgggcaaa ggcaggggct tcatggccat gctgggatgt gacgtggttg gaaaacaata 88320
agaatggaga cctctccaaa gacctcagac ataatttggc catgagaggc aagggtagag 88380
gcgagccccc tgtgggttgg aatgtatgga atccagatga agcaccatca acatgcatgg 88440
gctacatagg agagctgggt ctgggggaaa agatgggatt tgggtttggg tgtgcatgtt 88500
ccaggcatgg agggaagaat gggcagaatg acgaggatca agccctggtg gagccccccag 88560
accagggccc tgggcatatt tccacttgcc ttcttctgca aacttttgtg tgcctgttgg 88620
gtggaaggta ctatgctggg gccatccagg atccggagca gtgtaagaca tcatggcctg 88680
catggtgtga cccttgacat ctgaaaagaa cgagctggtg gagtgggaag gagacaagtg 88740
gcagcagagt tgacatcatc aggactgact gcaggacagg cggtgaaacg agccactgag 88800
gagttaccca gtgccctggg gagcttagat gtgagactta caccacccag cactccccag 88860
ctctgtgtcc ctgggtccca ctgaacttga ttgtatttta gttgcctctt ttctaagacc 88920
ggagcaacaa taccttcctt gagtgtgcat gtgcagtcca tagatggcag ccagtgttct 88980
cttcccatga gaagactctg agcctcctca ctagagggtg gtctaaaaac aaatggatcc 89040
atccacagaa ggtctgaaag gttttcatag aatcttgact tggtagcact tcaggatcta 89100
actcgtgctt tccagaagtg tggcctgtgg tgttctgtct ggagtatttg gtcctcccat 89160
ccacctccac cttgctgtcc tgtcctgtga ctctcactag ctcagtcacc gggtcaggaa 89220
gccctgccat gaaatgctag atttggaggc attgccaagg taccacaaac catactcaaa 89280
caaggtcata atagactagt gatctcactg tggctaacag gttcatgtga tttaaagaat 89340
gacagcattt tttctaaatt ttataaattt tataaatttc tcctaaatac aaatctgaat 89400
gtgtttacct ttagacagat tttcccagaa aattgtcagt gttctcgaat ttgaaagtag 89460
atcagatctc ctccctctag ttttgaaaat ctcaagtagg tttagcctct ccccagagtg 89520
acaacggcac aagaagttta taattttatg cacagctaaa tgcaaactga aaagtgtggt 89580
ttgtgggtat ttcatttttc ccataatgtt catcaatttg gcaattcaaa taggattcag 89640
aatccaaggt gttcgcagca ttttatatga aaatgtgcct gagagtttgg ggaatagaaa 89700
ttcttaccaa ataagttaaa tttgctcttg ataagaatat attttgtaaa atgtagaaaa 89760
ctgagaaaaa aagtttgaca cctgttttat ctgcatcctt ttattaaaca gtggcctgaa 89820
tttactaaag gacagagaac agggttgaga ggtaatcact gaataatagc ttcgctaatc 89880
ccacagtgac tgcttcttat gacaagcaag agggtcaact tagaggcagg actgtcttca 89940
ggggcaaaag caagtcagca cctacaaacc tctccaagag agtgagaaaa agcaggttgt 90000
atggctcatt ttgcagcttg ccagaagcaa tgtgggaata ttgtcagact gcacagacct 90060
ggggccagct ggctcctaga gtgcgaggag ctctcagtga ctgctgtgca tactcacctg 90120
ctctgtgact ttgttcagtc cctaccctgg atgtgtggtg aagggtgcca ggcttagctg 90180
ctggaccagt gaggtccctg agggggcagg gctaagaggt gtagcagtcg cacttgacca 90240
gtcattgatt cactggttgg gaatttgttc attgagggga caccattact ccccatgcct 90300
cacgtgcagg tgagtgtgtg tatatttgca ttaacacaca aacacactta tgtgtgtccc 90360
tgtatgtgca gctgcagtac cttacacatc ttccagtgcc tctcaagcat cataaaaaca 90420
gcttccacaa aacctctact acccacctgg catccacaga gctcccagtg attggctccc 90480
aaaagatact gaactttggc atggaacaga gtgagtttcc acatttgctg ttgtacataa 90540
ttacctgtcc agctagaata gtacacactt cttttactga gcccagaagt ttatgtgcct 90600
gaacacggat ggtacaggaa caagggtgag cgcttatcaa ttcagcatta ctctggagac 90660
atgaaacaaa ctaataggta cagctatatt ttgtttttta aacaattttg tgaaccacat 90720
atttgggaca aaaatcaaca agtaaatttg aattacacta ggcaaaggac tgattctttt 90780
gaaacgtgat tgacattcaa cgtctaactt tccaaaagaa gacatacatg tggcccacaa 90840
tcatatgaaa taaagttcat catcattgat cattagagaa atgcaaatca aaaccacaat 90900
gagataccat ctcacaccag tcagaatggt tattaataaa aagtcaaaga atgacagttg 90960
ctggtgaggt tgtagagaaa aaggaacgct tatacactgt tgaggggatt gtaaattagt 91020
tcaaccatgt ggaagacagt gtggcaattc ctcaaagacc tatataccat ttgacccagc 91080

-continued aatcccatta ctgcatatat acccaaagga atatgagtca ttctaccgta agacacatgc 91140
acgcatttgt ttgttgcagc actattcacg atagcaaaaa catggaatca acctacatgc 91200
ccatcaatga tagactggat aaagaaaatg tggtacatat accccatgga atactatgca 91260
gccataagaa aaagaatgag atcatgccct ttgcaggaac atggatggag ctggaggcca 91320
ttatccttag caaactaacc caggaacaga aaaccaagtg cagatgttct cacttttaag 91380
tgtgagctga atgaggagaa tacatgggca catagagggg cctatcagag ggtggagggt 91440
gggagaagga agagtatcag aaaaaataac aggtagtaga tttaataccg gatgacaaaa 91500
caatctgtat aacaaacccc catgacatga gtttacctat ataacaaacc cgcacatgta 91560
ctcctgaact taaaagttaa attaaaaaaa aattaatgtc taataatata ttacagtatt 91620
cttcatattc aatggcaatg tgtgaagtgg gaagtgtctt gacagaattc ggtgtttcaa 91680
ggcttacact ttgatgccca agactgcaca aggctacatt ttctactggt gagacaaatt 91740
ccagacgcat tgcattcaga tctaatctct tagctcctta atcttcaggg tactggtaaa 91800
catgaagacc tccccagtgc tgtagtcatc atgatatgta cagcaggtgg ctgagctctg 91860
gatgtagact gcagggatat attaggaagt taattctcaa ggcaagtcat cttcaagcac 91920
catatcagca tgatcagcaa tataagtagt atctcagtgc tttgttgttt agtcagagtt 91980
ttgtactcta tcacccattg taatgttcct atttgcaaaa ggtaatacat accctttaaa 92040
acatctttgc tttttctccc attatcgaga tgctagcagc ttcataaagc agaataacta 92100
agggcaaaca gattatataa agggttggag ctcaatgaag acaacaagaa cagcaaaggt 92160
tattgtaaaa ctggctgctt gcaggccaac aagcacatcc atatggaggc aatcagttta 92220
tgctacctct gtctgtttga tgggattcat aatattgact ttatccatta gatttggact 92280
accagggaat aaaataagca gatggagagt aaggatttgc taggaaataa ttcagccagt 92340
cactttgaaa gctgttcaag aaacagcttt caaagtgtct ctcaaactat gtttgcccat 92400
tatcccaata atttatttcc caataatttc atgggaaaag aaggaagttc tgtggtcaga 92460
taaatctgga aaacactggt ttaagcaaag ttcagtaggt ctgcttccct gcaggtcacc 92520
tcagagtctt tactctgcta acctaggaac tcatccaaca agtttaattt aacagctaca 92580
ctgtgtacgt cactttaaca gtcactgagc tgtgactctt gggggaaaga ttgtgcgtgt 92640
gtgtgtgtgt gtgtacacat gtgtgcacat gtgcagaatc taccaaatct taagagaaag 92700
gaacatgctg ggaaactgtc ctgtgaaaga gaatagaaac ctgaagattt gaggcagtga 92760
tagcatttat gaaagcagca gataaggact aatcaccaaa aggggtagct cttttgttgg 92820
ttggggaaaa caggaatttt tcccccaccc aatgtgctgc attttctaat tttctatgaa 92880
cacttcctaa gaaaaagctg aatgaagaac atttgcgatg caatcagctc attaagaaac 92940
acgcactttt gtggagatac gtgctgtccc aggagatgct ctgcgaggag ccgagtgttt 93000
ggactggagc tgctgaatgg tttctcacag ttctagaatg tttggggctg caccctctaa 93060
gatgttgaac ccatcagtaa ttgctccaaa ccactttatg ggatataatg ctgtgagttg 93120
acacctgagg ggattgtggt cctgttcatg agtaattact tttctgttgc ctatagaagg 93180
gccagcaata gcagatgagt agctgaacag tggttttgag taataaaacg ttctttttta 93240
aaaaaaagta atgctttctg ttaaactctg actatactct ctcctggtat cacaacccag 93300
ctttcttttt gccttcttta ttgcagttac atatggggct gatgacttta gggatttcca 93360
tgcaataatt cccaaatctt tctctcgtaa gtatatgcct tgcttctgga aacaaaagc 93420

-continued

```
atgccttcat ctcctatcat gtaaatatcg tacgtgcatg ttccttcatc aacccccgag  93480
atacattaaa tattcactgt tctattcgtt agacacctac catatcattt ttgggtattt  93540
ataccataaa gtgcaaaacg aaggtctagg cagttgtgcg gtgtcctggg agcatggcag  93600
tggagtaaca gtaagggttg gagtcacagt agcactgatg ggattgttac ttcgcagatg  93660
ctgctggaca gctttgagat tactcctgta atccttttta ttgagtgtga ggataaaatg  93720
gccatatttt ctgtcaccaa caaagaactg aacatggttt caagataatt tttacaattt  93780
tgtgggacag gagaaggaga tatgctcttc atctgtggtt ctggagtatt aatttcagaa  93840
ctgagaagag aaaattgcag gcctccaggc cgttattctg tggtgcatcg ctgctggagc  93900
caacgtactg ttcctgcttg gtgcccgcag gaccttctct gatctgagct gttaaaccaa  93960
aaacagatgt gaatttcatt tttctttttt agatattgag ctgataaatg ataaatatat  94020
ttgggtaaca tcctcaaatg agtactttaa agaacagaga gtgcttttga aaatgtatag  94080
agagctgaat atttaaagcc atacaagttg ataatcccct taggacctgt attagtaaat  94140
cctctaatac tataaagcaa catcagaaaa caggtcgcat ttgttaacac tgtgacaatt  94200
ataattatag gctctaattt gaacagtgcc agtaacagtt aaagacaggt gtctgacatc  94260
ctggttatca aaaactatct ggtgtctaag gaatttaaca gtatcaaagt acatcttttt  94320
gctcacaaac tagattggct acttttccag cctatagaag ttacagaaat ctttctttta  94380
ctgatattcc tttgattcca ctttaaagca atagcttgat acctactttt tgagatgtat  94440
atgtatgtac ttgtaaatgc ttatatatgt gtatttgttt acacgtgagc ttatatgaac  94500
atataaaaca ttatggtatt ggacagagaa atgatattga tttgaagaat catattgttg  94560
aagtattttg agaagtcaaa tgcacttgag agtaagctaa tgcatcctaa aacatgtttc  94620
tgtgaagtct gaggaaggtg tcagccagag catatgttga agcagaccct tcagtgaagc  94680
cttcagtctg taagaatcgc tgcatgtgaa gatgtgttaa tgttatgata gttacagttt  94740
ttataaaaga gatgatatac acttggatat gctttctgtc tatatttatg caaatgtgtc  94800
cataaggtat tggtgtctct ctttctctcc cactctcccc agtgttggaa ttgtgactat  94860
cttctcacac aagcggctac ttggtcttga tgccttcccc cgcaaaacag caaccaaact  94920
gttctgggcc aatatcacca ccttgtggtc atgatgaaga attgcccccct ttgccctcaa  94980
cacctctttt cttcttgaaa attaaaaaca accccttca cccctctac tgtccttatt  95040
ccagtttgtg tccgtagttg ctggaggaaa gaaaatgcct attgctcttt tttttattct  95100
ctttatctgt ttactcttct gcctttcttt tctctccctg acttcattcc atttaaaggc  95160
cttaaattgc aaataacgaa aaaagtattt tctaataata taccctagtg ggacgaaaac  95220
aaccttctac attttaaatg atattaagtt ataataaatg gttccatgaa ctttaaaacg  95280
cttaaaagtt ttataaatct cttttagagg caacacaaaa atatctatat atatatcttc  95340
tcttcacctc aaattttcat ttaattaccg tgattcaaga tatatcttaa atatttccat  95400
ttcatttgat ttttacttgc tagtcaccag tgttgcaaga atatttctgt accatttttc  95460
aagtaaaata ttgagcattt caagcttaca tggcctaaac tcacactaga gtgactactt  95520
cggactatct tttcaatgga aaaatgcgtt ctgagtacca aacatttact ttttcagtaa  95580
atatgaagac acattctaaa aaggaaaggg aaatgaagag gaagcttaat tcattggtca  95640
ggtggggact aacagtgtac attataccta tgcattaaaa aatgtttaat tatccatgag  95700
cacatacagt gcctggcaca gattcaggcc tcttggctcc tcttggcatc tgagttcctt  95760
ggattctcca gattcttcaa tccaaacttg tctatctacc aaagtccacc ttccatacag  95820
```

gggtgtgggg tctctcttag tactgttggg tgccaataac atagaagccc tccaagatag 95880
gtcaatgaga ttttaatttt tcccaacttt aaatagcatc tgggaaggaa agcagctttt 95940
gactaggagt ttgaaaacat ccactcttca tatttattgt cacatttatt gagtaataaa 96000
attgggctct tgtccattat ctctcagtca atgaaagagc ccacggtggg catgagccag 96060
agtgttccgg agaaagagag gaccagtctc catttcatgt tctatattta atcagttcaa 96120
ttcagcacct tactgagttt gacatttttc taagtaatgg ggtggggggt tacaaaatat 96180
ttataactat ctttcctatc ttcagggaga tgtaccattt cactgaagca ataccacagc 96240
taagcagttc cagctccgag taacagagga aggagtgagc gatttaggaa ctcacagaag 96300
ggcacggcca ggcaactcgg gccctggcaa atgttccata gagacagcat ccatggggtt 96360
gaaccaagca caatgcctgc aaatcgggca ggcgggttca tggaattgat tctagggcag 96420
gtatgatcag caccatttaa ggagtggcag ttgttaagaa actgaaggga tttctcatat 96480
ggcattttca acagaattca gcaggagcct tgcatatccc ttgggatggg ttccggggta 96540
ttatggagct gccaggaggt gctcagcttc agtaagtgcc agtcattcct tcccaacctc 96600
ctccttcatt agtggaagta tcagctggtg tcattgcctt cttcaggagg atggatttca 96660
aaatgaaggg ccaacaaaac tcacattctc gcagagcctc cgtcacaact gcatgtgttc 96720
actgccatca acaggccaac acccacttgt tcttttcttc taggtaaagg aaaaggtctg 96780
tgggacaaag gccctgaact cctcactcct tgaatgggag gcatattggt ggaggctgtc 96840
acacaactac aggtggcagg aacctgccat cagggttccc atcagcctcc agggcttgct 96900
tctctgccct gtgtgtggac accttccatc actggaaacc cctctctcag aagaaccact 96960
tcttgccctc atctcccact tgcctctcct cggcaccttc tccaccctca ggggccaagc 97020
tgaggaagtg tgcatcctgt gccaccaacc ttgctcgcag gaattagttt cagtccccag 97080
tgactgactc ttccaaacct gcaccagcct atgctgccct tttgaaagga ggcgtgcgta 97140
cagcctggct ggtacagaag attccagatt tcagtgacta caggacgctg tcaccccttc 97200
tgtttttctt ttttctgtcc acatctctga ttgagcatac cttcagggaa aaccccagaa 97260
accttttca cacttacatg ggaagccaag acactctcat cctgggcttg tgtttttaaa 97320
atctatattt taatttcaca ggtccttaca tttatgacta atagatttca gattttgaga 97380
tacaatctgt agttgcaact tatgaagata gtttcaagcc ctgatttctg tcatctatga 97440
aaacagtaag caagttgctt gtattctcct cctagctgga taagagaccc ccgttttcat 97500
ggacagcctc cttgggtgga cagaagtctc ctgatcttgt ctatgtaacc agcacccact 97560
ttgcattttt ccgcaaagaa aagaggagct taaccccatt tacgggaaat ccacgcactg 97620
cttgaatctt acgcgccccg tggtgacggt gttgcccact ctgttccctt cccaccaaat 97680
cctgccagca cctggcagtc atccagtcct tgtcttagac ttcaccaacc tttcccgtca 97740
taacatggct tagaagttgt ccgaatagtg ctagaagctt tcagccctgg aatgctcagc 97800
atctgccatc taacttccat ttaaaacgtt ttgagcattt gctgatacag gttcctctgt 97860
cctttcccca ttattttcag ttccttggcc ttgcccatag tgatctgtgg atattgtctg 97920
catactcttt tttagaaacc tagagcatcg cagtgtcctt aattttcctc ttcaaactct 97980
atatattcct gagctgatca tccctactgc tgttcctaca gaactgtgtg actaatcttc 98040
tatatatgtc cctacatcta gccatctagg tggagatcta ggtacctatc tccctaaaat 98100
tgtacttggt atccacattg acctcaggac agtatgtgat aggctcttgt gccttttcga 98160

-continued

```
ctaggagttt gaaaacatcc actcttcata tttattgtca catttgttga ataataaaat  98220
tgggctcttg tccattatgt ctcagtcagt gaaagagccc agggtgggcc tgagccagag  98280
tgtttgtgtc cctagttctc ttttggttct gttacagctc tcagtgacag tgtcattgag  98340
gctaacaagg acagagtact gctttcagcc accatttgtc caatgagtgg ctgatctcca  98400
ggcctctggc tttgagaaca tctgtgatat ctaaggcagc atccattgtg ggctttcccc  98460
catgcttctg tttccttcct gtcacatagc tttgcctcct cctgcaagca gcctgctgta  98520
gcagaaccgg tgttcctgaa gccagaaacc caaaggtcgt gtccaatgct tccctgctgt  98580
tctgctcccc acctgcaagc gcccacacac tgatcaacag cacacgccat agagcatgcc  98640
aaagaatccc agaaatactc attcttaatg atccagaaga acaagtgata gcttctggca  98700
agttctaata ggccatatgt gcccatggga aagcaagagt caattctctc tagctggttg  98760
cctctgaatt tatgaagtca agccgcgtag gggaacatgc caagaggatt atcccaatgc  98820
ctgttctgcg tggtgtcctt tttctagcct cggaagcact aggcctacac cttcgctata  98880
gccctcgtct tagcgcctgt atttgaaaaa cttgccacac caatcttaat ttgctccatt  98940
gtgttctaat ctcattttaa aaaccacaag gtaaatgatt aaaaataatc ttagattaag  99000
gagtacacag atctttgcag cctcattgtg tttccagagc gggctagtgt agacactggt  99060
gaacaaggag ggcctagaga attagctttc tcccagaaag atgcacagcc tctacctgag  99120
agtaccaatt ccagagaact caatggtcat taagcaccat tgcctcgaca gccagccagc  99180
ctcacttgcc tgcctatctc ctttattttc caagtatctt gtccctggca gtggggagag  99240
gttagcagga ggctgctcag atgctctcgg tctctgatct tcaggatctg aaggggagag  99300
catttgaaga atccccattg ctggatttct caggacaatc ctgcataatg ccaggatctg  99360
atggaggaga caggcagctc tgttaatcct ctggtgcatc ctcacttctg tggtctccaa  99420
gtccaccatg tcccagttaa ttcatttcat tattcatctg taagtcattt ccctaaagag  99480
ctaataagaa aacactggca gtacaatcag ccctccatat ccatgggttc agcctctgga  99540
aattcaaccc actgtggctt gaaaatacag tattcaagag acatggaacc tgtggatata  99600
gaaggcagat ttttcgtatc cataggttct atagggccat tttagggact tgcacatcta  99660
cagaccttca ggagtctcag aactgatgca ctgcagatac caagagatga ctgtaagtgg  99720
ttaggaattt ggatgctggg gccaggctgc ctgcagttac cttccagctc tgccacttgc  99780
cagctatgtg accttagcaa gttgttcaac ctctctgtgc cttggcttct tcaactgtaa  99840
aataggataa tgatagcact tcccttatgg agtccttgtg aaggttaaat ggcagagtac  99900
aattaatgtg ctgtgtgccc agcgtgtggt attggggtta ggtgaaagac tgtactggga  99960
tcactggggg tgagcctcca tgtgccatgc cccaaccact atcctcagct aacttcttgt 100020
ctgtcagtgt taggctggtg ctataataat ttccattttc atggatgagg aaatcaaggc 100080
acagagaagt tacatgactt gcctaagatc tcagtgcttt taaatagtgc agctaagatt 100140
ccagaccagg tatttttatt tcagtgtctg gactgtagat ctctaaatcg agaggaactc 100200
cctgaataaa ataagcttgg agtgctgtta actaagttgg ttatttaaga cagttgttct 100260
cagtcctcag tgtacattag aatcttctgg agggtatgtt aaaacagact gctgggccca 100320
ccgagagttc ctgagcctgc aactctgggt tgagcctgag agtctgtgct tctagtaagt 100380
tctcaggtga tgcttatgct gcttctccca aattttgaga accattgatt gaaaatgttg 100440
atcaaaaatt atgtggtcta ggctgagcac agtggctcac aactgtaatc tcaacacttt 100500
gggaggccaa gtcaggtgga tcactgagct caggagttcg agagcagcct ggtcaacatg 100560
```

acaagaccca tctctacaaa aaacaccaaa aaaaaatggc tggatgtggt ggtgcacacc 100620
tgtagtcaca actactgggg aggctgaggt gggaggatca cttgagcccg ggagacagag 100680
caagaccctg tctcaaaaaa gaaacattta gtcttgattg tcatctatct cattgatcat 100740
tttacttggc aaaatttacc tacttactct tattagtctg taaaaatggt tattaaaatg 100800
gtggctttca gtgtaactac aaattctctt agtcattata gtgttggatt caccaatgta 100860
tcatcagtca gtgtttctga agtgtgtaaa tgaaataact cctactttct ttaggaagaa 100920
aaatattcaa atgacataat taccttgtga tgtgtgactt aaaggtaaca gtaatgcaga 100980
gtcaatagtg gtcattgtat tcaagacact aaaagttcac ctcccacccc cccccccac 101040
ccaccaccca acaaacacac aagcttcttt ccctttggaa aaaaaagctc ttccagatac 101100
ctacattcat aaactatccc aattaaccct tcagcaagtg gaagaagtgt aagaaaggat 101160
acctcttctt tagaacacag ggtttgtttt tatgttattt aagataaaca ggaattcaaa 101220
tggtcatgta ccaaagcaac acaaagaact tccggaaatc tgaaagggaa ctgtggtcag 101280
aactctgagc atttttatgt ttactgagtt ttgtcccaaa gtttattaat gtttacatgc 101340
cacaaggaaa ggtagcatca caataagaga cgtttttcag gcttgataac cacttattag 101400
gtattttgcc aaacaagttc acacatccta gagagctgga ttgtgtgacc cagaacccac 101460
cctctagggc aaggtgccca tctgatgggt agggtgtagg agtaggcctc agaccactcc 101520
tgacgtgaac ctgcttaaag tgagggccca attctaaagt gggaactatg taaatacctt 101580
tctagtgcat tttcagataa tcgccactgg gcctatggat ggagagggct ggcagatctc 101640
cctgtaaccc caggtgcatc ccgaggcctg ccaccgaagc ccactcaagg ctgaatgcac 101700
ggcgagctca ggctgctctc cccttggtat ttgctaagaa cttctgttta gtagctctcc 101760
acacctattt gattgtcttt ttgctgctgt gttgttttgt tgagtttttt ttttgcaatg 101820
acactgagtg gcctcctgta ttgtttcttt cagccagtaa tgttaaagta gagactcaga 101880
gtgatgaaga gaatgggcgt gcctgtgaaa tgaatgggga agaatgtgcg gaggatttac 101940
gaatgcttga tgcctcggga gagaaaatga atggctccca cagggaccaa ggcagctcgg 102000
ctttgtcggg agttggaggc attcgacttc ctaacggaaa actaaagtgt gatatctgtg 102060
ggatcatttg catcgggccc aatgtgctca tggttcacaa aagaagccac actggtaagg 102120
cctggctcag tttttccttt agtggcctgg agaaggtgca tggggtttga aggaggaaag 102180
catcctgtct tccttgtgtt ctgagcatgt ttctaattga ctggtagctc agttgttgca 102240
agcgattggt tccaagtggt accgagtcat agagtccttg ttctggtaca gccttgtaaa 102300
ggacttctca acacgtacca attccaccct ataaataaaa caagggaaaa gtgaacagca 102360
tcacatgaga ggcttggcga gggctgctat tatagtaaca catactaagt agtctcagct 102420
gagccctcag ggtacgtgtg ctgagtggtc accctccaca aaacaaaaaa tcctgataca 102480
ccaaaactta ctcctcaaag tttccactga gaaaccatga gtaaaatgtg tgtttaaatt 102540
gtatccaaac taacagggtt tgatgtttag aaacaataat caatgatgga atagcagcaa 102600
aatcgagttt tcagaaagac ctcagatgag ctttcaaatg gcttgccctc taacaggaaa 102660
gactttgaat cagatgcttc tattgccact ggttatcagc tcaaattcct aaagaacttc 102720
atcccaaata ccctgtcttg ctgaaaggtt tactggaagt ataagagaat gtcatgttct 102780
gtgtccagaa aggaaggaac acgggcaccc tagtgtcagc gagttgtgct caggctcaca 102840
ggatgccccc tcaccagagg cgtgggaaca cggcgagccc cagctggccg cgctctgcca 102900

-continued ctgtttctaa tagccggtca cgttgatgga agtgtcacag agttgtccaa cagaactgtc 102960
cagtcagaaa accaccactc atggtgctgg agtgtcttag aagtaaaata tgaataacac 103020
acacttattt aactataggc aggaggtttc ttatgaattg aagagaaact tttctttgcg 103080
tgggaagctg ttctaaagtt gggtaaaaca caatagatcc accacctcta gcagccactg 103140
atagctgaaa cgtgaaacat agagacccta agctatcact gcctctgagc tggcattgtt 103200
aggtcatcat aaagctagcg tctcccactg caaaacccaa gaggaaaaaa atagttgaaa 103260
atcctatttt aaaggcctag cagattctat aagatacctt gggaaaatga tgacgatgac 103320
ttgaaatcag accctcgtat gctgcttccg tgggggcgaa caaaaatatg ttcatcaaaa 103380
attaagcaga aatgcagaaa attttgtgag ccaaaaaagc tgtgttatca ggaaatgcag 103440
atatttgtgg ggttgtaatt ttttatattt gaatcgggcg gttttcaaaa tgatctattc 103500
catttgtagt gtatctgaaa acctataaaa ataagttgat atcaatagat atccatcttc 103560
cataaaaatt caacttctaa aattaagcaa actttgcttt ttctaatggc ccctttatcc 103620
tcaaattacc cactgaaata gacggatcac actcagccct aagtgaagca agcgtgcatg 103680
agagtagtcc cagcctcgcc tttgtaatga ggtggaaatt aacatgaagg taggctaccc 103740
tgtgatagac acttaacagg atactcgggg acccatggta atacatccct gataaggaat 103800
agacctcaca aatgaactac ttgcctgtta attcatttaa agcctgactg tacagtgaaa 103860
attctcttaa ataaatattt gataagtgaa tcaaattctg gcttactaaa ttgccaaaat 103920
ataatgactg cctgccttga taaaaagaat aattacattt aatgaataaa cctgccaagt 103980
acagatatgc caggtggcac ctgctgtttg ctgctcactt ctcccaacaa atagcagcta 104040
ggtgccacct gcacaccaat aagctgagtt tttcacttac ggaacaaata actttcagaa 104100
gtcaatttta tagtttctgc cttgcccttt gttaaaaaaa tacacacact tgaagcaatg 104160
aactcatgaa ttgttttcat catgcatttc cacttgccta aatataaagg gtcccaggta 104220
gatacagaaa tacctggttt ggccaaactt ggtttgaata actagacatg ctagaaaagg 104280
ttttcatttt cctgggatct gagtggaata tgttagaaaa ggcatgcttt ctgaattctc 104340
tatgcttaaa acatttctag agcagtgctt ctcaaacttg aaagagcatg taaatcacct 104400
gagatctcgt gaacatacaa ctctgcttca gacctggggg gaggcaggag agcaagcatt 104460
cctaacaagc tcccagcttg tggagcacag agccgcctca ggcagcaggg cagtgcagct 104520
gagcagtgac agtgaacagg gccattcaga gggctctcca cctggggctt aggtacgacg 104580
ggaatcccca ctggacaggc taggacttgc actgtggcca ttgttcctcc tcctgcccat 104640
ggctgagtca gcttctcagt cccttccagg atacactgag aggattcagg ggcggtctcg 104700
cctctgccca tatccccacg ttggtgaagt accactggcg ccattttcta atcagctcat 104760
cggcaccagc acgtcacttc ccctgttgtg cagctcagtt ttatatttct gactcgggtg 104820
taatagtaac atcttcccca ccaatgtctc agggttattg tgagaaccag agaggagaga 104880
ggtaggaagg aagcaggaaa tgcagggtgc aaatacacca cattattatt ctaaataatg 104940
ggatttttaa taacaaagac caagaagatt gtctgtgcct atctagttcc catctgtaag 105000
ataaaaaggt gcagtccctg agcctcctaa aaacagcacc ctaatggcac tgctcctccc 105060
aggtatgatt gcagtagacc tacgtcagtt cttgcagttc aaacacattt tttcactttc 105120
ttctgaaatg ccctcaaatt ctatgacata gtatccatga agacttccct ttttacccag 105180
tgaagttact agagggggtt caaaccttct tacagagggt tcctaaaatg ggagatctgt 105240
ggagtcattg ggattaaaaa ttaaatttca aattcatgac atcaatgtcc tcatcccagt 105300

-continued taaataaaag taaatacaac cttgaagaaa tttgacctac tcagctgcaa tagctgttga 105360
cctgcagaag gcaaatgatg gaccccggcc acgcaagaac acacatggcg tgggctgcgt 105420
tcttgtgccc cagctccatg gacgtgtctt cttagctgtg gacccctcca aaggaaactg 105480
cttgagtgga gtgctctgta ttgtcactcc tgggaatgct ctcttaacac ccccatgcct 105540
tgtgctatgt gttcatacca gcataggcac tcagaagcaa aaaaggtttc cagtgaaatt 105600
tgtttgcagg caggtattaa gacatcagac actgcaggat ccaagtgaac ccctgcccgc 105660
ctgcctgcct gccctgctct gctctgcaga agggcatgtg tctgtagcaa tctgcccttt 105720
ctgtctgcga tgggcagaga ccctggctct gcctcctgtt ttccctgtag ccctccagac 105780
ctggggagag acatgggact ccagcacctg cccagcacgg aagggggtct ttcccaggtg 105840
taagtgtagg gctgcattca ctaatttagg gtcataccac aaacactgtt gtgtcaccag 105900
gatgttgtca catgcttatt gtgagcattt ttgtgacatg agctttctcc tgagaggcca 105960
ccctgtccaa atgagagctg tagttggagg cacatccgtc tcatgctgcc tgggtctccc 106020
tgcaccagct cactctactt ttccttttta tccacttgga gttaaatgca cacatttatg 106080
cacaagtgca cagaaggccc agaactgttc ctaatagata attaaatgat ctctctccag 106140
tggaaactct cctgggctac ctggctgcta gctgttttag cctcttcatc cagtattgat 106200
ttacatgcat cggtttgtaa ctcagacagt atagttagtt agtttgtttc accatcacct 106260
tccaacctgc ttacgtttaa actccttctc tctgcttagc taatacagat ttctgtaagg 106320
atttggagaa ataccagata cctcctggtt agtatcagga cctctccatt ggcctataat 106380
tgaacatcac tgtaaattag tttcagcttt tatagtaatg catctaaccc gccagcttaa 106440
aaaaaaagtg atgataatca tgaaattcaa gtgtcaatat agacttttaa atctggtgtg 106500
gatgttaata gtgccagata tgcttctgtg taatcatttt tgagaagtgc tgtcttcttt 106560
accataatca cattaatcaa tcgggaaatg gttaaataga cattttaata cattgttttt 106620
tcctgagaaa aaaagtgact ccaggaaata tgttgttaca atatctcaac accaggaatt 106680
gtggtcacat agcattcttc ttctaaataa agcatttgtt ttacaaaaga gtttcatgtt 106740
tacttaaacg tgacaaatgt atcactcttc gaagtgagag ttaaatgaaa tgttccctga 106800
tttagattcc aagacctgtg actactcagt aggacaatag catatttctt ttactcagat 106860
acctgtttat ccctttgtca gctccagaat ggagacacag gtgctgccac acagaggaga 106920
gggtcaggtg ttttcttagt cacaaatgca gcagtctcac ccctgaaaga attccttcat 106980
aacaactaaa ttgcacctct tagaatacct gtacttaaaa tataatttgt cttctatgga 107040
tatagacaaa taatagctta aatgttttag gatttgtaaa gaaagaaaaa gctagaaatc 107100
tcaatgcaac tctgacttgt atgtcctgcc ataggaaggt ttgggacttt tctttggaag 107160
atgggaggct tccttcacag tttcttaact tctcatttta ttcaatcttt ctccatctct 107220
ctctctcttt ctctcatcct cacgctctct gtctgtctct ctcctgattt gtctgcttag 107280
ggacagacag gtaatggaga agaaattgaa agggaaaata cagggaaaat gtaaatgaaa 107340
agaagttatt ataactgtta taatgaagtg cctttcattt aaatataaga atgtaacgct 107400
gaaatgaact tgtgatcctg aaatgcattt ttaatgagtt tcctttttat tttgctgctt 107460
cagtggcata ttttaaagac cctttgaaaa aagccacatt aaaaaacccc accaaatgcc 107520
acaacacgca aaattggata ttggtttatt ccaaaactgc tgatcaggaa gagtggctct 107580
tcatcacaaa atgttgcagt cactttattt aaatgagttt gaatttgcat tgtgatgtgc 107640
cattctgatt tagggaaaaa aaattagatt ttcagatcaa attgacccag ccagtgaagc 107700
gttaaggagc tggcaggttt agtctgaaag cctcatgttc tatcaaacct gcagccggtg 107760
gaagtcacca ggcccccgtg ggaaacaact ttctcgtagc atcgtcctca tgtccccacg 107820
ctgagtttag ttctcaccag ctctcctctc tccgtcccag gagaacggcc cttccagtgc 107880
aatcagtgcg gggcctcatt cacccagaag ggcaacctgc tccggcacat caagctgcat 107940
tccggggaga agcccttcaa atgccacctc tgcaactacg cctgccgccg gagggacgcc 108000
ctcactggcc acctgaggac gcactccggt aggtcccctg gatgcagtcc ggggctgtct 108060
gggtgtcccg ggattcctcc actctgcccg cctgggtccc ggattgtgtc cttgctggct 108120
aaccctgagt ccctcccagc tcgcagtcct gcatcgggtg tgagctgttg cttctttgac 108180
attgccccat ccccccctccc catattctcc ttttcccact gcaccaggga gattgggcgc 108240
aggaccccca tgcacataca cacacagaag tctcacctta ggtagcatgt ttcagaacag 108300
gcctcctcat cccgtttgtc aggctggtat ggtttcccta aaggattttg cgggaaatgt 108360
tttcaccaag tgtactgcta agacccaaaa cgttttcaag tacaattctt tctgttgtta 108420
agtcccgctt tggagtgttt tacacaggtg taatggatag ctttttttgca gagctggtag 108480 agaagggtga tttagggcgc acccacccag actgagcccc gtgtggctct cacaccaaaa 108540
accagccaag gccacagtta cagaggccag tctggggctg ttaccagatt ttagacagca 108600
gcctttctct ttgaattaga cagttaaagt acaacccaca taatctggag tcttgacaag 108660
atcatcatag gcataaacgc tctatcattc tcaaaacagt ctcagcctgc aaagttcaaa 108720
tccactaaag tttggttaga tcctctgcct cctgagaaat ggtcctgggt gtttcattat 108780
ccagcagtcc cataattcta cagggcagag gaagagaggg ctcttggccg gcctgtcatg 108840
gatcatgttt gcctacagtg tggtctatac aacatgacat ggcacaggtc tccttcatac 108900
cgtccagttg gggatatttg ctgtagcata ctgcatgaga cttcggaggc gaaaggttga 108960
tggcttttgt ccttcccctc aaggagcttc ctgccccagc cagccaccag ccagggccct 109020
tctccaagca gcagcctctc taagccggtg ccctggggga tggcaatgcc tcagaccagc 109080
tactcctcac ccaccctggg tagcaggata aggaggagcc tccctcaggg aggcagacgt 109140
gtgttctttg tgaaatatct gcagcggccc aggccatctc ttcccaaatg tgatgcgtgt 109200
atttgatggt tgagggtttt agaggctgct cattgtgtcc atctctttat cacacattta 109260
ctgagcaccc ctgggtgccc attctgcaca gaagacctca ggtgcacaca aggaaagcac 109320
caatgtgtta caggaggcat gacagagtgt ctgaggggac agtgggagca taaggaaggg 109380
gacagtgggt cctggggtgg aaagtcagga gagacttccc atagaaggga ggggcttctg 109440
aagtacatgc tggaaggcga gtgtctgagg tttgctttag agacattcta aactagtgtg 109500
tgagtcggca gtaatcccag agaggggtgc ggcacccatg ttggcaagaa ctcggtctca 109560
ctcctggcag gtggtccctg cagtagttca cccagttggc tggagacaaa aaggagagga 109620
gtcacagggg ctggtgcatc acctcctctc catcctgacc tccttcctgg cggtgcacat 109680
ggagaaggat ccccacatgc tcgccatcag aaaattgtca tgatttgggt gatttgactt 109740
cctaaaaact tccaagaaag gagctatacc aagctgagga gttgcttgcc cgagagggcg 109800
ggcagatcag cagggggggcc atggagtggg acacttgcct tgttacagag ggacagggag 109860
aacaggtggt tcccctgaga taggaagaca gtagcatgac ggtgagcatc tttaaatgtt 109920
cacatgggtg atgagcatgt atggtggtcc cacctggaga caaaggtggt acctgggcct 109980
gataagcaag gcccatggag gcctcagcta agagaactgt gcagtctgtc tgccatgcta 110040
accagtggtc taggaagaag cttcacatct gttgtttcta aggagccatg tagacataga 110100
cacagttggc agcaatattg ccttgggtta gtgggaagca ccacttccca tgtcagtgga 110160
aaacacagac actcgttctt aggttgacac caaccatagg tcatcatcac tcctagatta 110220
ctctgattgc aatggaatct ctcatgccca tcagtcctta aaagcagagc tgctctcttt 110280
cctttcttgt tgtggagtta ggaacatgta gtggagtatt ttatgttatt ctggctccag 110340
gcctatgtat ttcatttgag gcatgatggt ttcctattct aagtaccact aagtattgag 110400
tagttataaa atggtggtag actttggact gtgtatttct attctggatc cacggatgag 110460
caagtggaga aaacccatca tggatgcagg gctgctgggg atctgtctgt ccgaaaatgc 110520
tatagagaca cacactgctc ttggggaaaa aaacagtgat gatttcttca aaatgatttc 110580
actgaagtga aataaggact ttggccttgc tctggcaaat tcaaatgtgg ccacactcta 110640
ctccattgtg gaatggtgac tcccctgtcc catgaaaaac caggatcaac atcacagctt 110700
tctctagcaa ctggtggtgg cctgaggtct tatgaactag catgttagca gggatagagt 110760
tagggaattt gtccgatgct gacagcaaga gggtgctggg ggagctggag gggtggagaa 110820
gtgatctccc ttcctgcctc atggcttcct ttggaagttg caagcttaga atttctttcc 110880
caaagaatat tggactatgc ttcaagagac acttgagttc agttgcttac agtgaacata 110940
cttcttatgt tccagagtta aactcaatca tattttcaga aaaatagata ttcagacatc 111000
atgtcatatt tacaggaagc tatttgatca tggaatttac tgaagtgaca gctttttcag 111060
gaaagggtat cgagtggtta tctatatcct attaatttct aaaagcaatg ctcaataaaa 111120
tgtgcaattt taggcaatat tctgtgtttc aacattattt ccttatgttg ggggtacatc 111180
actttatata gataaagaaa gatccttttc attctctatt aaatggtcga gaagtcaaat 111240
tttggctttc atgttggtct tcttactgta gcttctgttc acctaagaaa gagatttaac 111300
caacataagc tttggctaaa ccattgtacc aaacatttct atttggatgc tcttaacttt 111360
tatacaatac tttgaaatgt gttcaataaa acaacatgag aaagaagtag aagattctgc 111420
tattaggttg gaaattgata ttccttacat aagtgattaa agatacttta ttcagtttat 111480
cccttaaaat ggtatctact gaagtcctta aacttaggca tgatattaat tcctggctag 111540
tctttctttt tcctaaaata tcactcaata aaatccaaga aggactaaaa ctcattatat 111600
agaactgcac tgcccaatac agcagccact agccacatgc agtattttta attataataa 111660
gttaaaatta aacaaaatta aaacttcagc cctcagtggc actagccaca ctttttgtgt 111720
ccaacagcta catatggctg gtggctgcca tattggacag cactaataga gagcatttct 111780
atcatcatag gaagttctgt tgaacaaggc tgatctggaa gctacaccat cctaaagctc 111840
tttggcaaga aagcagagct tttccataag ctcagtttat gaacaatata ttttgtattt 111900
tctatgtata tgtatatgag aatacgtata catagaaata tatgaaaata catatacata 111960
taaatataca tatacataaa atagaaatac atatacatag aaaatacaaa atattttgta 112020
ttacatatac atatgcatgg aaatacaaaa tattttgtat tatataatgc aaatgtaaga 112080
tatatttata ttatgtaaga aaatacattt gtgcaataaa acgcttattt cattcaagca 112140
tatttgtcca gcatggtttc ttagagactg aagttaccca gtttagcacc tggaactgaa 112200
ttcactctgg ctgtgttaga tgtagcacca gcgtcatgac agatccagcc cacagcatag 112260
actgaggcct actctggagg caaatctgca gacaatgtgg ccaacacatg ggccttcctc 112320
acatctctgt ccagtcgctg gcatccacgt tataacacag cagtggctcg ttttctccag 112380

-continued ttaaaggcta ggcttccgtg attgaagcag gagagaattt ggtagtcagt aaagtagaca 112440
aactaagaca aaacaagagt cgcatgagtt cttggtacaa ttaaagaaac ccttggccac 112500
caacgttttt aaattcagga atttcaccaa gtccgtaaca gttttagctc tcaagggtag 112560
aatttttttt ttaacttttt tggtaataat tgtattgcat gcattcccct tacacagaag 112620
gctggcattt aattggggtc ttgaactcaa ttgtgttttc tgcagttggt aaacctcaca 112680
aatgtggata ttgtggccga agctataaac agcgaagctc tttagaggaa cataaagagc 112740
gctgccacaa ctacttggaa agcatgggcc ttccgggcac actgtaccca ggtaagcgct 112800
gctgctcgga ggccagcctg gtgggctctc cccccagcac ggtggggaag gagggcgctc 112860
tgcatgcagc cttaggagca gagccttggg cctgcttcct gccggggcta ggagggaggg 112920
aagtttttgg ccaatagcat cagtttcacc agaagcacgt tgtgcttccc agctttctag 112980
gtcctcatct gaccagagag agcttgattt taaaaccctt cccacttcca atcgggagaa 113040
actcctagga tagcagtgac cttgaaagtt ttggggttgt tttttggatg ttggtgattt 113100
taaaacaaca acaaaaaaaa cacctcaagt agtgatattt ctttgtaaac aaaataaaat 113160
gtaaaatatt gttttgaaac aattttttaa caaagttgat caaataagaa ctttcaggct 113220
gtgattttaa gcatcagttc agactgaggg cagggtatcc actcctgcat ggagtgtgag 113280
gttgaagttt gttggaagcc cctggtagtt gataatattg aggttgttga aggatgagag 113340
gaaaggtcgc ttctttctta ggagctgtga tgctccactg tattgcataa cgagatagca 113400
cttgattcag accccagagc ctgtagaata aatgatgtgg agagagtatt gaaaaaggct 113460
ggatttatct gggggaatgg caatgttata aaaggttctt ccctaatttt ttaagagata 113520
agcaatttat aaagagatca aataaaacta atctctttca aaacagtatt catttagcac 113580
tacccctgga aaaatcatca ctagactgtg agtcgaaatt taacgaatgg aggaaaattt 113640
attaagcctc attcaccttt cggactttaa caaatggttc aaaagggaaa attcaccaga 113700
gtaccctcag attattaatg gcagatgaga gcaggaaaaa agaatgttga gaatggctaa 113760
aaattgattc caattagtct tggcatggag aggcaacatc tcacctggcc agagccctgc 113820
agccagagtg ctgtctcctc tgccagtcag ccagggatct ggggcttaca ggcgattcct 113880
ccaggcctca atcttctcac ctgtgaaatg ggaagatacc attaaattgt catttggctt 113940
ctttcaaaat ctcaggtcta gaatggaaag gcattgaagg tgagtggaag agaagaaact 114000
ggatgttaaa ataataataa tgtaacagtt attaattcac atggccagac cccagggcag 114060
aagactaatg gacgagagga tgattatgtt cctttgaaat aaaatgtcaa cattcaaata 114120
ttgttttttt ctgtaaaaaa taagtgaatg ggtcttggaa ggaagtgctc ctaatgatgt 114180
agtttacata ttaatgctta ataaaccatt ttatttactc aacaaatatt cactgaggac 114240
ttataatcaa taataccaag ccctattgaa tacagtaatc taatatacac atagaattga 114300
aaagacaaaa tgaacaaaag aaacagacag tatatcattt ctgtttcctc cactgttttc 114360
attactaaag aaacaagctg cagtacacag ccggctgaga gctgcttccg ggggagcagg 114420
agaagcagca ctcatttcac tgagacctgg gtttgagttc tctgtttttg aatgtgaccc 114480
agagctcatc gcttaaatgc gactgataat tcgtgcctgg ccaccctcat agcagcgctc 114540
tgaaagaaac ataaaggagt ggatacacgt gtgagcagga gcctagacat gtgtcaggta 114600
cttacctaaa catggatgtt taggtcactg acatactgac accatcaagc taattcttct 114660
ctattggtct ctatgtcagt aaggctacgt gccagtaatg tgtattaaat attaccctgt 114720
ggtgagtatc aatttcaccc taaaatgttc atttattccc tttggtggtt aagttacttg 114780
gactaccaca gtgatgcctc tatgtcccca cactcaggag gtatgaaagc gtctctagga 114840
aggagcagtg gtctggtctc agtgtggcag cagacaaagc caggctcgca cttaattaca 114900
ttgaattatt tctgtctggt atggcctcaa aaggtgcaaa atgatcataa atatctttcg 114960
acagtcacct ttggtttttg cccttgccag cacctggccc ttgtaggtgc tgctggttta 115020
aggaacttgg agtattaagg ggatccataa aaggactttg acagaagtct tcctgaactg 115080
tgcttagggc caggaaggca ggcaggggct tggtcatttc agctgtgctg tacccggatg 115140
agtggaaact gtgccttctg atgcatctct cctcctctgt tcccctctaa gaaccccttg 115200
tctgtgctca gatggatgag caagtagtct cttctcccac cccaaaaacc tccttagatg 115260
gggtggattc agtaaaatca aagcctcagt taggcaatat aggaaaagat gaatttttgt 115320
gaatataatt ttctttagta aaaggctttt ggtcacctct tataatttct caatgtcttt 115380
atggaaaaaa taagtttctc ttgagccttt ggtgcacaaa cagagtcacc agcccttgga 115440
ggtgcatgca tctaatgaca gagcagcctg tgactcgcga gcatcaggct cacttgttcc 115500
ttgctgtgat tgactctggg gggtggaggc ttttgggagg ccctgcgcca tggtgcagag 115560
gaagacccct gacctctggg agccctgggc aggctgtggg tgtggcttgg cagagaagga 115620
tggacatgtc aggaagcata ttagcttaat agatgaagtg tgtgaccagt gtaattgggt 115680
tttatggatt tatatttatc ttgcatataa atcagggtgt ggcctatata tgtttgccca 115740
tttaataaaa aacacatatt ccaaatgtta aaatataaaa tataccagca acaatagcca 115800
atttgaaata tatgttttca aagtaacatt cataatagca atgaagacat aaatacttag 115860
aaatgaagaa aaccagcaag ccatagtgag gcaagaaaga aaacatggga gattggagag 115920
gtagagaggt ctggatgccg tccatgggcc tctgcccaaa ttagtgtatc atttcaacat 115980
aaaactggct tgtaaatttt actggaatct ggtaaccatg tatcataaag tatctggata 116040
tatacatgag ataattggca actttttaga agaagaataa tgtcaagtga tgtatgaaaa 116100
tgtagctgaa atggatggaa ctctttgaag aatagacaaa caaatcaata atagagatgg 116160
ataccctact gaagacccca tgataaatca gcatgaaata tccgaggcag gaggaagcat 116220
aaggcaggaa cggtattgga agaattgatc aggcatttaa gataatcagt ttacattatc 116280
atctccttat acactaggat aaattgccgg gaaatgaaag agttatattt ttataactcc 116340
aaccacaata actgatgtaa atatagatcc agctatgcag gatacaaagt tgtatcttca 116400
attatggaaa gagatgacat agaacaattg agaatgacta gaaatggccc acacatcagc 116460
atttacctcc ataatttcta aattttctac agcagtcagg ggtgctttga ttttcaggag 116520
tttgttgtat gctcagggat aaggggctct gggtttttcc tccacattgc ccagatctgc 116580
tgtaggctct tgggggccac atttttgtat ctccgttcac tgtgctggtc catgaagtca 116640
gatgttagat cacacagttc tttgcgtctc agagggctgc tgttagggac tgactgaggt 116700
agcagatttg ggagtattat gaaaagttaa aaggacttgt caaagggaca tcaatactta 116760
atcccagtcc agcctctggt gatggtggtg gtgcctgtgc atttggactt aaagaggatg 116820
atgtgtggtg agcagctgtt ggaggaagaa gcatttgcag gtggctggtc attggcattg 116880
ctccggctgc ctctgcctgt ctggaagtgt tgctgggaag attagaatta atctctagga 116940
agggcctggc tcttgtaggc acttaacaaa tgtcagattt aacattggac gcgactgaac 117000
cctttaaaca taagcctttc taaactggcc tctctgtctt tgactttagt cattaaagaa 117060
gaaactaatc acagtgaaat ggcagaagac ctgtgcaaga taggatcaga gagatctctc 117120

-continued

```
gtgctggaca gactagcaag taacgtcgcc aaacgtaaga gctctatgcc tcagaaattt 117180
cttggtaaga gttaaatgtt tgctgtctct taaaaaaaaa ctatgtgggt gttttagatg 117240
caagtagaaa tgagttgagg gtggaagaaa gggaaaaaaa tcttattttt tcaaaaggaa 117300
aaattggtaa gcttaacatt ccttaaatat cttagaattt tttccaataa gtatcttaaa 117360
aataacaaac ctcccatcag tttttcctag atttgatttt gcagcatctg gggcctgccc 117420
tgtgatctgc ctgtggacat cgctcttagg ggcggctgca ccagcgtgca cagggtggag 117480
agtttgggcc tggctcgtcc gggggacacc acactgcagg acactccagg cctggccggc 117540
ttctcagagc ttcagatcct catttttcat atgaagctcc taatgctccc cttatggggg 117600
actctgaagg gttaatggga ggaatcatac agtgactgac ccctgagaag tgtccagtga 117660
agacagggct tagctaggat tgctgttttg cctaatgctc tgcgggatta aaaaaaaaga 117720
agaagaagaa caagaccatt cgtctctcta ggagcattgc ccagagtagg tattagacac 117780
accaacacca ccatccagcc agacgctgca gggacagtga gccagggtcc gagtggaaag 117840
gcgctaggct tgggaaccag ctcagagtca atacagagcc accgccactc accaactctg 117900
tcagcttagt aaaatggctc tgcccctaga gccctggttc catcctttag tatctcacag 117960
ggtgattgtg aatatcccat gactccaaga ttgagaaaac gtttagaatc cctcggtgtg 118020
aaggttaact ctgtccggaa agaggaccag taaaagcttc atgaggctga gatgcacttt 118080
ggaagaggaa tagagtttca gcacattcta ggtgttggag gaatggggga atctaggcag 118140
atgtttaaaa tcaatgagaa accagaatgc tgaccatgag ggttggagtg gggcctaag 118200
gacatgacgg aggagcaggg tgtgttccca gcttaactca ggtacccatg gggaagcagg 118260
aaaagtgaag gtgtcctagg cagctctgcc acaggatgaa tggcttcaga tgccaggtga 118320
gcgagggacc cttcattcag tcagcaggaa agaagcactg gcatattttt tatgagaaca 118380
aaggctagga tagtaaagac agcaagtacc aaaaaatgac tggaaaaggg agactgtgga 118440
ggcagtggca gcaggcatgg aaagaagggc ttgtgaaggg gaaggggtgg tgtcagagga 118500
acatagggct gggggcaggg attaggtgag ggaaaccatg agtcacactg attctagagt 118560
agtgtgccct tgatgaaaag gataacacca ggttctagga aaagatgggg ttctgttttt 118620
gacgtgttga ttttcaagga cttctggtgt ttgtgacaca tggggaaatt gtggtgggag 118680
agaggtgggg ccagaacagg ggctggtgag gccaagggtc ccagagggca cctgttgacc 118740
tgcaggatga catgaagggg gaaggacaga ggcaaggcca agtcctgggc accagcctcc 118800
ctcttgcagc ttcaaatagg gctccatttt gaccttttga ttaattagag gtttgtcata 118860
ggttgggggt tgagaggagc aagggagaga aggattcagt gtacaaaaag aatgaaagcc 118920
actggctgag ccagtgggga gttgtccaca cacacatgag cctttggacc atgagaacga 118980
gggaggcctt gccttcctga acggagtagg agtgaggtcc tgtgctgagc gtaagcagtg 119040
ggattcccac agcactgggc acagagccca cgggctgcct cctgagcagc cagcatctgc 119100
ctggggtgga cacagtgaca gagagatggg tggtgactgg ggtatgggca gagataaggc 119160
agcaagtgtg tgcaagggga gtgaagggtt actgacctta agaagcaggg atggcgtcct 119220
ctgtcaggtg aggagcctgg agaatgcttt ggtgaatgaa cgtttgcagc cccttttagc 119280
ttttggagac ttgaaaccaa aggagagatt catctgtgaa actctactgg agccactccc 119340
caaccccccac ccttgtgaga ccacaatgtg ggcgttggct tgagatgctt ctgtgttagt 119400
agaagaaata aacaacacag tgctctgatg aggcaaagcg aagatgaaaa aggagttccc 119460
aggggacata gtaggaacag tggacgaggg tagcagaaga ggagtttgga gcaaaagact 119520
```

cacaagcagc tgcataatct gttggtgctt ggcagttcat ttgtaaaaat gatgcctctt 119580
cctgccctaa aatacctacc ttacccccgc ttcaacttga tgagatttcc atcagtcact 119640
cccaatgtgt cacagcttct gcagccctaa aattaaaagg tgagtgagtc tctgaggccc 119700
ctctccactt ctcggatgct gagtttagcc ttcatgtgaa tgtggaaaga ctaggaatac 119760
agctgttatc acacaagctg gcccaatagt ggttcagttg agagagcccc atccttcaga 119820
gtcagctcca gctaggagtg actggtggcc ttgagcatgg tgctgggctt agtgttgcca 119880
tctgtggaat gggtgtgggt ctgttgccct gcctcctccc agagctattc tgaggctcag 119940
aaggggtgat ggatgtgatg gtgctcccaa cactagaaag catcttaaga atgtaagatt 120000
ttcatgatga ctgttgctca gagtggctat tatagttttg ctttattgtt ctataaccta 120060
tgattaaaat ttttacctta aactttgacg tgagtgtgaa taagtatttg ttttgccagc 120120
aacattcctc accactgggg ccattaaaga tctccccctc tgagaccatc aaatacaggt 120180
caacaggact gattaatcta attagaaaag ggcttgtatt aaatagcaat gataattgtt 120240
gtttttagtc tgtctggtgt ttgacttggg aacgttttta aaatagagaa aagcacaaag 120300
aggaaaacaa caattaccaa tattcctgct acccattata attatctagg tatattttct 120360
tcttttgtaa gaaaaagaaa ccctgttata ttgttaaaat aacacaaagt taatataaag 120420
aattttaatg caaagattaa tgttttcaaa tcaccacaaa acccaacatc cagaaattac 120480
caatattaaa agtagaaaag tatcattcta aatattttct gttgcatatg tatgtgagtg 120540
gataggctga tgaattaggt ggattgatgg ataggtaaat atgaaataaa tactttcata 120600
aatattccaa cttatcatac atgccttaaa ttcaagaggt gaaaaaagac ccaaacaaaa 120660
ctagagaagc ggcttatttt aaatatcctc tgacataaag gaatattata tttaaaggat 120720
cctctaagat taaaaatatg tactatgaaa aacattaaga aatttgaatt ttttttaatc 120780
catttgtttc aatttaagca gcatctactg gctcactgct ttgaaaaata aggacagtat 120840
tccagttcac attcagtgtt ccagtgttca cattatctta ttatttttac attgtccagc 120900
tttgtaatat tcacattcta ttctgtaatc ataattcata gtagtttagt tatttattac 120960
taactctatt taaatagatt caaggatcag accctgccct tttcttctta tttatgttta 121020
ttttgattaa tctcttaatt gattggactt tacattcaag caactttttt aaaaaaaagt 121080
ttctatagat gttctatttc tatcattgta ttgtttttga ggatgttggc ctgttgcctt 121140
tgtatttgat gagcattttg acagagtcta tggtcttggg ccactctttc tttttctccc 121200
ttgagaactt tttagatttt gctgatggca ttgcttgttg aatgttgctg tggaaacatc 121260
aagtctagtg taactgtttc ttcttcaagg tgatttgcat tttattcctg aatgcctgag 121320
ggttctttat ttaaccttga agttaaatac cctaattagg atgtatcttg gtctattcat 121380
tcggaataaa aaattcctgc cattttgtct agagagtccc tttttttttct ctttatttct 121440
gggaaattct cttttatata aatatgtttt gttccatcta ttgtgatctc tgttgaggga 121500
taccagttgt ccatatgtta gataatttgt cttccatatc tgttaacagt tcttaaagtt 121560
ttttgtttat ttctttgtct atttttacat ttactcactg ttctcttgtg gttttcctct 121620
gtcagtaatt taatttttag tagttcctgt tctattactt gctattttta atccatgcat 121680
taattttata ataatattat tttgctcctt attttgtctc ctgagacccg aaatctcttt 121740
tttcctctta ctctgttgct tttgcatttt attttgaata cttttaaaat tgattccatg 121800
ttatgaagca attatgaggc atttcctctc ttgttggaat taacgatttt ttcccctagg 121860
agggactcta tggtctgtgt tttacttcct ttcttcccct gtatttctag aaaatatttt 121920
cctagtaacc ctgacatttc ttttcatctt gcttattcta gttggtctga tatagcttga 121980
ttgacatttc agccttcttc ccactatatt ttttttcct gtgagagcta ttgggttttc 122040
taaatcctga aagaatgcca aagatggggt tggaggagtt tggtgaggca aagtgcagcc 122100
tttgttaaaa tacttttcct ttgctctctc tccctcatct gaaatttagt taaataccct 122160
aagccatcag cactgtacct agttggggaa tgctttcatc cccacaggag attctctggg 122220
gctttgggcc atcttcccct tcagtgtaga ccacagagga ctttgcttct gtcccaggga 122280
gcccgcaggg gctcacttct ccatgttcat ctgattcttg tcagccaagg tttcaaatgc 122340
ttttctgatc agaacaggga aaagatacct atctgaatca tgtctttata gatatgaggc 122400
tatgagggaa aattctgagg ttattcttga ctcacaccta aagatttgga aatgagatta 122460
gcagcaaagc tttgccctac atctcatgtc agaattttct gtttctttct agtctttgag 122520
tgtatgtgtg ttctcacaca cgccataatg aaatgcatat tatatataat tatgtgtata 122580
tataatattc tatgactata catgacatgt tcctttagct gattgctgtt aagagaaatt 122640
tataggtttt tatttttctt gttttgttgg gtattaagga agagaaattc tatggtaatt 122700
ttcatgtggc acagtaatct ggcatatatg ttgatttttt tcctacaccc atttgttgtg 122760
ataccaagtt tgaaaacaac agatttcagt ggttgcttgg gaaaccacag aaccatgact 122820
tggggagaga caggatgatt aggtgggaaa gcaccctttt ggtggggctg taaagacttt 122880
tatatttagc aaaattggct acaaagtcca ttcccctcct tttcttgcct tgatttggta 122940
gagggataga cttggataca aactagaatg gattcattct tctctggagt tagtgtaaca 123000
agacatttag ctgctcaaca caaaaacaga aacaaaaaaa ttgtgtggtt tcagcagtgc 123060
tatacaatta ctttttctga cctttaatgg agagaaacac cacttctttg gtccctacca 123120
tcagcttcat agggttttca tcctgttctg tttctgggag ggcgtaactg gccatgcaca 123180
agtttttttt ctctaatcag agtatgtgcc acttctgacc accagtagat gaaaacgaat 123240
ggaaaccagg ctattatatg atacatatcc attacaaaat aagacatgaa actcaaaggt 123300
actttatggt ataatggggc atatattcct ggacaattct taatggtcac agattttata 123360
aaaggactat tagtaaatgt atgaattaca gagtaattta tccttctgtt agtaagaacc 123420
agctgatgac ctcagtgtca ggtgcatcgt ggaaggtgtt gggaccttcc cttgccacca 123480
ccctcaccag ccatcatcag ccataacctg cacattgggg aagttttgac ttatccctca 123540
cttttgcccc tcttcaagct gttctttcca cagtgaatga gaaggccact tcttccttca 123600
aacctttcag tggtttccat tttcctttag acaaagtctc tgcctagctg gcctctgcct 123660
gcccctcctg cctacctctc gagcactgcc cccacctagg gctctggttc cccaaccttc 123720
actcggtcct gccacacctc ccagcccctt ctcccttcag aactttcctt cttgttgtcc 123780
ccaacactgg gacacaaaac cctccttatc aaccctcctt atctggctga ctcttacaag 123840
atcagaaacc tgtgtaatgc tctcatggca cgctcccctt gtcttcgtgg atttctcaga 123900
tgggaaggaa ttatccatgc aatcacacat aaacttctac ctaccctccc ctagtagctg 123960
tctgctgcta aggatgggga ccattctcac ttactcactg ttctgtccct ctgcccagtc 124020
cagatgtgtt gaaggatgga aatatacaga gtagtggtaa aatataaacc gttcagacat 124080
tccaaggatg ggctcatgtg ctttgactca ttaatgtacc actgctgaaa acagaacaca 124140
gccgcagtct tgccagtaag agtgcagtta ctgtaattaa tgaatttgct aattaagcca 124200
tgatttcata ctgaacttat gaccaacata ttgagaaggt gtgtcttcaa gaaaatttat 124260

-continued

```
tttttgtatt aagatattta ctccaaagct aattgaagaa gccaaatcta ggctctggtt 124320
tcaccattgc cagggaaatg agctcatgga ctcctatgaa ctgatgatgt tagatcagaa 124380
gtttctcaag gccagggccc aatcactgct gaggcgtcaa cagtagttcc ttgtacatca 124440
ataattctca ttacttttaa aaaataacag atgaatagca actattttcc ctgtagctcc 124500
cttgctgtgc ctcctaccct ccaccacatg tttctgggga gccctgcttc gggcctgcca 124560
actacagaga attacttttg agtatccctt ccactctcat ctcaagacag agttcatcta 124620
cctttgggtt atttgtcaaa aatgtgtcat tttattacaa aaaatataca atcatcatgt 124680
attttgatta aattttacac tagattatta aaattattaa atacaattat taaaattaat 124740
aatttaacat atcacatatt ttaaatatat tgtatataat gaataataat ataattattg 124800
tctattttaa ttcaataaat gtatagtaag ttagccagtt gtaaattact gagaacactc 124860
tactgaaaaa gcatcatttc aaatacacta tttaaaatat taaatgaaat acaataacat 124920
aattaaacta atctttggtt cccctattta tgtattcatt tatccaacaa aatctcctta 124980
agtgcttata atgggtaggt cctggctcgg tgtcccctag acagacgcat gggccttccc 125040
ccagcccgtc agtatggtgc aggtgtgatg tgtccgcagg tgtgtgtgta tgtgtgcagg 125100
tgtggggtcc gcaggcgtgc tgggccccca ggccgtgttc cccttcccct ccccggttgt 125160
agatttcagc tgttgctgcc agacctgacc ggttccggag gtggccgcgc cccactcact 125220
gtcgcctgct ttccacaggg gacaagggcc tgtccgacac gccctacgac agcagcgcca 125280
gctacgagaa ggagaacgaa atgatgaagt cccacgtgat ggaccaagcc atcaacaacg 125340
ccatcaacta cctgggggcc gagtccctgc gcccgctggt gcagacgccc ccgggcggtt 125400
ccgaggtggt cccggtcatc agcccgatgt accagctgca caagccgctc gcggagggca 125460
ccccgcgctc caaccactcg gcccaggaca gcgccgtgga gaacctgctg ctgctctcca 125520
aggccaagtt ggtgccctcg gagcgcgagg cgtccccgag caacagctgc caagactcca 125580
cggacaccga gagcaacaac gaggagcagc gcagcggtct catctacctg accaaccaca 125640
tcgccccgca cgcgcgcaac gggctgtcgc tcaaggagga gcaccgcgcc tacgacctgc 125700
tgcgcgccgc ctccgagaac tcgcaggacg cgctccgcgt ggtcagcacc agcggggagc 125760
agatgaaggt gtacaagtgc gaacactgcc gggtgctctt cctggatcac gtcatgtaca 125820
ccatccacat gggctgccac ggcttccgtg atccttttga gtgcaacatg tgcggctacc 125880
acagccagga ccggtacgag ttctcgtcgc acataacgcg aggggagcac cgcttccaca 125940
tgagctaaag ccctcccgcg cccccacccc agaccccgag ccaccccagg aaaagcacaa 126000
ggactgccgc cttctcgctc ccgccagcag catagactgg actggaccag acaatgttgt 126060
gtttggattt gtaactgttt tttgtttttt gtttgagttg gttgattggg gtttgatttg 126120
cttttgaaaa gatttttatt tttagaggca gggctgcatt gggagcatcc agaactgcta 126180
ccttcctaga tgtttcccca gaccgctggc tgagattccc tcacctgtcg cttcctagaa 126240
tccccttctc caaacgatta gtctaaattt tcagagagaa atagataaaa cacgccacag 126300
cctgggaagg agcgtgctct accctgtgct aagcacgggg ttcgcgcacc aggtgtcttt 126360
ttccagtccc cagaagcaga gagcacagcc cctgctgtgt gggtctgcag gtgagcagac 126420
aggacaggtg tgccgccacc caagtgccaa gacacagcag ggccaacaac ctgtgcccag 126480
gccagcttcg agctacatgc atctagggcg gagaggctgc acttgtgaga gaaaatacta 126540
tttcaagtca tattctgcgt aggaaaatga attggttggg gaaagtcgtg tctgtcagac 126600
```

-continued tgccctgggt ggagggagac gccgggctag agcctttggg atcgtcctgg attcactggc 126660
tttgcggagg ctgctcagat ggcctgagcc tcccgaggct tgctgccccg taggaggaga 126720
ctgtcttccc gtgggcatat ctggggagcc ctgttccccg ctttttcact cccatacctt 126780
taatggcccc caaaatctgt cactacaatt taaacaccag tcccgaaatt tggatcttct 126840
ttctttttga atctctcaaa cggcaacatt cctcagaaac caaagcttta tttcaaatct 126900
cttccttccc tggctggttc catctagtac cagaggcctc ttttcctgaa gaaatccaat 126960
cctagccctc attttaatta tgtacatctg tttgtagcca caagcctgaa tttctcagtg 127020
ttggtaagtt tctttaccta ccctcactat atattattct cgttttaaaa cccataaagg 127080
agtgatttag aacagtcatt aattttcaac tcaatgaaat atgtgaagcc cagcatctct 127140
gttgctaaca cacagagctc acctgtttga aaccaagctt tcaaacatgt tgaagctctt 127200
tactgtaaag gcaagccagc atgtgtgtcc acacatacat aggatggctg gctctgcacc 127260
tgtaggatat tggaatgcac agggcaattg agggactgag ccagaccttc ggagagtaat 127320
gccaccagat cccctaggaa agaggaggca aatggcactg caggtgagaa ccccgcccat 127380
ccgtgctatg acatggaggc actgaagccc gaggaaggtg tgtggagatt ctaatcccaa 127440
caagcaaggg tctccttcaa gattaatgct atcaatcatt aaggtcatta ctctcaacca 127500
cctaggcaat gaagaatata ccatttcaaa tatttacagt acttgtcttc accaacactg 127560
tcccaaggtg aaatgaagca acagagagga aattgtacat aagtacctca gcatttaatc 127620
caaacagggg ttcttagtct cagcactatg acattttggg ctgactactt atttgttagg 127680
cgggagctct cctgtgcatt gtaggataat tagcagtatc cctggtggct acccaataga 127740
cgccagtagc accccgaatt gacaacccaa actctccaga catcaccaac tgtcccctgc 127800
gaggagaaat cactcctggg ggagaaccac tgacccaaat gaattctaaa ccaatcaaat 127860
gtctgggaag ccctccaaga aaaaaaatag aaaagcactt gaagaatatt cccaatattc 127920
ccggtcagca gtatcaaggc tgacttgtgt tcatgtggag tcattataaa ttctataaat 127980
caattattcc ccttcggtct taaaaatata tttcctcata aacatttgag ttttgttgaa 128040
aagatggagt ttacaaagat accattcttg agtcatggat ttctctgctc acagaagggt 128100
gtggcatttg gaaacgggaa taaacaaaat tgctgcacca atgcactgag tgaaggaaga 128160
gagacagagg atcaagggct ttagacagca ctccttcaat atgcaatcac agagaaagat 128220
gcgccttatc caagttaata tctctaaggt gagagccttc ttagagtcag tttgttgcaa 128280
atttcaccta ctctgttctt ttccatccat ccccctgagt cagttggttg aagggagtta 128340
ttttttcaag tggaattcaa acaaagctca aaccagaact gtaaatagtg attgcaggaa 128400
ttcttttcta aactgctttg ccctttcctc tcactgcctt ttatagccaa tataaatgtc 128460
tctttgcaca ccttttgttg tggttttata ttgtaacacc atttttcttt gaaactattg 128520
tatttaaagt aaggtttcat attatgtcag caagtaatta acttatgttt aaaaggtggc 128580
catatcatgt accaaaagtt gctgaagttt ctcttctagc tggtaaagta ggagtttgca 128640
tgacttcaca cttttttttgc gtagtttctt ctgttgtatg atggcgtgag tgtgtgtctt 128700
gggtaccgct gtgtactact gtgtgcctag attccatgca ctctcgttgt gtttgaagta 128760
aatattggag accggagggt aacaggttgg cctgttgatt acagctagta atcgctgtgt 128820
cttgttccgc cccctccctg acaccccagc ttcccaggat gtggaaagcc tggatctcag 128880
ctccttgccc catatccctt ctgtaatttg tacctaaaga gtgtgattat cctaattcaa 128940
gagtcactaa aactcatcac attatcattg catatcagca aagggtaaag tcctagcacc 129000

-continued

```
aattgcttca cataccagca tgttccattt ccaatttaga attagccaca taataaaatc 129060
ttagaatctt ccttgagaaa gagctgcctg agatgtagtt ttgttatatg gttccccacc 129120
gaccattttt gtgctttttt cttgttttgt tttgttttga ctgcactgtg agttttgtag 129180
tgtcctcttc ttgccaaaac aaacgcgaga tgaactggac ttatgtagac aaatcgtgat 129240
gccagtgtat ccttcctttc ttcagttcca gcaataatga atggtcaact tttttaaaat 129300
ctagatctct ctcattcatt tcaatgtatt tttactttaa gatgaaccaa aattattaga 129360
cttatttaag atgtacaggc atcagaaaaa agaagcacat aatgcttttg gtgcgatggc 129420
actcactgtg aacatgtgta accacatatt aatatgcaat attgtttcca atactttcta 129480
atacagtttt ttataatgtt gtgtgtggtg attgttcagg tcgaatctgt tgtatccagt 129540
acagctttag gtcttcagct gcccttctgg cgagtacatg cacaggattg taaatgagaa 129600
atgcagtcat atttccagtc tgcctctatg atgatgttaa attattgctg tttagctgtg 129660
aacaagggat gtaccactgg aggaatagag tatccttttg tacacatttt gaaatgcttc 129720
ttctgtagtg atagaacaaa taaatgcaac gaatactctg tctgccctat cccgtgaagt 129780
ccacactggc gtaagagaag gcccagcaga gcaggaatct gcctagactt tctcccaatg 129840
agatcccaat atgagaggga gaagagatgg gcctcaggac agctgcaata ccacttggga 129900
acacatgtgg tgtcttgatg tggccagcgc agcagttcag cacaacgtac ctcccatcta 129960
caacagtgct ggacgtggga attctaagtc ccagtcttga gggtgggtgg agatggaggg 130020
caacaagaga tacatttcca gttctccact gcagcatgct tcagtcattc tgtgagtggc 130080
cgggcccagg gccctcacaa tttcactacc ttgtctttta catagtcata agaattatcc 130140
tcaacatagc cttttgacgc tgtaaatctt gagtattcat ttaccctttt ctgatctcct 130200
ggaaacagct gcctgcctgc attgcacttc tcttcccgag gagtggggta aatttaaaag 130260
tcaagttata gtttggatgt tagtatagaa ttttgaaatt gggaattaaa aatcaggact 130320
ggggactggg agaccaaaaa tttctgatcc catttctgat ggatgtgtca caccttttct 130380
gtcaaaataa aatgtcttgg aggttatgac tccttggtga a                    130421
```